US 8,598,164 B2
Dec. 3, 2013

(12) United States Patent
Hadida-Ruah et al.

(54) HETEROCYCLIC CHROMENE-SPIROCYCLIC PIPERIDINE AMIDES AS MODULATORS OF ION CHANNELS

(75) Inventors: Sara Sabina Hadida-Ruah, La Jolla, CA (US); Edward Adam Kallel, Escondido, CA (US); Mark Thomas Miller, San Diego, CA (US); Joseph Pontillo, San Diego, CA (US); Vijayalaksmi Arumugam, San Marcos, CA (US); Nicole Hilgraf, San Diego, CA (US); Jason McCartney, Cardiff by the Sea, CA (US); Peter Diederik Jan Grootenhuis, San Diego, CA (US); Corey Anderson, San Diego, CA (US); Mehdi Numa, San Diego, CA (US); Bryan A. Frieman, San Diego, CA (US); Brian Richard Bear, Oceanside, CA (US); James Philip Johnson, Jr., San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 187 days.

(21) Appl. No.: 13/102,335

(22) Filed: May 6, 2011

(65) Prior Publication Data
US 2011/0306607 A1     Dec. 15, 2011

Related U.S. Application Data

(60) Provisional application No. 61/331,882, filed on May 6, 2010, provisional application No. 61/438,688, filed on Feb. 2, 2011.

(51) Int. Cl.
| | | |
|---|---|---|
| *C07D 491/22* | (2006.01) | |
| *C07D 498/22* | (2006.01) | |
| *A61K 31/5386* | (2006.01) | |
| *A61K 31/438* | (2006.01) | |

(52) U.S. Cl.
USPC ............ 514/229.5; 544/71; 546/17; 514/278

(58) Field of Classification Search
USPC ................... 544/71; 546/17; 514/229.5, 278
See application file for complete search history.

(56) References Cited

U.S. PATENT DOCUMENTS

| | | | |
|---|---|---|---|
| 3,939,159 | A | 2/1976 | Dornauer et al. |
| 4,353,901 | A | 10/1982 | Clark |
| 5,206,240 | A | 4/1993 | Baldwin et al. |
| 2002/0013325 | A1 | 1/2002 | Fisher et al. |
| 2002/0082264 | A1 | 6/2002 | Nikolic et al. |
| 2002/0151712 | A1 | 10/2002 | Lin et al. |
| 2004/0014744 | A1 | 1/2004 | Haviv et al. |
| 2004/0266802 | A1 | 12/2004 | Calvet et al. |
| 2005/0209262 | A1 | 9/2005 | Tomori et al. |
| 2006/0052597 | A1 | 3/2006 | Best et al. |
| 2007/0066584 | A1 | 3/2007 | Yao et al. |
| 2007/0078120 | A1 | 4/2007 | Ban et al. |
| 2007/0117824 | A1 | 5/2007 | Berk et al. |
| 2008/0255154 | A1 | 10/2008 | Yao et al. |
| 2009/0169567 | A1 | 7/2009 | Kokubo et al. |
| 2009/0192182 | A1 | 7/2009 | Kusumi et al. |
| 2009/0325992 | A1 | 12/2009 | Hanada et al. |
| 2010/0113418 | A1 | 5/2010 | Fukatsu et al. |
| 2012/0196869 | A1 | 8/2012 | Hadida Ruah et al. |
| 2012/0245136 | A1 | 9/2012 | Hadida-Ruah et al. |
| 2012/0264749 | A1 | 10/2012 | Hadida-Ruah et al. |

FOREIGN PATENT DOCUMENTS

| | | |
|---|---|---|
| CA | 2489255 | 12/2003 |
| EP | 0 002 937 | 7/1979 |
| EP | 0 370 732 | 5/1990 |
| EP | 0 431 943 | 6/1991 |
| EP | 2 123 652 | 11/2009 |
| GB | 1 590 155 | 8/1981 |
| JP | 4 297458 | 10/1992 |
| WO | WO 92/15304 | 9/1992 |
| WO | WO 95/15327 | 6/1995 |
| WO | WO 95/30642 | 11/1995 |
| WO | WO 97/02248 | 1/1997 |
| WO | WO 97/11940 | 4/1997 |
| WO | WO 97/16729 | 5/1997 |
| WO | WO 02/20509 | 5/2002 |
| WO | WO 03/095427 | 11/2003 |
| WO | WO 03/104240 | 12/2003 |
| WO | WO 2004/037800 | 5/2004 |
| WO | WO 2004/037828 | 5/2004 |
| WO | WO 2004/054974 | 7/2004 |
| WO | WO 2004/076418 | 9/2004 |
| WO | WO 2004/092179 | 10/2004 |
| WO | WO 2005/003128 | 1/2005 |
| WO | WO 2005/110992 | 11/2005 |
| WO | WO 2005/121090 | 12/2005 |
| WO | WO 2006/105442 | 10/2006 |
| WO | WO 2006/117669 | 11/2006 |
| WO | WO 2007/011809 | 1/2007 |
| WO | WO 2007/011811 | 1/2007 |
| WO | WO 2007/050124 | 5/2007 |
| WO | WO 2007/124045 | 11/2007 |
| WO | WO 2007/128782 | 11/2007 |
| WO | WO 2007/136605 | 11/2007 |
| WO | WO 2008/045564 | 4/2008 |
| WO | WO 2008/065508 | 6/2008 |
| WO | WO 2008/088688 | 7/2008 |

(Continued)

OTHER PUBLICATIONS

Artico, M., et al., "One-Pot Synthesis of Novel Spiro-Annelated Pyrrole-Containing Heterocyclic Systems from Suitable Synthons", Journal of Heterocyclic Chemistry, Jan. 1, 1992, p. 241-245, vol. 29, No. 1.

(Continued)

*Primary Examiner* — Kahsay Habte
(74) *Attorney, Agent, or Firm* — Brinks Gilson & Lione

(57) ABSTRACT

The invention relates to heterocyclic chromene-spirocyclic piperidine amides useful as inhibitors of ion channels. The invention also provides pharmaceutically acceptable compositions comprising the compounds of the invention and methods of using the compositions in the treatment of various disorders.

68 Claims, No Drawings

(56) References Cited

FOREIGN PATENT DOCUMENTS

| WO | WO 2008/088692 | 7/2008 |
| WO | WO 2009/127609 | 10/2009 |
| WO | WO 2009/144554 | 12/2009 |
| WO | WO 2010/002010 | 1/2010 |
| WO | WO 2010/009195 | 1/2010 |
| WO | WO 2010/027567 | 3/2010 |
| WO | WO 2010/051476 | 5/2010 |
| WO | WO 2010/051497 | 5/2010 |
| WO | WO 2010/114957 | 10/2010 |
| WO | WO 2010/151595 | 12/2010 |
| WO | WO 2010/151597 | 12/2010 |
| WO | WO 2011/025690 | 3/2011 |
| WO | WO 2011/092198 | 8/2011 |
| WO | WO 2012/106499 | 8/2012 |
| WO | WO 2012/112743 | 8/2012 |
| WO | WO 2012/125613 | 9/2012 |

OTHER PUBLICATIONS

Fletcher, Stephen, et al., "4-(Phenylsulfonyl)piperidines: Novel, Selective, and Bioavailable 5-$HT_{2A}$ Receptor Antagonists", J. Med. Chem, 2002, p. 492-503, vol. 45.

Shen, Hong C., et al. "Discovery of spirocyclic secondary amine-derived ureas as highly potent, selective and bioavailable soluble epoxide hydrolase inhibitors", Bioorganic & Medicinal Chemistry Letters, 2009, p. 3398-3404, vol. 19.

International Search Report dated Jun. 21, 2011, prepared in International Application No. PCT/US2011/035493, filed May 6, 2011.

HETEROCYCLIC CHROMENE-SPIROCYCLIC PIPERIDINE AMIDES AS MODULATORS OF ION CHANNELS

CROSS REFERENCE TO RELATED APPLICATIONS

This application claims priority under 35 U.S.C. §119 to U.S. provisional patent application Ser. Nos. 61/331,882, filed May 6, 2010; and 61/438,688, filed Feb. 2, 2011, the entire contents of all applications are incorporated herein by reference.

TECHNICAL FIELD OF THE INVENTION

The invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Pain is a protective mechanism that allows healthy animals to avoid tissue damage and to prevent further damage to injured tissue. Nonetheless there are many conditions where pain persists beyond its usefulness, or where patients would benefit from inhibition of pain. Voltage-gated sodium channels are believed to play a critical role in pain signaling. This belief is based on the known roles of these channels in normal physiology, pathological states arising from mutations in sodium channel genes, preclinical work in animal models of disease, and the clinical usefulness of known sodium channel modulating agents (Cummins, T. R., Sheets, P. L., and Waxman, S. G., The roles of sodium channels in nociception: Implications for mechanisms of pain. *Pain* 131 (3), 243 (2007); England, S., Voltage-gated sodium channels: the search for subtype-selective analgesics. *Expert Opin Investig Drugs* 17 (12), 1849 (2008); Krafte, D. S. and Bannon, A. W., Sodium channels and nociception: recent concepts and therapeutic opportunities. *Curr Opin Pharmacol* 8 (1), 50 (2008)).

Voltage-gated sodium channels (NaV's) are key biological mediators of electrical signaling. NaV's are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role NaV's play in the initiation and propagation of neuronal signals, antagonists that reduce NaV currents can prevent or reduce neural signaling. Thus NaV channels are considered likely targets in pathologic states where reduced excitability is predicted to alleviate the clinical symptoms, such as pain, epilepsy, and some cardiac arrhythmias (Chahine, M., Chatelier, A., Babich, O., and Krupp, J. J., Voltage-gated sodium channels in neurological disorders. *CNS Neurol Disord Drug Targets* 7 (2), 144 (2008)).

The NaV's form a subfamily of the voltage-gated ion channel super-family and comprises 9 isoforms, designated NaV 1.1-NaV 1.9. The tissue localizations of the nine isoforms vary greatly. NaV 1.4 is the primary sodium channel of skeletal muscle, and NaV 1.5 is primary sodium channel of cardiac myocytes. NaV's 1.7, 1.8 and 1.9 are primarily localized to the peripheral nervous system, while NaV's 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), 397 (2005)).

NaV channels have been identified as the primary target for some clinically useful pharmaceutical agents that reduce pain (Cummins, T. R., Sheets, P. L., and Waxman, S. G., The roles of sodium channels in nociception: Implications for mechanisms of pain. *Pain* 131 (3), 243 (2007)). The local anesthetic drugs such as lidocaine block pain by inhibiting NaV channels. These compounds provide excellent local pain reduction but suffer the drawback of abolishing normal acute pain and sensory inputs. Systemic administration of these compounds results in dose limiting side effects that are generally ascribed to block of neural channels in the CNS (nausea, sedation, confusion, ataxia). Cardiac side effects can also occur, and indeed these compounds are also used as class 1 anti-arrhythmics, presumably due to block of NaV 1.5 channels in the heart. Other compounds that have proven effective at reducing pain have also been suggested to act by sodium channel blockade including carbamazepine, lamotragine, and tricyclic antidepressants (Soderpalm, B., Anticonvulsants: aspects of their mechanisms of action. *Eur J Pain* 6 Suppl A, 3 (2002); Wang, G. K., Mitchell, J., and Wang, S. Y., Block of persistent late Na+ currents by antidepressant sertraline and paroxetine. *J Membr Biol* 222 (2), 79 (2008)). These compounds are likewise dose limited by adverse effects similar to those seen with the local anesthetics. Antagonists that specifically block only the isoform(s) critical for nociception are expected to have increased efficacy since the reduction of adverse effects caused by block of off-target channels should enable higher dosing and thus more complete block of target channels isoforms.

Four NaV isoforms, NaV 1.3, 1.7, 1.8, and 1.9, have been specifically indicated as likely pain targets. NaV 1.3 is normally found in the pain sensing neurons of the dorsal root ganglia (DRG) only early in development and is lost soon after birth both in humans and in rodents. Nonetheless, nerve damaging injuries have been found to result in a return of the NaV 1.3 channels to DRG neurons and this may contribute to the abnormal pain signaling in various chronic pain conditions resulting from nerve damage (neuropathic pain). These data have led to the suggestion that pharmaceutical block of NaV 1.3 could be an effective treatment for neuropathic pain. In opposition to this idea, global genetic knockout of NaV 1.3 in mice does not prevent the development of allodynia in mouse models of neuropathic pain (Nassar, M. A. et al., Nerve injury induces robust allodynia and ectopic discharges in NaV 1.3 null mutant mice. *Mol Pain* 2, 33 (2006)). It remains unknown whether compensatory changes in other channels allow for normal neuropathic pain in NaV 1.3 knockout mice, though it has been reported that knockout of NaV 1.1 results in drastic upregulation of NaV 1.3. The converse effect in NaV 1.3 knockouts might explain these results.

NaV 1.7, 1.8, and 1.9 are highly expressed in DRG neurons, including the neurons whose axons make up the C-fibers and Aδ nerve fibers that are believed to carry most pain signals from the nociceptive terminals to the central nervous. Like NaV 1.3, NaV 1.7 expression increases after nerve injury and may contribute to neuropathic pain states. The localization of NaV 1.7, 1.8, and 1.9 in nociceptors led to the hypothesis that reducing the sodium currents through these channels might alleviate pain. Indeed, specific interventions that reduce the levels of these channels have proven effective in animal models of pain.

Specific reduction of NaV 1.7 in rodents by multiple different techniques has resulted in the reduction of observable pain behaviors in model animals. Injection of a viral antisense NaV 1.7 cDNA construct greatly reduces normal pain responses due to inflammation or mechanical injury (Yeomans, D. C. et al., Decrease in inflammatory hyperalgesia by herpes vector-mediated knockdown of NaV 1.7 sodium channels in primary afferents. *Hum Gene Ther* 16 (2), 271 (2005)). Likewise, a genetic knockout of NaV 1.7 in a subset of nociceptor neurons reduced acute and inflammatory pain in mouse models (Nassar, M. A. et al., Nociceptor-specific gene deletion reveals a major role for NaV 1.7 (PNI) in acute and inflammatory pain. *Proc Natl Acad Sci USA* 101 (34), 12706 (2004)). Global knockouts of NaV 1.7 in mice lead to animals that die on the first day after birth. These mice fail to feed and this is the presumed cause of death.

Treatments that specifically reduce NaV 1.8 channels in rodent models effectively reduce pain sensitivity. Knockdown of NaV 1.8 in rats by intrathecal injection of antisense oligodeoxynucleotides reduces neuropathic pain behaviors, while leaving acute pain sensation intact (Lai, J. et al., Inhibition of neuropathic pain by decreased expression of the tetrodotoxin-resistant sodium channel, NaV1.8. *Pain* 95 (1-2), 143 (2002); Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)). Global genetic knockout of NaV 1.8 in mice or specific destruction of NaV 1.8 expressing neurons greatly reduces perception of acute mechanical, inflammatory, and visceral pain (Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)). In contrast to the antisense experiments in rats, genetic knockout mice appear to develop neuropathic pain behaviors normally after nerve injury (Lai, J. et al., Inhibition of neuropathic pain by decreased expression of the tetrodotoxin-resistant sodium channel, NaV1.8. *Pain* 95 (1-2), 143 (2002); Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)).

NaV 1.9 global knock out mice have decreased sensitivity to inflammation induced pain, despite normal acute, and neuropathic pain behaviors (Amaya, F. et al., The voltage-gated sodium channel Na(v)1.9 is an effector of peripheral inflammatory pain hypersensitivity. *J Neurosci* 26 (50), 12852 (2006); Priest, B. T. et al., Contribution of the tetrodotoxin-resistant voltage-gated sodium channel NaV 1.9 to sensory transmission and nociceptive behavior. *Proc Natl Acad Sci USA* 102 (26), 9382 (2005)). Spinal knockdown of NaV 1.9 had no apparent effect on pain behavior in rats (Porreca, F. et al., A comparison of the potential role of the tetrodotoxin-insensitive sodium channels, PN3/SNS and NaN/SNS2, in rat models of chronic pain. *Proc Natl Acad Sci* 96 (14), 7640 (1999)).

The understanding of the role of NaV channels in human physiology and pathology has been greatly advanced by the discovery and analysis of naturally occurring human mutations. NaV 1.1 and NaV 1.2 mutations result in various forms of epilepsy (Fujiwara, T., Clinical spectrum of mutations in SCN1A gene: severe myoclonic epilepsy in infancy and related epilepsies. *Epilepsy Res* 70 Suppl 1, S223 (2006); George, A. L., Jr., Inherited disorders of voltage-gated sodium channels. *J Clin Invest* 115 (8), 1990 (2005); Misra, S, N., Kahlig, K. M., and George, A. L., Jr., Impaired NaV1.2 function and reduced cell surface expression in benign familial neonatal-infantile seizures. *Epilepsia* 49 (9), 1535 (2008)). Mutations of the NaV 1.4 cause muscular disorders like paramyotonia congenita (Vicart, S., Sternberg, D., Fontaine, B., and Meola, G., Human skeletal muscle sodium channelopathies. *Neurol Sci* 26 (4), 194 (2005)). NaV 1.5 mutations result in cardiac abnormalities like Brugada Syndrome and long QT syndrome (Bennett, P. B., Yazawa, K., Makita, N., and George, A. L., Jr., Molecular mechanism for an inherited cardiac arrhythmia. *Nature* 376 (6542), 683 (1995); Darbar, D. et al., Cardiac sodium channel (SCN5A) variants associated with atrial fibrillation. *Circulation* 117 (15), 1927 (2008); Wang, Q. et al., SCN5A mutations associated with an inherited cardiac arrhythmia, long QT syndrome. *Cell* 80 (5), 805 (1995)).

Recent discoveries have demonstrated that mutations in the gene that encodes the NaV 1.7 channel (SCN9A) can cause both enhanced and reduced pain syndromes. Work by Waxman's group and others have identified at least 15 mutations that result in enhanced current through NaV 1.7 and are linked to dominant congenital pain syndromes. Mutations that lower the threshold for NaV 1.7 activation cause inherited erythromelalgia (IEM). IEM patients exhibit abnormal burning pain in their extremities. Mutations that interfere with the normal inactivation properties of NaV 1.7 lead to prolonged sodium currents and cause paroxysmal extreme pain disorder (PEPD). PEPD patients exhibit periocular, perimandibular, and rectal pain symptoms that progresses throughout life (Drenth, J. P. et al., SCN9A mutations define primary erythermalgia as a neuropathic disorder of voltage gated sodium channels. *J Invest Dermatol* 124 (6), 1333 (2005); Estacion, M. et al., NaV 1.7 gain-of-function mutations as a continuum: A1632E displays physiological changes associated with erythromelalgia and paroxysmal extreme pain disorder mutations and produces symptoms of both disorders. *J Neurosci* 28 (43), 11079 (2008)).

NaV 1.7 null mutations in human patients were recently described by several groups (Ahmad, S. et al., A stop codon mutation in SCN9A causes lack of pain sensation. *Hum Mol Genet* 16 (17), 2114 (2007); Cox, J. J. et al., An SCN9A channelopathy causes congenital inability to experience pain. *Nature* 444 (7121), 894 (2006); Goldberg, Y. P. et al., Loss-of-function mutations in the NaV 1.7 gene underlie congenital indifference to pain in multiple human populations. *Clin Genet* 71 (4), 311 (2007)). In all cases patients exhibit congenital indifference to pain. These patients report no pain under any circumstances. Many of these patients suffer dire injuries early in childhood since they do not have the protective, normal pain that helps to prevent tissue damage and develop appropriate protective behaviors. Aside from the striking loss of pain sensation and reduced or absent of smell (Goldberg, Y. P. et al., Loss-of-function mutations in the NaV 1.7 gene underlie congenital indifference to pain in multiple human populations. *Clin Genet* 71 (4), 311 (2007)), these patients appear completely normal. Despite the normally high expression of NaV 1.7 in sympathetic neurons (Toledo-Aral, J. J. et al., Identification of PN1, a predominant voltage-dependent sodium channel expressed principally in peripheral neurons. *Proc Natl Acad Sci USA* 94 (4), 1527 (1997)) and adrenal chromafin cells (Klugbauer, N., Lacinova, L., Flockerzi, V., and Hofmann, F., Structure and functional expression of a new member of the tetrodotoxin-sensitive voltage-activated sodium channel family from human neuroendocrine cells. *EMBO J* 14 (6), 1084 (1995)), these NaV 1.7-null patients show no sign of neuroendocrine or sympathetic nervous dysfunction.

The gain of NaV 1.7 function mutations that cause pain, coupled with the loss of NaV 1.7 function mutations that abolish pain, provide strong evidence that NaV 1.7 plays an important role in human pain signaling. The relative good health of NaV 1.7-null patients indicates that ablation of NaV 1.7 is well tolerated in these patients.

Unfortunately, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

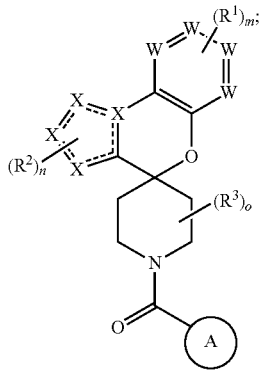

I or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

In one aspect, the invention provides compounds of formula I:

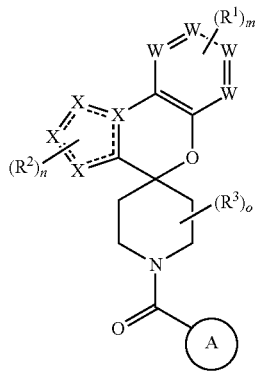

I or a pharmaceutically acceptable salt thereof,
wherein, independently for each occurrence and optionally substituted as valency allows:

$R^1$ is C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl or (C1-C6)-$R^8$ wherein up to two $CH_2$ units may be replaced with O, CO, S, SO, $SO_2$, or $NR^7$;

$R^2$ is H, C1-C6 alkyl, C1-C6 haloalkyl, C3-C8 cycloalkyl, halo, aryl, an electron withdrawing group, $OR^7$, $CH_2CF_3$, $CHF_2$, $CF_3$, CN, $CON(R^7)_2$, $SO_2R^7$, $SR^7$, $SOR^7$, $SO_2N(R^7)_2$, or (C1-C6)-$R^8$ wherein up to two $CH_2$ units may be replaced with O, CO, S, SO, $SO_2$, $CF_2$, or $NR^7$;

$R^3$ is halo, C1-C6 alkyl or C3-C8 cycloalkyl, wherein up to two $CH_2$ units may be replaced by O, CO, S, SO, $SO_2$, or $NR^8$, or 2 occurrences of $R^3$ taken together form a C3-C8 cycloalkyl group;

$R^7$ is H, C1-C6 alkyl, $CHF_2$, $CF_3$, or C3-C8 cycloalkyl, or 2 $R^7$ taken together with the atoms to which they are attached form a ring;

$R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$;

A is aryl, heteroaryl or heterocyclic;

X is N, S, or $CR^2$ wherein at least one X is N;

W is N or CH, wherein up to 2 W are N;

a - - - - line denotes an optionally double bond depending on the identity of X;

m is an integer from 0 to 4 inclusive;

n is an integer from 0 to 3 inclusive; and o is an integer from 0 to 4 inclusive.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. The phrase "optionally substituted" is used interchangeably with the phrase "substituted or unsubstituted." As described herein, the variables $R^1$-$R^8$ in formula I encompass specific groups, such as, for example, alkyl and aryl. Unless otherwise noted, each of the specific groups for the variables $R^1$-$R^8$ can be optionally substituted with one or more substituents of halo, cyano, oxoalkoxy, hydroxy, amino, nitro, aryl, haloalkyl, and alkyl. For instance, an alkyl group can be optionally substituted with one or more of halo, cyano, oxoalkoxy, hydroxy, amino, nitro, aryl, haloalkyl, and alkyl. As an additional example, an aryl group can be optionally substituted with one or more of halo, cyano, alkoxy, hydroxy, nitro, haloalkyl, and alkyl. As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The term "aliphatic", "aliphatic group" or "alkyl" as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" or "cycloalkyl" mean a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

The term "electron withdrawing group", as used herein means an atom or a group that is electronegative relative to hydrogen. See, e.g., "Advanced Organic Chemistry: Reactions, Mechanisms, and Structure," Jerry March, 4$^{th}$ Ed., John Wiley & Sons (1992), e.g., pp. 14-16, 18-19, etc. Exemplary such substituents include halo such as Cl, Br, or F, CN, COOH, $CF_3$, etc.

Unless otherwise specified, the term "heterocycle", "heterocyclyl", "heterocycloaliphatic", "heterocycloalkyl" or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", "heterocycloaliphatic", "heterocycloalkyl" or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I.

Additionally, unless otherwise stated, structures depicted herein are also meant to include compounds that differ only in the presence of one or more isotopically enriched atoms. For example, compounds of formula I, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or sodium channel blockers with improved therapeutic profile.

In the formulas and drawings, a line transversing a ring and bonded to an R group such as in

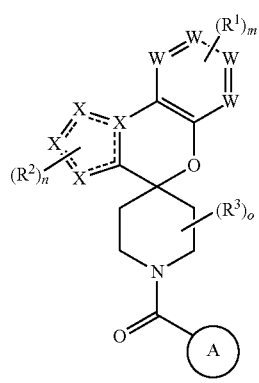

means that the R group can be bonded to any carbon, or if applicable, heteroatom such as N, of that ring as valency allows.

Within a definition of a term as, for example, $R^3$, $R^4$, $R^5$, or $R^6$, when a $CH_2$ unit or, interchangeably, methylene unit may be replaced by O, $NR^7$, or S, it is meant to include any $CH_2$ unit, including a $CH_2$ within a terminal methyl group. For example, —$CH_2CH_2CH_2SH$ is within the definition of C1-C6 alkyl wherein up to two $CH_2$ units may be replaced by S because the $CH_2$ unit of the terminal methyl group has been replaced by S.

In another embodiment, the invention relates to a compound of formula I and the attendant definitions, wherein all W's are CH. In another embodiment, one W is N.

In another embodiment, the invention relates to a compound of formula I and the attendant definitions, wherein $R^1$ is C1-C6 alkyl, C1-C6 alkoxy, halo, CN, $OR^7$, $CON(R^7)_2$, or (C1-C6)-$R^8$ wherein up to two $CH_2$ units may be replaced with O, CO, S, SO, $SO_2$, or $NR^7$. In another embodiment, $R^1$ is F, Cl, $CH_3$, CN, $OCH_3$, $CH_2OH$, $CH_2N(CH_3)_2$, $CH_2NH_2$, $CONHCH_3$, $CON(CH_3)_2$, $CH_2OCH_3$.

In another embodiment, the invention relates to a compound of formula I and the attendant definitions, wherein $R^2$ is C1-C6 alkyl, C1-C6-haloalkyl, halo, CN, $OR^7$, $CF_3$, $CON(R^7)_2$, $SO_2R^7$, or (C1-C6)-$R^8$ wherein up to two $CH_2$ units may be replaced with O, CO, S, SO, $SO_2$, or $NR^7$. In another embodiment, $R^2$ is $CH_3$, $CF_3$, $CHF_2$, $C_2H_5$, $CH_2OH$, halo, CN, $(CH_2)_2OCH_3$, $SO_2CH_3$, $SOCH_3$, $CH_2CF_3$, $CH_2NH_2$, $CH_2NHCOCH_3$, $CH_2NHCOH$, $COCH_3$, or $CONHCH_3$.

In another embodiment, the invention relates to a compound of formula I and the attendant definitions, wherein $R^3$ is C1-C6 alkyl. In another embodiment, $R^3$ is methyl. In another embodiment, 2 occurrences of $R^3$ taken together form a C3-C8 cycloalkyl group.

In another embodiment, the invention relates to a compound of formula I and the attendant definitions, wherein m is 0, 1 or 2. In another embodiment, m is 0.

In another embodiment, the invention relates to a compound of formula I and the attendant definitions, wherein n is 0, 1 or 2. In another embodiment, n is 0. In another embodiment, n is 1.

In another embodiment, o is 0.

In another embodiment, the invention relates to a compound of formula I and the attendant definitions, wherein A is

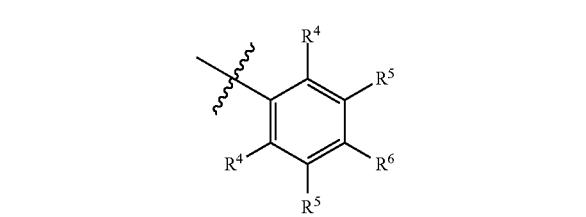

wherein:

$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CHF_2$, $CF_3$, $OCF_3$, $OCHF_2$, heterocycloalkyl, aryl, heteroaryl, or a straight chain, branched, or cyclic (C1-C8)-$R^8$ wherein up to three $CH_2$ units may be replaced with O, CO, S, SO, $SO_2$, or $NR^7$;

$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ wherein up to three $CH_2$ units may be replaced with O, CO, S, SO, $SO_2$, or $NR^7$;

$R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ wherein up to three $CH_2$ units may be replaced with O, CO, S, SO, $SO_2$, or $NR^7$; or two occurrences of $R^4$ and $R^5$, or $R^5$ and $R^6$ are both C1-C6 alkyl and together with the carbons to which they are attached form an optionally substituted ring comprising up to 2 heteroatoms.

In another embodiment, $R^4$ is H, C1-C6 alkyl, C1-C6 alkoxy, halo, CN, OH, $OR^7$, $CON(R^7)_2$, $NR^7SO_2R^7$, $SO_2R^7$, $SOR^7$, $SR^7$, $CO_2R^7$, $NR^7CO_2R^7$, $CF_3$, $CHF_2$, $OCF_3$, $OCHF_2$, heteroaryl, or a straight chain, branched, or cyclic (C1-C8)-$R^8$ wherein up to three $CH_2$ units may be replaced with O, CO, S, SO, $SO_2$, or $NR^7$. In another embodiment, $R^4$ is H, F, Cl, OH, $CH_3$, $CHF_2$, $CF_3$, $OCH_3$, $OCHF_2$, $OCF_3$, $CO_2CH_3$, $CH_2OH$, $SO_2CH_3$, CN, $NHSO_2CH_3$, $C_2H_5$, $OC_2H_5$, $OCF_2CHFCl$, $OCH_2CF_3$, $O(CH_2)_2CH_3$, $OCH(CH_3)_2$, $O(CH_2)_2OH$, $OCH_2OCH_3$, $SCH_3$, $CON(CH_3)_2$, $NHCO_2tBu$,

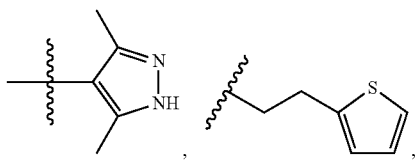

,

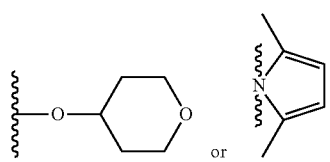 or .

In another embodiment, $R^5$ is H, C1-C6 alkyl, C1-C6 alkoxy, halo, CN, OH, $OR^7$, $NR^7SO_2R^7$, $SO_2R^7$, $SR^7$, $SOR^7$, $CO_2R^7$, $CON(R^7)_2$, $SO_2N(R^7)_2$, $CF_3$, $OCF_3$, or a straight chain, branched, or cyclic (C1-C8)-$R^8$ wherein up to three $CH_2$ units may be replaced with O, CO, S, SO, $SO_2$, or $NR^7$. In another embodiment, $R^5$ is H, F, Cl, $CH_3$, $C_2H_5$, $CH(CH_3)_2$, tBu, OH, $OCH_3$, $OC_2H_5$, $OCH(CH_3)_2$, $CH_2OH$, $CF_3$, $OCF_3$, CN, $CO_2CH_3$, $CONH_2$, $N(CH_3)SO_2CH_3$, $SO_2NH_2$ or $SO_2CH_3$.

In another embodiment, $R^6$ is H, C1-C6 alkyl, C3-C8 cycloalkyl, C1-C6 alkoxy, halo, CN, OH, $OR^7$, $SR^7$, $SOR^7$, $SO_2R^7$, $NR^7COR^7$, $SO_2N(R^7)_2$, $CON(R^7)_2$, $CF_3$, $OCF_3$, $OCHF_2$, heterocycloalkyl, heteroaryl or a straight chain, branched, or cyclic (C1-C8)-$R^8$ wherein up to three $CH_2$ units may be replaced with O, CO, S, SO, $SO_2$, or $NR^7$. In another embodiment, $R^6$ is H, F, Cl, $CH_3$, $CF_3$, $OCH_3$, $OC_2H_5$, $CH_2CH_2OH$, $OCF_3$, $OCHF_2$, $SOCH(CH_3)_2$, $SO_2CH_3$, $SO_2CH(CH_3)_2$, $SO_2CHF_2$, $SO_2CF_3$, $SO_2C_2H_5$, $SO_2CH_2CH(CH_3)_2$, $SO_2tBu$, OH, CN, $CH_2CH_3$, $OCH_2CF_3$, $O(CH_2)_2OH$, $NHC(=O)CH_3$, $OCH_2C(=O)NH_2$,

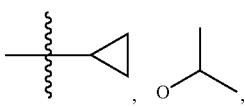

$O(CH_2)_2CH_3$,

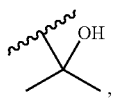

$O(CH_2)_3OH$, $O(CH_2)_2OCH_3$,

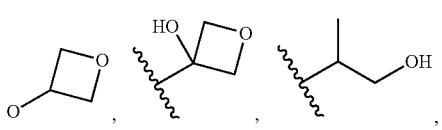

$O(CH_2)_2OCF_3$,

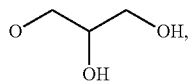

$O(CH_2)_2SO_2CH_3$, tBu,

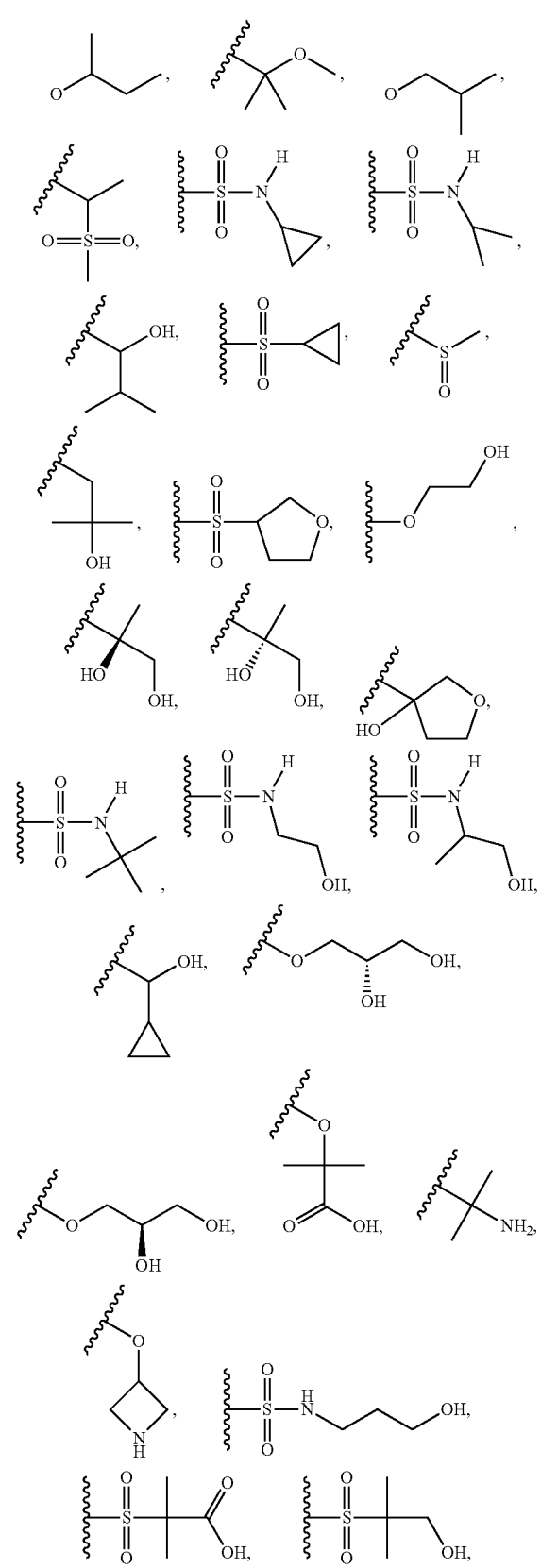

OtBu

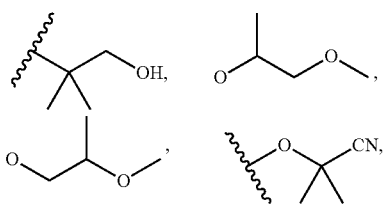

O(CH$_2$)$_3$OCH$_3$, O(CH$_2$)$_2$OC$_2$H$_5$,

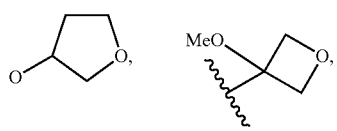 [SMILES: OC1CCOC1 ; *C1(OC)COC1]

O(CH$_2$)$_2$N(CH$_3$)$_2$,

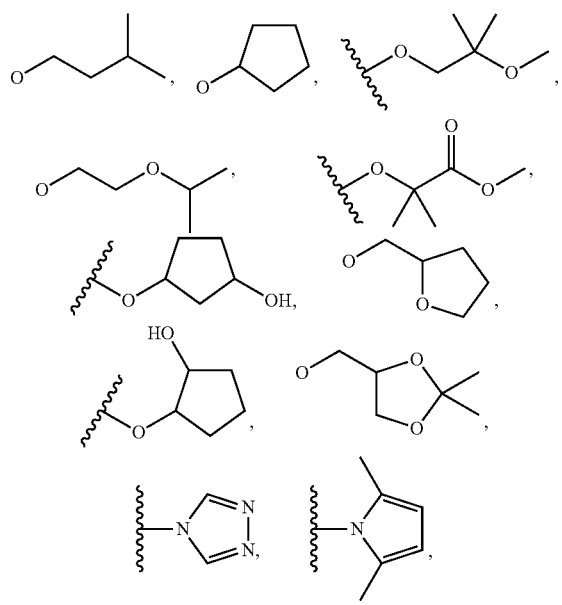

OCH$_2$Ph, SO$_2$NHCH$_3$, SO$_2$N(CH$_3$)$_2$, SO$_2$NHCH$_2$CH$_3$, SO$_2$N(CH$_3$)CH(CH$_3$)$_2$, SO$_2$CH$_2$CH$_2$OH, CONHCH(CH$_3$)$_2$ or OCH$_2$CO$_2$H.

In another embodiment, two occurrences of R$^4$ and R$^5$ are both C1-C6 alkyl and together with the carbons to which they are attached form an optionally substituted ring comprising up to 2 heteroatoms. In another embodiment, two occurrences of R$^5$ and R$^6$ are C1-C6 alkyl and together with the carbons to which they are attached form an optionally substituted ring comprising up to 2 heteroatoms.

In another embodiment, R$^4$ is H. In another embodiment, R$^5$ is halo, CF$_3$, C1-C6 alkyl, or C1-C6 alkoxy. In another embodiment, R$^5$ is C1-C6 alkoxy. In another embodiment, R$^6$ is C1-C6 alkyl or C1-C6 alkoxy. In another embodiment, R$^6$ is C1-C6 alkyl.

In another embodiment, R$^4$ is H; R$^5$ is halo, CF$_3$, C1-C6 alkyl, or C1-C6 alkoxy; and R$^6$ is C1-C6 alkyl or C1-C6 alkoxy. In another embodiment, R$^4$ is H, R$^5$ is C1-C6 alkoxy, and R$^6$ is C1-C6 alkyl.

In another embodiment, R$^4$ is H, and R$^5$ and R$^6$ are alkoxy. In another embodiment, R$^4$ is halo, R$^5$ is H, and R$^6$ is alkoxy.

In another embodiment, R$^4$ and R$^5$ are H, and R$^6$ is SO$_2$R$^7$. In another embodiment, R$^4$ and R$^5$ are H, and R$^6$ is SO$_2$NR$^7$.

In another embodiment,

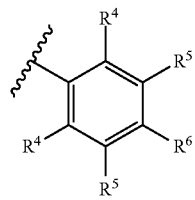

is selected from:

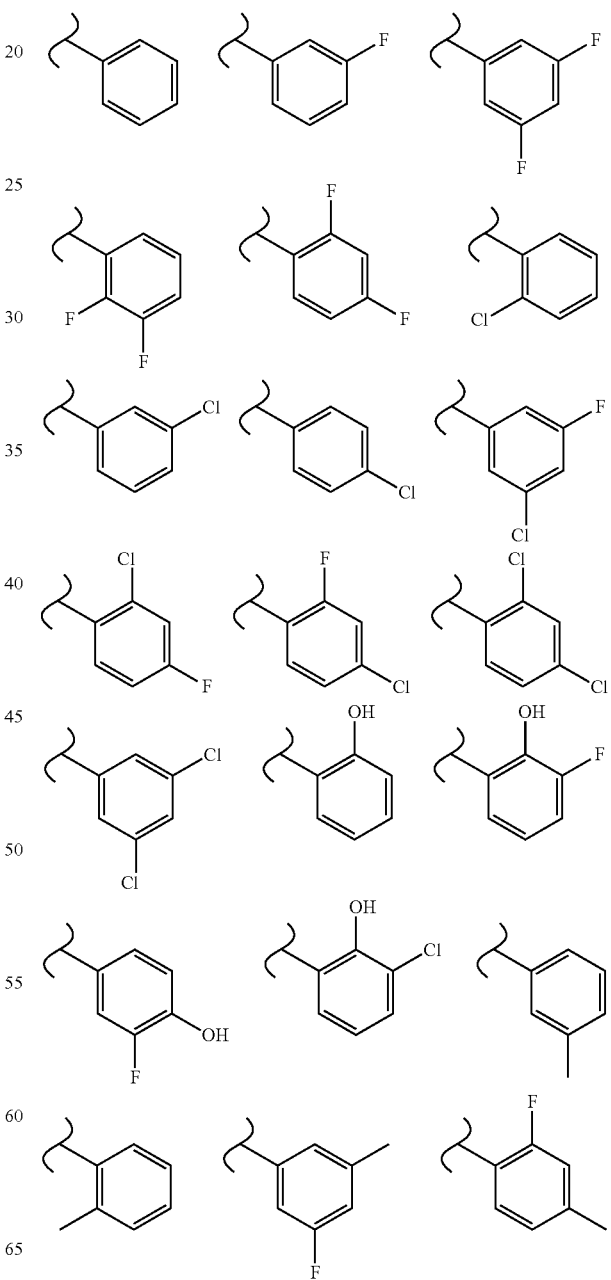

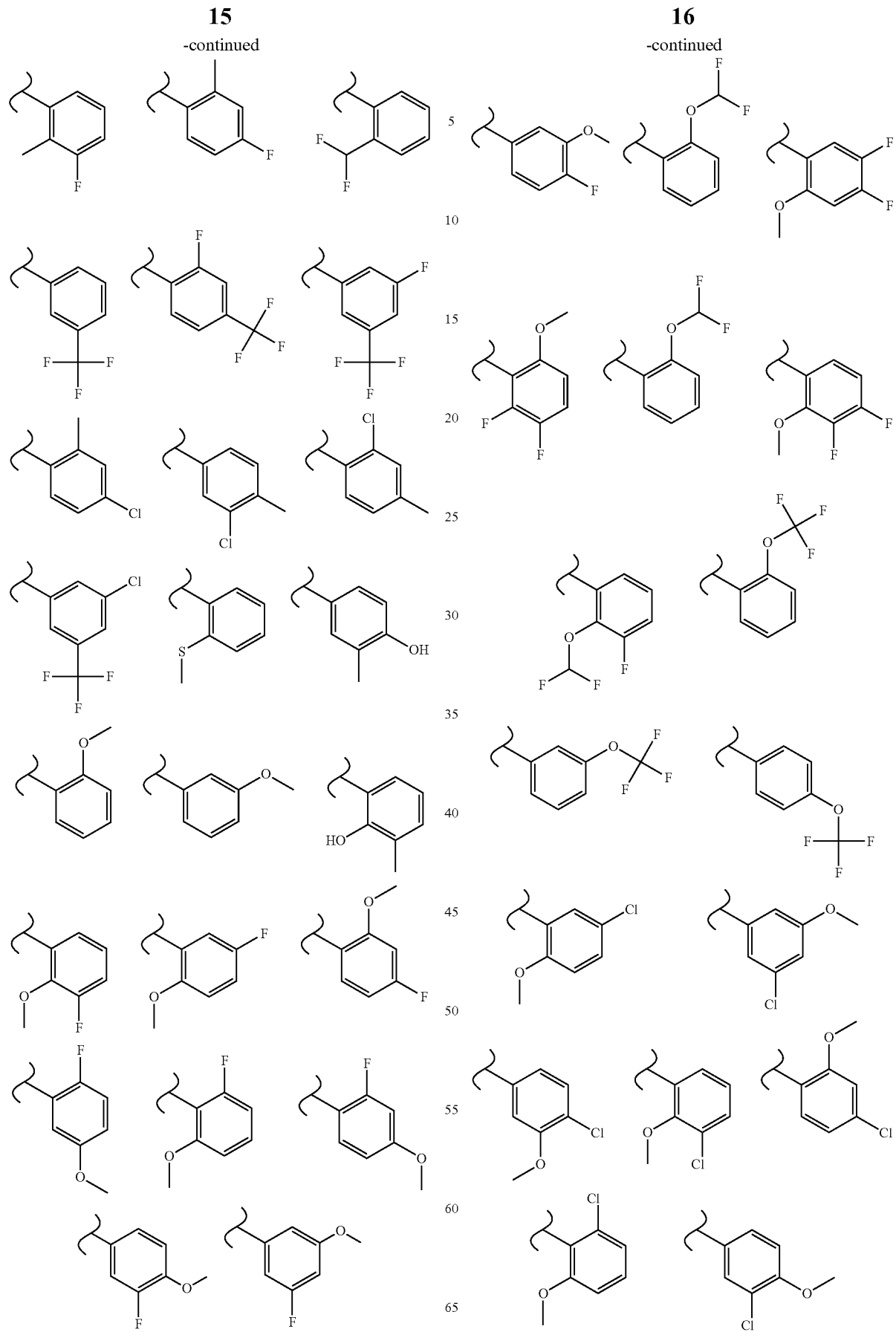

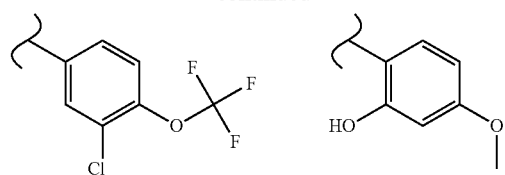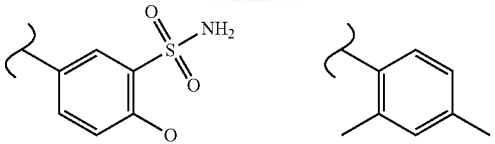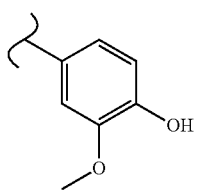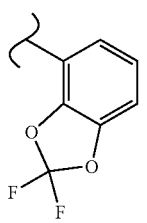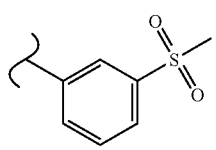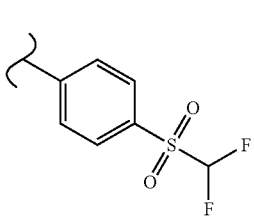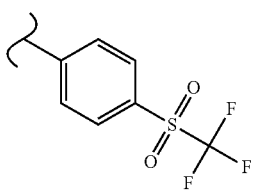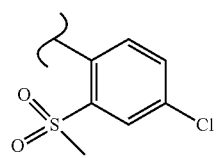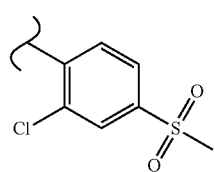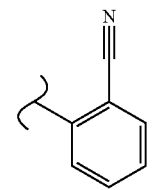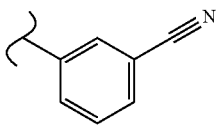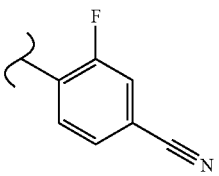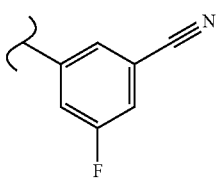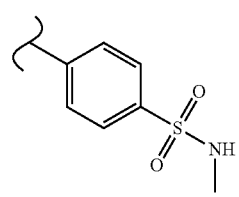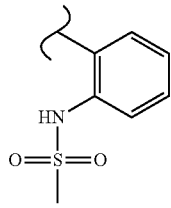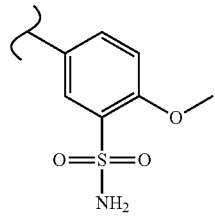

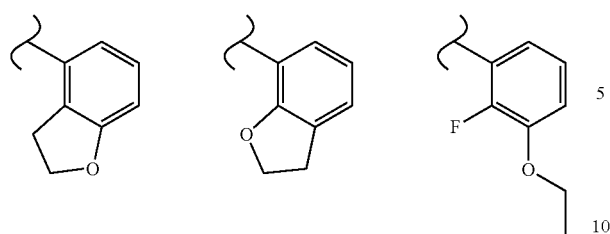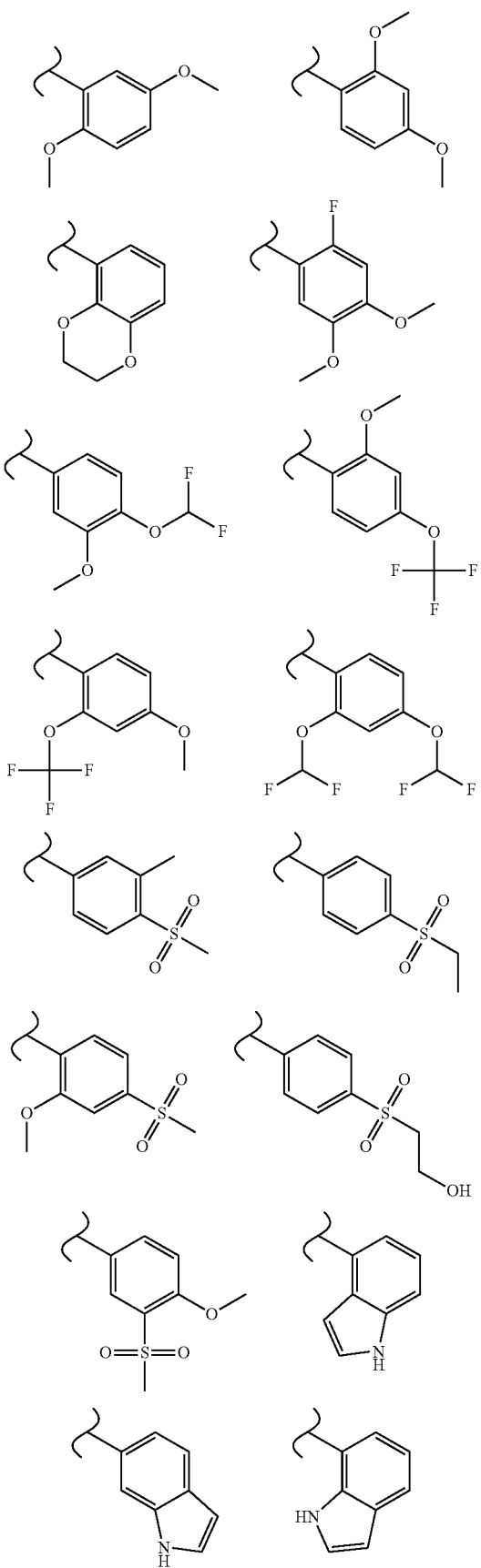

-continued

-continued
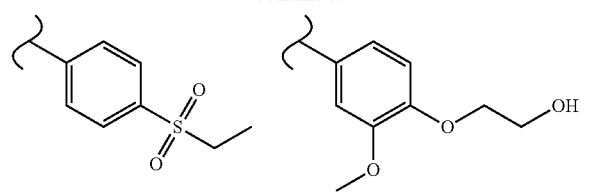
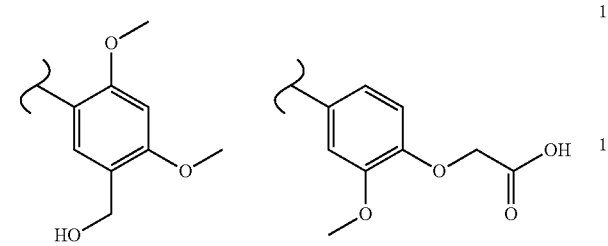
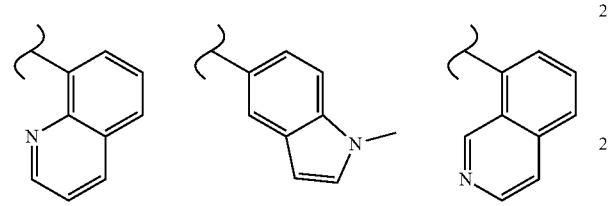
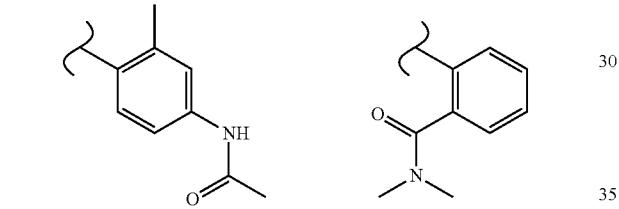
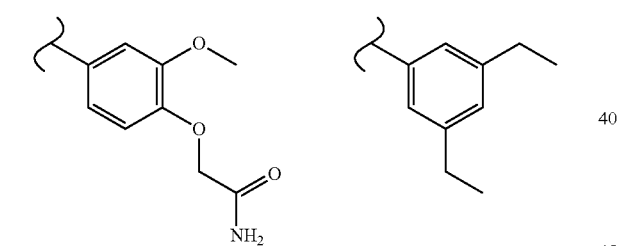
-continued

25
-continued
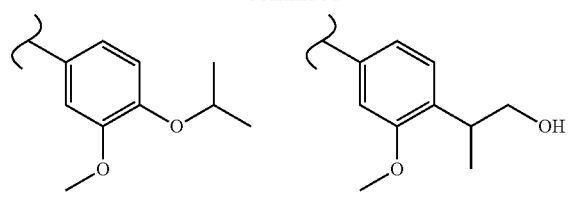
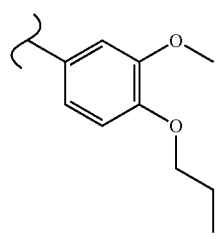
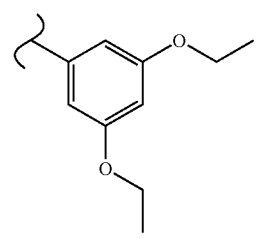
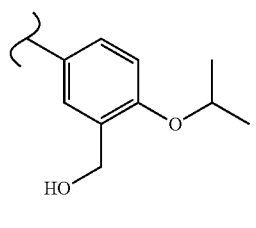
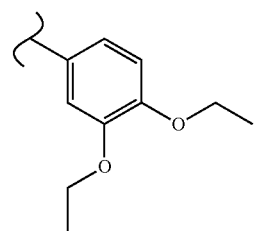
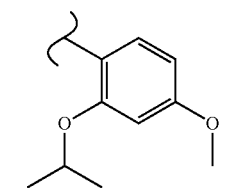
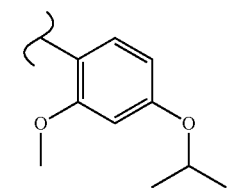
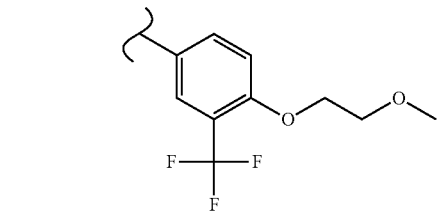
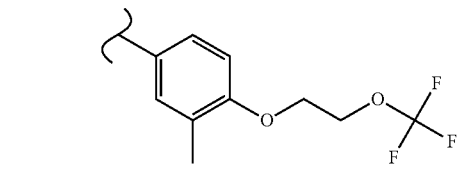
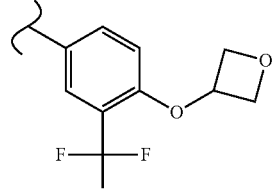
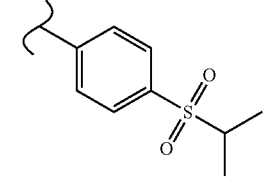
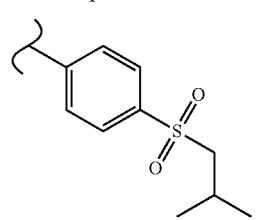
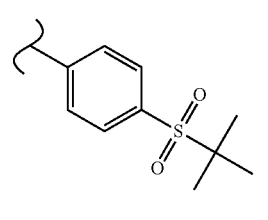
26
-continued
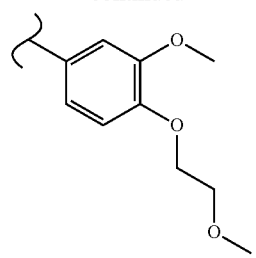
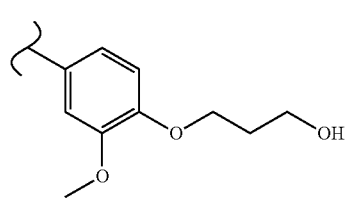
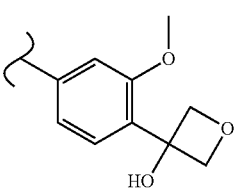
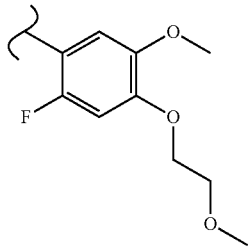
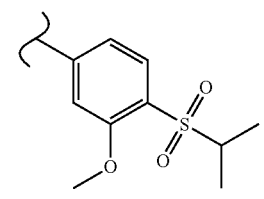
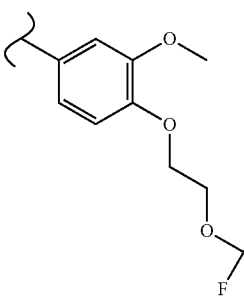
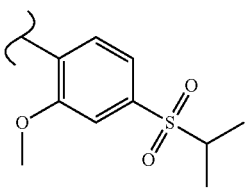
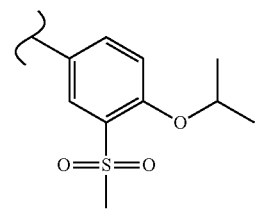
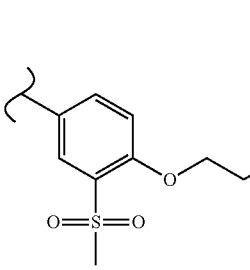
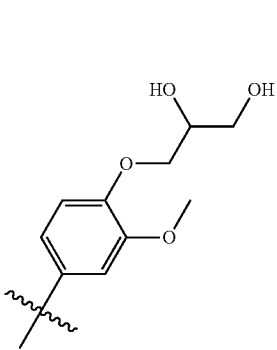

27
-continued
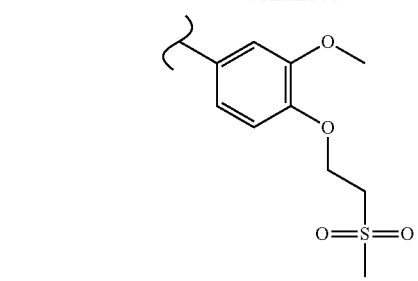
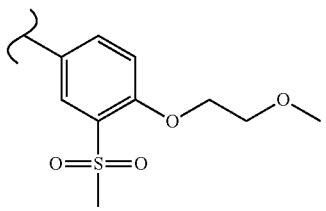
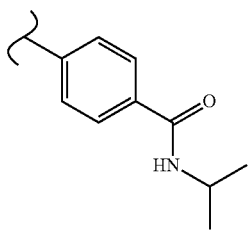
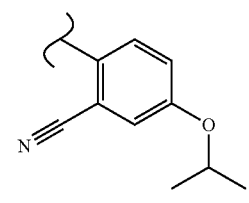
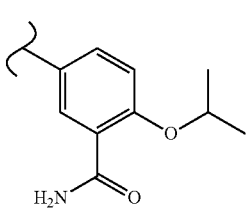
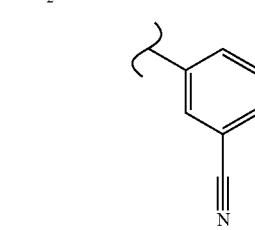
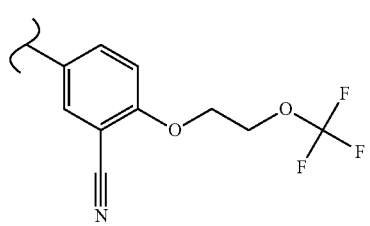
28
-continued
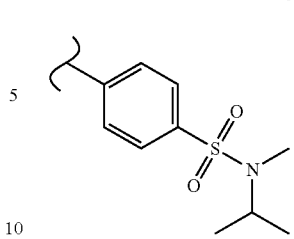
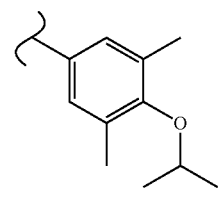
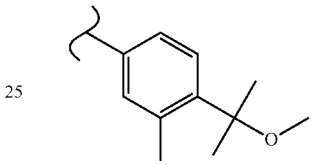
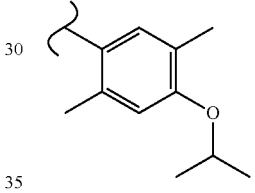
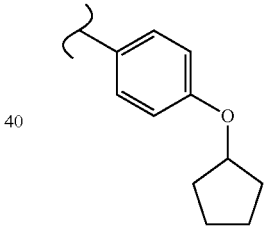
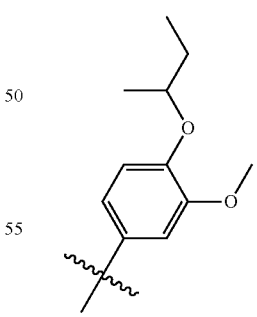
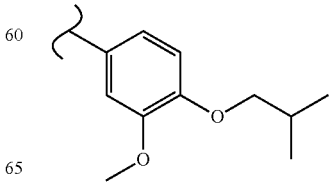
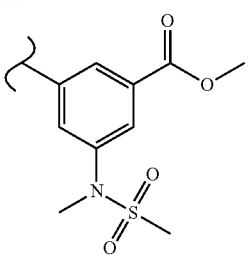
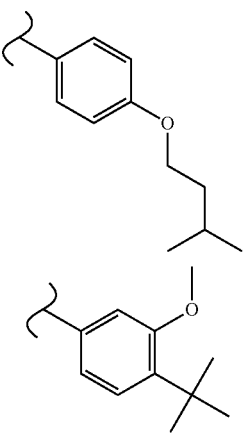
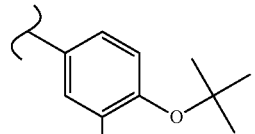
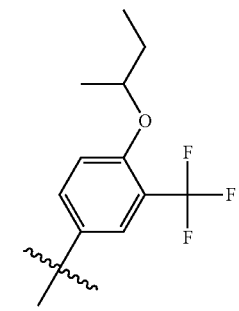
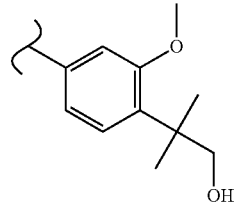
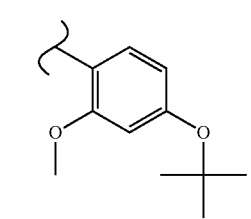

-continued
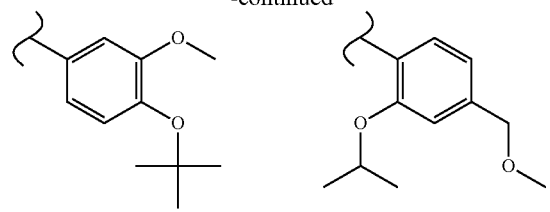
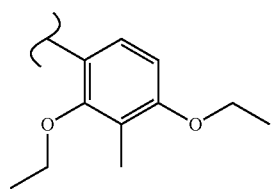
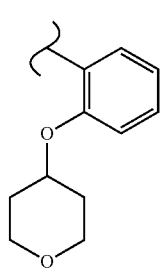
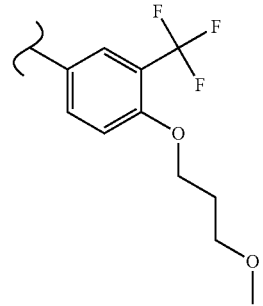
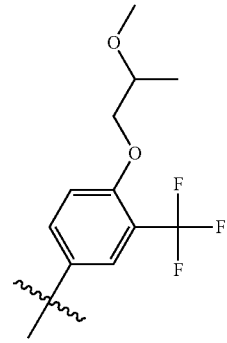
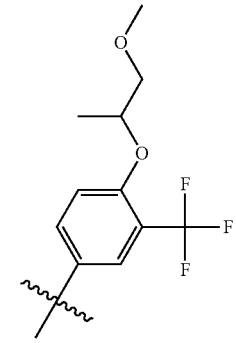
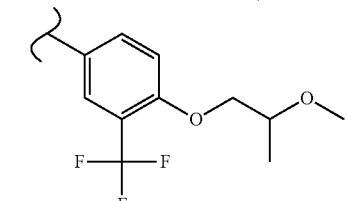
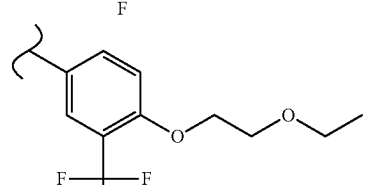
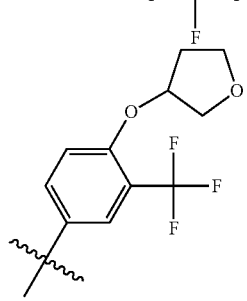
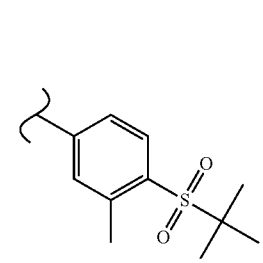
-continued
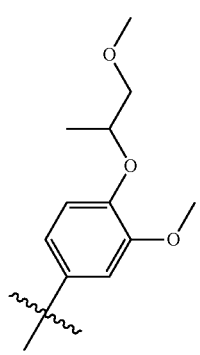
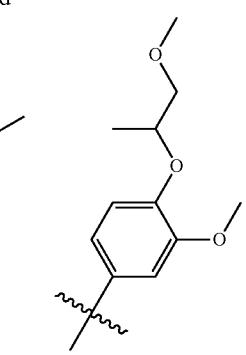
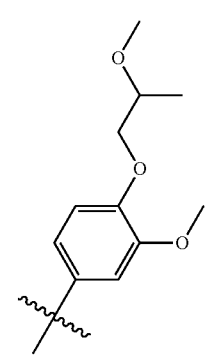
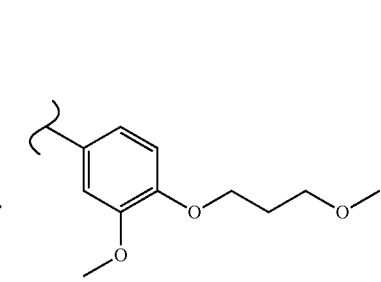
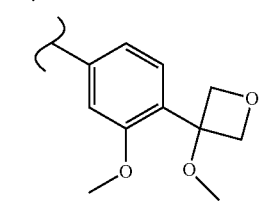
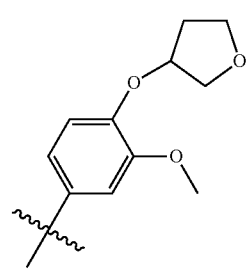
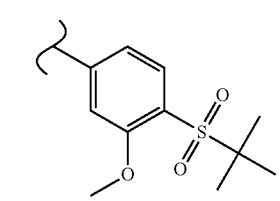
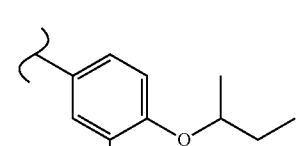
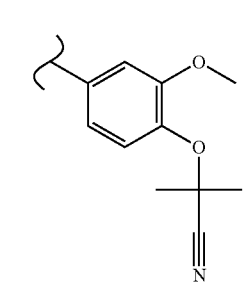

31
-continued
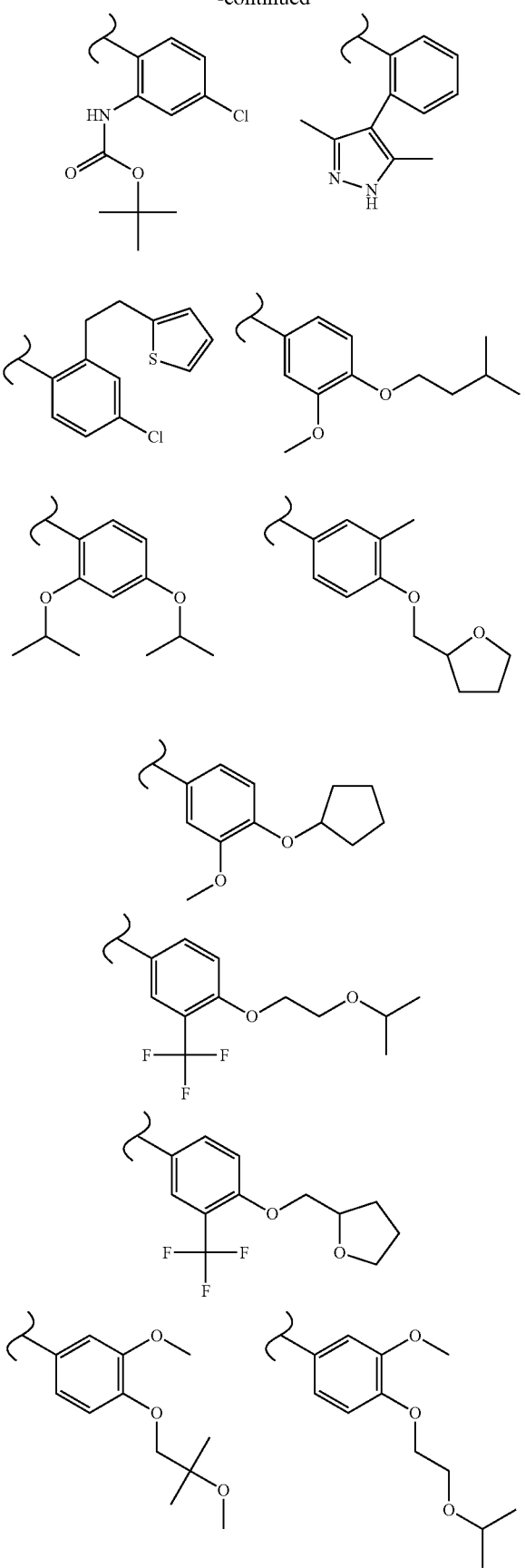
32
-continued
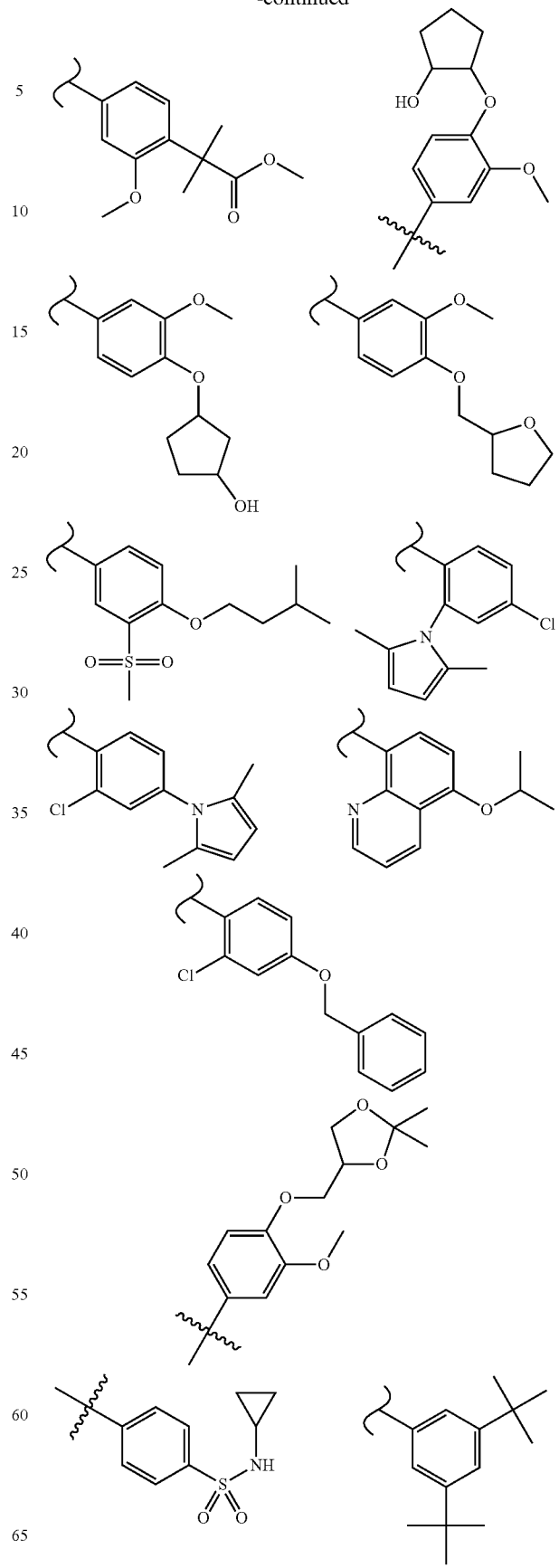

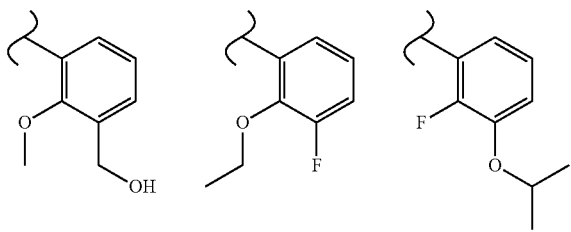
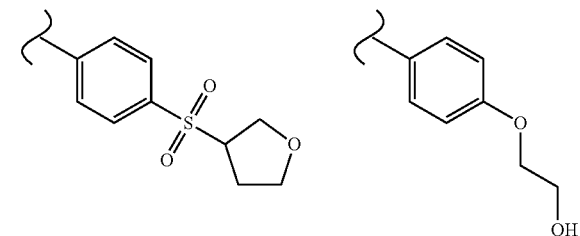
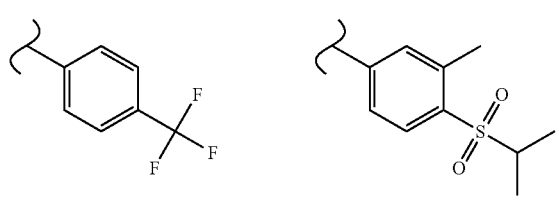
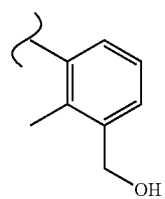
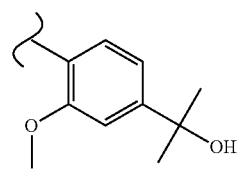
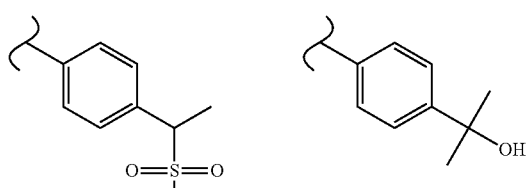
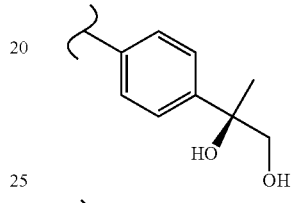
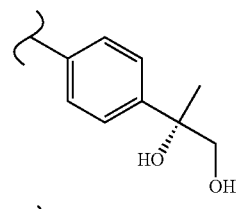
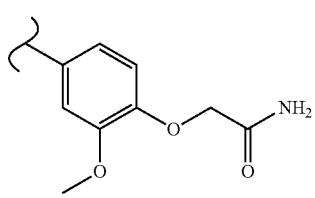
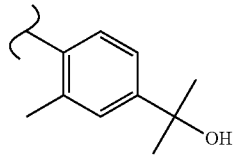
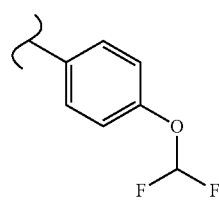
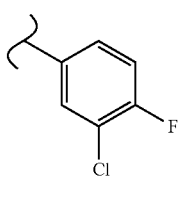
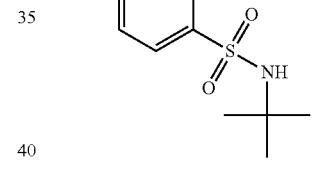
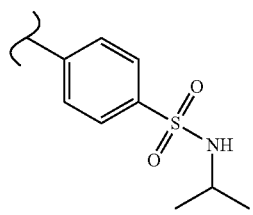
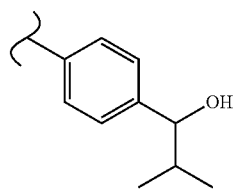
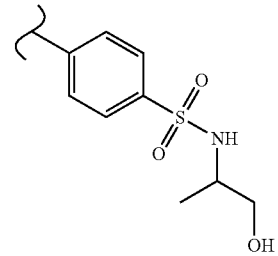
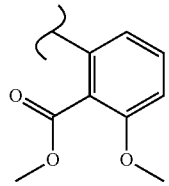
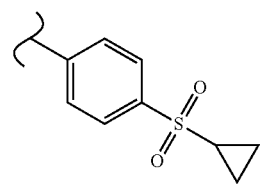
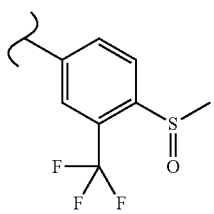
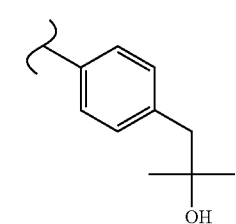
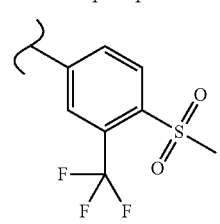
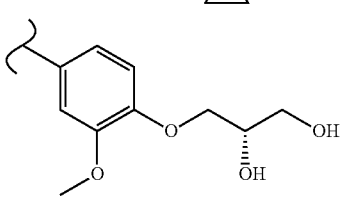

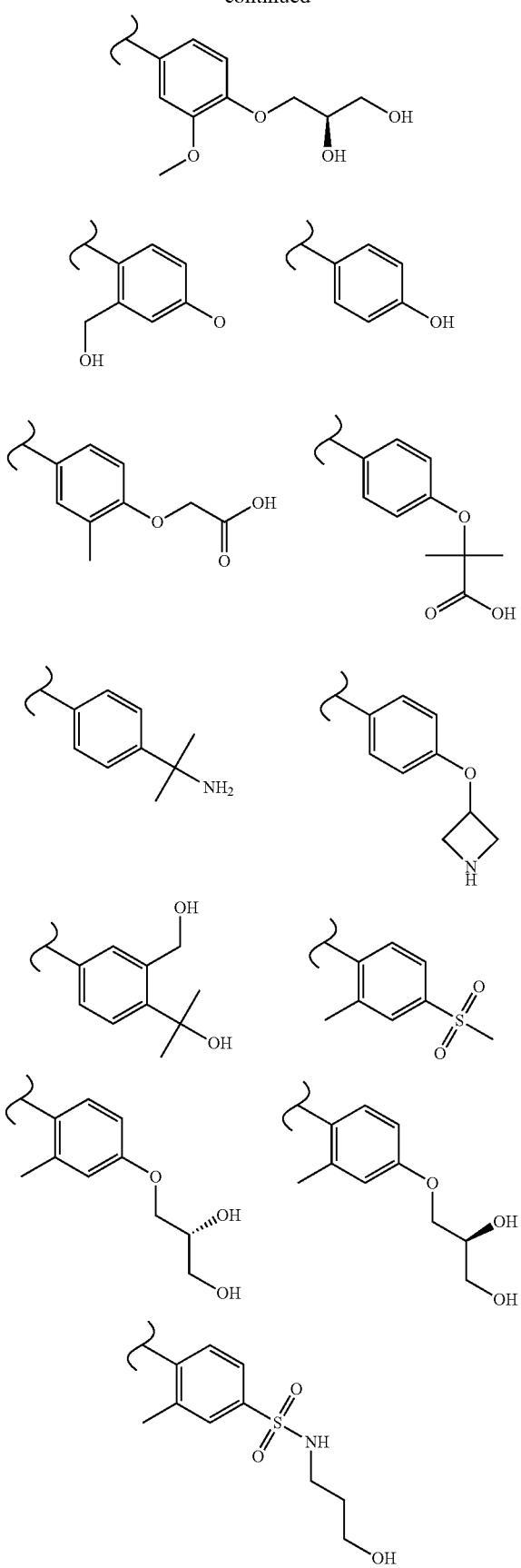
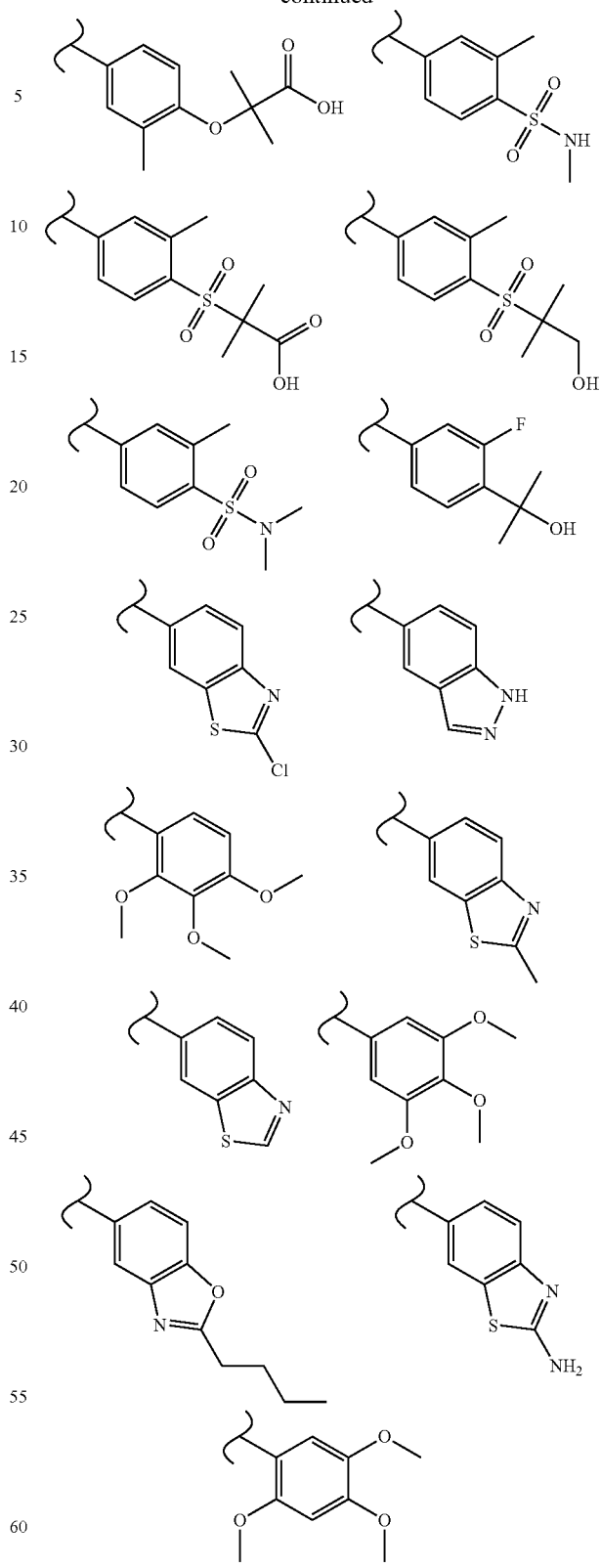
In another embodiment, the invention relates to a compound of formula I and the attendant definitions, wherein A is heteroaryl or heterocyclic. In another embodiment, A is selected from:

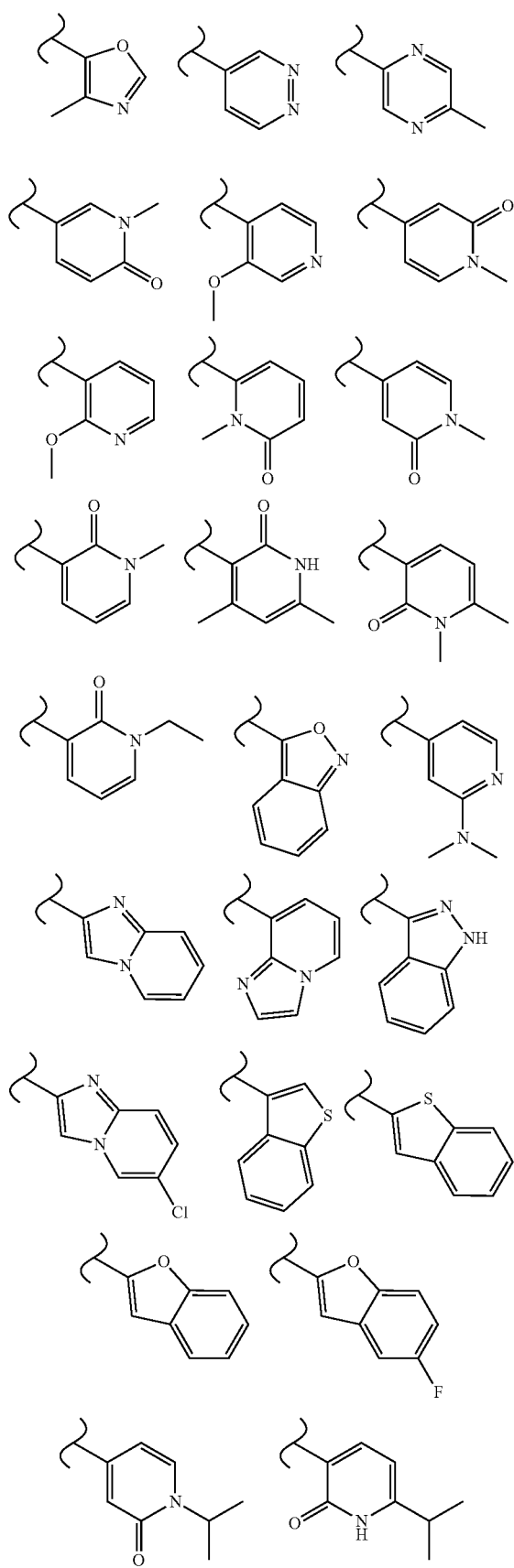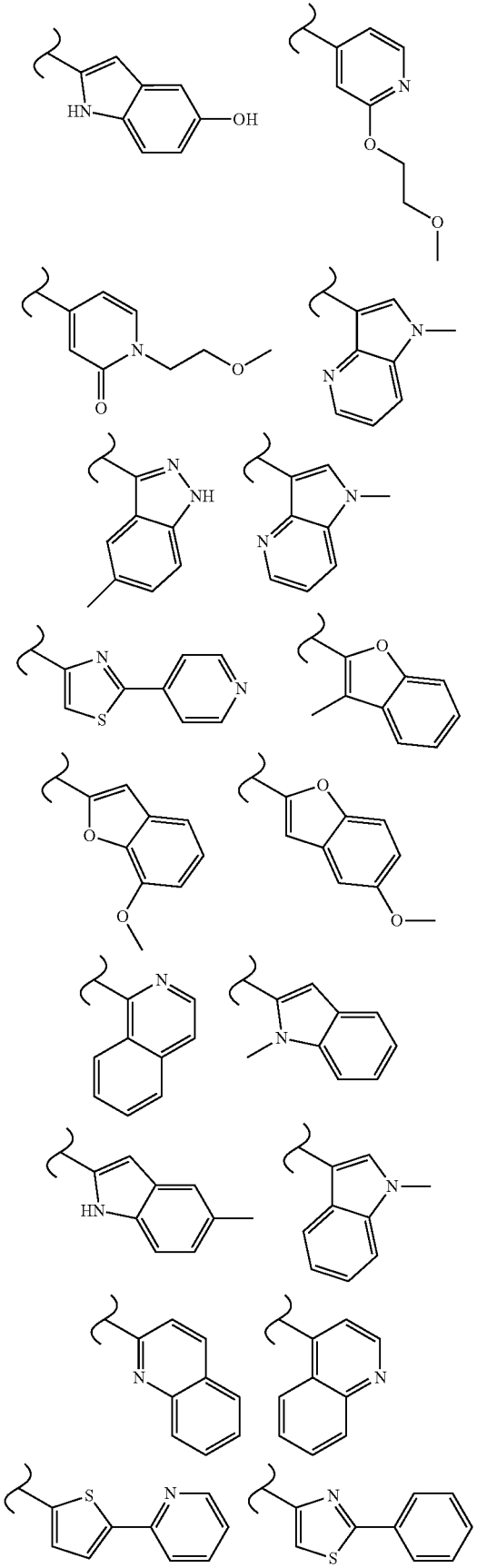

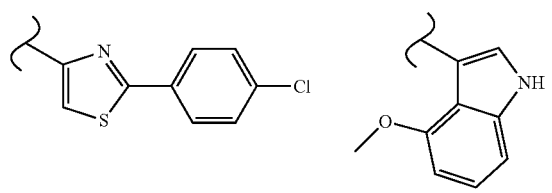
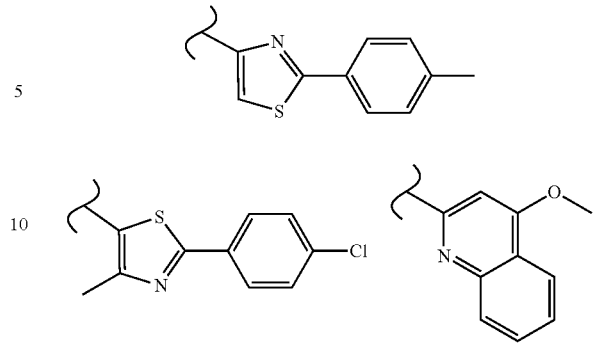
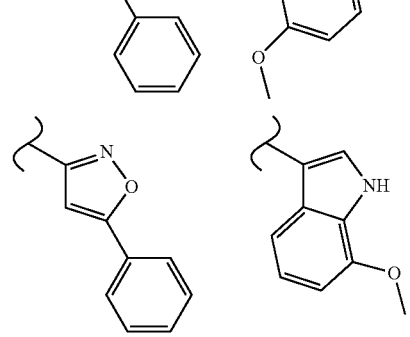
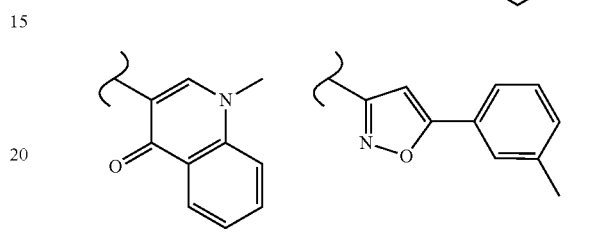
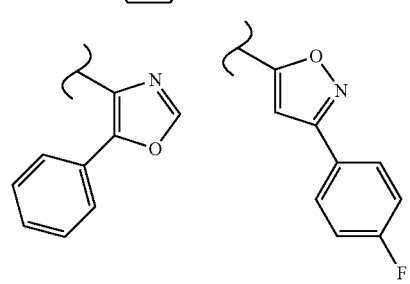
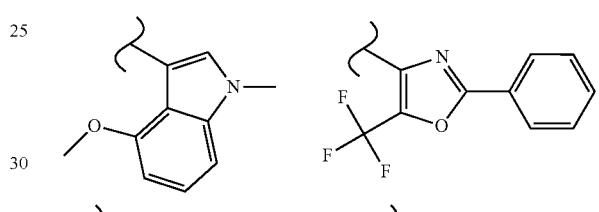
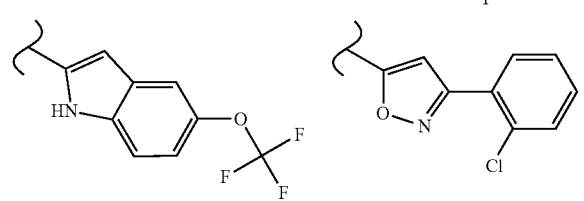
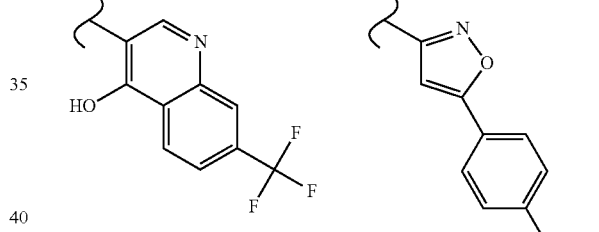
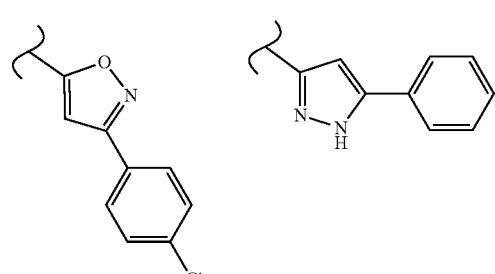
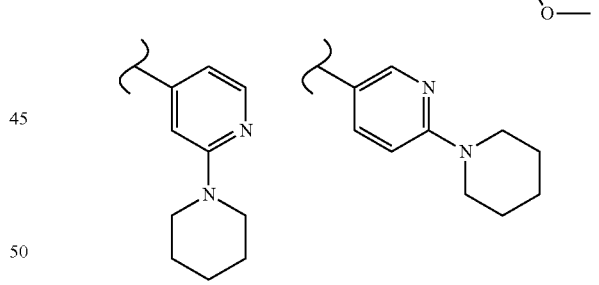
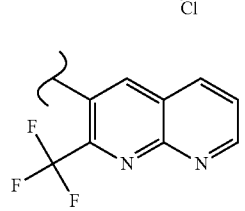
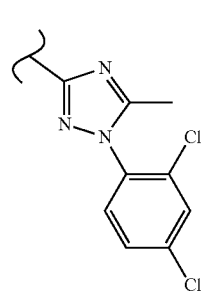

-continued

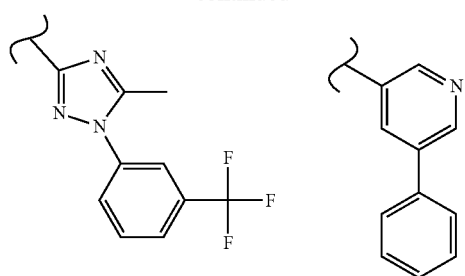

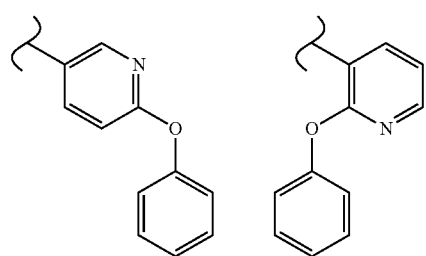

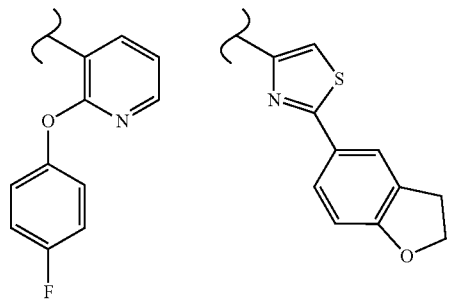

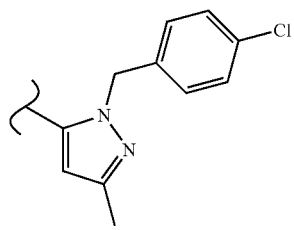

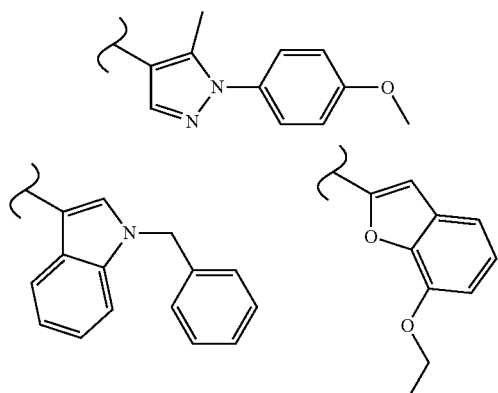

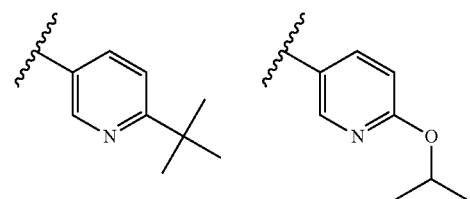

-continued

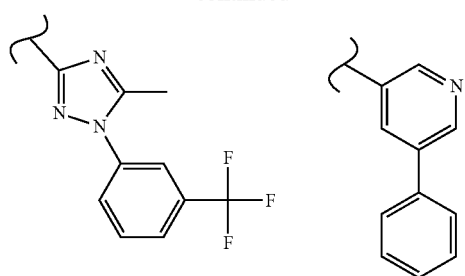

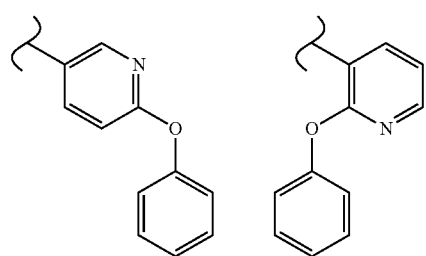

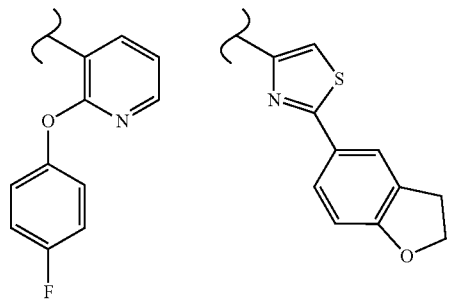

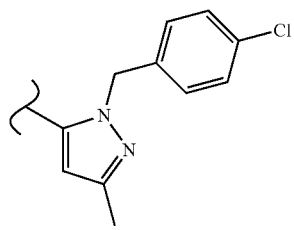

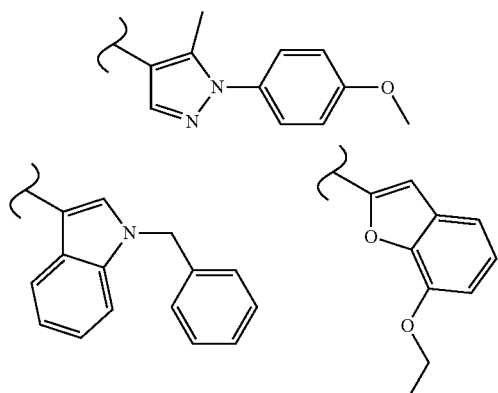

In another embodiment, the invention relates to a compound of formula I and the attendant definitions, wherein the compound has formula IA:

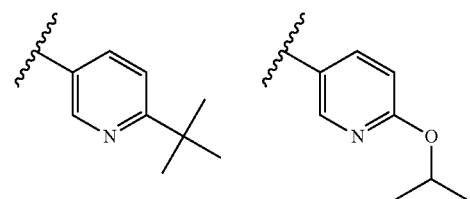

wherein:

$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl or a straight chain, branched, or cyclic (C1-C8)-$R^8$ wherein up to three $CH_2$ units may be replaced with O, CO, S, SO, $SO_2$, or $NR^7$;

$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl or a straight chain, branched, or cyclic (C1-C8)-$R^8$ wherein up to three $CH_2$ units may be replaced with O, CO, S, SO, $SO_2$, or $NR^7$;

$R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl or a straight chain, branched, or cyclic (C1-C8)-$R^8$ wherein up to three $CH_2$ units may be replaced with O, CO, S, SO, $SO_2$, or $NR^7$; or two occurrences of $R^4$ and $R^5$, or $R^5$ and $R^6$ are both C1-C6 alkyl and together with the carbons to which they are attached form an optionally substituted ring comprising up to 2 heteroatoms.

In another embodiment, the invention relates to a compound of formula IA and the attendant definitions, wherein $R^1$ is C1-C6 alkyl, C1-C6 alkoxy, halo, CN, $CON(R^7)_2$, or (C1-C6)-$R^8$ wherein up to two $CH_2$ units may be replaced with O or $NR^7$. In another embodiment, $R^1$ is F, Cl, CN, $CH_3$, $CH_2OH$, $CH_2N(CH_3)_2$, $CH_2NH_2$, $CONHCH_3$, $CON(CH_3)_2$, $CH_2OCH_3$.

In another embodiment, the invention relates to a compound of formula IA and the attendant definitions, wherein $R^2$ is C1-C6 alkyl, CN, $CF_3$, $CON(R^7)_2$, $SO_2R^7$, or (C1-C6)-$R^8$ wherein up to two $CH_2$ units may be replaced with O or $NR^7$. In another embodiment, $R^2$ is $CH_3$, $CF_3$, $CH_2OH$, CN, $SO_2CH_3$, $SOCH_3$, $CH_2NH_2$, $CH_2NHCOCH_3$, $CH_2NHCOH$, $COCH_3$, or $CONHCH_3$.

In another embodiment, the invention relates to a compound of formula IA and the attendant definitions, wherein $R^3$ is C1-C6 alkyl or 2 occurrences of $R^3$ taken together form a C3-C8 cycloalkyl group. In another embodiment, $R^3$ is $CH_3$. In another embodiment, 2 occurrences of $R^3$ taken together form a C3-C8 cycloalkyl group.

In another embodiment, the invention relates to a compound of formula IA and the attendant definitions, wherein $R^4$ is H, C1-C6 alkyl, C1-C6 alkoxy, halo, CN, OH, $OR^7$, $CHF_2$, $CF_3$, $OCF_3$, $OCHF_2$, $SO_2R^7$, $SOR^7$, $SR^7$, $NR^7CO_2R^7$, heteroaryl, or a straight chain, branched, or cyclic (C1-C8)-$R^8$ wherein up to three $CH_2$ units may be replaced with O, CO, S, SO, $SO_2$, or $NR^7$. In another embodiment, $R^4$ is H, F, Cl, OH, $CH_3$, $CHF_2$, $CF_3$, $OCH_3$, $OCHF_2$, $OCF_3$, $CO_2CH_3$, $CH_2OH$, $SO_2CH_3$, CN, $NHCO_2tBu$, $C_2H_5$, $OCF_2CHFCl$,

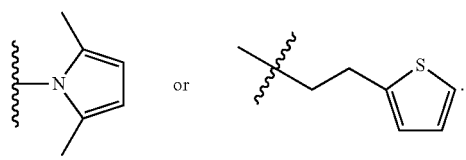

In another embodiment, the invention relates to a compound of formula IA and the attendant definitions, wherein $R^5$ is H, C1-C6 alkyl, C1-C6 alkoxy, halo, CN, OH, $OR^7$, $NR^7SO_2R^7$, $SO_2R^7$, $SR^7$, SOW, $CO_2R^7$, $CON(R^7)_2$, $SO_2N(R^7)_2$, $CF_3$, $OCF_3$, or a straight chain, branched, or cyclic (C1-C8)-$R^8$ wherein up to three $CH_2$ units may be replaced with O, CO, S, SO, $SO_2$, or $NR^7$. In another embodiment, $R^5$ is H, F, Cl, $CH_3$, $C_2H_5$, tBu, OH, $OCH_3$, $OC_2H_5$, $OCH(CH_3)_2$, $CH_2OH$, $CF_3$, $OCF_3$, CN, $CO_2CH_3$, $CONH_2$, $N(CH_3)SO_2CH_3$, $SO_2NH_2$ or $SO_2CH_3$.

In another embodiment, the invention relates to a compound of formula IA and the attendant definitions, wherein $R^6$ is H, C1-C6 alkyl, C3-C8 cycloalkyl, C1-C6 alkoxy, halo, CN, OH, $OR^7$, $SOR^7$, $SO_2R^7$, $NR^7COR^7$, $SO_2N(R^7)_2$, $CF_3$, $OCF_3$, heteroaryl, or a straight chain, branched, or cyclic (C1-C8)-$R^8$, wherein up to three $CH_2$ units may be replaced with O, CO, S, SO, $SO_2$, or $NR^7$. In another embodiment, $R^6$ is H, F, $CH_3$, $CF_3$, $OCH_3$, $OCF_3$, $SO_2CH_3$, $SO_2C_2H_5$, $SO_2CH(CH_3)_2$, $SO_2CH_2CH(CH_3)_2$, $SO_2tBu$, $SO_2CHF_2$, CN, $CH_2CH_3$, tBu, $CH_2CH_2OH$, $C(CH_3)_2OH$, $OCH_2CF_3$, $O(CH_2)_2OH$, $NHC(=O)CH_3$, $OCH_2C(=O)NH_2$,

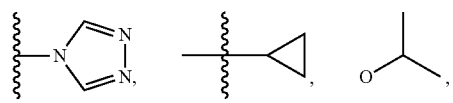

$O(CH_2)_2CH_3$,

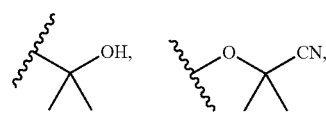

$O(CH_2)_3OH$, $O(CH_2)_2OCH_3$,

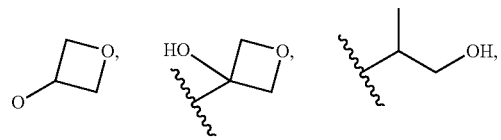

$O(CH_2)_2OCF_3$,

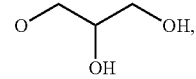

$O(CH_2)_2SO_2CH_3$, tBu,

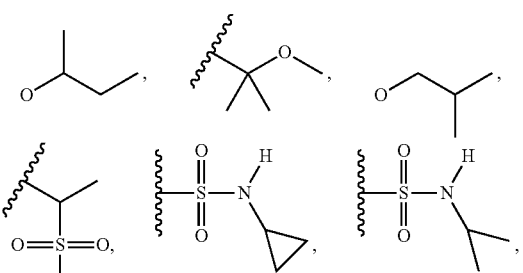

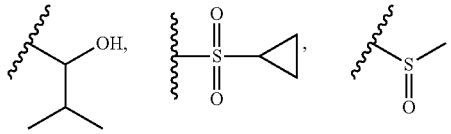

-continued

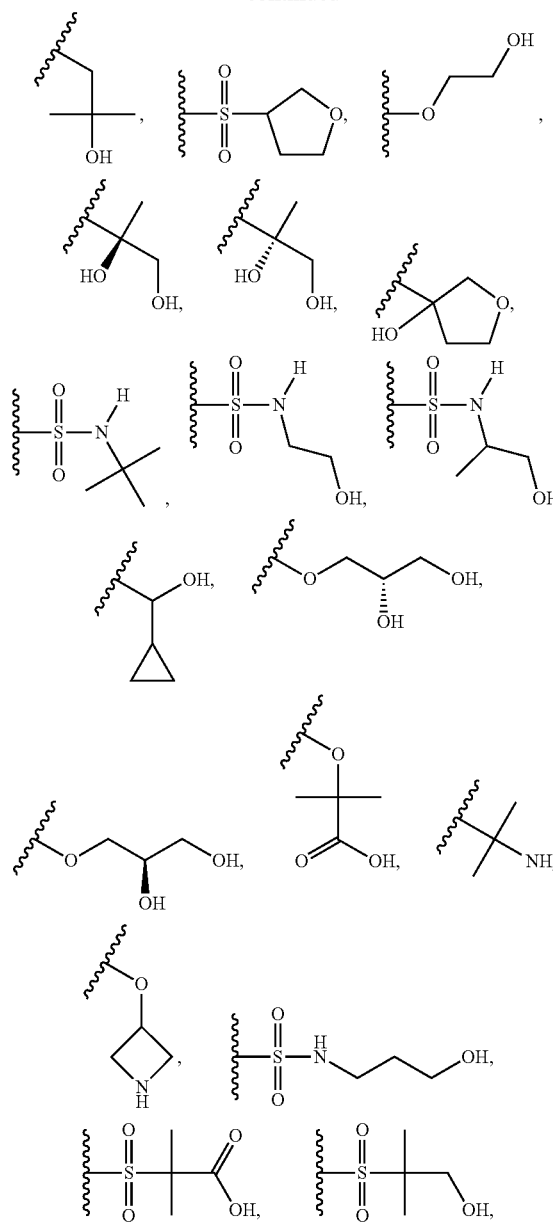

OtBu,

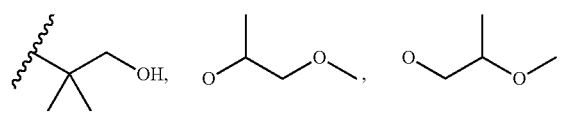

$O(CH_2)_3OCH_3$, $O(CH_2)_2OC_2H_5$,

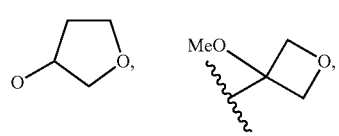 [SMILES: OC1CCOC1 ; *C1(OC)COC1]

$O(CH_2)_2N(CH_3)_2$,

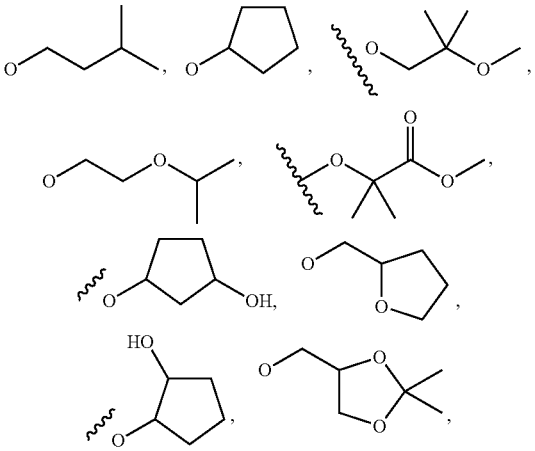

$OCH_2Ph$, $SO_2NHCH_3$, $SO_2NHCH_2CH_3$, $SO_2CH_2CH_2OH$ or $OCH_2CO_2H$.

In another embodiment, the invention relates to a compound of formula IA and the attendant definitions, wherein m is 0 or 1. In another embodiment, m is 0.

In another embodiment, the invention relates to a compound of formula IA and the attendant definitions, wherein n is 0, 1 or 2. In another embodiment, n is 0. In another embodiment, n is 1. In another embodiment, n is 2.

In another embodiment, the invention relates to a compound of formula IA and the attendant definitions, wherein o is 0, 1 or 2. In another embodiment, o is 0. In another embodiment, o is 1. In another embodiment, o is 2, and the two occurrences of $R^3$ form a C3-C8 cycloalkyl group.

In another embodiment, the invention relates to a compound of formula IA and the attendant definitions, wherein

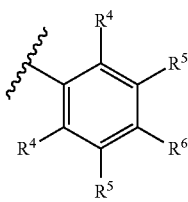

is selected from:

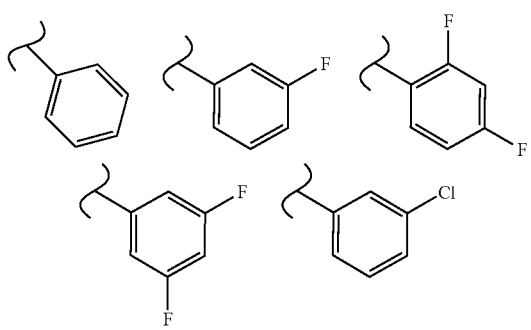

47
-continued
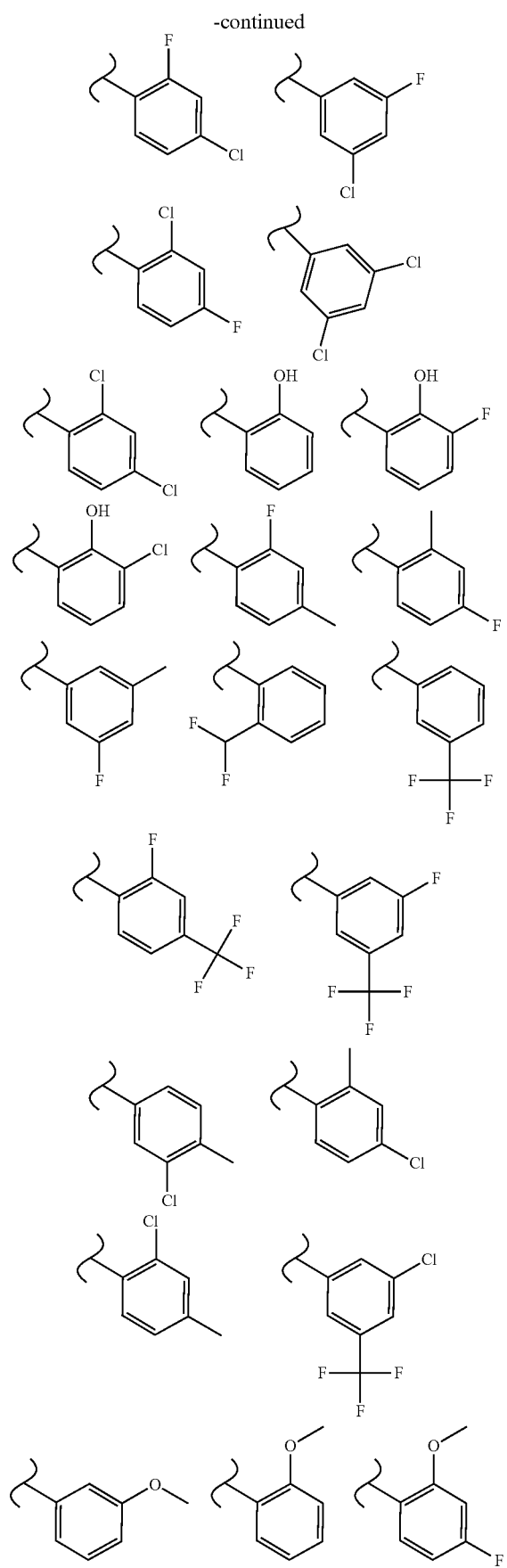
48
-continued
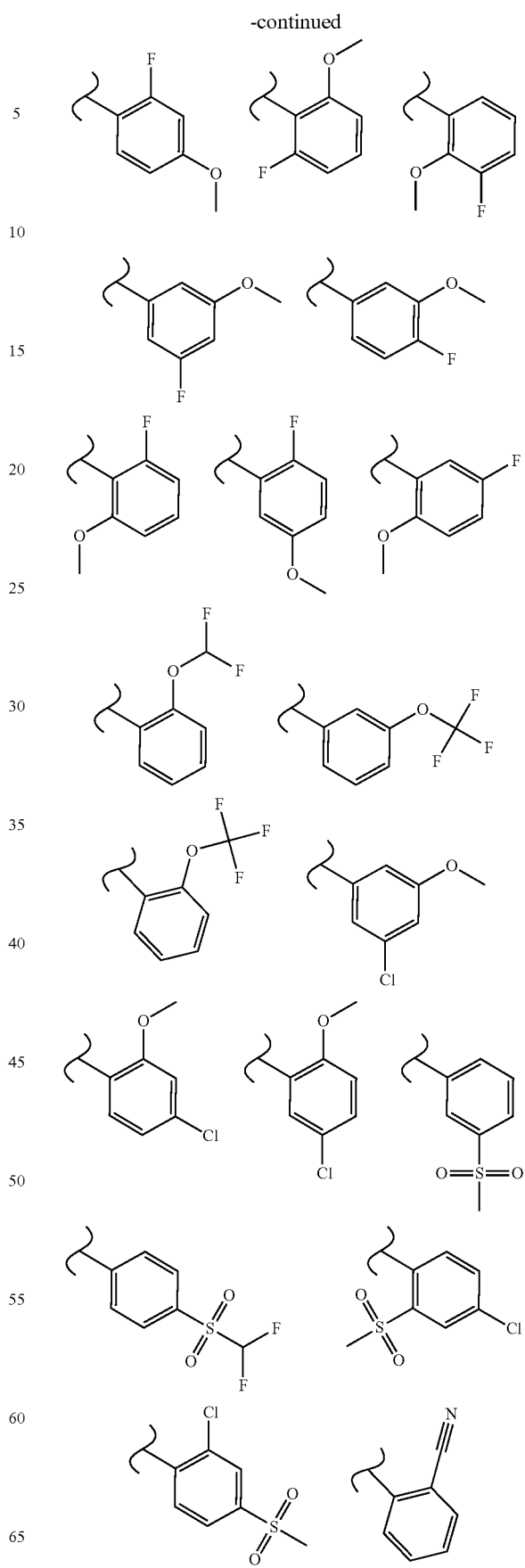

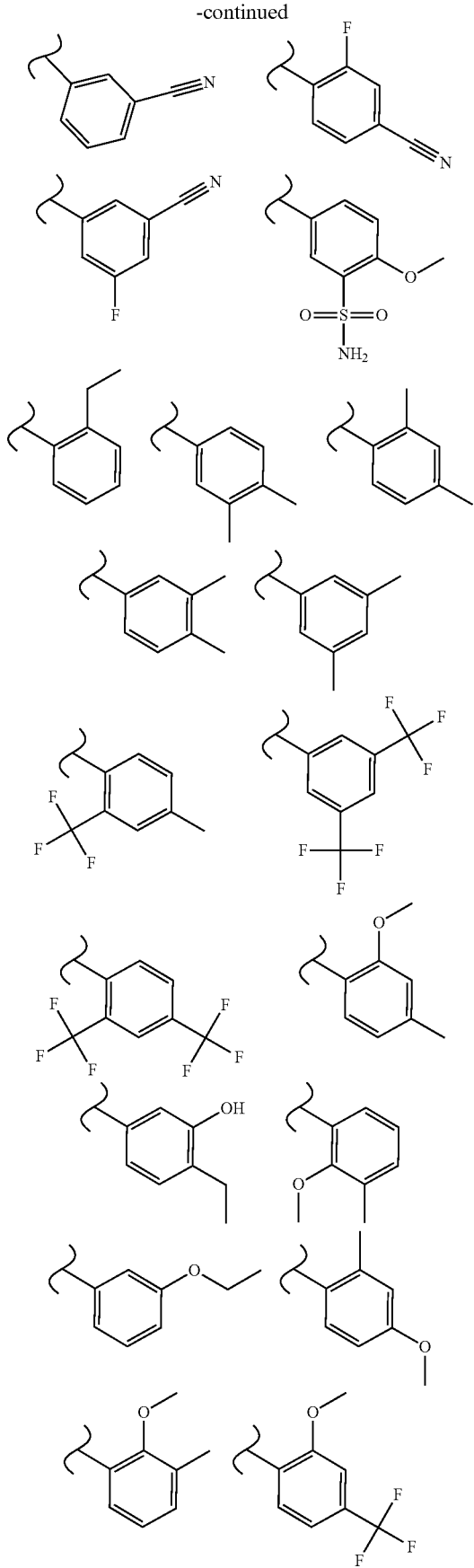
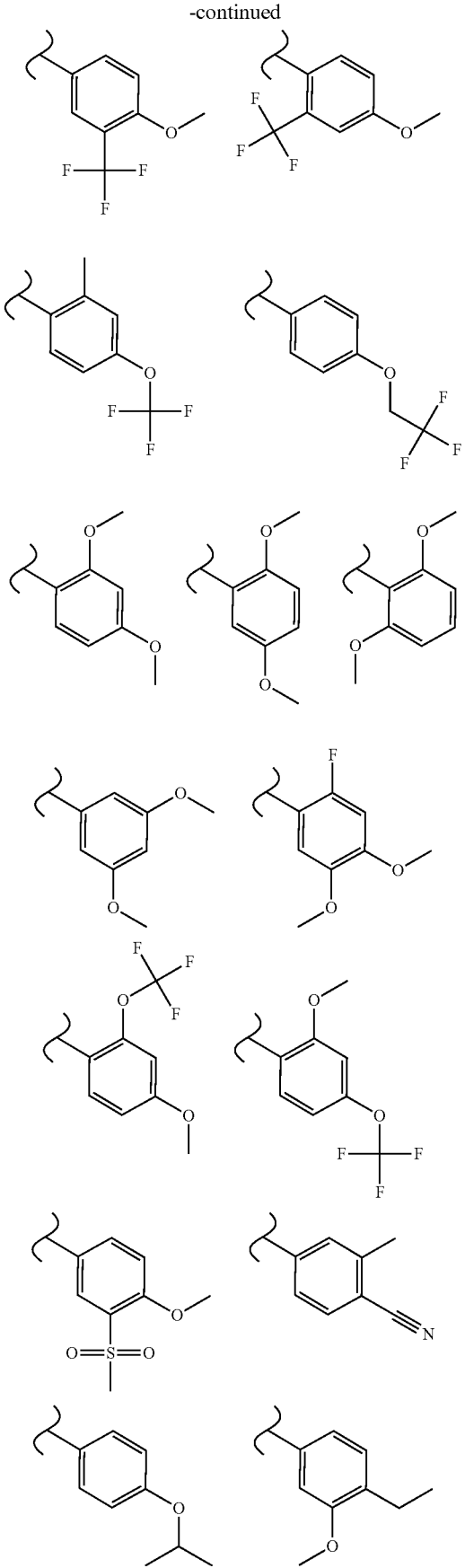

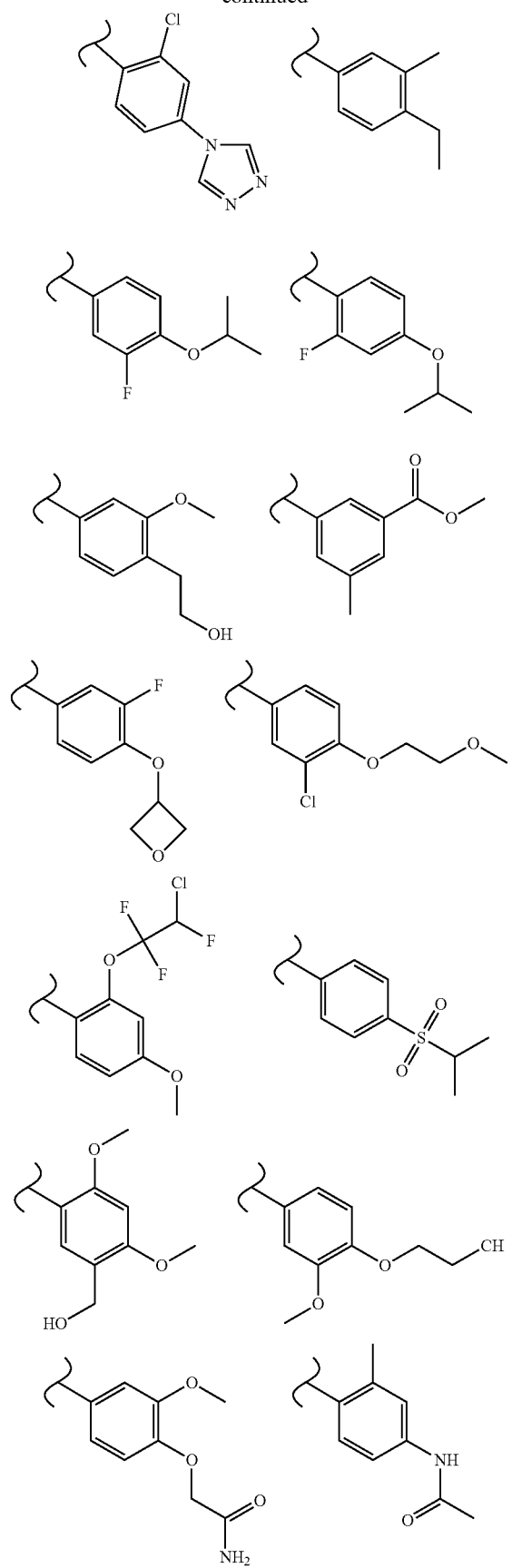
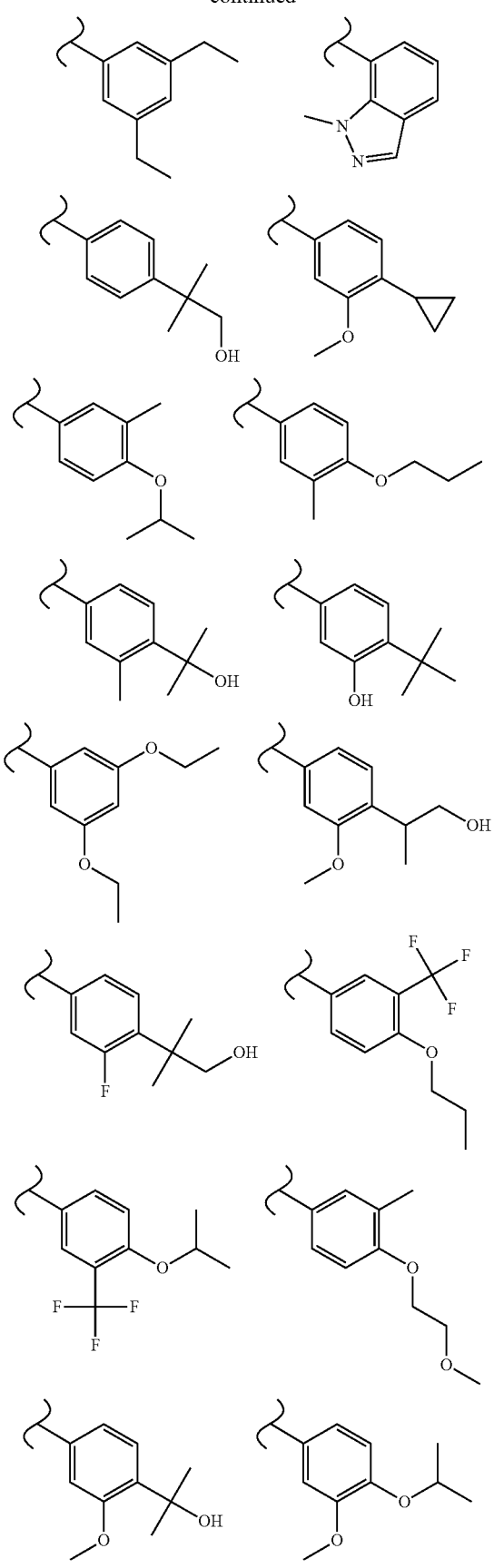

53
-continued
54
-continued
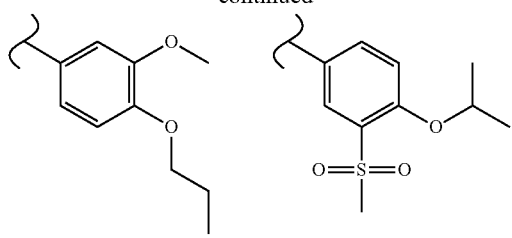
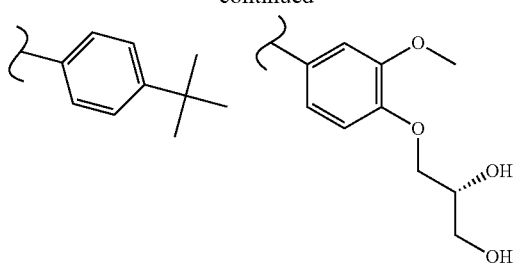

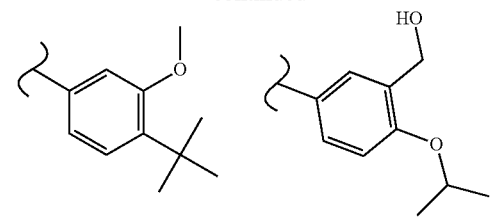
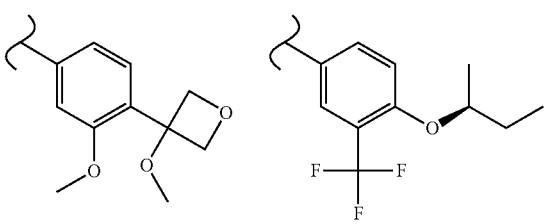
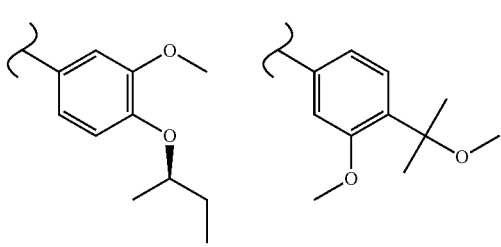
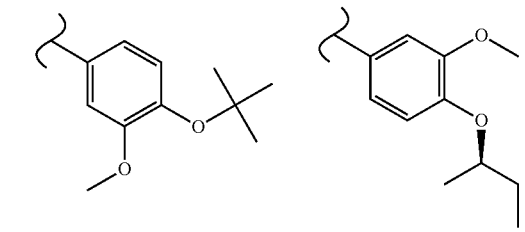
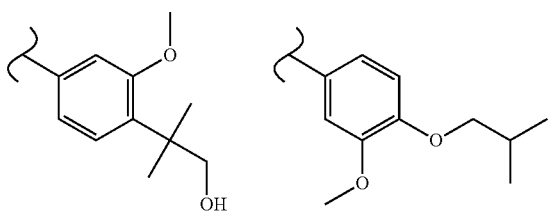
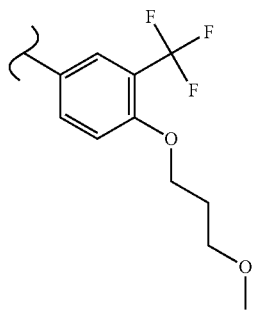
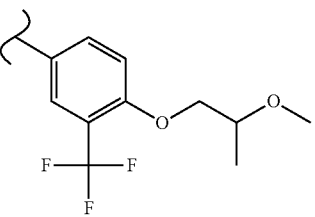
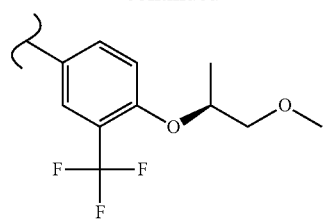
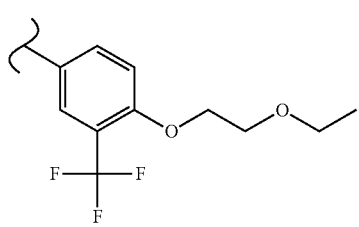
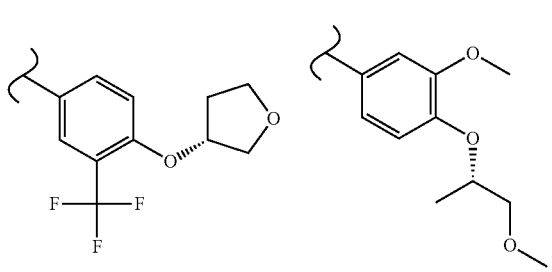
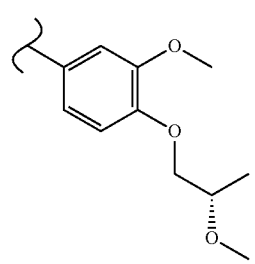
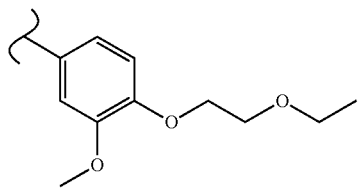
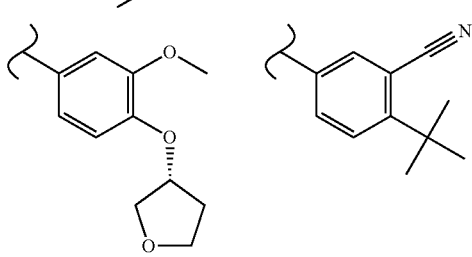

57
-continued
58
-continued
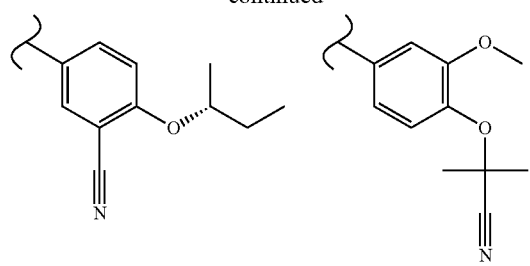
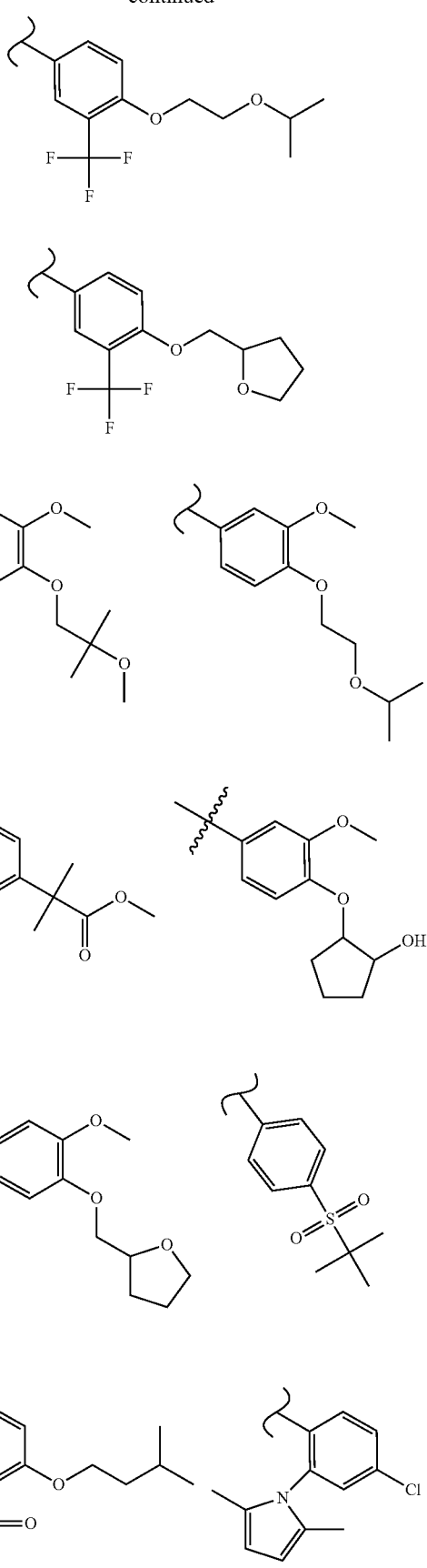

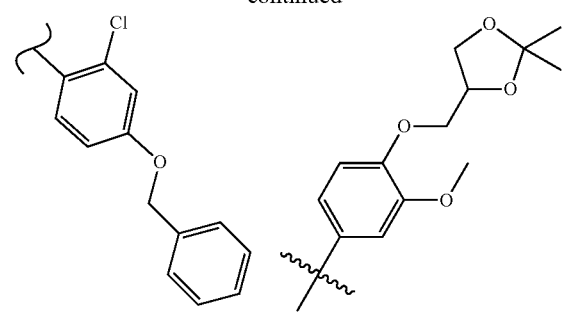
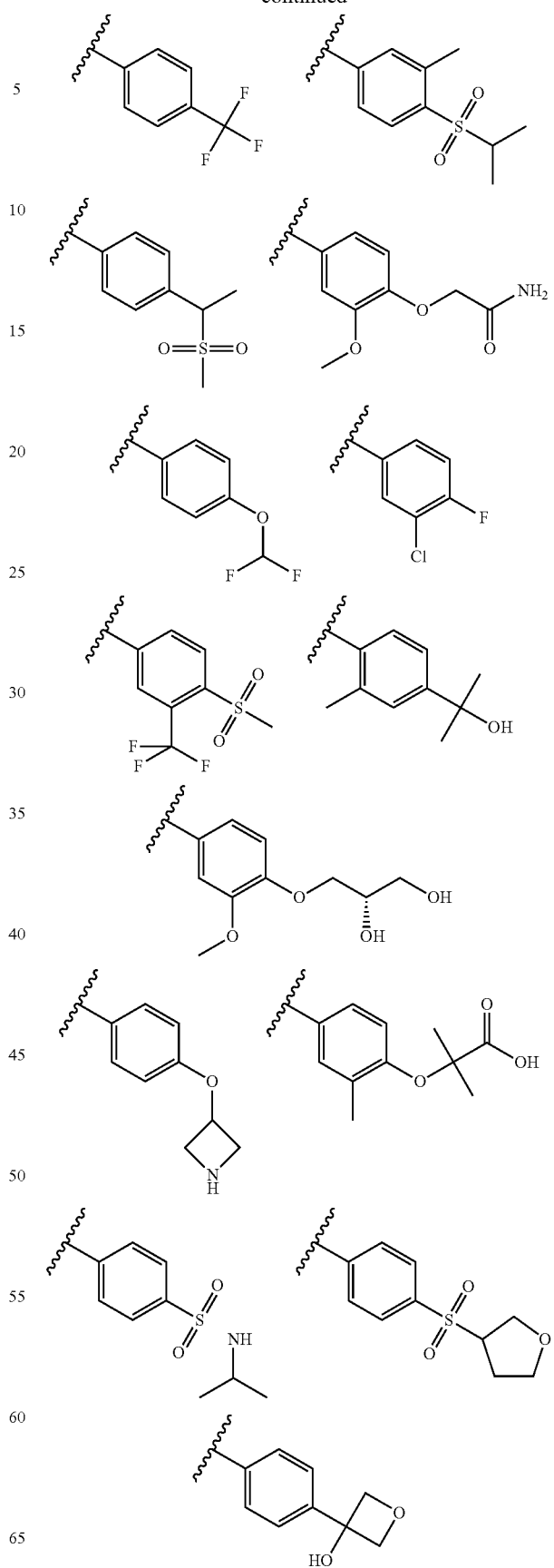

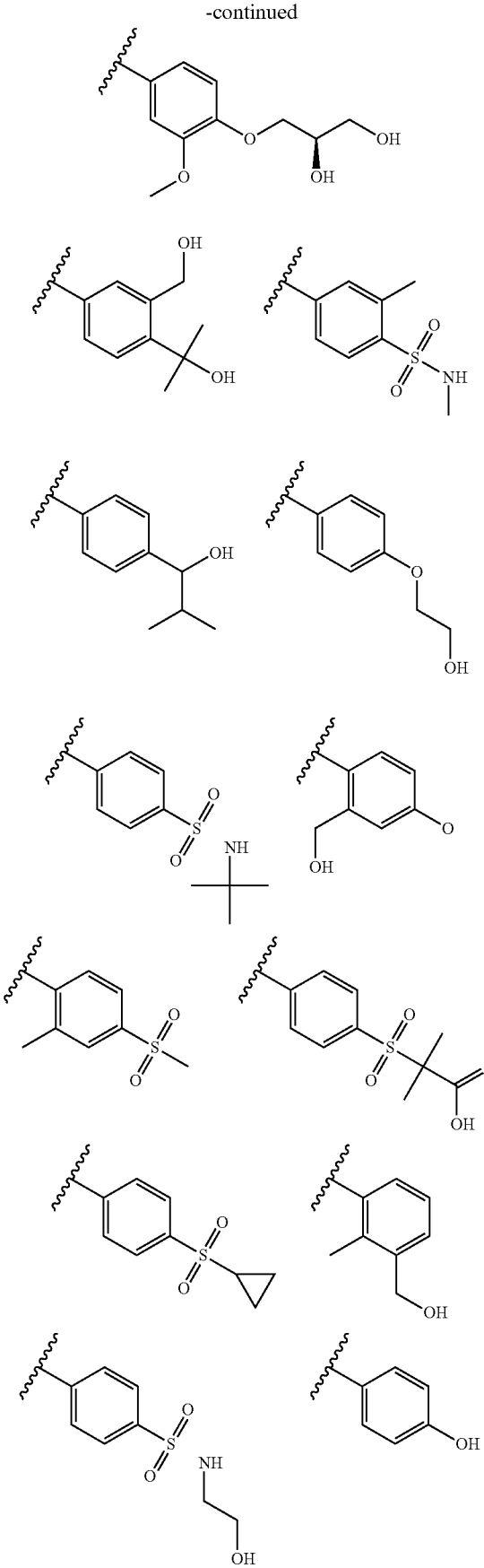
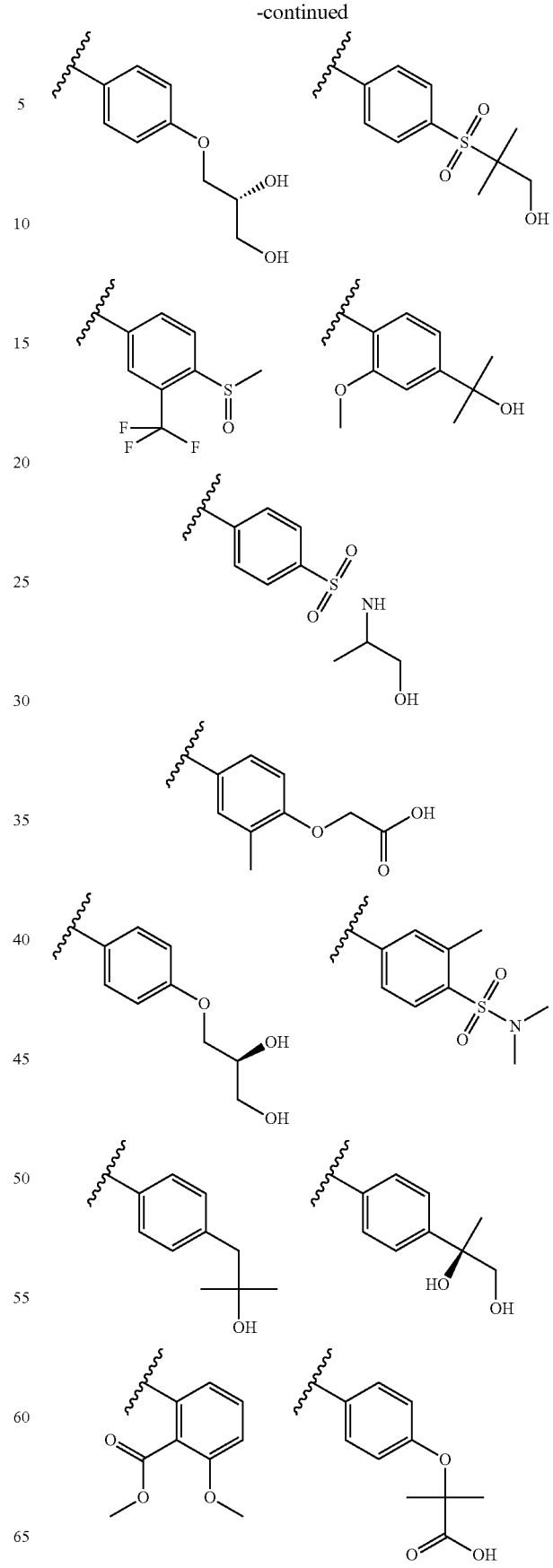

-continued

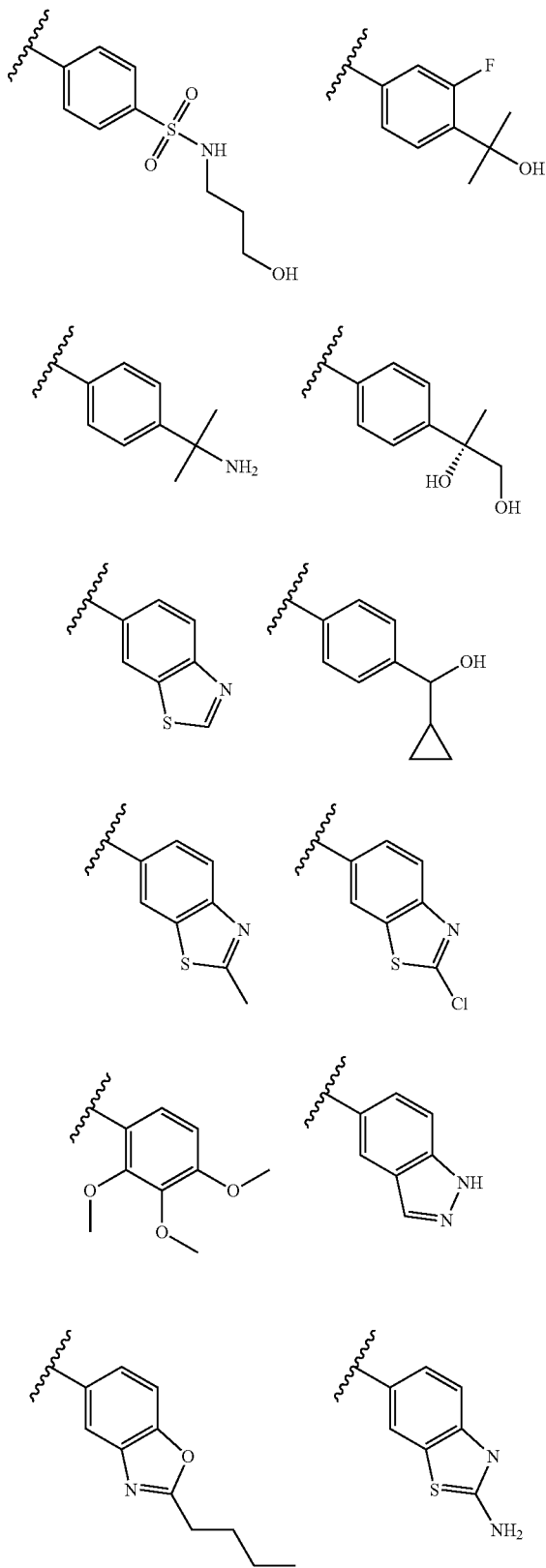

In another embodiment, the invention relates to a compound of formula I and the attendant definitions, wherein the compound has formula IB:

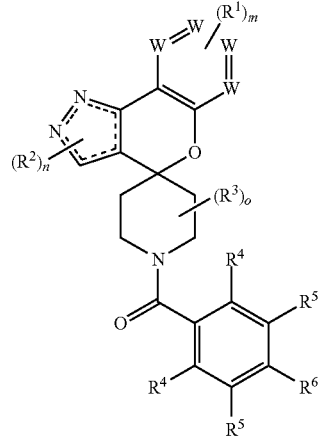

wherein:

R⁴ is H, C1-C6 alkyl, C3-C8 cycloalkyl, C1-C6 alkoxy, halo, CN, OH, OR⁷, N(R⁷)₂, NR⁷SO₂R⁷, SO₂R⁷, SR⁷, SOR⁷, CO₂R⁷, NR⁷COR⁷, NR⁷CO₂R⁷, CON(R⁷)₂, SO₂N(R⁷)₂, CF₃, OCF₃, OCHF₂, heterocycloalkyl, aryl, heteroaryl or a straight chain, branched, or cyclic (C1-C8)-R⁸ wherein up to three CH₂ units may be replaced with O, CO, S, SO, SO₂, or NR⁷;

R⁵ is H, C1-C6 alkyl, C3-C8 cycloalkyl, C1-C6 alkoxy, C3-C8 cycloalkoxy, halo, CN, OH, OR⁷, N(R⁷)₂, NR⁷SO₂R⁷, SO₂R⁷, SR⁷, SOR⁷, CO₂R⁷, NR⁷COR⁷, NR⁷CO₂R⁷, CON(R⁷)₂, SO₂N(R⁷)₂, CF₃, OCF₃, OCHF₂, heterocycloalkyl, aryl, heteroaryl or a straight chain, branched, or cyclic (C1-C8)-R⁸ wherein up to three CH₂ units may be replaced with O, CO, S, SO, SO₂, or NR⁷;

R⁶ is H, C1-C6 alkyl, C3-C8 cycloalkyl, C1-C6 alkoxy, halo, CN, OH, OR⁷, N(R⁷)₂, NR⁷SO₂R⁷, SOR⁷, SO₂R⁷, SR⁷, CO₂R⁷, NR⁷COR⁷, NR⁷CO₂R⁷, CON(R⁷)₂, SO₂N(R⁷)₂, CF₃, OCF₃, OCHF₂, heterocycloalkyl, aryl, heteroaryl or a straight chain, branched, or cyclic (C1-C8)-R⁸ wherein up to three CH₂ units may be replaced with O, CO, S, SO, SO₂, or NR⁷; or two occurrences of R⁴ and R⁵, or R⁵ and R⁶ are both C1-C6 alkyl and together with the carbons to which they are attached form an optionally substituted ring comprising up to 2 heteroatoms.

In another embodiment, the invention relates to a compound of formula IB and the attendant definitions, wherein R¹ is halo or C1-C6 alkoxy. In another embodiment, R¹ is F, Cl or OCH₃.

In another embodiment, the invention relates to a compound of formula IB and the attendant definitions, wherein R² is C1-C6 alkyl, CF₃ or (C1-C6)-R⁸ wherein up to two CH₂ units may be replaced with O or NR⁷. In another embodiment, R² is CH₃, CF₃, C₂H₅, CH₂CF₃, or (CH₂)₂OCH₃.

In another embodiment, the invention relates to a compound of formula IB and the attendant definitions, wherein R⁴ is H, C1-C6 alkyl, C1-C6 alkoxy, halo, CN, OH, OR⁷, CON(R⁷)₂, NR⁷SO₂R⁷, SO₂R⁷, SR⁷, SOR⁷, CO₂R⁷, NR⁷CO₂R⁷, CHF₂, CF₃, OCF₃, OCHF₂, heteroaryl, or a straight chain, branched, or cyclic (C1-C8)-R⁸ wherein up to three CH₂ units may be replaced with O, CO, S, SO, SO₂, or NR⁷. In another embodiment, R⁴ is H, F, Cl, OH, CH₃, CHF₂, CF₃, OCH₃, OCHF₂, OCF₃, SO₂CH₃, CN, NHSO₂CH₃, C₂H₅, OC₂H₅, OCF₂CHFCl, OCH₂CF₃, O(CH₂)₂CH₃, OCH₂OCH₃, OCH(CH₃)₂, O(CH₂)₂OH, SCH₃, CON(CH₃)₂, NHCO₂tBu,

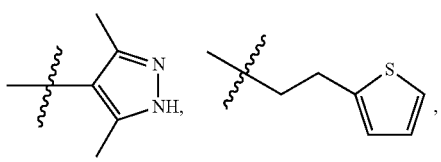

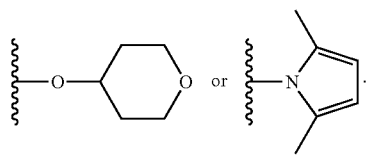

In another embodiment, the invention relates to a compound of formula IB and the attendant definitions, wherein $R^5$ is H, C1-C6 alkyl, C1-C6 alkoxy, halo, CN, OH, $OR^7$, $CF_3$, $OCF_3$, $SO_2R^7$, $SR^7$, $SOR^7$, or a straight chain, branched, or cyclic (C1-C8)-$R^8$ wherein up to three $CH_2$ units may be replaced with O, CO, S, SO, $SO_2$, or $NR^7$. In another embodiment, $R^5$ is H, F, Cl, $CH_3$, $CF_3$, $OCH_3$, $CH(CH_3)_2$, $OCH_2CH_3$, $CH_2OH$, $OCF_3$, CN, $SO_2CH_3$ or tBu.

In another embodiment, $R^6$ is H, C1-C6 alkyl, C1-C6 alkoxy, halo, CN, OH, $OR^7$, $CON(R^7)_2$, $NR^7SO_2R^7$, $SO_2R^7$, $SR^7$, $SOR^7$, $CO_2R^7$, $NR^7CO_2R^7$, $CHF_2$, $CF_3$, $OCF_3$, $OCHF_2$, heteroaryl, or a straight chain, branched, or cyclic (C1-C8)-$R^8$ wherein up to three $CH_2$ units may be replaced with O, CO, S, SO, $SO_2$, or $NR^7$. In another embodiment, the invention relates to a compound of formula IB and the attendant definitions, wherein $R^6$ is H, F, Cl, OH, $CH_3$, $CF_3$, $OCH_3$, $OCF_3$, $OCHF_2$, $SOCH(CH_3)_2$, $SO_2CH_3$, $SO_2CHF_2$, $SO_2CF_3$, $SO_2C_2H_5$, $SO_2CH(CH_3)_2$, $SO_2CH_2CH(CH_3)_2$, $SO_2tBu$, $SO_2NHCH_3$, $SO_2N(CH_3)_2$, $SO_2NHCH_2CH_3$, $SO_2N(CH_3)CH(CH_3)_2$, $CONHCH(CH_3)_2$, $CH_2CH_3$, $OCH_2CH_3$,

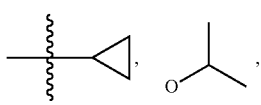

$O(CH_2)_2CH_3$,

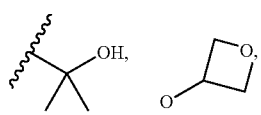

$O(CH_2)_2OCH_3$, $O(CH_2)_2OCF_3$, tBu,

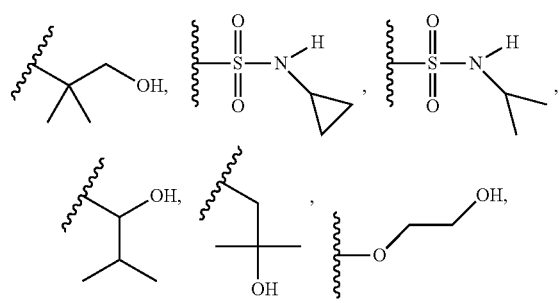

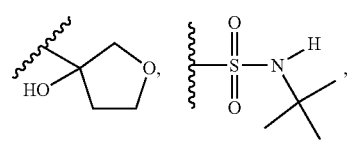

OtBu,

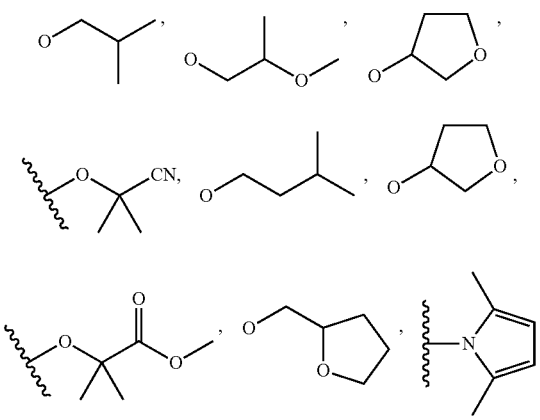

or $OCH_2Ph$.

In another embodiment, the invention relates to a compound of formula IB and the attendant definitions, wherein two occurrences of $R^4$ and $R^5$ are both C1-C6 alkyl and together with the carbons to which they are attached form an optionally substituted ring comprising up to 2 heteroatoms. In another embodiment, two occurrences of $R^5$ and $R^6$ are both C1-C6 alkyl and together with the carbons to which they are attached form an optionally substituted ring comprising up to 2 heteroatoms.

In another embodiment, the invention relates to a compound of formula IB and the attendant definitions, wherein m is 0 or 1. In another embodiment, m is 0. In another embodiment, m is 1.

In another embodiment, the invention relates to a compound of formula IB and the attendant definitions, wherein n is 0, 1 or 2. In another embodiment, n is 1.

In another embodiment, the invention relates to a compound of formula IB and the attendant definitions, wherein o is 0.

In another embodiment, the invention relates to a compound of formula IB and the attendant definitions, wherein

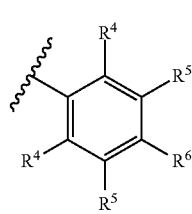

is selected from:
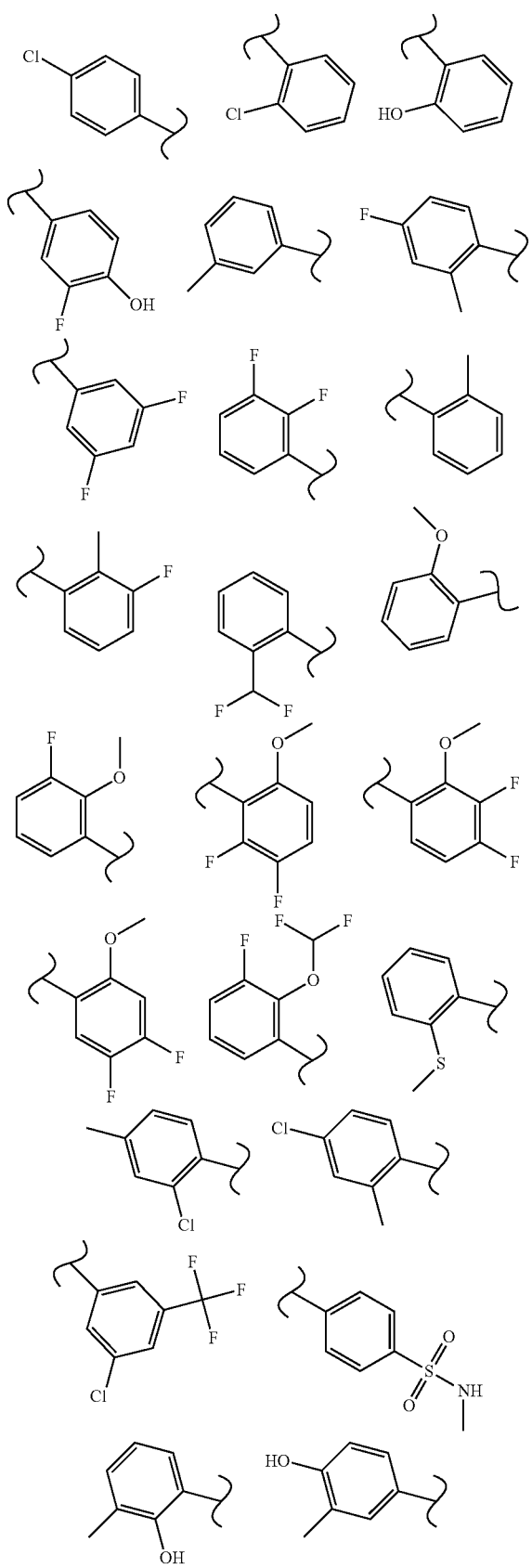
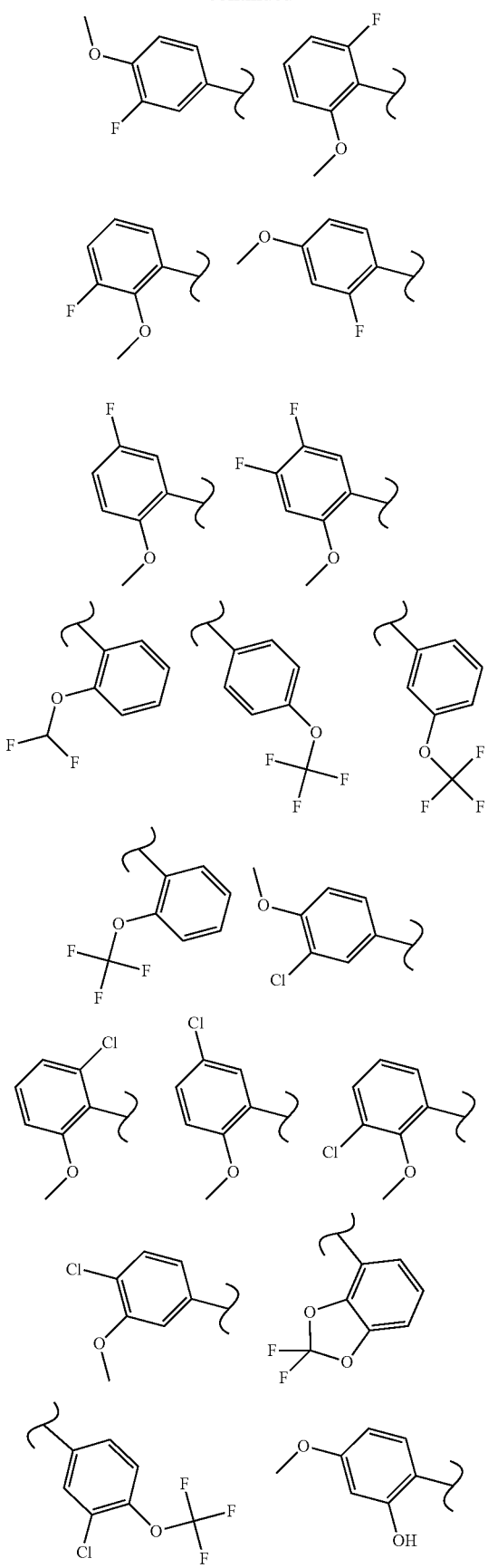

-continued
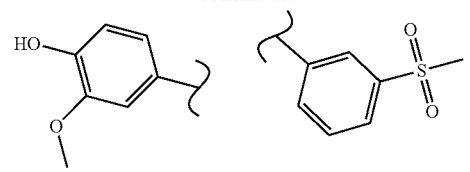
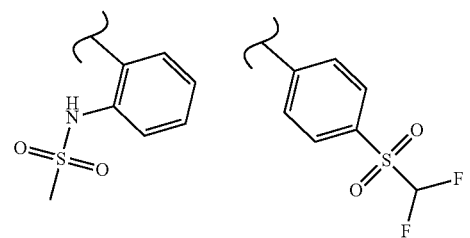
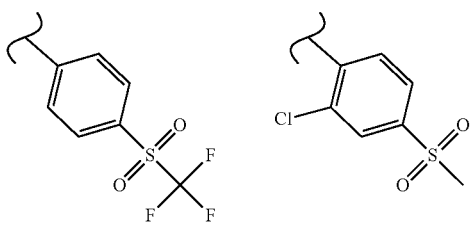
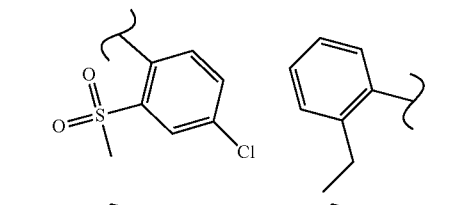
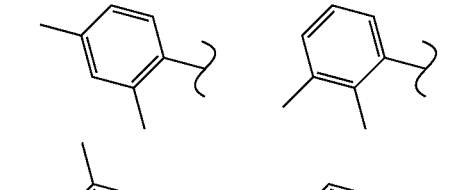
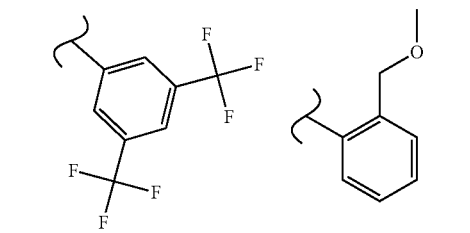
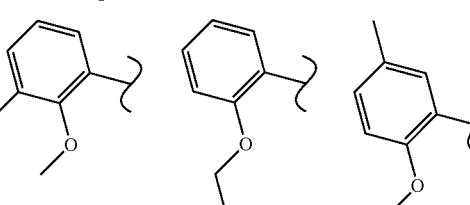
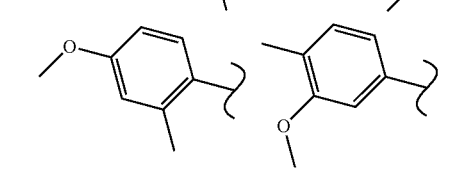
-continued
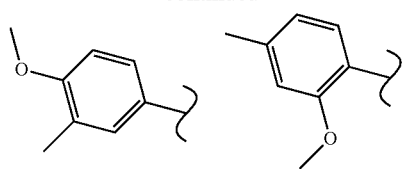
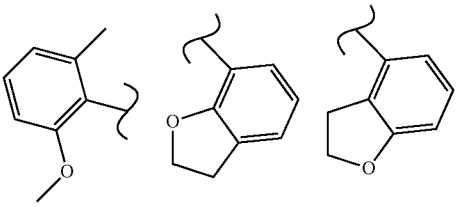
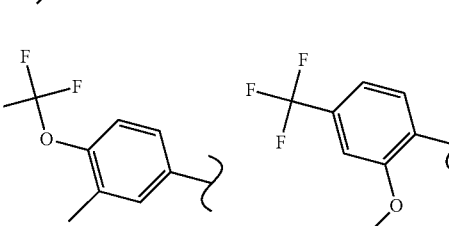
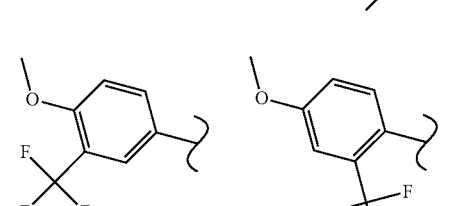
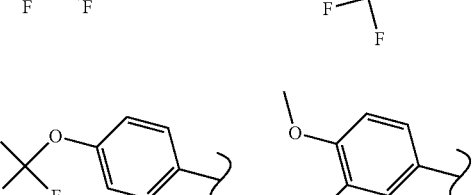
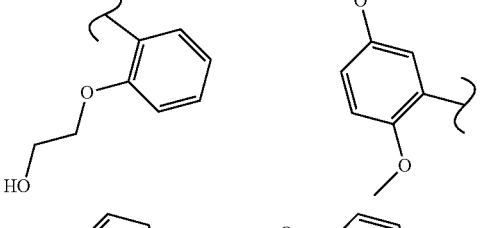
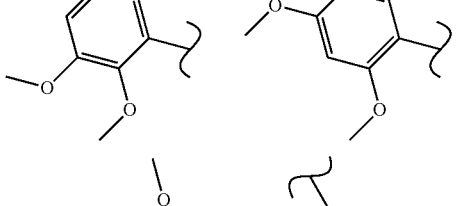
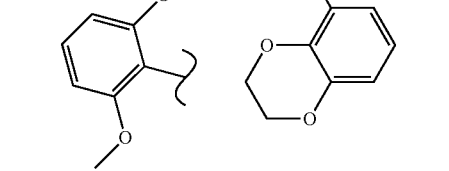

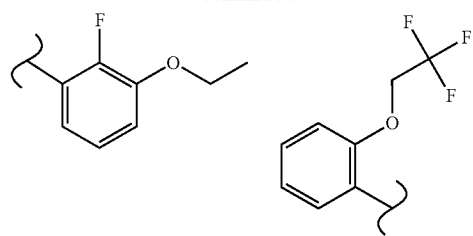
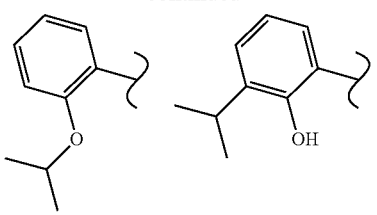
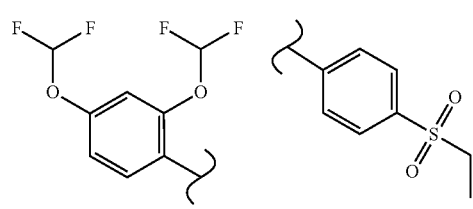
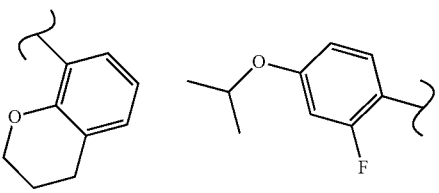
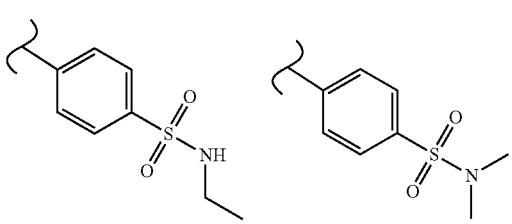
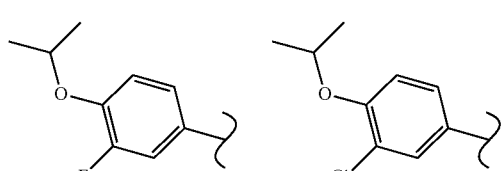
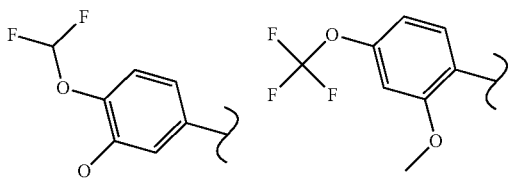
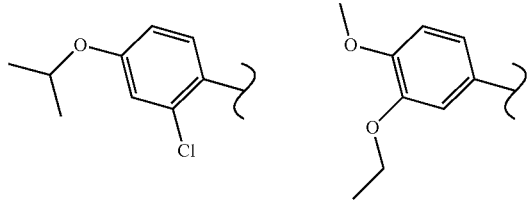
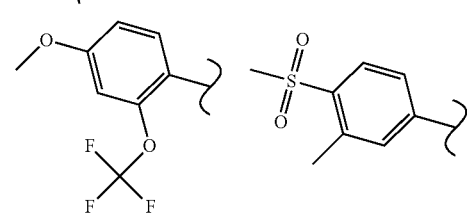
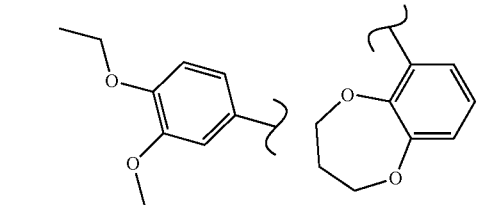
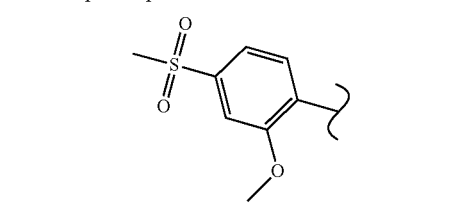
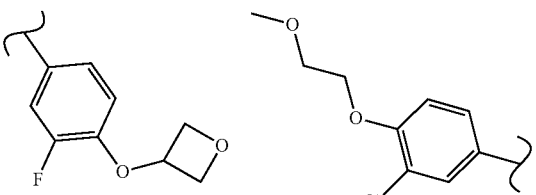
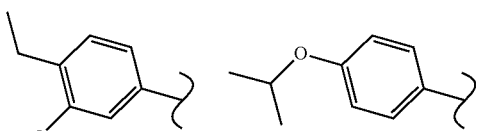

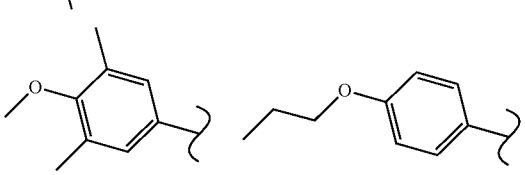
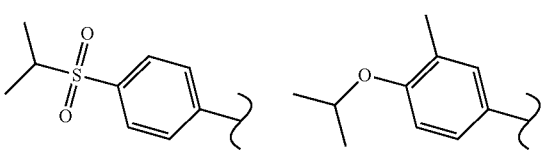

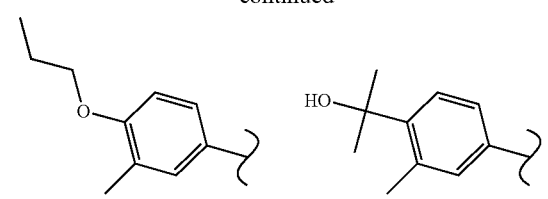
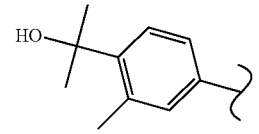
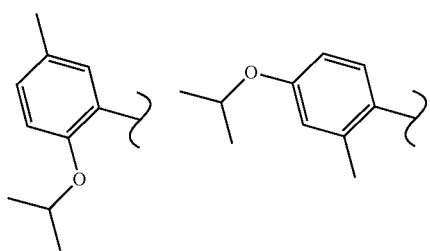
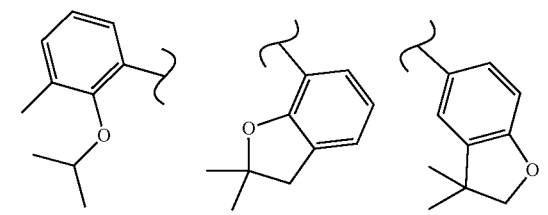
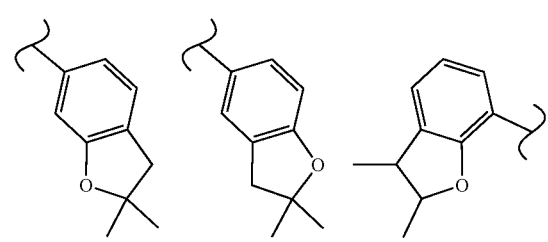
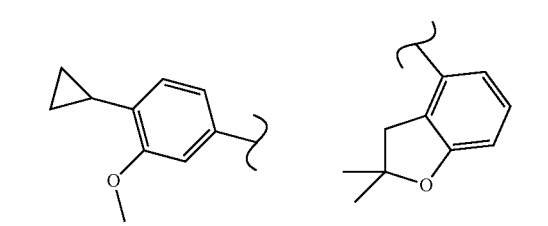
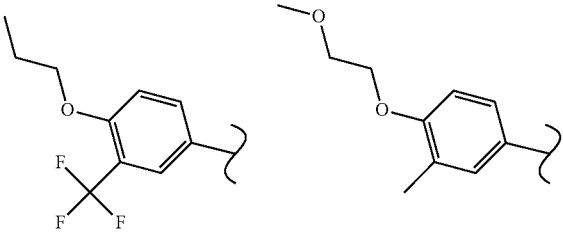
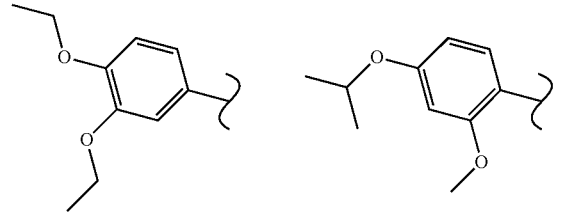
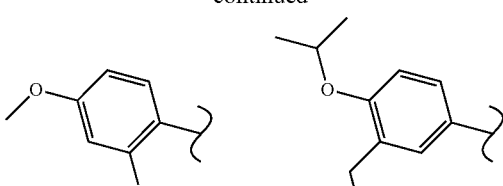
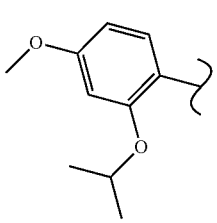
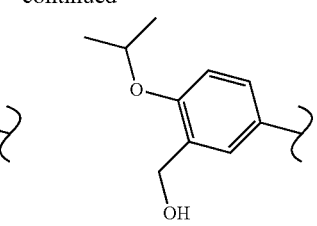
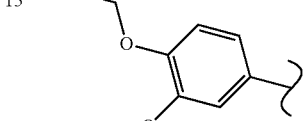
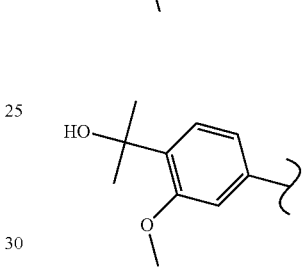
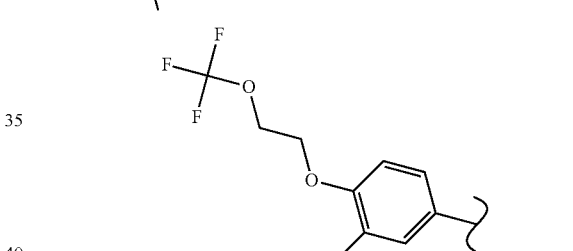
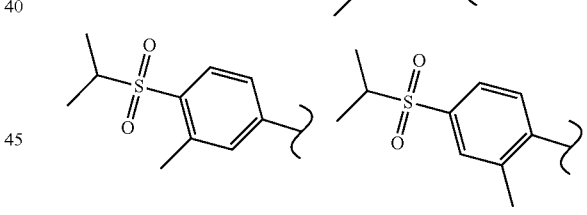
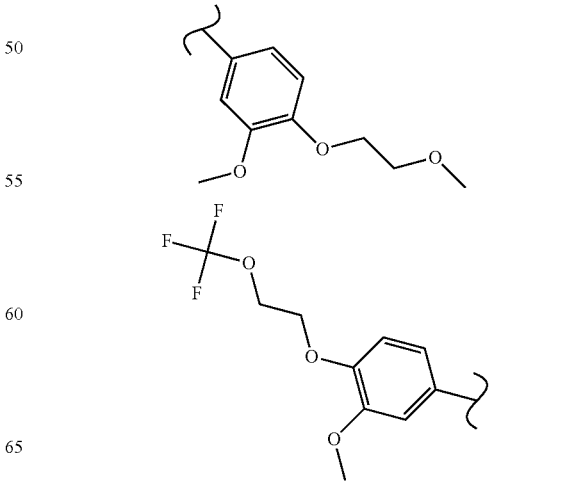

75
-continued
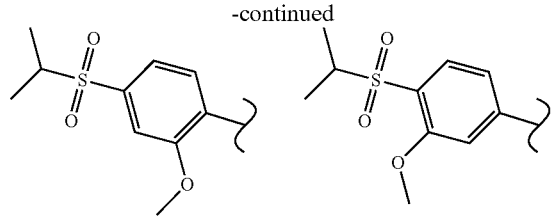
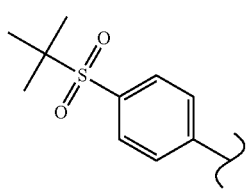 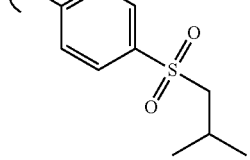
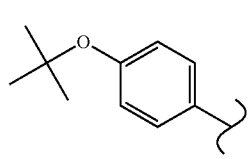 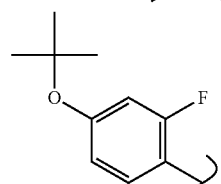
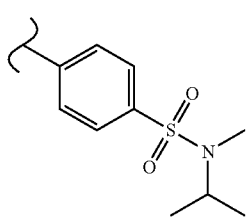 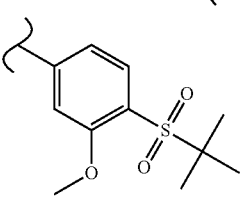
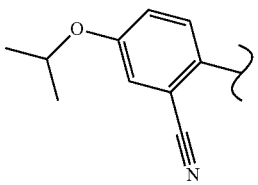 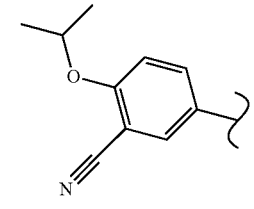
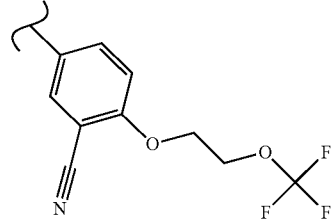
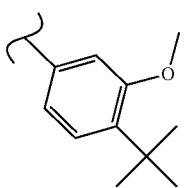 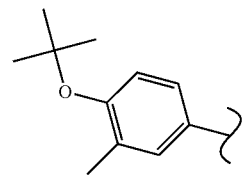
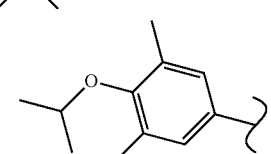
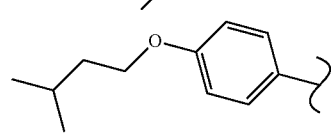
76
-continued
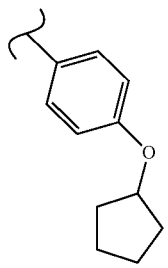 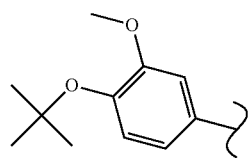
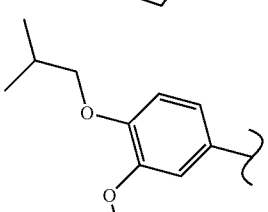 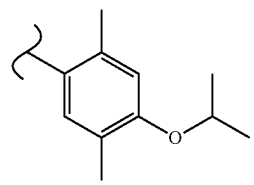
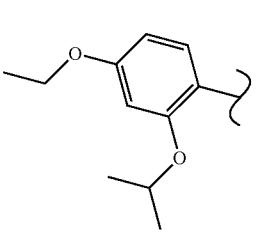 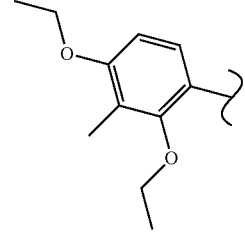
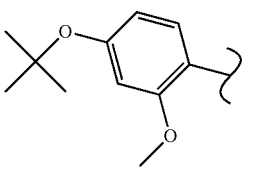 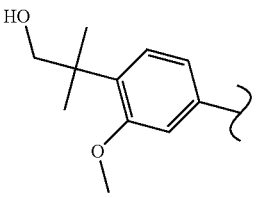
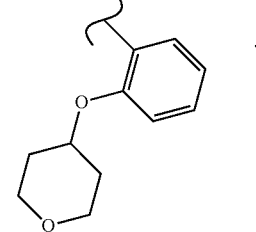 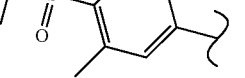
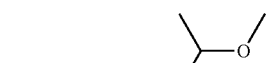 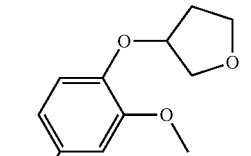
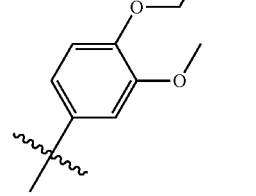 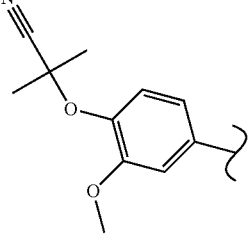

77
-continued
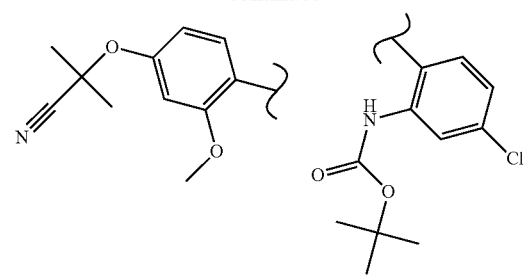
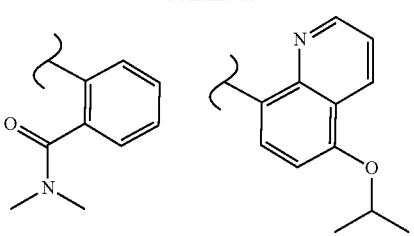
78
-continued
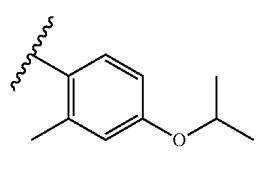
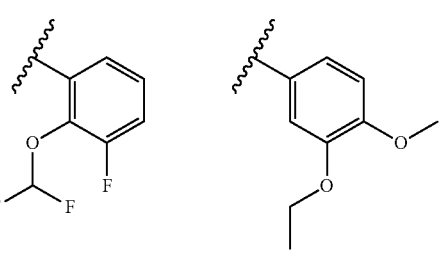
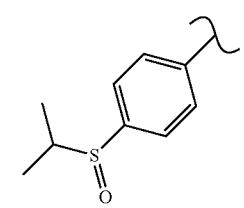
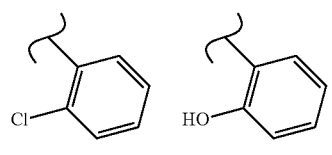
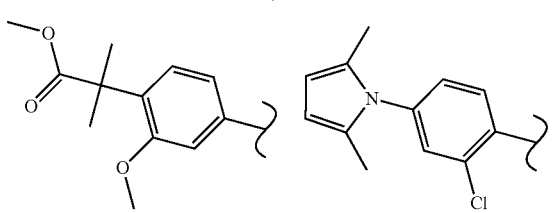
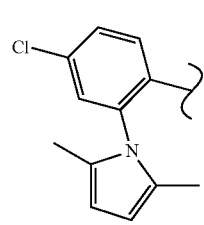
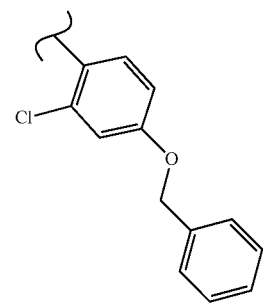
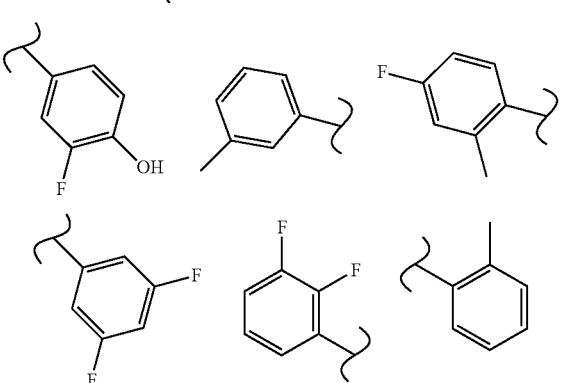
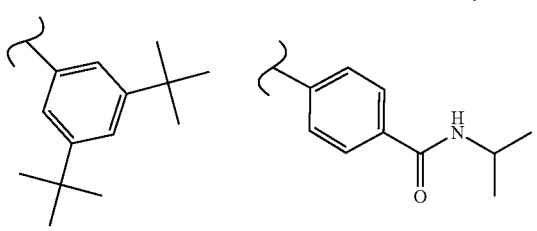

-continued
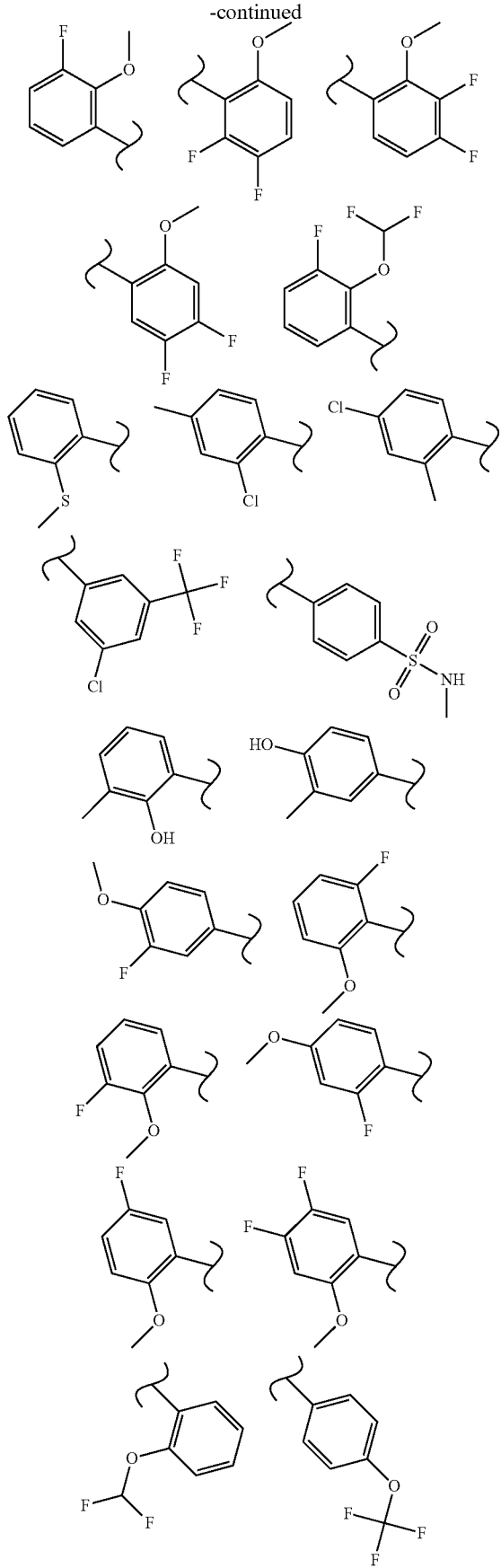
-continued
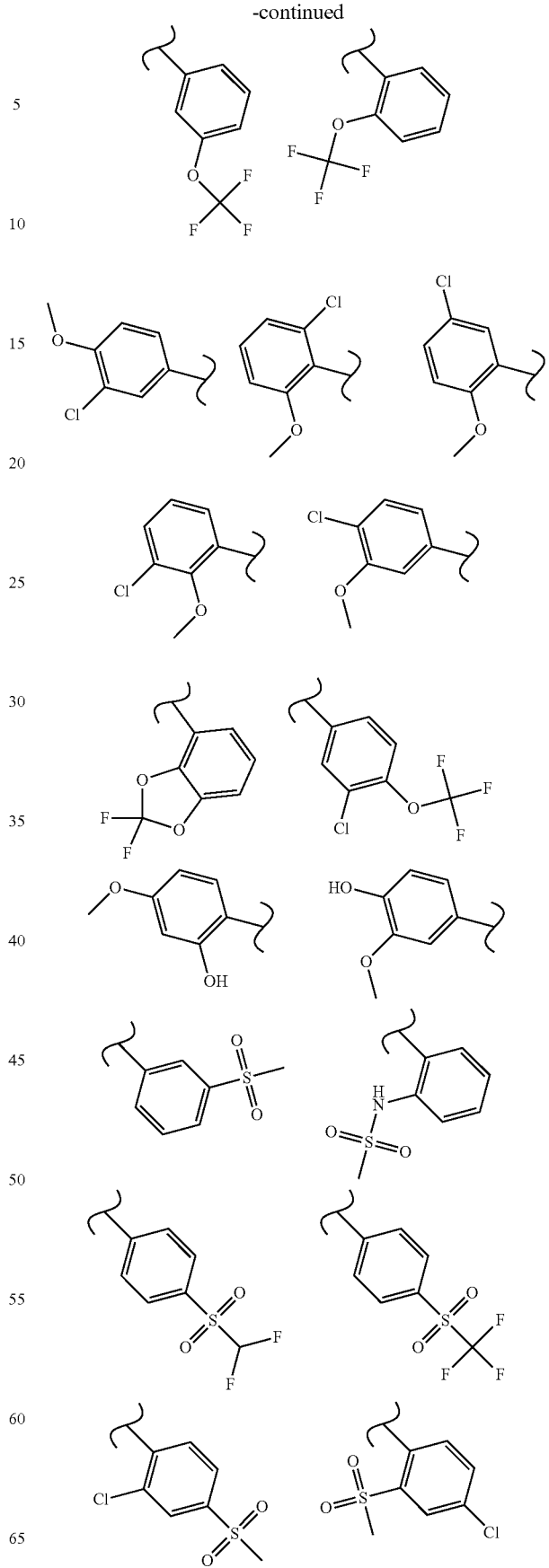

81
-continued
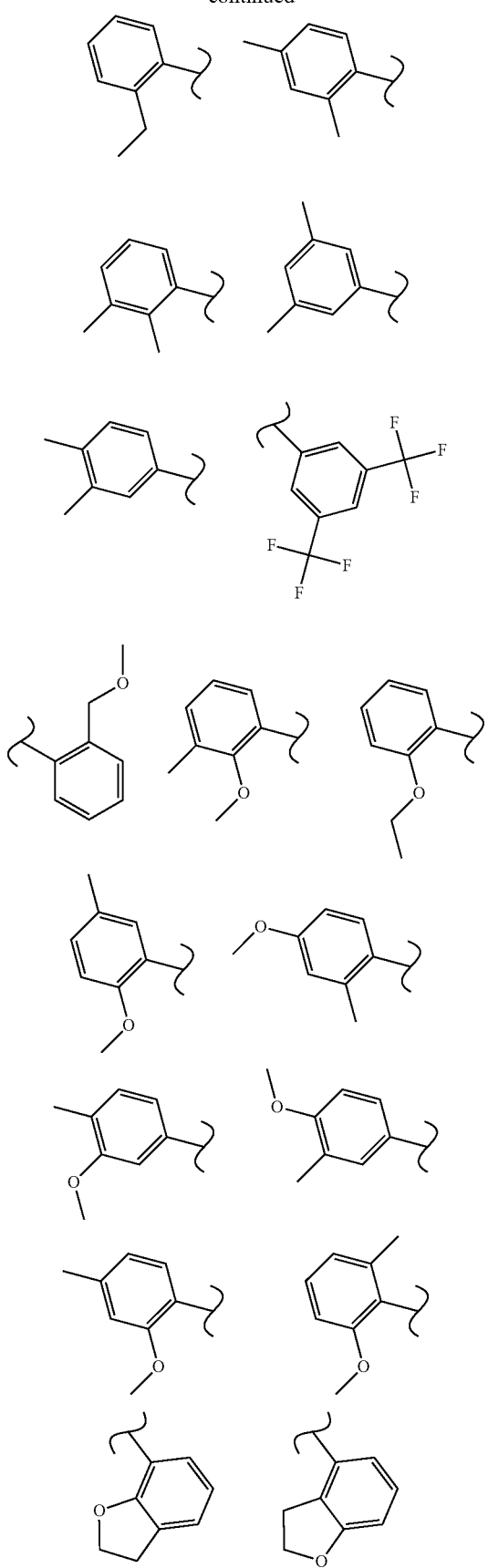
82
-continued
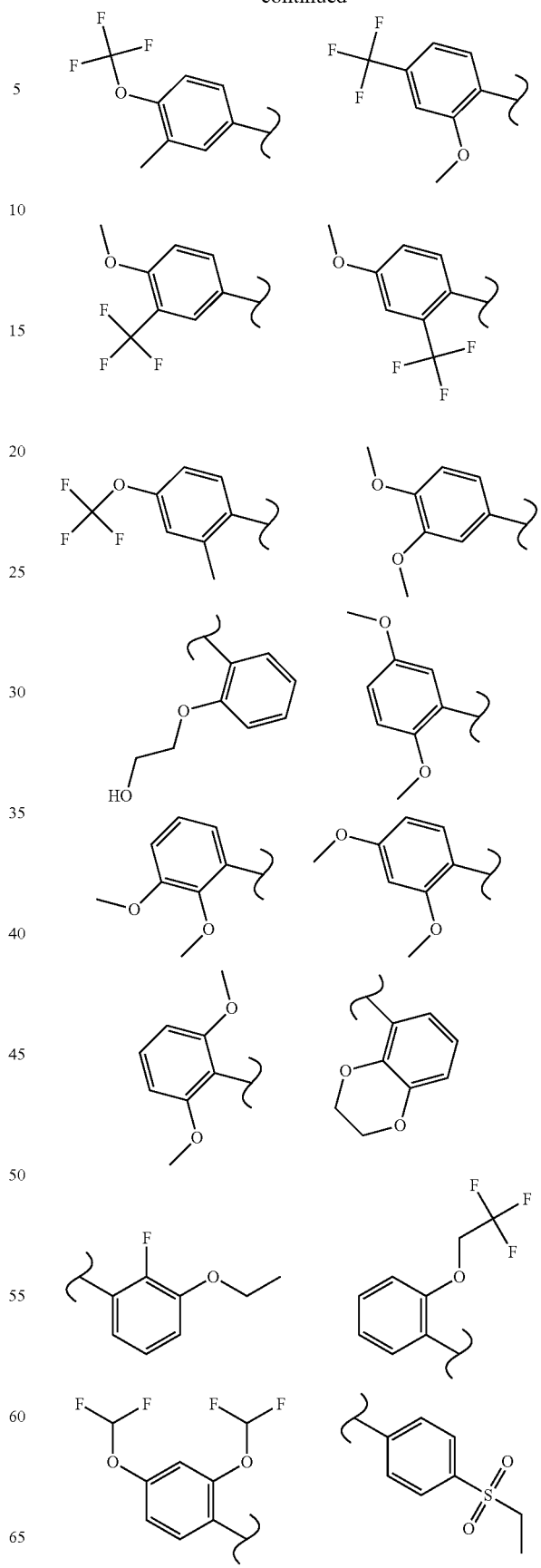

83
-continued
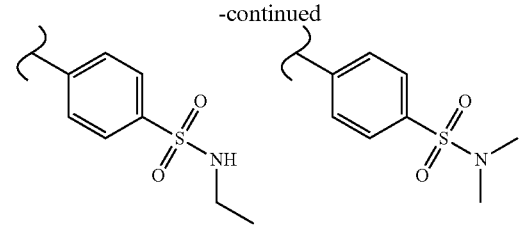
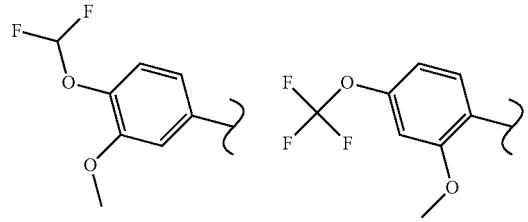
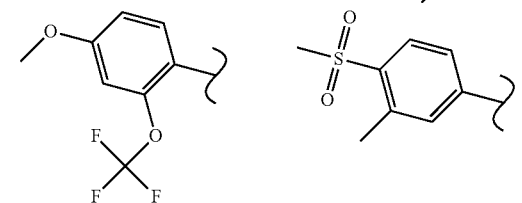
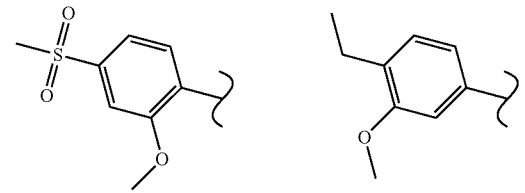
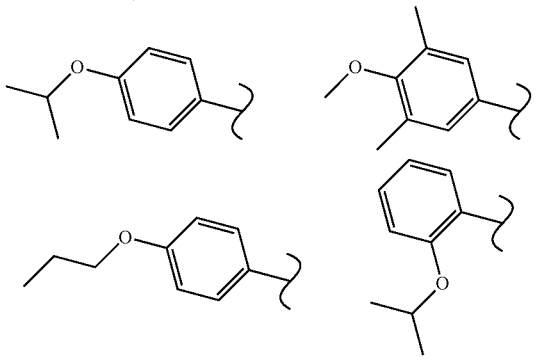
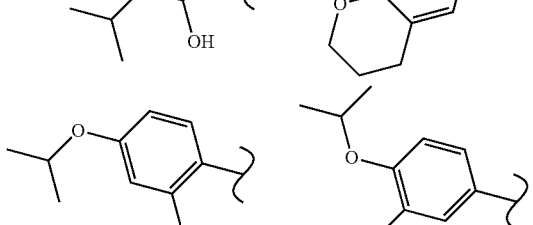
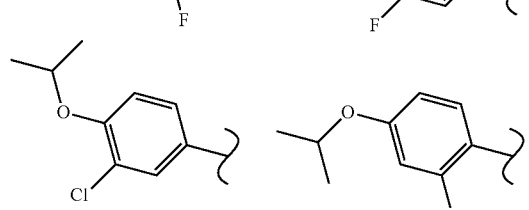
84
-continued

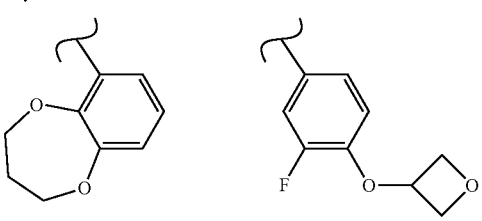
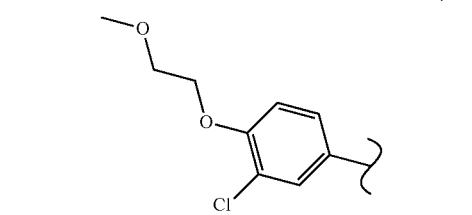
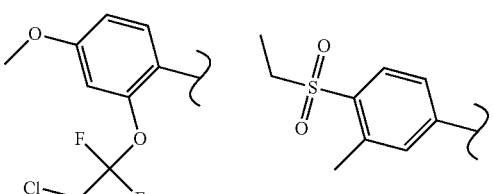
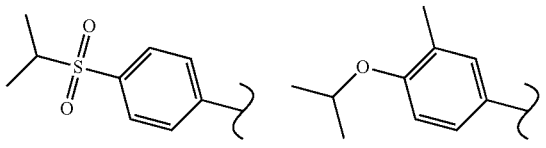
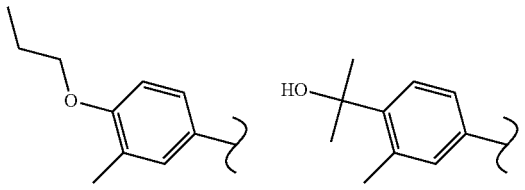
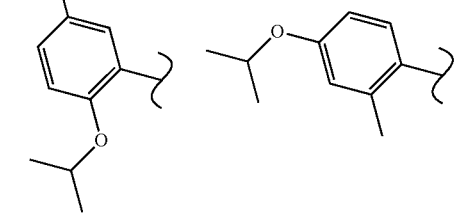
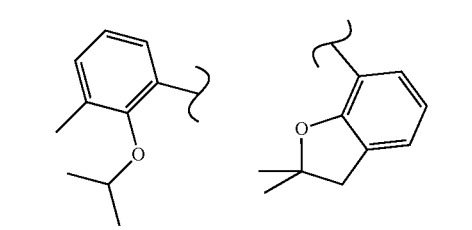

-continued
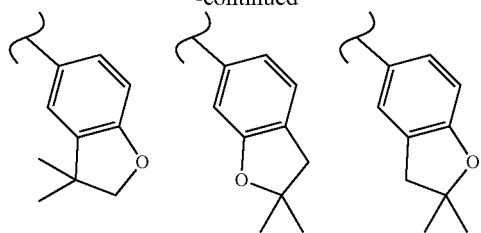
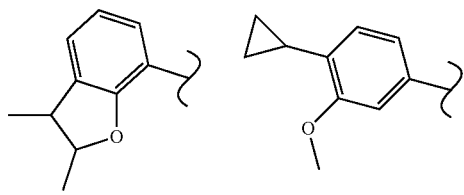
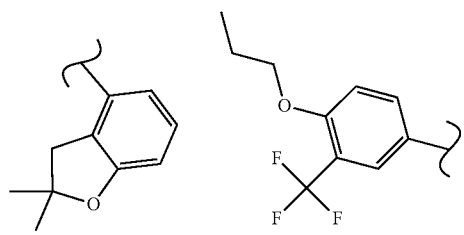
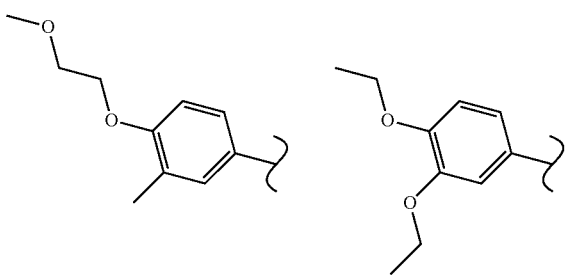
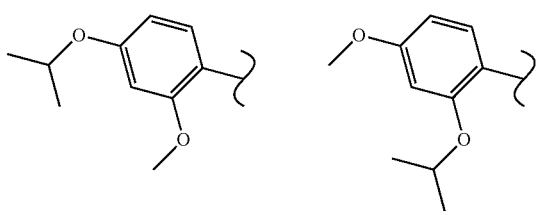
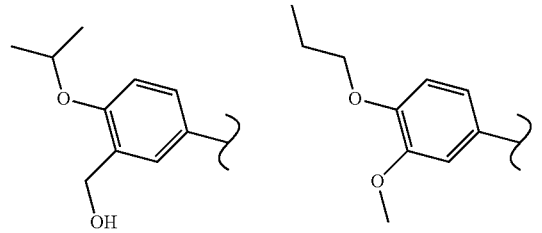
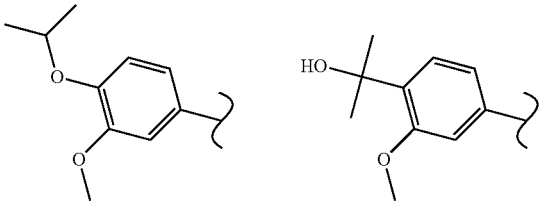
-continued
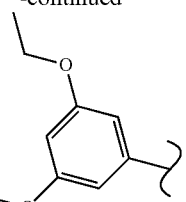
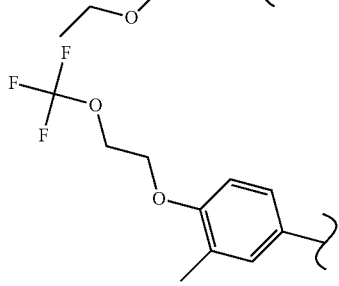
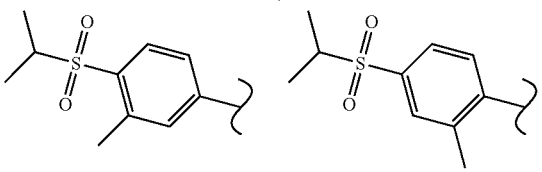
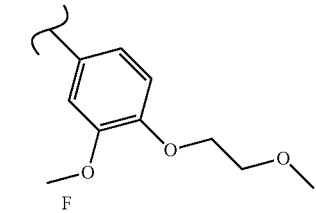
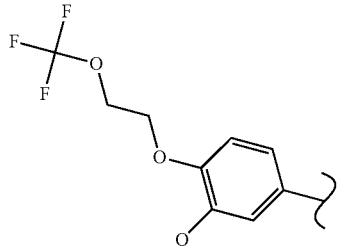
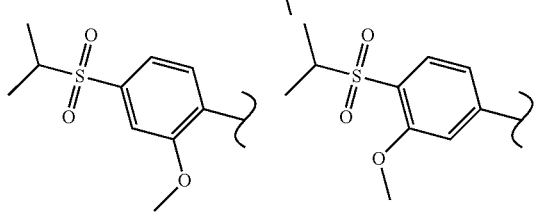
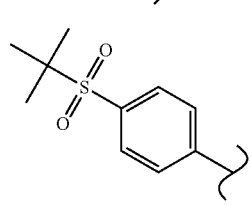
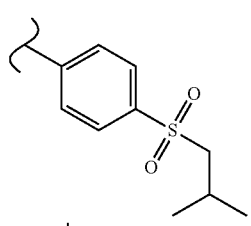
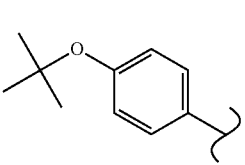
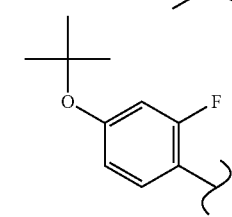

-continued
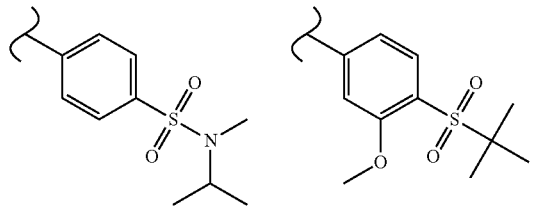
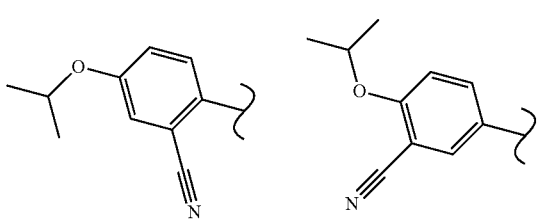
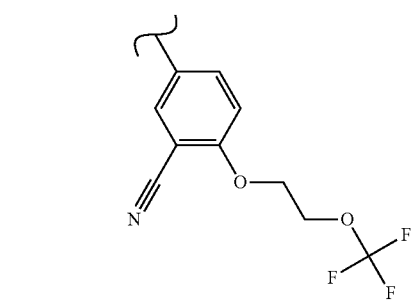
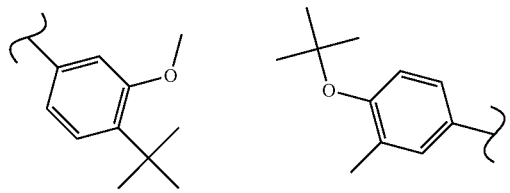
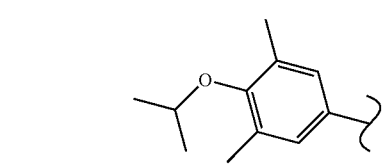
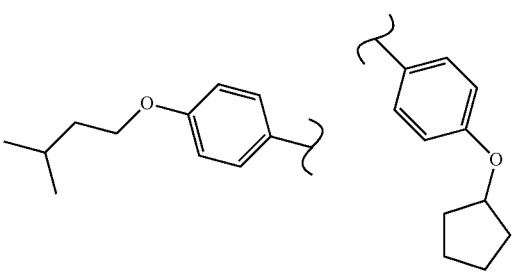
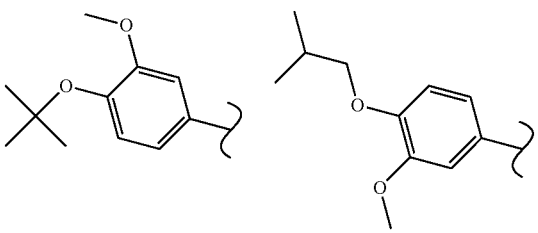
-continued
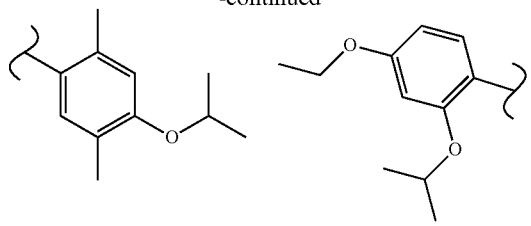
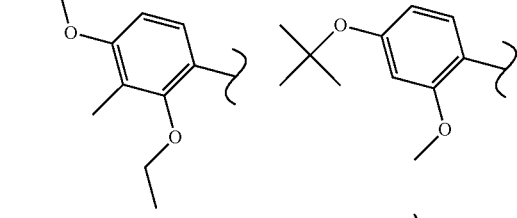
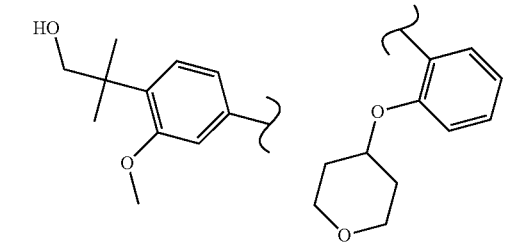
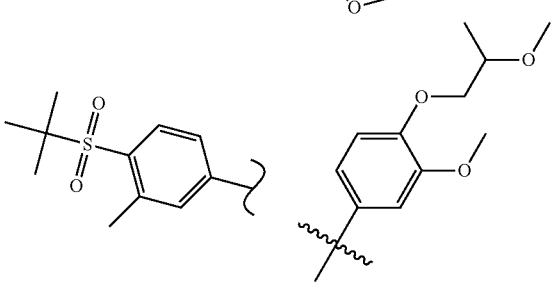
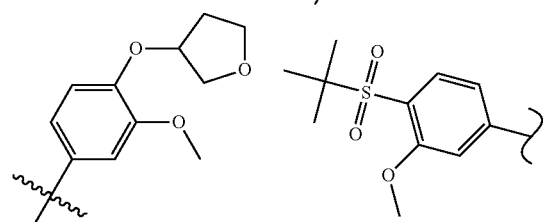
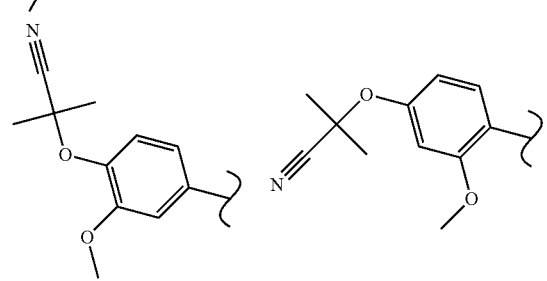
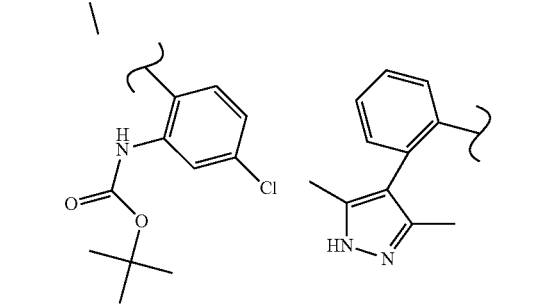

89
-continued
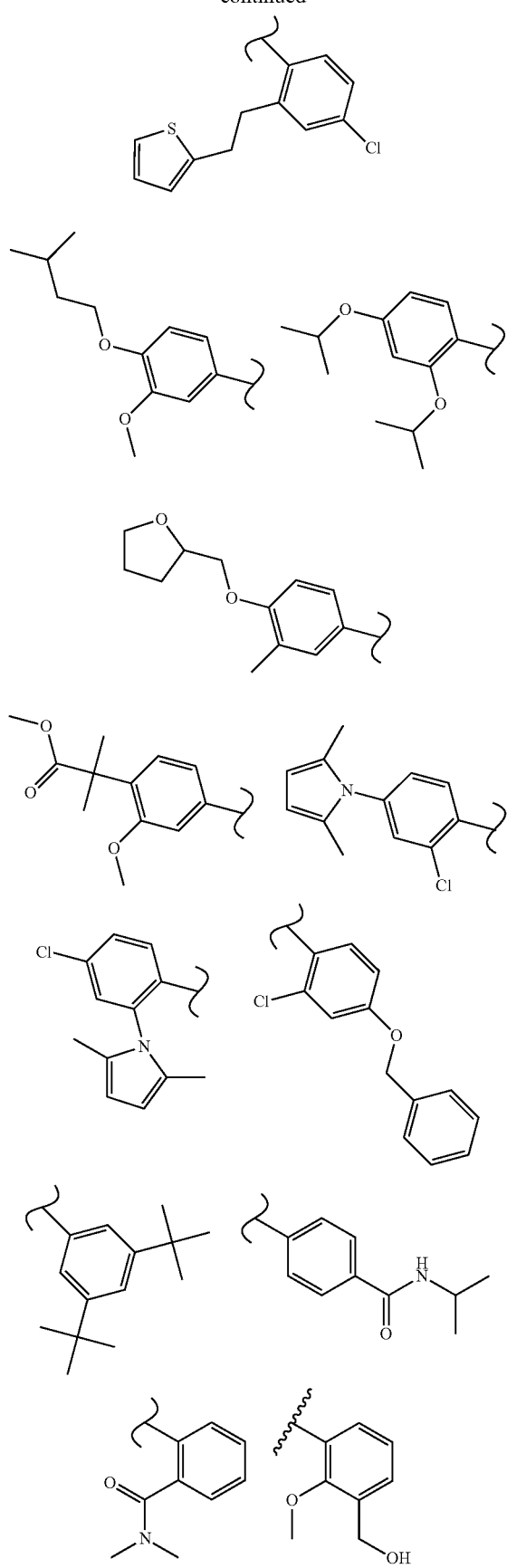
90
-continued
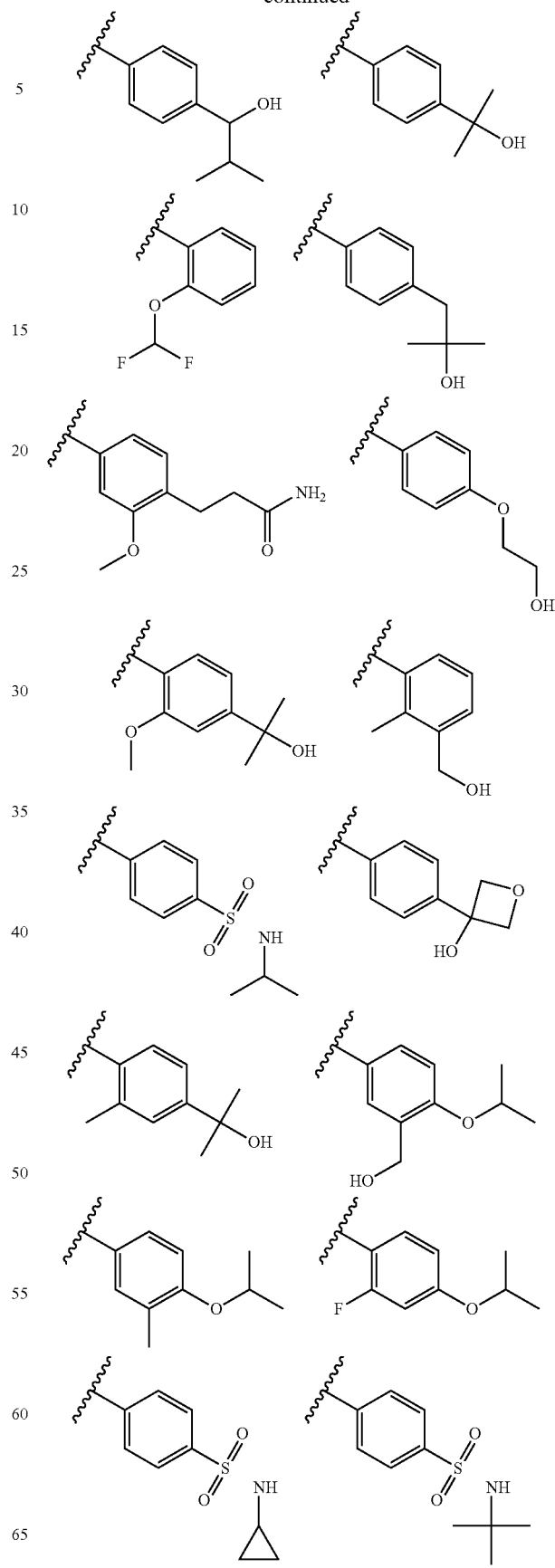

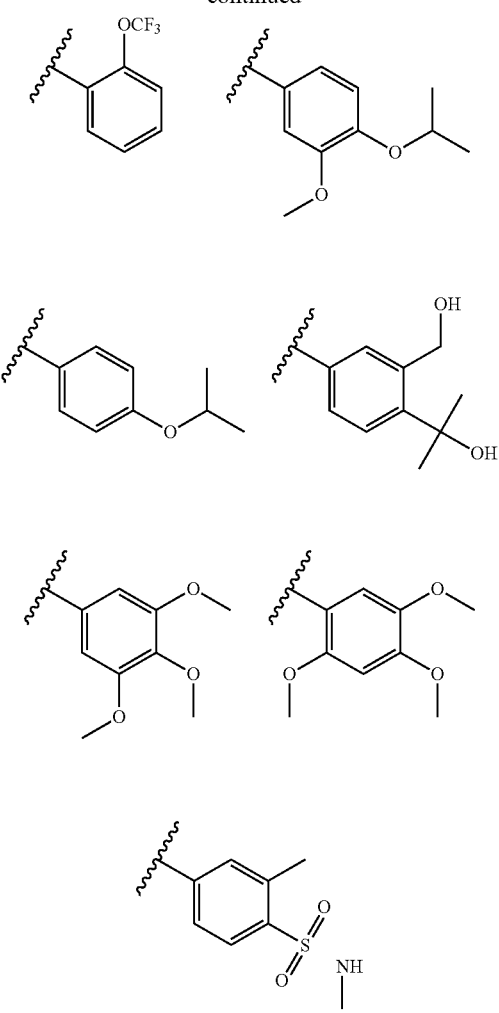
In another embodiment, the invention relates to a compound selected from Table 1:
TABLE 1
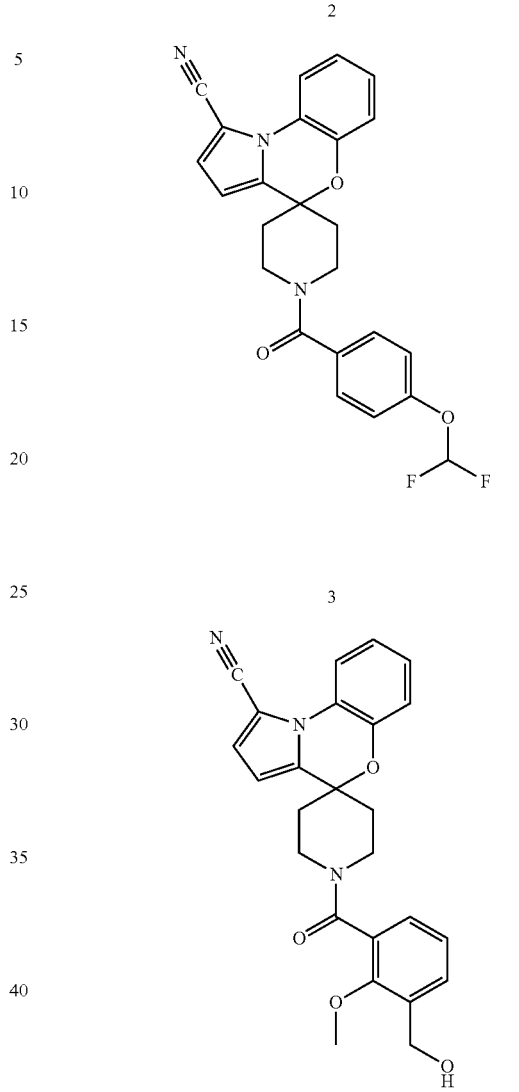
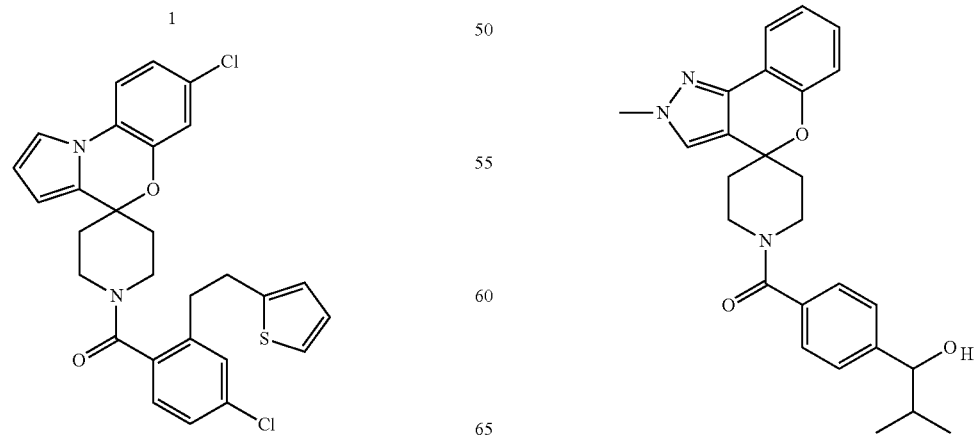

TABLE 1-continued
5
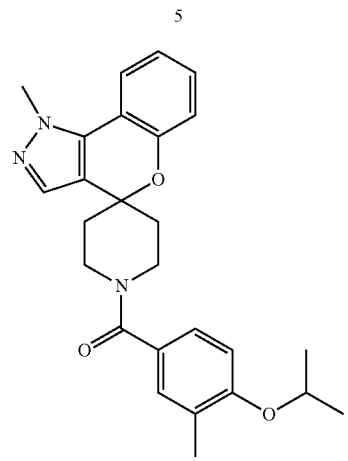
6
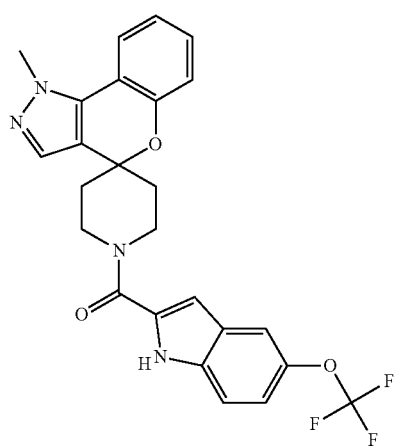
7
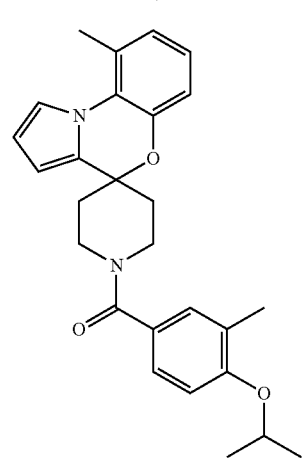 [SMILES: Cc1cc(C(=O)N2CCC3(CC2)Oc2cccc(C)c2-n2cccc23)ccc1OC(C)C]
TABLE 1-continued
8
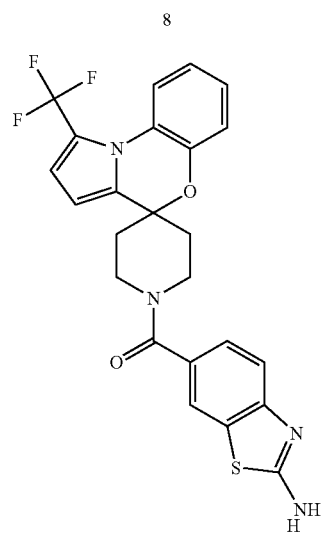
9
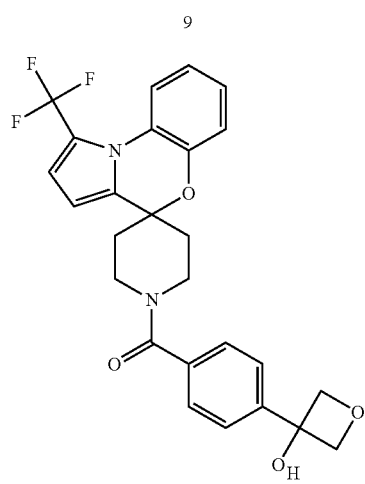
10
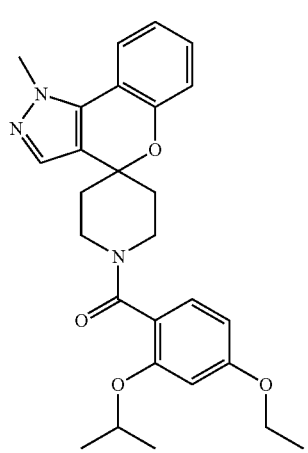 [SMILES: CCOc1ccc(C(=O)N2CCC3(CC2)Oc2ccccc2-c2c3cnn2C)c(OC(C)C)c1]

TABLE 1-continued
11
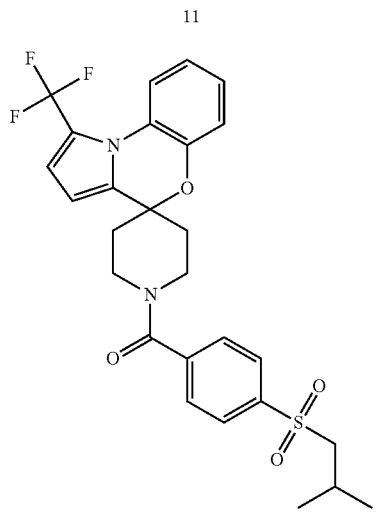
12
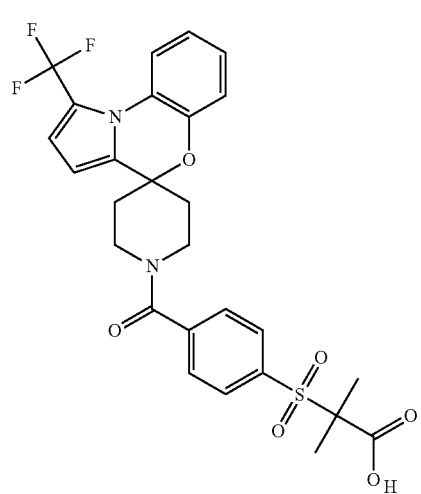
13
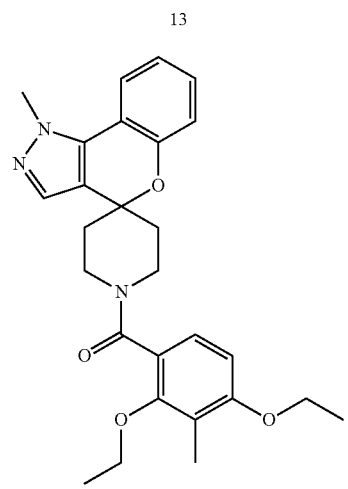
TABLE 1-continued
14
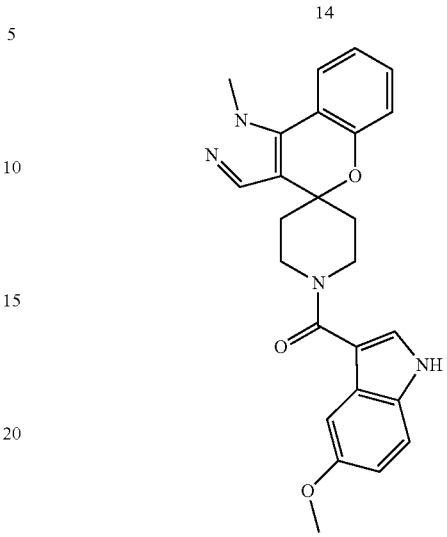
15
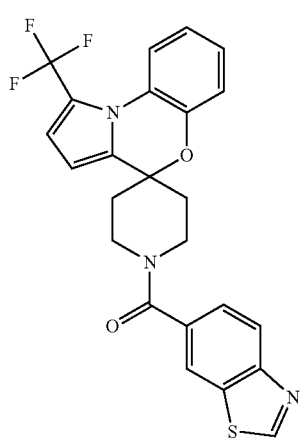 [SMILES: O=C(c1ccc2ncsc2c1)N1CCC2(CC1)Oc1ccccc1-n1c(C(F)(F)F)ccc12]
16
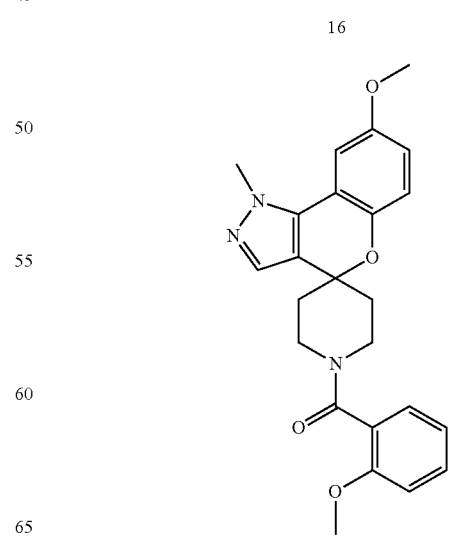

TABLE 1-continued
17
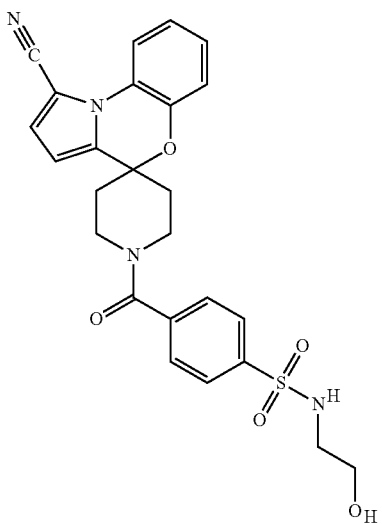
18
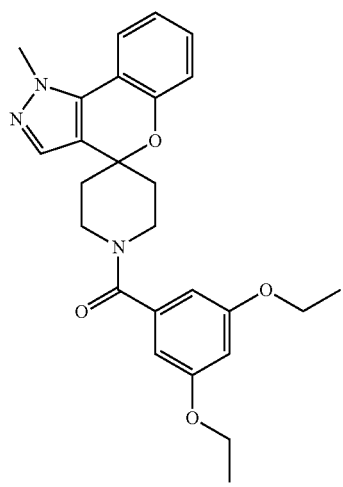 [SMILES: CCOc1cc(OCC)cc(C(=O)N2CCC3(CC2)Oc2ccccc2-c2c3cnn2C)c1]
19
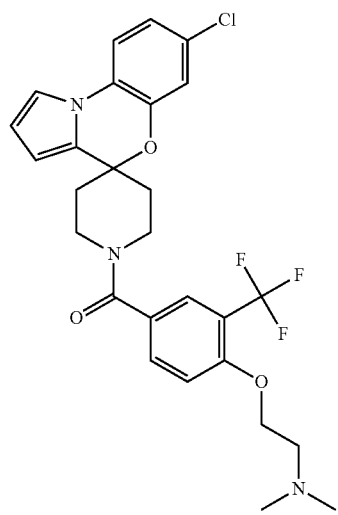
TABLE 1-continued
20
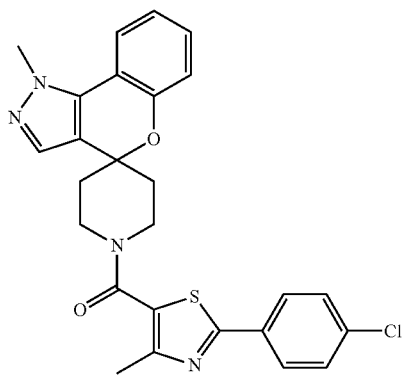 [SMILES: Cc1nc(-c2ccc(Cl)cc2)sc1C(=O)N1CCC2(CC1)Oc1ccccc1-c1c2cnn1C]
21
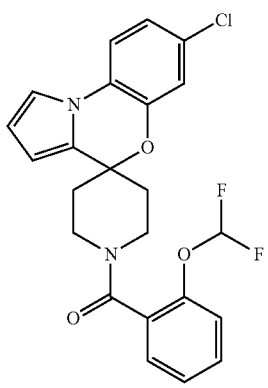 [SMILES: O=C(c1ccccc1OC(F)F)N1CCC2(CC1)Oc1cc(Cl)ccc1-n1cccc12]
22
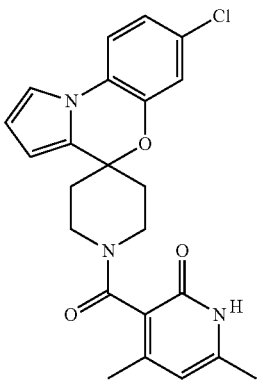

TABLE 1-continued
23
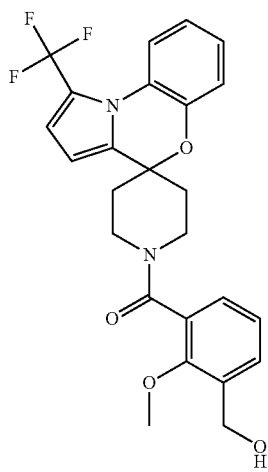 [SMILES: COc1c(CO)cccc1C(=O)N1CCC2(CC1)Oc1ccccc1-n1c(C(F)(F)F)ccc12]
24
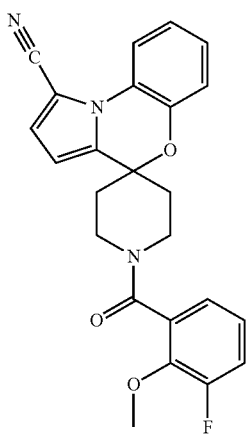
25
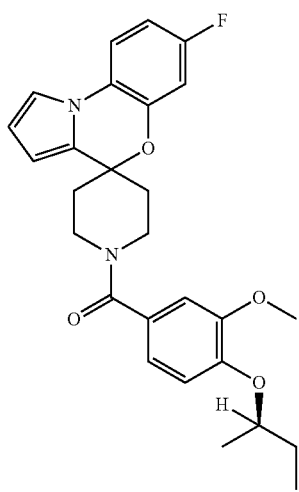 [SMILES: CC[C@@H](C)Oc1ccc(C(=O)N2CCC3(CC2)Oc2cc(F)ccc2-n2cccc23)cc1OC]
TABLE 1-continued
26
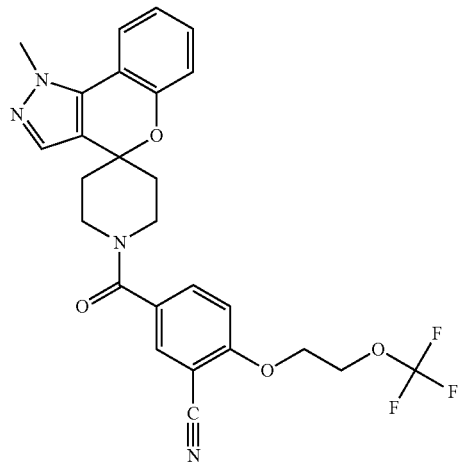 [SMILES: Cn1ncc2c1-c1ccccc1OC21CCN(C(=O)c2ccc(OCCOC(F)(F)F)c(C#N)c2)CC1]
27
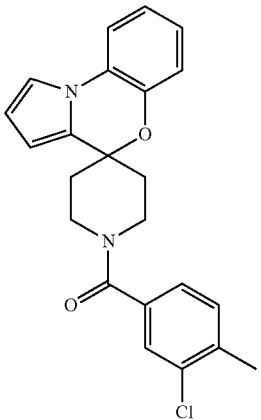 [SMILES: Cc1ccc(C(=O)N2CCC3(CC2)Oc2ccccc2-n2cccc23)cc1Cl]
28
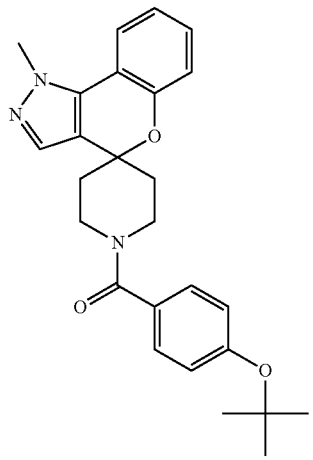 [SMILES: Cn1ncc2c1-c1ccccc1OC21CCN(C(=O)c2ccc(OC(C)(C)C)cc2)CC1]

TABLE 1-continued
29
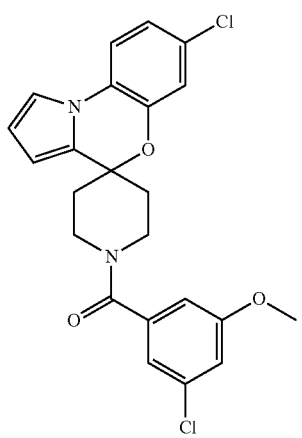
30
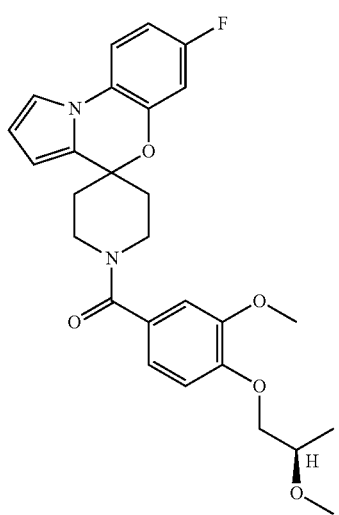
31
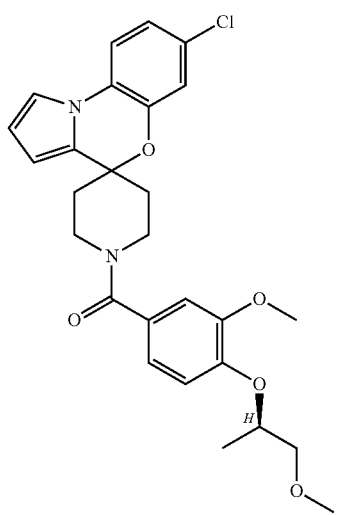
TABLE 1-continued
32
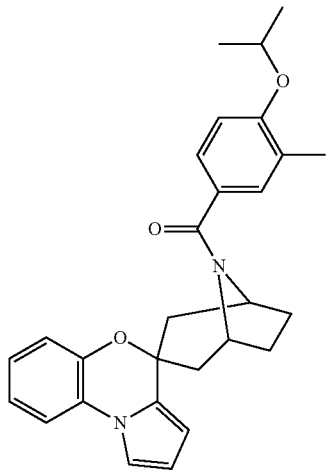 [SMILES: Cc1cc(C(=O)N2C3CCC2CC2(C3)Oc3ccccc3-n3cccc32)ccc1OC(C)C]
33
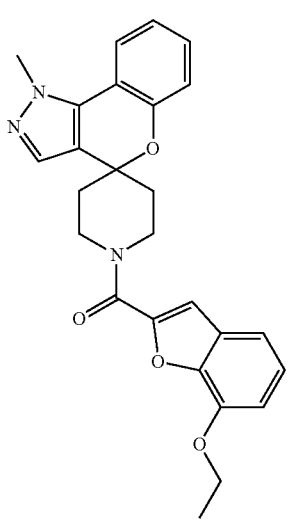 [SMILES: CCOc1cccc2cc(C(=O)N3CCC4(CC3)Oc3ccccc3-c3c4cnn3C)oc12]
34
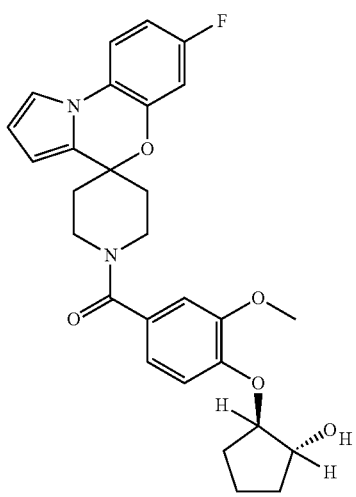

TABLE 1-continued
35
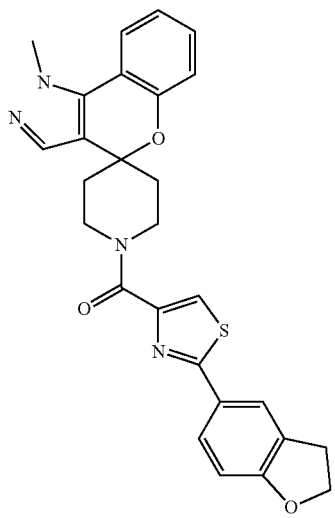 [SMILES: CNC1=C(C=N)C2(CCN(C(=O)c3csc(-c4ccc5c(c4)CCO5)n3)CC2)Oc2ccccc21]
36
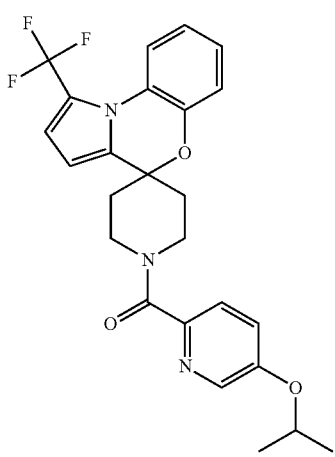 [SMILES: CC(C)Oc1ccc(C(=O)N2CCC3(CC2)Oc2ccccc2-n2c(C(F)(F)F)ccc23)nc1]
37
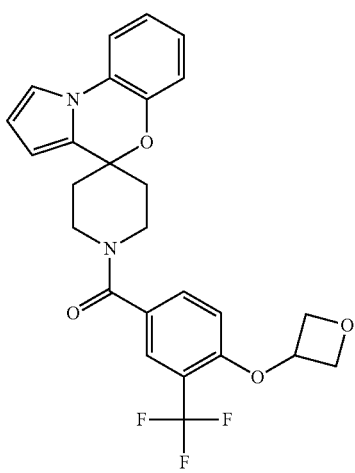 [SMILES: O=C(c1ccc(OC2COC2)c(C(F)(F)F)c1)N1CCC2(CC1)Oc1ccccc1-n1cccc12]
TABLE 1-continued
38
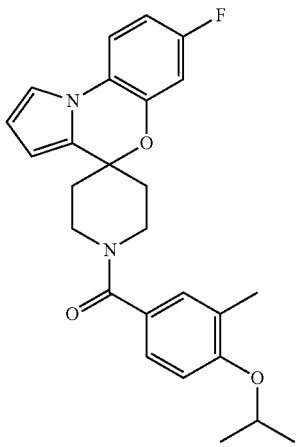 [SMILES: Cc1cc(C(=O)N2CCC3(CC2)Oc2cc(F)ccc2-n2cccc23)ccc1OC(C)C]
39
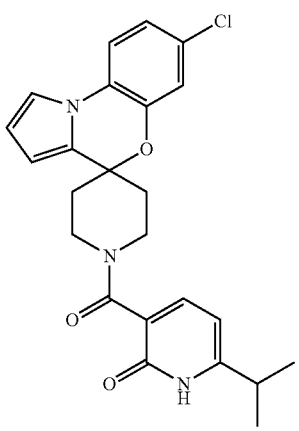 [SMILES: CC(C)c1ccc(C(=O)N2CCC3(CC2)Oc2cc(Cl)ccc2-n2cccc23)c(=O)[nH]1]
40
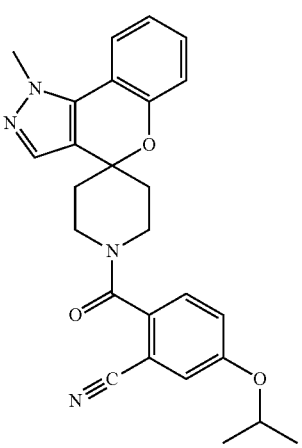 [SMILES: CC(C)Oc1ccc(C(=O)N2CCC3(CC2)Oc2ccccc2-c2c3cnn2C)c(C#N)c1]

TABLE 1-continued
41
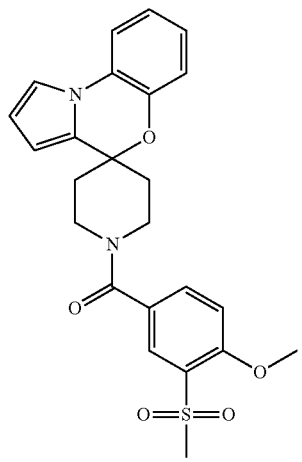 [SMILES: COc1ccc(C(=O)N2CCC3(CC2)Oc2ccccc2-n2cccc23)cc1S(C)(=O)=O]
42
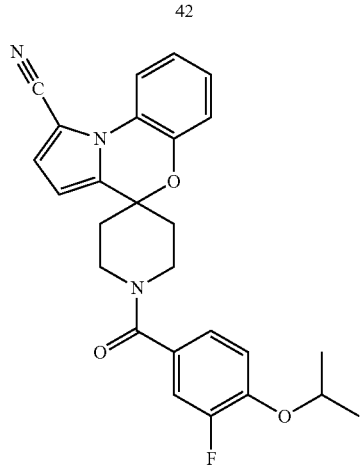
43
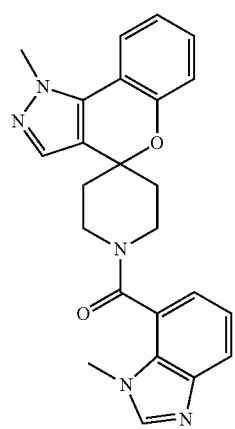 [SMILES: Cn1ncc2c1-c1ccccc1OC21CCN(C(=O)c2cccc3ncn(C)c23)CC1]
TABLE 1-continued
44
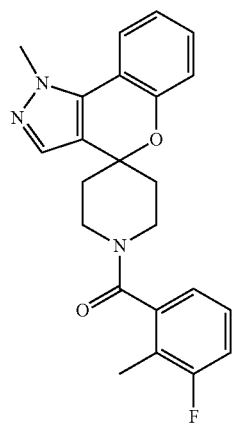 [SMILES: Cc1c(F)cccc1C(=O)N1CCC2(CC1)Oc1ccccc1-c1c2cnn1C]
45
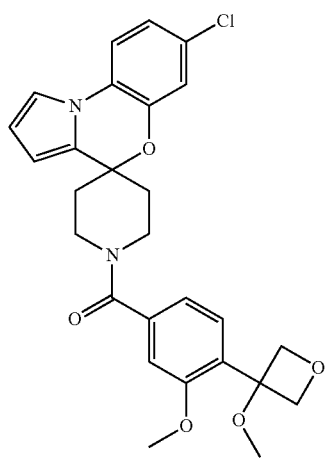 [SMILES: COc1cc(C(=O)N2CCC3(CC2)Oc2cc(Cl)ccc2-n2cccc23)ccc1C1(OC)COC1]
46
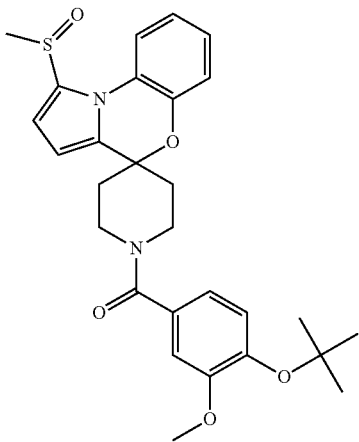 [SMILES: COc1cc(C(=O)N2CCC3(CC2)Oc2ccccc2-n2c(S(C)=O)ccc23)ccc1OC(C)(C)C]

TABLE 1-continued
47
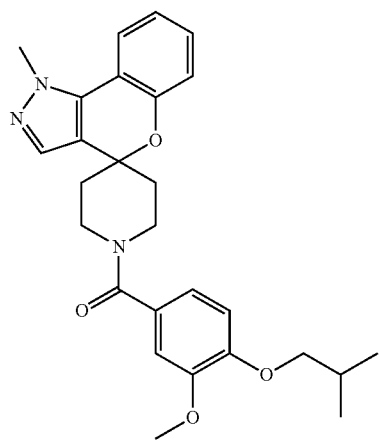 [SMILES: COc1cc(C(=O)N2CCC3(CC2)Oc2ccccc2-c2c3cnn2C)ccc1OCC(C)C]
48
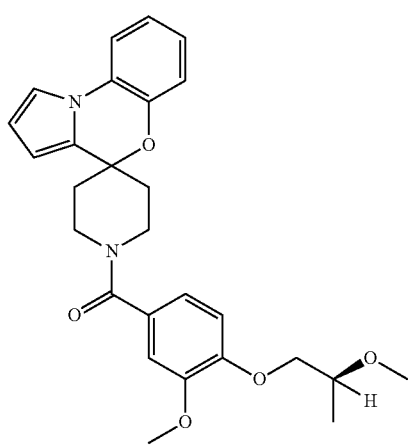 [SMILES: COc1cc(C(=O)N2CCC3(CC2)Oc2ccccc2-n2cccc23)ccc1OC[C@H](C)OC]
49
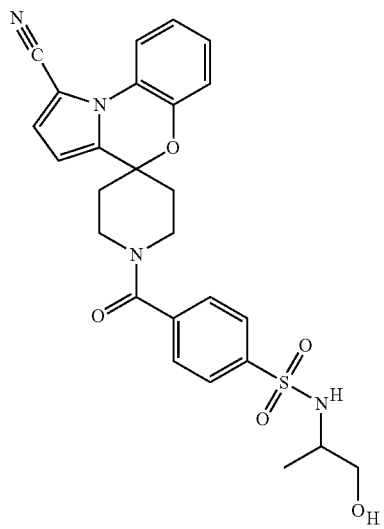
TABLE 1-continued
50
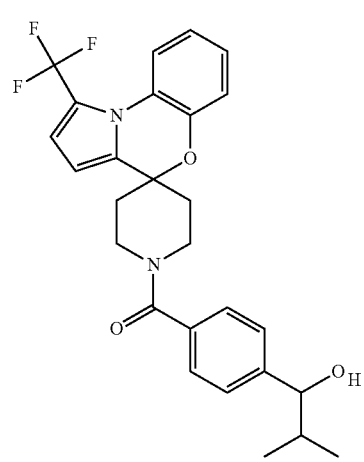
51
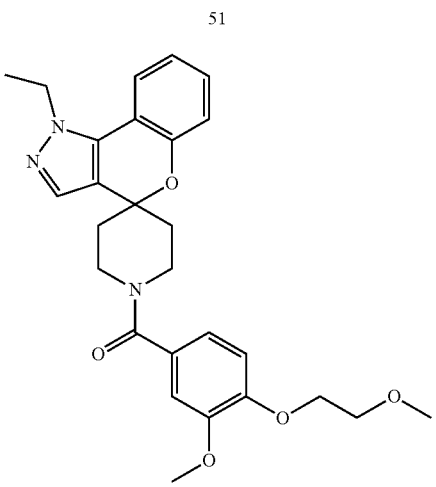
52
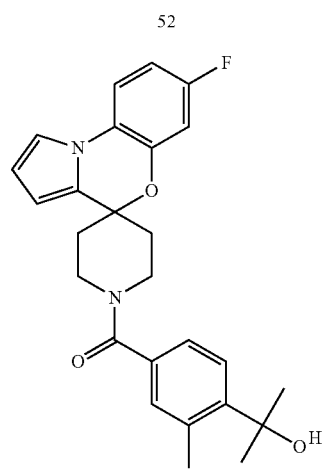

TABLE 1-continued
53
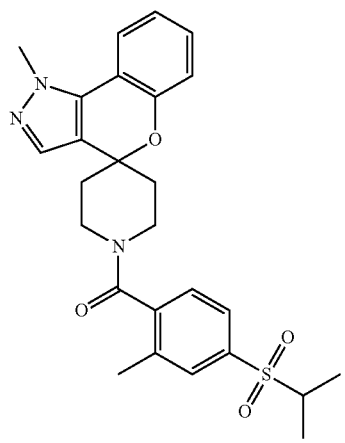
54
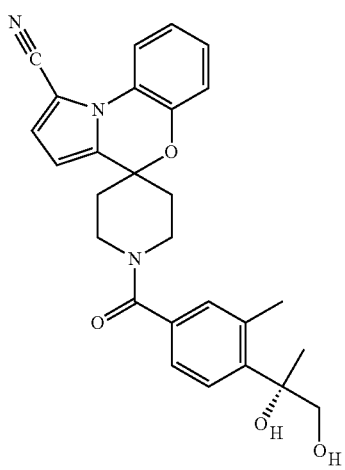
55
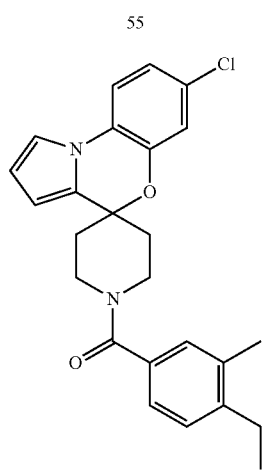
TABLE 1-continued
56
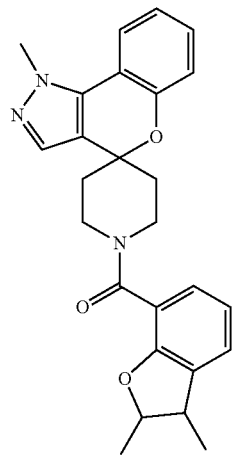 [SMILES: CC1Oc2c(C(=O)N3CCC4(CC3)Oc3ccccc3-c3c4cnn3C)cccc2C1C]
57
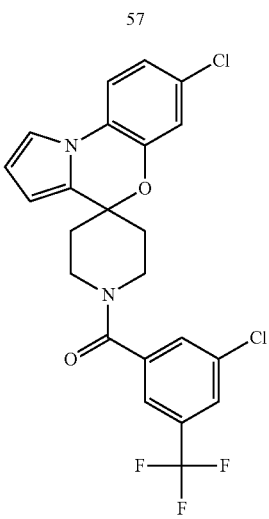
58
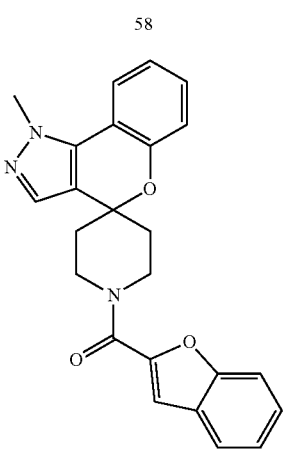

TABLE 1-continued
59
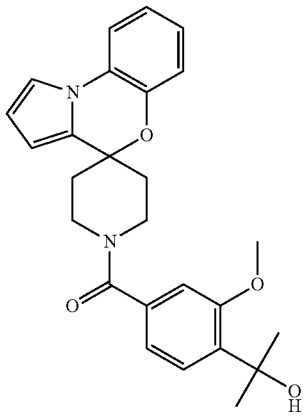 [SMILES: COc1cc(C(=O)N2CCC3(CC2)Oc2ccccc2-n2cccc23)ccc1C(C)(C)O]
60
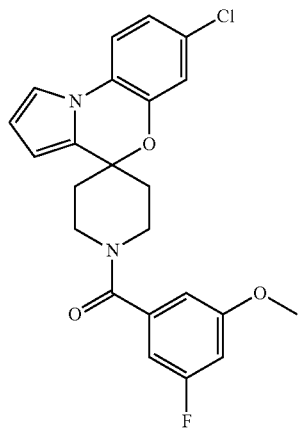 [SMILES: COc1cc(F)cc(C(=O)N2CCC3(CC2)Oc2cc(Cl)ccc2-n2cccc23)c1]
61
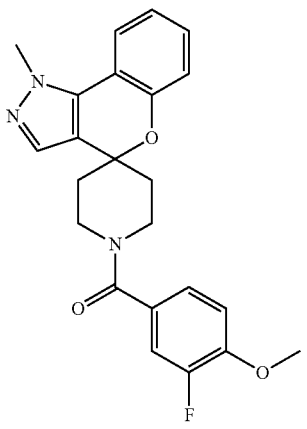 [SMILES: COc1ccc(C(=O)N2CCC3(CC2)Oc2ccccc2-c2c3cnn2C)cc1F]
TABLE 1-continued
62
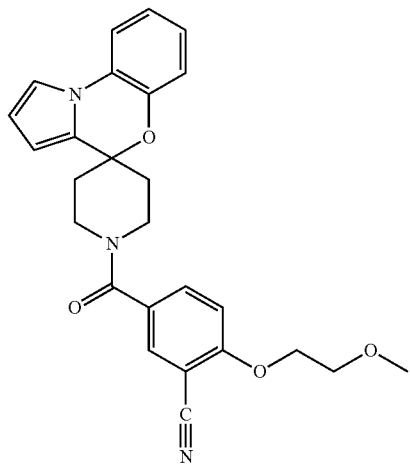 [SMILES: COCCOc1ccc(C(=O)N2CCC3(CC2)Oc2ccccc2-n2cccc23)cc1C#N]
63
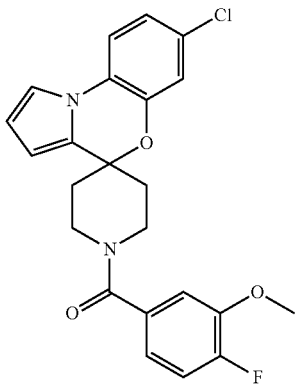 [SMILES: COc1cc(C(=O)N2CCC3(CC2)Oc2cc(Cl)ccc2-n2cccc23)ccc1F]
64
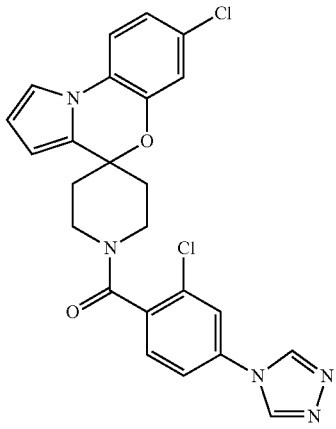 [SMILES: O=C(c1ccc(-n2cnnc2)cc1Cl)N1CCC2(CC1)Oc1cc(Cl)ccc1-n1cccc12]

TABLE 1-continued
65
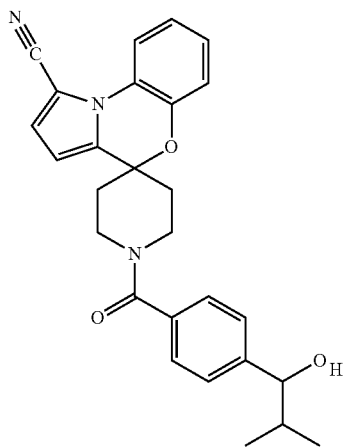
66
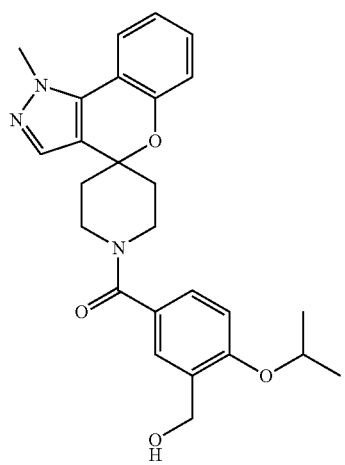 [SMILES: CC(C)Oc1ccc(C(=O)N2CCC3(CC2)Oc2ccccc2-c2c3cnn2C)cc1CO]
67
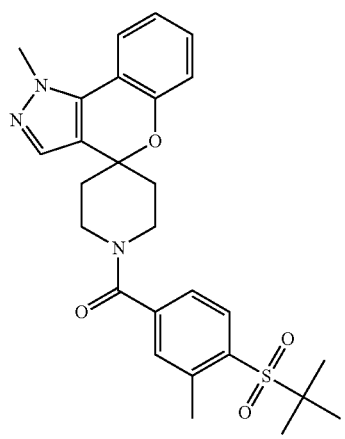
TABLE 1-continued
68
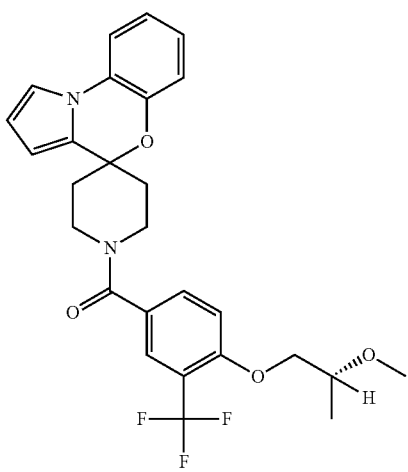 [SMILES: CO[C@H](C)COc1ccc(C(=O)N2CCC3(CC2)Oc2ccccc2-n2cccc23)cc1C(F)(F)F]
69
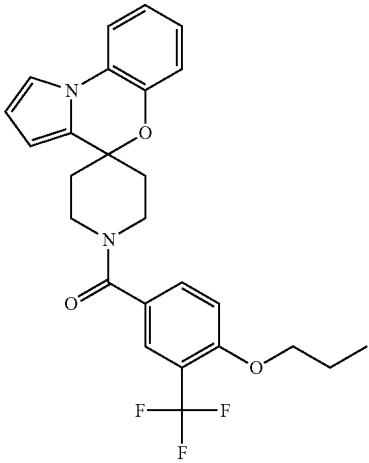 [SMILES: CCCOc1ccc(C(=O)N2CCC3(CC2)Oc2ccccc2-n2cccc23)cc1C(F)(F)F]
70
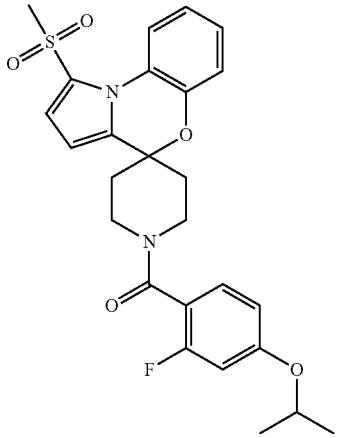 [SMILES: CC(C)Oc1ccc(C(=O)N2CCC3(CC2)Oc2ccccc2-n2c3ccc2S(C)(=O)=O)c(F)c1]

TABLE 1-continued
71
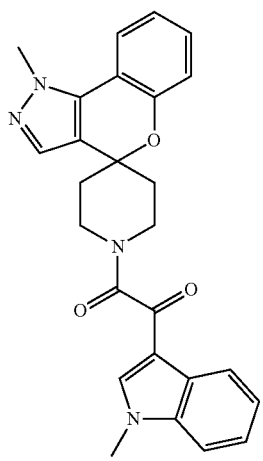 [SMILES: Cn1ncc2c1-c1ccccc1OC21CCN(C(=O)C(=O)c2cn(C)c3ccccc23)CC1]
72
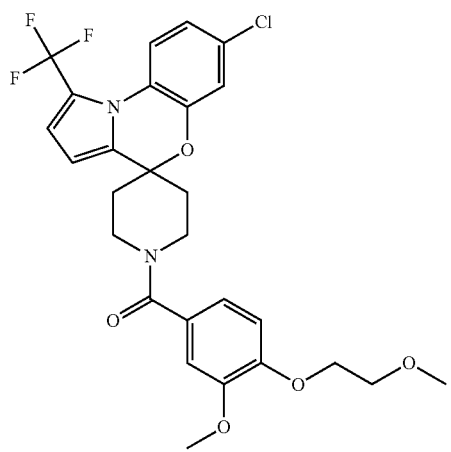 [SMILES: COCCOc1ccc(C(=O)N2CCC3(CC2)Oc2cc(Cl)ccc2-n2c(C(F)(F)F)ccc23)cc1OC]
73
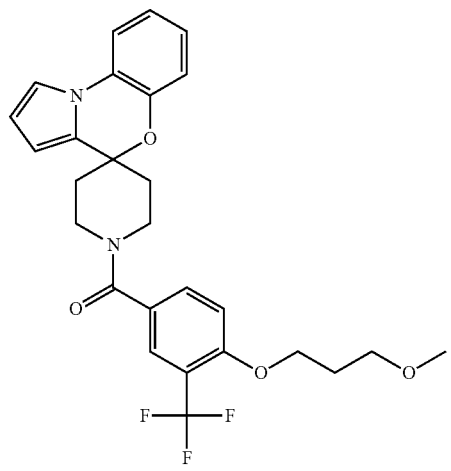 [SMILES: COCCCOc1ccc(C(=O)N2CCC3(CC2)Oc2ccccc2-n2cccc23)cc1C(F)(F)F]
TABLE 1-continued
74
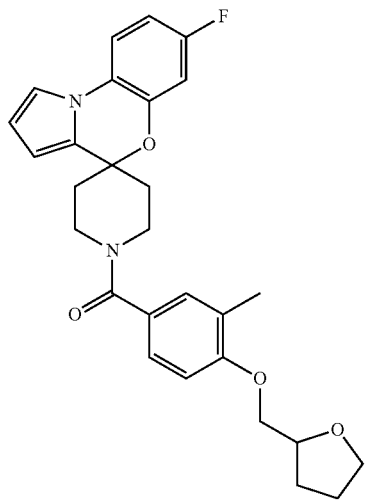 [SMILES: Cc1cc(C(=O)N2CCC3(CC2)Oc2cc(F)ccc2-n2cccc23)ccc1OCC1CCCO1]
75
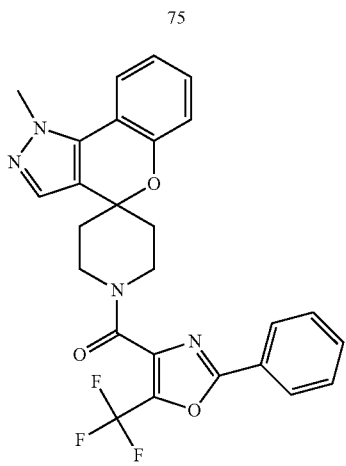
76
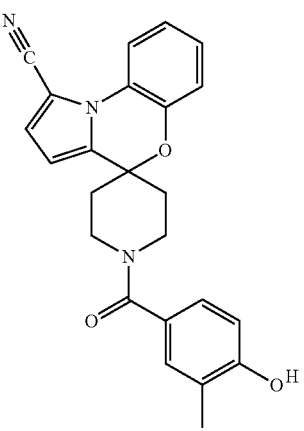

TABLE 1-continued
77
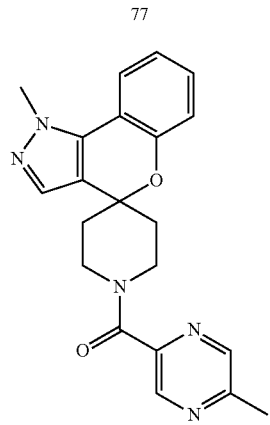
78
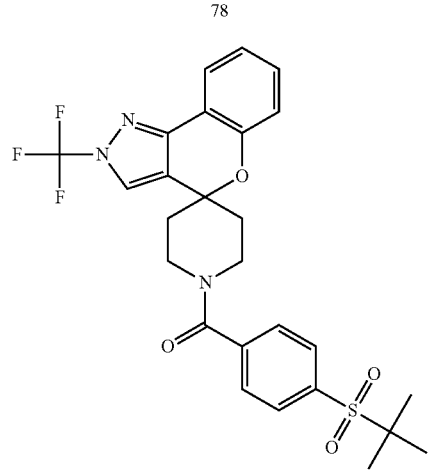
79
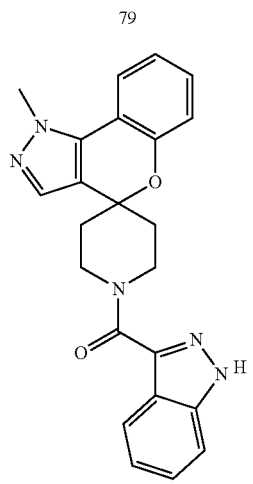
TABLE 1-continued
80
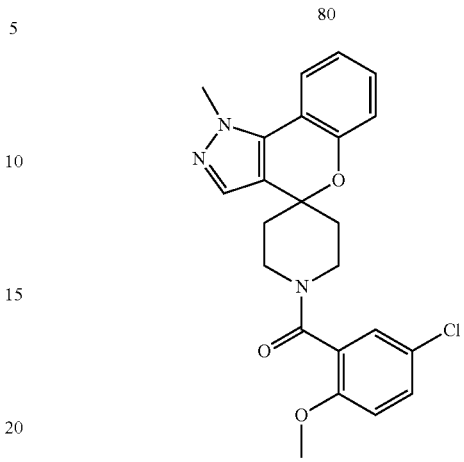
81
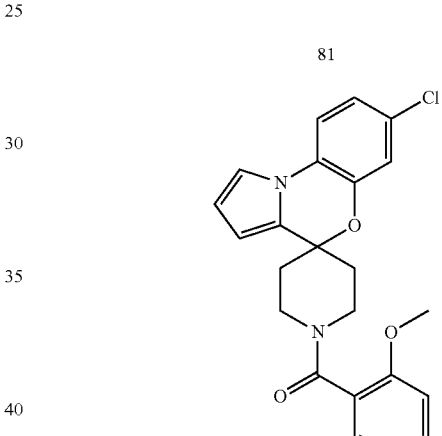
82
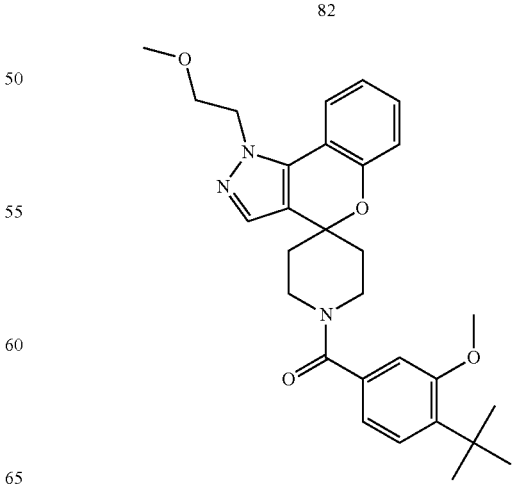

TABLE 1-continued
83
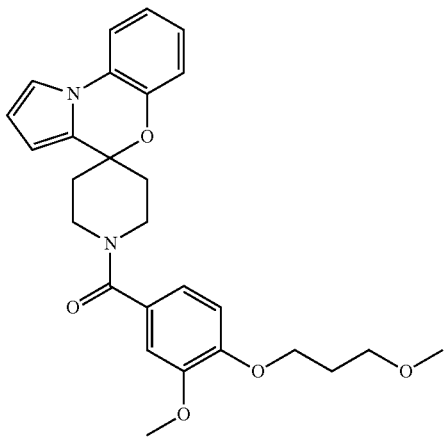 [SMILES: COCCCOc1ccc(C(=O)N2CCC3(CC2)Oc2ccccc2-n2cccc23)cc1OC]
84
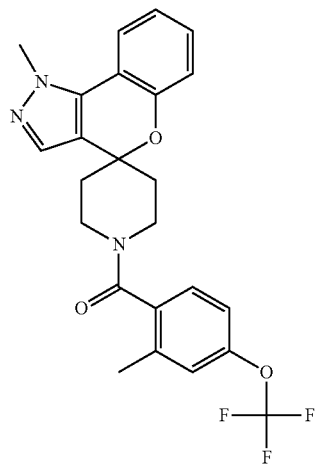 [SMILES: Cc1cc(OC(F)(F)F)ccc1C(=O)N1CCC2(CC1)Oc1ccccc1-c1c2cnn1C]
85
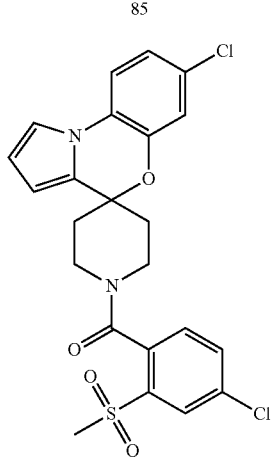
TABLE 1-continued
86
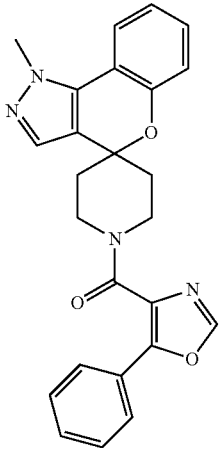 [SMILES: Cn1ncc2c1-c1ccccc1OC21CCN(C(=O)c2ncoc2-c2ccccc2)CC1]
87
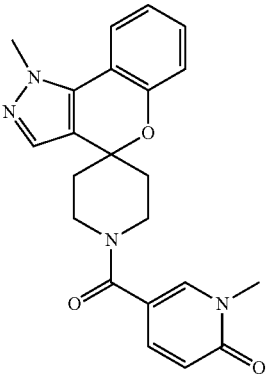 [SMILES: Cn1ncc2c1-c1ccccc1OC21CCN(C(=O)c2ccc(=O)n(C)c2)CC1]
88
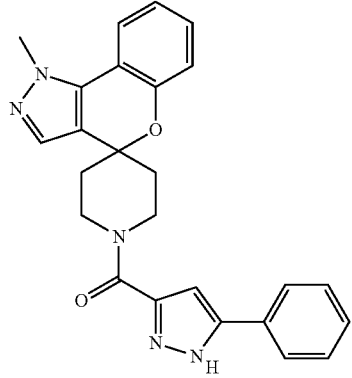

TABLE 1-continued
89
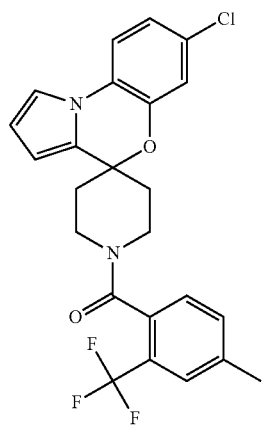 [SMILES: Cc1ccc(C(=O)N2CCC3(CC2)Oc2cc(Cl)ccc2-n2cccc23)c(C(F)(F)F)c1]
90
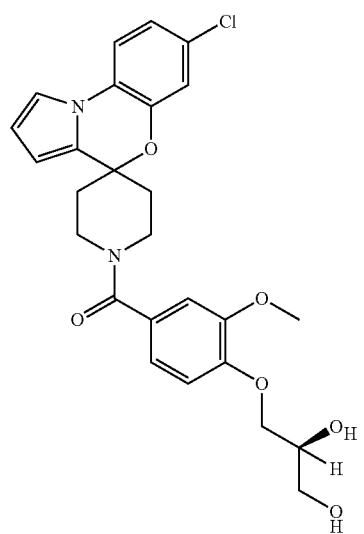
91
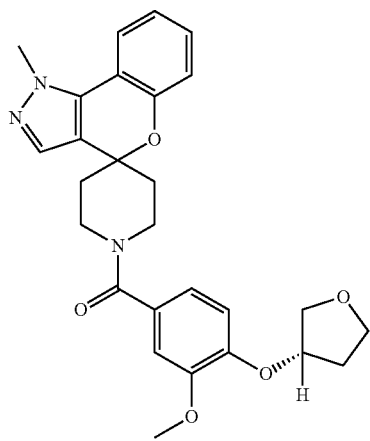 [SMILES: COc1cc(C(=O)N2CCC3(CC2)Oc2ccccc2-c2c3cnn2C)ccc1O[C@H]1CCOC1]
TABLE 1-continued
92
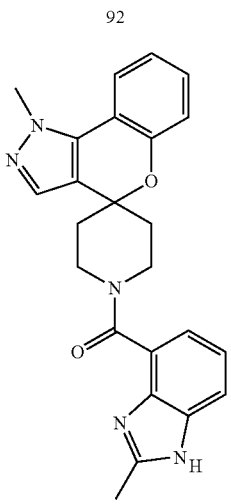
93
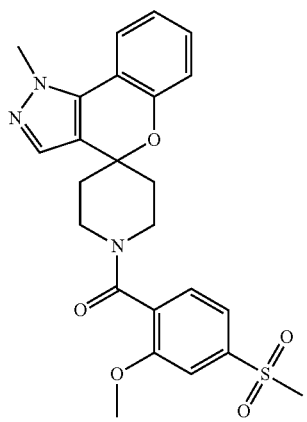
94
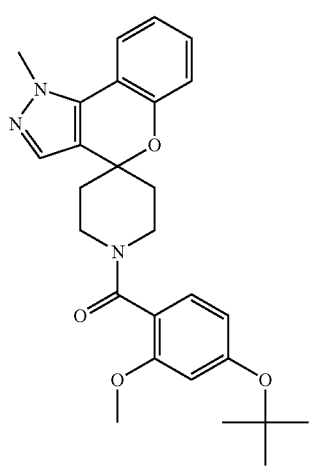 [SMILES: COc1cc(OC(C)(C)C)ccc1C(=O)N1CCC2(CC1)Oc1ccccc1-c1c2cnn1C]

TABLE 1-continued
95
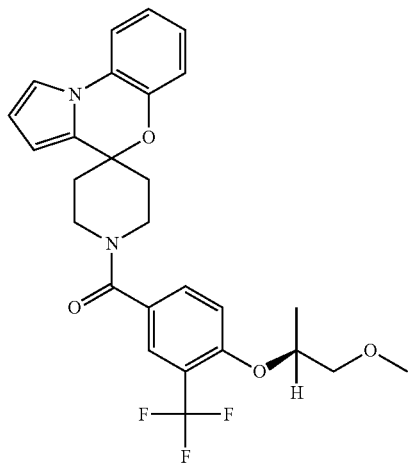 [SMILES: COC[C@H](C)Oc1ccc(C(=O)N2CCC3(CC2)Oc2ccccc2-n2cccc23)cc1C(F)(F)F]
96
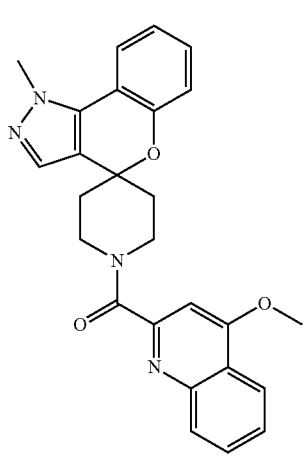 [SMILES: COc1cc(C(=O)N2CCC3(CC2)Oc2ccccc2-c2c3cnn2C)nc2ccccc12]
97
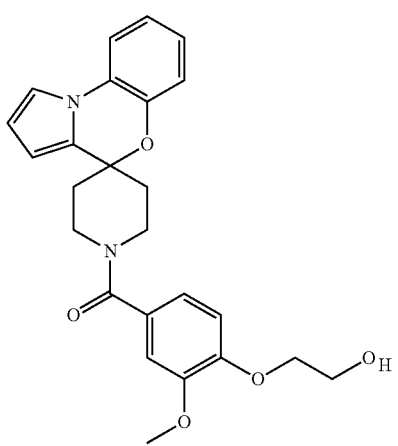
TABLE 1-continued
98
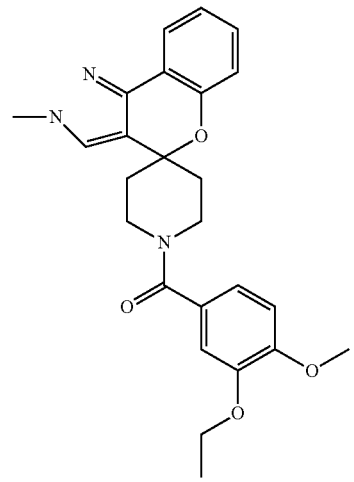
99
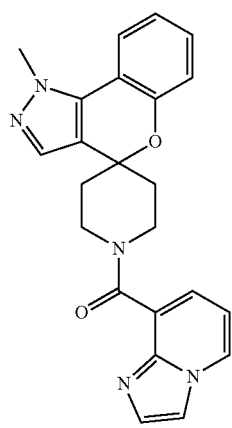 [SMILES: Cn1ncc2c1-c1ccccc1OC21CCN(C(=O)c2cccn3ccnc23)CC1]
100
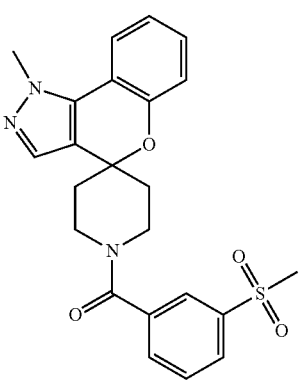 [SMILES: Cn1ncc2c1-c1ccccc1OC21CCN(C(=O)c2cccc(S(C)(=O)=O)c2)CC1]

TABLE 1-continued
101
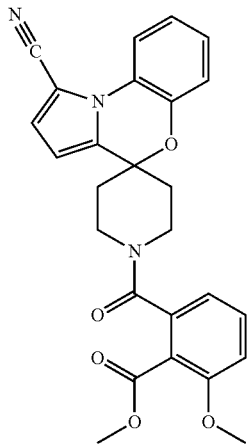
102
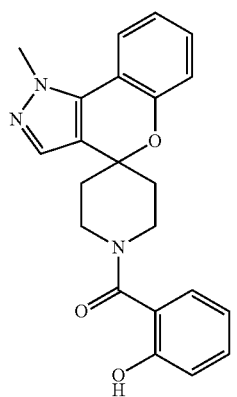 [SMILES: Cn1ncc2c1-c1ccccc1OC21CCN(C(=O)c2ccccc2O)CC1]
103
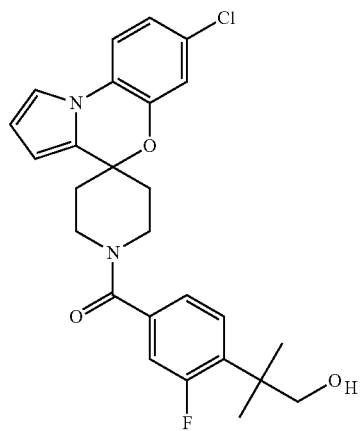
TABLE 1-continued
104
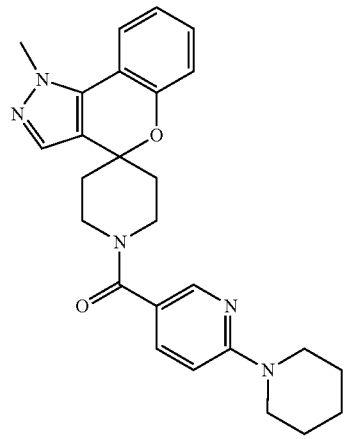 [SMILES: Cn1ncc2c1-c1ccccc1OC21CCN(C(=O)c2ccc(N3CCCCC3)nc2)CC1]
105
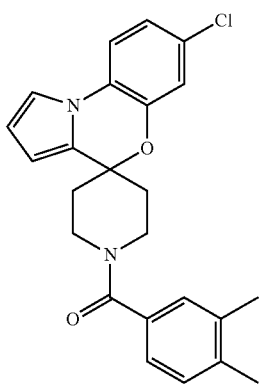 [SMILES: Cc1ccc(C(=O)N2CCC3(CC2)Oc2cc(Cl)ccc2-n2cccc23)cc1C]
106
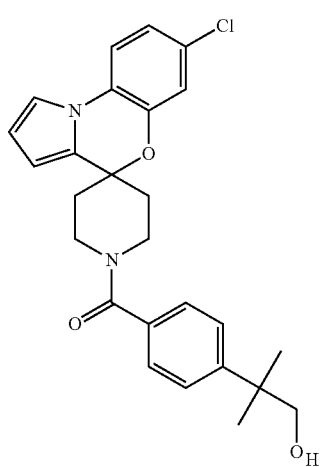

TABLE 1-continued
107
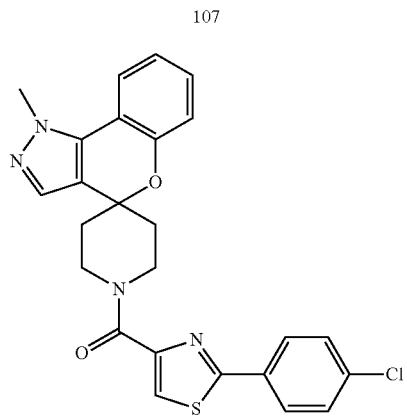
108
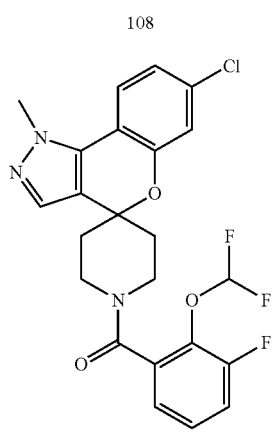
109
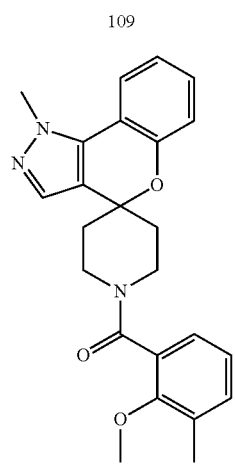
TABLE 1-continued
110
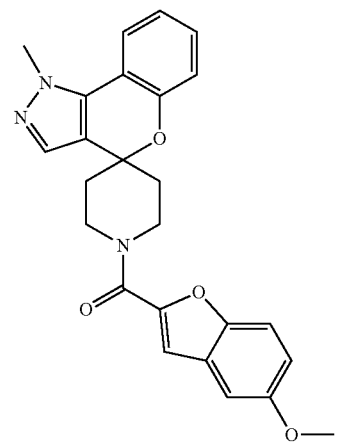 [SMILES: COc1ccc2oc(C(=O)N3CCC4(CC3)Oc3ccccc3-c3c4cnn3C)cc2c1]
111
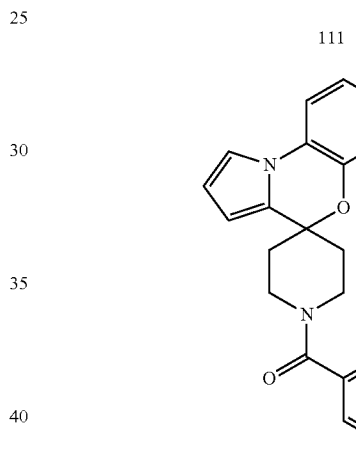
112
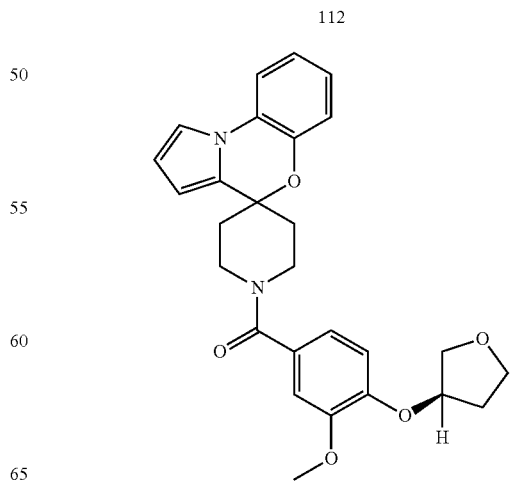

TABLE 1-continued
113
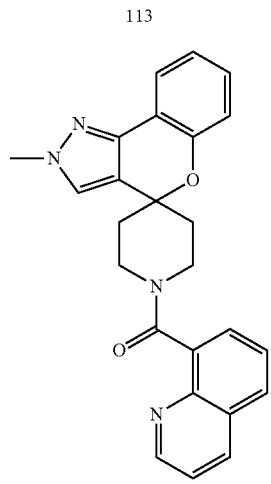
114
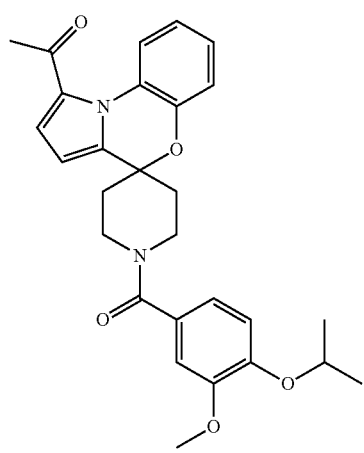 [SMILES: COc1cc(C(=O)N2CCC3(CC2)Oc2ccccc2-n2c(C(C)=O)ccc23)ccc1OC(C)C]
115
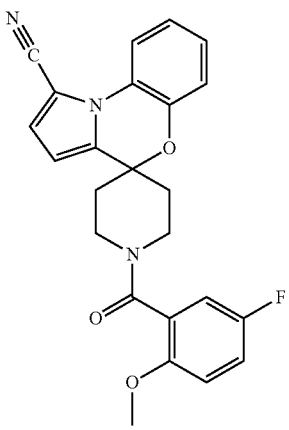 [SMILES: COc1ccc(F)cc1C(=O)N1CCC2(CC1)Oc1ccccc1-n1c(C#N)ccc12]
TABLE 1-continued
116
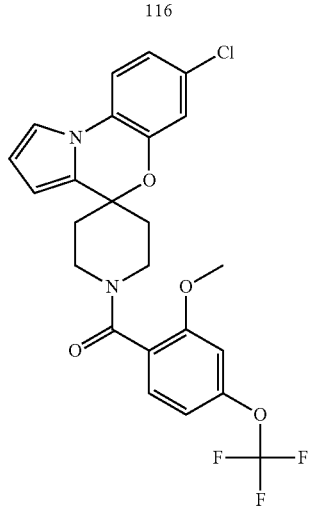
117
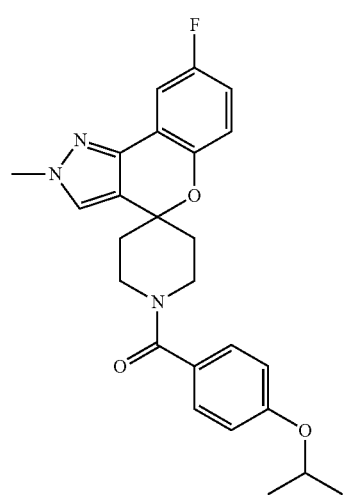 [SMILES: CC(C)Oc1ccc(C(=O)N2CCC3(CC2)Oc2ccc(F)cc2-c2nn(C)cc23)cc1]
118
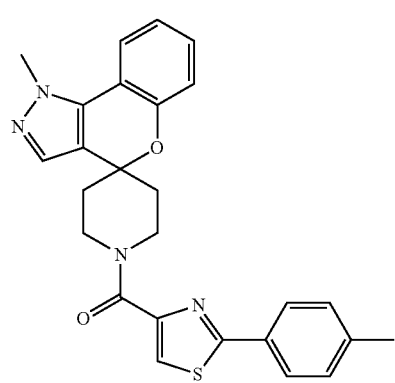 [SMILES: Cc1ccc(-c2nc(C(=O)N3CCC4(CC3)Oc3ccccc3-c3c4cnn3C)cs2)cc1]

TABLE 1-continued
119
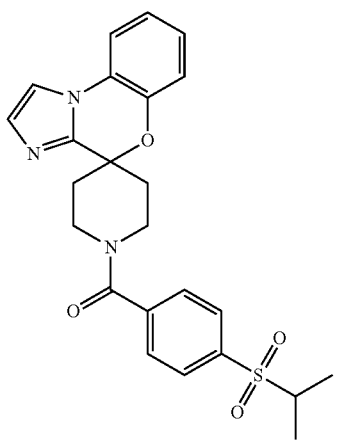 [SMILES: CC(C)S(=O)(=O)c1ccc(C(=O)N2CCC3(CC2)Oc2ccccc2-n2ccnc23)cc1]
120
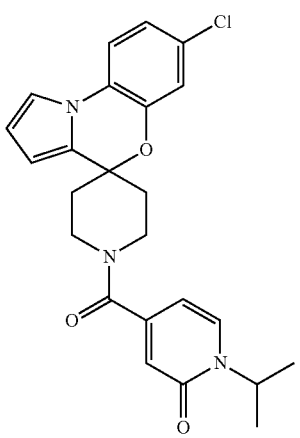 [SMILES: CC(C)n1ccc(C(=O)N2CCC3(CC2)Oc2cc(Cl)ccc2-n2cccc23)cc1=O]
121
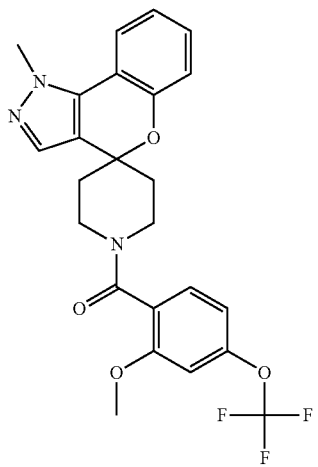 [SMILES: COc1cc(OC(F)(F)F)ccc1C(=O)N1CCC2(CC1)Oc1ccccc1-c1c2cnn1C]
TABLE 1-continued
122
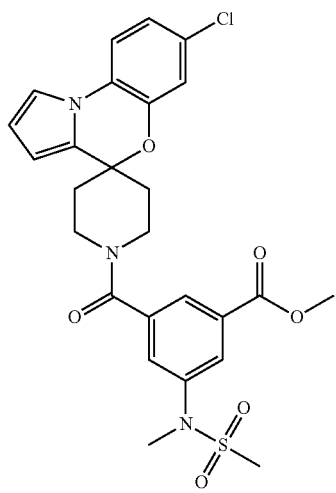 [SMILES: COC(=O)c1cc(C(=O)N2CCC3(CC2)Oc2cc(Cl)ccc2-n2cccc23)cc(N(C)S(C)(=O)=O)c1]
123
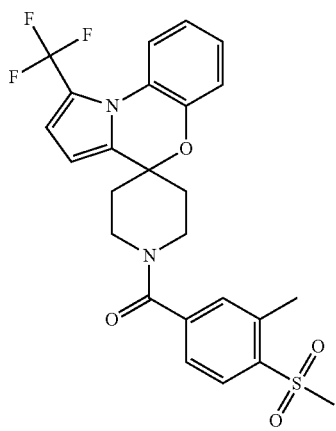 [SMILES: Cc1cc(C(=O)N2CCC3(CC2)Oc2ccccc2-n2c(C(F)(F)F)ccc23)ccc1S(C)(=O)=O]
124
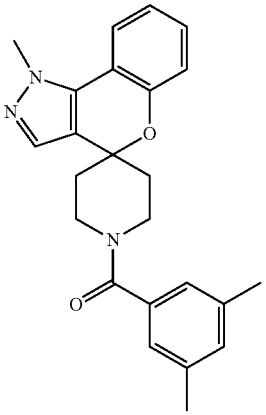 [SMILES: Cc1cc(C)cc(C(=O)N2CCC3(CC2)Oc2ccccc2-c2c3cnn2C)c1]

TABLE 1-continued
125
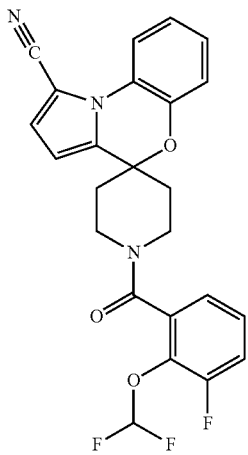
126
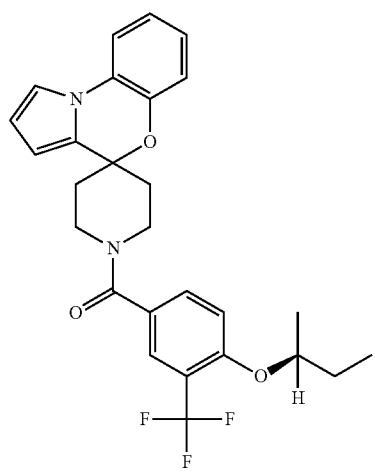 [SMILES: CC[C@H](C)Oc1ccc(C(=O)N2CCC3(CC2)Oc2ccccc2-n2cccc23)cc1C(F)(F)F]
127
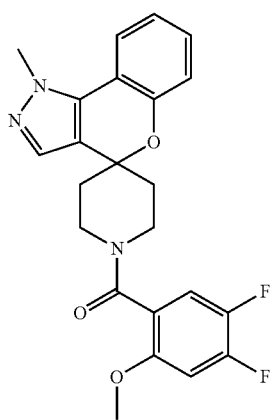 [SMILES: COc1cc(F)c(F)cc1C(=O)N1CCC2(CC1)Oc1ccccc1-c1c2cnn1C]
TABLE 1-continued
128
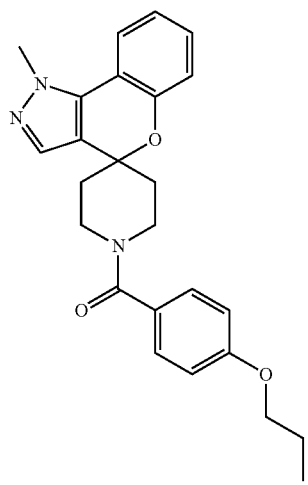 [SMILES: CCCOc1ccc(C(=O)N2CCC3(CC2)Oc2ccccc2-c2c3cnn2C)cc1]
129
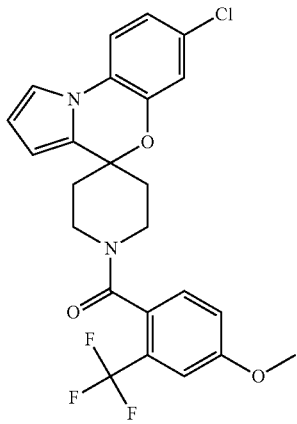 [SMILES: COc1ccc(C(=O)N2CCC3(CC2)Oc2cc(Cl)ccc2-n2cccc23)c(C(F)(F)F)c1]
130
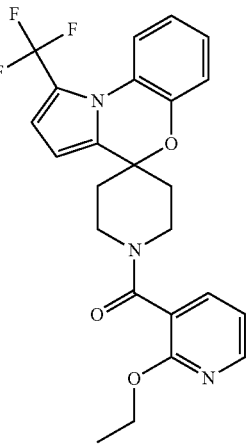

TABLE 1-continued
131
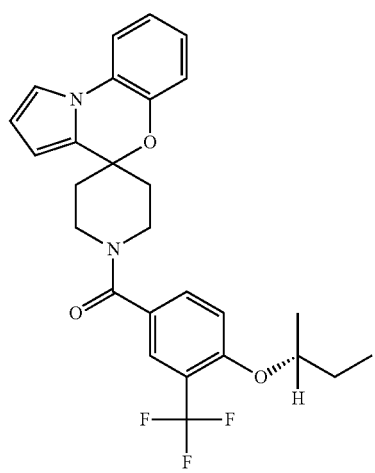 [SMILES: CC[C@@H](C)Oc1ccc(C(=O)N2CCC3(CC2)Oc2ccccc2-n2cccc23)cc1C(F)(F)F]
132
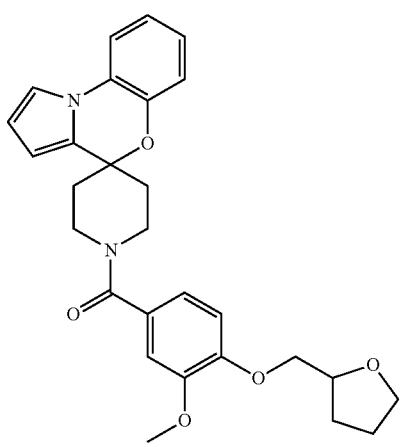 [SMILES: COc1cc(C(=O)N2CCC3(CC2)Oc2ccccc2-n2cccc23)ccc1OCC1CCCO1]
133
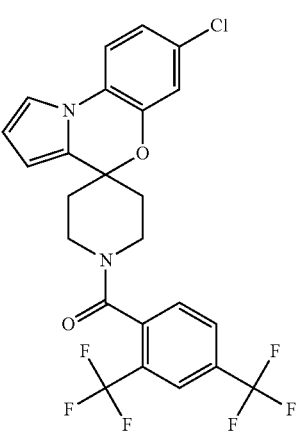 [SMILES: O=C(c1ccc(C(F)(F)F)cc1C(F)(F)F)N1CCC2(CC1)Oc1cc(Cl)ccc1-n1cccc12]
TABLE 1-continued
134
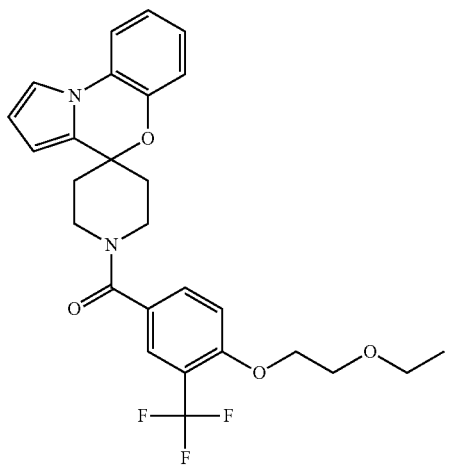
135
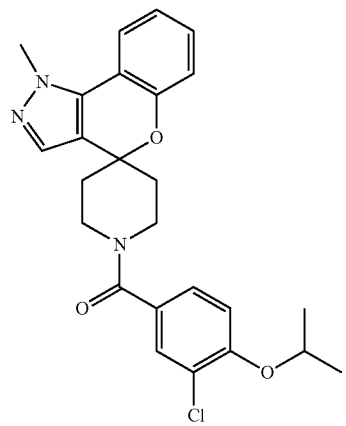 [SMILES: CC(C)Oc1ccc(C(=O)N2CCC3(CC2)Oc2ccccc2-c2c3cnn2C)cc1Cl]
136
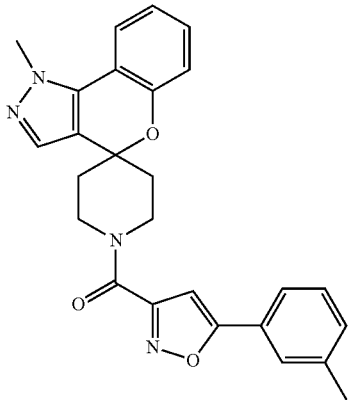

TABLE 1-continued
137
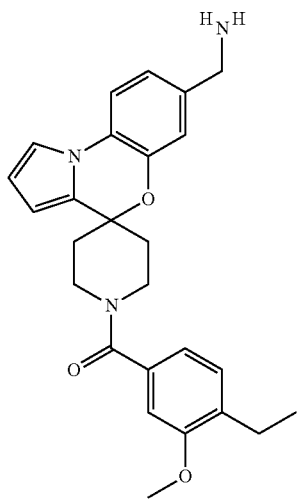
138
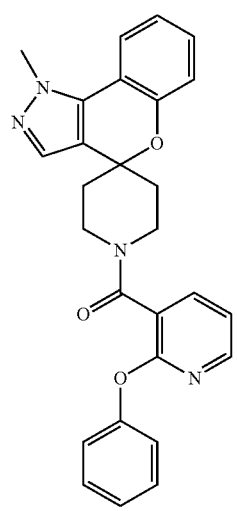 [SMILES: Cn1ncc2c1-c1ccccc1OC21CCN(C(=O)c2cccnc2Oc2ccccc2)CC1]
139
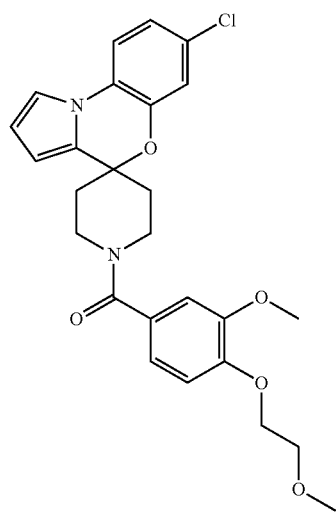
TABLE 1-continued
140
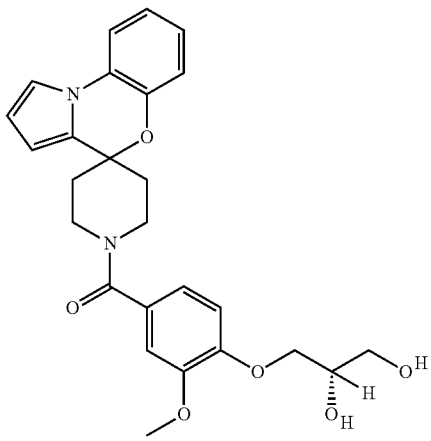
141
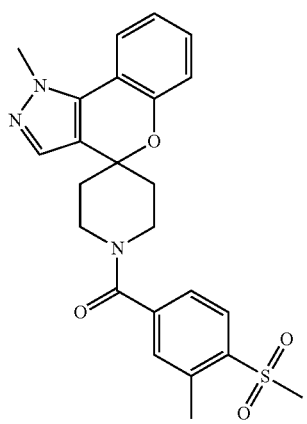 [SMILES: Cc1cc(C(=O)N2CCC3(CC2)Oc2ccccc2-c2c3cnn2C)ccc1S(C)(=O)=O]
142
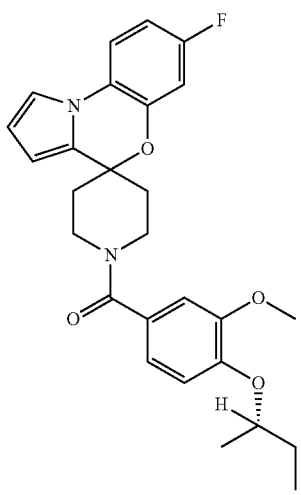

TABLE 1-continued
143
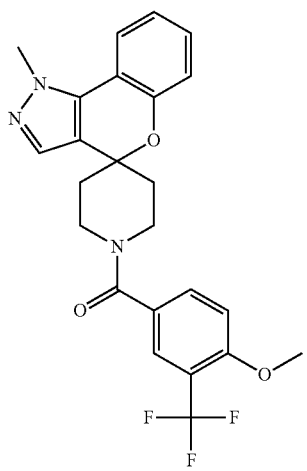 [SMILES: COc1ccc(C(=O)N2CCC3(CC2)Oc2ccccc2-c2c3cnn2C)cc1C(F)(F)F]
144
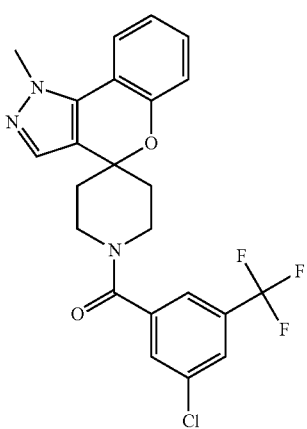 [SMILES: Cn1ncc2c1-c1ccccc1OC21CCN(C(=O)c2cc(Cl)cc(C(F)(F)F)c2)CC1]
145
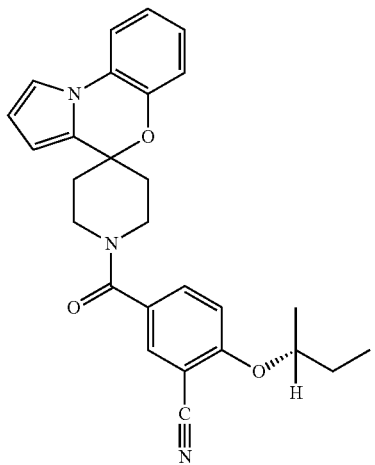 [SMILES: CC[C@@H](C)Oc1ccc(C(=O)N2CCC3(CC2)Oc2ccccc2-n2cccc23)cc1C#N]
TABLE 1-continued
146
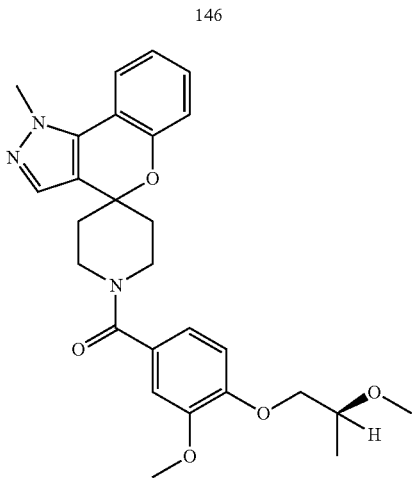
147
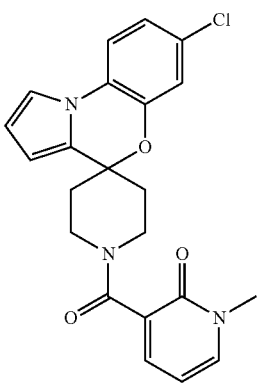 [SMILES: Cn1cccc(C(=O)N2CCC3(CC2)Oc2cc(Cl)ccc2-n2cccc23)c1=O]
148
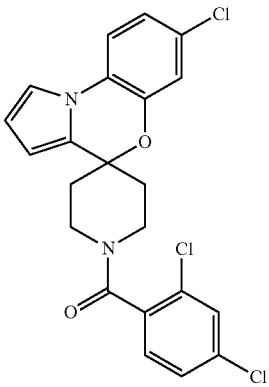

TABLE 1-continued
149
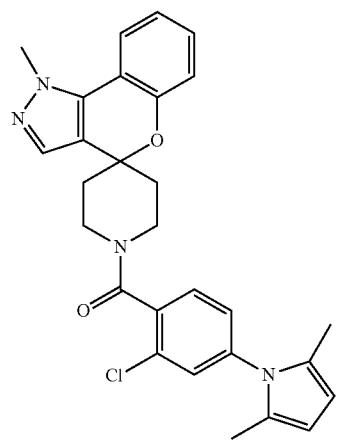 [SMILES: Cc1ccc(C)n1-c1ccc(C(=O)N2CCC3(CC2)Oc2ccccc2-c2c3cnn2C)c(Cl)c1]
150
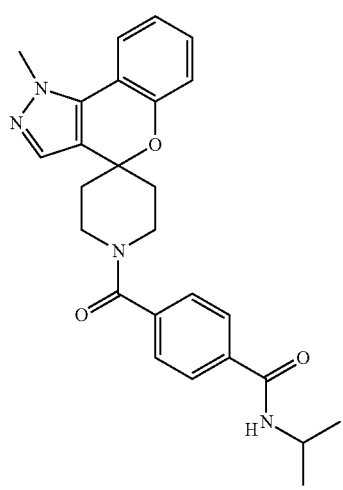
151
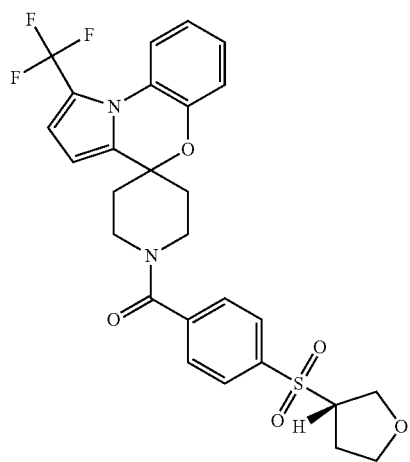 [SMILES: O=C(c1ccc(S(=O)(=O)[C@H]2CCOC2)cc1)N1CCC2(CC1)Oc1ccccc1-n1c(C(F)(F)F)ccc12]
TABLE 1-continued
152
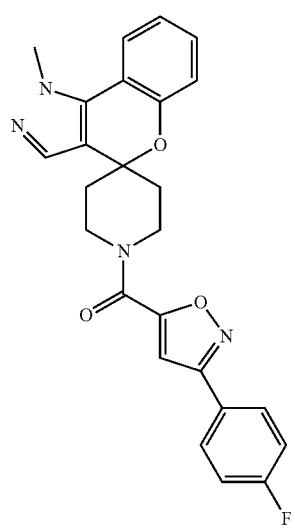 [SMILES: CNC1=C(C=N)C2(CCN(C(=O)c3cc(-c4ccc(F)cc4)no3)CC2)Oc2ccccc21]
153
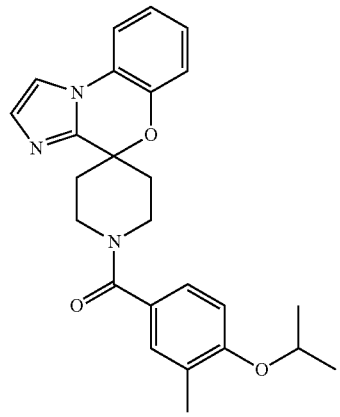 [SMILES: Cc1cc(C(=O)N2CCC3(CC2)Oc2ccccc2-n2ccnc23)ccc1OC(C)C]
154
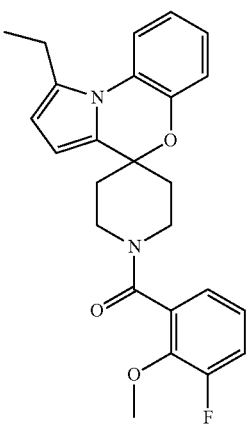 [SMILES: CCc1ccc2n1-c1ccccc1OC21CCN(C(=O)c2cccc(F)c2OC)CC1]

TABLE 1-continued
155
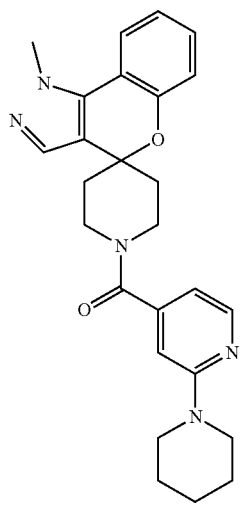 [SMILES: CNC1=C(C=N)C2(CCN(C(=O)c3ccnc(N4CCCCC4)c3)CC2)Oc2ccccc21]
156
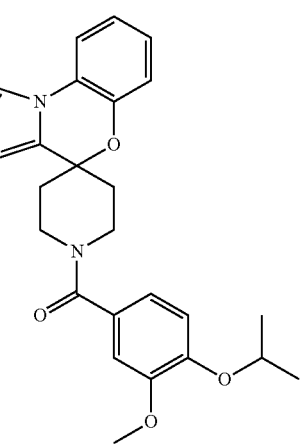
157
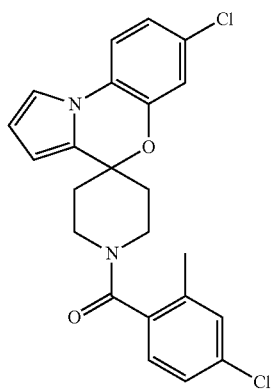 [SMILES: Cc1cc(Cl)ccc1C(=O)N1CCC2(CC1)Oc1cc(Cl)ccc1-n1cccc12]
158
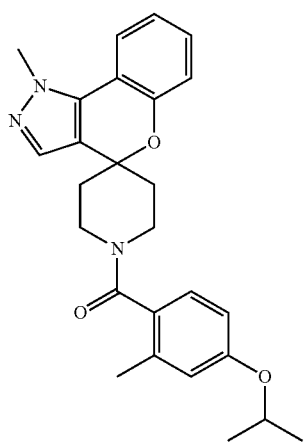
159
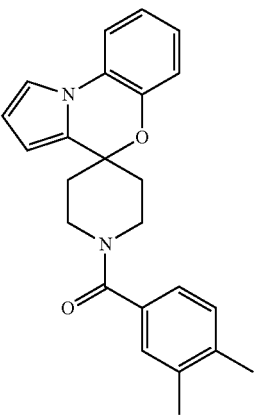 [SMILES: Cc1ccc(C(=O)N2CCC3(CC2)Oc2ccccc2-n2cccc23)cc1C]
160
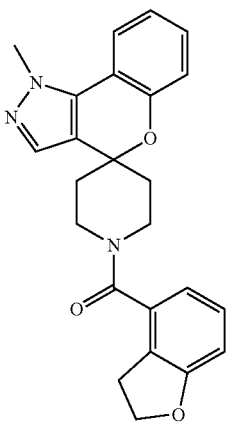 [SMILES: Cn1ncc2c1-c1ccccc1OC21CCN(C(=O)c2cccc3c2CCO3)CC1]

TABLE 1-continued
161
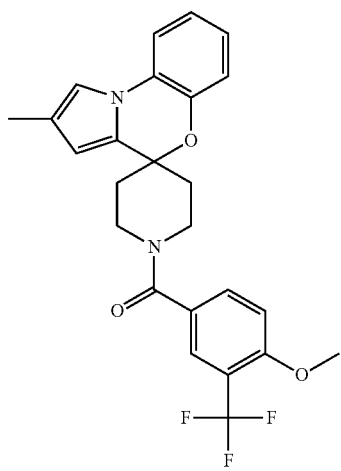
162
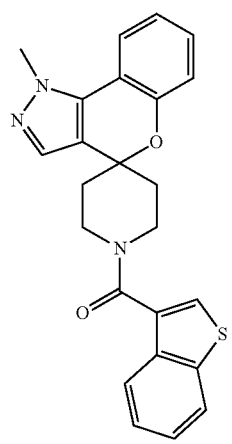 [SMILES: Cn1ncc2c1-c1ccccc1OC21CCN(C(=O)c2csc3ccccc23)CC1]
163
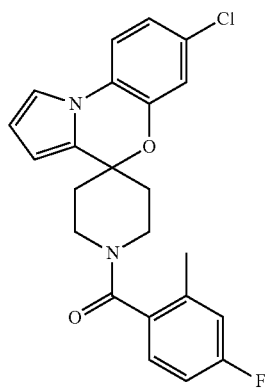
TABLE 1-continued
164
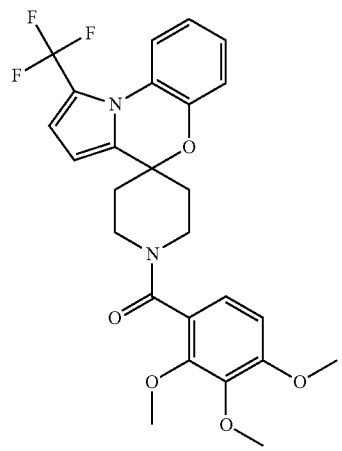
165
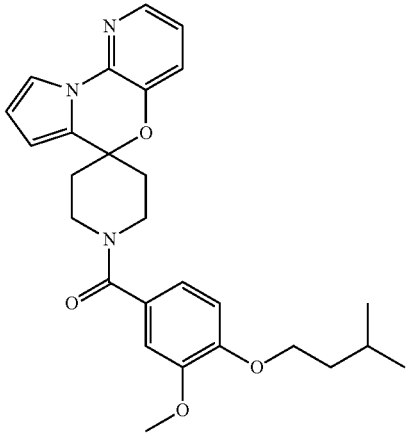 [SMILES: COc1cc(C(=O)N2CCC3(CC2)Oc2cccnc2-n2cccc23)ccc1OCCC(C)C]
166
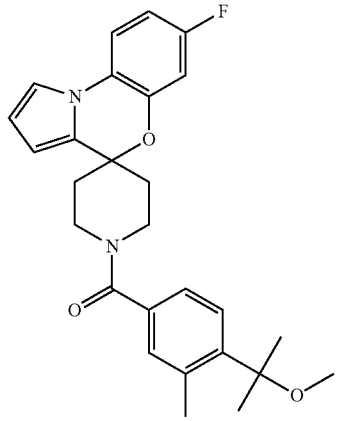 [SMILES: COC(C)(C)c1ccc(C(=O)N2CCC3(CC2)Oc2cc(F)ccc2-n2cccc23)cc1C]

TABLE 1-continued
167
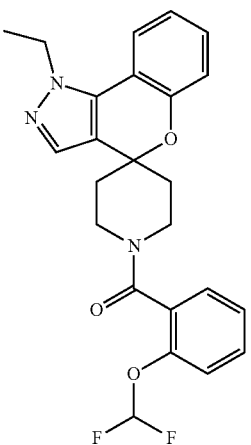 [SMILES: CCn1ncc2c1-c1ccccc1OC21CCN(C(=O)c2ccccc2OC(F)F)CC1]
168
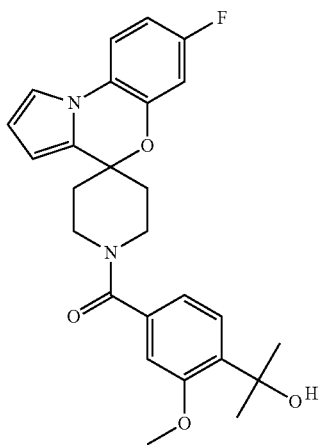
169
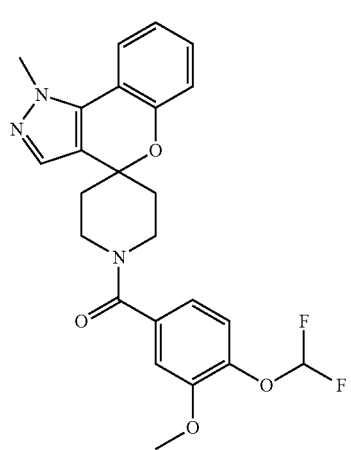
TABLE 1-continued
170
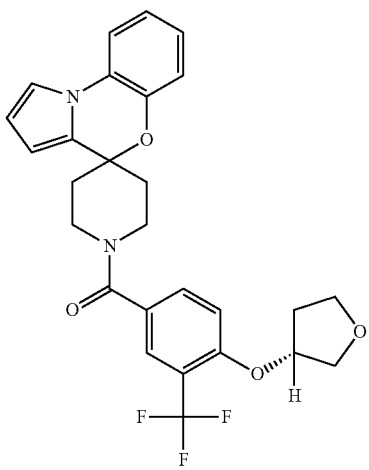 [SMILES: O=C(c1ccc(O[C@@H]2CCOC2)c(C(F)(F)F)c1)N1CCC2(CC1)Oc1ccccc1-n1cccc12]
171
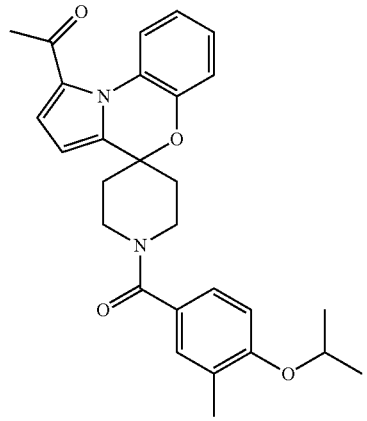 [SMILES: CC(=O)c1ccc2n1-c1ccccc1OC21CCN(C(=O)c2ccc(OC(C)C)c(C)c2)CC1]
172
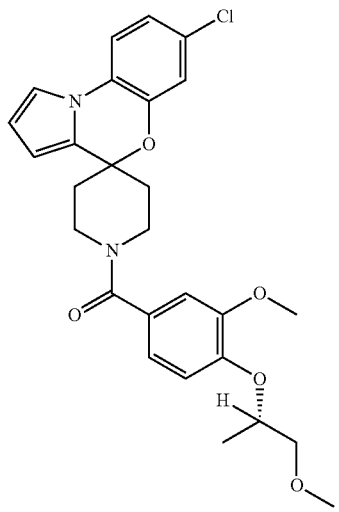 [SMILES: COC[C@H](C)Oc1ccc(C(=O)N2CCC3(CC2)Oc2cc(Cl)ccc2-n2cccc23)cc1OC]

TABLE 1-continued
173
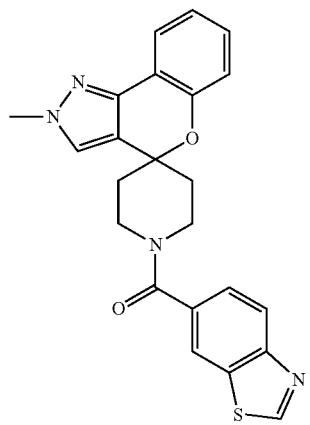 [SMILES: Cn1cc2c(n1)-c1ccccc1OC21CCN(C(=O)c2ccc3ncsc3c2)CC1]
174
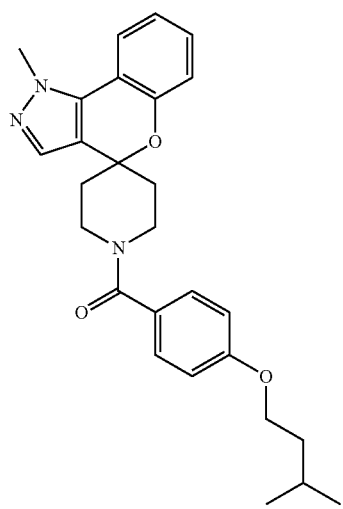 [SMILES: CC(C)CCOc1ccc(C(=O)N2CCC3(CC2)Oc2ccccc2-c2c3cnn2C)cc1]
175
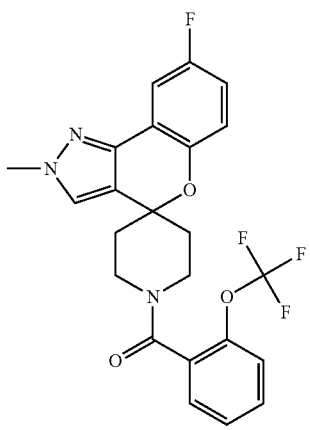 [SMILES: Cn1cc2c(n1)-c1cc(F)ccc1OC21CCN(C(=O)c2ccccc2OC(F)(F)F)CC1]
TABLE 1-continued
176
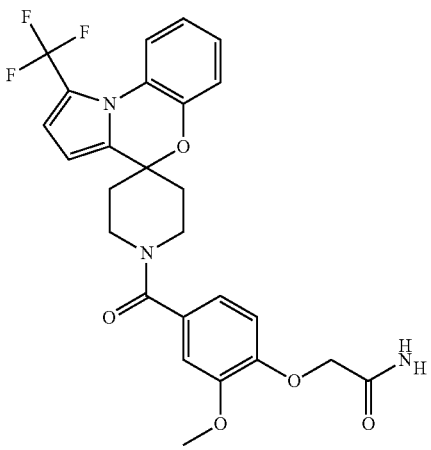
177
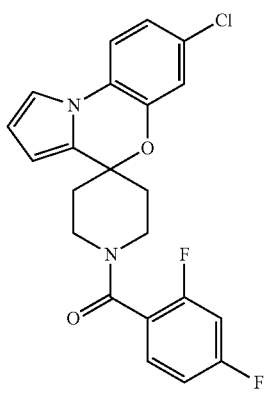
178
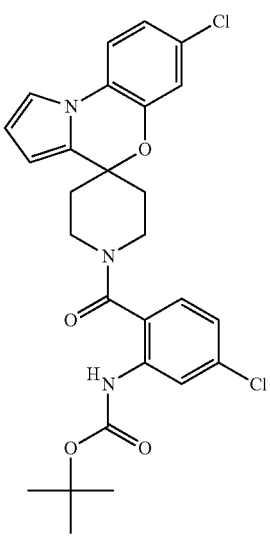

TABLE 1-continued
179
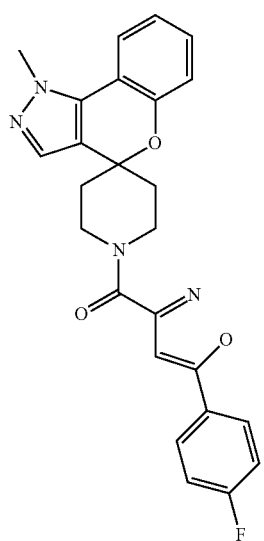 [SMILES: Cn1ncc2c1-c1ccccc1OC21CCN(C(=O)C(=N)/C=C(\O)c2ccc(F)cc2)CC1]
180
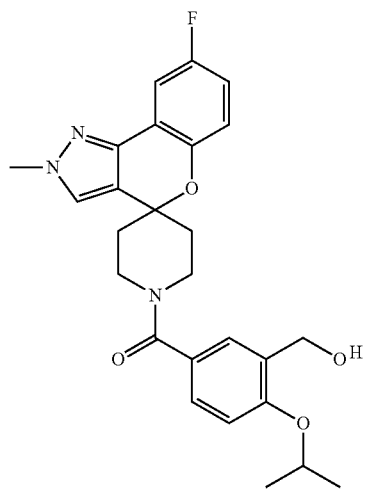
181
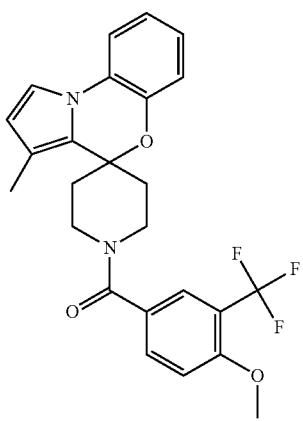 [SMILES: COc1ccc(C(=O)N2CCC3(CC2)Oc2ccccc2-n2ccc(C)c23)cc1C(F)(F)F]
TABLE 1-continued
182
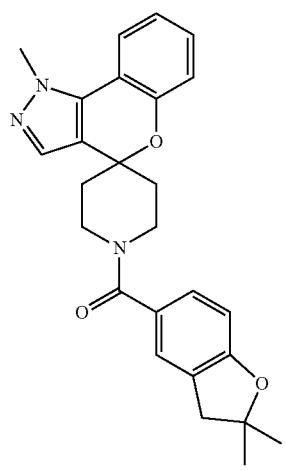 [SMILES: Cn1ncc2c1-c1ccccc1OC21CCN(C(=O)c2ccc3c(c2)CC(C)(C)O3)CC1]
183
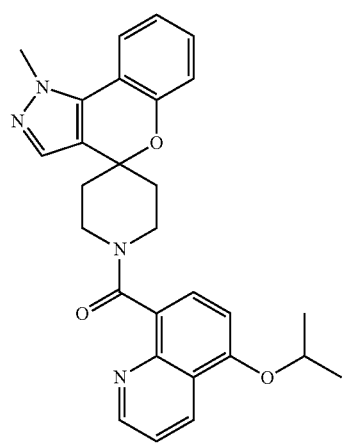 [SMILES: CC(C)Oc1ccc(C(=O)N2CCC3(CC2)Oc2ccccc2-c2c3cnn2C)c2ncccc12]
184
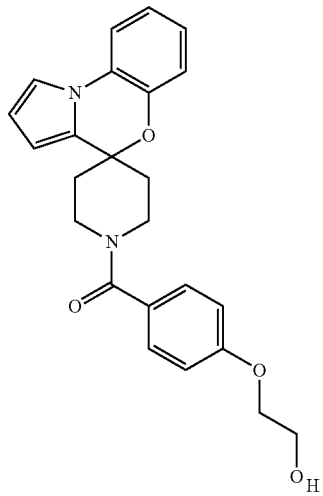

TABLE 1-continued
185
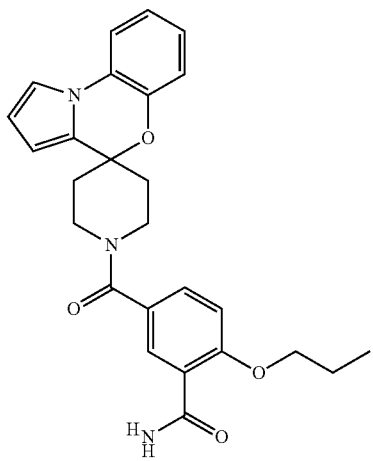
186
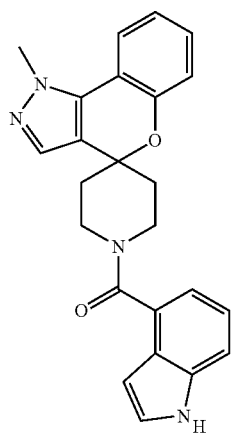
187
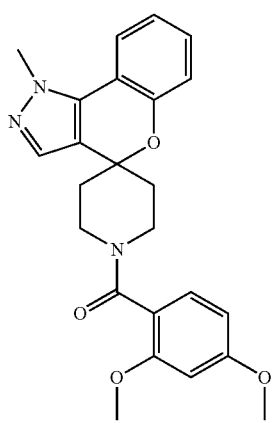 [SMILES: COc1ccc(C(=O)N2CCC3(CC2)Oc2ccccc2-c2c3cnn2C)c(OC)c1]
TABLE 1-continued
188
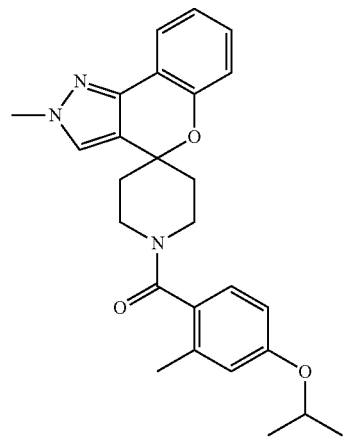 [SMILES: Cc1cc(OC(C)C)ccc1C(=O)N1CCC2(CC1)Oc1ccccc1-c1nn(C)cc12]
189
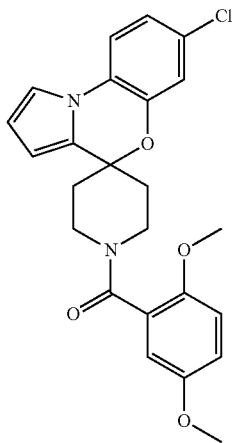 [SMILES: COc1ccc(OC)c(C(=O)N2CCC3(CC2)Oc2cc(Cl)ccc2-n2cccc23)c1]
190
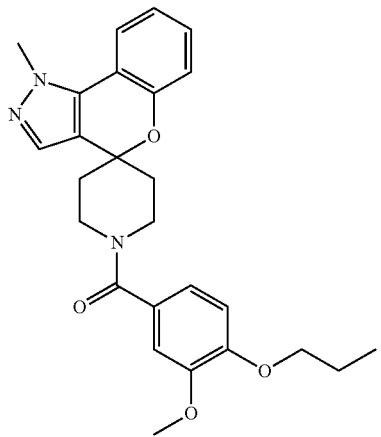 [SMILES: CCCOc1ccc(C(=O)N2CCC3(CC2)Oc2ccccc2-c2c3cnn2C)cc1OC]

TABLE 1-continued
191
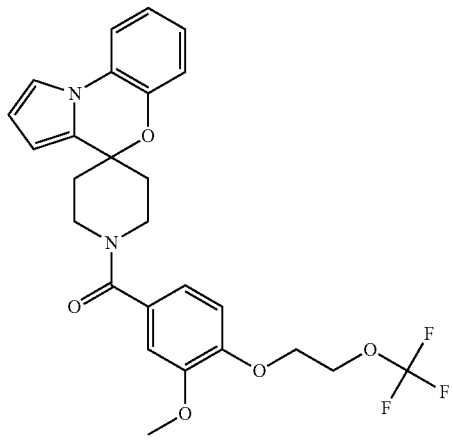 [SMILES: COc1cc(C(=O)N2CCC3(CC2)Oc2ccccc2-n2cccc23)ccc1OCCOC(F)(F)F]
192
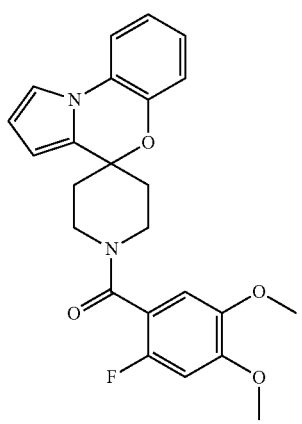 [SMILES: COc1cc(F)c(C(=O)N2CCC3(CC2)Oc2ccccc2-n2cccc23)cc1OC]
193
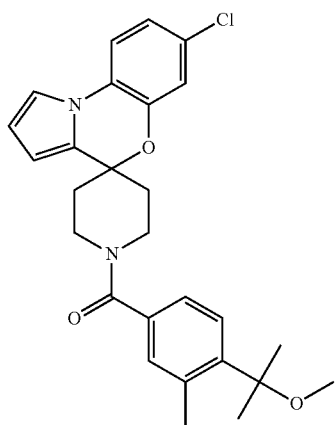 [SMILES: COC(C)(C)c1ccc(C(=O)N2CCC3(CC2)Oc2cc(Cl)ccc2-n2cccc23)cc1C]
TABLE 1-continued
194
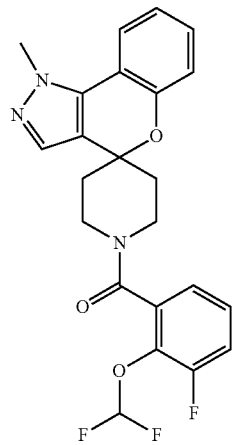 [SMILES: Cn1ncc2c1-c1ccccc1OC21CCN(C(=O)c2cccc(F)c2OC(F)F)CC1]
195
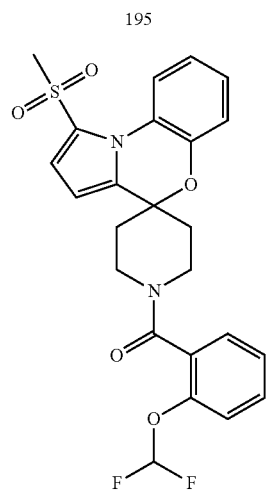
196
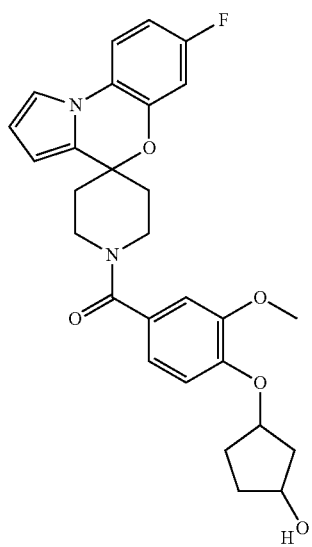

TABLE 1-continued
197
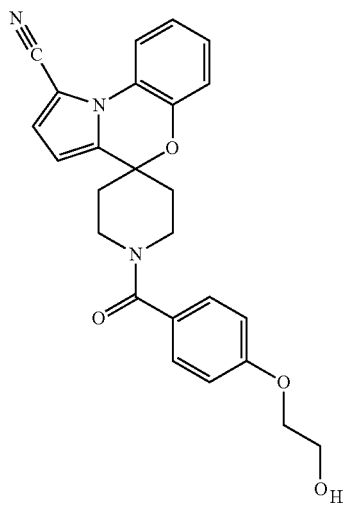
198
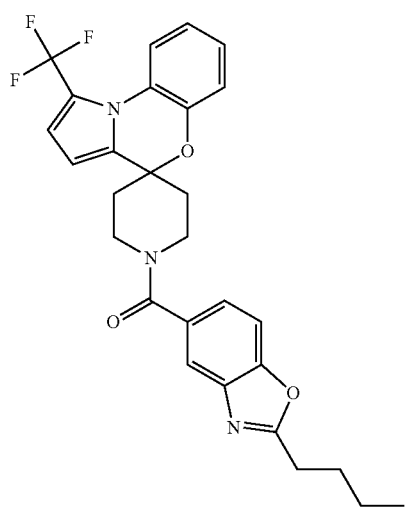 [SMILES: CCCCc1nc2cc(C(=O)N3CCC4(CC3)Oc3ccccc3-n3c(C(F)(F)F)ccc34)ccc2o1]
199
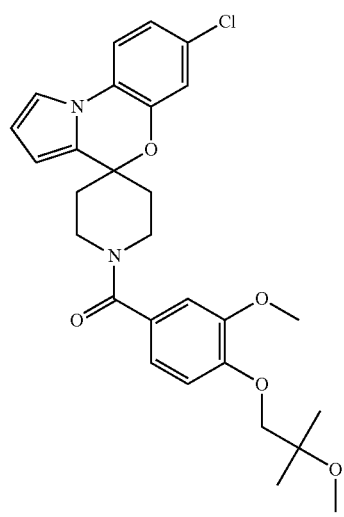
TABLE 1-continued
200
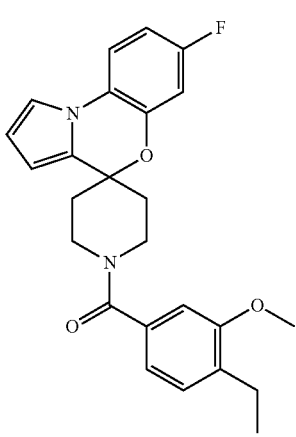 [SMILES: CCc1ccc(C(=O)N2CCC3(CC2)Oc2cc(F)ccc2-n2cccc23)cc1OC]
201
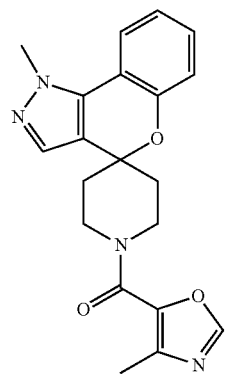 [SMILES: Cc1ncoc1C(=O)N1CCC2(CC1)Oc1ccccc1-c1c2cnn1C]
202
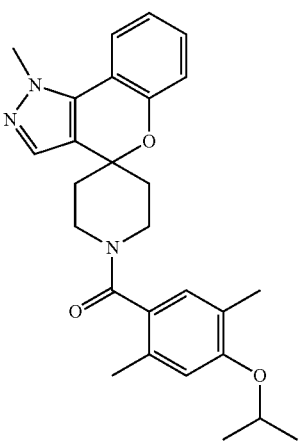 [SMILES: Cc1cc(C(=O)N2CCC3(CC2)Oc2ccccc2-c2c3cnn2C)c(C)cc1OC(C)C]

TABLE 1-continued
203
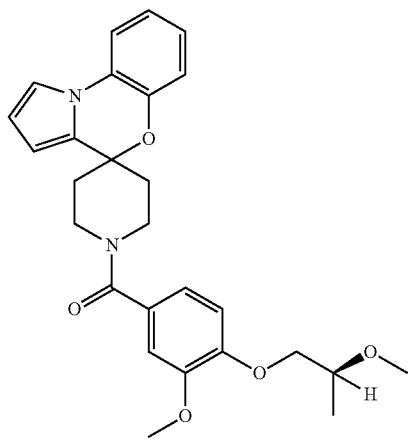 [SMILES: COc1cc(C(=O)N2CCC3(CC2)Oc2ccccc2-n2cccc23)ccc1OC[C@H](C)OC]
204
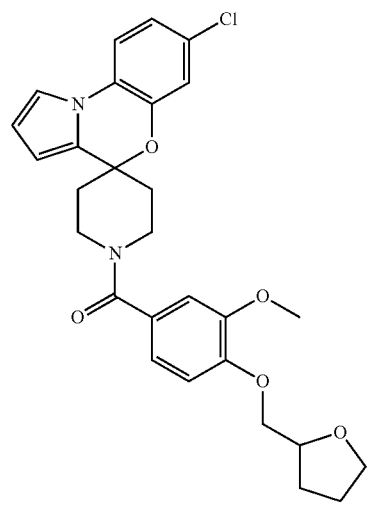 [SMILES: COc1cc(C(=O)N2CCC3(CC2)Oc2cc(Cl)ccc2-n2cccc23)ccc1OCC1CCCO1]
205
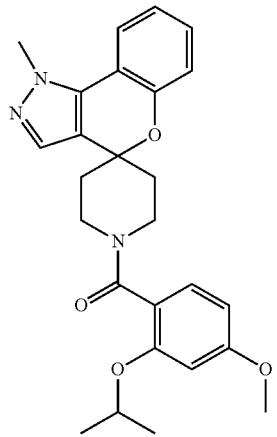
TABLE 1-continued
206
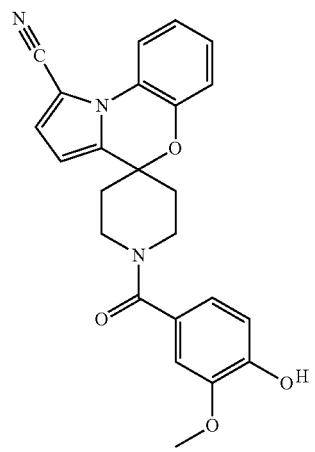
207
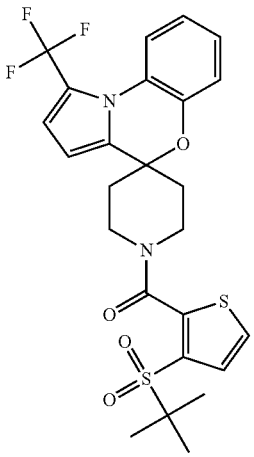 [SMILES: CC(C)(C)S(=O)(=O)c1ccsc1C(=O)N1CCC2(CC1)Oc1ccccc1-n1c(C(F)(F)F)ccc12]
208
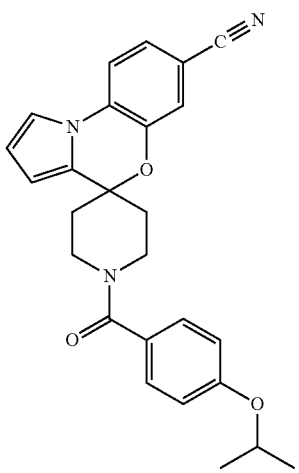 [SMILES: CC(C)Oc1ccc(C(=O)N2CCC3(CC2)Oc2cc(C#N)ccc2-n2cccc23)cc1]

TABLE 1-continued
209
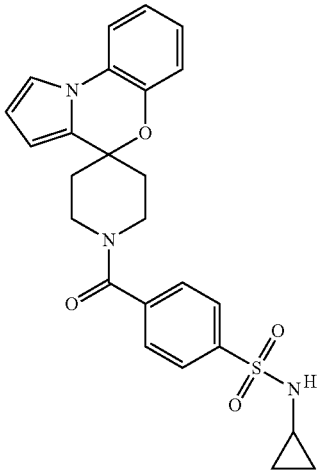
210
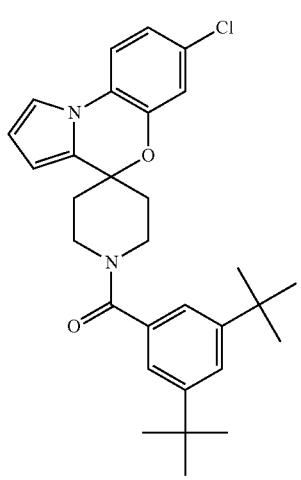 [SMILES: CC(C)(C)c1cc(C(=O)N2CCC3(CC2)Oc2cc(Cl)ccc2-n2cccc23)cc(C(C)(C)C)c1]
211
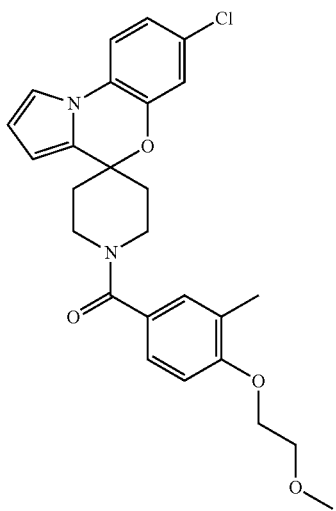
TABLE 1-continued
212
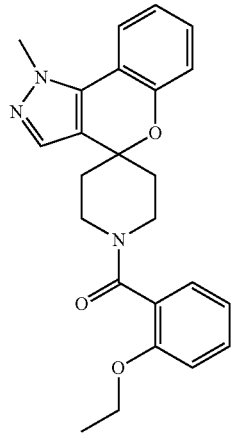 [SMILES: CCOc1ccccc1C(=O)N1CCC2(CC1)Oc1ccccc1-c1c2cnn1C]
213
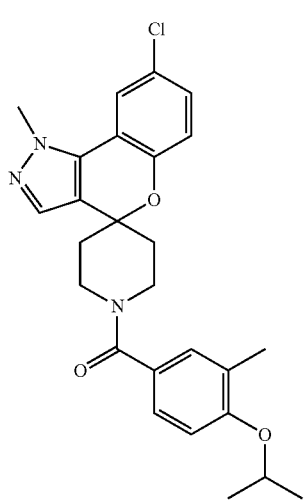 [SMILES: Cc1cc(C(=O)N2CCC3(CC2)Oc2ccc(Cl)cc2-c2c3cnn2C)ccc1OC(C)C]
214
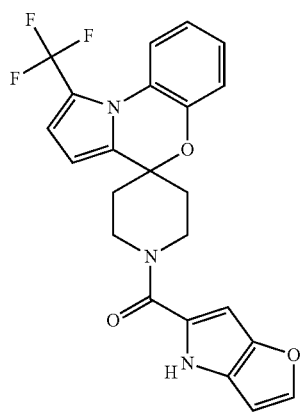

TABLE 1-continued
215
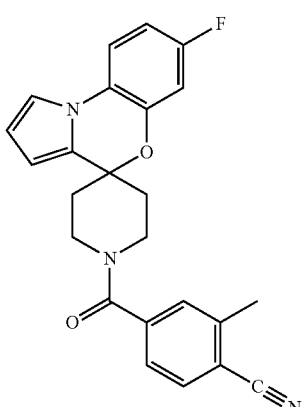
216
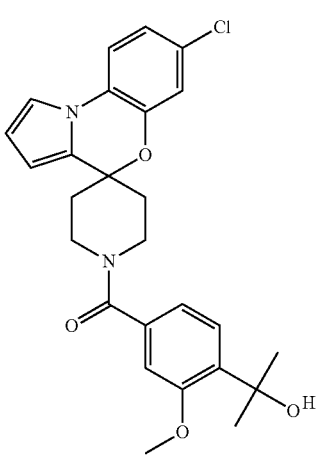
217
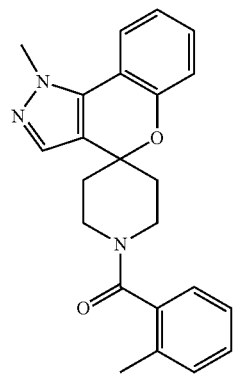 [SMILES: Cc1ccccc1C(=O)N1CCC2(CC1)Oc1ccccc1-c1c2cnn1C]
TABLE 1-continued
218
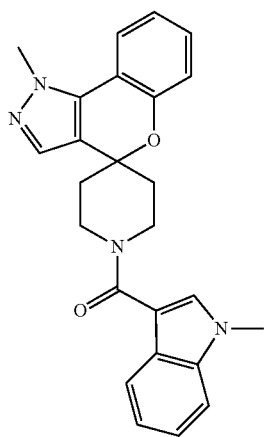 [SMILES: Cn1ncc2c1-c1ccccc1OC21CCN(C(=O)c2cn(C)c3ccccc23)CC1]
219
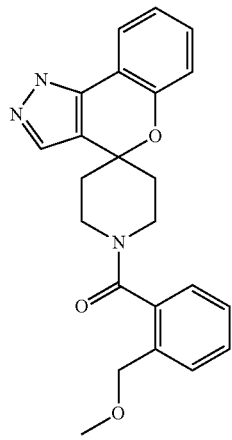 [SMILES: COCc1ccccc1C(=O)N1CCC2(CC1)Oc1ccccc1-c1[nH]ncc12]
220
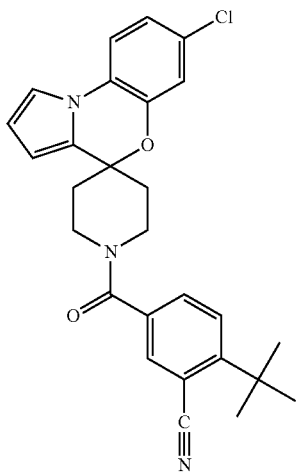 [SMILES: CC(C)(C)c1ccc(C(=O)N2CCC3(CC2)Oc2cc(Cl)ccc2-n2cccc23)cc1C#N]

TABLE 1-continued
221
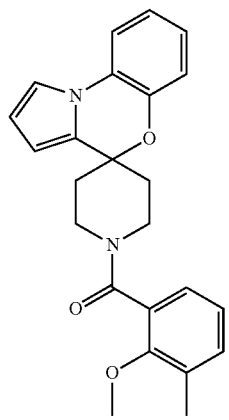 [SMILES: COc1c(C)cccc1C(=O)N1CCC2(CC1)Oc1ccccc1-n1cccc12]
222
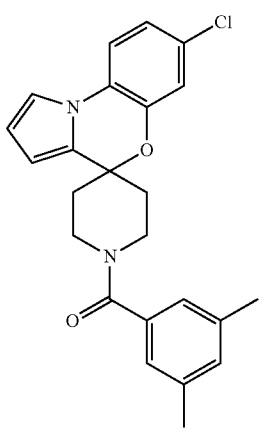 [SMILES: Cc1cc(C)cc(C(=O)N2CCC3(CC2)Oc2cc(Cl)ccc2-n2cccc23)c1]
223
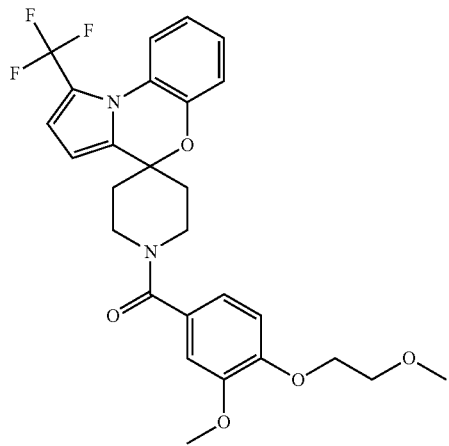
TABLE 1-continued
224
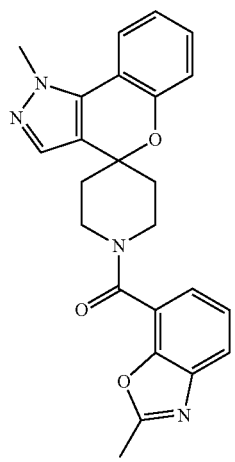 [SMILES: Cc1nc2cccc(C(=O)N3CCC4(CC3)Oc3ccccc3-c3c4cnn3C)c2o1]
225
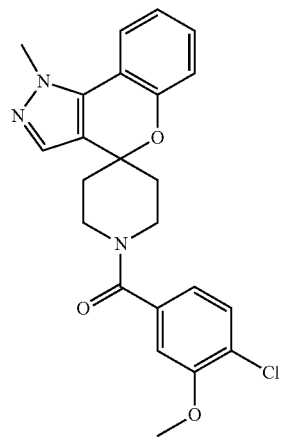 [SMILES: COc1cc(C(=O)N2CCC3(CC2)Oc2ccccc2-c2c3cnn2C)ccc1Cl]
226
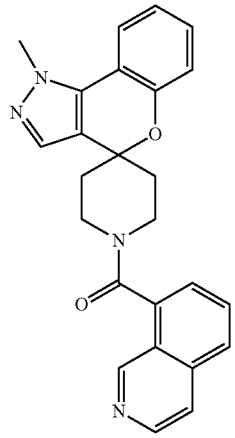 [SMILES: Cn1ncc2c1-c1ccccc1OC21CCN(C(=O)c2cccc3ccncc23)CC1]

TABLE 1-continued
227
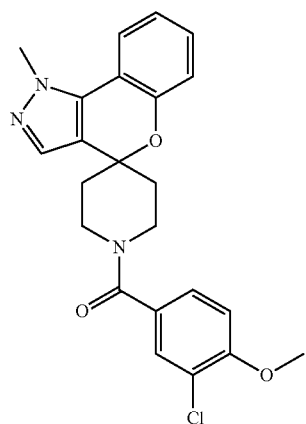
228
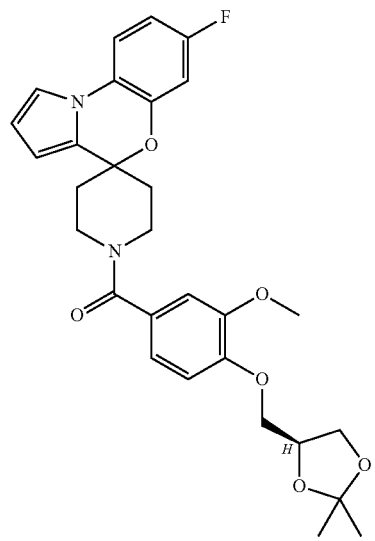
229
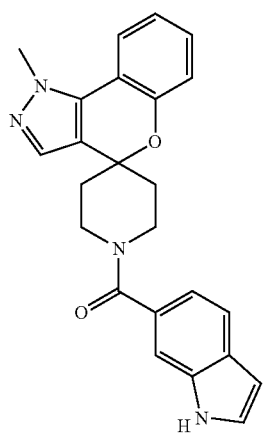
TABLE 1-continued
230
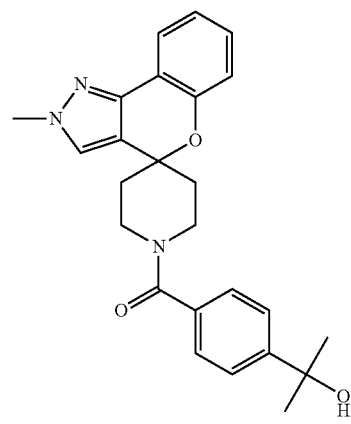 [SMILES: Cn1cc2c(n1)-c1ccccc1OC21CCN(C(=O)c2ccc(C(C)(C)O)cc2)CC1]
231
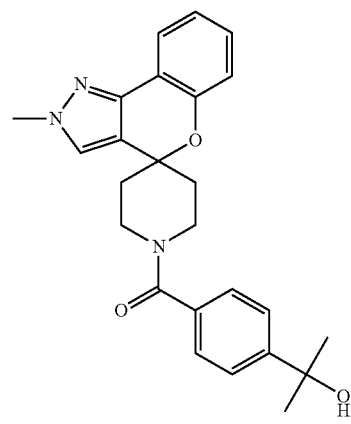 [SMILES: Cn1cc2c(n1)-c1ccccc1OC21CCN(C(=O)c2ccc(C(C)(C)O)cc2)CC1]
232
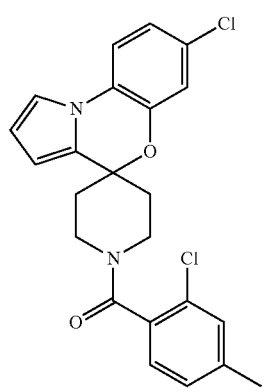 [SMILES: Cc1ccc(C(=O)N2CCC3(CC2)Oc2cc(Cl)ccc2-n2cccc23)c(Cl)c1]

TABLE 1-continued
233
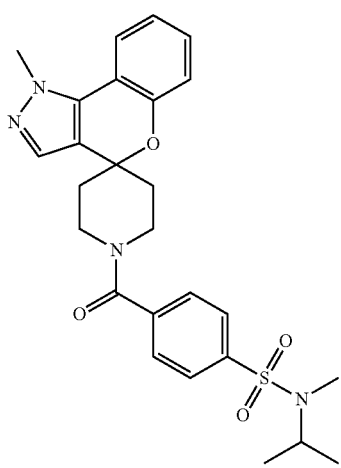 [SMILES: CC(C)N(C)S(=O)(=O)c1ccc(C(=O)N2CCC3(CC2)Oc2ccccc2-c2c3cnn2C)cc1]
234
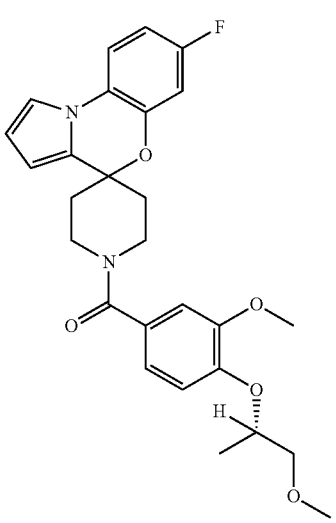 [SMILES: COC[C@H](C)Oc1ccc(C(=O)N2CCC3(CC2)Oc2cc(F)ccc2-n2cccc23)cc1OC]
235
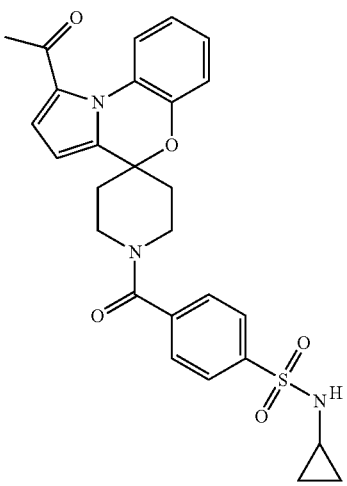
TABLE 1-continued
236
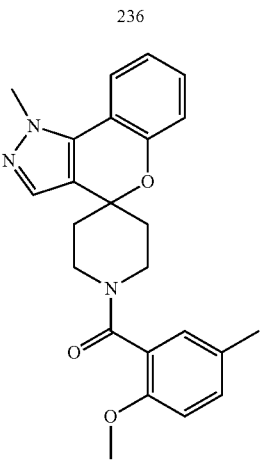
237
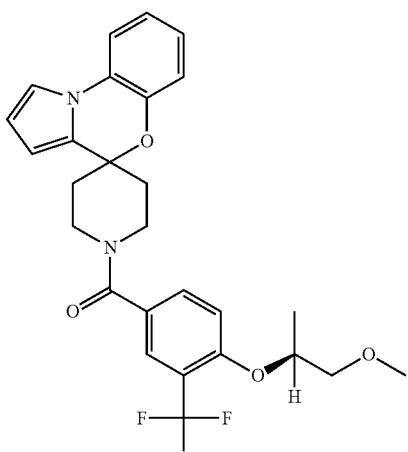
238
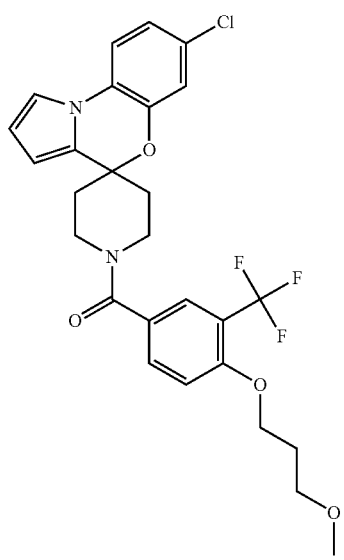 [SMILES: COCCCOc1ccc(C(=O)N2CCC3(CC2)Oc2cc(Cl)ccc2-n2cccc23)cc1C(F)(F)F]

TABLE 1-continued
239
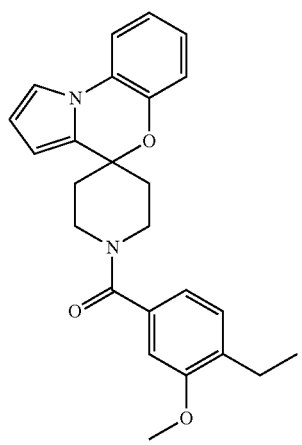 [SMILES: CCc1ccc(C(=O)N2CCC3(CC2)Oc2ccccc2-n2cccc23)cc1OC]
240
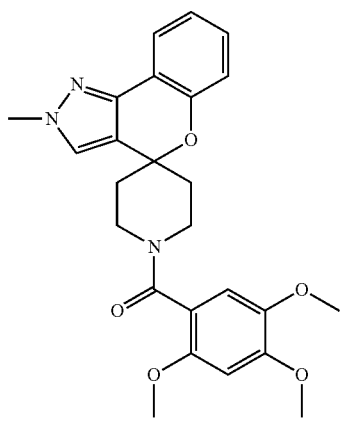
241
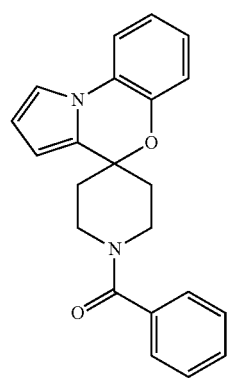
TABLE 1-continued
242
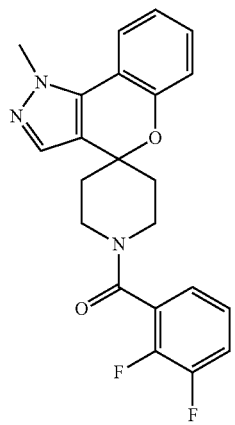 [SMILES: Cn1ncc2c1-c1ccccc1OC21CCN(C(=O)c2cccc(F)c2F)CC1]
243
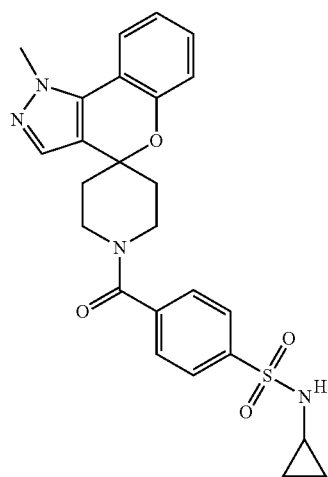
244
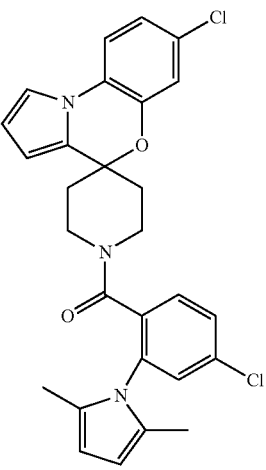 [SMILES: Cc1ccc(C)n1-c1cc(Cl)ccc1C(=O)N1CCC2(CC1)Oc1cc(Cl)ccc1-n1cccc12]

TABLE 1-continued
245
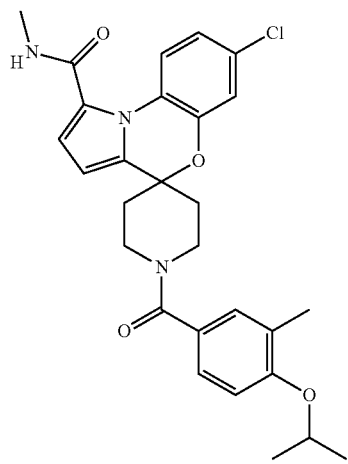
246
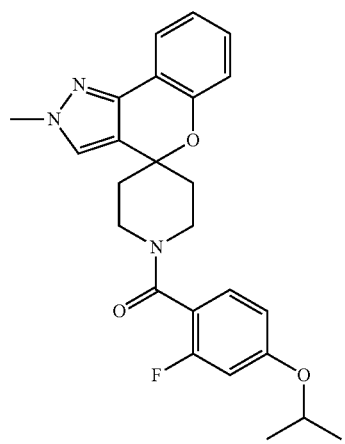
247
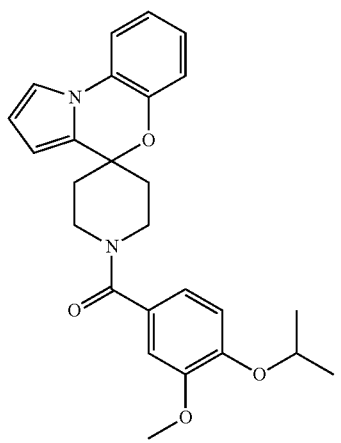 [SMILES: COc1cc(C(=O)N2CCC3(CC2)Oc2ccccc2-n2cccc23)ccc1OC(C)C]
TABLE 1-continued
248
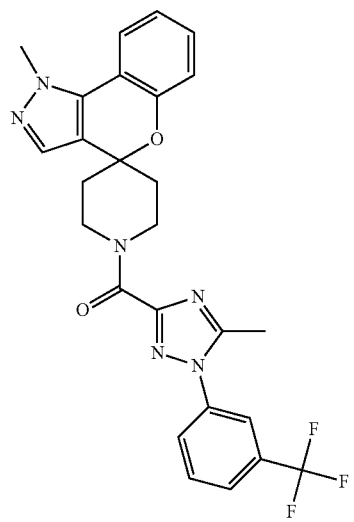 [SMILES: Cc1nc(C(=O)N2CCC3(CC2)Oc2ccccc2-c2c3cnn2C)nn1-c1cccc(C(F)(F)F)c1]
249
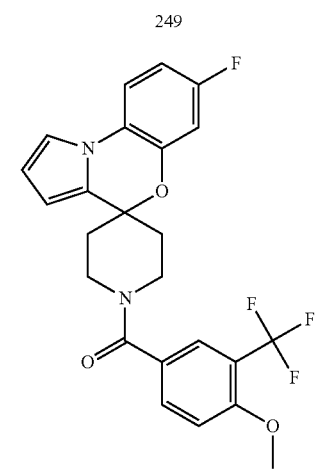
250
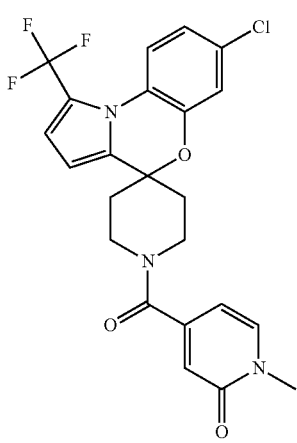 [SMILES: Cn1ccc(C(=O)N2CCC3(CC2)Oc2cc(Cl)ccc2-n2c(C(F)(F)F)ccc23)cc1=O]

TABLE 1-continued
251
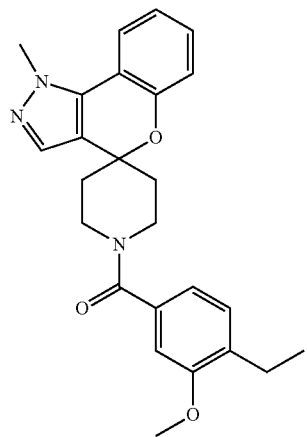 [SMILES: CCc1ccc(C(=O)N2CCC3(CC2)Oc2ccccc2-c2c3cnn2C)cc1OC]
252
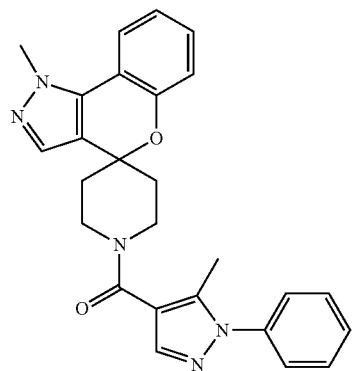 [SMILES: Cc1c(C(=O)N2CCC3(CC2)Oc2ccccc2-c2c3cnn2C)cnn1-c1ccccc1]
253
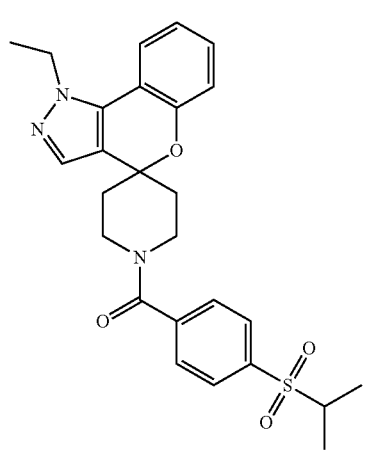 [SMILES: CCn1ncc2c1-c1ccccc1OC21CCN(C(=O)c2ccc(S(=O)(=O)C(C)C)cc2)CC1]
TABLE 1-continued
254
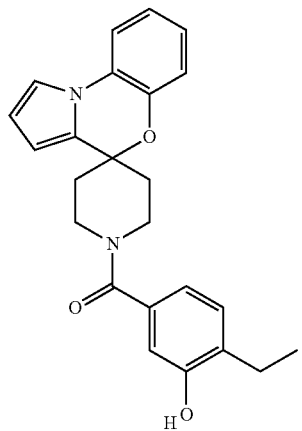
255
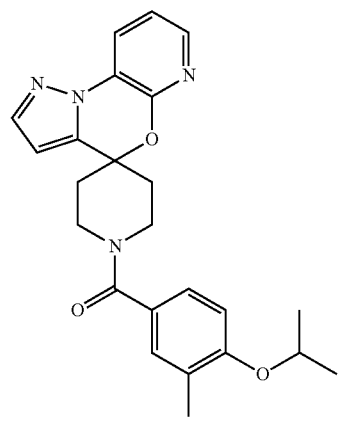 [SMILES: Cc1cc(C(=O)N2CCC3(CC2)Oc2ncccc2-n2nccc23)ccc1OC(C)C]
256
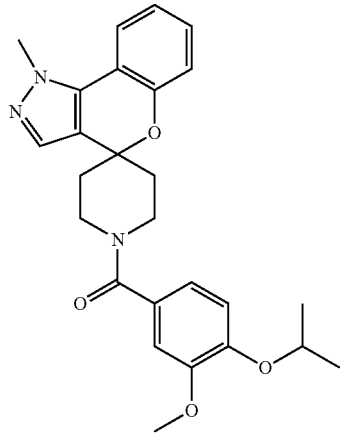 [SMILES: COc1cc(C(=O)N2CCC3(CC2)Oc2ccccc2-c2c3cnn2C)ccc1OC(C)C]

TABLE 1-continued
257
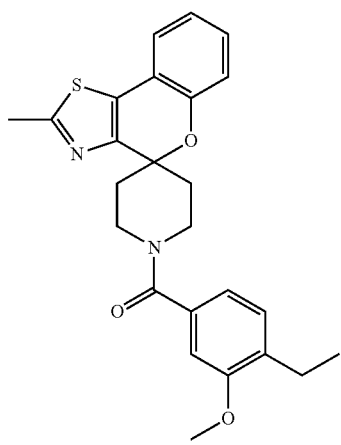 [SMILES: CCc1ccc(C(=O)N2CCC3(CC2)Oc2ccccc2-c2sc(C)nc23)cc1OC]
258
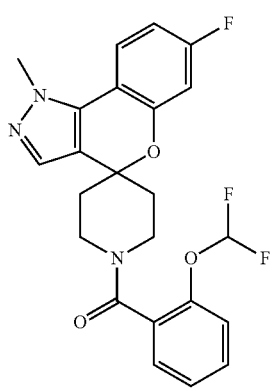 [SMILES: Cn1ncc2c1-c1ccc(F)cc1OC21CCN(C(=O)c2ccccc2OC(F)F)CC1]
259
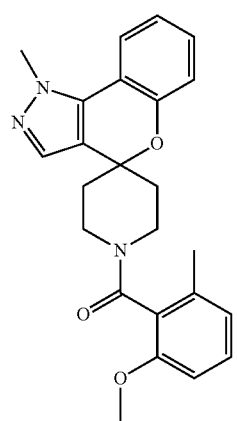 [SMILES: COc1cccc(C)c1C(=O)N1CCC2(CC1)Oc1ccccc1-c1c2cnn1C]
TABLE 1-continued
260
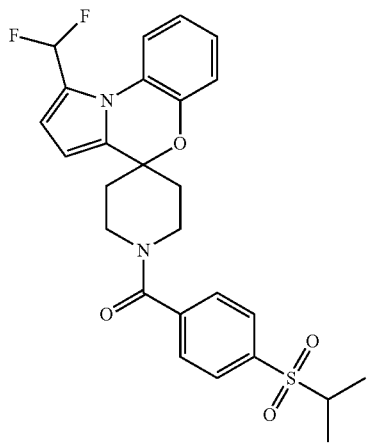 [SMILES: CC(C)S(=O)(=O)c1ccc(C(=O)N2CCC3(CC2)Oc2ccccc2-n2c(C(F)F)ccc23)cc1]
261
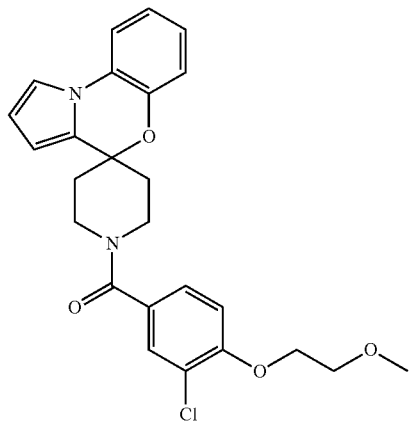
262
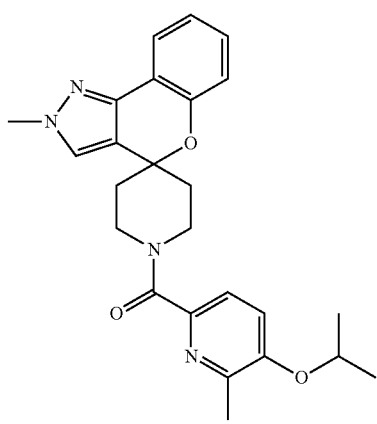 [SMILES: Cc1nc(C(=O)N2CCC3(CC2)Oc2ccccc2-c2nn(C)cc23)ccc1OC(C)C]

TABLE 1-continued
263
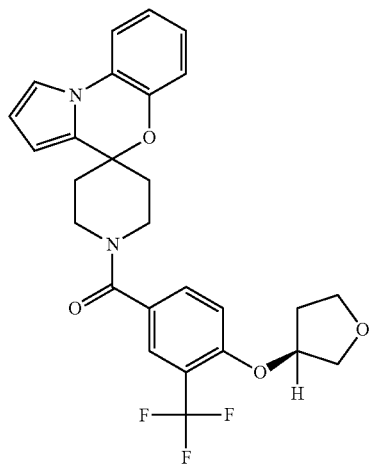 [SMILES: O=C(c1ccc(O[C@H]2CCOC2)c(C(F)(F)F)c1)N1CCC2(CC1)Oc1ccccc1-n1cccc12]
264
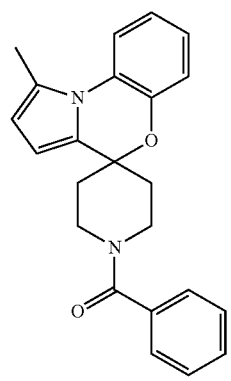 [SMILES: Cc1ccc2n1-c1ccccc1OC21CCN(C(=O)c2ccccc2)CC1]
265
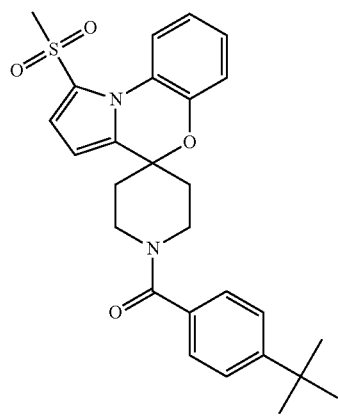 [SMILES: CC(C)(C)c1ccc(C(=O)N2CCC3(CC2)Oc2ccccc2-n2c3ccc2S(C)(=O)=O)cc1]
TABLE 1-continued
266
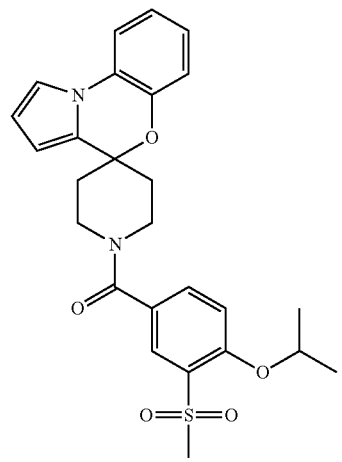 [SMILES: CC(C)Oc1ccc(C(=O)N2CCC3(CC2)Oc2ccccc2-n2cccc23)cc1S(C)(=O)=O]
267
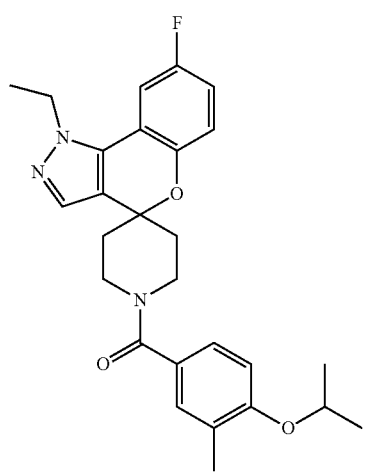 [SMILES: CCn1ncc2c1-c1cc(F)ccc1OC21CCN(C(=O)c2ccc(OC(C)C)c(C)c2)CC1]
268
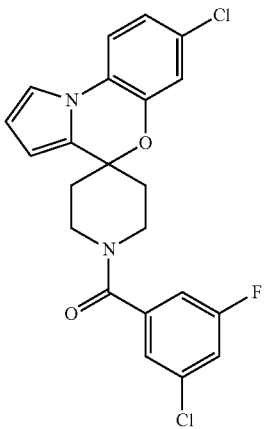

TABLE 1-continued
269
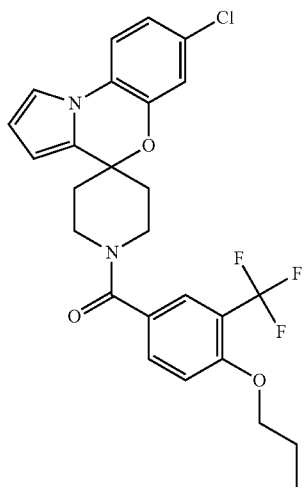 [SMILES: CCCOc1ccc(C(=O)N2CCC3(CC2)Oc2cc(Cl)ccc2-n2cccc23)cc1C(F)(F)F]
270
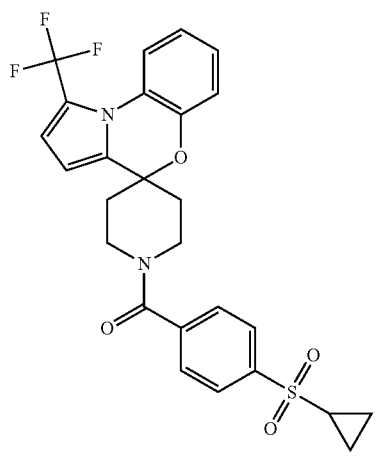 [SMILES: O=C(c1ccc(S(=O)(=O)C2CC2)cc1)N1CCC2(CC1)Oc1ccccc1-n1c(C(F)(F)F)ccc12]
271
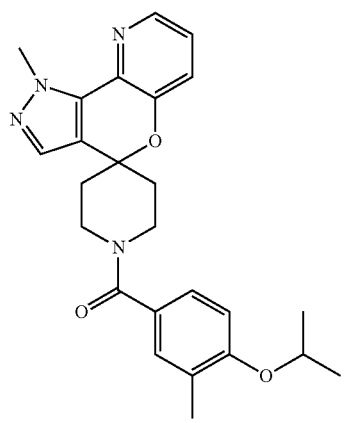 [SMILES: Cc1cc(C(=O)N2CCC3(CC2)Oc2cccnc2-c2c3cnn2C)ccc1OC(C)C]
TABLE 1-continued
272
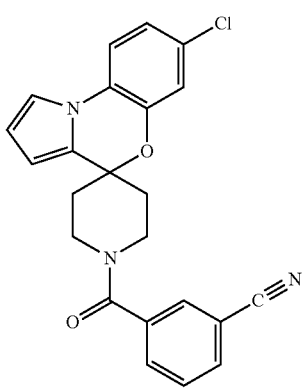 [SMILES: N#Cc1cccc(C(=O)N2CCC3(CC2)Oc2cc(Cl)ccc2-n2cccc23)c1]
273
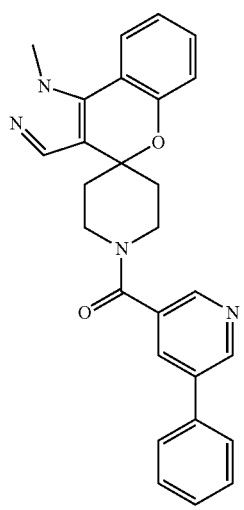 [SMILES: CNC1=C(C=N)C2(CCN(C(=O)c3cncc(-c4ccccc4)c3)CC2)Oc2ccccc21]
274
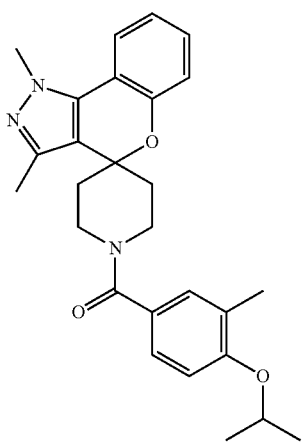 [SMILES: Cc1cc(C(=O)N2CCC3(CC2)Oc2ccccc2-c2c3c(C)nn2C)ccc1OC(C)C]

TABLE 1-continued
275
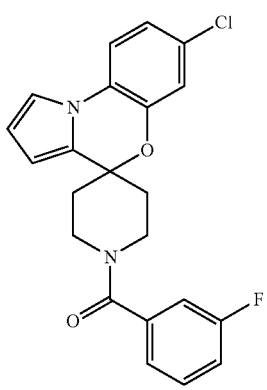 [SMILES: O=C(c1cccc(F)c1)N1CCC2(CC1)Oc1cc(Cl)ccc1-n1cccc12]
276
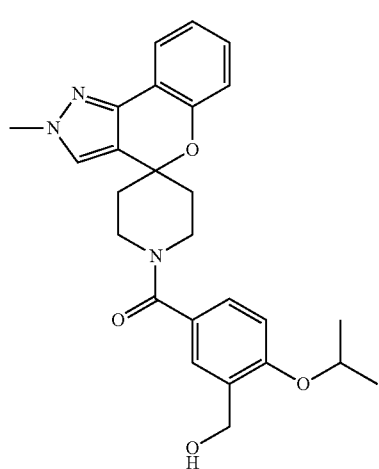 [SMILES: CC(C)Oc1ccc(C(=O)N2CCC3(CC2)Oc2ccccc2-c2nn(C)cc23)cc1CO]
277
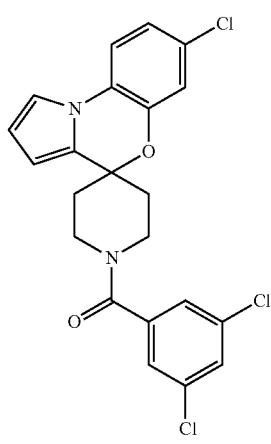 [SMILES: O=C(c1cc(Cl)cc(Cl)c1)N1CCC2(CC1)Oc1cc(Cl)ccc1-n1cccc12]
TABLE 1-continued
278
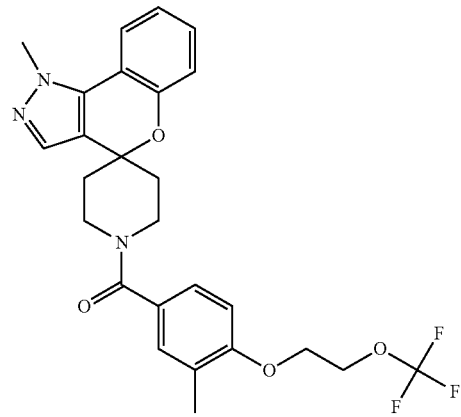 [SMILES: Cc1cc(C(=O)N2CCC3(CC2)Oc2ccccc2-c2c3cnn2C)ccc1OCCOC(F)(F)F]
279
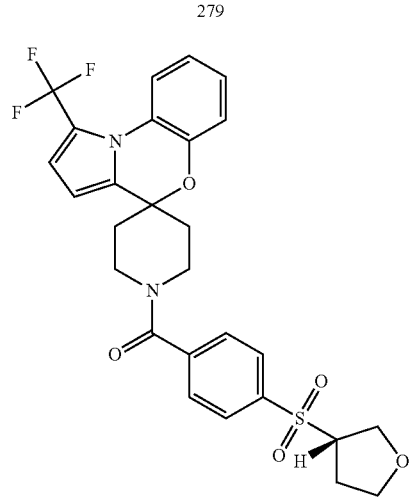
280
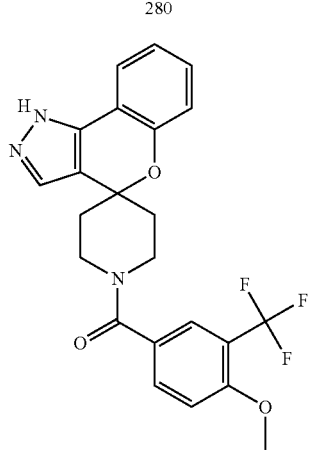

TABLE 1-continued
281
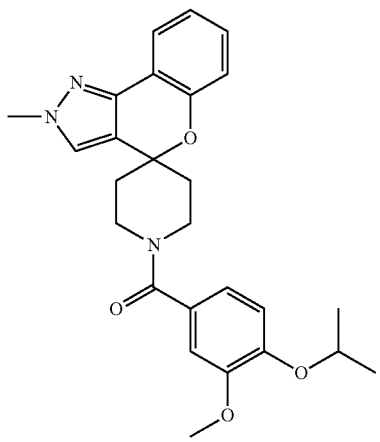 [SMILES: COc1cc(C(=O)N2CCC3(CC2)Oc2ccccc2-c2nn(C)cc23)ccc1OC(C)C]
282
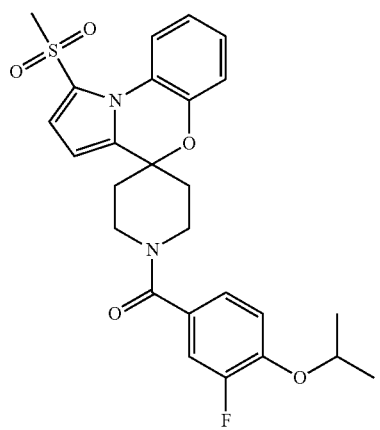 [SMILES: CC(C)Oc1ccc(C(=O)N2CCC3(CC2)Oc2ccccc2-n2c3ccc2S(C)(=O)=O)cc1F]
283
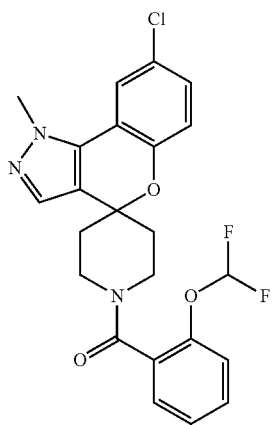 [SMILES: Cn1ncc2c1-c1cc(Cl)ccc1OC21CCN(C(=O)c2ccccc2OC(F)F)CC1]
TABLE 1-continued
284
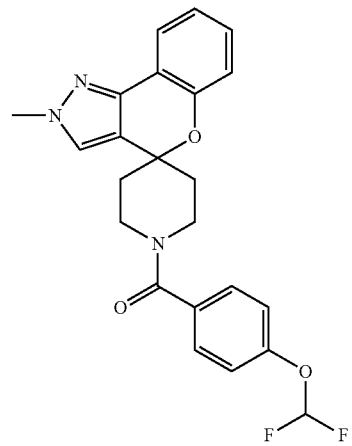 [SMILES: Cn1cc2c(n1)-c1ccccc1OC21CCN(C(=O)c2ccc(OC(F)F)cc2)CC1]
285
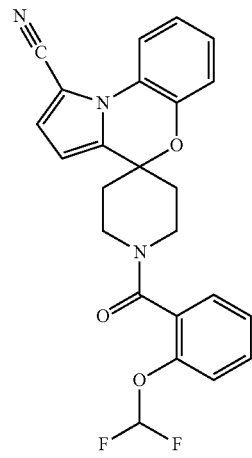 [SMILES: N#Cc1ccc2n1-c1ccccc1OC21CCN(C(=O)c2ccccc2OC(F)F)CC1]
286
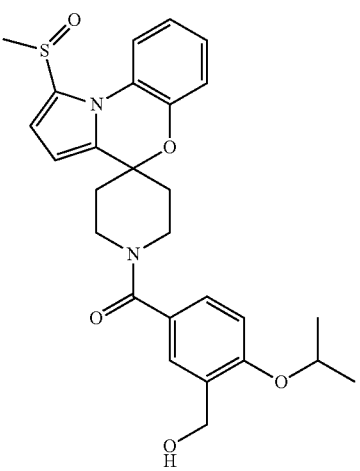 [SMILES: CC(C)Oc1ccc(C(=O)N2CCC3(CC2)Oc2ccccc2-n2c(S(C)=O)ccc23)cc1CO]

TABLE 1-continued
287
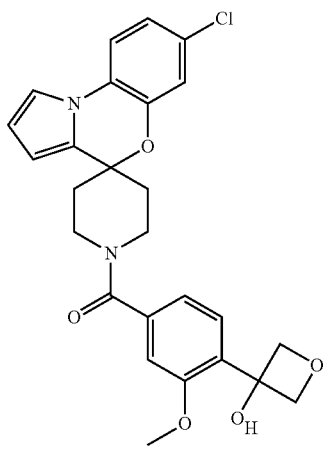
288
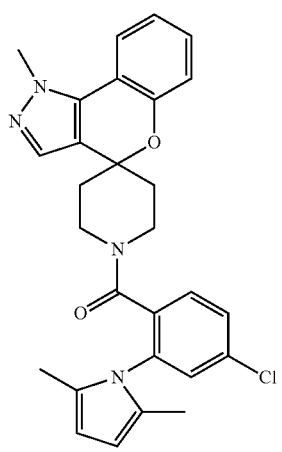 [SMILES: Cc1ccc(C)n1-c1cc(Cl)ccc1C(=O)N1CCC2(CC1)Oc1ccccc1-c1c2cnn1C]
289
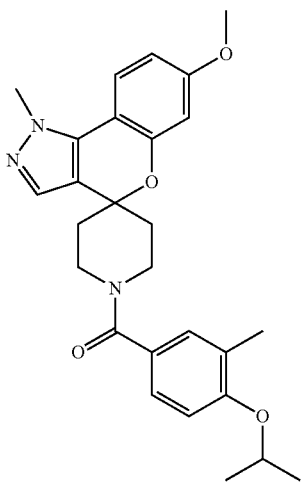 [SMILES: COc1ccc2c(c1)OC1(CCN(C(=O)c3ccc(OC(C)C)c(C)c3)CC1)c1cnn(C)c1-2]
TABLE 1-continued
290
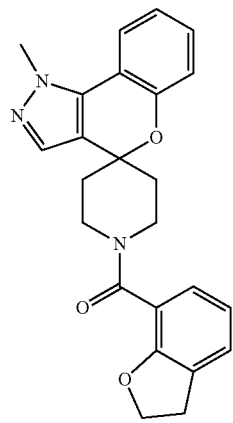 [SMILES: Cn1ncc2c1-c1ccccc1OC21CCN(C(=O)c2cccc3c2OCC3)CC1]
291
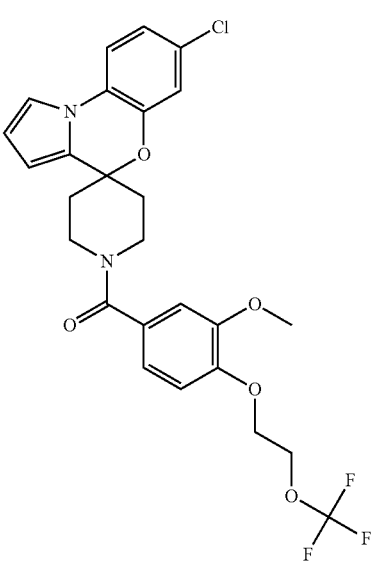 [SMILES: COc1cc(C(=O)N2CCC3(CC2)Oc2cc(Cl)ccc2-n2cccc23)ccc1OCCOC(F)(F)F]
292
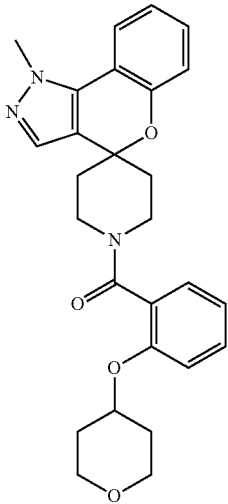 [SMILES: Cn1ncc2c1-c1ccccc1OC21CCN(C(=O)c2ccccc2OC2CCOCC2)CC1]

TABLE 1-continued
293
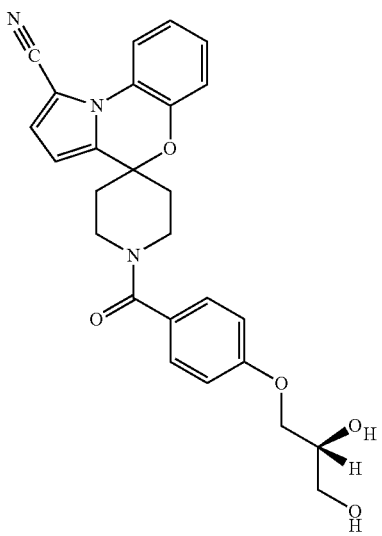
294
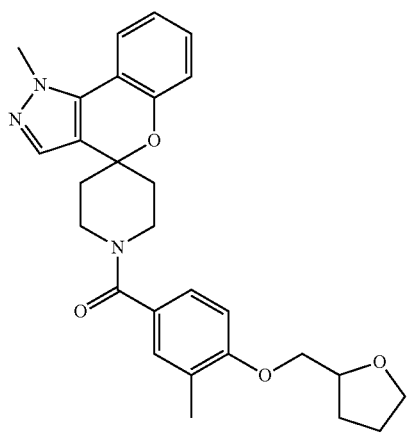 [SMILES: Cc1cc(C(=O)N2CCC3(CC2)Oc2ccccc2-c2c3cnn2C)ccc1OCC1CCCO1]
295
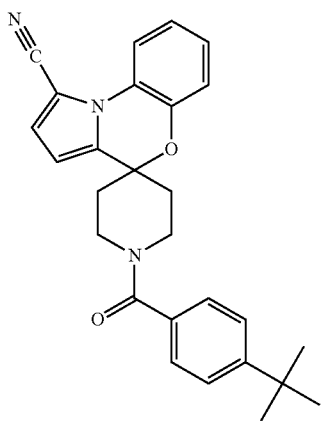 [SMILES: CC(C)(C)c1ccc(C(=O)N2CCC3(CC2)Oc2ccccc2-n2c(C#N)ccc23)cc1]
TABLE 1-continued
296
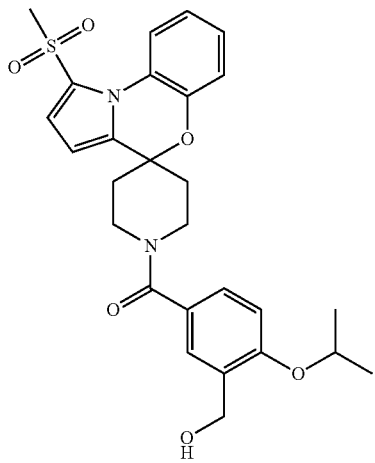 [SMILES: CC(C)Oc1ccc(C(=O)N2CCC3(CC2)Oc2ccccc2-n2c3ccc2S(C)(=O)=O)cc1CO]
297
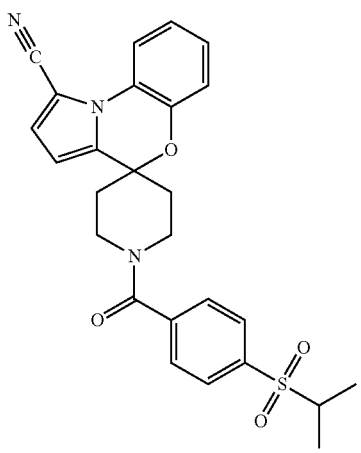 [SMILES: CC(C)S(=O)(=O)c1ccc(C(=O)N2CCC3(CC2)Oc2ccccc2-n2c(C#N)ccc23)cc1]
298
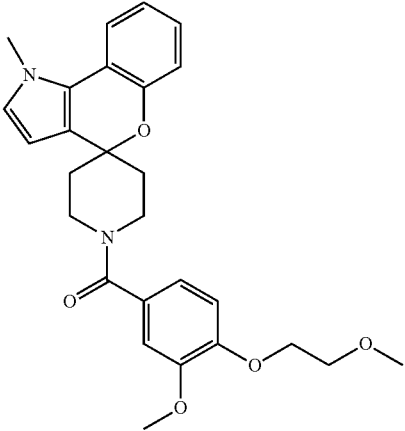 [SMILES: COCCOc1ccc(C(=O)N2CCC3(CC2)Oc2ccccc2-c2c3ccn2C)cc1OC]

TABLE 1-continued
299
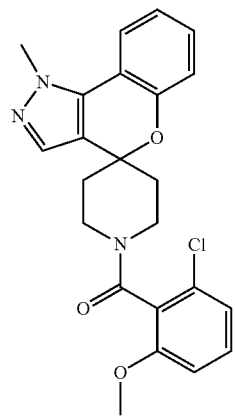 [SMILES: COc1cccc(Cl)c1C(=O)N1CCC2(CC1)Oc1ccccc1-c1c2cnn1C]
300
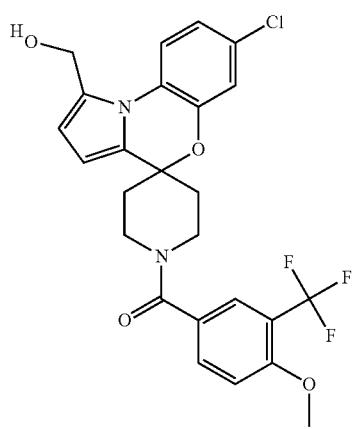
301
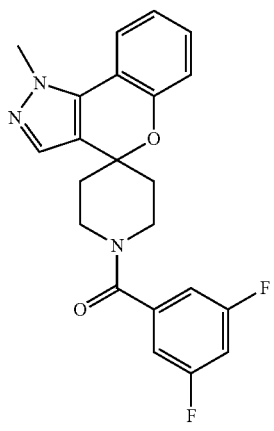 [SMILES: Cn1ncc2c1-c1ccccc1OC21CCN(C(=O)c2cc(F)cc(F)c2)CC1]
TABLE 1-continued
302
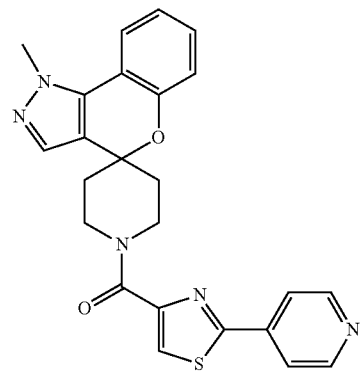 [SMILES: Cn1ncc2c1-c1ccccc1OC21CCN(C(=O)c2csc(-c3ccncc3)n2)CC1]
303
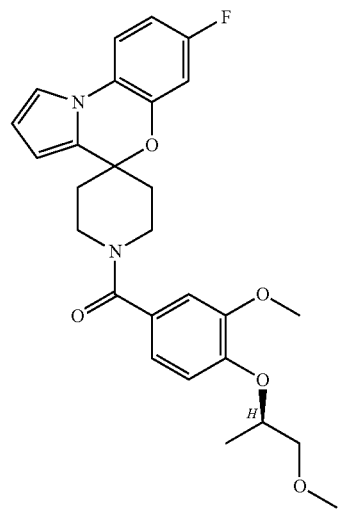
304
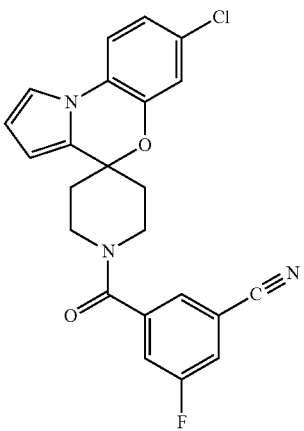 [SMILES: N#Cc1cc(F)cc(C(=O)N2CCC3(CC2)Oc2cc(Cl)ccc2-n2cccc23)c1]

TABLE 1-continued
305
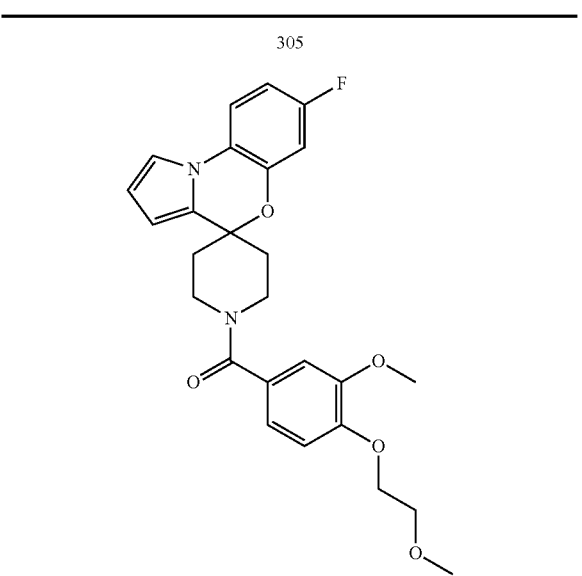
306
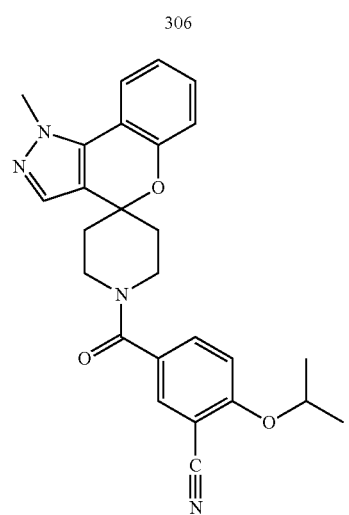
307
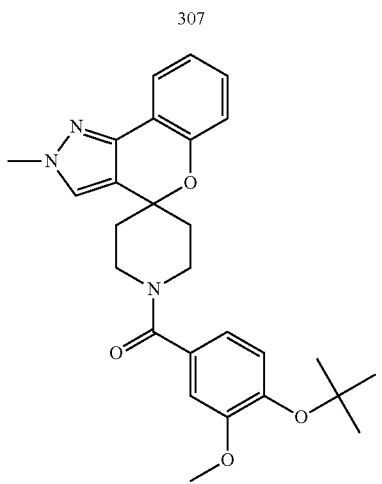
TABLE 1-continued
308
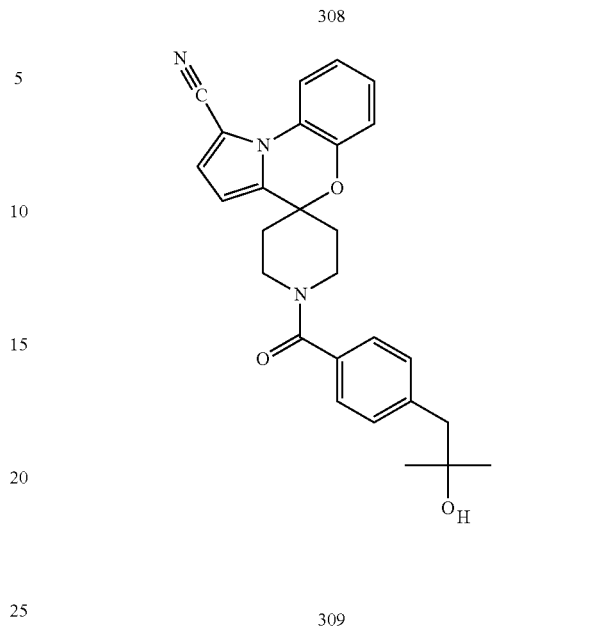
309
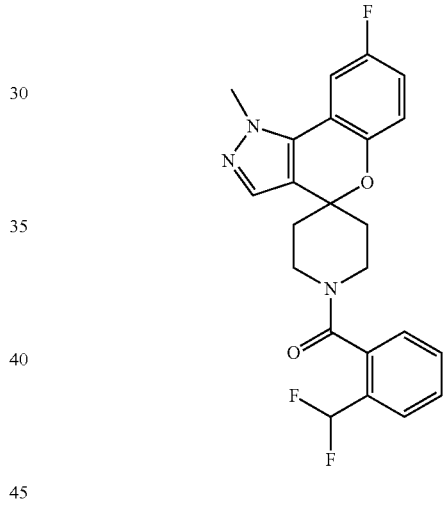
310
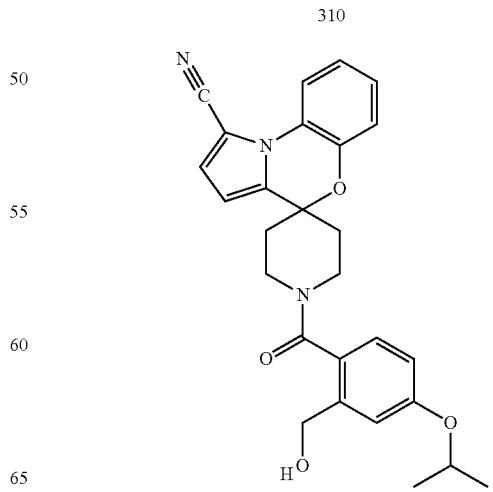

TABLE 1-continued
311
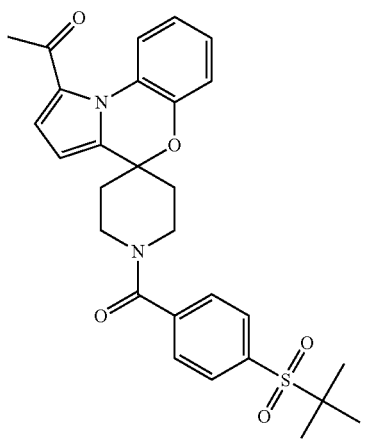 [SMILES: CC(=O)c1ccc2n1-c1ccccc1OC21CCN(C(=O)c2ccc(S(=O)(=O)C(C)(C)C)cc2)CC1]
312
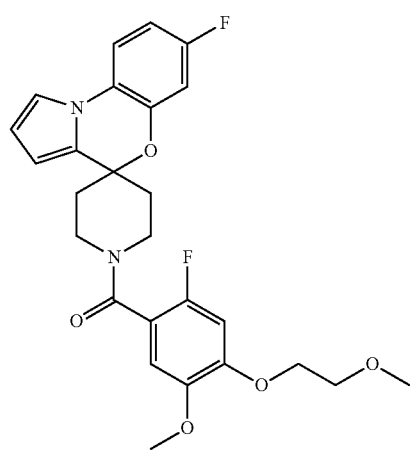 [SMILES: COCCOc1cc(F)c(C(=O)N2CCC3(CC2)Oc2cc(F)ccc2-n2cccc23)cc1OC]
313
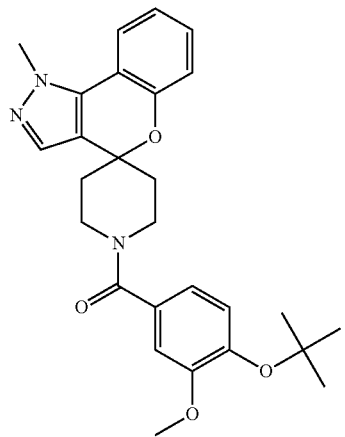 [SMILES: COc1cc(C(=O)N2CCC3(CC2)Oc2ccccc2-c2c3cnn2C)ccc1OC(C)(C)C]
TABLE 1-continued
314
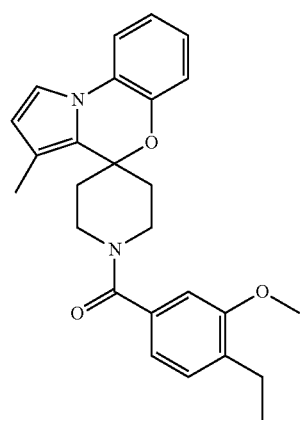 [SMILES: CCc1ccc(C(=O)N2CCC3(CC2)Oc2ccccc2-n2ccc(C)c23)cc1OC]
315
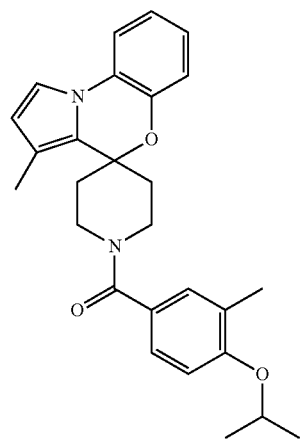 [SMILES: Cc1cc(C(=O)N2CCC3(CC2)Oc2ccccc2-n2ccc(C)c23)ccc1OC(C)C]
316
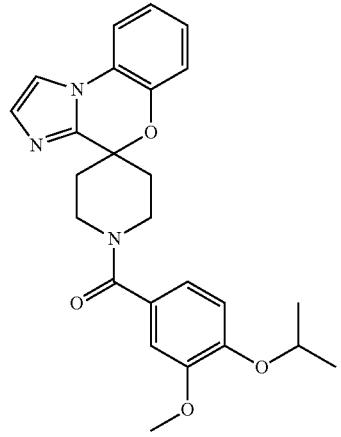 [SMILES: COc1cc(C(=O)N2CCC3(CC2)Oc2ccccc2-n2ccnc23)ccc1OC(C)C]

TABLE 1-continued
317
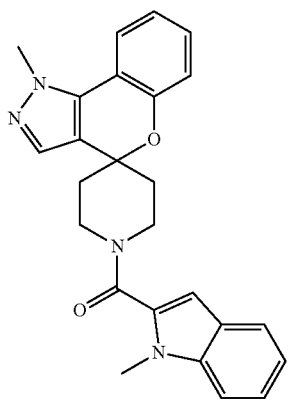 [SMILES: Cn1ncc2c1-c1ccccc1OC21CCN(C(=O)c2cc3ccccc3n2C)CC1]
318
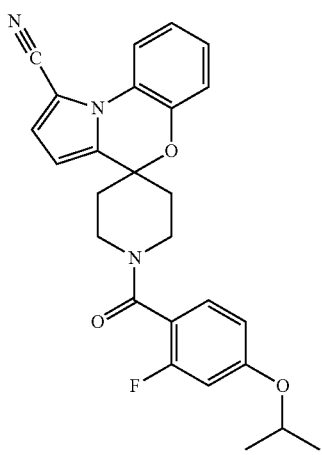 [SMILES: CC(C)Oc1ccc(C(=O)N2CCC3(CC2)Oc2ccccc2-n2c(C#N)ccc23)c(F)c1]
319
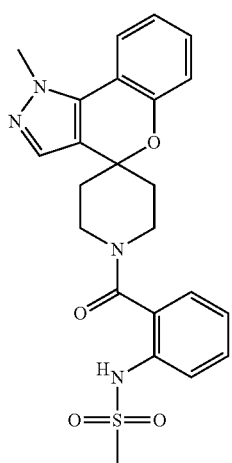
TABLE 1-continued
320
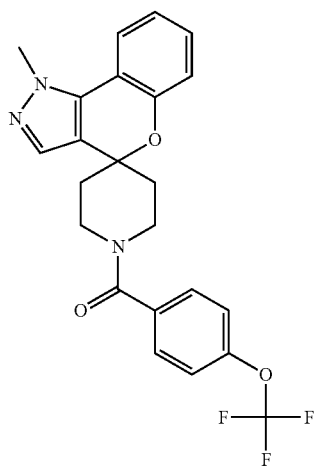 [SMILES: Cn1ncc2c1-c1ccccc1OC21CCN(C(=O)c2ccc(OC(F)(F)F)cc2)CC1]
321
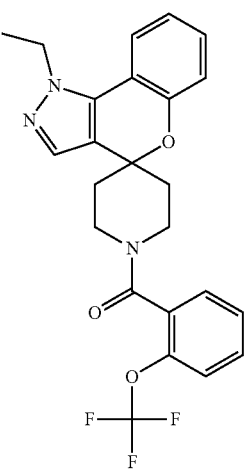 [SMILES: CCn1ncc2c1-c1ccccc1OC21CCN(C(=O)c2ccccc2OC(F)(F)F)CC1]
322
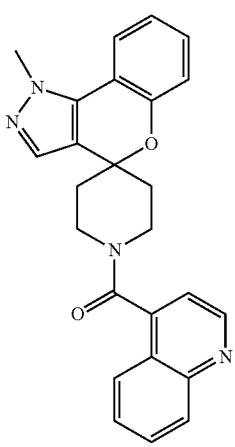 [SMILES: Cn1ncc2c1-c1ccccc1OC21CCN(C(=O)c2ccnc3ccccc23)CC1]

TABLE 1-continued
323
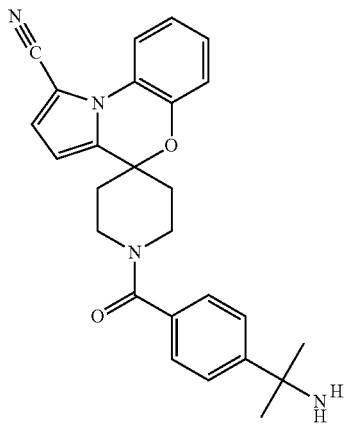
324
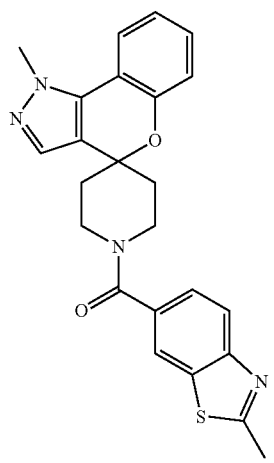 [SMILES: Cc1nc2ccc(C(=O)N3CCC4(CC3)Oc3ccccc3-c3c4cnn3C)cc2s1]
325
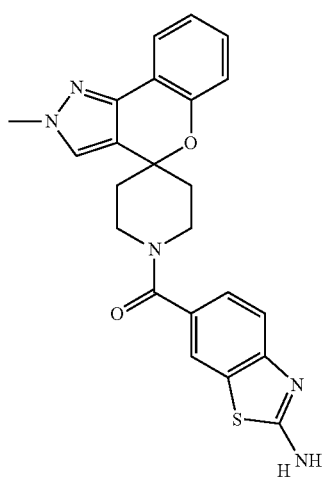
TABLE 1-continued
326
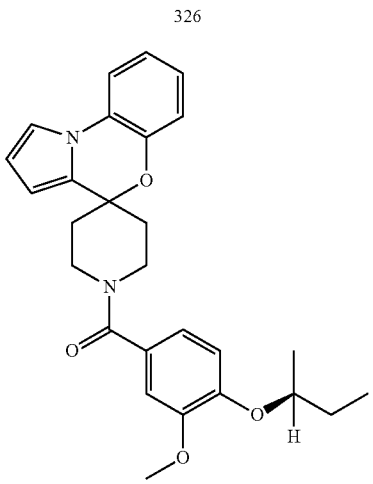
327
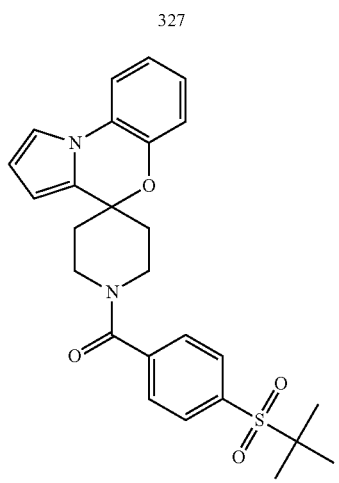
328
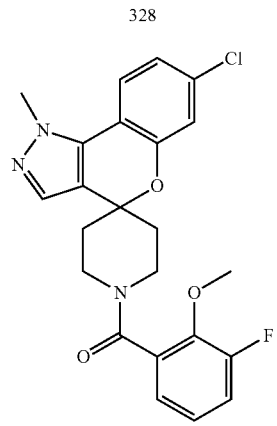

TABLE 1-continued
329
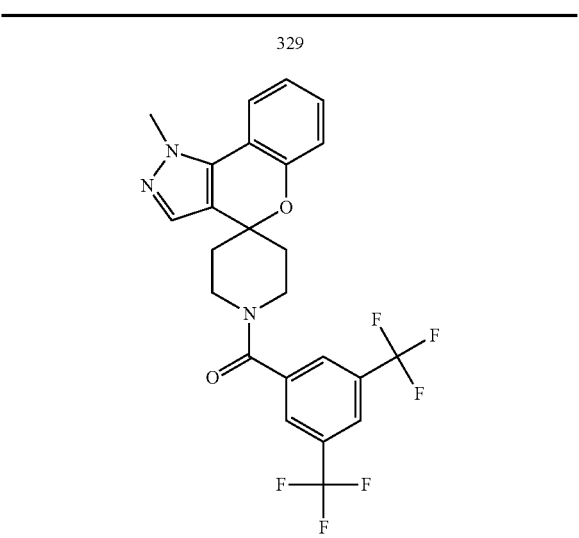
330
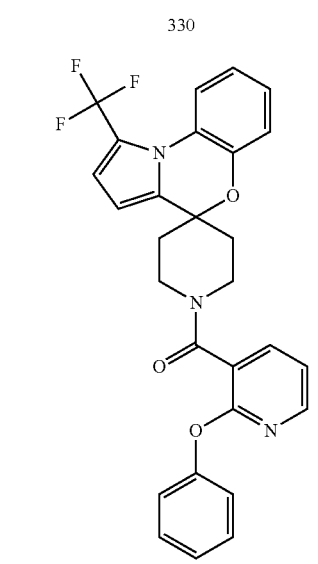
331
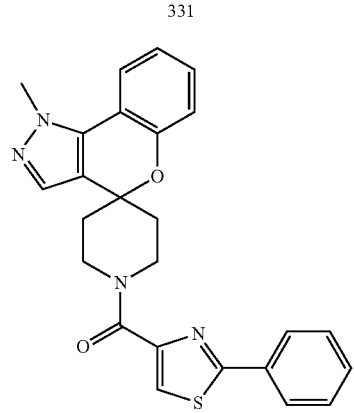
TABLE 1-continued
332
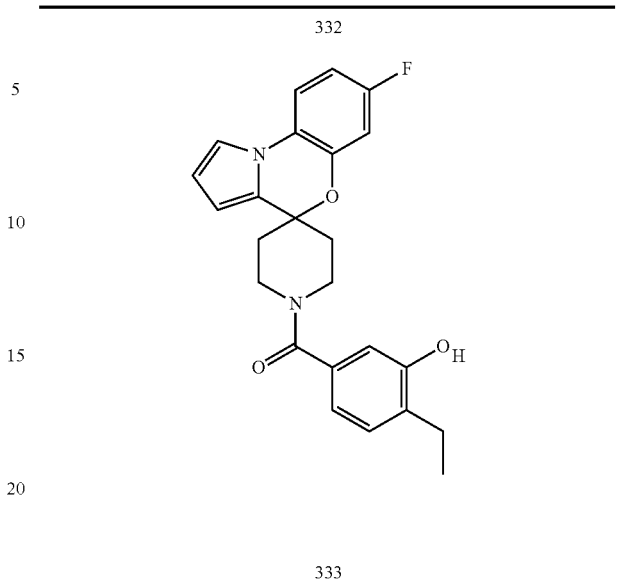
333
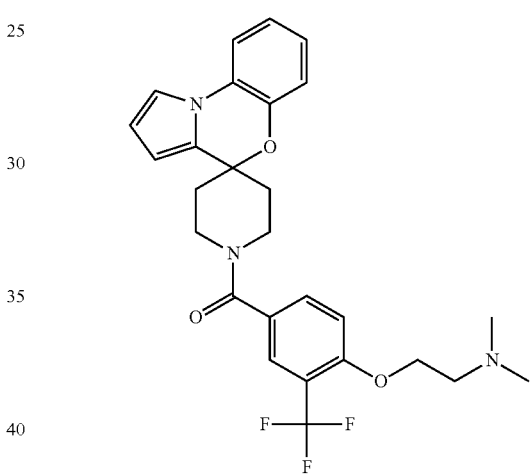
334
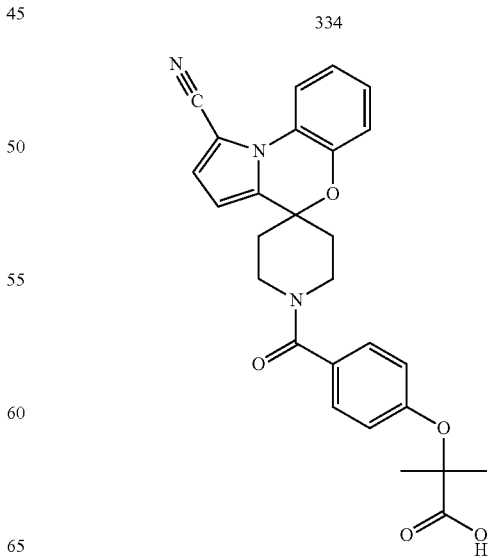

TABLE 1-continued
335
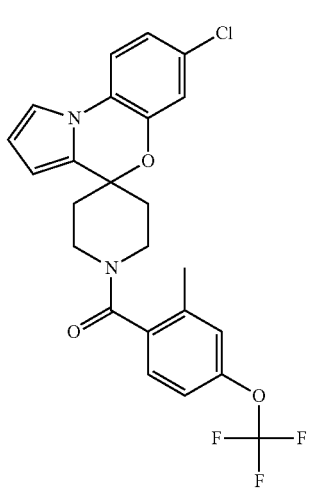 [SMILES: Cc1cc(OC(F)(F)F)ccc1C(=O)N1CCC2(CC1)Oc1cc(Cl)ccc1-n1cccc12]
336
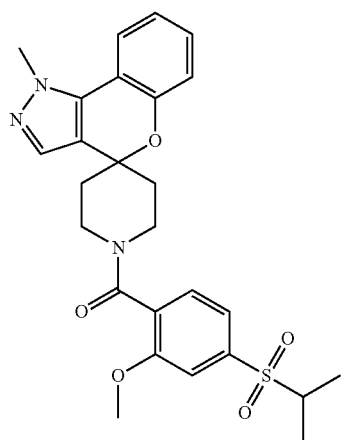 [SMILES: COc1cc(S(=O)(=O)C(C)C)ccc1C(=O)N1CCC2(CC1)Oc1ccccc1-c1c2cnn1C]
337
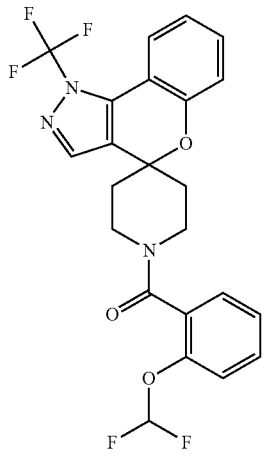 [SMILES: O=C(c1ccccc1OC(F)F)N1CCC2(CC1)Oc1ccccc1-c1c2cnn1C(F)(F)F]
TABLE 1-continued
338
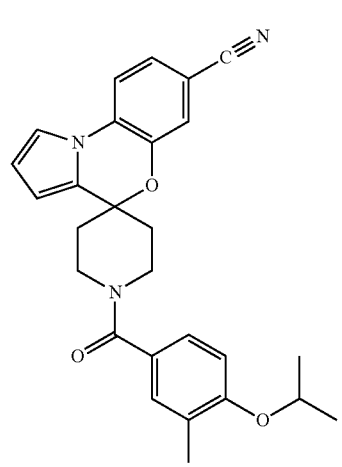 [SMILES: Cc1cc(C(=O)N2CCC3(CC2)Oc2cc(C#N)ccc2-n2cccc23)ccc1OC(C)C]
339
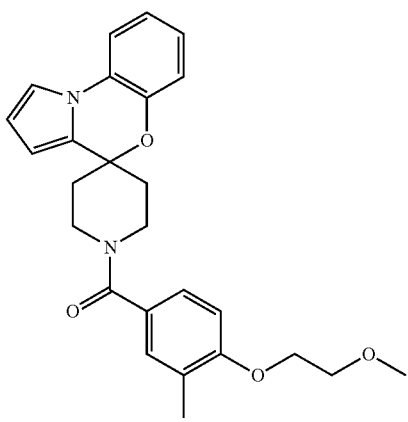 [SMILES: COCCOc1ccc(C(=O)N2CCC3(CC2)Oc2ccccc2-n2cccc23)cc1C]
340
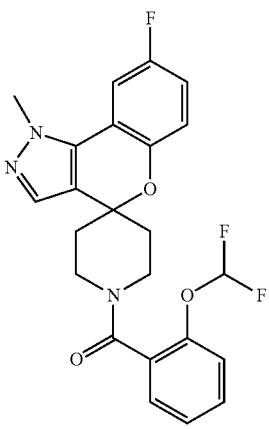 [SMILES: Cn1ncc2c1-c1cc(F)ccc1OC21CCN(C(=O)c2ccccc2OC(F)F)CC1]

TABLE 1-continued
341
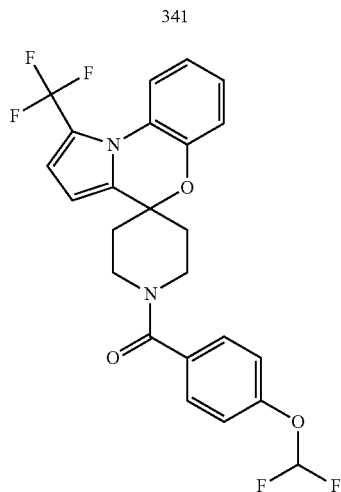
342
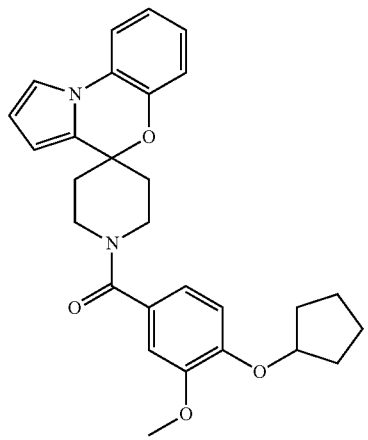 [SMILES: COc1cc(C(=O)N2CCC3(CC2)Oc2ccccc2-n2cccc23)ccc1OC1CCCC1]
343
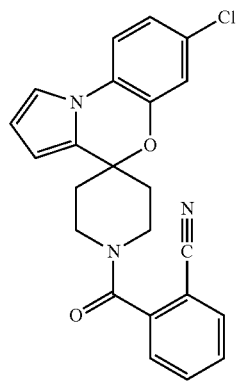 [SMILES: N#Cc1ccccc1C(=O)N1CCC2(CC1)Oc1cc(Cl)ccc1-n1cccc12]
TABLE 1-continued
344
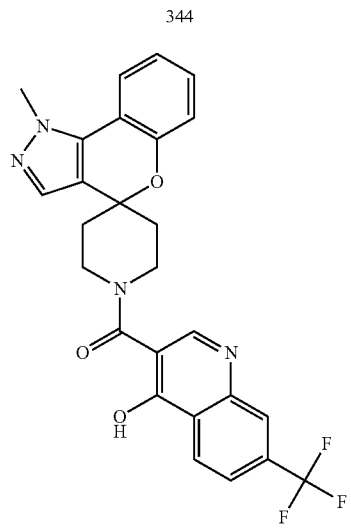
345
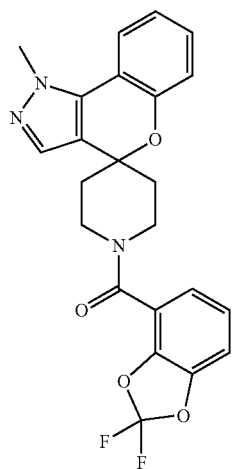 [SMILES: Cn1ncc2c1-c1ccccc1OC21CCN(C(=O)c2cccc3c2OC(F)(F)O3)CC1]
346
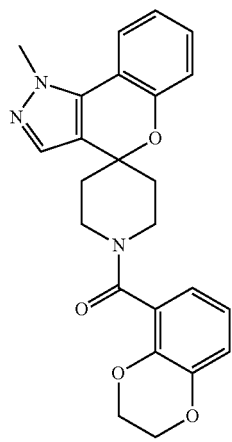 [SMILES: Cn1ncc2c1-c1ccccc1OC21CCN(C(=O)c2cccc3c2OCCO3)CC1]

TABLE 1-continued
347
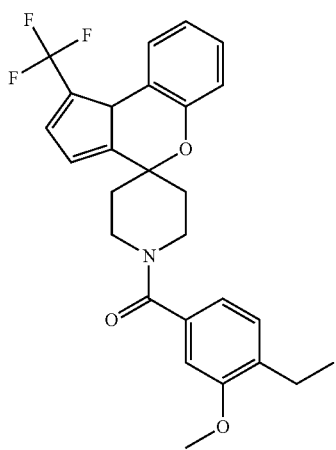 [SMILES: CCc1ccc(C(=O)N2CCC3(CC2)Oc2ccccc2C2C(C(F)(F)F)=CC=C23)cc1OC]
348
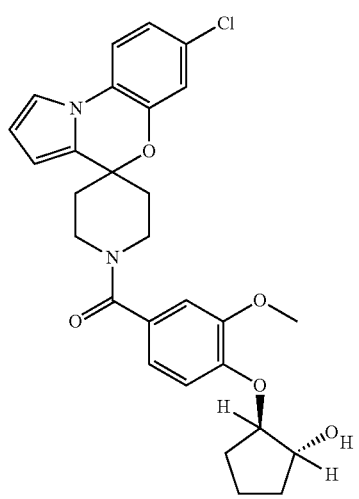
349
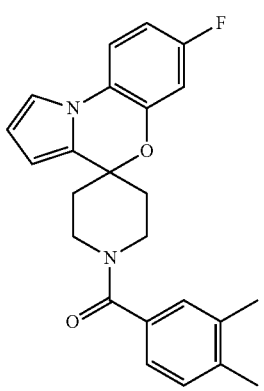 [SMILES: Cc1ccc(C(=O)N2CCC3(CC2)Oc2cc(F)ccc2-n2cccc23)cc1C]
TABLE 1-continued
350
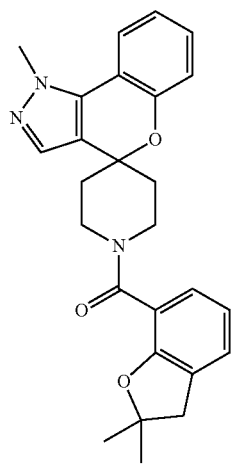 [SMILES: Cn1ncc2c1-c1ccccc1OC21CCN(C(=O)c2cccc3c2OC(C)(C)C3)CC1]
351
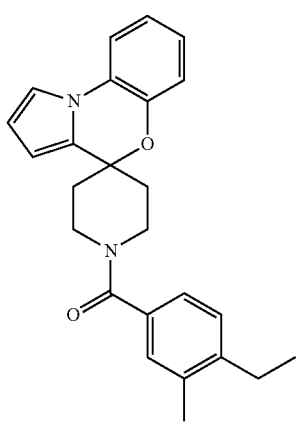 [SMILES: CCc1ccc(C(=O)N2CCC3(CC2)Oc2ccccc2-n2cccc23)cc1C]
352
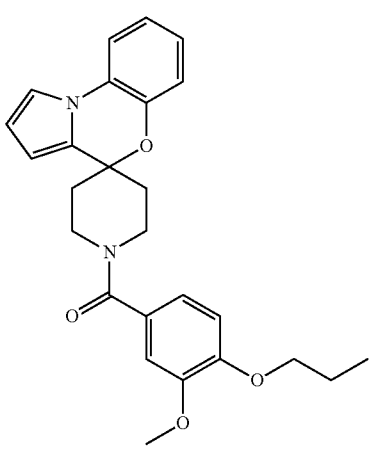 [SMILES: CCCOc1ccc(C(=O)N2CCC3(CC2)Oc2ccccc2-n2cccc23)cc1OC]

TABLE 1-continued
353
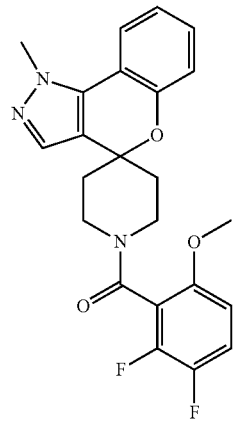 [SMILES: COc1ccc(F)c(F)c1C(=O)N1CCC2(CC1)Oc1ccccc1-c1c2cnn1C]
354
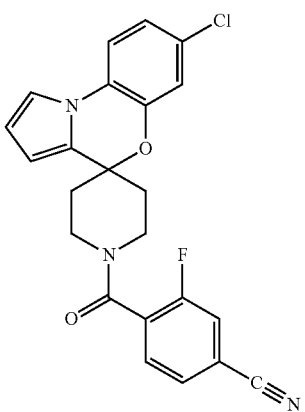 [SMILES: N#Cc1ccc(C(=O)N2CCC3(CC2)Oc2cc(Cl)ccc2-n2cccc23)c(F)c1]
355
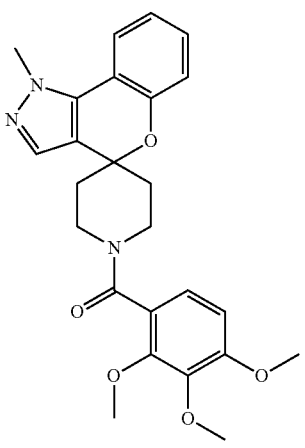 [SMILES: COc1ccc(C(=O)N2CCC3(CC2)Oc2ccccc2-c2c3cnn2C)c(OC)c1OC]
TABLE 1-continued
356
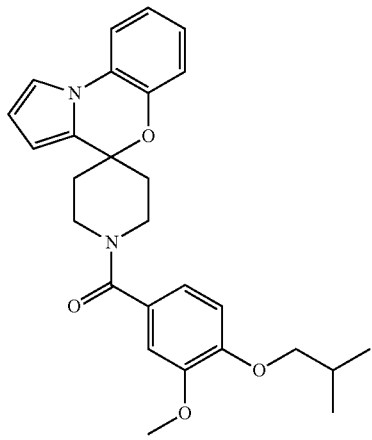 [SMILES: COc1cc(C(=O)N2CCC3(CC2)Oc2ccccc2-n2cccc23)ccc1OCC(C)C]
357
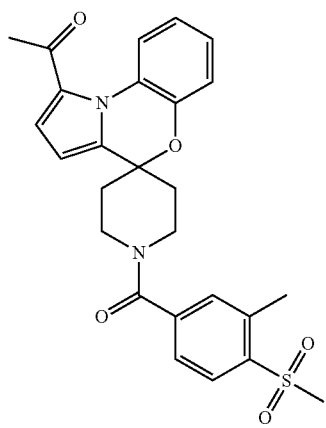 [SMILES: CC(=O)c1ccc2n1-c1ccccc1OC21CCN(C(=O)c2ccc(S(C)(=O)=O)c(C)c2)CC1]
358
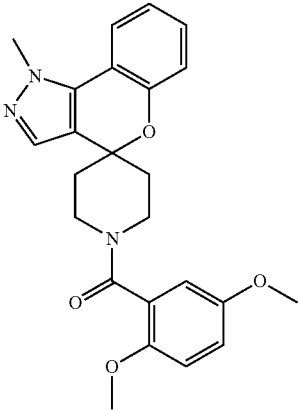 [SMILES: COc1ccc(OC)c(C(=O)N2CCC3(CC2)Oc2ccccc2-c2c3cnn2C)c1]

TABLE 1-continued
359
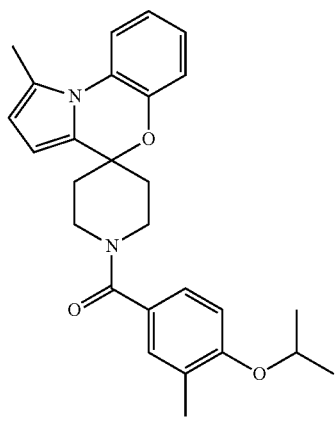 [SMILES: Cc1cc(C(=O)N2CCC3(CC2)Oc2ccccc2-n2c(C)ccc23)ccc1OC(C)C]
360
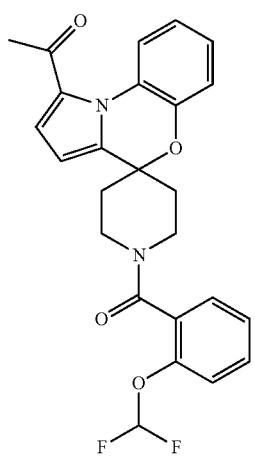 [SMILES: CC(=O)c1ccc2n1-c1ccccc1OC21CCN(C(=O)c2ccccc2OC(F)F)CC1]
361
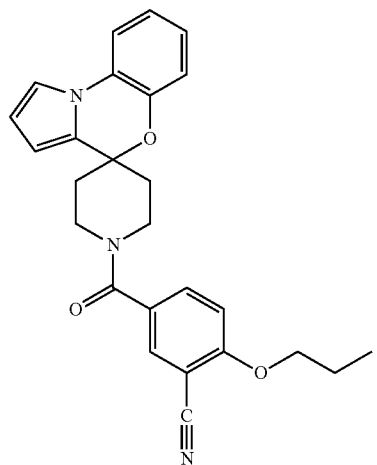 [SMILES: CCCOc1ccc(C(=O)N2CCC3(CC2)Oc2ccccc2-n2cccc23)cc1C#N]
TABLE 1-continued
362
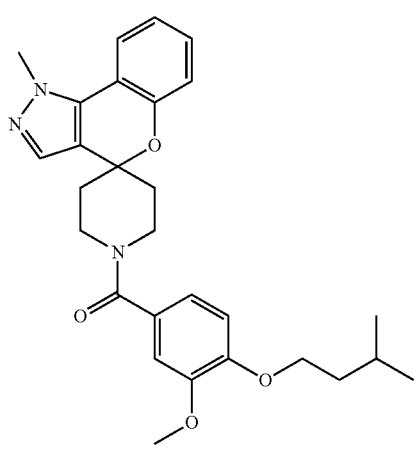 [SMILES: COc1cc(C(=O)N2CCC3(CC2)Oc2ccccc2-c2c3cnn2C)ccc1OCCC(C)C]
363
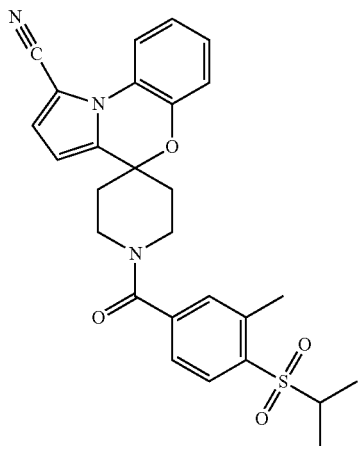 [SMILES: Cc1cc(C(=O)N2CCC3(CC2)Oc2ccccc2-n2c(C#N)ccc23)ccc1S(=O)(=O)C(C)C]
364
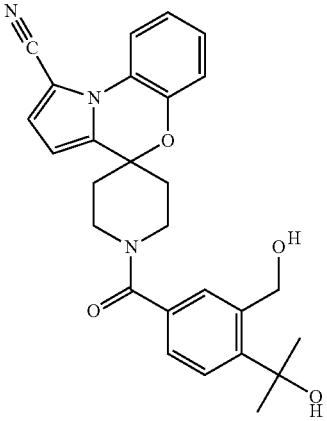

TABLE 1-continued
365
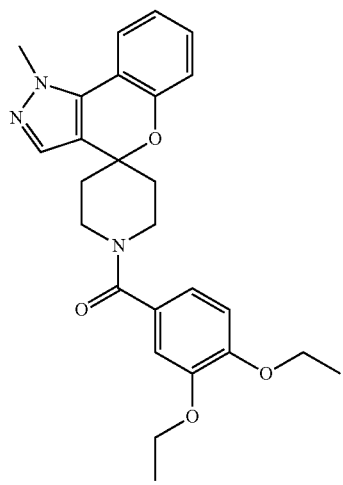 [SMILES: CCOc1ccc(C(=O)N2CCC3(CC2)Oc2ccccc2-c2c3cnn2C)cc1OCC]
366
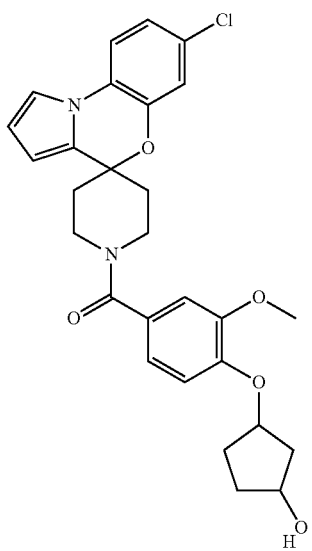
367
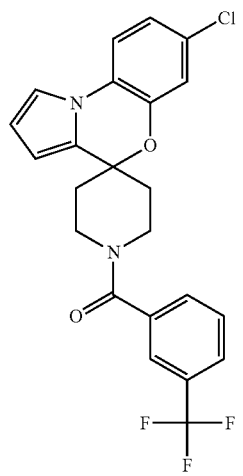 [SMILES: O=C(c1cccc(C(F)(F)F)c1)N1CCC2(CC1)Oc1cc(Cl)ccc1-n1cccc12]
TABLE 1-continued
368
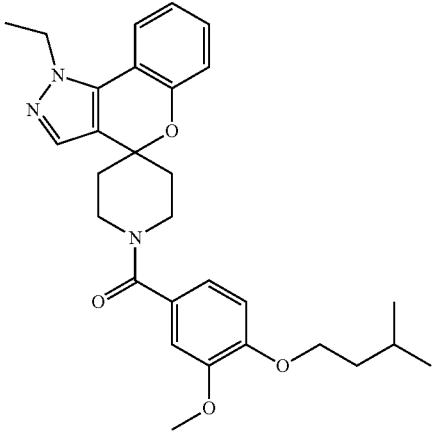 [SMILES: CCn1ncc2c1-c1ccccc1OC21CCN(C(=O)c2ccc(OCCC(C)C)c(OC)c2)CC1]
369
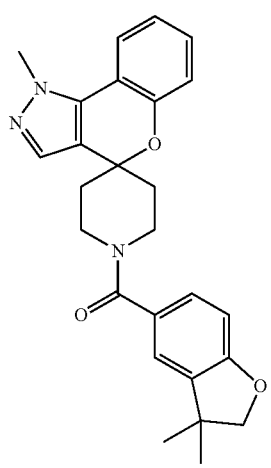 [SMILES: Cn1ncc2c1-c1ccccc1OC21CCN(C(=O)c2ccc3c(c2)C(C)(C)CO3)CC1]
370
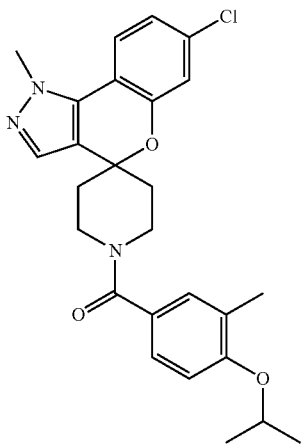 [SMILES: Cc1cc(C(=O)N2CCC3(CC2)Oc2cc(Cl)ccc2-c2c3cnn2C)ccc1OC(C)C]

TABLE 1-continued
371
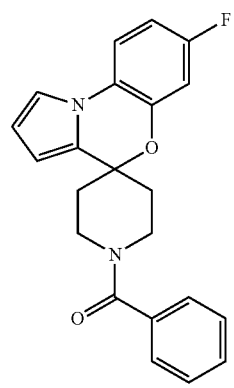 [SMILES: O=C(c1ccccc1)N1CCC2(CC1)Oc1cc(F)ccc1-n1cccc12]
372
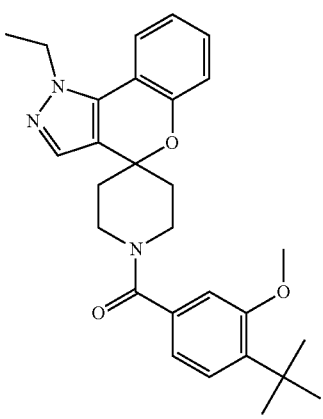 [SMILES: CCn1ncc2c1-c1ccccc1OC21CCN(C(=O)c2ccc(C(C)(C)C)c(OC)c2)CC1]
373
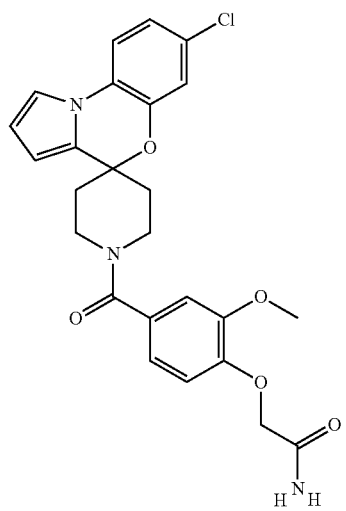
TABLE 1-continued
374
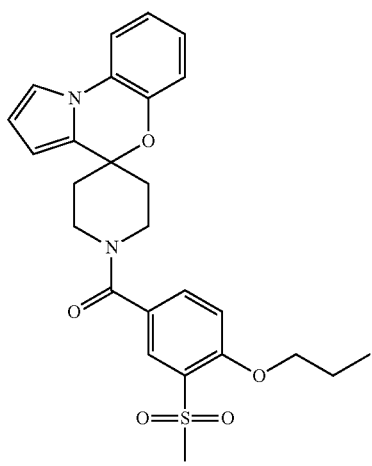 [SMILES: CCCOc1ccc(C(=O)N2CCC3(CC2)Oc2ccccc2-n2cccc23)cc1S(C)(=O)=O]
375
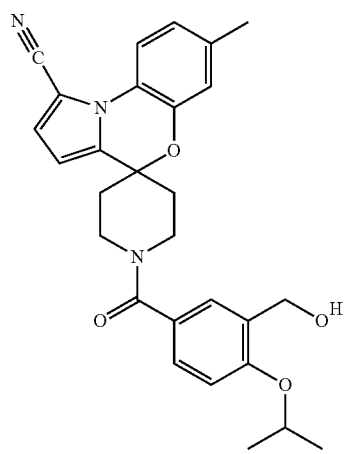
376
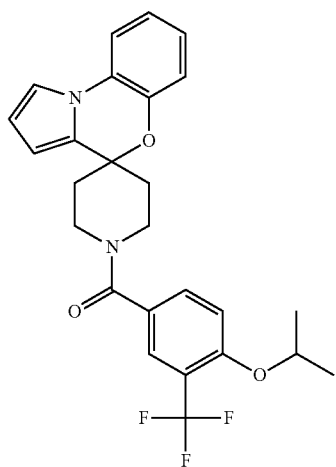 [SMILES: CC(C)Oc1ccc(C(=O)N2CCC3(CC2)Oc2ccccc2-n2cccc23)cc1C(F)(F)F]

TABLE 1-continued
377
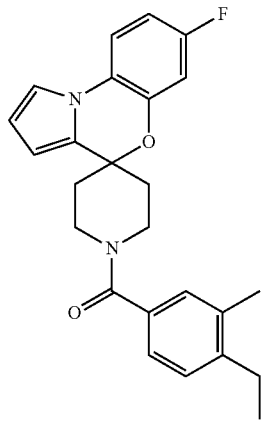 [SMILES: CCc1ccc(C(=O)N2CCC3(CC2)Oc2cc(F)ccc2-n2cccc23)cc1C]
378
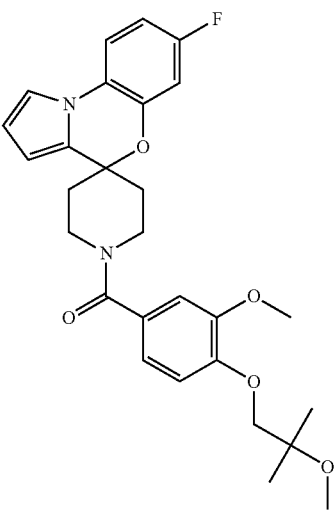 [SMILES: COc1cc(C(=O)N2CCC3(CC2)Oc2cc(F)ccc2-n2cccc23)ccc1OCC(C)(C)OC]
379
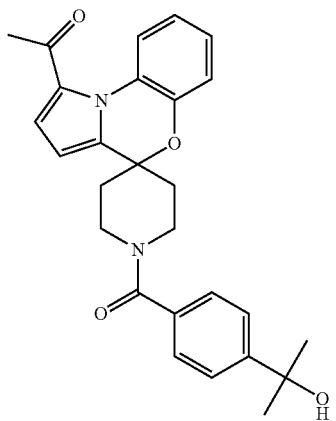 [SMILES: CC(=O)c1ccc2n1-c1ccccc1OC21CCN(C(=O)c2ccc(C(C)(C)O)cc2)CC1]
TABLE 1-continued
380
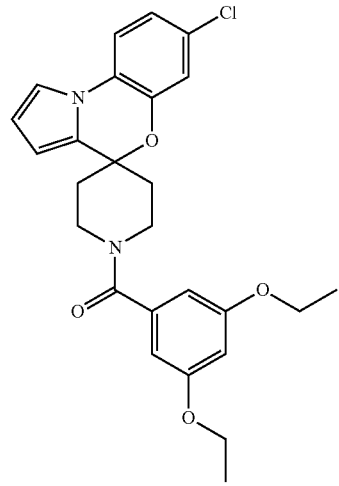 [SMILES: CCOc1cc(OCC)cc(C(=O)N2CCC3(CC2)Oc2cc(Cl)ccc2-n2cccc23)c1]
381
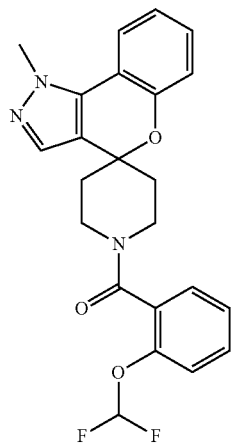 [SMILES: Cn1ncc2c1-c1ccccc1OC21CCN(C(=O)c2ccccc2OC(F)F)CC1]
382
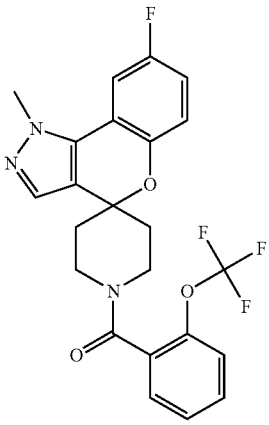 [SMILES: Cn1ncc2c1-c1cc(F)ccc1OC21CCN(C(=O)c2ccccc2OC(F)(F)F)CC1]

TABLE 1-continued
383
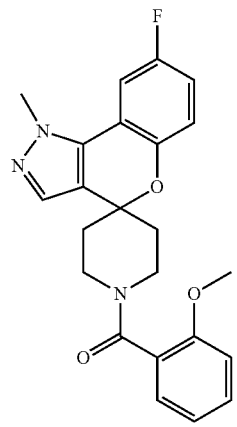 [SMILES: COc1ccccc1C(=O)N1CCC2(CC1)Oc1ccc(F)cc1-c1c2cnn1C]
384
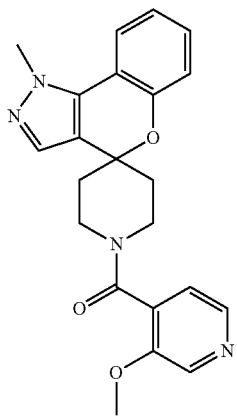 [SMILES: COc1cnccc1C(=O)N1CCC2(CC1)Oc1ccccc1-c1c2cnn1C]
385
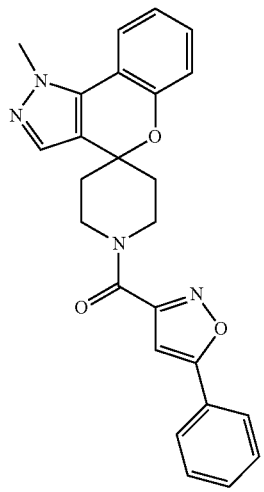 [SMILES: Cn1ncc2c1-c1ccccc1OC21CCN(C(=O)c2cc(-c3ccccc3)on2)CC1]
TABLE 1-continued
386
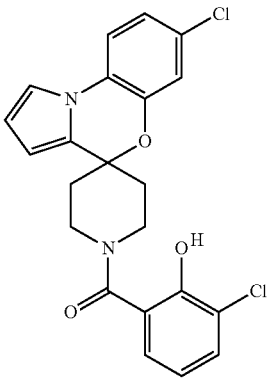
387
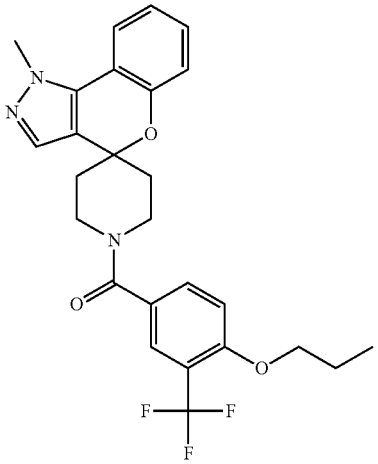 [SMILES: CCCOc1ccc(C(=O)N2CCC3(CC2)Oc2ccccc2-c2c3cnn2C)cc1C(F)(F)F]
388
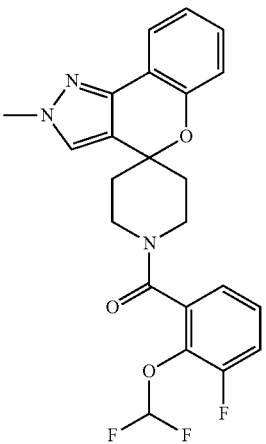 [SMILES: Cn1cc2c(n1)-c1ccccc1OC21CCN(C(=O)c2cccc(F)c2OC(F)F)CC1]

TABLE 1-continued
390
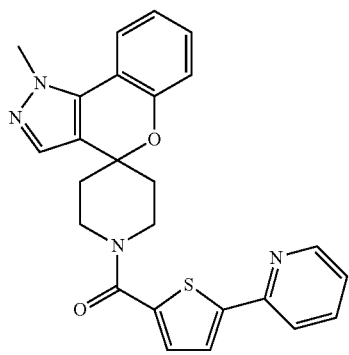 [SMILES: Cn1ncc2c1-c1ccccc1OC21CCN(C(=O)c2ccc(-c3ccccn3)s2)CC1]
391
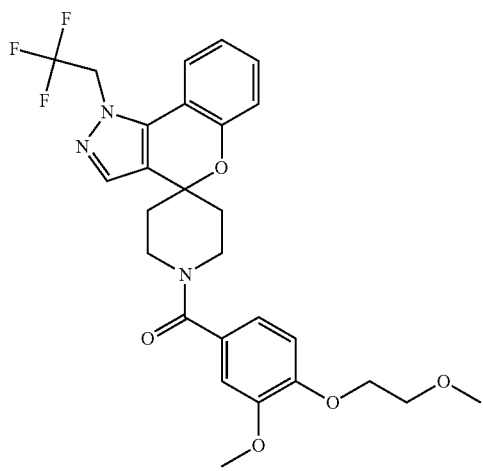 [SMILES: COCCOc1ccc(C(=O)N2CCC3(CC2)Oc2ccccc2-c2c3cnn2CC(F)(F)F)cc1OC]
392
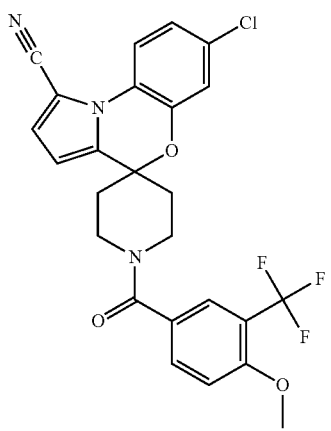 [SMILES: COc1ccc(C(=O)N2CCC3(CC2)Oc2cc(Cl)ccc2-n2c(C#N)ccc23)cc1C(F)(F)F]
TABLE 1-continued
393
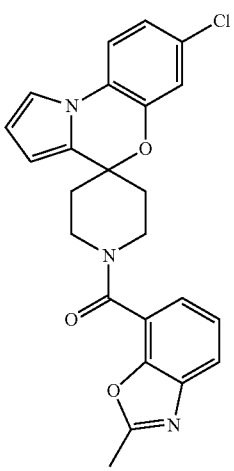 [SMILES: Cc1nc2cccc(C(=O)N3CCC4(CC3)Oc3cc(Cl)ccc3-n3cccc34)c2o1]
394
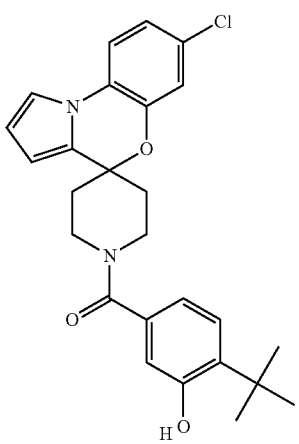
395
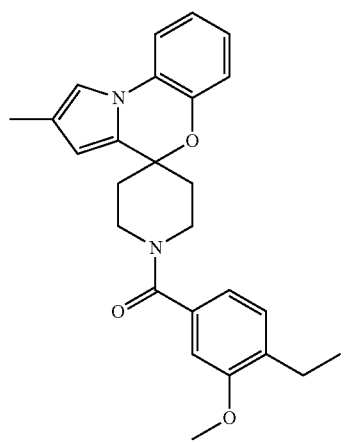 [SMILES: CCc1ccc(C(=O)N2CCC3(CC2)Oc2ccccc2-n2cc(C)cc23)cc1OC]

TABLE 1-continued
396
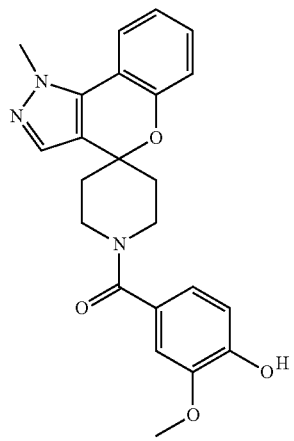
397
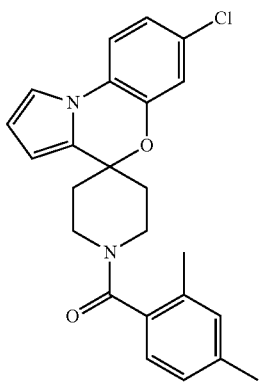 [SMILES: Cc1ccc(C(=O)N2CCC3(CC2)Oc2cc(Cl)ccc2-n2cccc23)c(C)c1]
398
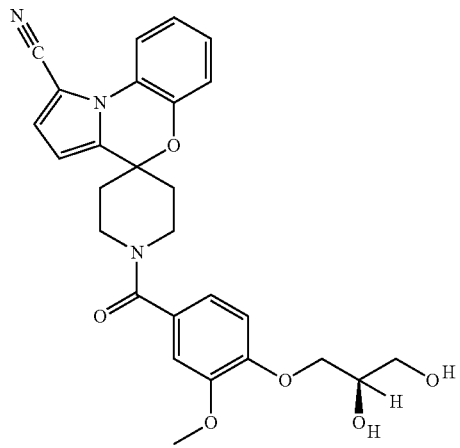
TABLE 1-continued
399
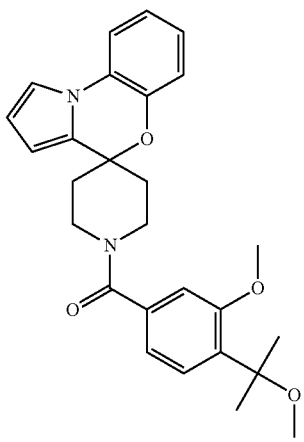 [SMILES: COc1cc(C(=O)N2CCC3(CC2)Oc2ccccc2-n2cccc23)ccc1C(C)(C)OC]
400
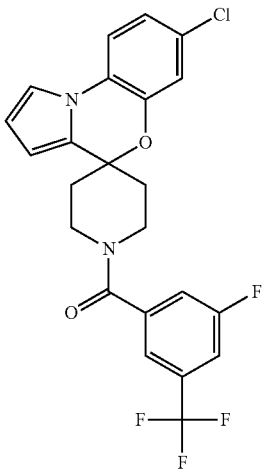 [SMILES: O=C(c1cc(F)cc(C(F)(F)F)c1)N1CCC2(CC1)Oc1cc(Cl)ccc1-n1cccc12]
401
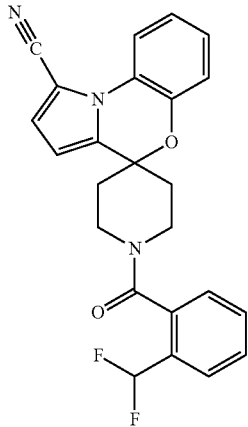

TABLE 1-continued
402
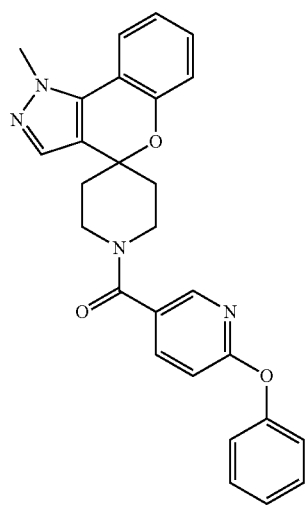 [SMILES: Cn1ncc2c1-c1ccccc1OC21CCN(C(=O)c2ccc(Oc3ccccc3)nc2)CC1]
403
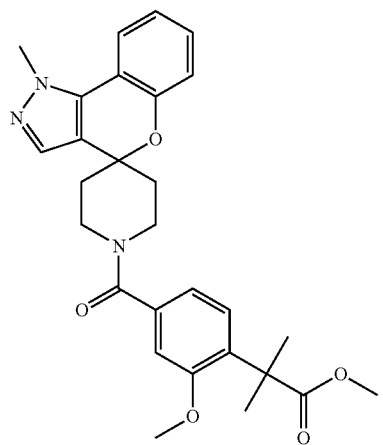 [SMILES: COC(=O)C(C)(C)c1ccc(C(=O)N2CCC3(CC2)Oc2ccccc2-c2c3cnn2C)cc1OC]
404
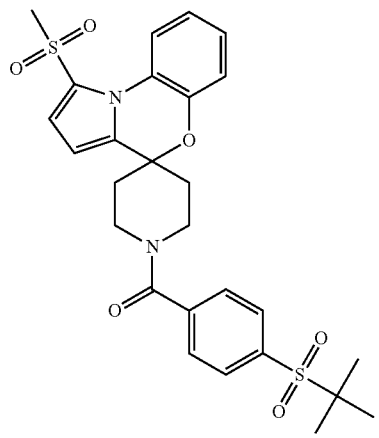 [SMILES: CC(C)(C)S(=O)(=O)c1ccc(C(=O)N2CCC3(CC2)Oc2ccccc2-n2c3ccc2S(C)(=O)=O)cc1]
TABLE 1-continued
405
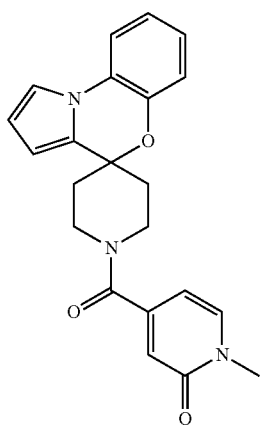 [SMILES: Cn1ccc(C(=O)N2CCC3(CC2)Oc2ccccc2-n2cccc23)cc1=O]
406
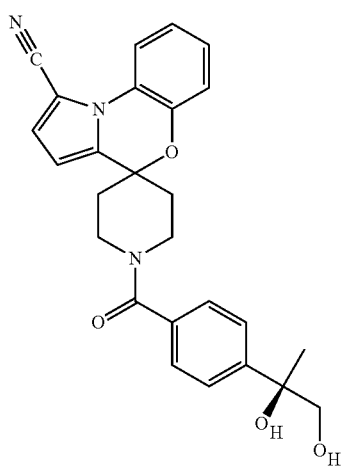
407
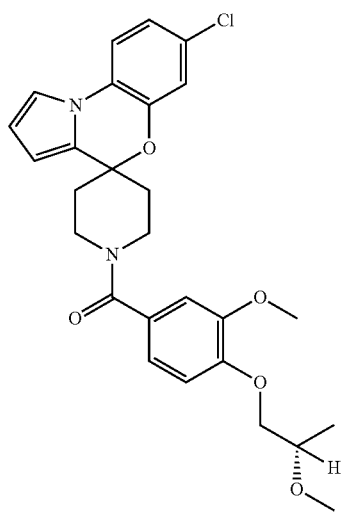 [SMILES: COc1cc(C(=O)N2CCC3(CC2)Oc2cc(Cl)ccc2-n2cccc23)ccc1OC[C@H](C)OC]

TABLE 1-continued
408
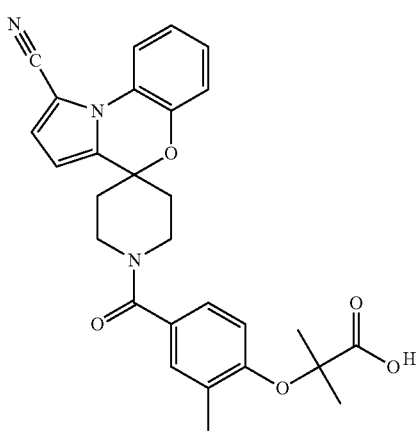
409
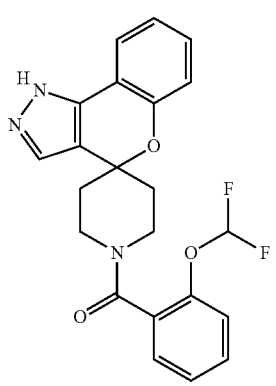
410
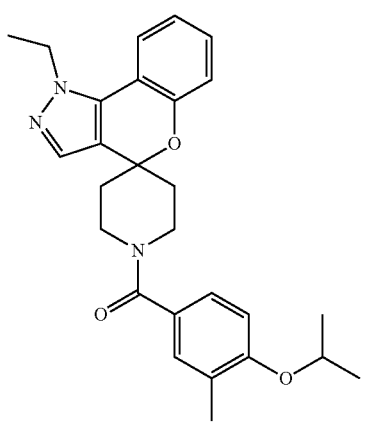 [SMILES: CCn1ncc2c1-c1ccccc1OC21CCN(C(=O)c2ccc(OC(C)C)c(C)c2)CC1]
TABLE 1-continued
411
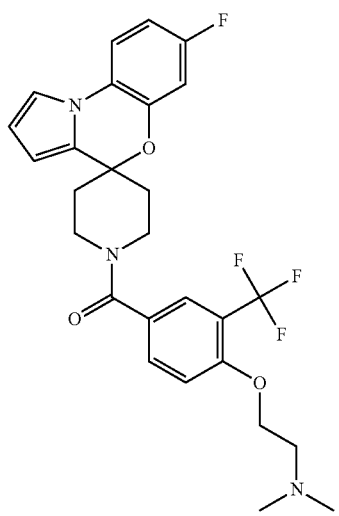 [SMILES: CN(C)CCOc1ccc(C(=O)N2CCC3(CC2)Oc2cc(F)ccc2-n2cccc23)cc1C(F)(F)F]
412
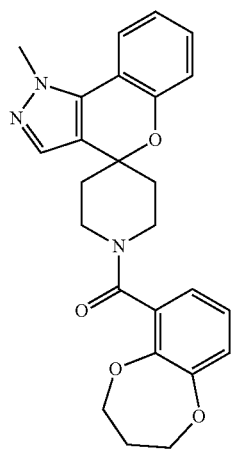 [SMILES: Cn1ncc2c1-c1ccccc1OC21CCN(C(=O)c2cccc3c2OCCCO3)CC1]
413
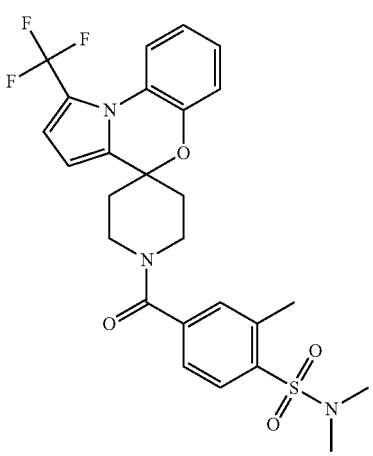 [SMILES: Cc1cc(C(=O)N2CCC3(CC2)Oc2ccccc2-n2c(C(F)(F)F)ccc23)ccc1S(=O)(=O)N(C)C]

TABLE 1-continued
414
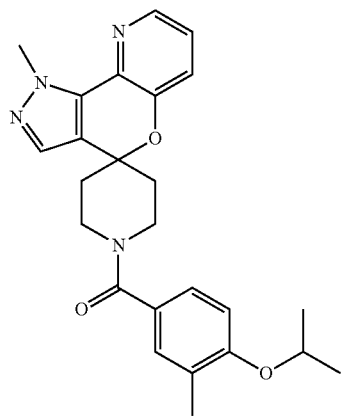 [SMILES: Cc1cc(C(=O)N2CCC3(CC2)Oc2cccnc2-c2c3cnn2C)ccc1OC(C)C]
415
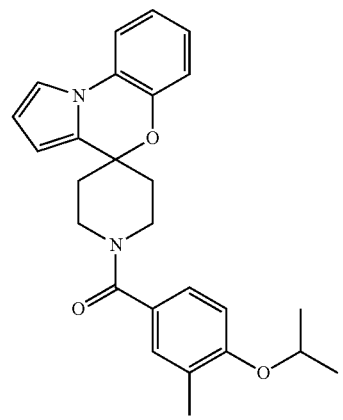 [SMILES: Cc1cc(C(=O)N2CCC3(CC2)Oc2ccccc2-n2cccc23)ccc1OC(C)C]
416
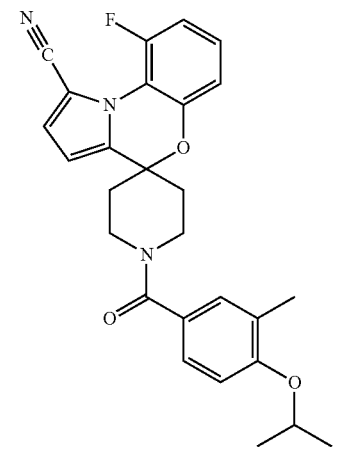 [SMILES: Cc1cc(C(=O)N2CCC3(CC2)Oc2cccc(F)c2-n2c(C#N)ccc23)ccc1OC(C)C]
TABLE 1-continued
417
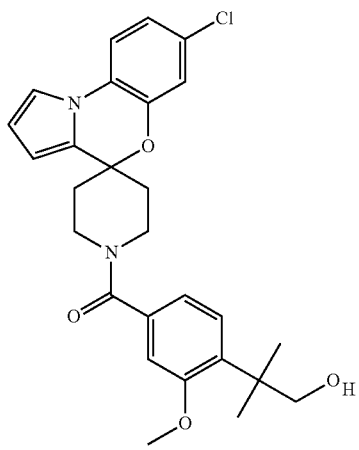
418
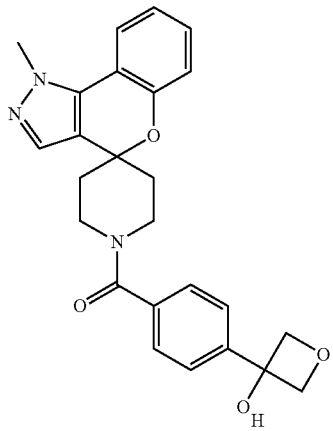
419
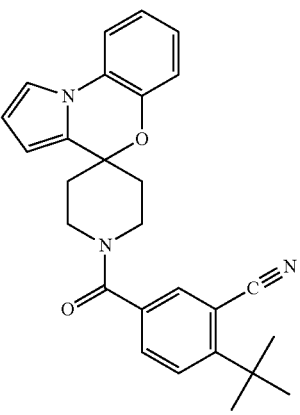

TABLE 1-continued
420
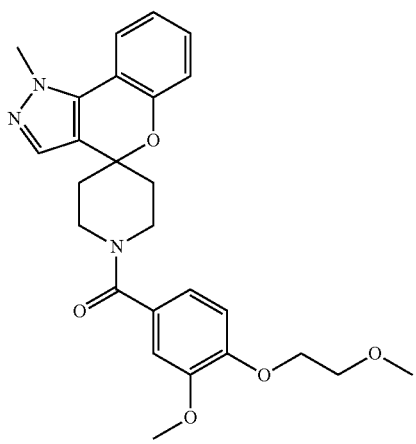 [SMILES: COCCOc1ccc(C(=O)N2CCC3(CC2)Oc2ccccc2-c2c3cnn2C)cc1OC]
421
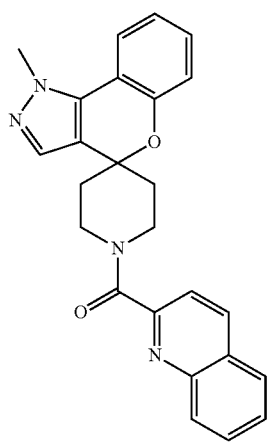
422
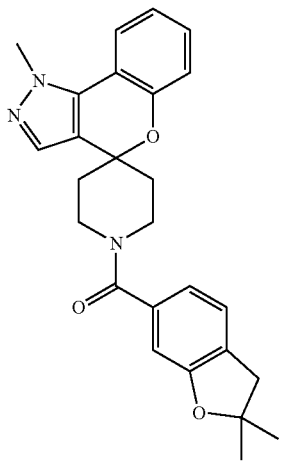 [SMILES: Cn1ncc2c1-c1ccccc1OC21CCN(C(=O)c2ccc3c(c2)OC(C)(C)C3)CC1]
TABLE 1-continued
423
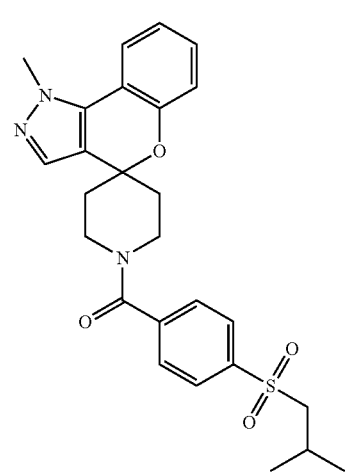 [SMILES: CC(C)CS(=O)(=O)c1ccc(C(=O)N2CCC3(CC2)Oc2ccccc2-c2c3cnn2C)cc1]
424
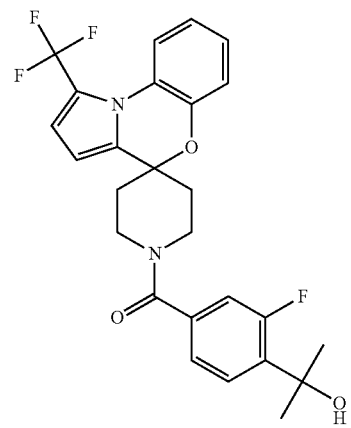 [SMILES: CC(C)(O)c1ccc(C(=O)N2CCC3(CC2)Oc2ccccc2-n2c(C(F)(F)F)ccc23)cc1F]
425
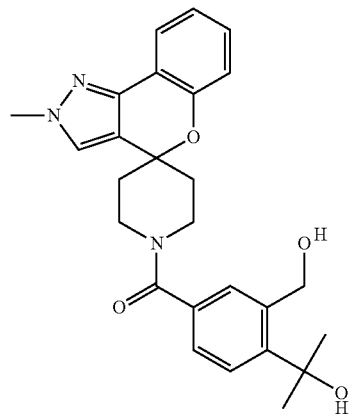

TABLE 1-continued
426
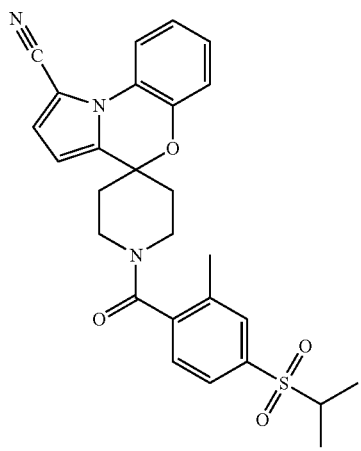 [SMILES: Cc1cc(S(=O)(=O)C(C)C)ccc1C(=O)N1CCC2(CC1)Oc1ccccc1-n1c(C#N)ccc12]
427
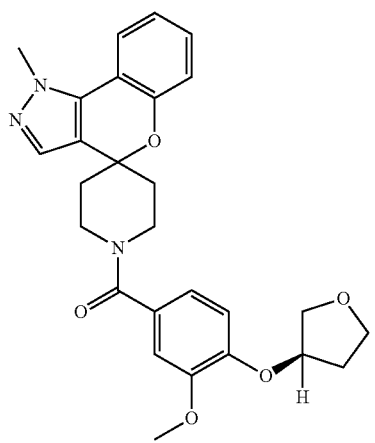 [SMILES: COc1cc(C(=O)N2CCC3(CC2)Oc2ccccc2-c2c3cnn2C)ccc1O[C@@H]1CCOC1]
428
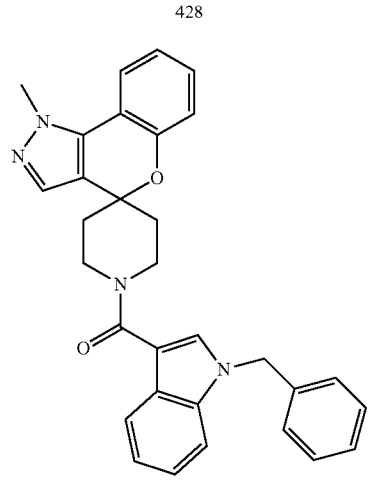
TABLE 1-continued
429
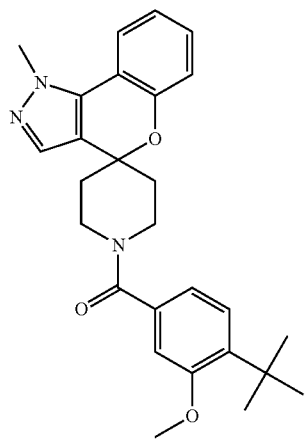 [SMILES: COc1cc(C(=O)N2CCC3(CC2)Oc2ccccc2-c2c3cnn2C)ccc1C(C)(C)C]
430
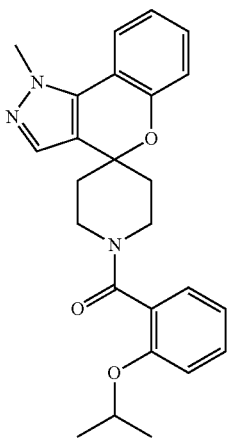 [SMILES: CC(C)Oc1ccccc1C(=O)N1CCC2(CC1)Oc1ccccc1-c1c2cnn1C]
431
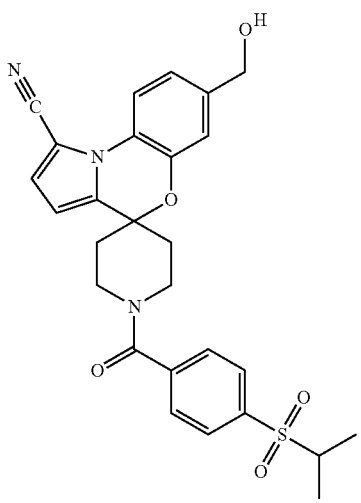

TABLE 1-continued
432
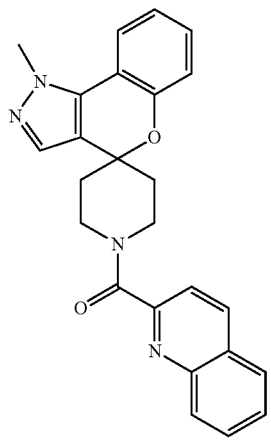 [SMILES: Cn1ncc2c1-c1ccccc1OC21CCN(C(=O)c2ccc3ccccc3n2)CC1]
433
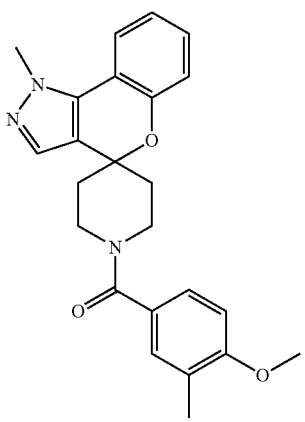 [SMILES: COc1ccc(C(=O)N2CCC3(CC2)Oc2ccccc2-c2c3cnn2C)cc1C]
434
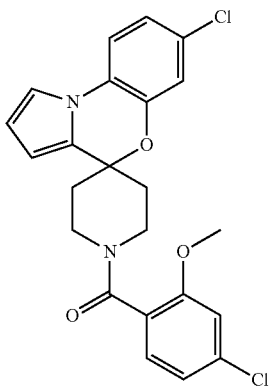 [SMILES: COc1cc(Cl)ccc1C(=O)N1CCC2(CC1)Oc1cc(Cl)ccc1-n1cccc12]
TABLE 1-continued
435
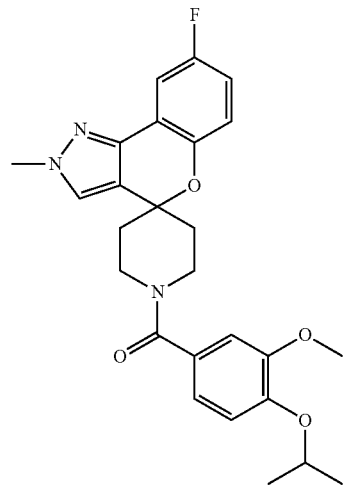
436
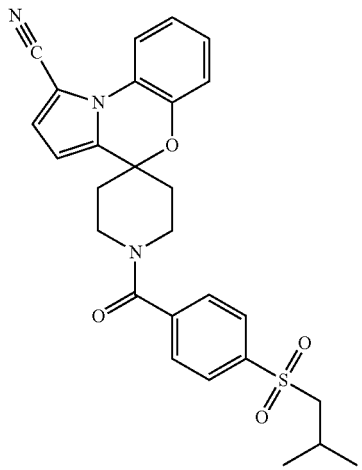 [SMILES: CC(C)CS(=O)(=O)c1ccc(C(=O)N2CCC3(CC2)Oc2ccccc2-n2c(C#N)ccc23)cc1]
437
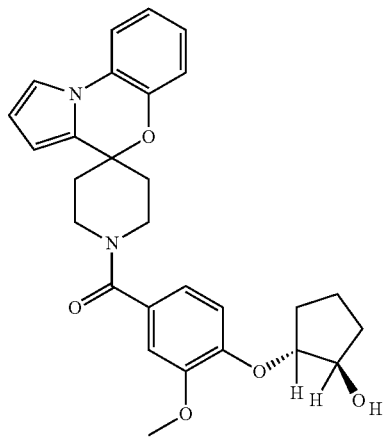

TABLE 1-continued
438
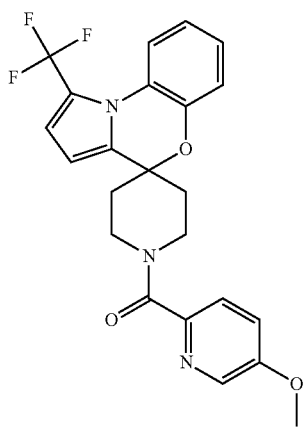 [SMILES: COc1ccc(C(=O)N2CCC3(CC2)Oc2ccccc2-n2c(C(F)(F)F)ccc23)nc1]
439
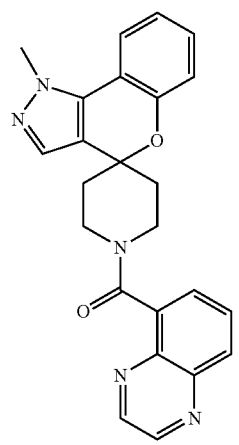 [SMILES: Cn1ncc2c1-c1ccccc1OC21CCN(C(=O)c2cccc3nccnc23)CC1]
440
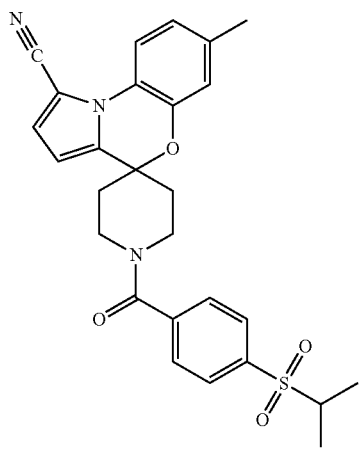 [SMILES: Cc1ccc2c(c1)OC1(CCN(C(=O)c3ccc(S(=O)(=O)C(C)C)cc3)CC1)c1ccc(C#N)n1-2]
TABLE 1-continued
441
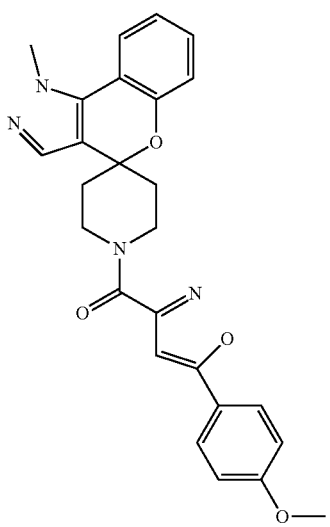 [SMILES: CNC1=C(C=N)C2(CCN(C(=O)C(=N)/C=C(\O)c3ccc(OC)cc3)CC2)Oc2ccccc21]
442
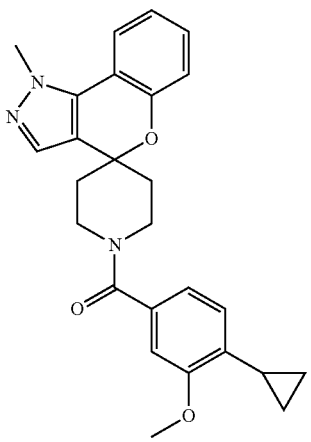 [SMILES: COc1cc(C(=O)N2CCC3(CC2)Oc2ccccc2-c2c3cnn2C)ccc1C1CC1]
443
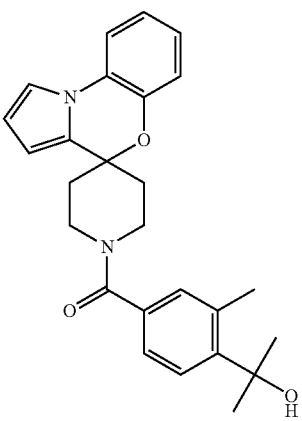 [SMILES: Cc1cc(C(=O)N2CCC3(CC2)Oc2ccccc2-n2cccc23)ccc1C(C)(C)O]

TABLE 1-continued

444

445

446

447

448

449

TABLE 1-continued
450
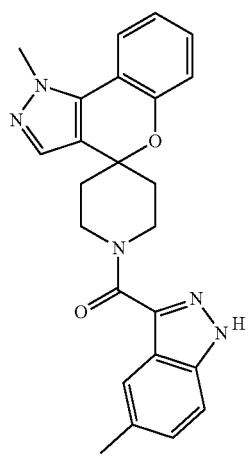
451
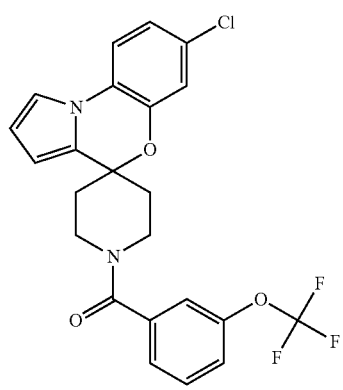 [SMILES: O=C(c1cccc(OC(F)(F)F)c1)N1CCC2(CC1)Oc1cc(Cl)ccc1-n1cccc12]
452
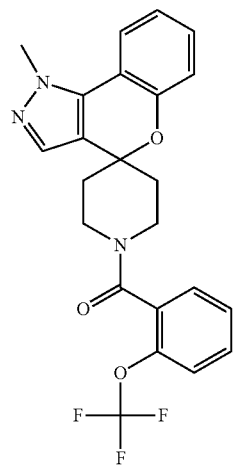 [SMILES: Cn1ncc2c1-c1ccccc1OC21CCN(C(=O)c2ccccc2OC(F)(F)F)CC1]
TABLE 1-continued
453
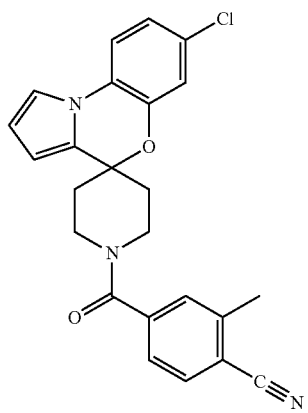
454
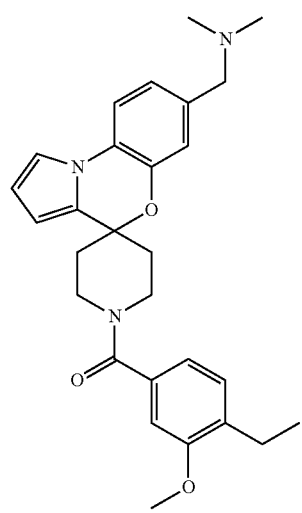 [SMILES: CCc1ccc(C(=O)N2CCC3(CC2)Oc2cc(CN(C)C)ccc2-n2cccc23)cc1OC]
455
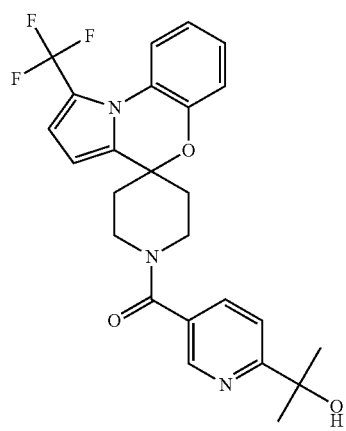 [SMILES: CC(C)(O)c1ccc(C(=O)N2CCC3(CC2)Oc2ccccc2-n2c(C(F)(F)F)ccc23)cn1]

TABLE 1-continued
456
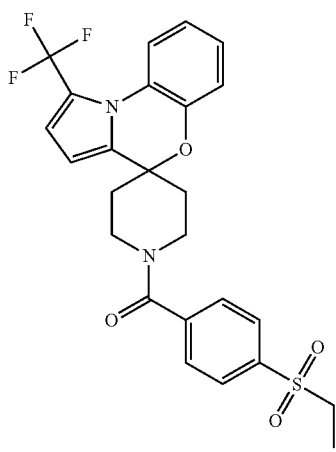 [SMILES: CCS(=O)(=O)c1ccc(C(=O)N2CCC3(CC2)Oc2ccccc2-n2c(C(F)(F)F)ccc23)cc1]
457
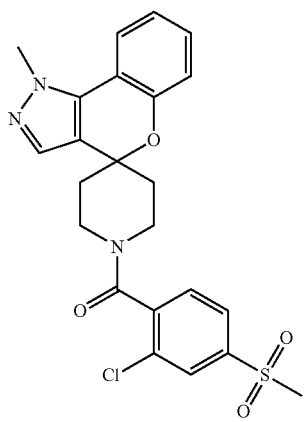 [SMILES: Cn1ncc2c1-c1ccccc1OC21CCN(C(=O)c2ccc(S(C)(=O)=O)cc2Cl)CC1]
458
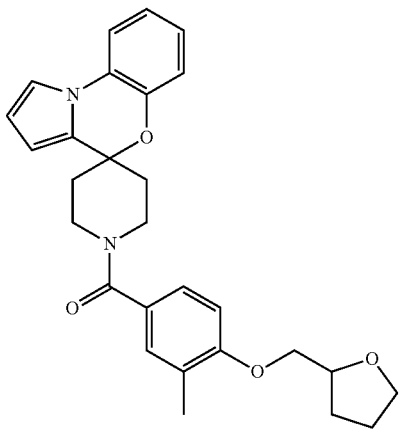 [SMILES: Cc1cc(C(=O)N2CCC3(CC2)Oc2ccccc2-n2cccc23)ccc1OCC1CCCO1]
TABLE 1-continued
459
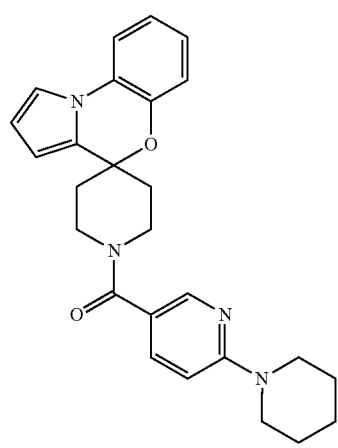 [SMILES: O=C(c1ccc(N2CCCCC2)nc1)N1CCC2(CC1)Oc1ccccc1-n1cccc12]
460
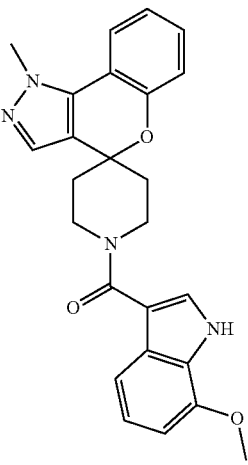 [SMILES: COc1cccc2c(C(=O)N3CCC4(CC3)Oc3ccccc3-c3c4cnn3C)c[nH]c12]
461
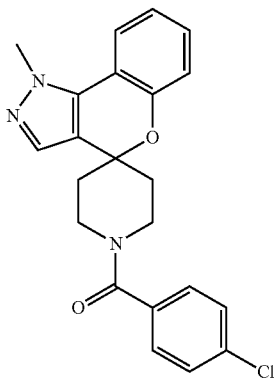 [SMILES: Cn1ncc2c1-c1ccccc1OC21CCN(C(=O)c2ccc(Cl)cc2)CC1]

TABLE 1-continued
462
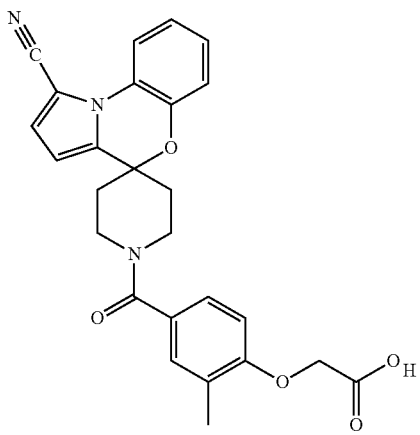
463
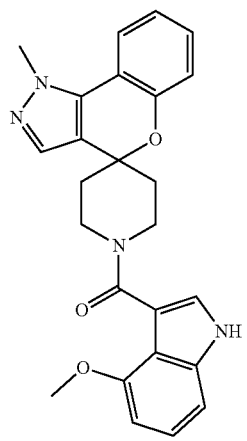 [SMILES: COc1cccc2[nH]cc(C(=O)N3CCC4(CC3)Oc3ccccc3-c3c4cnn3C)c12]
464
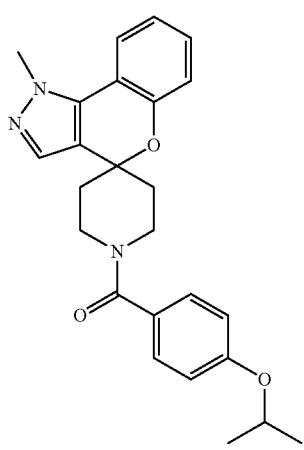 [SMILES: CC(C)Oc1ccc(C(=O)N2CCC3(CC2)Oc2ccccc2-c2c3cnn2C)cc1]
TABLE 1-continued
465
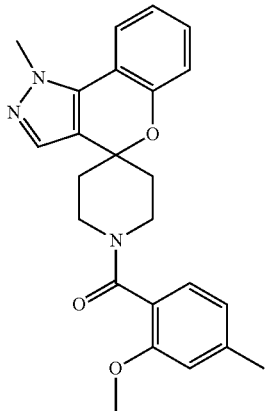 [SMILES: COc1cc(C)ccc1C(=O)N1CCC2(CC1)Oc1ccccc1-c1c2cnn1C]
466
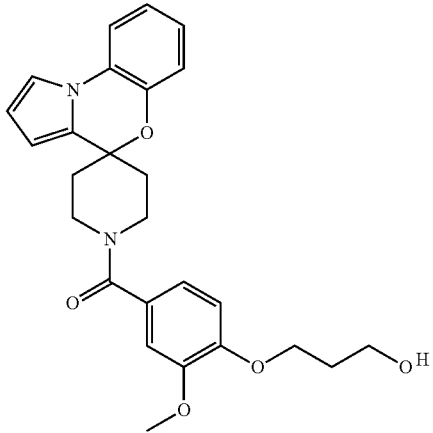
467
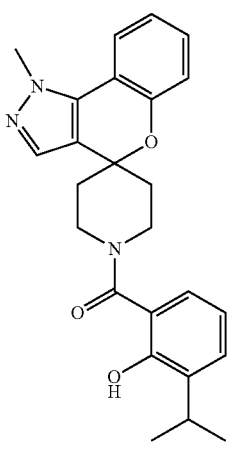 [SMILES: CC(C)c1cccc(C(=O)N2CCC3(CC2)Oc2ccccc2-c2c3cnn2C)c1O]

TABLE 1-continued
468
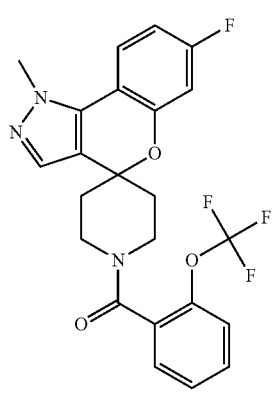 [SMILES: Cn1ncc2c1-c1ccc(F)cc1OC21CCN(C(=O)c2ccccc2OC(F)(F)F)CC1]
469
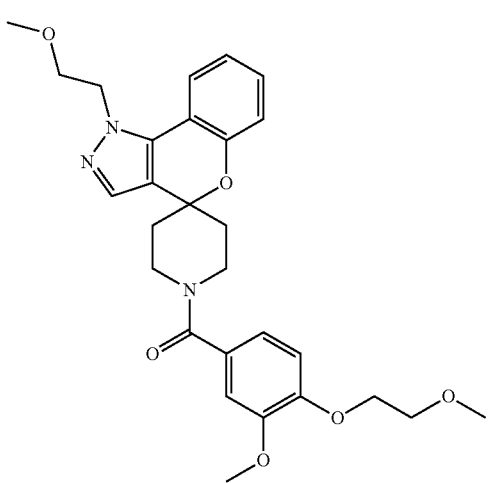
470
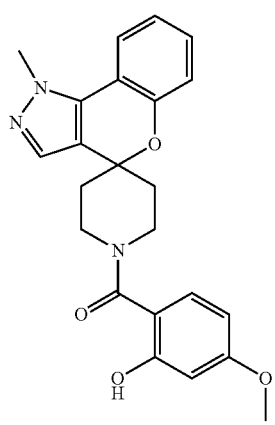 [SMILES: COc1ccc(C(=O)N2CCC3(CC2)Oc2ccccc2-c2c3cnn2C)c(O)c1]
TABLE 1-continued
471
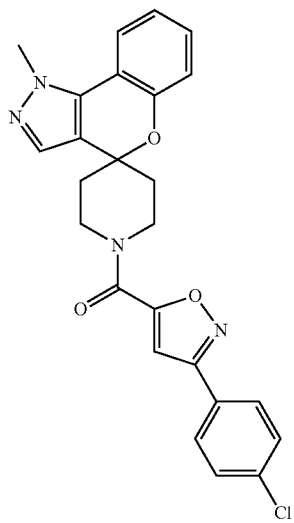 [SMILES: Cn1ncc2c1-c1ccccc1OC21CCN(C(=O)c2cc(-c3ccc(Cl)cc3)no2)CC1]
472
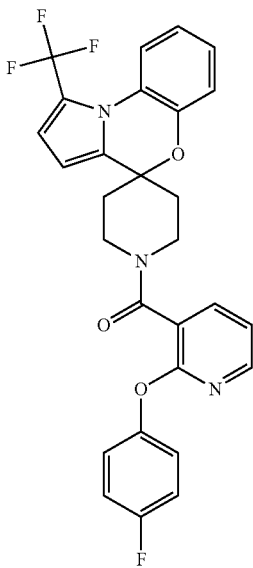 [SMILES: O=C(c1cccnc1Oc1ccc(F)cc1)N1CCC2(CC1)Oc1ccccc1-n1c(C(F)(F)F)ccc12]
473
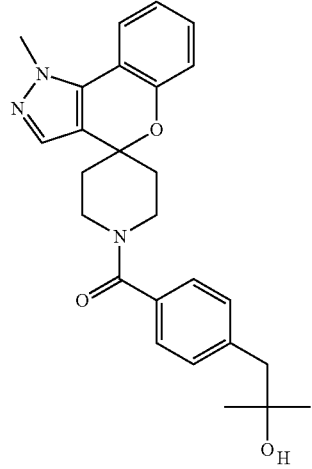

TABLE 1-continued
474
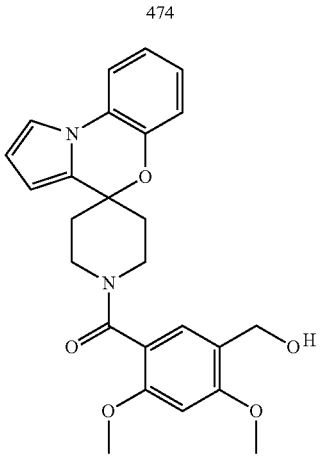
475
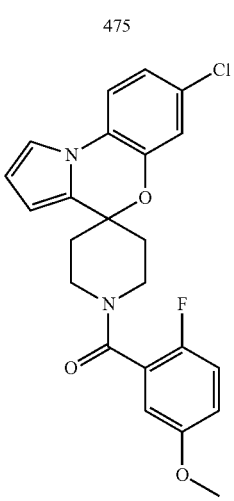
476
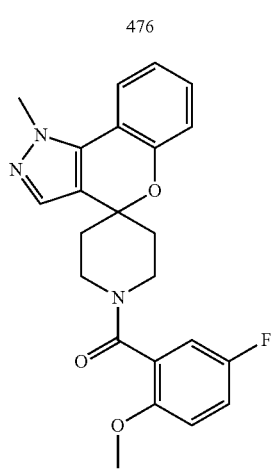
TABLE 1-continued
477
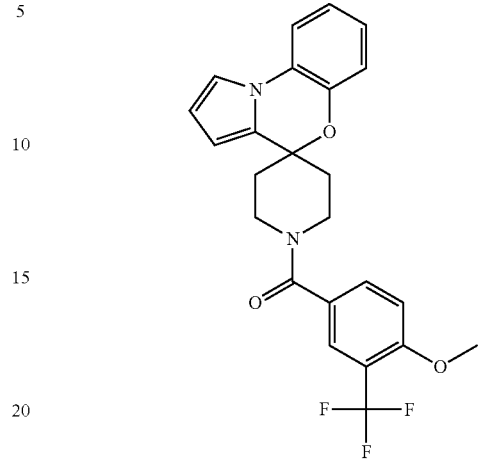
478
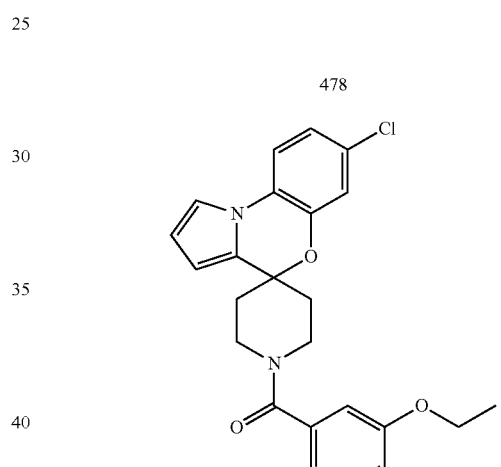
479
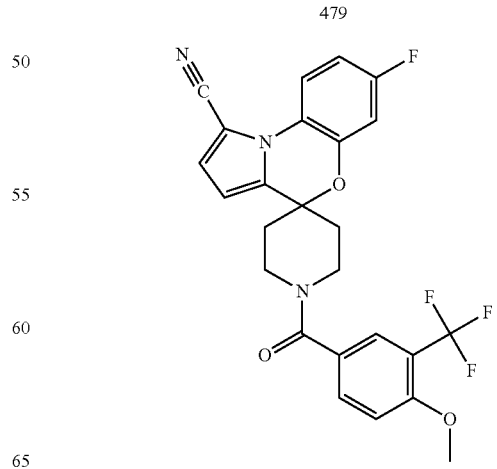

TABLE 1-continued
480
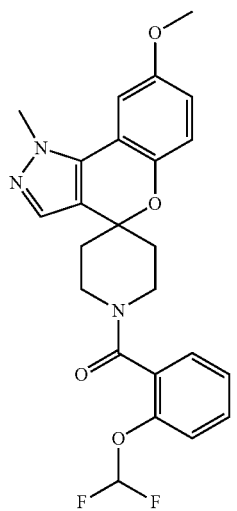 [SMILES: COc1ccc2c(c1)-c1c(cnn1C)C1(CCN(C(=O)c3ccccc3OC(F)F)CC1)O2]
481
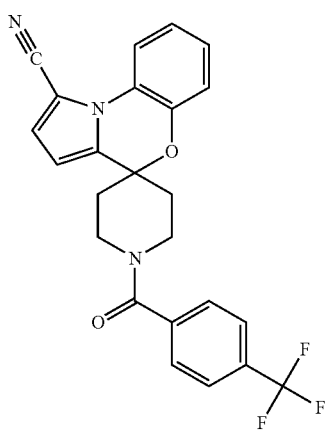 [SMILES: N#Cc1ccc2n1-c1ccccc1OC21CCN(C(=O)c2ccc(C(F)(F)F)cc2)CC1]
482
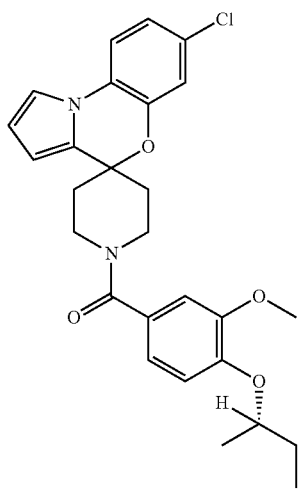 [SMILES: CC[C@H](C)Oc1ccc(C(=O)N2CCC3(CC2)Oc2cc(Cl)ccc2-n2cccc23)cc1OC]
TABLE 1-continued
483
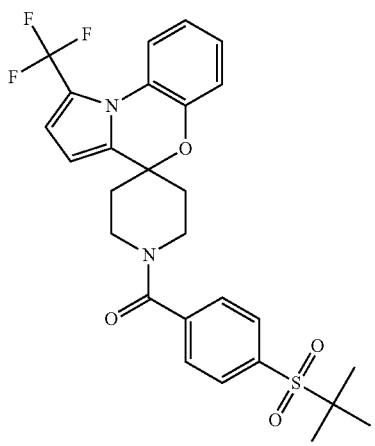 [SMILES: CC(C)(C)S(=O)(=O)c1ccc(C(=O)N2CCC3(CC2)Oc2ccccc2-n2c(C(F)(F)F)ccc23)cc1]
484
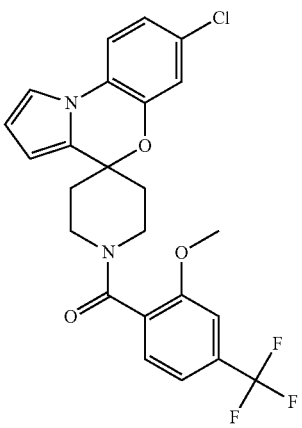 [SMILES: COc1cc(C(F)(F)F)ccc1C(=O)N1CCC2(CC1)Oc1cc(Cl)ccc1-n1cccc12]
485
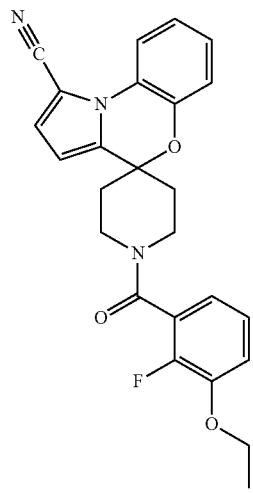 [SMILES: CCOc1cccc(C(=O)N2CCC3(CC2)Oc2ccccc2-n2c(C#N)ccc23)c1F]

TABLE 1-continued
486
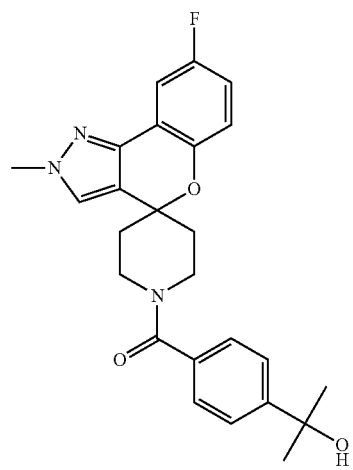 [SMILES: Cn1cc2c(n1)-c1cc(F)ccc1OC21CCN(C(=O)c2ccc(C(C)(C)O)cc2)CC1]
487
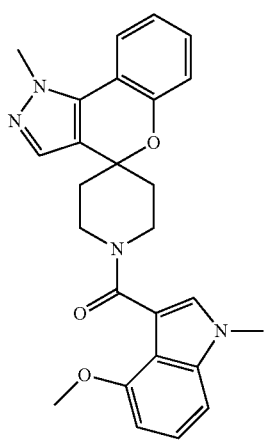 [SMILES: COc1cccc2c1c(C(=O)N1CCC3(CC1)Oc1ccccc1-c1c3cnn1C)cn2C]
488
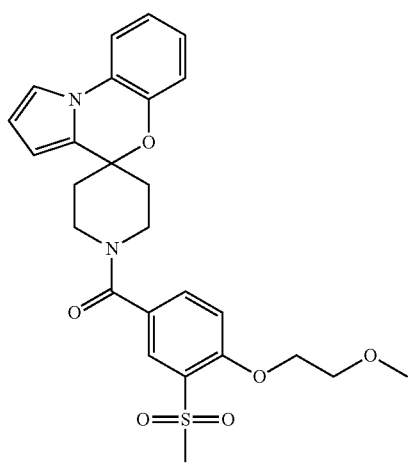 [SMILES: COCCOc1ccc(C(=O)N2CCC3(CC2)Oc2ccccc2-n2cccc23)cc1S(C)(=O)=O]
TABLE 1-continued
489
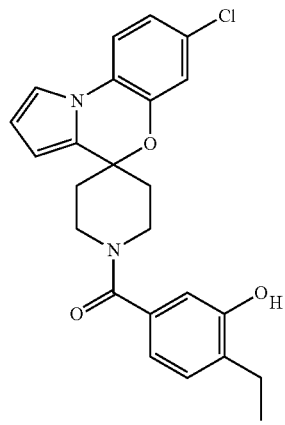
490
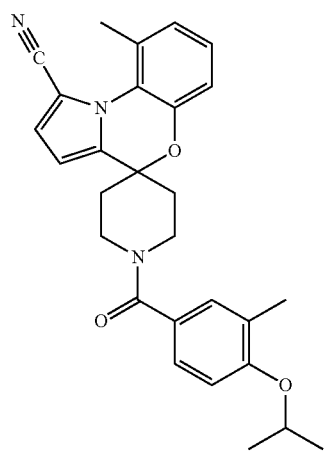 [SMILES: Cc1cc(C(=O)N2CCC3(CC2)Oc2cccc(C)c2-n2c(C#N)ccc23)ccc1OC(C)C]
491
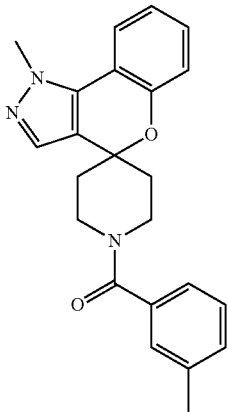 [SMILES: Cc1cccc(C(=O)N2CCC3(CC2)Oc2ccccc2-c2c3cnn2C)c1]

TABLE 1-continued
492
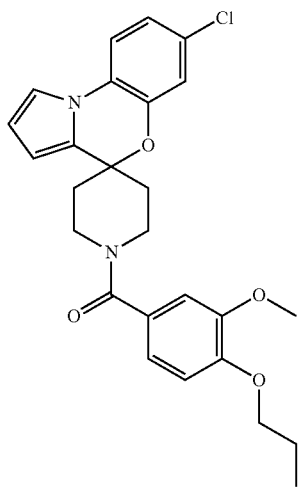 [SMILES: CCCOc1ccc(C(=O)N2CCC3(CC2)Oc2cc(Cl)ccc2-n2cccc23)cc1OC]
493
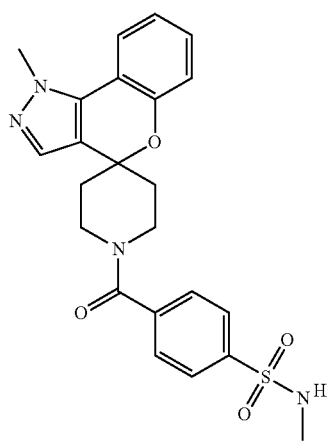
494
495
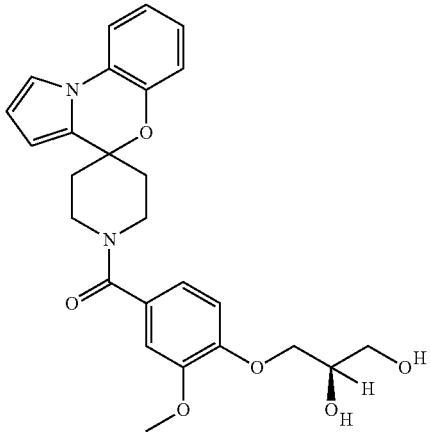
496
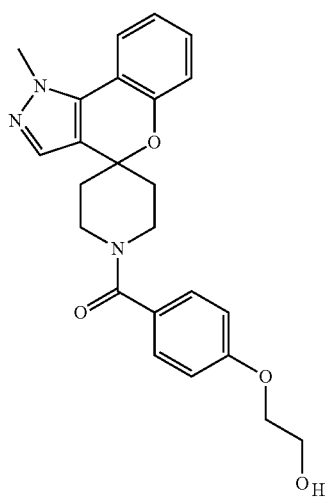
497
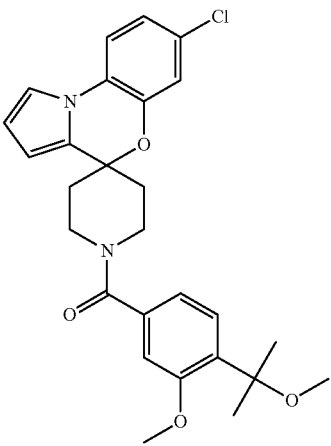

TABLE 1-continued
498
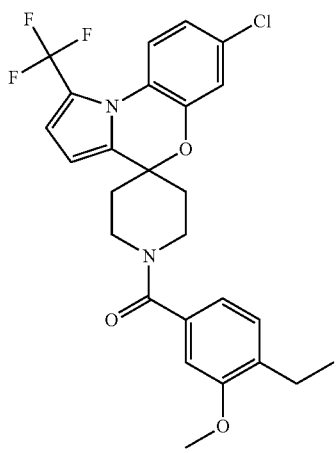 [SMILES: CCc1ccc(C(=O)N2CCC3(CC2)Oc2cc(Cl)ccc2-n2c(C(F)(F)F)ccc23)cc1OC]
499
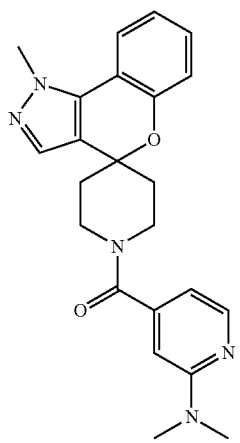 [SMILES: CN(C)c1cc(C(=O)N2CCC3(CC2)Oc2ccccc2-c2c3cnn2C)ccn1]
500
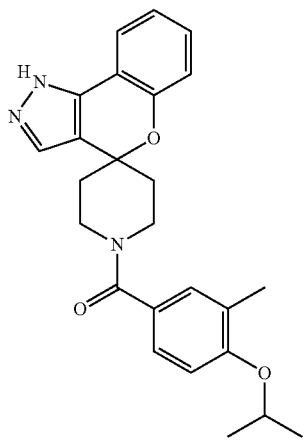
TABLE 1-continued
501
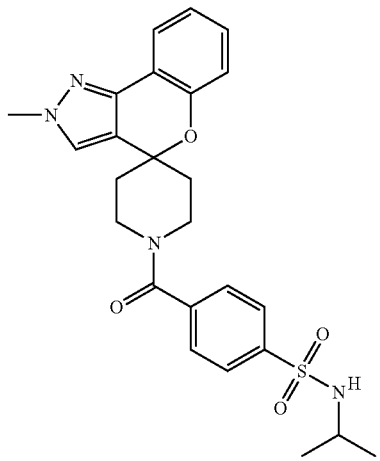
502
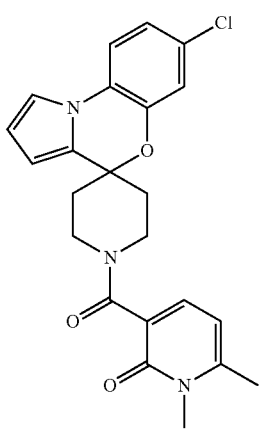 [SMILES: Cc1ccc(C(=O)N2CCC3(CC2)Oc2cc(Cl)ccc2-n2cccc23)c(=O)n1C]
503
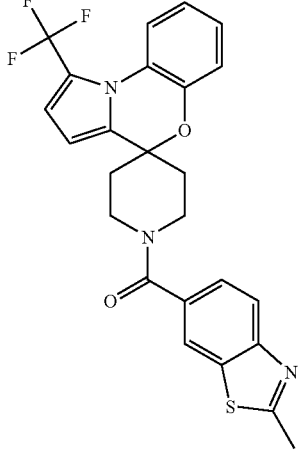

TABLE 1-continued
504
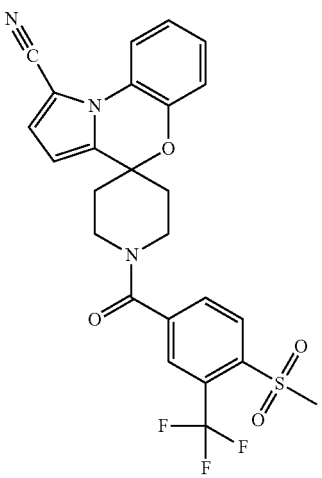 [SMILES: CS(=O)(=O)c1ccc(C(=O)N2CCC3(CC2)Oc2ccccc2-n2c(C#N)ccc23)cc1C(F)(F)F]
505
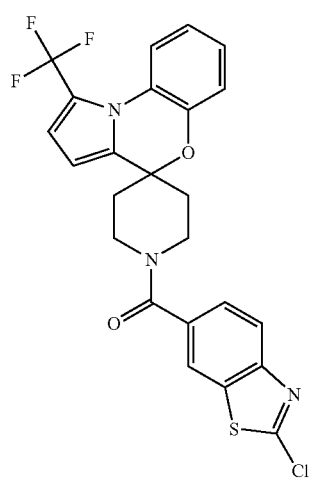 [SMILES: O=C(c1ccc2nc(Cl)sc2c1)N1CCC2(CC1)Oc1ccccc1-n1c(C(F)(F)F)ccc12]
506
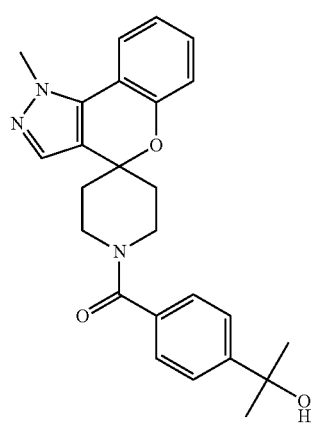 [SMILES: Cn1ncc2c1-c1ccccc1OC21CCN(C(=O)c2ccc(C(C)(C)O)cc2)CC1]
TABLE 1-continued
507
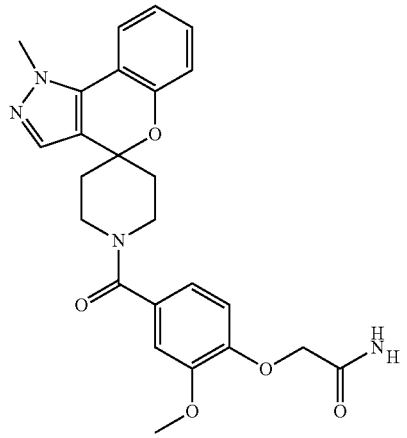
508
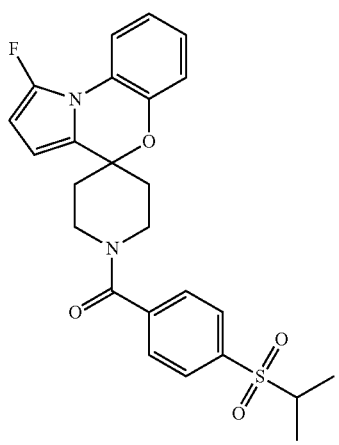 [SMILES: CC(C)S(=O)(=O)c1ccc(C(=O)N2CCC3(CC2)Oc2ccccc2-n2c(F)ccc23)cc1]
509
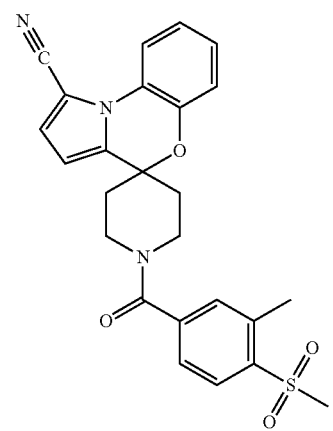 [SMILES: Cc1cc(C(=O)N2CCC3(CC2)Oc2ccccc2-n2c(C#N)ccc23)ccc1S(C)(=O)=O]

TABLE 1-continued
510
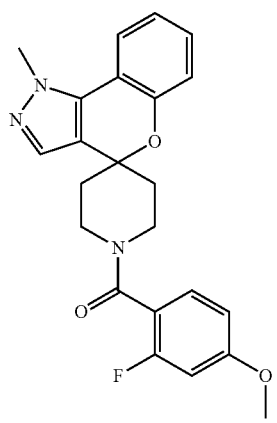 [SMILES: COc1ccc(C(=O)N2CCC3(CC2)Oc2ccccc2-c2c3cnn2C)c(F)c1]
511
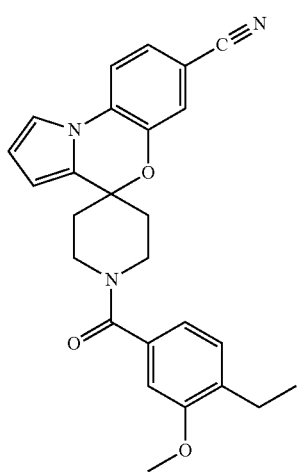 [SMILES: CCc1ccc(C(=O)N2CCC3(CC2)Oc2cc(C#N)ccc2-n2cccc23)cc1OC]
512
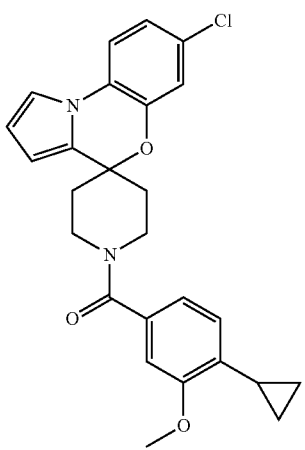 [SMILES: COc1cc(C(=O)N2CCC3(CC2)Oc2cc(Cl)ccc2-n2cccc23)ccc1C1CC1]
TABLE 1-continued
513
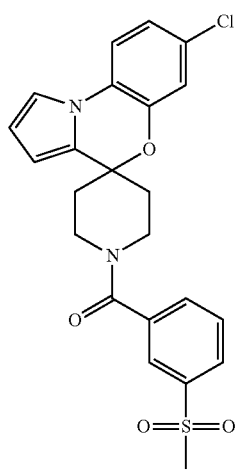 [SMILES: CS(=O)(=O)c1cccc(C(=O)N2CCC3(CC2)Oc2cc(Cl)ccc2-n2cccc23)c1]
514
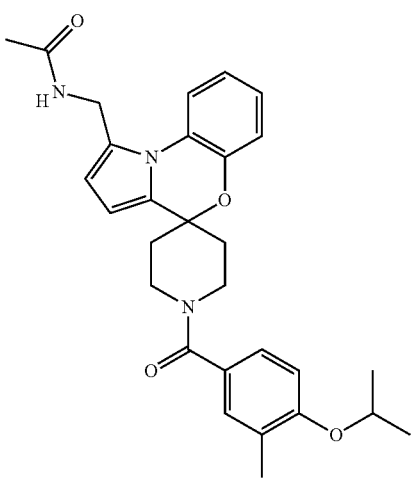
515
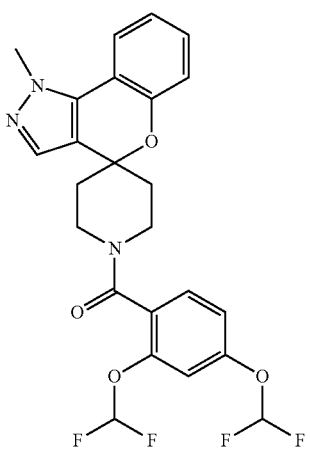 [SMILES: Cn1ncc2c1-c1ccccc1OC21CCN(C(=O)c2ccc(OC(F)F)cc2OC(F)F)CC1]

TABLE 1-continued
516
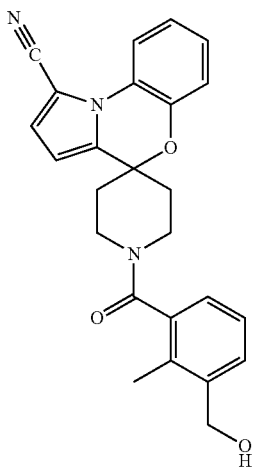 [SMILES: Cc1c(CO)cccc1C(=O)N1CCC2(CC1)Oc1ccccc1-n1c(C#N)ccc12]
517
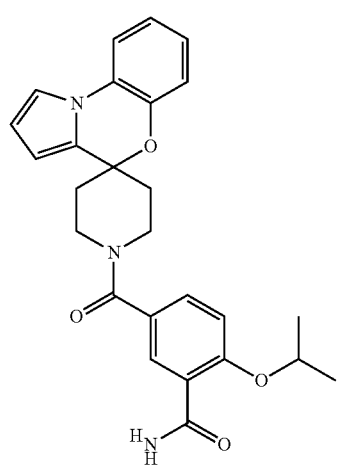
518
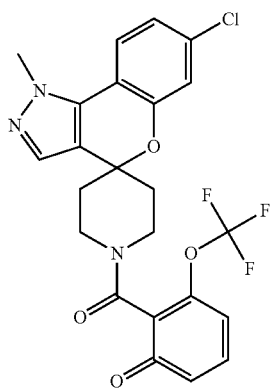
TABLE 1-continued
519
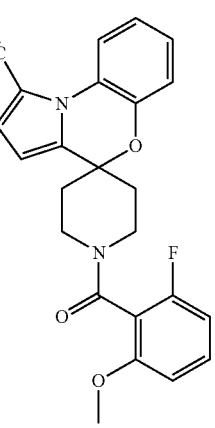
520
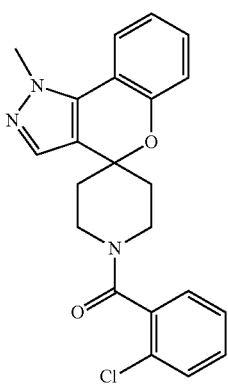 [SMILES: Cn1ncc2c1-c1ccccc1OC21CCN(C(=O)c2ccccc2Cl)CC1]
521
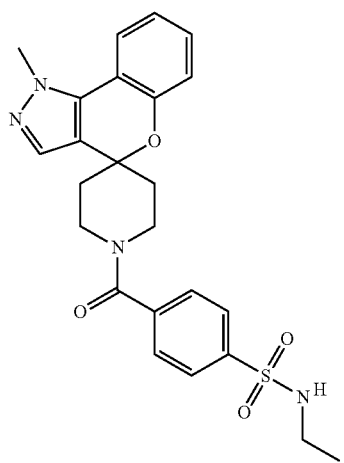

TABLE 1-continued
522
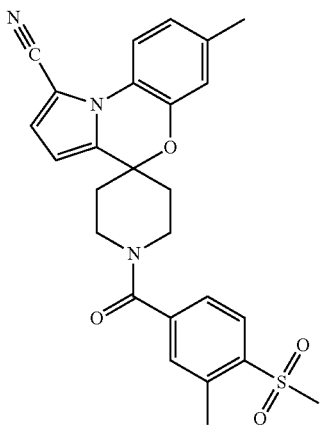 [SMILES: Cc1ccc2c(c1)OC1(CCN(C(=O)c3ccc(S(C)(=O)=O)c(C)c3)CC1)c1ccc(C#N)n1-2]
523
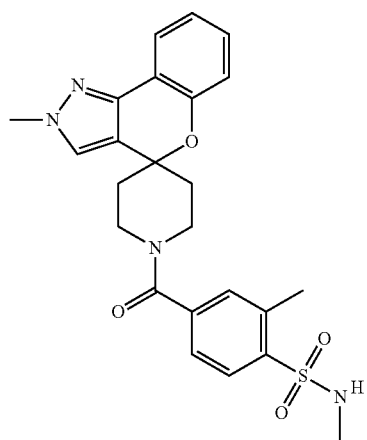
524
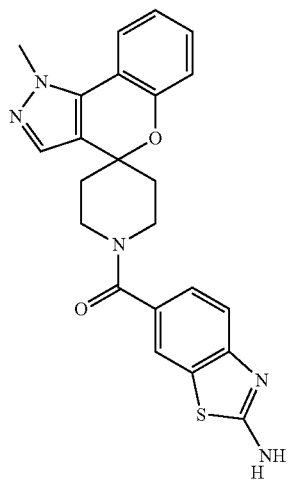
TABLE 1-continued
525
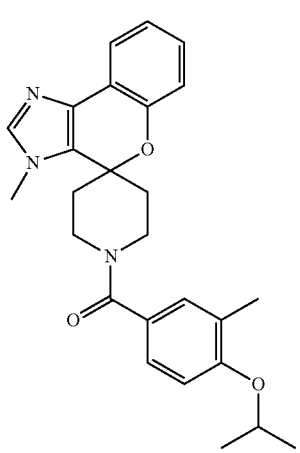 [SMILES: Cc1cc(C(=O)N2CCC3(CC2)Oc2ccccc2-c2ncn(C)c23)ccc1OC(C)C]
526
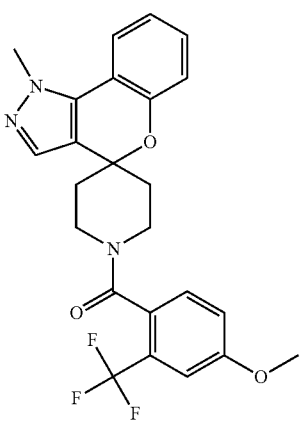 [SMILES: COc1ccc(C(=O)N2CCC3(CC2)Oc2ccccc2-c2c3cnn2C)c(C(F)(F)F)c1]
527
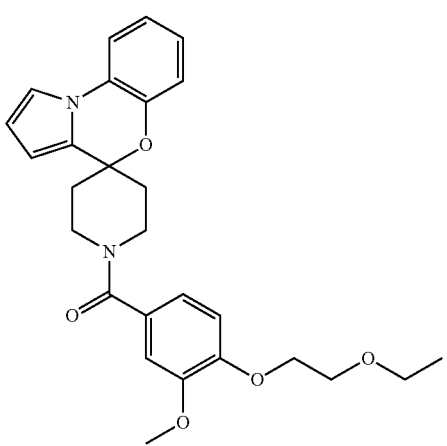 [SMILES: CCOCCOc1ccc(C(=O)N2CCC3(CC2)Oc2ccccc2-n2cccc23)cc1OC]

TABLE 1-continued
528
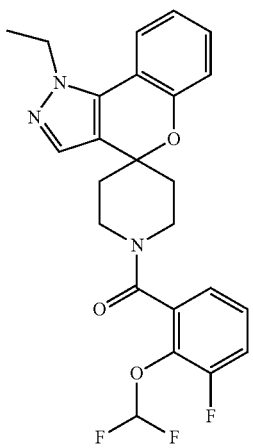 [SMILES: CCn1ncc2c1-c1ccccc1OC21CCN(C(=O)c2cccc(F)c2OC(F)F)CC1]
529
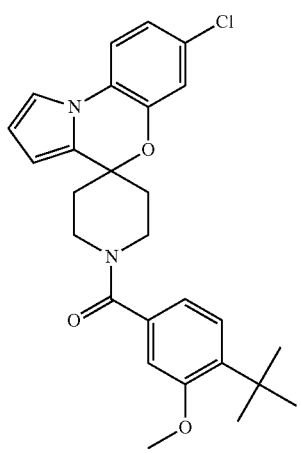 [SMILES: COc1cc(C(=O)N2CCC3(CC2)Oc2cc(Cl)ccc2-n2cccc23)ccc1C(C)(C)C]
530
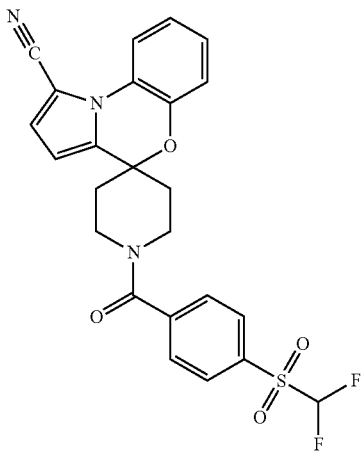 [SMILES: N#Cc1ccc2n1-c1ccccc1OC21CCN(C(=O)c2ccc(S(=O)(=O)C(F)F)cc2)CC1]
TABLE 1-continued
531
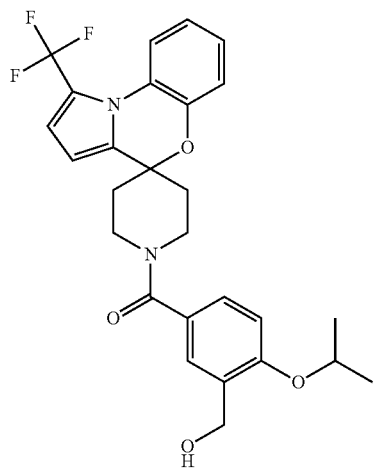 [SMILES: CC(C)Oc1ccc(C(=O)N2CCC3(CC2)Oc2ccccc2-n2c(C(F)(F)F)ccc23)cc1CO]
532
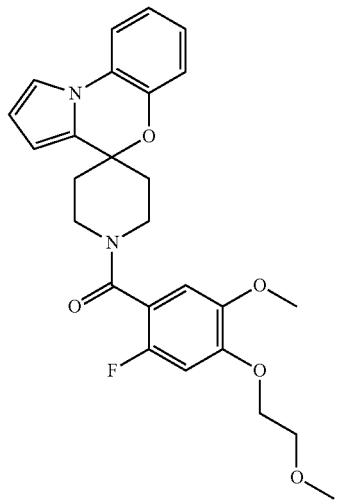 [SMILES: COCCOc1cc(F)c(C(=O)N2CCC3(CC2)Oc2ccccc2-n2cccc23)cc1OC]
533
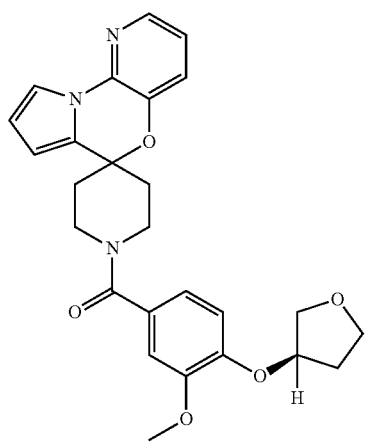 [SMILES: COc1cc(C(=O)N2CCC3(CC2)Oc2cccnc2-n2cccc23)ccc1O[C@@H]1CCOC1]

TABLE 1-continued
534
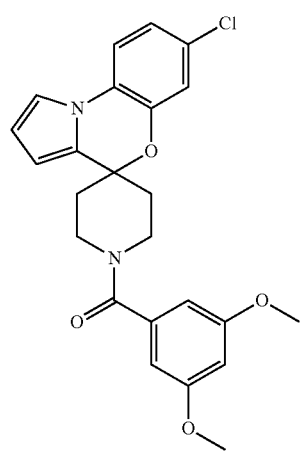
535
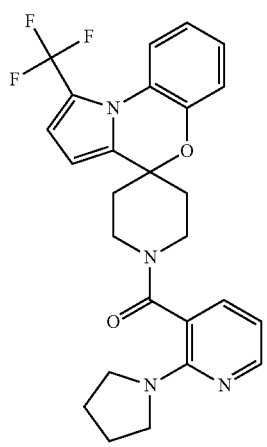 [SMILES: O=C(c1cccnc1N1CCCC1)N1CCC2(CC1)Oc1ccccc1-n1c(C(F)(F)F)ccc12]
536
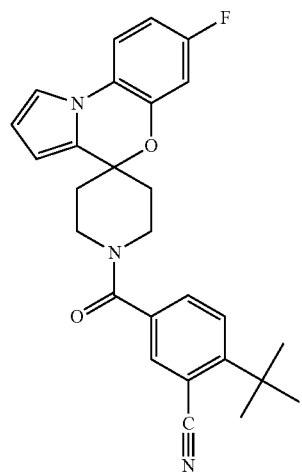 [SMILES: CC(C)(C)c1ccc(C(=O)N2CCC3(CC2)Oc2cc(F)ccc2-n2cccc23)cc1C#N]
TABLE 1-continued
537
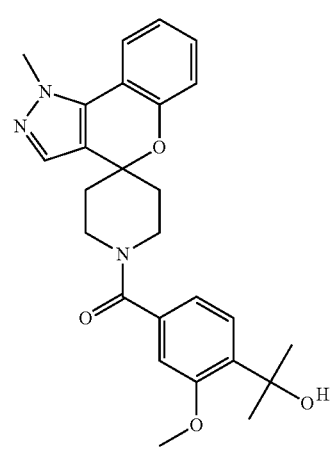
538
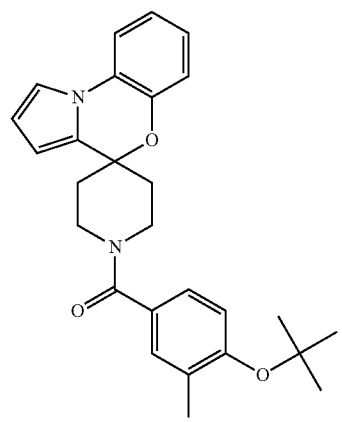 [SMILES: Cc1cc(C(=O)N2CCC3(CC2)Oc2ccccc2-n2cccc23)ccc1OC(C)(C)C]
539
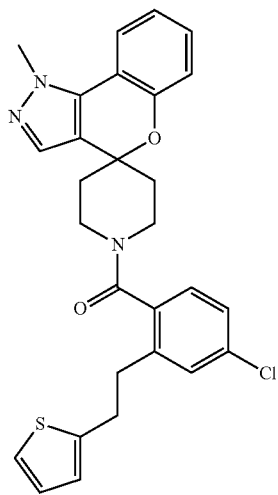 [SMILES: Cn1ncc2c1-c1ccccc1OC21CCN(C(=O)c2ccc(Cl)cc2CCc2cccs2)CC1]

TABLE 1-continued
540
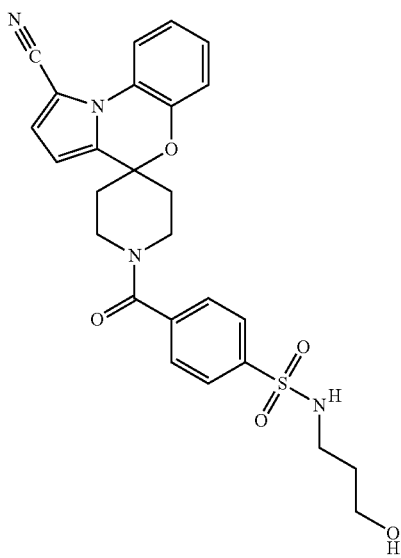
541
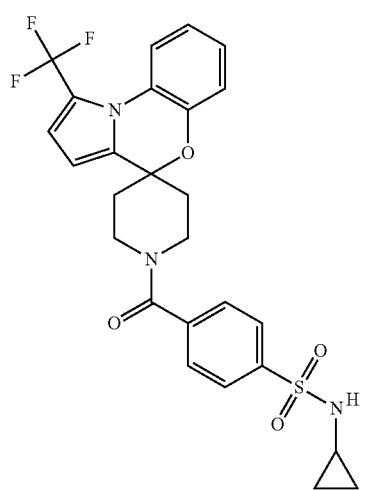
542
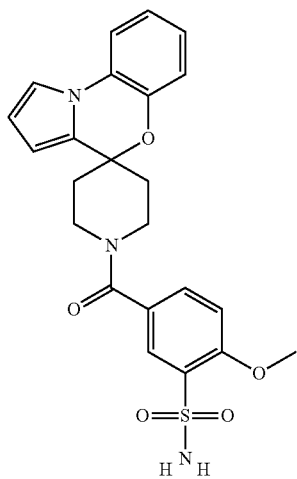
TABLE 1-continued
543
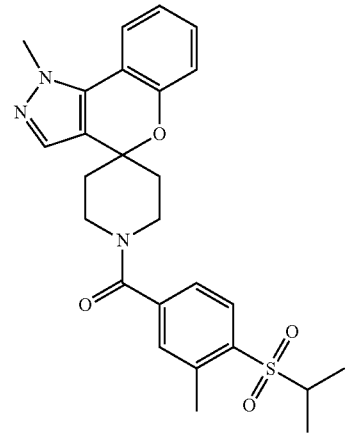 [SMILES: Cc1cc(C(=O)N2CCC3(CC2)Oc2ccccc2-c2c3cnn2C)ccc1S(=O)(=O)C(C)C]
544
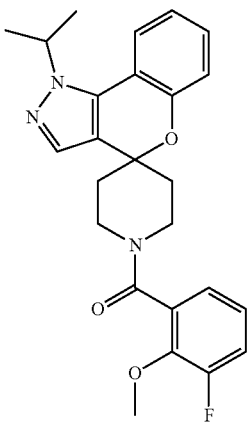 [SMILES: COc1c(F)cccc1C(=O)N1CCC2(CC1)Oc1ccccc1-c1c2cnn1C(C)C]
545
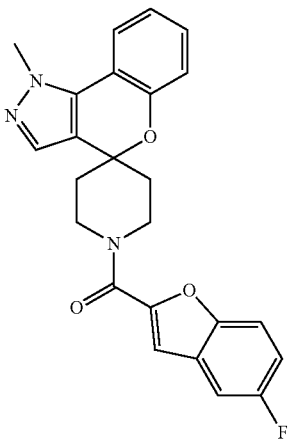 [SMILES: Cn1ncc2c1-c1ccccc1OC21CCN(C(=O)c2cc3cc(F)ccc3o2)CC1]

TABLE 1-continued
546
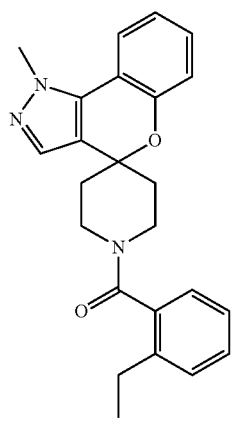 [SMILES: CCc1ccccc1C(=O)N1CCC2(CC1)Oc1ccccc1-c1c2cnn1C]
547
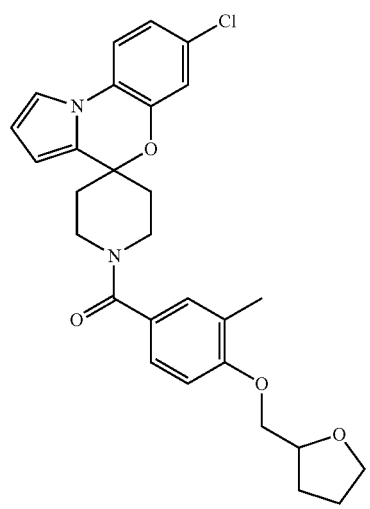 [SMILES: Cc1cc(C(=O)N2CCC3(CC2)Oc2cc(Cl)ccc2-n2cccc23)ccc1OCC1CCCO1]
548
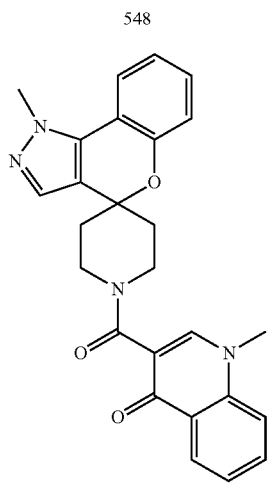
TABLE 1-continued
549
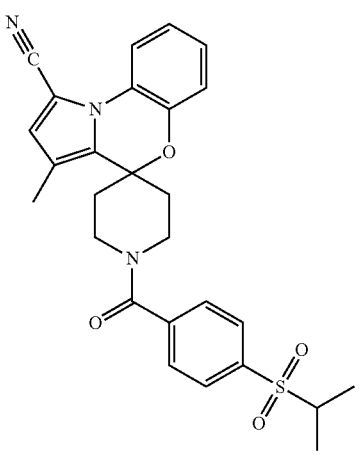 [SMILES: Cc1cc(C#N)n2c1C1(CCN(C(=O)c3ccc(S(=O)(=O)C(C)C)cc3)CC1)Oc1ccccc1-2]
550
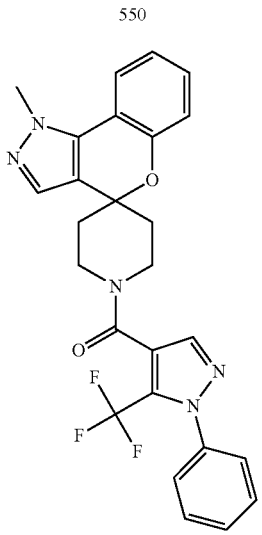
551
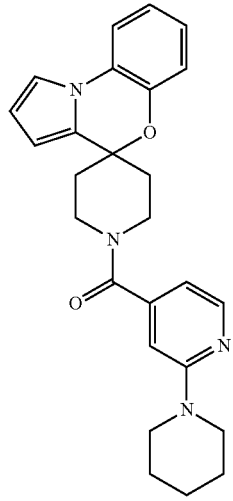 [SMILES: O=C(c1ccnc(N2CCCCC2)c1)N1CCC2(CC1)Oc1ccccc1-n1cccc12]

TABLE 1-continued
552
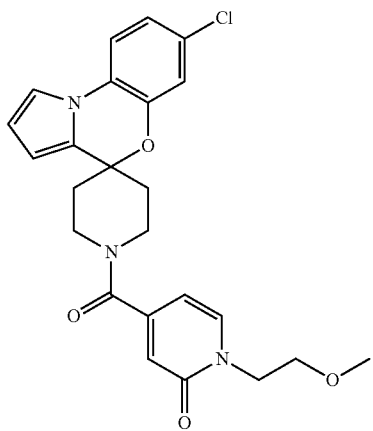 [SMILES: COCCn1ccc(C(=O)N2CCC3(CC2)Oc2cc(Cl)ccc2-n2cccc23)cc1=O]
553
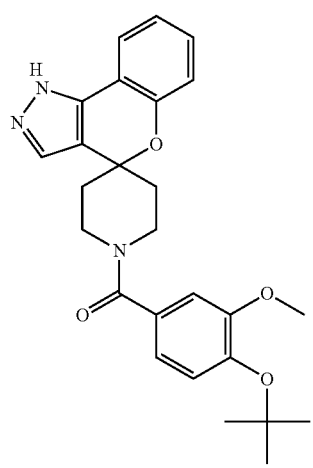
554
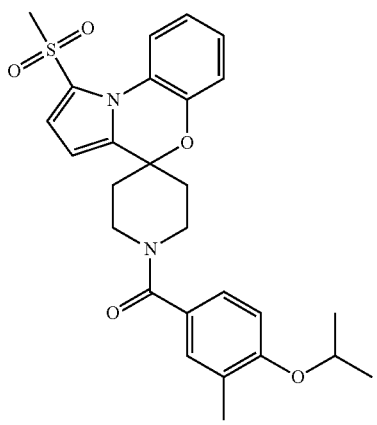 [SMILES: Cc1cc(C(=O)N2CCC3(CC2)Oc2ccccc2-n2c3ccc2S(C)(=O)=O)ccc1OC(C)C]
TABLE 1-continued
555
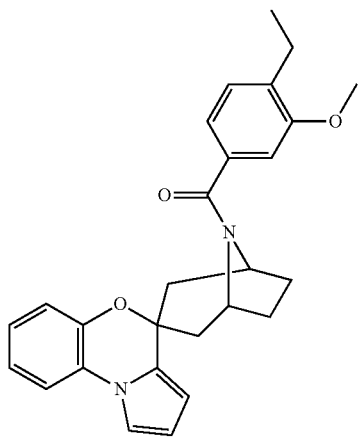 [SMILES: CCc1ccc(C(=O)N2C3CCC2CC2(C3)Oc3ccccc3-n3cccc32)cc1OC]
556
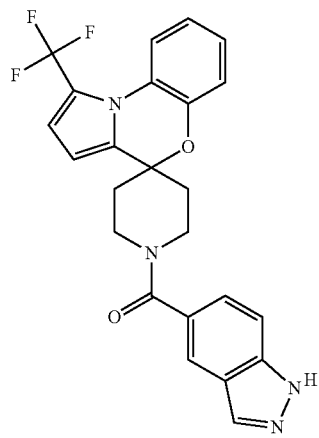
557
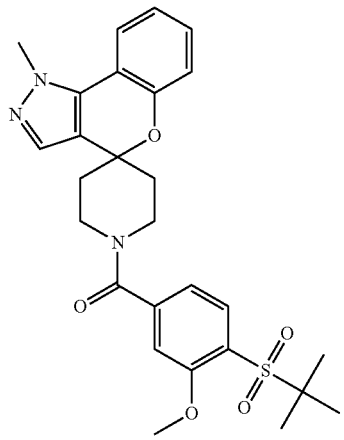 [SMILES: COc1cc(C(=O)N2CCC3(CC2)Oc2ccccc2-c2c3cnn2C)ccc1S(=O)(=O)C(C)(C)C]

277
TABLE 1-continued
558
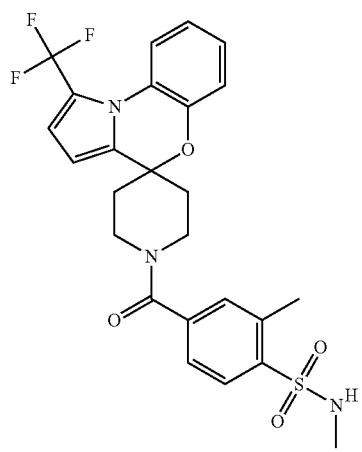
559
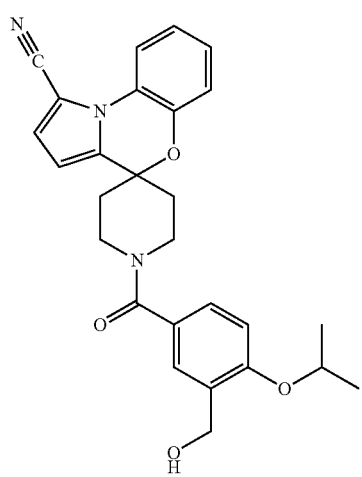 [SMILES: CC(C)Oc1ccc(C(=O)N2CCC3(CC2)Oc2ccccc2-n2c(C#N)ccc23)cc1CO]
560
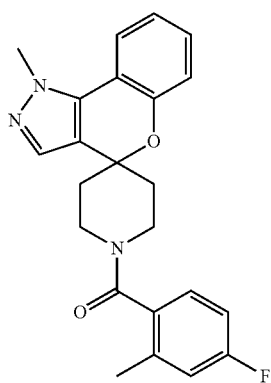 [SMILES: Cc1cc(F)ccc1C(=O)N1CCC2(CC1)Oc1ccccc1-c1c2cnn1C]
278
TABLE 1-continued
561
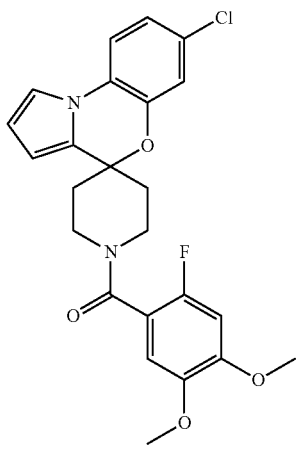
562
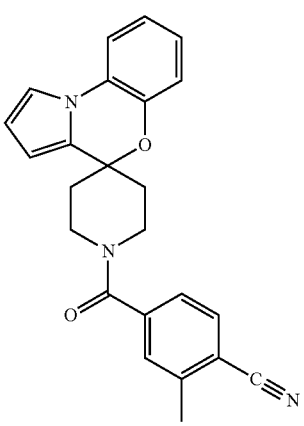 [SMILES: Cc1cc(C(=O)N2CCC3(CC2)Oc2ccccc2-n2cccc23)ccc1C#N]
563
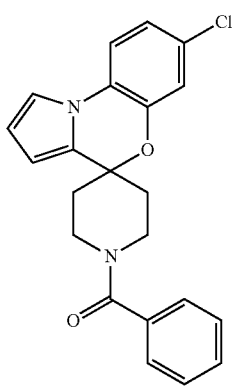 [SMILES: O=C(c1ccccc1)N1CCC2(CC1)Oc1cc(Cl)ccc1-n1cccc12]

TABLE 1-continued
564
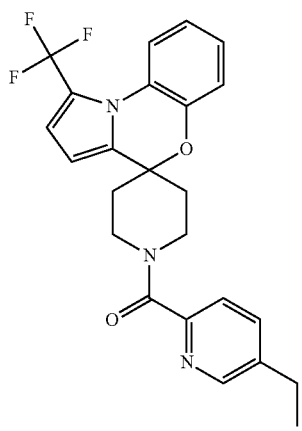 [SMILES: CCc1ccc(C(=O)N2CCC3(CC2)Oc2ccccc2-n2c(C(F)(F)F)ccc23)nc1]
565
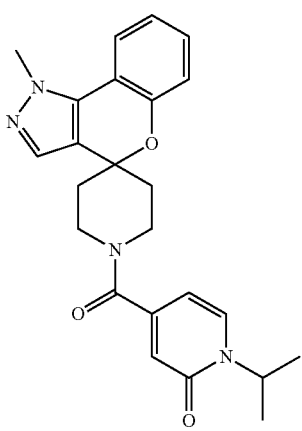 [SMILES: CC(C)n1ccc(C(=O)N2CCC3(CC2)Oc2ccccc2-c2c3cnn2C)cc1=O]
566
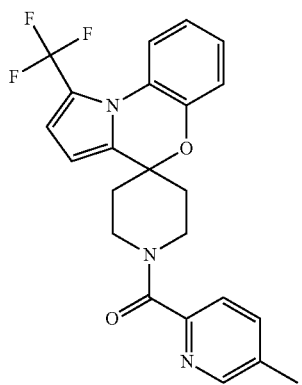 [SMILES: Cc1ccc(C(=O)N2CCC3(CC2)Oc2ccccc2-n2c(C(F)(F)F)ccc23)nc1]
TABLE 1-continued
567
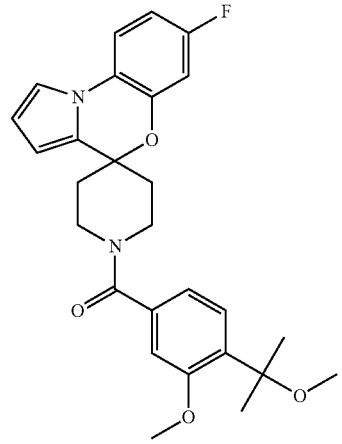 [SMILES: COc1cc(C(=O)N2CCC3(CC2)Oc2cc(F)ccc2-n2cccc23)ccc1C(C)(C)OC]
568
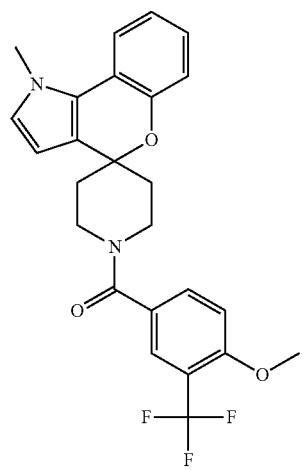 [SMILES: COc1ccc(C(=O)N2CCC3(CC2)Oc2ccccc2-c2c3ccn2C)cc1C(F)(F)F]
569
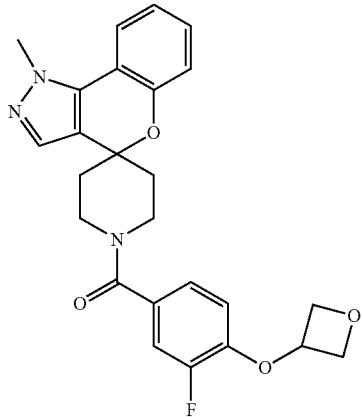 [SMILES: Cn1ncc2c1-c1ccccc1OC21CCN(C(=O)c2ccc(OC3COC3)c(F)c2)CC1]

TABLE 1-continued
570
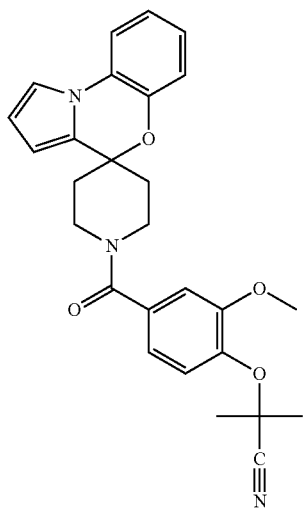 [SMILES: COc1cc(C(=O)N2CCC3(CC2)Oc2ccccc2-n2cccc23)ccc1OC(C)(C)C#N]
571
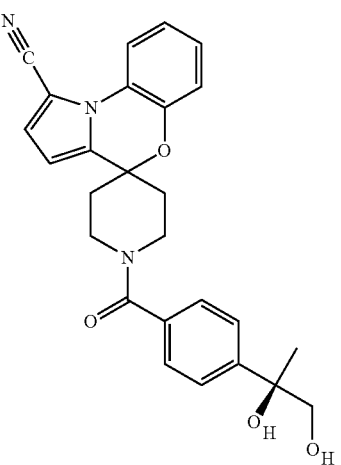
572
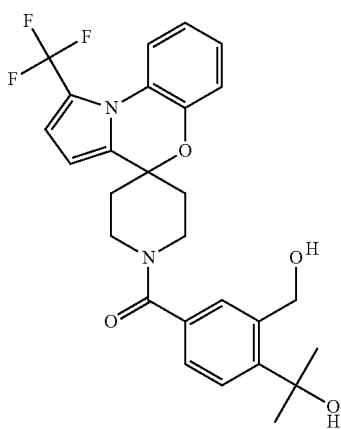
TABLE 1-continued
573
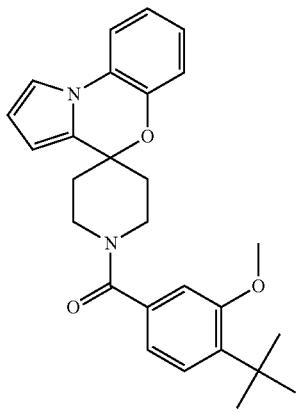
574
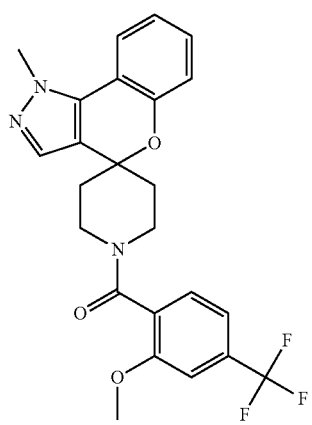 [SMILES: COc1cc(C(F)(F)F)ccc1C(=O)N1CCC2(CC1)Oc1ccccc1-c1c2cnn1C]
575
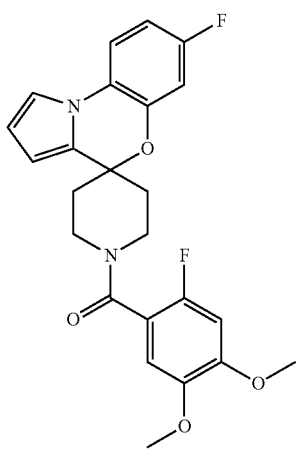

TABLE 1-continued
576
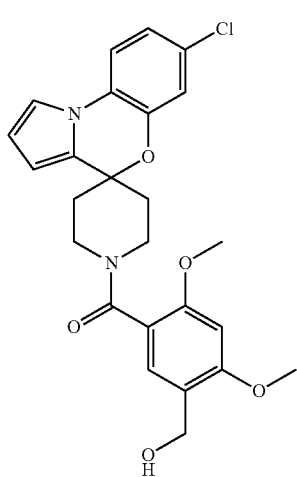 [SMILES: COc1cc(OC)c(C(=O)N2CCC3(CC2)Oc2cc(Cl)ccc2-n2cccc23)cc1CO]
577
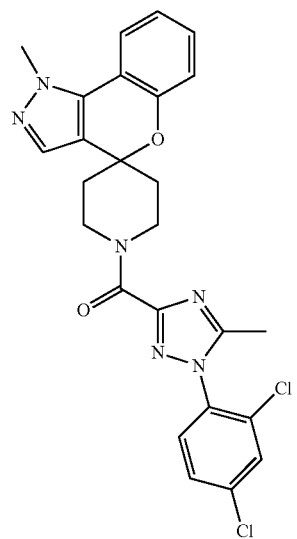 [SMILES: Cc1nc(C(=O)N2CCC3(CC2)Oc2ccccc2-c2c3cnn2C)nn1-c1ccc(Cl)cc1Cl]
578
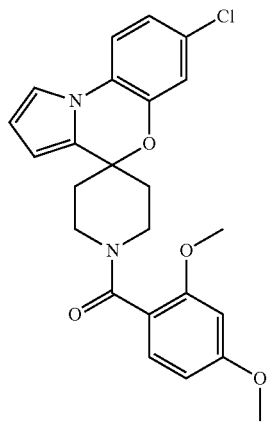 [SMILES: COc1ccc(C(=O)N2CCC3(CC2)Oc2cc(Cl)ccc2-n2cccc23)c(OC)c1]
TABLE 1-continued
579
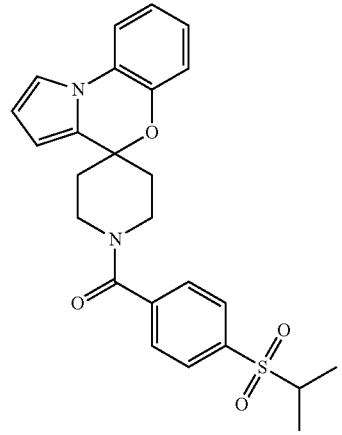
580
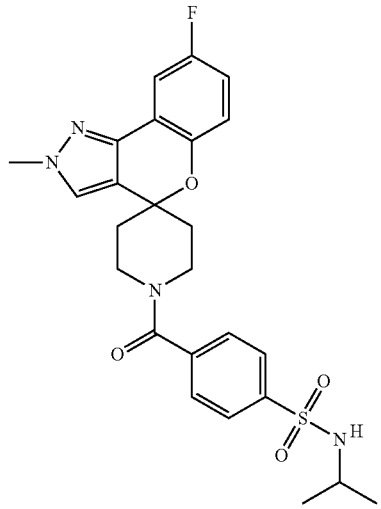
581
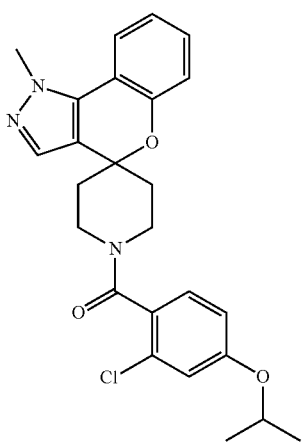

TABLE 1-continued
582
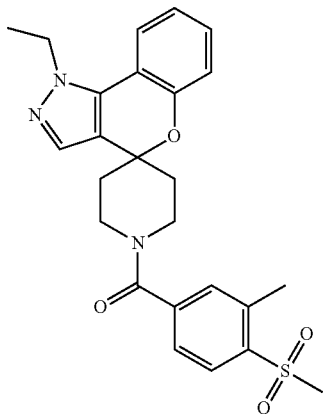 [SMILES: CCn1ncc2c1-c1ccccc1OC21CCN(C(=O)c2ccc(S(C)(=O)=O)c(C)c2)CC1]
583
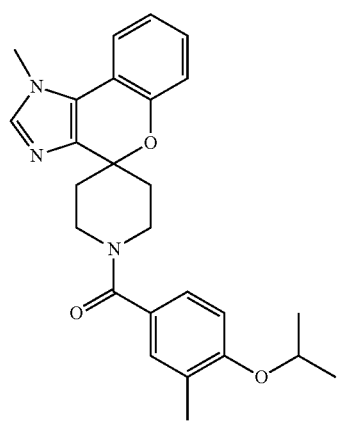 [SMILES: Cc1cc(C(=O)N2CCC3(CC2)Oc2ccccc2-c2c3ncn2C)ccc1OC(C)C]
584
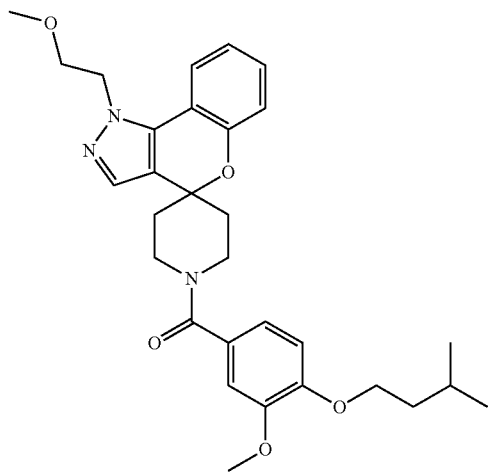 [SMILES: COCCn1ncc2c1-c1ccccc1OC21CCN(C(=O)c2ccc(OCCC(C)C)c(OC)c2)CC1]
TABLE 1-continued
585
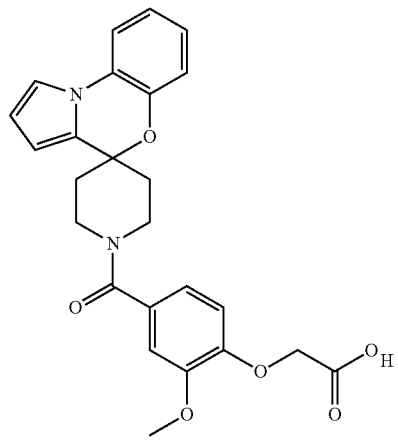
586
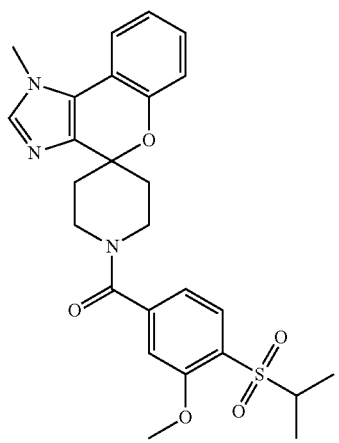 [SMILES: COc1cc(C(=O)N2CCC3(CC2)Oc2ccccc2-c2c3ncn2C)ccc1S(=O)(=O)C(C)C]
587
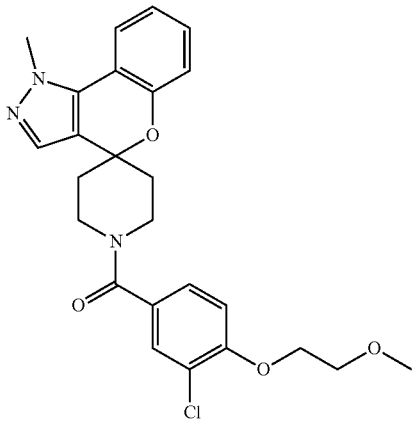 [SMILES: COCCOc1ccc(C(=O)N2CCC3(CC2)Oc2ccccc2-c2c3cnn2C)cc1Cl]

TABLE 1-continued
588
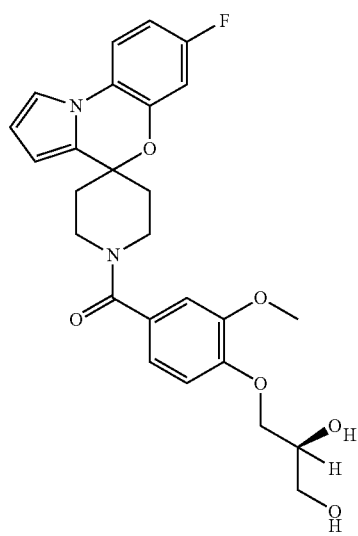
589
591
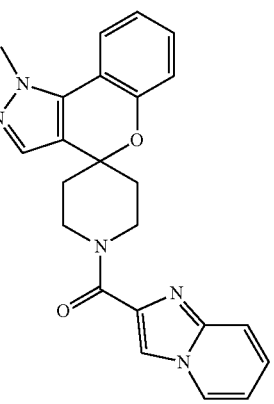
592
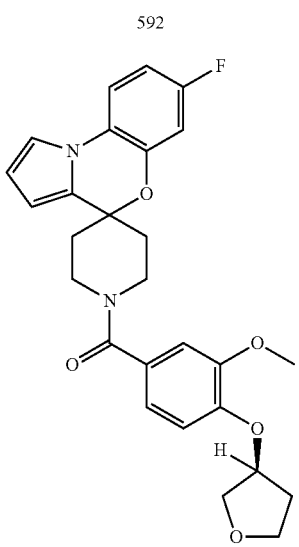
590
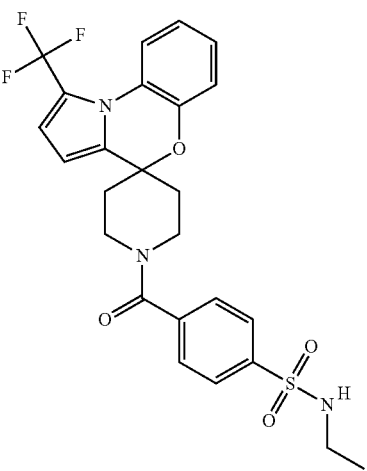
593
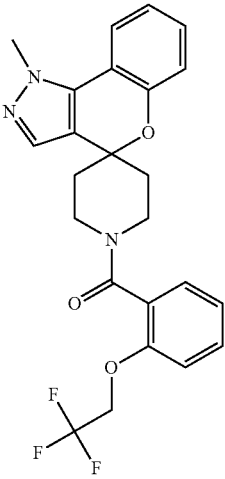 [SMILES: Cn1ncc2c1-c1ccccc1OC21CCN(C(=O)c2ccccc2OCC(F)(F)F)CC1]

TABLE 1-continued
594
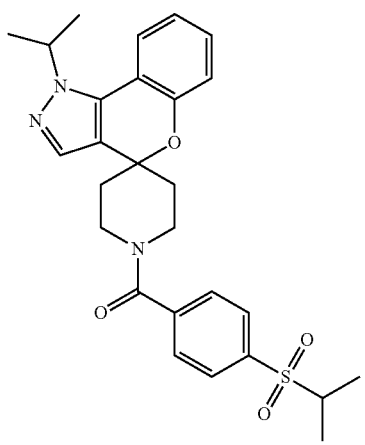 [SMILES: CC(C)n1ncc2c1-c1ccccc1OC21CCN(C(=O)c2ccc(S(=O)(=O)C(C)C)cc2)CC1]
595
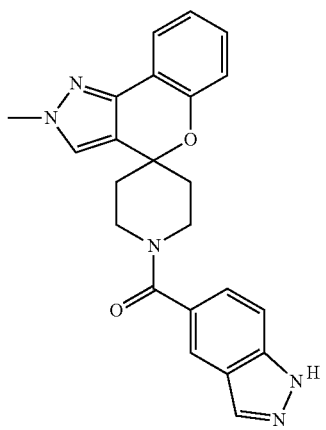
596
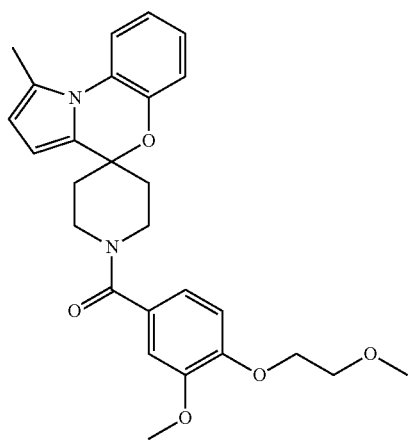 [SMILES: COCCOc1ccc(C(=O)N2CCC3(CC2)Oc2ccccc2-n2c(C)ccc23)cc1OC]
TABLE 1-continued
597
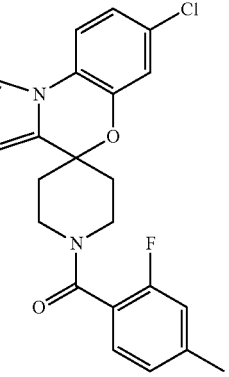
598
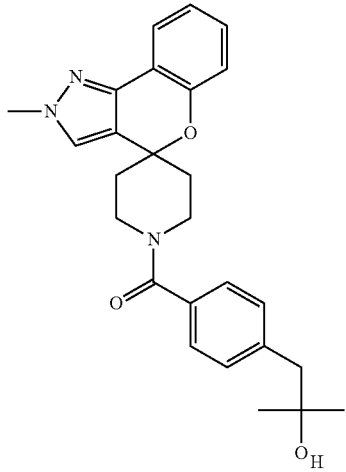
599
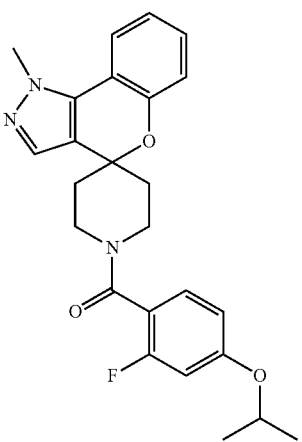

TABLE 1-continued
600
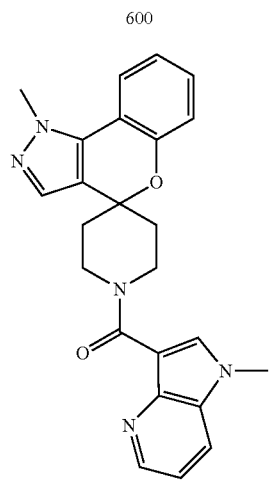
601
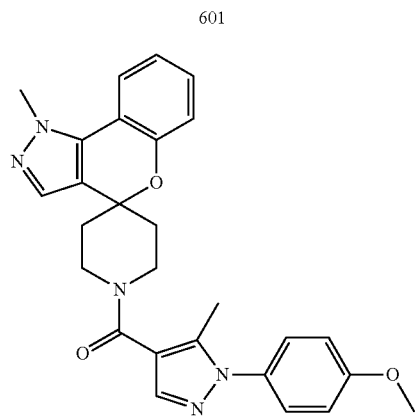
602
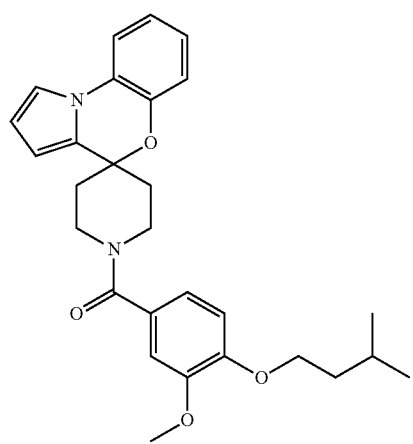
TABLE 1-continued
603
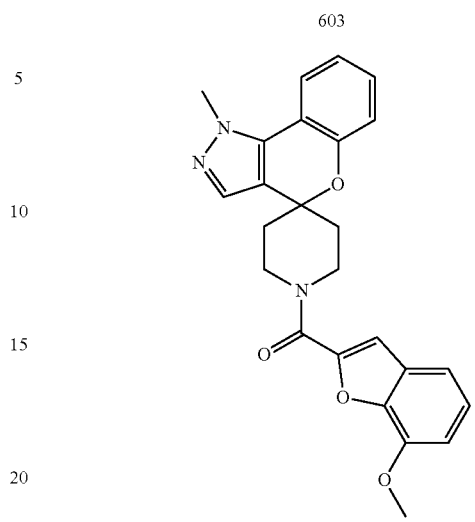
604
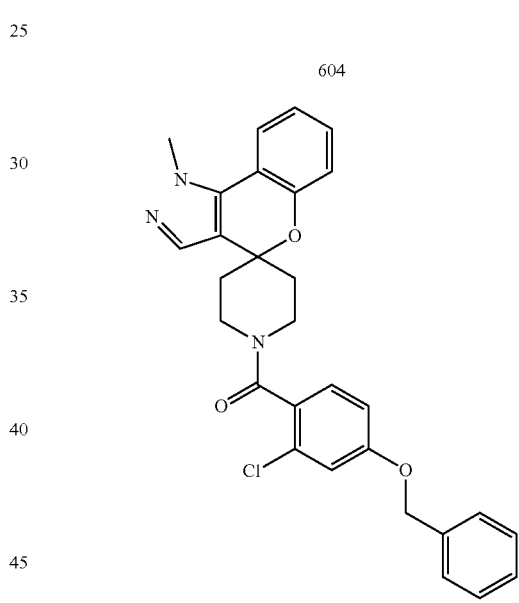
605
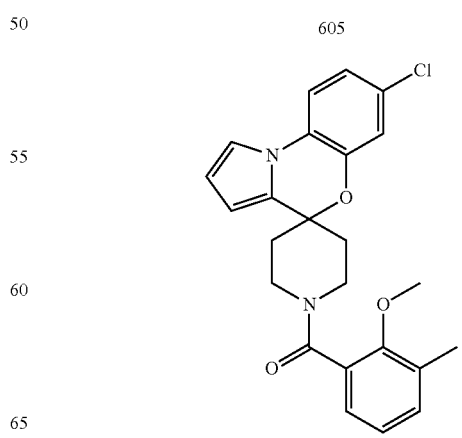

TABLE 1-continued
606
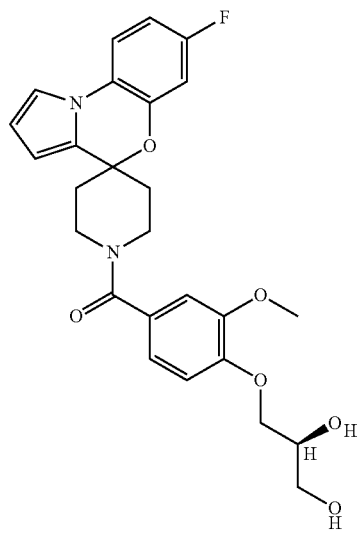
607
609
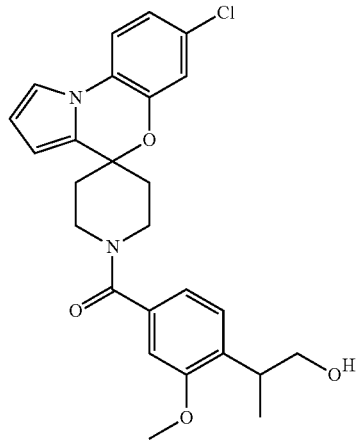
610
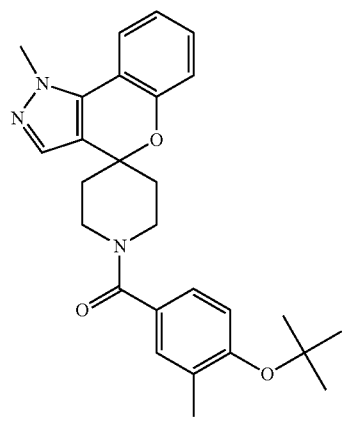 [SMILES: Cc1cc(C(=O)N2CCC3(CC2)Oc2ccccc2-c2c3cnn2C)ccc1OC(C)(C)C]
608
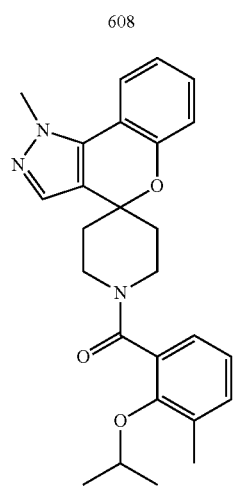
611
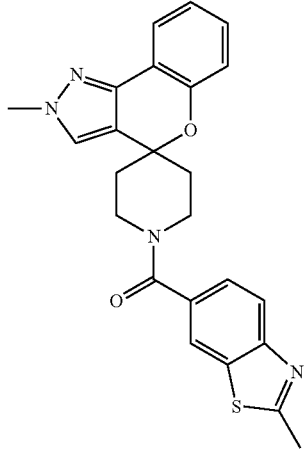

TABLE 1-continued
612
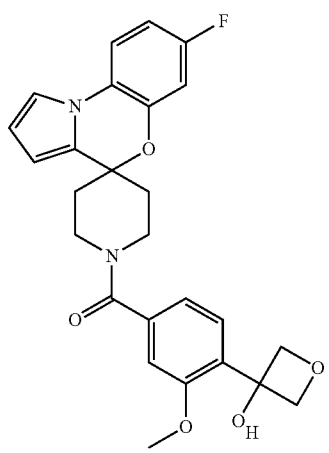
613
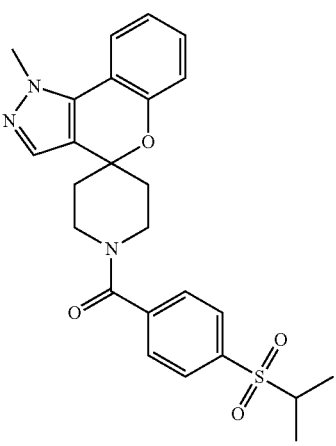 [SMILES: CC(C)S(=O)(=O)c1ccc(C(=O)N2CCC3(CC2)Oc2ccccc2-c2c3cnn2C)cc1]
614
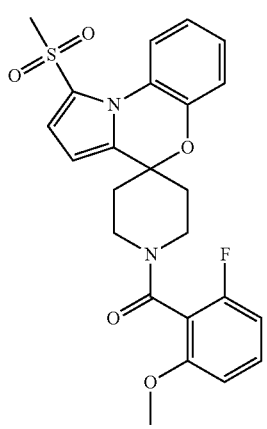 [SMILES: COc1cccc(F)c1C(=O)N1CCC2(CC1)Oc1ccccc1-n1c2ccc1S(C)(=O)=O]
TABLE 1-continued
615
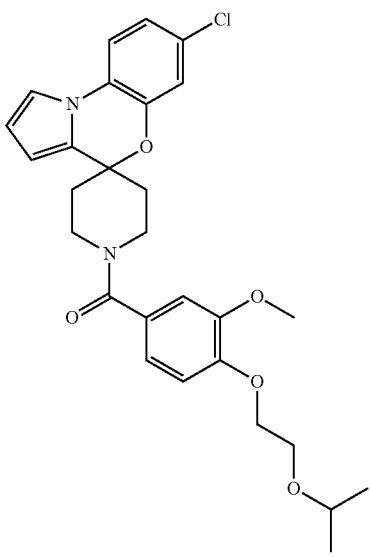 [SMILES: COc1cc(C(=O)N2CCC3(CC2)Oc2cc(Cl)ccc2-n2cccc23)ccc1OCCOC(C)C]
616
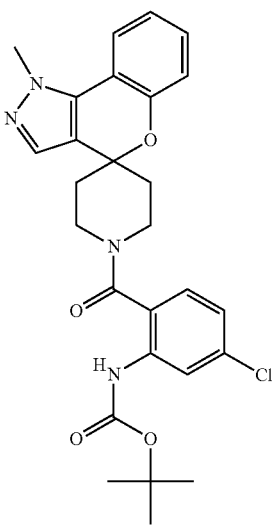
617
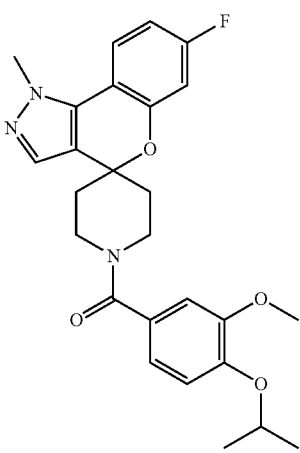 [SMILES: COc1cc(C(=O)N2CCC3(CC2)Oc2cc(F)ccc2-c2c3cnn2C)ccc1OC(C)C]

TABLE 1-continued
618
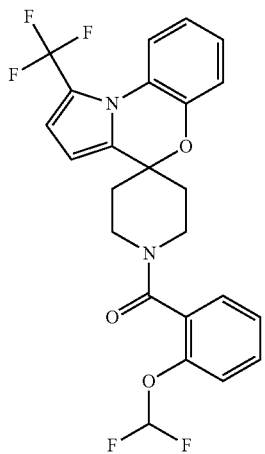 [SMILES: O=C(c1ccccc1OC(F)F)N1CCC2(CC1)Oc1ccccc1-n1c(C(F)(F)F)ccc12]
619
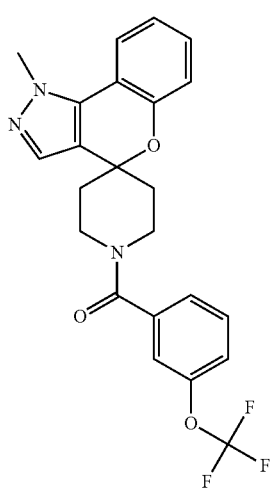 [SMILES: Cn1ncc2c1-c1ccccc1OC21CCN(C(=O)c2cccc(OC(F)(F)F)c2)CC1]
620
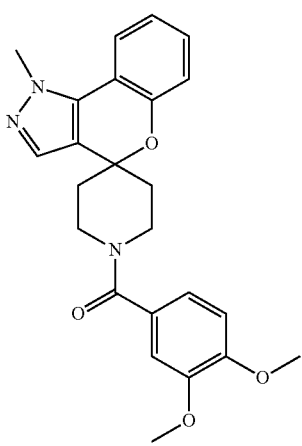 [SMILES: COc1ccc(C(=O)N2CCC3(CC2)Oc2ccccc2-c2c3cnn2C)cc1OC]
TABLE 1-continued
621
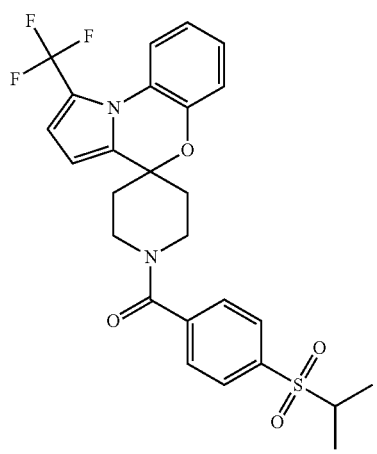 [SMILES: CC(C)S(=O)(=O)c1ccc(C(=O)N2CCC3(CC2)Oc2ccccc2-n2c(C(F)(F)F)ccc23)cc1]
622
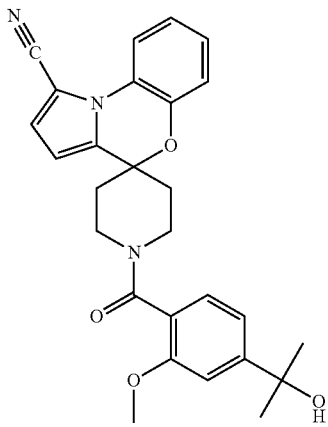 [SMILES: COc1cc(C(C)(C)O)ccc1C(=O)N1CCC2(CC1)Oc1ccccc1-n1c(C#N)ccc12]
623
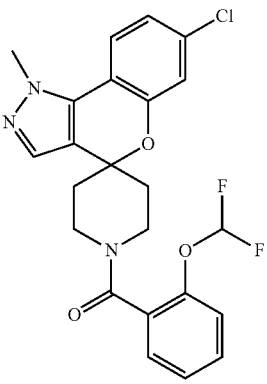 [SMILES: Cn1ncc2c1-c1ccc(Cl)cc1OC21CCN(C(=O)c2ccccc2OC(F)F)CC1]

TABLE 1-continued
624
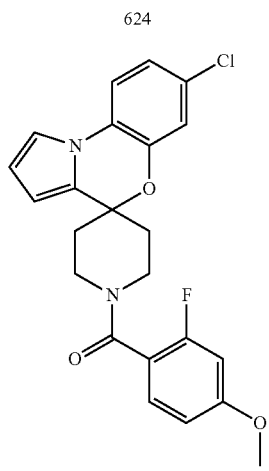
625
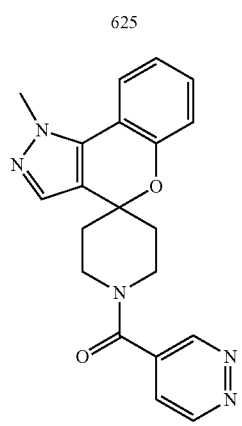
626
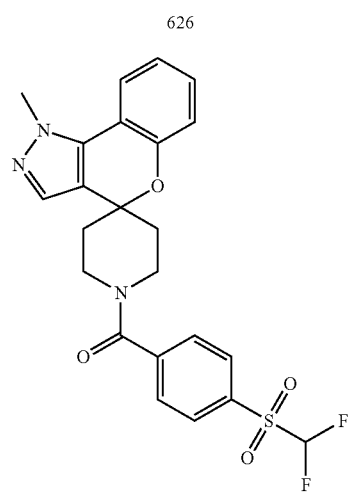
TABLE 1-continued
627
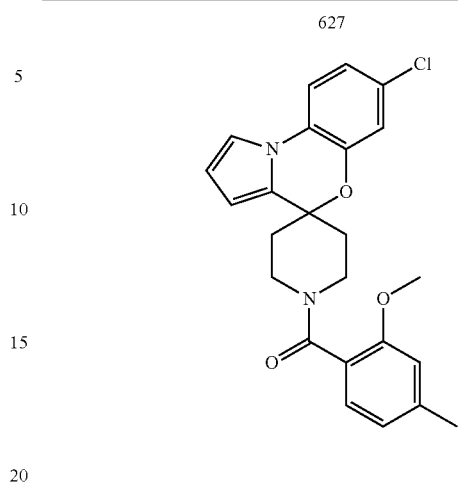
628
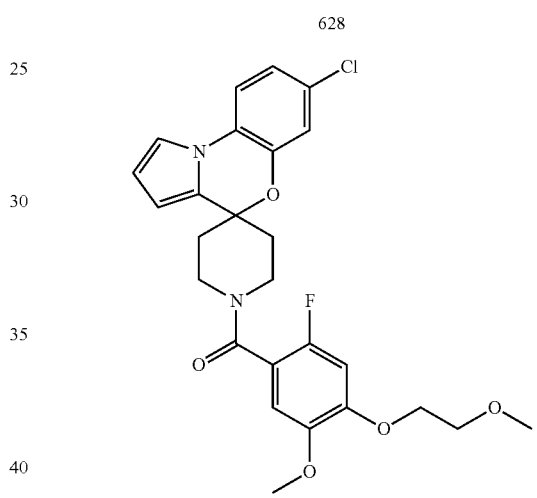
629
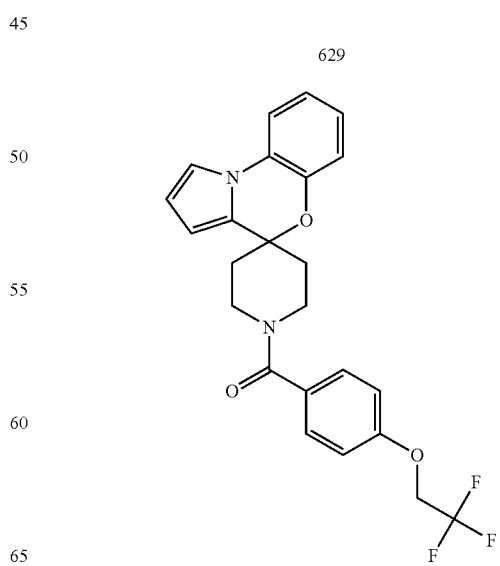

TABLE 1-continued
630
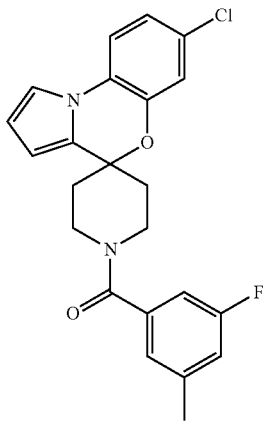 [SMILES: Cc1cc(F)cc(C(=O)N2CCC3(CC2)Oc2cc(Cl)ccc2-n2cccc23)c1]
631
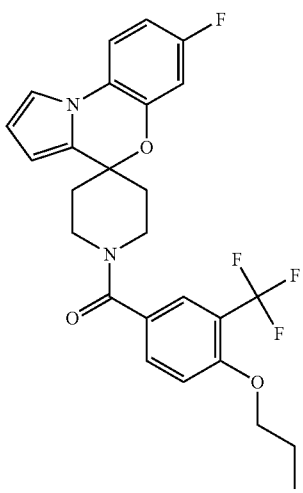 [SMILES: CCCOc1ccc(C(=O)N2CCC3(CC2)Oc2cc(F)ccc2-n2cccc23)cc1C(F)(F)F]
632
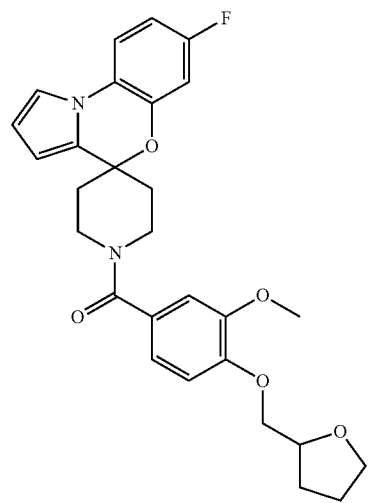 [SMILES: COc1cc(C(=O)N2CCC3(CC2)Oc2cc(F)ccc2-n2cccc23)ccc1OCC1CCCO1]
TABLE 1-continued
633
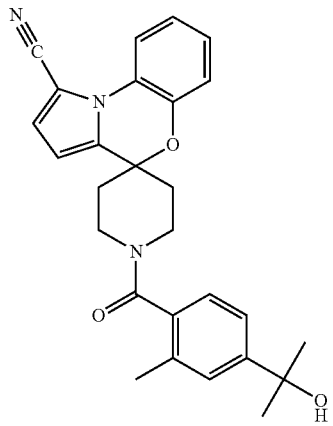 [SMILES: Cc1cc(C(C)(C)O)ccc1C(=O)N1CCC2(CC1)Oc1ccccc1-n1c(C#N)ccc12]
634
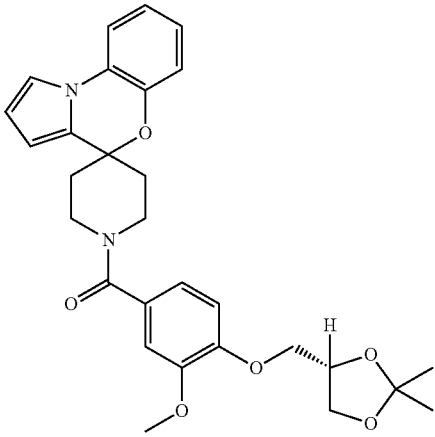 [SMILES: COc1cc(C(=O)N2CCC3(CC2)Oc2ccccc2-n2cccc23)ccc1OC[C@H]1COC(C)(C)O1]
635
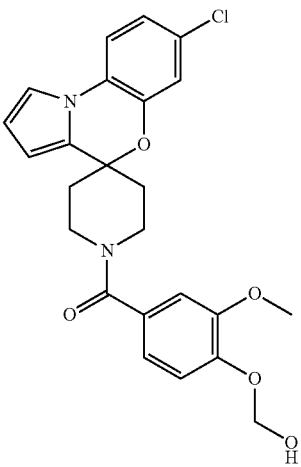 [SMILES: COc1cc(C(=O)N2CCC3(CC2)Oc2cc(Cl)ccc2-n2cccc23)ccc1OCO]

303
TABLE 1-continued
636
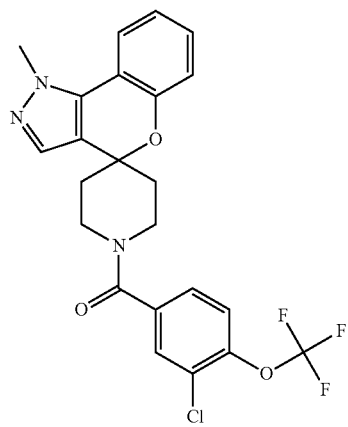
637
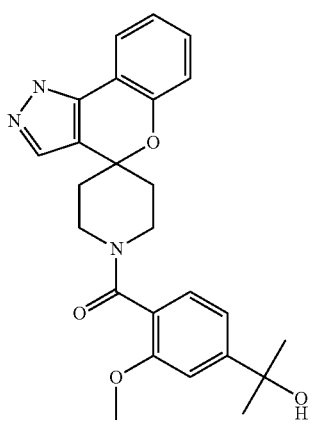 [SMILES: COc1cc(C(C)(C)O)ccc1C(=O)N1CCC2(CC1)Oc1ccccc1-c1[nH]ncc12]
638
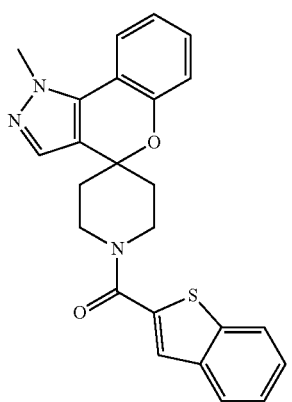
304
TABLE 1-continued
639
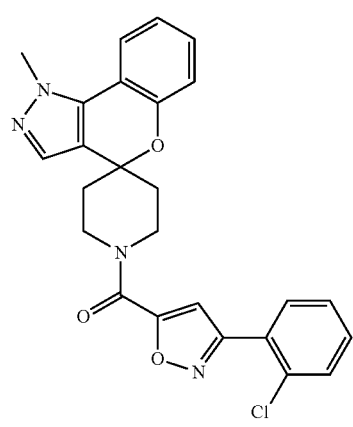 [SMILES: Cn1ncc2c1-c1ccccc1OC21CCN(C(=O)c2cc(-c3ccccc3Cl)no2)CC1]
640
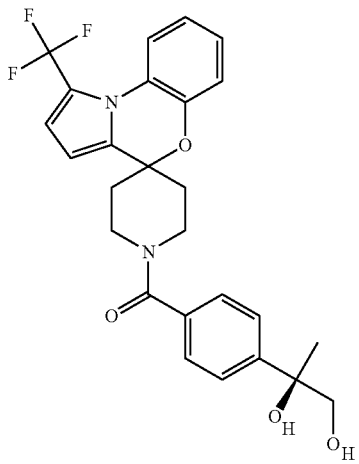
641
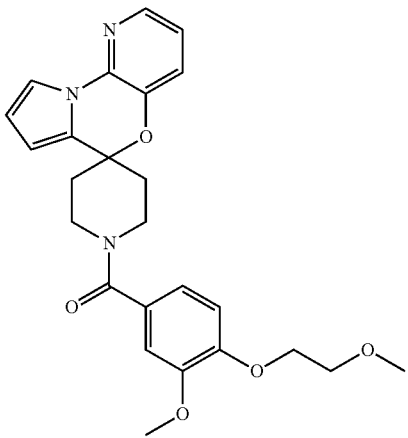 [SMILES: COCCOc1ccc(C(=O)N2CCC3(CC2)Oc2cccnc2-n2cccc23)cc1OC]

TABLE 1-continued
642
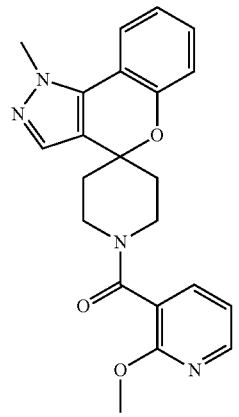 [SMILES: COc1ncccc1C(=O)N1CCC2(CC1)Oc1ccccc1-c1c2cnn1C]
643
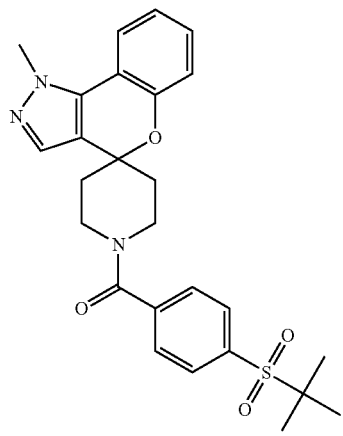 [SMILES: Cn1ncc2c1-c1ccccc1OC21CCN(C(=O)c2ccc(S(=O)(=O)C(C)(C)C)cc2)CC1]
644
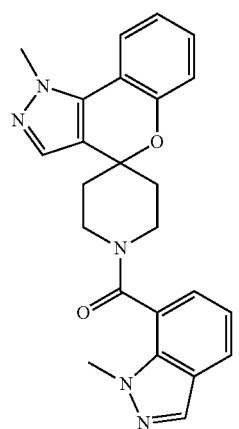 [SMILES: Cn1ncc2c1-c1ccccc1OC21CCN(C(=O)c2cccc3cnn(C)c23)CC1]
TABLE 1-continued
645
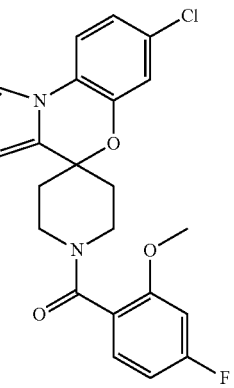
646
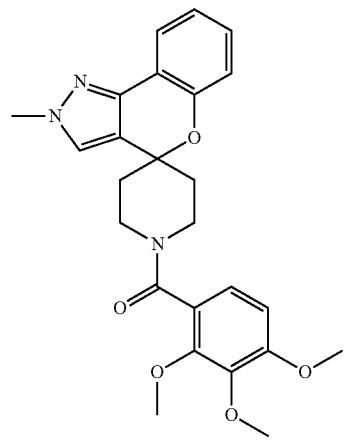
647
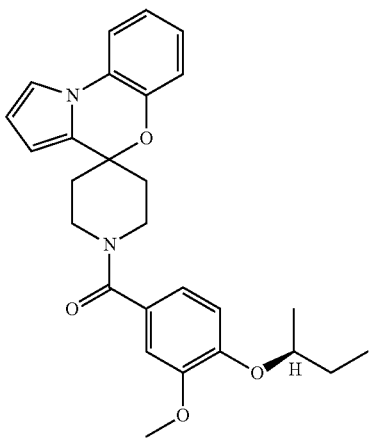

TABLE 1-continued
648
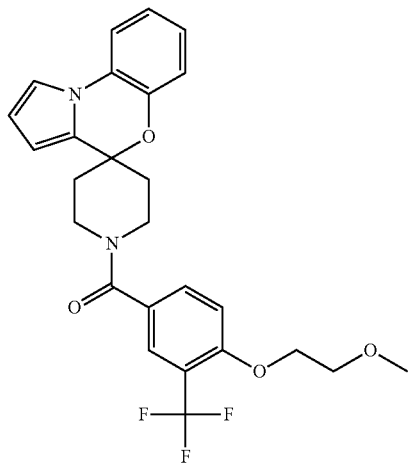 [SMILES: COCCOc1ccc(C(=O)N2CCC3(CC2)Oc2ccccc2-n2cccc23)cc1C(F)(F)F]
649
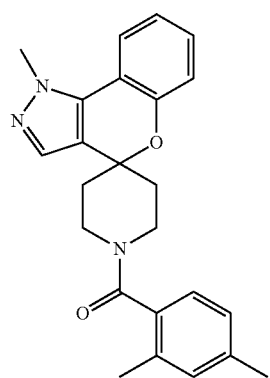 [SMILES: Cc1ccc(C(=O)N2CCC3(CC2)Oc2ccccc2-c2c3cnn2C)c(C)c1]
650
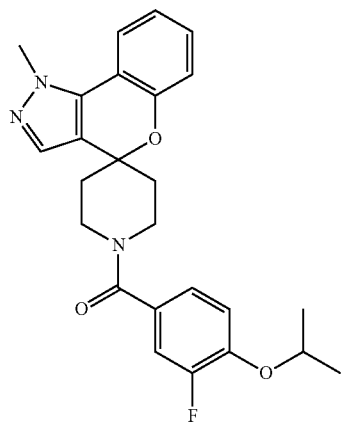 [SMILES: CC(C)Oc1ccc(C(=O)N2CCC3(CC2)Oc2ccccc2-c2c3cnn2C)cc1F]
TABLE 1-continued
651
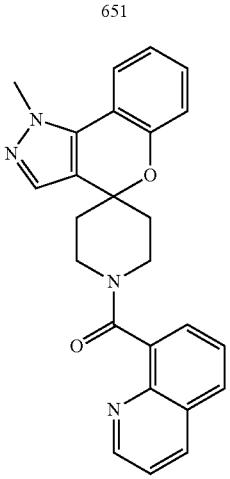
652
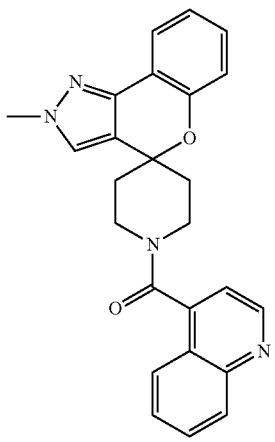 [SMILES: Cn1cc2c(n1)-c1ccccc1OC21CCN(C(=O)c2ccnc3ccccc23)CC1]
653
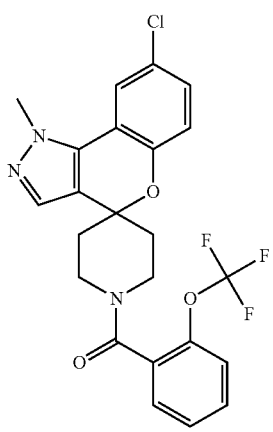 [SMILES: Cn1ncc2c1-c1cc(Cl)ccc1OC21CCN(C(=O)c2ccccc2OC(F)(F)F)CC1]

TABLE 1-continued
654
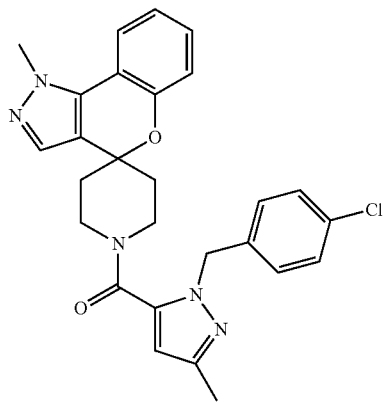 [SMILES: Cc1cc(C(=O)N2CCC3(CC2)Oc2ccccc2-c2c3cnn2C)n(Cc2ccc(Cl)cc2)n1]
655
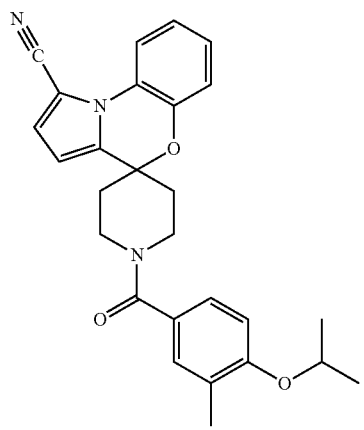 [SMILES: Cc1cc(C(=O)N2CCC3(CC2)Oc2ccccc2-n2c(C#N)ccc23)ccc1OC(C)C]
656
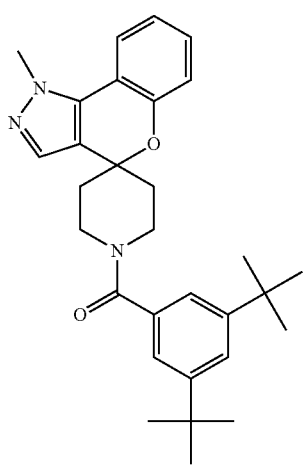 [SMILES: Cn1ncc2c1-c1ccccc1OC21CCN(C(=O)c2cc(C(C)(C)C)cc(C(C)(C)C)c2)CC1]
TABLE 1-continued
657
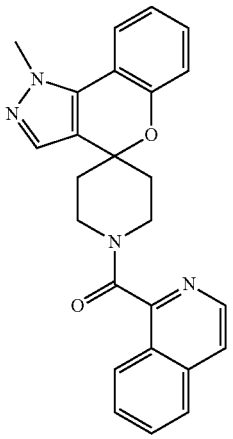 [SMILES: Cn1ncc2c1-c1ccccc1OC21CCN(C(=O)c2nccc3ccccc23)CC1]
658
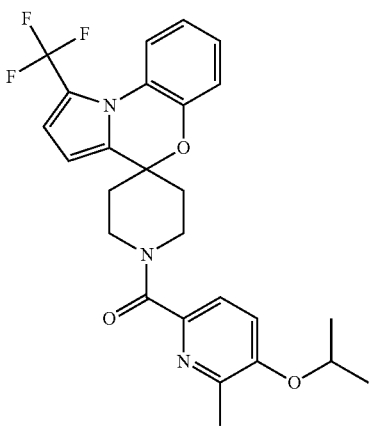 [SMILES: Cc1nc(C(=O)N2CCC3(CC2)Oc2ccccc2-n2c(C(F)(F)F)ccc23)ccc1OC(C)C]
659
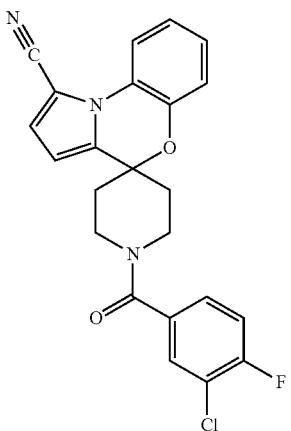 [SMILES: N#Cc1ccc2n1-c1ccccc1OC21CCN(C(=O)c2ccc(F)c(Cl)c2)CC1]

TABLE 1-continued
660
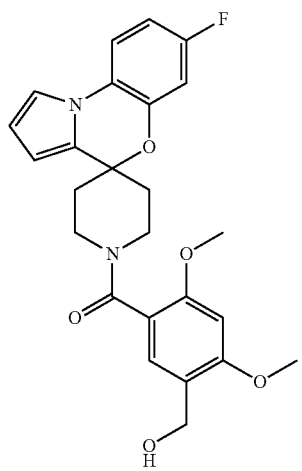
661
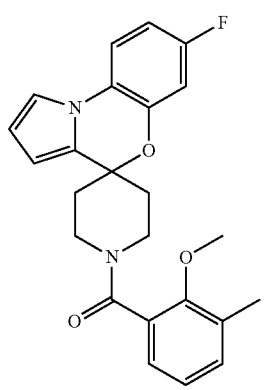 [SMILES: COc1c(C)cccc1C(=O)N1CCC2(CC1)Oc1cc(F)ccc1-n1cccc12]
662
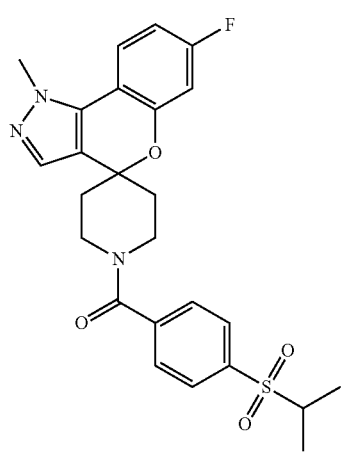 [SMILES: CC(C)S(=O)(=O)c1ccc(C(=O)N2CCC3(CC2)Oc2cc(F)ccc2-c2c3cnn2C)cc1]
TABLE 1-continued
663
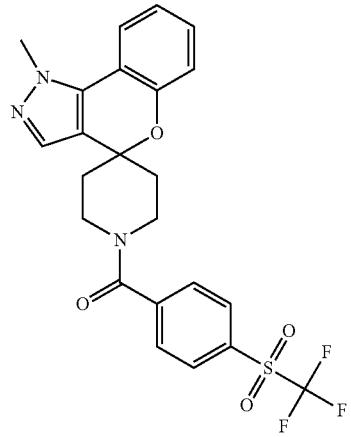 [SMILES: Cn1ncc2c1-c1ccccc1OC21CCN(C(=O)c2ccc(S(=O)(=O)C(F)(F)F)cc2)CC1]
664
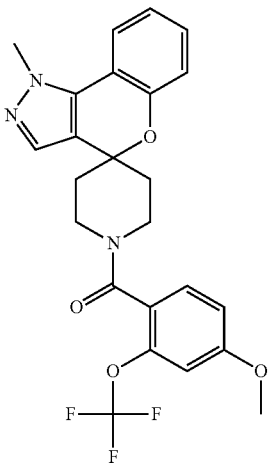 [SMILES: COc1ccc(C(=O)N2CCC3(CC2)Oc2ccccc2-c2c3cnn2C)c(OC(F)(F)F)c1]
665
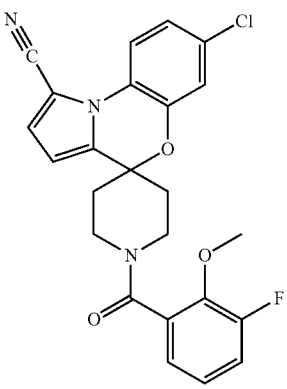 [SMILES: COc1c(F)cccc1C(=O)N1CCC2(CC1)Oc1cc(Cl)ccc1-n1c(C#N)ccc12]

TABLE 1-continued
666
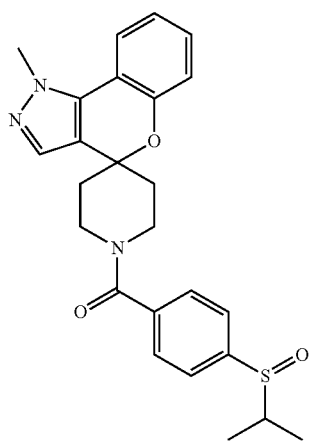 [SMILES: CC(C)S(=O)c1ccc(C(=O)N2CCC3(CC2)Oc2ccccc2-c2c3cnn2C)cc1]
667
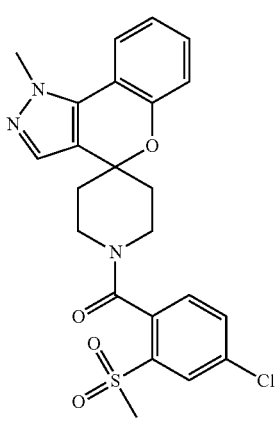 [SMILES: Cn1ncc2c1-c1ccccc1OC21CCN(C(=O)c2ccc(Cl)cc2S(C)(=O)=O)CC1]
668
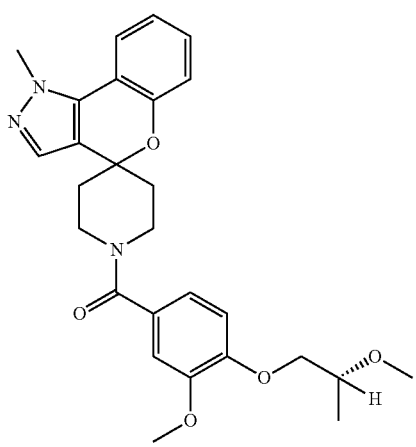
TABLE 1-continued
669
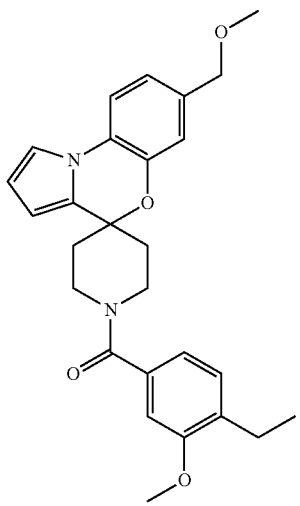 [SMILES: CCc1ccc(C(=O)N2CCC3(CC2)Oc2cc(COC)ccc2-n2cccc23)cc1OC]
670
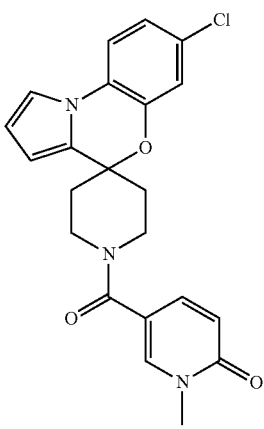 [SMILES: Cn1cc(C(=O)N2CCC3(CC2)Oc2cc(Cl)ccc2-n2cccc23)ccc1=O]
671
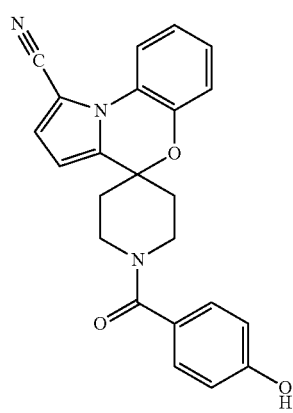 [SMILES: N#Cc1ccc2n1-c1ccccc1OC21CCN(C(=O)c2ccc(O)cc2)CC1]

TABLE 1-continued
672
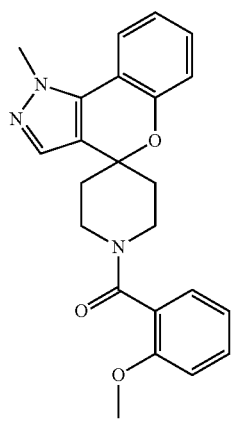 [SMILES: COc1ccccc1C(=O)N1CCC2(CC1)Oc1ccccc1-c1c2cnn1C]
673
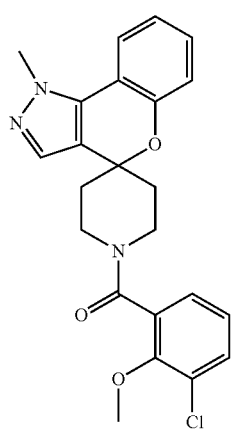 [SMILES: COc1c(Cl)cccc1C(=O)N1CCC2(CC1)Oc1ccccc1-c1c2cnn1C]
674
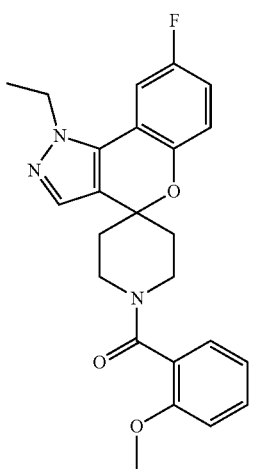 [SMILES: CCn1ncc2c1-c1cc(F)ccc1OC21CCN(C(=O)c2ccccc2OC)CC1]
TABLE 1-continued
675
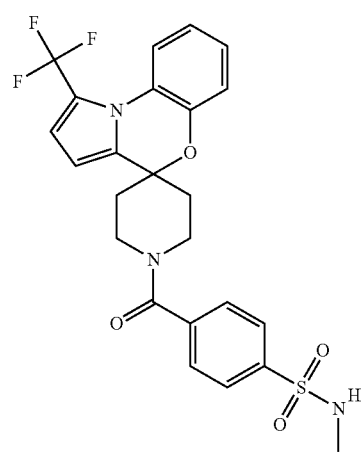
676
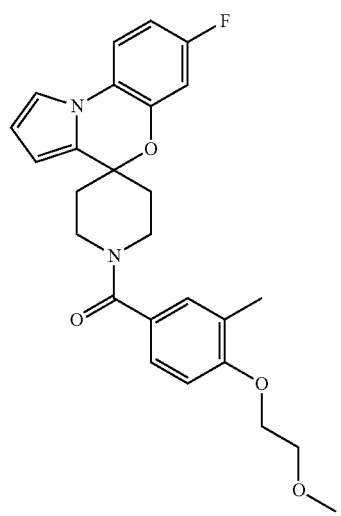 [SMILES: COCCOc1ccc(C(=O)N2CCC3(CC2)Oc2cc(F)ccc2-n2cccc23)cc1C]
677
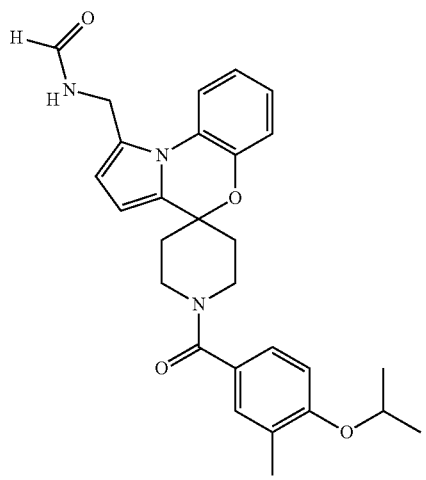

TABLE 1-continued
678
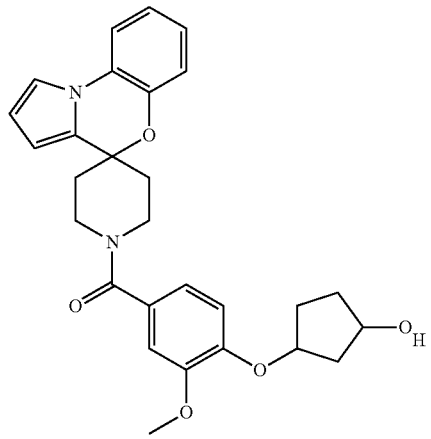
679
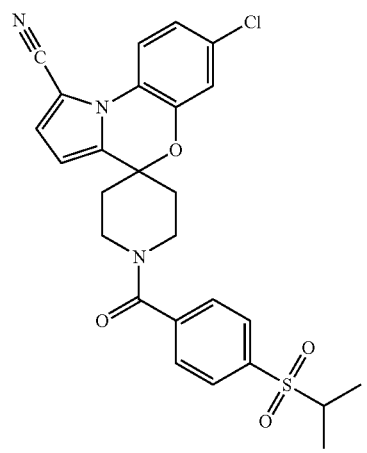 [SMILES: CC(C)S(=O)(=O)c1ccc(C(=O)N2CCC3(CC2)Oc2cc(Cl)ccc2-n2c(C#N)ccc23)cc1]
680
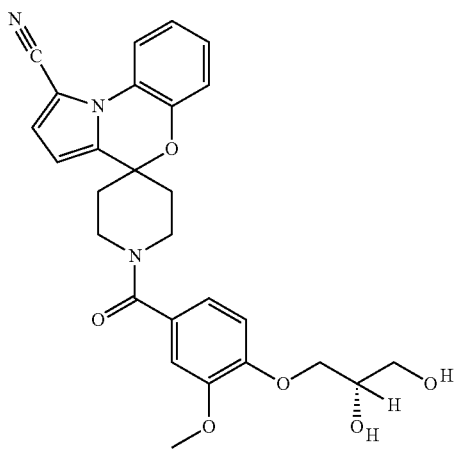
TABLE 1-continued
681
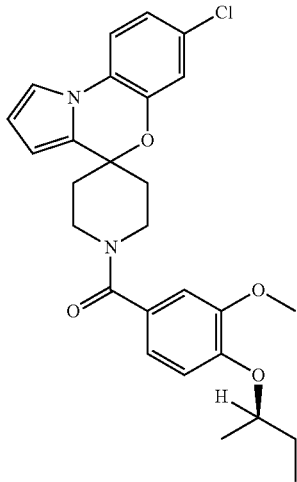
682
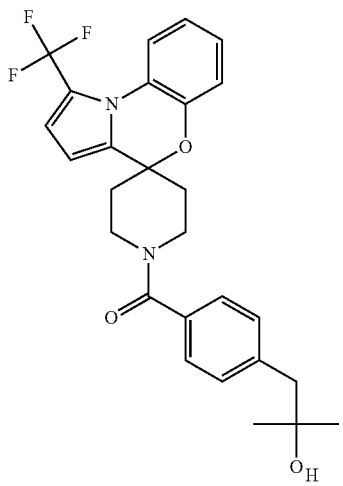
683
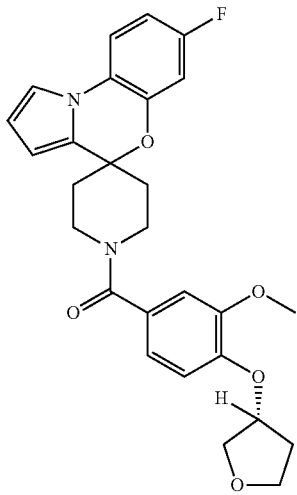 [SMILES: COc1cc(C(=O)N2CCC3(CC2)Oc2cc(F)ccc2-n2cccc23)ccc1O[C@@H]1CCOC1]

TABLE 1-continued
684
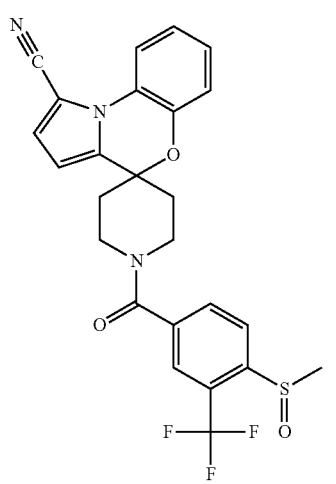 [SMILES: CS(=O)c1ccc(C(=O)N2CCC3(CC2)Oc2ccccc2-n2c(C#N)ccc23)cc1C(F)(F)F]
685
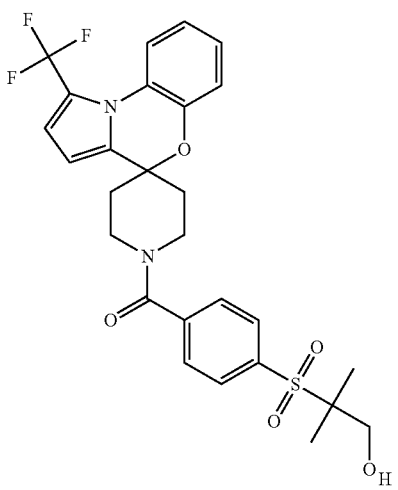
686
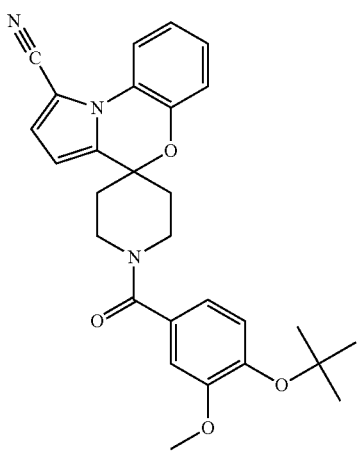 [SMILES: COc1cc(C(=O)N2CCC3(CC2)Oc2ccccc2-n2c(C#N)ccc23)ccc1OC(C)(C)C]
TABLE 1-continued
687
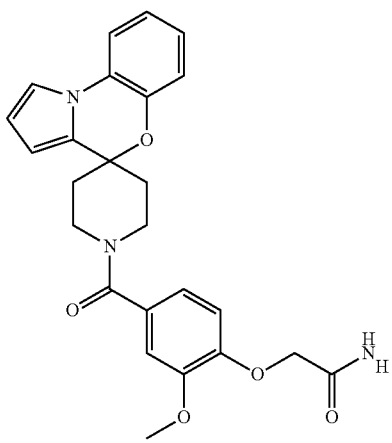
688
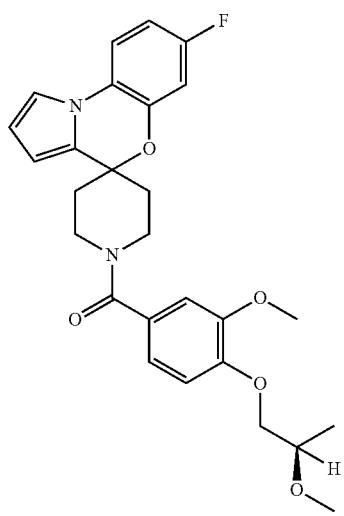 [SMILES: COc1cc(C(=O)N2CCC3(CC2)Oc2cc(F)ccc2-n2cccc23)ccc1OC[C@@H](C)OC]
689
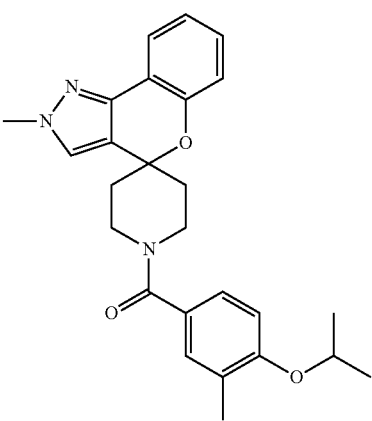 [SMILES: Cc1cc(C(=O)N2CCC3(CC2)Oc2ccccc2-c2nn(C)cc23)ccc1OC(C)C]

TABLE 1-continued
690
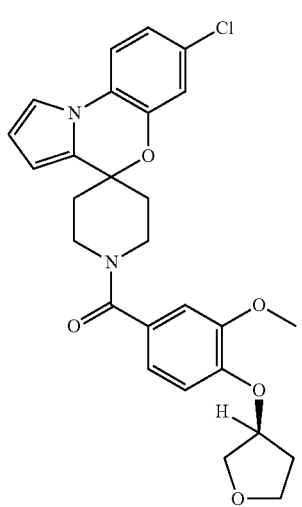 [SMILES: COc1cc(C(=O)N2CCC3(CC2)Oc2cc(Cl)ccc2-n2cccc23)ccc1O[C@H]1CCOC1]
691
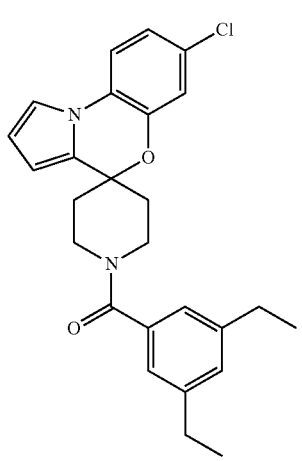 [SMILES: CCc1cc(CC)cc(C(=O)N2CCC3(CC2)Oc2cc(Cl)ccc2-n2cccc23)c1]
692
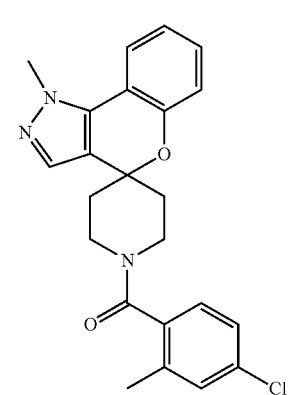 [SMILES: Cc1cc(Cl)ccc1C(=O)N1CCC2(CC1)Oc1ccccc1-c1c2cnn1C]
TABLE 1-continued
693
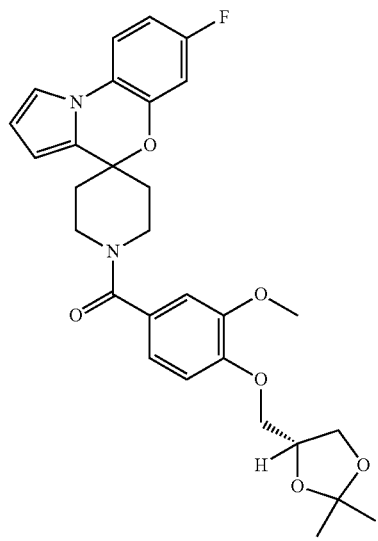
694
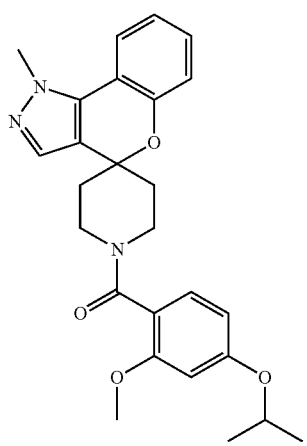 [SMILES: COc1cc(OC(C)C)ccc1C(=O)N1CCC2(CC1)Oc1ccccc1-c1c2cnn1C]
695
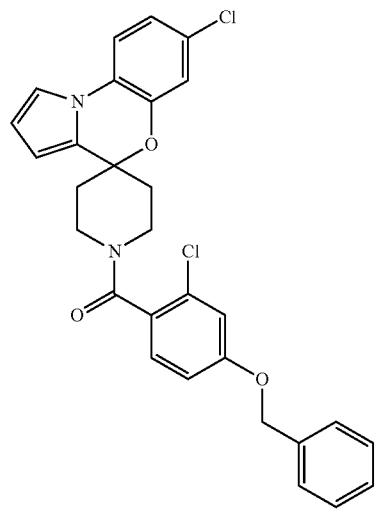 [SMILES: O=C(c1ccc(OCc2ccccc2)cc1Cl)N1CCC2(CC1)Oc1cc(Cl)ccc1-n1cccc12]

TABLE 1-continued
696
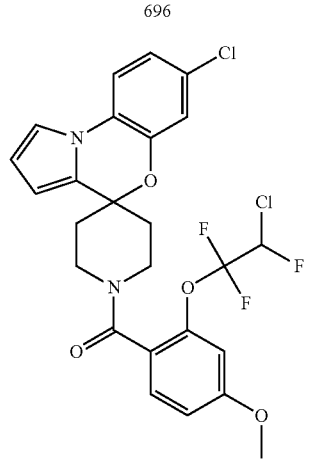
697
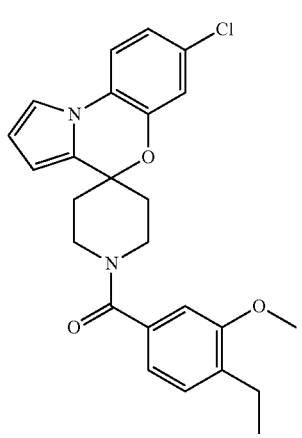 [SMILES: CCc1ccc(C(=O)N2CCC3(CC2)Oc2cc(Cl)ccc2-n2cccc23)cc1OC]
698
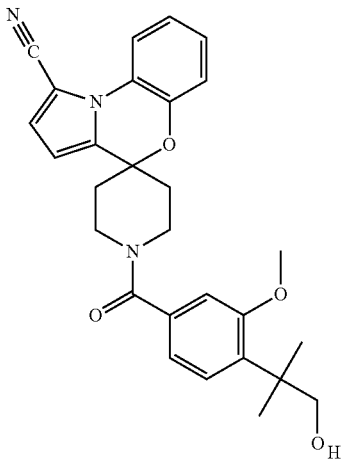
TABLE 1-continued
699
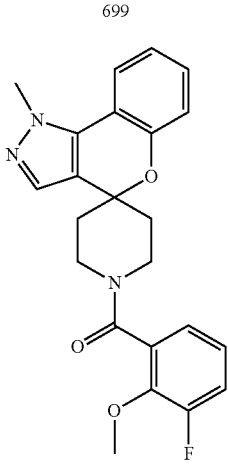
700
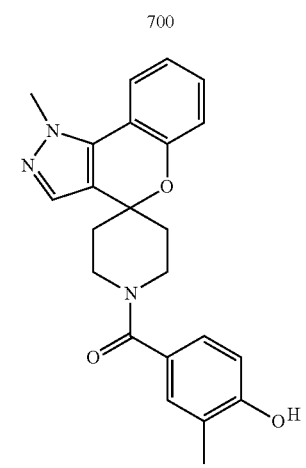
701
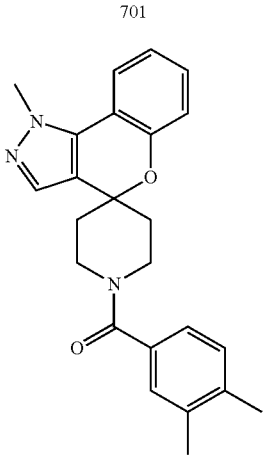

TABLE 1-continued
702
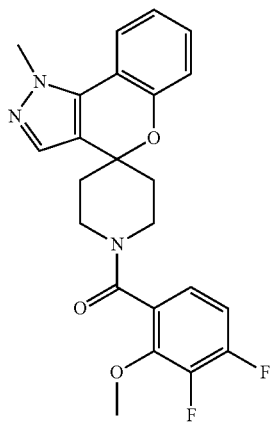 [SMILES: COc1c(C(=O)N2CCC3(CC2)Oc2ccccc2-c2c3cnn2C)ccc(F)c1F]
703
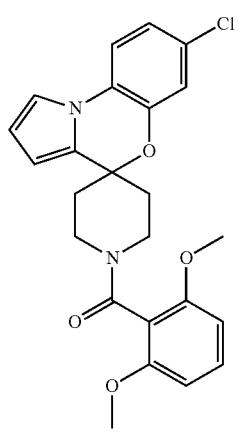 [SMILES: COc1cccc(OC)c1C(=O)N1CCC2(CC1)Oc1cc(Cl)ccc1-n1cccc12]
704
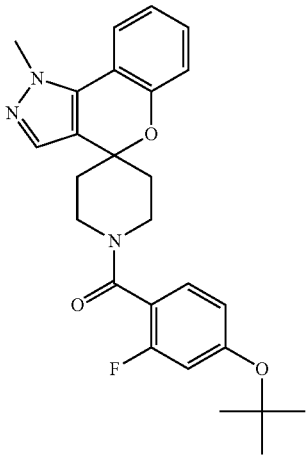 [SMILES: Cn1ncc2c1-c1ccccc1OC21CCN(C(=O)c2ccc(OC(C)(C)C)cc2F)CC1]
TABLE 1-continued
705
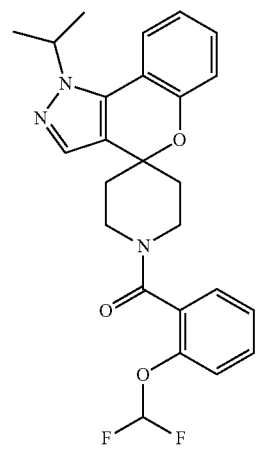 [SMILES: CC(C)n1ncc2c1-c1ccccc1OC21CCN(C(=O)c2ccccc2OC(F)F)CC1]
706
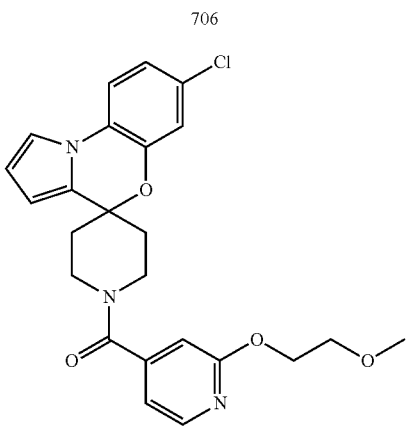
707
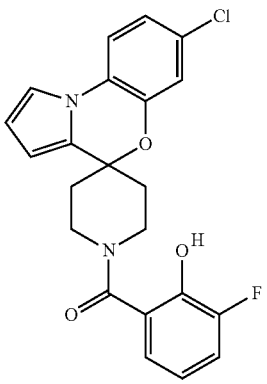

TABLE 1-continued
708
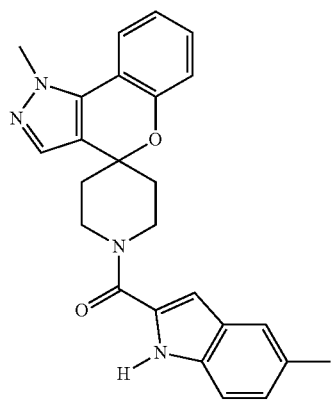 [SMILES: Cc1ccc2[nH]c(C(=O)N3CCC4(CC3)Oc3ccccc3-c3c4cnn3C)cc2c1]
709
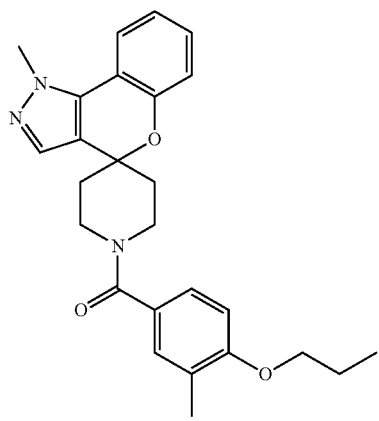 [SMILES: CCCOc1ccc(C(=O)N2CCC3(CC2)Oc2ccccc2-c2c3cnn2C)cc1C]
710
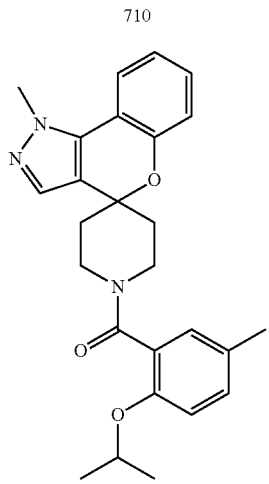
TABLE 1-continued
711
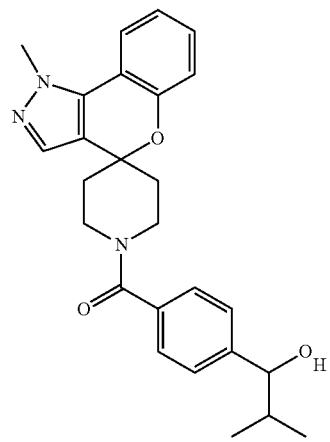
712
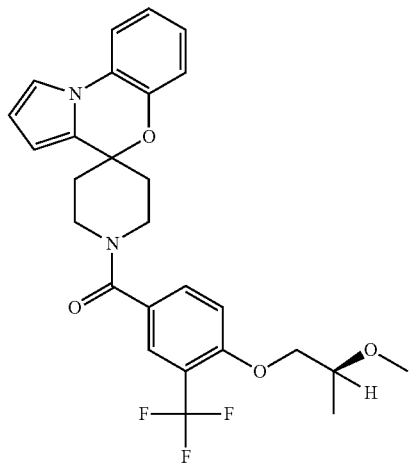 [SMILES: CO[C@@H](C)COc1ccc(C(=O)N2CCC3(CC2)Oc2ccccc2-n2cccc23)cc1C(F)(F)F]
713
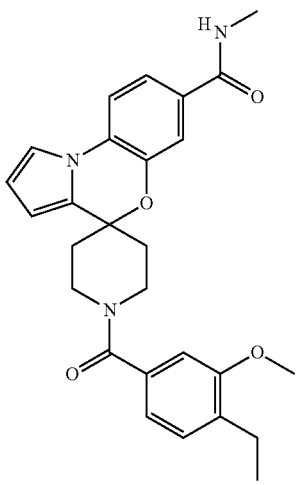

TABLE 1-continued
714
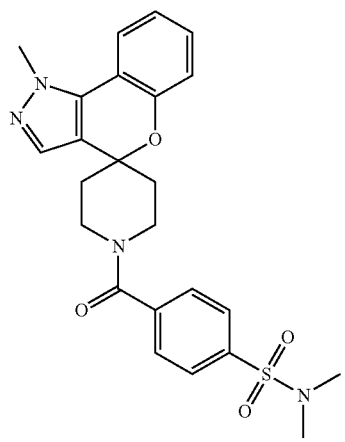 [SMILES: CN(C)S(=O)(=O)c1ccc(C(=O)N2CCC3(CC2)Oc2ccccc2-c2c3cnn2C)cc1]
715
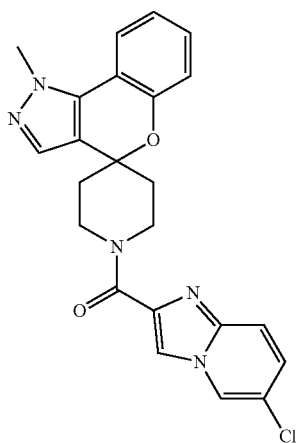 [SMILES: Cn1ncc2c1-c1ccccc1OC21CCN(C(=O)c2cn3cc(Cl)ccc3n2)CC1]
716
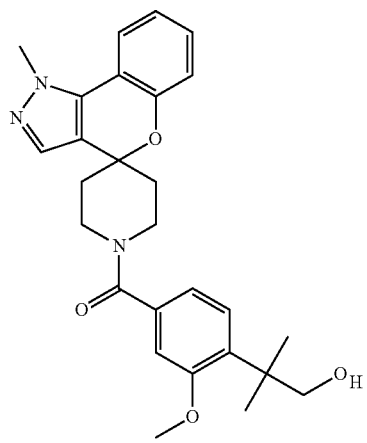
TABLE 1-continued
717
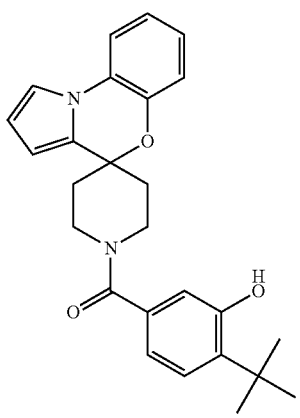 [SMILES: CC(C)(C)c1ccc(C(=O)N2CCC3(CC2)Oc2ccccc2-n2cccc23)cc1O]
718
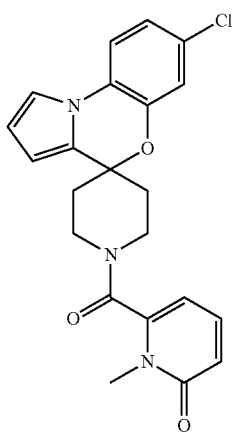 [SMILES: Cn1c(C(=O)N2CCC3(CC2)Oc2cc(Cl)ccc2-n2cccc23)cccc1=O]
719
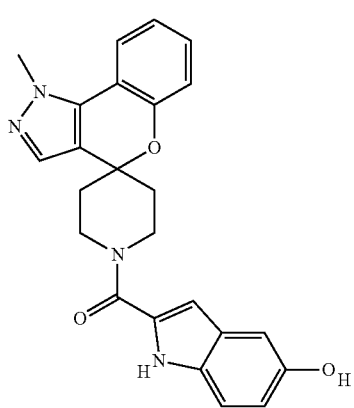

TABLE 1-continued
720
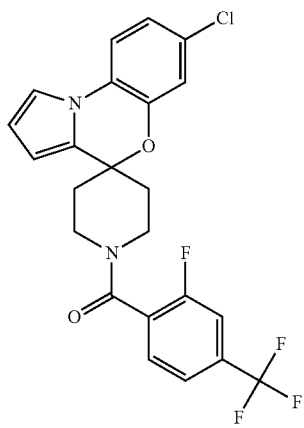 [SMILES: O=C(c1ccc(C(F)(F)F)cc1F)N1CCC2(CC1)Oc1cc(Cl)ccc1-n1cccc12]
721
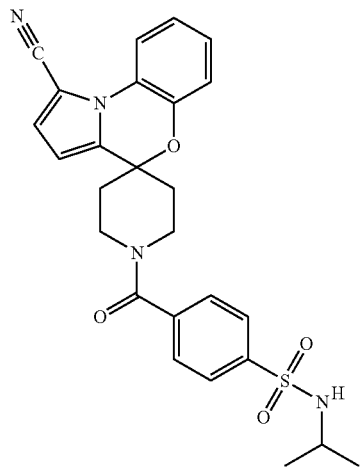
722
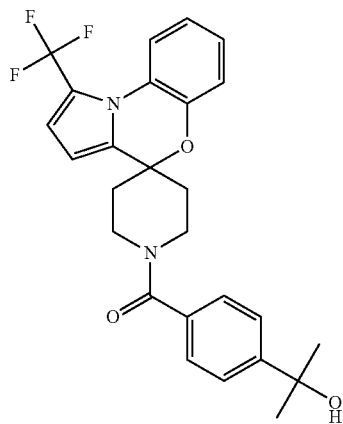 [SMILES: CC(C)(O)c1ccc(C(=O)N2CCC3(CC2)Oc2ccccc2-n2c(C(F)(F)F)ccc23)cc1]
TABLE 1-continued
723
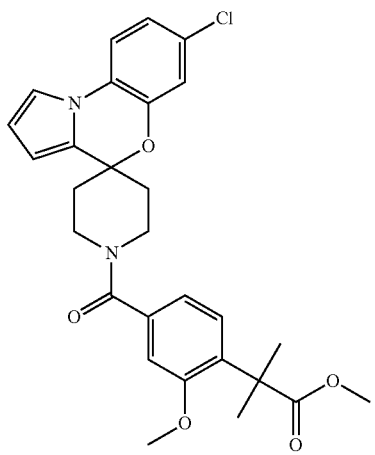 [SMILES: COC(=O)C(C)(C)c1ccc(C(=O)N2CCC3(CC2)Oc2cc(Cl)ccc2-n2cccc23)cc1OC]
724
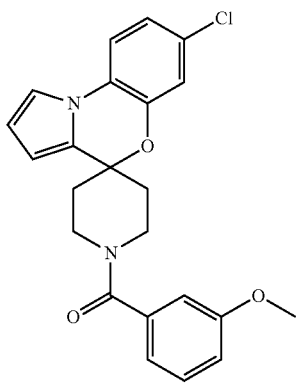 [SMILES: COc1cccc(C(=O)N2CCC3(CC2)Oc2cc(Cl)ccc2-n2cccc23)c1]
725
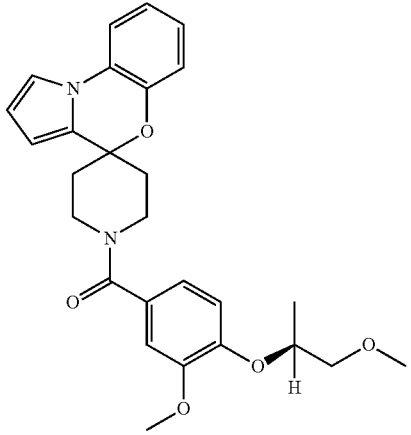 [SMILES: COC[C@H](C)Oc1ccc(C(=O)N2CCC3(CC2)Oc2ccccc2-n2cccc23)cc1OC]

TABLE 1-continued
726
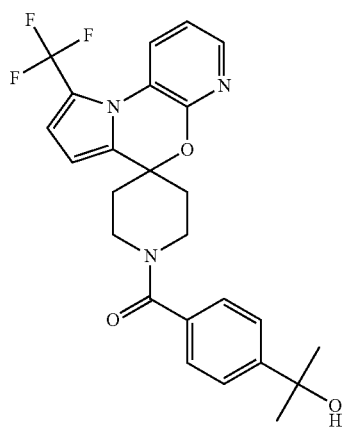 [SMILES: CC(C)(O)c1ccc(C(=O)N2CCC3(CC2)Oc2ncccc2-n2c(C(F)(F)F)ccc23)cc1]
727
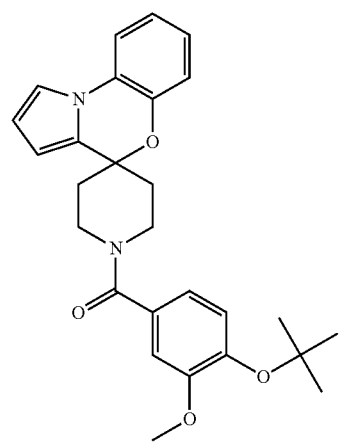 [SMILES: COc1cc(C(=O)N2CCC3(CC2)Oc2ccccc2-n2cccc23)ccc1OC(C)(C)C]
728
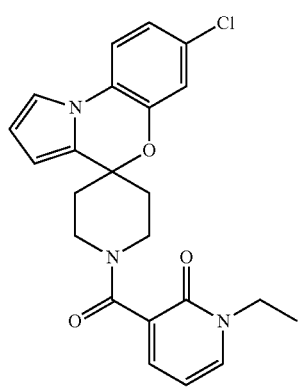 [SMILES: CCn1cccc(C(=O)N2CCC3(CC2)Oc2cc(Cl)ccc2-n2cccc23)c1=O]
TABLE 1-continued
729
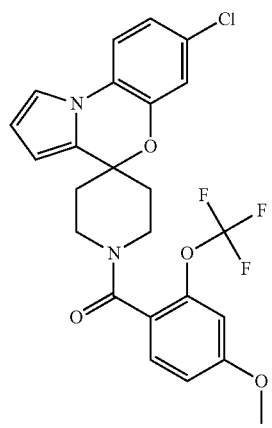
730
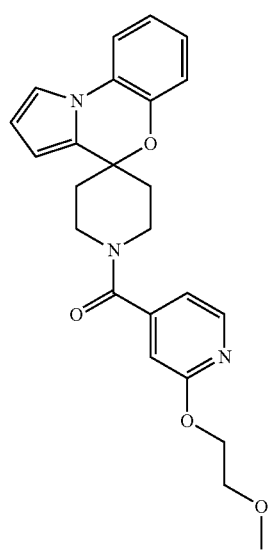
731
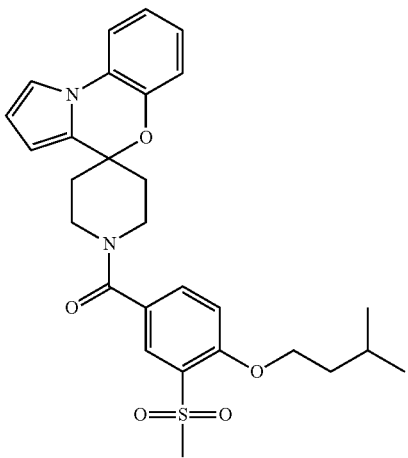 [SMILES: CC(C)CCOc1ccc(C(=O)N2CCC3(CC2)Oc2ccccc2-n2cccc23)cc1S(C)(=O)=O]

TABLE 1-continued
732
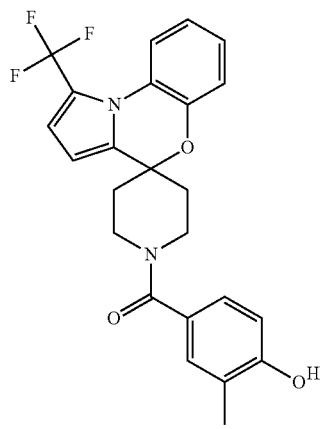
733
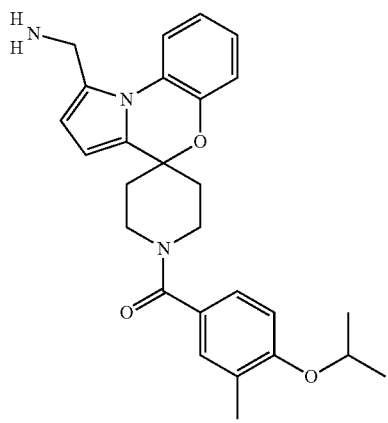
734
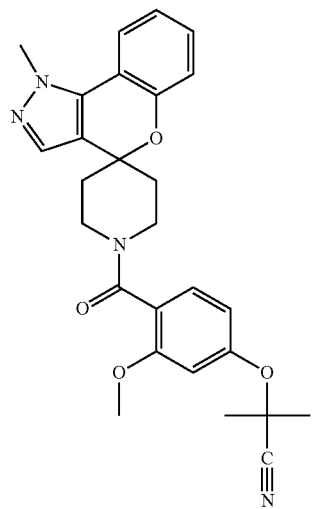 [SMILES: COc1cc(OC(C)(C)C#N)ccc1C(=O)N1CCC2(CC1)Oc1ccccc1-c1c2cnn1C]
TABLE 1-continued
735
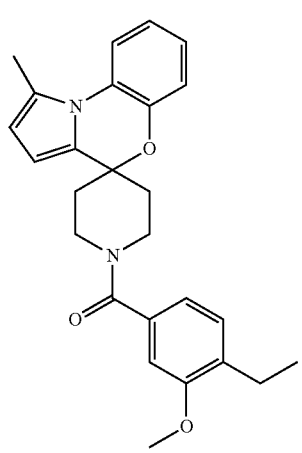 [SMILES: CCc1ccc(C(=O)N2CCC3(CC2)Oc2ccccc2-n2c(C)ccc23)cc1OC]
736
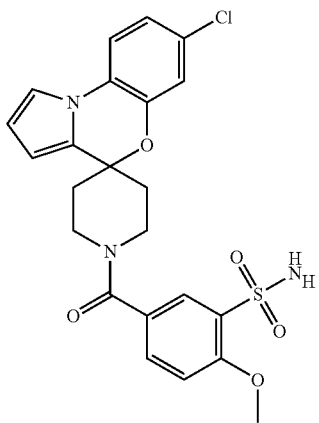
737
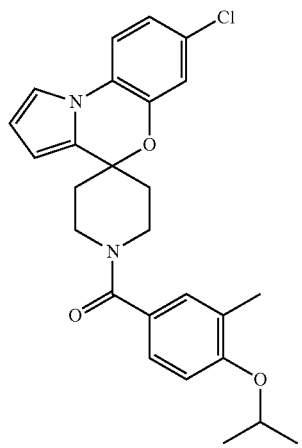 [SMILES: Cc1cc(C(=O)N2CCC3(CC2)Oc2cc(Cl)ccc2-n2cccc23)ccc1OC(C)C]

TABLE 1-continued
738
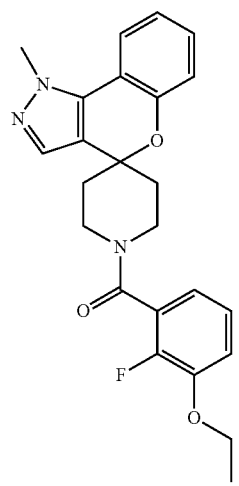 [SMILES: CCOc1cccc(C(=O)N2CCC3(CC2)Oc2ccccc2-c2c3cnn2C)c1F]
739
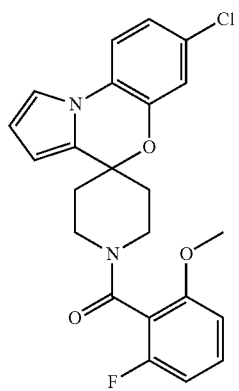 [SMILES: COc1cccc(F)c1C(=O)N1CCC2(CC1)Oc1cc(Cl)ccc1-n1cccc12]
740
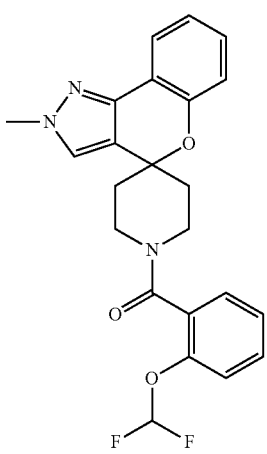 [SMILES: Cn1cc2c(n1)-c1ccccc1OC21CCN(C(=O)c2ccccc2OC(F)F)CC1]
TABLE 1-continued
741
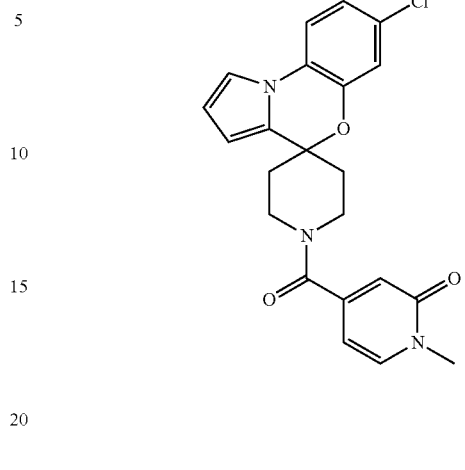
742
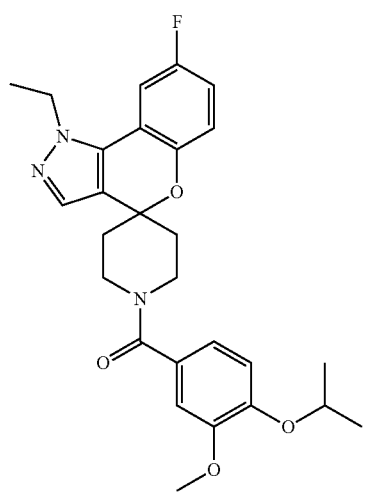 [SMILES: CCn1ncc2c1-c1cc(F)ccc1OC21CCN(C(=O)c2ccc(OC(C)C)c(OC)c2)CC1]
743
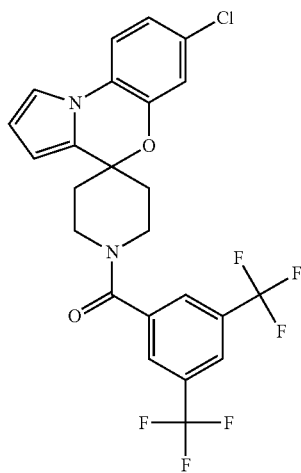 [SMILES: O=C(c1cc(C(F)(F)F)cc(C(F)(F)F)c1)N1CCC2(CC1)Oc1cc(Cl)ccc1-n1cccc12]

TABLE 1-continued
744
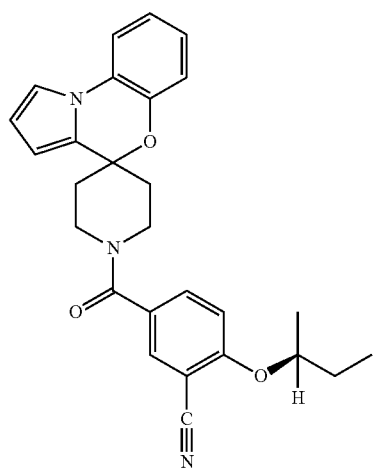 [SMILES: CC[C@H](C)Oc1ccc(C(=O)N2CCC3(CC2)Oc2ccccc2-n2cccc23)cc1C#N]
745
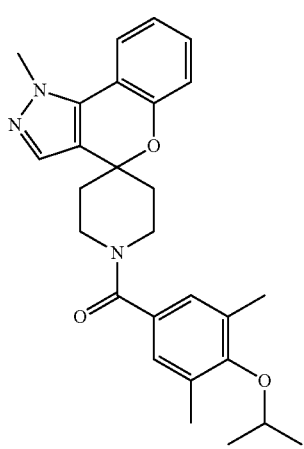 [SMILES: Cc1cc(C(=O)N2CCC3(CC2)Oc2ccccc2-c2c3cnn2C)cc(C)c1OC(C)C]
746
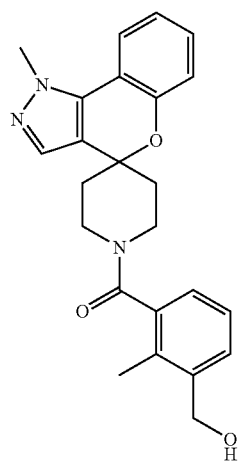 [SMILES: Cc1c(CO)cccc1C(=O)N1CCC2(CC1)Oc1ccccc1-c1c2cnn1C]
TABLE 1-continued
747
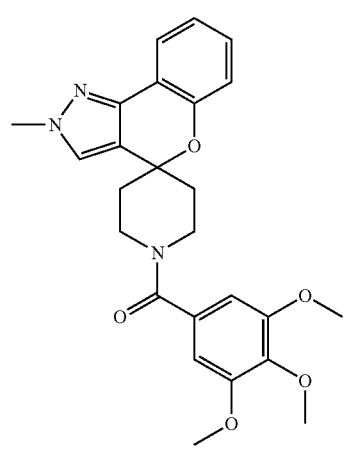
748
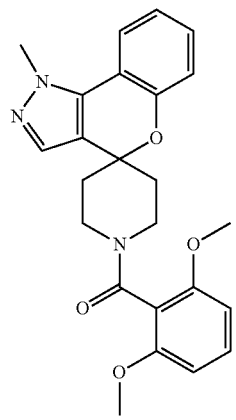
749
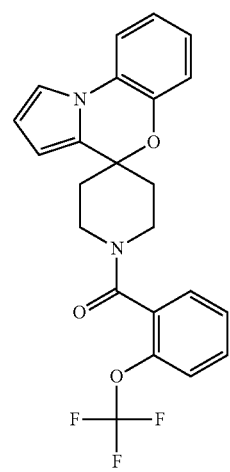 [SMILES: O=C(c1ccccc1OC(F)(F)F)N1CCC2(CC1)Oc1ccccc1-n1cccc12]

TABLE 1-continued
750
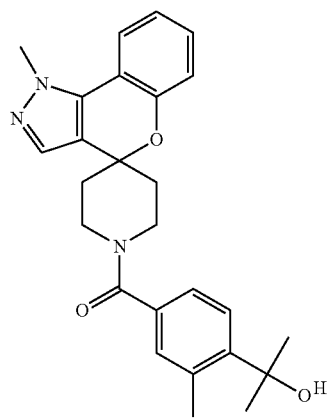
751
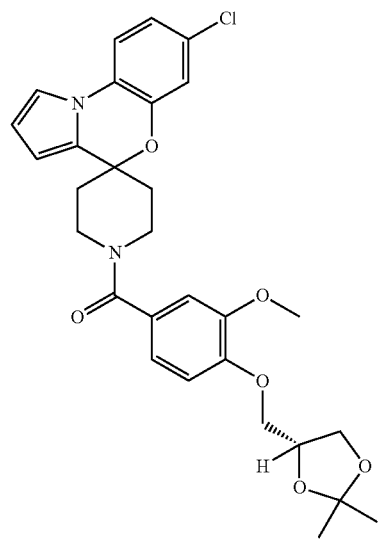 [SMILES: COc1cc(C(=O)N2CCC3(CC2)Oc2cc(Cl)ccc2-n2cccc23)ccc1OC[C@@H]1COC(C)(C)O1]
752
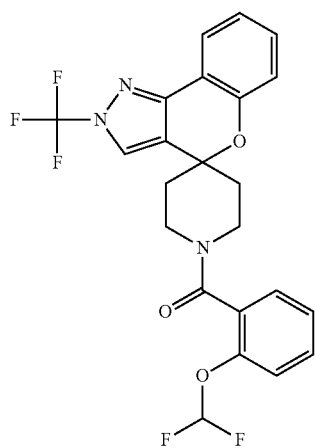 [SMILES: O=C(c1ccccc1OC(F)F)N1CCC2(CC1)Oc1ccccc1-c1nn(C(F)(F)F)cc12]
TABLE 1-continued
753
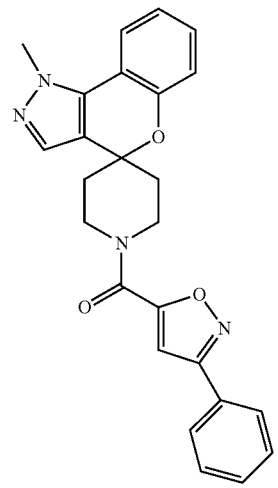 [SMILES: Cn1ncc2c1-c1ccccc1OC21CCN(C(=O)c2cc(-c3ccccc3)no2)CC1]
754
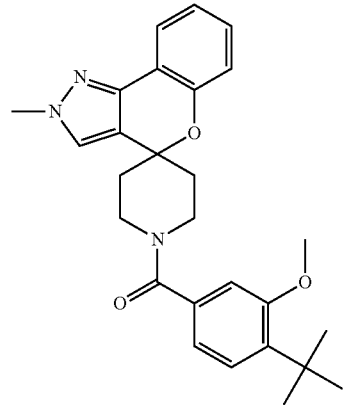 [SMILES: COc1cc(C(=O)N2CCC3(CC2)Oc2ccccc2-c2nn(C)cc23)ccc1C(C)(C)C]
755
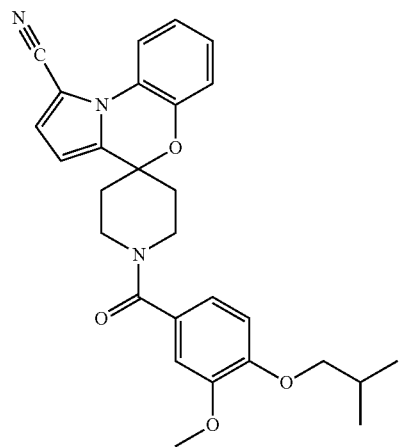 [SMILES: COc1cc(C(=O)N2CCC3(CC2)Oc2ccccc2-n2c(C#N)ccc23)ccc1OCC(C)C]

TABLE 1-continued
756
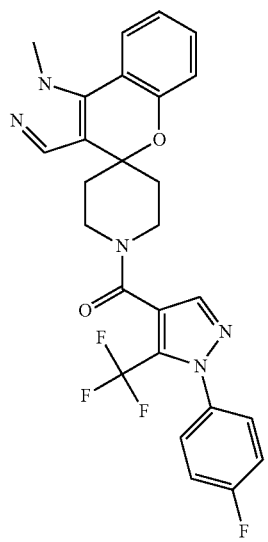 [SMILES: CNC1=C(C=N)C2(CCN(C(=O)c3cnn(-c4ccc(F)cc4)c3C(F)(F)F)CC2)Oc2ccccc21]
757
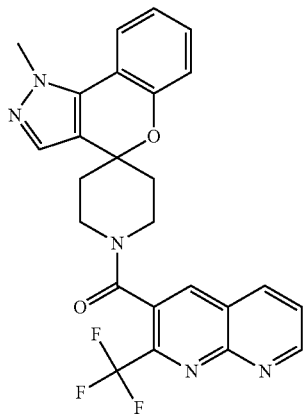 [SMILES: Cn1ncc2c1-c1ccccc1OC21CCN(C(=O)c2cc3cccnc3nc2C(F)(F)F)CC1]
758
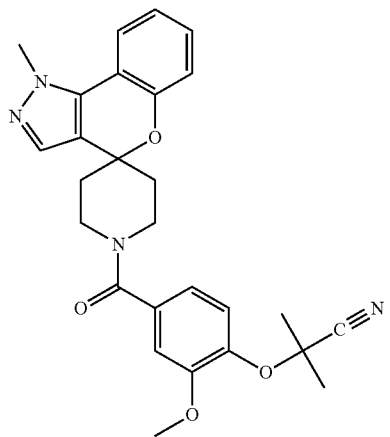 [SMILES: COc1cc(C(=O)N2CCC3(CC2)Oc2ccccc2-c2c3cnn2C)ccc1OC(C)(C)C#N]
TABLE 1-continued
759
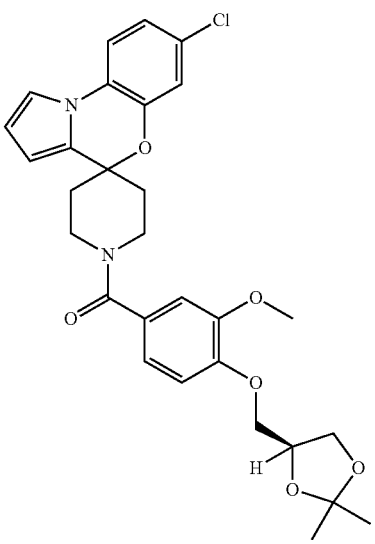 [SMILES: COc1cc(C(=O)N2CCC3(CC2)Oc2cc(Cl)ccc2-n2cccc23)ccc1OC[C@H]1COC(C)(C)O1]
760
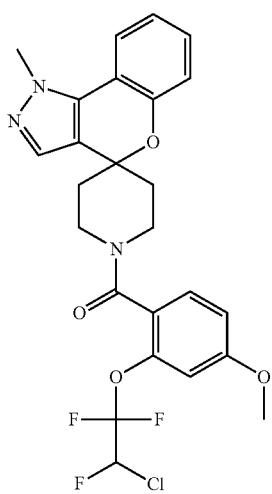 [SMILES: COc1ccc(C(=O)N2CCC3(CC2)Oc2ccccc2-c2c3cnn2C)c(OC(F)(F)C(F)Cl)c1]
761
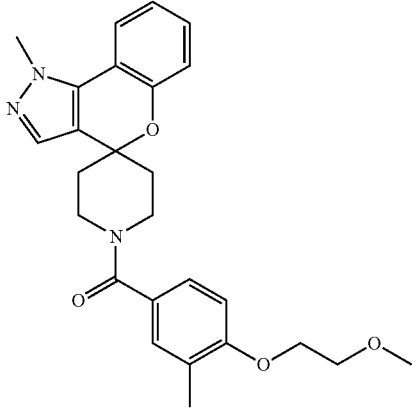 [SMILES: COCCOc1ccc(C(=O)N2CCC3(CC2)Oc2ccccc2-c2c3cnn2C)cc1C]

TABLE 1-continued
762
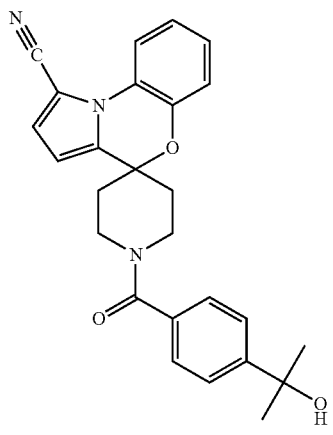 [SMILES: CC(C)(O)c1ccc(C(=O)N2CCC3(CC2)Oc2ccccc2-n2c(C#N)ccc23)cc1]
763
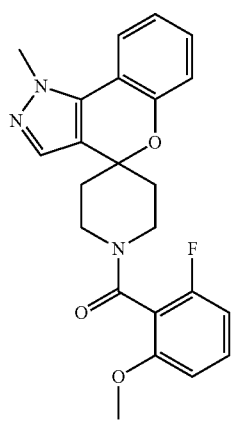 [SMILES: COc1cccc(F)c1C(=O)N1CCC2(CC1)Oc1ccccc1-c1c2cnn1C]
764
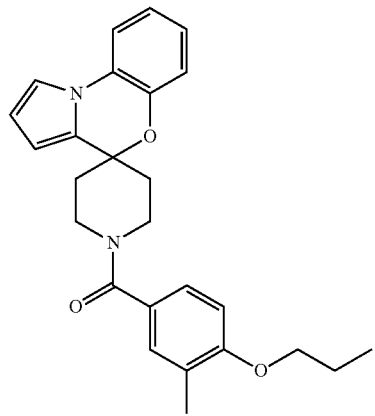 [SMILES: CCCOc1ccc(C(=O)N2CCC3(CC2)Oc2ccccc2-n2cccc23)cc1C]
TABLE 1-continued
765
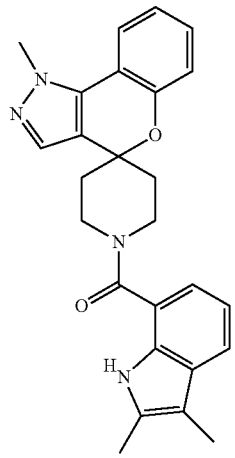
766
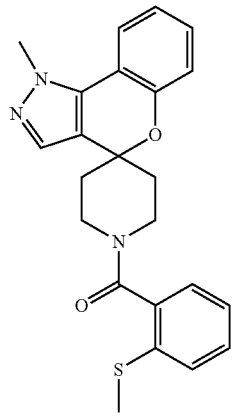 [SMILES: CSc1ccccc1C(=O)N1CCC2(CC1)Oc1ccccc1-c1c2cnn1C]
767
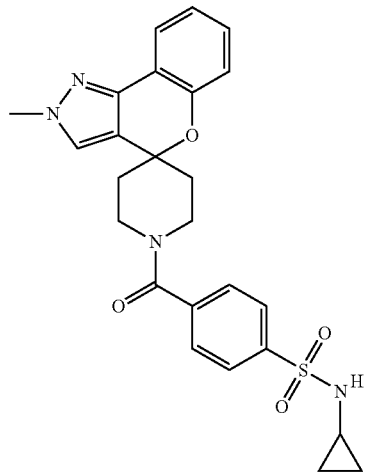

TABLE 1-continued
768
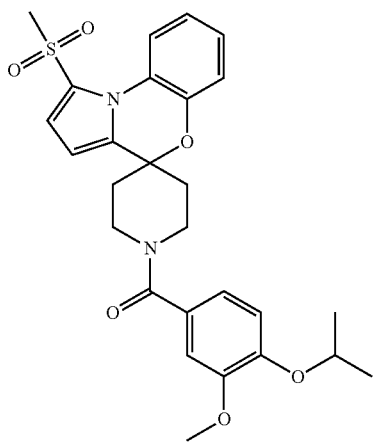 [SMILES: COc1cc(C(=O)N2CCC3(CC2)Oc2ccccc2-n2c3ccc2S(C)(=O)=O)ccc1OC(C)C]
769
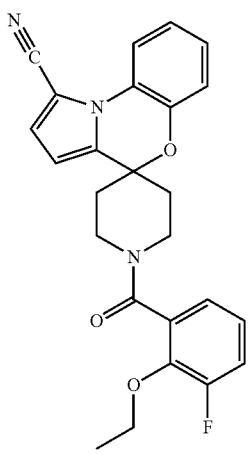
770
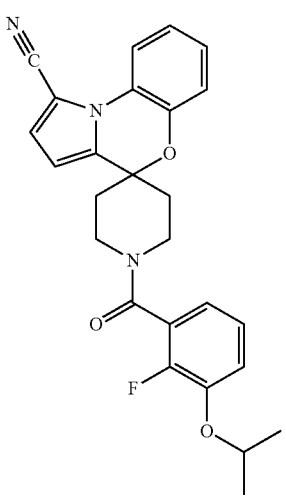 [SMILES: CC(C)Oc1cccc(C(=O)N2CCC3(CC2)Oc2ccccc2-n2c(C#N)ccc23)c1F]
TABLE 1-continued
771
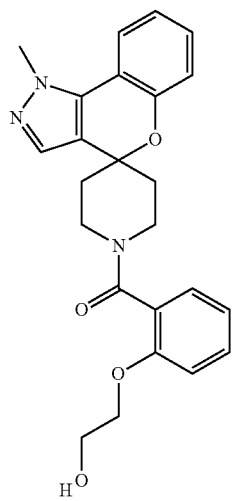
772
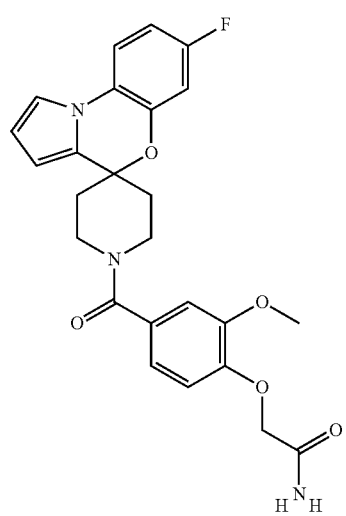
773
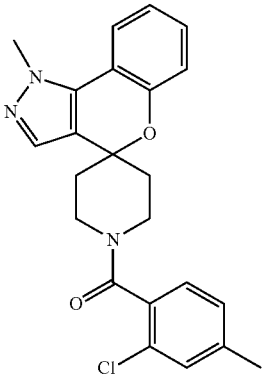 [SMILES: Cc1ccc(C(=O)N2CCC3(CC2)Oc2ccccc2-c2c3cnn2C)c(Cl)c1]

TABLE 1-continued
774
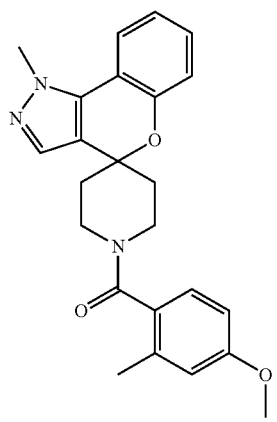 [SMILES: COc1ccc(C(=O)N2CCC3(CC2)Oc2ccccc2-c2c3cnn2C)c(C)c1]
775
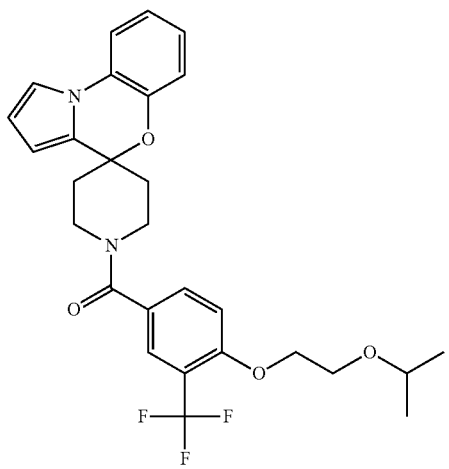
776
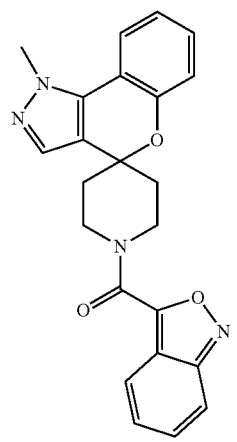 [SMILES: Cn1ncc2c1-c1ccccc1OC21CCN(C(=O)c2onc3ccccc23)CC1]
TABLE 1-continued
777
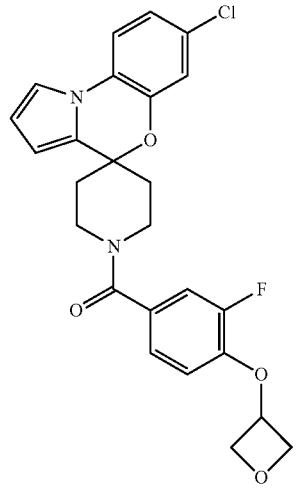 [SMILES: O=C(c1ccc(OC2COC2)c(F)c1)N1CCC2(CC1)Oc1cc(Cl)ccc1-n1cccc12]
778
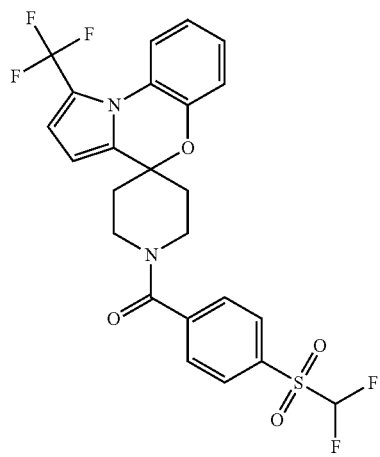 [SMILES: O=C(c1ccc(S(=O)(=O)C(F)F)cc1)N1CCC2(CC1)Oc1ccccc1-n1c(C(F)(F)F)ccc12]
779
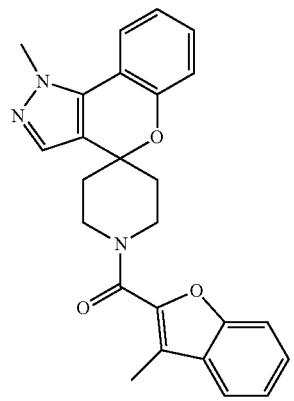 [SMILES: Cc1c(C(=O)N2CCC3(CC2)Oc2ccccc2-c2c3cnn2C)oc2ccccc12]

TABLE 1-continued
780
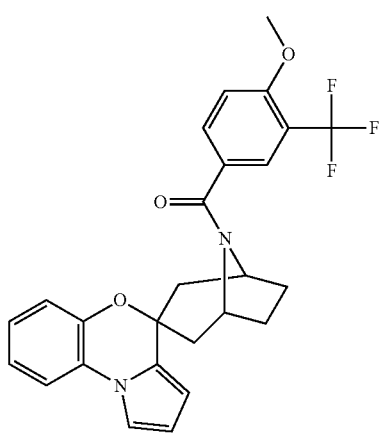 [SMILES: COc1ccc(C(=O)N2C3CCC2CC2(C3)Oc3ccccc3-n3cccc32)cc1C(F)(F)F]
781
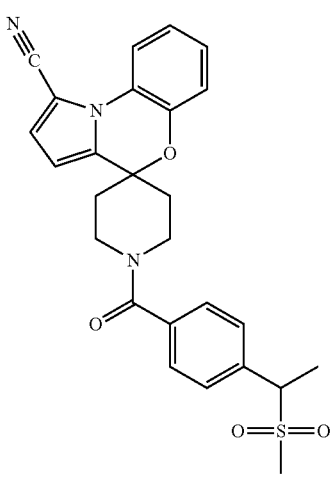 [SMILES: CC(c1ccc(C(=O)N2CCC3(CC2)Oc2ccccc2-n2c(C#N)ccc23)cc1)S(C)(=O)=O]
782
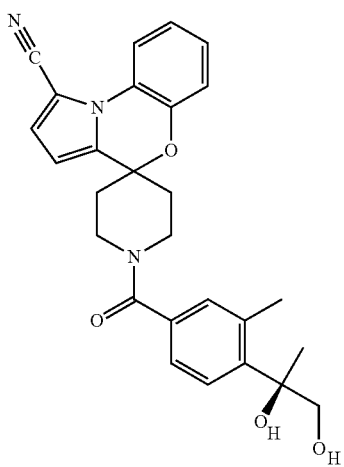
TABLE 1-continued
783
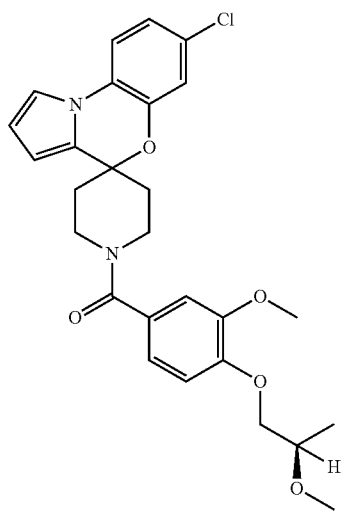
784
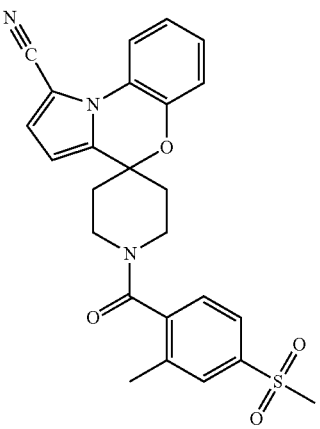 [SMILES: Cc1cc(S(C)(=O)=O)ccc1C(=O)N1CCC2(CC1)Oc1ccccc1-n1c(C#N)ccc12]
785
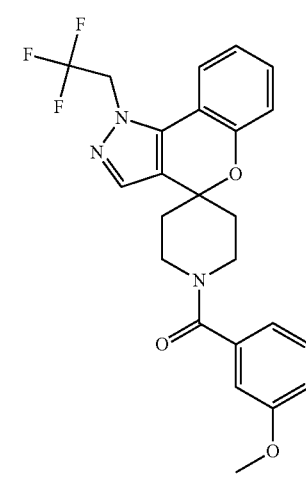

TABLE 1-continued
786
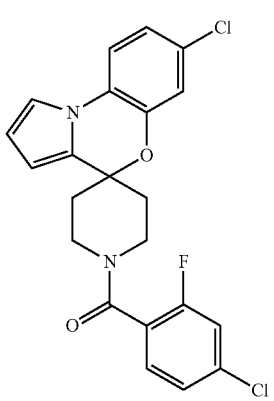
787
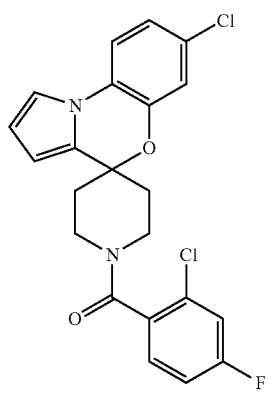 [SMILES: O=C(c1ccc(F)cc1Cl)N1CCC2(CC1)Oc1cc(Cl)ccc1-n1cccc12]
788
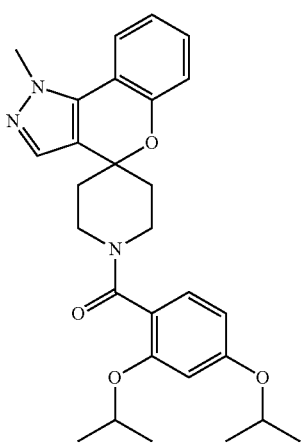 [SMILES: CC(C)Oc1ccc(C(=O)N2CCC3(CC2)Oc2ccccc2-c2c3cnn2C)c(OC(C)C)c1]
TABLE 1-continued
789
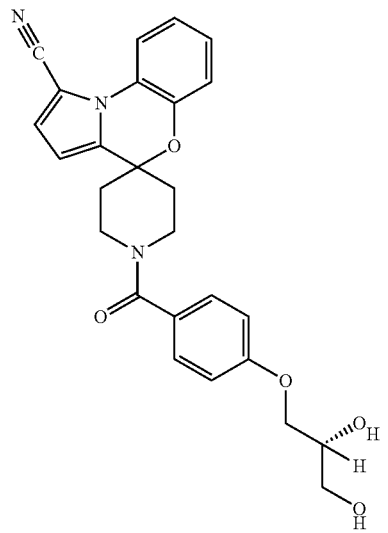
790
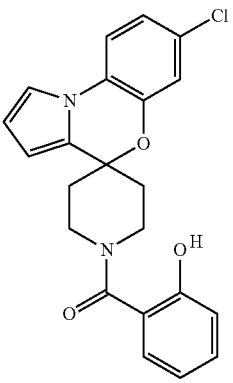
791
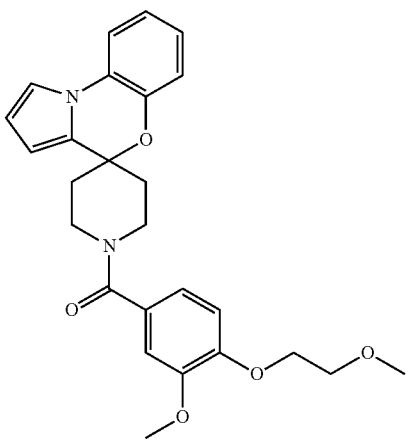 [SMILES: COCCOc1ccc(C(=O)N2CCC3(CC2)Oc2ccccc2-n2cccc23)cc1OC]

TABLE 1-continued
792
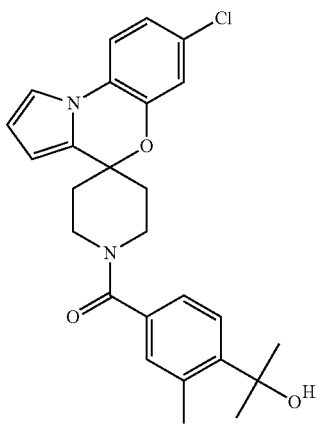
793
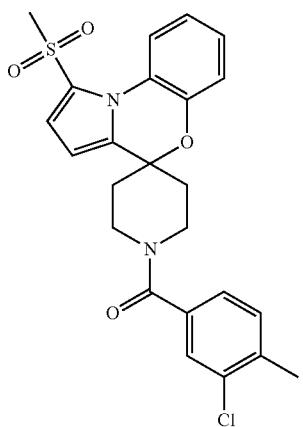 [SMILES: Cc1ccc(C(=O)N2CCC3(CC2)Oc2ccccc2-n2c3ccc2S(C)(=O)=O)cc1Cl]
794
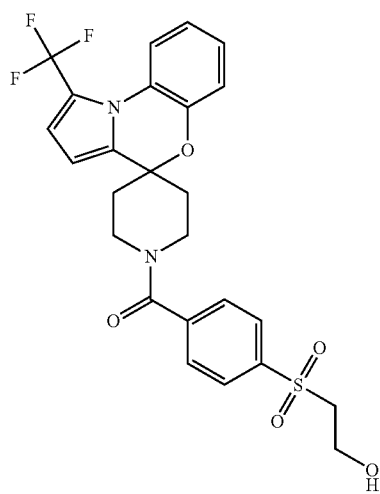 [SMILES: O=C(c1ccc(S(=O)(=O)CCO)cc1)N1CCC2(CC1)Oc1ccccc1-n1c(C(F)(F)F)ccc12]
TABLE 1-continued
795
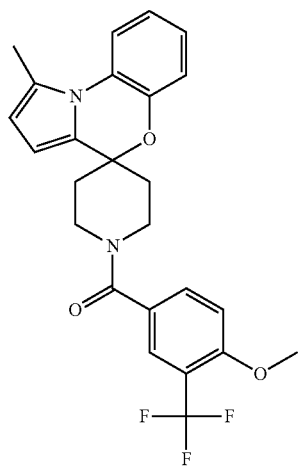 [SMILES: COc1ccc(C(=O)N2CCC3(CC2)Oc2ccccc2-n2c(C)ccc23)cc1C(F)(F)F]
796
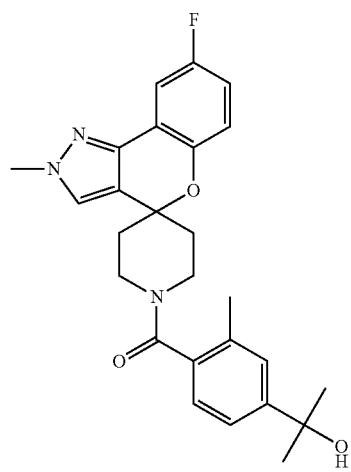 [SMILES: Cc1cc(C(C)(C)O)ccc1C(=O)N1CCC2(CC1)Oc1ccc(F)cc1-c1nn(C)cc12]
797
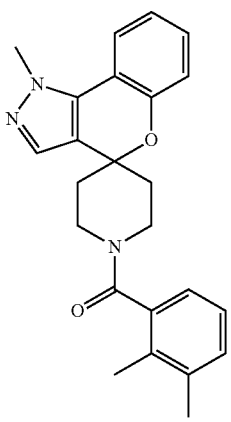 [SMILES: Cc1cccc(C(=O)N2CCC3(CC2)Oc2ccccc2-c2c3cnn2C)c1C]

TABLE 1-continued
798
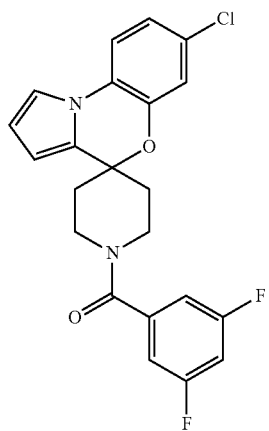 [SMILES: O=C(c1cc(F)cc(F)c1)N1CCC2(CC1)Oc1cc(Cl)ccc1-n1cccc12]
799
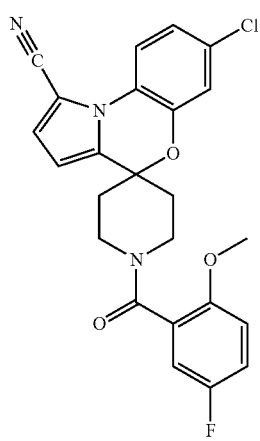 [SMILES: COc1ccc(F)cc1C(=O)N1CCC2(CC1)Oc1cc(Cl)ccc1-n1c(C#N)ccc12]
800
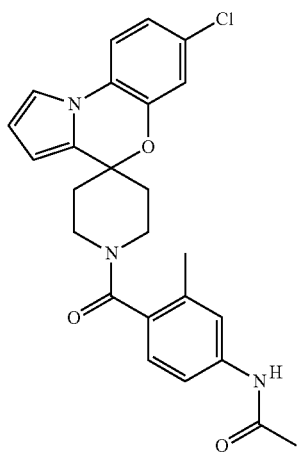
TABLE 1-continued
801
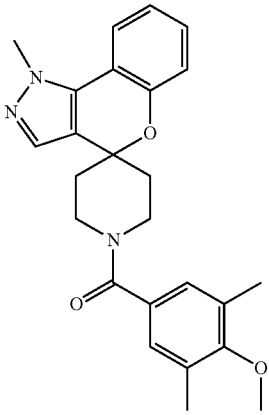 [SMILES: COc1c(C)cc(C(=O)N2CCC3(CC2)Oc2ccccc2-c2c3cnn2C)cc1C]
802
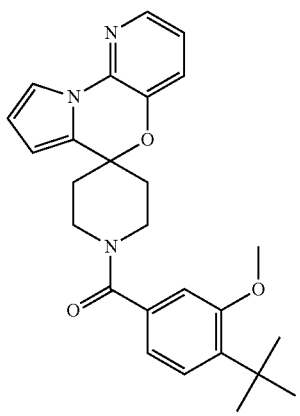 [SMILES: COc1cc(C(=O)N2CCC3(CC2)Oc2cccnc2-n2cccc23)ccc1C(C)(C)C]
803
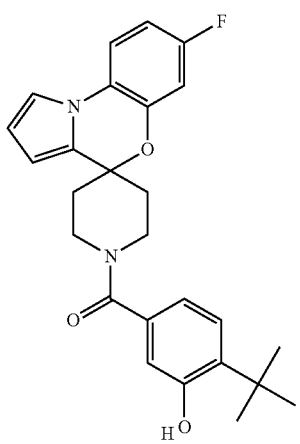

TABLE 1-continued
804
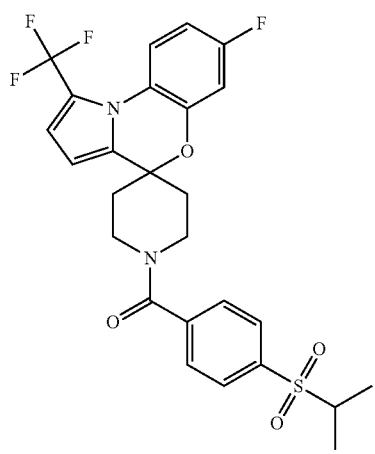 [SMILES: CC(C)S(=O)(=O)c1ccc(C(=O)N2CCC3(CC2)Oc2cc(F)ccc2-n2c(C(F)(F)F)ccc23)cc1]
805
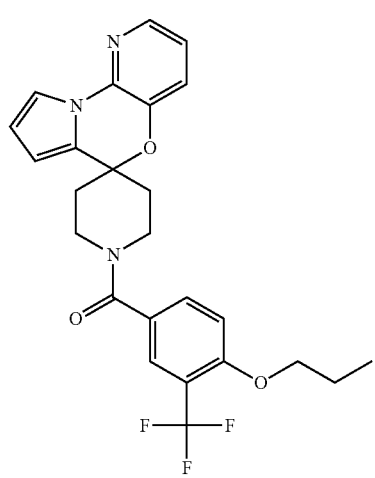 [SMILES: CCCOc1ccc(C(=O)N2CCC3(CC2)Oc2cccnc2-n2cccc23)cc1C(F)(F)F]
806
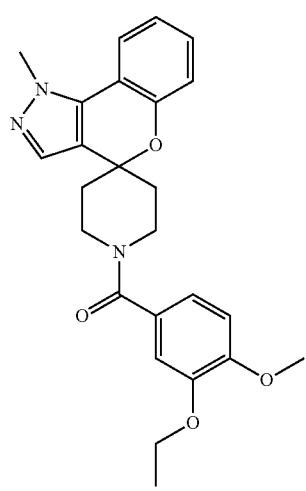 [SMILES: CCOc1cc(C(=O)N2CCC3(CC2)Oc2ccccc2-c2c3cnn2C)ccc1OC]
TABLE 1-continued
807
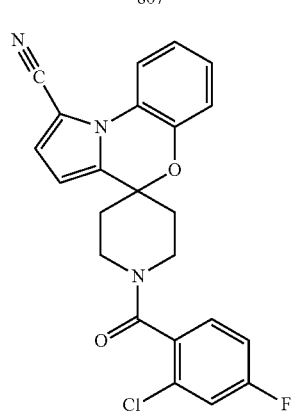
808
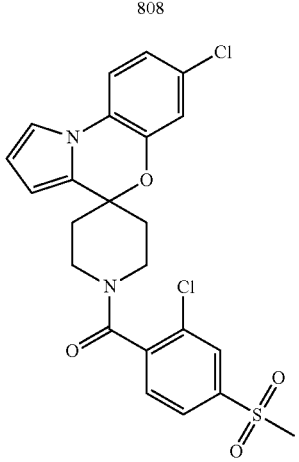
809
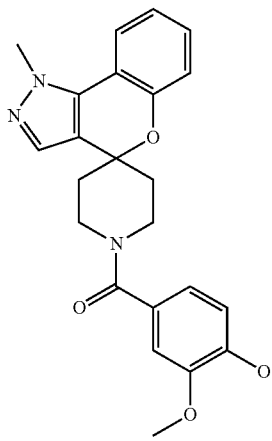 [SMILES: COc1cc(C(=O)N2CCC3(CC2)Oc2ccccc2-c2c3cnn2C)ccc1O]

TABLE 1-continued
810
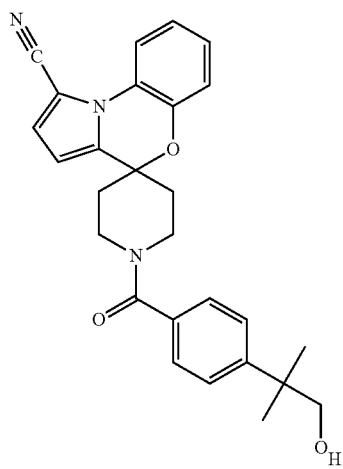
811
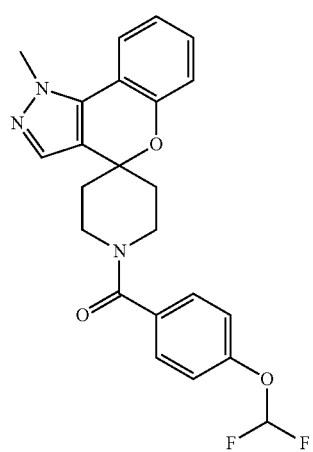 [SMILES: Cn1ncc2c1-c1ccccc1OC21CCN(C(=O)c2ccc(OC(F)F)cc2)CC1]
812
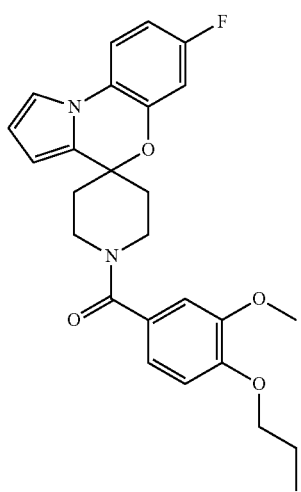 [SMILES: CCCOc1ccc(C(=O)N2CCC3(CC2)Oc2cc(F)ccc2-n2cccc23)cc1OC]
TABLE 1-continued
813
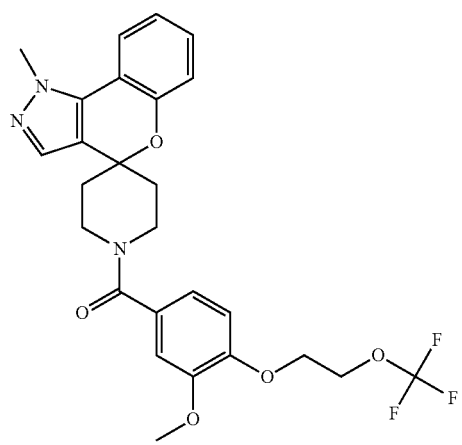 [SMILES: COc1cc(C(=O)N2CCC3(CC2)Oc2ccccc2-c2c3cnn2C)ccc1OCCOC(F)(F)F]
814
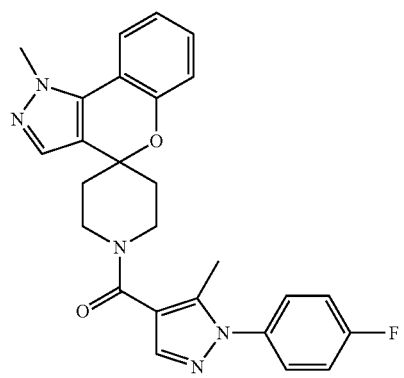 [SMILES: Cc1c(C(=O)N2CCC3(CC2)Oc2ccccc2-c2c3cnn2C)cnn1-c1ccc(F)cc1]
815
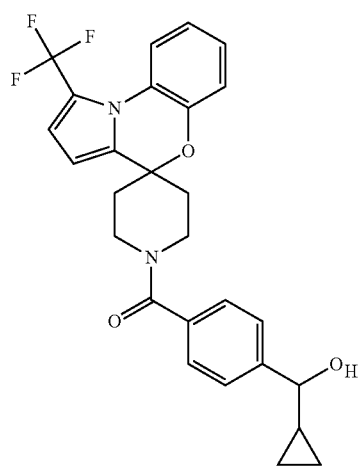

TABLE 1-continued
816
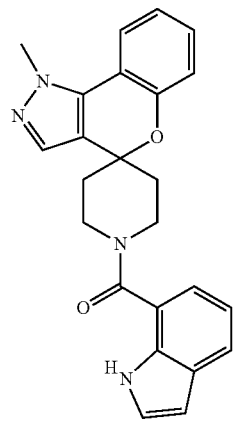
817
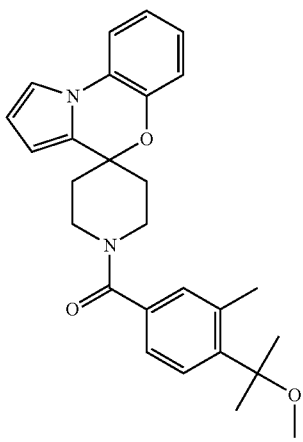 [SMILES: COC(C)(C)c1ccc(C(=O)N2CCC3(CC2)Oc2ccccc2-n2cccc23)cc1C]
818
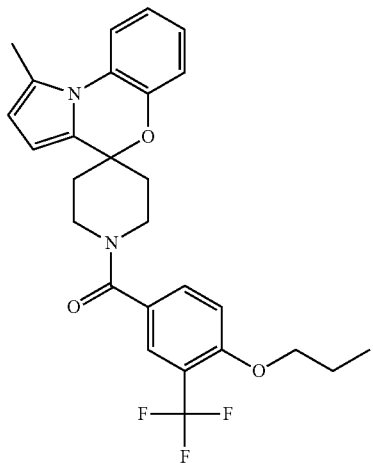 [SMILES: CCCOc1ccc(C(=O)N2CCC3(CC2)Oc2ccccc2-n2c(C)ccc23)cc1C(F)(F)F]
TABLE 1-continued
819
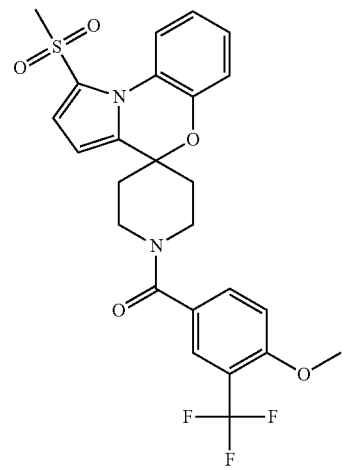 [SMILES: COc1ccc(C(=O)N2CCC3(CC2)Oc2ccccc2-n2c3ccc2S(C)(=O)=O)cc1C(F)(F)F]
820
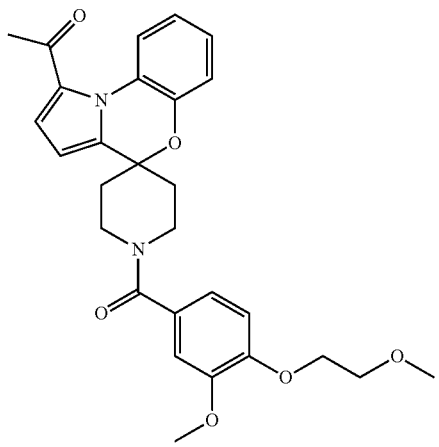 [SMILES: COCCOc1ccc(C(=O)N2CCC3(CC2)Oc2ccccc2-n2c(C(C)=O)ccc23)cc1OC]
821
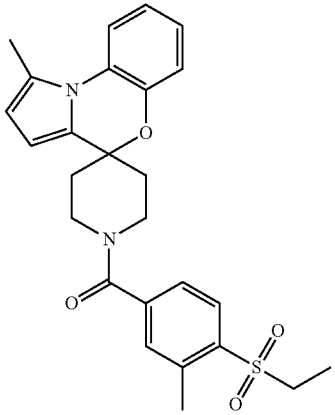 [SMILES: CCS(=O)(=O)c1ccc(C(=O)N2CCC3(CC2)Oc2ccccc2-n2c(C)ccc23)cc1C]

TABLE 1-continued
822
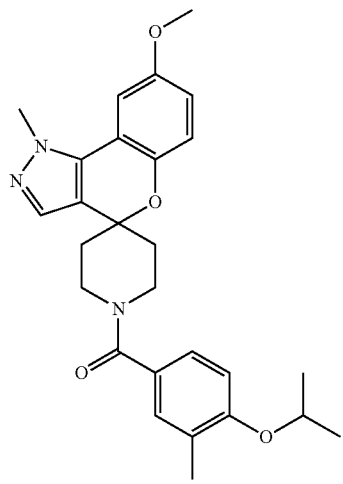 [SMILES: COc1ccc2c(c1)-c1c(cnn1C)C1(CCN(C(=O)c3ccc(OC(C)C)c(C)c3)CC1)O2]
823
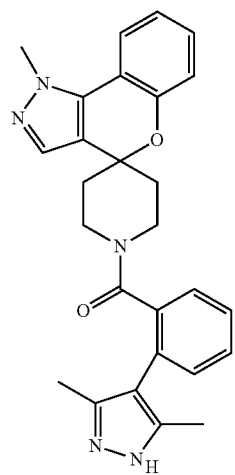
824
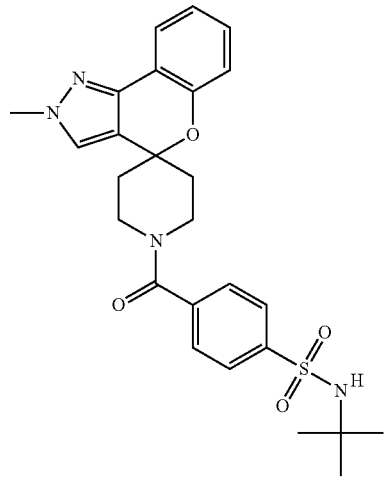
TABLE 1-continued
825
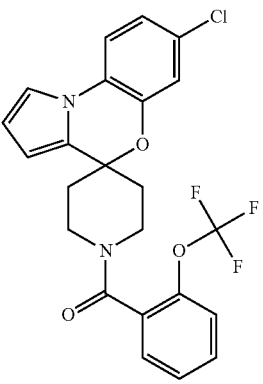 [SMILES: O=C(c1ccccc1OC(F)(F)F)N1CCC2(CC1)Oc1cc(Cl)ccc1-n1cccc12]
826
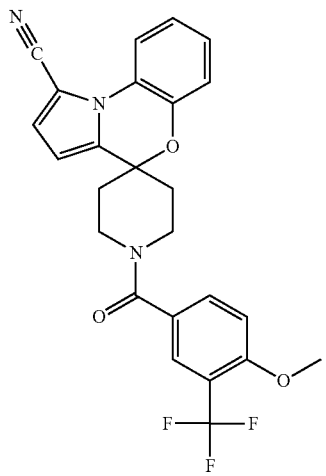 [SMILES: COc1ccc(C(=O)N2CCC3(CC2)Oc2ccccc2-n2c(C#N)ccc23)cc1C(F)(F)F]
827
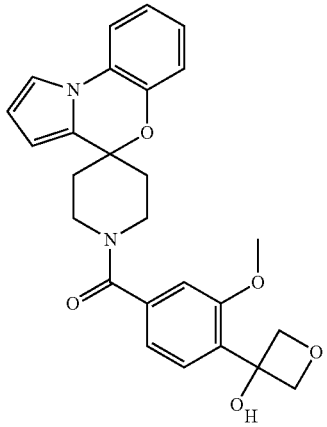

TABLE 1-continued
828
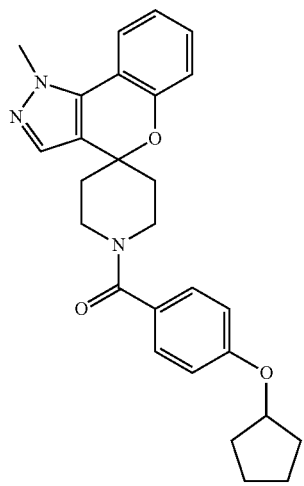 [SMILES: Cn1ncc2c1-c1ccccc1OC21CCN(C(=O)c2ccc(OC3CCCC3)cc2)CC1]
829
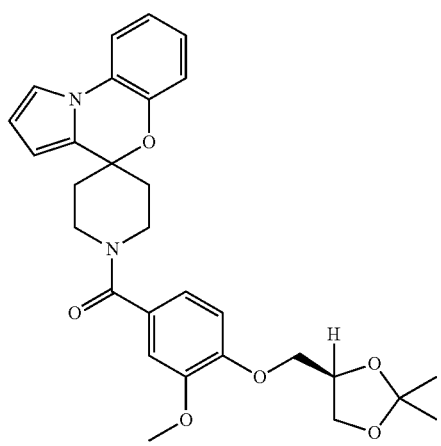 [SMILES: COc1cc(C(=O)N2CCC3(CC2)Oc2ccccc2-n2cccc23)ccc1OC[C@@H]1COC(C)(C)O1]
830
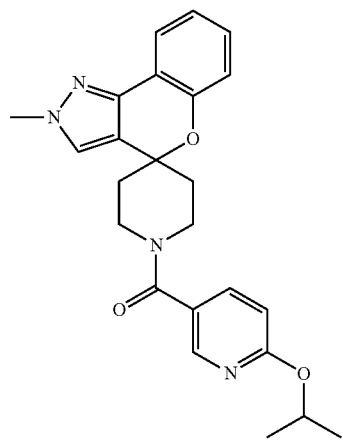 [SMILES: CC(C)Oc1ccc(C(=O)N2CCC3(CC2)Oc2ccccc2-c2nn(C)cc23)cn1]
TABLE 1-continued
831
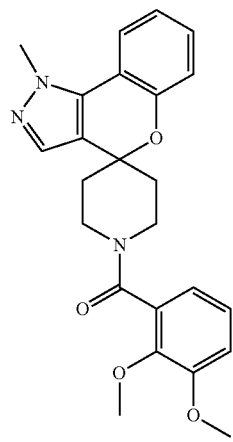 [SMILES: COc1cccc(C(=O)N2CCC3(CC2)Oc2ccccc2-c2c3cnn2C)c1OC]
832
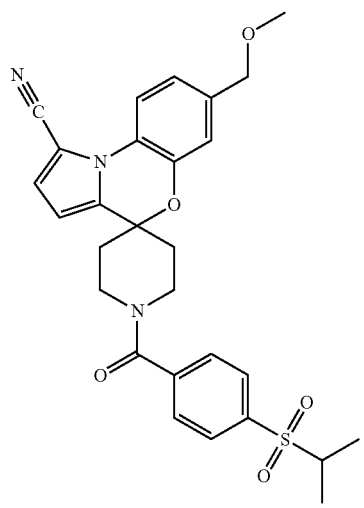 [SMILES: COCc1ccc2c(c1)OC1(CCN(C(=O)c3ccc(S(=O)(=O)C(C)C)cc3)CC1)c1ccc(C#N)n1-2]
833
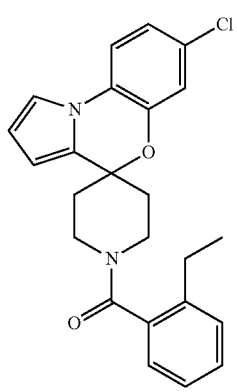 [SMILES: CCc1ccccc1C(=O)N1CCC2(CC1)Oc1cc(Cl)ccc1-n1cccc12]

TABLE 1-continued
834
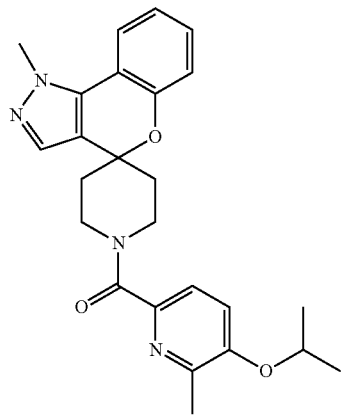 [SMILES: Cc1nc(C(=O)N2CCC3(CC2)Oc2ccccc2-c2c3cnn2C)ccc1OC(C)C]
835
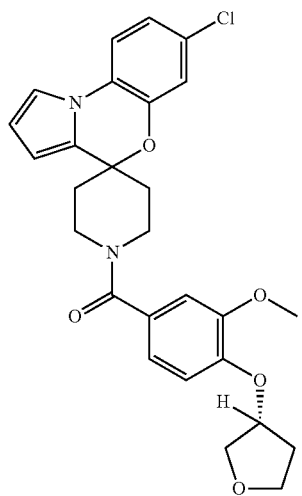 [SMILES: COc1cc(C(=O)N2CCC3(CC2)Oc2cc(Cl)ccc2-n2cccc23)ccc1O[C@@H]1CCOC1]
836
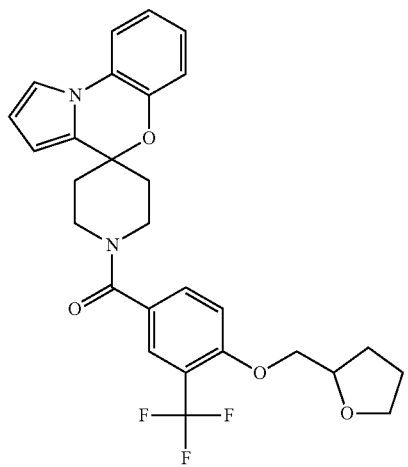 [SMILES: O=C(c1ccc(OCC2CCCO2)c(C(F)(F)F)c1)N1CCC2(CC1)Oc1ccccc1-n1cccc12]
TABLE 1-continued
837
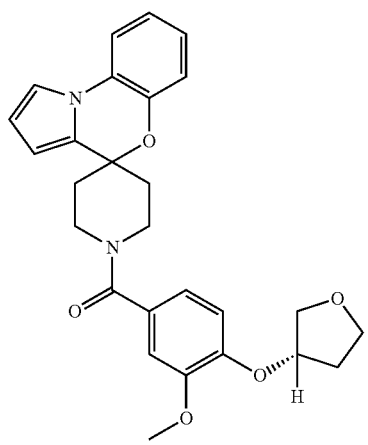 [SMILES: COc1cc(C(=O)N2CCC3(CC2)Oc2ccccc2-n2cccc23)ccc1O[C@H]1CCOC1]
838
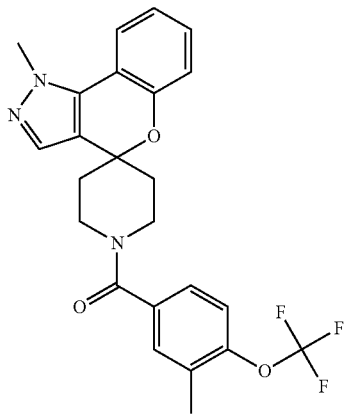 [SMILES: Cc1cc(C(=O)N2CCC3(CC2)Oc2ccccc2-c2c3cnn2C)ccc1OC(F)(F)F]
839
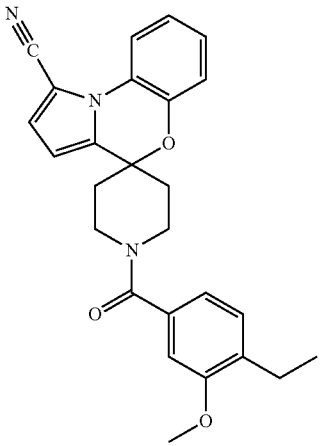 [SMILES: CCc1ccc(C(=O)N2CCC3(CC2)Oc2ccccc2-n2c(C#N)ccc23)cc1OC]

TABLE 1-continued
840
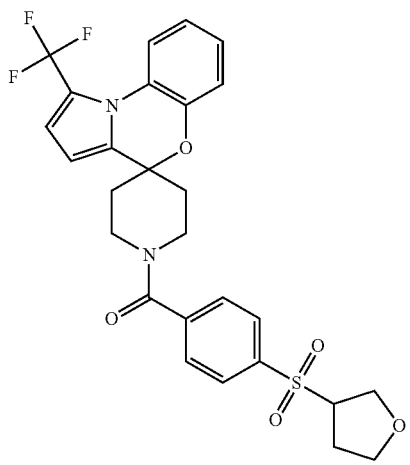 [SMILES: O=C(c1ccc(S(=O)(=O)C2CCOC2)cc1)N1CCC2(CC1)Oc1ccccc1-n1c(C(F)(F)F)ccc12]
841
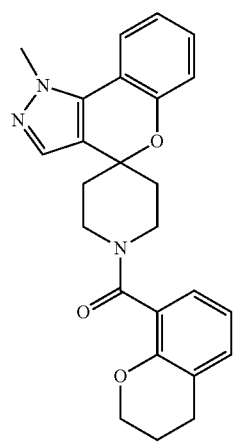 [SMILES: Cn1ncc2c1-c1ccccc1OC21CCN(C(=O)c2cccc3c2OCCC3)CC1]
842
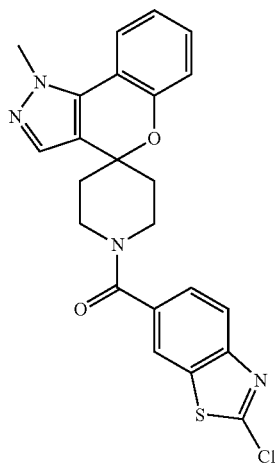 [SMILES: Cn1ncc2c1-c1ccccc1OC21CCN(C(=O)c2ccc3nc(Cl)sc3c2)CC1]
TABLE 1-continued
843
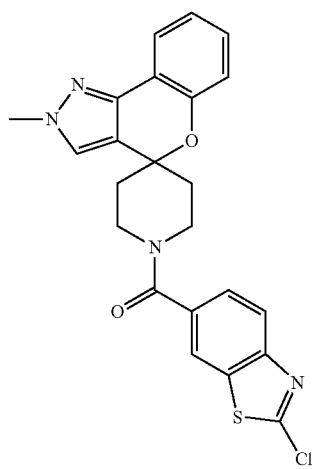 [SMILES: Cn1cc2c(n1)-c1ccccc1OC21CCN(C(=O)c2ccc3nc(Cl)sc3c2)CC1]
844
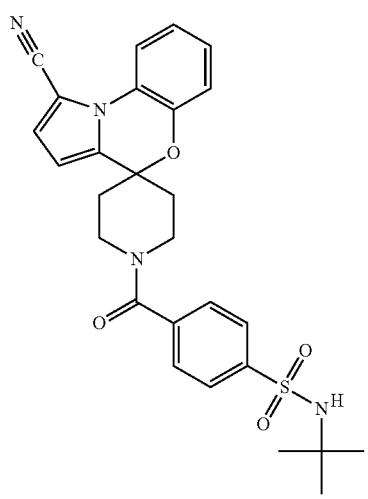
845
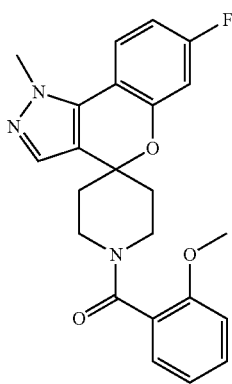 [SMILES: COc1ccccc1C(=O)N1CCC2(CC1)Oc1cc(F)ccc1-c1c2cnn1C]

TABLE 1-continued
846
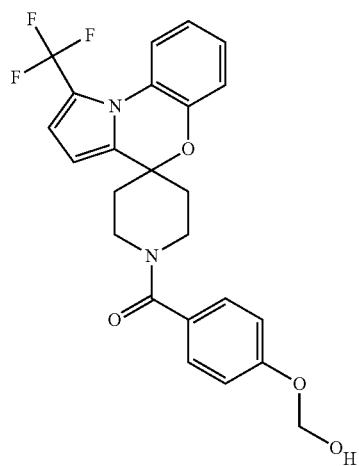
847
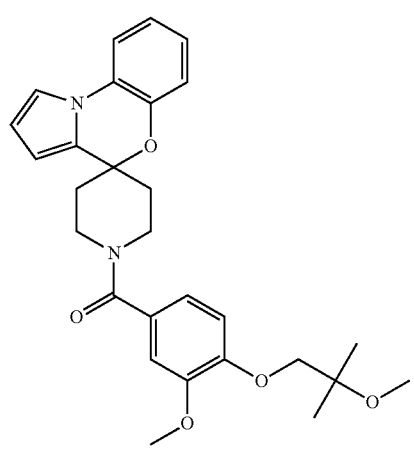 [SMILES: COc1cc(C(=O)N2CCC3(CC2)Oc2ccccc2-n2cccc23)ccc1OCC(C)(C)OC]
848
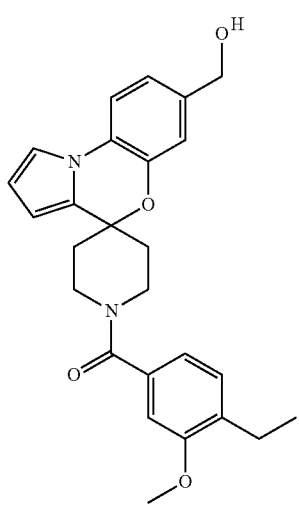
TABLE 1-continued
849
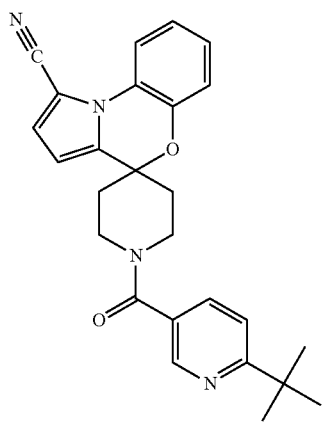 [SMILES: CC(C)(C)c1ccc(C(=O)N2CCC3(CC2)Oc2ccccc2-n2c(C#N)ccc23)cn1]
850
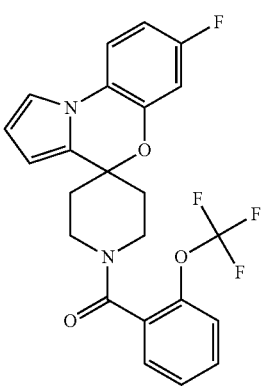 [SMILES: O=C(c1ccccc1OC(F)(F)F)N1CCC2(CC1)Oc1cc(F)ccc1-n1cccc12]
851
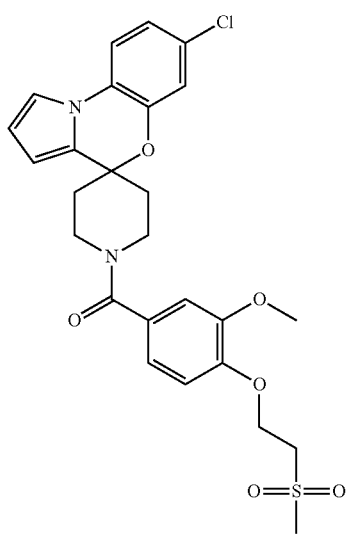 [SMILES: COc1cc(C(=O)N2CCC3(CC2)Oc2cc(Cl)ccc2-n2cccc23)ccc1OCCS(C)(=O)=O]

TABLE 1-continued
852
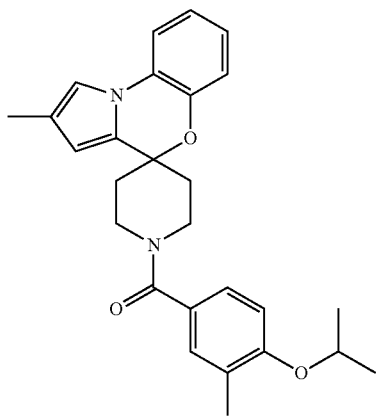 [SMILES: Cc1cc2n(c1)-c1ccccc1OC21CCN(C(=O)c2ccc(OC(C)C)c(C)c2)CC1]
853
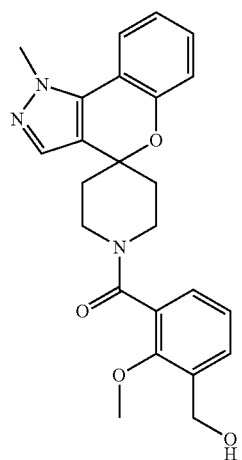 [SMILES: COc1c(CO)cccc1C(=O)N1CCC2(CC1)Oc1ccccc1-c1c2cnn1C]
854
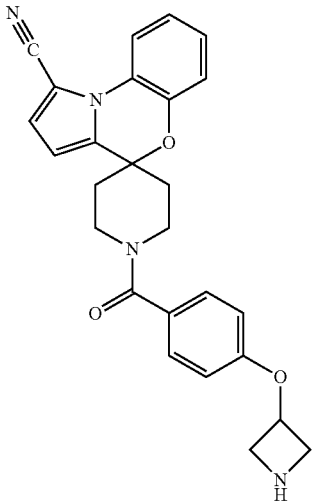 [SMILES: N#Cc1ccc2n1-c1ccccc1OC21CCN(C(=O)c2ccc(OC3CNC3)cc2)CC1]
TABLE 1-continued
855
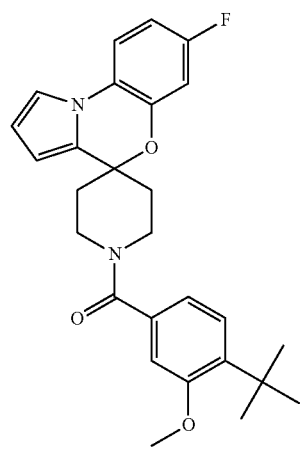
856
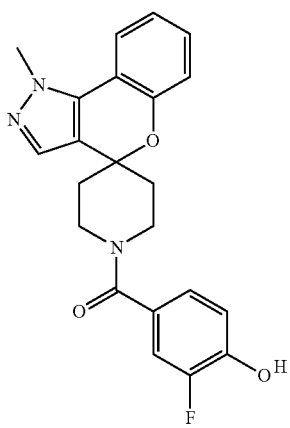
857
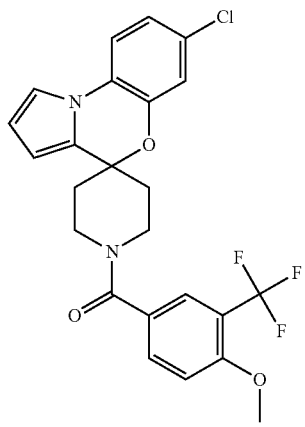

TABLE 1-continued
858
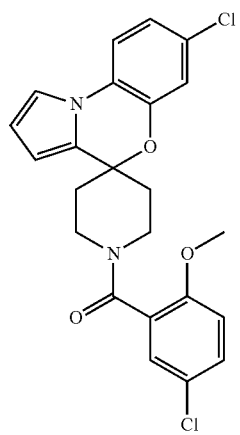 [SMILES: COc1ccc(Cl)cc1C(=O)N1CCC2(CC1)Oc1cc(Cl)ccc1-n1cccc12]
859
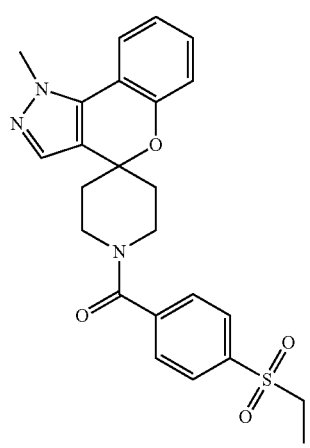 [SMILES: CCS(=O)(=O)c1ccc(C(=O)N2CCC3(CC2)Oc2ccccc2-c2c3cnn2C)cc1]
860
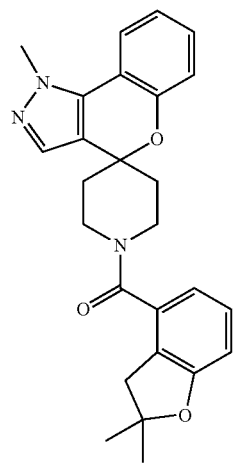 [SMILES: Cn1ncc2c1-c1ccccc1OC21CCN(C(=O)c2cccc3c2CC(C)(C)O3)CC1]
TABLE 1-continued
861
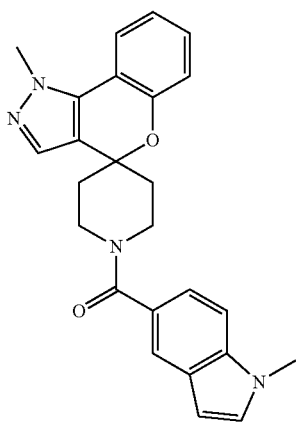 [SMILES: Cn1ncc2c1-c1ccccc1OC21CCN(C(=O)c2ccc3c(ccn3C)c2)CC1]
862
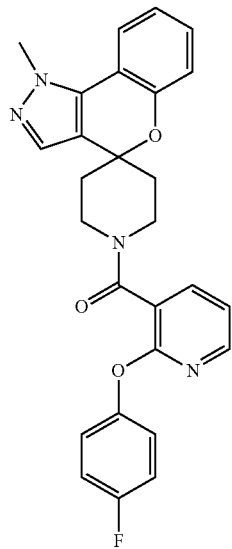 [SMILES: Cn1ncc2c1-c1ccccc1OC21CCN(C(=O)c2cccnc2Oc2ccc(F)cc2)CC1]

TABLE 1-continued
863
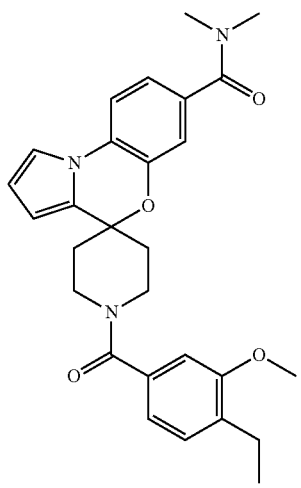 [SMILES: CCc1ccc(C(=O)N2CCC3(CC2)Oc2cc(C(=O)N(C)C)ccc2-n2cccc23)cc1OC]
864
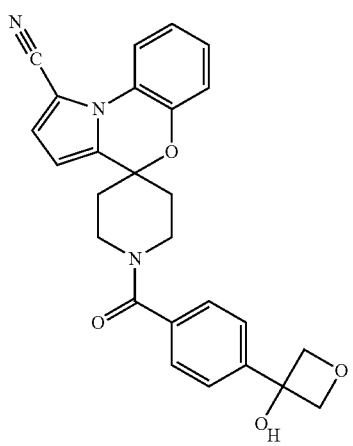
865
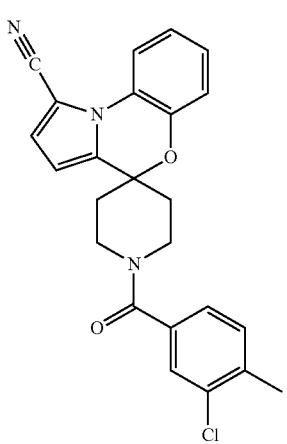 [SMILES: Cc1ccc(C(=O)N2CCC3(CC2)Oc2ccccc2-n2c(C#N)ccc23)cc1Cl]
TABLE 1-continued
866
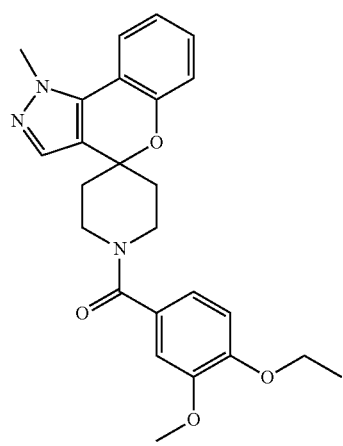 [SMILES: CCOc1ccc(C(=O)N2CCC3(CC2)Oc2ccccc2-c2c3cnn2C)cc1OC]
867
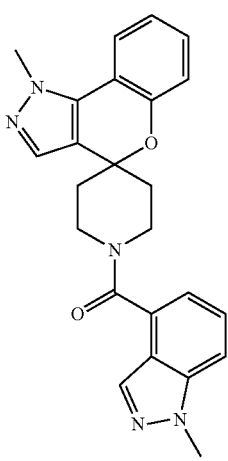 [SMILES: Cn1ncc2c1-c1ccccc1OC21CCN(C(=O)c2cccc3c2cnn3C)CC1]
868
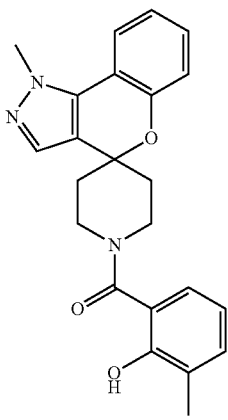 [SMILES: Cc1cccc(C(=O)N2CCC3(CC2)Oc2ccccc2-c2c3cnn2C)c1O]

TABLE 1-continued

869

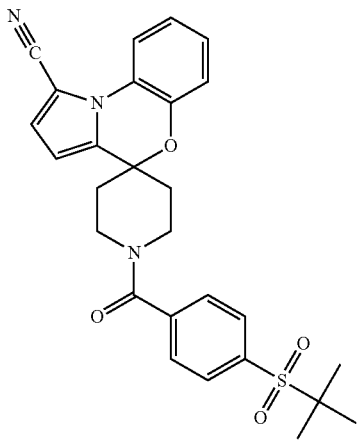 [SMILES: CC(C)(C)S(=O)(=O)c1ccc(C(=O)N2CCC3(CC2)Oc2ccccc2-n2c(C#N)ccc23)cc1]

870

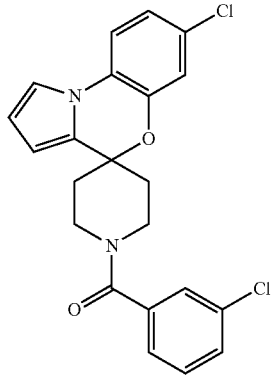 [SMILES: O=C(c1cccc(Cl)c1)N1CCC2(CC1)Oc1cc(Cl)ccc1-n1cccc12]

In another aspect, the invention relates to a pharmaceutical composition comprising a compound of formula I and a pharmaceutically acceptable carrier.

In another aspect, the invention relates to a method of inhibiting a voltage-gated sodium ion channel in:
(a) a patient; or
(b) a biological sample;

comprising administering to the patient, or contacting the biological sample, with a compound of formula I or a pharmaceutical composition comprising a compound of formula I. In another embodiment, the voltage-gated sodium ion channel is NaV1.7.

In another aspect, the invention relates to a method of treating or lessening the severity in a subject of acute, chronic, neuropathic, or inflammatory pain, arthritis, migraine, cluster headaches, trigeminal neuralgia, herpatic neuralgia, general neuralgias, epilepsy or epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abormal gastro-intestinal motility, comprising administering an effective amount of a compound of formula I or a pharmaceutical composition comprising a compound of formula I.

In another embodiment, said method is used for treating or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, including, cluster headaches; chronic and acute neuropathic pain, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritis, tinnitis, or angina-induced pain.

The compounds of the invention may be prepared readily using the following methods. Illustrated below in Scheme 1 through Scheme 24 are methods for preparing the compounds of the invention.

General Scheme 1
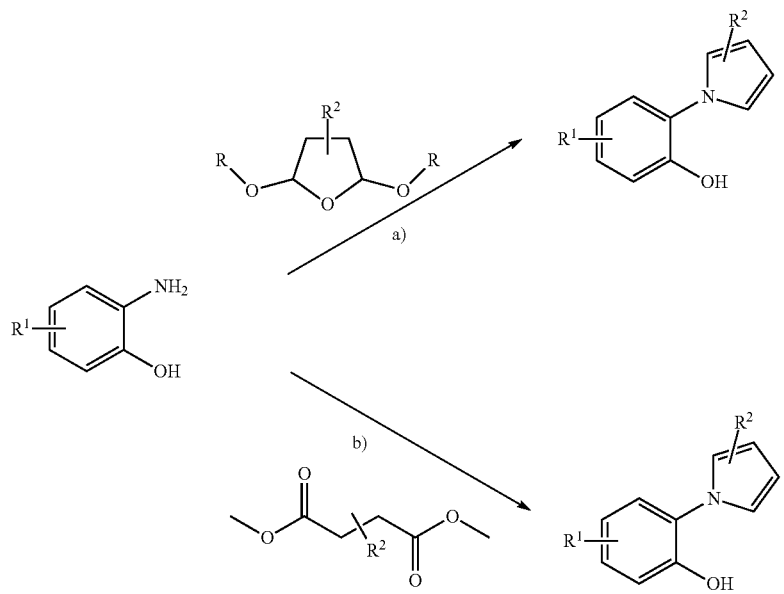
R is alkyl such as methyl.
a) H⁺: protic acid such as acetic acid or para-toluene sulfonic acid; b) diisobutylaluminium hydride, CH₂Cl₂.
General Scheme 2
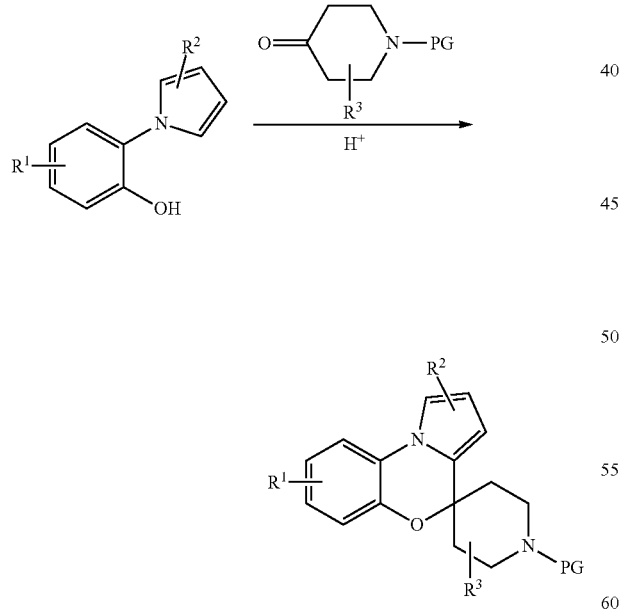
PG=protective group such as BOC, benzyl, CBZ.
H⁺: protic acid such as trifluoroacetic acid, para-toluene sulfonic acid, propionic acid, or dichloroacetic acid.
General Scheme 3
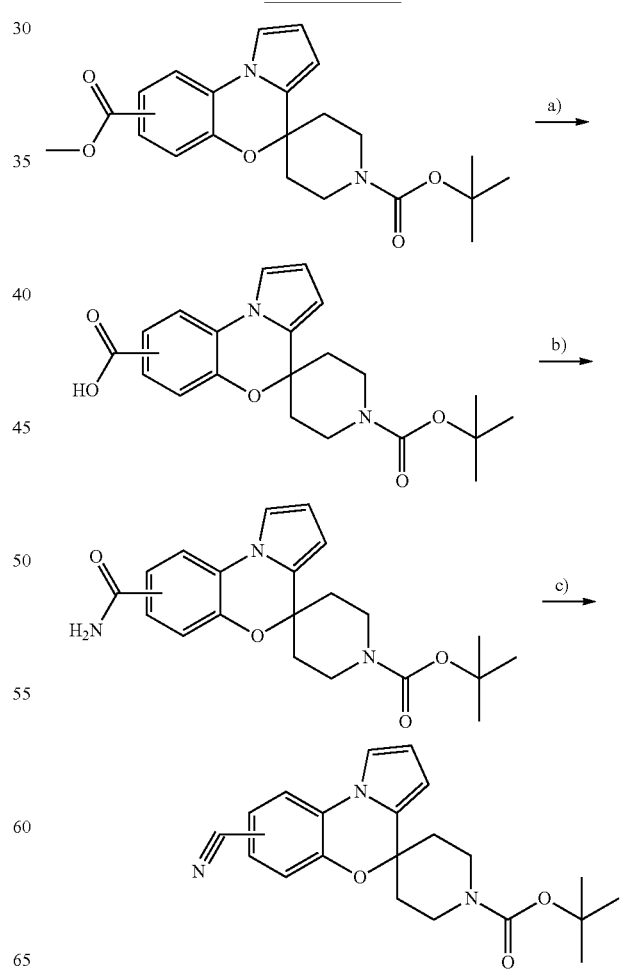

a) aqueous MOH (i.e. NaOH, LiOH), polar solvent miscible with water like dioxane or THF;
b) coupling agent (i.e. HATU), base (i.e. TEA, NH₄Cl or NH₃ in DMF or CH₂Cl₂; c) cyanuric chloride, DMF.
General Scheme 4
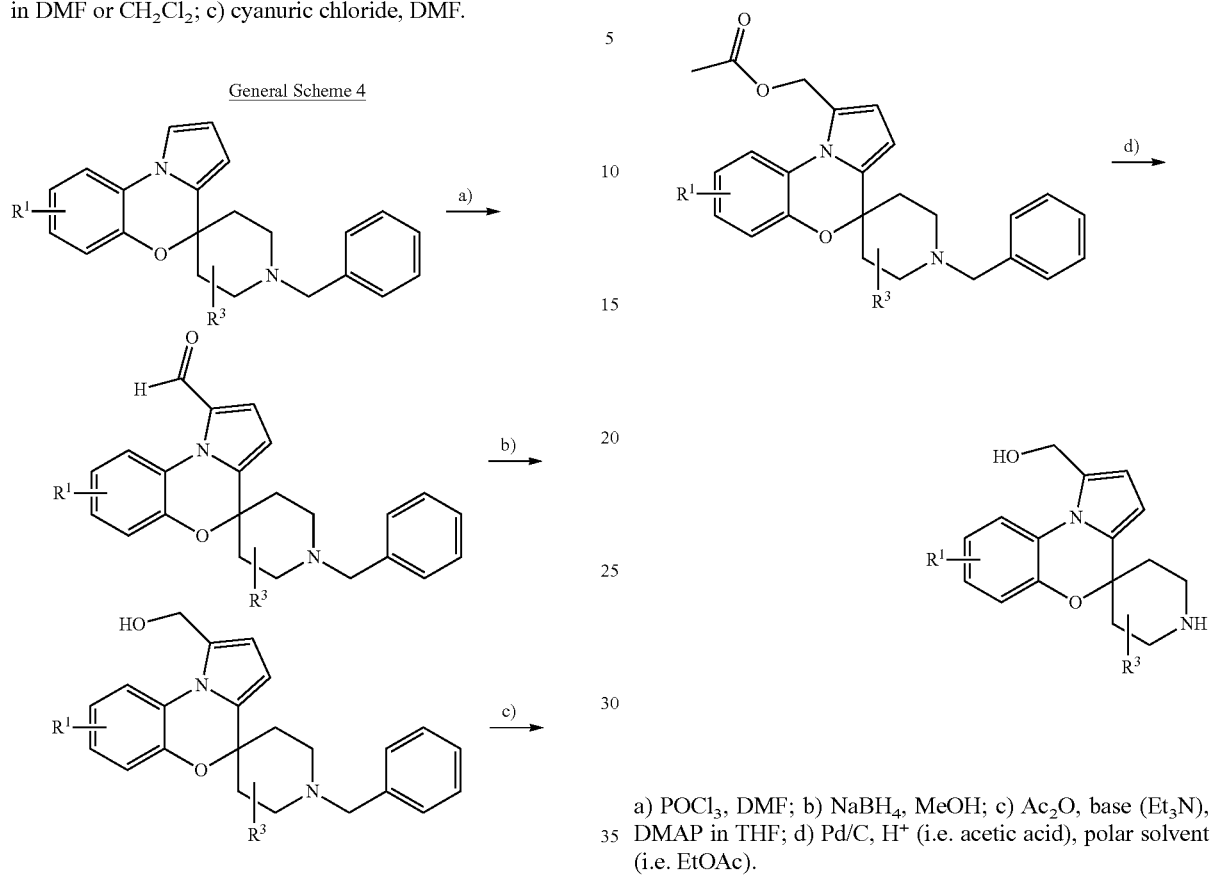
-continued
a) POCl₃, DMF; b) NaBH₄, MeOH; c) Ac₂O, base (Et₃N), DMAP in THF; d) Pd/C, H⁺ (i.e. acetic acid), polar solvent (i.e. EtOAc).
General Scheme 5
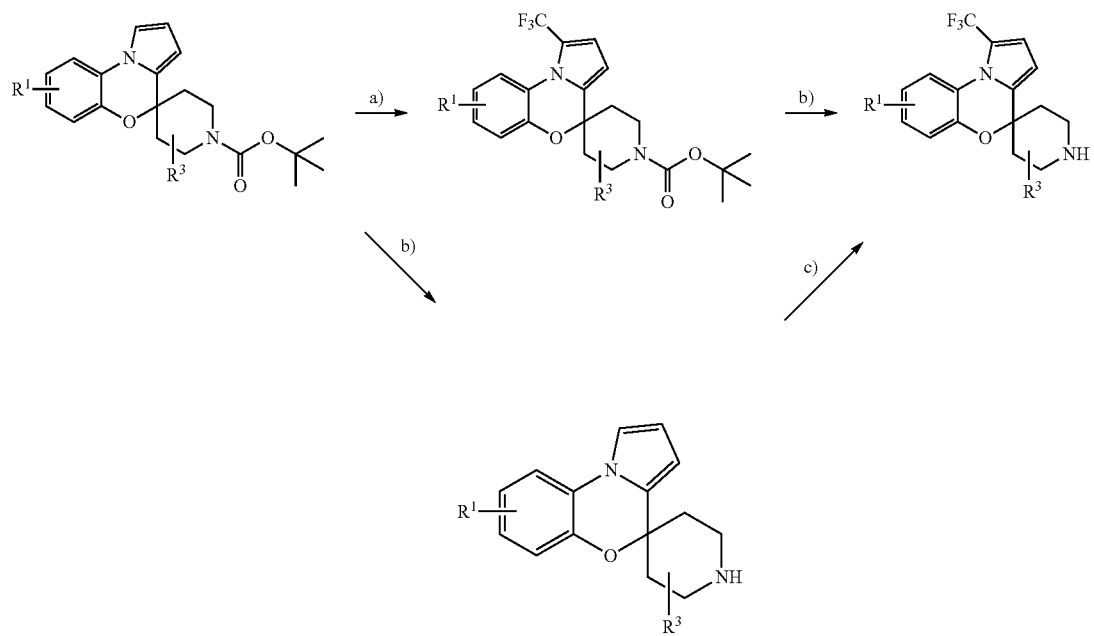

a) trifluoromethanesulfonate 5-(trifluoromethyl)dibenzothiophen-5-ium, $K_2CO_3$, DMF; b) protic acid (i.e. HCl, TFA), solvent (i.e. dioxane, $CH_2Cl_2$); c) $CF_3I$, $FeSO_4 \cdot 7H_2O$, $H_2SO_4$, $H_2O_2$, DMSO.

-continued

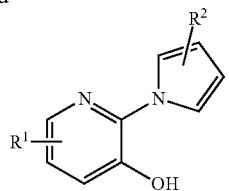

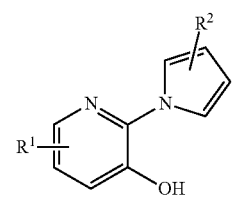

a) $H^+$: protic acid such as acetic acid or para-toluene sulfonic acid; b) diisobutylaluminium hydride, $CH_2Cl_2$.

General Scheme 6

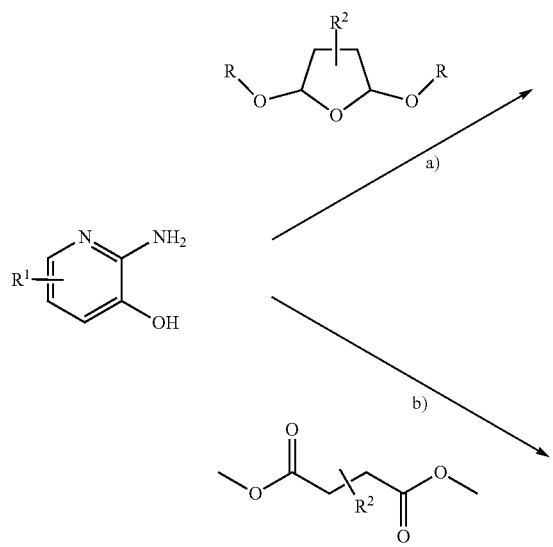

General Scheme 7

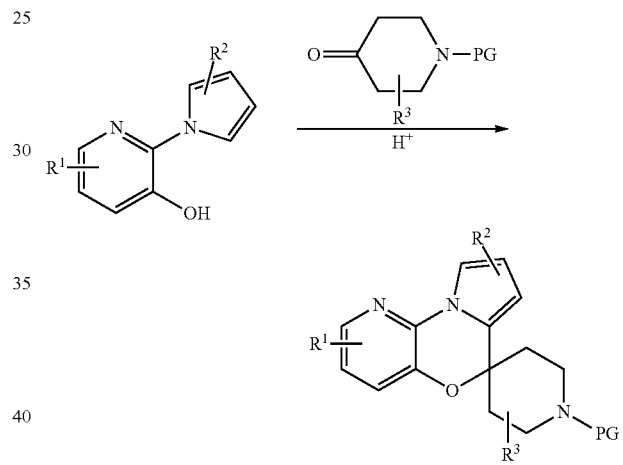

PG=protective group such as BOC, benzyl, CBZ.
$H^+$: protic acid such as trifluoroacetic acid, para-toluene sulfonic acid, propionic acid, or dichloroacetic acid.

General Scheme 8

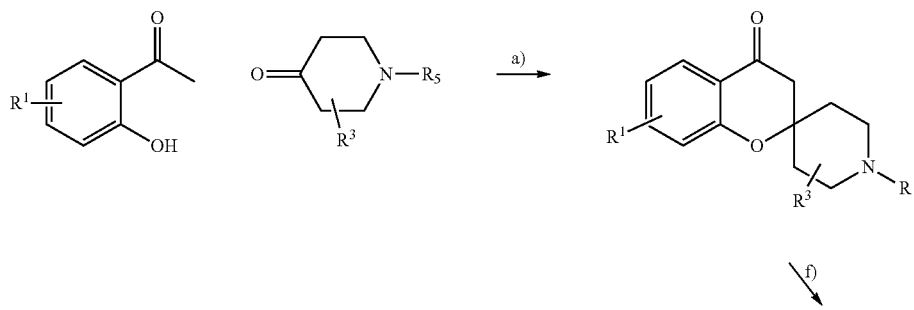

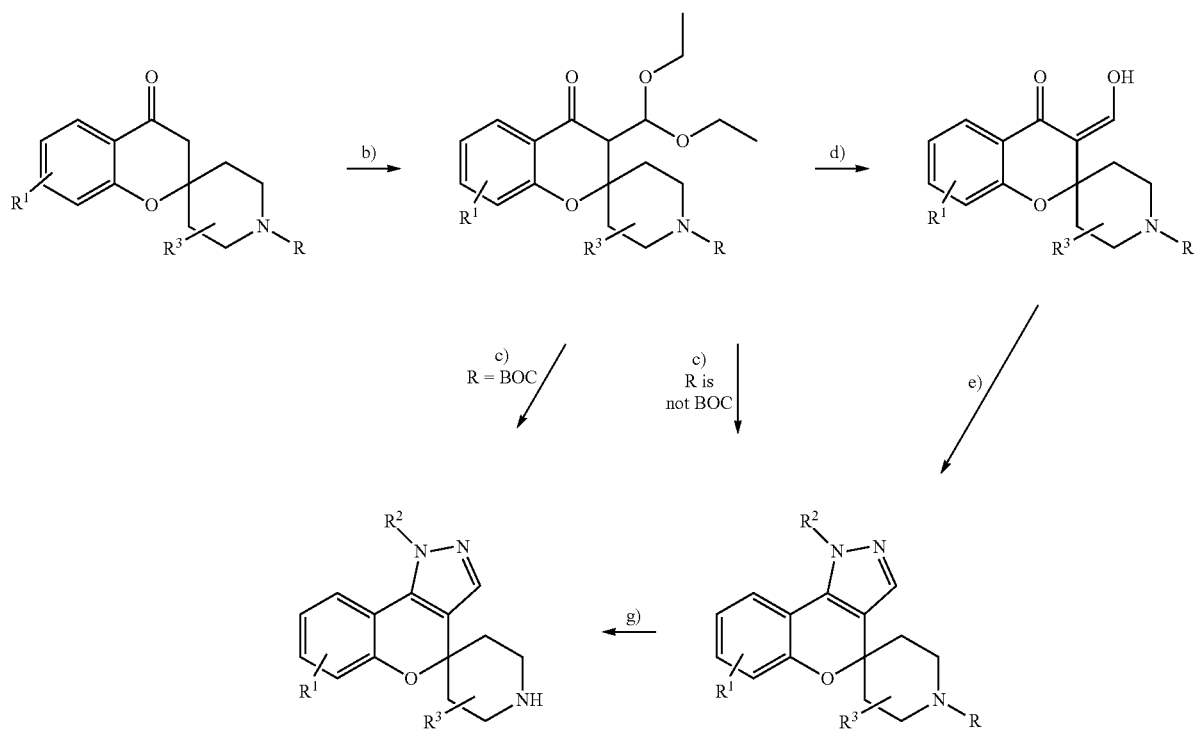

R=benzyl, CO₂Bn, BOC, COCH₃, COCF₃, COAryl.
a) pyrrolidine, MeOH; b) BF₃.OEt₂, (EtO)₃CH, CH₂Cl₂; c) 1) HCl, dioxane; 2) NH₂—NR²BOC; 3) R=BOC, HCl, dioxane; d) I₂, acetone; e) 1) NH₂—NHR²BOC, EtOH; 2) R=BOC, HCl, dioxane; f) NaH, HCO₂Et; g) deprotection: R=benzyl or CO₂Bn, Pd/C, H₂; R=COCF₃ or COCH₃, NaOH, MeOH; R=BOC, HCl, dioxane.

a) LDA, R'COH, THF; (R'=aliphatic) b) oxidation (i.e. Dess-Martin periodinane) in CH₂Cl₂; c) NH₂NR²BOC, para-toluene sulfonic acid, EtOH; d) deprotection: Pd/C, H₂; NaOH, MeOH; HCl, dioxane.

General Scheme 9

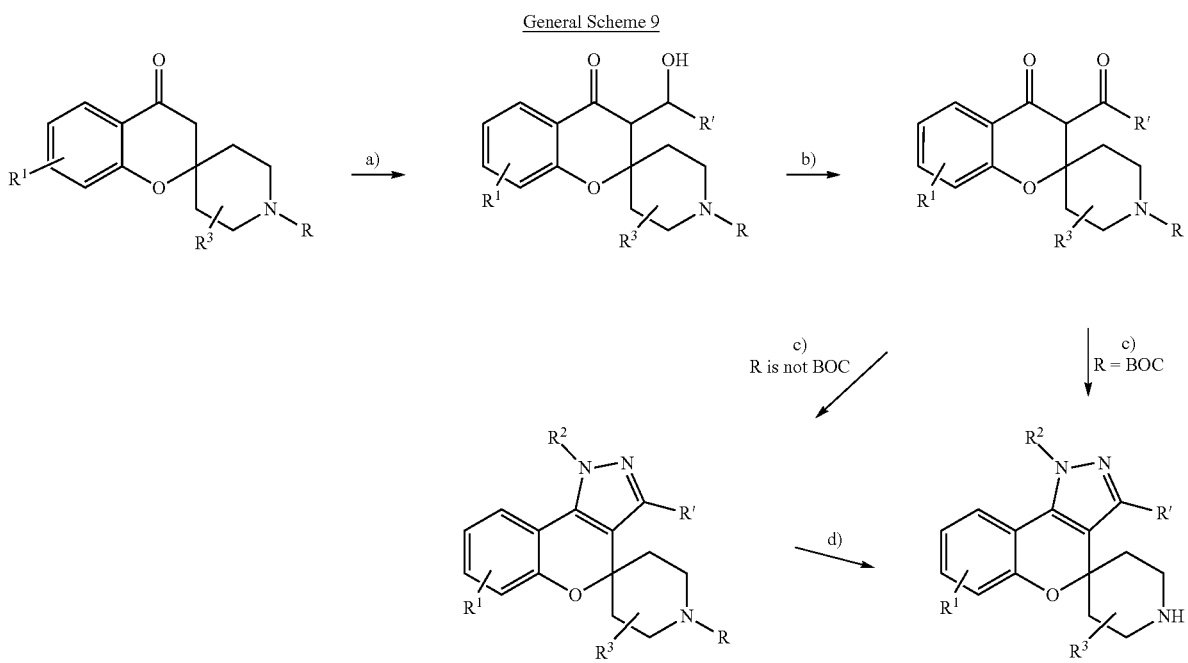

General Scheme 10
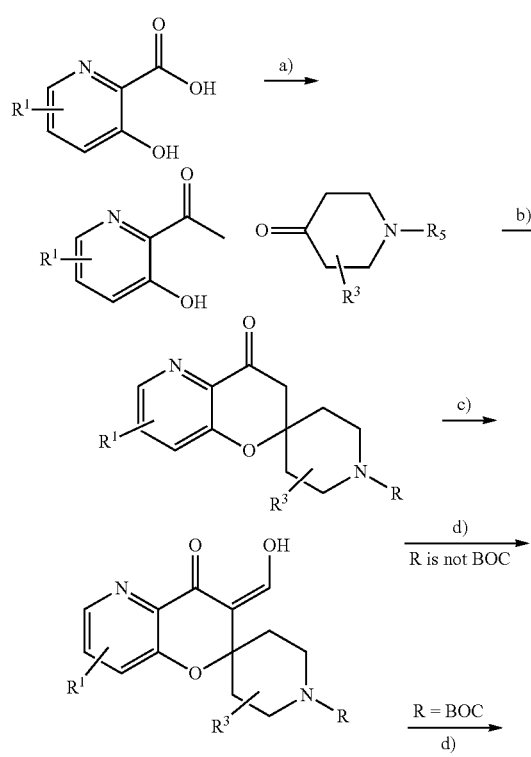
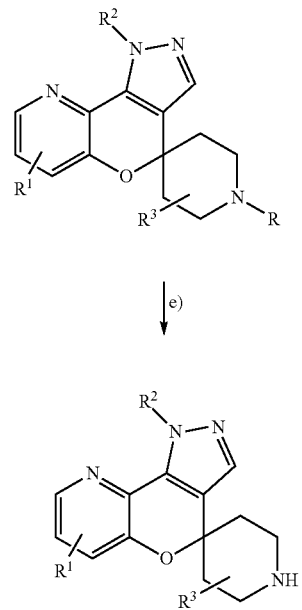
R=benzyl, BOC, COCH₃, COCF₃, COAryl.
a) MeMgX (X=Br, I); Et₃N, THF; MeCOH; b) pyrrolidine, MeOH; c) NaH, HCO₂Et; d) 1) NH₂—NR²BOC, EtOH; 2) HCl, dioxane e) deprotection: Pd/C, H₂; NaOH, MeOH; HCl, dioxane.
General Scheme 11
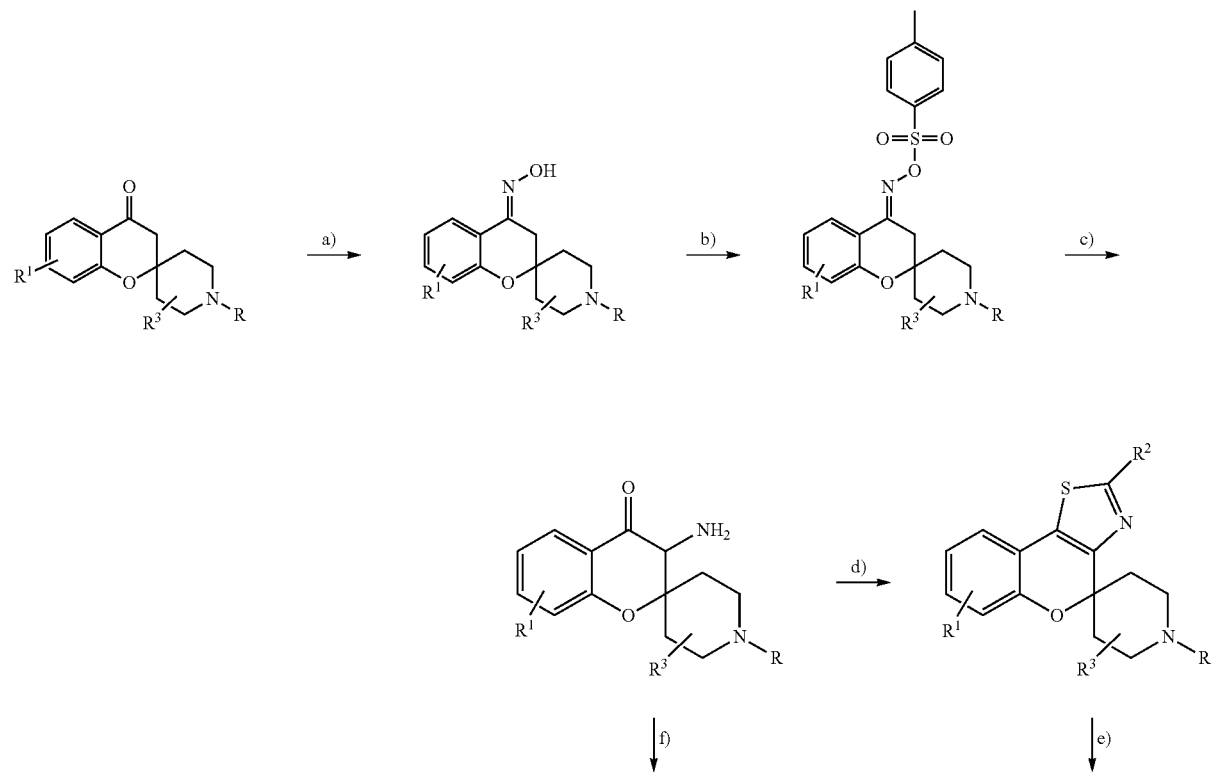

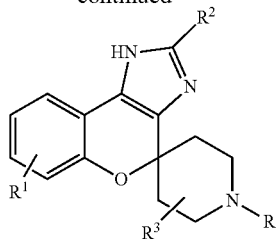

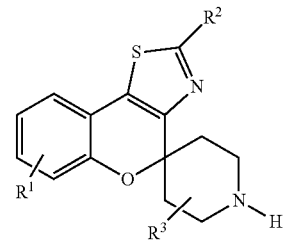

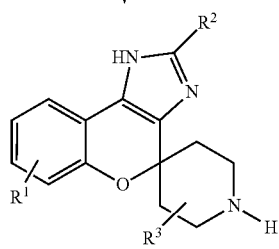

a) NH₂OH, H₂O, MeOH b) p-TSCl, pyridine; c) NaOEt; toluene d) 1) R²COCl, Et₃N, CH₂Cl₂; 2) Lawesson's reagent, toluene; e) Deprotection: R=BOC: HCl, dioxane; f) R²CONH₂, 180° C.; g) Deprotection: R=CBZ; Pd/C, H₂; NaOH, MeOH.

General Scheme 12

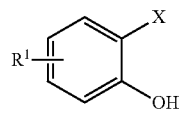 + 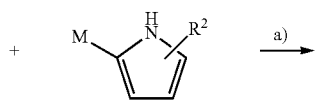 →a)

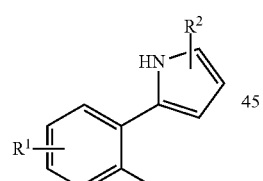

X=Cl, Br, I, OTf; M=B(OR)₂, ZnCl, MgBr.

a) Pd(0) such as Pd(PPh₃)₄, base such as Et₃N or K₂CO₃ in a solvent such as THF, DMF or DCE, 80° C.

General Scheme 13

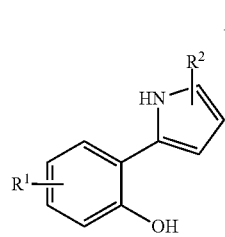 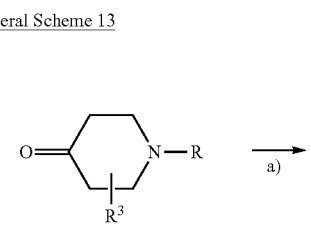 →a)

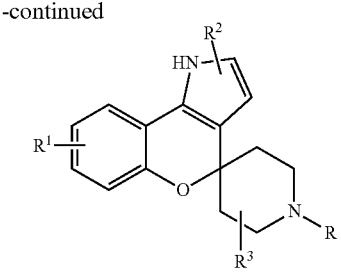

a) protic acid (i.e. para-toluene sulfonic acid.H₂O), DCE, 80° C.; b) deprotection (i.e R=BOC: HCl, dioxane).

General Scheme 14

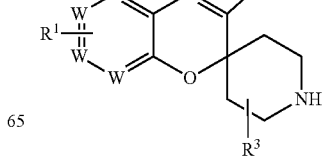 a or b

395

-continued

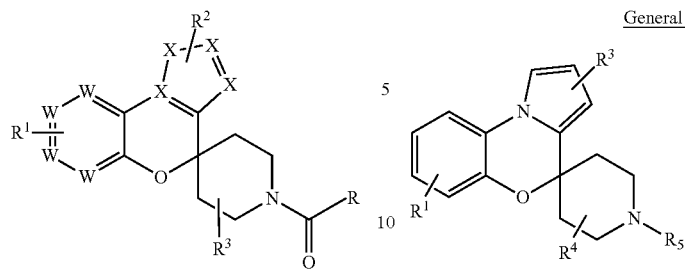

a) RCO₂H, coupling agent (i.e. HATU, EDCl), base (i.e. TEA), polar aprotic solvent (i.e. DMF, CH₂Cl₂); b) RCOCl, base (i.e. TEA), polar aprotic solvent (i.e. DMF, CH₂Cl₂).

General Scheme 15

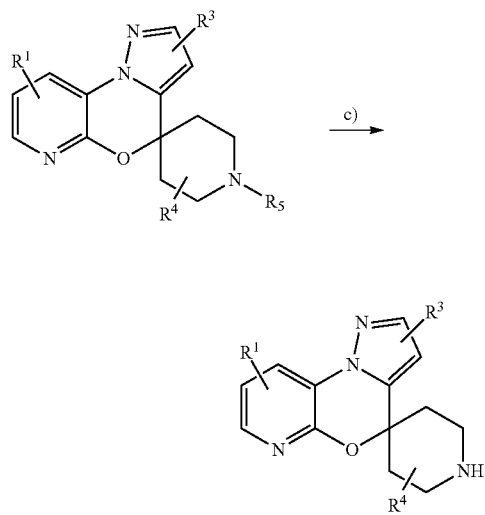

$R_5$=benzyl, CO₂Bn, BOC, COCH₃, COCF₃, COAryl.

a) K₂CO₃, DMF; b) nBuLi, THF; c) $R_5$=BOC: protic acid (i.e. HCl, TFA), solvent (i.e. dioxane, MeOH, CH₂Cl₂); $R_5$=benzyl, CO₂Bn: H₂, Pd/C, solvent (i.e. MeOH, EtOH, iPrOH, EOAc); $R_5$=COCH₃, COCF₃: base (i.e. NaOH, K₂CO₃), solvent (i.e. MeOH, EtOH, water).

396

General Scheme 16

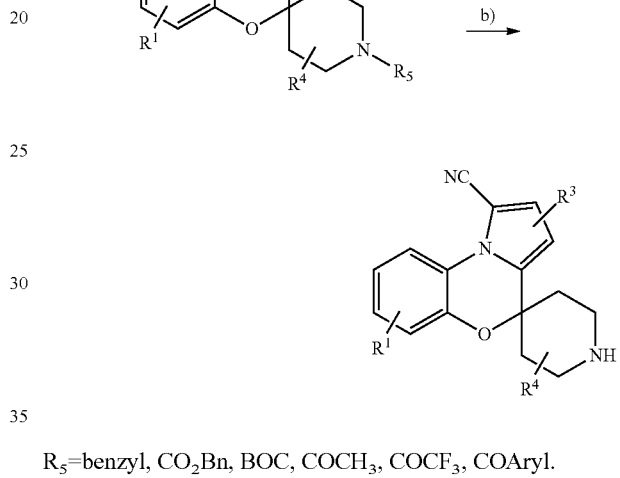

$R_5$=benzyl, CO₂Bn, BOC, COCH₃, COCF₃, COAryl.

a) chlorosulfonyl isocyanate, THF; b) $R_5$=BOC: protic acid (i.e. HCl, TFA), solvent (i.e. dioxane, MeOH, CH₂Cl₂); $R_5$=benzyl, CO₂Bn: H₂, Pd/C, solvent (i.e. MeOH, EtOH, iPrOH, EOAc); $R_5$=COCH₃, COCF₃: base (i.e. NaOH, K₂CO₃), solvent (i.e. MeOH, EtOH, water).

General Scheme 17

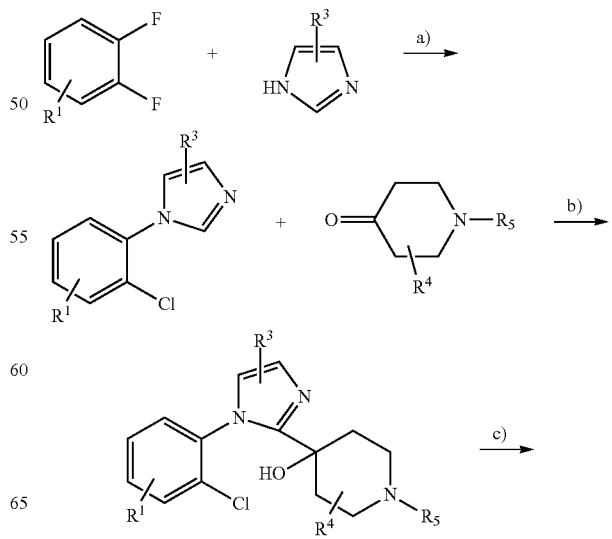

397

-continued

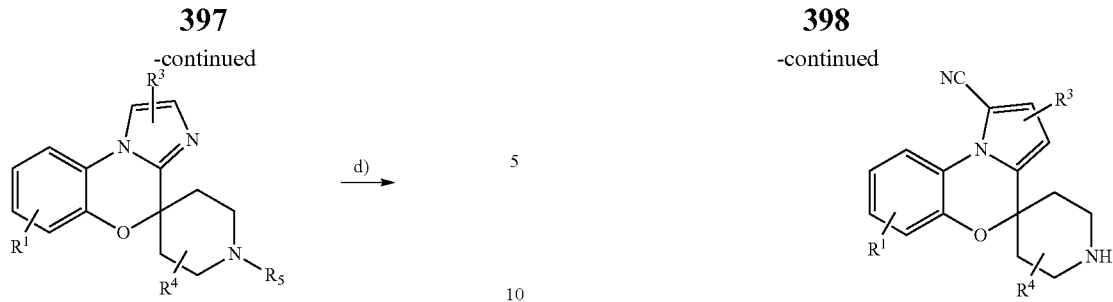

$R_5$=BOC, benzyl, $CO_2Bn$, $COCH_3$, $COCF_3$, COAryl.
a) $K_2CO_3$, DMSO; b) nBuLi, THF; c) $K_2CO_3$, DMF; d) $R_5$=BOC: protic acid (i.e. HCl, TFA), solvent (i.e. dioxane, MeOH, $CH_2Cl_2$); $R_5$=benzyl, $CO_2Bn$: $H_2$, Pd/C, solvent (i.e. MeOH, EtOH, iPrOH, EOAc); $R_5$=$COCH_3$, $COCF_3$: base (i.e. NaOH, $K_2CO_3$), solvent (i.e. MeOH, EtOH, water).

General Scheme 18

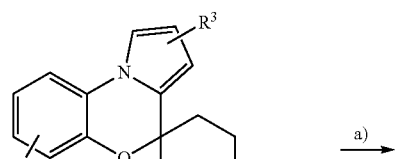

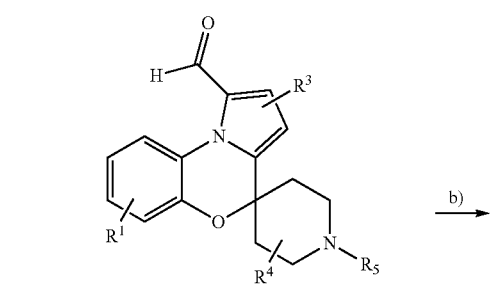

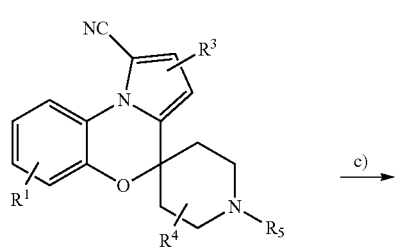

398

-continued

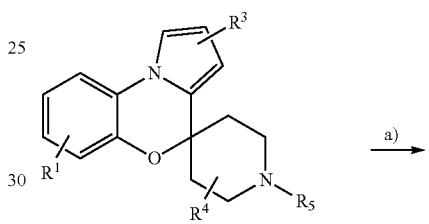

$R_5$=benzyl, $CO_2Bn$, $COCH_3$, $COCF_3$, COAryl.
a) $POCl_3$, DMF; b) HO—$NH_2$·HCl, EtOH, NaOAc, $H_2O$; c) $R_5$=benzyl, $CO_2Bn$: $H_2$, Pd/C, solvent (i.e. MeOH, EtOH, iPrOH, EOAc); $R_5$=$COCH_3$, $COCF_3$: base (i.e. NaOH, $K_2CO_3$), solvent (i.e. MeOH, EtOH, water).

General Scheme 19

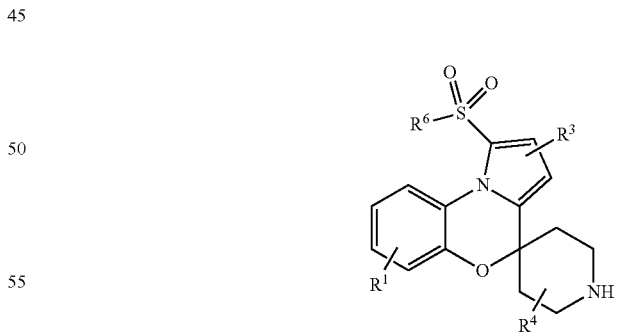

$R_5$=BOC, benzyl, $CO_2Bn$, $COCH_3$, $COCF_3$, COAryl; $R^6$=alkyl.

a) 1) NCS, $CH_2Cl_2$, $(R^6)_2S$ or $R^6SCl$; 2) oxidating conditions (i.e. $H_2O_2$, AcOH, or mCPBA, $CH_2Cl_2$; b) $R_5$=BOC: protic acid (i.e. HCl, TFA), solvent (i.e. dioxane, MeOH, $CH_2Cl_2$); $R_5$=benzyl, $CO_2Bn$: $H_2$, Pd/C, solvent (i.e. MeOH, EtOH, iPrOH, EOAc); $R_5$=$COCH_3$, $COCF_3$: base (i.e. NaOH, $K_2CO_3$), solvent (i.e. MeOH, EtOH, water).

General Scheme 20

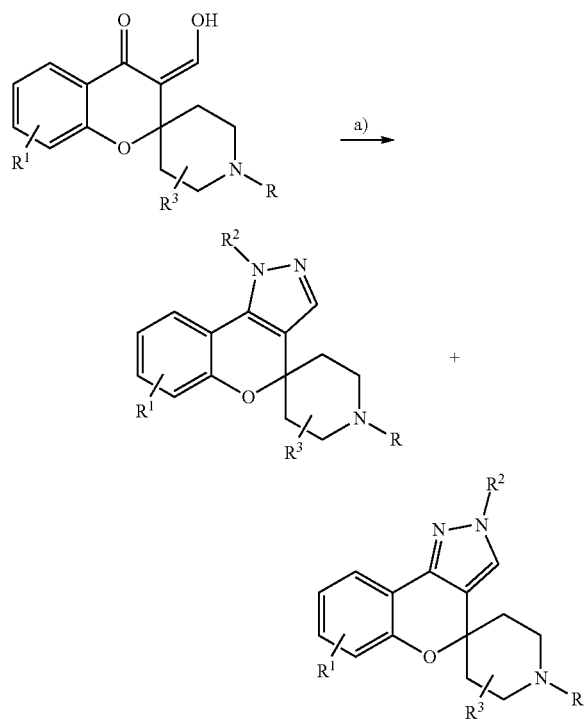

R=benzyl, CO₂Bn, BOC, COCH₃, COCF₃, or COAryl.
a) H₂NNHR², solvent (e.g. EtOH).

General Scheme 21

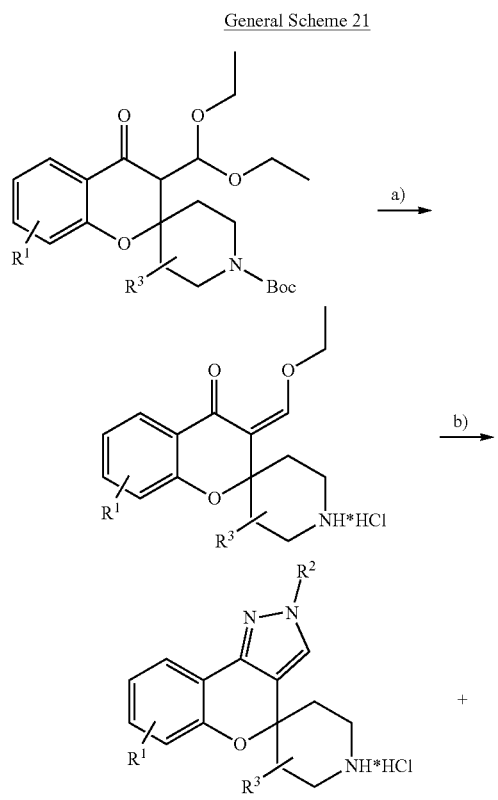

-continued

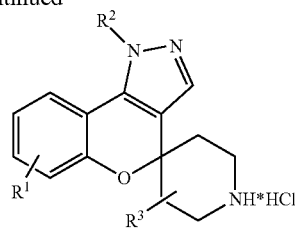

a) acid (i.e. HCl), solvent (i.e. dioxane, toluene); b) NH₂—NHR², solvent (i.e.) EtOH.

General Scheme 22

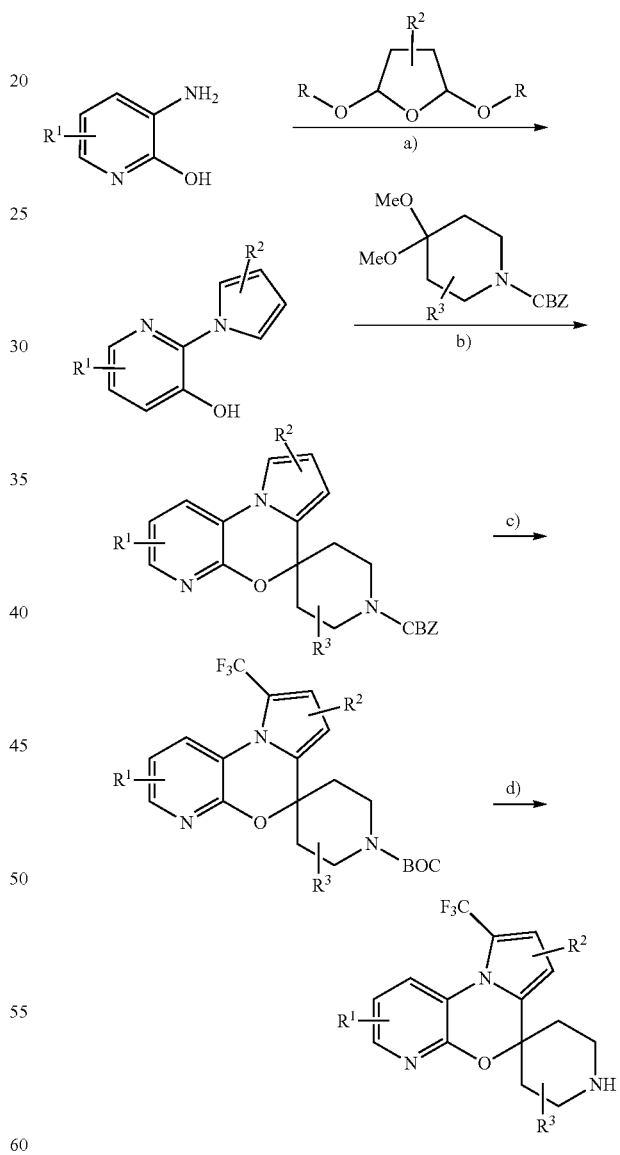

a) H⁺: protic acid such as acetic acid or para-toluene sulfonic acid; b) BF₃·OEt₂, CH₂Cl₂; c) i) H₂, Pd/C, solvent (i.e. AcOH, MeOH), ii) BOC₂O, base (i.e. Na₂CO₃), solvent (i.e. THF), iii) trifluoromethanesulfonate 5-(trifluoromethyl)dibenzothiophen-5-ium, K₂CO₃, DMF; d) protic acid (i.e. HCl, TFA), solvent (i.e. dioxane, CH₂Cl₂).

General Scheme 23

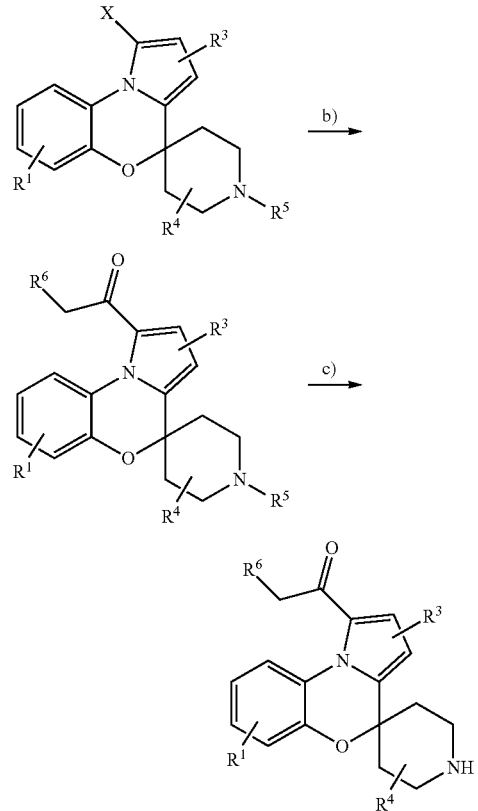

$R_5$=BOC, benzyl, $CO_2Bn$, $COCH_3$, $COCF_3$, COAryl; $R^6$=H, alkyl; X=Br, Cl.

a) X=Br; NBS, solvent (i.e. $CH_2Cl_2$); X=Cl; NCS, solvent (i.e. $CH_2Cl_2$); b) catalyst (i.e. $Pd_2(dba)_3$·$CHCl_3$), alkene (i.e. $R^6CH=CHOR^7$), ligand (i.e. $tBu_3P$), base (i.e. MeN(cHex)$_2$), solvent (i.e. dioxane); c) $R_5$=BOC: protic acid (i.e. HCl, TFA), solvent (i.e. dioxane, MeOH, $CH_2Cl_2$); $R_5$=benzyl, $CO_2Bn$: $H_2$, Pd/C, solvent (i.e. MeOH, EtOH, iPrOH, EOAc); $R_5$=$COCH_3$, $COCF_3$: base (i.e. NaOH, $K_2CO_3$), solvent (i.e. MeOH, EtOH, water).

General Scheme 24

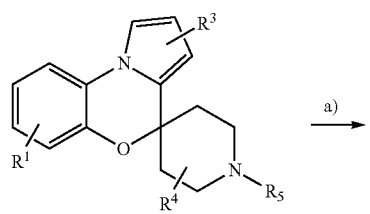

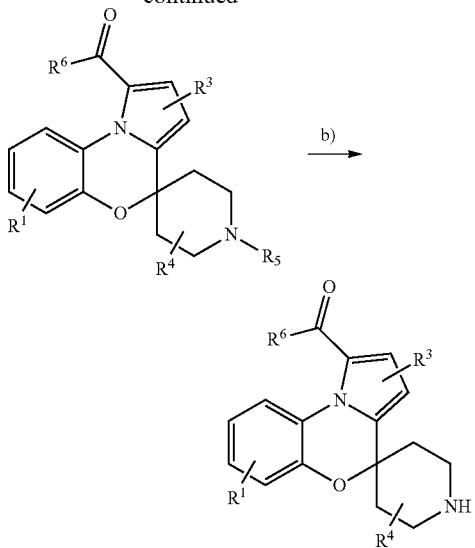

$R_5$=BOC, benzyl, $CO_2Bn$, $COCH_3$, $COCF_3$, COAryl; $R^6$=alkyl, aryl.

a) Acylating agent (ex: $R^6C(O)_2O$, $R^6C(O)Cl$), base (ex: pyridine, $Et_3N$, or DBN), solvent (ex: $CH_2Cl_2$, DCE, or THF) or acylating agent (ex: $R^6C(O)_2O$), Lewis acid (ex: $BF_3$·$OEt_2$), base (ex: pyridine), solvent (ex: $CH_2Cl_2$); b) $R_5$=BOC: protic acid (i.e. HCl, TFA), solvent (i.e. dioxane, MeOH, $CH_2Cl_2$); $R_5$=benzyl, $CO_2Bn$: $H_2$, Pd/C, solvent (i.e. MeOH, EtOH, iPrOH, EOAc); $R_5$=$COCH_3$, $COCF_3$: base (i.e. NaOH, $K_2CO_3$), solvent (i.e. MeOH, EtOH, water).

Uses, Formulation and Administration

Pharmaceutically Acceptable Compositions

As discussed above, the invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitus or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitus or cancer pain.

The compounds and compositions, according to the method of the invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject" or "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV 1.2, NaV 1.3, NaV 1.4, NaV 1.5, NaV 1.6, NaV1.7, NaV 1.8, or NaV 1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV 1.1, NaV 1.2, NaV 1.3, NaV 1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV 1.1, NaV 1.2, NaV 1.3, NaV 1.4, NaV1.5, NaV1.6, NaV 1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.7 and/or NaV1.8.

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) an Hi antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(R), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

(12) a tachykinin (NK) antagonist, particularly an NK-3, NK-2 or NK-1 antagonist, e.g. ([alpha]R,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g. oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(R) or sarizotan;

(17) a vanilloid receptor agonist (e.g. resinferatoxin) or antagonist (e.g. capsazepine);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-HTi B/1 D agonist such as eletriptan, sumatriptan, naratriptan, zolmitriptan or rizatriptan;

(22) a 5-HT2A receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol(R);

(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7//-pyrazolo[4,3-<i]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-<i]pyrimidm-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide; (z) an alpha-2-delta ligand such as gabapentin, pregabalin, 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(26) a cannabinoid;

(27) metabotropic glutamate subtype 1 receptor (mGluR1) antagonist;

(28) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(29) a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan(R)), especially a selective noradrenaline reuptake inhibitor such as reboxetine, in particular (S,S)-reboxetine;

(30) a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

(31) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S, 5Z)-2-amino-2-methyl-7-[(1-iminoethyl)amino]-5-heptenoic acid, 2-[[(1R,3S)-3-amino-4-hydroxy-1-(5-thiazolyl)-butyl]thioJ-S-chloro-5-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

(32) an acetylcholinesterase inhibitor such as donepezil;

(33) a prostaglandin E2 subtype 4 (EP4) antagonist such as 7V-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy)pyridin-3-yl]carbonyl}amino)ethyl]benzoic acid;

(34) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,

(35) a 5-lipoxygenase inhibitor, such as zileuton, 6-[(3-fluoro-5-[4-methoxy-3,4,5,6-tetrahydro-2H-pyran-4-yl]) phenoxy-methyl]-1-methyl-2-quinolone (ZD-2138), or 2,3,5-trimethyl-6-(3-pyridylmethyl), 1,4-benzoquinone (CV-6504);

(36) a sodium channel blocker, such as lidocaine;

(36) a 5-HT3 antagonist, such as ondansetron; and the pharmaceutically acceptable salts and solvates thereof.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General methods. $^1$H NMR (400 MHz) and $^{13}$C NMR (100 MHz) spectra were obtained as solutions in deuterioacetonitrile (CD$_3$CN), chloroform-d (CDCl$_3$) or dimethyl sulfoxide-D$_6$ (DMSO). Mass spectra (MS) were obtained using an Applied Biosystems API EX LC/MS system equipped with a Phenomenex 50×4.60 mm luna-5μ C18 column. The LC/MS eluting system was 1-99% or 10-99% acetonitrile in H$_2$O with 0.035% v/v trifluoroacetic acid, 0.035% v/v formic acid, 5 mM HCl or 5 mM ammonium formate using a 3 or 15 minute linear gradient and a flow rate of 12 mL/minute. Silica gel chromatography was performed using silica gel-60 with a particle size of 230-400 mesh. Pyridine, dichloromethane (CH$_2$Cl$_2$), tetrahydrofuran (THF), dimethylformamide (DMF), acetonitrile (ACN), methanol (MeOH), and 1,4-dioxane were from Aldrich Sure-Seal bottles kept under dry nitrogen. All reactions were stirred magnetically unless otherwise noted.

Spiro[benzo[b]pyrrolo[1,2-d][1,4]oxazine-4,4'-piperidine]hydrochloride salt

Step 1: 2-(1H-Pyrrol-1-yl)phenol

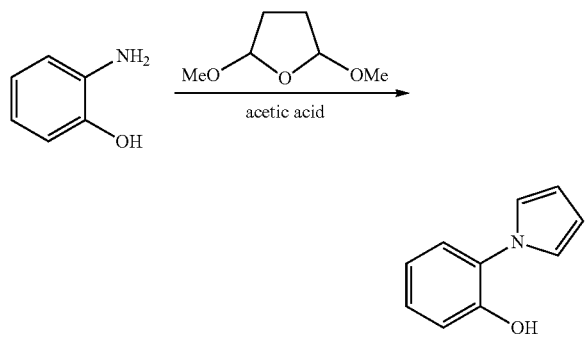

A 5 L 3-neck round bottom flask was fitted with a mechanical stirrer, a heating mantle, a water cooled reflux condenser, a temperature probe/controller and a nitrogen inlet/outlet. The vessel was charged with (50 g, 0.46 mol) of 2-aminophenol and acetic acid (750 mL) which provided a very dark solution. Stirring was commenced and the vessel was charged with 2,5-dimethoxytetrahydrofuran (59.4 mL, 0.458 mol) dropwise over 2 minutes. The dark mixture was then heated at 100° C. for 15 min. The mixture was allowed to cool to room temperature and was filtered through a pad of Celite to remove residual solids. The filtrate was concentrated under reduced pressure azeotroping with toluene. The residual oil was dissolved in ethyl acetate (1000 mL) and was partitioned with water (500 mL). The organic layer was separated and was washed with water (500 mL), dried over sodium sulfate and filtered. The filtrate was concentrated under reduced pressure to provide 2-(1H-pyrrol-1-yl)phenol (54 g, 74%) as a dark oil. ESI-MS m/z calc. 159.1. found 160.2 (M+1)$^+$. Retention time: 2.67 minutes (3 min run). $^1$H NMR (400 MHz, CDCl$_3$) δ 7.37-7.23 (m, 2H), 7.13-6.97 (m, 2H), 6.91 (t, J=1.9 Hz, 2H), 6.43 (t, J=1.9 Hz, 2H), 5.35 (s, 1H). 3-(1H-Pyrrol-1-yl)pyridin-2-ol was also synthesized using the procedure described above.

Step 2: tert-Butyl spiro[benzo[b]pyrrolo[1,2-d][1,4]oxazine-4,4'-piperidine]-1'-carboxylate

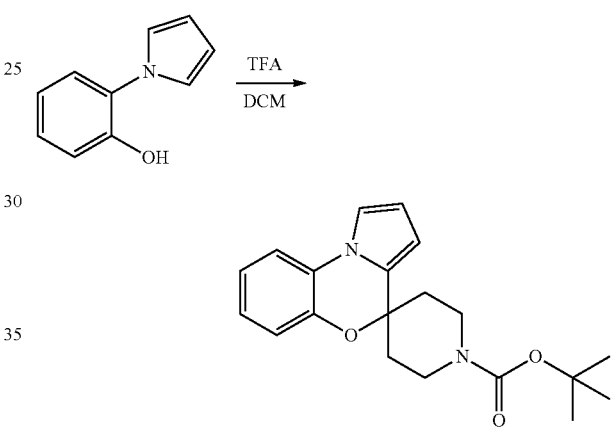

A 5 L 3-neck round bottom flask was fitted with a mechanical stirrer, an addition funnel, a temperature probe/controller and a nitrogen inlet/outlet. The vessel was charged under nitrogen with 2-(1H-pyrrol-1-yl)phenol (40 g, 0.25 mol) and dichloromethane (800 mL). Stirring was commenced and the dark solution was charged with tert-butyl 4-oxopiperidine-1-carboxylate (55.1 g, 0.276 mol) added as a solid in one portion. An addition funnel was charged with TFA (38.7 ml, 0.503 mol) which was subsequently added dropwise over 15 minutes. The dark mixture was continued to stir at ambient temperature for 5 hours at which point the contents of the reaction vessel were transferred to a separatory funnel and were partitioned with water (500 mL). The organic layer was separated and was washed with 1M NaOH (2×250 mL), dried over sodium sulfate and filtered. The filtrate was concentrated under reduced pressure to provide a clear amber oil (105 g). The material was purified by silica gel column flash chromatography (4:1 Hex/EtOAc, 250 mL fractions) to provide (51 g, 60%) of tert-butyl spiro[benzo[b]pyrrolo[1,2-d][1,4]oxazine-4,4'-piperidine]-1'-carboxylate as a clear amber oil. ESI-MS m/z calc. 340.2. found 341.3 (M+1)$^+$. Retention time: 2.17 minutes (3 min run). $^1$H NMR (400 MHz, CDCl$_3$) δ 7.35 (d, J=7.5 Hz, 1H), 7.19-7.13 (m, 1H), 7.10-7.01 (m, 3H), 6.34 (t, J=3.1 Hz, 1H), 6.03 (d, J=3.4 Hz, 1H), 4.02 (s, 2H), 3.30 (s, 2H), 2.14-1.99 (m, 2H), 1.90 (td, J=13.3, 4.9 Hz, 2H), 1.48 (s, 9H).

Step 3: Spiro[benzo[b]pyrrolo[1,2-d][1,4]oxazine-4,4'-piperidine]hydrochloride salt

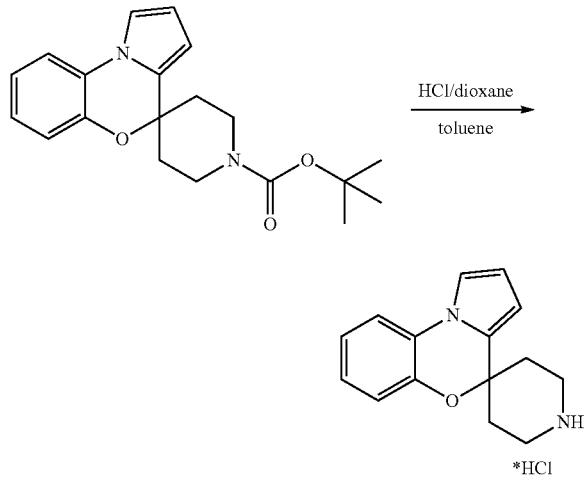 [SMILES: CC(C)(C)OC(=O)N1CCC2(CC1)Oc1ccccc1-n1cccc12 ; c1ccc2c(c1)OC1(CCNCC1)c1cccn1-2]

A 5 L 3-neck round bottom flask was fitted with a mechanical stirrer, an addition funnel, a temperature probe/controller and a nitrogen inlet/outlet. The vessel was charged under nitrogen with a clear amber solution of tert-butyl spiro[benzo[b]pyrrolo[1,2-d][1,4]oxazine-4,4'-piperidine]-1'-carboxylate and (50 g, 0.15 mol) and toluene (250 mL). Stirring was commenced and the addition funnel was charged with (73 mL, 0.29 mol) of 4M HCl in 1,4-dioxane which was added dropwise over 10 minutes resulting in a very dark solution. The mixture was continued to stir at ambient temperature for 1 h before the reaction mixture was filtered to remove the residual solids. The filtrate was concentrated under reduced pressure to provide a solid which was triturated with diethyl ether (2×200 mL) and was then dried under vacuum to provide (31 g, 76%) of spiro[benzo[b]pyrrolo[1,2-d][1,4]oxazine-4,4'-piperidine]hydrochloride as an off-white solid. ESI-MS m/z calc. 240.1. found 241.3 (M+1)$^+$. Retention time: 1.21 minutes (3 min run). $^1$H NMR (400 MHz, DMSO) δ 9.45 (s, 2H), 7.76-7.62 (m, 1H), 7.55 (dd, J=2.8, 1.3 Hz, 1H), 7.23-7.08 (m, 3H), 6.31 (t, J=3.2 Hz, 1H), 6.11 (dd, J=3.4, 1.3 Hz, 1H), 3.29-3.13 (m, 4H), 2.25 (td, J=14.4, 5.0 Hz, 2H), 2.09 (d, J=14.1 Hz, 2H).

The following compounds were prepared using the procedures described above: 7-Fluorospiro[benzo[b]pyrrolo[1,2-d][1,4]oxazine-4,4'-piperidine]hydrochloride: ESI-MS m/z calc. 258.1 (—HCl). found 259.2 (M+1)$^+$. Retention time: 1.29 minutes (3 min run). $^1$H NMR (400 MHz, DMSO) δ 9.52 (s, 2H), 7.76 (dd, J=8.9, 5.6 Hz, 1H), 7.58-7.54 (m, 1H), 7.20 (dd, J=9.6, 2.8 Hz, 1H), 6.97 (td, J=8.7, 2.8 Hz, 1H), 6.31 (t, J=3.2 Hz, 1H), 6.11 (dd, J=3.4, 1.2 Hz, 1H), 3.30-3.14 (m, 4H), 2.28 (td, J=14.7, 5.5 Hz, 2H), 2.11 (d, J=14.1 Hz, 2H) and 7-chlorospiro[benzo[b]pyrrolo[1,2-d][1,4]oxazine-4,4'-piperidine]hydrochloride: ESI-MS m/z calc. 274.1 (—HCl). found 275.2 (M+1)$^+$. Retention time: 1.38 minutes (3 min run). $^1$H NMR (400 MHz, DMSO) δ 9.38 (s, 2H), 7.75 (d, J=8.6 Hz, 1H), 7.57 (d, J=1.6 Hz, 1H), 7.39 (d, J=2.2 Hz, 1H), 7.17 (dd, J=8.6, 2.2 Hz, 1H), 6.33 (t, J=3.2 Hz, 1H), 6.13 (d, J=3.0 Hz, 1H), 3.30-3.11 (m, 4H), 2.32-2.17 (m, 2H), 2.10 (d, J=14.1 Hz, 2H).

Spiro[benzo[b]pyrrolo[1,2-d][1,4]oxazine-4,4'-piperidine]-7-carbonitrile

Step 1: 1'-tert-Butyl 7-methyl spiro[benzo[b]pyrrolo[1,2-d][1,4]oxazine-4,4'-piperidine]-1',7-dicarboxylate

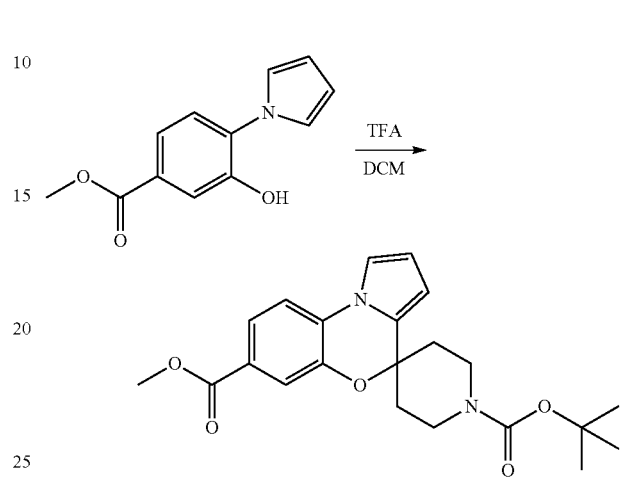

Trifluoroacetic acid (3.15 g, 2.13 mL, 27.6 mmol) was added dropwise to a solution of methyl 3-hydroxy-4-pyrrol-1-yl-benzoate (3.00 g, 13.8 mmol) and tert-butyl 4-oxopiperidine-1-carboxylate (3.00 g, 15.2 mmol) in dichloromethane (60 mL) and the reaction mixture was stirred at room temperature for 6 hours. The reaction mixture was washed with water and 1N NaOH. The organics were dried over sodium sulfate, filtered and evaporated. The residue was purified by silica gel chromatography eluting with 0-30% EtOAc in Hexanes. The pure fractions were combined and concentrated to give 1'-tert-butyl 7-methyl spiro[benzo[b]pyrrolo[1,2-d][1,4]oxazine-4,4'-piperidine]-1',7-dicarboxylate. ESI-MS m/z calc. 398.4. found 399.5 (M+1)$^+$. Retention time: 2.13 minutes (3 min run).

Step 2: 1'-(tert-Butoxycarbonyl)spiro[benzo[b]pyrrolo[1,2-d][1,4]oxazine-4,4'-piperidine]-7-carboxylic acid

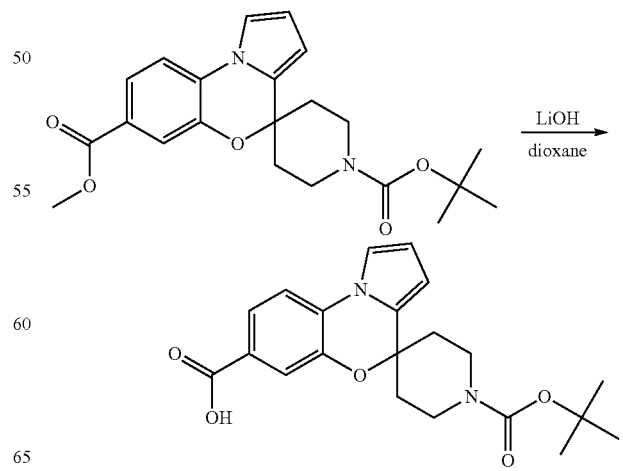

A solution of 1'-tert-butyl 7-methyl spiro[benzo[b]pyrrolo [1,2-d][1,4]oxazine-4,4'-piperidine]-1',7-dicarboxylate (3.5 g, 8.8 mmol) in LiOH (18 mL of 2.0 M, 35.1 mmol) and dioxane (18 mL) was stirred at 55° C. for 1 hour. The reaction mixture was diluted with ethyl acetate and was washed with water. The aqueous layer was acidified with 1N HCl and the product was extracted into ethyl acetate. The organics were dried over sodium sulfate, filtered and evaporated to yield 1'-(tert-butoxycarbonyl)spiro[benzo[b]pyrrolo[1,2-d][1,4]oxazine-4,4'-piperidine]-7-carboxylic acid which was used without further purification. ESI-MS m/z calc. 384.4. found 385.3 (M+1)$^+$. Retention time: 1.81 minutes (3 min run).

Step 3: tert-Butyl 7-carbamoylspiro[benzo[b]pyrrolo [1,2-d][1,4]oxazine-4,4'-piperidine]-1'-carboxylate

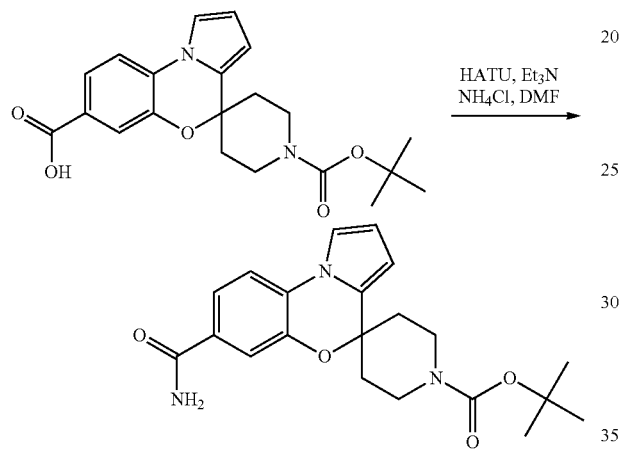

A solution of NH$_4$Cl (1.4 mL, 40 mmol) and Et$_3$N (5.6 mL, 40 mmol) in DMF (6 mL) was added to a solution of 1-tert-butoxycarbonylspiro[piperidine-4,4'-pyrrolo[2,1-c][1,4]benzoxazine]-7'-carboxylic acid (3.1 g, 8.0 mmol), HATU (3.3 g, 8.8 mmol), and Et$_3$N (2.5 mL, 18 mmol) in DMF (6 mL). The mixture was stirred at room temperature for 1 h. The reaction mixture was diluted with ethyl acetate and was washed with saturated sodium bicarbonate solution. The organics were dried over sodium sulfate, filtered and evaporated. Purification of the residue by silica gel chromatography eluting with 0-100% EtOAc in Hexanes gave tert-butyl 7'-carbamoylspiro[piperidine-4,4'-pyrrolo[2,1-c][1,4]benzoxazine]-1-carboxylate (2.7 g, 89%). ESI-MS m/z calc. 383.4. found 384.7 (M+1)$^+$. Retention time: 1.60 minutes (3 min run).

Step 4: tert-Butyl 7-cyanospiro[benzo[b]pyrrolo[1,2-d][1,4]oxazine-4,4'-piperidine]-1'-carboxylate

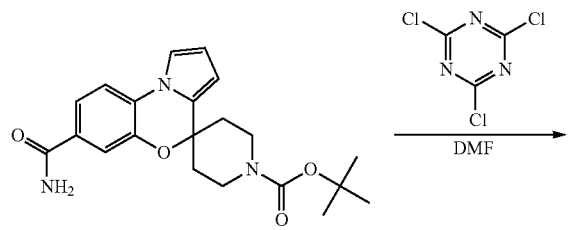

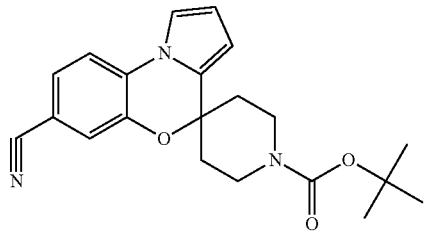

A solution of tert-butyl 7'-carbamoylspiro[piperidine-4,4'-pyrrolo[2,1-c][1,4]benzoxazine]-1-carboxylate (2.7 g, 7.1 mmol) and cyanuric chloride (1.3 g, 7.1 mmol) in DMF (10 mL) was stirred at room temperature for 1 hour. The reaction was poured into water and the product was extracted into ethyl acetate. The organics were dried over sodium sulfate, filtered and evaporated to yield a crude mixture that was purified by silica gel chromatography eluting with 0-100% EtOAc in Hexanes. Pure fractions were combined and concentrated to yield tert-butyl 7-cyanospiro[benzo[b]pyrrolo[1,2-d][1,4]oxazine-4,4'-piperidine]-1'-carboxylate (1.1 g, 44%). ESI-MS m/z calc. 365.4. found 366.3 (M+1)$^+$. Retention time: 2.00 minutes (3 min run).

Step 5: Spiro[benzo[b]pyrrolo[1,2-d][1,4]oxazine-4,4'-piperidine]-7-carbonitrile

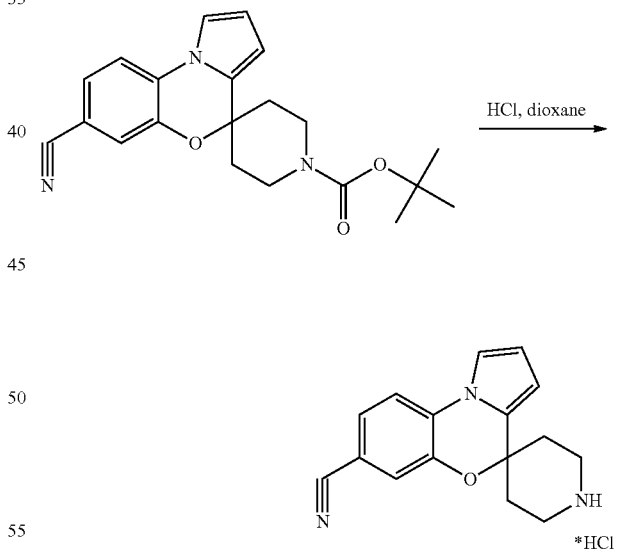

A solution of tert-butyl 7'-cyanospiro[piperidine-4,4'-pyrrolo[2,1-c][1,4]benzoxazine]-1-carboxylate (1.1 g, 3.1 mmol) in HCl in dioxane (3.1 mL of 4.0 M, 12 mmol) was stirred at room temperature for 1 hour. The reaction mixture was evaporated to dryness to yield spiro[benzo[b]pyrrolo[1,2-d][1,4]oxazine-4,4'-piperidine]-7-carbonitrile (880 mg, 94%). ESI-MS m/z calc. 265.3. found 266.1 (M+1)$^+$. Retention time: 0.92 minutes (3 min run).

419

Methyl spiro[benzo[b]pyrrolo[1,2-d][1,4]oxazine-4,4'-piperidine]-7-carboxylate hydrochloride

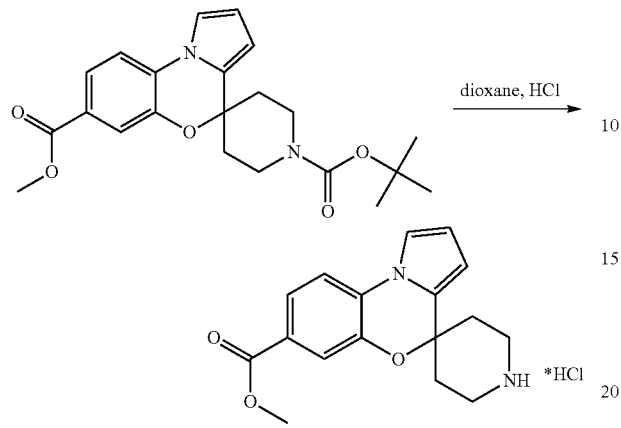

A solution of 1'-tert-butyl 7-methyl spiro[benzo[b]pyrrolo[1,2-d][1,4]oxazine-4,4'-piperidine]-1',7-dicarboxylate (1.8 g, 4.5 mmol) in HCl (4.5 mL, 4.0M in dioxanes, 18 mmol) was stirred at room temperature for 2 hours. The reaction mixture was evaporated to dryness to give methyl spiro[benzo[b]pyrrolo[1,2-d][1,4]oxazine-4,4'-piperidine]-7-carboxylate hydrochloride (1.5 g, quant). ESI-MS m/z calc. 298.3. found 299.5 (M+1)$^+$. Retention time: 1.06 minutes (3 min run).

1-Methylspiro[benzo[b]pyrrolo[1,2-d][1,4]oxazine-4,4'-piperidine]

Step 1: 1'-Benzylspiro[benzo[b]pyrrolo[1,2-d][1,4]oxazine-4,4'-piperidine]

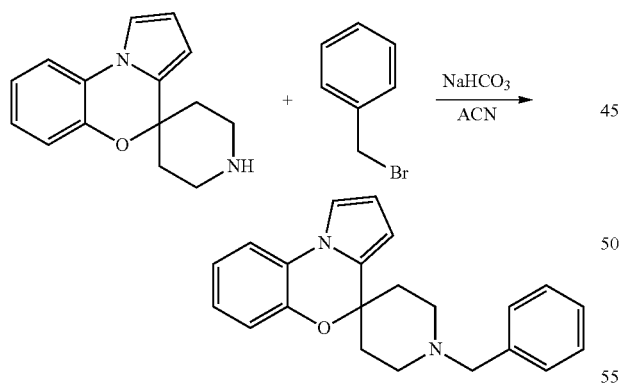

To a 0° C. solution of spiro[piperidine-4,4'-pyrrolo[2,1-c][1,4]benzoxazine] (HCl salt) (1.0 g, 3.6 mmol) in dry acetonitrile (10 mL), under nitrogen, was added NaHCO$_3$ (1.5 g, 18 mmol) followed by dropwise addition of benzyl bromide (560 μL, 4.7 mmol). The cooling bath was removed. Water (25 ml) was then added, and the organic solvent was removed under vacuum. The product was extracted from the aqueous solution with EtOAc (3×150 mL). The organic phases were combined, washed with brine, dried with sodium sulfate, filtered, and concentrated under reduced pressure. The product was purified by column chromatography (silica gel: 5-70% EtOAc in hexanes) to give 1'-benzylspiro[benzo[b]pyrrolo[1,2-d][1,4]oxazine-4,4'-piperidine] 660 mg, 55%). ESI-MS m/z calc. 330.4. found 331.5 (M+1)$^+$; Retention time: 1.23 minutes (3 min run).

Step 2: 1'-Benzylspiro[benzo[b]pyrrolo[1,2-d][1,4]oxazine-4,4'-piperidine]-1-carbaldehyde

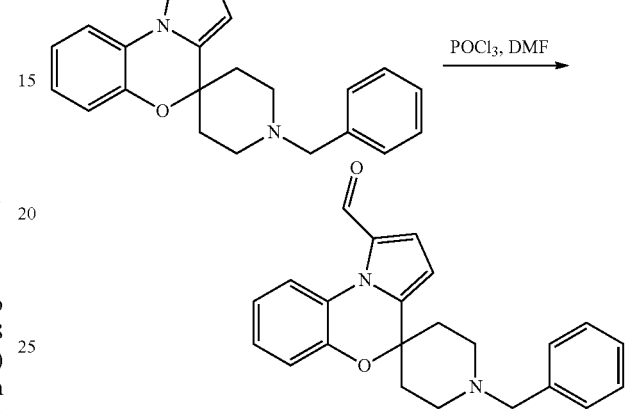

N,N-Dimethylformamide (723 μL, 9.40 mmol), under nitrogen, was cooled to 0° C. and POCl$_3$ (876 μL, 9.40 mmol) was added dropwise. The reaction was stirred for 20 min at 0° C. and a white solid formed. A solution of 1-benzylspiro[piperidine-4,4'-pyrrolo[2,1-c][1,4]benzoxazine] (2.07 g, 6.27 mmol) in dry DMF (15.5 mL) was added dropwise and the cooling bath was removed. The reaction mixture was stirred for 2 h at 50° C., then cooled down to room temperature and poured onto ice. Sodium hydroxide (1M) was added until the pH reached 10, then the solution was acidified to pH 6 with 3 M HCl. The mixture was then extracted with EtOAc. The organics were dried over sodium sulfate, filtered and concentrated. The residue was purified by column chromatography (silica gel: 10-70% EtOAc in hexanes) to give 1'-benzylspiro[benzo[b]pyrrolo[1,2-d][1,4]oxazine-4,4'-piperidine]-1-carbaldehyde (1.94 g, 86%). ESI-MS m/z calc. 358.4. found 359.3 (M+1)$^+$; Retention time: 1.16 minutes (3 min run). $^1$H NMR (400 MHz, CDCl$_3$) δ 9.66 (s, 1H), 8.17-8.07 (m, 1H), 7.38-7.30 (m, 4H), 7.29-7.24 (m, 1H), 7.20-7.13 (m, 2H), 7.09 (m, 2H), 6.20 (d, J=4.1 Hz, 1H), 3.59 (s, 2H), 2.76 (m, 2H), 2.58-2.45 (m, 2H), 2.10-1.96 (m, 4H).

Step 3: (1'-Benzylspiro[benzo[b]pyrrolo[1,2-d][1,4]oxazine-4,4'-piperidine]-1-yl)methanol

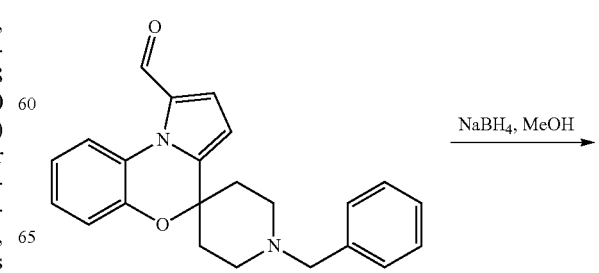

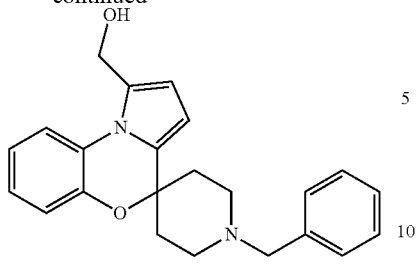

A solution of 1'-benzylspiro[benzo[b]pyrrolo[1,2-d][1,4] oxazine-4,4'-piperidine]-1-carbaldehyde (1.94 g, 5.40 mmol) in methanol (40 mL) was cooled to 0° C. Sodium borohydride (409 mg, 10.8 mmol) was added in one portion and the cooling bath was removed. After stirring for 1 h at room temperature, the reaction was diluted with saturated aqueous NaHCO$_3$ (50 mL) and DCM (150 mL). The organic layer was separated and the aqueous layer was extracted twice more with DCM (150 mL). The organic layers were combined, dried, filtered and concentrated to give (1'-benzylspiro[benzo[b]pyrrolo[1,2-d][1,4]oxazine-4,4'-piperidine]-1-yl)methanol (1.66 g) as a white solid. The crude material was used in the next step without purification.

Step 4: (1'-Benzylspiro[benzo[b]pyrrolo[1,2-d][1,4]oxazine-4,4'-piperidine]-1-yl)methyl acetate

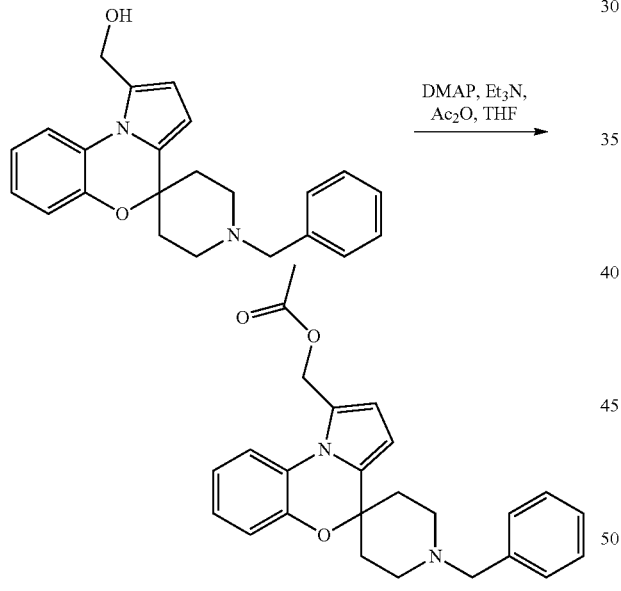

A solution of (r-benzylspiro[benzo[b]pyrrolo[1,2-d][1,4]oxazine-4,4'-piperidine]-1-yl)methanol (1.66 g, 4.60 mmol) and 4-(dimethylamino)pyridine (561 mg, 4.60 mmol) in dry THF (40 mL) was cooled to 0° C. Triethylamine (2.56 mL, 18.4 mmol) was then added to the reaction mixture followed by dropwise addition of acetic anhydride (1.27 mL, 13.5 mmol). The reaction mixture was allowed to warm to room temperature and was stirred overnight. It was then concentrated and purified by column chromatography (silica gel: 10-40% EtOAc in hexanes) to give (1'-benzylspiro[benzo[b]pyrrolo[1,2-d][1,4]oxazine-4,4'-piperidine]-1-yl)methyl acetate (1.32 g, 61% yield over two steps). ESI-MS m/z calc. 402.5. found 403.7 (M+1)$^+$; Retention time: 1.31 minutes (3 min run).

Step 5: 1-Methylspiro[benzo[b]pyrrolo[1,2-d][1,4]oxazine-4,4'-piperidine]

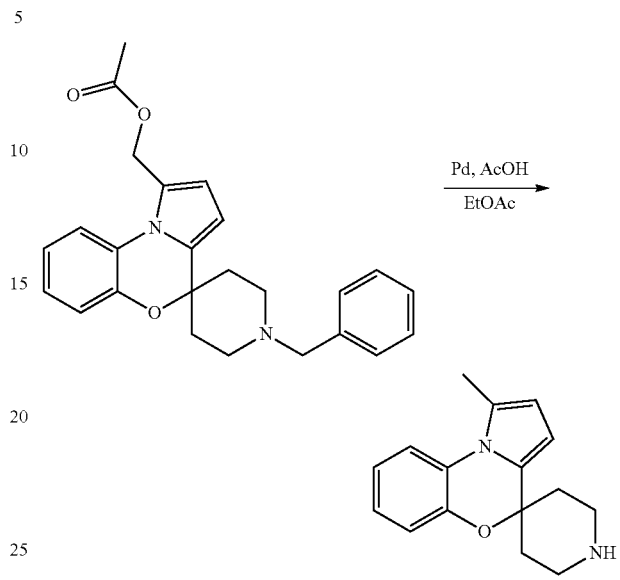

To a solution of (1'-benzylspiro[benzo[b]pyrrolo[1,2-d][1,4]oxazine-4,4'-piperidine]-1-yl)methyl acetate (300 mg, 0.75 mmol) in ethyl acetate (30 mL) was added acetic acid (17 μL, 0.30 mmol). The reaction was flushed with nitrogen then 10% Pd/C (40 mg, 0.37 mmol) was added. The reaction was placed under hydrogen gas and was stirred for 20 h at room temperature. The suspension was filtered through celite, concentrated, then purified by column chromatography (silica gel: 0.1-15% methanol in dichloromethane) to give 1-methylspiro[benzo[b]pyrrolo[1,2-d][1,4]oxazine-4,4'-piperidine] (65 mg, 34%). ESI-MS m/z calc. 254.3. found 255.3 (M+1)$^+$; Retention time: 1.93 minutes (3 min run). NMR (400 MHz, CDCl$_3$) δ 7.56 (d, J=7.9 Hz, 1H), 7.16-6.99 (m, 3H), 6.03 (d, J=3.2 Hz, 1H), 5.94 (d, J=3.4 Hz, 1H), 3.14 (t, J=12.2 Hz, 2H), 2.94 (d, J=12.3 Hz, 2H), 2.56 (s, 3H), 2.19 (m, 1H), 2.04 (d, J=12.7 Hz, 2H), 1.97-1.84 (m, 2H).

1-(Trifluoromethyl)spiro[benzo[b]pyrrolo[1,2-d][1,4]oxazine-4,4'-piperidine]

Step 1: tert-Butyl 1-(trifluoromethyl)spiro[benzo[b]pyrrolo[1,2-d][1,4]oxazine-4,4'-piperidine]-1'-carboxylate

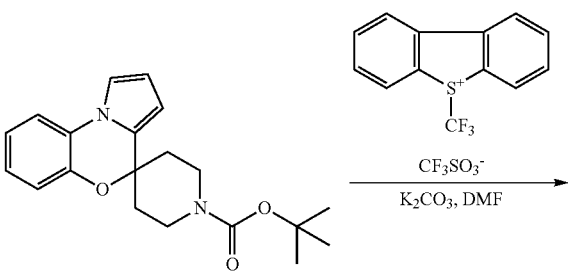

-continued

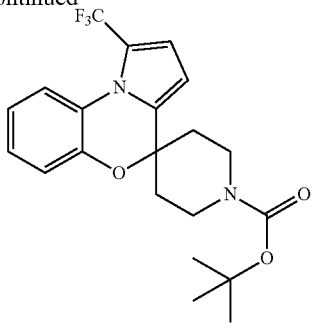

tert-Butyl spiro[piperidine-4,4'-pyrrolo[2,1-c][1,4]benzoxazine]-1-carboxylate (100 mg, 0.29 mmol), trifluoromethanesulfonate 5-(trifluoromethyl)dibenzothiophen-5-ium (300 mg, 0.73 mmol) and $K_2CO_3$ (110 mg, 0.76 mmol) were combined in N,N-dimethylformamide (1 mL). The reaction mixture was heated at 80° C. for 16 hours. The reaction mixture was filtered and then purified by reverse phase HPLC 10-99% methanol in water to give tert-butyl 1-(trifluoromethyl)spiro[benzo[b]pyrrolo[1,2-d][1,4]oxazine-4,4'-piperidine]-1'-carboxylate (57 mg, 48%). $^1$H NMR (400 MHz, $CDCl_3$) δ 7.66 (d, J=8.1 Hz, 1H), 7.22-7.03 (m, 3H), 6.79 (d, J=3.9 Hz, 1H), 6.03 (d, J=3.9 Hz, 1H), 4.27-3.75 (m, 2H), 3.39-3.10 (m, 2H), 2.13-1.96 (m, 2H), 1.95-1.78 (m, 2H), 1.48 (s, 9H). ESI-MS m/z calc. 408.4. found 409.5 (M+1)$^+$; Retention time: 2.38 minutes (3 min run).

Step 2: 1-(Trifluoromethyl)spiro[benzo[b]pyrrolo[1,2-d][1,4]oxazine-4,4'-piperidine]hydrochloric acid

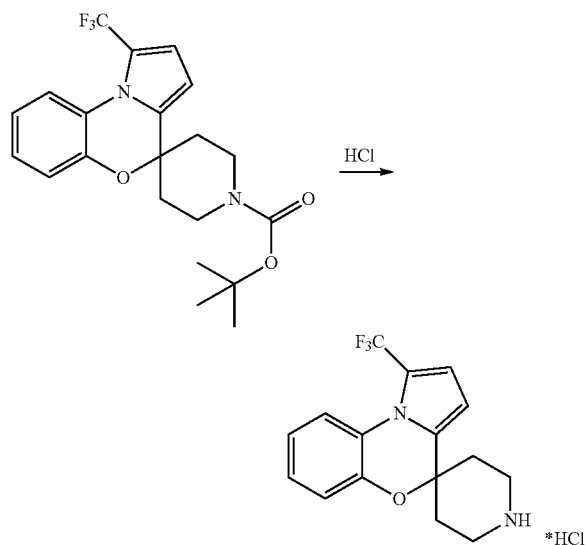

tert-Butyl 1'-(trifluoromethyl)spiro[piperidine-4,4'-pyrrolo[2,1-c][1,4]benzoxazine]-1-carboxylate (30 mg, 0.074 mmol) was dissolved in hydrogen chloride in dioxane (700 µL of 4.0 M, 2.8 mmol). The reaction mixture was allowed to stand for 20 minutes. The solvent was evaporated to give 1-(trifluoromethyl)spiro[benzo[b]pyrrolo[1,2-d][1,4]oxazine-4,4'-piperidine]hydrochloride was then used without further purification (25 mg, 99%). $^1$H NMR (400 MHz, DMSO) δ 9.23 (br s, 2H), 7.59 (d, J=8.1 Hz, 1H), 7.40-7.19 (m, 3H), 7.05 (d, J=3.9 Hz, 1H), 6.38 (d, J=4.0 Hz, 1H), 3.42-3.04 (m, 4H), 2.37-2.00 (m, 4H). ESI-MS m/z calc. 308.3. found 309.5 (M+1)$^+$; Retention time: 1.53 minutes (3 min run).

1-(Trifluoromethyl)spiro[benzo[b]pyrrolo[1,2-d][1,4]oxazine-4,4'-piperidine]sulfate

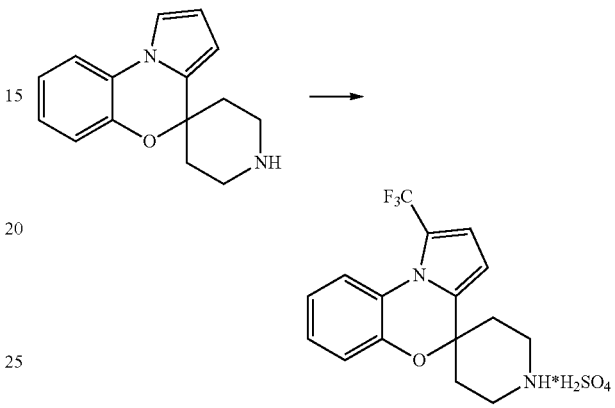

To spiro[piperidine-4,4'-pyrrolo[2,1-c][1,4]benzoxazine] (5.20 g, 21.6 mmol) in DMSO (104 mL) was added $H_2SO_4$ (1.27 mL, 23.8 mmol) (note: exothermic), ferrous sulfate heptahydrate (6.5 mL of 1.0 M, 6.5 mmol) followed by $CF_3I$ (4.24 g, 21.6 mmol) by slow bubbling through the solution and taking weight difference of cannister. The mixture cooled with a ice-water bath before $H_2O_2$ (2.45 mL of 30% w/v, 21.6 mmol) was added drop-wise over 10 min keeping temperature <23° C. The mixture was allowed to stir for 15 min before it was poured onto ice (250 g) producing a white precipitate. The slurry was stirred for 5 min and then the solid was collected via filtration. The off-white solid was taken up in acetonitrile (150 mL) and was heated at reflux of 1 h. The solvent was removed and the solid was recrystallized from EtOH (15 mL/g) and water (5 mL/g). The solid was collected and dried to give 1-(trifluoromethyl)spiro[benzo[b]pyrrolo[1,2-d][1,4]oxazine-4,4'-piperidine]sulfate (2.9 g, 33%). ESI-MS m/z calc. 308.1. found 309.1 (M+1)$^+$; Retention time: 1.23 minutes (3 min run).

7-Chloro-1-(trifluoromethyl)spiro[benzo[b]pyrrolo[1,2-d][1,4]oxazine-4,4'-piperidine]

Step 1: tert-Butyl 7-chloro-1-(trifluoromethyl)spiro[benzo[b]pyrrolo[1,2-d][1,4]oxazine-4,4'-piperidine]-1'-carboxylate

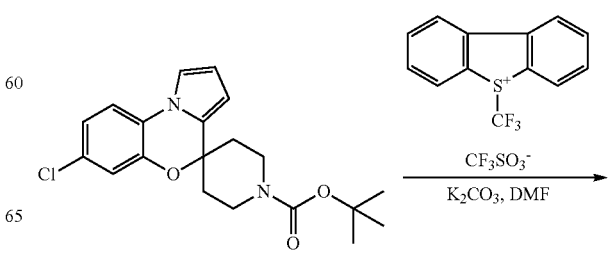

425
-continued

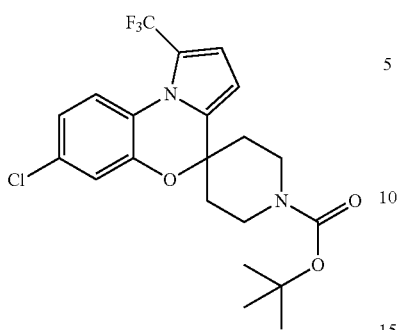

tert-Butyl 7'-chlorospiro[piperidine-4,4'-pyrrolo[2,1-c][1,4]benzoxazine]-1-carboxylate (370 mg, 1.0 mmol), potassium carbonate (360 mg, 2.6 mmol) and trifluoromethanesulfonate 5-(trifluoromethyl)dibenzothiophen-5-ium (1.0 g, 2.5 mmol) were combined in N,N-dimethylformamide (3.7 mL). The reaction mixture was heated at 80° C. for 90 minutes. Trifluoromethanesulfonate 5-(trifluoromethyl)dibenzothiophen-5-ium (200 mg, 0.50 mmol) and potassium carbonate (69 mg, 0.50 mmol) were added and stirring was continued for an additional 40 minutes. The reaction mixture was partitioned between 50 mL of water and 50 mL of dichloromethane. The layers were separated and the organic layer was washed with a saturated aqueous solution of sodium chloride. The organic layer was dried over sodium sulfate, filtered, and evaporated to dryness to yield a pale yellow solid. The crude material was purified on silica gel utilizing a gradient of 0-5% ethyl acetate in hexanes to yield tert-butyl 7-chloro-1-(trifluoromethyl)spiro[benzo[b]pyrrolo[1,2-d][1,4]oxazine-4,4'-piperidine]-1'-carboxylate (210 mg, 63%) as a white solid. $^1$H NMR (400 MHz, CDCl$_3$) δ 7.58 (d, J=8.8 Hz, 1H), 7.13 (d, J=2.4 Hz, 1H), 7.06 (dd, J=8.8, 2.4 Hz, 1H), 6.80 (d, J=3.9 Hz, 1H), 6.04 (d, J=3.9 Hz, 1H), 4.07-3.96 (m, 2H), 3.26-3.14 (m, 2H), 2.07-1.81 (m, 4H), 1.47 (s, 9H). ESI-MS m/z calc. 442.9. found 443.1 (M+1)$^+$; Retention time: 2.34 minutes (3 min run).

Step 2: 7-Chloro-1-(trifluoromethyl)spiro[benzo[b]pyrrolo[1,2-d][1,4]oxazine-4,4'-piperidine]hydrochloric acid

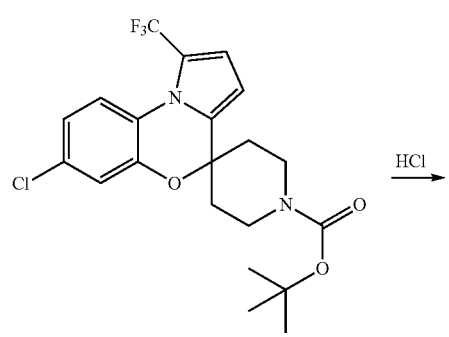

426
-continued

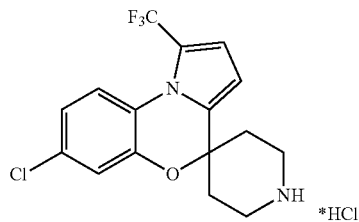

tert-Butyl 7-chloro-1-(trifluoromethyl)spiro[benzo[b]pyrrolo[1,2-d][1,4]oxazine-4,4'-piperidine]-1'-carboxylate (210 mg, 0.14 mmol) was dissolved in HCl in dioxane (2.0 mL of 4.0 M, 8.0 mmol). The reaction mixture was allowed to stand for 30 minutes. The reaction mixture was then evaporated to dryness to give 7-chloro-1-(trifluoromethyl)spiro[benzo[b]pyrrolo[1,2-d][1,4]oxazine-4,4'-piperidine]hydrochloric acid. ESI-MS m/z calc. 342.7. found 343.3 (M+1)$^+$; Retention time: 1.46 minutes (3 min run).

2-Methylspiro[benzo[b]pyrrolo[1,2-d][1,4]oxazine-4,4'-piperidine] and 3-methylspiro[benzo[b]pyrrolo[1,2-d][1,4]oxazine-4,4'-piperidine]

Step 1: 2-(3-Methyl-1H-pyrrol-1-yl)phenol

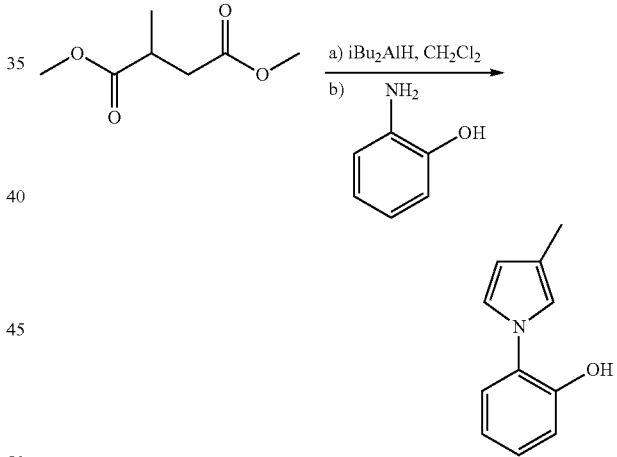

Diisobutylaluminum (100 mL of 1.0 M, 100 mmol) was added dropwise to a solution of dimethyl 2-methylbutanedioate (7.6 g, 48 mmol) in dichloromethane (15 mL) at −78° C., and the solution was stirred for 1 h. A suspension of 2-aminophenol HCl salt (6.6 g, 45 mmol) in water (110 mL) was added initially dropwise with vigorous stirring, then in small portions. About midway through the addition, the cooling bath was removed to help facilitate stirring. The mixture was stirred vigourously at room temperature overnight, then filtered over celite and the filter cake was washed several times with dichloromethane. The filtrate was separated, and the aqueous layer was extracted with dichloromethane (2×20 mL). The combined organics were washed with brine (50 mL), dried over MgSO$_4$, concentrated and purified by column chromatography (0-40% EtOAc/hexane) to give 2-(3-methylpyrrol-1-yl)phenol (3.7 g, 48%) as a yellow oil. ESI-MS m/z calc. 173.2. found 174.3 (M+1)⁺; Retention time: 1.51 minutes (3 min run).

Step 2: tert-Butyl 2-methylspiro[benzo[b]pyrrolo[1,2-d][1,4]oxazine-4,4'-piperidine]-1'-carboxylate and tert-butyl 3-methylspiro[benzo[b]pyrrolo[1,2-d][1,4]oxazine-4,4'-piperidine]-1'-carboxylate

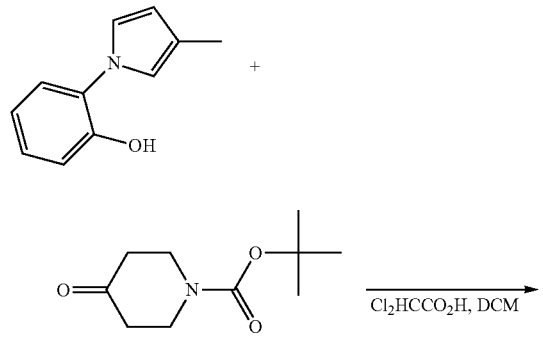

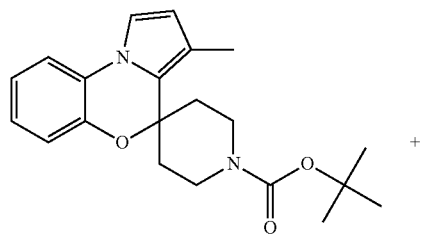

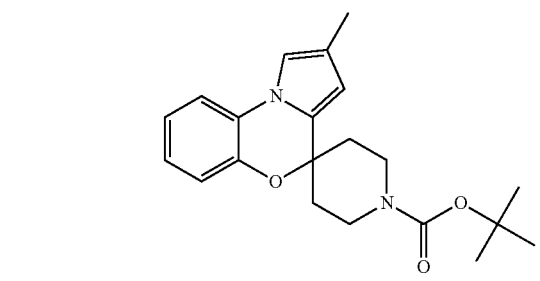

To 2-(3-methylpyrrol-1-yl)phenol (2.0 g, 12 mmol) and tert-butyl 4-oxopiperidine-1-carboxylate (2.5 g, 13 mmol) in dichloromethane (36 mL) under N₂ was added, dropwise at 0° C., dichloroacetic acid (1.9 mL, 23 mmol) over 5 min. The mixture was stirred at that temperature for 2 h then held at 5° C. overnight. The mixture was washed with water (10 mL), 1M NaOH (20 mL) and brine (10 mL), dried over MgSO₄ and purified by column chromatography (0-30% EtOAc/hexane) to give a mixture of product isomers (~2.7 g, 68%, 2:1 ratio by NMR). The mixture was subjected to SFC separation using ChiralPak OD-H (30% MeOH w/0.1% DEA, 70% CO₂) to give tert-butyl 3-methylspiro[benzo[b]pyrrolo[1,2-d][1,4]oxazine-4,4'-piperidine]-1'-carboxylate as the first eluting fraction (1.0 g, 37%) and tert-butyl 2'-methylspiro[piperidine-4,4'-pyrrolo[2,1-c][1,4]benzoxazine]-1-carboxylate as the second eluting fraction (0.40 g, 30%).

Step 3a: 3-Methylspiro[benzo[b]pyrrolo[1,2-d][1,4]oxazine-4,4'-piperidine]hydrochloric acid

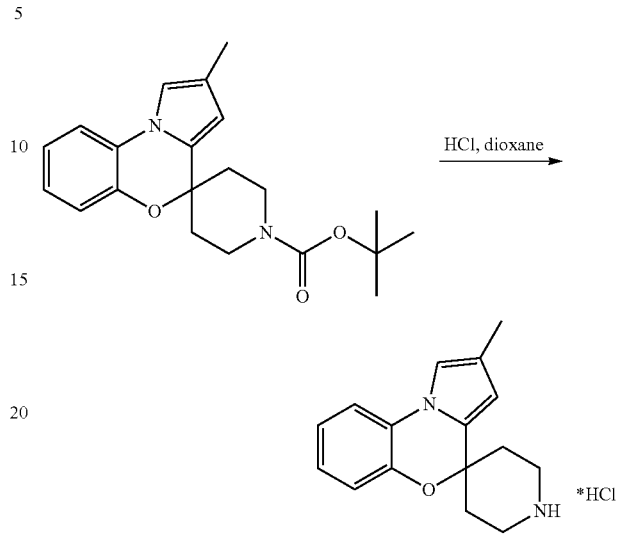

To tert-butyl 2'-methylspiro[piperidine-4,4'-pyrrolo[2,1-c][1,4]benzoxazine]-1-carboxy late (second eluting fraction from step 2) (0.40 g, 1.1 mmol) was added hydrogen chloride in 1,4-dioxane (2.8 mL of 4.0 M, 11 mmol) and the mixture stirred 1 h, then filtered and rinsed with 1:1 ether/isopropanol to give 2'-methylspiro[piperidine-4,4'-pyrrolo[2,1-c][1,4]benzoxazine] as a pink solid. ESI-MS m/z calc. 254.3. found 255.3 (M+1)⁺; Retention time: 1.16 minutes (3 min run).

Step 3b: 3-Methylspiro[benzo[b]pyrrolo[1,2-d][1,4]oxazine-4,4'-piperidine]hydrochloric acid

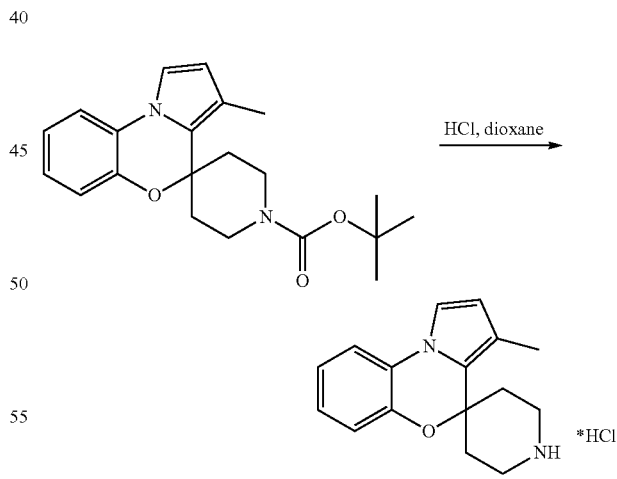

To tert-butyl 3-methylspiro[benzo[b]pyrrolo[1,2-d][1,4]oxazine-4,4'-piperidine]-1'-carboxylate (first eluting peak from step 2 (1.0 g, 2.8 mmol) was added hydrogen chloride in 1,4-dioxane (7.0 mL of 4.0 M, 28 mmol) and the mixture stirred 1 h, then filtered and rinsed with 1:1 ether/isopropanol to give 3'-methylspiro[piperidine-4,4'-pyrrolo[2,1-c][1,4]benzoxazine] as a pink solid. ESI-MS m/z calc. 254.3. found 255.3 (M+1)⁺; Retention time: 1.14 minutes (3 min run).

2'-Methylspiro[benzo[b]pyrrolo[1,2-d][1,4]oxazine-4,4'-piperidine]

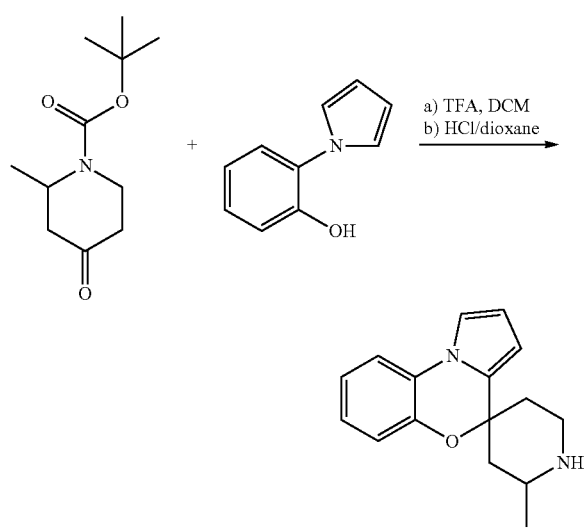

Trifluoroacetic acid (443 µL, 5.75 mmol) was added to a solution of 2-pyrrol-1-ylphenol (457 mg, 2.87 mmol) and tert-butyl 2-methyl-4-oxo-piperidine-1-carboxylate (613 mg, 2.87 mmol) in dichloromethane (19 mL) and the solution was vigorously stirred for 16 h. The reaction mixture was quenched with saturated aqueous NaHCO₃, and the organics were extracted with EtOAc (3×200 mL). The combined organics were washed with water, brine, dried over Na₂SO₄, filtered and concentrated. The residue was purified by column chromatography (silica gel: 0-10% EtOAc in dichloromethane) to give tert-butyl 2'-methylspiro[benzo[b]pyrrolo[1,2-d][1,4]oxazine-4,4'-piperidine]-1'-carboxylate as a brown oil. The crude residue was dissolved in a solution of HCl in dioxane (1.4 mL of 4.0 M, 5.6 mmol) and stirred for 30 min at room temperature. The volatiles were removed in vacuo and the residue was dissolved in diethylether. The solids were collected by filtration to provide 2'-methylspiro [benzo[b]pyrrolo[1,2-d][1,4]oxazine-4,4'-piperidine]hydrochloride (386 mg, 46%) as a reddish brown solid. ESI-MS m/z calc. 254.1. found 255.5 (M+1)⁺; Retention time: 1.12 minutes (3 min run).

8'-Azaspiro[benzo[b]pyrrolo[1,2-d][1,4]oxazine-4,3'-bicyclo[3.2.1]octane]

Step 1: (1R,5S)-8-(2,2,2-Trifluoroacetyl)-8-azabicyclo[3.2.1]octan-3-one

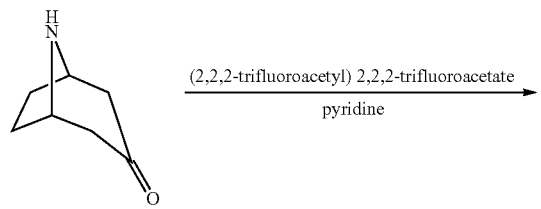

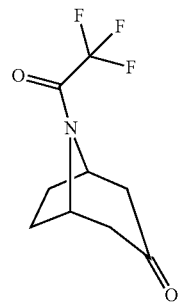

A solution of (1S,5R)-8-azabicyclo[3.2.1]octan-3-one (500 mg, 4.00 mmol) in pyridine (16 mL) was stirred in an ice bath and (2,2,2-trifluoroacetyl) 2,2,2-trifluoroacetate (1.11 mL, 7.99 mmol) was added dropwise. The solution was gently warmed to room temperature and stirred for 1 h. The reaction was then quenched with ice and was extracted with EtOAc (3×100 mL). The organic layers were combined and washed with saturated aqueous NaHCO₃, followed by 1M NaOH, and brine. The organic layer was dried over Na₂SO₄, filtered and concentrated to provide (1R,5S)-8-(2,2,2-trifluoroacetyl)-8-azabicyclo[3.2.1]octan-3-one as a clear oil (620 mg, 70%). NMR (400 MHz, CDCl₃) δ 5.08-4.94 (m, 1H), 4.79-4.67 (m, 1H), 2.87-2.63 (m, 2H), 2.52 (d, J=16.2 Hz, 2H), 2.35-2.08 (m, 2H), 2.01-1.86 (m, 1H), 1.85-1.73 (m, 1H).

Step 2: 2,2,2-Trifluoro-1-(8'-azaspiro[benzo[b]pyrrolo[1,2-d][1,4]oxazine-4,3'-bicyclo[3.2.1]octane]-8'-yl)ethanone

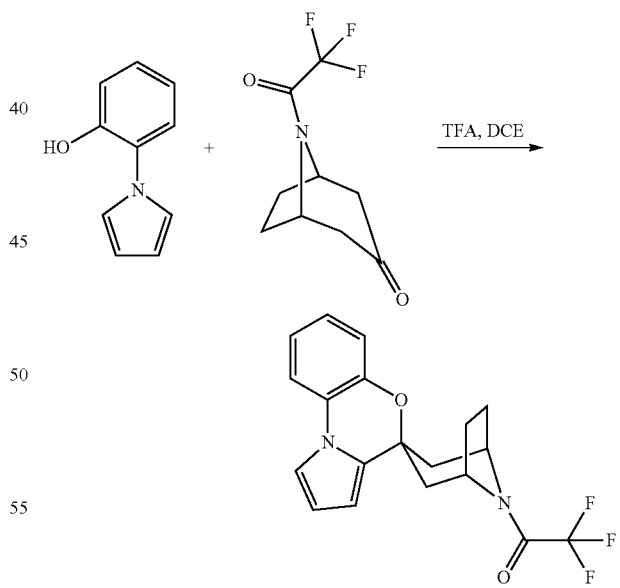

A solution of TFA (387 µL, 5.02 mmol) in dichloroethane (18 mL) was added to 2-pyrrol-1-ylphenol (401 mg, 2.52 mmol) and (1R,5S)-8-(2,2,2-trifluoroacetyl)-8-azabicyclo[3.2.1]octan-3-one (620 mg, 2.80 mmol). The solution was heated at 70° C. overnight. The solvent was evaporated and the crude residue was purified by column chromatography (silica gel: 0-10% EtOAc in hexanes) to afford 2,2,2-trifluoro-1-(8'-azaspiro[benzo[b]pyrrolo[1,2-d][1,4]oxazine-4,3'-bicyclo

[3.2.1]octane]-8'-yl)ethanone as a clear oil (469 mg, 46%). $^1$H NMR (400 MHz, CDCl$_3$) δ 7.27 (d, J=7.5 Hz, 1H), 7.07-6.94 (m, 4H), 6.23 (t, J=3.2 Hz, 1H), 5.87 (d, J=3.4 Hz, 1H), 4.74 (d, J=7.4 Hz, 1H), 4.42 (s, 1H), 2.50-2.34 (m, 2H), 2.34-2.16 (m, 3H), 2.16-1.89 (m, 3H). ESI-MS m/z calc. 362.4. found 363.3 (M+1)$^+$; Retention time: 2.07 minutes (3 min run).

Step 3: 8'-Azaspiro[benzo[b]pyrrolo[1,2-d][1,4]oxazine-4,3'-bicyclo[3.2.1]octane]

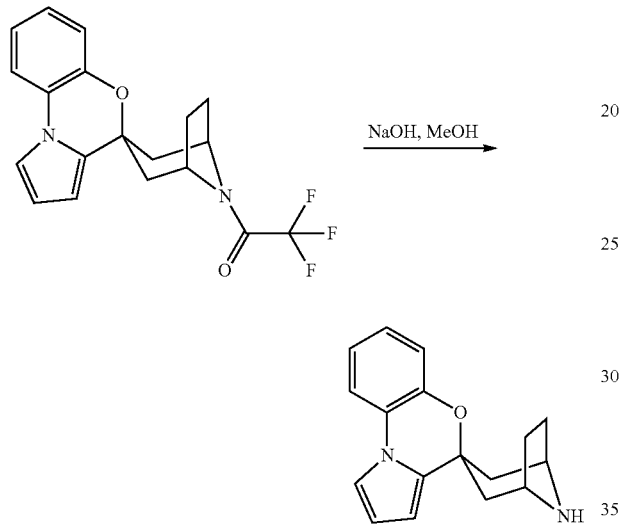

To a solution of 2: 2,2,2-trifluoro-1-(8'-azaspiro[benzo[b]pyrrolo[1,2-d][1,4]oxazine-4,3'-bicyclo[3.2.1]octane]-8'-yl)ethanone (469 mg, 1.29 mmol) in MeOH (5 mL) was added NaOH (1.3 mL of 2.0 M, 2.6 mmol). The solution was heated at 70° C. overnight. The reaction was then cooled to room temperature and the organics were extracted with EtOAc (3×100 mL), combined, and dried over Na$_2$SO$_4$. The organic layer was then filtered and concentrated to provide 8'-azaspiro[benzo[b]pyrrolo[1,2-d][1,4]oxazine-4,3'-bicyclo[3.2.1]octane] as an opaque oil in quantitative yield. $^1$H NMR (400 MHz, CDCl$_3$) δ 7.28 (d, J=7.7 Hz, 1H), 7.09-6.96 (m, 4H), 6.26 (t, J=3.2 Hz, 1H), 5.97 (d, J=3.4 Hz, 1H), 3.58 (s, 2H), 2.40-2.29 (m, 2H), 2.21-2.15 (m, 2H), 2.09 (dd, J=15.0, 3.1 Hz, 2H), 1.86-1.77 (m, 2H). ESI-MS m/z calc. 266.3. found 267.3 (M+1)$^+$; Retention time: 1.04 minutes (3 min run).

Spiro[piperidine-4,6'-pyrido[3,2-b]pyrrolo[1,2-d][1,4]oxazine]

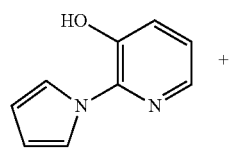

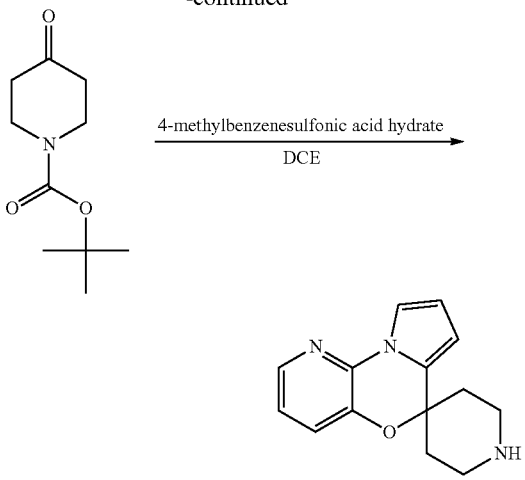

A mixture of 2-pyrrol-1-ylpyridin-3-ol (1.00 g, 6.24 mmol), tert-butyl 4-oxopiperidine-1-carboxylate (1.24 g, 6.24 mmol), 4-methylbenzenesulfonic acid hydrate (119 mg, 0.625 mmol), molecular sieves (442 mg) and dichloroethane (8.9 mL) was heated at 130° C. for 162 hours. The reaction was filtered and washed with dichloroethane. The solid was dissolved in MeOH and filtered through a plug of Celite. The solvent was evaporated under reduced pressure to yield spiro[piperidine-4,6'-pyrido[3,2-b]pyrrolo[1,2-d][1,4]oxazine] (1.4 g, 38%). ESI-MS m/z calc. 241.1. found 242.5 (M+1)$^+$; Retention time: 1.10 minutes (4 min run).

9'-(Trifluoromethyl)spiro[piperidine-4,6'-pyrido[2,3-b]pyrrolo[1,2-d][1,4]oxazine]

Step 1: Benzyl spiro[piperidine-4,6'-pyrido[2,3-b]pyrrolo[1,2-d][1,4]oxazine]-1-carboxylate

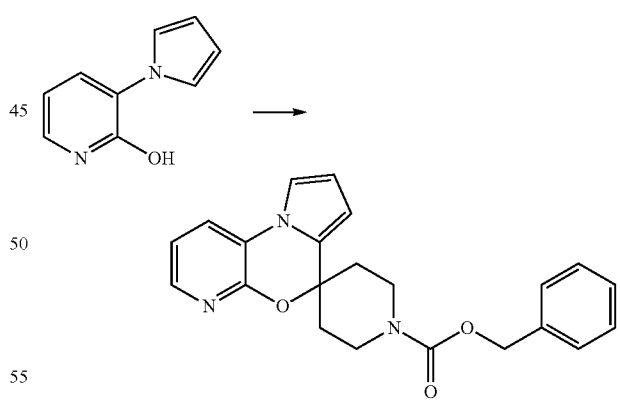

To a stirred solution of 3-pyrrol-1-ylpyridin-2-ol (481 mg, 3.00 mmol) and benzyl 4,4-dimethoxypiperidine-1-carboxylate (922 g, 3.3 mol) in CH$_2$Cl$_2$ (20 mL) at 40° C. was added BF$_3$.OEt$_2$ (407.3 μL, 3.300 mmol) drop-wise. The reaction mixture was stirred at 40° C. for 16 hours. The mixture was poured into sat. aq. Na$_2$CO$_3$ and was stirred for 5 min before it was extracted with EtOAc (3×). Organic layers were combined, washed with sat. aq. Na$_2$CO$_3$, water, brine, dried (Na$_2$SO$_4$) and evaporated to dryness. The residue was purified by column chromatography (1-30% EtOAc/CH$_2$Cl$_2$) to give benzyl spiro[piperidine-4,6'-pyrido[2,3-b]pyrrolo[1,2-d][1,4]oxazine]-1-carboxylate as an oil. ESI-MS m/z calc. 375.2. found 376.5 (M+1)+; Retention time: 1.70 minutes (3 min run). $^1$H NMR (400 MHz, DMSO) δ 8.10 (dd, J=7.7, 1.1 Hz, 1H), 8.00 (dd, J=4.9, 1.5 Hz, 1H), 7.60-7.52 (m, 1H), 7.42-7.36 (m, 4H), 7.36-7.29 (m, 1H), 7.16 (dd, J=7.8, 4.9 Hz, 1H), 6.33 (t, J=3.2 Hz, 1H), 6.20 (d, J=3.4 Hz, 1H), 5.11 (s, 2H), 3.97 (d br, J=13.2 Hz, 2H), 3.28 (s br, 2H), 1.98-1.92 (m, 4H).

Step 2: tert-Butyl spiro[piperidine-4,6'-pyrido[2,3-b]pyrrolo[1,2-d][1,4]oxazine]-1-carboxylate

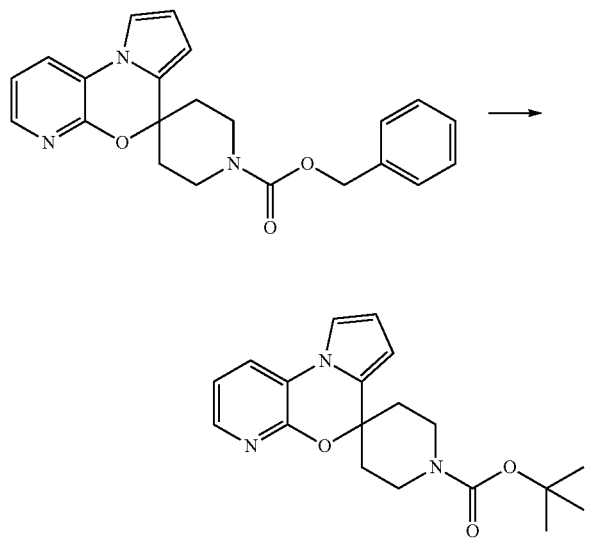

A solution of benzyl spiro[piperidine-4,6'-pyrido[2,3-b]pyrrolo[1,2-d][1,4]oxazine]-1-carboxylate (220 mg, 0.586 mmol), AcOH (33 µL, 0.59 mmol) and Pd/C (22 mg, 0.21 mmol) in MeOH (2 mL) was stirred under a balloon on H$_2$ for 6 hours. The mixture was filtered through celite and the fitrate was evaporated to give spiro[piperidine-4,6'-pyrido[2,3-b]pyrrolo[1,2-d][1,4]oxazine] (ESI-MS m/z calc. 241.1. found 242.5 (M+1)+; Retention time: 0.46 minutes (3 min run)). The residue was then taken up in THF (3 mL) before Na$_2$CO$_3$ (1.2 mL of 2.0 M, 2.4 mmol) was added. Boc$_2$O (156 mg, 0.70 mmol) was added and the mixture was stirred at room temperature for 12 hours. N,N-dimethylethylenediamine (0.5 mL) was added and the mixture was stirred at room temperature for 30 min. The mixture was poured into water and was extracted with EtOAc (3×). The organics were combined, washed with 0.1N HCl (3×), brine, dried (Na$_2$SO$_4$) and filtered through a plug of silica to give tert-butyl spiro[piperidine-4,6'-pyrido[2,3-b]pyrrolo[1,2-d][1,4]oxazine]-1-carboxylate (134 mg, 67%). $^1$H NMR (400 MHz, DMSO) δ 8.18-8.13 (m, 1H), 8.12-8.00 (m, 1H), 7.69-7.56 (m, 1H), 7.32-7.12 (m, 1H), 6.39 (dd, J=5.8, 3.0 Hz, 1H), 6.33-6.20 (m, 1H), 3.94 (d, J=11.9 Hz, 2H), 3.26 (s, 2H), 2.02 (s br, 4H), 1.48 (d, J=2.3 Hz, 9H).

Step 3: tert-Butyl 9'-(trifluoromethyl)spiro[piperidine-4,6'-pyrido[2,3-b]pyrrolo[1,2-d][1,4]oxazine]-1-carboxylate

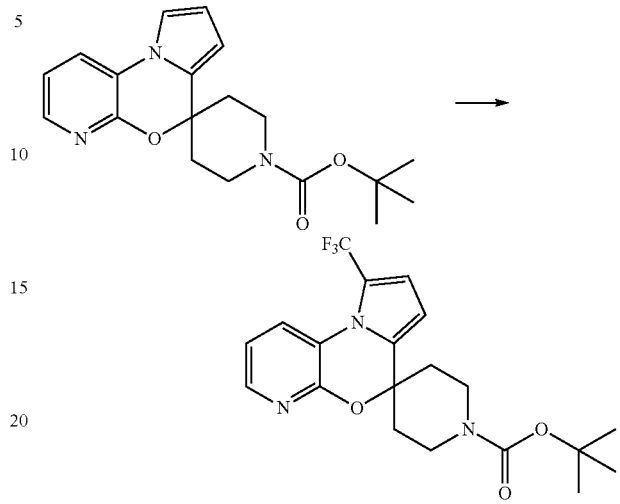

A solution of tert-butyl spiro[piperidine-4,6'-pyrido[2,3-b]pyrrolo[1,2-d][1,4]oxazine]-1-carboxylate (134 mg, 0.393 mmol) and 5-(trifluoromethyl)dibenzothiophen-5-ium (99.4 mg, 0.393 mmol) in DMF (2 mL) was stirred at 80° C. for 1.5 hours. The mixture was poured into water and was extracted with EtOAc (3×). The organics were combined, washed with water and brine, dried (Na$_2$SO$_4$) and evaporated to dryness. The residue was purified by column chromatography (1-30% EtOAc/hexanes) to give tert-butyl 9'-(trifluoromethyl)spiro-[piperidine-4,6'-pyrido[2,3-b]pyrrolo[1,2-d][1,4]oxazine]-1-carboxylate (83 mg, 56%). ESI-MS m/z calc. 409.2. found 410.5 (M+1)+; Retention time: 1.92 minutes (3 min run).

Step 4: 9'-(Trifluoromethyl)spiro[piperidine-4,6'-pyrido[2,3-b]pyrrolo[1,2-d][1,4]oxazine]

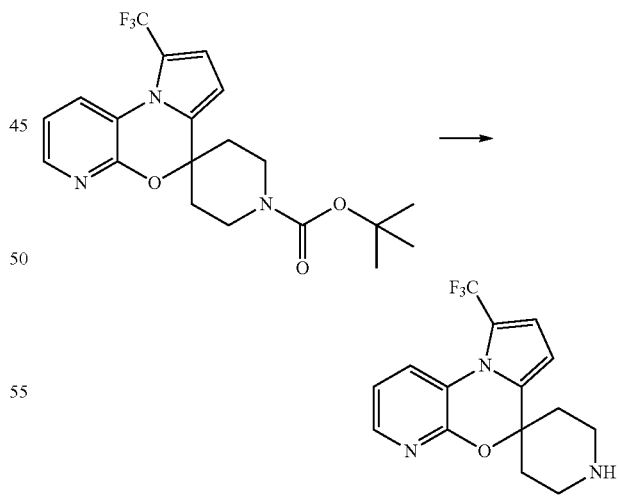

To a solution of tert-butyl 9'-(trifluoromethyl)spiro[piperidine-4,6'-pyrido[2,3-b]pyrrolo[1,2-d][1,4]oxazine]-1-carboxylate (83 mg, 0.20 mmol) in CH$_2$Cl$_2$ (3 mL) was added TFA (1.0 mL, 13 mmol) and the mixture was stirred at room temperature for 15 min before being evaporated to dryness. The residue was taken up in EtOAc and sat. aq. Na$_2$CO$_3$, the layers were separated, and aqueous layer was extracted with EtOAc (2×). The organics were combined, washed with sat. aq. Na₂CO₃, brine, dried (Na₂SO₄) and evaporated to dryness to give 9'-(trifluoromethyl)-spiro[piperidine-4,6'-pyrido[2,3-b]pyrrolo[1,2-d][1,4]oxazine] as a pale yellow solid (59 mg). ESI-MS m/z calc. 309.1. found 310.3 (M+1)⁺; Retention time: 1.32 minutes (3 min run).

7-Chlorospiro[benzo[b]pyrrolo[1,2-d][1,4]oxazine-4,4'-piperidine]-1-carbaldehyde Step 1: 1-(7-Chlorospiro[benzo[b]pyrrolo[1,2-d][1,4]oxazine-4,4'-piperidine]-1'-yl)-2,2,2-trifluoroethanone

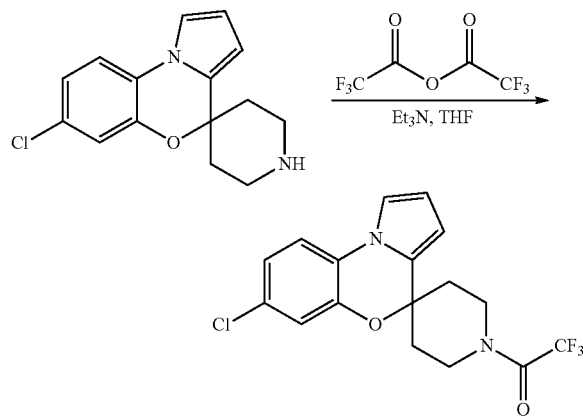

To a solution of 7'-chlorospiro[piperidine-4,4'-pyrrolo[2,1-c][1,4]benzoxazine] (3.5 g, 11.3 mmol) in dry THF (70.00 mL) at 0° C. was added Et₃N (6.27 mL, 45.0 mmol) dropwise followed by DMAP (1.374 g, 11.25 mmol). (2,2,2-Trifluoroacetyl) 2,2,2-trifluoroacetate (2.82 mL, 20.3 mmol) was added and the mixture was stirred for 8 h at room temperature. The solvent was removed and the residue was partitioned between sat. aq. NaHCO₃ (50 mL) and DCM (250 mLl). The layers were separated and the aqueous phase was extracted with DCM (2×250 mL). The organics were combined, dried, filtered, purified by column chromatography (3-15% AcOEt in hexanes) to give 1-(7-chlorospiro[benzo[b]pyrrolo[1,2-d][1,4]oxazine-4,4'-piperidine]-1'-yl)-2,2,2-trifluoroethanone (85%). ESI-MS m/z calc. 370.1. found 370.3 (M+1)⁺; Retention time: 2.15 minutes (3 min run).

Step 2: 7-Chloro-1'-(2,2,2-trifluoroacetyl)spiro[benzo[b]pyrrolo[1,2-d][1,4]oxazine-4,4'-piperidine]-1-carbaldehyde

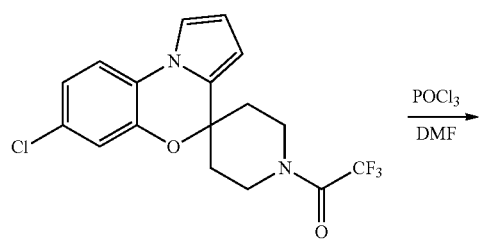

-continued

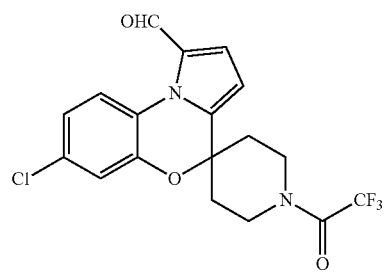

POCl₃ (1.33 mL, 14.3 mmol) was added dropwise at 0° C. under N₂ to dry DMF (1.1 mL, 14 mmol). The reaction mixture was left for 20 min at this temperature, which led to the formation of a white solid. A solution of 1-(7'-chlorospiro[piperidine-4,4'-pyrrolo[2,1-c][1,4]benzoxazine]-1-yl)-2,2,2-trifluoro-ethanone (353 mg, 9.535 mmol) in dry DMF (26.5 mL) was added dropwise and the cooling bath was removed. The reaction was allowed to stir at room temperature for 1 h. The mixture was poured over ice and 1M NaOH (25 ml) was added. The pH was adjusted to 7 with 3M HCl and the mixture was extracted with DCM three times. The combined organics were dried, filtered and concentrated. Column chromatography (5-30% AcOEt in hexanes) on the residue gave 7-chloro-1'-(2,2,2-trifluoroacetyl)spiro[benzo[b]pyrrolo[1,2-d][1,4]oxazine-4,4'-piperidine]-1-carbaldehyde. ESI-MS m/z calc. 398.1. found 399.3 (M+1)⁺; Retention time: 1.96 minutes (3 min run).

Step 3: 7-Chlorospiro[benzo[b]pyrrolo[1,2-d][1,4]oxazine-4,4'-piperidine]-1-carbaldehyde

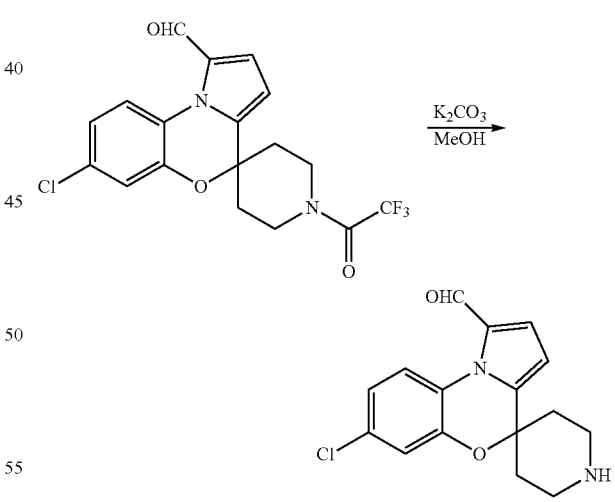

To 7'-chloro-1-(2,2,2-trifluoroacetyl)spiro[piperidine-4,4'-pyrrolo[2,1-c][1,4]benzoxazine]-1'-carbaldehyde (510 mg, 1.28 mmol) dissolved in MeOH (5.1 mL) was added K₂CO₃ (371 mg, 2.69 mmol) in one portion at room temperature. Water was added (2 mL), and organic solvent was removed under vacuum. The mixture was extracted with DCM (3×10 mL). The organics were combined, dried, filtered, and concentrated to give 7-chlorospiro[benzo[b]pyrrolo[1,2-d][1,4]oxazine-4,4'-piperidine]-1-carbaldehyde as a yellow oil, which was used as is for the following step. ESI-MS m/z calc. 302.1. found 303.3 (M+1)+; Retention time: 1.07 minutes (3 min run).

1-Methyl-1H-spiro[chromeno[4,3-c]pyrazole-4,4'-piperidine]dihydrochloride

Step 1: tert-Butyl 4-oxospiro[chroman-2,4'-piperidine]-1'-carboxylate

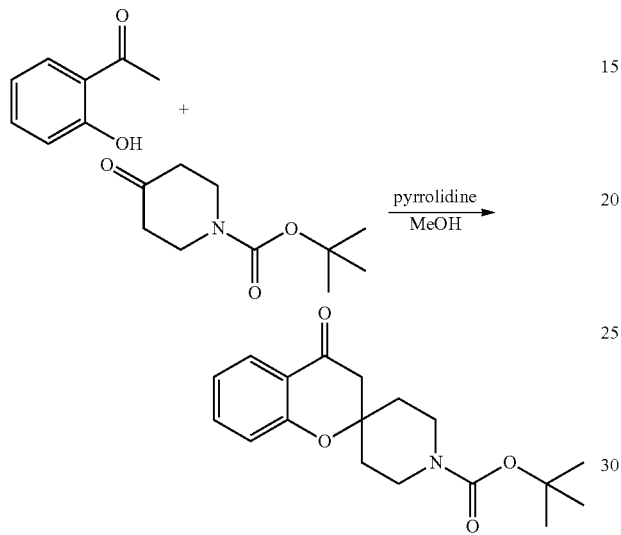

To a solution of tert-butyl 4-oxopiperidine-1-carboxylate (93.7 g, 470 mmol) in pyrrolidine (56.0 mL, 673 mmol) and anhydrous MeOH (112 mL) was added 1-(2-hydroxyphenyl)ethanone (56 mL, 468 mmol). The reaction mixture was stirred at 80° C. for 2.5 hours. Methanol was removed under reduced pressure. The resulting residue was dissolved in ethyl acetate (150 mL), washed with 1M aqueous HCl (1×150 mL) and brine (2×100 mL). The organic layer was dried over sodium sulfate, filtered and concentrated under reduced pressure to afford a yellow oil. This oil was diluted with hexane (400 mL) and was heated at 60° C. until in solution. Once dissolved, the solution was allowed to cool to 25° C. Crystals were collected via vacuum filtration and rinsed with hexane to obtain tert-butyl 4-oxospiro[chromane-2,4'-piperidine]-1'-carboxylate (105 g, 70%) as a light yellow solid. ESI-MS m/z calc. 317.2. found 318.2 (M+1)+; Retention time: 1.78 minutes (3 min run). $^1$H NMR (400 MHz, CDCl$_3$) δ 7.87 (dd, J=7.8, 1.5 Hz, 1H), 7.55-7.45 (m, 1H), 7.10-6.90 (m, 2H), 3.95-3.80 (m, 2H), 3.26-3.17 (m, 2H), 2.72 (s, 2H), 2.03 (d, J=13.0 Hz, 2H), 1.68-1.58 (m, 2H), 1.46 (s, 9H).

The following compounds were synthesized using the procedure described above: tert-butyl 6-chloro-4-oxospiro[chroman-2,4'-piperidine]-1'-carboxylate: ESI-MS m/z calc. 351.1. found 352.4 (M+1)+; Retention time: 3.13 minutes (4 min run). $^1$H NMR (400 MHz, CDCl$_3$) δ 7.82 (d, J=2.7 Hz, 1H), 7.44 (dd, J=8.8, 2.7 Hz, 1H), 6.95 (d, J=8.8 Hz, 1H), 3.92-3.83 (m, 2H), 3.24-3.13 (m, 2H), 2.71 (s, 2H), 2.01 (d, J=12.7 Hz, 2H), 1.66-1.56 (m, 2H), 1.46 (s, 9H); tert-butyl 7-chloro-4-oxospiro-[chroman-2,4'-piperidine]-1'-carboxylate: ESI-MS m/z calc. 351.1. found 352.2 (M+1)+; Retention time: 3.18 minutes (4 min run). $^1$H NMR (400 MHz, CDCl$_3$) δ 7.80 (d, J=8.4 Hz, 1H), 7.03 (d, J=1.8 Hz, 1H), 6.99 (dd, J=8.4, 1.9 Hz, 1H), 3.94-3.83 (m, 2H), 3.25-3.16 (m, 2H), 2.04-1.97 (m, 2H), 1.66-1.56 (m, 2H), 1.46 (s, 9H); tert-butyl 6-methoxy-4-oxospiro[chroman-2,4'-piperidine]-1'-carboxylate: ESI-MS m/z calc. 347.2. found 348.4 (M+1)+; Retention time: 3.07 minutes (4 min run). $^1$H NMR (400 MHz, CDCl$_3$) δ 7.28 (dd, J=16.3, 2.4 Hz, 1H), 7.11 (dd, J=9.0, 2.6 Hz, 1H), 6.91 (dd, J=9.0, 2.0 Hz, 1H), 3.90-3.84 (m, 2H), 3.80 (s, 3H), 3.26-3.15 (m, 2H), 2.69 (s, 2H), 2.07-1.97 (m, 2H), 1.64-1.52 (m, 2H), 1.46 (s, 9H).

Step 2: tert-Butyl 3-(diethoxymethyl)-4-oxospiro[chroman-2,4'-piperidine]-1'-carboxylate

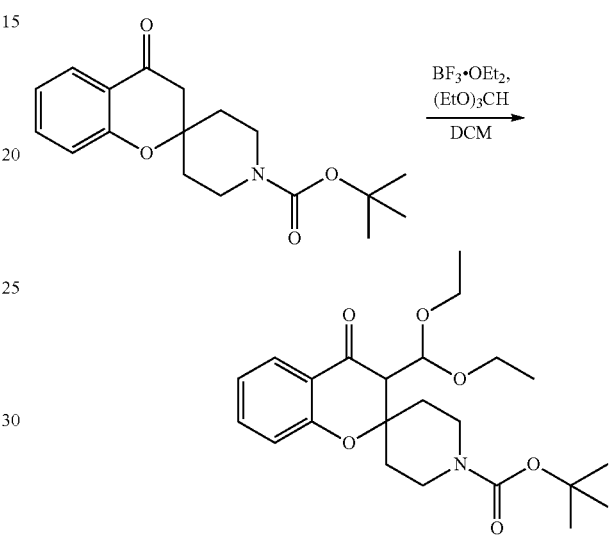

To triethyl orthoformate (85 mL, 510 mmol) in dry dichloromethane (460 mL) under nitrogen at −10° C. was added dropwise BF$_3$OEt$_2$ (65 mL, 510 mmol). The solution was allowed to warm to 0° C. and was stirred for 10 minutes. The solution was cooled to −78° C. prior to the slow dropwise addition of tert-butyl 4-oxospiro[chromane-2,4'-piperidine]-1'-carboxylate (55 g, 170 mmol) in dichloromethane (25 mL). N-ethyl-N-isopropylpropan-2-amine (100 mL, 600 mmol) was added over a 30 minutes period, and the mixture was slowly warmed to 25° C. and was stirred at this temperature overnight. The reaction mixture was diluted with dichloromethane (500 mL) followed by saturated aqueous sodium bicarbonate solution (500 mL). The layers were separated, and the organic layer was washed with additional sodium bicarbonate (500 mL). The organic layer was dried over sodium sulfate, filtered and concentrated. The residue was purified by silica gel column chromatography (0-25% ethyl acetate in hexane) to provide tert-butyl 3-(diethoxymethyl)-4-oxo-spiro[chromane-2,4'-piperidine]-1'-carboxylate (72 g, 91%) as an orange oil. ESI-MS m/z calc. 419.5. found 420.3 (M+1)+; Retention time: 2.50 minutes (3 min run).

The following compounds were synthesized using the procedure described above: tert-butyl 6-chloro-3-(diethoxymethyl)-4-oxospiro[chroman-2,4'-piperidine]-1'-carboxylate: ESI-MS m/z calc. 453.2. found 454.4 (M+1)+; Retention time: 3.41 minutes (4 min run); tert-butyl 7-chloro-3-(diethoxymethyl)-4-oxospiro[chroman-2,4'-piperidine]-1'-carboxylate: ESI-MS m/z calc. 453.2. found 454.3 (M+1)+; Retention time: 2.41 minutes (3 min run); tert-butyl 3-(diethoxymethyl)-6-methoxy-4-oxospiro[chroman-2,4'-piperi-

Step 3: 1-Methyl-1H-spiro[chromeno[4,3-c]pyrazole-4,4'-piperidine]dihydrochloride

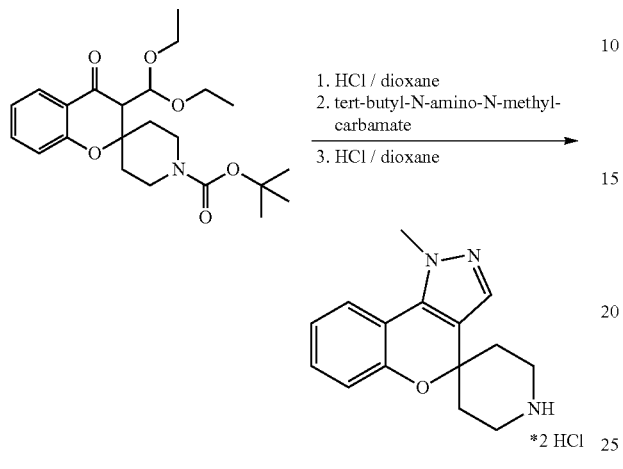

To tert-butyl 3-(diethoxymethyl)-4-oxo-spiro[chromane-2,4'-piperidine]-1'-carboxylate (72 g, 160 mmol) was added hydrochloric acid (610 mL of 4.0 M, 2.5 mol). The reaction mixture was allowed to stir at 25° C. for 2 hours. Solvent was removed under vacuum, and the obtained solid was azeotroped with EtOH (3×700 mL). The resulting beige-white solid was dissolved in EtOH (685 mL) at 25° C. prior to the addition of tert-butyl N-amino-N-methyl-carbamate (29 mL, 200 mmol). The solution was allowed to stir at 25° C. overnight. To the thick beige-white slurry that formed was added hydrochloric acid (200 mL of 4.0 M, 800 mmol). The mixture was heated at 60° C. to yield a clear yellow solution. After 1 hour at 60° C., a thick white slurry developed. The slurry was allowed to slowly cool to 25° C., and solids were collected by vacuum filtration. The filter cake was rinsed with a 10% solution of EtOH in hexane (2×500 mL). The solid was placed in a vacuum oven overnight (20 mm Hg/45° C.). 1-Methyl-1H-spiro[chromeno[4,3-c]pyrazole-4,4'-piperidine]dihydrochloride (42 g, 78%) was obtained as an off-white solid. ESI-MS m/z calc. 255.3. found 256.3 (M+1)$^+$; Retention time: 1.30 minutes (3 min run). $^1$H NMR (400 MHz, MeOD) δ 7.82-7.76 (m, 1H), 7.61 (s, 1H), 7.40-7.34 (s, 1H), 7.22-7.14 (m, 2H), 4.19 (s, 3H), 3.52-3.42 (m, 2H), 3.41-3.33 (m, 2H), 2.39-2.07 (m, 4H).

The following compounds were synthesized using the procedure described above: 8-chloro-1-methyl-1H-spiro[chromeno[4,3-c]pyrazole-4,4'-piperidine]dihydrochloride: ESI-MS m/z calc. 289.1. found 290.3 (M+1)$^+$; Retention time: 1.29 minutes (3 min run). NMR (400 MHz, DMSO) δ 7.74 (d, J=2.4 Hz, 1H), 7.43 (s, 1H), 7.36 (dd, J=8.7, 2.4 Hz, 1H), 7.21 (d, J=8.7 Hz, 1H), 4.12 (s, 3H), 3.26-3.13 (m, 4H), 2.24-2.04 (m, 4H); 7-chloro-1-methyl-1H-spiro[chromeno[4,3-c]pyrazole-4,4'-piperidine]dihydrochloride: ESI-MS m/z calc. 289.1. found 290.2 (M+1)$^+$; Retention time: 2.00 minutes (4 min run). $^1$H NMR (400 MHz, CDCl$_3$) δ 7.50 (d, J=8.3 Hz, 1H), 7.36 (s, 1H), 7.17-6.97 (m, 2H), 4.15 (s, 3H), 3.48-3.37 (m, 4H), 2.45-2.22 (m, 4H); 8-methoxy-1-methyl-1H-spiro[chromeno[4,3-c]pyrazole-4,4'-piperidine]dihydrochloride: ESI-MS m/z calc. 285.2. found 286.5 (M+1)$^+$; Retention time: 1.14 minutes (3 min run). NMR (400 MHz, CDCl$_3$) δ 7.36 (s, 1H), 7.12 (d, J=2.7 Hz, 1H), 7.01 (d, J=8.9 Hz, 1H), 6.87-6.79 (m, 1H), 4.16 (s, 3H), 3.83 (s, 3H), 3.48-3.39 (m, 4H), 2.48-2.18 (m, 4H).

2-Methyl-2H-spiro[chromeno[4,3-c]pyrazole-4,4'-piperidine]hydrochloride

Step 1: (Z)-3-(ethoxymethylene)spiro[chroman-2,4'-piperidin]-4-one hydrochloride

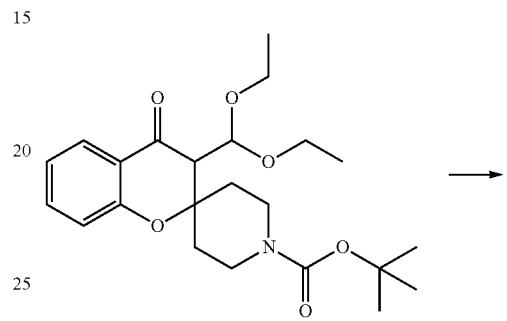

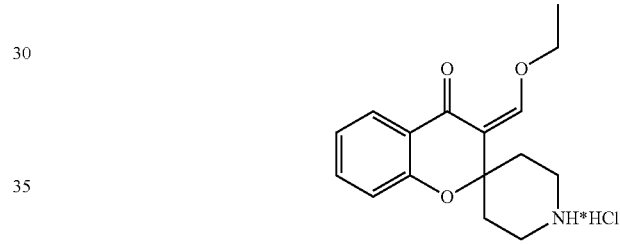

To tert-butyl 3-(diethoxymethyl)-4-oxo-spiro[chromane-2,4'-piperidine]-1'-carboxylate (33.0 g, 78.7 mmol) in toluene (73.33 mL) was added hydrochloric acid (68.8 mL of 4.0 M in dioxane, 275 mmol). The reaction mixture was heated at 60° C. for 15 min. Most of the solvent was removed under vacuum, and the tan slurry was filtered using a medium frit. The solids were washed with 500 mL of toluene. The solids were dried to give (Z)-3-(ethoxymethylene)spiro[chroman-2,4'-piperidin]-4-one hydrochloride (15.4 g, 63%). ESI-MS m/z calc. 273.1. found 274.3 (M+1)$^+$; Retention time: 0.85 minutes (3 min run).

Step 2: 2-Methyl-2H-spiro[chromeno[4,3-c]pyrazole-4,4'-piperidine]hydrochloride

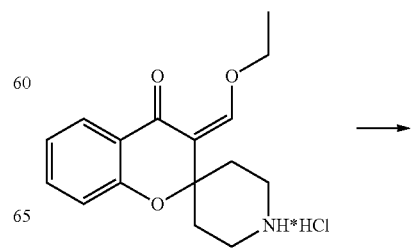

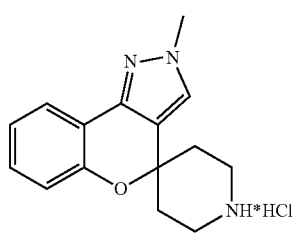

(Z)-3-(Ethoxymethylene)spiro[chroman-2,4'-piperidin]-4-one hydrochloride (2.46 g, 7.94 mmol) in ethanol (24.6 mL) was treated with methylhydrazine (423 μL, 7.94 mmol). The reaction mixture was heated at 70° C. for 1 h and then at 100° C. for 10 min. The mixture was allowed to cool to room temperature overnight. The yellow solid was filtered off and was washed with ethanol to give 2-methylspiro[chromeno[4,3-c]pyrazole-4,4'-piperidine]hydrochloride (1.20 g, 74%). ESI-MS m/z calc. 255.1. found 256.3 (M+1)$^+$; Retention time: 0.65 minutes. $^1$H NMR (400 MHz, DMSO) δ 9.01 (s, 2H), 7.75 (s, 1H), 7.61 (dd, J=7.5, 1.2 Hz, 1H), 7.28-7.20 (m, 1H), 7.10-6.99 (m, 2H), 3.89 (s, 3H), 3.28-3.18 (m, 4H), 2.18-2.02 (m, 4H).

2-(Trifluoromethyl)-2H-spiro[chromeno[4,3-c]pyrazole-4,4'-piperidine]

Step 1: tert-Butyl 1H-spiro[chromeno[4,3-c]pyrazole-4,4'-piperidine]-1'-carboxylate

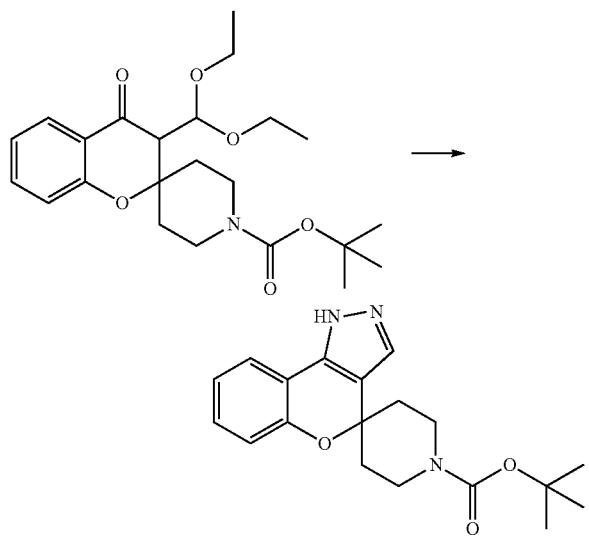

To tert-butyl 3-(diethoxymethyl)-4-oxo-spiro[chromane-2,4'-piperidine]-1'-carboxylate (15.1 g, 35.9 mmol) and hydrazine (1.35 mL, 43.1 mmol) in EtOH (120 mL) was added hydrochloric acid (900 μL of 4.0 M in dioxanes, 3.6 mmol). The mixture was heated at 60° C. for 2 h before it was cooled and the solvent was evaporated. The residue was purified by silica gel chromatography eluting with 0-100% ethyl acetate in hexanes to give tert-butyl spiro[1H-chromeno[4,3-c]pyrazole-4,4'-piperidine]-1'-carboxylate (8.76 g, 71%). ESI-MS m/z calc. 341.2. found 342.3 (M+1)$^+$; Retention time: 1.69 minutes (3 min run).

Step 2: tert-Butyl 2-(bromodifluoromethyl)-2H-spiro[chromeno[4,3-c]pyrazole-4,4'-piperidine]-1'-carboxylate and tert-butyl 1-(bromodifluoromethyl)-1H-spiro[chromeno[4,3-c]pyrazole-4,4'-piperidine]-1'-carboxylate

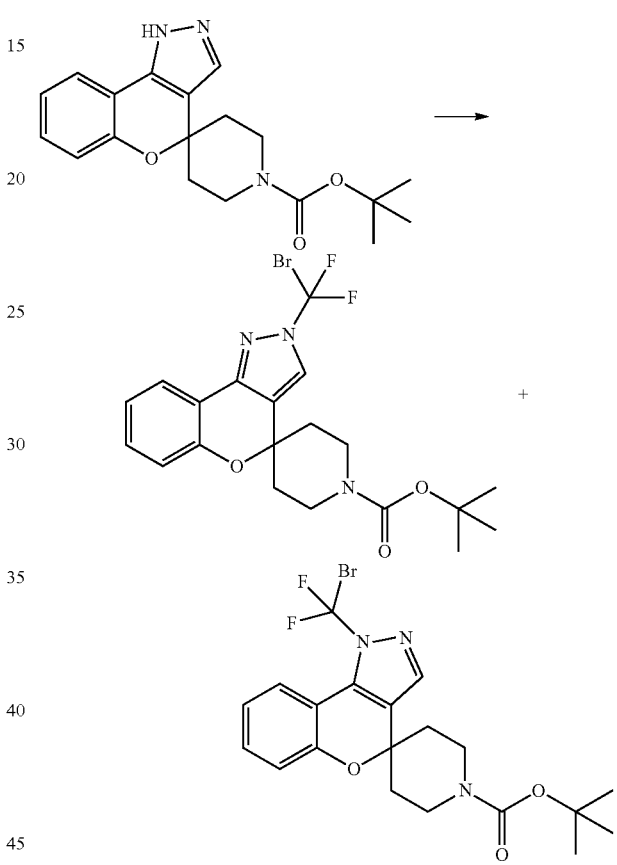

A solution of tert-butyl spiro[1H-chromeno[4,3-c]pyrazole-4,4'-piperidine]-1'-carboxylate (1.80 g, 5.26 mmol) in DMF (4.4 mL) was cooled to 0° C. Sodium hydride (242 mg, 6.05 mmol) was added and the reaction mixture was stirred for 30 min. Dibromodifluoromethane (11.0 g, 4.78 mL, 52.6 mmol) was added and the reaction mixture was allowed to warm to room temperature over 2 h. The mixture was poured into water and was extracted with dichloromethane. The organics were washed with brine, dried over sodium sulfate and evaporated. The crude material was purified by silica gel chromatography eluting with 100% dichloromethane until the first peak eluted then 0-10% ethyl acetate in dichloromethane to collect the second peak. Peak 1: tert-butyl 2-[bromo(difluoro)methyl]spiro[chromeno[4,3-c]pyrazole-4,4'-piperidine]-1'-carboxylate (251 mg, 10%). ESI-MS m/z calc. 469.1. found 470.5 (M+1)$^+$; Retention time: 2.30 minutes (3 min run). Peak 2: tert-butyl 1-[bromo(difluoro)methyl]spiro[chromeno[4,3-c]pyrazole-4,4'-piperidine]-1'-carboxylate (200 mg, 8%). ESI-MS m/z calc. 469.1. found 470.3/472.3 (M+1)$^+$; Retention time: 1.69 minutes (3 min run).

Step 3: 2-(Trifluoromethyl)-2H-spiro[chromeno[4,3-c]pyrazole-4,4'-piperidine]

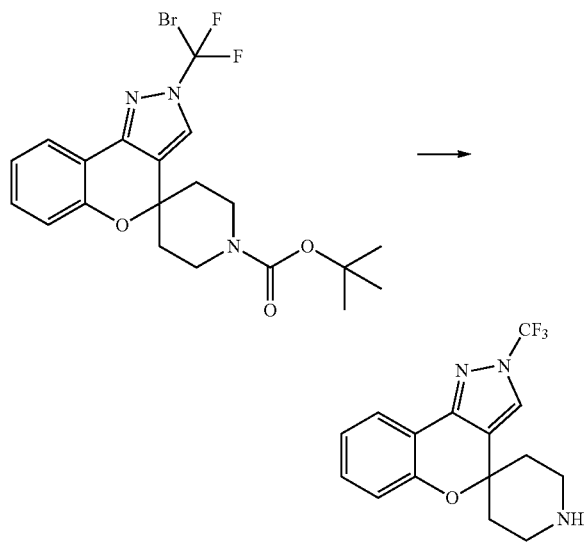

tert-butyl 2-[bromo(difluoro)methyl]spiro[chromeno[4,3-c]pyrazole-4,4'-piperidine]-1'-carboxylate (251 mg, 0.534 mmol) was dissolved in 2-isopropoxypropane (377 µL) at 0° C. before pyridine hydrofluoride (250 µL, 2.78 mmol) was added. The reaction mixture was stirred for 15 min and oxomercury (98.3 mg, 0.454 mmol) was added in three portions. The reaction was warmed to 25° C. and was stirred for 16 h. The reaction mixture was poured into water and was extracted with dichloromethane. The organics were washed with sodium bicarbonate and brine, dried over sodium sulfate, and concentrated under reduced pressure to give a mixture of 2-(trifluoromethyl)-2H-spiro[chromeno[4,3-c]pyrazole-4,4'-piperidine] (ESI-MS m/z calc. 309.1. found 310.5 (M+1)$^+$; Retention time: 1.22 minutes (3 min run)) and 1H-spiro[chromeno[4,3-c]pyrazole-4,4'-piperidine]. 1-(Trifluoromethyl)-1H-spiro[chromeno[4,3-c]pyrazole-4,4'-piperidine] was also prepared using the procedure described above. ESI-MS m/z calc. 309.1. found 310.5 (M+1)$^+$; Retention time: 1.07 minutes (3 min run)

1,3-Dimethyl-1H-spiro[chromeno[4,3-c]pyrazole-4,4'-piperidine]dihydrochloride

Step 1: tert-Butyl 3-(1-hydroxyethyl)-4-oxospiro[chroman-2,4'-piperidine]-1'-carboxylate

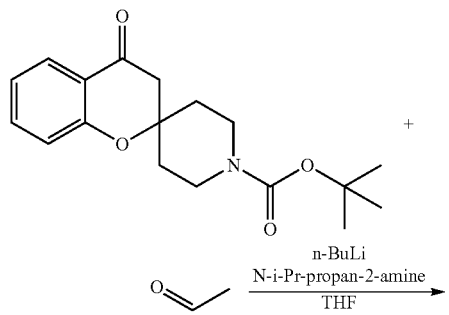

To a solution of N-isopropylpropan-2-amine (0.57 mL, 4.1 mmol) in THF (3.5 mL) was added a solution of n-butyllithium in hexane (2.6 mL of 1.6 M, 4.1 mmol) dropwise at −78° C. under Ar. The solution was allowed to stir at −20° C. for 15 min and then cooled to −78° C. tert-Butyl 4-oxospiro[chromane-2,4'-piperidine]-1'-carboxylate (1.1 g, 3.5 mmol) in THF (3.5 mL) was added at −78° C. followed by the addition of acetaldehyde (0.22 mL, 3.9 mmol) in THF (3 mL). The reaction was quenched with saturated aqueous ammonium chloride at −78° C., warmed to 25° C. and extracted with ethyl acatate (2×). The combined organic layers were washed with brine, dried over MgSO$_4$ and concentrated to dryness. Purification by silica gel chromatography (20-30% ethyl acetate in hexane) provided tert-butyl 3-(1-hydroxyethyl)-4-oxospiro[chroman-2,4'-piperidine]-1'-carboxylate (0.80 g, 63%) as a colorless oil. ESI-MS m/z calc. 361.2. found 362.5 (M+1)$^+$; Retention time: 1.79 minutes (3 min run). $^1$H NMR (400 MHz, CDCl$_3$) δ 7.87 (dd, J=7.8, 1.6 Hz, 1H), 7.55-7.48 (m, 1H), 7.06-6.96 (m, 2H), 4.33-4.23 (m, 1H), 4.10-3.93 (m, 1H), 3.88-3.67 (m, 1H), 3.41-3.27 (m, 1H), 3.07-2.94 (m, 1H), 2.62 (d, J=5.2 Hz, 1H), 2.45 (d, J=8.5 Hz, 1H), 2.20-2.00 (m, 2H), 1.85-1.76 (m, 1H), 1.58-1.49 (m, 1H), 1.46 (s, 9H), 1.26 (t, J=7.1 Hz, 1H) 1.13 (d, J=6.6 Hz, 3H).

Step 2: tert-Butyl 3-acetyl-4-oxospiro[chroman-2,4'-piperidine]-1'-carboxylate

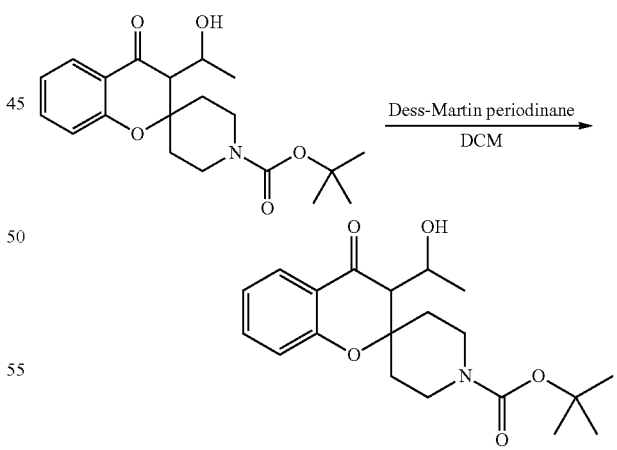

A mixture of tert-butyl 3-(1-hydroxyethyl)-4-oxospiro[chroman-2,4'-piperidine]-1'-carboxylate (600 mg, 1.66 mmol) and Dess-Martin periodinane (8.3 mL of 0.30 M, 2.5 mmol) was stirred at 25° C. for 5 h. The reaction mixture was diluted with dichloromethane, washed with saturated aqueous NaHCO$_3$ (2×), 5% Na$_2$S$_2$O$_3$ (2×), brine, dried over MgSO$_4$, filtered and concentrated to dryness. Purification by silica gel chromatography provided tert-butyl 3-acetyl-4-oxospiro[chroman-2,4'-piperidine]-1'-carboxylate (435 mg, 73%). ESI-MS m/z calc. 359.2. found 360.4 (M+1)$^+$; Retention time: 2.84 minutes (4 min run). $^1$H NMR (400 MHz, CDCl$_3$) δ 7.86 (dd, J=7.8, 1.5 Hz, 1H), 7.60-7.52 (m, 1H), 7.07-7.01 (m, 2H), 4.10-3.79 (m, 2H), 3.76 (s, 1H), 3.29-3.03 (m, 2H), 2.27 (s, 3H), 2.10-1.85 (m, 3H), 1.68-1.58 (m, 1H), 1.47 (s, 9H).

Step 3: 1,3-Dimethyl-1H-spiro[chromeno[4,3-c]pyrazole-4,4'-piperidine]dihydrochloride

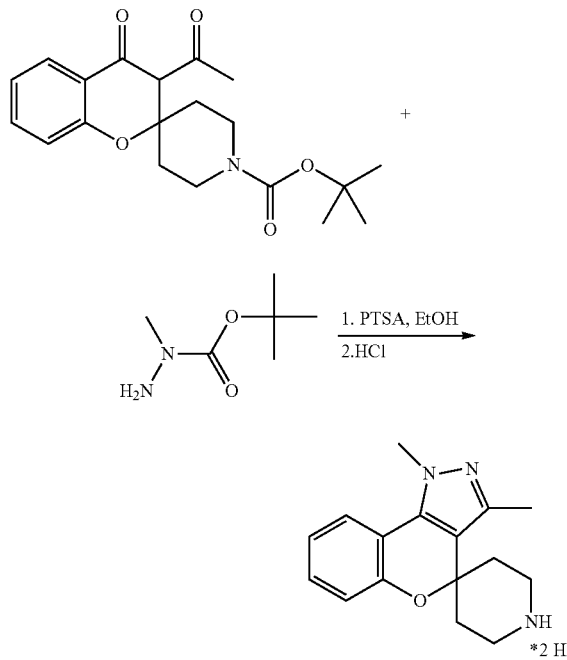

A mixture of tert-butyl 3-acetyl-4-oxospiro[chroman-2,4'-piperidine]-1'-carboxylate (250 mg, 0.70 mmol), tert-butyl N-amino-N-methyl-carbamate (120 μL, 0.84 mmol) and p-toluene sulfonic acid monohydrate (27 mg, 0.14 mmol) in ethanol (8 mL) was heated at 80° C. overnight. Additional tert-butyl N-amino-N-methyl-carbamate (120 μL, 0.84 mmol) was added and the mixture was heated at 80° C. for 6.5 h, then another portion of ten-butyl N-amino-N-methyl-carbamate (120 μL, 0.84 mmol) was added and the mixture was heated at 80° C. for 2 h. HCl (0.87 mL of 4.0 M in dioxane, 3.5 mmol) was added and the mixture was stirred at 80° C. for 1 h. After cooling, the precipitate was collected via filtration and washed with cold EtOH to provide 1,3-dimethyl-1H-spiro[chromeno[4,3-c]pyrazole-4,4'-piperidine]dihydrochloride (295 mg, >100%, may contain some methyl hydrazine HCl salt) as a solid. ESI-MS m/z calc. 269.2. found 270.5 (M+1)$^+$; Retention time: 1.11 minutes (3 min run). $^1$H NMR (400 MHz, DMSO) δ 7.71 (dd, J=7.8, 1.3 Hz, 1H), 7.33-7.27 (m, 1H), 7.17-7.14 (m, 1H), 7.11-7.05 (m, 1H), 4.02 (s, 3H), 3.28-3.15 (m, 4H), 2.40-2.30 (m, 2H), 2.23 (s, 3H), 2.07-1.97 (m 2H).

1H-Spiro[chromeno[4,3-c]pyrazole-4,4'-piperidine]

Step 1: Benzyl 4-oxospiro[chroman-2,4'-piperidine]-1'-carboxylate

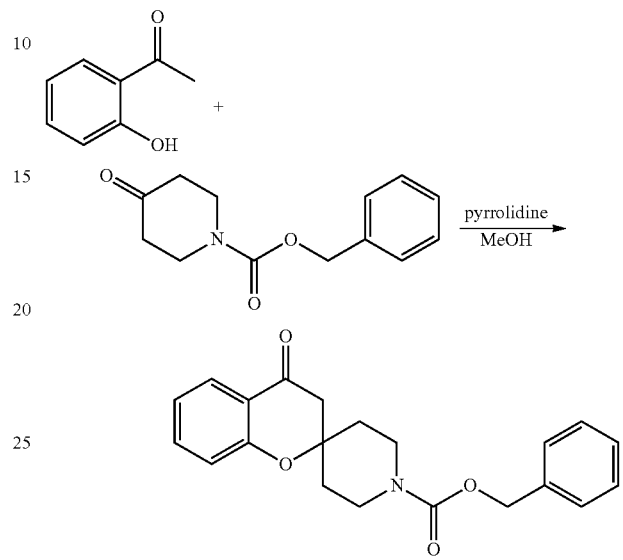

A mixture of 1-(2-hydroxyphenyl)ethanone (50 g, 0.37 mol), benzyl 4-oxopiperidine-1-carboxylate (94 g, 0.40 mol), pyrrolidine (61 mL, 0.73 mol) and methanol (24 mL) was heated at 80° C. for 20 hours. After cooling to 25° C., the reaction mixture was diluted with ethyl acetate (1000 mL) and partitioned with 1M aqueous HCl (500 mL). The organic phase was washed with 1M aqueous HCl (2×500 mL), water (500 mL), saturated sodium chloride solution (500 mL), dried over magnesium sulfate, filtered and concentrated. Purification by silica gel chromatography (0-30% ethyl acetate in hexane) afforded benzyl 4-oxospiro[chroman-2,4'-piperidine]-1'-carboxylate (105 g, 81% yield) as a yellow oil. ESI-MS m/z calc. 351.2. found 352.2 (M+1)$^+$; Retention time: 2.30 minutes (3 min run). $^1$H NMR (400 MHz, CDCl$_3$) δ 7.88 (d, J=7.8 Hz, 1H), 7.54-7.47 (m, 1H), 7.44-7.29 (m, 5H), 7.02 (dd, J=14.8, 7.8 Hz, 2H), 5.16 (s, 2H), 4.10-3.90 (m, 2H), 3.36-3.24 (m, 2H), 2.73 (s, 2H), 2.12-2.00 (m, 2H), 1.71-1.58 (m, 2H).

Step 2: Benzyl 3-(diethoxymethyl)-4-oxospiro[chroman-2,4'-piperidine]-1'-carboxylate

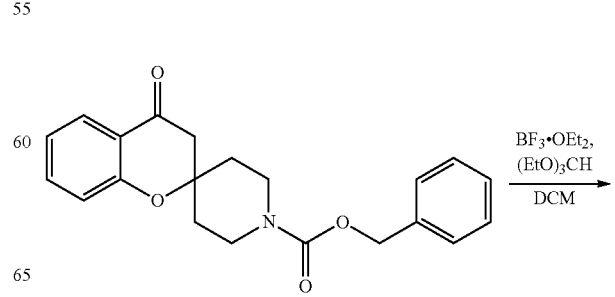

-continued

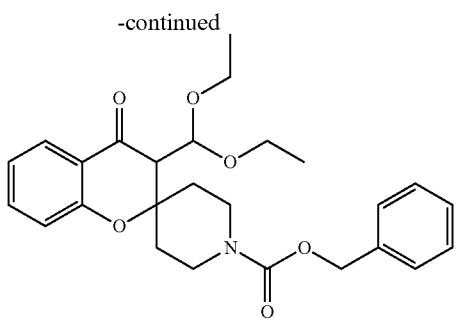

To a solution of triethyl orthoformate (71 mL, 0.43 mol)] in dichloromethane (250 mL) at −10° C. under nitrogen was added boron trifluoride diethyletherate (54 mL, 0.43 mol) dropwise over 30 minutes. The mixture was allowed to warm to 0° C. and stirring was continued at 0° C. for 15 minutes. The mixture was then cooled to −78° C. and a solution of benzyl 4-oxospiro[chroman-2,4'-piperidine]-1'-carboxylate (50 g, 0.14 mol) in dichloromethane (250 mL) was added dropwise over 1 hour, followed by N-ethyl-N-isopropylpropan-2-amine (87 mL, 0.50 mol) over 1 hour at −78° C. The mixture was continued to stir at −78° C. for 30 minutes and then at 25° C. for 15 hours. The reaction mixture was diluted with dichloromethane (750 mL) and then partitioned with saturated sodium bicarbonate solution (500 mL). The organic phase was washed with water (500 mL), saturated sodium chloride solution (500 mL), dried over magnesium sulfate and concentrated under reduced pressure. Purification by silica gel flash chromatography (0-50% ethyl acetate in hexane) afforded benzyl 3-(diethoxymethyl)-4-oxospiro[chroman-2,4'-piperidine]-1'-carboxylate (50 g, 78%) as a yellow oil. ESI-MS m/z calc. 453.2. found 408.5 (M+1-OEt)$^+$; Retention time: 2.08 minutes (3 min run).

Step 3: Benzyl 3-(hydroxymethylene)-4-oxospiro[chroman-2,4'-piperidine]-1'-carboxylate

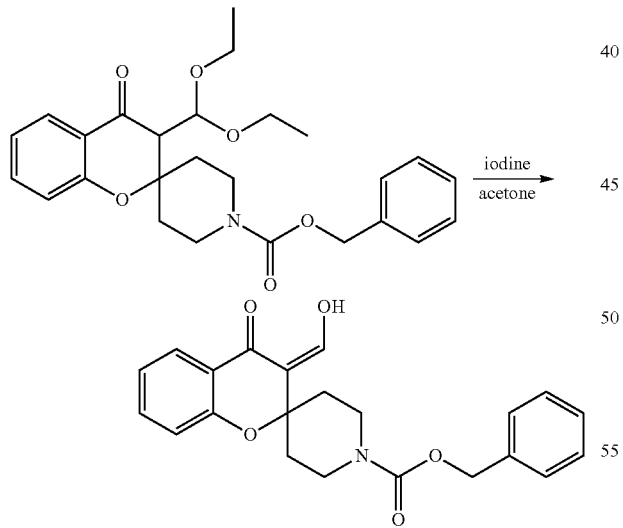

Iodine (2.88 g, 11.4 mmol) was slowly added to a solution of benzyl 3-(diethoxymethyl)-4-oxospiro[chroman-2,4'-piperidine]-1'-carboxylate (20.6 g, 45.4 mmol) in acetone (515 mL) and the mixture was stirred at 35° C. overnight. The reaction mixture was concentrated and the residue was purified by silica gel column chromatography (0-40% ethyl acetate in hexane) to afford benzyl 3-(hydroxymethylene)-4-oxospiro[chroman-2,4'-piperidine]-1'-carboxylate (15.2 g, 88%). ESI-MS m/z calc. 379.1. found 380.3 (M+1)$^+$; Retention time: 2.00 minutes (3 min run).

Step 4: Benzyl 1H-spiro[chromeno[4,3-c]pyrazole-4,4'-piperidine]-1'-carboxylate

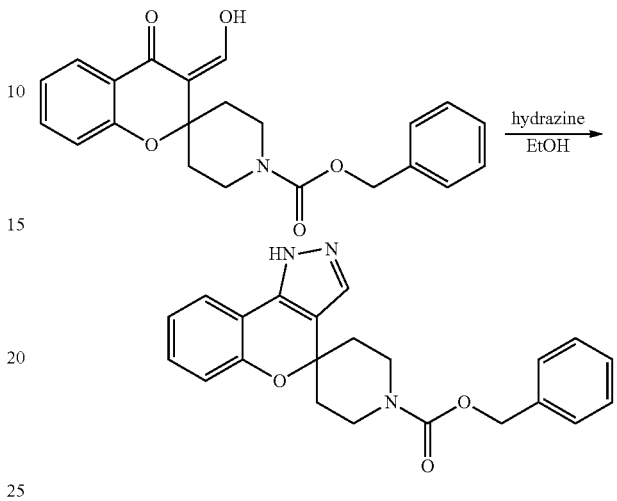

A solution of benzyl 3-(hydroxymethylene)-4-oxo-spiro[chromane-2,4'-piperidine]-1'-carboxylate (1.95 g, 5.10 mmol) and hydrazine (161 µL, 5.10 mmol) in EtOH (39 mL) was stirred at room temperature for 1 hour and then at 50° C. for 3 hours. The reaction mixture was concentrated and the residue was purified by silica gel chromatography (10-100% ethyl acetate in hexane) to afford benzyl 1H-spiro[chromeno-[4,3-c]pyrazole-4,4'-piperidine]-1'-carboxylate (1.11 g, 58%). ESI-MS m/z calc. 375.2. found 376.3 (M+1)$^+$; Retention time: 1.71 minutes (3 min run).

Step 5: 1H-Spiro[chromeno[4,3-c]pyrazole-4,4'-piperidine]

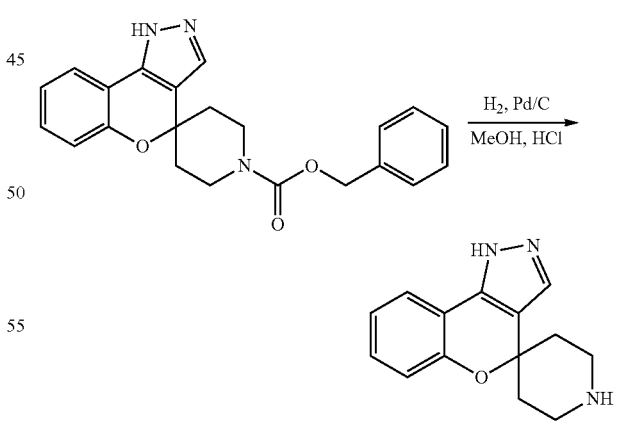

A mixture of benzyl spiro[1H-chromeno[4,3-c]pyrazole-4,4'-piperidine]-1'-carboxylate (1.11 g, 2.96 mmol) and palladium (10% wt on carbon, 157 mg, 0.15 mmol) in MeOH (15 mL) was set under hydrogen (1 atm) and stirred vigorously at room temperature for 3 hours. The reaction mixture was filtered through Celite and the filtrate was concentrated to afford 1H-spiro[chromeno[4,3-c]pyrazole-4,4'-piperidine]

(570 mg, 80%). ESI-MS m/z calc. 241.1. found 242.5 (M+1)⁺; Retention time: 0.42 minutes (3 min run).

1-(2-Methoxyethyl)-1H-spiro[chromeno[4,3-c]pyrazole-4,4'-piperidine]hydrochloride Step 1: tert-Butyl 3-(hydroxymethylene)-4-oxospiro[chroman-2,4'-piperidine]-1'-carboxylate

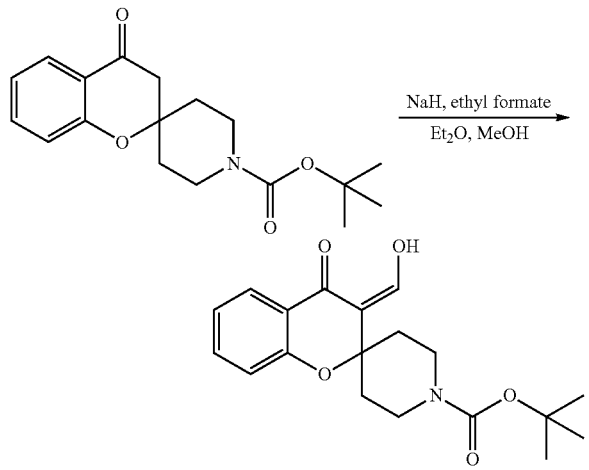

NaH (1.89 g, 47.3 mmol) was added in small portions to a mixture of tert-butyl 4-oxospiro[chroman-2,4'-piperidine]-1'-carboxylate (3.0 g, 9.5 mmol), Et₂O (75 mL), and MeOH (120 µL) at rt. The mixture was allowed to stir for 1 h before ethyl formate (9.2 mL, 110 mmol) was added dropwise. The mixture was allowed to stir at 25° C. overnight before it was quenched with 1M aqueous HCl. The layers were separated and the aqueous layer was extracted with ethyl acetate (3×). The combined organics were washed with brine, dried over sodium sulfate, and concentrated in vacuo. Column chromatography (0-100% ethyl acetate in hexanes) provided tert-butyl 3-(hydroxymethylene)-4-oxospiro[chroman-2,4'-piperidine]-1'-carboxylate (1.2 g, 36%) as a light yellow solid. ESI-MS m/z calc. 345.2. found 246.2 (M+1-Boc)⁺; Retention time: 2.62 minutes (4 min run). ¹H NMR (400 MHz, CDCl₃) δ 15.13 (d, J=8.3 Hz, 1H), 7.93 (d, J=8.1 Hz, 1H), 7.88 (dd, J=7.8, 1.5 Hz, 1H), 7.50-7.44 (m, 1H), 7.06 (t, J=7.5 Hz, 1H), 6.96 (d, J=8.2 Hz, 1H), 4.10-3.95 (m, 2H), 3.25-3.15 (m 2H), 2.15 (d, J=12.7 Hz, 2H), 1.80-1.66 (m, 2H), 1.47 (s, 9H).

Step 2: 1-(2-Methoxyethyl)-1H-spiro[chromeno[4,3-c]pyrazole-4,4'-piperidine]hydrochloride

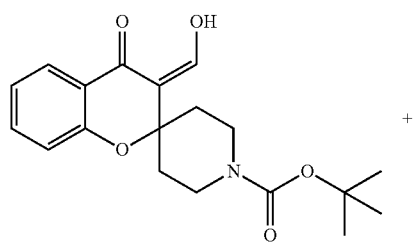

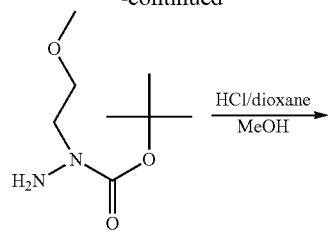

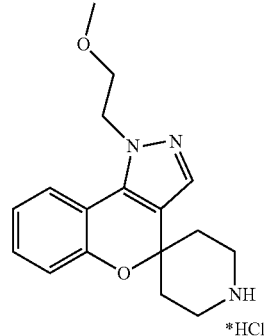

A mixture of tert-butyl 3-(hydroxymethylene)-4-oxospiro[chroman-2,4'-piperidine]-1'-carboxylate (200 mg, 0.58 mmol) and tert-butyl N-amino-N-(2-methoxyethyl)carbamate (130 mg, 0.70 mmol) in ethanol (5 mL) was allowed to stir at rt for 2 h. A solution of hydrogen chloride in 1,4-dioxane (150 µL of 4.0 M, 0.60 mmol) was added and the mixture was stirred at 50° C. for 1.5 h before it was concentrated in vacuo to give 1-(2-methoxyethyl)-1H-spiro[chromeno[4,3-c]pyrazole-4,4'-piperidine]hydrochloride (85 mg, 44%). ESI-MS m/z calc. 299.2. found 300.3 (M+1)⁺; Retention time: 0.95 minutes (3 min run).

1-(2,2,2-Trifluoroethyl)-1H-spiro[chromeno[4,3-c]pyrazole-4,4'-piperidine] and 2-(2,2,2-trifluoroethyl)-2H-spiro[chromeno[4,3-c]pyrazole-4,4'-piperidine]

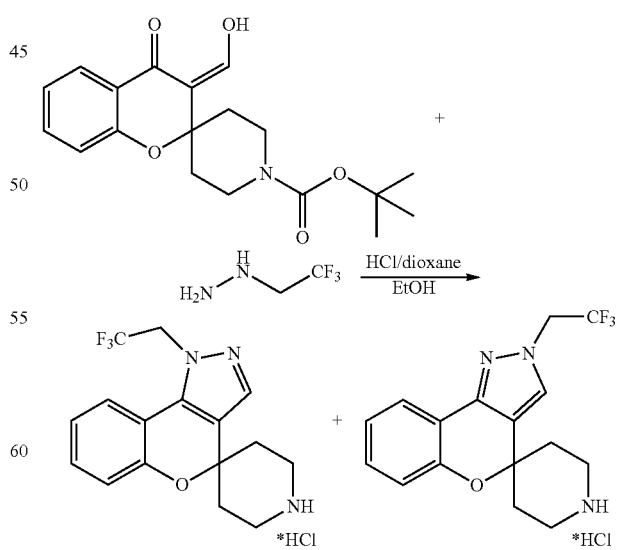

A mixture of tert-butyl 3-(hydroxymethylene)-4-oxospiro[chroman-2,4'-piperidine]-1'-carboxylate (100 mg, 0.29 mmol) and 2,2,2-trifluoroethylhydrazine (57 mg, 0.35 mmol) in ethanol (2.5 mL) was allowed to stir at 25° C. for 2 h. A solution of hydrogen chloride in 1,4-dioxane (72 µL of 4.0 M, 0.29 mmol) was added and the mixture was stirred at 50° C. for 1.5 h before it was concentrated in vacuo to give a mixture of 1-(2,2,2-trifluoroethyl)-1H-spiro[chromeno[4,3-c]pyrazole-4,4'-piperidine] and 2-(2,2,2-trifluoroethyl)-2H-spiro[chromeno[4,3-c]pyrazole-4,4'-piperidine] (60 mg, 58%). ESI-MS m/z calc. 323.1. found 324.2 (M+1)$^+$; Retention time: 1.11 minutes (3 min run).

(4-tert-Butyl-3-methoxyphenyl)(1-methyl-1H-spiro[chromeno[4,3-c]pyrazole-4,4'-piperidine]-1'-yl)methanone and (4-tert-butyl-3-methoxyphenyl)(2-methyl-2H-spiro[chromeno[4,3-c]pyrazole-4,4'-piperidine]-1'-yl)methanone Step 1:
1-(4-tert-Butyl-3-methoxybenzoyl)piperidin-4-one

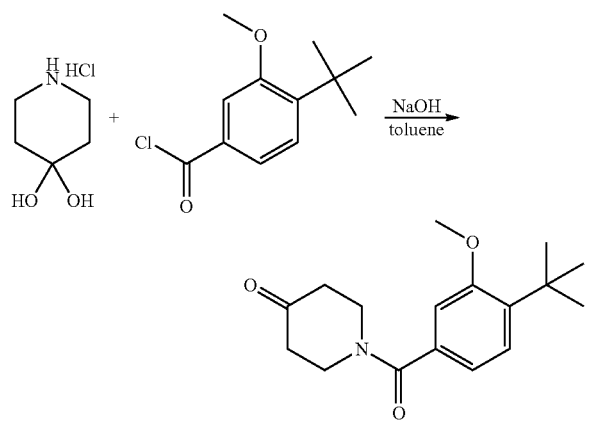

A solution of 4-tert-butyl-3-methoxybenzoyl chloride (650 mg, 4.2 mmol) in toluene (4.4 mL) and a solution of NaOH (1.1 mL of 4.0 M, 4.4 mmol) were contemporaneously added dropwise to a solution of 4-tert-butyl-3-methoxybenzoyl chloride (960 mg, 4.2 mmol) in NaOH (2.1 mL of 2.0 M, 4.2 mmol) at 25° C. The mixture was stirred for 90 min before the toluene was removed in vacuo. The alkaline phase was extracted with dichloromethane (3×). The organics were combined, washed with brine, dried over sodium sulfate, and concentrated in vacuo to provide 1-(4-tert-butyl-3-methoxybenzoyl)-piperidin-4-one (1.2 g, 94%). ESI-MS m/z calc. 289.2. found 290.3 (M+1)$^+$; Retention time: 1.60 minutes (3 min run).

Step 2: 1'-(4-tert-Butyl-3-methoxybenzoyl)spiro[chroman-2,4'-piperidin]-4-one

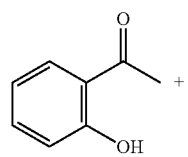 +

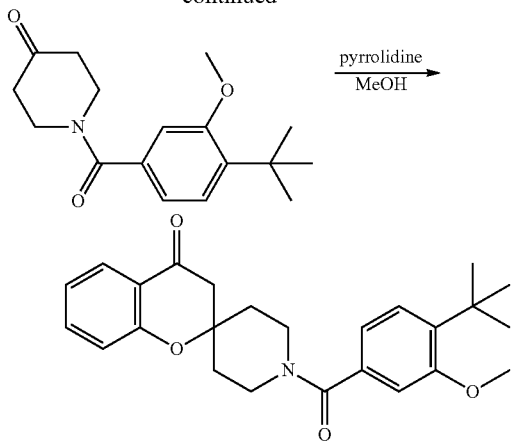

1-(2-Hydroxyphenyl)ethanone (260 µL, 2.2 mmol) was added portion-wise at room temperature to pyrrolidine (370 µL, 4.4 mmol) followed by portion-wise addition of 1-(4-tert-butyl-3-methoxy-benzoyl)piperidin-4-one (630 mg, 2.2 mmol). Anhydrous methanol (140 µL) was added and the slurry was heated at 80° C. for 3 h. The mixture was then partitioned between ethyl acetate and 1M aqueous HCl. The layers were separated and the aqueous layer was discarded. Saturated aqueous sodium bicarbonate was added and the layers were separated. The organic layer was washed with brine, dried over sodium sulfate, and concentrated under reduced pressure. The residue was purified by column chromatography (0-25% ethyl acetate/hexanes) to give 1'-(4-tert-butyl-3-methoxybenzoyl)spiro[chroman-2,4'-piperidin]-4-one (840 mg, 94%) as a light yellow solid. ESI-MS m/z calc. 407.2. found 408.2 (M+1)$^+$; Retention time: 2.07 minutes (3 min run).

Step 3: 1'-(4-tert-Butyl-3-methoxybenzoyl)-3-(hydroxymethylene)-spiro[chroman-2,4'-piperidin]-4-one

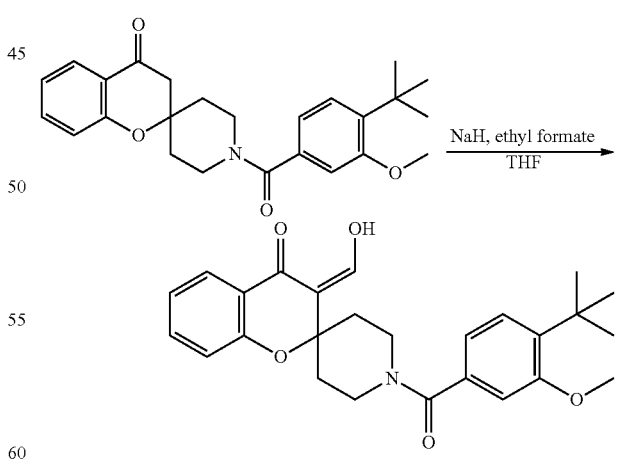

NaH (57 mg, 1.4 mmol) was added in small portions to a mixture of 1'-(4-tert-butyl-3-methoxy-benzoyl)spiro[chromane-2,4'-piperidin]-4-one (250 mg, 0.61 mmol) in THF (2.5 mL) at 25° C. A solution of ethyl formate (74 µL, 0.90 mmol) in THF (0.5 mL) was added and the mixture was allowed to stir at 25° C. for 3 h before it was quenched with 0.5M aqueous HCl. The layers were separated and the aqueous layer was extracted with ethyl acetate (3×). The combined organics were washed with brine, dried over sodium sulfate, and concentrated in vacuo to provide 1'-(4-tert-butyl-3-methoxybenzoyl)-3-(hydroxymethylene)spiro[chroman-2,4'-piperidin]-4-one (50 mg, 19%) as an orange oil. ESI-MS m/z calc. 435.2. found 436.2 (M+1)⁺; Retention time: 1.87 minutes (3 min run).

Step 4: (4-tert-Butyl-3-methoxyphenyl)(1-methyl-1H-spiro[chromeno[4,3-c]pyrazole-4,4'-piperidine]-1'-yl)methanone and (4-tert-butyl-3-methoxyphenyl)(2-methyl-2H-spiro[chromeno[4,3-c]pyrazole-4,4'-piperidine]-1'-yl)methanone

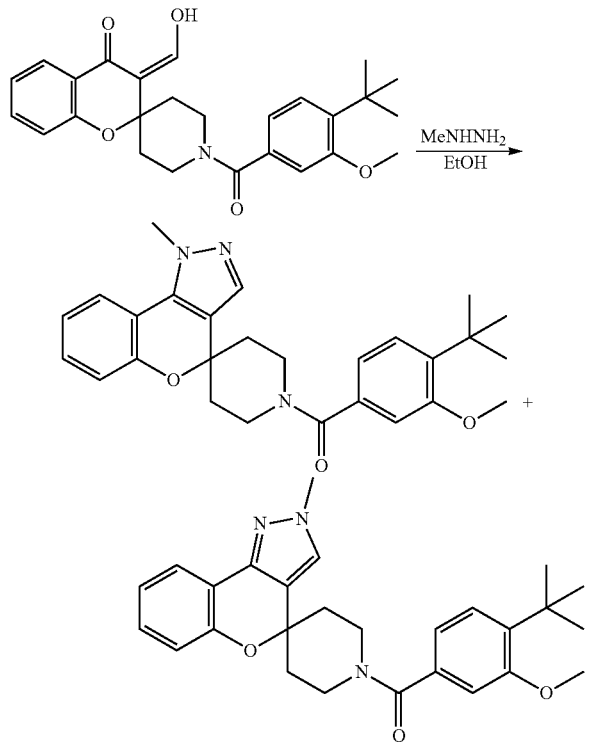

A mixture of 1'-(4-tert-butyl-3-methoxy-benzoyl)-3-(hydroxymethylene)-spiro[chromane-2,4'-piperidine]-4-one (50 mg, 0.12 mmol) and methylhydrazine (6.7 µL, 0.13 mmol) in ethanol (1.6 mL) was allowed to stir at 25° C. for 3 h. The mixture was filtered and then purified by reverse phase HPLC to provide (4-tert-butyl-3-methoxy-phenyl)-(2-methylspiro[chromeno[4,3-c]pyrazole-4,4'-piperidine]-1'-yl)methanone (8 mg, 15%) (peak 1) and (4-tert-butyl-3-methoxy-phenyl)-(1-methylspiro[chromeno[4,3-c]pyrazole-4,4'-piperidine]-1'-yl)methanone (peak 2). (4-tert-Butyl-3-methoxy-phenyl)-(2-methylspiro[chromeno[4,3-c]pyrazole-4,4'-piperidine]-1'-yl)methanone: ESI-MS m/z calc. 445.2. found 446.3 (M+1)⁺; Retention time: 1.87 minutes (3 min run). ¹H NMR (400 MHz, CDCl₃) δ 7.56 (s, 1H), 7.33 (t, J=7.5 Hz, 1H), 7.2-7.20 (m, 1H), 7.17-7.10 (m, 1H), 7.06-6.94 (m, 2H), 6.93-6.83 (m, 2H), 4.25-4.05 (m, 1H), 4.02-3.93 (m, 1H), 3.85-3.75 (m, 1H), 3.79 (s, 3H), 3.63 (s, 3H), 3.55-3.40 (m, 1H), 2.37-2.18 (m, 2H), 1.35 (s, 9H), 1.30-1.15 (m, 2H). (4-tert-Butyl-3-methoxy-phenyl)-(1-methylspiro-[chromeno[4,3-c]pyrazole-4,4'-piperidine]-1'-yl)methanone: ESI-MS m/z calc. 445.2. found 446.3 (M+1)⁺; Retention time: 2.10 minutes (3 min run). ¹H NMR (400 MHz, CDCl₃) δ 7.50 (d, J=7.5 Hz, 1H), 7.32-7.25 (m, 2H), 7.18 (t, J=7.7 Hz, 1H), 7.08-6.88 (m, 3H), 6.84 (t, J=7.5 Hz, 1H), 4.43-4.32 (m, 1H), 4.20-4.05 (m, 1H), 3.93 (s, 3H), 3.84 (s, 3H), 3.76-3.55 (m, 2H), 2.26-2.25 (m, 2H), 1.80-1.50 (m, 2H), 1.36 (s, 9H).

(4-Methoxy-3-(trifluoromethyl)phenyl)(1-methyl-1H-spiro[chromeno[4,3-c]pyrazole-4,4'-piperidine]-1'-yl)methanone Step 1: 1-(4-Methoxy-3-(trifluoromethyl)benzoyl)piperidin-4-one

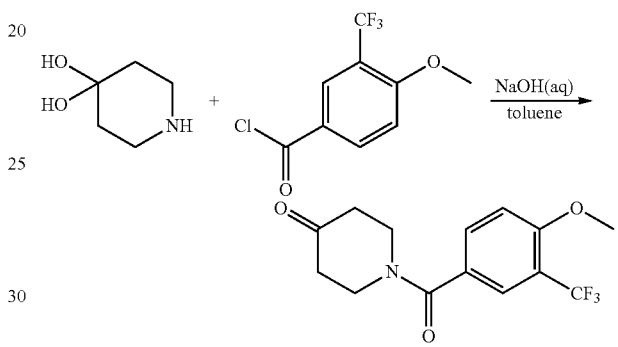

A solution of 4-methoxy-3-(trifluoromethyl)benzoyl chloride (4.00 g, 16.8 mmol) in toluene (16 mL) and a solution of NaOH (3.8 mL of 4.0 M, 15 mmol) were contemporaneously added drop-wise to a solution of piperidine-4,4-diol hydrochloride (2.30 g, 15.2 mmol) in NaOH (7.6 mL of 2.0 M, 15 mmol) at 25° C. The mixture was stirred for 90 min before the toluene was removed in vacuo. The alkaline phase was extracted with dichloromethane (3 times). The organics were combined, washed with brine, dried over Na₂SO₄, and concentrated in vacuo to provide 1-(4-methoxy-3-(trifluoromethyl)benzoyl)piperidin-4-one (4.2 g, 91%). ESI-MS m/z calc. 301.3. found 302.2 (M+1)⁺. Retention time: 0.95 minutes (3 min run). ¹H NMR (400 MHz, CDCl₃) δ 7.77 (d, J=1.9 Hz, 1H), 7.70 (dd, J=8.6, 2.1 Hz, 1H), 7.09 (d, J=8.6 Hz, 1H), 3.98 (s, 3H), 3.94 (s, 4H), 2.55 (s, 4H).

Step 2: 1'-(4-Methoxy-3-(trifluoromethyl)benzoyl)spiro[chroman-2,4'-piperidin]-4-one

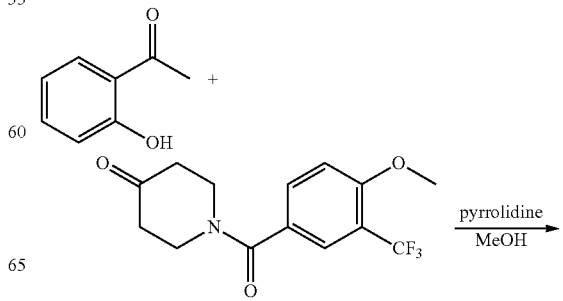

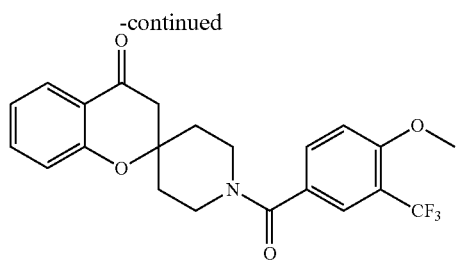

1-(2-Hydroxyphenyl)ethanone (1.80 g, 13.3 mmol) was added portion wise at 25° C. to pyrrolidine (2.20 mL, 26.6 mmol) followed by portion-wise addition of 1-(4-methoxy-3-(trifluoromethyl)benzoyl)piperidin-4-one (4.00 g, 13.3 mmol). Anhydrous methanol (868 µL) was then added and the red slurry was heated at 80° C. for 3 hours. The reaction was cooled to 25° C. and was stirred overnight. Ethyl acetate (5 mL) and 1M HCl (aq, 5 mL) were added. The aqueous layer was separated and discarded. 1M NaOH (aq, 5 mL) was added and the aqueous layer was separated and discarded. A brine solution was added (10 mL) and the aqueous layer was separated and discarded. The organic layer was dried over Na$_2$SO$_4$, filtered and the solvent was evaporated to provide an oil. The crude oil was dissolved in dichloromethane and was purified by column chromatography using 0-50% ethyl acetate/hexanes to provide 1'-(4-methoxy-3-(trifluoromethyl)benzoyl)spiro[chroman-2,4'-piperidin]-4-one (4.4 g, 79%) as a off-white solid. ESI-MS m/z calc. 419.4. found 420.2 (M+1)$^+$. Retention time: 2.63 minutes (4 min run).

Step 3: (Z)-3-(Hydroxymethylene)-1'-(4-methoxy-3-(trifluoromethyl)benzoyl)spiro[chroman-2,4'-piperidin]-4-one

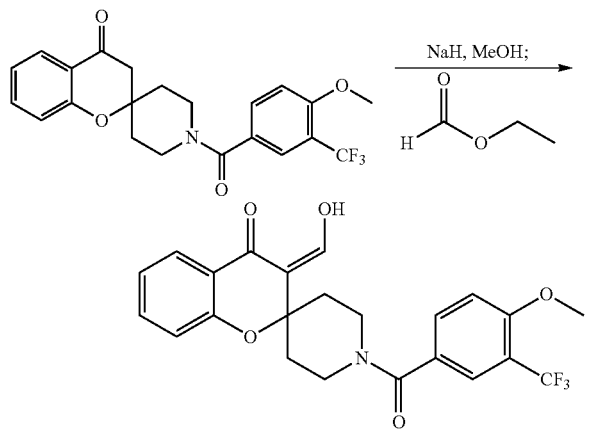

NaH (120 mg, 3.0 mmol) was added to a mixture of 1'-(4-methoxy-3-(trifluoromethyl)benzoyl)spiro[chroman-2,4'-piperidin]-4-one (250 mg, 0.60 mmol) in diethyl ether (6.2 mL) at 0° C. MeOH (0.01 mL) was added and the mixture was allowed to warm to 25° C. over 1 h. The mixture was cooled to 0° C. before ethyl formate (600 µL, 7.4 mmol) was added slowly. The mixture was allowed to stir at 25° C. overnight. The mixture was slowly partitioned between ethyl acetate and water. The layers were separated and the aqueous layer was extracted with ethyl acetate (twice). The combined organics were washed with brine, dried over sodium sulfate, and concentrated in vacuo to yield a crude mixture containing the desired product that was taken to the next step without further purification. ESI-MS m/z calc. 447.4. found 448.1 (M+1)$^+$. Retention time: 2.38 minutes (4 min run).

Step 4: (4-Methoxy-3-(trifluoromethyl)phenyl)(1-methyl-1H-spiro[chromeno[4,3-c]pyrazole-4,4'-piperidine]-1'-yl)methanone

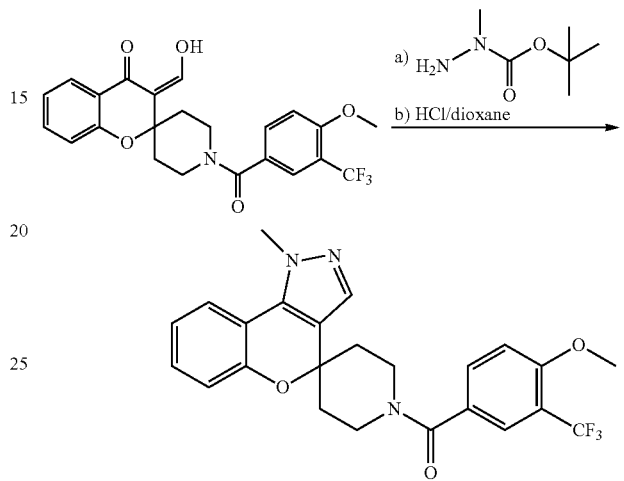

tert-Butyl N-amino-N-methyl-carbamate (21 mg, 0.14 mmol) was added to a mixture of (Z)-3-(hydroxymethylene)-1'-(4-methoxy-3-(trifluoromethyl)benzoyl)spiro[chroman-2,4'-piperidin]-4-one (53 mg, 0.12 mmol) in ethanol (1.6 mL) at 25° C. The mixture was allowed to stir at 25° C. for 2 hours before hydrogen chloride (150 µL of 4.0 M, 0.60 mmol) was added. The mixture was heated at 50° C. for 1 h before it was cooled to 25° C. and concentrated in vacuo. The residue was taken up in DMF and was purified by reverse phase HPLC to give (4-methoxy-3-(trifluoromethyl)phenyl)(1-methyl-1H-spiro[chromeno[4,3-c]pyrazole-4,4'-piperidine]-1'-yl)methanone. ESI-MS m/z calc. 457.2. found 45.8.1 (M+1)$^+$. Retention time: 2.66 minutes (4 min run). $^1$H NMR (400 MHz, CDCl$_3$) δ 7.73 (s, 1H), 7.68 (d, J=8.5 Hz, 1H), 7.62 (d, J=6.8 Hz, 1H), 7.43 (s, 1H), 7.36 (t, J=7.2 Hz, 1H), 7.16-7.03 (m, 3H), 4.30 (s, 3H), 3.97 (s, 3H), 3.51 (s, 2H), 2.73 (s, 2H), 2.16 (s, 2H), 1.92 (s, 2H).

(4-Methoxy-3-(trifluoromethyl)phenyl)(1H-spiro[chromeno[4,3-c]pyrazole-4,4'-piperidine]-1'-yl)methanone

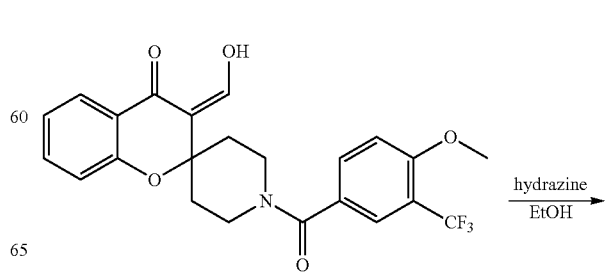

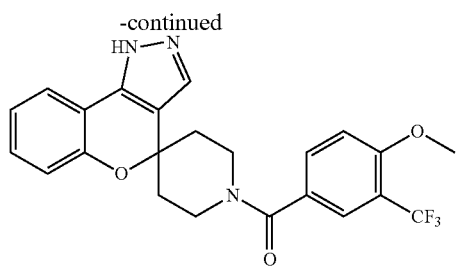

A mixture of 3-(hydroxymethylene)-1'-[4-methoxy-3-(trifluoromethyl)-benzoyl]spiro[chromane-2,4'-piperidine]-4-one (54 mg, 0.12 mmol) and hydrazine (3.8 µL, 0.12 mmol) in ethanol (1.7 mL) was allowed to stir for 1 h at 25° C., then for 2.5 h at 50° C. The mixture was cooled and then concentrated in vacuo. The residue was taken up in DMF and was purified by reverse phase HPLC to give (4-methoxy-3-(trifluoromethyl)phenyl)(1H-spiro[chromeno[4,3-c]pyrazole-4,4'-piperidine]-1'-yl)methanone. ESI-MS m/z calc. 443.2. found 444.1 (M+1)+; Retention time: 2.40 minutes (4 min run). $^1$H NMR (400 MHz, CDCl$_3$) δ 9.15-8.90 (m, 1H), 7.73 (s, 1H), 7.67 (d, J=8.3 Hz, 1H), 7.58 (s, 1H), 7.52 (d, J=7.7 Hz, 1H), 7.33-7.18 (m, 1H), 7.04 (dd, J=18.8, 8.3 Hz, 2H), 6.91 (t, J=7.5 Hz, 1H), 6.05-5.60 (m, 1H), 4.50-4.05 (m, 2H), 4.08-3.55 (m, 3H), 3.97 (s, 3H), 2.50-2.32 (m, 2H).

1-Ethyl-1H-spiro[chromeno[4,3-c]pyrazole-4,4'-piperidine]

Step 1: tert-Butyl 1,3-dioxoisoindolin-2-yl(ethyl)carbamate

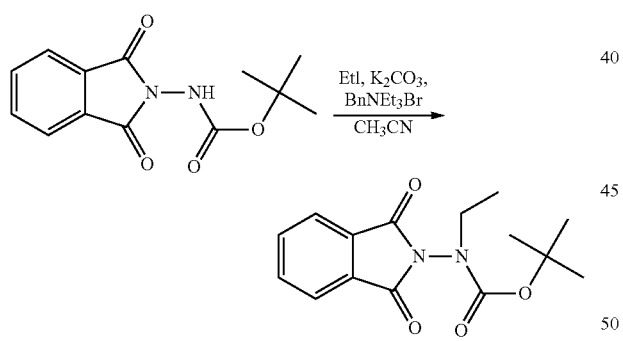

tert-Butyl N-(1,3-dioxoisoindolin-2-yl)carbamate (1.0 g, 3.8 mmol), iodoethane (460 µL, 5.7 mmol), potassium carbonate (2.1 g, 15 mmol), and benzyl-triethyl-ammonium bromide (210 mg, 0.80 mmol) were combined in acetonitrile (15 mL) and heated at 50° C. for 48 h. The reaction mixture was diluted with water (30 mL) and was extracted with ether (3×15 mL). The combined organics were washed with brine, dried over sodium sulfate and evaporated to dryness. The crude material was purified by column chromatography (0-20% ethyl acetate in hexanes) to afford tert-butyl 1,3-dioxoisoindolin-2-yl(ethyl)-carbamate (0.79 g, 71%). ESI-MS m/z calc. 290.1. found 291.3 (M+1)+; Retention time: 1.64 minutes (3 min run). $^1$H NMR (400 MHz, CDCl$_3$) δ 7.98-7.85 (m, 2H), 7.84-7.69 (m, 2H), 3.86-3.57 (m, 2H), 1.52 (s, 3H), 1.32 (s, 6H), 1.27-1.04 (m, 3H).

Step 2: tert-Butyl 1-ethylhydrazinecarboxylate

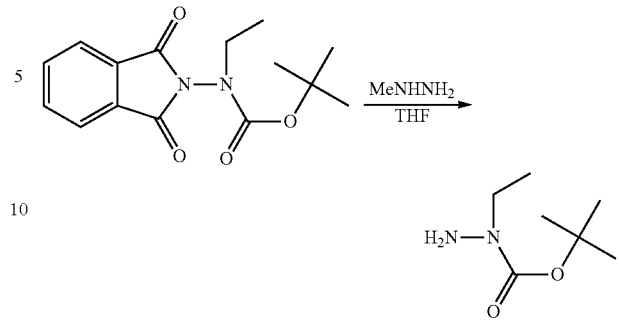

tert-Butyl 1,3-dioxoisoindolin-2-yl(ethyl)-carbamate (790 mg, 2.7 mmol) in THF (16 mL) was cooled to 0° C. and methylhydrazine (250 µL, 4.8 mmol) was added. The reaction mixture was warmed to room temperature and was stirred until all starting material was consumed. The mixture was filtered through a pad of Celite and the solvent was evaporated. The residue was purified by column chromatography (0-10% methanol in dichloromethane) to afford tert-butyl 1-ethylhydrazinecarboxylate (320 mg, 74%). Retention time: 1.13 minutes (3 min run).

Step 3: Benzyl 1-ethyl-1H-spiro[chromeno[4,3-c] pyrazole-4,4'-piperidine]-1'-carboxylate

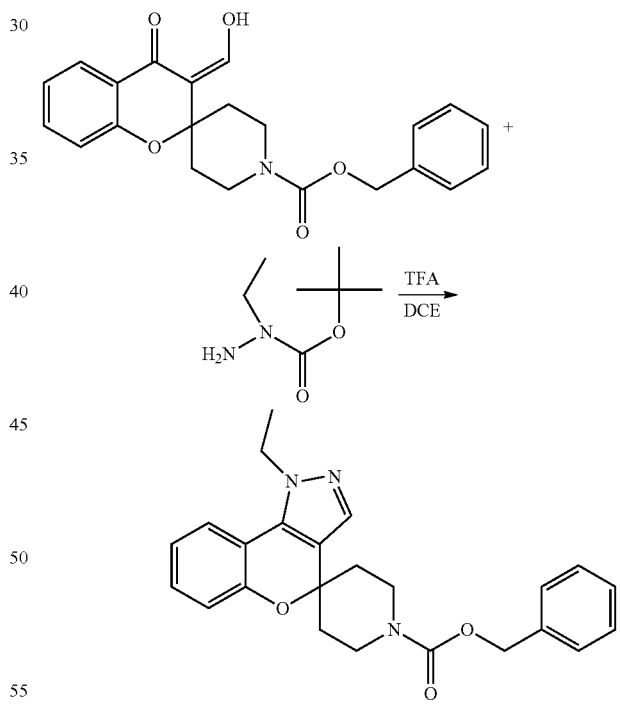

A mixture of tert-butyl 1-ethylhydrazinecarboxylate (320 mg, 2.0 mmol) and benzyl 3-(hydroxymethylene)-4-oxo-spiro[chromane-2,4'-piperidine]-1'-carboxylate (770 mg, 2.0 mmol) in dichloroethane (5 mL) was allowed to stir at 25° C. with TFA (78 µL, 1.0 mmol) for 2 h. Once LC/MS analysis showed complete imine formation, more TFA was added to deprotect the hydrazine and cyclize the product. The reaction was diluted with dichloromethane, and aqueous sodium bicarbonate was added with stirring. The layers were separated and the organics were further washed with saturated aqueous sodium bicarbonate and brine. The organics were dried over sodium sulfate and evaporated to dryness. The crude material was purified by column chromatography (0-100% ethyl acetate in hexanes) to afford benzyl 1-ethyl-1H-spiro[chromeno[4,3-c]pyrazole-4,4'-piperidine]-1'-carboxylate (530 mg, 65%). ESI-MS m/z calc. 403.2. found 404.7 (M+1)$^+$; Retention time: 1.94 minutes (3 min run). $^1$H NMR (400 MHz, CDCl$_3$) δ 7.49 (d, J=7.6 Hz, 1H), 7.40-7.29 (m, 4H), 7.29-7.19 (m, 2H), 7.10-6.99 (m, 2H), 5.16 (s, 2H), 4.47 (q, J=7.3 Hz, 2H), 4.15-3.95 (m, 2H), 3.45-3.26 (m, 2H), 2.15-2.03 (m, 2H), 1.88-1.78 (m 2H), 1.54 (t, J=7.3 Hz, 4H).

Step 4: 1-Ethyl-1H-spiro[chromeno[4,3-c]pyrazole-4,4'-piperidine]

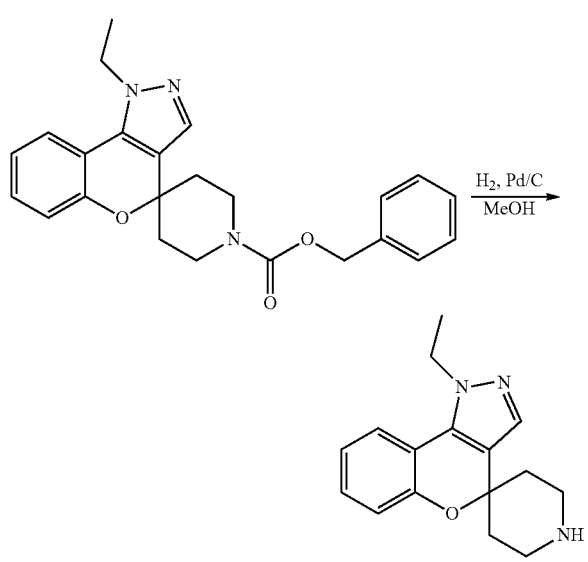

Benzyl 1-ethyl-1H-spiro[chromeno[4,3-c]pyrazole-4,4'-piperidine]-1'-carboxylate (530 mg, 1.3 mmol) was stirred in methanol (9.5 mL) with Pd/C (70 mg, 0.070 mmol) under a balloon of hydrogen for 16 h. The reaction was filtered through a syringe filter and the solvent evaporated to give 1-ethyl-1H-spiro[chromeno[4,3-c]pyrazole-4,4'-piperidine] (350 mg, 99%). ESI-MS m/z calc. 269.2. found 270.5 (M+1)$^+$; Retention time: 0.80 minutes (3 min run).

9-Aza-1-methyl-1H-spiro[chromeno[4,3-c]pyrazole-4,4'-piperidine]

Step 1: 1-(3-Hydroxypyridin-2-yl)ethanone

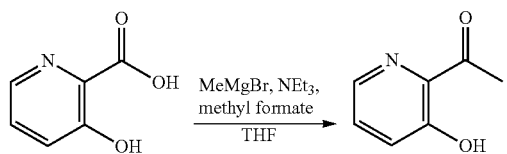

A solution of MeMgBr (390 mL of 1.4 M in toluene/THF (75:25), 540 mmol) was heated at 60° C. and a solution of 3-hydroxypyridine-2-carboxylic acid (15 g, 110 mmol) and triethylamine (15 mL, 110 mmol) in THF (75 mL) was added dropwise over 3 hours. The resulting mixture was then stirred for 2 hours at 60° C. The reaction mixture was cooled on an ice/brine bath and methyl formate (13 mL, 220 mmol) was added keeping the internal temperature below 20° C. The reaction mixture was then acidified to pH 5-6 with 1M aqueous HCl, and the layers were separated, and the aqueous layer was extracted with ethyl acetate (3×). The organic phases were combined, washed with brine, dried over sodium sulfate and evaporated to dryness to afford 1-(3-hydroxypyridin-2-yl)ethanone (4.0 g, 27%). ESI-MS m/z calc. 137.1. found 138.3 (M+1)$^+$; Retention time: 0.62 minutes (3 min run).

Step 2: tert-Butyl 4'-oxo-3',4'-dihydrospiro[piperidine-4,2'-pyrano[3,2-b]pyridine]-1-carboxylate

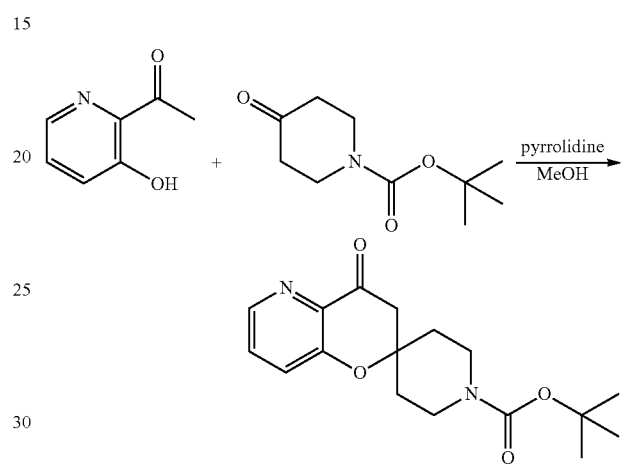

A solution of 1-(3-hydroxy-2-pyridyl)ethanone (2.4 g, 18 mmol), tert-butyl 4-oxopiperidine-1-carboxylate (3.5 g, 18 mmol) and pyrrolidine (1.5 mL, 18 mmol) in MeOH (12 mL) was stirred at 80° C. for 2 hours. After cooling to room temperature 1M aqueous HCl was added until pH 4 was reached and the reaction mixture was stirred for further 30 minutes. Methanol was evaporated, the remaining mixture was poured into water, and the pH adjusted to pH 7 with saturated aqueous sodium carbonate. The aqueous phase was extracted with ethyl acetate (3×), washed with brine (3×), dried over sodium sulfate and evaporated to dryness. Purification by silica gel chromatography (50-100% ethyl acetate in hexane) afforded tert-butyl 4'-oxo-3',4'-dihydrospiro-[piperidine-4,2'-pyrano[3,2-b]pyridine]-1-carboxylate (2.2 g, 40%) as an orange oil that solidified upon standing. ESI-MS m/z calc. 318.2. found 319.3 (M+1)$^+$; Retention time: 1.16 minutes (3 min run).

Step 3: tert-Butyl 3'-(hydroxymethylene)-4'-oxo-3',4'-dihydrospiro-[piperidine-4,2'-pyrano[3,2-b]pyridine]-1-carboxylate

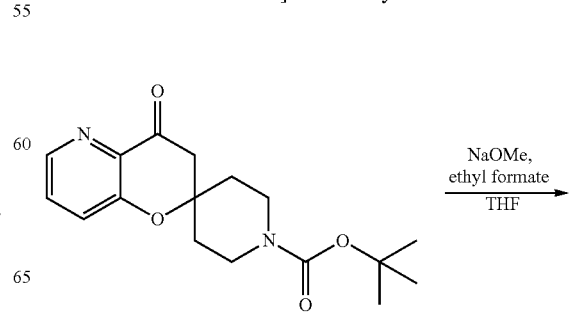

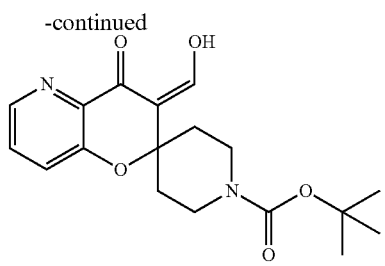

To a suspension of sodium methoxide (594 mg, 11.0 mmol) in THF (5 mL) was added a suspension of tert-butyl 4'-oxo-3',4'-dihydrospiro[piperidine-4,2'-pyrano[3,2-b]pyridine]-1-carboxylate (1.0 g, 3.1 mmol) in THF (10 mL), followed by ethyl formate (2.5 mL, 31 mmol) and the reaction mixture was stirred at 25° C. for 3 hours. Additional sodium methoxide (170 mg, 3.1 mmol) and ethyl formate (0.25 mL, 3.1 mmol) were added and the reaction mixture was stirred at 25° C. for 1 hour. The reaction mixture was poured into water and was extracted with ethyl acetate (4×). The aqueous layer was saturated with solid NaCl and was extracted with ethyl acetate (5×). The organic layers were combined and dried over sodium sulfate. The precipitate formed was filtered and washed with ether (2×). The solid product was dissolved in hot dichloromethane/MeOH (1:1) and filtered, and the filter cake was rinsed with additional hot dichloromethane/MeOH (1:1) (4×) to dissolve all product and remove solid sodium sulfate. The combined filtrates were evaporated to afford tert-butyl 3'-(hydroxymethylene)-4'-oxo-3',4'-dihydrospiro-[piperidine-4,2'-pyrano[3,2-b]pyridine]-1-carboxylate (560 mg, 52%) as a yellow solid. ESI-MS m/z calc. 346.2. found 347.5 (M+1)+; Retention time: 0.98 minutes (3 min run).

Step 4: 9-Aza-1-methyl-1H-spiro[chromeno[4,3-c]pyrazole-4,4'-piperidine]

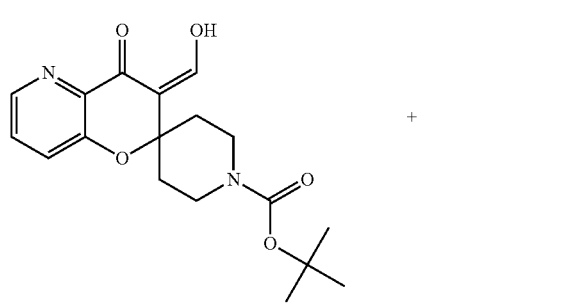

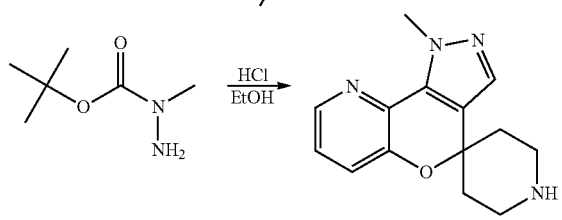

tert-Butyl 3'-(hydroxymethylene)-4'-oxo-3',4'-dihydrospiro-[piperidine-4,2'-pyrano[3,2-b]pyridine]-1-carboxylate (160 mg, 0.46 mmol), tert-butyl N-amino-N-methyl-carbamate (68 mg, 0.46 mmol) and HCl in dioxane (0.64 mL of 4.0 M, 2.5 mmol) in EtOH (1.6 mL) was heated at 50° C. for 3 hours. Another portion of HCl in dioxane (0.64 mL of 4.0 M, 2.5 mmol) was added and the reaction mixture was stirred at 50° C. for 4 hours. The reaction mixture was poured into saturated aqueous sodium carbonate and extracted with 10% MeOH in dichloromethane (3×). The organic phases were combined, dried over sodium sulfate and concentrated to give 9-aza-1-methyl-1H-spiro[chromeno[4,3-c]pyrazole-4,4'-piperidine]. ESI-MS m/z calc. 256.1. found 257.3 (M+1)+; Retention time: 0.64 minutes (3 min run).

2-Methylspiro[chromeno[3,4-d]thiazole-4,4'-piperidine]hydrochloric acid

Step 1: (E)-tert-Butyl 4-(hydroxyimino)spiro[chroman-2,4'-piperidine]-1'-carboxylate

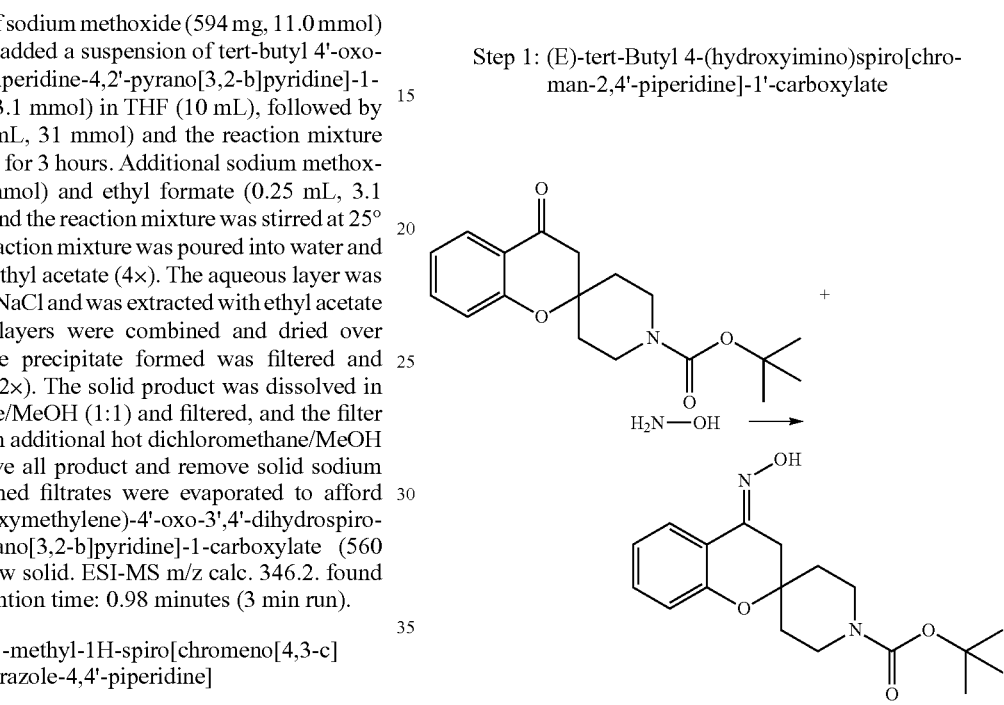

tert-Butyl 4-oxospiro[chroman-2,4'-piperidine]-1'-carboxylate (450 mg, 1.41 mmol) and hydroxylamine 50 wt % in water (940 µL, of 50% w/v, 14 mmol) were combined in methanol (9.0 mL) and heated at reflux. After 24 hours, the reaction mixture was diluted with ethyl acetate and was washed with water. The organics were dried over MgSO4, filtered and evaporated to dryness to yield (E)-tert-butyl 4-(hydroxyimino)spiro[chroman-2,4'-piperidine]-1'-carboxylate (450 mg, 98%). ESI-MS m/z calc. 332.4. found 333.3 (M+1)+; Retention time: 1.68 minutes (3 min run).

Step 2: (E)-tert-Butyl 4-(tosyloxyimino)spiro[chroman-2,4'-piperidine]-1'-carboxylate

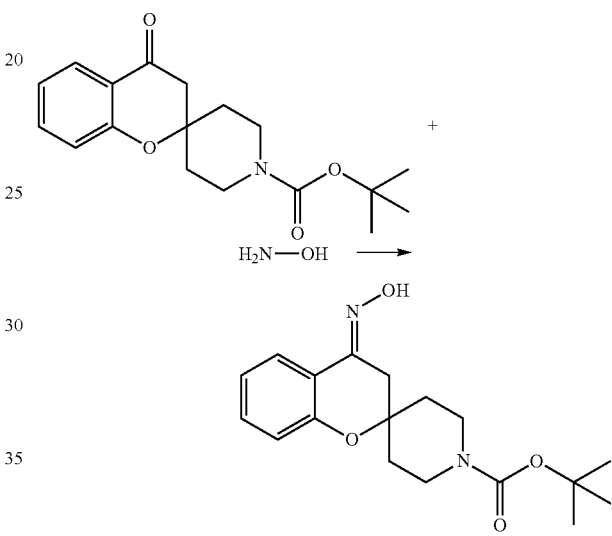

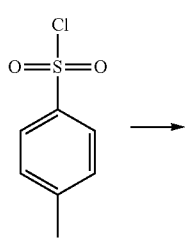

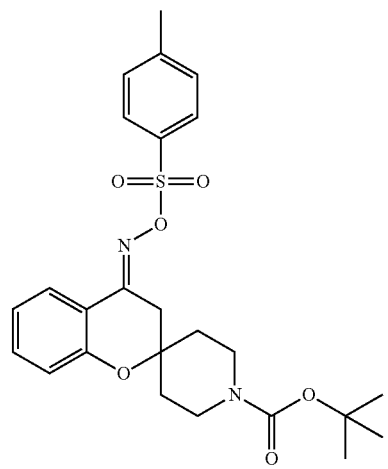

A mixture of tert-butyl (4E)-4-hydroxyiminospiro[chromane-2,4'-piperidine]-1'-carboxylate (448 mg, 1.34 mmol) and 4-methylbenzenesulfonyl chloride (514 mg, 2.70 mmol) were stirred in pyridine (2.1 mL) at 0° C. for 6 hours. The reaction mixture was poured over ice and the mixture was extracted with ethyl acetate. The organics were dried over sodium sulfate and evaporated to give (E)-tert-butyl 4-(tosyloxyimino)spiro[chroman-2,4'-piperidine]-1'-carboxylate (532 mg, 81%). ESI-MS m/z calc. 486.2. found 487.5 (M+1)$^+$; Retention time: 2.20 minutes (3 min run).

Step 3: tert-Butyl 3-amino-4-oxospiro[chroman-2,4'-piperidine]-1'-carboxylate

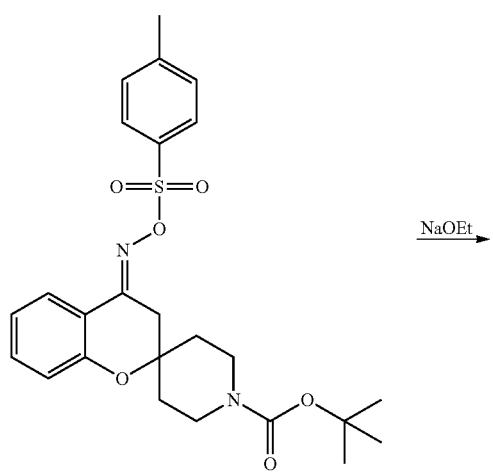

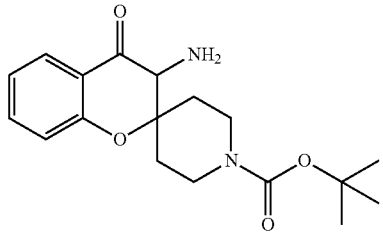

tert-Butyl (4E)-4-(p-tolylsulfonyloxyimino)spiro[chromane-2,4'-piperidine]-1'-carboxylate (3.36 g, 6.90 mmol) was dissolved in toluene (40 mL) and cooled in an ice bath. Sodium ethoxide (2.5 mL of 21% w/v, 7.6 mmol) was added dropwise and the reaction was allowed to warm to room temperature overnight. The reaction was filtered through a pad of Celite. The celite was washed with a 1N HCl solution and the two resulting layers were separated. The aqueous layer was neutralized with 4 M NaOH and was extracted with ethyl acetate. The organics were dried over sodium sulfate and evaporated to yield tert-butyl 3-amino-4-oxospiro[chroman-2,4'-piperidine]-1'-carboxylate (33 mg, 1%). ESI-MS m/z calc. 332.4. found 333.7 (M+1)$^+$; Retention time: 1.14 minutes (3 min run).

Step 4: 2-Methylspiro[chromeno[3,4-d]thiazole-4,4'-piperidine]

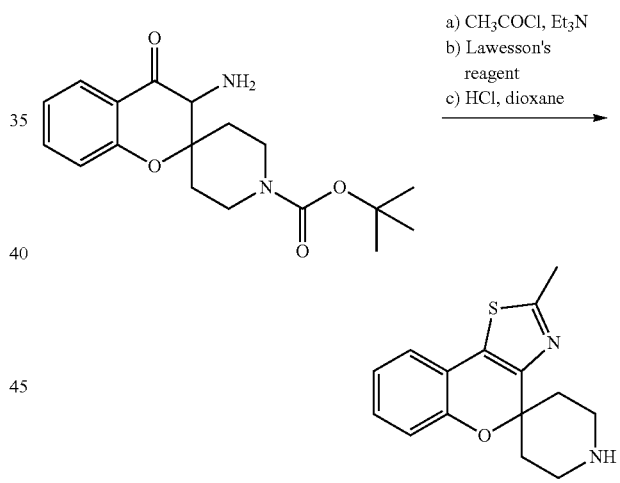

tert-Butyl 3-amino-4-oxo-spiro[chromane-2,4'-piperidine]-1'-carboxylate (33 mg, 0.10 mmol), acetyl chloride (7.8 µL, 0.11 mmol), and N,N-diethylethanamine (28 µL, 0.20 mmol) were combined in dichloromethane and stirred for 30 minutes. The reaction mixture was diluted with dichloromethane and was washed with 1N HCl, a saturated solution of NaHCO$_3$, and brine. The organics were dried over sodium sulfate and evaporated to dryness. The residue was stirred in toluene with Lawesson's reagent (40 mg, 0.10 mmol) at 70° C. overnight. The reaction was diluted with dichloromethane and filtered through a pad of Celite. The filtrate was evaporated and stirred with HCl in dioxane (1.0 mL of 4.0 M, 4.0 mmol) for 1 h at room temperature. The reaction mixture was evaporated to dryness to yield 2-methylspiro[chromeno[3,4-d]thiazole-4,4'-piperidine] (27 mg, 20%). ESI-MS m/z calc. 272.4. found 273.1 (M+1)$^+$; Retention time: 1.05 minutes (3 min run).

1H-spiro[chromeno[4,3-d]imidazole-4,4'-piperidine]

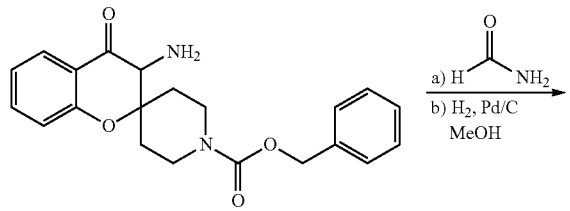

Benzyl 3-amino-4-oxo-spiro[chromane-2,4'-piperidine]-1'-carboxylate (600 mg, 1.64 mmol) was added portion-wise to formamide (3.0 mL, 75 mmol) and the mixture was heated at 180° C. for 2 h. After cooling to room temperature, 3 mL of 1N NaOH was added and the resulting solution was extracted with dichloromethane. The organics were combined and washed with brine, dried over sodium sulfate, and evaporated to dryness. The crude material was filtered through silica gel eluting with 0-10% methanol in dichloromethane. The combined fractions were evaporated, and the residue (400 mg) was dissolved in methanol (5 mL). Pd/C (210 mg, 0.20 mmol) was added and the mixture was stirred under a balloon of hydrogen. The reaction was filtered and the filtrate evaporated to give 1H-spiro[chromeno[4,3-d]imidazole-4,4'-piperidine]. ESI-MS m/z calc. 241.3. found 242.5 (M+1)+; Retention time: 0.27 minutes (3 min run).

1-Methyl-1H-spiro[chromeno[4,3-b]pyrrole-4,4'-piperidine]

Step 1: 2-(1-Methyl-1H-pyrrol-2-yl)phenol

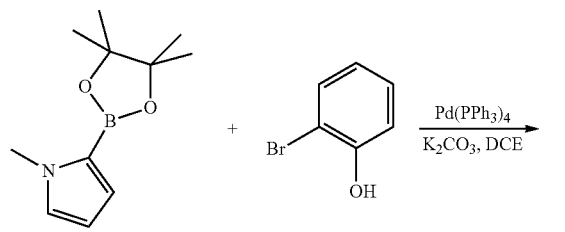

1-Methyl-2-(4,4,5,5-tetramethyl-1,3,2-dioxaborolan-2-yl)pyrrole (5.0 g, 24 mmol), tetrakis(triphenylphosphine)palladium (0) (1.4 g, 1.2 mmol), 2-bromophenol (4.2 g, 24 mmol), and potassium carbonate (24 mL of 2.0 M, 48 mmol) were combined in 1,2-dichloroethane (291 mL). The mixture was heated at 80° C. for 16 h. The mixture was cooled to 25° C. before it was partitioned between ethyl acetate and water. The layers were separated and the organic layer was washed with brine, dried over Na₂SO₄, and concentrated. Column chromatography (0-100% ethyl acetate/hexanes) on the residue gave 2-(1-methylpyrrol-2-yl)phenol (1.4 g, 34%). ESI-MS m/z calc. 173.2. found 174.2 (M+1)+; Retention time: 1.76 minutes (3 min run).

Step 2: 1-Methyl-1H-spiro[chromeno[4,3-b]pyrrole-4,4'-piperidine]

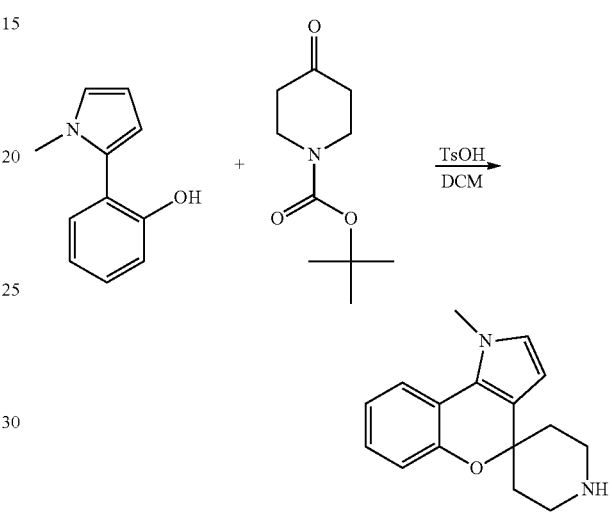

A mixture of 2-(1-methylpyrrol-2-yl)phenol (1.20 g, 6.90 mmol), tert-butyl 4-oxopiperidine-1-carboxylate (1.38 g, 6.93 mmol), 4-methylbenzenesulfonic acid hydrate (264 mg, 1.39 mmol), and dichloroethane (24 mL) was heated at 80° C. for 2 h. To the mixture was added HCl (1.7 mL of 4.0 M, 6.9 mmol) and the mixture was allowed to stir at 50° C. for 1 h. The mixture was cooled to 25° C. and was concentrated in vacuo. The residue was taken up in dichloromethane and was washed with saturated aqueous NaHCO₃. The organic layer was dried over sodium sulfate and concentrated. Column chromatography (0-100% ethyl acetate/hexanes) on the residue gave 1-methyl-1H-spiro[chromeno[4,3-b]pyrrole-4,4'-piperidine]. ESI-MS m/z calc. 254.3. found 255.2 (M+1)+; Retention time: 1.51 minutes (3 min run).

Spiro[piperidine-4,4'-pyrazolo[1,5-d]pyrido[2,3-b][1,4]oxazine]

Step 1: 2-Chloro-3-(1H-pyrazol-1-yl)pyridine

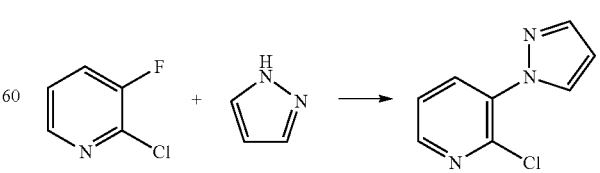

A solution of 2-chloro-3-fluoro-pyridine (1.3 g, 10.0 mmol), 1H-pyrazole (749 mg, 11.0 mmol) and K₂CO₃ (4.1 g, 30.0 mmol) was stirred in DMF (15 mL) at 80° C. for 16 hours. The reaction mixture was poured into water and extracted with EtOAc (3×). The organics were combined, washed with water (3×), brine, dried (Na₂SO₄) and evaporated to dryness. Purification by column chromatography (5 to 30% EtOAc in hexanes) gave the desired product (0.7 g, 40%) as a white solid. ESI-MS m/z calc. 179.3. found 180.3 (M+1)⁺. Retention time: 0.74 minutes (3 min run).

Step 2: tert-Butyl spiro[piperidine-4,4'-pyrazolo[1,5-d]pyrido[2,3-b][1,4]oxazine]-1-carboxylate

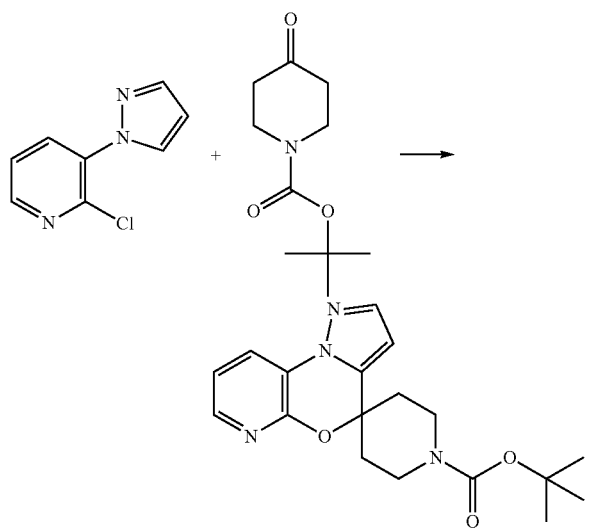

To a solution of 2-chloro-3-pyrazol-1-yl-pyridine (338 mg, 1.88 mmol) in THF (3.4 mL) at −78° C. was added butyl-lithium (979 µL of 2.5 M, 2.45 mmol) dropwise over 5 minutes. The reaction mixture was then stirred at the temperature for 15 minutes before the addition of tert-butyl 4-oxopiperidine-1-carboxylate (562.5 mg, 2.82 mmol). The reaction was allowed to come to 25° C., then heated at 70° C. for 4 hours. The reaction mixture was poured into water, and extracted with EtOAc (3×). The organics were combined, washed with brine, dried (Na₂SO₄) and evaporated to dryness to yield a crude mixture that was purified by column chromatography (5 to 30% EtOAC in hexanes) to give the title product (35 mg, 5%) that was used in the next step without further purification. ESI-MS m/z calc. 342.2. found 343.3 (M+1)⁺. Retention time: 1.46 minutes (3 min run).

Step 3: Spiro[piperidine-4,4'-pyrazolo[1,5-d]pyrido[2,3-b][1,4]oxazine]hydrochloride

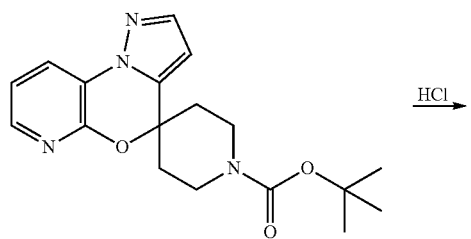

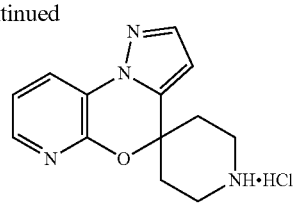

To a solution of tert-butyl spiro[piperidine-4,4'-pyrazolo[1,5-d]pyrido[2,3-b][1,4]oxazine]-1-carboxylate (35 mg, 0.10 mmol) in CH₂Cl₂ (1 mL) and MeOH (0.1 mL) was added HCl in dioxane (256 µL of 4 M, 1.02 mmol) and the mixture was stirred at 40° C. for 4 hours. The reaction mixture was evaporated and the hydrochloric acid salt of the product was used without further purification. ESI-MS m/z calc. 242.1. found 243.5 (M+1)⁺. Retention time: 0.32 minutes (3 min run).

Spiro[benzo[b]pyrrolo[1,2-d][1,4]oxazine-4,4'-piperidine]-1-carbonitrile]

Step 1: tert-Butyl 1-cyanospiro[benzo[b]pyrrolo[1,2-d][1,4]oxazine-4,4'-piperidine]-1'-carboxylate

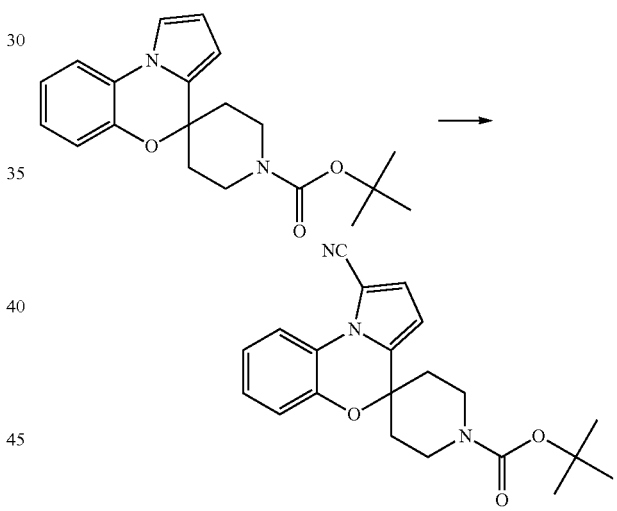

To tert-butyl spiro[piperidine-4,4'-pyrrolo[2,1-c][1,4]benzoxazine]-1-carboxylate (54.6 g, 160.5 mmol) in THF (500 mL) at −75° C. was added chlorosulfonyl isocyanate (17.5 mL, 200.6 mmol) in THF (100 mL) dropwise over a 30 minutes period keeping the temperature below −70° C. and the mixture was stirred at −75° C. for 1 hr. To this mixture was added DMF (37.3 mL, 481.5 mmol) dropwise at −75° C. and the mixture was warmed to ambient temperature, stirring for a total of 2 h. The mixture was quenched with 1 L of 1N NaOH and transferred to a separatory funnel with 500 mL of methyl-tert-butyl ether. The aqueous phase was separated and extracted with an additional 500 mL of methyl-tert-butyl ether. The combined organic phases were washed twice with 500 mL of brine, dried over MgSO₄, filtered and concentrated in vacuo to yield a crude mixture that was purified by column chromatography with a 0-100% EtOAc/hexane gradient to yield tert-butyl 1-cyanospiro[benzo[b]pyrrolo[1,2-d][1,4]oxazine-4,4'-piperidine]-1'-carboxylate (45 g, 76%) as an oil that crystallized upon standing. ESI-MS m/z calc. 365.2. found 266.2 (M-Boc+1)⁺. Retention time: 2.43 minutes (3 min run).

Step 2: tert-Butyl 1-cyanospiro[benzo[b]pyrrolo[1,2-d][1,4]oxazine-4,4'-piperidine]-1'-carboxylate

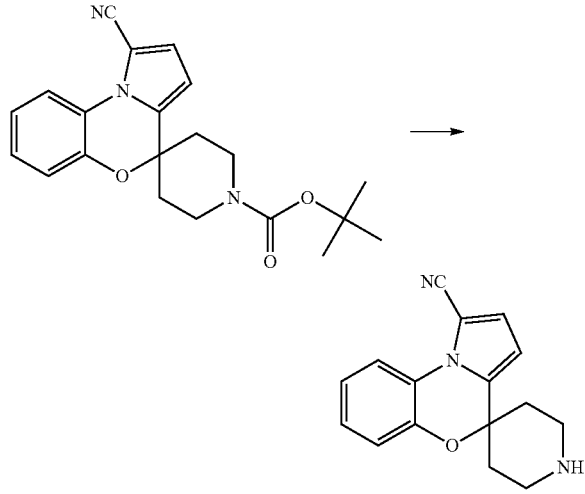

To a mixture of tert-butyl 1'-cyanospiro[piperidine-4,4'-pyrrolo[2,1-c][1,4]benzoxazine]-1-carboxylate (27.0 g, 73.9 mmol) in DCM (200 mL) was added TFA (28.5 mL, 369 mmol). The mixture was stirred at room temperature for 3 h. The solvent was removed in vacuo and the mixture was diluted with 200 mL of MTBE and neutralized with 175 mL of 2N NaOH. The layers were separated and the aqueous phase was extracted with 200 mL of MTBE. The combined organics were washed with brine and were dried over $MgSO_4$, filtered and concentrated in vacuo. The residue solidified upon standing. The solids were slurried with 100 mL of MTBE and 200 mL of hexane. The precipitate was collected on a Buchner funnel to give tert-butyl 1-cyanospiro[benzo[b]pyrrolo[1,2-d][1,4]oxazine-4,4'-piperidine]-1'-carboxylate. ESI-MS m/z calc. 265.1. found 266.2 (M+1)⁺. Retention time: 1.21 minutes (3 min run).

7-Chlorospiro[benzo[b]pyrrolo[1,2-d][1,4]oxazine-4,4'-piperidine]-1-carbonitrile and 7-fluorospiro[benzo[b]pyrrolo[1,2-d][1,4]oxazine-4,4'-piperidine]-1-carbonitrile was also prepared using the procedures described above.

9-Methylspiro[benzo[b]pyrrolo[1,2-d][1,4]oxazine-4,4'-piperidine]

Step 1: 3-Methyl-2-(1H-pyrrol-1-yl)phenol

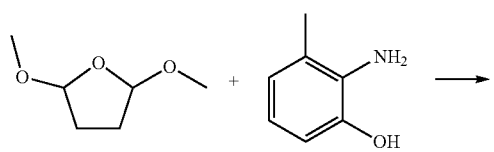

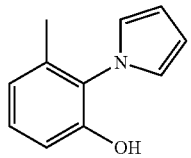

A round bottom flask was charged with 2-amino-3-methylphenol (2.5 g, 20.3 mmol) and acetic acid (37.5 mL) which provided a very dark solution. Stirring was commenced and the vessel was charged with 2,5-dimethoxytetrahydrofuran (2.6 mL, 20.3 mmol) added neat dropwise over a period of 2 minutes. The dark mixture was then heated at 100° C. for 3 h then 80° C. for 12 hours. The solvent was evaporated under vacuum and the crude residue purified by column chromatography using a gradient of 0.5-50% EtOAc in hexanes to yield 3-methyl-2-(1H-pyrrol-1-yl)phenol (2.9 g, 83%). ESI-MS m/z calc. 173.1. found 174.3 (M+1)⁺. Retention time: 1.31 minutes (3 min run).

Step 2: 9-Methylspiro[benzo[b]pyrrolo[1,2-d][1,4]oxazine-4,4'-piperidine]

To a solution of 3-methyl-2-(1H-pyrrol-1-yl)phenol (2.9 g, 16.6 mmol) and tert-butyl 4-oxopiperidine-1-carboxylate (3.6 g, 18.2 mmol) in dry dichloromethane (57.4 mL) was added TFA (2.5 mL, 33.1 mmol) over a 15 minutes period and the reaction was stirred at 25° C. for 12 hours. Another portion of TFA (2.5 mL, 33.1 mmol) was added at 25° C. and the reaction was stirred for 2 hours after which time a third portion of TFA (2.55 mL, 33.1 mmol) was added and the mixture was stirred at 25° C. for an additional 12 hours. The reaction mixture was diluted with $CH_2Cl_2$ (350 ml) and washed with 1M NaOH (50 ml). The organic phase was dried with $MgSO_4$, filtered, evaporated to dryness and the resulting residue was purified by silica gel chromatography eluting with 0.5-40% MeOH in $CH_2Cl_2$ to yield 9-methylspiro[benzo[b]pyrrolo[1,2-d][1,4]oxazine-4,4'-piperidine] (2.0 g, 48%) obtained as a yellow oil. ESI-MS m/z calc. 254.1. found 255.3 (M+1)⁺. Retention time: 1.08 minutes (3 min run).

471

8-Fluoro-1-methyl-1H-spiro[chromeno[4,3-c]pyrazole-4,4'-piperidine]hydrochloride

Step 1: tert-Butyl 6-fluoro-4-oxospiro[chroman-2,4'-piperidine]-1'-carboxylate

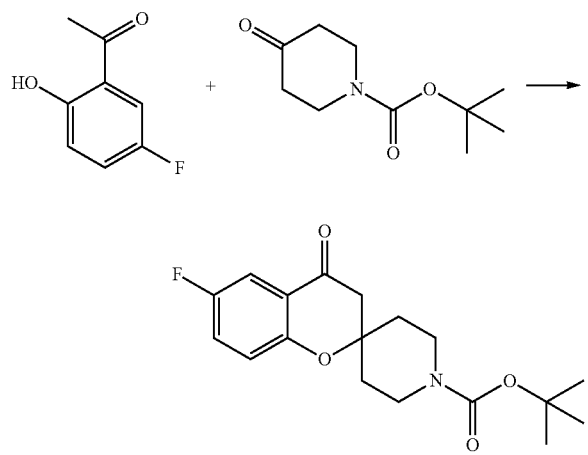

To a solution of tert-butyl 4-oxopiperidine-1-carboxylate (12.1 g, 60.9 mmol) in pyrrolidine (7.3 mL, 87.2 mmol) and anhydrous methanol (16.5 mL) was added 1-(5-fluoro-2-hydroxy-phenyl)ethanone (9.3 g, 60.7 mmol). The reaction mixture was stirred at 80° C. for 2.5 hours. The methanol was removed under reduced pressure and the resulting residue was dissolved in ethyl acetate (150 mL), washed with 1N HCl (1×150 mL) and brine (2×100 mL). The organic layer was dried over sodium sulfate, filtered and concentrated under reduced pressure to yield a yellow oil. The oil was diluted with hexanes (400 mL) and was heated at 60° C. until in solution. Once dissolved, the solution was allowed to cool to 25° C. The crystals were collected via vacuum filtration, rinsed with hexanes to obtain tert-butyl 6-fluoro-4-oxo-spiro[chromane-2,4'-piperidine]-1'-carboxylate (13.6 g, 67%) as a light yellow solid. ESI-MS m/z calc. 335.2. found 336.7 (M+1)$^+$. Retention time 1.85 minutes (3 min run).

Step 2: tert-Butyl 3-(diethoxymethyl)-6-fluoro-4-oxospiro[chroman-2,4'-piperidine]-1'-carboxylate

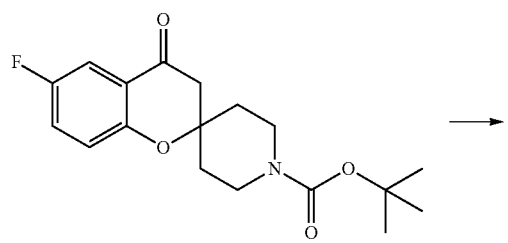

472

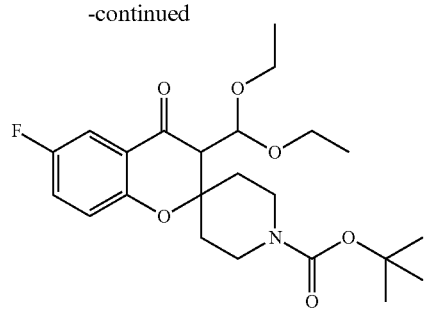

To triethyl orthoformate (20.2 mL, 121.5 mmol) in dry dichloromethane (115 mL) under argon at −10° C. was added drop-wise BF$_3$.OEt$_2$ (15.4 mL, 121.5 mmol). The solution was allowed to warm to 0° C. and was stirred for 10 minutes. After, the solution was cooled to −78° C. prior to the slow drop-wise addition of tert-butyl 6-fluoro-4-oxo-spiro[chromane-2,4'-piperidine]-1'-carboxylate (13.6 g, 40.5 mmol) in dichloromethane (10 mL). iPr$_2$NEt (24.7 mL, 141.7 mmol) was added drop-wise over 30 minutes, and the mixture was slowly warmed to room temperature and was stirred at 25° C. for 2 hours. The reaction mixture was diluted with the addition of dichloromethane (200 mL) followed by saturated aqueous sodium bicarbonate solution (200 mL). The mixture was shaken in a separatory funnel and separated. The organic layer was washed with additional sodium bicarbonate solution (200 mL) and brine (200 mL). The organic layer was dried over sodium sulfate, filtered and concentrated to yield a residue that was purified by silica gel column chromatography (0-25% EtOAc/hexanes gradient) to give tert-butyl 3-(diethoxymethyl)-6-fluoro-4-oxospiro[chroman-2,4'-piperidine]-1'-carboxylate (3.9 g, 22%). ESI-MS m/z calc. 437.2. found 438.7 (M+1)$^+$. Retention time 2.14 minutes (3 min run).

Step 3: 8-Fluoro-1-methyl-1H-spiro[chromeno[4,3-c]pyrazole-4,4'-piperidine]hydrochloride

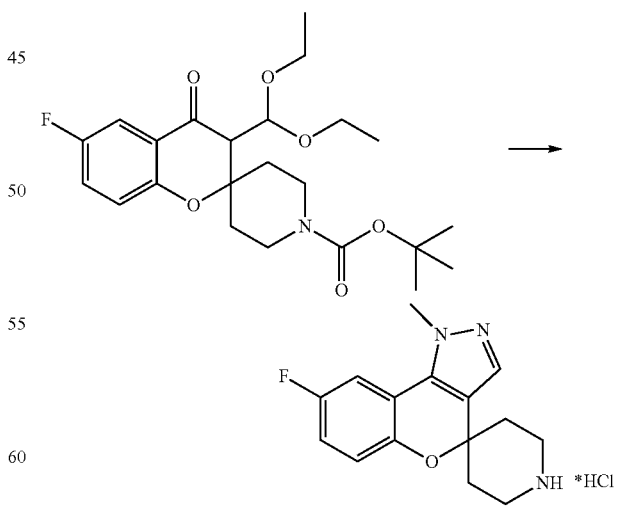

To a solution of tert-butyl 3-(diethoxymethyl)-6-fluoro-4-oxo-spiro[chromane-2,4'-piperidine]-1'-carboxylate (2.6 g, 6.0 mmol) in ethanol (20 mL) was added hydrochloric acid (22.5 mL of 4 M, 89.8 mmol) (4 M in dioxane). The reaction mixture was allowed to stir at 25° C. for 2 hours. The solvent was removed under vacuum, and the obtained solid was azeotroped with ethanol (3×30 mL). The resulting beige-white solid was fully dissolved in ethanol (21 mL) at 25° C. prior to the addition of tert-butyl N-amino-N-methyl-carbamate (1.1 mL, 7.2 mmol). The solution was allowed to stir overnight. To the thick beige-white slurry that formed was added hydrochloric acid (7.5 mL of 4 M, 29.9 mmol) (4 M in dioxane). The mixture was heated at 60° C. to yield a clear yellow solution. After 1 hour at 60° C., a white thick slurry developed. The slurry was allowed to slowly cool to 25° C. over 4 hours, and solids were collected by vacuum filtration. The cake was rinsed with a 10% solution of ethanol in hexanes (2×). Residual solvents were further removed under reduced pressure providing 8-fluoro-1-methyl-spiro[chromeno[4,3-c]pyrazole-4,4'-piperidine]hydrochloride (1.9 g, 92%). $^1$H NMR (400 MHz, DMSO) δ 7.59 (dd, J=9.3, 2.8 Hz, 1H), 7.43 (s, 1H), 7.27-7.10 (m, 2H), 4.12 (s, 3H), 3.28-3.11 (m, 4H), 2.59 (s, 1H), 2.22-2.02 (m, 4H). ESI-MS m/z calc. 273.1. found 274.1 (M+1)+. Retention time 0.84 minutes (3 min run).

1-Ethyl-8-fluoro-1H-spiro[chromeno[4,3-c]pyrazole-4,4'-piperidine]hydrochloride

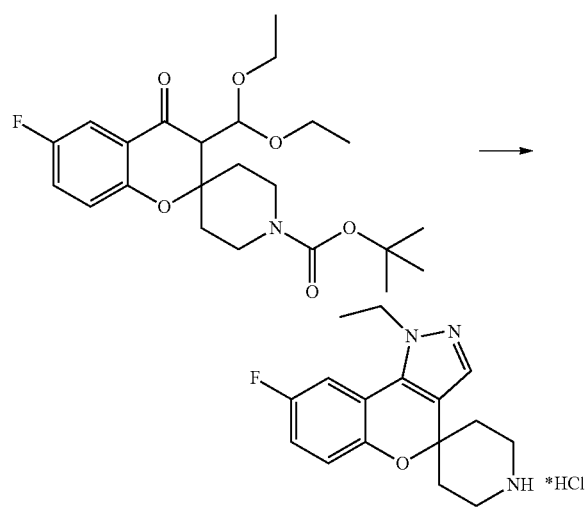

To a solution of tert-butyl 3-(diethoxymethyl)-6-fluoro-4-oxo-spiro[chromane-2,4'-piperidine]-1'-carboxylate (1.3 g, 3.0 mmol) in ethanol (10.4 mL) was added hydrochloric acid (11.1 mL of 4 M, 44.6 mmol) (4 M in dioxane). The reaction mixture was allowed to stir at 25° C. for 2 hours. The solvent was removed under vacuum, and the obtained solid was azeotroped with ethanol (3×30 mL). The resulting beige-white solid was fully dissolved in ethanol (10.40 mL) at 25° C. prior to the addition of tert-butyl N-amino-N-ethyl-carbamate (571.2 mg, 3.6 mmol). The solution was allowed to stir at 25° C. overnight. To the thick beige-white slurry that formed was added hydrochloric acid (3.7 mL of 4 M in dioxane, 14.9 mmol). The mixture was heated at 60° C. to yield a clear yellow solution. After 1 hour at 60° C., a thick white slurry developed. The slurry was allowed to slowly, cool to 25° C. over 4 hours, and solids were collected by vacuum filtration. The cake was rinsed with a 10% solution of EtOH in hexanes (2×). Residual solvent was further removed under reduced pressure providing 1-ethyl-8-fluoro-spiro[chromeno[4,3-c]pyrazole-4,4'-piperidine]hydrochloride (880 mg, 82%). ESI-MS m/z calc. 287.1. found 288.1 (M+1)$^+$. Retention time 0.79 minutes (3 min run). $^1$H NMR (400 MHz, DMSO) δ 7.52 (dd, J=9.4, 2.8 Hz, 1H), 7.47 (s, 1H), 7.26-7.13 (m, 2H), 5.24 (s, 1H), 4.47 (q, J=7.2 Hz, 2H), 3.30-3.12 (m, 4H), 2.18-2.01 (m, 4H), 1.37 (t, J=7.2 Hz, 3H).

8-Fluoro-2-methyl-2H-spiro[chromeno[4,3-c]pyrazole-4,4'-piperidine]hydrochloride

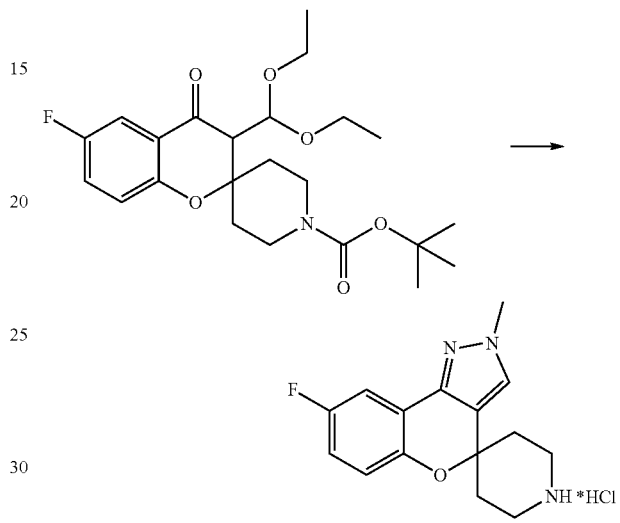

To tert-butyl 3-(diethoxymethyl)-6-fluoro-4-oxo-spiro[chromane-2,4'-piperidine]-1'-carboxylate (3.81 g, 8.71 mmol) was added hydrochloric acid (32.7 mL of 4.0 M in dioxane, 130 mmol). The reaction mixture was allowed to stir at room temperature for 2 hours. The solvent was removed under vacuum, and the obtained solid was azeotroped with EtOH (1×30 mL). The resulting solid was suspended in EtOH (30.5 mL) and was treated with methylhydrazine (556 μL, 10.5 mmol) at 40° C. for 4 h. The mixture was then heated at 80° C. for 1 h resulting in a yellow solution with an off white precipitate. The solid was collected to give 8-fluoro-2-methyl-2H-spiro[chromeno[4,3-c]pyrazole-4,4'-piperidine]hydrochloride (798 mg, 26%). ESI-MS m/z calc. 273.1. found 274.5 (M+1)$^+$. Retention time 0.83 minutes (3 min run). Note: The yellow mother liquor was evaporated to give a mixture of methyl regioisomers (1.71 g).

Spiro[benzo[b]imidazo[1,2-d][1,4]oxazine-4,4'-piperidine]dihydrochloride

Step 1: 1-(2-Fluorophenyl)-1H-imidazole

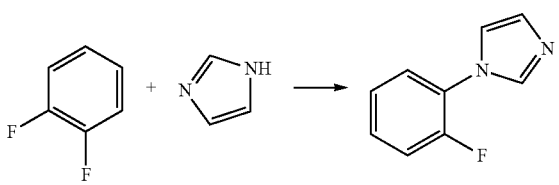 [SMILES: Fc1ccccc1F ; c1c[nH]cn1 ; Fc1ccccc1-n1ccnc1]

1,2-Difluorobenzene (25 mL, 254.0 mmol), imidazole (15.6 g, 228.6 mmol), and potassium carbonate (70.2 g, 508.0 mmol) were suspended in dimethyl sulfoxide (15 mL). The reaction mixture was heated at 110° C. for 72 hours. The reaction mixture was then partitioned between ethyl acetate and was water and washed several times with a saturated aqueous solution of ammonium chloride to remove a small amount of di-imidazole material. The organic layer was then dried over sodium sulfate and evaporated to dryness to yield 1-(2-fluorophenyl)imidazole (430 mg, 1%) that was used without further purification. ESI-MS m/z calc. 162.1. found 163.3 (M+1)⁺. Retention time 0.26 minutes (3 min run). ¹H NMR (400 MHz, DMSO) δ 8.04 (s, 1H), 7.69-7.62 (m, 1H), 7.57 (s, 1H), 7.54-7.45 (m, 2H), 7.41-7.33 (m, 1H), 7.13 (s, 1H).

Step 2: tert-Butyl 4-(1-(2-fluorophenyl)-1H-imidazol-2-yl)-4-hydroxypiperidine-1-carboxylate

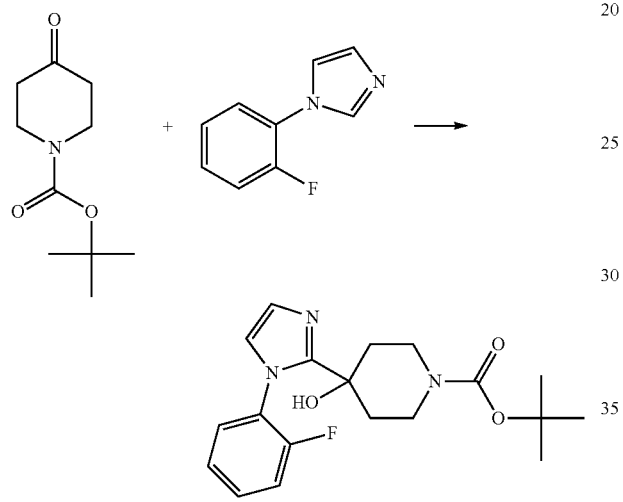

1-(2-Fluorophenyl)imidazole (484 mg, 2.99 mmol) was dissolved in a tetrahydrofuran (5 mL) under an atmosphere of argon. The reaction mixture was cooled to −78° C. n-Butyllithium (2.2 mL of 1.6 M, 3.58 mmol) in hexanes was slowly added and the resulting mixture was stirred at −78° C. for 1 hour. tert-Butyl 4-oxopiperidine-1-carboxylate (892.2 mg, 4.48 mmol) was then added as a solution in tetrahydrofuran (2 mL). The reaction mixture was allowed to slowly warm to room temperature and stir for 10 days. The crude material was evaporated to dryness and taken to the next step without further purification. ESI-MS m/z calc. 361.2. found 362.1 (M+1)⁺. Retention time 1.12 minutes (3 min run).

Step 3: Spiro[benzo[b]imidazo[1,2-d][1,4]oxazine-4,4'-piperidine]

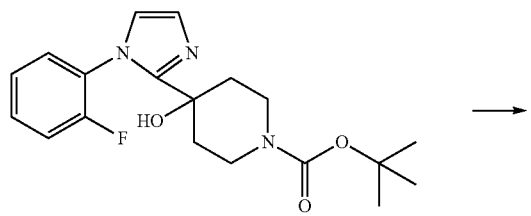

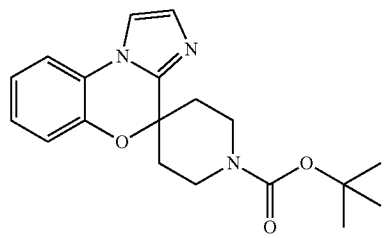

tert-Butyl 4-[1-(2-fluorophenyl)imidazol-2-yl]-4-hydroxypiperidine-1-carboxylate (294 mg, 0.81 mmol) and K₂CO₃ (337 mg, 2.44 mmol) were heated at 110° C. for 16 h in DMF (5 mL). The solvent was evaporated and the resulting material was partitioned between dichloromethane and water. The organics were separated and washed with brine, dried over sodium sulfate and evaporated. The crude material was purified by column chromatography (0-50% ethyl acetate in hexanes) to give tert-butyl spiro[imidazo[2,1-c][1,4]benzoxazine-4,4'-piperidine]-1'-carboxylate (139 mg, 50%). ESI-MS m/z calc. 341.2. found 342.3 (M+1)⁺. Retention time 1.31 minutes (3 min run).

Step 4: Spiro[benzo[b]imidazo[1,2-d][1,4]oxazine-4,4'-piperidine]dihydrochloride

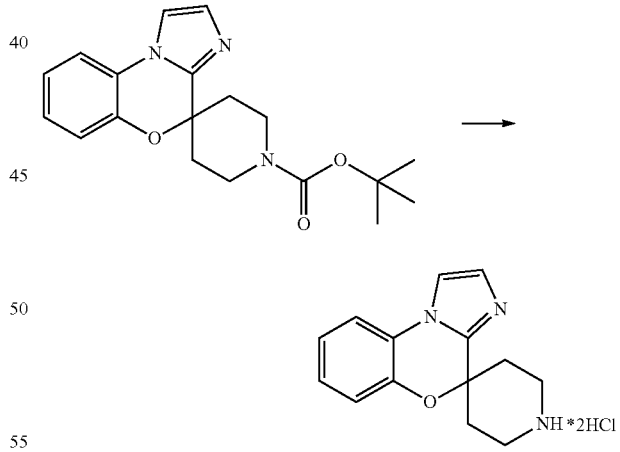

tert-Butyl spiro[imidazo[2,1-c][1,4]benzoxazine-4,4'-piperidine]-1'-carboxylate (138 mg, 0.40 mmol) was stirred for 10 min in 4M HCl in dioxane (2 mL of 4 M, 8.00 mmol). The reaction was evaporated to dryness to yield the spiro[benzo[b]imidazo[1,2-d][1,4]oxazine-4,4'-piperidine]dihydrochloride (97 mg, quantitative) that was used in next step without further purification. ESI-MS m/z calc. 241.1. found 242.3 (M+1)⁺. Retention time 0.40 minutes (3 min run).

477

7-Fluoro-1-methyl-1H-spiro[chromeno[4,3-c]pyrazole-4,4'-piperidine]dihydrochloride Step 1: tert-Butyl 7-fluoro-4-oxospiro[chroman-2,4'-piperidine]-1'-carboxylate

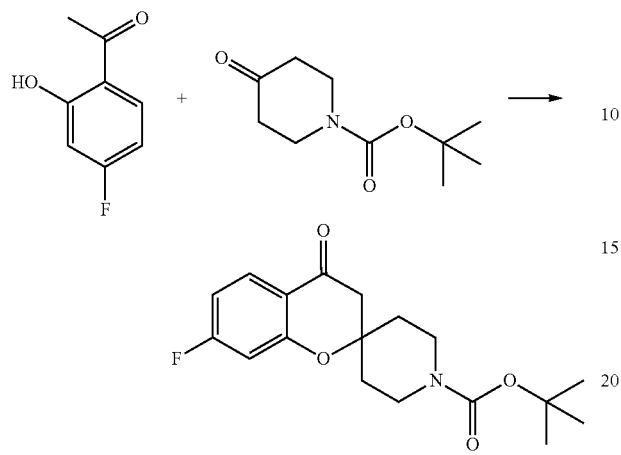

To a solution of tert-butyl 4-oxopiperidine-1-carboxylate (7.5 g, 37.8 mmol) in pyrrolidine (4.5 mL, 54.1 mmol) and anhydrous methanol (10.2 mL) was added 1-(4-fluoro-2-hydroxyphenyl)ethanone (5.8 g, 37.6 mmol). The reaction mixture was stirred at 80° C. for 2.5 hours. The methanol was removed under reduced pressure and the resulting residue was dissolved in ethyl acetate (150 mL), washed with 1N HCl (1×150 mL) and brine (2×100 mL). The organic layer was dried over sodium sulfate, filtered and concentrated under reduced pressure to yield a yellow oil. The oil was diluted with hexanes (400 mL) and was heated at 60° C. until in solution. Once dissolved, the solution was allowed to cool to 25° C. The crystals were collected via vacuum filtration, rinsing with hexanes to remove tert-butyl 4-oxo-7-pyrrolidin-1-yl-spiro[chromane-2,4'-piperidine]-1'-carboxylate (8.6 g), which was collected as light yellow solid; ESI-MS m/z calc. 386.2. found 387.2 (M+1)+; Retention time: 2.59 minutes (3 min run). The filtrate was concentrated and the residue was subjected to column chromatography (0-100% ethyl acetate/hexanes) to give tert-butyl 7-fluoro-4-oxo-spiro[chromane-2,4'-piperidine]-1'-carboxylate (2.7 g, 21%) as a light yellow solid; ESI-MS m/z calc. 335.2. found 336.2 (M+1)+; Retention time: 2.49 minutes (3 min run). $^{1}$H NMR (400 MHz, CDCl$_3$) δ 7.89 (dd, J=8.6, 6.7 Hz, 1H), 6.80-6.62 (m, 2H), 3.88 (d, J=12.1 Hz, 2H), 3.21 (t, J=12.0 Hz, 2H), 2.71 (s, 2H), 2.02 (d, J=12.8 Hz, 2H), 1.62 (td, J=14.1, 4.8 Hz, 2H), 1.46 (s, 9H).

Step 2: (Z)-tert-Butyl 3-(ethoxymethylene)-7-fluoro-4-oxospiro[chroman-2,4'-piperidine]-1'-carboxylate and tert-butyl 3-(diethoxymethyl)-7-fluoro-4-oxospiro[chroman-2,4'-piperidine]-1'-carboxylate

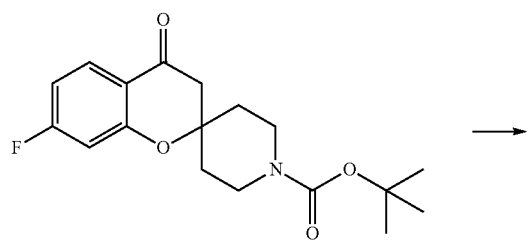

478

-continued

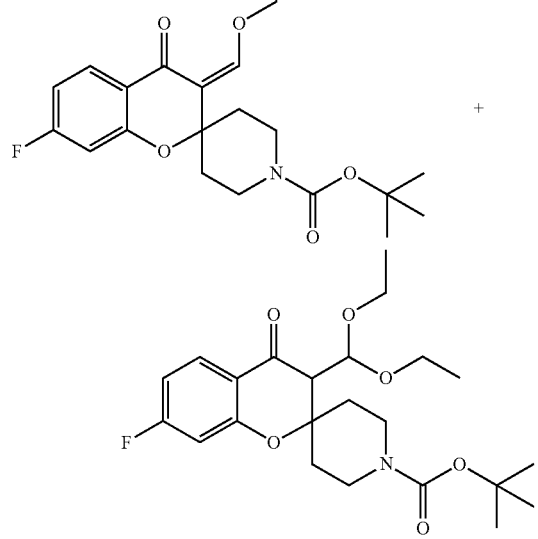

To Triethyl orthoformate (4.0 mL, 24.1 mmol) in dry dichloromethane (23 mL) under argon at −10° was added dropwise BF$_3$.OEt$_2$ (3.1 mL, 24.2 mmol). The solution was allowed to warm to 0° C. and was stirred for 10 minutes. After, the solution was cooled to −78° C. prior to the slow drop-wise addition of tert-butyl 7-fluoro-4-oxo-spiro[chromane-2,4'-piperidine]-1'-carboxylate (2.7 g, 8.0 mmol) in dichloromethane (1.2 mL). Diisopropylethylamine (4.9 mL, 28.2 mmol) was added over 10 minutes, and the mixture was slowly warmed to 25° C. and was stirred at this temperature overnight. The reaction mixture was diluted with dichloromethane (500 mL) followed by saturated aqueous sodium bicarbonate solution (500 mL). The mixture was shaken in a separatory funnel and separated. The organic layer was washed with sodium bicarbonate (500 mL). The organic layer was dried over sodium sulfate, filtered and concentrated. The residue was purified by silica gel column chromatography (0-25% EtOAc/hexanes) to provide a mixture of ten-butyl (3Z)-3-(ethoxymethylene)-7-fluoro-4-oxo-spiro[chromane-2,4'-piperidine]-1'-carboxylate (2.6 g, 82%) and tert-butyl 3-(diethoxymethyl)-7-fluoro-4-oxo-spiro[chromane-2,4'-piperidine]-1'-carboxylate. ESI-MS m/z calc. 391.2. found 392.2 (M+1)+; Retention time: 2.69 minutes (3 min run).

Step 3: 7-Fluoro-1-methyl-1H-spiro[chromeno[4,3-c]pyrazole-4,4'-piperidine]dihydrochloride

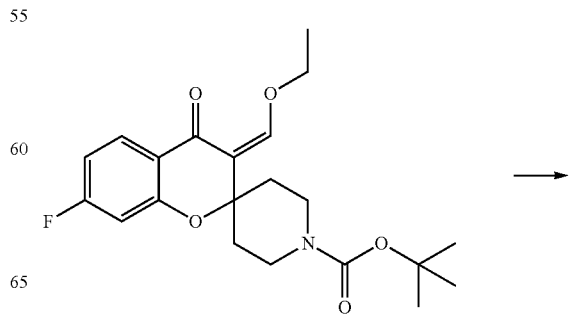

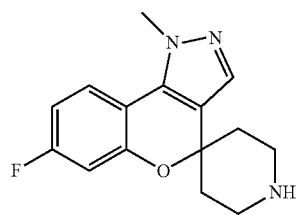

To tert-butyl (3Z)-3-(ethoxymethylene)-7-fluoro-4-oxo-spiro[chromane-2,4'-piperidine]-1'-carboxylate (2.6 g, 5.9 mmol) was added hydrochloric acid (22.3 mL, 89.1 mmol) (4 M in dioxane). The reaction mixture was allowed to stir at 25° C. for 2 hours. Solvent was removed under vacuum, and the obtained solid was dissolved in EtOH (3×25 mL) and the solvent was evaporated to dryness. The resulting beige-white solid was fully dissolved in ethanol (21 mL) at 25° C. prior to the addition of tert-butyl N-amino-N-methyl-carbamate (1.0 g, 7.1 mmol). The solution was allowed to stir at 25° C. overnight. To the thick beige-white slurry that formed was added hydrochloric acid, 4 M in dioxane (7.4 mL, 29.7 mmol). The mixture was heated at 60° C. to yield a clear yellow solution. After 1"hour at 60° C., a thick beige-white slurry developed. The slurry was allowed to slowly cool to 25° C. over 1 hour, and solids were collected by vacuum filtration. The cake was rinsed with a 10% solution of ethanol in hexanes (2×). Residual solvent was further removed under reduced pressure providing 7-fluoro-1-methyl-spiro[chromeno[4,3-c]pyrazole-4,4'-piperidine]dihydrochloride (1.4 g, 67%) as a light tan solid. ESI-MS m/z calc. 273.1. found 274.3 (M+1)$^+$; Retention time: 1.59 minutes (3 min run). $^1$H NMR (400 MHz, MeOD) δ 7.80 (dd, J=8.7, 6.1 Hz, 1H), 7.45 (d, J=1.7 Hz, 1H), 7.00 (dd, J=9.8, 2.6 Hz, 1H), 6.91 (td, J=8.6, 2.6 Hz, 1H), 4.14 (s, 3H), 3.53-3.42 (m, 2H), 3.41-3.33 (m, 2H), 2.29 (d, J=13.9 Hz, 2H), 2.23-2.11 (m, 2H).

1-Isopropyl-1H-spiro[chromeno[4,3-c]pyrazole-4,4'-piperidine]

Step 1: Benzyl 1-isopropyl-1H-spiro[chromeno[4,3-c]pyrazole-4,4'-piperidine]-1'-carboxylate

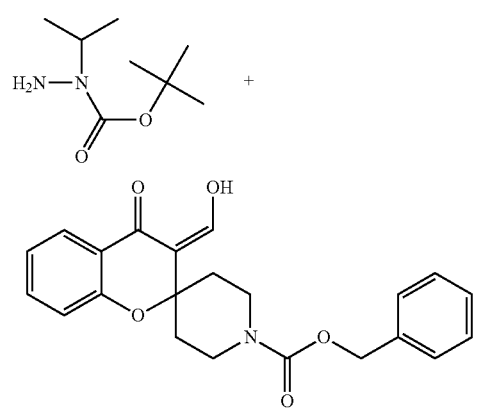

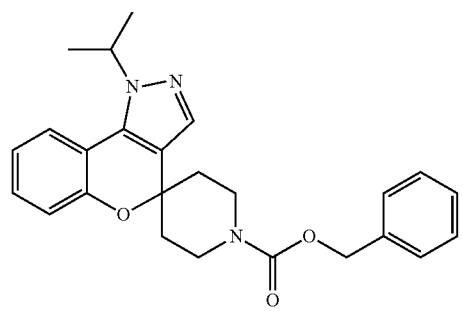

A mixture of tert-butyl N-amino-N-isopropyl-carbamate (530.4 mg, 3.0 mmol), (Z)-benzyl 3-(hydroxymethylene)-4-oxospiro[chroman-2,4'-piperidine]-1'-carboxylate (1.10 g, 2.9 mmol) and TFA (223.4 μL, 2.9 mmol) in dichloromethane (10 mL) was stirred 2 h. The reaction was concentrated to ⅓ volume, then TFA (~1.5 mL) was added. The mixture was stirred for 30 min, then concentrated, neutralized with excess Et$_3$N, re-concentrated, and purified by column chromatography (0-60% EtOAc/hexanes) to give benzyl 1-isopropyl-1H-spiro[chromeno[4,3-c]pyrazole-4,4'-piperidine]-1'-carboxylate (1.1 g, 91%) as a pale yellow oil. ESI-MS m/z calc. 417.2. found 418.3 (M+1)$^+$; Retention time: 2.07 minutes (3 min run).

Step 2: 1-Isopropyl-1H-spiro[chromeno[4,3-c]pyrazole-4,4'-piperidine]

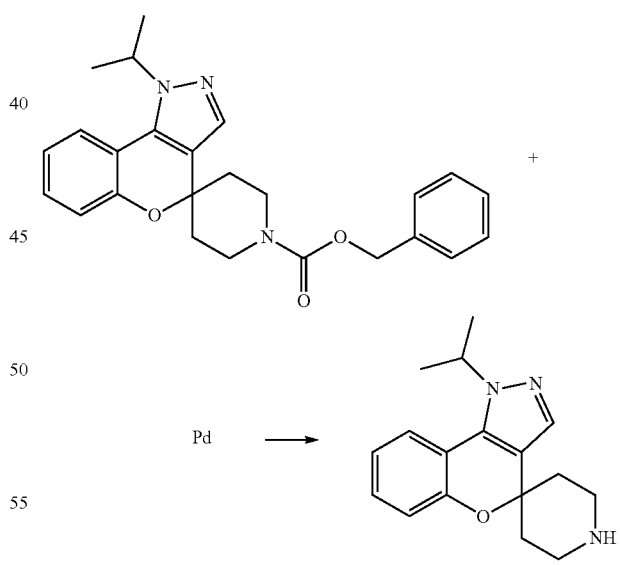

Benzyl 1-isopropylspiro[chromeno[4,3-c]pyrazole-4,4'-piperidine]-1'-carboxylate (1.1 g, 2.6 mmol) was stirred in methanol (14.4 mL) with Pd/C (140.3 mg, 0.1318 mmol) under a balloon of hydrogen for 16 h. The reaction was filtered through a syringe filter and the solvent evaporated to give 1-isopropylspiro[chromeno[4,3-c]pyrazole-4,4'-piperidine] (750 mg, 100%). ESI-MS m/z calc. 283.2. found 284.3 (M+1)$^+$; Retention time: 1.01 minutes (3 min run).

481

7-Methylspiro[benzo[b]pyrrolo[1,2-d][1,4]oxazine-4,4'-piperidine]-1-carbonitrile Step 1: tert-Butyl 7-methylspiro[benzo[b]pyrrolo[1,2-d][1,4]oxazine-4,4'-piperidine]-1'-carboxylate

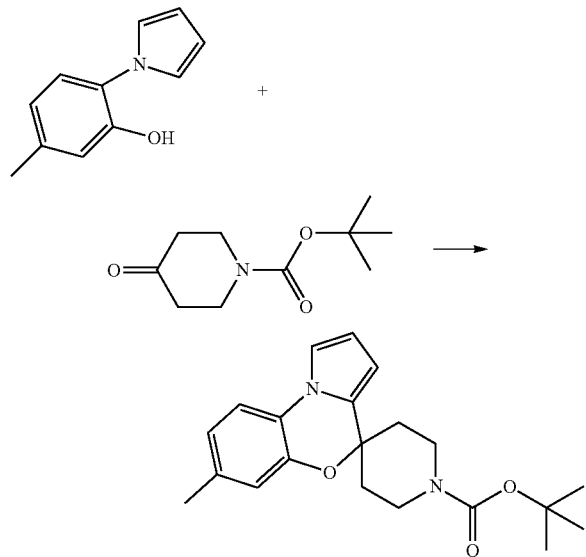

To 5-methyl-2-pyrrol-1-yl-phenol (6.0 g, 33.6 mmol) in dichloromethane (75 mL) was added tert-butyl 4-oxopiperidine-1-carboxylate (6.61 g, 33.6 mmol) then trifluoroacetic acid (3.1 mL, 40.3 mmol) and the mixture was stirred at room temperature for 5.5 hours. The solvent was evaporated and the crude residue was purified by column chromatography utilizing a gradient of 0-100% dichloromethane in hexanes to yield tert-butyl 7'-methylspiro[piperidine-4,4'-pyrrolo[2,1-c][1,4]benzoxazine]-1-carboxylate (7.1 g, 59%). ¹H NMR (400 MHz, CDCl₃) δ 7.22 (d, J=8.1 Hz, 1H), 7.12-7.09 (m, 1H), 6.88 (s, 1H), 6.82 (d, J=8.0 Hz, 1H), 6.29 (t, J=3.2 Hz, 1H), 6.00-5.98 (m, 1H), 5.30 (s, 1H), 3.97 (s, 2H), 3.26 (t, J=12.2 Hz, 2H), 2.32 (s, 3H), 2.09-2.01 (m, 2H), 1.87 (dt, J=13.3, 4.9 Hz, 2H), 1.48 (s, 9H). ESI-MS m/z calc. 354.4. found 355.5 (M+1)⁺; Retention time 2.28 minutes (3 min run).

Step 2: tert-Butyl 1-cyano-7-methylspiro[benzo[b]pyrrolo[1,2-d][1,4]oxazine-4,4'-piperidine]-1'-carboxylate and 7-methylspiro[benzo[b]pyrrolo[1,2-d][1,4]oxazine-4,4'-piperidine]-1-carbonitrile

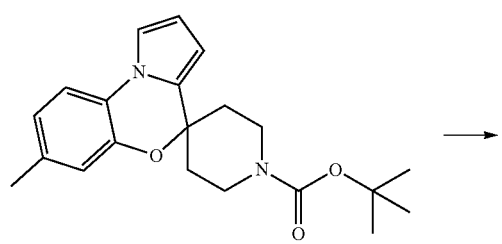

482

-continued

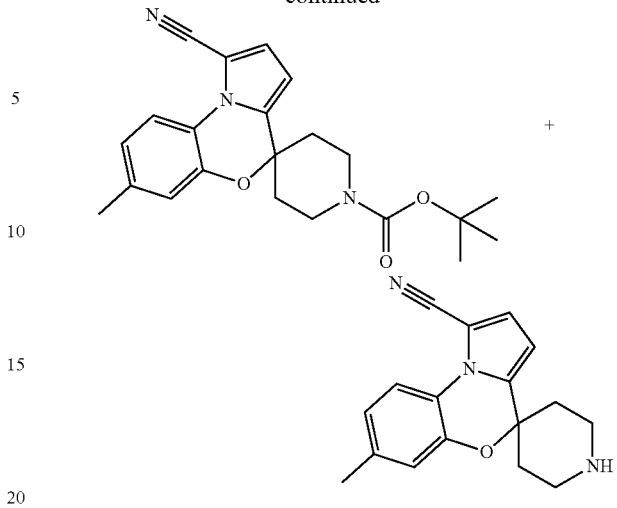

To tert-butyl 7'-methylspiro[piperidine-4,4'-pyrrolo[2,1-c][1,4]benzoxazine]-1-carboxylate (5.0 g, 14.1 mmol) in THF (150 mL) at −78° C. was added dropwise chlorosulfonyl isocyanate (1.5 mL, 16.9 mmol) in THF (50 mL) over a period of 10 minutes. The mixture was stirred at that temperature for 4 hours and then DMF (3.5 mL, 45.9 mmol) was added dropwise and the mixture allowed to stir at room temperature overnight. The mixture was concentrated, diluted with DCM (500 mL) and washed with sat. NaHCO₃ (200 mL), brine (200 mL), dried over MgSO₄ and evaporated to yield a crude residue that was purified by column chromatography (50-100% dichloromethane/hexane) to give tert-butyl 1'-(methoxysulfonylcarbamoyl)-7'-methyl-spiro[piperidine-4,4'-pyrrolo[2,1-c][1,4]benzoxazine]-1-carboxylate as a pale yellow oil (1.3 g, 24%). ¹H NMR (400 MHz, CDCl₃) δ 7.98 (d, J=8.0 Hz, 1H), 6.98 (d, J=4.0 Hz, 1H), 6.96-6.88 (m, 2H), 6.05 (d, J=4.0 Hz, 1H), 4.09-3.95 (m, 2H), 3.31-3.15 (m, 2H), 2.35 (s, 3H), 2.04 (d, J=14.0 Hz, 2H), 1.92-1.79 (m, 2H), 1.48 (s, 9H). ESI-MS m/z calc. 379.5. found 380.1 (M+1)⁺; Retention time 2.20 minutes (3 min run), and 7-methylspiro[benzo[b]pyrrolo[1,2-d][1,4]oxazine-4,4'-piperidine]-1-carbonitrile (0.5 g, 12%). ¹H NMR (400 MHz, DMSO) δ 8.40 (s, 1H), 7.88 (d, J=8.3 Hz, 1H), 7.33 (d, J=4.1 Hz, 1H), 7.17 (s, 1H), 7.06 (d, J=8.4 Hz, 1H), 6.42 (d, J=4.1 Hz, 1H), 3.26-3.09 (m, 4H), 2.33 (s, 3H), 2.19-2.04 (m, 4H). ESI-MS m/z calc. 279.3. found 280.3 (M+1)⁺; Retention time 1.12 minutes (3 min run).

(1-Cyanospiro[benzo[b]pyrrolo[1,2-d][1,4]oxazine-4,4'-piperidine]-7-yl)methyl acetate Step 1: tert-Butyl 7-(bromomethyl)-1-cyanospiro[benzo[b]pyrrolo[1,2-d][1,4]oxazine-4,4'-piperidine]-1'-carboxylate

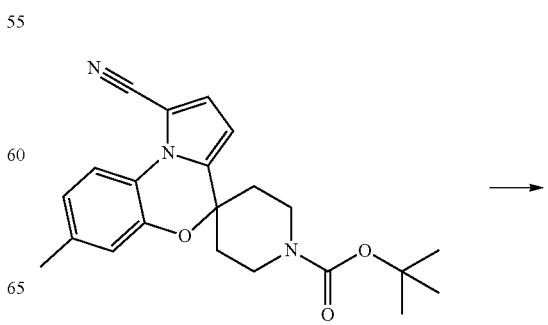

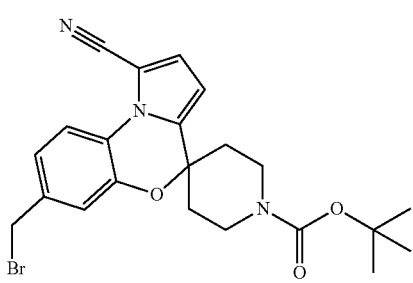

tert-Butyl 1'-cyano-7'-methyl-spiro[piperidine-4,4'-pyrrolo[2,1-c][1,4]benzoxazine]-1-carboxylate (200 mg, 0.527 mmol), 1-bromopyrrolidine-2,5-dione (93.8 mg, 0.527 mmol), and 2-(1-cyano-1-methyl-ethyl)azo-2-methyl-propanenitrile (8.66 mg, 0.0527 mmol) were combined in carbon tetrachloride (10 mL) and the mixture was heated at 80° C. for 4 hours. The mixture was washed with water, dried over sodium sulfate and concentrated under reduced pressure. The residue was purified by column chromatography (50-100% CH$_2$Cl$_2$/hexanes) to yield tert-butyl 7'-(bromomethyl)-1'-cyano-spiro[piperidine-4,4'-pyrrolo[2,1-c][1,4]benzoxazine]-1-carboxylate (115 mg, 47%). ESI-MS m/z calc. 457.1. found 458.5 (M+1)$^+$; Retention time 2.43 minutes (3 min run).

Step 2: (1-Cyanospiro[benzo[b]pyrrolo[1,2-d][1,4]oxazine-4,4'-piperidine]-7-yl)methyl acetate

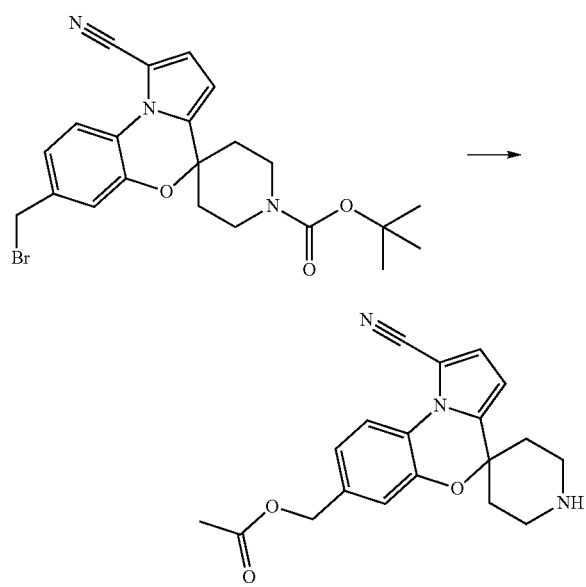

tert-Butyl 7'-(bromomethyl)-1'-cyano-spiro[piperidine-4,4'-pyrrolo[2,1-c][1,4]benzoxazine]-1-carboxylate (33.0 mg, 0.0720 mmol) and potassium acetate (35.3 mg, 0.360 mmol) were combined in DMF (0.5 mL) and the mixture was stirred at 80° C. for 18 hours. The mixture was taken up in NH$_4$Cl (10 mL) and was extracted with CH$_2$Cl$_2$ (10 mL). Solvent was removed under reduced pressure and the residue was purified by column chromatography (0-10% EtOAc/CH$_2$Cl$_2$) to obtain tert-butyl 7'-(acetoxymethyl)-1'-cyano-spiro[piperidine-4,4'-pyrrolo[2,1-c][1,4]benzoxazine]-1-carboxylate (19.5 mg, 62%) as a clear oil. ESI-MS m/z calc. 437.2. found 438.5 (M+1)$^+$; Retention time 2.05 minutes (3 min run).

tert-Butyl 7'-(acetoxymethyl)-1'-cyano-spiro[piperidine-4,4'-pyrrolo[2,1-c][1,4]benzoxazine]-1-carboxylate was dissolved in CH$_2$Cl$_2$ (10 mL) before TFA (5.0 mL, 65 mmol) was added. The solvent was removed under reduced pressure to give (1'-cyanospiro[piperidine-4,4'-pyrrolo[2,1-c][1,4]benzoxazine]-7'-yl)methyl acetate (15 mg, 62%). ESI-MS m/z calc. 337.1. found 338.3 (M+1)$^+$; Retention time 1.16 minutes (3 min run).

7-(Methoxymethyl)spiro[benzo[b]pyrrolo[1,2-d][1,4]oxazine-4,4'-piperidine]-1-carbonitrile Step 1: 7-Methyl-1'-(2,2,2-trifluoroacetyl)spiro[benzo[b]pyrrolo-[1,2-d][1,4]oxazine-4,4'-piperidine]-1-carbonitrile

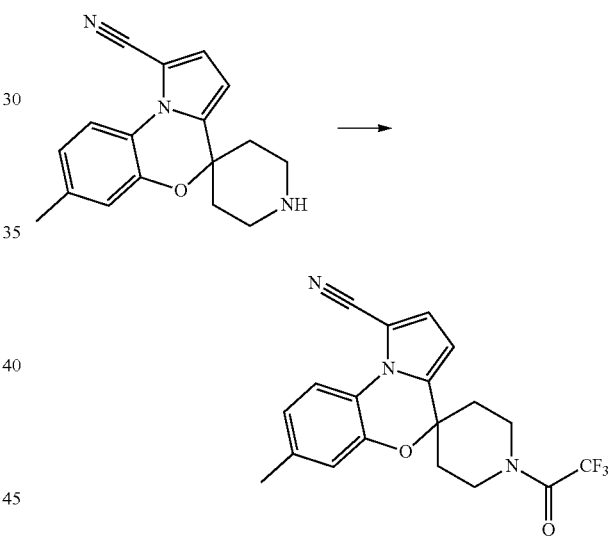

To a solution of 7'-methylspiro[piperidine-4,4'-pyrrolo[2,1-c][1,4]benzoxazine]-1'-carbonitrile (250 mg, 0.895 mmol) in dichloromethane (5.0 mL) at 0° C. was added triethylamine (374 µL, 2.69 mmol) and (2,2,2-trifluoroacetyl) 2,2,2-trifluoroacetate (124 µL, 0.895 mmol). The mixture was allowed to warm up to room temperature and was stirred overnight. The mixture was concentrated under reduced pressure and the residue was purified by column chromatography (0-100% ethyl acetate/hexanes) to give 7'-methyl-1-(2,2,2-trifluoroacetyl)spiro[piperidine-4,4'-pyrrolo[2,1-c][1,4]benzoxazine]-1'-carbonitrile (250 mg, 74%) ESI-MS m/z calc. 375.3. found 376.3 (M+1)$^+$; Retention time 2.01 minutes (3 min run). $^1$H NMR (400 MHz, CDCl$_3$) δ 8.01 (d, J=8.8 Hz, 1H), 6.99 (d, J=4.0 Hz, 1H), 6.96 (s, 1H), 6.94 (d, J=6.3 Hz, 1H), 6.07 (d, J=4.0 Hz, 1H), 4.54-4.48 (m, 1H), 3.94 (d, J=14.2 Hz, 1H), 3.71-3.62 (m, 1H), 3.34-3.25 (m, 1H), 2.36 (s, 3H), 2.20 (d, J=13.4 Hz, 2H), 1.66-1.45 (m, 2H).

Step 2: 7-(Bromomethyl)-1'-(2,2,2-trifluoroacetyl) spiro[benzo-[b]pyrrolo[1,2-d][1,4]oxazine-4,4'-piperidine]-1-carbonitrile

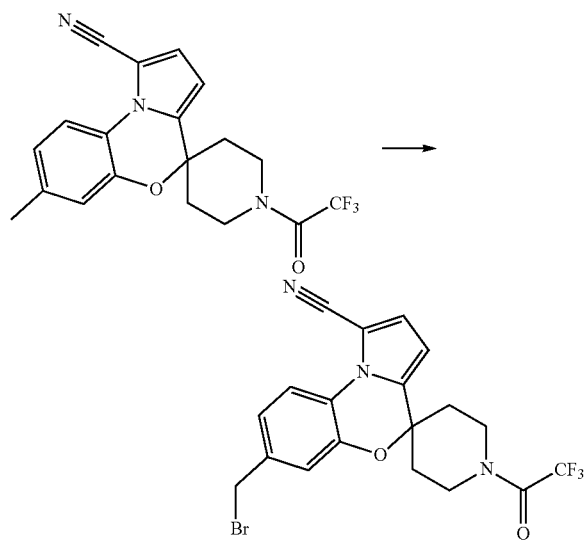

7'-Methyl-1-(2,2,2-trifluoroacetyl)spiro[piperidine-4,4'-pyrrolo[2,1-c][1,4]benzoxazine]-1'-carbonitrile (250 mg, 0.666 mmol), 1-bromopyrrolidine-2,5-dione (119 mg, 0.666 mmol) and 2-(1-cyano-1-methyl-ethyl)azo-2-methyl-propanenitrile (10.9 mg, 0.0666 mmol) were combined in carbon tetrachloride and the mixture was heated at 80° C. for 4 hours. The mixture was concentrated under reduced pressure and the residue was purified by column chromatography to give 7'-(bromomethyl)-1-(2,2,2-trifluoroacetyl)spiro[piperidine-4,4'-pyrrolo[2,1-c][1,4]benzoxazine]-1'-carbonitrile (53.2 mg, 18%).

Step 3: 7-(Methoxymethyl)spiro[benzo[b]pyrrolo[1,2-d][1,4]oxazine-4,4'-piperidine]-1-carbonitrile

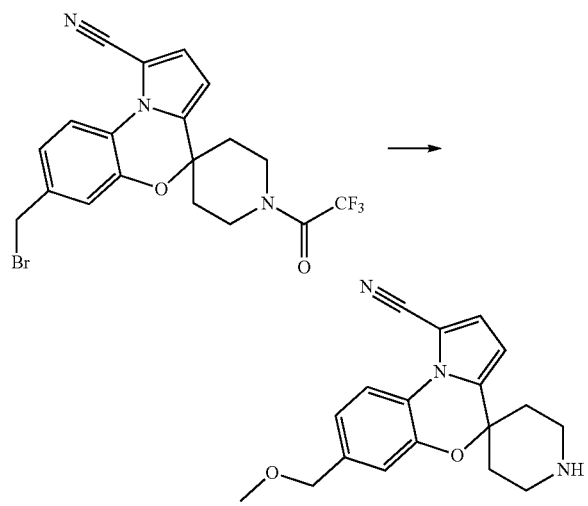

7'-(Bromomethyl)-1-(2,2,2-trifluoroacetyl)spiro[piperidine-4,4'-pyrrolo[2,1-c][1,4]-benzoxazine]-1'-carbonitrile (53.2 mg, 0.117 mmol) was treated with sodium methoxide (36 mg, 0.67 mmol) at room temperature. The mixture was allowed to stir for 5 h at room temperature before it was concentrated under reduced pressure. The residue was taken up in ethyl acetate, filtered, and concentrated to give 7'-(methoxymethyl)spiro[piperidine-4,4'-pyrrolo[2,1-c][1,4]benzoxazine]-1'-carbonitrile (9.0 mg, 4%). ESI-MS m/z calc. 309.2. found 310.3 (M+1)+; Retention time 0.97 minutes (3 min run).

3-Methylspiro[benzo[b]pyrrolo[1,2-d][1,4]oxazine-4,4'-piperidine]-1-carbonitrile

Step 1: 2,2,2-Trifluoro-1-(3-methylspiro[benzo[b]pyrrolo[1,2-d][1,4]oxazine-4,4'-piperidine]-1'-yl) ethanone

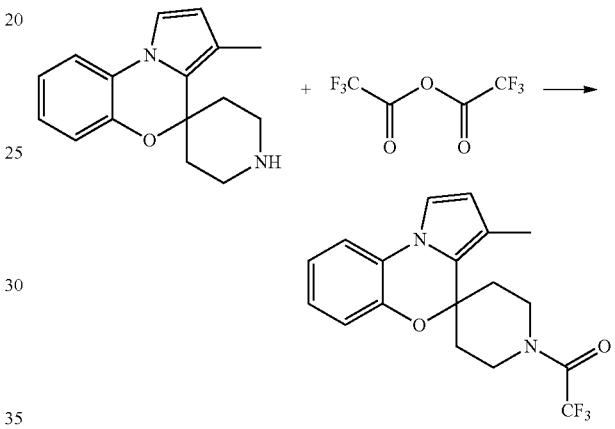

To a solution of 3'-methylspiro[piperidine-4,4'-pyrrolo[2,1-c][1,4]benzoxazine] (120 mg, 0.41 mmol), and Et$_3$N (173 µL, 1.24 mmol) in dry dichloromethane (2.1 mL) at 0° C. under N$_2$, was added (2,2,2-trifluoroacetyl) 2,2,2-trifluoroacetate (86 µL, 0.62 mmol) dropwise. After 5 min, the cooling bath was removed and the mixture was stirred for 3 h at 25° C. The solvent was removed under reduced pressure and the oily residue was purified by silica-gel column chromatography eluting with 0.5-60% EtOAc in hexanes. The product 2,2,2-trifluoro-1-(3'-methylspiro[piperidine-4,4'-pyrrolo[2,1-c][1,4]benzoxazine]-1'-yl)ethanone (95 mg, 66%) was isolated as an off-white foamy solid. ESI-MS m/z calc. 350.1. found 351.3 (M+1)$^+$; Retention time 2.03 minutes (3 min run).

Step 2: 3-Methyl-1'-(2,2,2-trifluoroacetyl)spiro[benzo[b]pyrrolo[1,2-d][1,4]oxazine-4,4'-piperidine]-1-carbaldehyde

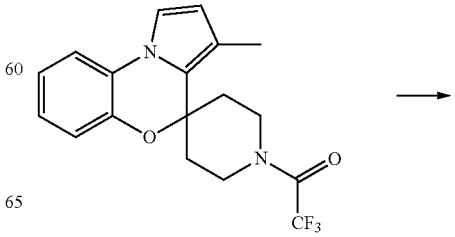

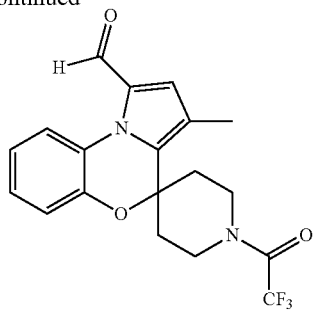

POCl₃ (38 μL, 0.41 mmol) was added dropwise at 0° C. under N₂ to DMF (32 μL, 0.41 mmol). The reaction was stirred for 30 min at this temperature and a white solid formed, to which was slowly added a solution of 2,2,2-trifluoro-1-(3'-methyl-spiro[piperidine-4,4'-pyrrolo[2,1-c][1,4]benzoxazine]-1-yl)ethanone (95 mg, 0.27 mmol) in dry DMF (0.7 mL). The reaction stirred for 4 h, poured onto ice, 0.8 ml of 1M NaOH was added and the product was extracted with dichloromethane (3×5 mL). The organic phases were combined, washed with brine, dried, filtered and concentrated and the residue was purified by silica-gel column chromatography eluting with 5-40% EtOAc in hexanes to yield 3-methyl-1'-(2,2,2-trifluoroacetyl)spiro[benzo[b]pyrrolo[1,2-d][1,4]oxazine-4,4'-piperidine]-1-carbaldehyde (25 mg, 24%). ESI-MS m/z calc. 378.1. found 379.3 (M+1)+; Retention time 1.83 minutes (3 min run).

Step 3: 3-Methyl-1'-(2,2,2-trifluoroacetyl)spiro[benzo[b]pyrrolo[1,2-d][1,4]oxazine-4,4'-piperidine]-1-carbonitrile

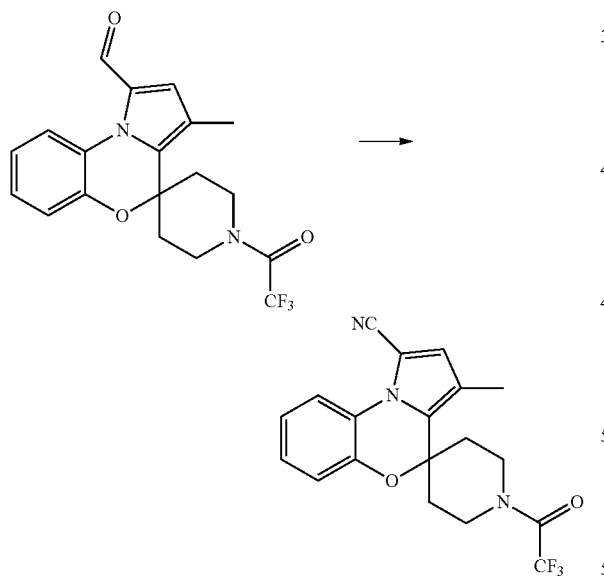

To a solution of 3'-methyl-1-(2,2,2-trifluoroacetyl)spiro[piperidine-4,4'-pyrrolo[2,1-c][1,4]benzoxazine]-1'-carbaldehyde (25 mg, 0.07 mmol) in ethanol (125 μL) at 60° C. was added an aqueous solution of hydroxylamine hydrochloride (20.7 mg, 0.30 mmol) and sodium acetate (41.2 mg, 0.50 mmol) in water (125.0 μL). The solution was stirred at 60° C. for 2 hours. The reaction was cooled to 25° C., water added and the precipitate that formed was collected by filtration. The solids were washed thoroughly with water and dried under vacuum, dissolved in Ac₂O (119.1 μL, 1.26 mmol) and heated at 140° C. for 5 h. The reaction was cooled to 25° C., poured onto ice, basified by addition of solid NaHCO₃ until no more foaming occurred and extracted with dichloromethane (3×5 mL). The organic phases were combined, dried, filtered and concentrated to yield a residue that was purified by silica gel chromatography using a gradient of 0.5-45% EtOAc in hexanes to yield 3-methyl-1'-(2,2,2-trifluoroacetyl)spiro[benzo[b]pyrrolo[1,2-d][1,4]oxazine-4,4'-piperidine]-1-carbonitrile (10 mg, 40%). ESI-MS m/z calc. 375.1. found 376.3 (M+1)⁺; Retention time 2.01 minutes (3 min run).

Step 4: 3-Methylspiro[benzo[b]pyrrolo[1,2-d][1,4]oxazine-4,4'-piperidine]-1-carbonitrile

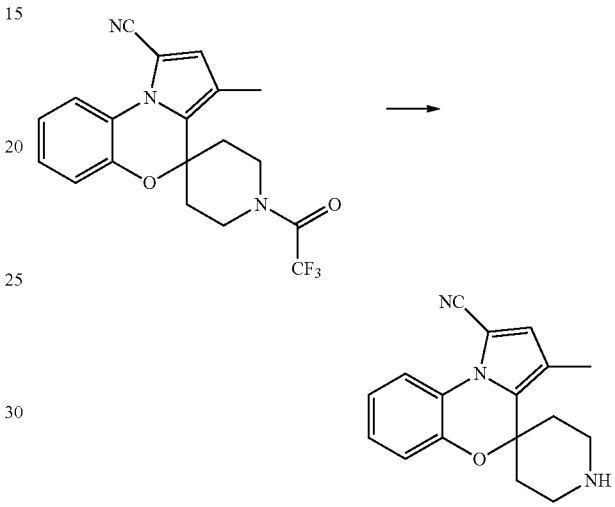

To a solution of 3'-methyl-1-(2,2,2-trifluoroacetyl)spiro[piperidine-4,4'-pyrrolo[2,1-c][1,4]benzoxazine]-1'-carbonitrile (10 mg, 0.027 mmol) in MeOH (159 μL) was added K₂CO₃ (7.7 mg, 0.056 mmol) in one portion at 25° C. Water was added (35 mL), and the organics were removed under vacuum and the aqueous layer was extracted with dichloromethane (3×100 ml). The organic phases were combined, dried, filtered, concentrated to a white solid, which was used directly in the next step without further purification (7 mg, 93%).

9-Fluorospiro[benzo[b]pyrrolo[1,2-d][1,4]oxazine-4,4'-piperidine]-1-carbonitrile Step 1: 9-Fluorospiro[benzo[b]pyrrolo[1,2-d][1,4]oxazine-4,4'-piperidine]

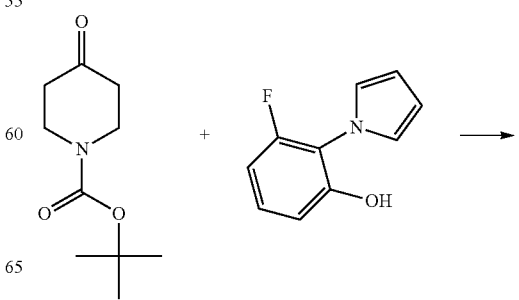

-continued

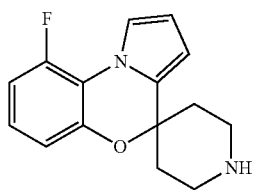

3-Fluoro-2-(1H-pyrrol-1-yl)phenol (2.7 g, 16.6 mmol) and tert-butyl 4-oxopiperidine-1-carboxylate (3.3 g, 16.6 mmol) were dissolved in dry dichloromethane (53.6 mL). TFA (2.3 mL, 30.3 mmol) was added over 15 min and stirring was continued for 12 hours. Additional TFA (2.3 mL, 30.3 mmol) was added at 25° C. The reaction mixture was concentrated under vacuum and the residue diluted with dichloromethane (350 mL) then washed with 1M NaOH (2×50 ml), dried, filtered and evaporated to dryness. The resulting material was purified by silica gel chromatography eluting with 0.5-40% MeOH in dichloromethane to yield 9-fluorospiro[benzo[b]pyrrolo[1,2-d][1,4]oxazine-4,4'-piperidine] (3.4 g, 86%). ESI-MS m/z calc. 258.1. found 259.1 (M+1)+; Retention time 0.90 minutes (3 min run).

Step 2: 2,2,2-Trifluoro-1-(9-fluorospiro[benzo[b]pyrrolo[1,2-d][1,4]oxazine-4,4'-piperidine]-1'-yl)ethanone

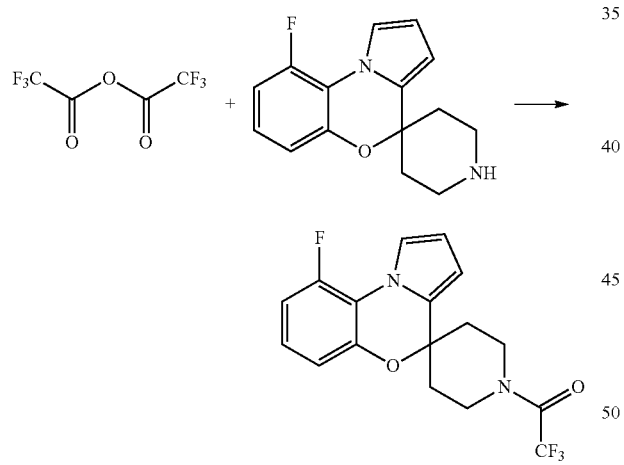

To a cold solution of 9-fluorospiro[benzo[b]pyrrolo[1,2-d][1,4]oxazine-4,4'-piperidine] (3.1 g, 12.2 mmol) in dry dichloromethane (54 mL) under $N_2$ was successively added $Et_3N$ (5.1 mL, 36.6 mmol) and (2,2,2-trifluoroacetyl) 2,2,2-trifluoroacetate (2.5 mL, 18.3 mmol). The cooling bath was removed and the mixture was stirred overnight at room temperature. The mixture was concentrated, then purified by silica-gel column chromatography eluting with 0.5-50% EtOAc in hexanes to yield 2,2,2-trifluoro-1-(9-fluorospiro[benzo[b]pyrrolo[1,2-d][1,4]oxazine-4,4'-piperidine]-1'-yl)ethanone (2.2 g, 50%) as a white foamy solid. ESI-MS m/z calc. 354.1. found 355.3 (M+1)+; Retention time 2.11 minutes (3 min run).

Step 3: 9-Fluoro-1'-(2,2,2-trifluoroacetyl)spiro[benzo[b]pyrrolo[1,2-d][1,4]oxazine-4,4'-piperidine]-1-carbaldehyde

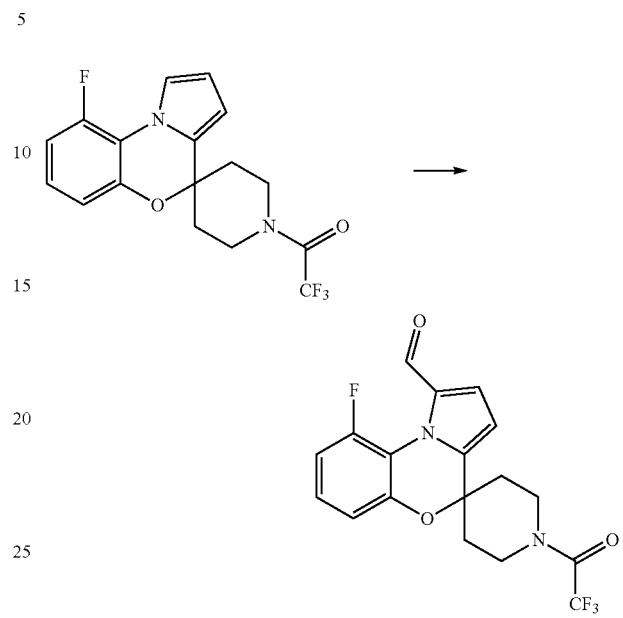

$POCl_3$ (282 μL, 3.0 mmol) was added dropwise at 0° C. under $N_2$ to dry DMF (234 μL, 3.0 mmol). The reaction mixture was left for 20 min at this temperature, which led to the formation of a white solid. A solution of 2,2,2-trifluoro-1-(9'-fluorospiro[piperidine-4,4'-pyrrolo[2,1-c][1,4]benzoxazine]-1-yl)ethanone (715 mg, 2.0 mmol) dry DMF (5.4 mL) was added drop-wise and the cooling bath was removed. The reaction was poured over ice, 1M NaOH was added (5 mL), then the pH was adjusted to 7 with 2M HCl. The mixture was extracted with dichloromethane (3×10 mL). The organics were combined, dried with $MgSO_4$, filtered and evaporated to yield a residue that was purified by silica-gel column chromatography eluting with 5-30% EtOAc in hexanes to yield 9-fluoro-1'-(2,2,2-trifluoroacetyl)spiro[benzo[b]pyrrolo[1,2-d][1,4]oxazine-4,4'-piperidine]-1-carbaldehyde (770 mg, quant). ESI-MS m/z calc. 382.1. found 383.3 (M+1)+; Retention time 1.71 minutes (3 min run).

Step 4: 9-Fluoro-1'-(2,2,2-trifluoroacetyl)spiro[benzo[b]pyrrolo[1,2-d][1,4]oxazine-4,4'-piperidine]-1-carbonitrile

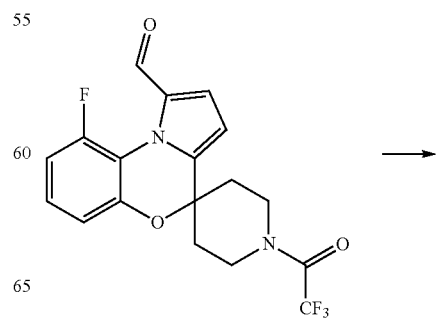

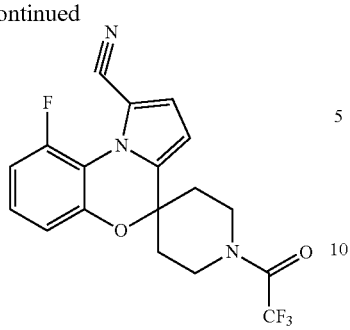

To a solution of 9'-fluoro-1-(2,2,2-trifluoroacetyl)spiro[piperidine-4,4'-pyrrolo[2,1-c][1,4]benzoxazine]-1'-carbaldehyde (715 mg, 1.9 mmol) in ethanol (3.5 mL) heated at 70° C. was added an aqueous solution of hydroxylamine hydrochloride (587 mg, 8.4 mmol) and sodium acetate (1.16 g, 14.20 mmol) in water (3.6 mL). The mixture was heated at 60° C. for 2 h. The mixture was cooled to 25° C., water added and the precipitate formed was collected by filtration and washed thoroughly with water and dried under vacuum. The residue was dissolved in Ac$_2$O (3.37 mL, 35.74 mmol) and heated at 140° C. for 5 h. The reaction was cooled down to 25° C., poured onto ice, basified by addition of NaHCO$_3$ (solid) until no more foaming occurred and was extracted with dichloromethane (3×5 mL). The combined organic phases were dried, filtered and concentrated to yield a residue that was purified by silica gel chromatography (gradient: 0.5-45% EtOAc in hexanes) to yield 9-fluoro-1'-(2,2,2-trifluoroacetyl)spiro[benzo[b]pyrrolo[1,2-d][1,4]oxazine-4,4'-piperidine]-1-carbonitrile (50 mg, 7%). ESI-MS m/z calc. 379.1. found 380.3 (M+1)+; Retention time 1.82 minutes (3 min run).

Step 5: 9-Fluorospiro[benzo[b]pyrrolo[1,2-d][1,4]oxazine-4,4'-piperidine]-1-carbonitrile

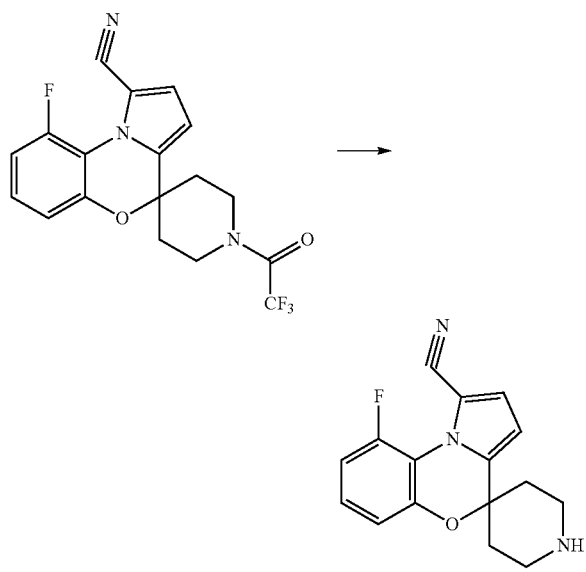

To a solution of 9'-fluoro-1-(2,2,2-trifluoroacetyl)spiro[piperidine-4,4'-pyrrolo[2,1-c][1,4]benzoxazine]-1'-carbonitrile (170 mg, 0.45 mmol) dissolved in MeOH (2.7 mL) was added K$_2$CO$_3$ (130 mg, 0.94 mmol) in one portion at rt. The reaction was monitored by LCMS until no starting material remained. Water was added (10 mL), and the organic solvent removed under vacuum. The product was extracted with dichloromethane (3×30 mL), the organic phases were combined, dried with sodium sulfate, filtered, concentrated to a white solid, which was used directly in next step without further purification (104 mg, 82%). ESI-MS m/z calc. 283.1. found 284.1 (M+1)+; Retention time 0.94 minutes (3 min run).

1-(Methylsulfonyl)spiro[benzo[b]pyrrolo[1,2-d][1,4]oxazine-4,4'-piperidine]

Step 1: tert-Butyl 1-(methylsulfonyl)spiro[benzo[b]pyrrolo[1,2-d][1,4]oxazine-4,4'-piperidine]-1'-carboxylate]

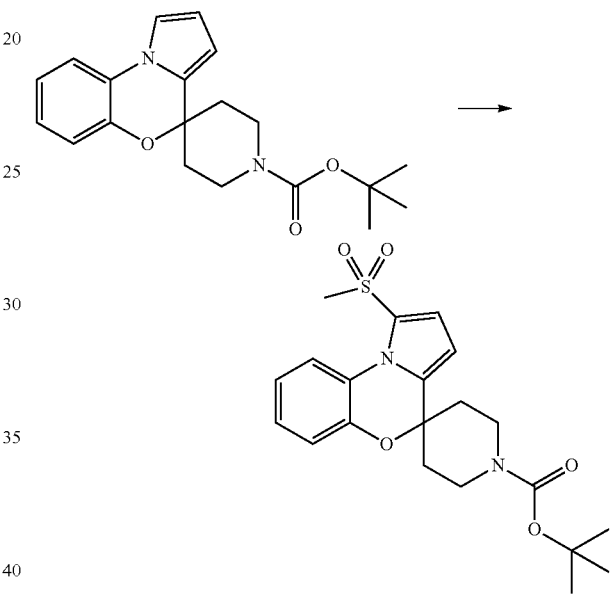

To a solution of NCS (466 mg, 3.49 mmol) in dichloromethane (9.2 mL) at −10° C. was added dimethyl sulfide (393.9 μL, 5.38 mmol) dropwise and the reaction mixture was stirred at this temperature for 10 min. The solution was cooled to −55° C. and a solution of tert-butyl spiro[piperidine-4,4'-pyrrolo[2,1-c][1,4]benzoxazine]-1-carboxylate (915 mg, 2.69 mmol) in dichloromethane (5 mL) was added dropwise over 10 min. The cooling bath was removed and the mixture was stirred until the solution reached 25° C. Water (10 ml) and EtOAc (40 ml) were added. The organic phase was separated, dried on sodium sulfate, filtered and concentrated under reduced pressure to yield an orange oil (1.4 g) that was used in the next step without further purification. The orange oily residue obtained (1.4 g) was taken up in AcOH (5 mL) then H$_2$O$_2$ (671 μL of 30% w/v, 5.91 mmol) was added dropwise. After 15 min at 25° C., another portion of H$_2$O$_2$ (671 μL of 30% w/v, 5.91 mmol) was added dropwise and the reaction was monitored by HPLC until disappearance of starting materials. EtOAc (50 ml) and aqueous saturated NaHCO$_3$ (150 ml) were added and the product was carefully extracted (gas emission). The organic phase was washed with 150 mL of aq sat NaHCO$_3$, then with brine (50 ml). The organic phase was dried, filtered, concentrated under reduced pressure. Purification by silica-gel column chromatography eluting with 5-100% EtOAc in hexanes yielded tert-butyl 1'-methylsulfinylspiro[piperidine-4,4'-pyrrolo[2,1-c][1,4]benzoxazine]-1-carboxylate (276 mg, 0.68 mmol) that was taken up in dry dichloromethane (1 mL). mCPBA (116.0 mg, 0.67 mmol) was added at 25° C. and the mixture was stirred for 1 h. Another 30 mg of mCPBA was added and after 30 min, aqueous saturated NaHCO$_3$ (3 mL) was added and the product extracted twice with dichloromethane (10 mL). The organic phases were combined, washed with brine, dried, filtered and concentrated to yield a residue that was purified by silica-gel chromatography eluting with 5-100% EtOAc in hexanes. The desired product tert-butyl 1'-methylsulfonyl-spiro[piperidine-4,4'-pyrrolo[2,1-c][1,4]benzoxazine]-1-carboxylate (200 mg, 18% over 3 steps) was isolated as a yellow oil. ESI-MS m/z calc. 418.2. found 419.5 (M+1)+; Retention time 1.93 minutes (3 min run).

Step 2: 1-(Methylsulfonyl)spiro[benzo[b]pyrrolo[1,2-d][1,4]oxazine-4,4'-piperidine]

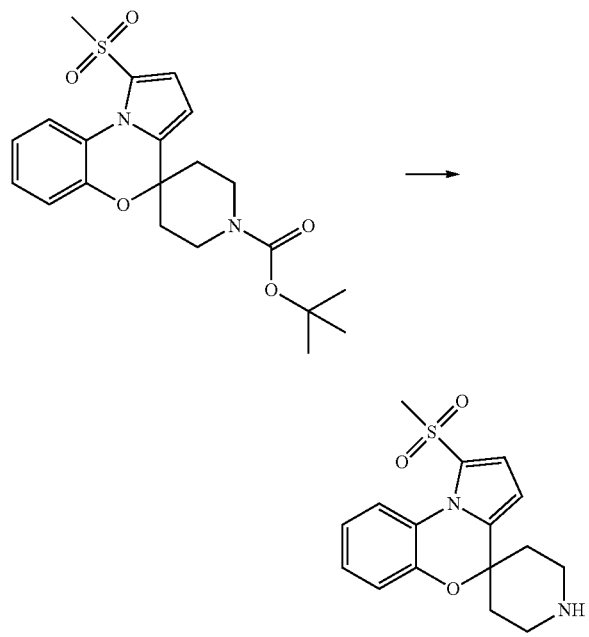

To a solution of tert-butyl 1'-methylsulfonylspiro[piperidine-4,4'-pyrrolo[2,1-c][1,4]benzoxazine]-1-carboxylate (200 mg, 0.48 mmol) in dry dichloromethane (1 mL) at 0° C. was added TFA (147 µL, 1.91 mmol). The cooling bath was removed and the mixture was stirred for 1.5 h at 25° C. The mixture was concentrated under reduced pressure and the residue obtained was taken up in dichloromethane (10 ml) and was washed with aqueous saturated NaHCO$_3$ (5 ml). The aqueous phase was extracted twice with dichloromethane (2×10 ml) and the organic phases were combined, dried, filtered and concentrated to yield 1'-methylsulfonylspiro[piperidine-4,4'-pyrrolo[2,1-c][1,4]benzoxazine] as a light yellow foamy solid (150 mg, 99%). ESI-MS m/z calc. 318.1. found 319.3 (M+1)+; Retention time 0.93 minutes (3 min run).

1-(Methylsulfinyl)spiro[benzo[b]pyrrolo[1,2-d][1,4]oxazine-4,4'-piperidine] was also prepared using the procedure described above where only one aliquot of H$_2$O$_2$ was used in Step 1.

1-(Spiro[benzo[b]pyrrolo[1,2-d][1,4]oxazine-4,4'-piperidine]-1-yl)ethanone hydrochloride Step 1: tert-Butyl 1-bromospiro[benzo[b]pyrrolo[1,2-d][1,4]oxazine-4,4'-piperidine]-1'-carboxylate

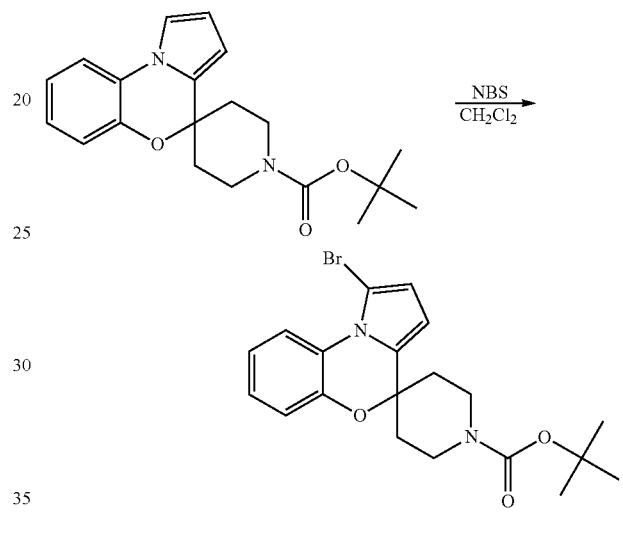

To tert-butyl spiro[piperidine-4,4'-pyrrolo[2,1-c][1,4]benzoxazine]-1-carboxylate (13.2 g, 38.8 mmol) in CH$_2$Cl$_2$ (125 mL) at 0° C. was added NBS (7.25 g, 40.7 mmol) in CH$_2$Cl$_2$ (25 mL) dropwise over 10 min. The mixture was stirred at 0° C. for 5 min before it was diluted with 200 mL of 0.5M Na$_2$S$_2$O$_3$. The aqueous phase was removed and the organic phase was washed with 200 mL of brine. The organic phase was separated, dried over MgSO$_4$, filtered and concentrated in vacuo. The residue was purified by column chromatography (0-30% EtOAc/hexanes) to give tert-butyl 1-bromospiro[benzo[b]pyrrolo[1,2-d][1,4]oxazine-4,4'-piperidine]-1'-carboxylate. ESI-MS m/z calc. 418.1. found 419.0 (M+1)+; Retention time: 2.29 minutes (3 min run).

Step 2: tert-Butyl 1-acetylspiro[benzo[b]pyrrolo[1,2-d][1,4]oxazine-4,4'-piperidine]-1'-carboxylate

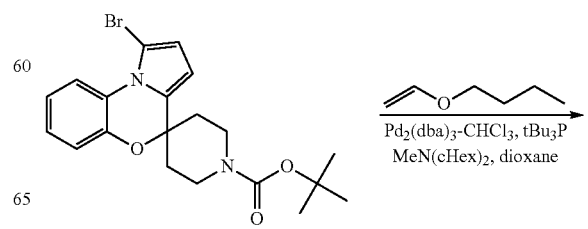

-continued

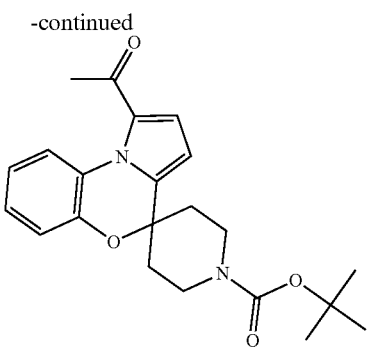

To a solution of tert-butyl 1'-bromospiro[piperidine-4,4'-pyrrolo[2,1-c][1,4]benzoxazine]-1-carboxylate (1.10 g, 2.60 mmol) and Pd$_2$(dba)$_3$.CHCl$_3$ (543 mg, 0.525 mmol) in 1,4-dioxane (4.4 mL) was added tri-tert-butylphosphane (360 μL, 1.31 mmol), 1-vinyloxybutane (3.55 mL, 26.2 mmol) and N-cyclohexyl-N-methyl-cyclohexanamine (843 μL, 3.94 mmol). The mixture was heated at 80° C. for 5 hours. The mixture was cooled to room temperature before 1N HCl (3 mL) was added and the mixture was stirred for 1 hour. The mixture was poured into water and was extracted with ethyl acetate (4×). The organics were combined, washed with water (2×), brine and evaporated. The residue was purified by column chromatography (0-20% ethyl acetate in hexanes) to give tert-butyl 1'-acetylspiro[piperidine-4,4'-pyrrolo[2,1-c][1,4]benzoxazine]-1-carboxylate (610 mg, 61%) as a yellow solid. ESI-MS m/z calc. 382.2. found 383.1 (M+1)+; Retention time: 1.97 minutes (3 min run). $^1$H NMR (400 MHz, DMSO) δ 7.52 (dd, J=8.1, 1.3 Hz, 1H), 7.35 (d, J=4.1 Hz, 1H), 7.24-7.12 (m, J=9.4, 8.0, 1.6 Hz, 2H), 7.08-6.98 (m, 1H), 6.35 (d, J=4.1 Hz, 1H), 3.88 (d br, J=11.3 Hz, 2H), 3.13 (s br, 2H), 2.49 (s, 3H), 1.92-1.76 (m, 4H), 1.41 (s, 9H).

Step 3: 1-(Spiro[benzo[b]pyrrolo[1,2-d][1,4]oxazine-4,4'-piperidine]-1-yl)ethanone hydrochloride

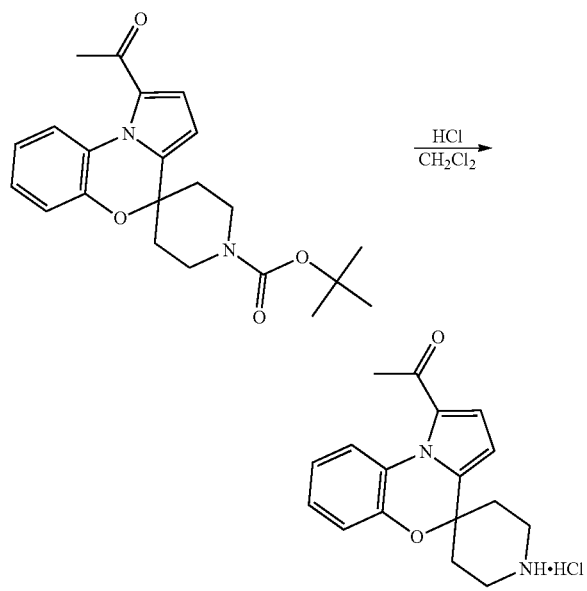

To a solution of tert-butyl 1'-acetylspiro[piperidine-4,4'-pyrrolo[2,1-c][1,4]benzoxazine]-1-carboxylate (600 mg, 1.57 mmol) in CH$_2$Cl$_2$ (6 mL) was added HCl in Dioxane (3.9 mL of 4 M, 15.7 mmol) and the mixture was stirred at room temperature for 1 hour. The mixture was evaporated to dryness to give 1-spiro[piperidine-4,4'-pyrrolo[2,1-c][1,4]benzoxazine]-1'-ylethanone hydrochloride (499 mg, 99%) which was used without further purification. ESI-MS m/z calc. 282.1. found 283.3 (M+1)+; Retention time: 0.86 minutes (3 min run).

4-(2-Methoxyethoxy)-3-methylbenzoic acid

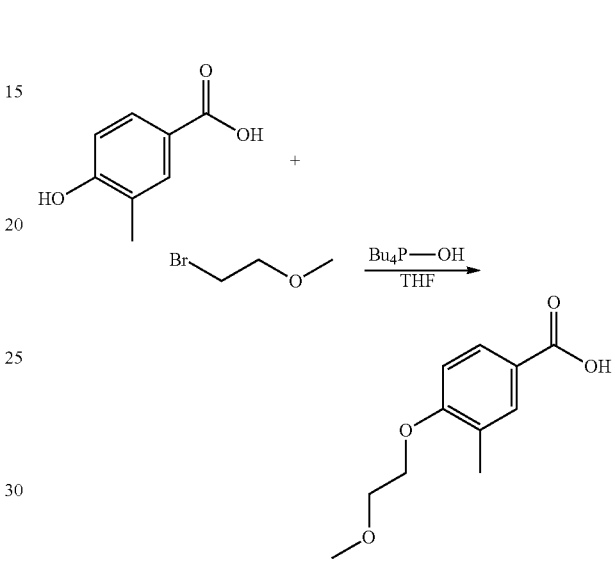

To a solution of 4-hydroxy-3-methyl-benzoic acid (2.0 g, 13 mmol) in THF (24 mL) was added tetrabutylphosphonium hydroxide (18 mL of 40% w/v, 26 mmol). The reaction mixture was cooled to 0° C. in an ice water bath and then 1-bromo-2-methoxy-ethane (1.8 g, 1.2 mL, 13 mmol) was added. The reaction mixture was then allowed to warm to room temperature and stir overnight. The reaction mixture was made acidic by addition of 1M HCl and the reaction was extracted with ethyl acetate. The organics were dried over sodium sulfate and evaporated to yield 180 mg of 4-(2-methoxyethoxy)-3-methylbenzoic acid (yield: 6%). ESI-MS m/z calc. 210.2. found 209.2 (M-H)$^-$. Retention time: 0.96 minutes (3 min run).

The following compounds were synthesized using the procedures described above: 3-methyl-4-propoxybenzoic acid, 4-(2-isopropoxyethoxy)-3-methylbenzoic acid, and 4-(3-methoxypropoxy)-3-methylbenzoic acid.

3-Cyano-4-(2-methoxyethoxy)benzoic acid

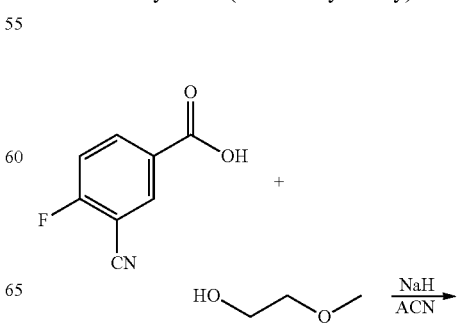

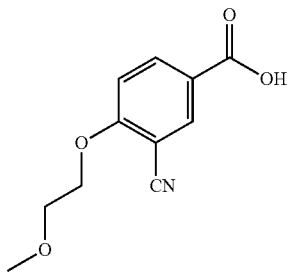

3-Cyano-4-fluorobenzoic acid (500 mg, 3.03 mmol), 2-methoxyethanol (461 mg, 6.06 mmol), and 60% w/w NaH (363 mg, 9.08 mmol) were combined in acetonitrile (15 mL) and the reaction mixture was heated at 70° C. overnight. The reaction mixture was made acidic by the addition of 1N HCl and was extracted with ethyl acetate. The organics were dried over sodium sulfate, evaporated and purified by column chromatography (0-10% methanol in dichloromethane) to yield 3-cyano-4-(2-methoxyethoxy)benzoic acid (625 mg, 93%). $^1$H NMR (400 MHz, CD$_3$CN) δ 9.60 (s, 1H), 8.26 (d, J=1.9 Hz, 1H), 8.22 (dd, J=8.9, 2.2 Hz, 1H), 7.22 (d, J=8.9 Hz, 1H), 4.34 (dd, J=5.2, 3.7 Hz, 2H), 3.79 (dd, J=5.2, 3.6 Hz, 2H), 3.41 (s, 3H).

The following compound was synthesized using the procedures described above: 3-cyano-4-propoxybenzoic acid.

3-Methoxy-4-(2-(trifluoromethoxy)ethoxy)benzoic acid

Step 1: Methyl 3-methoxy-4-(2-(trifluoromethoxy)ethoxy)benzoate

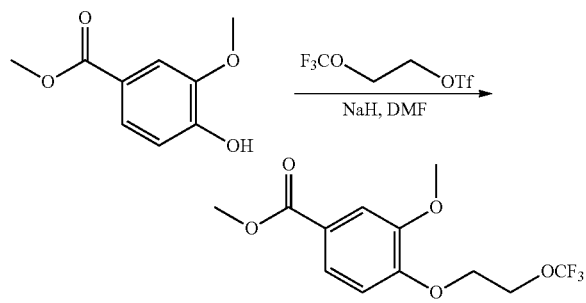

To sodium hydride (200 mg, 5.0 mmol) in DMF (6 mL) under N$_2$ was added methyl 4-hydroxy-3-methoxy-benzoate (920 mg, 5.0 mmol) and the mixture was stirred for 10 min. 2-(Trifluoromethoxy)ethyl trifluoromethanesulfonate (prepared according to the procedure described by Blazejewski, et. al. JOC, 2001, 66(3), 1061-1063) (1.2 g, 4.6 mmol) was then added dropwise and the solution was stirred at room temperature for 2 h, then at 50° C. for 2 h. The mixture was concentrated to a solid, and the residue was taken up in 50 mL of DCM before it was washed with brine (20 mL), dried over MgSO$_4$ and purified by column chromatography (0-25% EtOAc/hexane) to give methyl 3-methoxy-4-(2-(trifluoromethoxy)ethoxy)benzoate as a white solid. ESI-MS m/z calc. 294.1. found 295.3 (M+1)$^+$; Retention time: 1.63 minutes (3 min run).

Step 2: 3-Methoxy-4-(2-(trifluoromethoxy)ethoxy)benzoic acid

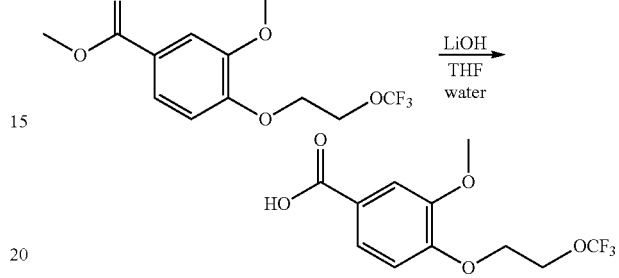

Methyl 3-methoxy-4-(2-(trifluoromethoxy)ethoxy)benzoate (crude from Step 1) was dissolved in THF (5 mL) and a suspension of LiOH (550 mg, 23 mmol) in water (5 mL) was added. The mixture was stirred vigorously and heated at 60° C. for 6 h before it was concentrated to half volume. Water (5 mL) was added and the mixture was extracted with diethyl ether (1×10 mL). The aqueous layer was acidified with 4N HCl to pH 2. The resulting mixture was extracted with ethyl acetate (3×10 mL) and the combined organics were washed (1×10 mL H$_2$O, 1×10 mL brine), dried over MgSO$_4$ and evaporated to give 3-methoxy-4-(2-(trifluoromethoxy)ethoxy)benzoic acid (1.0 g, 82%) as a white solid. ESI-MS m/z calc. 280.1. found 281.3 (M+1)$^+$; Retention time: 1.34 minutes (3 min run).

3-Methoxy-4-(2-(methylsulfonyl)ethoxy)benzoic acid

Step 1: Methyl 4-(2-bromoethoxy)-3-methoxybenzoate

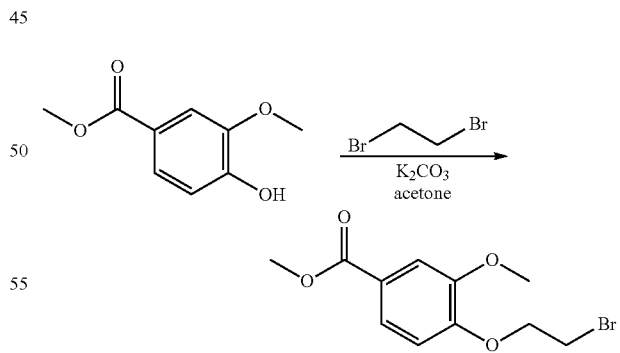

To a solution of methyl 4-hydroxy-3-methoxy-benzoate (2.0 g, 11 mmol) in acetone (330 mL) was added K$_2$CO$_3$ (6.1 g, 44 mmol) followed by 1,2-dibromoethane (6.2 g, 2.8 mL, 33 mmol). The mixture was stirred for 2 d at 75° C. The mixture was cooled to ambient temperature and the solids were removed by filtration. The filtrate was concentrated and the residue was purified by column chromatography (10-25% ethyl acetate/hexanes) to give methyl 4-(2-bromoethoxy)-3-

Step 2: Ethyl 3-methoxy-4-(2-(methylthio)ethoxy)benzoate

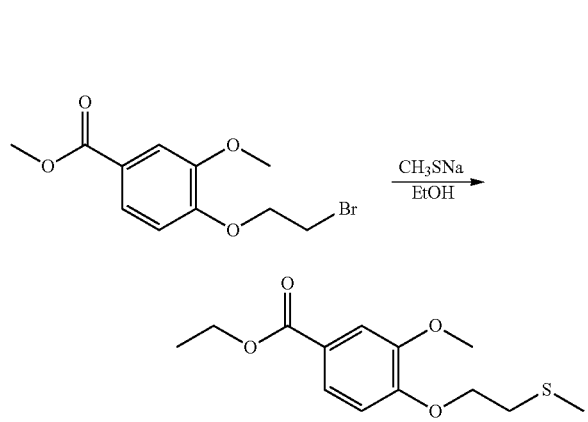

To a solution of methyl 4-(2-bromoethoxy)-3-methoxybenzoate (258 mg, 0.892 mmol) in ethanol (2 mL) was added CH₃SNa (81.3 mg, 1.16 mmol). The reaction mixture was stirred for 3 h at 90° C. before it was cooled to rt and concentrated. Column chromatography (5-25% ethyl acetate/hexanes) gave ethyl 3-methoxy-4-(2-(methylthio)ethoxy)benzoate. ESI-MS m/z calc. 270.1. found 271.5 (M+1)⁺; Retention time: 1.61 minutes (3 min run).

Step 3: Ethyl 3-methoxy-4-(2-(methylsulfonyl)ethoxy)benzoate

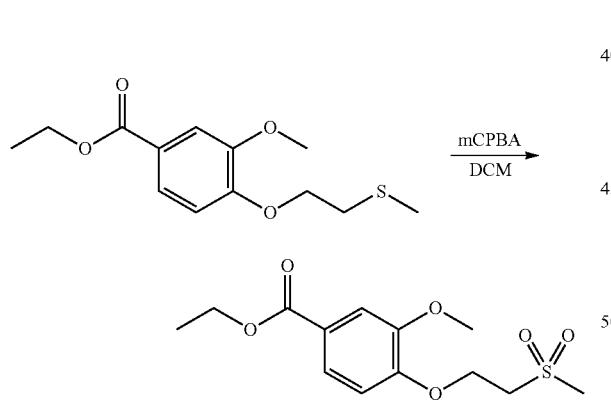

mCPBA (91 mg, 0.53 mmol) was added to a solution of ethyl 3-methoxy-4-(2-(methylthio)ethoxy)benzoate (68 mg, 0.25 mmol) in DCM (3 mL) at 0° C. The ice bath was removed, and the mixture was allowed to stir at ambient temperature for 2 h. To the mixture was added sat. aq. NaHCO₃ (2 mL) and DCM (3 mL). The layers were separated and the organic layer was washed with sat. aq. NaHCO₃ (2 mL), dried over sodium sulfate, filtered, and concentrated. The residue was purified by column chromatography (5-70% ethyl acetate/hexanes) to give ethyl 3-methoxy-4-(2-(methylsulfonyl)ethoxy)benzoate. ESI-MS m/z calc. 302.1. found 303.5 (M+1)⁺; Retention time: 1.21 minutes (3 min run).

Step 4: 3-Methoxy-4-(2-(methylsulfonyl)ethoxy)benzoic acid

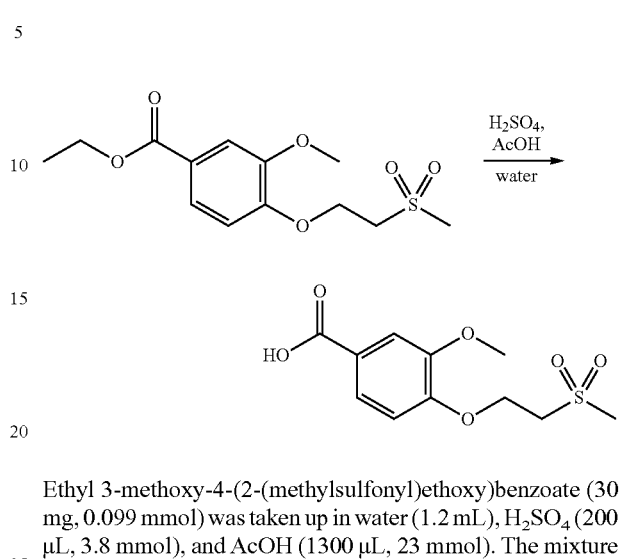

Ethyl 3-methoxy-4-(2-(methylsulfonyl)ethoxy)benzoate (30 mg, 0.099 mmol) was taken up in water (1.2 mL), H₂SO₄ (200 µL, 3.8 mmol), and AcOH (1300 µL, 23 mmol). The mixture was heated at 90° C. for 6 h before it was cooled to ambient temperature and was concentrated under vacuum. The residue was purified by column chromatography (1-40% MeOH/DCM) to give 3-methoxy-4-(2-(methylsulfonyl)ethoxy)benzoic acid. ESI-MS m/z calc. 274.1. found 275.1 (M+1)⁺; Retention time: 0.69 minutes (3 min run).

3-Carbamoyl-4-isopropoxybenzoic acid

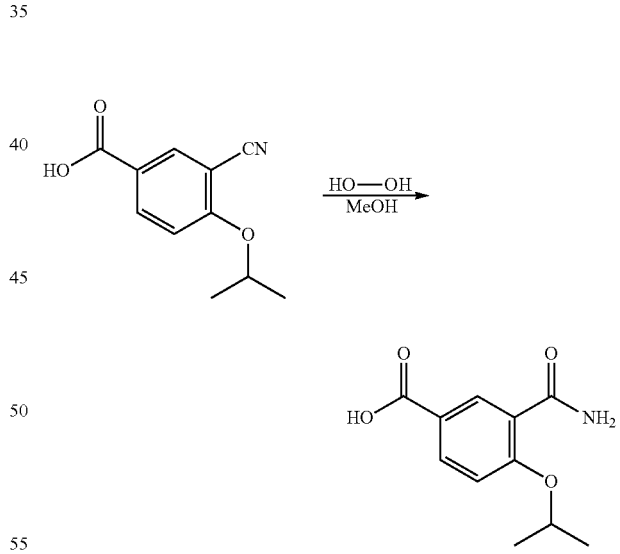

3-Cyano-4-isopropoxy-benzoic acid (50 mg, 0.24 mmol), hydrogen peroxide (280 µL of 30% w/v, 2.4 mmol), and 10% NaOH (240 µL of 10% w/v, 0.61 mmol) were combined and stirred at room temperature for 16 h. The mixture was acidified with 4M HCl and was extracted with ethyl acetate (2×7 mL). The combined organics were washed with brine, dried over sodium sulfate and evaporated to give 3-carbamoyl-4-isopropoxy-benzoic acid (45 mg, 83%). ESI-MS m/z calc. 223.1. found 224.3 (M+1)⁺; Retention time: 1.49 minutes (4 min run).

4-tert-Butoxy-3-methoxybenzoic acid

Step 1: 4-tert-Butoxy-3-methoxybenzaldehyde

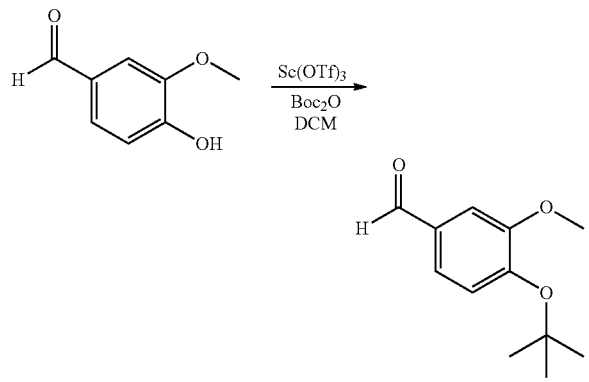

4-Hydroxy-3-methoxy-benzaldehyde (500 mg, 3.29 mmol), Boc$_2$O (1.74 g, 7.97 mmol), and Sc(OTf)$_3$ (0.080 g, 0.16 mmol) were combined in dichloromethane (5 mL). The reaction mixture was allowed to stir at room temperature for 24 h. Water (5 mL) and dichloromethane (5 mL) were added and the two phases were separated. The aqueous layer was extracted with dichloromethane (3×5 mL) and the combined organics were stirred with 10% aqueous potassium hydroxide until all remaining starting material was not observed in the organic phase (TLC, 40% ethyl acetate in hexanes). The two phases were separated and the dichloromethane layer was then washed twice with a saturated aqueous solution of sodium chloride, dried over sodium sulfate, filtered, and evaporated to dryness to give 4-tert-butoxy-3-methoxybenzaldehyde (130 mg, 19%) as a yellow oil. Rf=0.66 (SiO$_2$, 40% ethyl acetate in hexanes); ESI-MS m/z calc. 208.1. found 209.2 (M+1)$^+$. Retention time: 0.96 minutes (6 min run).

Step 2: 4-tert-Butoxy-3-methoxybenzoic acid

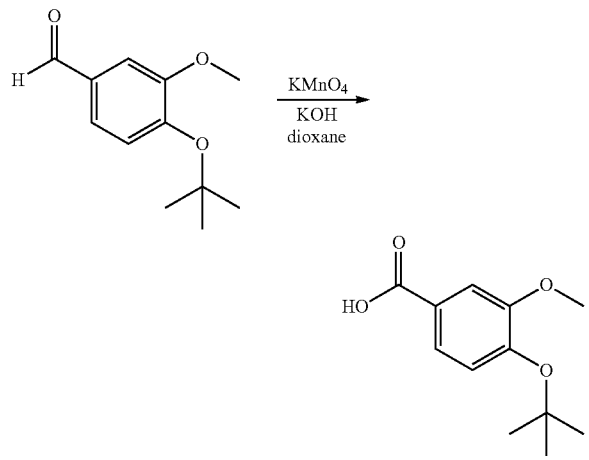

4-tert-Butoxy-3-methoxybenzaldehyde (130 mg, 0.62 mmol) was suspended in a mixture of dioxane (520 µL) and potassium hydroxide (6.5 mL of 0.20 M, 1.3 mmol). KMnO$_4$ (150 mg, 0.93 mmol) was added and the reaction was stirred vigorously for 16 h. The reaction mixture was filtered and then concentrated to 3 mL. Hydrochloric acid (1M, 4 mL) was added and the resulting precipitate was filtered (after standing for 15 minutes) and washed with 1M HCl and a small amount of water to yield 4-tert-butoxy-3-methoxy-benzoic acid (68 mg, 49%) as a white solid. Rf=0.23 (SiO$_2$, 40% ethyl acetate in hexanes); ESI-MS m/z calc. 224.1. found 225.2 (M+1)$^+$. Retention time: 1.66 minutes (3 min run). $^1$H NMR (400 MHz, DMSO) δ 12.80 (s, 1H), 7.66-7.41 (m, 2H), 7.09 (d, J=8.8 Hz, 1H), 3.78 (s, 3H), 1.32 (s, 9H).

The following compounds were synthesized using the procedures described above: 4-tert-butoxy-3-methylbenzoic acid from 4-hydroxy-3-methylbenzaldehyde, 2-fluoro-4,5-dimethoxybenzoic acid from 2-fluoro-4,5-dimethoxybenzaldehyde, 4-tert-butoxy-2-methoxybenzoic acid from 4-hydroxy-2-methoxybenzaldehyde, 4-tert-butoxy-2-fluorobenzoic acid from 2-fluoro-4-hydroxybenzaldehyde, and 4-tert-butoxybenzoic acid from 4-hydroxybenzaldehyde.

2-Fluoro-5-methoxy-4-(2-methoxyethoxy)benzoic acid

Step 1: 2-Fluoro-4-hydroxy-5-methoxybenzaldehyde

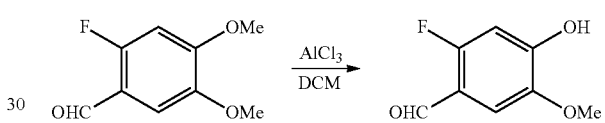

AlCl$_3$ (8.69 g, 65.2 mmol) was added to a solution of 2-fluoro-4,5-dimethoxy-benzaldehyde (2.00 g, 10.9 mmol) in DCM (100 mL) under an atmosphere of argon. The reaction mixture was allowed to stir at room temperature for 16 h. The reaction mixture was slowly quenched with water. The layers were separated and the aqueous layer was then extracted with ethyl acetate (3×). The combined organic layers were dried over sodium sulfate and then evaporated to dryness to yield 2-fluoro-4-hydroxy-5-methoxy-benzaldehyde (1.82 g, 98%) as an off white solid. ESI-MS m/z calc. 170.0. found 171.0 (M+1)$^+$. Retention time: 0.84 minutes (3 min run). $^1$H NMR (400 MHz, DMSO) δ 10.04 (s, 1H), 7.22 (d, J=6.7 Hz, 1H), 6.73 (d, J=11.9 Hz, 1H), 3.81 (s, 3H).

Step 2: 2-Fluoro-5-methoxy-4-(2-methoxyethoxy)benzaldehyde

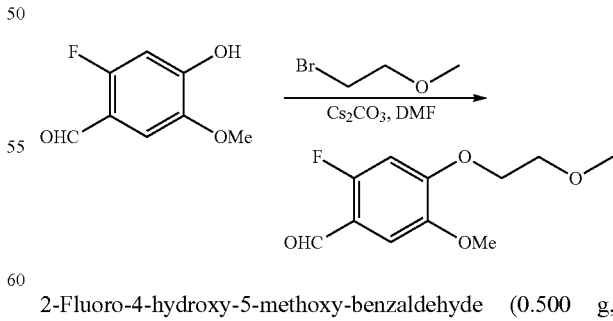

2-Fluoro-4-hydroxy-5-methoxy-benzaldehyde (0.500 g, 2.94 mmol) was dissolved in DMF (2.6 mL) containing Cs$_2$CO$_3$ (2.88 g, 8.82 mmol). 1-Bromo-2-methoxy-ethane (1.23 g, 828 µL, 8.82 mmol) was added and the reaction mixture was allowed to stir for 86 h. The reaction mixture was filtered and the filtrate was evaporated to dryness to give 2-fluoro-5-methoxy-4-(2-methoxyethoxy)benzaldehyde.

ESI-MS m/z calc. 228.1. found 229.0 (M+1)+. Retention time: 1.14 minutes (3 min run).

Step 3:
2-Fluoro-5-methoxy-4-(2-methoxyethoxy)benzoic acid

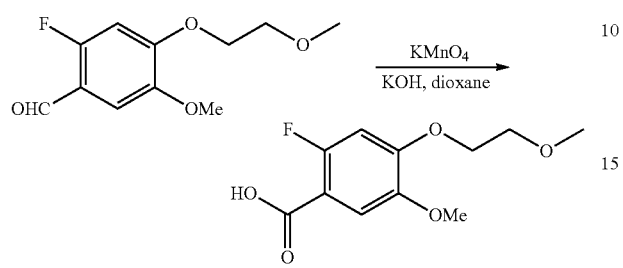

2-Fluoro-5-methoxy-4-(2-methoxyethoxy)benzaldehyde (0.36 g, 1.6 mmol) was suspended in a mixture of dioxane (1.5 mL) and KOH (16 mL of 0.2 M, 3.2 mmol). KMnO$_4$ (370 mg, 2.4 mmol) was added and the mixture was stirred vigorously for 30 minutes. The reaction mixture was filtered and the filtrate was concentrated to 10 mL (blue soln). HCl (4M, ~2 mL) was added and the resulting precipitate was filtered and washed with 1M HCl and then water (1 mL) to yield 2-fluoro-5-methoxy-4-(2-methoxyethoxy)benzoic acid (300 mg, 78%) as a white solid. ESI-MS m/z calc. 244.1. found 245.1 (M+1)+. Retention time: 1.01 minutes (3 min run). $^1$H NMR (400 MHz, DMSO) δ 12.96 (s, 1H), 7.30 (d, J=7.0 Hz, 1H), 6.98 (d, J=12.5 Hz, 1H), 4.20-4.13 (m, 2H), 3.78 (s, 3H), 3.71-3.63 (m, 2H), 3.31 (s, 3H).

4-tert-Butyl-3-cyanobenzoic acid

Step 1: Methyl 3-bromo-4-tert-butyl-benzoate

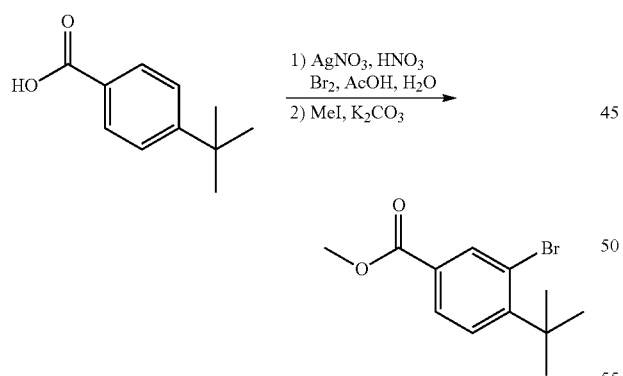

4-tert-Butylbenzoic acid (3.00 g, 16.8 mmol) was mixed with nitric acid (11 mL), water (8.4 mL), glacial acetic acid (51 mL), and bromine (2.9 g, 19 mmol) in a two-neck flask containing an addition funnel and a reflux condenser. An aqueous solution of silver nitrate (2.9 g, 17 mmol) in water (8.5 mL) was added dropwise over 30 minutes with vigorous stirring. The mixture was stirred at room temperature for 16 h before it was poured into ice water. The solids were collected by vacuum filtration. The solids were taken up in ethyl acetate and were washed with water, then brine. The organic layer was dried over sodium sulfate and was concentrated in vacuo to give 3.2 g of a solid that was taken up in DMF (10 mL). To the solution was added potassium carbonate (4.7 g, 34 mmol) and methyl iodide (4.8 g, 34 mmol). The mixture was concentrated to dryness and the residue was dissolved in dichloromethane and washed with a 1N HCl solution, then brine. The organics were dried over sodium sulfate and evaporated. The crude material was purified by column chromatography (0-10% ethyl acetate in hexanes) to give methyl 3-bromo-4-tert-butyl-benzoate (2.26 g, 25%). $^1$H NMR (400 MHz, CD$_3$CN) δ 8.19 (d, J=1.9 Hz, 1H), 7.91 (dd, J=8.3, 1.9 Hz, 1H), 7.65 (d, J=8.3 Hz, 1H), 3.89 (s, 3H), 1.54 (s, 9H).

Step 2: Methyl 4-tert-butyl-3-cyanobenzoate

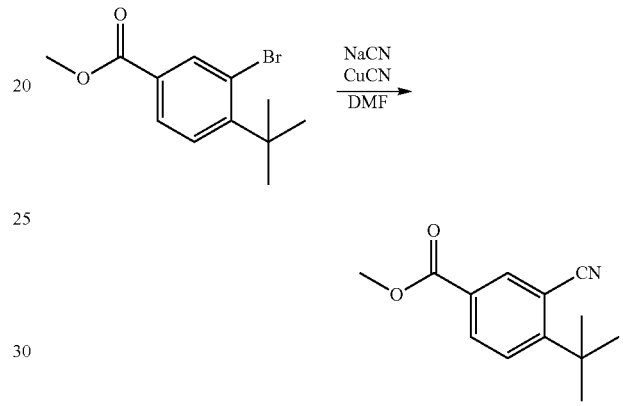

Methyl 3-bromo-4-tert-butyl-benzoate (2.26 g, 4.17 mmol) was dissolved in dry DMF (2.1 mL) before CuCN (821 mg, 9.17 mmol) and NaCN (1.0 mg, 0.021 mmol) were added. The mixture was flushed with nitrogen and was stirred at 110° C. for 24 h. The reaction mixture was diluted with ethyl acetate (70 mL) and was washed with water. The organics were dried over sodium sulfate and were evaporated to dryness. The crude material was purified by column chromatography eluting with 0-10% ethyl acetate in hexanes to give methyl 4-tert-butyl-3-cyano-benzoate (390 mg, 43%). ESI-MS m/z calc. 217.1. found 218.5 (M+1)+; Retention time: 2.07 minutes (3 min run). NMR (400 MHz, CD$_3$CN) δ 8.31 (d, J=1.8 Hz, 1H), 8.16 (dd, J=8.4, 2.0 Hz, 1H), 7.72 (d, J=8.4 Hz, 1H), 3.92 (s, 3H), 1.55 (s, 9H).

Step 3: 4-tert-Butyl-3-cyanobenzoic acid

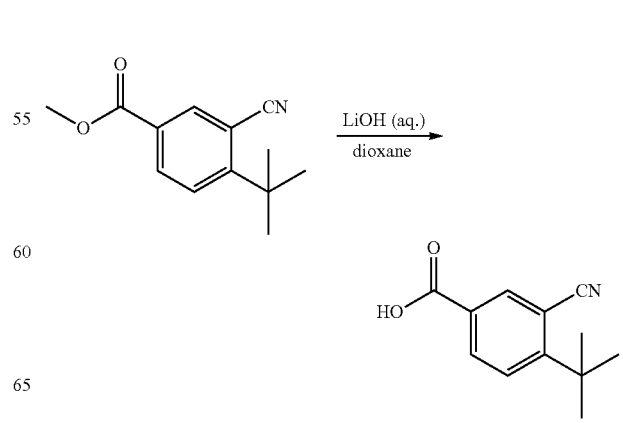

A mixture of methyl 4-tert-butyl-3-cyano-benzoate (380 mg, 1.75 mmol), LiOH (3.5 mL of 2.0 M, 7.0 mmol) and 1,4-dioxane (3.5 mL) was heated at 60° C. for 2 h. The reaction mixture was made acidic and was washed with dichloromethane (2×8 mL). The organics were combined, dried over sodium sulfate and evaporated to dryness to give 4-tert-butyl-3-cyanobenzoic acid (348 mg, 98%). $^1$H NMR (400 MHz, CD$_3$CN) δ 9.77 (s, 1H), 8.31 (d, J=1.8 Hz, 1H), 8.17 (dd, J=8.4, 1.9 Hz, 1H), 7.71 (d, J=8.4 Hz, 1H), 1.55 (s, 9H). 4-Cyano-3-methylbenzoic acid was also prepared using the procedures described above.

(R)-3-Methoxy-4-(tetrahydrofuran-3-yloxy)benzoic acid

Step 1: (R)-Methyl 3-methoxy-4-(tetrahydrofuran-3-yloxy)benzoate

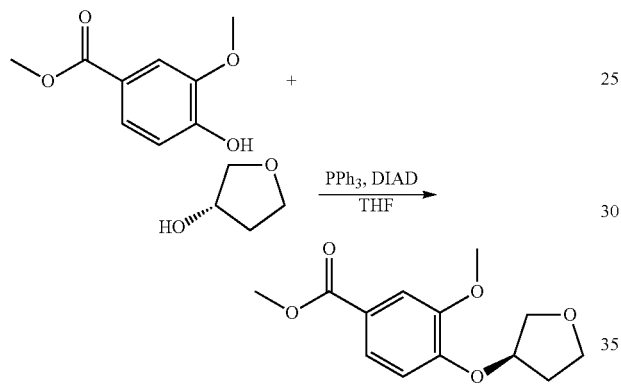

To a stirred solution of (3S)-tetrahydrofuran-3-ol (403 mg, 4.57 mmol), methyl 4-hydroxy-3-methoxy-benzoate (1.00 g, 5.49 mmol) and triphenylphosphane (1.44 g, 1.27 mL, 5.49 mmol) in THF (13 mL) at 0° C. was added DIAD (1.11 g, 1.06 mL, 5.49 mmol). The ice bath was removed and the reaction mixture was stirred at room temperature for 16 h, then at 55° C. for 4 h. The mixture was diluted with EtOAc and was washed with sat. aq. NaHCO$_3$ (×2) and brine (×2). The organic layer was dried over Na$_2$SO$_4$, filtered and the solvent was evaporated under reduced pressure. The crude product was purified by column chromatography on silica gel (0-30% ethyl acetate in hexane) to yield (R)-methyl 3-methoxy-4-(tetrahydrofuran-3-yloxy)benzoate (0.97 g, 84%) as a viscous liquid. ESI-MS m/z calc. 252.1. found 253.3 (M+1)$^+$; Retention time: 1.72 minutes (3 min run).

Step 2: (R)-3-methoxy-4-(tetrahydrofuran-3-yloxy)benzoic acid

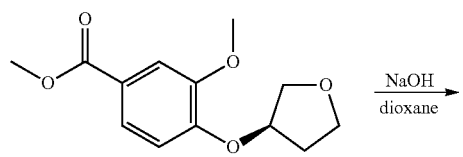

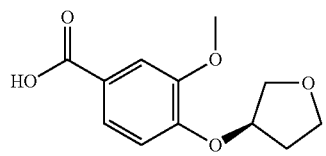

To (R)-methyl 3-methoxy-4-(tetrahydrofuran-3-yloxy)benzoate (0.95 g, 3.8 mmol) were added dioxane (10 mL) and NaOH (10 mL, 1M) and the mixture was heated at 80° C. for 0.5 h. The solvent was evaporated under reduced pressure and the residue was dissolved in water and was washed with EtOAc (×3). The aqueous layer was acidified and a solid was formed. The aqueous layer (with the solid) was washed with EtOAc (×3). The combined organics were dried over Na$_2$SO$_4$, filtered and the solvent was evaporated under reduced pressure to yield (R)-3-methoxy-4-(tetrahydrofuran-3-yloxy) benzoic acid (0.71 g, 79%) as a white solid. ESI-MS m/z calc. 238.1. found 239.3 (M+1)$^+$; Retention time: 1.21 minutes (4 min run). $^1$H NMR (400 MHz, DMSO) δ 12.70 (s, 1H), 7.54 (dd, J=8.3, 1.4 Hz, 1H), 7.46 (d, J=1.3 Hz, 1H), 7.03 (d, J=8.4 Hz, 1H), 5.13-5.02 (m, 1H), 4.04-3.62 (m, 7H), 2.40-2.12 (m, 1H), 2.10-1.86 (m, 1H).

The following compounds were synthesized using the procedures described above: (R)-4-((2,2-dimethyl-1,3-dioxolan-4-yl)methoxy)-3-methoxybenzoic acid, (S)-4-((2,2-dimethyl-1,3-dioxolan-4-yl)methoxy)-3-methoxybenzoic acid, and 4-(3-hydroxycyclopentyloxy)-3-methoxybenzoic acid.

3-Methoxy-4-(2-methoxy-2-methylpropoxy)benzoic acid

Step 1: Methyl 3-methoxy-4-(2-methylallyloxy)benzoate

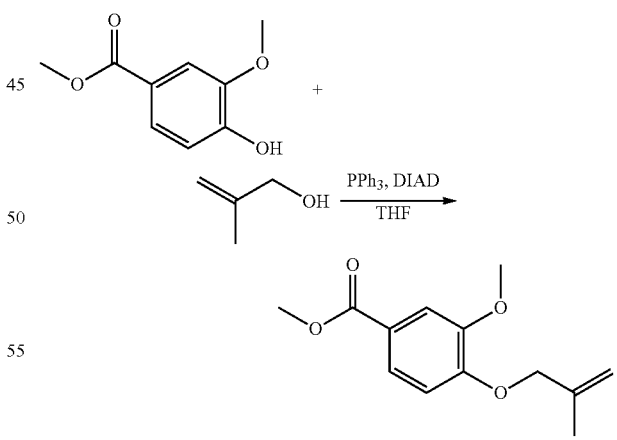

Methyl 3-methoxy-4-(2-methylallyloxy)benzoate was synthesized using the procedure described above. ESI-MS m/z calc. 236.1. found 237.1 (M+1)$^+$; Retention time: 1.63 minutes (3 min run). $^1$H NMR (400 MHz, DMSO) δ 7.56 (dd, J=8.4, 2.0 Hz, 1H), 7.47 (d, J=1.9 Hz, 1H), 7.06 (d, J=8.5 Hz, 1H), 5.07 (br s, 1H), 4.97 (br s, 1H), 4.55 (s, 2H), 3.83 (s, 3H), 3.82 (s, 3H), 1.78 (s, 3H).

Step 2: Methyl 3-methoxy-4-(2-methoxy-2-methylpropoxy)benzoate

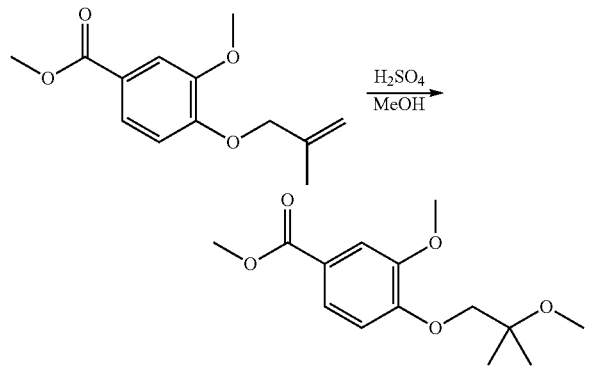

To methyl 3-methoxy-4-(2-methylallyloxy)benzoate (313 mg, 1.33 mmol) in MeOH (2.5 mL) was added H$_2$SO$_4$ (71 µL, 1.3 mmol) and the mixture was heated in a microwave vial at 100° C. for 15.5 h. The solvent was evaporated under reduced pressure and the crude product was purified by column chromatography on silica gel (0-30% ethyl acetate in hexane) to yield methyl 3-methoxy-4-(2-methoxy-2-methyl-propoxy) benzoate (208 mg, 59%). ESI-MS m/z calc. 268.1. found 269.5 (M+1)$^+$; Retention time: 1.46 minutes (3 min run). $^1$H NMR (400 MHz, DMSO) δ 7.57 (dd, J=8.4, 2.0 Hz, 1H), 7.45 (d, J=1.9 Hz, 1H), 7.10 (d, J=8.5 Hz, 1H), 3.90 (s, 2H), 3.83 (s, 3H), 3.82 (s, 3H), 3.17 (s, 3H), 1.22 (s, 6H).

Step 3: 3-Methoxy-4-(2-methoxy-2-methylpropoxy)benzoic acid

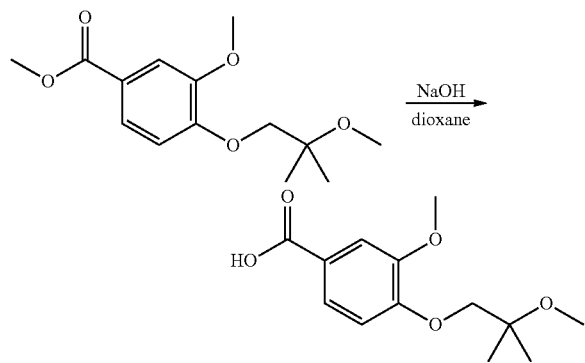

Methyl 3-methoxy-4-(2-methoxy-2-methyl-propoxy)benzoate (177 mg, 0.660 mmol), dioxane (1.9 mL) and NaOH (1.8 mL of 1.0 M, 1.8 mmol) were combined and the mixture was heated at 80° C. for 15 min. The solvent was evaporated under reduced pressure and the crude mixture was dissolved in water. The mixture was extracted with EtOAc (3×). The aqueous layer was acidified with 1N HCl before it was extracted with EtOAc (3×). The combined organic layers were dried over Na$_2$SO$_4$, filtered and the solvent was evaporated under reduced pressure to yield 3-methoxy-4-(2-methoxy-2-methyl-propoxy)benzoic acid (130 mg, 77%). ESI-MS m/z calc. 254.1. found 255.5 (M+1)$^+$; Retention time: 1.14 minutes (3 min run). $^1$H NMR (400 MHz, DMSO) δ 12.61 (s, 1H), 7.54 (dd, J=8.4, 1.9 Hz, 1H), 7.45 (d, J=1.8 Hz, 1H), 7.07 (d, J=8.5 Hz, 1H), 3.89 (s, 2H), 3.81 (s, 3H), 3.17 (s, 3H), 1.22 (s, 6H).

4-((1R,2R)-2-Hydroxycyclopentyloxy)-3-methoxybenzoic acid

Step 1: Methyl 4-((1R,2R)-2-hydroxycyclopentyloxy)-3-methoxybenzoate

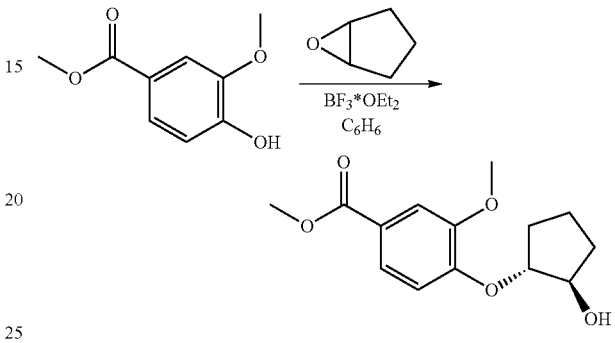

6-Oxabicyclo[3.1.0]hexane (2.43 g, 2.50 mL, 28.9 mmol) was added dropwise to a stirred solution of methyl 4-hydroxy-3-methoxy-benzoate (5.26 g, 28.9 mmol) and BF$_3$.OEt$_2$ (410 mg, 369 µL, 2.89 mmol) in benzene (10 mL) at ambient temperature. The mixture was stirred at room temperature overnight before it was diluted with ethyl acetate and was washed with 1N NaOH. The organic layer was dried over sodium sulfate, filtered and evaporated. The residue was purified by column chromatography eluting with 0-100% EtOAc in hexanes to give methyl 4-((1R,2R)-2-hydroxycyclopentyloxy)-3-methoxybenzoate. ESI-MS m/z calc. 266.1. found 267.1 (M+1)$^+$; Retention time: 1.16 minutes (3 min run).

Step 2: 4-((1R,2R)-2-Hydroxycyclopentyloxy)-3-methoxybenzoic acid

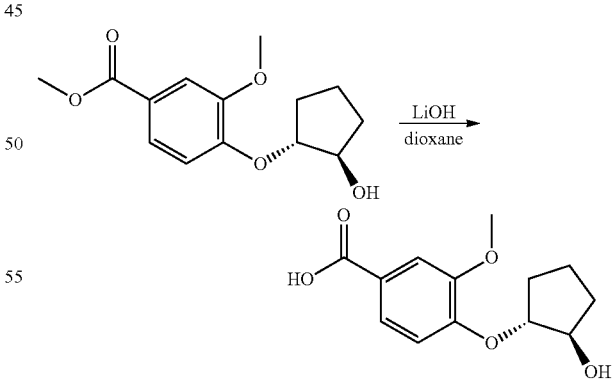

A solution of methyl 4-[(1R,2R)-2-hydroxycyclopentoxy]-3-methoxy-benzoate (2.8 g, 11 mmol) and LiOH (21 mL of 2.0 M, 42 mmol) in dioxane (20 mL) was stirred at 50° C. overnight. The mixture was diluted with ethyl acetate and was washed with water. The aqueous layer was acidified with 1N HCl and the product was extracted into ethyl acetate. The organics were dried over sodium sulfate, filtered and evaporated to give 4-((1R,2R)-2-hydroxycyclopentyloxy)-3-methoxybenzoic acid. ESI-MS m/z calc. 252.1. found 253.5 (M+1)⁺; Retention time: 1.07 minutes (3 min run).

4-(2-Methoxyethoxy)-3-(trifluoromethyl)benzoic acid

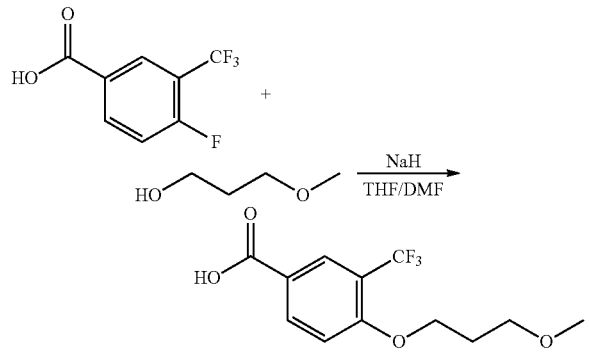

3-Methoxypropan-1-ol (217 mg, 2.40 mmol), 4-fluoro-3-(trifluoromethyl)benzoic acid (500 mg, 2.40 mmol), and NaH (240 mg, 6.0 mmol) were combined in THF (10 mL) and DMF (1 mL) at 0° C. under an atmosphere of nitrogen. The reaction mixture was stirred for 16 h at room temperature. The reaction mixture was partitioned between ethyl acetate and a 1M aqueous solution of hydrochloric acid. The layers were separated and then the organic layer was washed with a saturated aqueous solution of sodium chloride, dried over sodium sulfate, and evaporated to dryness. The crude material was purified by column chromatography utilizing a gradient of 0-5% methanol in dichloromethane to yield 4-(3-methoxypropoxy)-3-(trifluoromethyl)benzoic acid (213 mg, 32%) as a white solid. ESI-MS m/z calc. 278.1. found 279.3 (M+1)⁺; Retention time: 1.38 minutes (3 min run).
4-Propoxy-3-(trifluoromethyl)benzoic acid was prepared from 4-fluoro-3-(trifluoromethyl)benzoic acid and 3-fluoro-4-(2-methoxyethoxy)benzoic acid was prepared from 3,4-difluorobenzoic acid using the procedure described above.

4-(2-Hydroxypropan-2-yl)-3-methoxybenzoic acid

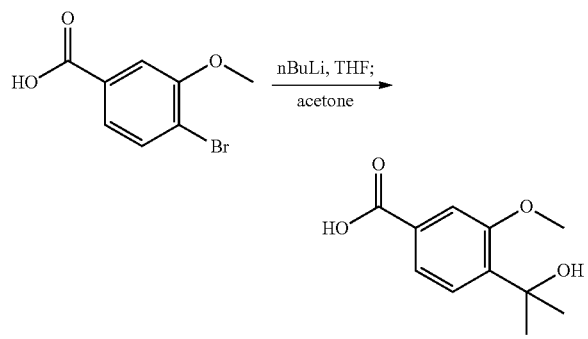

4-Bromo-3-methoxy-benzoic acid (2.00 g, 8.67 mmol) was dissolved in THF (50 mL) and the solution was cooled to −78° C. n-BuLi in hexanes (7.6 mL of 2.5 M, 19 mmol) was added dropwise over 15 minutes. The reaction mixture was allowed to stir for 30 minutes at −78° C. and then acetone (640 µL, 8.9 mmol) was added in a dropwise manner. The reaction mixture was allowed to stir for 30 minutes at −78° C., and then it was allowed to warm to room temperature. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography utilizing a gradient of 0-5% methanol in dichloromethane to give 4-(2-hydroxypropan-2-yl)-3-methoxybenzoic acid (618 mg, 34%). ESI-MS m/z calc. 210.1. found 209.1 (M−1)⁻; Retention time: 0.68 minutes (3 min run).

4-(3-Hydroxyoxetan-3-yl)-3-methoxybenzoic acid was also prepared using the method described above. ESI-MS m/z calc. 224.1. found 223 (M−1)⁻; Retention time: 0.69 minutes (3 min run).

1-(2-Methoxyethyl)-2-oxo-1,2-dihydropyridine-4-carboxylic acid

Step 1: Methyl 1-(2-methoxyethyl)-2-oxo-1,2-dihydropyridine-4-carboxylate and methyl 2-(2-methoxyethoxy)isonicotinate

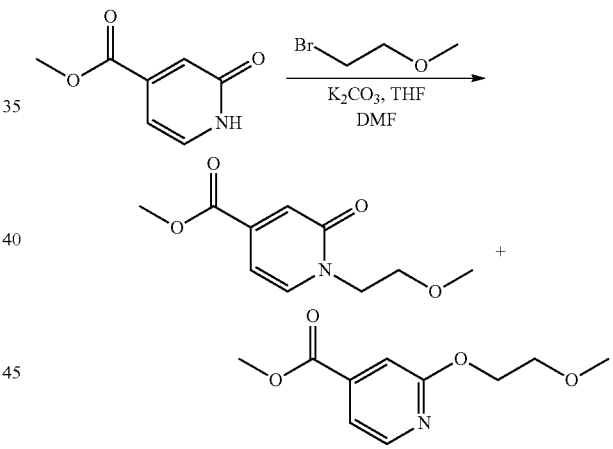

Methyl 2-oxo-1H-pyridine-4-carboxylate (2.00 g, 13.1 mmol), K₂CO₃ (3.61 g, 26.1 mmol), THF (48 mL), DMF (38 mL) and 1-bromo-2-methoxy-ethane (3.63 g, 2.45 mL, 26.1 mmol) were combined and the mixture was stirred at 80° C. for 2 d. The reaction was filtered using ethyl acetate and the solvent was evaporated under reduced pressure and the residue was purified by column chromatography on silica gel (0-100% ethyl acetate in hexane) to yield methyl 1-(2-methoxyethyl)-2-oxo-1,2-dihydropyridine-4-carboxylate [(1.22 g, 44%), ESI-MS m/z calc. 211.1. found 212.3 (M+1)⁺; Retention time: 0.57 minutes (3 min run); ¹H NMR (400 MHz, DMSO) δ 8.35 (d, J=5.2 Hz, 1H), 7.41 (d, J=5.2 Hz, 1H), 7.21 (s, 1H), 4.47-4.36 (m, 2H), 3.89 (s, 3H), 3.71-3.64 (m, 2H), 3.30 (s, 3H)] and methyl 2-(2-methoxyethoxy)isonicotinate [(405 mg), ESI-MS m/z calc. 211.1. found 212.1 (M+1)⁺; Retention time: 1.04 minutes (3 min run); ¹H NMR (400 MHz, DMSO) δ 7.75 (d, J=7.0 Hz, 1H), 6.86 (s, 1H), 6.55 (d, J=7.0 Hz, 1H), 4.09 (t, J=5.2 Hz, 2H), 3.85 (s, 3H), 3.58 (t, J=5.2 Hz, 2H), 3.23 (s, 3H)].

Step 2: 1-(2-Methoxyethyl)-2-oxo-1,2-dihydropyridine-4-carboxylic acid

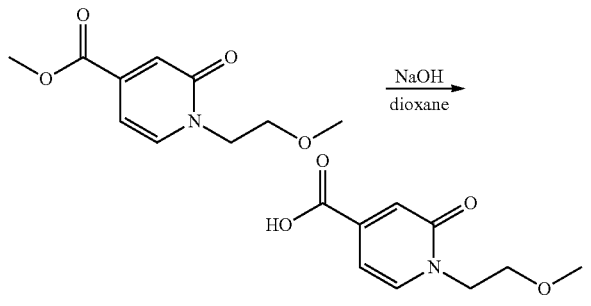

Methyl 1-(2-methoxyethyl)-2-oxo-pyridine-4-carboxylate (1.56 g, 7.39 mmol), dioxane (16 mL) and NaOH (20 mL of 1M, 20 mmol) were combined and the mixture was heated at 80° C. for 50 min. The solvent was evaporated under reduced pressure and the residue was dissolved in water before it was washed with EtOAc (3×). The aqueous layer was acidified with 1N HCl and was washed with EtOAc (3×). The combined organic layers were dried over $Na_2SO_4$, filtered and the solvent was evaporated under reduced pressure to yield 1-(2-methoxyethyl)-2-oxo-pyridine-4-carboxylic acid (1.0 g, 69%) as a white solid. ESI-MS m/z calc. 197.2. found 198.3 (M+1)+; Retention time: 0.29 minutes (3 min run); NMR (400 MHz, DMSO) δ 13.59 (s, 1H), 7.72 (d, J=7.0 Hz, 1H), 6.84 (d, J=1.6 Hz, 1H), 6.53 (dd, J=7.0, 1.6 Hz, 1H), 4.08 (t, J=5.2 Hz, 2H), 3.58 (t, J=5.2 Hz, 2H), 3.23 (s, 3H).

2-(2-Methoxyethoxy)isonicotinic acid

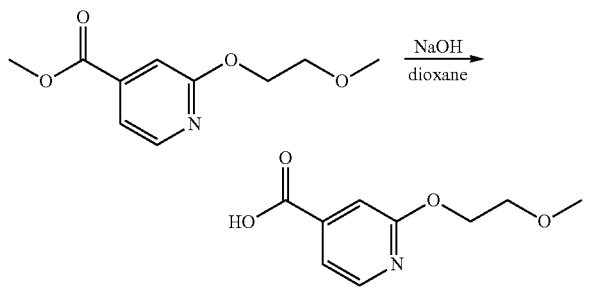

Methyl 2-(2-methoxyethoxy)pyridine-4-carboxylate (562 mg, 2.66 mmol), dioxane (6 mL) and NaOH (7.1 mL of 1M, 7.1 mmol) were combined and the mixture was heated at 80° C. for 50 min. The solvent was evaporated under reduced pressure and the residue was dissolved in water before it was washed with EtOAc (3×). The aqueous layer was acidified with 1N HCl and was washed with EtOAc (3×). The combined organic layers were dried over $Na_2SO_4$, filtered and the solvent was evaporated under reduced pressure to yield 2-(2-methoxyethoxy)pyridine-4-carboxylic acid (457 mg, 87%) as a white solid. ESI-MS m/z calc. 197.2. found 198.3 (M+1)+; Retention time: 0.66 minutes (3 min run); 1H NMR (400 MHz, DMSO) δ 13.64 (s, 1H), 8.32 (d, J=5.2 Hz, 1H), 7.39 (d, J=5.2 Hz, 1H), 7.18 (s, 1H), 4.51-4.27 (m, 2H), 3.78-3.54 (m, 2H), 3.30 (s, 3H).

4-tert-Butyl-3-hydroxybenzoic acid

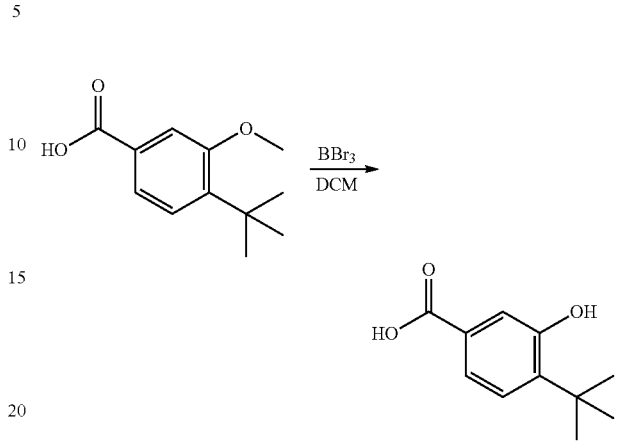

To a stirring solution of 4-tert-butyl-3-methoxy-benzoic acid (400 mg, 1.92 mmol) in anhydrous DCM (9 mL) under $N_2$ at −78° C. was added $BBr_3$ (5.76 mL of 1M in DCM, 5.763 mmol) dropwise over 30 minutes. The mixture was allowed to stir at −78° C. for 1 hour, allowed to warm to room temperature over 1 hour and then stirred at room temperature for 1 hour. The mixture was poured onto crushed ice and was stirred for 10 minutes. The organic layer was removed and the aqueous layer was extracted with DCM (3×). The combined organics were combined, dried over $Na_2SO_4$ and then concentrated under reduced pressure to give 4-tert-butyl-3-hydroxybenzoic acid. ESI-MS m/z calc. 194.1. found 195.1 (M+1)+; Retention time: 1.45 minutes (3 min run); 1H NMR (400 MHz, DMSO) δ 12.50 (s, 1H), 9.71 (s, 1H), 7.39 (d, J=1.1 Hz, 1H), 7.32 (dd, J=8.0 Hz, 1.1 Hz, 1H), 7.24 (d, J=8.1 Hz, 1H), 1.35 (s, 9H).

4-Ethyl-3-hydroxybenzoic acid

Step 1: 4-Ethyl-3-methoxybenzoic acid

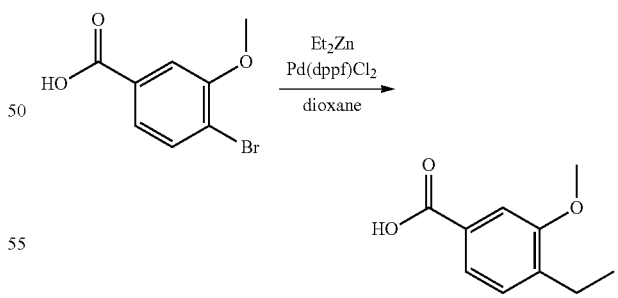

A mixture of 4-bromo-3-methoxy-benzoic acid (2.49 g, 10.9 mmol) and Pd(dppf)Cl₂ (158 mg, 0.216 mmol) were stirred in dioxane (25 mL) and Et₂Zn (22 mL, 1M in hexanes, 22 mmol) was added. The reaction mixture was heated at 70° C. for 1 h. The mixture was cooled to room temperature and was quenched with MeOH (1.1 mL). The solution was diluted with ethyl acetate (20 mL) and was washed with 1N HCl (10 mL). The combined organics were washed with brine, dried over sodium sulfate and evaporated to dryness to give 4-ethyl- 3-methoxybenzoic acid. ESI-MS m/z calc. 180.1. found 179.1 (M−1)⁻; Retention time: 1.77 minutes (3 min run).

Step 2: 4-Ethyl-3-hydroxybenzoic acid

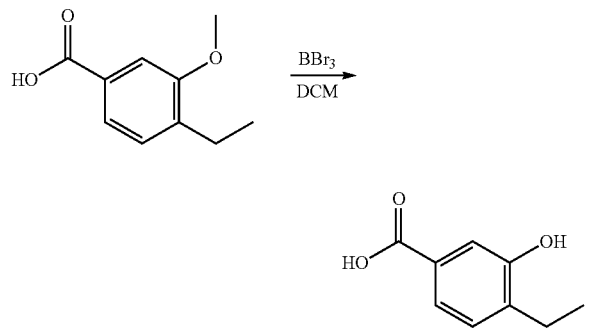

4-Ethyl-3-hydroxybenzoic acid was prepared using the method described above. ESI-MS m/z calc. 166.1. found 167.1 (M+1)⁺; Retention time: 1.09 minutes (3 min run). $^1$H NMR (400 MHz, DMSO) δ 12.62 (s, 1H), 9.64 (s, 1H), 7.37 (d, J=1.5 Hz, 1H), 7.33 (dd, J=7.8, 1.5 Hz, 1H), 7.17 (d, J=7.8 Hz, 1H), 2.57 (q, J=7.5 Hz, 2H), 1.12 (t, J=7.5 Hz, 3H).

4-Ethyl-3-methylbenzoic acid was also prepared using the procedures described above.

3-Methoxy-4-(1-methoxy-2-methyl-1-oxopropan-2-yl)benzoic acid

Step 1: tert-Butyl 4-bromo-3-methoxybenzoate

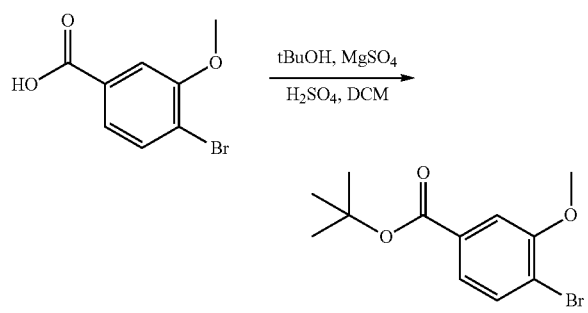

MgSO₄ (4.82 g, 40.0 mmol), DCM (40 mL), and H₂SO₄ (533 µL, 10.0 mmol) were combined at 0° C. and the mixture was allowed to stir for 30 minutes at 0° C. 4-Bromo-3-methoxybenzoic acid (2.31 g, 10.0 mmol) and 2-methylpropan-2-ol (4.78 mL, 50.0 mmol) were added and the mixture was allowed to stir at rt overnight. The mixture was filtered to remove the MgSO₄ and the filtrate was washed with 1N NaOH. The layers were separated and the organic layer was dried over sodium sulfate and the solvent was removed to yield 400 mg of tert-butyl 4-bromo-3-methoxybenzoate. ESI-MS m/z calc. 286.0. found 287.0 (M+1)⁺; Retention time: 3.11 minutes (4 min run).

Step 2: tert-Butyl 3-methoxy-4-(1-methoxy-2-methyl-1-oxopropan-2-yl)benzoate

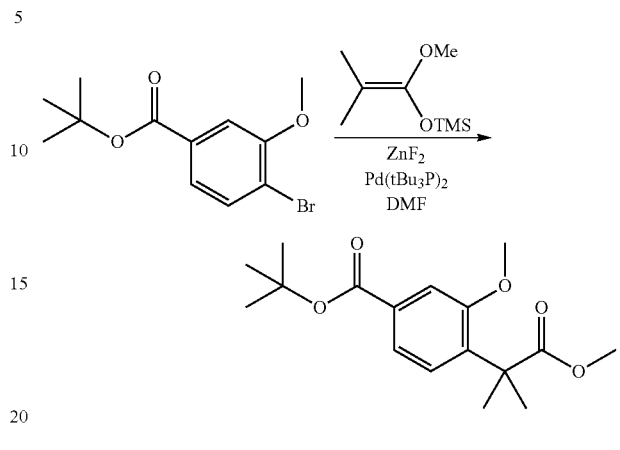

To a microwave vial was added ZnF₂ (36 mg, 0.35 mmol) and Pd(tBu₃P)₂ (7.2 mg, 0.014 mmol). The reaction vessel was purged with nitrogen for 10 minutes before tert-butyl 4-bromo-3-methoxy-benzoate (200 mg, 0.70 mmol) dissolved in DMF (2.5 mL) was added followed by (1-methoxy-2-methyl-prop-1-enoxy)-trimethyl-silane (180 mg, 1.1 mmol). The reaction vessel was placed in an 80° C. oil bath under an atmosphere of nitrogen and the mixture was allowed to stir overnight. The mixture was allowed to cool to rt and was filtered through a frit and was washed with brine and EtOAc. The organics were separated and dried over sodium sulfate. The solvent was removed and the residue was taken on to the next step without additional purification. ESI-MS m/z calc. 308.2. found 309.4 (M+1)⁺; Retention time: 3.12 minutes (4 min run).

Step 3: 3-Methoxy-4-(1-methoxy-2-methyl-1-oxopropan-2-yl)benzoic acid

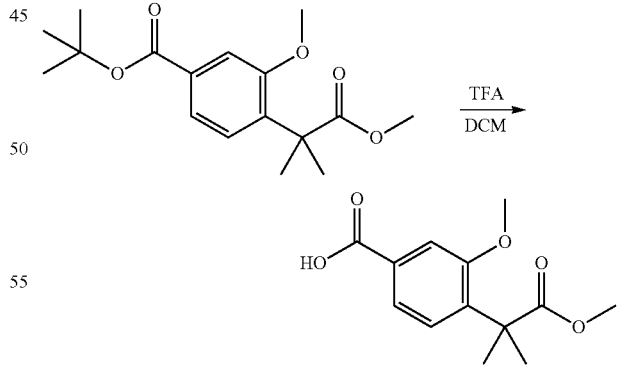

To the crude tert-butyl 3-methoxy-4-(1-methoxy-2-methyl-1-oxopropan-2-yl)benzoate from Step 2 was added DCM (1 mL) followed by TFA (540 µL, 7.0 mmol). The reaction was allowed to stir for 2 h before it was concentrated in vacuo. The residue was dissolved in DMF, filtered and was purified by prep-HPLC (MeOH:H₂O, 1-99% in an HCl modifier) to give 3-methoxy-4-(1-methoxy-2-methyl-1-oxopropan-2-yl)benzoic acid. ESI-MS m/z calc. 252.1. found 253.2 (M+1)⁺; Retention time: 2.45 minutes (4 min run).

3-Fluoro-4-(oxetan-3-yloxy)benzoic acid

Step 1: Methyl 3-fluoro-4-(oxetan-3-yloxy)benzoate

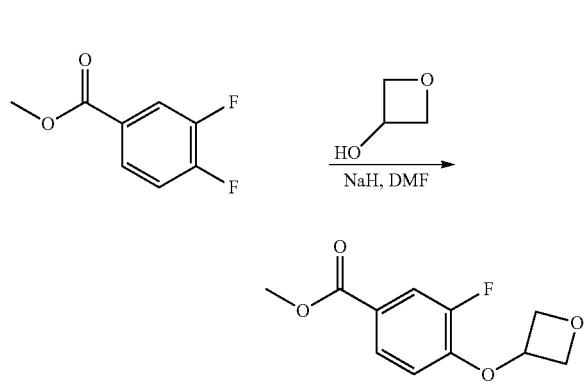 [SMILES: COC(=O)c1ccc(F)c(F)c1 ; OC1COC1 ; COC(=O)c1ccc(OC2COC2)c(F)c1]

NaH (80 mg, 2.0 mmol) was added to a mixture of oxetan-3-ol (150 mg, 2.0 mmol) and DMF (2 mL) at 0° C. The reaction was allowed to stir for 10 minutes before methyl 3,4-difluorobenzoate (170 mg, 1.0 mmol) was added. The reaction was then heated at 80° C. overnight. The reaction was quenched with brine and was extracted with EtOAc (3×). The combined organic layers were dried over sodium sulfate and the solvent was removed to give methyl 3-fluoro-4-(oxetan-3-yloxy)benzoate. ESI-MS m/z calc. 226.1. found 227.2 (M); Retention time: 2.36 minutes (4 min run).

Step 2: 3-Fluoro-4-(oxetan-3-yloxy)benzoic acid

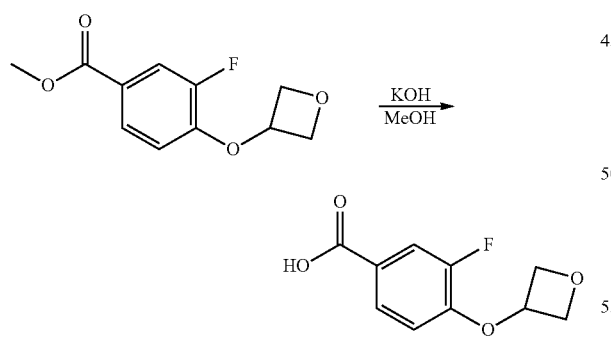

Crude methyl 3-fluoro-4-(oxetan-3-yloxy)benzoate from Step 1, MeOH (1 mL), and KOH (4.0 mL of 3.0 M, 12 mmol) were combined and the mixture was allowed to stir for 3 h at rt. The mixture was extracted with EtOAc and the organic layer was discarded. The aqueous layer was then treated with 1N HCl and the pH was adjusted to pH 3. The aqueous layer was extracted with EtOAc (3×) and the combined organic layers were dried over sodium sulfate and the solvent was removed. The crude acid was used without further purification. ESI-MS m/z calc. 212.1. found 213.0 (M+1)⁺; Retention time: 1.65 minutes (4 min run).

3-Formyl-4-isopropoxybenzoic acid

Step 1: Methyl 3-formyl-4-isopropoxybenzoate

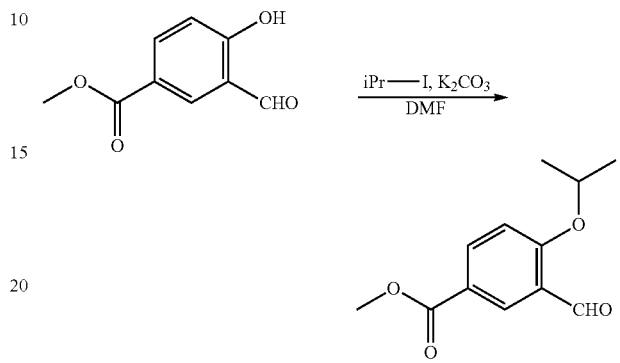

To methyl 3-formyl-4-hydroxy-benzoate (10.0 g, 55.5 mmol), potassium carbonate (30.7 g, 222 mmol) and N,N-dimethylformamide (63 mL) was added 2-iodopropane (11.1 mL, 111 mmol). The mixture was heated at 60° C. for 18 hours. The mixture was filtered using ethyl acetate (200 mL) and the solvent was evaporated under reduced pressure. The residue was dissolved in ethyl acetate (150 mL) and was washed with water (3×75 mL) and a saturated aqueous solution of sodium chloride (1×75 mL). The organic layer was dried over sodium sulfate, filtered and the solvent was evaporated under reduced pressure to yield methyl 3-formyl-4-isopropoxy-benzoate (98%) as a yellow viscous liquid. ESI-MS m/z calc. 222.2. found 223.3 (M+1)⁺; Retention time: 1.51 minutes (3 min run). ¹H NMR (400 MHz, DMSO) δ 10.35 (s, 1H), 8.23 (d, J=2.3 Hz, 1H), 8.17 (dd, J=8.8, 2.3 Hz, 1H), 7.39 (d, J=8.9 Hz, 1H), 4.98-4.83 (m, 1H), 3.85 (s, 3H), 1.38 (d, J=6.0 Hz, 6H).

Step 2: 3-Formyl-4-isopropoxybenzoic acid

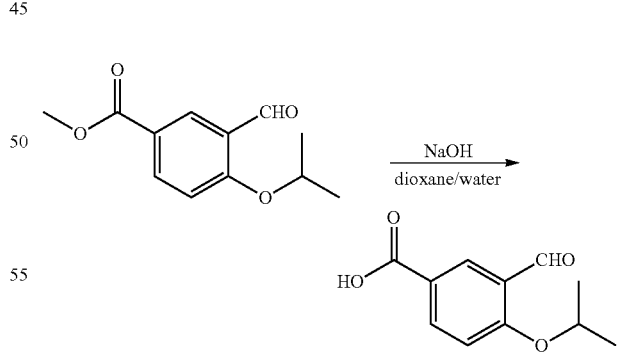

To a solution of the ester (from previous step) in dioxane (4 mL) was added 2 mL of sodium hydroxide solution (5N). The reaction mixture was heated at 65° C. for 4 hours. The reaction mixture was cooled to room temperature and was diluted with 20 mL of water. The water layer was extracted with 20 mL portion of ethyl acetate (2×). The organic extracts were discarded and the aqueous layer was made acidic with 1M HCl. The resulting product was then extracted into ethyl acetate, dried over MgSO$_4$, filtered, and evaporated to dryness to yield 3-formyl-4-isopropoxy-benzoic acid (320 mg, 55% over 2 steps) as a white solid. $^1$H NMR (400 MHz, DMSO) δ 10.36 (s, 1H), 8.23 (d, J=2.5 Hz, 1H), 8.15 (dd, J=2.5, 8.9 Hz, 1H), 7.37 (d, J=8.9 Hz, 1H), 4.96-4.87 (m, 1H), 1.37 (d, J=5.6 Hz, 6H).

4-(2-Cyanopropan-2-yloxy)-3-methoxybenzoic acid

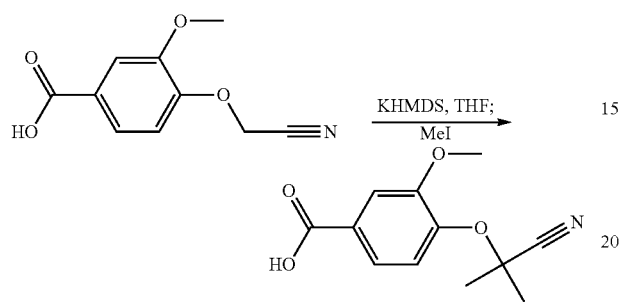

To oven dried (250 mL) 3-neck-flask with 4-(cyanomethoxy)-3-methoxy-benzoic acid (1.0 g, 4.8 mmol) and anhydrous THF (14 mL) cooled to −78° C. was added KHMDS in toluene (29 mL of 0.5 M, 15 mmol) slowly. After 1 h, iodomethane (960 μL, 15 mmol) was added drop-wise and the mixture was stirred at −78° C. for 30 min. THF (14 mL) was added and the reaction was cooled to −78° C. KHMDS (19 mL of 0.5 M, 9.5 mmol) was added. After 1 h, iodomethane was added (640 μL, 10 mmol) and the reaction was stirred for 30 min at −78° C. The reaction was allowed to warm up to room temperature overnight. The reaction was quenched with NH$_4$Cl. The aqueous layer was separated and was washed with ethyl acetate (×3). The aqueous layer was acidified and was extracted with ethyl acetate (×3). The organic layer was dried over Na$_2$SO$_4$ and filtered. The solvent was evaporated under reduced pressure to yield a mixture of mono and di-alkylated products as observed by LCMS (negative mode). ESI-MS m/z calc. 235.4. found 234.1 (M−1)$^-$. Retention time: 0.93 minutes (3 min run).

2-Cyano-4-isopropoxy-benzoic acid

Step 1: 2-Bromo-5-isopropoxybenzonitrile

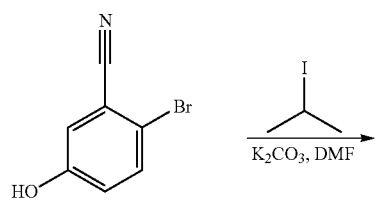

2-Bromo-5-hydroxy-benzonitrile (20.0 g, 10.1 mmol) and K$_2$CO$_3$ (5.60 g, 40.4 mmol) were taken-up in dry DMF (12.5 mL). 2-Iodopropane (2.00 mL, 20.2 mmol) was added and the reaction mixture was heated at 60° C. for 2 h. The mixture was diluted with ether (100 mL), filtered over celite and the filtrate was washed with water (3×50 mL) and brine (50 mL), dried over MgSO$_4$, evaporated and purified by column chromatography (5-45% EtOAc/hexanes) to give 1.9 g (81%) of 2-bromo-5-isopropoxybenzonitrile as a colorless oil. $^1$H NMR (400 MHz, CDCl$_3$) δ 7.53 (d, J=9.0 Hz, 1H), 7.15 (d, J=2.9 Hz, 1H), 6.99 (dd, J=9.0, 3.0 Hz, 1H), 4.58-4.49 (m, 1H), 1.36 (d, J=6.0 Hz, 6H). ESI-MS m/z calc. 239.0. found 240.1 (M+1)$^+$. Retention time: 1.81 minutes (3 min run).

Step 2: tert-Butyl 2-cyano-4-isopropoxybenzoate

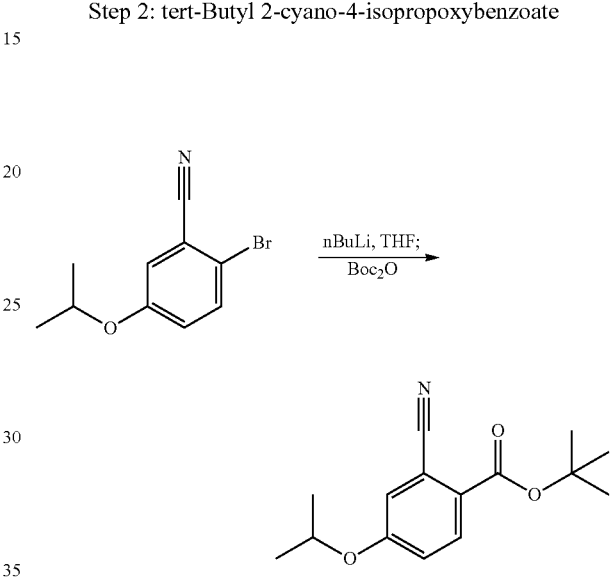

2-Bromo-5-isopropoxybenzonitrile (200 mg, 0.83 mmol) in dry THF (0.5 mL) was added to a solution of butyllithium (570 μL of 1.6 M, 0.91 mmol) in dry THF (0.5 mL) at −65° C. The mixture was stirred for 15 minutes and then a solution of BOC anhydride (380 μL, 1.7 mmol) in dry THF (1 mL) was added and the reaction was stirred for an additional 15 min at this temperature. The cooling bath was removed and water (2 mL) was added. The solvent was removed under vacuum and the mixture was extracted with dichloromethane (5 mL). The organic layer was dried, filtered and concentrated to yield a brown oil that was purified on silica gel chromatography using a gradient of 5-70% ethyl acetate in hexanes to give tert-butyl 2-cyano-4-isopropoxybenzoate (82 mg, 38%). ESI-MS m/z calc. 261.3. found 262.3 (M+1)$^+$. Retention time: 1.96 minutes (3 min run).

Step 3: 2-Cyano-4-isopropoxybenzoic acid

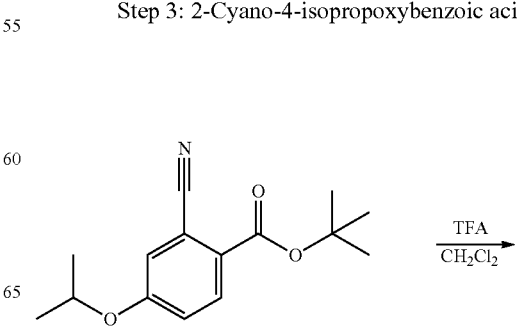

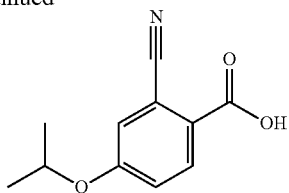

Trifluoroacetic acid (0.6 mL, 7.8 mmol) was added drop-wise to a solution of tert-butyl 2-cyano-4-isopropoxybenzoate (82 mg, 0.31 mmol) in dichloromethane (0.6 mL) at 0° C. under $N_2$ atmosphere. After the addition was complete, the cooling bath was removed and stirring was continued for an additional 2 h at 25° C. The solvent was removed under reduced pressure to yield 2-cyano-4-isopropoxybenzoic acid that was used directly in the next step without further purification.

1-Methylindazole-7-carboxylic acid

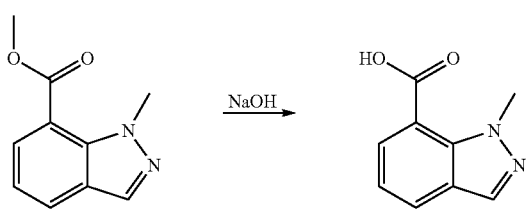

Methyl 1-methylindazole-7-carboxylate (1 g, 5.3 mmol) was suspended in a mixture of sodium hydroxide (12 mL of 1.0 M, 12 mmol) and 1,4-dioxane (8.7 mL). The reaction mixture was heated at 80° C. for 30 minutes. The dioxane was evaporated off and the aqueous layer was extracted with ethyl acetate three times and the extracts were discarded. The aqueous layer was then acidified with 4M hydrochloric acid and then filtered and washed with 1M hydrochloric acid to yield 1-methylindazole-7-carboxylic acid (0.9 g, 97%) as a white solid. $^1$H NMR (400 MHz, DMSO) δ 13.31 (s, 1H), 8.20 (s, 1H), 8.01 (d, J=8.0 Hz, 1H), 7.87 (d, J=7.2 Hz, 1H), 7.21 (t, J=7.6 Hz, 1H), 4.18 (s, 3H).

2,4-Diethoxy-3-methyl-benzoic acid

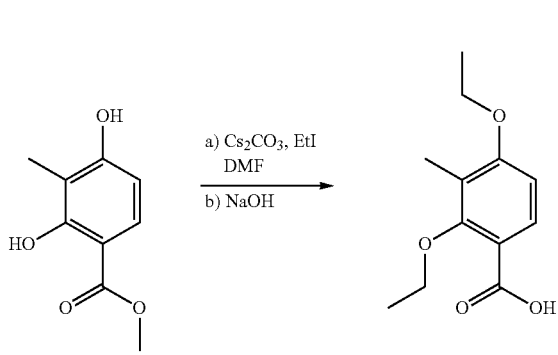

Methyl 2,4-dihydroxy-3-methyl-benzoate (193 mg, 1.06 mmol) was dissolved in DMF (1 mL) containing cesium carbonate (1.03 g, 3.18 mmol). Iodoethane (847 µL, 10.6 mmol) was added and the reaction mixture was allowed to stir for 86 hours. The reaction mixture was then filtered and evaporated to dryness. The crude material was then dissolved in a mixture of dioxane (2 mL) and sodium hydroxide (1.1 mL of 1.0 M, 1.1 mmol). The reaction mixture was then heated at 80° C. for 75 minutes. The dioxane was evaporated to dryness and the reaction mixture was made acidic with 4M hydrochloric acid. The aqueous layer was extracted 3 times with ethyl acetate. The combined ethyl acetate extracts were then dried over sodium sulfate, filtered, and evaporated to dryness to yield 2,4-diethoxy-3-methyl-benzoic acid (189 mg, 80%) as a pale yellow solid which was used without further purification. $^1$H NMR (400 MHz, DMSO) δ 12.37 (s, 1H), 7.62 (d, J=8.7 Hz, 1H), 6.79 (d, J=8.8 Hz, 1H), 4.08 (q, J=6.9 Hz, 2H), 3.87 (q, J=7.0 Hz, 2H), 2.06 (s, 3H), 1.36 (t, J=6.9 Hz, 3H), 1.30 (t, J=7.0 Hz, 3H).

4-(Isopropylsulfonyl)-3-methylbenzoic acid

Step 1: 4-(Isopropylthio)-3-methylbenzoic acid

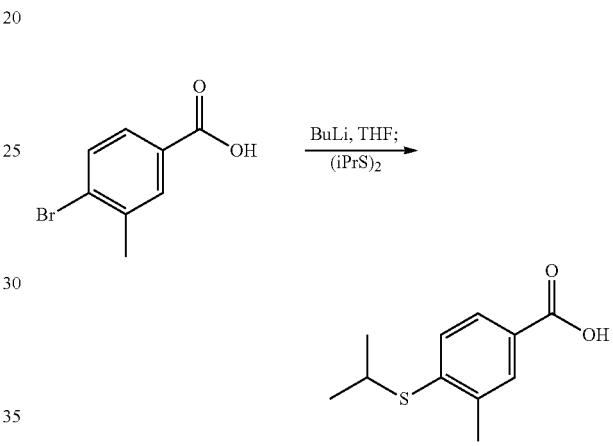

Butyllithium (16 mL of 1.6 M, 26 mmol) was added drop-wise to a mixture of 4-bromo-3-methyl-benzoic acid (2.5 g, 12 mmol) and THF (63 mL) at −78° C. The mixture was allowed to stir at −78° C. for 30 minutes before a solution of 2-isopropyldisulfanylpropane (1.7 g, 12 mmol) in THF (2 mL) was added drop-wise. The mixture was allowed to stir at −78° C. for 30 min, then 30 min at rt. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography using a gradient of 0-5% MeOH in dichloromethane to give 4-(isopropylthio)-3-methylbenzoic acid (870 mg, 18%). MS m/z calc. 210.3. found 211.2 $(M+1)^+$. Retention time: 2.32 minutes (3 min run).

Step 2: 4-(Isopropylsulfonyl)-3-methylbenzoic acid

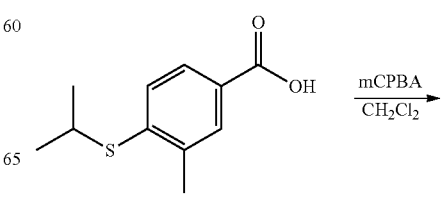

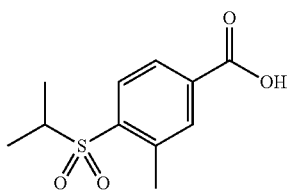

3-Chlorobenzenecarboperoxoic acid (930 mg, 4.2 mmol) was added to a mixture of 4-(isopropylthio)-3-methylbenzoic acid (250 mg, 1.2 mmol) and dichloromethane (5.0 mL) at 25° C. The mixture was allowed to stir at 25° C. for 2 h before it was concentrated in vacuo. The white solid material was taken up in dichloromethane and was subjected to column chromatography (0-2% MeOH/dichloromethane) to give 4-isopropylsulfonyl-3-methyl-benzoic acid (90 mg, 31%) as a white solid. ESI-MS m/z calc. 242.3. found 243.2 (M+1)$^+$. Retention time: 1.57 minutes (3 min run). $^1$H NMR (400 MHz, DMSO) δ 13.50 (s, 1H), 8.50-7.66 (m, 3H), 3.50-3.47 (m, 1H), 2.67 (s, 3H), 1.19 (d, J=1.16 Hz, 6H).

3-Methyl-4-(trifluoromethoxy)benzoic acid

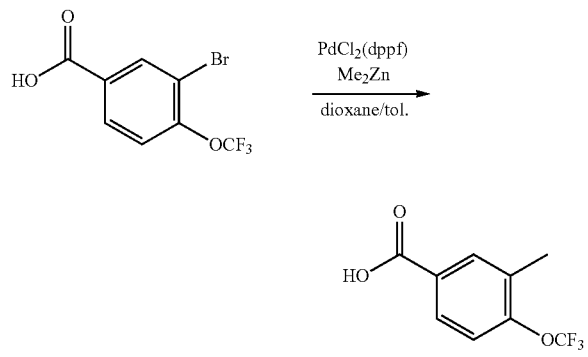

A mixture of 3-bromo-4-(trifluoromethoxy)benzoic acid (923 mg, 3.24 mmol) and PdCl$_2$(dppf) (95 mg, 0.13 mmol) were stirred in 1,4-dioxane (9 mL) in a three necked flask under argon atmosphere (a condenser was added to the flask). Dimethylzinc in toluene (3.2 mL of 2.0 M, 6.4 mmol) was added very slowly (caution: the reaction was very exothermic) and the mixture was stirred at room temperature for 1 hour before it was heated at 70° C. for 18 h. The mixture was cooled to room temperature before it was charged with additional dioxane (9 mL) and PdCl$_2$(dppf) (100 mg). The mixture was cooled to 0° C. before additional dimethyl zinc in toluene (3.0 mL, 2.0M) was added. The ice bath was removed and the mixture was heated at 70° C. overnight. The mixture was cooled to room temperature and was quenched with methanol (2 mL) very slowly. The solution was diluted with ethyl acetate and was washed with 1N HCl (3×). The organic layer was washed with brine, dried over sodium sulfate and evaporated to dryness to yield 3-methyl-4-(trifluoromethoxy) benzoic acid (56%).

4-Methoxy-3,5-dimethyl-benzoic acid

Step 1: Methyl 4-hydroxy-3,5-dimethyl-benzoate

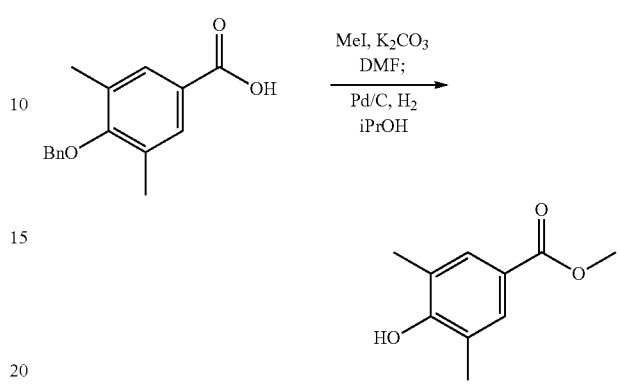

K$_2$CO$_3$ (3.0 g, 21 mmol) followed by iodomethane (1.2 mL, 20 mmol) were added to a solution of 4-benzyloxy-3,5-dimethyl-benzoic acid (5.0 g, 20 mmol) in DMF (100 mL) and the mixture was stirred at room temperature for 6 h. The solution was diluted with water and was acidified with 1% aq. HCl. The mixture was extracted with EtOAc (3×200 mL). The combined organics were washed with water (200 mL), dried over sodium sulfate, filtered, and concentrated. The residue was taken up in degassed 2-propanol (100 mL). Pd/C (10%, 500 mg) was added and the mixture was again degassed and was backfilled with Ar. The mixture was introduced to an atmosphere of H$_2$ (balloon) and was stirred overnight. The solids were removed by filtration through Celite and the filtrate was concentrated in vacuo to provide methyl 4-hydroxy-3,5-dimethyl-benzoate (91%) as a white solid. $^1$H NMR (400 MHz, DMSO) δ 7.56 (s, 2H), 3.76 (s, 3H), 3.38 (s, 9H), 2.19 (s, 6H).

Step 2: 4-Methoxy-3,5-dimethyl-benzoic acid

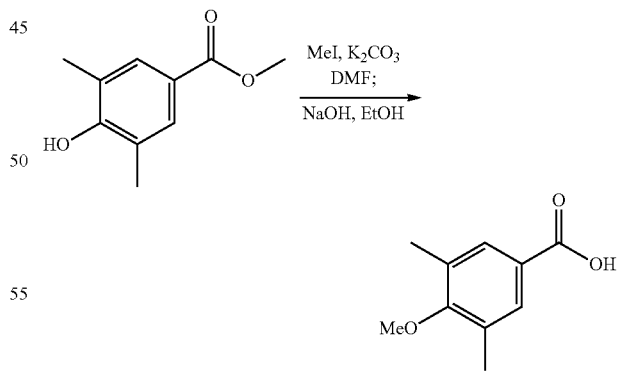

Iodomethane (350 μL, 5.6 mmol) was added to a vigorously stirring suspension of methyl 4-hydroxy-3,5-dimethyl-benzoate (0.50 g, 2.8 mmol) and K$_2$CO$_3$ (1.5 g, 11 mmol) in DMF (14 mL) and the mixture was stirred overnight at 60° C. The solution was cooled to room temperature and was concentrated in vacuo. The residue was taken up in water and mixture was extracted with ethyl acetate (3×100 mL). The combined organics were washed with water (300 mL) and dried over sodium sulfate, filtered and concentrated to provide the intermediate ester. The residue was taken up in EtOH (20 mL) and NaOH (1.4 mL of 2.0 M, 2.8 mmol) was added. The solution was heated at 60° C. overnight. The solution was cooled to room temperature and the volatiles were removed in vacuo. The residue was taken up in water and was extracted with EtOAc. The layers were separated and the organics were discarded. The aqueous layer was acidified with 1N aq HCl, and was extracted with ethyl acetate (3×100 mL). The combined organics were dried over sodium sulfate, filtered and concentrated to provide 4-methoxy-3,5-dimethyl-benzoic acid (85%) as a white solid. (4-Isopropoxy-3,5-dimethylphenyl)(1-methyl-1H-spiro[chromeno[4,3-c]pyrazole-4,4'-piperidine]-1'-yl)methanone was also prepared using the procedures described above.

1-Methyl-2-oxo-1,2-dihydropyridine-3-carboxylic acid

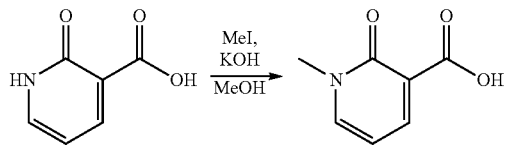

To 2-oxo-1H-pyridine-3-carboxylic acid (2.00 g, 14.4 mmol) in methanol (20 mL) was added a solution of KOH (1.60 g, 28.5 mmol) in water (3 mL) and the mixture was vigorously stirred until a thick suspension formed. Iodomethane (10 µL, 0.16 mmol) was added and the mixture was heated at reflux for 1.5 h. The mixture was concentrated to ⅓ volume and was acidified to pH 1 with 6N HCl. The solids were filtered off and were washed with water (3×2 mL) and acetonitrile (2×2 mL), and then dried in vacuo to give 1-methyl-2-oxo-pyridine-3-carboxylic acid as a white solid. ESI-MS m/z calc 153.0. found 154.1 (M−1)⁻. Retention time: 0.65 minutes (3 min run).
1-Ethyl-2-oxo-1,2-dihydropyridine-3-carboxylic acid was also synthesized using the procedure described above.

1-Isopropyl-2-oxo-pyridine-4-carboxylic acid

Step 1: Methyl 1-isopropyl-2-oxo-1,2-dihydropyridine-4-carboxylate

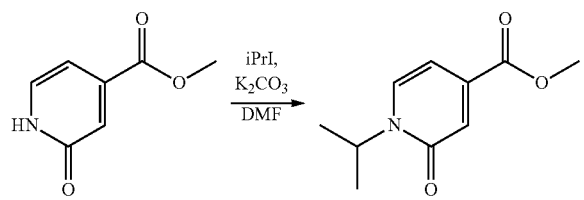

To methyl 2-oxo-1H-pyridine-4-carboxylate (700 mg, 4.57 mmol) in dry DMF (4.4 mL) was added finely ground K₂CO₃ (2.53 g, 18.3 mmol) followed by 2-iodopropane (914 µL, 9.14 mmol). The mixture was heated at 60° C. (external) for 1 h. The mixture was diluted with acetonitrile (10 mL) and was filtered. The filtrate was evaporated onto Celite and was purified by column chromatography (0-100% EtOAc/DCM) to give methyl 1-isopropyl-2-oxo-1,2-dihydropyridine-4-carboxylate (230 mg). ESI-MS m/z calc 195.1. found 196.3 (M−1)⁻. Retention time: 1.09 minutes (3 min run).

Step 2: 1-Isopropyl-2-oxo-pyridine-4-carboxylic acid

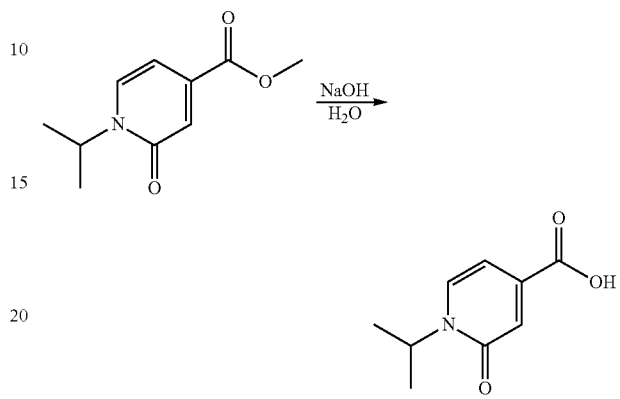

To methyl 1-isopropyl-2-oxo-1,2-dihydropyridine-4-carboxylate (225 mg) was added NaOH (550 µL of 25% w/w, 4.3 mmol) and water (0.6 mL). The mixture was rapidly stirred and heated at 50° C. for 1 h. The mixture was cooled, acidified to pH 2 with 6N aq. HCl and the solids collected, rinsing with water and ACN (2×). The solid was dried in vacuo to give 1-isopropyl-2-oxo-pyridine-4-carboxylic acid as a white solid. ESI-MS m/z calc 181.2. found 182.3 (M−1)⁻. Retention time: 0.86 minutes (3 min run).

3-Fluoro-4-isopropoxybenzoic acid

Step 1: Methyl 3-fluoro-4-isopropoxybenzoate

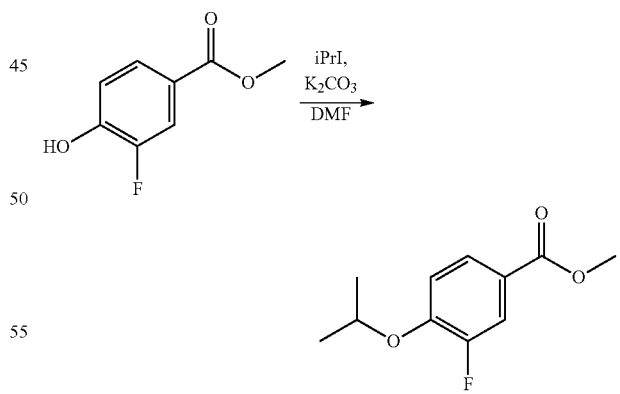

To methyl 3-fluoro-4-hydroxy-benzoate (2.00 g, 11.8 mmol) in DMF (12.5 mL) was added K₂CO₃ (6.50 g, 47.0 mmol) followed by 2-iodopropane (2.35 mL, 23.5 mmol). The mixture was heated at 60° C. for 1.5 h. The mixture was filtered using EtOAc and the filtrate was evaporated under reduced pressure. The residue was dissolved in EtOAc and was washed with water and brine. The organic layer was dried over sodium sulfate, filtered and concentrated under reduced pressure to give methyl 3-fluoro-4-isopropoxybenzoate. ESI-MS m/z calc 212.1. found 213.3 (M+1)⁺. Retention time: 1.70 minutes (3 min run).

Step 2: 3-Fluoro-4-isopropoxybenzoic acid

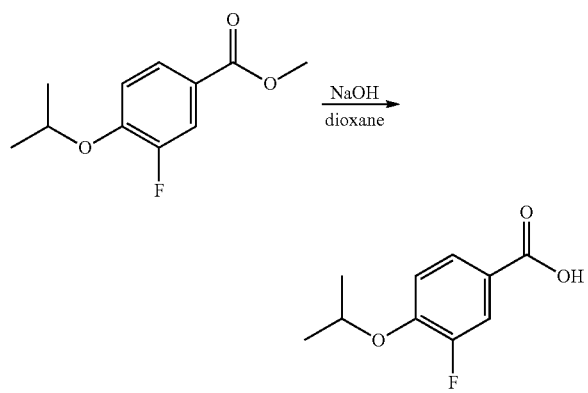

Methyl 3-fluoro-4-isopropoxybenzoate (from step 1), 1,4-dioxane (31 mL), and NaOH (31 mL of 1.0 M, 31 mmol) were combined and the mixture was heated at 80° C. for 20 min. The solvent was evaporated under reduced pressure. The crude mixture was dissolved in water and was washed with EtOAc (3×). The combined organics were discarded. The aqueous layer was acidified and was extracted with EtOAc (3×). The organic layer was dried over sodium sulfate, filtered and the concentrated under reduced pressure to yield 3-fluoro-4-isopropoxy-benzoic acid (1.25 g, 72%) as a white solid. ESI-MS m/z calc 198.1. found 199.3 (M+1)⁺. Retention time: 1.34 minutes (3 min run).

2-Fluoro-4-isopropoxybenzoic acid and 4-isopropoxy-3-methylbenzoic acid were also prepared using the procedures described above.

4-(1-Hydroxypropan-2-yl)-3-methoxybenzoic acid

Step 1: Benzyl 4-bromo-3-methoxybenzoate

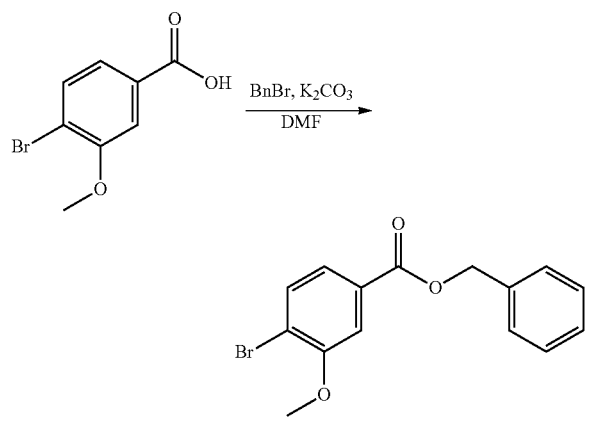

4-Bromo-3-methoxy-benzoic acid (1.50 g, 6.49 mmol), K₂CO₃ (2.69 g, 19.5 mmol), and DMF (10 mL) were combined and the mixture was allowed to stir for 10 minutes. Bromomethylbenzene (849 μL, 7.14 mmol) was added dropwise and the mixture was allowed to stir at rt for 1 h. The reaction mixture was quenched with brine and was extracted with EtOAc (3×). The organic layers were dried over sodium sulfate, filter and concentrated. The residue was purified using silica gel chromatography (5%-70% EtOAc in hexanes) to provide benzyl 4-bromo-3-methoxybenzoate (91%). ESI-MS m/z calc 320.0. found 321.0/323.0 (M+1)⁺. Retention time: 3.24 minutes (4 min run).

Step 2: Benzyl 3-methoxy-4-(4,4,5,5-tetramethyl-1,3,2-dioxaborolan-2-yl)benzoate

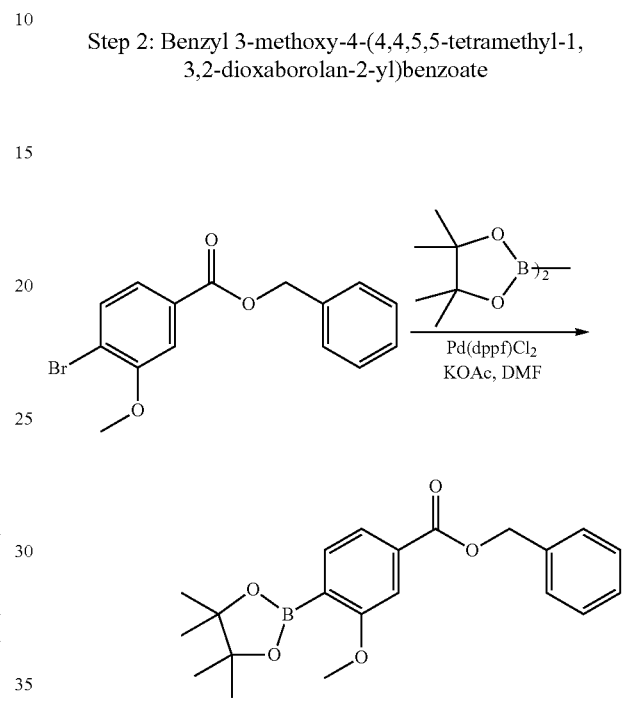

Pd(dppf)Cl₂ (197 mg, 0.269 mmol), KOAc (1.06 g, 10.8 mmol), benzyl 4-bromo-3-methoxy-benzoate (865 mg, 2.69 mmol), 4,4,5,5-tetramethyl-2-(4,4,5,5-tetramethyl-1,3,2-dioxaborolan-2-yl)-1,3,2-dioxaborolane (1.03 g, 4.04 mmol), and DMF (10 mL) were combined and heated overnight at 100° C. The reaction mixture was quenched with brine and was extracted with EtOAc (3×). The combined organic layers were dried over sodium sulfate, filtered, and concentrated. The residue was purified by silica gel chromatography (3%-80% EtOAc in hexanes) to give benzyl 3-methoxy-4-(4,4,5,5-tetramethyl-1,3,2-dioxaborolan-2-yl)benzoate (34%). ESI-MS m/z calc 368.2. found 369.3 (M+1)⁺. Retention time: 2.09 minutes (3 min run).

Step 3:
4-(1-Hydroxypropan-2-yl)-3-methoxybenzoic acid

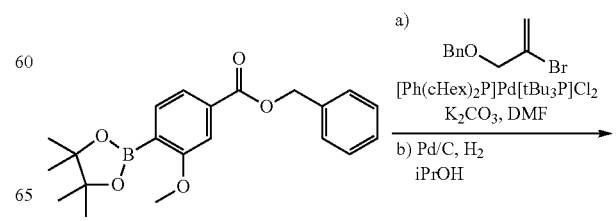

Step 2: 8-Bromo-5-isopropoxy-quinoline

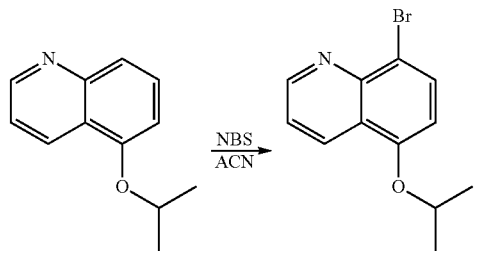

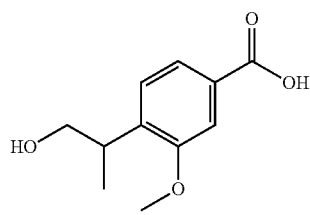

Dichloro-[dicyclohexyl(phenyl)phosphaniumyl]-tritert-butylphosphaniumyl-palladium (981 mg, 0.150 mmol) and 2-bromoallyloxymethylbenzene (341 mg, 1.50 mmol) were dissolved in DMF (1 mL). A solution of benzyl 3-methoxy-4-(4,4,5,5-tetramethyl-1,3,2-dioxaborolan-2-yl)benzoate (1.11 g, 3.00 mmol) in DMF (3 mL) was added the mixture was heated at 90° C. for 3 h. The mixture was then filtered through Celite using ethyl acetate. The filtrate was then washed with brine, dried over sodium sulfate, filtered, and concentrated. The residue from step 1 was taken up in isopropanol (2 mL) and was added to 10% Pd/C (160 mg, 0.150 mmol). The vessel was purged with nitrogen and a balloon of hydrogen was added and the reaction mixture was allowed to stir overnight. The reaction mixture was filtered through Celite and the filtrate was concentrated. The residue was partitioned between aqueous 2M $Na_2CO_3$ and ethyl acetate. The layers were separated and the organic phase was discarded. To the aqueous phase was added 1M HCl until the solution was pH 3. The solution was then extracted with EtOAc (3×) and the combined organic layers were dried over sodium sulfate, filtered, and concentrated to provide 4-(1-hydroxypropan-2-yl)-3-methoxybenzoic acid. ESI-MS m/z calc 210.1. found 211.1 (M+1)$^+$. Retention time: 1.19 minutes (3 min run).

To a solution of 5-isopropoxyquinoline (1.87 g, 10.0 mmol) in acetonitrile (100 mL) was added NBS (1.78 g, 10.0 mmol) at 0° C. The mixture was stirred at rt for 2 h before the solvent was removed. The residue was partitioned between EtOAc and $H_2O$. The layers were separated and the organic layer was washed with brine, dried over $MgSO_4$, and concentrated. The crude material was purified by column chromatography (0-10% EtOAc-Hex) to provide 8-bromo-5-isopropoxy-quinoline (92%) as a light brown solid. ESI-MS m/z calc 265.1. found 266.1 (M+1)$^+$. Retention time: 1.44 minutes (3 min run).

Step 3: 5-Isopropoxyquinoline-8-carboxylic acid

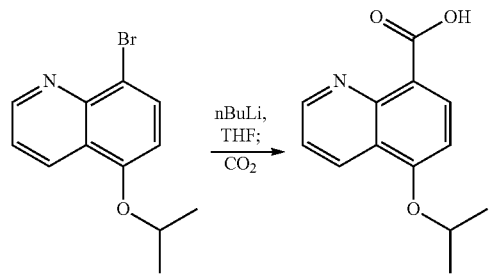

To a solution of 8-bromo-5-isopropoxy-quinoline (133 mg, 0.500 mmol) in THF (2 mL) was added nBuLi (310 μL of 1.6 M, 0.50 mmol) dropwise at −78° C. under Ar. The reaction mixture was stirred at −78° C. for 30 min. Carbon dioxide was bubbled through the solution for 10 min. The mixture was quenched with sat. aq. $NH_4Cl$ before it was extracted with EtOAc (2×). The aqueous layer was acidified with 6N HCl to pH ~4 and was extracted with EtOAc (3×). The combined organics were washed with brine, dried over $MgSO_4$, filtered, and concentrated to dryness to give 5-isopropoxyquinoline-8-carboxylic acid. ESI-MS m/z calc 231.1. found 232.1 (M+1)$^+$. Retention time: 1.28 minutes (3 min run).

5-Isopropoxyquinoline-8-carboxylic acid

Step 1: 5-Isopropoxyquinoline

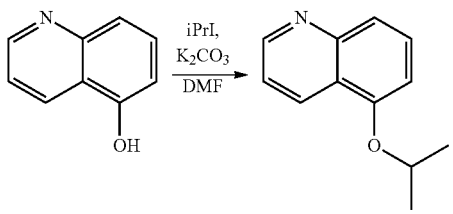

To a mixture of quinolin-5-ol (2.00 g, 13.8 mmol) and $K_2CO_3$ (7.62 g, 55.1 mmol) in DMF (20 mL) was added 2-iodopropane (2.76 mL, 27.6 mmol). The reaction mixture was heated at 80° C. overnight before it was partitioned between EtOAc and water. The layers were separated and the aqueous layer was extracted with EtOAc (2×). The combined organic layers were washed with brine, dried over $MgSO_4$ and concentrated to dryness. The crude material was purified by column chromatography (10-20% EtOAc-Hex) to provide 5-isopropoxyquinoline (91%) as a light yellow oil. ESI-MS m/z calc 187.1. found 188.3 (M+1)$^+$. Retention time: 1.06 minutes (3 min run).

4-(1-Cyano-1-methyl-ethoxy)-2-methoxy-benzoic acid

Step 1: Methyl 4-hydroxy-2-methoxy-benzoate

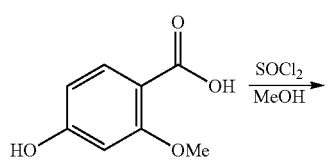

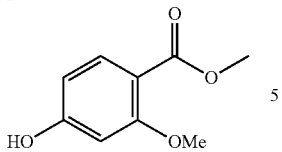

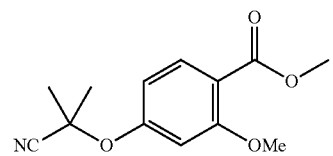

Thionyl chloride (953 μL, 13.1 mmol) was added dropwise to a solution of 4-hydroxy-2-methoxy-benzoic acid (733 mg, 4.36 mmol) in methanol (30 mL) at 0° C. The mixture was stirred at 50° C. overnight. The reaction mixture was concentrated and the residue was dissolved in water (40 mL). The solution was neutralized with saturated sodium bicarbonate solution and the product was extracted into ethyl acetate. The organics were dried over sodium sulfate, filtered and evaporated to dryness to give methyl 4-hydroxy-2-methoxy-benzoate (99%). ESI-MS m/z calc 182.1. found 183.1 (M+1)$^+$. Retention time: 0.73 minutes (3 min run).

Step 2: Methyl 4-(cyanomethoxy)-2-methoxy-benzoate

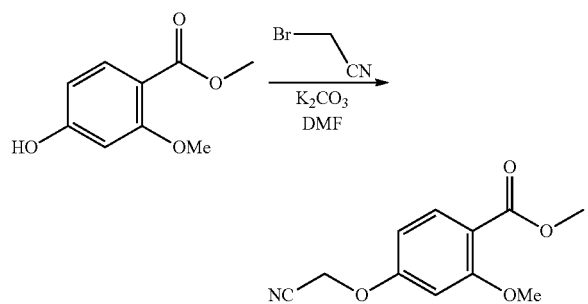

Methyl 4-hydroxy-2-methoxy-benzoate (0.790 g, 4.34 mmol), 2-bromoacetonitrile (361 μL, 5.42 mmol), and potassium carbonate (900 mg, 6.51 mmol) were combined in N,N-dimethylformamide (5 mL). The reaction mixture was stirred at room temperature for 16 hours. The reaction mixture was diluted with 50 mL of ethyl acetate and 25 mL of water. The layers were separated and the water layer was extracted with 50 mL of ethyl acetate. The combined organic layers were washed with a saturated aqueous solution of sodium chloride (2×). The organic layer was then dried over sodium sulfate, filtered, and evaporated to dryness to yield methyl 4-(cyanomethoxy)-2-methoxy-benzoate (99%) as a brown oil. ESI-MS m/z calc 221.1. found 222.1 (M+1)$^+$. Retention time: 1.08 minutes (3 min run).

Step 3: Methyl 4-(1-cyano-1-methyl-ethoxy)-2-methoxy-benzoate

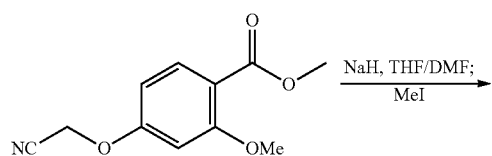

Methyl 4-(cyanomethoxy)-2-methoxy-benzoate (960 mg, 4.34 mmol) was dissolved in tetrahydrofuran (1 mL) and N,N-dimethylformamide (4 mL). Sodium hydride (521 mg, 13.0 mmol) was added and the reaction mixture was allowed to stir for 5 min. Iodomethane (1.35 mL, 21.7 mmol) was added and the reaction mixture was allowed to stir for 10 min. The reaction mixture was quenched with water and extracted with ethyl acetate. The ethyl acetate was dried over sodium sulfate, filtered and evaporated to dryness. The crude material was then dissolved in tetrahydrofuran (10 mL) and was cooled to −78° C. under an atmosphere of argon. LDA (2.2 mL of 2.0 M, 4.4 mmol) was added and the reaction mixture was stirred at −78° C. for 45 minutes. Iodomethane (1.35 mL, 21.7 mmol) was added and the reaction mixture was allowed to slowly warm to room temperature. The reaction mixture was evaporated to dryness, and then partitioned between ethyl acetate and a saturated aqueous solution of ammonium chloride. The organic layer was washed two times with a saturated aqueous solution of sodium chloride, dried over sodium sulfate, filtered, and evaporated to dryness. The crude product was then purified on 40 g of silica gel utilizing a gradient of 0-30% ethyl acetate in hexanes to give methyl 4-(1-cyano-1-methyl-ethoxy)-2-methoxy-benzoate (31%). ESI-MS m/z calc 249.1. found 250.3 (M+1)$^+$. Retention time: 1.59 minutes (3 min run).

Step 4: 4-(1-Cyano-1-methyl-ethoxy)-2-methoxy-benzoic acid

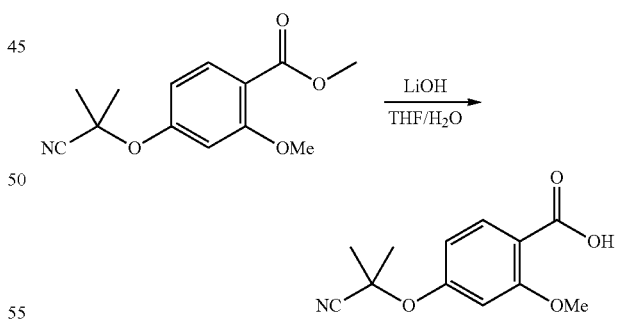

Methyl 4-(1-cyano-1-methyl-ethoxy)-2-methoxy-benzoate (340 mg, 1.36 mmol) was dissolved in tetrahydrofuran (5 mL) and water (5 mL). Lithium hydroxide (98 mg, 4.1 mmol) was added and reaction mixture was heated at 65° C. for 1 hour. The crude material was diluted with 10 mL of water and was extracted two times with ether. The ether extracts were discarded and the aqueous layer was made acidic with 4M HCl. The product was then extracted into ethyl acetate, dried over sodium sulfate, filtered, and evaporated to dryness to yield 4-(1-cyano-1-methyl-ethoxy)-2-methoxy-benzoic acid (78%) as a pale yellow solid. ESI-MS m/z calc 235.1. found 236.1 (M+1)$^+$. Retention time: 1.29 minutes (3 min run).

4-Isopropylsulfinylbenzoic acid

Step 1: Ethyl 4-isopropylsulfanylbenzoate

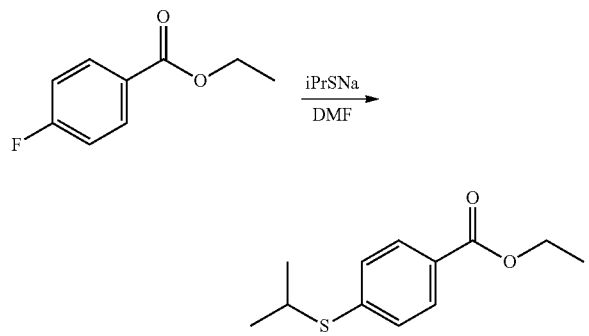

A mixture of ethyl 4-fluorobenzoate (390 mg, 2.32 mmol) and isopropylsulfanylsodium (273 mg, 2.78 mmol) in DMF (2.5 mL) was heated at 80° C. for 36 h. The reaction mixture was diluted with ethyl acetate before being washed with 1N NaOH and then brine. The organic layer was dried over sodium sulfate and evaporated. The residue was purified by column chromatography eluting with 50-100% ethyl acetate in hexanes to give ethyl 4-isopropylsulfanylbenzoate (350 mg).

Step 2: Ethyl 4-isopropylsulfinylbenzoate

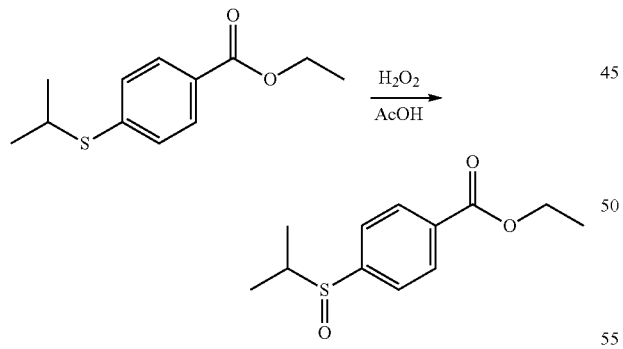

A solution of ethyl 4-isopropylsulfanylbenzoate (350 mg, 1.6 mmol) and H$_2$O$_2$ (180 μL of 30% w/v, 1.6 mmol) in AcOH (2 mL) was stirred at ambient temperature for 3 h. The mixture was poured into sat. aq. Na$_2$CO$_3$ and the pH was adjusted to 10 with solid Na$_2$CO$_3$. The mixture was extracted with EtOAc (3×). The organics were combined and washed with sat. aq. Na$_2$CO$_3$, water (2×), then brine. The organic layer was dried over magnesium sulfate and was evaporated to dryness. The residue was purified by column chromatography (20-50% EtOAc in hexanes) to give ethyl 4-isopropylsulfinylbenzoate (65%). ESI-MS m/z calc. 240.1. found 241.3 (M+1)$^+$. Retention time: 1.16 minutes (3 min run).

Step 3: 4-Isopropylsulfinylbenzoic acid

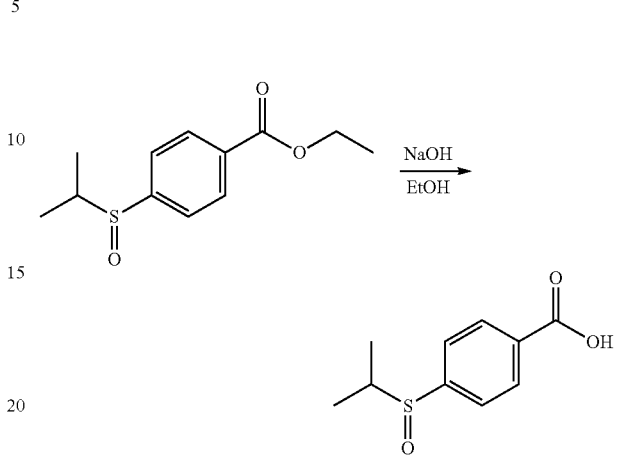

To a stirred solution of ethyl 4-isopropylsulfinylbenzoate (245 mg, 1.02 mmol) in EtOH (1 mL) at room temperature was added NaOH (300 μL of 5.0 M, 1.50 mmol) dropwise and the mixture stirred for 30 min. The pH of the mixture was adjusted to 2 with 1N HCl before it was evaporated to dryness. The solids were taken up in water, filtered, washed with water (2×), and desiccated to give 4-isopropylsulfinylbenzoic acid (80%) as a white solid. $^1$H NMR (400 MHz, DMSO) δ 13.30 (s, 1H), 8.11 (d, J=8.2 Hz, 2H), 7.73 (d, J=8.2 Hz, 2H), 3.07-2.97 (m, 1H), 1.22 (d, J=6.9 Hz, 3H), 0.90 (d, J=6.7 Hz, 3H).

4-(tert-Butylsulfonyl)benzoic acid

Step 1: 4-(tert-Butylthio)benzoic acid

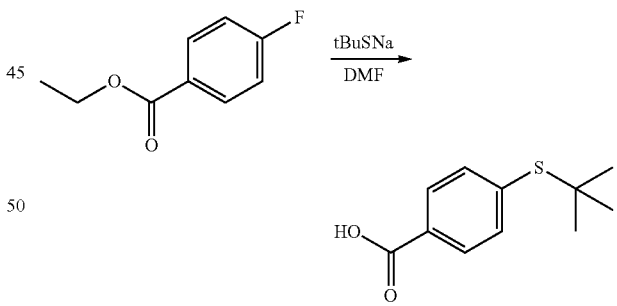

Ethyl 4-fluorobenzoate (1.5 g, 8.9 mmol) and tert-butylsulfanylsodium (2.00 g, 17.8 mmol) were combined in N,N-dimethylformamide (10 mL). The reaction mixture was heated at 80° C. for 2 hours. A large amount of precipitate formed and an additional 15 mL of N,N-dimethylformamide was added and the reaction mixture was stirred for an additional 20 hours at 80° C. The reaction mixture was partitioned between ethyl acetate (100 mL) and water (100 mL). The organic layer was discarded, and the water layer was made acidic with 4M hydrochloric acid. The water layer was extracted two times with ethyl acetate. The combined extracts were dried over sodium sulfate, filtered, and evaporated to dryness to yield 4-(tert-butylthio)benzoic acid as a colorless oil. ESI-MS m/z calc. 210.3. found 211.1 (M+1)$^+$. Retention time: 1.74 minutes (3 min run).

Step 2: 4-(tert-Butylsulfonyl)benzoic acid

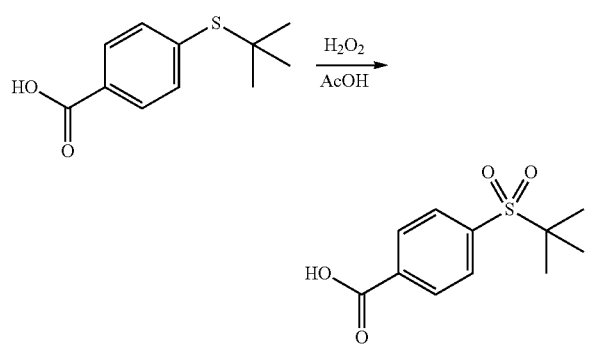

4-(tert-Butylthio)benzoic acid (from Step 1) was dissolved in AcOH (10 mL) and hydrogen peroxide (5.0 mL of 30% w/w, 52 mmol) was added to the reaction mixture. The resulting mixture was heated at 80° C. for 2 hours. The reaction mixture was then allowed to cool to room temperature, and was diluted with 50 mL of water and 100 mL of ethyl acetate. The layers were separated and the aqueous layer was extracted with ethyl acetate. The combined ethyl acetate extracts were dried over sodium sulfate, filtered, and evaporated to dryness to yield a white solid. The white solid was then dissolved in dichloromethane and was evaporated to dryness. The solid was then dried under vacuum for 16 hours to give 4-tert-butylsulfonylbenzoic acid (2.2 g, 92%) as a white solid. ESI-MS m/z calc. 242.1. found 243.1 (M+1)$^+$. Retention time: 1.15 minutes (3 min run). $^1$H NMR (400 MHz, DMSO) δ 8.18 (d, J=8.0 Hz, 2H), 7.94 (d, J=7.6 Hz, 2H), 1.25 (s, 9H).

4-(Ethylsulfonyl)benzoic acid was also synthesized using the procedures described above.

4-(Isobutylsulfonyl)benzoic acid

Step 1: Methyl 4-(isobutylthio)benzoate

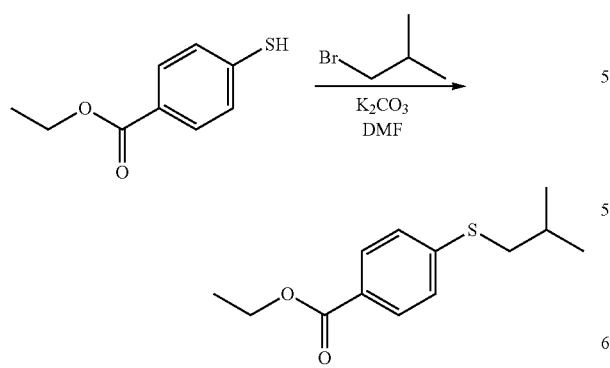

K$_2$CO$_3$ (1.23 g, 8.92 mmol) was added to a mixture of methyl 4-sulfanylbenzoate (1.00 g, 5.95 mmol), 1-bromo-2-methylpropane (970 µL, 8.92 mmol), and DMF (10 mL) at rt. The mixture was allowed to stir for 4 h at rt before the solids were filtered off. The solids were washed with ethyl acetate, and then were discarded. The combined filtrates were partitioned between ethyl acetate (100 mL) and water (100 mL). The layers were separated and the organic layer was washed with brine, dried over sodium sulfate, filtered and concentrated to give methyl 4-(isobutylthio)benzoate (82%) as a clear oil. ESI-MS m/z calc. 224.1. found 225.2 (M+1)$^+$. Retention time: 1.59 minutes (3 min run).

Step 2: Methyl 4-(isobutylsulfonyl)benzoate

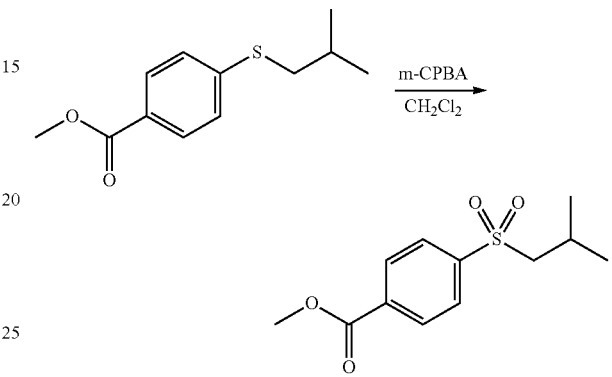

m-CPBA (3.59 g, 15.6 mmol) was added to a solution of methyl 4-(isobutylsulfanyl)benzoate (1.00 g, 4.46 mmol) in CH$_2$Cl$_2$ (20 mL) at rt. The mixture was allowed to stir for 2 h before it was concentrated in vacuo. Column chromatography (0-100% ethyl acetate/hexanes) on the residue gave methyl 4-(isobutylsulfonyl)benzoate. ESI-MS m/z calc. 256.1. found 257.2 (M+1)+; Retention time: 1.96 minutes (3 min run). $^1$H NMR (400 MHz, CDCl$_3$) δ 8.23 (d, J=8.4 Hz, 2H), 8.00 (d, J=8.3 Hz, 2H), 3.98 (s, 3H), 3.02 (d, J=6.5 Hz, 2H), 2.25 (dp, J=13.3, 6.6 Hz, 1H), 1.07 (d, J=6.7 Hz, 6H).

Step 3: 4-(Isobutylsulfonyl)benzoic acid

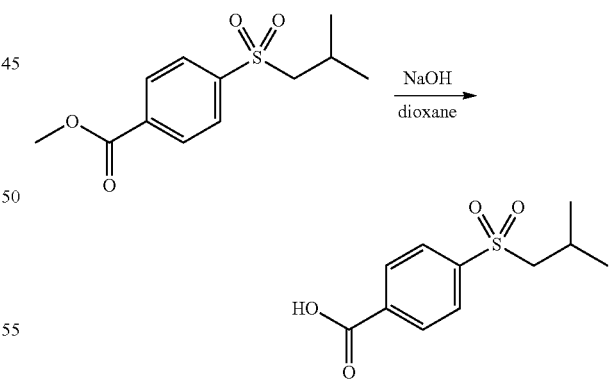

A mixture of methyl 4-isobutylsulfonylbenzoate (1.00 g, 3.90 mmol), NaOH (10 mL of 1.0 M, 10 mmol), and 1,4-dioxane (10 mL) was heated at 80° C. for 1.5 h. The mixture was cooled to rt before it was concentrated in vacuo. The solid residue was taken up in water and was washed with ethyl acetate which was discarded. The aqueous layer was acidified with 1N HCl and was extracted with ethyl acetate (2×). The combined organics were washed with brine, dried over sodium sulfate, and were concentrated in vacuo. Column chromatography (0-100% ethyl acetate/hexanes) on the residue gave 4-(isobutylsulfonyl)benzoic acid (98%). ESI-MS m/z calc. 242.1. found 243.2 (M+1)+; Retention time: 1.73 minutes (3 min run). $^1$H NMR (400 MHz, CDCl$_3$) δ 8.30 (d, J=8.3 Hz, 2H), 8.05 (d, J=8.3 Hz, 2H), 3.03 (d, J=6.5 Hz, 2H), 2.27 (dt, J=13.3, 6.6 Hz, 1H), 1.08 (d, J=6.7 Hz, 6H).

3-Ethoxy-2-fluorobenzoic acid

Step 1: 1-Ethoxy-2-fluorobenzene

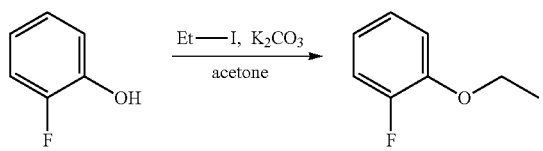

A mixture of 2-fluorophenol (8.6 g, 77 mmol), iodoethane (9.2 mL, 120 mmol) and potassium carbonate (21 g, 150 mmol) (finely powdered) was stirred in acetone (100 mL) at 50° C. overnight, then at room temperature for 24 h. The mixture was filtered over a pad of silica gel, and was rinsing with ether. The solution was carefully concentrated (due to volatility of product), then microfiltered to give 1-ethoxy-2-fluoro-benzene (92%) as a yellow oil. $^1$H NMR (CDCl$_3$, 500 MHz), δ 7.12-6.94 (m, 2H), 6.91-6.86 (m, 1H), 6.83-6.77 (m, 1H), 4.01 (q, J=7.0 Hz, 2H), 1.37 (t, J=7.0 Hz, 3H).

Step 2: 3-Ethoxy-2-fluorobenzoic acid

To 1-ethoxy-2-fluoro-benzene (1.0 g, 7.1 mmol) in THF (10 mL) at −78° C. was added dropwise butyllithium (4.5 mL of 1.6 M, 7.2 mmol) followed by N'-(2-dimethylaminoethyl)-N,N,N'-trimethyl-ethane-1,2-diamine (1.2 g, 7.2 mmol). The mixture was stirred for 3 h at −78° C. before it was transferred quickly via large cannula to a mixture of crushed dry ice (freshly crushed under N$_2$) under ether. The mixture was warmed to RT, diluted with 30 mL of 2M HCl (aq.), extracted with ethyl acetate (2×30 mL), washed with 10 mL brine, and dried over MgSO$_4$ to give 3-ethoxy-2-fluorobenzoic acid (65%) as a white solid. ESI-MS m/z calc. 184.1. found 185.1 (M+1)+; Retention time: 1.04 minutes (3 min run). $^1$H NMR (400 MHz, DMSO) δ 7.42-7.30 (m, 2H), 7.20-7.16 (m, 1H), 4.12 (q, J=7.0 Hz, 2H), 1.35 (t, J=7.0 Hz, 3H).

3-(Hydroxymethyl)-4-isopropoxy-benzoic acid

Step 1: Methyl 3-formyl-4-isopropoxy-benzoate

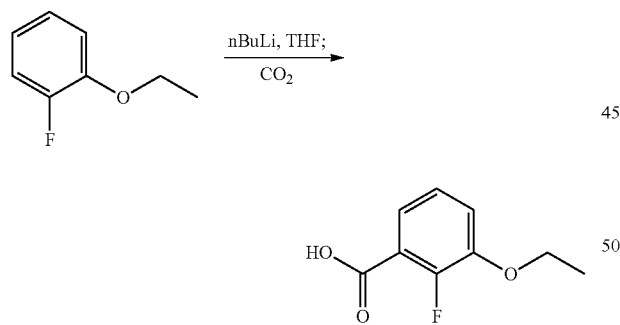

Methyl 3-formyl-4-isopropoxy-benzoate (180 mg, 0.81 mmol) was dissolved in tetrahydrofuran (4.8 mL) and LiBH$_4$ (35 mg, 1.6 mmol) was added. The reaction was stirred at room temperature for 30 minutes before it was quenched with methanol (3 mL). The reaction was neutralized by the addition of a saturated aqueous solution of sodium bicarbonate (3 mL) and was then extracted with ethyl acetate (3×10 mL). The combined organics were washed with a saturated aqueous solution of sodium chloride (1×10 mL), dried over sodium sulfate, filtered and the solvent was evaporated under reduced pressure to yield methyl 3-(hydroxymethyl)-4-isopropoxy-benzoate (99%) as a viscous liquid. ESI-MS m/z calc. 224.3. found 225.3 (M+1)+; Retention time: 1.26 minutes (3 min run). $^1$H NMR (400 MHz, DMSO) δ 8.09 (s, 1H), 7.89 (d, J=8.6 Hz, 1H), 7.13 (d, J=8.6 Hz, 1H), 5.25 (t, J=5.6 Hz, 1H), 4.86-4.68 (m, 1H), 4.54 (d, J=5.6 Hz, 2H), 3.87 (s, 3H), 1.35 (d, J=6.0 Hz, 6H).

Step 2: 3-(Hydroxymethyl)-4-isopropoxy-benzoic acid

To methyl 3-(hydroxymethyl)-4-isopropoxy-benzoate (180 mg, 0.80 mmol) and 1,4-dioxane (1.895 mL) was added sodium hydroxide (2.1 mL of 1.0 M, 2.1 mmol) and the mixture was heated at 80° C. for 50 minutes. The solvent was evaporated under reduced pressure. The crude mixture was dissolved in water (10 mL) and was washed with ethyl acetate (3×10 mL) which was discarded. The aqueous layer was acidified with hydrochloric acid. The aqueous layer was extracted with ethyl acetate (3×10 mL). The combined organics were dried over sodium sulfate, filtered and the solvent was evaporated under reduced pressure to yield 3-(hydroxymethyl)-4-isopropoxy-benzoic acid (89%) as a white solid. ESI-MS m/z calc. 210.2. found 211.3 (M+1)+; Retention time: 1.01 minutes (3 min run).

3-Methyl-4-methylsulfonyl-benzoic acid

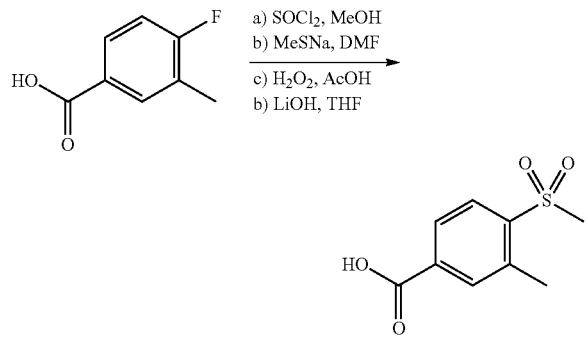

Thionyl chloride (3.55 mL, 48.7 mmol) was added dropwise to a solution of 4-fluoro-3-methyl-benzoic acid (2.50 g, 16.2 mmol) in methanol (102 mL) at 0° C. The mixture was stirred at 50° C. for 2 hours. The reaction mixture was evaporated to dryness and the crude ester was then dissolved in N,N-dimethylformamide (10 mL). Sodium thiomethoxide (2.50 g, 35.7 mmol) was added and the reaction mixture was heated at 80° C. for 15 hours. The reaction mixture was then partitioned between 1M hydrochloric acid and ethyl acetate. The layers were separated and the organic layer was washed with 1M hydrochloric acid. The ethyl acetate layer was then dried over sodium sulfate, filtered, and evaporated to dryness. The resultant acid and ester mixture was suspended in acetic acid (20 mL). Hydrogen peroxide (5.0 mL of 30% w/w) was added and the reaction mixture was heated at 80° C. for 2 hours. The reaction mixture was diluted with water (20 mL) and the resulting mixture was extracted three times with 50 mL portions of ethyl acetate. The combined organics were evaporated to dryness and the residue was dissolved in tetrahydrofuran (10 mL). Water (10 mL) and lithium hydroxide (1.17 g, 48.7 mmol) were then added and the reaction mixture was heated at 65° C. for 4 hours. The reaction mixture was diluted with water (20 mL) and the resulting mixture was extracted three times with 20 mL portions of ethyl acetate. The aqueous layer was then made acidic with aqueous 6M hydrochloric acid and was extracted 3 times with 50 mL portions of ethyl acetate. The combined ethyl acetate extracts were dried over sodium sulfate, filtered, and evaporated to dryness to yield 3-methyl-4-methylsulfonyl-benzoic acid (2.25 g, 72%) as a white solid. ESI-MS m/z calc. 214.0. found 215.0 (M+1)+; Retention time: 0.97 minutes (3 min run). $^1$H NMR (400 MHz, DMSO) δ 13.48 (s, 1H), 8.07-7.94 (m, 3H), 3.27 (s, 3H), 2.70 (s, 3H).

4-Isopropoxy-2,5-dimethylbenzoic acid

Step 1: 1-Iodo-4-isopropoxy-2,5-dimethylbenzene

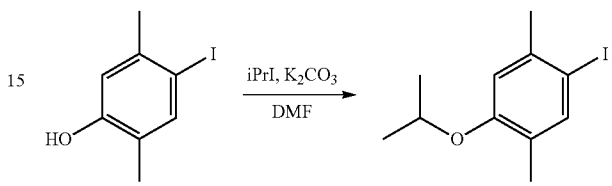

$K_2CO_3$ (1.23 g, 8.87 mmol) followed by 2-iodopropane (806 μL, 8.06 mmol) were added to a solution of 4-iodo-2,5-dimethyl-phenol (1.00 g, 4.03 mmol) in DMF (40 mL) and the solution was heated at 50° C. for 24 h. The mixture was then acidified with 1% aq HCl before it was extracted with EtOAc (3×100 mL). The combined organics were washed with 1N NaOH (3×200 mL), dried over $Na_2SO_4$, filtered, and concentrated. The residue was purified by column chromatography (0-10% ethyl acetate/hexanes) to provide 1-iodo-4-isopropoxy-2,5-dimethylbenzene (42%) as a yellow oil.

Step 2: 4-Isopropoxy-2,5-dimethylbenzoic acid

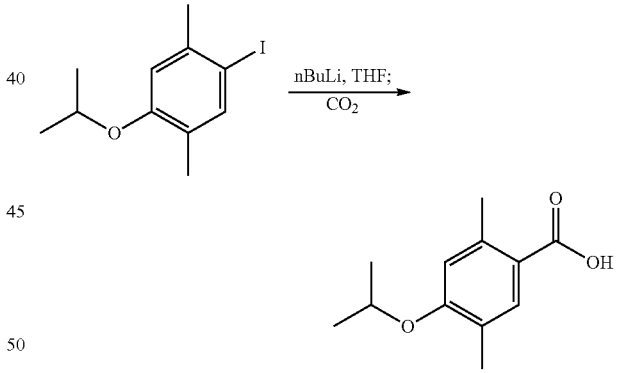

A solution of 1-iodo-4-isopropoxy-2,5-dimethylbenzene (450 mg, 1.6 mmol) in THF (7.8 mL) was cooled to −78° C. before nBuLi (620 mL, 2.5 M, 1.6 mmol) was added dropwise. The mixture was allowed to warm to 0° C., then it was cooled to −78° C. before it was added dropwise to a flask containing crushed, dry $CO_2$. The mixture was allowed to warm to room temperature and was stirred overnight. The mixture was poured over ice and was acidified with 1N HCl. The mixture was extracted with ethyl acetate (3×) and the combined organics were washed with brine, dried over sodium sulfate, and concentrated to give 4-isopropoxy-2,5-dimethylbenzoic acid (67 mg, 10%). ESI-MS m/z calc. 208.1. found 209.1 (M+1)+; Retention time: 1.55 minutes (3 min run).

539

Spiro[benzo[b]pyrrolo[1,2-d][1,4]oxazine-4,4'-piperidine]-1'-yl(4-(2,2,2-trifluoroethoxy)phenyl)methanone

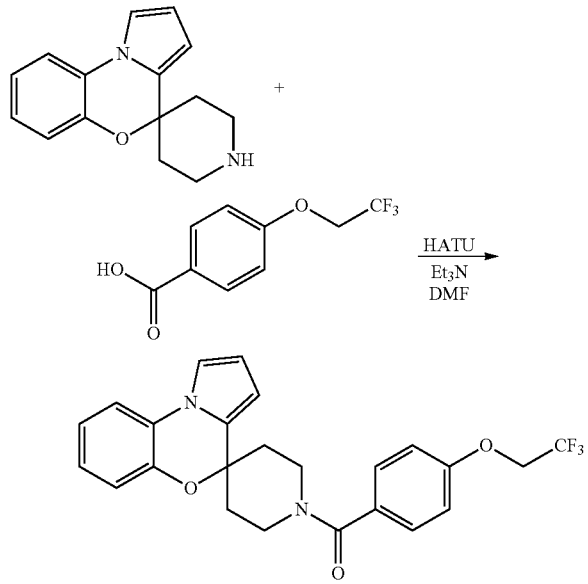

4-(2,2,2-Trifluoroethoxy)benzoic acid (22 mg, 0.10 mmol), HATU (42 mg, 0.11 mmol), and DMF (0.8 mL) were combined and allowed to sit at room temperature for 10 minutes. The activated acid was then added to spiro[benzo[b]pyrrolo[1,2-d][1,4]oxazine-4,4'-piperidine] (28 mg, 0.10 mmol) followed by the addition of Et₃N (84 μL, 0.60 mmol). The reaction mixture was stirred at room temperature for 17 h before it was filtered and purified by prep-HPLC (5 mM HCl/H₂O and MeOH) to provide spiro[benzo[b]pyrrolo[1,2-d][1,4]oxazine-4,4'-piperidine]-1'-yl(4-(2,2,2-trifluoroethoxy)phenyl)methanone. ESI-MS m/z calc. 442.2. found 443.4 (M+1)⁺. Retention time: 2.05 minutes (4 min run).

(4-(Isopropylsulfonyl)-3-methylphenyl)(1-methyl-1H-spiro[chromeno[4,3-e]pyrazole-4,4'-piperidine]-1'-yl)methanone

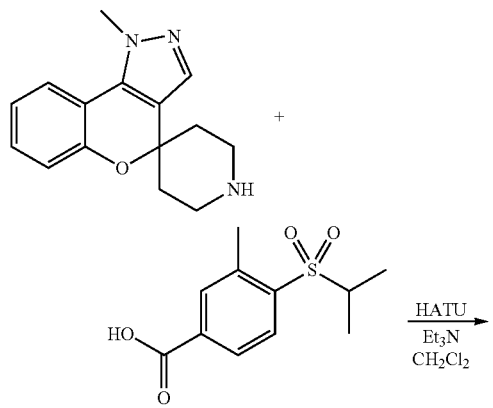

540

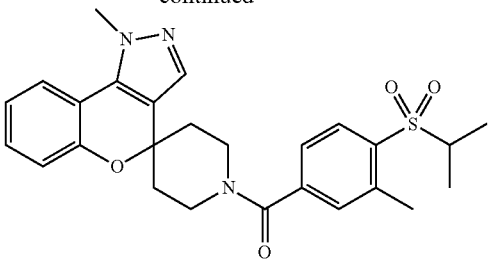

Triethylamine (152 μL, 1.1 mmol) was added to a mixture of 1-methylspiro[chromeno[4,3-c]pyrazole-4,4'-piperidine]dihydrochloride (108 mg, 0.33 mmol), 4-(isopropylsulfonyl)-3-methylbenzoic acid (80 mg, 0.33 mmol), HATU (126 mg, 0.33 mmol), and dichloromethane (2 mL) at 25° C. The mixture was heated at 40° C. for 3 h. The mixture was concentrated and the residue was purified by column chromatography (0-100% ethyl acetate/hexanes) to give (4-(isopropylsulfonyl)-3-methylphenyl)(1-methyl-1H-spiro[chromeno[4,3-c]pyrazole-4,4'-piperidine]-1'-yl)methanone (107 mg, 65%) as a fluffy white solid. ESI-MS m/z calc. 479.6. found 480.3 (M+1)⁺. Retention time: 2.24 minutes (3 min run).

9-Aza-(4-isopropoxy-3-methylphenyl)(1-methyl-1H-spiro[chromeno[4,3-c]pyrazole-4,4'-piperidine]-1'-yl)methanone

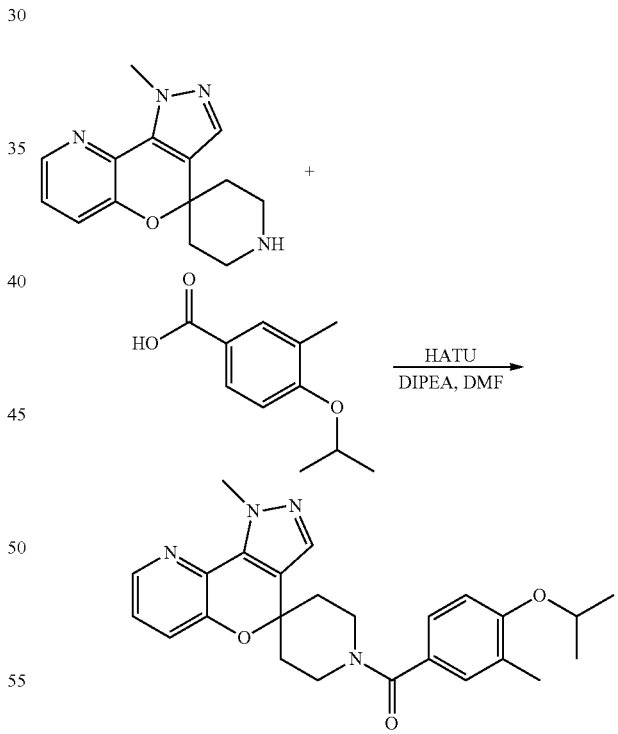

A solution of 9-aza-1-methyl-1H-spiro[chromeno[4,3-c]pyrazole-4,4'-piperidine] (64 mg, 0.19 mmol), 4-isopropoxy-3-methyl-benzoic acid (45 mg, 0.23 mmol), HATU (89 mg, 0.23 mmol) and iPr₂NEt (169 μL 0.97 mmol) in DMF (0.5 mL) was stirred at room temperature for 16 hours. Purification by HPLC (10-90% MeOH in Water (HCl modifier)) afforded the HCl salt of the product. This material was taken up in EtOAc and washed with saturated aqueous Na₂CO₃ (2×), brine, dried over Na₂SO₄ and evaporated to dryness to give 9-aza-(4-isopropoxy-3-methylphenyl)(1-methyl-1H-spiro[chromeno[4,3-c]pyrazole-4,4'-piperidine]-1'-yl)methanone (8 mg, 18%) as a white solid. ESI-MS m/z calc. 432.2. found 433.5 (M+1)$^+$; Retention time: 1.91 minutes (3 min run). $^1$H NMR (400 MHz, CDCl$_3$) δ 8.19 (dd, J=4.7, 1.3 Hz, 1H), 7.47-7.21 (m, 4H), 7.14 (dd, J=8.2, 4.7 Hz, 1H), 6.83 (d, J=8.0 Hz, 1H), 4.75-4.48 (m, J=12.0, 5.9 Hz, 1H), 4.36 (s, J=7.9 Hz, 3H), 3.44 (s br, 2H), 2.22 (s, J=7.5 Hz, 3H), 2.16 (s br, 2H), 1.94 (s br, 2H), 1.70 (s br, 2H), 1.36 (d, J=6.9 Hz, 6H).

The following compounds were prepared using procedures reported above:

| Product Name | Amine or Amine•HCl | Carboxylic Acid |
|---|---|---|
| (4-(2-methoxyethoxy)-3-methylphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(2-methoxyethoxy)-3-methylbenzoic acid |
| 2-(2-methoxyethoxy)-5-(spiro[benzo[b]pyrrolo[1,2-d][1,4]oxazine-4,4'-piperidine]-1'-ylcarbonyl)benzonitrile | spiro[benzo[b]pyrrolo[1,2-d][1,4]oxazine-4,4'-piperidine] | 3-cyano-4-(2-methoxyethoxy)benzoic acid |
| (3-chloro-4-(2-methoxyethoxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3-chloro-4-(2-methoxyethoxy)benzoic acid |
| (4-(isopentyloxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(isopentyloxy)-3-methoxybenzoic acid |
| (4-(cyclopentyloxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(cyclopentyloxy)-3-methoxybenzoic acid |
| (4-tert-butyl-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-tert-butyl-3-methoxybenzoic acid |
| 2-propoxy-5-(spiro[benzo[b]pyrrolo[1,2-d][1,4]oxazine-4,4'-piperidine]-1'-ylcarbonyl)benzonitrile | spiro[benzo[b]pyrrolo[1,2-d][1,4]oxazine-4,4'-piperidine] | 3-cyano-4-propoxybenzoic acid |
| (3-methyl-4-propoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3-methyl-4-propoxybenzoic acid |
| (4-isopropoxy-3-methylphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-isopropoxy-3-methylbenzoic acid |
| (3-methoxy-4-(2-methoxyethoxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3-methoxy-4-(2-methoxyethoxy)benzoic acid |
| 2-isopropoxy-5-(spiro[benzo[b]pyrrolo[1,2-d][1,4]oxazine-4,4'-piperidine]-1'-ylcarbonyl)benzamide | spiro[benzo[b]pyrrolo[1,2-d][1,4]oxazine-4,4'-piperidine] | 3-carbamoyl-4-isopropoxybenzoic acid |
| 2-propoxy-5-(spiro[benzo[b]pyrrolo[1,2-d][1,4]oxazine-4,4'-piperidine]-1'-ylcarbonyl)benzamide | spiro[benzo[b]pyrrolo[1,2-d][1,4]oxazine-4,4'-piperidine] | 3-carbamoyl-4-propoxybenzoic acid |
| (4-methoxy-3-(trifluoromethyl)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-methoxy-3-(trifluoromethyl)benzoic acid |
| (4-isobutoxy-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-isobutoxy-3-methoxybenzoic acid |
| (3-chloro-4-methylphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3-chloro-4-methylbenzoic acid |
| (4-ethyl-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-ethyl-3-methoxybenzoic acid |
| (4-propoxy-3-(trifluoromethyl)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-propoxy-3-(trifluoromethyl)benzoic acid |

| Product Name | Amine or Amine•HCl | Carboxylic Acid |
|---|---|---|
| (4-isopropoxy-3-(trifluoromethyl)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-isopropoxy-3-(trifluoromethyl)benzoic acid |
| (4-(2-methoxyethoxy)-3-(trifluoromethyl)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(2-methoxyethoxy)-3-(trifluoromethyl)benzoic acid |
| (4-tert-butoxy-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-tert-butoxy-3-methoxybenzoic acid |
| 2-tert-butyl-5-(spiro[benzo[b]pyrrolo[1,2-d][1,4]oxazine-4,4'-piperidine]-1'-ylcarbonyl)benzonitrile | spiro[benzo[b]pyrrolo[1,2-d][1,4]oxazine-4,4'-piperidine] | 4-tert-butyl-3-cyanobenzoic acid |
| (7-chlorospiro[benzo[b]pyrrolo[1,2-d][1,4]oxazine-4,4'-piperidine]-1'-yl)(3-methoxy-4-(2-methoxyethoxy)phenyl)methanone | 7-chlorospiro[benzo[b]pyrrolo[1,2-d][1,4]oxazine-4,4'-piperidine] | 3-methoxy-4-(2-methoxyethoxy)benzoic acid |
| (7-chlorospiro[benzo[b]pyrrolo[1,2-d][1,4]oxazine-4,4'-piperidine]-1'-yl)(4-(2-methoxyethoxy)-3-methylphenyl)methanone | 7-chlorospiro[benzo[b]pyrrolo[1,2-d][1,4]oxazine-4,4'-piperidine] | 4-(2-methoxyethoxy)-3-methylbenzoic acid |
| (7-chlorospiro[benzo[b]pyrrolo[1,2-d][1,4]oxazine-4,4'-piperidine]-1'-yl)(4-ethyl-3-methoxyphenyl)methanone | 7-chlorospiro[benzo[b]pyrrolo[1,2-d][1,4]oxazine-4,4'-piperidine] | 4-ethyl-3-methoxybenzoic acid |
| (7-chlorospiro[benzo[b]pyrrolo[1,2-d][1,4]oxazine-4,4'-piperidine]-1'-yl)(4-isopropoxy-3-methylphenyl)methanone | 7-chlorospiro[benzo[b]pyrrolo[1,2-d][1,4]oxazine-4,4'-piperidine] | 4-isopropoxy-3-methylbenzoic acid |
| (7-fluorospiro[benzo[b]pyrrolo[1,2-d][1,4]oxazine-4,4'-piperidine]-1'-yl)(4-isopropoxy-3-methylphenyl)methanone | 7-fluorospiro[benzo[b]pyrrolo[1,2-d][1,4]oxazine-4,4'-piperidine] | 4-isopropoxy-3-methylbenzoic acid |
| (7-fluorospiro[benzo[b]pyrrolo[1,2-d][1,4]oxazine-4,4'-piperidine]-1'-yl)(3-methoxy-4-(2-methoxyethoxy)phenyl)methanone | 7-fluorospiro[benzo[b]pyrrolo[1,2-d][1,4]oxazine-4,4'-piperidine] | 3-methoxy-4-(2-methoxyethoxy)benzoic acid |
| (7-fluorospiro[benzo[b]pyrrolo[1,2-d][1,4]oxazine-4,4'-piperidine]-1'-yl)(4-(2-methoxyethoxy)-3-methylphenyl)methanone | 7-fluorospiro[benzo[b]pyrrolo[1,2-d][1,4]oxazine-4,4'-piperidine] | 4-(2-methoxyethoxy)-3-methylbenzoic acid |
| (4-ethyl-3-methoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | 4-ethyl-3-methoxybenzoic acid |
| (4-(2-ethoxyethoxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(2-ethoxyethoxy)-3-methoxybenzoic acid |
| (R)-(3-methoxy-4-(tetrahydrofuran-3-yloxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (R)-3-methoxy-4-(tetrahydrofuran-3-yloxy)benzoic acid |
| (7-chlorospiro[benzo[b]pyrrolo[1,2-d][1,4]oxazine-4,4'-piperidine]-1'-yl)(4-propoxy-3-(trifluoromethyl)phenyl)methanone | 7-chlorospiro[benzo[b]pyrrolo[1,2-d][1,4]oxazine-4,4'-piperidine] | 4-propoxy-3-(trifluoromethyl)benzoic acid |
| (7-fluorospiro[benzo[b]pyrrolo[1,2-d][1,4]oxazine-4,4'-piperidine]-1'-yl)(4-propoxy-3-(trifluoromethyl)phenyl)methanone | 7-fluorospiro[benzo[b]pyrrolo[1,2-d][1,4]oxazine-4,4'-piperidine] | 4-propoxy-3-(trifluoromethyl)benzoic acid |
| (3-methoxy-4-(3-methoxypropoxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3-methoxy-4-(3-methoxypropoxy)benzoic acid |
| (4-(3-hydroxypropoxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(3-hydroxypropoxy)-3-methoxybenzoic acid |
| (4-(2-hydroxyethoxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(2-hydroxyethoxy)-3-methoxybenzoic acid |

-continued

| Product Name | Amine or Amine•HCl | Carboxylic Acid |
|---|---|---|
| (4-tert-butoxy-3-methylphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-tert-butoxy-3-methylbenzoic acid |
| (7-chlorospiro[benzo[b]pyrrolo[1,2-d][1,4]oxazine-4,4'-piperidine]-1'-yl)(4-(3-methoxypropoxy)-3-(trifluoromethyl)phenyl)methanone | 7-chlorospiro[benzo[b]pyrrolo[1,2-d][1,4]oxazine-4,4'-piperidine] | 4-(3-methoxypropoxy)-3-(trifluoromethyl)benzoic acid |
| 5-(7-chlorospiro[benzo[b]pyrrolo[1,2-d][1,4]oxazine-4,4'-piperidine]-1'-ylcarbonyl)-2-methoxybenzenesulfonamide | 7-chlorospiro[benzo[b]pyrrolo[1,2-d][1,4]oxazine-4,4'-piperidine] | 4-methoxy-3-sulfamoylbenzoic acid |
| (7-chlorospiro[benzo[b]pyrrolo[1,2-d][1,4]oxazine-4,4'-piperidine]-1'-yl)(4-(2-isopropoxyethoxy)-3-methoxyphenyl)methanone | 7-chlorospiro[benzo[b]pyrrolo[1,2-d][1,4]oxazine-4,4'-piperidine] | 4-(2-isopropoxyethoxy)-3-methoxybenzoic acid |
| (4-(3-methoxypropoxy)-3-(trifluoromethyl)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(3-methoxypropoxy)-3-(trifluoromethyl)benzoic acid |
| 2-methoxy-5-(spiro[benzo[b]pyrrolo[1,2-d][1,4]oxazine-4,4'-piperidine]-1'-ylcarbonyl)-benzenesulfonamide | spiro[benzo[b]pyrrolo[1,2-d][1,4]oxazine-4,4'-piperidine] | 4-methoxy-3-sulfamoylbenzoic acid |
| (R)-(7-chlorospiro[benzo[b]pyrrolo[1,2-d][1,4]oxazine-4,4'-piperidine]-1'-yl)(3-methoxy-4-(tetrahydrofuran-3-yloxy)phenyl)methanone | 7-chlorospiro[benzo[b]pyrrolo[1,2-d][1,4]oxazine-4,4'-piperidine] | (R)-3-methoxy-4-(tetrahydrofuran-3-yloxy)benzoic acid |
| (R)-(7-chlorospiro[benzo[b]pyrrolo[1,2-d][1,4]oxazine-4,4'-piperidine]-1'-yl)(3-methoxy-4-(1-methoxypropan-2-yloxy)phenyl)methanone | 7-chlorospiro[benzo[b]pyrrolo[1,2-d][1,4]oxazine-4,4'-piperidine] | (R)-3-methoxy-4-(1-methoxypropan-2-yloxy)benzoic acid |
| (7-chlorospiro[benzo[b]pyrrolo[1,2-d][1,4]oxazine-4,4'-piperidine]-1'-yl)(3-methoxy-4-((tetrahydrofuran-2-yl)methoxy)phenyl)methanone | 7-chlorospiro[benzo[b]pyrrolo[1,2-d][1,4]oxazine-4,4'-piperidine] | 3-methoxy-4-((tetrahydrofuran-2-yl)methoxy)benzoic acid |
| (R)-(3-methoxy-4-(1-methoxypropan-2-yloxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (R)-3-methoxy-4-(1-methoxypropan-2-yloxy)benzoic acid |
| (3-methoxy-4-((tetrahydrofuran-2-yl)methoxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3-methoxy-4-((tetrahydrofuran-2-yl)methoxy)benzoic acid |
| (S)-(7-chlorospiro[benzo[b]pyrrolo[1,2-d][1,4]oxazine-4,4'-piperidine]-1'-yl)(3-methoxy-4-(tetrahydrofuran-3-yloxy)phenyl)methanone | 7-chlorospiro[benzo[b]pyrrolo[1,2-d][1,4]oxazine-4,4'-piperidine] | (S)-3-methoxy-4-(tetrahydrofuran-3-yloxy)benzoic acid |
| (S)-(7-chlorospiro[benzo[b]pyrrolo[1,2-d][1,4]oxazine-4,4'-piperidine]-1'-yl)(3-methoxy-4-(1-methoxypropan-2-yloxy)phenyl)methanone | 7-chlorospiro[benzo[b]pyrrolo[1,2-d][1,4]oxazine-4,4'-piperidine] | (S)-3-methoxy-4-(1-methoxypropan-2-yloxy)benzoic acid |
| (S)-(3-methoxy-4-(1-methoxypropan-2-yloxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (S)-3-methoxy-4-(1-methoxypropan-2-yloxy)benzoic acid |
| (S)-(3-methoxy-4-(tetrahydrofuran-3-yloxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (S)-3-methoxy-4-(tetrahydrofuran-3-yloxy)benzoic acid |
| (S)-(4-sec-butoxy-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (S)-4-sec-butoxy-3-methoxybenzoic acid |
| (S)-(4-sec-butoxy-3-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | (S)-4-sec-butoxy-3-methoxybenzoic acid |
| (R)-(7-chlorospiro[benzo[b]pyrrolo[1,2-d][1,4]oxazine-4,4'- | 7-chlorospiro[benzo[b]pyrrolo[1, | (R)-3-methoxy-4-(2-methoxypropoxy)benzoic acid |

| Product Name | Amine or Amine•HCl | Carboxylic Acid |
|---|---|---|
| piperidine]-1'-yl)(3-methoxy-4-(2-methoxypropoxy)phenyl)methanone | 2-d][1,4]oxazine-4,4'-piperidine] | |
| (4-tert-butyl-3-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-tert-butyl-3-methoxybenzoic acid |
| (S)-(3-methoxy-4-(2-methoxypropoxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (S)-3-methoxy-4-(2-methoxypropoxy)benzoic acid |
| (S)-(7-fluorospiro[benzo[b]pyrrolo[1,2-d][1,4]oxazine-4,4'-piperidine]-1'-yl)(3-methoxy-4-(2-methoxypropoxy)phenyl)methanone | 7-fluorospiro[benzo[b]pyrrolo[1,2-d][1,4]oxazine-4,4'-piperidine] | (S)-3-methoxy-4-(2-methoxypropoxy)benzoic acid |
| (S)-(4-sec-butoxy-3-methoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | (S)-4-sec-butoxy-3-methoxybenzoic acid |
| (R)-(3-methoxy-4-(2-methoxypropoxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (R)-3-methoxy-4-(2-methoxypropoxy)benzoic acid |
| (R)-(7-fluorospiro[benzo[b]pyrrolo[1,2-d][1,4]oxazine-4,4'-piperidine]-1'-yl)(3-methoxy-4-(2-methoxypropoxy)phenyl)methanone | 7-fluorospiro[benzo[b]pyrrolo[1,2-d][1,4]oxazine-4,4'-piperidine] | (R)-3-methoxy-4-(2-methoxypropoxy)benzoic acid |
| (4-tert-butyl-3-methoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | 4-tert-butyl-3-methoxybenzoic acid |
| (7-chlorospiro[benzo[b]pyrrolo[1,2-d][1,4]oxazine-4,4'-piperidine]-1'-yl)(4-methoxy-3-(trifluoromethyl)phenyl)methanone | 7-chlorospiro[benzo[b]pyrrolo[1,2-d][1,4]oxazine-4,4'-piperidine] | 4-methoxy-3-(trifluoromethyl)benzoic acid |
| (7-fluorospiro[benzo[b]pyrrolo[1,2-d][1,4]oxazine-4,4'-piperidine]-1'-yl)(4-methoxy-3-(trifluoromethyl)phenyl)methanone | 7-fluorospiro[benzo[b]pyrrolo[1,2-d][1,4]oxazine-4,4'-piperidine] | 4-methoxy-3-(trifluoromethyl)benzoic acid |
| (3,4-dimethylphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3,4-dimethylbenzoic acid |
| (7-chlorospiro[benzo[b]pyrrolo[1,2-d][1,4]oxazine-4,4'-piperidine]-1'-yl)(3,4-dimethylphenyl)methanone | 7-chlorospiro[benzo[b]pyrrolo[1,2-d][1,4]oxazine-4,4'-piperidine] | 3,4-dimethylbenzoic acid |
| (3,4-dimethylphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | 3,4-dimethylbenzoic acid |
| (7-chlorospiro[benzo[b]pyrrolo[1,2-d][1,4]oxazine-4,4'-piperidine]-1'-yl)(4-(2-hydroxypropan-2-yl)-3-methoxyphenyl)methanone | 7-chlorospiro[benzo[b]pyrrolo[1,2-d][1,4]oxazine-4,4'-piperidine] | 4-(2-hydroxypropan-2-yl)-3-methoxybenzoic acid |
| (7-fluorospiro[benzo[b]pyrrolo[1,2-d][1,4]oxazine-4,4'-piperidine]-1'-yl)(4-(2-hydroxypropan-2-yl)-3-methoxyphenyl)methanone | 7-fluorospiro[benzo[b]pyrrolo[1,2-d][1,4]oxazine-4,4'-piperidine] | 4-(2-hydroxypropan-2-yl)-3-methoxybenzoic acid |
| 2-tert-butyl-5-(7-chlorospiro[benzo[b]pyrrolo[1,2-d][1,4]oxazine-4,4'-piperidine]-1'-ylcarbonyl)benzonitrile | 7-chlorospiro[benzo[b]pyrrolo[1,2-d][1,4]oxazine-4,4'-piperidine] | 4-tert-butyl-3-cyanobenzoic acid |
| 2-tert-butyl-5-(7-fluorospiro[benzo[b]pyrrolo[1,2-d][1,4]oxazine-4,4'-piperidine]-1'-ylcarbonyl)benzonitrile | 7-fluorospiro[benzo[b]pyrrolo[1,2-d][1,4]oxazine-4,4'-piperidine] | 4-tert-butyl-3-cyanobenzoic acid |
| (7-chlorospiro[benzo[b]pyrrolo[1,2-d][1,4]oxazine-4,4'-piperidine]-1'-yl)(4-(2-hydroxypropan-2-yl)-3-methylphenyl)methanone | 7-chlorospiro[benzo[b]pyrrolo[1,2-d][1,4]oxazine-4,4'-piperidine] | 4-(2-hydroxypropan-2-yl)-3-methylbenzoic acid |
| (7-fluorospiro[benzo[b]pyrrolo[1,2-d][1,4]oxazine-4,4'- | 7-fluorospiro[benzo[b]pyrrolo[1, | 4-(2-hydroxypropan-2-yl)-3-methylbenzoic acid |

| Product Name | Amine or Amine•HCl | Carboxylic Acid |
|---|---|---|
| piperidine]-1'-yl)(4-(2-hydroxypropan-2-yl)-3-methylphenyl)methanone | 2-d][1,4]oxazine-4,4'-piperidine] | |
| (4-(2-hydroxypropan-2-yl)-3-methylphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(2-hydroxypropan-2-yl)-3-methylbenzoic acid |
| phenyl(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | benzoic acid |
| (7-fluorospiro[benzo[b]pyrrolo[1,2-d][1,4]oxazine-4,4'-piperidine]-1'-yl)(phenyl)methanone | 7-fluorospiro[benzo[b]pyrrolo[1,2-d][1,4]oxazine-4,4'-piperidine] | benzoic acid |
| (7-chlorospiro[benzo[b]pyrrolo[1,2-d][1,4]oxazine-4,4'-piperidine]-1'-yl)(phenyl)methanone | 7-chlorospiro[benzo[b]pyrrolo[1,2-d][1,4]oxazine-4,4'-piperidine] | benzoic acid |
| spiro[benzo[b]pyrrolo[1,2-d][1,4]oxazine-4,4'-piperidine]-1'-yl(2-(trifluoromethoxy)phenyl)methanone | spiro[benzo[b]pyrrolo[1,2-d][1,4]oxazine-4,4'-piperidine] | 2-(trifluoromethoxy)benzoic acid |
| (7-fluorospiro[benzo[b]pyrrolo[1,2-d][1,4]oxazine-4,4'-piperidine]-1'-yl)(2-(trifluoromethoxy)phenyl)methanone | 7-fluorospiro[benzo[b]pyrrolo[1,2-d][1,4]oxazine-4,4'-piperidine] | 2-(trifluoromethoxy)benzoic acid |
| (7-chlorospiro[benzo[b]pyrrolo[1,2-d][1,4]oxazine-4,4'-piperidine]-1'-yl)(2-(trifluoromethoxy)phenyl)methanone | 7-chlorospiro[benzo[b]pyrrolo[1,2-d][1,4]oxazine-4,4'-piperidine] | 2-(trifluoromethoxy)benzoic acid |
| (3-methyl-4-((tetrahydrofuran-2-yl)methoxy)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 3-methyl-4-((tetrahydrofuran-2-yl)methoxy)benzoic acid |
| (7-fluorospiro[benzo[b]pyrrolo[1,2-d][1,4]oxazine-4,4'-piperidine]-1'-yl)(3-methyl-4-((tetrahydrofuran-2-yl)methoxy)phenyl)methanone | 7-fluorospiro[benzo[b]pyrrolo[1,2-d][1,4]oxazine-4,4'-piperidine] | 3-methyl-4-((tetrahydrofuran-2-yl)methoxy)benzoic acid |
| (7-chlorospiro[benzo[b]pyrrolo[1,2-d][1,4]oxazine-4,4'-piperidine]-1'-yl)(3-methyl-4-((tetrahydrofuran-2-yl)methoxy)phenyl)methanone | 7-chlorospiro[benzo[b]pyrrolo[1,2-d][1,4]oxazine-4,4'-piperidine] | 3-methyl-4-((tetrahydrofuran-2-yl)methoxy)benzoic acid |
| (7-fluorospiro[benzo[b]pyrrolo[1,2-d][1,4]oxazine-4,4'-piperidine]-1'-yl)(3-methoxy-4-((tetrahydrofuran-2-yl)methoxy)phenyl)methanone | 7-fluorospiro[benzo[b]pyrrolo[1,2-d][1,4]oxazine-4,4'-piperidine] | 3-methoxy-4-((tetrahydrofuran-2-yl)methoxy)benzoic acid |
| (S)-(7-fluorospiro[benzo[b]pyrrolo[1,2-d][1,4]oxazine-4,4'-piperidine]-1'-yl)(3-methoxy-4-(1-methoxypropan-2-yloxy)phenyl)methanone | 7-fluorospiro[benzo[b]pyrrolo[1,2-d][1,4]oxazine-4,4'-piperidine] | (S)-3-methoxy-4-(1-methoxypropan-2-yloxy)benzoic acid |
| (R)-(7-fluorospiro[benzo[b]pyrrolo[1,2-d][1,4]oxazine-4,4'-piperidine]-1'-yl)(3-methoxy-4-tetrahydrofuran-3-yloxy)phenyl)methanone | 7-fluorospiro[benzo[b]pyrrolo[1,2-d][1,4]oxazine-4,4'-piperidine] | (R)-3-methoxy-4-(tetrahydrofuran-3-yloxy)benzoic acid |
| (R)-(7-fluorospiro[benzo[b]pyrrolo[1,2-d][1,4]oxazine-4,4'-piperidine]-1'-yl)(3-methoxy-4-(1-methoxypropan-2-yloxy)phenyl)methanone | 7-fluorospiro[benzo[b]pyrrolo[1,2-d][1,4]oxazine-4,4'-piperidine] | (R)-3-methoxy-4-(1-methoxypropan-2-yloxy)benzoic acid |
| (S)-(7-fluorospiro[benzo[b]pyrrolo[1,2-d][1,4]oxazine-4,4'-piperidine]-1'-yl)(3-methoxy-4-tetrahydrofuran-3-yloxy)phenyl)methanone | 7-fluorospiro[benzo[b]pyrrolo[1,2-d][1,4]oxazine-4,4'-piperidine] | (S)-3-methoxy-4-(tetrahydrofuran-3-yloxy)benzoic acid |
| (R)-(4-((2,2-dimethyl-1,3-dioxolan-4-yl)methoxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (R)-4-((2,2-dimethyl-1,3-dioxolan-4-yl)methoxy)-3-methoxybenzoic acid |
| (R)-(7-chlorospiro[benzo[b]pyrrolo[1,2-d][1,4]oxazine-4,4'-piperidine]-1'-yl)(4-((2,2-dimethyl-1,3-dioxolan-4- | 7-chlorospiro[benzo[b]pyrrolo[1,2-d][1,4]oxazine-4,4'-piperidine] | (R)-4-((2,2-dimethyl-1,3-dioxolan-4-yl)methoxy)-3-methoxybenzoic acid |

| Product Name | Amine or Amine•HCl | Carboxylic Acid |
| --- | --- | --- |
| yl)methoxy)-3-methoxyphenyl)methanone | | |
| (R)-(4-sec-butoxy-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | (R)-4-sec-butoxy-3-methoxybenzoic acid |
| (R)-(4-sec-butoxy-3-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | (R)-4-sec-butoxy-3-methoxybenzoic acid |
| (R)-(4-sec-butoxy-3-methoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | (R)-4-sec-butoxy-3-methoxybenzoic acid |
| 2-(2-methoxy-4-(spiro[benzo[b]pyrrolo[1,2-d][1,4]oxazine-4,4'-piperidine]-1'-ylcarbonyl)phenoxy)-2-methylpropanenitrile | spiro[benzo[b]pyrrolo[1,2-d][1,4]oxazine-4,4'-piperidine] | 4-(2-cyanopropan-2-yloxy)-3-methoxybenzoic acid |
| (4-bromo-3-fluorophenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-bromo-3-fluorobenzoic acid |
| 4-(7-chloro-1-(trifluoromethyl)spiro[benzo[b]pyrrolo[1,2-d][1,4]oxazine-4,4'-piperidine]-1'-ylcarbonyl)-1-methylpyridin-2(1H)-one | 7-chloro-1-(trifluoromethyl)spiro[benzo[b]pyrrolo[1,2-d][1,4]oxazine-4,4'-piperidine] | 1-methyl-2-oxo-1,2-dihydropyridine-4-carboxylic acid |
| 5-(7-chlorospiro[benzo[b]pyrrolo[1,2-d][1,4]oxazine-4,4'-piperidine]-1'-ylcarbonyl)-1-methylpyridin-2(1H)-one | 7-chlorospiro[benzo[b]pyrrolo[1,2-d][1,4]oxazine-4,4'-piperidine] | 1-methyl-6-oxo-1,6-dihydropyridine-3-carboxylic acid |
| (7-chlorospiro[benzo[b]pyrrolo[1,2-d][1,4]oxazine-4,4'-piperidine]-1'-yl)(3-fluoro-2-hydroxyphenyl)methanone | 7-chlorospiro[benzo[b]pyrrolo[1,2-d][1,4]oxazine-4,4'-piperidine] | 3-fluoro-2-hydroxybenzoic acid |
| (3-chloro-2-hydroxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 3-chloro-2-hydroxybenzoic acid |
| (4-bromophenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-bromobenzoic acid |
| 3-(7-chlorospiro[benzo[b]pyrrolo[1,2-d][1,4]oxazine-4,4'-piperidine]-1'-ylcarbonyl)-1-methylpyridin-2(1H)-one | 7-chlorospiro[benzo[b]pyrrolo[1,2-d][1,4]oxazine-4,4'-piperidine] | 1-methyl-2-oxo-1,2-dihydropyridine-3-carboxylic acid |
| 3-(7-chlorospiro[benzo[b]pyrrolo[1,2-d][1,4]oxazine-4,4'-piperidine]-1'-ylcarbonyl)-1,6-dimethylpyridin-2(1H)-one | 7-chlorospiro[benzo[b]pyrrolo[1,2-d][1,4]oxazine-4,4'-piperidine] | 1,6-dimethyl-2-oxo-1,2-dihydropyridine-3-carboxylic acid |
| 3-(7-chlorospiro[benzo[b]pyrrolo[1,2-d][1,4]oxazine-4,4'-piperidine]-1'-ylcarbonyl)-6-isopropylpyridin-2(1H)-one | 7-chlorospiro[benzo[b]pyrrolo[1,2-d][1,4]oxazine-4,4'-piperidine] | 6-isopropyl-2-oxo-1,2-dihydropyridine-3-carboxylic acid |
| (7-chlorospiro[benzo[b]pyrrolo[1,2-d][1,4]oxazine-4,4'-piperidine]-1'-yl)(2-methylbenzo[d]oxazol-7-yl)methanone | 7-chlorospiro[benzo[b]pyrrolo[1,2-d][1,4]oxazine-4,4'-piperidine] | 2-methylbenzo[d]oxazole-7-carboxylic acid |
| 4-(7-chlorospiro[benzo[b]pyrrolo[1,2-d][1,4]oxazine-4,4'-piperidine]-1'-ylcarbonyl)-1-isopropylpyridin-2(1H)-one | 7-chlorospiro[benzo[b]pyrrolo[1,2-d][1,4]oxazine-4,4'-piperidine] | 1-isopropyl-2-oxo-1,2-dihydropyridine-4-carboxylic acid |
| 3-(7-chlorospiro[benzo[b]pyrrolo[1,2-d][1,4]oxazine-4,4'-piperidine]-1'-ylcarbonyl)-4,6-dimethylpyridin-2(1H)-one | 7-chlorospiro[benzo[b]pyrrolo[1,2-d][1,4]oxazine-4,4'-piperidine] | 4,6-dimethyl-2-oxo-1,2-dihydropyridine-3-carboxylic acid |
| 3-(7-chlorospiro[benzo[b]pyrrolo[1,2-d][1,4]oxazine-4,4'-piperidine]-1'-ylcarbonyl)-1-ethylpyridin-2(1H)-one | 7-chlorospiro[benzo[b]pyrrolo[1,2-d][1,4]oxazine-4,4'-piperidine] | 1-ethyl-2-oxo-1,2-dihydropyridine-3-carboxylic acid |
| 1'-(2-(difluoromethyl)benzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 2-(difluoromethyl)benzoic acid |
| 1'-(3-fluoro-4- | spiro[benzo[b]pyrrolo[1,2- | 3-fluoro-4-isopropoxybenzoic |

-continued

| Product Name | Amine or Amine•HCl | Carboxylic Acid |
|---|---|---|
| isopropoxybenzoyl)spiro[benzo[b]pyrrolo[1,2-d][1,4]oxazine-4,4'-piperidine]-1-carbonitrile | d][1,4]oxazine-4,4'-piperidine]-1-carbonitrile | acid |
| 1'-(2-fluoro-6-methoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 2-fluoro-6-methoxybenzoic acid |
| 1'-(2-(difluoromethoxy)benzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile |
| 1'-(2-fluoro-4-isopropoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 2-fluoro-4-isopropoxybenzoic acid |
| 1'-(3-chloro-4-methylbenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 3-chloro-4-methylbenzoic acid |
| 1'-(4-isopropoxy-3-methoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-isopropoxy-3-methoxybenzoic acid |
| 1'-(4-(isopropylsulfonyl)benzoyl)spiro[benzo[b]pyrrolo2-[1,d][1,4]oxazine-4,4'-piperidine]-1-carbonitrile | spiro[benzo[b]pyrrolo[1,2-d][1,4]oxazine-4,4'-piperidine]-1-carbonitrile | 4-(isopropylsulfonyl)benzoic acid |
| 1'-(4-bromo-3-methoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-bromo-3-methoxybenzoic acid |
| 1'-(3-fluoro-2-methoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 3-fluoro-2-methoxybenzoic acid |
| 1'-(5-fluoro-2-methoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 5-fluoro-2-methoxybenzoic acid |
| 1'-(4-(difluoromethylsulfonyl)benzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-(difluoromethylsulfonyl)benzoic acid |
| 7-chloro-1'-(3-fluoro-2-methoxybenzoyl)spiro[benzo[b]pyrrolo[1,2-d][1,4]oxazine-4,4'-piperidine]-1-carbonitrile | 7-chlorospiro[benzo[b]pyrrolo[1,2-d][1,4]oxazine-4,4'-piperidine]-1-carbonitrile | 3-fluoro-2-methoxybenzoic acid |
| 7-chloro-1'-(5-fluoro-2-methoxybenzoyl)spiro[benzo[b]pyrrolo[1,2-d][1,4]oxazine-4,4'-piperidine]-1-carbonitrile | 7-chlorospiro[benzo[b]pyrrolo[1,2-d][1,4]oxazine-4,4'-piperidine]-1-carbonitrile | 5-fluoro-2-methoxybenzoic acid |
| 7-chloro-1'-(4-(isopropylsulfonyl)benzoyl)spiro[benzo[b]pyrrolo[1,2-d][1,4]oxazine-4,4'-piperidine]-1-carbonitrile | 7-chlorospiro[benzo[b]pyrrolo[1,2-d][1,4]oxazine-4,4'-piperidine]-1-carbonitrile | 4-(isopropylsulfonyl)benzoic acid |
| 1'-(4-tert-butoxy-3-methoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-tert-butoxy-3-methoxybenzoic acid |
| 1'-(3-ethoxy-2-fluorobenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 3-ethoxy-2-fluorobenzoic acid |
| 1'-(4-(isopropylsulfonyl)benzoyl)-3-methylspiro[benzo[b]pyrrolo[1,2-d][1,4]oxazine-4,4'-piperidine]-1-carbonitrile | 3-methylspiro[benzo[b]pyrrolo[1,2-d][1,4]oxazine-4,4'-piperidine]-1-carbonitrile | 4-(isopropylsulfonyl)benzoic acid |
| 1'-(4-(tert-butylsulfonyl)benzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-(tert-butylsulfonyl)benzoic acid |
| 1'-(4-isobutoxy-3-methoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-isobutoxy-3-methoxybenzoic acid |
| 1'-(4-tert-butylbenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-tert-butylbenzoic acid |

-continued

| Product Name | Amine or Amine•HCl | Carboxylic Acid |
|---|---|---|
| 1'-(4-methoxy-3-(trifluoromethyl)benzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-methoxy-3-(trifluoromethyl)benzoic acid |
| 1'-(3-(hydroxymethyl)-4-isopropoxybenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 3-(hydroxymethyl)-4-isopropoxybenzoic acid |
| 1'-(3-(hydroxymethyl)-4-isopropoxybenzoyl)-7-methylspiro[benzo[b]pyrrolo[1,2-d][1,4]oxazine-4,4'-piperidine]-1-carbonitrile | 7-methylspiro[benzo[b]pyrrolo[1,2-d][1,4]oxazine-4,4'-piperidine]-1-carbonitrile | 3-(hydroxymethyl)-4-isopropoxybenzoic acid |
| 1'-(3-methyl-4-(methylsulfonyl)benzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 3-methyl-4-(methylsulfonyl)benzoic acid |
| 1'-(4-(isobutylsulfonyl)benzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 4-(isobutylsulfonyl)benzoic acid |
| 7-chloro-1'-(4-isopropoxy-3-methylbenzoyl)spiro[benzo[b]pyrrolo[1,2-d][1,4]oxazine-4,4'-piperidine]-1-carbaldehyde | 7-chlorospiro[benzo[b]pyrrolo[1,2-d][1,4]oxazine-4,4'-piperidine]-1-carbaldehyde | 4-isopropoxy-3-methylbenzoic acid |
| 9-fluoro-1'-(4-isopropoxy-3-methylbenzoyl)spiro[benzo[b]pyrrolo[1,2-d][1,4]oxazine-4,4'-piperidine]-1-carbonitrile | 9-fluorospiro[benzo[b]pyrrolo[1,2-d][1,4]oxazine-4,4'-piperidine]-1-carbonitrile | 4-isopropoxy-3-methylbenzoic acid |
| (4-isopropoxy-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-isopropoxy-3-methoxybenzoic acid |
| 1'-(4-(isopropylsulfonyl)benzoyl)-7-methylspiro[benzo[b]pyrrolo[1,2-d][1,4]oxazine-4,4'-piperidine]-1-carbonitrile | 7-methylspiro[benzo[b]pyrrolo[1,2-d][1,4]oxazine-4,4'-piperidine]-1-carbonitrile | 4-(isopropylsulfonyl)benzoic acid |
| 7-methyl-1'-(3-methyl-4-(methylsulfonyl)benzoyl)spiro[benzo[b]pyrrolo[1,2-d][1,4]oxazine-4,4'-piperidine]-1-carbonitrile | 7-methylspiro[benzo[b]pyrrolo[1,2-d][1,4]oxazine-4,4'-piperidine]-1-carbonitrile | 3-methyl-4-(methylsulfonyl)benzoic acid |
| (4-(isopropylsulfonyl)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(isopropylsulfonyl)benzoic acid |
| (4-(tert-butylsulfonyl)phenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(tert-butylsulfonyl)benzoic acid |
| (4-bromo-3-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-bromo-3-methoxybenzoic acid |
| (4-(difluoromethylsulfonyl)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 4-(difluoromethylsulfonyl)benzoic acid |
| (4-(isobutylsulfonyl)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 4-(isobutylsulfonyl)benzoic acid |
| N-methyl-4-(1-(trifluoromethyl)spiro[benzo[b]pyrrolo[1,2-d][1,4]oxazine-4,4'-piperidine]-1'-ylcarbonyl)benzenesulfonamide | 1-(trifluoromethyl)spiro[benzo[b]pyrrolo[1,2-d][1,4]oxazine-4,4'-piperidine] | 4-(N-methylsulfamoyl)benzoic acid |
| N-ethyl-4-(1-(trifluoromethyl)spiro[benzo[b]pyrrolo[1,2-d][1,4]oxazine-4,4'-piperidine]-1'-ylcarbonyl)benzenesulfonamide | 1-(trifluoromethyl)spiro[benzo[b]pyrrolo[1,2-d][1,4]oxazine-4,4'-piperidine] | 4-(N-ethylsulfamoyl)benzoic acid |
| (4-(isopropylsulfonyl)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 4-(isopropylsulfonyl)benzoic acid |

-continued

| Product Name | Amine or Amine•HCl | Carboxylic Acid |
|---|---|---|
| (1-(difluoromethyl)spiro[benzo[b]pyrrolo[1,2-d][1,4]oxazine-4,4'-piperidine]-1'-yl)(4-(isopropylsulfonyl)phenyl)methanone | 1-(difluoromethyl)spiro[benzo[b]pyrrolo[1,2-d][1,4]oxazine-4,4'-piperidine] | 4-(isopropylsulfonyl)benzoic acid |
| (3-ethoxy-2-fluorophenyl)(1-(methylsulfonyl)spiro[benzo[b]pyrrolo[1,2-d][1,4]oxazine-4,4'-piperidine]-1'-yl)methanone | 1-(methylsulfonyl)spiro[benzo[b]pyrrolo[1,2-d][1,4]oxazine-4,4'-piperidine] | 3-ethoxy-2-fluorobenzoic acid |
| (4-tert-butylphenyl)(1-(methylsulfonyl)spiro[benzo[b]pyrrolo[1,2-d][1,4]oxazine-4,4'-piperidine]-1'-yl)methanone | 1-(methylsulfonyl)spiro[benzo[b]pyrrolo[1,2-d][1,4]oxazine-4,4'-piperidine] | 4-tert-butylbenzoic acid |
| (3-chloro-4-methylphenyl)(1-(methylsulfonyl)spiro[benzo[b]pyrrolo[1,2-d][1,4]oxazine-4,4'-piperidine]-1'-yl)methanone | 1-(methylsulfonyl)spiro[benzo[b]pyrrolo[1,2-d][1,4]oxazine-4,4'-piperidine] | 3-chloro-4-methylbenzoic acid |
| (2-(difluoromethoxy)phenyl)(1-(methylsulfonyl)spiro[benzo[b]pyrrolo[1,2-d][1,4]oxazine-4,4'-piperidine]-1'-yl)methanone | 1-(methylsulfonyl)spiro[benzo[b]pyrrolo[1,2-d][1,4]oxazine-4,4'-piperidine] | 2-(difluoromethoxy)benzoic acid |
| (2-fluoro-4-isopropoxyphenyl)(1-(methylsulfonyl)spiro[benzo[b]pyrrolo[1,2-d][1,4]oxazine-4,4'-piperidine]-1'-yl)methanone | 1-(methylsulfonyl)spiro[benzo[b]pyrrolo[1,2-d][1,4]oxazine-4,4'-piperidine] | 2-fluoro-4-isopropoxybenzoic acid |
| (3-fluoro-4-isopropoxyphenyl)(1-(methylsulfonyl)spiro[benzo[b]pyrrolo[1,2-d][1,4]oxazine-4,4'-piperidine]-1'-yl)methanone | 1-(methylsulfonyl)spiro[benzo[b]pyrrolo[1,2-d][1,4]oxazine-4,4'-piperidine] | 3-fluoro-4-isopropoxybenzoic acid |
| (4-isopropoxy-3-methoxyphenyl)(1-(methylsulfonyl)spiro[benzo[b]pyrrolo[1,2-d][1,4]oxazine-4,4'-piperidine]-1'-yl)methanone | 1-(methylsulfonyl)spiro[benzo[b]pyrrolo[1,2-d][1,4]oxazine-4,4'-piperidine] | 4-isopropoxy-3-methoxybenzoic acid |
| (1-fluorospiro[benzo[b]pyrrolo[1,2-d][1,4]oxazine-4,4'-piperidine]-1'-yl)(4-(isopropylsulfonyl)phenyl)methanone | 1-fluorospiro[benzo[b]pyrrolo[1,2-d][1,4]oxazine-4,4'-piperidine] | 4-(isopropylsulfonyl)benzoic acid |
| (4-isopropoxy-3-methylphenyl)(9-methylspiro[benzo[b]pyrrolo[1,2-d][1,4]oxazine-4,4'-piperidine]-1'-yl)methanone | 9-methylspiro[benzo[b]pyrrolo[1,2-d][1,4]oxazine-4,4'-piperidine] | 4-isopropoxy-3-methoxybenzoic acid |
| (4-(isopropylsulfonyl)phenyl)(spiro[benzo[b]imidazo[1,2-d][1,4]oxazine-4,4'-piperidine]-1'-yl)methanone | spiro[benzo[b]imidazo[1,2-d][1,4]oxazine-4,4'-piperidine] | 4-(isopropylsulfonyl)benzoic acid |
| (4-tert-butoxy-3-methoxyphenyl)(spiro[benzo[b]imidazo[1,2-d][1,4]oxazine-4,4'-piperidine]-1'-yl)methanone | spiro[benzo[b]imidazo[1,2-d][1,4]oxazine-4,4'-piperidine] | 4-tert-butoxy-3-methoxybenzoic acid |
| (4-isopropoxy-3-methylphenyl)(spiro[benzo[b]imidazo[1,2-d][1,4]oxazine-4,4'-piperidine]-1'-yl)methanone | spiro[benzo[b]imidazo[1,2-d][1,4]oxazine-4,4'-piperidine] | 4-isopropoxy-3-methylbenzoic acid |
| 1-methyl-4-(spiro[benzo[b]pyrrolo[1,2-d][1,4]oxazine-4,4'-piperidine]-1'-ylcarbonyl)pyridin-2(1H)-one | spiro[benzo[b]pyrrolo[1,2-d][1,4]oxazine-4,4'-piperidine] | 1-methyl-2-oxo-pyridine-4-carboxylic acid |
| 2,4-dimethoxy-5-(spiro[benzo[b]pyrrolo[1,2-d][1,4]oxazine-4,4'-piperidine]-1'-ylcarbonyl)benzaldehyde | spiro[benzo[b]pyrrolo[1,2-d][1,4]oxazine-4,4'-piperidine] | 5-formyl-2,4-dimethoxybenzoic acid |
| (4-((1R,2R)-2-hydroxycyclopentyloxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-((1R,2R)-2-hydroxycyclopentyloxy)-3-methoxybenzoic acid |
| (4-(3-hydroxycyclopentyloxy)-3-methoxyphenyl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 4-(3-hydroxycyclopentoxy)-3-methoxy-benzoic acid |
| 2-methyl-4-(spiro[benzo[b]pyrrolo[1,2- | spiro[benzo[b]pyrrolo[1,2-d][1,4]oxazine-4,4'- | 4-cyano-3-methyl-benzoic acid |

| Product Name | Amine or Amine•HCl | Carboxylic Acid |
|---|---|---|
| d][1,4]oxazine-4,4'-piperidine]-1'-ylcarbonyl)benzonitrile | piperidine] | |
| (2-fluoro-5-methoxy-4-(2-methoxyethoxy)phenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 2-fluoro-5-methoxy-4-(2-methoxyethoxy)benzoic acid |
| 2-(2-methoxy-4-(spiro[benzo[b]pyrrolo[1,2-d][1,4]oxazine-4,4'-piperidine]-1'-ylcarbonyl)phenoxy)acetamide | spiro[benzo[b]pyrrolo[1,2-d][1,4]oxazine-4,4'-piperidine] | 4-(carbamoylmethoxy)-3-methoxy-benzoic acid |
| (2-(piperidin-1-yl)pyridin-4-yl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 2-(1-piperidyl)pyridine-4-carboxylic acid |
| (3-methoxy-4-(2-methoxy-2-methylpropoxy)phenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 3-methoxy-4-(2-methoxy-2-methyl-propoxy)-benzoic acid |
| (3-methoxy-4-(2-(trifluoromethoxy)ethoxy)phenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 3-methoxy-4-[2-(trifluoromethoxy)ethoxy]benzoic acid |
| (3-methoxy-4-propoxyphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 3-methoxy-4-propoxy-benzoic acid |
| (4-ethyl-3-hydroxyphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 4-ethyl-3-hydroxy-benzoic acid |
| (4-tert-butyl-3-hydroxyphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 3-hydroxy-4-tert-butyl-benzoic acid |
| (2-fluoro-4,5-dimethoxyphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 2-fluoro-4,5-dimethoxy-benzoic acid |
| (S)-(4-((2,2-dimethyl-1,3-dioxolan-4-yl)methoxy)-3-methoxyphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | (S)-4-((2,2-dimethyl-1,3-dioxolan-4-yl)methoxy)-3-methoxybenzoic acid |
| (6-(piperidin-1-yl)pyridin-3-yl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 6-(1-piperidyl)pyridine-3-carboxylic acid |
| (2-methoxy-3-methylphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 2-methoxy-3-methyl-benzoic acid |
| (4-(3-hydroxyoxetan-3-yl)-3-methoxyphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 4-(3-hydroxyoxetan-3-yl)-3-methoxy-benzoic acid |
| (S)-(4-((2,2-dimethyl-1,3-dioxolan-4-yl)methoxy)-3-methoxyphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | (S)-4-((2,2-dimethyl-1,3-dioxolan-4-yl)methoxy)-3-methoxybenzoic acid |
| (4-ethyl-3-methylphenyl)(spiro[benzo[b]pyrrolo [1,2-d][1,4]oxazine-4,4'-piperidine]-1'-yl)methanone | spiro[benzo[b]pyrrolo[1,2-d][1,4]oxazine-4,4'-piperidine] | 4-ethyl-3-methyl-benzoic acid |
| (2-(2-methoxyethoxy)pyridin-4-yl)(spiro[benzo[b]pyrrolo[1,2-d][1,4]oxazine-4,4'-piperidine]-1'-yl)methanone | spiro[benzo[b]pyrrolo[1,2-d][1,4]oxazine-4,4'-piperidine] | 2-(2-methoxyethoxy)pyridine-4-carboxylic acid |
| (2-fluoro-5-methoxy-4-(2-methoxyethoxy)phenyl)(7-fluorospiro[benzo[b]pyrrolo [1,2-d][1,4]oxazine-4,4'-piperidine]-1'-yl)methanone | 7-fluorospiro[benzo[b]pyrrolo[1,2-d][1,4]oxazine-4,4'-piperidine] | 2-fluoro-5-methoxy-4-(2-methoxyethoxy)benzoic acid |

| Product Name | Amine or Amine•HCl | Carboxylic Acid |
|---|---|---|
| 2-(4-(7-fluorospiro[benzo[b]pyrrolo[1,2-d][1,4]oxazine-4,4'-piperidine]-1'-ylcarbonyl)-2-methoxyphenoxy)acetamide | 7-fluorospiro[benzo[b]pyrrolo[1,2-d][1,4]oxazine-4,4'-piperidine] | 4-(carbamoylmethoxy)-3-methoxy-benzoic acid |
| 4-(7-fluorospiro[benzo[b]pyrrolo[1,2-d][1,4]oxazine-4,4'-piperidine]-1'-ylcarbonyl)-2-methylbenzonitrile | 7-fluorospiro[benzo[b]pyrrolo[1,2-d][1,4]oxazine-4,4'-piperidine] | 4-cyano-3-methyl-benzoic acid |
| 5-(7-fluorospiro[benzo[b]pyrrolo[1,2-d][1,4]oxazine-4,4'-piperidine]-1'-ylcarbonyl)-2,4-dimethoxybenzaldehyde | 7-fluorospiro[benzo[b]pyrrolo[1,2-d][1,4]oxazine-4,4'-piperidine] | 5-formyl-2,4-dimethoxybenzoic acid |
| (4-ethyl-3-methylphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | 4-ethyl-3-methyl-benzoic acid |
| (7-fluorospiro[benzo[b]pyrrolo[1,2-d][1,4]oxazine-4,4'-piperidine]-1'-yl)(4-(3-hydroxycyclopentyloxy)-3-methoxyphenyl)methanone | 7-fluorospiro[benzo[b]pyrrolo[1,2-d][1,4]oxazine-4,4'-piperidine] | 4-(3-hydroxycyclopentoxy)-3-methoxy-benzoic acid |
| (7-fluorospiro[benzo[b]pyrrolo[1,2-d][1,4]oxazine-4,4'-piperidine]-1'-yl)(4-((1R,2R)-2-hydroxycyclopentyloxy)-3-methoxyphenyl)methanone | 7-fluorospiro[benzo[b]pyrrolo[1,2-d][1,4]oxazine-4,4'-piperidine] | 4-((1R,2R)-2-hydroxycyclopentyloxy)-3-methoxybenzoic acid |
| (7-fluorospiro[benzo[b]pyrrolo[1,2-d][1,4]oxazine-4,4'-piperidine]-1'-yl)(4-(3-hydroxyoxetan-3-yl)-3-methoxyphenyl)methanone | 7-fluorospiro[benzo[b]pyrrolo[1,2-d][1,4]oxazine-4,4'-piperidine] | 4-(3-hydroxyoxetan-3-yl)-3-methoxy-benzoic acid |
| (S)-(4-((2,2-dimethyl-1,3-dioxolan-4-yl)methoxy)-3-methoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | (S)-4-((2,2-dimethyl-1,3-dioxolan-4-yl)methoxy)-3-methoxybenzoic acid |
| (7-fluorospiro[benzo[b]pyrrolo[1,2-d][1,4]oxazine-4,4'-piperidine]-1'-yl)(3-methoxy-4-(2-methoxy-2-methylpropoxy)phenyl)methanone | 7-fluorospiro[benzo[b]pyrrolo[1,2-d][1,4]oxazine-4,4'-piperidine] | 3-methoxy-4-(2-methoxy-2-methyl-propoxy)-benzoic acid |
| (7-fluorospiro[benzo[b]pyrrolo[1,2-d][1,4]oxazine-4,4'-piperidine]-1'-yl)(3-methoxy-4-propoxyphenyl)methanone | 7-fluorospiro[benzo[b]pyrrolo[1,2-d][1,4]oxazine-4,4'-piperidine] | 3-methoxy-4-propoxy-benzoic acid |
| (4-ethyl-3-hydroxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | 4-ethyl-3-hydroxy-benzoic acid |
| (R)-(4-((2,2-dimethyl-1,3-dioxolan-4-yl)methoxy)-3-methoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | (R)-4-((2,2-dimethyl-1,3-dioxolan-4-yl)methoxy)-3-methoxybenzoic acid |
| (S)-(4-((2,2-dimethyl-1,3-dioxolan-4-yl)methoxy)-3-methoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | (S)-4-((2,2-dimethyl-1,3-dioxolan-4-yl)methoxy)-3-methoxybenzoic acid |
| (4-tert-butyl-3-hydroxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | 3-hydroxy-4-tert-butyl-benzoic acid |
| (2-fluoro-4,5-dimethoxyphenyl)(7-fluorospiro[benzo[b]pyrrolo[1,2-d][1,4]oxazine-4,4'-piperidine]-1'-yl)methanone | 7-fluorospiro[benzo[b]pyrrolo[1,2-d][1,4]oxazine-4,4'-piperidine] | 2-fluoro-4,5-dimethoxy-benzoic acid |
| (7-fluorospiro[benzo[b]pyrrolo[1,2-d][1,4]oxazine-4,4'-piperidine]-1'-yl)(2-methoxy-3-methylphenyl)methanone | 7-fluorospiro[benzo[b]pyrrolo[1,2-d][1,4]oxazine-4,4'-piperidine] | 2-methoxy-3-methyl-benzoic acid |
| 2-(7-chlorospiro[benzo[b]pyrrolo[1,2-d][1,4]oxazine-4,4'-piperidine]-1'-ylcarbonyl)benzonitrile | 7-chlorospiro[benzo[b]pyrrolo[1,2-d][1,4]oxazine-4,4'-piperidine] | 2-cyanobenzoic acid |

-continued

| Product Name | Amine or Amine•HCl | Carboxylic Acid |
|---|---|---|
| 3-(7-chlorospiro[benzo[b]pyrrolo[1,2-d][1,4]oxazine-4,4'-piperidine]-1'-ylcarbonyl)benzonitrile | 7-chlorospiro[benzo[b]pyrrolo[1,2-d][1,4]oxazine-4,4'-piperidine] | 3-cyanobenzoic acid |
| (7-chlorospiro[benzo[b]pyrrolo[1,2-d][1,4]oxazine-4,4'-piperidine]-1'-yl)(4-ethyl-3-hydroxyphenyl)methanone | 7-chlorospiro[benzo[b]pyrrolo[1,2-d][1,4]oxazine-4,4'-piperidine] | 4-ethyl-3-hydroxy-benzoic acid |
| (2-chloro-4-(methylsulfonyl)phenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 2-chloro-4-methylsulfonyl-benzoic acid |
| 4-(7-chlorospiro[benzo[b]pyrrolo[1,2-d][1,4]oxazine-4,4'-piperidine]-1'-ylcarbonyl)-1-methylpyridin-2(1H)-one | 7-chlorospiro[benzo[b]pyrrolo[1,2-d][1,4]oxazine-4,4'-piperidine] | 1-methyl-2-oxo-pyridine-4-carboxylic acid |
| (7-chlorospiro[benzo[b]pyrrolo[1,2-d][1,4]oxazine-4,4'-piperidine]-1'-yl)(4-methoxy-2-(trifluoromethyl)phenyl)methanone | 7-chlorospiro[benzo[b]pyrrolo[1,2-d][1,4]oxazine-4,4'-piperidine] | 4-methoxy-2-(trifluoromethyl)benzoic acid |
| (7-chlorospiro[benzo[b]pyrrolo[1,2-d][1,4]oxazine-4,4'-piperidine]-1'-yl)(4-((1R,2R)-2-hydroxycyclopentyloxy)-3-methoxyphenyl)methanone | 7-chlorospiro[benzo[b]pyrrolo[1,2-d][1,4]oxazine-4,4'-piperidine] | 4-(2-hydroxycyclopentoxy)-3-methoxy-benzoic acid |
| (7-chlorospiro[benzo[b]pyrrolo[1,2-d][1,4]oxazine-4,4'-piperidine]-1'-yl)(2-hydroxyphenyl)methanone | 7-chlorospiro[benzo[b]pyrrolo[1,2-d][1,4]oxazine-4,4'-piperidine] | 2-hydroxybenzoic acid |
| (7-chlorospiro[benzo[b]pyrrolo[1,2-d][1,4]oxazine-4,4'-piperidine]-1'-yl)(2-fluoro-4,5-dimethoxyphenyl)methanone | 7-chlorospiro[benzo[b]pyrrolo[1,2-d][1,4]oxazine-4,4'-piperidine] | 2-fluoro-4,5-dimethoxy-benzoic acid |
| (7-chlorospiro[benzo[b]pyrrolo[1,2-d][1,4]oxazine-4,4'-piperidine]-1'-yl)(2,4-dimethoxyphenyl)methanone | 7-chlorospiro[benzo[b]pyrrolo[1,2-d][1,4]oxazine-4,4'-piperidine] | 2,4-dimethoxybenzoic acid |
| (7-chlorospiro[benzo[b]pyrrolo[1,2-d][1,4]oxazine-4,4'-piperidine]-1'-yl)(2,6-dimethoxyphenyl)methanone | 7-chlorospiro[benzo[b]pyrrolo[1,2-d][1,4]oxazine-4,4'-piperidine] | 2,6-dimethoxybenzoic acid |
| (7-chlorospiro[benzo[b]pyrrolo[1,2-d][1,4]oxazine-4,4'-piperidine]-1'-yl)(4-(3-hydroxyoxetan-3-yl)-3-methoxyphenyl)methanone | 7-chlorospiro[benzo[b]pyrrolo[1,2-d][1,4]oxazine-4,4'-piperidine] | 4-(3-hydroxyoxetan-3-yl)-3-methoxy-benzoic acid |
| 3-(7-chlorospiro[benzo[b]pyrrolo[1,2-d][1,4]oxazine-4,4'-piperidine]-1'-ylcarbonyl)-5-fluorobenzonitrile | 7-chlorospiro[benzo[b]pyrrolo[1,2-d][1,4]oxazine-4,4'-piperidine] | 3-cyano-5-fluoro-benzoic acid |
| 2-(4-(7-chlorospiro[benzo[b]pyrrolo[1,2-d][1,4]oxazine-4,4'-piperidine]-1'-ylcarbonyl)-2-methoxyphenoxy)acetamide | 7-chlorospiro[benzo[b]pyrrolo[1,2-d][1,4]oxazine-4,4'-piperidine] | 4-(carbamoylmethoxy)-3-methoxy-benzoic acid |
| (7-chlorospiro[benzo[b]pyrrolo[1,2-d][1,4]oxazine-4,4'-piperidine]-1'-yl)(4-ethyl-3-methylphenyl)methanone | 7-chlorospiro[benzo[b]pyrrolo[1,2-d][1,4]oxazine-4,4'-piperidine] | 4-ethyl-3-methyl-benzoic acid |
| (7-chlorospiro[benzo[b]pyrrolo[1,2-d][1,4]oxazine-4,4'-piperidine]-1'-yl)(3-methoxy-4-(2-(methylsulfonyl)ethoxy)phenyl)methanone | 7-chlorospiro[benzo[b]pyrrolo[1,2-d][1,4]oxazine-4,4'-piperidine] | 3-methoxy-4-(2-methylsulfonylethoxy)benzoic acid |
| 4-(7-chlorospiro[benzo[b]pyrrolo[1,2-d][1,4]oxazine-4,4'-piperidine]-1'-ylcarbonyl)-1-(2-methoxyethyl)pyridin-2(1H)-one | 7-chlorospiro[benzo[b]pyrrolo[1,2-d][1,4]oxazine-4,4'-piperidine] | 1-(2-methoxyethyl)-2-oxo-pyridine-4-carboxylic acid |
| (7-chlorospiro[benzo[b]pyrrolo[1,2-d][1,4]oxazine-4,4'-piperidine]-1'-yl)(4-fluoro-3-methoxyphenyl)methanone | 7-chlorospiro[benzo[b]pyrrolo[1,2-d][1,4]oxazine-4,4'-piperidine] | 4-fluoro-3-methoxy-benzoic acid |
| (5-chloro-2-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 5-chloro-2-methoxy-benzoic acid |
| (7-chlorospiro[benzo[b]pyrrolo[1,2-d][1,4]oxazine-4,4'-piperidine]-1'-yl)(2-fluoro-6- | 7-chlorospiro[benzo[b]pyrrolo[1,2-d][1,4]oxazine-4,4'- | 2-fluoro-6-methoxy-benzoic acid |

| Product Name | Amine or Amine•HCl | Carboxylic Acid |
|---|---|---|
| methoxyphenyl)methanone | piperidine] | |
| (7-chlorospiro[benzo[b]pyrrolo[1,2-d][1,4]oxazine-4,4'-piperidine]-1'-yl)(4-methoxy-2-methylphenyl)methanone | 7-chlorospiro[benzo[b]pyrrolo[1,2-d][1,4]oxazine-4,4'-piperidine] | 4-methoxy-2-methyl-benzoic acid |
| (7-chlorospiro[benzo[b]pyrrolo[1,2-d][1,4]oxazine-4,4'-piperidine]-1'-yl)(2-methoxy-3-methylphenyl)methanone | 7-chlorospiro[benzo[b]pyrrolo[1,2-d][1,4]oxazine-4,4'-piperidine] | 2-methoxy-3-methyl-benzoic acid |
| (7-chlorospiro[benzo[b]pyrrolo[1,2-d][1,4]oxazine-4,4'-piperidine]-1'-yl)(4-methoxy-2-(trifluoromethoxy)phenyl)methanone | 7-chlorospiro[benzo[b]pyrrolo[1,2-d][1,4]oxazine-4,4'-piperidine] | 4-methoxy-2-(trifluoromethoxy)benzoic acid |
| (4-bromo-3-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-bromo-3-methoxybenzoic acid |
| methyl 2-(4-(7-chlorospiro[benzo[b]pyrrolo[1,2-d][1,4]oxazine-4,4'-piperidine]-1'-ylcarbonyl)-2-methoxyphenyl)-2-methylpropanoate | 7-chlorospiro[benzo[b]pyrrolo[1,2-d][1,4]oxazine-4,4'-piperidine] | 3-methoxy-4-(1-methoxycarbonyl-1-methyl-ethyl)-benzoic acid |
| 5-(7-chlorospiro[benzo[b]pyrrolo[1,2-d][1,4]oxazine-4,4'-piperidine]-1'-ylcarbonyl)-2,4-dimethoxybenzaldehyde | 7-chlorospiro[benzo[b]pyrrolo[1,2-d][1,4]oxazine-4,4'-piperidine] | 5-formyl-2,4-dimethoxybenzoic acid |
| (7-chlorospiro[benzo[b]pyrrolo[1,2-d][1,4]oxazine-4,4'-piperidine]-1'-yl)(4-(3-hydroxycyclopentyloxy)-3-methoxyphenyl)methanone | 7-chlorospiro[benzo[b]pyrrolo[1,2-d][1,4]oxazine-4,4'-piperidine] | 4-(3-hydroxycyclopentoxy)-3-methoxy-benzoic acid |
| (7-chlorospiro[benzo[b]pyrrolo[1,2-d][1,4]oxazine-4,4'-piperidine]-1'-yl)(3-methoxy-4-(2-methoxy-2-methylpropoxy)phenyl)methanone | 7-chlorospiro[benzo[b]pyrrolo[1,2-d][1,4]oxazine-4,4'-piperidine] | 3-methoxy-4-(2-methoxy-2-methyl-propoxy)-benzoic acid |
| (7-chlorospiro[benzo[b]pyrrolo[1,2-d][1,4]oxazine-4,4'-piperidine]-1'-yl)(3-fluoro-5-methoxyphenyl)methanone | 7-chlorospiro[benzo[b]pyrrolo[1,2-d][1,4]oxazine-4,4'-piperidine] | 3-fluoro-5-methoxy-benzoic acid |
| (7-chlorospiro[benzo[b]pyrrolo[1,2-d][1,4]oxazine-4,4'-piperidine]-1'-yl)(2-ethylphenyl)methanone | 7-chlorospiro[benzo[b]pyrrolo[1,2-d][1,4]oxazine-4,4'-piperidine] | 2-ethylbenzoic acid |
| (3-chloro-5-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 3-chloro-5-methoxy-benzoic acid |
| (S)-(7-chlorospiro[benzo[b]pyrrolo[1,2-d][1,4]oxazine-4,4'-piperidine]-1'-yl)(4-((2,2-dimethyl-1,3-dioxolan-4-yl)methoxy)-3-methoxyphenyl)methanone | 7-chlorospiro[benzo[b]pyrrolo[1,2-d][1,4]oxazine-4,4'-piperidine] | (S)-4-((2,2-dimethyl-1,3-dioxolan-4-yl)methoxy)-3-methoxybenzoic acid |
| (7-chlorospiro[benzo[b]pyrrolo[1,2-d][1,4]oxazine-4,4'-piperidine]-1'-yl)(3-fluoro-4-(oxetan-3-yloxy)phenyl)methanone | 7-chlorospiro[benzo[b]pyrrolo[1,2-d][1,4]oxazine-4,4'-piperidine] | 3-fluoro-4-oxetan-3-yloxy-benzoic acid |
| (7-chlorospiro[benzo[b]pyrrolo[1,2-d][1,4]oxazine-4,4'-piperidine]-1'-yl)(3-methoxy-4-(2-(trifluoromethoxy)ethoxy)phenyl)methanone | 7-chlorospiro[benzo[b]pyrrolo[1,2-d][1,4]oxazine-4,4'-piperidine] | 3-methoxy-4-[2-(trifluoromethoxy)ethoxy]benzoic acid |
| (7-chlorospiro[benzo[b]pyrrolo[1,2-d][1,4]oxazine-4,4'-piperidine]-1'-yl)(4-(3-hydroxyoxetan-3-yl)-3-methoxyphenyl)methanone | 7-chlorospiro[benzo[b]pyrrolo[1,2-d][1,4]oxazine-4,4'-piperidine] | 4-(3-hydroxyoxetan-3-yl)-3-methoxybenzoic acid |
| (S)-(7-chlorospiro[benzo[b]pyrrolo[1,2-d][1,4]oxazine-4,4'-piperidine]-1'-yl)(3-methoxy-4-(2-methoxypropoxy)phenyl)methanone | 7-chlorospiro[benzo[b]pyrrolo[1,2-d][1,4]oxazine-4,4'-piperidine] | 3-methoxy-4-(2-methoxypropoxy)benzoic acid |
| (7-chlorospiro[benzo[b]pyrrolo[1,2-d][1,4]oxazine-4,4'-piperidine]-1'-yl)(2-(difluoromethoxy)phenyl)methanone | 7-chlorospiro[benzo[b]pyrrolo[1,2-d][1,4]oxazine-4,4'-piperidine] | 2-(difluoromethoxy)benzoic acid |
| (7-chlorospiro[benzo[b]pyrrolo[1,2-d][1,4]oxazine-4,4'-piperidine]-1'-yl)(3-(methylsulfonyl)phenyl)methanone | 7-chlorospiro[benzo[b]pyrrolo[1,2-d][1,4]oxazine-4,4'-piperidine] | 3-methylsulfonylbenzoic acid |

| Product Name | Amine or Amine•HCl | Carboxylic Acid |
|---|---|---|
| (7-chlorospiro[benzo[b]pyrrolo[1,2-d][1,4]oxazine-4,4'-piperidine]-1'-yl)(2,5-dimethoxyphenyl)methanone | 7-chlorospiro[benzo[b]pyrrolo[1,2-d][1,4]oxazine-4,4'-piperidine] | 2,5-dimethoxybenzoic acid |
| (3-chlorophenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 3-chlorobenzoic acid |
| (7-chlorospiro[benzo[b]pyrrolo[1,2-d][1,4]oxazine-4,4'-piperidine]-1'-yl)(3,5-dichlorophenyl)methanone | 7-chlorospiro[benzo[b]pyrrolo[1,2-d][1,4]oxazine-4,4'-piperidine] | 3,5-dichlorobenzoic acid |
| (7-chlorospiro[benzo[b]pyrrolo[1,2-d][1,4]oxazine-4,4'-piperidine]-1'-yl)(3-methoxyphenyl)methanone | 7-chlorospiro[benzo[b]pyrrolo[1,2-d][1,4]oxazine-4,4'-piperidine] | 3-methoxybenzoic acid |
| (7-chlorospiro[benzo[b]pyrrolo[1,2-d][1,4]oxazine-4,4'-piperidine]-1'-yl)(2-fluoro-5-methoxy-4-(2-methoxyethoxy)phenyl)methanone | 7-chlorospiro[benzo[b]pyrrolo[1,2-d][1,4]oxazine-4,4'-piperidine] | 2-fluoro-5-methoxy-4-(2-methoxyethoxy)benzoic acid |
| (7-chlorospiro[benzo[b]pyrrolo[1,2-d][1,4]oxazine-4,4'-piperidine]-1'-yl)(2-methoxyphenyl)methanone | 7-chlorospiro[benzo[b]pyrrolo[1,2-d][1,4]oxazine-4,4'-piperidine] | 2-methoxybenzoic acid |
| (7-chlorospiro[benzo[b]pyrrolo[1,2-d][1,4]oxazine-4,4'-piperidine]-1'-yl)(3,5-dimethoxyphenyl)methanone | 7-chlorospiro[benzo[b]pyrrolo[1,2-d][1,4]oxazine-4,4'-piperidine] | 3,5-dimethoxybenzoic acid |
| (7-chlorospiro[benzo[b]pyrrolo[1,2-d][1,4]oxazine-4,4'-piperidine]-1'-yl)(2-methoxy-4-(trifluoromethyl)phenyl)methanone | 7-chlorospiro[benzo[b]pyrrolo[1,2-d][1,4]oxazine-4,4'-piperidine] | 2-methoxy-4-(trifluoromethyl)benzoic acid |
| (7-chlorospiro[benzo[b]pyrrolo[1,2-d][1,4]oxazine-4,4'-piperidine]-1'-yl)(3,5-dimethylphenyl)methanone | 7-chlorospiro[benzo[b]pyrrolo[1,2-d][1,4]oxazine-4,4'-piperidine] | 3,5-dimethylbenzoic acid |
| (7-chlorospiro[benzo[b]pyrrolo[1,2-d][1,4]oxazine-4,4'-piperidine]-1'-yl)(3-(trifluoromethyl)phenyl)methanone | 7-chlorospiro[benzo[b]pyrrolo[1,2-d][1,4]oxazine-4,4'-piperidine] | 3-(trifluoromethyl)benzoic acid |
| 4-(7-chlorospiro[benzo[b]pyrrolo[1,2-d][1,4]oxazine-4,4'-piperidine]-1'-ylcarbonyl)-2-methylbenzonitrile | 7-chlorospiro[benzo[b]pyrrolo[1,2-d][1,4]oxazine-4,4'-piperidine] | 4-cyano-3-methyl-benzoic acid |
| (7-chlorospiro[benzo[b]pyrrolo[1,2-d][1,4]oxazine-4,4'-piperidine]-1'-yl)(2-methoxy-4-methylphenyl)methanone | 7-chlorospiro[benzo[b]pyrrolo[1,2-d][1,4]oxazine-4,4'-piperidine] | 2-methoxy-4-methyl-benzoic acid |
| (7-chlorospiro[benzo[b]pyrrolo[1,2-d][1,4]oxazine-4,4'-piperidine]-1'-yl)(2-(2-methoxyethoxy)pyridin-4-yl)methanone | 7-chlorospiro[benzo[b]pyrrolo[1,2-d][1,4]oxazine-4,4'-piperidine] | 2-(2-methoxyethoxy)pyridine-4-carboxylic acid |
| (7-chlorospiro[benzo[b]pyrrolo[1,2-d][1,4]oxazine-4,4'-piperidine]-1'-yl)(3-ethoxyphenyl)methanone | 7-chlorospiro[benzo[b]pyrrolo[1,2-d][1,4]oxazine-4,4'-piperidine] | 3-ethoxybenzoic acid |
| (4-chloro-2-(2-(thiophen-2-yl)ethyl)phenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-chloro-2-[2-(2-thienyl)ethyl]benzoic acid |
| (2,4-bis(trifluoromethyl)phenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 2,4-bis(trifluoromethyl)benzoic acid |
| (4-chloro-2-methylphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-chloro-2-methyl-benzoic acid |
| (4-chloro-2-(2,5-dimethyl-1H-pyrrol-1-yl)phenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-chloro-2-(2,5-dimethylpyrrol-1-yl)-benzoic acid |
| (3,5-bis(trifluoromethyl)phenyl)(7- | 7-chlorospiro[benzo[b]pyrrolo[1, | 3,5-bis(trifluoromethyl)benzoic acid |

-continued

| Product Name | Amine or Amine•HCl | Carboxylic Acid |
|---|---|---|
| chlorospiro[benzo[b]pyrrolo[1,2-d][1,4]oxazine-4,4'-piperidine]-1'-yl)methanone | 2-d][1,4]oxazine-4,4'-piperidine] | |
| (7-chlorospiro[benzo[b]pyrrolo[1,2-d][1,4]oxazine-4,4'-piperidine]-1'-yl)(3,5-di-tert-butylphenyl)methanone | 7-chlorospiro[benzo[b]pyrrolo[1,2-d][1,4]oxazine-4,4'-piperidine] | 3,5-di-tert-butylbenzoic acid |
| (4-chloro-2-(methylsulfonyl)phenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-chloro-2-methylsulfonyl-benzoic acid |
| (3-chloro-5-fluorophenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 3-chloro-5-fluoro-benzoic acid |
| tert-butyl 5-chloro-2-(7-chlorospiro[benzo[b]pyrrolo[1,2-d][1,4]oxazine-4,4'-piperidine]-1'-ylcarbonyl)phenylcarbamate | 7-chlorospiro[benzo[b]pyrrolo[1,2-d][1,4]oxazine-4,4'-piperidine] | 4-chloro-2-(tert-butoxycarbonylamino)-benzoic acid |
| (2-chloro-4-fluorophenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 2-chloro-4-fluoro-benzoic acid |
| methyl 3-(7-chlorospiro[benzo[b]pyrrolo[1,2-d][1,4]oxazine-4,4'-piperidine]-1'-ylcarbonyl)-5-(N-methylmethylsulfonamido)benzoate | 7-chlorospiro[benzo[b]pyrrolo[1,2-d][1,4]oxazine-4,4'-piperidine] | 3-methoxycarbonyl-5-(methyl-methylsulfonyl-amino)-benzoic acid |
| (4-chloro-2-fluorophenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-chloro-2-fluoro-benzoic acid |
| N-(4-(7-chlorospiro[benzo[b]pyrrolo[1,2-d][1,4]oxazine-4,4'-piperidine]-1'-ylcarbonyl)-3-methylphenyl)acetamide | 7-chlorospiro[benzo[b]pyrrolo[1,2-d][1,4]oxazine-4,4'-piperidine] | 4-acetamido-2-methyl-benzoic acid |
| (7-chlorospiro[benzo[b]pyrrolo[1,2-d][1,4]oxazine-4,4'-piperidine]-1'-yl)(3-fluorophenyl)methanone | 7-chlorospiro[benzo[b]pyrrolo[1,2-d][1,4]oxazine-4,4'-piperidine] | 3-fluorobenzoic acid |
| 4-(7-chlorospiro[benzo[b]pyrrolo[1,2-d][1,4]oxazine-4,4'-piperidine]-1'-ylcarbonyl)-3-fluorobenzonitrile | 7-chlorospiro[benzo[b]pyrrolo[1,2-d][1,4]oxazine-4,4'-piperidine] | 4-cyano-2-fluoro-benzoic acid |
| (7-chlorospiro[benzo[b]pyrrolo[1,2-d][1,4]oxazine-4,4'-piperidine]-1'-yl)(3,5-diethoxyphenyl)methanone | 7-chlorospiro[benzo[b]pyrrolo[1,2-d][1,4]oxazine-4,4'-piperidine] | 3,5-diethoxybenzoic acid |
| (7-chlorospiro[benzo[b]pyrrolo[1,2-d][1,4]oxazine-4,4'-piperidine]-1'-yl)(2-fluoro-4-methoxyphenyl)methanone | 7-chlorospiro[benzo[b]pyrrolo[1,2-d][1,4]oxazine-4,4'-piperidine] | 2-fluoro-4-methoxy-benzoic acid |
| (S)-(7-chlorospiro[benzo[b]pyrrolo[1,2-d][1,4]oxazine-4,4'-piperidine]-1'-yl)(4-((2,2-dimethyl-1,3-dioxolan-4-yl)methoxy)-3-methoxyphenyl)methanone | 7-chlorospiro[benzo[b]pyrrolo[1,2-d][1,4]oxazine-4,4'-piperidine] | (S)-4-((2,2-dimethyl-1,3-dioxolan-4-yl)methoxy)-3-methoxybenzoic acid |
| (4-tert-butyl-3-hydroxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 3-hydroxy-4-tert-butyl-benzoic acid |
| (7-chlorospiro[benzo[b]pyrrolo[1,2-d][1,4]oxazine-4,4'-piperidine]-1'-yl)(3-fluoro-5-(trifluoromethyl)phenyl)methanone | 7-chlorospiro[benzo[b]pyrrolo[1,2-d][1,4]oxazine-4,4'-piperidine] | 3-fluoro-5-(trifluoromethyl)benzoic acid |
| (7-chlorospiro[benzo[b]pyrrolo[1,2-d][1,4]oxazine-4,4'-piperidine]-1'-yl)(3,5-diethylphenyl)methanone | 7-chlorospiro[benzo[b]pyrrolo[1,2-d][1,4]oxazine-4,4'-piperidine] | 3,5-diethylbenzoic acid |
| (7-chlorospiro[benzo[b]pyrrolo[1,2-d][1,4]oxazine-4,4'-piperidine]-1'-yl)(3,5-difluorophenyl)methanone | 7-chlorospiro[benzo[b]pyrrolo[1,2-d][1,4]oxazine-4,4'-piperidine] | 3,5-difluorobenzoic acid |
| (7-chlorospiro[benzo[b]pyrrolo[1,2-d][1,4]oxazine-4,4'-piperidine]-1'-yl)(2-fluoro-4-(trifluoromethyl)phenyl)methanone | 7-chlorospiro[benzo[b]pyrrolo[1,2-d][1,4]oxazine-4,4'-piperidine] | 2-fluoro-4-(trifluoromethyl)benzoic acid |
| (7-chlorospiro[benzo[b]pyrrolo | 7- | 4-fluoro-2-methyl-benzoic acid |

| Product Name | Amine or Amine•HCl | Carboxylic Acid |
|---|---|---|
| (7-chlorospiro[benzo[b]pyrrolo[1,2-d][1,4]oxazine-4,4'-piperidine]-1'-yl)(4-fluoro-2-methylphenyl)methanone | 7-chlorospiro[benzo[b]pyrrolo[1,2-d][1,4]oxazine-4,4'-piperidine] | |
| (7-chlorospiro[benzo[b]pyrrolo[1,2-d][1,4]oxazine-4,4'-piperidine]-1'-yl)(2-methyl-4-(trifluoromethoxy)phenyl)methanone | 7-chlorospiro[benzo[b]pyrrolo[1,2-d][1,4]oxazine-4,4'-piperidine] | 2-methyl-4-(trifluoromethoxy)benzoic acid |
| (7-chlorospiro[benzo[b]pyrrolo[1,2-d][1,4]oxazine-4,4'-piperidine]-1'-yl)(2-fluoro-4-methylphenyl)methanone | 7-chlorospiro[benzo[b]pyrrolo[1,2-d][1,4]oxazine-4,4'-piperidine] | 2-fluoro-4-methyl-benzoic acid |
| (7-chlorospiro[benzo[b]pyrrolo[1,2-d][1,4]oxazine-4,4'-piperidine]-1'-yl)(2,4-dichlorophenyl)methanone | 7-chlorospiro[benzo[b]pyrrolo[1,2-d][1,4]oxazine-4,4'-piperidine] | 2,4-dichlorobenzoic acid |
| (2-chloro-4-(4H-1,2,4-triazol-4-yl)phenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 2-chloro-4-(1,2,4-triazol-4-yl)benzoic acid |
| (7-chlorospiro[benzo[b]pyrrolo[1,2-d][1,4]oxazine-4,4'-piperidine]-1'-yl)(4-methyl-2-(trifluoromethyl)phenyl)methanone | 7-chlorospiro[benzo[b]pyrrolo[1,2-d][1,4]oxazine-4,4'-piperidine] | 4-methyl-2-(trifluoromethyl)benzoic acid |
| (7-chlorospiro[benzo[b]pyrrolo[1,2-d][1,4]oxazine-4,4'-piperidine]-1'-yl)(4-fluoro-2-methoxyphenyl)methanone | 7-chlorospiro[benzo[b]pyrrolo[1,2-d][1,4]oxazine-4,4'-piperidine] | 4-fluoro-2-methoxy-benzoic acid |
| (2-(2-chloro-1,1,2-trifluoroethoxy)-4-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 2-(2-chloro-1,1,2-trifluoro-ethoxy)-4-methoxy-benzoic acid |
| (7-chlorospiro[benzo[b]pyrrolo[1,2-d][1,4]oxazine-4,4'-piperidine]-1'-yl)(2-methoxy-4-(trifluoromethoxy)phenyl)methanone | 7-chlorospiro[benzo[b]pyrrolo[1,2-d][1,4]oxazine-4,4'-piperidine] | 2-methoxy-4-(trifluoromethoxy)benzoic acid |
| (7-chlorospiro[benzo[b]pyrrolo[1,2-d][1,4]oxazine-4,4'-piperidine]-1'-yl)(3-fluoro-5-methylphenyl)methanone | 7-chlorospiro[benzo[b]pyrrolo[1,2-d][1,4]oxazine-4,4'-piperidine] | 3-fluoro-5-methyl-benzoic acid |
| (7-chlorospiro[benzo[b]pyrrolo[1,2-d][1,4]oxazine-4,4'-piperidine]-1'-yl)(2,4-dimethylphenyl)methanone | 7-chlorospiro[benzo[b]pyrrolo[1,2-d][1,4]oxazine-4,4'-piperidine] | 2,4-dimethylbenzoic acid |
| (4-chloro-2-methoxyphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-chloro-2-methoxy-benzoic acid |
| (7-chlorospiro[benzo[b]pyrrolo[1,2-d][1,4]oxazine-4,4'-piperidine]-1'-yl)(3-(trifluoromethoxy)phenyl)methanone | 7-chlorospiro[benzo[b]pyrrolo[1,2-d][1,4]oxazine-4,4'-piperidine] | 3-(trifluoromethoxy)benzoic acid |
| (2-chloro-4-methylphenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 2-chloro-4-methyl-benzoic acid |
| (4-(benzyloxy)-2-chlorophenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 4-benzyloxy-2-chloro-benzoic acid |
| methyl 3-(7-chlorospiro[benzo[b]pyrrolo[1,2-d][1,4]oxazine-4,4'-piperidine]-1'-ylcarbonyl)-5-methylbenzoate | 7-chlorospiro[benzo[b]pyrrolo[1,2-d][1,4]oxazine-4,4'-piperidine] | 3-methoxycarbonyl-5-methyl-benzoic acid |
| (7-chlorospiro[benzo[b]pyrrolo | 7-chlorospiro[benzo[b]pyrrolo[1, | 3-methoxy-4-propoxy-benzoic acid |

-continued

| Product Name | Amine or Amine•HCl | Carboxylic Acid |
|---|---|---|
| [1,2-d][1,4]oxazine-4,4'-piperidine]-1'-yl)(3-methoxy-4-propoxyphenyl)methanone | 2-d][1,4]oxazine-4,4'-piperidine] | |
| (7-chlorospiro[benzo[b]pyrrolo[1,2-d][1,4]oxazine-4,4'-piperidine]-1'-yl)(2,4-difluorophenyl)methanone | 7-chlorospiro[benzo[b]pyrrolo[1,2-d][1,4]oxazine-4,4'-piperidine] | 2,4-difluorobenzoic acid |
| (3-chloro-5-(trifluoromethyl)phenyl)(7-chlorospiro[benzo[b]pyrrolo[1,2-d][1,4]oxazine-4,4'-piperidine]-1'-yl)methanone | 7-chlorospiro[benzo[b]pyrrolo[1,2-d][1,4]oxazine-4,4'-piperidine] | 3-chloro-5-(trifluoromethyl)benzoic acid |
| (1-methyl-1H-spiro[chromeno[4,3-c]pyrazole-4,4'-piperidine]-1'-yl)(m-tolyl)methanone | 1-methylspiro[chromeno[4,3-c]pyrazole-4,4'-piperidine]dihydrochloride | 3-methylbenzoic acid |
| (1-methyl-1H-spiro[chromeno[4,3-c]pyrazole-4,4'-piperidine]-1'-yl)[3-(trifluoromethoxy)phenyl]-methanone | 1-methylspiro[chromeno[4,3-c]pyrazole-4,4'-piperidine]dihydrochloride | 3-(trifluoromethoxy)benzoic acid |
| (2-hydroxy-3-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-hydroxy-3-methyl-benzoic acid |
| (1-methyl-1H-spiro[chromeno[4,3-c]pyrazole-4,4'-piperidine]-1'-yl)(4-quinolyl)methanone | 1-methylspiro[chromeno[4,3-c]pyrazole-4,4'-piperidine]dihydrochloride | quinoline-4-carboxylic acid |
| (3,4-dimethylphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,4-dimethylbenzoic acid |
| (3-chloro-4-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-chloro-4-methoxy-benzoic acid |
| (1-methyl-1H-spiro[chromeno[4,3-c]pyrazole-4,4'-piperidine]-1'-yl)(4-propoxyphenyl)-methanone | 1-methylspiro[chromeno[4,3-c]pyrazole-4,4'-piperidine]dihydrochloride | 4-propoxybenzoic acid |
| (R)-(3-methoxy-4-(tetrahydrofuran-3-yloxy)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | (R)-3-methoxy-4-(tetrahydrofuran-3-yloxy)benzoic acid |
| [4-(2-methoxyethoxy)-3-methyl-phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-(2-methoxyethoxy)-3-methyl-benzoic acid |
| (4-ethyl-3-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-ethyl-3-methoxy-benzoic acid |
| (4-isopropoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-isopropoxybenzoic acid |
| (1-methyl-1H-spiro[chromeno[4,3-c]pyrazole-4,4'-piperidine]-1'-yl)[4-propoxy-3-(trifluoromethyl)phenyl]-methanone | 1-methylspiro[chromeno[4,3-c]pyrazole-4,4'-piperidine]dihydrochloride | 4-propoxy-3-(trifluoromethyl)benzoic acid |
| (3,4-dimethoxyphenyl)-(1-methyl-1H- | 1-methylspiro[chromeno[4,3- | 3,4-dimethoxybenzoic acid |

| Product Name | Amine or Amine•HCl | Carboxylic Acid |
|---|---|---|
| spiro[chromeno[4,3-c]pyrazole-4,4'-piperidine]-1'-yl)methanone | c]pyrazole-4,4'-piperidine]dihydrochloride | |
| (S)-(3-methoxy-4-(2-methoxypropoxy)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | (S)-3-methoxy-4-(2-methoxypropoxy)benzoic acid |
| [3-methoxy-4-(2-methoxyethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methoxy-4-(2-methoxyethoxy)benzoic acid |
| (4-cyclopentoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-cyclopentoxybenzoic acid |
| (R)-(3-methoxy-4-(2-methoxypropoxy)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | (R)-3-methoxy-4-(2-methoxypropoxy)benzoic acid |
| (4-ethoxy-3-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-ethoxy-3-methoxy-benzoic acid |
| (4-methoxy-3-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methoxy-3-methyl-benzoic acid |
| [4-(1-hydroxy-1-methyl-ethyl)-3-methyl-phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-(1-hydroxy-1-methyl-ethyl)-3-methyl-benzoic acid |
| [4-(1-hydroxy-1-methyl-ethyl)-3-methoxy-phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-(1-hydroxy-1-methyl-ethyl)-3-methoxy-benzoic acid |
| (1-methyl-1H-spiro[chromeno[4,3-c]pyrazole-4,4'-piperidine]-1'-yl)[2-(trifluoromethoxy)phenyl]-methanone | 1-methylspiro[chromeno[4,3-c]pyrazole-4,4'-piperidine]dihydrochloride | 2-(trifluoromethoxy)benzoic acid |
| (3-methyl-4-propoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methyl-4-propoxy-benzoic acid |
| (3-methoxy-4-tert-butyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methoxy-4-tert-butyl-benzoic acid |
| (4-isopentyloxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-isopentyloxybenzoic acid |
| (1-methyl-1H-spiro[chromeno[4,3-c]pyrazole-4,4'-piperidine]-1'-yl)(8-quinolyl)methanone | 1-methylspiro[chromeno[4,3-c]pyrazole-4,4'-piperidine]dihydrochloride | quinoline-8-carboxylic acid |
| [3-chloro-4-(2-methoxyethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-chloro-4-(2-methoxyethoxy)benzoic acid |

| Product Name | Amine or Amine•HCl | Carboxylic Acid |
|---|---|---|
| (4-isopropoxy-3-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-isopropoxy-3-methyl-benzoic acid |
| (2-methoxy-3-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-methoxy-3-methyl-benzoic acid |
| (3-methoxy-4-propoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methoxy-4-propoxy-benzoic acid |
| (2,3-dimethylphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,3-dimethylbenzoic acid |
| (4-isobutoxy-3-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-isobutoxy-3-methoxy-benzoic acid |
| (4-isopentyloxy-3-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-isopentyloxy-3-methoxy-benzoic acid |
| (4-chloro-3-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-chloro-3-methoxy-benzoic acid |
| (1-methyl-1H-spiro[chromeno[4,3-c]pyrazole-4,4'-piperidine]-1'-yl)[4-(trifluoromethoxy)phenyl]-methanone | 1-methylspiro[chromeno[4,3-c]pyrazole-4,4'-piperidine]dihydrochloride | 4-(trifluoromethoxy)benzoic acid |
| (3-fluoro-4-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-fluoro-4-methoxy-benzoic acid |
| (3-methoxy-4-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methoxy-4-methyl-benzoic acid |
| (S)-(3-methoxy-4-(tetrahydrofuran-3-yloxy)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | (S)-3-methoxy-4-(tetrahydrofuran-3-yloxy)benzoic acid |
| [3-methyl-4-(tetrahydrofuran-2-ylmethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methyl-4-(tetrahydrofuran-2-ylmethoxy)benzoic acid |
| (3-ethoxy-4-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-ethoxy-4-methoxy-benzoic acid |
| (3,4-diethoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,4-diethoxybenzoic acid |
| (3-fluoro-4-oxetan-3-yloxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-fluoro-4-oxetan-3-yloxy-benzoic acid |

| Product Name | Amine or Amine•HCl | Carboxylic Acid |
|---|---|---|
| (3-fluoro-4-(oxetan-3-yloxy)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(methanesulfonamido)benzoic acid |
| (2-hydroxy-4-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-hydroxy-4-methoxy-benzoic acid |
| methyl 2-(2-methoxy-4-(1-methyl-1H-spiro[chromeno[4,3-c]pyrazole-4,4'-piperidine]-1'-ylcarbonyl)phenyl)-2-methylpropanoate | 1-methylspiro[chromeno[4,3-c]pyrazole-4,4'-piperidine]dihydrochloride | 3-methoxy-4-(1-methoxycarbonyl-1-methyl-ethyl)-benzoic acid |
| (2,4-diisopropoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,4-diisopropoxybenzoic acid |
| (2,2-dimethyl-3H-benzofuran-5-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,2-dimethyl-3H-benzofuran-5-carboxylic acid |
| (3,3-dimethyl-2H-benzofuran-5-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,3-dimethyl-2H-benzofuran-5-carboxylic acid |
| 1-isoquinolyl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | isoquinoline-1-carboxylic acid |
| (1-methyl-1H-spiro[chromeno[4,3-c]pyrazole-4,4'-piperidine]-1'-yl)[6-(1-piperidyl)-3-pyridyl]-methanone | 1-methylspiro[chromeno[4,3-c]pyrazole-4,4'-piperidine]dihydrochloride | 6-(1-piperidyl)pyridine-3-carboxylic acid |
| (4-chloro-2-methylsulfonyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-chloro-2-methylsulfonyl-benzoic acid |
| (1-methyl-1H-spiro[chromeno[4,3-c]pyrazole-4,4'-piperidine]-1'-yl)(2-phenylthiazol-4-yl)-methanone | 1-methylspiro[chromeno[4,3-c]pyrazole-4,4'-piperidine]dihydrochloride | 2-phenylthiazole-4-carboxylic acid |
| (5-chloro-2-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-chloro-2-methoxy-benzoic acid |
| (2-hydroxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-hydroxybenzoic acid |
| (1-methylindol-2-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-methylindole-2-carboxylic acid |
| [1-(4-fluorophenyl)-5-methyl-pyrazol-4-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-(4-fluorophenyl)-5-methyl-pyrazole-4-carboxylic acid |
| (2,6-dimethoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,6-dimethoxybenzoic acid |
| (2,5-dimethoxyphenyl)-(1-methyl-1H- | 1-methylspiro[chromeno[4,3- | 2,5-dimethoxybenzoic acid |

| Product Name | Amine or Amine•HCl | Carboxylic Acid |
|---|---|---|
| spiro[chromeno[4,3-c]pyrazole-4,4'-piperidine]-1'-yl)methanone | c]pyrazole-4,4'-piperidine]dihydrochloride | |
| (5-methyl-1-phenyl-pyrazol-4-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-methyl-1-phenyl-pyrazole-4-carboxylic acid |
| (2-fluoro-6-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-fluoro-6-methoxy-benzoic acid |
| (2-dimethylamino-4-pyridyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-dimethylaminopyridine-4-carboxylic acid |
| [2-methyl-4-(trifluoromethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-methyl-4-(trifluoromethoxy)benzoic acid |
| (2-methyl-1H-benzoimidazol-4-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-methyl-1H-benzoimidazole-4-carboxylic acid |
| (1-methyl-1H-spiro[chromeno[4,3-c]pyrazole-4,4'-piperidine]-1'-yl)[1-phenyl-5-(trifluoromethyl)pyrazol-4-yl]-methanone | 1-methylspiro[chromeno[4,3-c]pyrazole-4,4'-piperidine]dihydrochloride | 1-phenyl-5-(trifluoromethyl)pyrazole-4-carboxylic acid |
| [2-methoxy-4-(trifluoromethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-methoxy-4-(trifluoromethoxy)benzoic acid |
| (1-methylindol-5-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-methylindole-5-carboxylic acid |
| (1-methyl-1H-spiro[chromeno[4,3-c]pyrazole-4,4'-piperidine]-1'-yl)[2-(1-piperidyl)-4-pyridyl]-methanone | 1-methylspiro[chromeno[4,3-c]pyrazole-4,4'-piperidine]dihydrochloride | 2-(1-piperidyl)pyridine-4-carboxylic acid |
| (5-methoxy-1H-indol-3-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-methoxy-1H-indole-3-carboxylic acid |
| [1-(4-methoxyphenyl)-5-methyl-pyrazol-4-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-(4-methoxyphenyl)-5-methyl-pyrazole-4-carboxylic acid |
| (4-methoxy-2-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methoxy-2-methyl-benzoic acid |
| (4-methoxy-1H-indol-3-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methoxy-1H-indole-3-carboxylic acid |
| (2-chloro-4-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-chloro-4-methyl-benzoic acid |

| Product Name | Amine or Amine•HCl | Carboxylic Acid |
|---|---|---|
| (2,3-dimethyl-1H-indol-7-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,3-dimethyl-1H-indole-7-carboxylic acid |
| 1H-indol-4-yl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1H-indole-4-carboxylic acid |
| (5-fluoro-2-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-fluoro-2-methoxy-benzoic acid |
| (7-methoxy-1H-indol-3-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 7-methoxy-1H-indole-3-carboxylic acid |
| (1-methylindol-3-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-methylindole-3-carboxylic acid |
| (2-isopropoxy-5-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-isopropoxy-5-methyl-benzoic acid |
| 2,5-dioxabicyclo[4.4.0]deca-6,8,10-trien-7-yl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,5-dioxabicyclo[4.4.0]deca-6,8,10-triene-10-carboxylic acid |
| (2,2-difluorobenzo[1,3]dioxol-4-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,2-difluorobenzo[1,3]dioxole-4-carboxylic acid |
| (4-methoxy-1-methyl-indol-3-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methoxy-1-methyl-indole-3-carboxylic acid |
| [2-methoxy-4-(trifluoromethyl)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-methoxy-4-(trifluoromethyl)benzoic acid |
| (2-ethylphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-ethylbenzoic acid |
| [2-(difluoromethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(difluoromethoxy)benzoic acid |
| (2,4-dimethoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,4-dimethoxybenzoic acid |
| (2-methoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-methoxybenzoic acid |
| [4-methoxy-2-(trifluoromethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methoxy-2-(trifluoromethoxy)benzoic acid |
| (4-isopropoxy-2-methoxy-phenyl)-(1-methyl-1H- | 1-methylspiro[chromeno[4,3- | 4-isopropoxy-2-methoxy-benzoic acid |

| Product Name | Amine or Amine•HCl | Carboxylic Acid |
| --- | --- | --- |
| spiro[chromeno[4,3-c]pyrazole-4,4'-piperidine]-1'-yl)methanone | c]pyrazole-4,4'-piperidine]dihydrochloride | |
| (2,2-dimethyl-3H-benzofuran-7-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,2-dimethyl-3H-benzofuran-7-carboxylic acid |
| (3,5-difluorophenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,5-difluorobenzoic acid |
| (4-chloro-2-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-chloro-2-methyl-benzoic acid |
| 1H-indol-7-yl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1H-indole-7-carboxylic acid |
| (1-methyl-1H-spiro[chromeno[4,3-c]pyrazole-4,4'-piperidine]-1'-yl)[5-(trifluoromethoxy)-1H-indol-2-yl]-methanone | 1-methylspiro[chromeno[4,3-c]pyrazole-4,4'-piperidine]dihydrochloride | 5-(trifluoromethoxy)-1H-indole-2-carboxylic acid |
| [2-(3,5-dimethyl-1H-pyrazol-4-yl)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(3,5-dimethyl-1H-pyrazol-4-yl)benzoic acid |
| (1-methyl-1H-spiro[chromeno[4,3-c]pyrazole-4,4'-piperidine]-1'-yl)[2-phenyl-5-(trifluoromethyl)oxazol-4-yl]-methanone | 1-methylspiro[chromeno[4,3-c]pyrazole-4,4'-piperidine]dihydrochloride | 2-phenyl-5-(trifluoromethyl)oxazole-4-carboxylic acid |
| [2-chloro-4-(2,5-dimethylpyrrol-1-yl)-phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-chloro-4-(2,5-dimethylpyrrol-1-yl)-benzoic acid |
| [4-chloro-2-[2-(2-thienyl)ethyl]phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-chloro-2-[2-(2-thienyl)ethyl]benzoic acid |
| (1-methyl-1H-spiro[chromeno[4,3-c]pyrazole-4,4'-piperidine]-1'-yl)pyridazin-4-yl-methanone | 1-methylspiro[chromeno[4,3-c]pyrazole-4,4'-piperidine]dihydrochloride | pyridazine-4-carboxylic acid |
| [4-hydroxy-7-(trifluoromethyl)-3-quinolyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-hydroxy-7-(trifluoromethyl)quinoline-3-carboxylic acid |
| (1-methyl-1H-spiro[chromeno[4,3-c]pyrazole-4,4'-piperidine]-1'-yl)(6-phenoxy-3-pyridyl)-methanone | 1-methylspiro[chromeno[4,3-c]pyrazole-4,4'-piperidine]dihydrochloride | 6-phenoxypyridine-3-carboxylic acid |
| benzo[c]isoxazol-3-yl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | benzo[c]isoxazole-3-carboxylic acid |
| [1-(4-fluorophenyl)-5-(trifluoromethyl)pyrazol-4-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-(4-fluorophenyl)-5-(trifluoromethyl)pyrazole-4-carboxylic acid |
| 1,7-diazabicyclo[4.3.0]nona-2,4,6,8-tetraen-8-yl-(1-methyl- | 1-methylspiro[chromeno[4,3- | 1,7-diazabicyclo[4.3.0]nona-2,4,6,8-tetraene-8-carboxylic |

-continued

| Product Name | Amine or Amine•HCl | Carboxylic Acid |
|---|---|---|
| 1H-spiro[chromeno[4,3-c]pyrazole-4,4'-piperidine]-1'-yl)methanone | c]pyrazole-4,4'-piperidine]dihydrochloride | acid |
| [3-(4-fluorophenyl)isoxazol-5-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-(4-fluorophenyl)isoxazole-5-carboxylic acid |
| (3,5-diethoxyphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,5-diethoxybenzoic acid |
| (4-fluoro-2-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-fluoro-2-methyl-benzoic acid |
| (7-methoxybenzofuran-2-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 7-methoxybenzofuran-2-carboxylic acid |
| (1-methyl-1H-spiro[chromeno[4,3-c]pyrazole-4,4'-piperidine]-1'-yl)[2-(4-pyridyl)thiazol-4-yl]-methanone | 1-methylspiro[chromeno[4,3-c]pyrazole-4,4'-piperidine]dihydrochloride | 2-(4-pyridyl)thiazole-4-carboxylic acid |
| (1-methyl-1H-spiro[chromeno[4,3-c]pyrazole-4,4'-piperidine]-1'-yl)(5-phenyl-3-pyridyl)-methanone | 1-methylspiro[chromeno[4,3-c]pyrazole-4,4'-piperidine]dihydrochloride | 5-phenylpyridine-3-carboxylic acid |
| (5-fluorobenzofuran-2-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-fluorobenzofuran-2-carboxylic acid |
| (5-methoxybenzofuran-2-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-methoxybenzofuran-2-carboxylic acid |
| [4-chloro-2-(2,5-dimethylpyrrol-1-yl)-phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-chloro-2-(2,5-dimethylpyrrol-1-yl)-benzoic acid |
| (1-methyl-1H-spiro[chromeno[4,3-c]pyrazole-4,4'-piperidine]-1'-yl)(3-phenylisoxazol-5-yl)-methanone | 1-methylspiro[chromeno[4,3-c]pyrazole-4,4'-piperidine]dihydrochloride | 3-phenylisoxazole-5-carboxylic acid |
| (5-methylpyrazin-2-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-methylpyrazine-2-carboxylic acid |
| 1-(1-methylindol-3-yl)-2-(1-methyl-1H-spiro[chromeno[4,3-c]pyrazole-4,4'-piperidine]-1'-yl)ethane-1,2-dione | 1-methylspiro[chromeno[4,3-c]pyrazole-4,4'-piperidine]dihydrochloride | 2-(1-methylindol-3-yl)-2-oxo-acetic acid |
| (1-methyl-1H-spiro[chromeno[4,3-c]pyrazole-4,4'-piperidine]-1'-yl)[5-(m-tolyl)isoxazol-3-yl]-methanone | 1-methylspiro[chromeno[4,3-c]pyrazole-4,4'-piperidine]dihydrochloride | 5-(m-tolyl)isoxazole-3-carboxylic acid |
| (3-chloro-1,7-diazabicyclo[4.3.0]nona-2,4,6,8-tetraen-8-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-chloro-1,7-diazabicyclo[4.3.0]nona-2,4,6,8-tetraene-8-carboxylic acid |
| (1-methyl-1H-spiro[chromeno[4,3- | 1-methylspiro[chromeno[4,3- | 5-phenyl-1H-pyrazole-3-carboxylic acid |

-continued

| Product Name | Amine or Amine•HCl | Carboxylic Acid |
|---|---|---|
| c]pyrazole-4,4'-piperidine]-1'-yl)(5-phenyl-1H-pyrazol-3-yl)-methanone | c]pyrazole-4,4'-piperidine]dihydrochloride | |
| [2-(4-chlorophenyl)thiazol-4-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(4-chlorophenyl)thiazole-4-carboxylic acid |
| [2-(4-chlorophenyl)-4-methyl-thiazol-5-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(4-chlorophenyl)-4-methyl-thiazole-5-carboxylic acid |
| (1-methyl-1H-spiro[chromeno[4,3-c]pyrazole-4,4'-piperidine]-1'-yl)(5-phenylisoxazol-3-yl)-methanone | 1-methylspiro[chromeno[4,3-c]pyrazole-4,4'-piperidine]dihydrochloride | 5-phenylisoxazole-3-carboxylic acid |
| (1-methyl-1H-spiro[chromeno[4,3-c]pyrazole-4,4'-piperidine]-1'-yl)(5-phenyloxazol-4-yl)-methanone | 1-methylspiro[chromeno[4,3-c]pyrazole-4,4'-piperidine]dihydrochloride | 5-phenyloxazole-4-carboxylic acid |
| (1-methyl-1H-spiro[chromeno[4,3-c]pyrazole-4,4'-piperidine]-1'-yl)[2-(p-tolyl)thiazol-4-yl]-methanone | 1-methylspiro[chromeno[4,3-c]pyrazole-4,4'-piperidine]dihydrochloride | 2-(p-tolyl)thiazole-4-carboxylic acid |
| [5-(4-fluorophenyl)isoxazol-3-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-(4-fluorophenyl)isoxazole-3-carboxylic acid |
| (2-fluoro-4-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-fluoro-4-methoxy-benzoic acid |
| (4-methoxy-2-quinolyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methoxyquinoline-2-carboxylic acid |
| (3,5-ditert-butylphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,5-ditert-butylbenzoic acid |
| (2-chloro-4-methylsulfonyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-chloro-4-methylsulfonyl-benzoic acid |
| (1-methyl-1H-spiro[chromeno[4,3-c]pyrazole-4,4'-piperidine]-1'-yl)[5-(2-pyridyl)-2-thienyl]-methanone | 1-methylspiro[chromeno[4,3-c]pyrazole-4,4'-piperidine]dihydrochloride | 5-(2-pyridyl)thiophene-2-carboxylic acid |
| tert-butyl 5-chloro-2-(1-methyl-1H-spiro[chromeno[4,3-c]pyrazole-4,4'-piperidine]-1'-ylcarbonyl)phenylcarbamate | 1-methylspiro[chromeno[4,3-c]pyrazole-4,4'-piperidine]dihydrochloride | 4-chloro-2-(tert-butoxycarbonylamino)-benzoic acid |
| [5-(4-methoxyphenyl)isoxazol-3-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 5-(4-methoxyphenyl)isoxazole-3-carboxylic acid |
| [3,5-bis(trifluoromethyl)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,5-bis(trifluoromethyl)benzoic acid |
| [5-methyl-1-[3-(trifluoromethyl)phenyl]-1,2,4-triazol-3-yl]-(1-methyl-1H-spiro[chromeno[4,3- | 1-methylspiro[chromeno[4,3-c]pyrazole-4,4'-piperidine]dihydrochloride | 5-methyl-1-[3-(trifluoromethyl)phenyl]-1,2,4-triazole-3-carboxylic acid |

| Product Name | Amine or Amine•HCl | Carboxylic Acid |
|---|---|---|
| c]pyrazole-4,4'-piperidine]-1'-yl)methanone | | |
| [2-[(4-chlorophenyl)methyl]-5-methyl-pyrazol-3-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-[(4-chlorophenyl)methyl]-5-methyl-pyrazole-3-carboxylic acid |
| (7-ethoxybenzofuran-2-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 7-ethoxybenzofuran-2-carboxylic acid |
| [1-(2,4-dichlorophenyl)-5-methyl-1,2,4-triazol-3-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-(2,4-dichlorophenyl)-5-methyl-1,2,4-triazole-3-carboxylic acid |
| 1-methyl-3-(methylBLAHyl)carbonyl-quinolin-4-one | 1-methylspiro[chromeno[4,3-c]pyrazole-4,4'-piperidine]dihydrochloride | 1-methyl-4-oxo-quinoline-3-carboxylic acid |
| 8-isoquinolyl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | isoquinoline-8-carboxylic acid |
| [2-(2,3-dihydrobenzofuran-5-yl)thiazol-4-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(2,3-dihydrobenzofuran-5-yl)thiazole-4-carboxylic acid |
| (2-methoxy-4-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-methoxy-4-methyl-benzoic acid |
| (3,5-dimethylphenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3,5-dimethylbenzoic acid |
| (4-methyloxazol-5-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methyloxazole-5-carboxylic acid |
| [4-methoxy-2-(trifluoromethyl)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-methoxy-2-(trifluoromethyl)benzoic acid |
| [2-(4-fluorophenoxy)-3-pyridyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(4-fluorophenoxy)pyridine-3-carboxylic acid |
| (4-benzyloxy-2-chloro-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-benzyloxy-2-chloro-benzoic acid |
| (1-methyl-1H-spiro[chromeno[4,3-c]pyrazole-4,4'-piperidine]-1'-yl)(2-phenoxy-3-pyridyl)-methanone | 1-methylspiro[chromeno[4,3-c]pyrazole-4,4'-piperidine]dihydrochloride | 2-phenoxypyridine-3-carboxylic acid |
| [2-(2-chloro-1,1,2-trifluoro-ethoxy)-4-methoxy-phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-(2-chloro-1,1,2-trifluoro-ethoxy)-4-methoxy-benzoic acid |
| 2,3-dihydrobenzofuran-7-yl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,3-dihydrobenzofuran-7-carboxylic acid |

| Product Name | Amine or Amine•HCl | Carboxylic Acid |
|---|---|---|
| [3-chloro-5-(trifluoromethyl)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-chloro-5-(trifluoromethyl)benzoic acid |
| [3-(4-chlorophenyl)isoxazol-5-yl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-(4-chlorophenyl)isoxazole-5-carboxylic acid |
| (1-benzylindol-3-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-benzylindole-3-carboxylic acid |
| 1,7-diazabicyclo[4.3.0]nona-2,4,6,8-tetraen-5-yl-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1,7-diazabicyclo[4.3.0]nona-2,4,6,8-tetraene-5-carboxylic acid |
| 5-isopropoxy-2-(1-methyl-1H-spiro[chromeno[4,3-c]pyrazole-4,4'-piperidine]-1'-ylcarbonyl)benzonitrile | 1-methylspiro[chromeno[4,3-c]pyrazole-4,4'-piperidine]dihydrochloride | 2-cyano-4-isopropoxy-benzoic acid |
| (2-chloro-4-isopropoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-chloro-4-isopropoxy-benzoic acid |
| (4-isopropoxy-2-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-isopropoxy-2-methyl-benzoic acid |
| (2-fluoro-4-isopropoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-fluoro-4-isopropoxy-benzoic acid |
| (2-isopropoxy-3-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2-isopropoxy-3-methyl-benzoic acid |
| 2-(2-methoxy-4-(1-methyl-1H-spiro[chromeno[4,3-c]pyrazole-4,4'-piperidine]-1'-ylcarbonyl)phenoxy)-2-methylpropanenitrile | 1-methylspiro[chromeno[4,3-c]pyrazole-4,4'-piperidine]dihydrochloride | 4-(1-cyano-1-methyl-ethoxy)-3-methoxy-benzoic acid |
| [3-chloro-4-(trifluoromethoxy)phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-chloro-4-(trifluoromethoxy)benzoic acid |
| (4-isopropoxy-3-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-isopropoxy-3-methoxy-benzoic acid |
| (4-hydroxy-3-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-hydroxy-3-methyl-benzoic acid |
| (3-fluoro-4-isopropoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-fluoro-4-isopropoxy-benzoic acid |
| (3-methyl-4-tert-butoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methyl-4-tert-butoxy-benzoic acid |
| (3-chloro-4-isopropoxy-phenyl)-(1-methyl-1H- | 1-methylspiro[chromeno[4,3- | 3-chloro-4-isopropoxy-benzoic acid |

-continued

| Product Name | Amine or Amine•HCl | Carboxylic Acid |
|---|---|---|
| spiro[chromeno[4,3-c]pyrazole-4,4'-piperidine]-1'-yl)methanone | c]pyrazole-4,4'-piperidine]dihydrochloride | |
| (7-chloro-1-methyl-1H-spiro[chromeno[4,3-c]pyrazole-4,4'-piperidine]-1'-yl)(4-isopropoxy-3-methylphenyl)methanone | 7-chloro-1-methyl-1H-spiro[chromeno[4,3-c]pyrazole-4,4'-piperidine] | 4-isopropoxy-3-methylbenzoic acid |
| (8-chloro-1-methyl-1H-spiro[chromeno[4,3-c]pyrazole-4,4'-piperidine]-1'-yl)(4-isopropoxy-3-methylphenyl)methanone | 8-chloro-1-methyl-1H-spiro[chromeno[4,3-c]pyrazole-4,4'-piperidine] | 4-isopropoxy-3-methylbenzoic acid |
| (4-isopropoxy-3-methylphenyl)(8-methoxy-1-methyl-1H-spiro[chromeno[4,3-c]pyrazole-4,4'-piperidine]-1'-yl)methanone | 8-methoxy-1-methyl-1H-spiro[chromeno[4,3-c]pyrazole-4,4'-piperidine] | 4-isopropoxy-3-methylbenzoic acid |
| (1,3-dimethyl-1H-spiro[chromeno[4,3-c]pyrazole-4,4'-piperidine]-1'-yl)(4-isopropoxy-3-methylphenyl)methanone | 1,3-dimethyl-1H-spiro[chromeno[4,3-c]pyrazole-4,4'-piperidine]dihydrochloride | 4-isopropoxy-3-methylbenzoic acid |
| (4-isopropoxy-3-methylphenyl)(1H-spiro[chromeno[4,3-c]pyrazole-4,4'-piperidine]-1'-yl)methanone | 1H-Spiro[chromeno[4,3-c]pyrazole-4,4'-piperidine] | 4-isopropoxy-3-methylbenzoic acid |
| (1-ethyl-1H-spiro[chromeno[4,3-c]pyrazole-4,4'-piperidine]-1'-yl)(3-methoxy-4-(2-methoxyethoxy)phenyl)methanone | 1-ethyl-1H-spiro[chromeno[4,3-c]pyrazole-4,4'-piperidine] | 3-methoxy-4-(2-methoxyethoxy)benzoic acid |
| (1-ethyl-1H-spiro[chromeno[4,3-c]pyrazole-4,4'-piperidine]-1'-yl)(4-isopropoxy-3-methylphenyl)methanone | 1-ethyl-1H-spiro[chromeno[4,3-c]pyrazole-4,4'-piperidine] | 4-isopropoxy-3-methylbenzoic acid |
| (1-ethyl-1H-spiro[chromeno[4,3-c]pyrazole-4,4'-piperidine]-1'-yl)(4-(isopentyloxy)-3-methoxyphenyl)methanone | 1-ethyl-1H-spiro[chromeno[4,3-c]pyrazole-4,4'-piperidine] | 4-(isopentyloxy)-3-methoxybenzoic acid |
| (4-tert-butyl-3-methoxyphenyl)(1-ethyl-1H-spiro[chromeno[4,3-c]pyrazole-4,4'-piperidine]-1'-yl)methanone | 1-ethyl-1H-spiro[chromeno[4,3-c]pyrazole-4,4'-piperidine] | 4-tert-butyl-3-methoxybenzoic acid |
| (3-methoxy-4-(2-methoxyethoxy)phenyl)(1-(2-methoxyethyl)-1H-spiro[chromeno[4,3-c]pyrazole-4,4'-piperidine]-1'-yl)methanone | 1-(2-methoxyethyl)-1H-spiro[chromeno[4,3-c]pyrazole-4,4'-piperidine]hydrochloride | 3-methoxy-4-(2-methoxyethoxy)benzoic acid |
| (4-tert-butyl-3-methoxyphenyl)(1-(2-methoxyethyl)-1H-spiro[chromeno[4,3-c]pyrazole-4,4'-piperidine]-1'-yl)methanone | 1-(2-methoxyethyl)-1H-spiro[chromeno[4,3-c]pyrazole-4,4'-piperidine]hydrochloride | 4-tert-butyl-3-methoxybenzoic acid |
| (4-(isopentyloxy)-3-methoxyphenyl)(1-(2-methoxyethyl)-1H-spiro[chromeno[4,3-c]pyrazole-4,4'-piperidine]-1'-yl)methanone | 1-(2-methoxyethyl)-1H-spiro[chromeno[4,3-c]pyrazole-4,4'-piperidine]hydrochloride | 4-(isopentyloxy)-3-methoxybenzoic acid |
| 3-methoxy-4-(2-methoxyethoxy)phenyl)(1-(2,2,2-trifluoroethyl)-1H-spiro[chromeno[4,3-c]pyrazole-4,4'-piperidine]-1'-yl)methanone | 1-(2,2,2-trifluoroethyl)-1H-spiro[chromeno[4,3-c]pyrazole-4,4'-piperidine] | 3-methoxy-4-(2-methoxyethoxy)benzoic acid |
| (4-(isopentyloxy)-3-methoxyphenyl)(1-(2,2,2-trifluoroethyl)-1H-spiro[chromeno[4,3- | 1-(2,2,2-trifluoroethyl)-1H-spiro[chromeno[4,3-c]pyrazole-4,4'-piperidine] | 4-(isopentyloxy)-3-methoxybenzoic acid |

-continued

| Product Name | Amine or Amine•HCl | Carboxylic Acid |
|---|---|---|
| c]pyrazole-4,4'-piperidine]-1'-yl)methanone | | |
| (4-(isopentyloxy)-3-methoxyphenyl)(2-(2,2,2-trifluoroethyl)-2H-spiro[chromeno[4,3-c]pyrazole-4,4'-piperidine]-1'-yl)methanone | 2-(2,2,2-trifluoroethyl)-2H-spiro[chromeno[4,3-c]pyrazole-4,4'-piperidine] | 4-(isopentyloxy)-3-methoxybenzoic acid |
| (1-methylspiro[benzo[b]pyrrolo[1,2-d][1,4]oxazine-4,4'-piperidine]-1'-yl)(phenyl)methanone | 1-methylspiro[benzo[b]pyrrolo[1,2-d][1,4]oxazine-4,4'-piperidine] | Benzoic acid |
| (4-ethyl-3-methoxyphenyl)(1-methylspiro[benzo[b]pyrrolo[1,2-d][1,4]oxazine-4,4'-piperidine]-1'-yl)methanone | 1-methylspiro[benzo[b]pyrrolo[1,2-d][1,4]oxazine-4,4'-piperidine] | 4-ethyl-3-methoxybenzoic acid |
| (4-ethyl-3-methoxyphenyl)(2-methylspiro[benzo[b]pyrrolo[1,2-d][1,4]oxazine-4,4'-piperidine]-1'-yl)methanone | 2-methylspiro[benzo[b]pyrrolo[1,2-d][1,4]oxazine-4,4'-piperidine] | 4-ethyl-3-methoxybenzoic acid |
| (4-ethyl-3-methoxyphenyl)(3-methylspiro[benzo[b]pyrrolo[1,2-d][1,4]oxazine-4,4'-piperidine]-1'-yl)methanone | 3-methylspiro[benzo[b]pyrrolo[1,2-d][1,4]oxazine-4,4'-piperidine] | 4-ethyl-3-methoxybenzoic acid |
| (4-isopropoxy-3-methylphenyl)(1-methylspiro[benzo[b]pyrrolo[1,2-d][1,4]oxazine-4,4'-piperidine]-1'-yl)methanone | 1-methylspiro[benzo[b]pyrrolo[1,2-d][1,4]oxazine-4,4'-piperidine] | 4-isopropoxy-3-methylbenzoic acid |
| (4-isopropoxy-3-methylphenyl)(2-methylspiro[benzo[b]pyrrolo[1,2-d][1,4]oxazine-4,4'-piperidine]-1'-yl)methanone | 2-methylspiro[benzo[b]pyrrolo[1,2-d][1,4]oxazine-4,4'-piperidine] | 4-isopropoxy-3-methylbenzoic acid |
| (4-isopropoxy-3-methylphenyl)(3-methylspiro[benzo[b]pyrrolo[1,2-d][1,4]oxazine-4,4'-piperidine]-1'-yl)methanone | 3-methylspiro[benzo[b]pyrrolo[1,2-d][1,4]oxazine-4,4'-piperidine] | 4-isopropoxy-3-methylbenzoic acid |
| (4-methoxy-3-(trifluoromethyl)phenyl)(1-methylspiro[benzo[b]pyrrolo[1,2-d][1,4]oxazine-4,4'-piperidine]-1'-yl)methanone | 1-methylspiro[benzo[b]pyrrolo[1,2-d][1,4]oxazine-4,4'-piperidine] | 4-methoxy-3-(trifluoromethyl)benzoic acid |
| (4-methoxy-3-(trifluoromethyl)phenyl)(2-methylspiro[benzo[b]pyrrolo[1,2-d][1,4]oxazine-4,4'-piperidine]-1'-yl)methanone | 2-methylspiro[benzo[b]pyrrolo[1,2-d][1,4]oxazine-4,4'-piperidine] | 4-methoxy-3-(trifluoromethyl)benzoic acid |
| (4-methoxy-3-(trifluoromethyl)phenyl)(3-methylspiro[benzo[b]pyrrolo[1,2-d][1,4]oxazine-4,4'-piperidine]-1'-yl)methanone | 3-methylspiro[benzo[b]pyrrolo[1,2-d][1,4]oxazine-4,4'-piperidine] | 4-methoxy-3-(trifluoromethyl)benzoic acid |
| (3-methoxy-4-(2-methoxyethoxy)phenyl)(1-methylspiro[benzo[b]pyrrolo[1,2-d][1,4]oxazine-4,4'-piperidine]-1'-yl)methanone | 1-methylspiro[benzo[b]pyrrolo[1,2-d][1,4]oxazine-4,4'-piperidine] | 3-methoxy-4-(2-methoxyethoxy)benzoic acid |
| (1-methylspiro[benzo[b]pyrrolo[1,2-d][1,4]oxazine-4,4'-piperidine]-1'-yl)(4-propoxy-3-(trifluoromethyl)phenyl)methanone | 1-methylspiro[benzo[b]pyrrolo[1,2-d][1,4]oxazine-4,4'-piperidine] | 4-propoxy-3-(trifluoromethyl)benzoic acid |
| (4-ethyl-3-methoxyphenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 4-ethyl-3-methoxybenzoic acid |
| (3-methoxy-4-(2-methoxyethoxy)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 3-methoxy-4-(2-methoxyethoxy)benzoic acid |
| (4-propoxy-3-(trifluoromethyl)phenyl)(spiro[piperidine- | spiro[piperidine-4,6'-pyrido[3,2-b]pyrrolo[1,2- | 4-propoxy-3-(trifluoromethyl)benzoic acid |

-continued

| Product Name | Amine or Amine•HCl | Carboxylic Acid |
|---|---|---|
| 4,6'-pyrido[3,2-b]pyrrolo[1,2-d][1,4]oxazine]-1-yl)methanone | | |
| (4-(isopentyloxy)-3-methoxyphenyl)(spiro[piperidine-4,6'-pyrido[3,2-b]pyrrolo[1,2-d][1,4]oxazine]-1-yl)methanone | spiro[piperidine-4,6'-pyrido[3,2-b]pyrrolo[1,2-d][1,4]oxazine] | 4-(isopentyloxy)-3-methoxybenzoic acid |
| (4-tert-butyl-3-methoxyphenyl)(spiro[piperidine-4,6'-pyrido[3,2-b]pyrrolo[1,2-d][1,4]oxazine]-1-yl)methanone | spiro[piperidine-4,6'-pyrido[3,2-b]pyrrolo[1,2-d][1,4]oxazine] | 4-tert-butyl-3-methoxybenzoic acid |
| (R)-(3-methoxy-4-(tetrahydrofuran-3-yloxy)phenyl)(spiro[piperidine-4,6'-pyrido[3,2-b]pyrrolo[1,2-d][1,4]oxazine]-1-yl)methanone | spiro[piperidine-4,6'-pyrido[3,2-b]pyrrolo[1,2-d][1,4]oxazine] | (R)-3-methoxy-4-(tetrahydrofuran-3-yloxy)benzoic acid |
| (3-methoxy-4-(2-methoxyethoxy)phenyl)(spiro[piperidine-4,6'-pyrido[3,2-b]pyrrolo[1,2-d][1,4]oxazine]-1-yl)methanone | spiro[piperidine-4,6'-pyrido[3,2-b]pyrrolo[1,2-d][1,4]oxazine] | 3-methoxy-4-(2-methoxyethoxy)benzoic acid |
| (4-ethyl-3-methoxyphenyl)(2-methylspiro[chromeno[3,4-d]thiazole-4,4'-piperidine]-1'-yl)methanone | 2-methylspiro[chromeno[3,4-d]thiazole-4,4'-piperidine] | 4-ethyl-3-methoxybenzoic acid |
| (4-methoxy-3-(trifluoromethyl)phenyl)(1-methyl-1H-spiro[chromeno[4,3-b]pyrrole-4,4'-piperidine]-1'-yl)methanone | 1-methyl-1H-spiro[chromeno[4,3-b]pyrrole-4,4'-piperidine] | 4-methoxy-3-(trifluoromethyl)benzoic acid |
| (3-methoxy-4-(2-methoxyethoxy)phenyl)(1-methyl-1H-spiro[chromeno[4,3-b]pyrrole-4,4'-piperidine]-1'-yl)methanone | spiro[chromeno[4,3-b]pyrrole-4,4'-piperidine] | 3-methoxy-4-(2-methoxyethoxy)benzoic acid |
| (1-methyl-1H-spiro[chromeno[4,3-c]pyrazole-4,4'-piperidine]-1'-yl)(3-(methylsulfonyl)phenyl)methanone | 1-methyl-1H-spiro[chromeno[4,3-c]pyrazole-4,4'-piperidine] | 3-(methylsulfonyl)benzoic acid |
| (4-chlorophenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-chlorobenzoic acid |
| (2-methoxypyridin-3-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-methoxynicotinic acid |
| (1-methyl-1H-spiro[chromeno[4,3-c]pyrazole-4,4'-piperidine]-1'-yl)(quinolin-2-yl)methanone | 1-methyl-1H-spiro[chromeno[4,3-c]pyrazole-4,4'-piperidine] | quinoline-2-carboxylic acid |
| (3-(2-chlorophenyl)isoxazol-5-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3-(2-chlorophenyl)isoxazole-5-carboxylic acid |
| (1-methyl-1H-spiro[chromeno[4,3-c]pyrazole-4,4'-piperidine]-1'-yl)(2-(trifluoromethyl)-1,8-naphthyridin-3-yl)methanone | 1-methyl-1H-spiro[chromeno[4,3-c]pyrazole-4,4'-piperidine] | 2-(trifluoromethyl)-1,8-naphthyridine-3-carboxylic acid |
| (2,4-dimethylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2,4-dimethylbenzoic acid |
| (2-methoxy-5-methylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-methoxy-5-methylbenzoic acid |

| Product Name | Amine or Amine•HCl | Carboxylic Acid |
|---|---|---|
| (4-tert-butoxy-3-methoxyphenyl)(1H-spiro[chromeno[4,3-c]pyrazole-4,4'-piperidine]-1'-yl)methanone | 1H-spiro[chromeno[4,3-c]pyrazole-4,4'-piperidine] | 4-tert-butoxy-3-methoxybenzoic acid |
| (2,3-dimethoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2,3-dimethoxybenzoic acid |
| (3-fluoro-2-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3-fluoro-2-methoxybenzoic acid |
| (2-methoxy-6-methylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-methoxy-6-methylbenzoic acid |
| (2,3-dihydrobenzofuran-4-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2,3-dihydrobenzofuran-4-carboxylic acid |
| chroman-8-yl(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | chroman-8-carboxylic acid |
| (3,4-dihydro-2H-benzo[b][1,4]dioxepin-6-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3,4-dihydro-2H-benzo[b][1,4]dioxepine-6-carboxylic acid |
| (3-chloro-2-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3-chloro-2-methoxybenzoic acid |
| (2-chloro-6-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-chloro-6-methoxybenzoic acid |
| (4,5-difluoro-2-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4,5-difluoro-2-methoxybenzoic acid |
| (2-ethoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-ethoxybenzoic acid |
| (2-isopropoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-isopropoxybenzoic acid |
| (3-methoxypyridin-4-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3-methoxyisonicotinic acid |
| (1-methyl-1H-spiro[chromeno[4,3-c]pyrazole-4,4'-piperidine]-1'-yl)(3-methyl-4-(trifluoromethoxy)phenyl)methanone | 1-methyl-1H-spiro[chromeno[4,3-c]pyrazole-4,4'-piperidine] | 3-methyl-4-(trifluoromethoxy)benzoic acid |
| (2-hydroxy-3-isopropylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-hydroxy-3-isopropylbenzoic acid |
| (4-methoxy-3,5-dimethylphenyl)(1-methyl-1H- | 1-methyl-1H-spiro[chromeno[4,3- | 4-methoxy-3,5-dimethylbenzoic acid |

| Product Name | Amine or Amine•HCl | Carboxylic Acid |
| --- | --- | --- |
| spiro[chromeno[4,3-c]pyrazole-4,4'-piperidine]-1'-yl)methanone | c]pyrazole-4,4'-piperidine] | |
| (1-methyl-1H-spiro[chromeno[4,3-c]pyrazole-4,4'-piperidine]-1'-yl)(4-(trifluoromethylsulfonyl)phenyl)methanone | 1-methyl-1H-spiro[chromeno[4,3-c]pyrazole-4,4'-piperidine] | 4-(trifluoromethylsulfonyl)benzoic acid |
| (4-(difluoromethylsulfonyl)phenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-(difluoromethylsulfonyl)benzoic acid |
| (4-isopropoxy-3,5-dimethylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-isopropoxy-3,5-dimethylbenzoic acid |
| (1-methyl-1H-spiro[chromeno[4,3-c]pyrazole-4,4'-piperidine]-1'-yl)(2-methylbenzo[d]oxazol-7-yl)methanone | 1-methyl-1H-spiro[chromeno[4,3-c]pyrazole-4,4'-piperidine] | 2-methylbenzo[d]oxazole-7-carboxylic acid |
| (4-fluoro-2-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-fluoro-2-methoxybenzoic acid |
| (8-methoxy-1-methyl-1H-spiro[chromeno[4,3-c]pyrazole-4,4'-piperidine]-1'-yl)(2-methoxyphenyl)methanone | 8-methoxy-1-methyl-1H-spiro[chromeno[4,3-c]pyrazole-4,4'-piperidine] | 2-methoxybenzoic acid |
| (2-(difluoromethoxy)phenyl)(8-methoxy-1-methyl-1H-spiro[chromeno[4,3-c]pyrazole-4,4'-piperidine]-1'-yl)methanone | 8-methoxy-1-methyl-1H-spiro[chromeno[4,3-c]pyrazole-4,4'-piperidine] | 2-(difluoromethoxy)benzoic acid |
| (2-chlorophenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-chlorobenzoic acid |
| (2-(2-hydroxyethoxy)phenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-(2-hydroxyethoxy)benzoic acid |
| (1-methyl-1H-spiro[chromeno[4,3-c]pyrazole-4,4'-piperidine]-1'-yl)(2-(tetrahydro-2H-pyran-4-yloxy)phenyl)methanone | 1-methyl-1H-spiro[chromeno[4,3-c]pyrazole-4,4'-piperidine] | 2-(tetrahydro-2H-pyran-4-yloxy)benzoic acid |
| (1-methyl-1H-spiro[chromeno[4,3-c]pyrazole-4,4'-piperidine]-1'-yl)(2-(methylthio)phenyl)methanone | 1-methyl-1H-spiro[chromeno[4,3-c]pyrazole-4,4'-piperidine] | 2-(methylthio)benzoic acid |
| (2,3-dimethyl-2,3-dihydrobenzofuran-7-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2,3-dimethyl-2,3-dihydrobenzofuran-7-carboxylic acid |
| (4-fluoro-2-methylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-fluoro-2-methylbenzoic acid |
| (5-isopropoxyquinolin-8-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 5-isopropoxyquinoline-8-carboxylic acid |
| (4-bromo-3-methylphenyl)(1-methyl-1H- | 1-methyl-1H-spiro[chromeno[4,3- | 4-bromo-3-methylbenzoic acid |

-continued

| Product Name | Amine or Amine•HCl | Carboxylic Acid |
|---|---|---|
| spiro[chromeno[4,3-c]pyrazole-4,4'-piperidine]-1'-yl)methanone | c]pyrazole-4,4'-piperidine] | |
| (4-bromo-3-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-bromo-3-methoxybenzoic acid |
| (4-tert-butoxy-2-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-tert-butoxy-2-methoxybenzoic acid |
| (1-methyl-1H-pyrrolo[3,2-b]pyridin-3-yl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 1-methyl-1H-pyrrolo[3,2-b]pyridine-3-carboxylic acid |
| 2-(3-methoxy-4-(1-methyl-1H-spiro[chromeno[4,3-c]pyrazole-4,4'-piperidine]-1'-ylcarbonyl)phenoxy)-2-methylpropanenitrile | 1-methyl-1H-spiro[chromeno[4,3-c]pyrazole-4,4'-piperidine] | 4-(2-cyanopropan-2-yloxy)-2-methoxybenzoic acid |
| (4-tert-butoxy-2-fluorophenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-tert-butoxy-2-fluorobenzoic acid |
| (1-methyl-1H-spiro[chromeno[4,3-c]pyrazole-4,4'-piperidine]-1'-yl)(o-tolyl)methanone | 1-methyl-1H-spiro[chromeno[4,3-c]pyrazole-4,4'-piperidine] | 2-methylbenzoic acid |
| (3-fluoro-2-methylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3-fluoro-2-methylbenzoic acid |
| (2,3-difluorophenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2,3-difluorobenzoic acid |
| (2-(methoxymethyl)phenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-(methoxymethyl)benzoic acid |
| (3,4-difluoro-2-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3,4-difluoro-2-methoxybenzoic acid |
| (2,3-difluoro-6-methoxyphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2,3-difluoro-6-methoxybenzoic acid |
| (4-(isobutylsulfonyl)phenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-(isobutylsulfonyl)benzoic acid |
| (4-isopropoxy-2,5-dimethylphenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 4-isopropoxy-2,5-dimethylbenzoic acid |
| (3-ethoxy-2-fluorophenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 3-ethoxy-2-fluorobenzoic acid |
| (8-fluoro-1-methyl-1H-spiro[chromeno[4,3-c]pyrazole-4,4'-piperidine]-1'-yl)(2-methoxyphenyl)methanone | 8-fluoro-1-methyl-1H-spiro[chromeno[4,3-c]pyrazole-4,4'-piperidine] | 2-methoxybenzoic acid |
| (1-ethyl-8-fluoro-1H-spiro[chromeno[4,3- | 1-ethyl-8-fluoro-1H-spiro[chromeno[4,3- | 2-methoxybenzoic acid |

| Product Name | Amine or Amine•HCl | Carboxylic Acid |
|---|---|---|
| c]pyrazole-4,4'-piperidine]-1'-yl)(2-methoxyphenyl)methanone | c]pyrazole-4,4'-piperidine] | |
| (2-(difluoromethyl)phenyl)(8-fluoro-1-methyl-1H-spiro[chromeno[4,3-c]pyrazole-4,4'-piperidine]-1'-yl)methanone | 8-fluoro-1-methyl-1H-spiro[chromeno[4,3-c]pyrazole-4,4'-piperidine] | 2-(difluoromethyl)benzoic acid |
| (8-fluoro-1-methyl-1H-spiro[chromeno[4,3-c]pyrazole-4,4'-piperidine]-1'-yl)(2-(trifluoromethoxy)phenyl)methanone | 8-fluoro-1-methyl-1H-spiro[chromeno[4,3-c]pyrazole-4,4'-piperidine] | 2-(trifluoromethoxy)benzoic acid |
| (7-chloro-1-methyl-1H-spiro[chromeno[4,3-c]pyrazole-4,4'-piperidine]-1'-yl)(3-fluoro-2-methoxyphenyl)methanone | 7-chloro-1-methyl-1H-spiro[chromeno[4,3-c]pyrazole-4,4'-piperidine] | 3-fluoro-2-methoxybenzoic acid |
| (7-chloro-1-methyl-1H-spiro[chromeno[4,3-c]pyrazole-4,4'-piperidine]-1'-yl)(2-(difluoromethoxy)-3-fluorophenyl)methanone | 7-chloro-1-methyl-1H-spiro[chromeno[4,3-c]pyrazole-4,4'-piperidine] | 2-(difluoromethoxy)-3-fluorobenzoic acid |
| (2-(difluoromethoxy)-3-fluorophenyl)(1-methyl-1H-spiro[chromeno[4,3-c]pyrazole-4,4'-piperidine]-1'-yl)methanone | 1-methyl-1H-spiro[chromeno[4,3-c]pyrazole-4,4'-piperidine] | 2-(difluoromethoxy)-3-fluorobenzoic acid |
| N-methyl-4-(1-methyl-1H-spiro[chromeno[4,3-c]pyrazole-4,4'-piperidine]-1'-ylcarbonyl)benzenesulfonamide | 1-methyl-1H-spiro[chromeno[4,3-c]pyrazole-4,4'-piperidine] | 4-(N-methylsulfamoyl)benzoic acid |
| N-ethyl-4-(1-methyl-1H-spiro[chromeno[4,3-c]pyrazole-4,4'-piperidine]-1'-ylcarbonyl)benzenesulfonamide | 1-methyl-1H-spiro[chromeno[4,3-c]pyrazole-4,4'-piperidine] | 4-(N-ethylsulfamoyl)benzoic acid |
| N,N-dimethyl-4-(1-methyl-1H-spiro[chromeno[4,3-c]pyrazole-4,4'-piperidine]-1'-ylcarbonyl)benzenesulfonamide | 1-methyl-1H-spiro[chromeno[4,3-c]pyrazole-4,4'-piperidine] | 4-(N,N-dimethylsulfamoyl)benzoic acid |
| (3-fluoro-2-methoxyphenyl)(1-isopropyl-1H-spiro[chromeno[4,3-c]pyrazole-4,4'-piperidine]-1'-yl)methanone | 1-isopropyl-1H-spiro[chromeno[4,3-c]pyrazole-4,4'-piperidine] | 3-fluoro-2-methoxybenzoic acid |
| (2-(difluoromethoxy)phenyl)(1-isopropyl-1H-spiro[chromeno[4,3-c]pyrazole-4,4'-piperidine]-1'-yl)methanone | 1-isopropyl-1H-spiro[chromeno[4,3-c]pyrazole-4,4'-piperidine] | 2-(difluoromethoxy)benzoic acid |
| (1-isopropyl-1H-spiro[chromeno[4,3-c]pyrazole-4,4'-piperidine]-1'-yl)(4-(isopropylsulfonyl)phenyl)methanone | 1-isopropyl-1H-spiro[chromeno[4,3-c]pyrazole-4,4'-piperidine] | 4-(isopropylsulfonyl)benzoic acid |
| (2-(difluoromethoxy)phenyl)(8-fluoro-1-methyl-1H-spiro[chromeno[4,3-c]pyrazole-4,4'-piperidine]-1'-yl)methanone | 8-fluoro-1-methyl-1H-spiro[chromeno[4,3-c]pyrazole-4,4'-piperidine] | 2-(difluoromethoxy)benzoic acid |
| (2-(difluoromethoxy)phenyl)(1-ethyl-8-fluoro-1H-spiro[chromeno[4,3-c]pyrazole-4,4'-piperidine]-1'-yl)methanone | 1-ethyl-8-fluoro-1H-spiro[chromeno[4,3-c]pyrazole-4,4'-piperidine] | 2-(difluoromethoxy)benzoic acid |
| (1-ethyl-1H-spiro[chromeno[4,3-c]pyrazole-4,4'-piperidine]-1'-yl)(3-methyl-4-(methylsulfonyl)phenyl)methanone | 1-ethyl-1H-spiro[chromeno[4,3-c]pyrazole-4,4'-piperidine] | 3-methyl-4-(methylsulfonyl)benzoic acid |
| (1-ethyl-8-fluoro-1H-spiro[chromeno[4,3-c]pyrazole-4,4'-piperidine]-1'-yl)(4-isopropoxy-3-methoxyphenyl)methanone | 1-ethyl-8-fluoro-1H-spiro[chromeno[4,3-c]pyrazole-4,4'-piperidine] | 4-isopropoxy-3-methoxybenzoic acid |

| Product Name | Amine or Amine•HCl | Carboxylic Acid |
|---|---|---|
| (1-ethyl-8-fluoro-1H-spiro[chromeno[4,3-c]pyrazole-4,4'-piperidine]-1'-yl)(4-isopropoxy-3-methylphenyl)methanone | 1-ethyl-8-fluoro-1H-spiro[chromeno[4,3-c]pyrazole-4,4'-piperidine] | 4-isopropoxy-3-methylbenzoic acid |
| (4-isopropoxy-3-methylphenyl)(spiro[piperidine-4,4'-pyrazolo[1,5-d]pyrido[2,3-b][1,4]oxazine]-1-yl)methanone | spiro[piperidine-4,4'-pyrazolo[1,5-d]pyrido[2,3-b][1,4]oxazine] | 4-isopropoxy-3-methylbenzoic acid |
| [1'-(trifluoromethyl)spiro[piperidine-4,4'-pyrrolo[2,1-c][1,4]benzoxazine]-1-yl]-(2,3,4-trimethoxyphenyl)methanone | 1'-(trifluoromethyl)spiro[piperidine-4,4'-pyrrolo[2,1-c][1,4]benzoxazine] | 2,3,4-trimethoxybenzoic acid |
| (2-methylspiro[chromeno[4,3-c]pyrazole-4,4'-piperidine]-1'-yl)-(3,4,5-trimethoxyphenyl)methanone | 2-methylspiro[chromeno[4,3-c]pyrazole-4,4'-piperidine] | 3,4,5-trimethoxybenzoic acid |
| (2-methylspiro[chromeno[4,3-c]pyrazole-4,4'-piperidine]-1'-yl)-(2,4,5-trimethoxyphenyl)methanone | 2-methylspiro[chromeno[4,3-c]pyrazole-4,4'-piperidine] | 2,4,5-trimethoxybenzoic acid |
| (2-methylspiro[chromeno[4,3-c]pyrazole-4,4'-piperidine]-1'-yl)-(2,3,4-trimethoxyphenyl)methanone | 2-methylspiro[chromeno[4,3-c]pyrazole-4,4'-piperidine] | 2,3,4-trimethoxybenzoic acid |
| (1-methylspiro[chromeno[4,3-c]pyrazole-4,4'-piperidine]-1'-yl)-(2,3,4-trimethoxyphenyl)methanone | 1-methylspiro[chromeno[4,3-c]pyrazole-4,4'-piperidine] | 2,3,4-trimethoxybenzoic acid |
| (2-amino-1,3-benzothiazol-6-yl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-amino-1,3-benzothiazole-6-carboxylic acid |
| (2-amino-1,3-benzothiazol-6-yl)-(2-methylspiro[chromeno[4,3-c]pyrazole-4,4'-piperidine]-1'-yl)methanone | 2-methylspiro[chromeno[4,3-c]pyrazole-4,4'-piperidine] | 2-amino-1,3-benzothiazole-6-carboxylic acid |
| 1H-indazol-5-yl-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 1H-indazole-5-carboxylic acid |
| 1H-indazol-5-yl-(1-methylspiro[chromeno[4,3-c]pyrazole-4,4'-piperidine]-1'-yl)methanone | 1-methylspiro[chromeno[4,3-c]pyrazole-4,4'-piperidine] | 1H-indazole-5-carboxylic acid |
| 1H-indazol-5-yl-(2-methylspiro[chromeno[4,3-c]pyrazole-4,4'-piperidine]-1'-yl)methanone | 2-methylspiro[chromeno[4,3-c]pyrazole-4,4'-piperidine] | 1H-indazole-5-carboxylic acid |
| [4-(difluoromethoxy)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-(difluoromethoxy)benzoic acid |
| [4-(difluoromethoxy)phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(difluoromethoxy)benzoic acid |
| [4-(difluoromethoxy)phenyl]-(2-methylspiro[chromeno[4,3-c]pyrazole-4,4'-piperidine]-1'-yl)methanone | 2-methylspiro[chromeno[4,3-c]pyrazole-4,4'-piperidine] | 4-(difluoromethoxy)benzoic acid |
| (2-amino-1,3-benzothiazol-6-yl)-(1-methylspiro[chromeno[4,3-c]pyrazole-4,4'-piperidine]-1'-yl)methanone | 1-methylspiro[chromeno[4,3-c]pyrazole-4,4'-piperidine] | 2-amino-1,3-benzothiazole-6-carboxylic acid |
| (2-chloro-1,3-benzothiazol-6-yl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-chloro-1,3-benzothiazole-6-carboxylic acid |
| (2-chloro-1,3-benzothiazol-6-yl)- | 1-methylspiro[chromeno[4,3- | 2-chloro-1,3-benzothiazole-6- |

| Product Name | Amine or Amine•HCl | Carboxylic Acid |
|---|---|---|
| (1-methylspiro[chromeno[4,3-c]pyrazole-4,4'-piperidine]-1'-yl)methanone | c]pyrazole-4,4'-piperidine] | carboxylic acid |
| (2-chloro-1,3-benzothiazol-6-yl)-(2-methylspiro[chromeno[4,3-c]pyrazole-4,4'-piperidine]-1'-yl)methanone | 2-methylspiro[chromeno[4,3-c]pyrazole-4,4'-piperidine] | 2-chloro-1,3-benzothiazole-6-carboxylic acid |
| (2-methyl-1,3-benzothiazol-6-yl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-methyl-1,3-benzothiazole-6-carboxylic acid |
| (2-methyl-1,3-benzothiazol-6-yl)-(1-methylspiro[chromeno[4,3-c]pyrazole-4,4'-piperidine]-1'-yl)methanone | 1-methylspiro[chromeno[4,3-c]pyrazole-4,4'-piperidine] | 2-methyl-1,3-benzothiazole-6-carboxylic acid |
| (2-methyl-1,3-benzothiazol-6-yl)-(2-methylspiro[chromeno[4,3-c]pyrazole-4,4'-piperidine]-1'-yl)methanone | 2-methylspiro[chromeno[4,3-c]pyrazole-4,4'-piperidine] | 2-methyl-1,3-benzothiazole-6-carboxylic acid |
| 1,3-benzothiazol-6-yl-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 1,3-benzothiazole-6-carboxylic acid |
| 1,3-benzothiazol-6-yl-(2-methylspiro[chromeno[4,3-c]pyrazole-4,4'-piperidine]-1'-yl)methanone | 2-methylspiro[chromeno[4,3-c]pyrazole-4,4'-piperidine] | 1,3-benzothiazole-6-carboxylic acid |
| (2-butyl-1,3-benzoxazol-5-yl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-butyl-1,3-benzoxazole-5-carboxylic acid |
| 1-[1-(4-tert-butylsulfonylbenzoyl)spiro[piperidine-4,4'-pyrrolo[2,1-c][1,4]benzoxazine]-1'-yl]ethanone | 1-spiro[piperidine-4,4'-pyrrolo[2,1-c][1,4]benzoxazine]-1'-ylethanone | 4-tert-butylsulfonylbenzoic acid |
| 4-(1'-acetylspiro[piperidine-4,4'-pyrrolo[2,1-c][1,4]benzoxazine]-1-carbonyl)-N-cyclopropyl-benzenesulfonamide | 1-spiro[piperidine-4,4'-pyrrolo[2,1-c][1,4]benzoxazine]-1'-ylethanone | 4-(cyclopropylsulfamoyl)benzoic acid |
| 1-[1-(3-methyl-4-methylsulfonyl-benzoyl)spiro[piperidine-4,4'-pyrrolo[2,1-c][1,4]benzoxazine]-1'-yl]ethanone | 1-spiro[piperidine-4,4'-pyrrolo[2,1-c][1,4]benzoxazine]-1'-ylethanone | 3-methyl-4-methylsulfonyl-benzoic acid |
| 1-[1-[4-(1-hydroxy-1-methyl-ethyl)benzoyl]spiro[piperidine-4,4'-pyrrolo[2,1-c][1,4]benzoxazine]-1'-yl]ethanone | 1-spiro[piperidine-4,4'-pyrrolo[2,1-c][1,4]benzoxazine]-1'-ylethanone | 4-(1-hydroxy-1-methyl-ethyl)benzoic acid |
| 1-[1-(4-isopropoxy-3-methoxy-benzoyl)spiro[piperidine-4,4'-pyrrolo[2,1-c][1,4]benzoxazine]-1'-yl]ethanone | 1-spiro[piperidine-4,4'-pyrrolo[2,1-c][1,4]benzoxazine]-1'-ylethanone | 4-isopropoxy-3-methoxy-benzoic acid |
| 1-[1-(4-isopropoxy-3-methyl-benzoyl)spiro[piperidine-4,4'-pyrrolo[2,1-c][1,4]benzoxazine]-1'-yl]ethanone | 1-spiro[piperidine-4,4'-pyrrolo[2,1-c][1,4]benzoxazine]-1'-ylethanone | 4-isopropoxy-3-methyl-benzoic acid |
| 1-[1-[3-methoxy-4-(2-methoxyethoxy)benzoyl]spiro[piperidine-4,4'-pyrrolo[2,1-c][1,4]benzoxazine]-1'-yl]ethanone | 1-spiro[piperidine-4,4'-pyrrolo[2,1-c][1,4]benzoxazine]-1'-ylethanone | 3-methoxy-4-(2-methoxyethoxy)benzoic acid |
| 1-[1-[2-(difluoromethoxy)benzoyl]spiro[piperidine-4,4'-pyrrolo[2,1-c][1,4]benzoxazine]-1'-yl]ethanone | 1-spiro[piperidine-4,4'-pyrrolo[2,1-c][1,4]benzoxazine]-1'-ylethanone | 2-(difluoromethoxy)benzoic acid |

613

(7-Chlorospiro[benzo[b]pyrrolo[1,2-d][1,4]oxazine-4,4'-piperidine]-1'-yl)(2-fluoro-5-methoxyphenyl)methanone

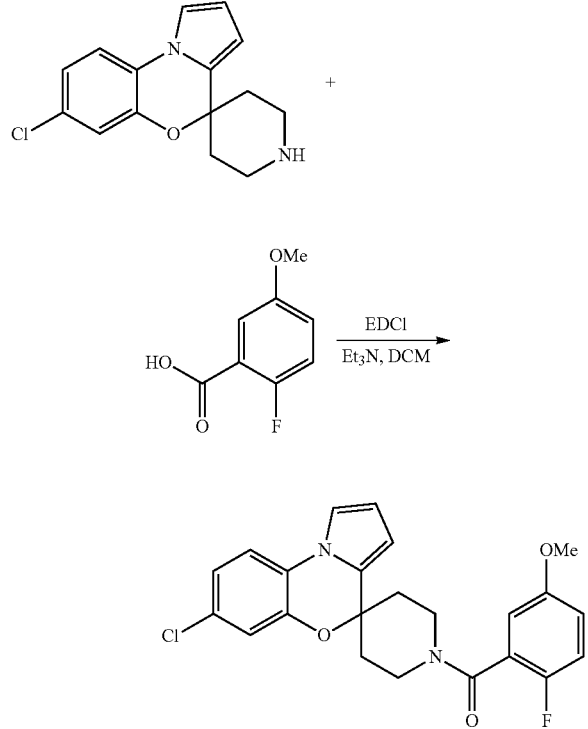

7-Chlorospiro[benzo[b]pyrrolo[1,2-d][1,4]oxazine-4,4'-piperidine] (62 mg, 0.20 mmol), 2-fluoro-5-methoxybenzoic acid (34 mg, 0.20 mmol), EDCI (38 mg, 0.20 mmol), and Et₃N (56 µL, 0.40 mmol) were combined in DCM (1 mL) and the mixture was stirred for 6 h. The mixture was diluted with DCM and was washed with 1N HCl, sat. aq. sodium bicarbonate and brine. The organics were dried over sodium sulfate and were evaporated. The crude material was purified by silica gel chromatography eluting with 0-40% ethyl acetate in hexanes to provide (7-chlorospiro[benzo[b]pyrrolo[1,2-d][1,4]oxazine-4,4'-piperidine]-1'-yl)(2-fluoro-5-methoxyphenyl)methanone. ESI-MS m/z calc. 426.1. found 427.5 (M+1)⁺. Retention time: 2.12 minutes (3 min run). NMR (400 MHz, CDCl₃) δ 7.26 (d, J=8.4 Hz, 1H), 7.13-7.07 (m, 2H), 7.05-6.96 (m, 2H), 6.94-6.85 (m, 2H), 6.33 (t, J=3.2 Hz, 1H), 6.08-5.98 (m, 1H), 4.69 (d, J=13.1 Hz, 1H), 3.80 (s, 3H), 3.63-3.44 (m, 2H), 3.33 (t, J=12.8 Hz, 1H), 2.19 (d, J=13.8 Hz, 1H), 2.09-1.96 (m, 2H), 1.60 (s, 1H).

614

(4-(tert-Butylsulfonyl)phenyl)(1-(trifluoromethyl)spiro-[benzo[b]pyrrolo[1,2-d][1,4]oxazine-4,4'-piperidine]-1'-yl)methanone

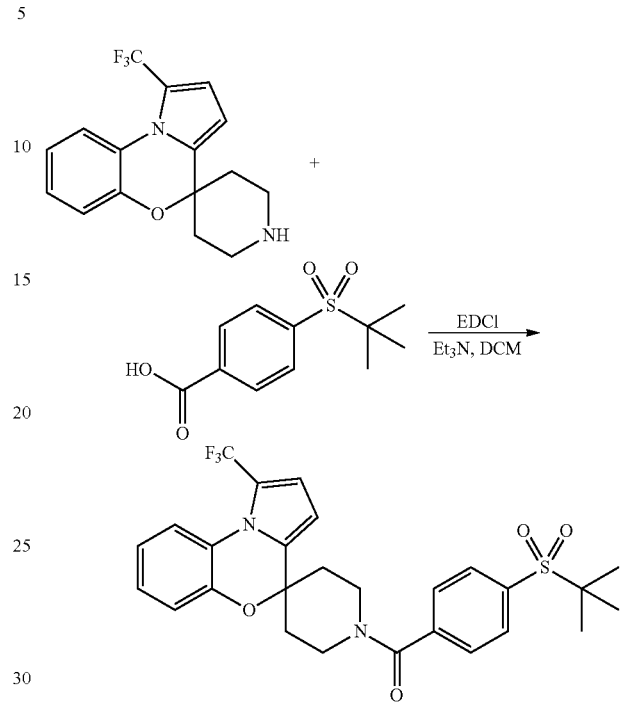

1'-(Trifluoromethyl)spiro[piperidine-4,4'-pyrrolo[2,1-c][1,4]benzoxazine] (172 mg, 0.559 mmol), 4-tert-butylsulfonylbenzoic acid (176 mg, 0.727 mmol), 3-(ethyliminomethyleneamino)-N,N-dimethyl-propan-1-amine hydrochloride (150 mg, 0.783 mmol), and triethylamine (312 µL, 2.24 mmol) were combined in dichloromethane (3.4 mL). The reaction mixture was allowed to stir for 72 hours at room temperature. The reaction mixture was washed three times with a 1M solution of hydrochloric acid, followed by three washes with a saturated aqueous solution of sodium bicarbonate, followed by three washes of a saturated aqueous solution of sodium chloride. The organic layer was dried over sodium sulfate, filtered, and evaporated to dryness to yield the crude product. The crude material was purified by reverse phase preparative chromatography utilizing a gradient of 10-99% acetonitrile in water to yield (4-tert-butylsulfonylphenyl)-[1'-(trifluoromethyl)spiro[piperidine-4,4'-pyrrolo[2,1-c][1,4]benzoxazine]-1-yl]methanone (49 mg, 16%) as a white solid. ESI-MS m/z calc. 532.2. found 533.5 (M+1)⁺. Retention time: 2.10 minutes (3 min run). 1H NMR (400 MHz, DMSO) δ 7.89 (d, J=8.0 Hz, 2H), 7.73 (d, J=8.0 Hz, 2H), 7.57 (d, J=8.0 Hz, 1H), 7.35-7.25 (m, 2H), 7.25-7.16 (m, 1H), 7.03 (d, J=3.9 Hz, 1H), 6.40 (d, J=3.9 Hz, 1H), 4.53-4.37 (m, 1H), 3.57-3.14 (m, 3H), 2.17-1.78 (m, 4H), 1.26 (s, 9H).

The following compound was prepared using procedures reported above:

| Product Name | Amine or Amine•HCl | Carboxylic Acid |
|---|---|---|
| (7-chlorospiro[benzo[b]pyrrolo[1,2-d][1,4]oxazine-4,4'-piperidine]-1'-yl)(4-fluoro-3-methoxyphenyl)methanone | 7-chlorospiro[benzo[b]pyrrolo[1,2-d][1,4]oxazine-4,4'-piperidine] | 4-fluoro-3-methoxybenzoic acid |

| Product Name | Amine or Amine•HCl | Carboxylic Acid |
| --- | --- | --- |
| (4-(ethylsulfonyl)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo][b]pyrrolo[1,2-d][1,4]oxazine-4,4'-piperidine] | 4-(ethylsulfonyl)benzoic acid |
| (4-(isopropylsulfonyl)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 4-(isopropylsulfonyl)benzoic acid |
| 1'-(2-(difluoromethoxy)-3-fluorobenzoyl)spiro[benzo[b]pyrrolo[1,2-d][1,4]oxazine-4,4'-piperidine]-1-carbonitrile | spiro[benzo[b]pyrrolo[1,2-d][1,4]oxazine-4,4'-piperidine]-1-carbonitrile | 2-(difluoromethoxy)-3-fluorobenzoic acid |
| (4-(2-hydroxyethylsulfonyl)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 4-(2-hydroxyethylsulfonyl)benzoic acid |
| (3-methyl-4-(methylsulfonyl)phenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 3-methyl-4-(methylsulfonyl)benzoic acid |
| (3-(hydroxymethyl)-4-isopropoxyphenyl)(1-(trifluoromethyl)spiro[benzo[b]pyrrolo[1,2-d][1,4]oxazine-4,4'-piperidine]-1'-yl)methanone | 1-(trifluoromethyl)spiro[benzo[b]pyrrolo[1,2-d][1,4]oxazine-4,4'-piperidine] | 3-(hydroxymethyl)-4-isopropoxybenzoic acid |
| 1-[3-(hydroxymethyl)-2-methoxy-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 3-(hydroxymethyl)-2-methoxy-benzoic acid |
| 1-(2-ethoxy-3-fluoro-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 2-ethoxy-3-fluoro-benzoic acid |
| 1-(2-fluoro-3-isopropoxy-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 2-fluoro-3-isopropoxy-benzoic acid |
| 1-[4-(trifluoromethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(trifluoromethyl)benzoic acid |
| 7'-fluoro-1-[4-methoxy-3-(trifluoromethyl)benzoyl]spiro[piperidine-4,4'-pyrrolo[2,1-c][1,4]benzoxazine]-1'-carbonitrile | 7'-fluorospiro[piperidine-4,4'-pyrrolo[2,1-c][1,4]benzoxazine]-1'-carbonitrile | 4-methoxy-3-(trifluoromethyl)benzoic acid |
| 1-(4-isopropylsulfonyl-3-methyl-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-isopropylsulfonyl-3-methyl-benzoic acid |
| 1-(4-isopropylsulfonyl-2-methyl-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-isopropylsulfonyl-2-methyl-benzoic acid |
| 1-[4-(1-methylsulfonylethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(1-methylsulfonylethyl)benzoic acid |

-continued

| Product Name | Amine or Amine•HCl | Carboxylic Acid |
| --- | --- | --- |
| 1-[4-(1-hydroxy-1-methyl-ethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(1-hydroxy-1-methyl-ethyl)benzoic acid |
| 1-[4-(difluoromethoxy)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(difluoromethoxy)benzoic acid |
| 1-(3-chloro-4-fluoro-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 3-chloro-4-fluoro-benzoic acid |
| 1-(2-chloro-4-fluoro-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 2-chloro-4-fluoro-benzoic acid |
| (1-cyano-1'-(4-(isopropylsulfonyl)benzoyl)spiro[benzo[b]pyrrolo[1,2-d][1,4]oxazine-4,4'-piperidine]-7-yl)methyl acetate | (1-cyanospiro[benzo[b]pyrrolo[1,2-d][1,4]oxazine-4,4'-piperidine]-7-yl)methyl acetate | 4-isopropylsulfonylbenzoic acid |
| 4-(1'-cyanospiro[piperidine-4,4'-pyrrolo[2,1-c][1,4]benzoxazine]-1-carbonyl)-N-isopropyl-benzenesulfonamide | spiro[piperidine-4,4'-pyrrolo[2,1-c][1,4]benzoxazine]-1'-carbonitrile | 4-(isopropylsulfamoyl)benzoic acid |
| 1-[4-(1-hydroxy-2-methyl-propyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(1-hydroxy-2-methyl-propyl)benzoic acid |
| 1-[4-methylsulfinyl-3-(trifluoromethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-methylsulfinyl-3-(trifluoromethyl)benzoic acid |
| 1-[4-(2-hydroxy-2-methyl-propyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(2-hydroxy-2-methyl-propyl)benzoic acid |
| 1-(4-isopropylsulfonylbenzoyl)-7'-(methoxymethyl)spiro[piperidine-4,4'-pyrrolo[2,1-c][1,4]benzoxazine]-1'-carbonitrile | 7'-(methoxymethyl)spiro[piperidine-4,4'-pyrrolo[2,1-c][1,4]benzoxazine]-1'-carbonitrile | 4-isopropylsulfonylbenzoic acid |
| 1-[4-methylsulfonyl-3-(trifluoromethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-methylsulfonyl-3-(trifluoromethyl)benzoic acid |
| 1-(6-tert-butylpyridine-3-carbonyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 6-tert-butylpyridine-3-carboxylic acid |
| 1-[4-(2-hydroxy-1,1-dimethyl-ethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(2-hydroxy-1,1-dimethyl-ethyl)benzoic acid |
| 1-[3-(hydroxymethyl)-2-methyl-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 3-(hydroxymethyl)-2-methyl-benzoic acid |
| 1-[4-(1-hydroxy-1-methyl-ethyl)-2-methoxy-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(1-hydroxy-1-methyl-ethyl)-2-methoxy-benzoic acid |

-continued

| Product Name | Amine or Amine•HCl | Carboxylic Acid |
|---|---|---|
| 1-[4-(2-hydroxyethoxy)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(2-hydroxyethoxy)benzoic acid |
| 1-[4-[(1R)-1,2-dihydroxy-1-methyl-ethyl]benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(1R)-1,2-dihydroxy-1-methyl-ethyl]benzoic acid |
| 1-[4-[(1S)-1,2-dihydroxy-1-methyl-ethyl]benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(1S)-1,2-dihydroxy-1-methyl-ethyl]benzoic acid |
| 1-[4-(1-hydroxy-1-methyl-ethyl)-2-methyl-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(1-hydroxy-1-methyl-ethyl)-2-methyl-benzoic acid |
| 1-[4-(3-hydroxyoxetan-3-yl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(3-hydroxyoxetan-3-yl)benzoic acid |
| 4-(1'-cyanospiro[piperidine-4,4'-pyrrolo[2,1-c][1,4]benzoxazine]-1-carbonyl)-N-(2-hydroxyethyl)benzenesulfonamide | spiro[piperidine-4,4'-pyrrolo[2,1-c][1,4]benzoxazine]-1'-carbonitrile | 4-(2-hydroxyethylsulfamoyl)benzoic acid |
| 4-(1'-cyanospiro[piperidine-4,4'-pyrrolo[2,1-c][1,4]benzoxazine]-1-carbonyl)-N-(2-hydroxy-1-methyl-ethyl)benzenesulfonamide | spiro[piperidine-4,4'-pyrrolo[2,1-c][1,4]benzoxazine]-1'-carbonitrile | 4-[(2-hydroxy-1-methyl-ethyl)sulfamoyl]benzoic acid |
| N-tert-butyl-4-(1'-cyanospiro[piperidine-4,4'-pyrrolo[2,1-c][1,4]benzoxazine]-1-carbonyl)benzenesulfonamide | spiro[piperidine-4,4'-pyrrolo[2,1-c][1,4]benzoxazine]-1'-carbonitrile | 4-(tert-butylsulfamoyl)benzoic acid |
| methyl 2-(1'-cyanospiro[piperidine-4,4'-pyrrolo[2,1-c][1,4]benzoxazine]-1-carbonyl)-6-methoxy-benzoate | spiro[piperidine-4,4'-pyrrolo[2,1-c][1,4]benzoxazine]-1'-carbonitrile | 3-methoxy-2-methoxycarbonyl-benzoic acid |
| 1-[4-[(1S)-1,2-dihydroxy-1-methyl-ethyl]-3-methyl-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(1S)-1,2-dihydroxy-1-methyl-ethyl]-3-methyl-benzoic acid |
| 1-[4-[(1R)-1,2-dihydroxy-1-methyl-ethyl]-3-methyl-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(1R)-1,2-dihydroxy-1-methyl-ethyl]-3-methyl-benzoic acid |
| 1-[4-[(2S)-2,3-dihydroxypropoxy]-3-methoxy-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(2S)-2,3-dihydroxypropoxy]-3-methoxy-benzoic acid |
| 1-[4-[(2R)-2,3-dihydroxypropoxy]-3-methoxy-benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(2R)-2,3-dihydroxypropoxy]-3-methoxy-benzoic acid |
| 1-[2-(hydroxymethyl)-4-isopropoxy-benzoyl]spiro[piperidine-4,4'- | spiro[piperidine-4,4'-pyrrolo[2,1-c][1,4]benzoxazine]-1'- | 2-(hydroxymethyl)-4-isopropoxy-benzoic acid |

-continued

| Product Name | Amine or Amine•HCl | Carboxylic Acid |
|---|---|---|
| pyrrolo[2,1-c][1,4]benzoxazine]-1'-carbonitrile | carbonitrile | |
| 1-(4-hydroxybenzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-hydroxybenzoic acid |
| 1-(4-hydroxy-3-methyl-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-hydroxy-3-methyl-benzoic acid |
| 2-[4-(1'-cyanospiro[piperidine-4,4'-pyrrolo[2,1-c][1,4]benzoxazine]-1-carbonyl)-2-methyl-phenoxy]acetic acid | spiro[piperidine-4,4'-pyrrolo[2,1-c][1,4]benzoxazine]-1'-carbonitrile | 4-(carboxymethyloxy)-3-methyl-benzoic acid |
| 2-[4-(1'-cyanospiro[piperidine-4,4'-pyrrolo[2,1-c][1,4]benzoxazine]-1-carbonyl)phenoxy]-2-methyl-propanoic acid | spiro[piperidine-4,4'-pyrrolo[2,1-c][1,4]benzoxazine]-1'-carbonitrile | 4-(2-hydroxy-1,1-dimethyl-2-oxo-ethoxy)benzoic acid |
| 1-(4-hydroxy-3-methoxy-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-hydroxy-3-methoxy-benzoic acid |
| 1-[4-(1-amino-1-methyl-ethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(1-amino-1-methyl-ethyl)benzoic acid |
| 1-[4-(azetidin-3-yloxy)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-(azetidin-3-yloxy)benzoic acid |
| 1-(2-methyl-4-methylsulfonyl-benzoyl)spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 2-methyl-4-methylsulfonyl-benzoic acid |
| 1-[4-[(2R)-2,3-dihydroxypropoxy]benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(2R)-2,3-dihydroxypropoxy]benzoic acid |
| 1-[4-[(2S)-2,3-dihydroxypropoxy]benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 4-[(2S)-2,3-dihydroxypropoxy]benzoic acid |
| 4-(1'-cyanospiro[piperidine-4,4'-pyrrolo[2,1-c][1,4]benzoxazine]-1-carbonyl)-N-(3-hydroxypropyl)benzenesulfonamide | spiro[piperidine-4,4'-pyrrolo[2,1-c][1,4]benzoxazine]-1'-carbonitrile | 4-(3-hydroxypropylsulfamoyl)benzoic acid |
| 2-[4-(1'-cyanospiro[piperidine-4,4'-pyrrolo[2,1-c][1,4]benzoxazine]-1-carbonyl)-2-methyl-phenoxy]-2-methyl-propanoic acid | spiro[piperidine-4,4'-pyrrolo[2,1-c][1,4]benzoxazine]-1'-carbonitrile | 4-(2-hydroxy-1,1-dimethyl-2-oxo-ethoxy)-3-methyl-benzoic acid |
| 1-[3-(hydroxymethyl)-4-(1-hydroxy-1-methyl-ethyl)benzoyl]spiro[piperidine-4,4'-pyrrolo[2,1-c][1,4]benzoxazine]-1'-carbonitrile | spiro[piperidine-4,4'-pyrrolo[2,1-c][1,4]benzoxazine]-1'-carbonitrile | 3-(hydroxymethyl)-4-(1-hydroxy-1-methyl-ethyl)benzoic acid |
| [4-methoxy-3-(trifluoromethyl)phenyl]-(1'-methylsulfonylspiro[piperidine-4,4'-pyrrolo[2,1-c][1,4]benzoxazine]-1-yl)methanone | 1'-methylsulfonylspiro[piperidine-4,4'-pyrrolo[2,1-c][1,4]benzoxazine] | 4-methoxy-3-(trifluoromethyl)benzoic acid |
| [4-(1-hydroxy-1-methyl-ethyl)phenyl]-(1'-methylsulfonylspiro[piperidine- | 1'-methylsulfonylspiro[piperidine-4,4'-pyrrolo[2,1- | 4-(1-hydroxy-1-methyl-ethyl)benzoic acid |

-continued

| Product Name | Amine or Amine•HCl | Carboxylic Acid |
|---|---|---|
| 4,4'-pyrrolo[2,1-c][1,4]benzoxazine]-1-yl)methanone | c][1,4]benzoxazine] | |
| [3-(hydroxymethyl)-4-isopropoxy-phenyl]-(1'-methylsulfinylspiro[piperidine-4,4'-pyrrolo[2,1-c][1,4]benzoxazine]-1-yl)methanone | 1'-methylsulfinylspiro[piperidine-4,4'-pyrrolo[2,1-c][1,4]benzoxazine] | 3-(hydroxymethyl)-4-isopropoxy-benzoic acid |
| (4-tert-butoxy-3-methoxy-phenyl)-(1'-methylsulfinylspiro[piperidine-4,4'-pyrrolo[2,1-c][1,4]benzoxazine]-1-yl)methanone | 1'-methylsulfinylspiro[piperidine-4,4'-pyrrolo[2,1-c][1,4]benzoxazine] | 4-tert-butoxy-3-methoxy-benzoic acid |
| (4-tert-butylsulfonylphenyl)-(1'-methylsulfonylspiro[piperidine-4,4'-pyrrolo[2,1-c][1,4]benzoxazine]-1-yl)methanone | 1'-methylsulfonylspiro[piperidine-4,4'-pyrrolo[2,1-c][1,4]benzoxazine] | 4-tert-butylsulfonylbenzoic acid |
| [3-(hydroxymethyl)-4-isopropoxy-phenyl]-(1'-methylsulfonylspiro[piperidine-4,4'-pyrrolo[2,1-c][1,4]benzoxazine]-1-yl)methanone | 1'-methylsulfonylspiro[piperidine-4,4'-pyrrolo[2,1-c][1,4]benzoxazine] | 3-(hydroxymethyl)-4-isopropoxy-benzoic acid |
| 2-[2-methoxy-4-[1'-(trifluoromethyl)spiro[piperidine-4,4'-pyrrolo[2,1-c][1,4]benzoxazine]-1-carbonyl]phenoxy]acetamide | 1'-(trifluoromethyl)spiro[piperidine-4,4'-pyrrolo[2,1-c][1,4]benzoxazine] | 4-(2-amino-2-oxo-ethoxy)-3-methoxy-benzoic acid |
| [4-(1-hydroxy-1-methyl-ethyl)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-(1-hydroxy-1-methyl-ethyl)benzoic acid |
| (4-cyclopropylsulfonylphenyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-cyclopropylsulfonylbenzoic acid |
| [4-(2-hydroxy-2-methyl-propyl)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-(2-hydroxy-2-methyl-propyl)benzoic acid |
| [4-(1-hydroxy-2-methyl-propyl)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-(1-hydroxy-2-methyl-propyl)benzoic acid |
| (4-tetrahydrofuran-3-ylsulfonylphenyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-tetrahydrofuran-3-ylsulfonylbenzoic acid |
| [4-(3-hydroxyoxetan-3-yl)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-(3-hydroxyoxetan-3-yl)benzoic acid |
| [4-(2-hydroxyethoxy)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-(2-hydroxyethoxy)benzoic acid |
| [3-(hydroxymethyl)-2-methoxy-phenyl]-[1'-(trifluoromethyl)spiro[piperidine- | 1'-(trifluoromethyl)spiro[piperidine-4,4'-pyrrolo[2,1- | 3-(hydroxymethyl)-2-methoxy-benzoic acid |

-continued

| Product Name | Amine or Amine•HCl | Carboxylic Acid |
|---|---|---|
| 4,4'-pyrrolo[2,1-c][1,4]benzoxazine]-1-yl]methanone | c][1,4']benzoxazine] | |
| [6-(1-hydroxy-1-methyl-ethyl)-3-pyridyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 6-(1-hydroxy-1-methyl-ethyl)pyridine-3-carboxylic acid |
| [4-[cyclopropyl(hydroxy)methyl]phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-[cyclopropyl(hydroxy)methyl]benzoic acid |
| [3-(hydroxymethyl)-4-(1-hydroxy-1-methyl-ethyl)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 3-(hydroxymethyl)-4-(1-hydroxy-1-methyl-ethyl)benzoic acid |
| [4-[(1S)-1,2-dihydroxy-1-methyl-ethyl]phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-[(1S)-1,2-dihydroxy-1-methyl-ethyl]benzoic acid |
| [4-[(1R)-1,2-dihydroxy-1-methyl-ethyl]phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-[(1R)-1,2-dihydroxy-1-methyl-ethyl]benzoic acid |
| [4-[(3S)-tetrahydrofuran-3-yl]sulfonylphenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-[(3S)-tetrahydrofuran-3-yl]sulfonylbenzoic acid |
| [4-[(3R)-tetrahydrofuran-3-yl]sulfonylphenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-[(3R)-tetrahydrofuran-3-yl]sulfonylbenzoic acid |
| N,2-dimethyl-4-[1'-(trifluoromethyl)spiro[piperidine-4,4'-pyrrolo[2,1-c][1,4]benzoxazine]-1-carbonyl]benzenesulfonamide | 1'-(trifluoromethyl)spiro[piperidine-4,4'-pyrrolo[2,1-c][1,4]benzoxazine] | 3-methyl-4-(methylsulfamoyl)benzoic acid |
| 2-methyl-2-[4-[1'-(trifluoromethyl)spiro[piperidine-4,4'-pyrrolo[2,1-c][1,4]benzoxazine]-1-carbonyl]phenyl]sulfonyl-propanoic acid | 1'-(trifluoromethyl)spiro[piperidine-4,4'-pyrrolo[2,1-c][1,4]benzoxazine] | 4-(2-hydroxy-1,1-dimethyl-2-oxo-ethyl)sulfonylbenzoic acid |
| [4-(2-hydroxy-1,1-dimethyl-ethyl)sulfonylphenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4-(2-hydroxy-1,1-dimethyl-ethyl)sulfonylbenzoic acid |
| N,N,2-trimethyl-4-[1'-(trifluoromethyl)spiro[piperidine-4,4'-pyrrolo[2,1-c][1,4]benzoxazine]-1-carbonyl]benzenesulfonamide | 1'-(trifluoromethyl)spiro[piperidine-4,4'-pyrrolo[2,1-c][1,4]benzoxazine] | 4-(dimethylsulfamoyl)-3-methyl-benzoic acid |
| (5-isopropoxy-6-methyl-2-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 5-isopropoxy-6-methyl-pyridine-2-carboxylic acid |
| (4-hydroxy-3-methyl-phenyl)-[1'-(trifluoromethyl)spiro[piperidine- | 1'-(trifluoromethyl)spiro[piperidine-4,4'-pyrrolo[2,1- | 4-hydroxy-3-methyl-benzoic acid |

| Product Name | Amine or Amine•HCl | Carboxylic Acid |
|---|---|---|
| 4,4'-pyrrolo[2,1-c][1,4]benzoxazine]-1-yl]methanone | c][1,4]benzoxazine] | |
| [2-(difluoromethoxy)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-(difluoromethoxy)benzoic acid |
| [3-fluoro-4-(1-hydroxy-1-methyl-ethyl)phenyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 3-fluoro-4-(1-hydroxy-1-methyl-ethyl)benzoic acid |
| (5-methoxy-2-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 5-methoxypyridine-2-carboxylic acid |
| (5-methyl-2-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 5-methylpyridine-2-carboxylic acid |
| (5-ethyl-2-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 5-ethylpyridine-2-carboxylic acid |
| (5-isopropoxy-2-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 5-isopropoxypyridine-2-carboxylic acid |
| (2-ethoxy-3-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-ethoxypyridine-3-carboxylic acid |
| (2-pyrrolidin-1-yl-3-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-pyrrolidin-1-ylpyridine-3-carboxylic acid |
| [2-(4-fluorophenoxy)-3-pyridyl]-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-(4-fluorophenoxy)pyridine-3-carboxylic acid |
| (2-phenoxy-3-pyridyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 2-phenoxypyridine-3-carboxylic acid |
| (3-tert-butylsulfonyl-2-thienyl)-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 3-tert-butylsulfonylthiophene-2-carboxylic acid |
| 4H-furo[3,2-b]pyrrol-5-yl-[1'-(trifluoromethyl)spiro[piperidine-4,4'-pyrrolo[2,1-c][1,4]benzoxazine]-1-yl]methanone | 1'-(trifluoromethyl)spiro[piperidine-4,4'-pyrrolo[2,1-c][1,4]benzoxazine] | 4H-furo[3,2-b]pyrrole-5-carboxylic acid |
| [3-(hydroxymethyl)-2-methoxy-phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 3-(hydroxymethyl)-2-methoxy-benzoic acid |
| N-cyclopropyl-4-(1-methylspiro[chromeno[4,3-c]pyrazole-4,4'-piperidine]-1'-carbonyl)benzenesulfonamide | 1-methylspiro[chromeno[4,3-c]pyrazole-4,4'-piperidine] | 4-(cyclopropylsulfamoyl)benzoic acid |

| Product Name | Amine or Amine•HCl | Carboxylic Acid |
| --- | --- | --- |
| [4-(1-hydroxy-2-methyl-propyl)phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(1-hydroxy-2-methyl-propyl)benzoic acid |
| [4-(1-hydroxy-1-methyl-ethyl)phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(1-hydroxy-1-methyl-ethyl)benzoic acid |
| [4-(2-hydroxy-2-methyl-propyl)phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(2-hydroxy-2-methyl-propyl)benzoic acid |
| [2-(difluoromethoxy)phenyl]-[1-(trifluoromethyl)spiro[chromeno[4,3-c]pyrazole-4,4'-piperidine]-1'-yl]methanone | 1-(trifluoromethyl)spiro[chromeno[4,3-c]pyrazole-4,4'-piperidine] | 2-(difluoromethoxy)benzoic acid |
| 2-[2-methoxy-4-(1-methylspiro[chromeno[4,3-c]pyrazole-4,4'-piperidine]-1'-carbonyl)phenoxy]acetamide | ammonia; 1-methylspiro[chromeno[4,3-c]pyrazole-4,4'-piperidine] | 4-(2-amino-2-oxo-ethoxy)-3-methoxy-benzoic acid |
| [4-(2-hydroxyethoxy)phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(2-hydroxyethoxy)benzoic acid |
| [4-(1-hydroxy-1-methyl-ethyl)-2-methoxy-phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(1-hydroxy-1-methyl-ethyl)-2-methoxy-benzoic acid |
| [3-(hydroxymethyl)-2-methyl-phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 3-(hydroxymethyl)-2-methyl-benzoic acid |
| [4-(3-hydroxyoxetan-3-yl)phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(3-hydroxyoxetan-3-yl)benzoic acid |
| [4-(1-hydroxy-1-methyl-ethyl)-2-methyl-phenyl]-(1-methylspiro[chromeno[4,3-c]pyrazole-4,4'-piperidine]-1'-yl)methanone | 1-methylspiro[chromeno[4,3-c]pyrazole-4,4'-piperidine] | 4-(1-hydroxy-1-methyl-ethyl)-2-methyl-benzoic acid |
| (5-isopropoxy-6-methyl-2-pyridyl)-(1-methylspiro[chromeno[4,3-c]pyrazole-4,4'-piperidine]-1'-yl)methanone | 1-methylspiro[chromeno[4,3-c]pyrazole-4,4'-piperidine] | 5-isopropoxy-6-methyl-pyridine-2-carboxylic acid |
| [2-(difluoromethoxy)phenyl]-[2-(trifluoromethyl)spiro[chromeno[4,3-c]pyrazole-4,4'-piperidine]-1'-yl]methanone | 2-(trifluoromethyl)spiro[chromeno[4,3-c]pyrazole-4,4'-piperidine] | 2-(difluoromethoxy)benzoic acid |
| (4-isopropoxy-3-methoxy-phenyl)-(2-methylspiro[chromeno[4,3-c]pyrazole-4,4'-piperidine]-1'-yl)methanone | 2-methylspiro[chromeno[4,3-c]pyrazole-4,4'-piperidine] | 4-isopropoxy-3-methoxy-benzoic acid |
| (4-tert-butylsulfonylphenyl)-[2-(trifluoromethyl)spiro[chromeno[4,3-c]pyrazole-4,4'-piperidine]-1'-yl]methanone | 2-(trifluoromethyl)spiro[chromeno[4,3-c]pyrazole-4,4'-piperidine] | 4-tert-butylsulfonylbenzoic acid |
| [2-(difluoromethoxy)phenyl]-(2-methylspiro[chromeno[4,3-c]pyrazole-4,4'-piperidine]-1'-yl)methanone | 2-methylspiro[chromeno[4,3-c]pyrazole-4,4'-piperidine] | 2-(difluoromethoxy)benzoic acid |
| N-isopropyl-4-(2-methylspiro[chromeno[4,3-c]pyrazole-4,4'-piperidine]-1'-carbonyl)benzenesulfonamide | 2-methylspiro[chromeno[4,3-c]pyrazole-4,4'-piperidine] | 4-(isopropylsulfamoyl)benzoic acid |
| [4-(1-hydroxy-2-methyl-propyl)phenyl]-(2- | 2-methylspiro[chromeno[4,3- | 4-(1-hydroxy-2-methyl-propyl)benzoic acid |

| Product Name | Amine or Amine•HCl | Carboxylic Acid |
|---|---|---|
| methylspiro[chromeno[4,3-c]pyrazole-4,4'-piperidine]-1'-yl)methanone | c]pyrazole-4,4'-piperidine] | |
| [4-(1-hydroxy-1-methyl-ethyl)phenyl]-(2-methylspiro[chromeno[4,3-c]pyrazole-4,4'-piperidine]-1'-yl)methanone | 2-methylspiro[chromeno[4,3-c]pyrazole-4,4'-piperidine] | 4-(1-hydroxy-1-methyl-ethyl)benzoic acid |
| [3-(hydroxymethyl)-4-isopropoxy-phenyl]-(2-methylspiro[chromeno[4,3-c]pyrazole-4,4'-piperidine]-1'-yl)methanone | 2-methylspiro[chromeno[4,3-c]pyrazole-4,4'-piperidine] | 3-(hydroxymethyl)-4-isopropoxy-benzoic acid |
| (4-isopropoxy-3-methyl-phenyl)-(2-methylspiro[chromeno[4,3-c]pyrazole-4,4'-piperidine]-1'-yl)methanone | 2-methylspiro[chromeno[4,3-c]pyrazole-4,4'-piperidine] | 4-isopropoxy-3-methyl-benzoic acid |
| (2-fluoro-4-isopropoxy-phenyl)-(2-methylspiro[chromeno[4,3-c]pyrazole-4,4'-piperidine]-1'-yl)methanone | 2-methylspiro[chromeno[4,3-c]pyrazole-4,4'-piperidine] | 2-fluoro-4-isopropoxy-benzoic acid |
| [4-(2-hydroxy-2-methyl-propyl)phenyl]-(2-methylspiro[chromeno[4,3-c]pyrazole-4,4'-piperidine]-1'-yl)methanone | 2-methylspiro[chromeno[4,3-c]pyrazole-4,4'-piperidine] | 4-(2-hydroxy-2-methyl-propyl)benzoic acid |
| N-cyclopropyl-4-(2-methylspiro[chromeno[4,3-c]pyrazole-4,4'-piperidine]-1'-carbonyl)benzenesulfonamide | 2-methylspiro[chromeno[4,3-c]pyrazole-4,4'-piperidine] | 4-(cyclopropylsulfamoyl)benzoic acid |
| N-tert-butyl-4-(2-methylspiro[chromeno[4,3-c]pyrazole-4,4'-piperidine]-1'-carbonyl)benzenesulfonamide | 2-methylspiro[chromeno[4,3-c]pyrazole-4,4'-piperidine] | 4-(tert-butylsulfamoyl)benzoic acid |
| (8-fluoro-2-methyl-spiro[chromeno[4,3-c]pyrazole-4,4'-piperidine]-1'-yl)-[2-(trifluoromethoxy)phenyl]methanone | 8-fluoro-2-methyl-spiro[chromeno[4,3-c]pyrazole-4,4'-piperidine] | 2-(trifluoromethoxy)benzoic acid |
| 4-(8-fluoro-2-methyl-spiro[chromeno[4,3-c]pyrazole-4,4'-piperidine]-1'-carbonyl)-N-isopropyl-benzenesulfonamide | 8-fluoro-2-methyl-spiro[chromeno[4,3-c]pyrazole-4,4'-piperidine] | 4-(isopropylsulfamoyl)benzoic acid |
| (8-fluoro-2-methyl-spiro[chromeno[4,3-c]pyrazole-4,4'-piperidine]-1'-yl)-(4-isopropoxy-3-methoxy-phenyl)methanone | 8-fluoro-2-methyl-spiro[chromeno[4,3-c]pyrazole-4,4'-piperidine] | 4-isopropoxy-3-methoxy-benzoic acid |
| (8-fluoro-2-methyl-spiro[chromeno[4,3-c]pyrazole-4,4'-piperidine]-1'-yl)-[3-(hydroxymethyl)-4-isopropoxy-phenyl]methanone | 8-fluoro-2-methyl-spiro[chromeno[4,3-c]pyrazole-4,4'-piperidine] | 3-(hydroxymethyl)-4-isopropoxy-benzoic acid |
| (8-fluoro-2-methyl-spiro[chromeno[4,3-c]pyrazole-4,4'-piperidine]-1'-yl)-[4-(1-hydroxy-1-methyl-ethyl)phenyl]methanone | 8-fluoro-2-methyl-spiro[chromeno[4,3-c]pyrazole-4,4'-piperidine] | 4-(1-hydroxy-1-methyl-ethyl)benzoic acid |
| (8-fluoro-2-methyl-spiro[chromeno[4,3-c]pyrazole-4,4'-piperidine]-1'-yl)-[4-(1-hydroxy-1-methyl-ethyl)-2-methyl-phenyl]methanone | 8-fluoro-2-methyl-spiro[chromeno[4,3-c]pyrazole-4,4'-piperidine] | 4-(1-hydroxy-1-methyl-ethyl)-2-methyl-benzoic acid |
| (8-fluoro-2-methyl-spiro[chromeno[4,3-c]pyrazole-4,4'-piperidine]-1'-yl)-(4-isopropoxyphenyl)methanone | 8-fluoro-2-methyl-spiro[chromeno[4,3-c]pyrazole-4,4'-piperidine] | 4-isopropoxybenzoic acid |
| [3-(hydroxymethyl)-4-(1-hydroxy-1-methyl-ethyl)phenyl]-(2-methylspiro[chromeno[4,3-c]pyrazole-4,4'-piperidine]-1'-yl)methanone | 2-methylspiro[chromeno[4,3-c]pyrazole-4,4'-piperidine] | 3-(hydroxymethyl)-4-(1-hydroxy-1-methyl-ethyl)benzoic acid |

-continued

| Product Name | Amine or Amine•HCl | Carboxylic Acid |
|---|---|---|
| N,2-dimethyl-4-(2-methylspiro[chromeno[4,3-c]pyrazole-4,4'-piperidine]-1'-carbonyl)benzenesulfonamide | 2-methylspiro[chromeno[4,3-c]pyrazole-4,4'-piperidine] | 3-methyl-4-(methylsulfamoyl)benzoic acid |
| (4-tert-butoxy-3-methoxy-phenyl)-(2-methylspiro[chromeno[4,3-c]pyrazole-4,4'-piperidine]-1'-yl)methanone | 2-methylspiro[chromeno[4,3-c]pyrazole-4,4'-piperidine] | 4-tert-butoxy-3-methoxy-benzoic acid |
| (4-isopropoxy-2-methyl-phenyl)-(2-methylspiro[chromeno[4,3-c]pyrazole-4,4'-piperidine]-1'-yl)methanone | 2-methylspiro[chromeno[4,3-c]pyrazole-4,4'-piperidine] | 4-isopropoxy-2-methyl-benzoic acid |
| (2-methylspiro[chromeno[4,3-c]pyrazole-4,4'-piperidine]-1'-yl)-(8-quinolyl)methanone | 2-methylspiro[chromeno[4,3-c]pyrazole-4,4'-piperidine] | quinoline-8-carboxylic acid |
| (6-isopropoxy-3-pyridyl)-(2-methylspiro[chromeno[4,3-c]pyrazole-4,4'-piperidine]-1'-yl)methanone | 2-methylspiro[chromeno[4,3-c]pyrazole-4,4'-piperidine] | 6-isopropoxypyridine-3-carboxylic acid |
| (2-methylspiro[chromeno[4,3-c]pyrazole-4,4'-piperidine]-1'-yl)-(4-quinolyl)methanone | 2-methylspiro[chromeno[4,3-c]pyrazole-4,4'-piperidine] | quinoline-4-carboxylic acid |
| [2-(difluoromethoxy)-3-fluoro-phenyl]-(2-methylspiro[chromeno[4,3-c]pyrazole-4,4'-piperidine]-1'-yl)methanone | 2-methylspiro[chromeno[4,3-c]pyrazole-4,4'-piperidine] | 2-(difluoromethoxy)-3-fluoro-benzoic acid |
| (3-ethoxy-4-methoxy-phenyl)-(2-methylspiro[chromeno[4,3-c]pyrazole-4,4'-piperidine]-1'-yl)methanone | 2-methylspiro[chromeno[4,3-c]pyrazole-4,4'-piperidine] | 3-ethoxy-4-methoxy-benzoic acid |
| (5-isopropoxy-6-methyl-2-pyridyl)-(2-methylspiro[chromeno[4,3-c]pyrazole-4,4'-piperidine]-1'-yl)methanone | 2-methylspiro[chromeno[4,3-c]pyrazole-4,4'-piperidine] | 5-isopropoxy-6-methyl-pyridine-2-carboxylic acid |

(1-Methyl-1H-spiro[chromeno[4,3-c]pyrazole-4,4'-piperidine]-1'-yl)(m-tolyl)methanone

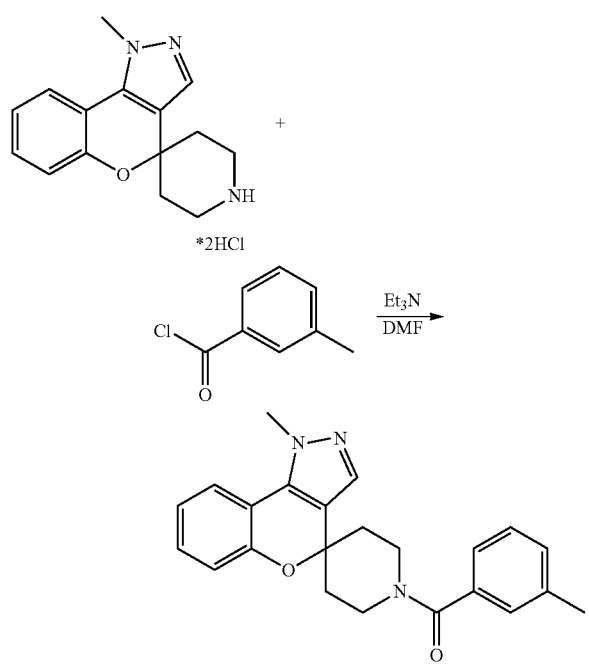

3-Methylbenzoyl chloride (14 mg, 0.09 mmol) was added to a mixture of 1-methyl-1H-spiro[chromeno[4,3-c]pyrazole-4,4'-piperidine]dihydrochloride (30 mg, 0.09 mmol), triethylamine (64 µL, 0.46 mmol), and DMF (0.7 mL) at 25° C. The mixture was allowed to stir at 50° C. overnight before it was cooled to 25° C. The mixture was filtered and then purified by reverse phase-HPLC to give (1-methyl-1H-spiro[chromeno[4,3-c]pyrazole-4,4'-piperidine]-1'-yl)(m-tolyl)methanone. ESI-MS m/z calc. 373.2. found 374.2 $(M+1)^+$. Retention time: 2.04 minutes (4 min run).

The following compound was prepared using procedures reported above:

| Product Name | Amine or Amine•HCl | Acid Chloride |
|---|---|---|
| (7-chloro-1-methyl-1H-spiro[chromeno[4,3-c]pyrazole-4,4'-piperidine]-1'-yl)(2-(trifluoromethoxy)phenyl)methanone | 7-chloro-1-methyl-1H-spiro[chromeno[4,3-c]pyrazole-4,4'-piperidine] | 2-(trifluoromethoxy)benzoyl chloride |
| (8-chloro-1-methyl-1H-spiro[chromeno[4,3-c]pyrazole-4,4'-piperidine]-1'-yl)(2-(trifluoromethoxy)phenyl)methanone | 8-chloro-1-methyl-1H-spiro[chromeno[4,3-c]pyrazole-4,4'-piperidine] | 2-(trifluoromethoxy)benzoyl chloride |

(3-Fluoro-4-hydroxy-phenyl)-(1-methyl-1H-spiro [chromeno[4,3-c]pyrazole-4,4'-piperidine]-1'-yl) methanone

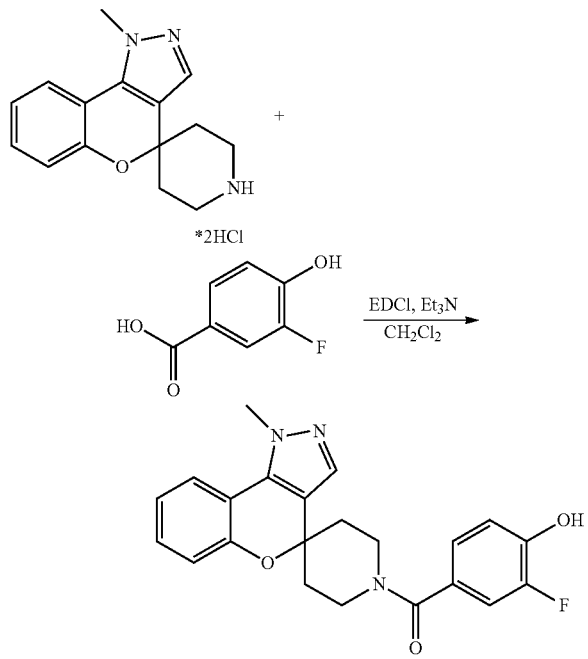

A mixture of 1-methylspiro[chromeno[4,3-c]pyrazole-4,4'-piperidine]bis hydrochloric acid (507 mg, 1.7 mmol), 3-fluoro-4-hydroxy-benzoic acid (271 mg, 1.7 mmol), triethylamine (727 µL, 5.2 mmol), and EDCI (333 mg, 1.7 mmol) in dichloromethane (10 mL) were stirred at room temperature for 16 hours. The reaction was diluted with dichloromethane and washed with 1N HCl, saturated sodium bicarbonate solution, and brine. The organics were dried over sodium sulfate and evaporated. The crude material was purified by column chromatography eluting with 0-10% methanol in dichloromethane to yield (3-fluoro-4-hydroxy-phenyl)-(1-methyl-1H-spiro[chromeno[4,3-c]pyrazole-4,4'-piperidine]-1'-yl)methanone (330 mg, 48%). ESI-MS m/z calc 393.4. found 394.3 (M+1)+. Retention time: 1.39 minutes (3 min run). $^1$H NMR (400 MHz, DMSO) δ 10.41 (s, 1H), 7.73 (d, J=7.7 Hz, 1H), 7.46 (s, 1H), 7.32-7.23 (m, 2H), 7.15-7.04 (m, 3H), 6.98 (t, J=8.5 Hz, 1H), 4.10 (s, 3H), 3.52-3.19 (m, 4H), 1.99-1.85 (m, 4H).

The following compounds were prepared using the procedure reported above:

| Product Name | Amine or Amine•HCl | Carboxylic Acid |
| --- | --- | --- |
| 2-isopropoxy-5-(1-methyl-1H-spiro[chromeno[4,3-c]pyrazole-4,4'-piperidine]-1'-ylcarbonyl)benzonitrile | 1-methylspiro[chromeno[4,3-c]pyrazole-4,4'-piperidine]dihydrochloride | 3-cyano-4-isopropoxy-benzoic acid |
| 5-(1-methyl-1H-spiro[chromeno[4,3-c]pyrazole-4,4'-piperidine]-1'-ylcarbonyl)-2-(2-(trifluoromethoxy)ethoxy)benzonitrile | 1-methylspiro[chromeno[4,3-c]pyrazole-4,4'-piperidine]dihydrochloride | 3-cyano-4-[2-(trifluoromethoxy)ethoxy]benzoic acid |
| [3-methyl-4-[2-(trifluoromethoxy)ethoxy]phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methyl-4-[2-(trifluoromethoxy)ethoxy]benzoic acid |
| [3-methoxy-4-[2-(trifluoromethoxy)ethoxy]phenyl]-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methoxy-4-[2-(trifluoromethoxy)ethoxy]benzoic acid |
| (1-methylindazol-7-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-methylindazole-7-carboxylic acid |
| (1-methylindazol-4-yl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 1-methylindazole-4-carboxylic acid |
| (1-methyl-1H-spiro[chromeno[4,3-c]pyrazole-4,4'-piperidine]-1'-yl)quinoxalin-5-yl-methanone | 1-methylspiro[chromeno[4,3-c]pyrazole-4,4'-piperidine]dihydrochloride | quinoxaline-5-carboxylic acid |
| (4-hydroxy-3-methoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-hydroxy-3-methoxy-benzoic acid |

| Product Name | Amine or Amine•HCl | Carboxylic Acid |
|---|---|---|
| (3-methoxy-4-tert-butoxy-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 3-methoxy-4-tert-butoxy-benzoic acid |
| (2,4-diethoxy-3-methyl-phenyl)-(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,4-diethoxy-3-methyl-benzoic acid |
| (4-(difluoromethoxy)-3-methoxyphenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-(difluoromethoxy)-3-methoxybenzoic acid |
| 1-isopropyl-4-(1-methyl-1H-spiro[chromeno[4,3-c]pyrazole-4,4'-piperidine]-1'-ylcarbonyl)pyridin-2(1H)-one | 1-methylspiro[chromeno[4,3-c]pyrazole-4,4'-piperidine]dihydrochloride | 1-isopropyl-2-oxo-1,2-dihydropyridine-4-carboxylic acid |
| (4-fluoro-3-methylphenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-fluoro-3-methylbenzoic acid |
| (1-ethyl-1H-spiro[chromeno[4,3-c]pyrazole-4,4'-piperidine]-1'-yl)(4-(isopropylsulfonyl)phenyl)methanone | 1-ethyl-1H-spiro[chromeno[4,3-c]pyrazole-4,4'-piperidine] | 4-(isopropylsulfonyl)benzoic acid |
| N-isopropyl-N-methyl-4-(1-methyl-1H-spiro[chromeno[4,3-c]pyrazole-4,4'-piperidine]-1'-ylcarbonyl)benzenesulfonamide | 1-methylspiro[chromeno[4,3-c]pyrazole-4,4'-piperidine]dihydrochloride | 4-(N-isopropyl-N-methylsulfamoyl)benzoic acid |
| (4-(isopropylsulfinyl)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-(isopropylsulfinyl)benzoic acid |
| (8-chloro-1-methyl-1H-spiro[chromeno[4,3-c]pyrazole-4,4'-piperidine]-1'-yl)(2-(difluoromethoxy)phenyl)methanone | 8-chloro-1-methyl-1H-spiro[chromeno[4,3-c]pyrazole-4,4'-piperidine] | 2-(difluoromethoxy)benzoic acid |
| (7-chloro-1-methyl-1H-spiro[chromeno[4,3-c]pyrazole-4,4'-piperidine]-1'-yl)(2-(difluoromethoxy)phenyl)methanone | 7-chloro-1-methyl-1H-spiro[chromeno[4,3-c]pyrazole-4,4'-piperidine] | 2-(difluoromethoxy)benzoic acid |
| (4-tert-butoxyphenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-tert-butoxybenzoic acid |
| (2,4-bis(difluoromethoxy)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 2,4-bis(difluoromethoxy)benzoic acid |
| (4-(ethylsulfonyl)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-(ethylsulfonyl)benzoic acid |
| (4-(tert-butylsulfonyl)phenyl)(1-methyl-1H-spiro[chromeno[4,3-c]pyrazole-4,4'-piperidine]-1'-yl)methanone | 1-methylspiro[chromeno[4,3-c]pyrazole-4,4'-piperidine]dihydrochloride | 4-(tert-butylsulfonyl)benzoic acid |
| (1-methyl-1H-spiro[chromeno[4,3-c]pyrazole-4,4'-piperidine]-1'-yl)(2-(2,2,2-trifluoroethoxy)phenyl)methanone | 1-methylspiro[chromeno[4,3-c]pyrazole-4,4'-piperidine]dihydrochloride | 2-(2,2,2-trifluoroethoxy)benzoic acid |

| Product Name | Amine or Amine•HCl | Carboxylic Acid |
| --- | --- | --- |
| (1-ethyl-1H-spiro[chromeno[4,3-c]pyrazole-4,4'-piperidine]-1'-yl)(3-fluoro-2-methoxyphenyl)methanone | 1-ethyl-1H-spiro[chromeno[4,3-c]pyrazole-4,4'-piperidine] | 3-fluoro-2-methoxybenzoic acid |
| (2-(difluoromethoxy)phenyl)(1-ethyl-1H-spiro[chromeno[4,3-c]pyrazole-4,4'-piperidine]-1'-yl)methanone | 1-ethyl-1H-spiro[chromeno[4,3-c]pyrazole-4,4'-piperidine] | 2-(difluoromethoxy)benzoic acid |
| (1-ethyl-1H-spiro[chromeno[4,3-c]pyrazole-4,4'-piperidine]-1'-yl)(2-(trifluoromethoxy)phenyl)methanone | 1-ethyl-1H-spiro[chromeno[4,3-c]pyrazole-4,4'-piperidine] | 2-(trifluoromethoxy)benzoic acid |
| (2-(difluoromethoxy)-3-fluorophenyl)(1-ethyl-1H-spiro[chromeno[4,3-c]pyrazole-4,4'-piperidine]-1'-yl)methanone | 1-ethyl-1H-spiro[chromeno[4,3-c]pyrazole-4,4'-piperidine] | 2-(difluoromethoxy)-3-fluorobenzoic acid |
| methyl 2-(1-ethyl-1H-spiro[chromeno[4,3-c]pyrazole-4,4'-piperidine]-1'-ylcarbonyl)benzoate | 1-methylspiro[chromeno[4,3-c]pyrazole-4,4'-piperidine]dihydrochloride | 2-(methoxycarbonyl)benzoic acid |
| (7-fluoro-1-methyl-1H-spiro[chromeno[4,3-c]pyrazole-4,4'-piperidine]-1'-yl)(2-(trifluoromethoxy)phenyl)methanone | 7-fluoro-1-methyl-1H-spiro[chromeno[4,3-c]pyrazole-4,4'-piperidine] | 2-(trifluoromethoxy)benzoic acid |
| (2-(difluoromethoxy)phenyl)(7-fluoro-1-methyl-1H-spiro[chromeno[4,3-c]pyrazole-4,4'-piperidine]-1'-yl)methanone | 7-fluoro-1-methyl-1H-spiro[chromeno[4,3-c]pyrazole-4,4'-piperidine] | 2-(difluoromethoxy)benzoic acid |
| (7-fluoro-1-methyl-1H-spiro[chromeno[4,3-c]pyrazole-4,4'-piperidine]-1'-yl)(4-(isopropylsulfonyl)phenyl)methanone | 7-fluoro-1-methyl-1H-spiro[chromeno[4,3-c]pyrazole-4,4'-piperidine] | 4-(isopropylsulfonyl)benzoic acid |
| (7-fluoro-1-methyl-1H-spiro[chromeno[4,3-c]pyrazole-4,4'-piperidine]-1'-yl)(4-isopropoxy-3-methoxyphenyl)methanone | 7-fluoro-1-methyl-1H-spiro[chromeno[4,3-c]pyrazole-4,4'-piperidine] | 4-isopropoxy-3-methoxybenzoic acid |
| (7-fluoro-1-methyl-1H-spiro[chromeno[4,3-c]pyrazole-4,4'-piperidine]-1'-yl)(2-methoxyphenyl)methanone | 7-fluoro-1-methyl-1H-spiro[chromeno[4,3-c]pyrazole-4,4'-piperidine] | 2-methoxybenzoic acid |
| methyl 4-(7-fluoro-1-methyl-1H-spiro[chromeno[4,3-c]pyrazole-4,4'-piperidine]-1'-ylcarbonyl)benzoate | 1-methylspiro[chromeno[4,3-c]pyrazole-4,4'-piperidine]dihydrochloride | 4-(methoxycarbonyl)benzoic acid |

(4-Propoxy-3-(trifluoromethyl)phenyl)(spiro[benzo[b]pyrrolo[1,2-d][1,4]oxazine-4,4'-piperidine]-1'-yl)methanone Step 1: (4-Fluoro-3-(trifluoromethyl)phenyl)(spiro[benzo[b]pyrrolo[1,2-d][1,4]oxazine-4,4'-piperidine]-1'-yl)methanone

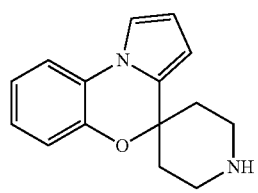

+

-continued

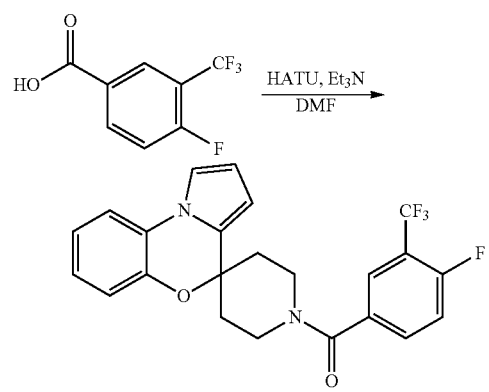

Spiro[piperidine-4,4'-pyrrolo[2,1-c][1,4]benzoxazine] (100 mg, 0.361 mmol), 4-fluoro-3-(trifluoromethyl)benzoic acid (75.2 mg, 0.361 mmol), and triethylamine (110 mg, 151 µL, 1.08 mmol) were combined in DMF (3 mL) and HATU (137 mg, 0.361 mmol) was added. The reaction was stirred at room temperature for 1 h and was concentrated. The residue was purified by column chromatography (silica gel: 0-50% ethyl acetate in hexanes) to give (4-fluoro-3-(trifluoromethyl)phenyl)(spiro[benzo[b]pyrrolo[1,2-d][1,4]oxazine-4,4'-piperidine]-1'-yl)methanone (113 mg, 73%). ESI-MS m/z calc. 430.1. found 431.1 (M+1)$^+$; Retention time: 2.24 minutes (4 min run).

Step 2: (4-Propoxy-3-(trifluoromethyl)phenyl)(spiro[benzo[b]pyrrolo[1,2-d][1,4]oxazine-4,4'-piperidine]-1'-yl)methanone

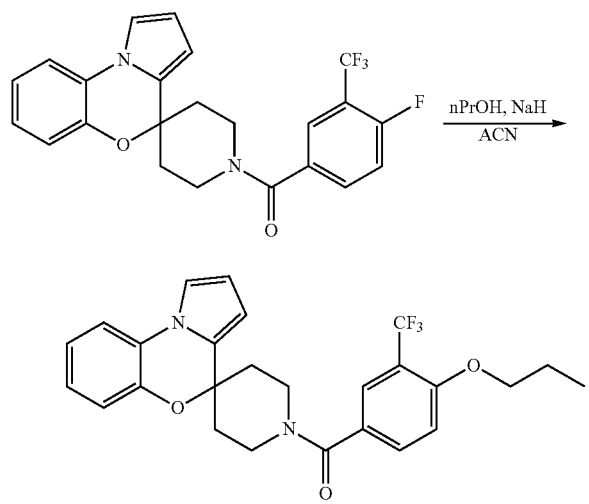

(4-Fluoro-3-(trifluoromethyl)phenyl)(spiro[benzo[b]pyrrolo[1,2-d][1,4]oxazine-4,4'-piperidine]-1'-yl)methanone (22 mg, 0.051 mmol), nPrOH (12 µL, 0.15 mmol), and NaH (60%, 6.1 mg, 0.15 mmol) were combined in acetonitrile (1 mL) and the reaction mixture was heated at 70° C. for 1 h. The reaction mixture was filtered and purified by reverse phase HPLC to provide (4-propoxy-3-(trifluoromethyl)phenyl)(spiro[benzo[b]pyrrolo[1,2-d][1,4]oxazine-4,4'-piperidine]-1'-yl)methanone. ESI-MS m/z calc. 470.2. found 471.2 (M−1)$^−$; Retention time: 2.83 minutes (4 min run).

The following compounds were synthesized using the procedures described above: (R)-spiro[benzo[b]pyrrolo[1,2-d][1,4]oxazine-4,4'-piperidine]-1'-yl(4-(tetrahydrofuran-3-yloxy)-3-(trifluoromethyl)phenyl)methanone, (S)-spiro[benzo[b]pyrrolo[1,2-d][1,4]oxazine-4,4'-piperidine]-1'-yl(4-(tetrahydrofuran-3-yloxy)-3-(trifluoromethyl)phenyl)methanone, spiro[benzo[b]pyrrolo[1,2-d][1,4]oxazine-4,4'-piperidine]-1'-yl(4-((tetrahydrofuran-2-yl)methoxy)-3-(trifluoromethyl)phenyl)methanone, (4-(2-(dimethylamino)ethoxy)-3-(trifluoromethyl)phenyl)(spiro[benzo[b]pyrrolo[1,2-d][1,4]oxazine-4,4'-piperidine]-1'-yl)methanone, and (S)-(4-(2-methoxypropoxy)-3-(trifluoromethyl)phenyl)(spiro[benzo[b]pyrrolo[1,2-d][1,4]oxazine-4,4'-piperidine]-1'-yl)methanone.

2-(2-Methoxy-4-(spiro[benzo[b]pyrrolo[1,2-d][1,4]oxazine-4,4'-piperidine]-1'-ylcarbonyl)phenoxy)acetic acid Step 1: (4-Hydroxy-3-methoxyphenyl)(spiro[benzo[b]pyrrolo[1,2-d][1,4]oxazine-4,4'-piperidine]-1'-yl)methanone

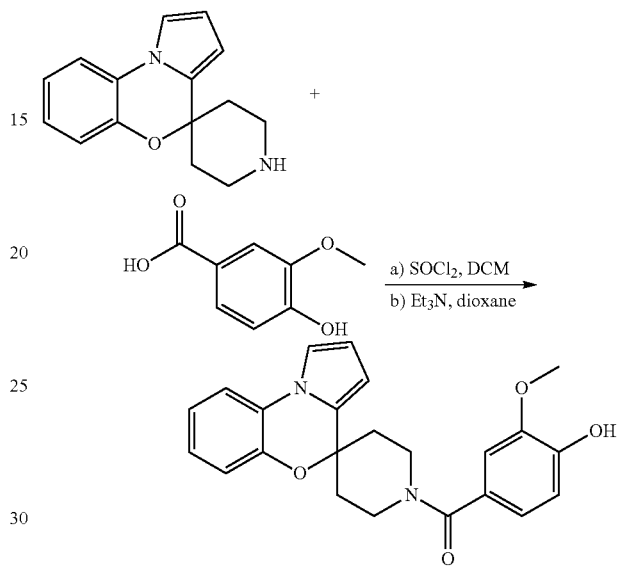

4-Hydroxy-3-methoxy-benzoic acid (304 mg, 1.81 mmol) was stirred with thionyl chloride (645 mg, 395 µL, 5.42 mmol) in dichloromethane and 2 drops of DMF were added. After stirring for 2.5 h, the excess thionyl chloride and dichloromethane were removed in vacuo. The residue was added to a mixture of spiro[piperidine-4,4'-pyrrolo[2,1-c][1,4]benzoxazine] (500 mg, 1.81 mmol), 1,4-dioxane (6.5 mL), and triethylamine (760 µL, 5.42 mmol). The mixture was stirred for 18 h at 90° C. before it was cooled to room temperature and was evaporated to dryness. The residue was dissolved in ethyl acetate, filtered and washed with 1N HCl (2×), a saturated sodium bicarbonate solution (2×), and brine. The organic layer was dried over sodium sulfate and was evaporated to dryness. The residue was purified by column chromatography (0-100% EtOAc/hexane) to give (4-hydroxy-3-methoxyphenyl)(spiro[benzo[b]pyrrolo[1,2-d][1,4]oxazine-4,4'-piperidine]-1'-yl)methanone (394 mg, 56%). ESI-MS m/z calc. 390.2. found 391.2 (M+1)$^+$; Retention time: 2.56 minutes (4 min run).

Step 2: Methyl 2-(2-methoxy-4-(spiro[benzo[b]pyrrolo[1,2-d][1,4]oxazine-4,4'-piperidine]-1'-ylcarbonyl)phenoxy)acetate

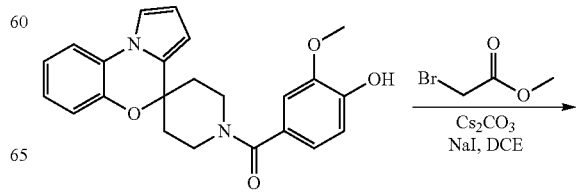

643

-continued

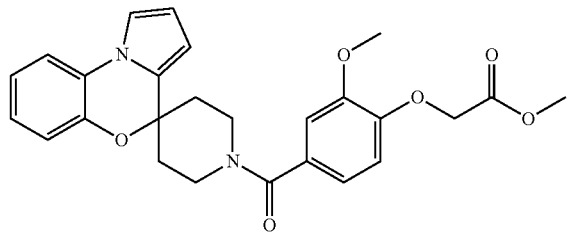

To (4-hydroxy-3-methoxyphenyl)(spiro[benzo[b]pyrrolo[1,2-d][1,4]oxazine-4,4'-piperidine]-1'-yl)methanone (200 mg, 0.512 mmol), sodium iodide (38.4 mg, 0.256 mmol), $Cs_2CO_3$ (334 mg, 1.03 mmol), and DCE (5.0 mL) was added methyl 2-bromoacetate (49 µL, 0.51 mmol). The mixture was stirred at 60° C. for 18 h. Additional methyl 2-bromoacetate (1.0 mmol) was added and the mixture was heated for 3 h at 60° C. The mixture was cooled and then filtered. The solvent was evaporated under reduced pressure and the crude product was purified by column chromatography on silica gel (0-30% ethyl acetate/DCM) to yield methyl 2-(2-methoxy-4-(spiro[benzo[b]pyrrolo[1,2-d][1,4]oxazine-4,4'-piperidine]-1'-ylcarbonyl)phenoxy)acetate (140 mg, 59%). ESI-MS m/z calc. 462.2. found 463.5 (M+1)⁺; Retention time: 2.68 minutes (4 min run).

Step 3: 2-(2-Methoxy-4-(spiro[benzo[b]pyrrolo[1,2-d][1,4]oxazine-4,4'-piperidine]-1'-ylcarbonyl)phenoxy)acetic acid

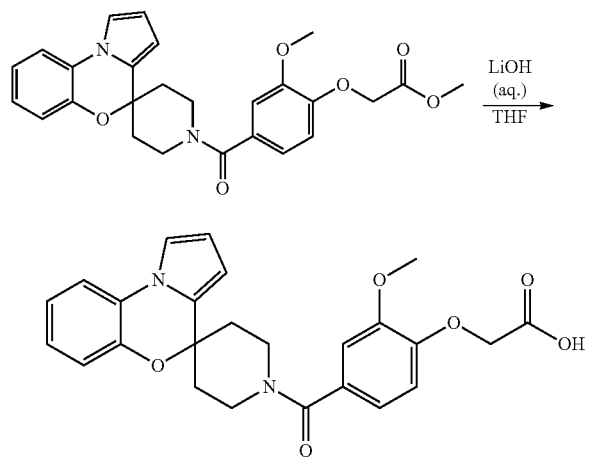

To a solution of methyl 2-(2-methoxy-4-(spiro[benzo[b]pyrrolo[1,2-d][1,4]oxazine-4,4'-piperidine]-1'-ylcarbonyl)phenoxy)acetate (140 mg, 0.303 mmol) in THF (4 mL) was added LiOH (600 µL of 2.0 M, 1.2 mmol) and the mixture was stirred at room temperature for 19 h. The mixture was filtered and was purified by HPLC using 5 mM HCl/water and MeOH to yield 2-(2-methoxy-4-(spiro[benzo[b]pyrrolo[1,2-d][1,4]oxazine-4,4'-piperidine]-1'-ylcarbonyl)phenoxy)acetic acid. ESI-MS m/z calc. 448.2. found 449.3 (M+1)⁺; Retention time: 5.90 minutes (15 min run).

644

(3-Methoxy-4-(2-methoxypropan-2-yl)phenyl)(spiro[benzo[b]pyrrolo[1,2-d][1,4]oxazine-4,4'-piperidine]-1'-yl)methanone

Step 1: (4-(2-Hydroxypropan-2-yl)-3-methoxyphenyl)(spiro[benzo[b]pyrrolo[1,2-d][1,4]oxazine-4,4'-piperidine]-1'-yl)methanone

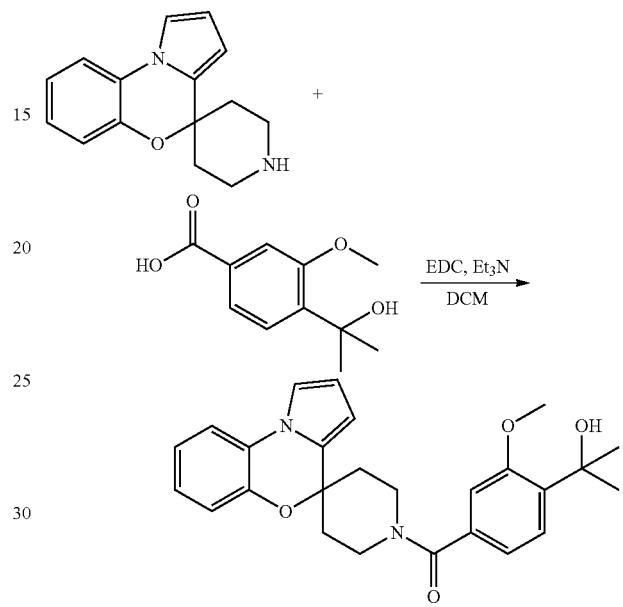

4-(1-Hydroxy-1-methyl-ethyl)-3-methoxy-benzoic acid (120 mg, 0.573 mmol), spiro[piperidine-4,4'-pyrrolo[2,1-c][1,4]benzoxazine] (167 mg, 0.573 mmol), triethylamine (320 µL, 2.29 mmol), and EDC (110 mg, 0.573 mmol) were combined in DCM (5.8 mL). The reaction mixture was allowed to stir at room temperature for 16 h. The reaction mixture was washed three times with a 1M solution of hydrochloric acid, followed by three washes with a saturated aqueous solution of sodium bicarbonate, followed by three washes of a saturated aqueous solution of sodium chloride. The organic layer was dried over sodium sulfate, filtered, and evaporated to dryness to provide (4-(2-hydroxypropan-2-yl)-3-methoxyphenyl)(spiro[benzo[b]pyrrolo[1,2-d][1,4]oxazine-4,4'-piperidine]-1'-yl)methanone. ESI-MS m/z calc. 432.0. found 433.1 (M+1)⁺; Retention time: 1.61 minutes (3 min run).

Step 2: (3-Methoxy-4-(2-methoxypropan-2-yl)phenyl)(spiro[benzo[b]pyrrolo[1,2-d][1,4]oxazine-4,4'-piperidine]-1'-yl)methanone

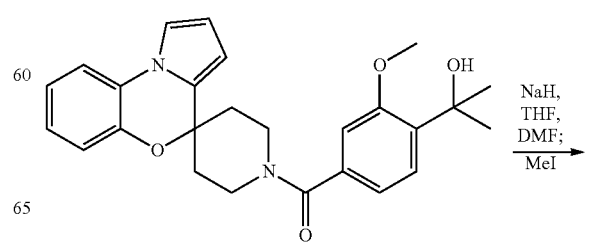

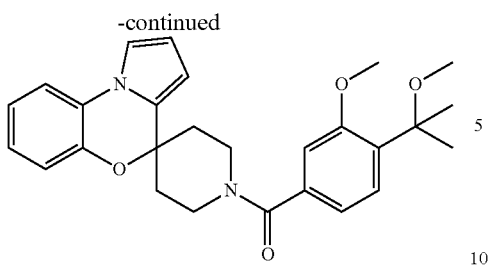

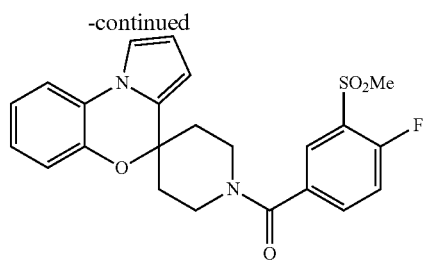

(4-(2-Hydroxypropan-2-yl)-3-methoxyphenyl)(spiro[benzo[b]pyrrolo[1,2-d][1,4]oxazine-4,4'-piperidine]-1'-yl)methanone (crude material from step 1) was dissolved in a mixture of THF (3 mL) and DMF (3 mL). NaH (28 mg, 0.69 mmol) was added and the reaction mixture was allowed to stir for 2 minutes. MeI (54 µL, 0.86 mmol) was then added and the reaction mixture was allowed to stir for 1 h. The reaction mixture was evaporated to dryness and the residue was suspended in 25 mL of dichloromethane. The suspension was washed two times with a 1M solution of hydrochloric acid, followed by two washes with a saturated aqueous solution of sodium bicarbonate, followed by two washes of a saturated aqueous solution of sodium chloride. The organic layer was dried over sodium sulfate, filtered, and evaporated to dryness to yield the crude product. The crude material was purified by column chromatography utilizing a gradient of 0-35% ethyl acetate in hexanes give (3-methoxy-4-(2-methoxypropan-2-yl)phenyl)(spiro[benzo[b]pyrrolo[1,2-d][1,4]oxazine-4,4'-piperidine]-1'-yl)methanone (94 mg, 35% over 2 steps). ESI-MS m/z calc. 446.2. found 447.5 (M+1)$^+$; Retention time: 7.60 minutes (15 min run). $^1$H NMR (400 MHz, DMSO) δ 7.68-7.65 (m, 1H), 7.50-7.49 (m, 1H), 7.40 (d, J=7.9 Hz, 1H), 7.17-6.98 (m, 5H), 6.29-6.28 (m, 1H), 6.18-6.17 (m, 1H), 4.49-4.34 (m, 1H), 3.83 (s, 3H), 3.80-3.41 (m, 3H), 3.13 (s, 3H), 2.11-1.81 (m, 4H) and 1.50 (s, 6H).

(7-Chlorospiro[benzo[b]pyrrolo[1,2-d][1,4]oxazine-4,4'-piperidine]-1'-yl)(3-methoxy-4-(3-methoxyoxetan-3-yl)phenyl)methanone was also prepared using the procedures described above.

(4-Methoxy-3-(methylsulfonyl)phenyl)(spiro[benzo[b]pyrrolo[1,2-d][1,4]oxazine-4,4'-piperidine]-1'-yl)methanone Step 1: (4-Fluoro-3-(methylsulfonyl)phenyl)(spiro[benzo[b]pyrrolo[1,2-d][1,4]oxazine-4,4'-piperidine]-1'-yl)methanone

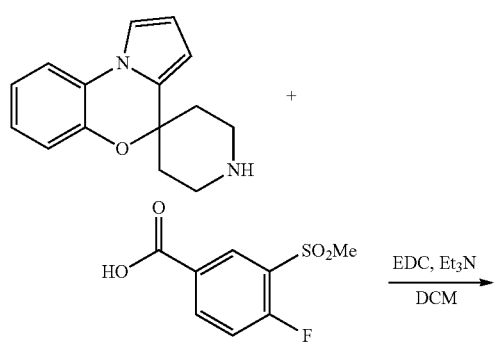

Spiro[piperidine-4,4'-pyrrolo[2,1-c][1,4]benzoxazine] (257 mg, 0.928 mmol), 4-fluoro-3-methylsulfonyl-benzoic acid (203 mg, 0.928 mmol), triethylamine (518 µL, 3.71 mmol), and EDC (196 mg, 1.02 mmol) were combined in dichloromethane (10 mL) and the reaction mixture was stirred at room temperature for 4 d. The reaction mixture was washed three times with a 1M solution of hydrochloric acid, followed by three washes with a saturated aqueous solution of sodium bicarbonate, followed by three washes of a saturated aqueous solution of sodium chloride. The organic layer was dried over sodium sulfate, filtered, and evaporated to dryness to yield the crude product. The crude material was purified column chromatography utilizing a gradient of 0-75% ethyl acetate in hexanes to yield (4-fluoro-3-methylsulfonyl-phenyl)-spiro[piperidine-4,4'-pyrrolo[2,1-c][1,4]benzoxazine]-1-yl-methanone (222 mg, 54%) as a colorless oil. ESI-MS m/z calc. 440.1. found 441.1 (M+1)$^+$; Retention time: 1.51 minutes (3 min run).

Step 2: (4-Methoxy-3-(methylsulfonyl)phenyl)(spiro[benzo[b]pyrrolo[1,2-d][1,4]oxazine-4,4'-piperidine]-1'-yl)methanone

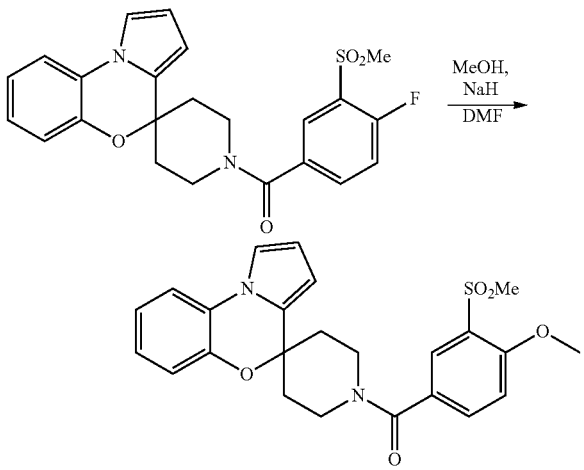

(4-Fluoro-3-methylsulfonyl-phenyl)-spiro[piperidine-4,4'-pyrrolo[2,1-c][1,4]benzoxazine]-1-yl-methanone (44 mg, 0.10 mmol) and MeOH (12 µL, 0.30 mmol) were combined in DMF (1 mL). NaH (60%, 12 mg, 0.30 mmol) was added and the reaction mixture was stirred for 10 minutes. The mixture was filtered and was purified by reverse phase preparative liquid chromatography utilizing a gradient of 10-99% acetonitrile in water containing 5 mM hydrochloric acid to give (4-methoxy-3-(methylsulfonyl)phenyl)(spiro[benzo[b]pyrrolo[1,2-d][1,4]oxazine-4,4'-piperidine]-1'-yl)methanone. ESI-MS m/z calc. 452.1. found 453.5 (M+1)$^+$; Retention time: 1.78 minutes (3 min run). $^1$H NMR (400 MHz, DMSO) δ 7.87 (d, J=2.0 Hz, 1H), 7.86-7.81 (m, 1H), 7.67 (d, J=7.6 Hz, 1H), 7.50 (s, 1H), 7.36 (d, J=8.6 Hz, 1H), 7.22-7.02 (m, 3H), 6.28 (t, J=3.1 Hz, 1H), 6.16 (d, J=2.3 Hz, 1H), 4.52-4.18 (m, 1H), 4.00 (s, 3H), 3.58 (s, 3H), 3.28 (s, 3H), 1.98 (s, 4H).

The following compounds were synthesized using the procedures described above: (3-(methylsulfonyl)-4-propoxyphenyl)(spiro[benzo[b]pyrrolo[1,2-d][1,4]oxazine-4,4'-piperidine]-1'-yl)methanone, (4-isopropoxy-3-(methylsulfonyl)phenyl)(spiro[benzo[b]pyrrolo[1,2-d][1,4]oxazine-4,4'-piperidine]-1'-yl)methanone, (4-(isopentyloxy)-3-(methylsulfonyl)phenyl)(spiro[benzo[b]pyrrolo[1,2-d][1,4]oxazine-4,4'-piperidine]-1'-yl)methanone, and (4-(2-methoxyethoxy)-3-(methylsulfonyl)phenyl)(spiro[benzo[b]pyrrolo[1,2-d][1,4]oxazine-4,4'-piperidine]-1'-yl)methanone.

(5-(Hydroxymethyl)-2,4-dimethoxyphenyl)(spiro[benzo[b]pyrrolo[1,2-d][1,4]oxazine-4,4'-piperidine]-1'-yl)methanone

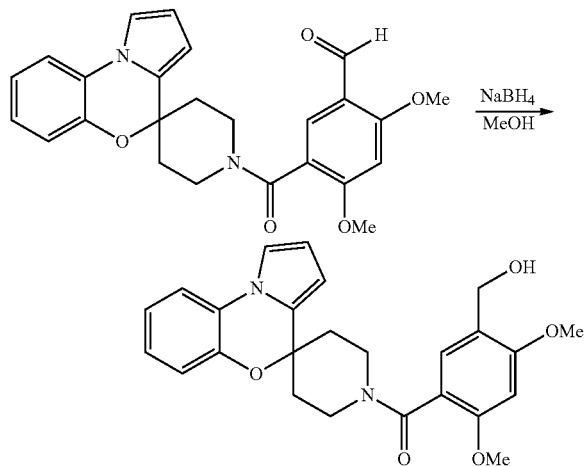

2,4-Dimethoxy-5-(spiro[benzo[b]pyrrolo[1,2-d][1,4]oxazine-4,4'-piperidine]-1'-ylcarbonyl)benzaldehyde (65 mg, 0.15 mmol) was suspended in MeOH (1 mL). NaBH$_4$ (60 mg, 1.6 mmol) was added and the reaction mixture was allowed to stir for 15 minutes. The reaction mixture was filtered and was then purified by reverse phase preparative liquid chromatography utilizing a gradient of 20-99% methanol in water containing no modifier to give (5-(hydroxymethyl)-2,4-dimethoxyphenyl)(spiro[benzo[b]pyrrolo[1,2-d][1,4]oxazine-4,4'-piperidine]-1'-yl)methanone. ESI-MS m/z calc. 434.2. found 435.5 (M+1)$^+$; Retention time: 1.63 minutes (3 min run).

(7-Chlorospiro[benzo[b]pyrrolo[1,2-d][1,4]oxazine-4,4'-piperidine]-1'-yl)(4-cyclopropyl-3-methoxyphenyl)methanone

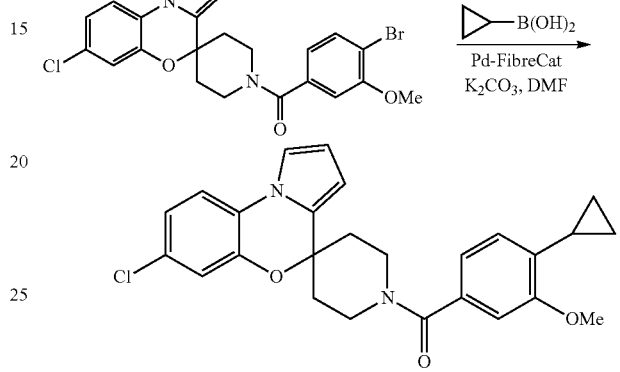

To a microwave vial was added Pd-FibreCat (42 mg, 0.0065 mmol), (4-bromo-3-methoxyphenyl)(7-chlorospiro[benzo[b]pyrrolo[1,2-d][1,4]oxazine-4,4'-piperidine]-1'-yl)methanone (63 mg, 0.13 mmol), cyclopropylboronic acid (17 mg, 0.19 mmol), DMF (0.7 mL), and K$_2$CO$_3$ (190 μL of 2.0 M, 0.39 mmol). The reaction vessel was purged with nitrogen and the mixture was heated at 120° C. overnight. The mixture was filtered and was purified by prep-HPLC (20-99% MeOH:H$_2$O with HCl modifier) to give (7-chlorospiro[benzo[b]pyrrolo[1,2-d][1,4]oxazine-4,4'-piperidine]-1'-yl)(4-cyclopropyl-3-methoxyphenyl)methanone. ESI-MS m/z calc. 448.2. found 449.4 (M+1)$^+$; Retention time: 3.32 minutes (4 min run).

(S)-(8-Chlorospiro[benzo[b]pyrrolo[1,2-d][1,4]oxazine-4,4'-piperidine]-1'-yl)(4-(2,3-dihydroxypropoxy)-3-methoxyphenyl)methanone

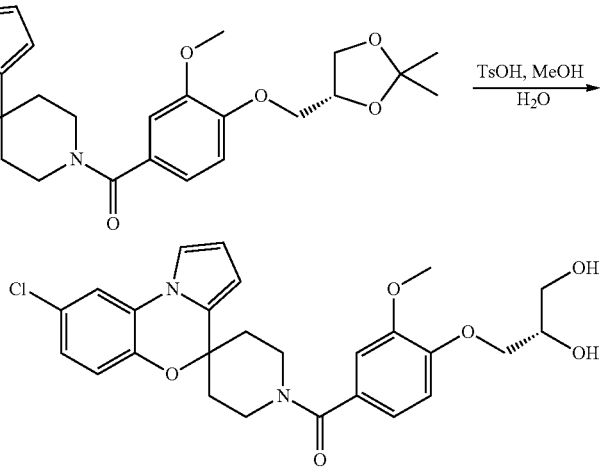

(R)-(8-Chlorospiro[benzo[b]pyrrolo[1,2-d][1,4]oxazine-4,4'-piperidine]-1'-yl)(4-((2,2-dimethyl-1,3-dioxolan-4-yl)methoxy)-3-methoxyphenyl)methanone (41 mg, 0.076 mmol) and 4-methylbenzenesulfonic acid hydrate (2.9 mg, 0.015 mmol) were dissolved in MeOH (760 μL) and H$_2$O (76 μL) was added. The reaction mixture was heated at 80° C. for 45 min. The mixture was filtered and the residue was purified by reverse phase HPLC using 5 mM HCl/H$_2$O and MeOH to yield (S)-(8-chlorospiro[benzo[b]pyrrolo[1,2-d][1,4]oxazine-4,4'-piperidine]-1'-yl)(4-(2,3-dihydroxypropoxy)-3-methoxyphenyl)methanone. ESI-MS m/z calc. 498.2. found 499.3 (M+1)$^+$; Retention time: 4.72 minutes (15 min run).

The following compounds were synthesized using the procedures described above: (S)-(4-(2,3-dihydroxypropoxy)-3-methoxyphenyl)(spiro[benzo[b]pyrrolo[1,2-d][1,4]oxazine-4,4'-piperidine]-1'-yl)methanone and (R)-(4-(2,3-dihydroxypropoxy)-3-methoxyphenyl)(spiro[benzo[b]pyrrolo[1,2-d][1,4]oxazine-4,4'-piperidine]-1'-yl)methanone.

(4-Ethyl-3-methoxyphenyl)(7-(hydroxymethyl)spiro[benzo[b]pyrrolo[1,2-d][1,4]oxazine-4,4'-piperidine]-1'-yl)methanone

Step 1: Methyl 1'-(4-ethyl-3-methoxybenzoyl)spiro[benzo[b]pyrrolo[1,2-d][1,4]oxazine-4,4'-piperidine]-7-carboxylate

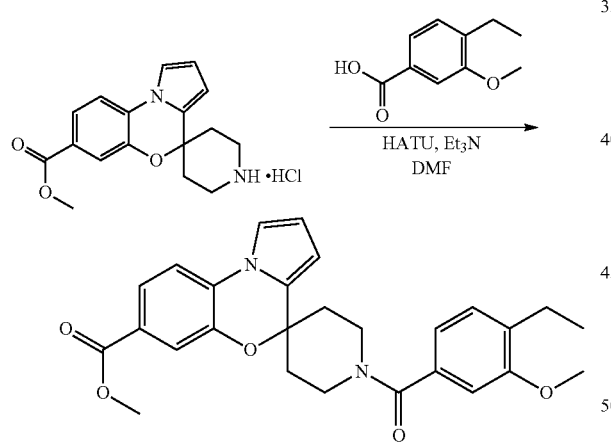

A solution of 4-ethyl-3-methoxy-benzoic acid (450 mg, 2.5 mmol), HATU (940 mg, 2.5 mmol), methyl spiro[piperidine-4,4'-pyrrolo[2,1-c][1,4]benzoxazine]-7'-carboxylate (830 mg, 2.5 mmol), and Et$_3$N (1.7 mL, 9.9 mmol) in DMF (8 mL) was stirred at room temperature overnight. The reaction was diluted with ethyl acetate and washed with saturated sodium bicarbonate solution. The organics were dried over sodium sulfate, filtered and evaporated to yield a crude mixture that was purified by silica gel chromatography eluting with 0-30% EtOAc in hexanes to yield methyl F-(4-ethyl-3-methoxybenzoyl)spiro[benzo[b]pyrrolo[1,2-d][1,4]oxazine-4,4'-piperidine]-7-carboxylate (1.1 g, quant). ESI-MS m/z calc. 460.5. found 461.5 (M+1)$^+$; Retention time: 2.08 minutes (3 min run).

Step 2: 1'-(4-Ethyl-3-methoxybenzoyl)spiro[benzo[b]pyrrolo[1,2-d][1,4]oxazine-4,4'-piperidine]-7-carboxylic acid

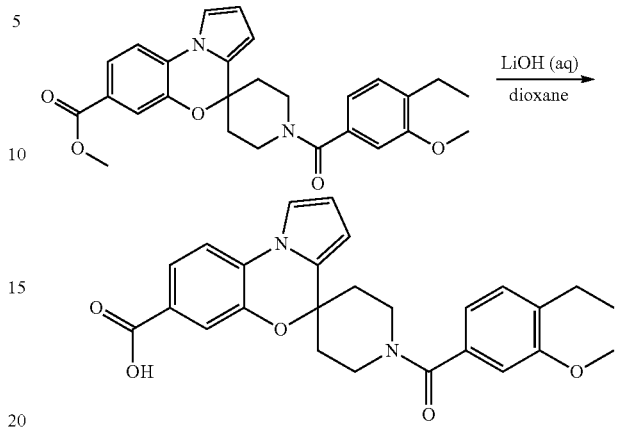

A solution of methyl 1-(4-ethyl-3-methoxy-benzoyl)spiro[piperidine-4,4'-pyrrolo[2,1-c][1,4]benzoxazine]-7'-carboxylate (1.1 g, 2.5 mmol) in LiOH (2.5 mL of 4.0 M, 9.9 mmol) and dioxane (5 mL) was stirred at 50° C. for 1 hour. The reaction was diluted with ethyl acetate and washed with water. The aqueous was acidified with 1N HCl and the product was extracted into ethyl acetate. The organics were dried over sodium sulfate, filtered and evaporated to yield a crude product that was used in the next step without further purification (0.60 g, 53%). ESI-MS m/z calc. 446.5. found 447.5 (M+1)$^+$; Retention time: 1.84 minutes (3 min run).

Step 3: (4-Ethyl-3-methoxyphenyl)(7-(hydroxymethyl)spiro[benzo[b]pyrrolo[1,2-d][1,4]oxazine-4,4'-piperidine]-1'-yl)methanone

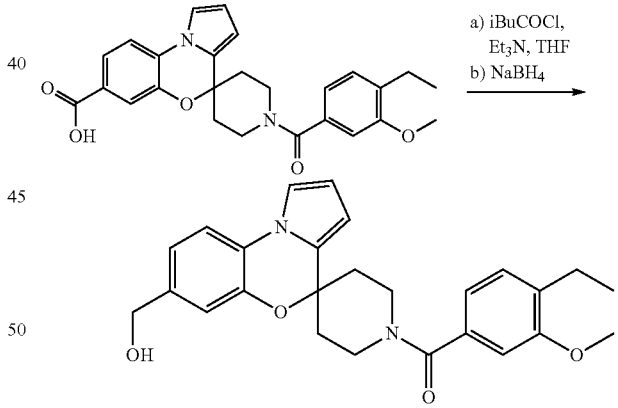

To 1-(4-ethyl-3-methoxy-benzoyl)spiro[piperidine-4,4'-pyrrolo[2,1-c][1,4]benzoxazine]-7'-carboxylic acid (550 mg, 1.2 mmol) in tetrahydrofuran (2.2 mL) at 0° C. was added triethylamine (200 μL, 1.4 mmol) then isobutyl chloroformate (180 μL, 1.4 mmol). The mixture was stirred for 30 min then filtered. The filtrate was added dropwise to a solution of sodium borohydride (70 mg, 1.8 mmol) in water (770 μL) at 0° C. The mixture was allowed to slowly reach room temperature before it was concentrated to ⅓ volume, diluted with ethyl acetate and washed with 1M HCl. The organics were dried over sodium sulfate, filtered and evaporated to yield (4-ethyl-3-methoxyphenyl)(7-(hydroxymethyl)spiro[benzo[b]pyrrolo[1,2-d][1,4]oxazine-4,4'-piperidine]-1'-yl)methanone (330 mg, 62%). ESI-MS m/z calc. 432.5. found 433.5 (M+1)⁺; Retention time: 1.78 minutes (3 min run).

(4-Ethyl-3-methoxyphenyl)(7-(methoxymethyl)spiro[benzo[b]pyrrolo[1,2-d][1,4]oxazine-4,4'-piperidine]-1'-yl)methanone

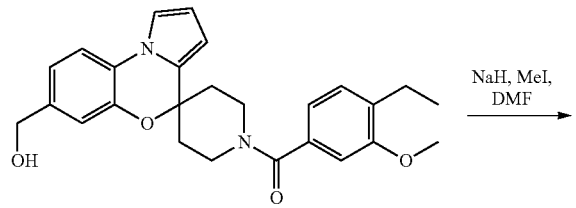

MeI (7.2 μL, 0.12 mmol) was added to a solution of (4-ethyl-3-methoxy-phenyl)-[7'-(hydroxymethyl)spiro[piperidine-4,4'-pyrrolo[2,1-c][1,4]benzoxazine]-1-yl]methanone (50 mg, 0.12 mmol) and NaH (4.6 mg, 0.12 mmol) in DMF (1 mL) and was stirred at room temperature for 1 hour. The reaction was filtered and purified by reverse phase LC-MS (10-99% CH₃CN/H₂O). Pure fractions were combined and evaporated to yield (4-ethyl-3-methoxyphenyl)(7-(methoxymethyl)spiro[benzo[b]pyrrolo[1,2-d][1,4]oxazine-4,4'-piperidine]-1'-yl)methanone. ESI-MS m/z calc. 446.5. found 447.5 (M+1)⁺; Retention time: 2.11 minutes (3 min run).

(7-((Dimethylamino)methyl)spiro[benzo[b]pyrrolo[1,2-d][1,4]oxazine-4,4'-piperidine]-1'-yl)(4-ethyl-3-methoxyphenyl)methanone Step 1: 1'-(4-Ethyl-3-methoxybenzoyl)spiro[benzo[b]pyrrolo[1,2-d][1,4]oxazine-4,4'-piperidine]-7-carbaldehyde

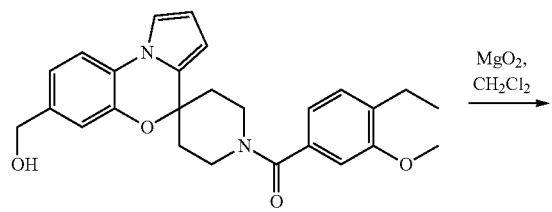

A solution of (4-ethyl-3-methoxy-phenyl)-[7'-(hydroxymethyl)spiro[piperidine-4,4'-pyrrolo[2,1-c][1,4]benzoxazine]-1-yl]methanone (270 mg, 0.62 mmol) and manganese dioxide (270 mg, 3.1 mmol) in dichloromethane (5 mL) was stirred at 60° C. overnight. The reaction was filtered, evaporated and submitted to the next step without further purification. ESI-MS m/z calc. 430.5. found 431.7 (M+1)⁺; Retention time: 2.01 minutes (3 min run).

Step 2: (7-((Dimethylamino)methyl)spiro[benzo[b]pyrrolo[1,2-d][1,4]oxazine-4,4'-piperidine]-1'-yl)(4-ethyl-3-methoxyphenyl)methanone

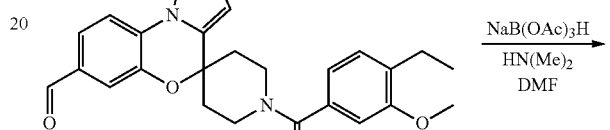

A solution of 1'-(4-ethyl-3-methoxybenzoyl)spiro[benzo[b]pyrrolo[1,2-d][1,4]oxazine-4,4'-piperidine]-7-carbaldehyde (88 mg, 0.20 mmol) N,N-dimethylamine hydrochloride (83 mg, 1.0 mmol), Et₃N (140 μL, 1.0 mmol) and NaHB(OAc)₃ (130 mg, 0.60 mmol) in DMF (1 mL) was stirred at room temperature overnight. The reaction mixture was filtered and purified by reverse phase LC-MS (10-99% CH₃CN/H₂O) to yield (7-((dimethylamino)methyl)spiro[benzo[b]pyrrolo[1,2-d][1,4]oxazine-4,4'-piperidine]-1'-yl)(4-ethyl-3-methoxyphenyl)methanone. ESI-MS m/z calc. 459.6. found 460.5 (M+1)⁺; Retention time: 1.40 minutes (3 min run).

1'-(4-Ethyl-3-methoxybenzoyl)-N,N-dimethylspiro[benzo[b]pyrrolo[1,2-d][1,4]oxazine-4,4'-piperidine]-7-carboxamide

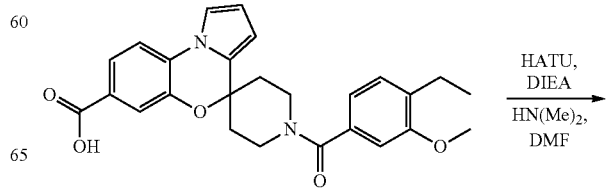

653

-continued

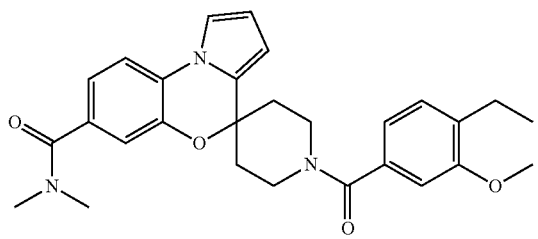

A solution of 1'-(4-ethyl-3-methoxybenzoyl)spiro[benzo[b]pyrrolo[1,2-d][1,4]oxazine-4,4'-piperidine]-7-carboxylic acid (40 mg, 0.09 mmol), HATU (34 mg, 0.090 mmol), N,N-dimethylamine hydrochloride (7.3 mg, 0.090 mmol) and iPr$_2$NEt (62 µL, 0.36 mmol) in DMF (1 mL) was stirred at room temperature overnight. The reaction mixture was filtered and purified by reverse phase LC-MS (10-99% CH$_3$CN/H$_2$O). Pure fractions were combined and evaporated to yield 1'-(4-ethyl-3-methoxybenzoyl)-N,N-dimethylspiro[benzo[b]pyrrolo[1,2-d][1,4]oxazine-4,4'-piperidine]-7-carboxamide. ESI-MS m/z calc. 473.6. found 474.5 (M+1)$^+$; Retention time: 1.80 minutes (3 min run).

1'-(4-Ethyl-3-methoxybenzoyl)-N-methylspiro[benzo[b]pyrrolo[1,2-d][1,4]oxazine-4,4'-piperidine]-7-carboxamide

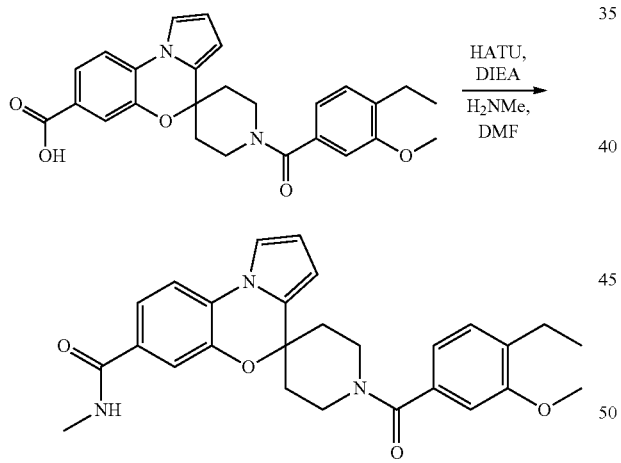

A solution of 1'-(4-ethyl-3-methoxybenzoyl)spiro[benzo[b]pyrrolo[1,2-d][1,4]oxazine-4,4'-piperidine]-7-carboxylic acid (40 mg, 0.090 mmol), HATU (34 mg, 0.090 mmol), N-methylamine hydrochloride (6.0 mg, 0.090 mmol) and iPr$_2$NEt (62 µL, 0.36 mmol) in DMF (1 mL) was stirred at room temperature overnight. The reaction mixture was filtered and purified by reverse phase LC-MS (10-99% CH$_3$CN/H$_2$O). Pure fractions were combined and evaporated to yield 1'-(4-ethyl-3-methoxybenzoyl)-N-methylspiro[benzo[b]pyrrolo[1,2-d][1,4]oxazine-4,4'-piperidine]-7-carboxamide. ESI-MS m/z calc. 459.5. found 460.5 (M+1)$^+$; Retention time: 1.73 minutes (3 min run).

654

(7-(Aminomethyl)spiro[benzo[b]pyrrolo[1,2-d][1,4]oxazine-4,4'-piperidine]-1'-yl)(4-ethyl-3-methoxyphenyl)methanone

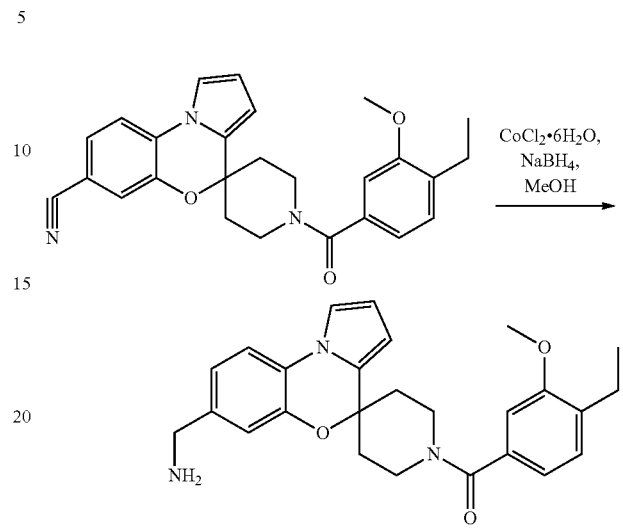

NaBH$_4$ (17.7 mg, 0.47 mmol) was slowly added to a solution of 1-(4-ethyl-3-methoxy-benzoyl)spiro[piperidine-4,4'-pyrrolo[2,1-c][1,4]benzoxazine]-7'-carbonitrile (20 mg, 0.050 mmol) and dichlorocobalt hexahydrate (22 mg, 0.090 mmol) in MeOH (1 mL) and was stirred at room temperature for 10 minutes. The reaction mixture was filtered and purified by reverse phase LC-MS (10-99% CH$_3$CN/H$_2$O) to yield (7-(aminomethyl)spiro[benzo[b]pyrrolo[1,2-d][1,4]oxazine-4,4'-piperidine]-1'-yl)(4-ethyl-3-methoxyphenyl)methanone. ESI-MS m/z calc. 431.5. found 432.5 (M+1)$^+$; Retention time: 1.44 minutes (3 min run).

(4-Isopropoxy-3-methylphenyl)(1-(methylsulfonyl)spiro[benzo[b]pyrrolo[1,2-d][1,4]oxazine-4,4'-piperidine]-1'-yl)methanone Step 1: (4-Isopropoxy-3-methylphenyl)(1-(methylthio)spiro[benzo[b]pyrrolo[1,2-d][1,4]oxazine-4,4'-piperidine]-1'-yl)methanone

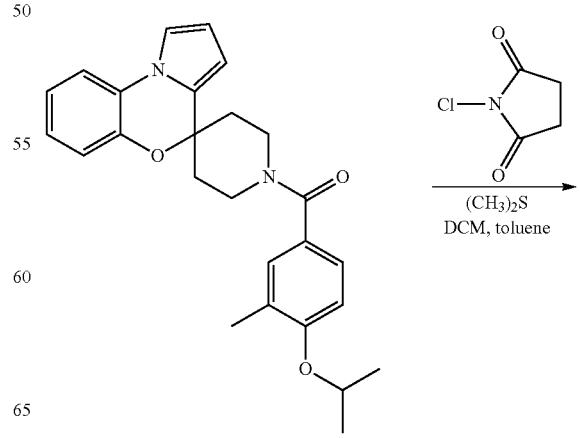

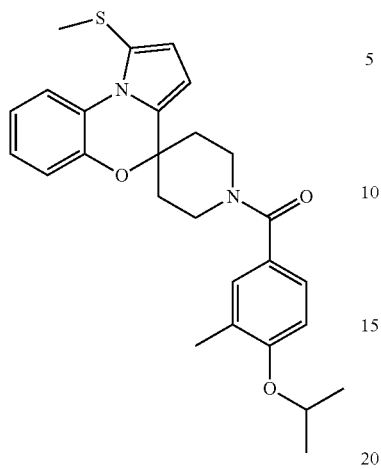

A solution of 1-chloropyrrolidine-2,5-dione (92 mg, 0.70 mmol) in dry dichloromethane (3.2 mL) was added dropwise at −10° C. to a solution of methylsulfanylmethane (82 μL, 1.1 mmol) in dry dichloromethane (800 μL) over a period of 5 minutes. The reaction was allowed to warm to room temperature and was stirred for 30 minutes. The mixture was then cooled to −55° C. and a solution of (4-isopropoxy-3-methylphenyl)-spiro[piperidine-4,4'-pyrrolo[2,1-c][1,4]benzoxazine]-1-yl-methanone (210 mg, 0.49 mmol) in dry dichloromethane (800 μL) was added dropwise. The cooling bath was removed and the mixture was gradually warmed up to room temperature and was stirred overnight. The solvent was removed under vacuum and the pink residue that was obtained was dissolved in dry toluene (7 mL) and was heated at 50° C. for 5 minutes. The solvent was removed to afford (4-isopropoxy-3-methylphenyl)(1-(methylthio)spiro[benzo[b]pyrrolo[1,2-d][1,4]oxazine-4,4'-piperidine]-1'-yl)methanone (250 mg, 78%). ESI-MS m/z calc. 462.2. found 463.5 (M+1)$^+$; Retention time: 2.43 minutes (3 min run).

Step 2: (4-Isopropoxy-3-methylphenyl)(1-(methylsulfonyl)spiro[benzo[b]pyrrolo[1,2-d][1,4]oxazine-4,4'-piperidine]-1'-yl)methanone

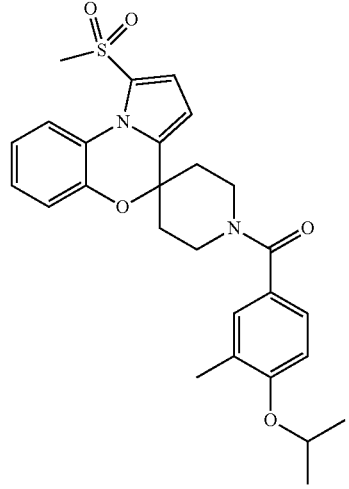

To a solution of (4-isopropoxy-3-methylphenyl)(1-(methylthio)spiro[benzo[b]-pyrrolo[1,2-d][1,4]oxazine-4,4'-piperidine]-1'-yl)methanone (250 mg, 0.54 mmol) in dry dichloromethane (2 mL) at 0° C. was added 3-chlorobenzenecarboperoxoic acid (93 mg, 0.54 mmol). After stirring 10 minutes at 0° C. the cooling bath was removed. The reaction was diluted with dichloromethane (25 mL) and saturated sodium bicarbonate (10 mL). The organic layer was separated and the aqueous layer was extracted twice with dichloromethane (2×25 mL). The combined organic layers were washed with brine, dried over sodium sulfate, filtered and concentrated. The residue was purified by column chromatography (silica gel: 5-40% EtOAc in hexanes) then reverse phase HPLC 10-99% acetonitrile in water (HCl modifier) to give (4-isopropoxy-3-methylphenyl)(1-(methylsulfonyl)spiro[benzo[b]pyrrolo[1,2-d][1,4]oxazine-4,4'-piperidine]-1'-yl)methanone. $^1$H NMR (400 MHz, CDCl$_3$) δ 8.60 (d, J=7.9 Hz, 1H), 7.31-7.21 (m, 4H), 7.21-7.13 (m, 2H), 6.84 (d, J=8.7 Hz, 1H), 6.17 (d, J=4.0 Hz, 1H), 4.65-4.52 (m, 1H), 4.25 (bs, 2H), 3.55-3.36 (m, 2H), 3.10 (s, 3H), 2.22 (s, 3H), 2.18-1.87 (m, 4H) and 1.36 (d, J=6.0 Hz, 6H). ESI-MS m/z calc. 494.6. found 495.5 (M+1)$^+$; Retention time: 1.98 minutes (3 min run).

1'-(4-Ethyl-3-methoxybenzoyl)spiro[benzo[b]pyrrolo[1,2-d][1,4]oxazine-4,4'-piperidine]-1-carbonitrile Step 1: (Z)-1'-(4-Ethyl-3-methoxybenzoyl)spiro[benzo[b]-pyrrolo[1,2-d][1,4]oxazine-4,4'-piperidine]-1-carbaldehyde oxime

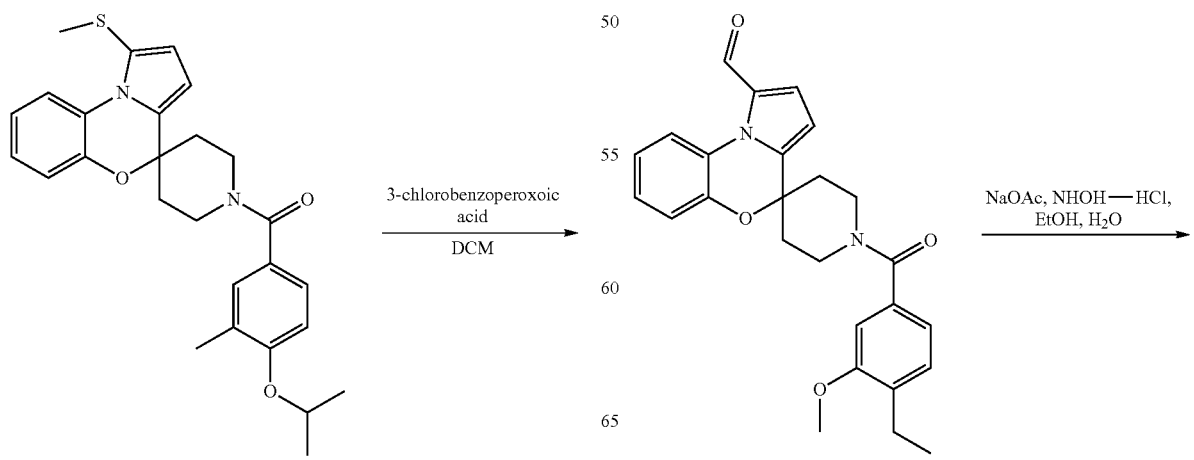

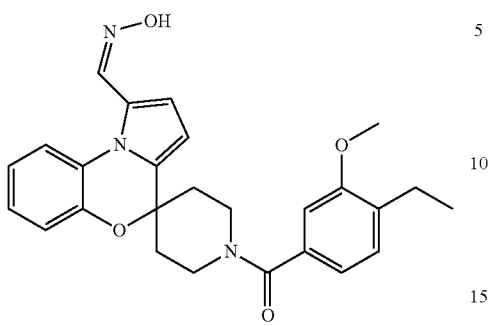

A solution of 1'-(4-ethyl-3-methoxybenzoyl)spiro[benzo[b]pyrrolo[1,2-d][1,4]oxazine-4,4'-piperidine]-1-carbaldehyde (950 mg, 2.21 mmol) in ethanol (4.7 mL) was heated at 60° C. A solution of hydroxylamine hydrochloride (693 mg, 9.97 mmol) and sodium acetate (1.38 g, 16.8 mmol) in water (4.7 mL) was added to the carbaldehyde solution. The reaction mixture was heated at 70° C. for 30 minutes before it was cooled to room temperature. Water was added and the product formed a white precipitate which was collected by filtration. The solids were washed with water and toluene, and dried under reduced pressure to give (Z)-1'-(4-ethyl-3-methoxybenzoyl)spiro[benzo[b]pyrrolo[1,2-d][1,4]oxazine-4,4'-piperidine]-1-carbaldehyde oxime (847 mg).

Acetic anhydride (4.0 mL, 42 mmol) was added to (Z)-1'-(4-ethyl-3-methoxybenzoyl)spiro[benzo[b]pyrrolo[1,2-d][1,4]oxazine-4,4'-piperidine]-1-carbaldehyde oxime (847 mg from previous step). The reaction mixture was heated at 140° C. for 3.5 h then cooled to room temperature and poured onto ice. Dichloromethane (30 mL) was added followed by sodium bicarbonate (0.7 g). The organic phase was then separated and the aqueous layer was extracted twice with dichloromethane. The combined organic layers were washed with brine, dried, filtered, and concentrated to give a yellow oil. The crude material was purified by column chromatography (silica gel: 5-45% EtOAc in hexanes) to give 1'-(4-ethyl-3-methoxybenzoyl)spiro[benzo[b]pyrrolo[1,2-d][1,4]oxazine-4,4'-piperidine]-1-carbonitrile (944 mg, 69%). $^1$H NMR (400 MHz, CDCl$_3$) δ 8.10 (d, J=8.0 Hz, 1H), 7.22-7.16 (m, 1H), 7.15-7.08 (m, J=7.6 Hz, 3H), 7.00 (d, J=4.0 Hz, 1H), 6.93-6.87 (m, 2H), 6.08 (d, J=4.0 Hz, 1H), 4.64 (s, 1H), 3.83 (s, 3H), 3.65-3.14 (m, 3H), 2.62 (q, J=7.5 Hz, 2H), 2.27-1.67 (m, 4H), 1.16 (t, J=7.5 Hz, 3H). ESI-MS m/z calc. 427.5. found 428.5 (M+1)$^+$; Retention time: 2.08 minutes (3 min run).

Step 2: 1'-(4-Ethyl-3-methoxybenzoyl)spiro[benzo[b]pyrrolo[1,2-d][1,4]oxazine-4,4'-piperidine]-1-carbonitrile (1-(Aminomethyl)spiro[benzo[b]pyrrolo[1,2-d][1,4]oxazine-4,4'-piperidine]-1'-yl)(4-isopropoxy-3-methylphenyl)methanone

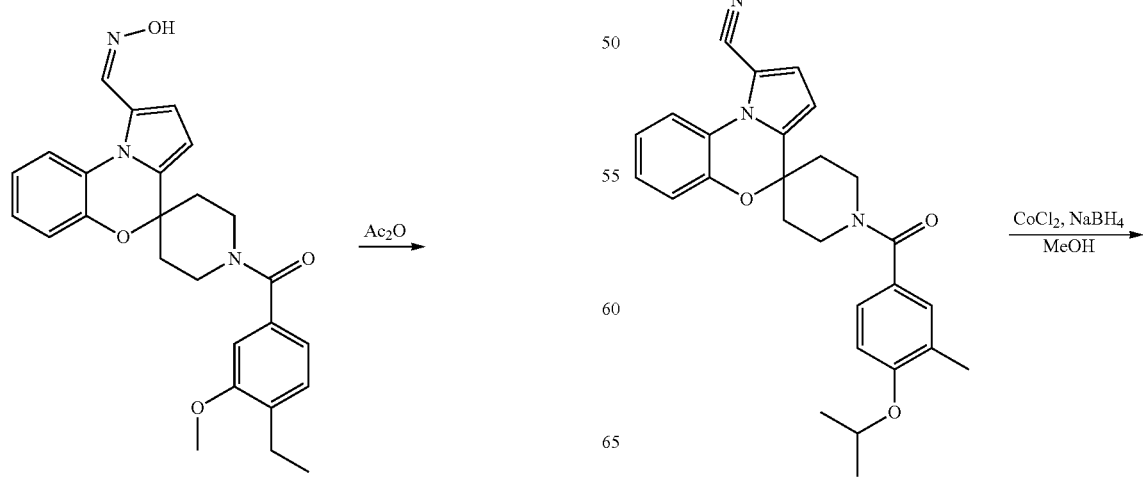

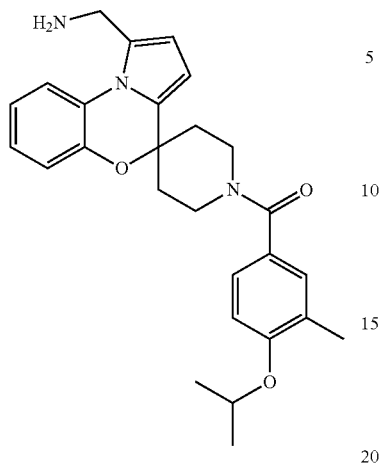

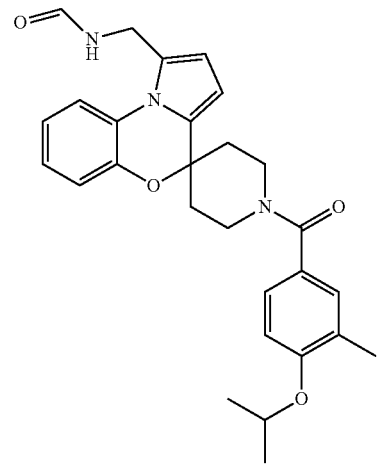

To a solution of 1'-(4-isopropoxy-3-methylbenzoyl)spiro[benzo[b]pyrrolo[1,2-d][1,4]oxazine-4,4'-piperidine]-1-carbonitrile (255 mg, 0.572 mmol) in MeOH (15.3 mL) at 0° C. was added dichlorocobalt (149 mg, 1.14 mmol) followed by portion wise addition of NaBH$_4$ (216. mg, 5.72 mmol). The reaction mixture was allowed to stir for 15 minutes at room temperature before it was cooled to 0° C. and acidified with 1M HCl. The solvent was removed under reduced pressure, and the residue was partitioned between EtOAc (50 mL) and aqueous saturated NaHCO$_3$ (15 mL). The aqueous phase was extracted with EtOAc (2×50 mL). The combined organic phases were dried with Na$_2$SO$_4$, filtered and concentrated to give (1-(aminomethyl)spiro[benzo[b]pyrrolo[1,2-d][1,4]oxazine-4,4'-piperidine]-1'-yl)(4-isopropoxy-3-methylphenyl)methanone (170 mg, 67%). ESI-MS m/z calc. 445.6. found 446.5 (M+1)$^+$; Retention time: 1.45 minutes (3 min run).

N-((1'-(4-isopropoxy-3-methylbenzoyl)spiro[benzo[b]pyrrolo-[1,2-d][1,4]oxazine-4,4'-piperidine]-1-yl)methyl)formamide A solution of (1-(aminomethyl)spiro[benzo[b]pyrrolo[1,2-d][1,4]oxazine-4,4'-piperidine]-1'-yl)(4-isopropoxy-3-methylphenyl)methanone hydrochloride (60 mg, 0.13 mmol) in ethyl formate (109 μL, 1.35 mmol) was heated at 50° C. overnight. The solvent was removed under reduced pressure and the product was purified by reverse phase HPLC 10-99% acetonitrile in water (HCl modifier) to give N-((1'-(4-isopropoxy-3-methylbenzoyl)spiro[benzo[b]pyrrolo-[1,2-d][1,4]oxazine-4,4'-piperidine]-1-yl)methyl)formamide. $^1$H NMR (400 MHz, CDCl$_3$) δ 8.23 (s, 1H), 7.40 (d, J=7.8 Hz, 1H), 7.30-7.22 (m, 1H), 7.20-7.01 (m, 3H), 6.83 (d, J=8.1 Hz, 1H), 6.28 (d, J=3.5 Hz, 1H), 5.99 (d, J=3.6 Hz, 1H), 5.89 (s, 1H), 4.77 (d, J=5.0 Hz, 2H), 4.62-4.52 (m, 1H), 3.50 (s, 2H), 2.21 (s, 3H), 2.17-1.78 (m, 4H), 1.70 (s, 2H), 1.36 (d, J=6.0 Hz, 6H). ESI-MS m/z calc. 473.6. found 474.5 (M+1)$^+$; Retention time: 1.80 minutes (3 min run).

N-((1'-(4-isopropoxy-3-methylbenzoyl)spiro[benzo[b]-pyrrolo[1,2-d][1,4]oxazine-4,4'-piperidine]-1-yl)methyl)acetamide

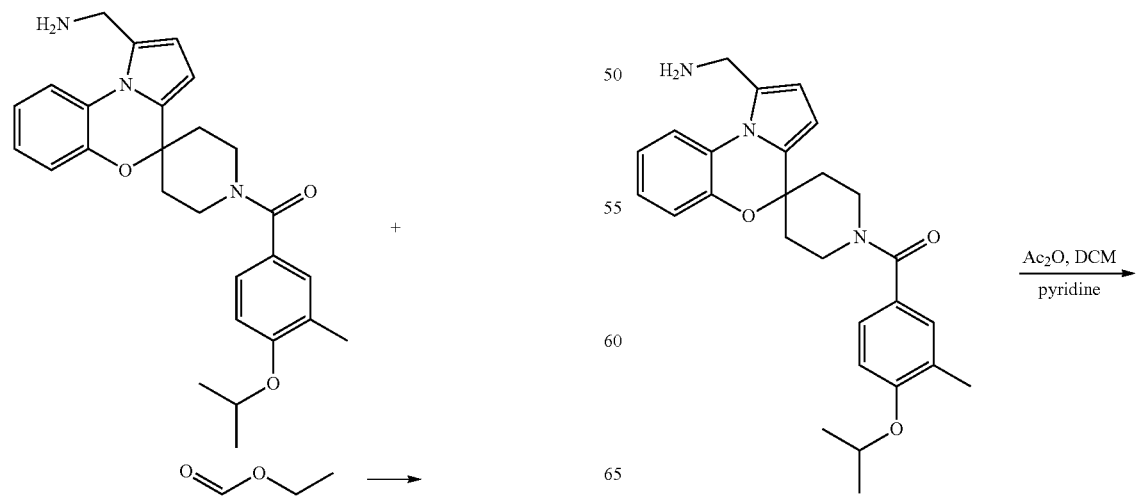

-continued

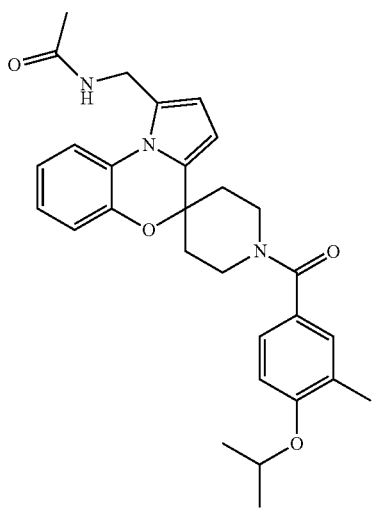

Crude (1-(aminomethyl)spiro[benzo[b]pyrrolo[1,2-d][1,4]oxazine-4,4'-piperidine]-1'-yl)(4-isopropoxy-3-methylphenyl)methanone (49 mg, 0.11 mmol) was dissolved in a solution of dry dichloromethane (0.5 mL) and pyridine (0.3 mL) and was cooled to 0° C. Acetic anhydride (52 µL, 0.55 mmol) was added and the reaction mixture was stirred for 30 minutes. The reaction mixture was quenched by the addition of methanol (0.5 mL), concentrated, and purified by reverse phase HPLC [10-99% acetonitrile in water (HCl modifier)] to give N-((1'-(4-isopropoxy-3-methylbenzoyl)spiro[benzo[b]pyrrolo[1,2-d][1,4]oxazine-4,4'-piperidine]-1-yl)methyl)acetamide. $^1$H NMR (400 MHz, CDCl$_3$) δ 7.41 (d, J=7.9 Hz, 1H), 7.33-7.21 (m, 2H), 7.13 (d, J=4.2 Hz, 2H), 7.10-7.02 (m, 1H), 6.83 (d, J=8.1 Hz, 1H), 6.26 (d, J=3.4 Hz, 1H), 5.99 (d, J=3.5 Hz, 1H), 5.68 (s, 1H), 4.71 (d, J=4.7 Hz, 2H), 4.64-4.50 (m, 1H), 3.50 (s, 2H), 2.22 (s, 3H), 2.17-1.76 (m, 7H), 1.67 (s, 2H), 1.36 (d, J=6.0 Hz, 6H). ESI-MS m/z calc. 487.6. found 488.5 (M+1)$^+$; Retention time: 1.81 minutes (3 min run).

(7-Chloro-1-(hydroxymethyl)spiro[benzo[b]pyrrolo[1,2-d][1,4]oxazine-4,4'-piperidine]-1'-yl)(3-methoxy-4-(trifluoromethyl)phenyl)methanone Step 1: 7-Chloro-1'-(3-methoxy-4-(trifluoromethyl)benzoyl)spiro[benzo[b]pyrrolo[1,2-d][1,4]oxazine-4,4'-piperidine]-1-carbaldehyde -continued

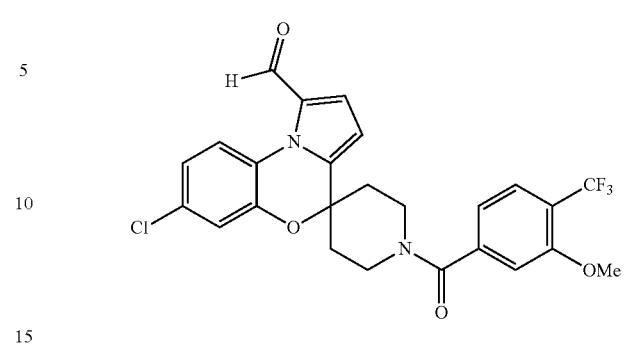

POCl$_3$ (150 µL, 1.5 mmol) was added dropwise at 0° C. under N$_2$ to dry DMF (120 µL, 1.5 mmol). The reaction mixture was left for 20 min at this temperature, which led to the formation of a white solid. A solution of (7'-chlorospiro[piperidine-4,4'-pyrrolo[2,1-c][1,4]benzoxazine]-1-yl)-[4-methoxy-3-(trifluoromethyl)phenyl]methanone (490 mg, 1.0 mmol) in dry DMF (3.7 mL) was added dropwise and the cooling bath was removed and stirring was continued for an additional hour. The mixture was poured over ice-water, 1M NaOH (7 ml) was added and the pH was adjusted to 7 with 2M HCl. The reaction was extracted with dichloromethane (3×10 mL). The combined organics were dried with MgSO$_4$, filtered and evaporated to yield a residue that was purified by silica gel chromatography eluting with 5-20% AcOEt in dichloromethane to yield 7-chloro-1'-(3-methoxy-4-(trifluoromethyl)benzoyl)spiro[benzo[b]pyrrolo[1,2-d][1,4]oxazine-4,4'-piperidine]-1-carbaldehyde (400 mg, 77%). ESI-MS m/z calc. 504.9. found 505.3 (M+1)$^+$; Retention time: 2.04 minutes (3 min run).

1'-(4-Isopropoxy-3-methylbenzoyl)-9-methylspiro[benzo[b]pyrrolo[1,2-d][1,4]oxazine-4,4'-piperidine]-1-carbaldehyde was synthesized from (4-isopropoxy-3-methylphenyl)(9-methylspiro[benzo[b]pyrrolo[1,2-d][1,4]oxazine-4,4'-piperidine]-1'-yl)methanone using the procedure described above.

Step 2: (7-Chloro-1-(hydroxymethyl)spiro[benzo[b]pyrrolo[1,2-d][1,4]oxazine-4,4'-piperidine]-1'-yl)(3-methoxy-4-(trifluoromethyl)phenyl)methanone

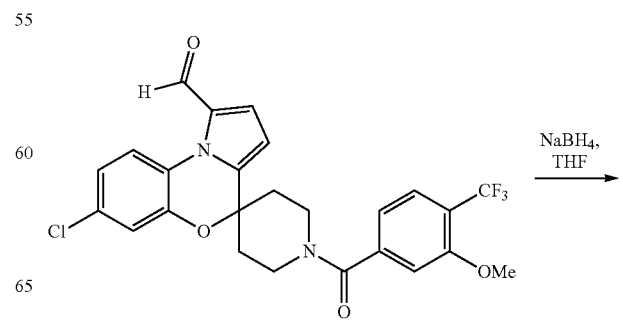

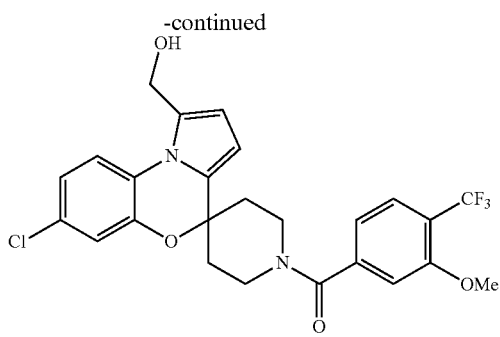

7-Chloro-1'-(3-methoxy-4-(trifluoromethyl)benzoyl)spiro[benzo[b]pyrrolo[1,2-d][1,4]oxazine-4,4'-piperidine]-1-carbaldehyde (50 mg, 0.10 mmol) dissolved in dry THF (3 mL) was cooled to 0° C. NaBH$_4$ (3.9 mg, 0.10 mmol) was added and stirring was continued for 30 min. The mixture was filtered through Celite, evaporated and purified by column chromatography (5-30% AcOEt in dichloromethane) to yield (7-chloro-1-(hydroxymethyl)spiro[benzo[b]pyrrolo[1,2-d][1,4]oxazine-4,4'-piperidine]-1'-yl)(3-methoxy-4-(trifluoromethyl)phenyl)methanone. ESI-MS m/z calc. 506.9. found 507.0 (M+1)$^+$; Retention time: 1.96 minutes (3 min run).

7-Chloro-1'-(3-methoxy-4-(trifluoromethyl)benzoyl)spiro[benzo[b]pyrrolo[1,2-d][1,4]oxazine-4,4'-piperidine]-1-carbonitrile

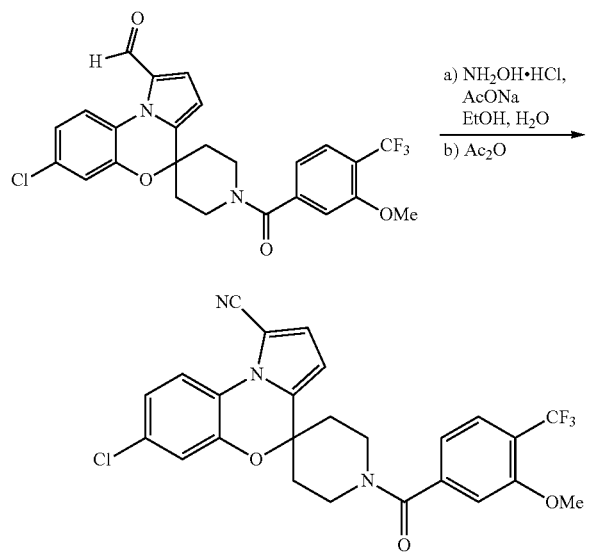 [SMILES: COc1cc(C(=O)N2CCC3(CC2)Oc2cc(Cl)ccc2-n2c(C=O)ccc23)ccc1C(F)(F)F ; COc1cc(C(=O)N2CCC3(CC2)Oc2cc(Cl)ccc2-n2c(C#N)ccc23)ccc1C(F)(F)F]

To a solution of 7-chloro-1'-(3-methoxy-4-(trifluoromethyl)benzoyl)spiro-[benzo[b]pyrrolo[1,2-d][1,4]oxazine-4,4'-piperidine]-1-carbaldehyde (310 mg, 0.61 mmol) in ethanol (1.5 mL) was added an aqueous solution of hydroxylamine hydrochloride (190 mg, 2.7 mmol) and sodium acetate (380 mg, 4.6 mmol) in water (1.5 mL). The mixture was heated at 95° C. for 2 hours. The reaction mixture was cooled to 25° C., water was added and the white precipitate that formed was collected by filtration, washed thoroughly with water and dried by azeotrope with toluene. The solid was dissolved in Ac$_2$O (1.1 mL, 12 mmol) and was heated at 140° C. for 3.5 hours. The mixture was cooled to 25° C., poured into ice, diluted with dichloromethane (30 mL), and neutralized with NaHCO$_3$ (2 g). The organic phase was separated, and the aqueous phase further extracted twice with dichloromethane. The organic layers were combined, washed with brine, dried, filtered, concentrated to a yellow oil that was purified by column chromatography (silica gel, 5-30% AcOEt in hexanes) to yield 7-chloro-1'-(3-methoxy-4-(trifluoromethyl)benzoyl)spiro[benzo-[b]pyrrolo[1,2-d][1,4]oxazine-4,4'-piperidine]-1-carbonitrile. $^1$H NMR (400 MHz, CDCl$_3$) δ 8.06 (t, J=10.1 Hz, 1H), 7.70 (s, 1H), 7.64 (dd, J=8.6, 1.6 Hz, 1H), 7.17 (d, J=2.2 Hz, 1H), 7.10 (dd, J=8.7, 2.2 Hz, 1H), 7.03 (dd, J=10.4, 6.3 Hz, 2H), 6.13 (d, J=4.0 Hz, 1H), 4.61 (s, 1H), 3.96 (d, J=20.2 Hz, 3H), 3.89-3.06 (m, 3H), 2.16-1.81 (m, 4H). ESI-MS m/z calc. 501.9. found 502.0 (M+1)$^+$; Retention time: 2.17 minutes (3 min run).

1'-(4-Isopropoxy-3-methylbenzoyl)spiro[benzo[b]pyrrolo[1,2-d][1,4]oxazine-4,4'-piperidine]-9-carbonitrile was synthesized from 1'-(4-isopropoxy-3-methylbenzoyl)spiro[benzo[b]pyrrolo[1,2-d][1,4]oxazine-4,4'-piperidine]-9-carbaldehyde using the procedure described above.

(4-Isopropoxy-3-methylphenyl)(1H-spiro[chromeno[3,4-d]imidazole-4,4'-piperidine]-1'-yl)methanone

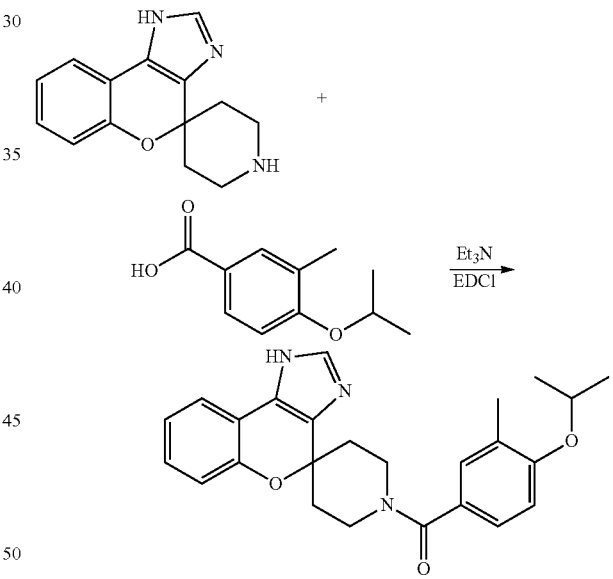

A mixture of 1H-spiro[chromeno[3,4-d]imidazole-4,4'-piperidine] (210 mg, 0.88 mmol), 4-isopropoxy-3-methyl-benzoic acid (170 mg, 0.89 mmol), triethylamine (370 μL, 2.6 mmol), and EDCI (170 mg, 0.89 mmol) in dichloromethane (5 mL) was stirred for 16 h. The reaction mixture was diluted with dichloromethane and was washed with 1M HCl, saturated solution of NaHCO$_3$, and brine. The organics were dried over sodium sulfate and evaporated to dryness. The crude product was purified by silica gel chromatography eluting with 0-100% methanol in dichloromethane to yield (4-isopropoxy-3-methylphenyl)(1H-spiro[chromeno[3,4-d]imidazole-4,4'-piperidine]-1'-yl)methanone (44 mg, 12%). ESI-MS m/z calc. 417.5. found 418.5 (M+1)$^+$; Retention time: 1.44 minutes (3 min run).

(4-Isopropoxy-3-methylphenyl)(1-Methyl-1H-spiro[chromeno[3,4-d]imidazole-4,4'-piperidine]-1'-yl)methanone and (4-isopropoxy-3-methylphenyl)(3-methyl-3H-spiro[chromeno[3,4-d]imidazole-4,4'-piperidine]-1'-yl)methanone

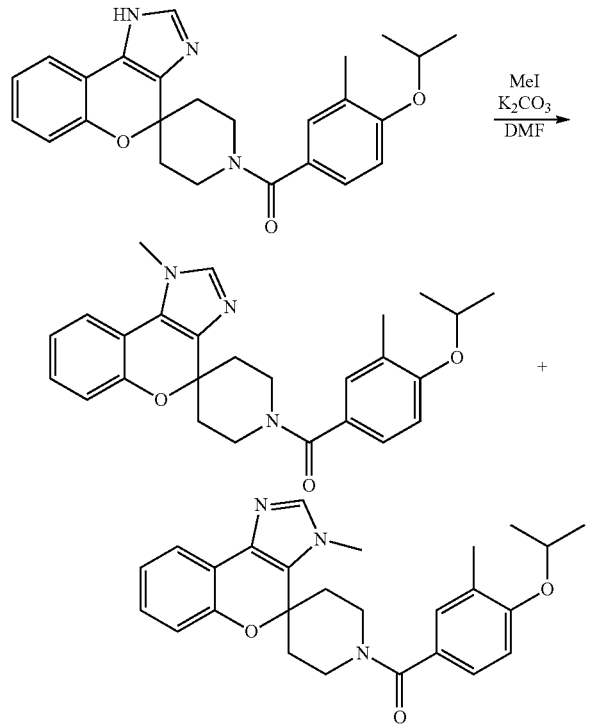

(4-Isopropoxy-3-methylphenyl)(1H-spiro[chromeno[3,4-d]imidazole-4,4'-piperidine]-1'-yl)methanone (44 mg, 0.11 mmol), iodomethane (20 µL, 0.32 mmol), and potassium carbonate (29 mg, 0.21 mmol) were stirred in DMF (1 mL) for 16 h. The reaction was filtered and evaporated. The crude material was purified by column chromatography eluting with 0-10% methanol in dichloromethane followed by reverse phase HPLC (gradient: 1-99% ACN in water with formic acid as the modifier) to separate the two regioisomers. First eluting product: ESI-MS m/z calc. 431.5. found 432.7 (M+1)$^+$; Retention time: 1.51 minutes (3 min run). Second eluting product: ESI-MS m/z calc. 431.5. found 432.7 (M+1)$^+$; Retention time: 1.54 minutes (3 min run).

(4-Cyclopropyl-3-methoxy-phenyl)-(1-methyl-1H-spiro[chromeno[4,3-c]pyrazole-4,4'-piperidine]-1'-yl)methanone

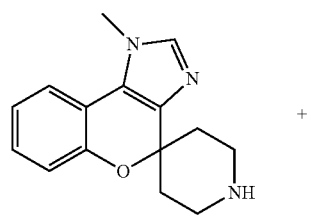

+

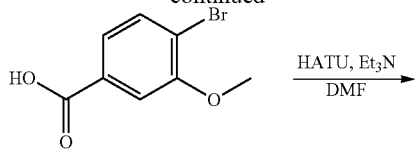

Step 1: (4-Bromo-3-methoxyphenyl)(1-methyl-1H-spiro[chromeno[4,3-c]pyrazole-4,4'-piperidine]-1'-yl)methanone To a 100 mL round bottom flask was added 4-bromo-3-methoxy-benzoic acid (860 mg, 3.7 mmol), HATU (1.4 g, 3.7 mmol), DMF (6 mL) and triethylamine (1.4 mL, 10 mmol). The reaction mixture was allowed to stir for 10 minutes. 1-Methylspiro[chromeno[4,3-c]pyrazole-4,4'-piperidine] (860 mg, 3.4 mmol) dissolved in DMF (6 mL) was added, and the mixture was allowed to stir at 25° C. After 2 h, the reaction was quenched with brine and was extracted with ethyl acetate. The combined organic layers were washed with brine 3 times. The combined organic layer were dried over sodium sulfate and evaporated. The residue was purified via silica gel chromatography (5-90% EtOAc:hexanes) to give (4-bromo-3-methoxyphenyl)(1-methyl-1H-spiro[chromeno[4,3-c]pyrazole-4,4'-piperidine]-1'-yl)methanone as white foam. ESI-MS m/z calc. 467.1. found 468.2 (M+1)$^+$. Retention time: 3.04 minutes (4 min run).

Step 2: (4-Cyclopropyl-3-methoxy-phenyl)-(1-methyl-1H-spiro[chromeno[4,3-e]pyrazole-4,4'-piperidine]-1'-yl)methanone

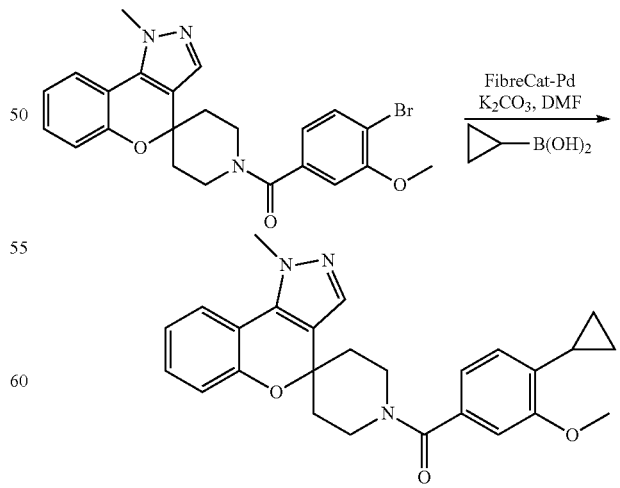

To a microwave vial was added (4-bromo-3-methoxyphenyl)(1-methyl-1H-spiro[chromeno[4,3-c]pyrazole-4,4'-piperidine]-1'-yl)methanone (70 mg, 0.15 mmol), cyclopropylboronic acid (26 mg, 0.30 mmol), Fibre cat (49 mg, 0.0075 mmol), DMF (0.7 mL), and K$_2$CO$_3$ (150 µL of 3.0 M, 0.45 mmol). The vial was purged with nitrogen and was heated at 120° C. for 2 hours. The reaction was filtered and purified by HPLC (20-99%) MeOH:H$_2$O. ESI-MS m/z calc. 429.2. found 430.4 (M+1)$^+$. Retention time: 2.95 minutes (4 min run).

(3-Methylbenzoimidazol-4-yl)-(1-methyl-1H-spiro[chromeno[4,3-c]pyrazole-4,4'-piperidine]-1'-yl)methanone

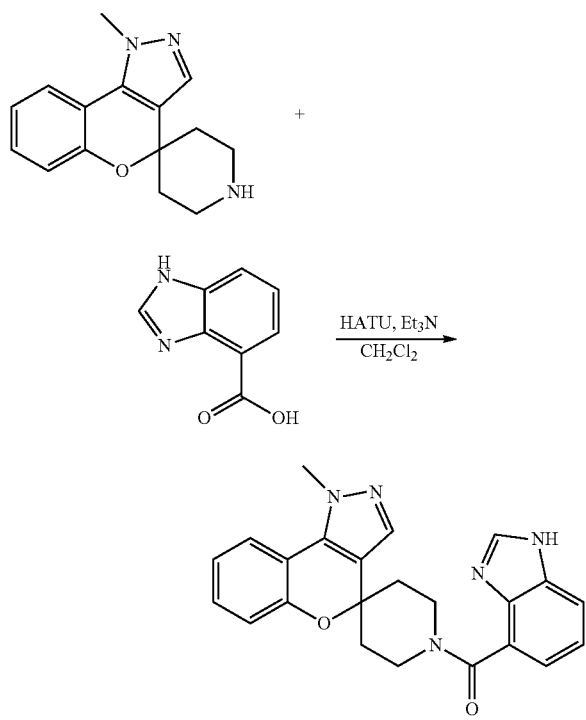

Step 1: (1H-Benzo[d]imidazol-4-yl)(1-methyl-1H-spiro[chromeno[4,3-e]pyrazole-4,4'-piperidine]-1'-yl)methanone To a solution of 1-methylspiro[chromeno[4,3-c]pyrazole-4,4'-piperidine] (211 mg, 0.830 mmol), 1H-benzimidazole-4-carboxylic acid (134 mg, 0.830 mmol) and triethylamine (346 µL, 2.50 mmol) in dichloromethane (2 mL) was added HATU (314 mg, 0.830 mmol) in one portion and the mixture was stirred for 12 hours. The reaction mixture was treated with 1M NaOH (1 mL) for 10 minutes. Dichloromethane (5 mL) was added. The two layers were separated and the aqueous layer was extracted with dichloromethane (2×5 mL). The organic layers were combined, washed with brine, dried over MgSO$_4$, filtered and evaporated to yield a residue that was purified on silica using a gradient of 0.5-30% MeOH in dichloromethane to yield (1H-benzo[d]imidazol-4-yl)(1-methyl-1H-spiro[chromeno[4,3-c]pyrazole-4,4'-piperidine]-1'-yl)methanone. ESI-MS m/z calc. 399.5. found 400.5 (M+1)$^+$. Retention time: 1.12 minutes (4 min run).

Step 2: (3-Methylbenzoimidazol-4-yl)-(1-methyl-1H-spiro[chromeno[4,3-c]pyrazole-4,4'-piperidine]-1'-yl)methanone

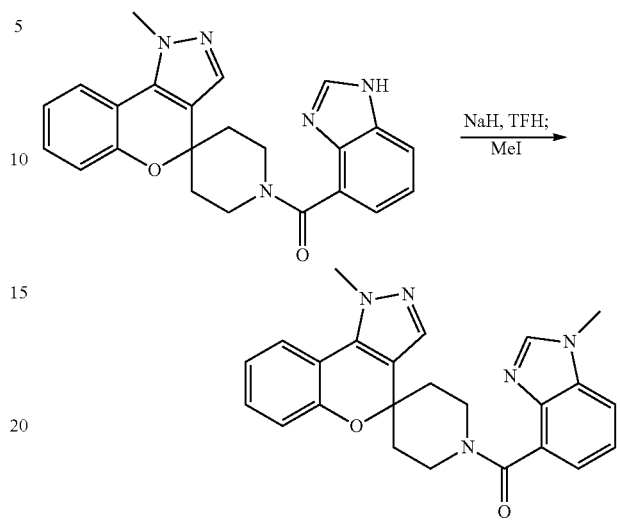

To a solution of (1H-benzo[d]imidazol-4-yl)(1-methyl-1H-spiro[chromeno[4,3-c]pyrazole-4,4'-piperidine]-1'-yl)methanone (21 mg, 0.052 mmol) in dry THF (0.2 mL) under N$_2$ was added NaH (1.9 mg, 0.079 mmol) at 0° C. After 30 min, MeI (3.3 µL, 0.052 mmol) was added and the mixture was stirred at 0° C. for 1 h. The reaction mixture was quenched with water and the solvent removed under vacuum to yield a crude residue that was taken up in methanol and purified by reverse phase HPLC to give (3-methylbenzoimidazol-4-yl)-(1-methyl-1H-spiro[chromeno[4,3-c]pyrazole-4,4'-piperidine]-1'-yl)methanone. ESI-MS m/z calc. 413.5. found 414.5 (M+1)$^+$. Retention time: 1.13 minutes (3 min run).

[4-(2-Hydroxy-1,1-dimethyl-ethyl)-3-methoxy-phenyl]-(1-methyl-1H-spiro[chromeno[4,3-c]pyrazole-4,4'-piperidine]-1'-yl)methanone

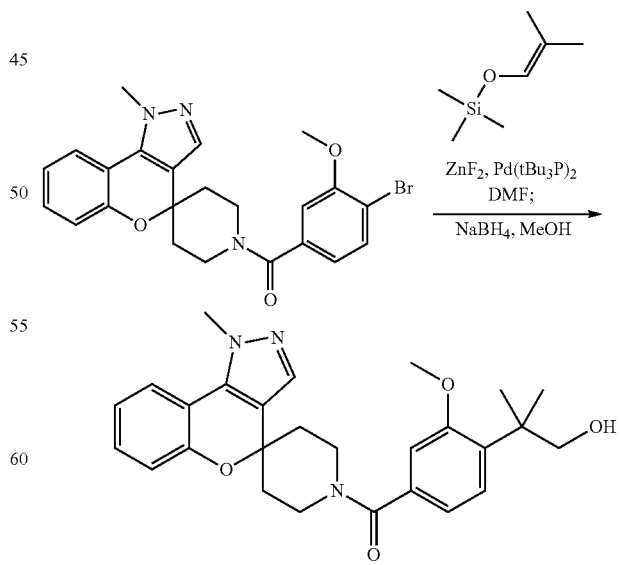

To a microwave vial was added difluorozinc (16 mg, 0.15 mmol) and Pd(tBu$_3$P)$_2$ (7.6 mg, 0.015 mmol). The vial was capped and purged with nitrogen for 10 minutes. DMF (1 mL) was added and the reaction mixture was allowed to stir for 10 minutes. (4-Bromo-3-methoxyphenyl)(1-methyl-1H-spiro[chromeno[4,3-c]pyrazole-4,4'-piperidine]-1'-yl)methanone (140 mg, 0.30 mmol) dissolved in DMF (0.5 mL) was added followed by trimethyl(2-methylprop-1-enoxy)silane (83 μL, 0.45 mmol). The reaction vessel was placed in an oil bath held at 80° C. for 16 hours. The reaction mixture was filtered, quenched with brine and extracted with ethyl acetate. The organic layer was dried over sodium sulfate, filtered and evaporated to dryness. The residue was dissolved in MeOH (2 mL). NaBH$_4$ (34 mg, 0.90 mmol) was added and the reaction mixture immediately turned from yellow to brown. The mixture was filtered and purified by HPLC (1-99%) MeOH:H$_2$O to provide [4-(2-hydroxy-1,1-dimethyl-ethyl)-3-methoxy-phenyl]-(1-methyl-1H-spiro[chromeno[4,3-c]pyrazole-4,4'-piperidine]-1'-yl)methanone. ESI-MS m/z calc. 461.5. found 462.2 (M+1)$^+$. Retention time: 2.73 minutes (4 min run). 1'-(4-(1-Hydroxy-2-methylpropan-2-yl)-3-methoxybenzoyl)spiro[benzo[b]pyrrolo-[1,2-d][1,4]oxazine-4,4'-piperidine]-1-carbonitrile was synthesized from 1'-(4-bromo-3-methoxybenzoyl)spiro[benzo[b]pyrrolo[1,2-d][1,4]oxazine-4,4'-piperidine]-1-carbonitrile using the procedures described above.

(4-Ethoxy-2-isopropoxy-phenyl)-(1-methyl-1H-spiro[chromeno[4,3-c]pyrazole-4,4'-piperidine]-1'-yl)methanone Step 1: (4-Ethoxy-2-hydroxyphenyl)(1-methyl-1H-spiro[chromeno[4,3-c]pyrazole-4,4'-piperidine]-1'-yl)methanone

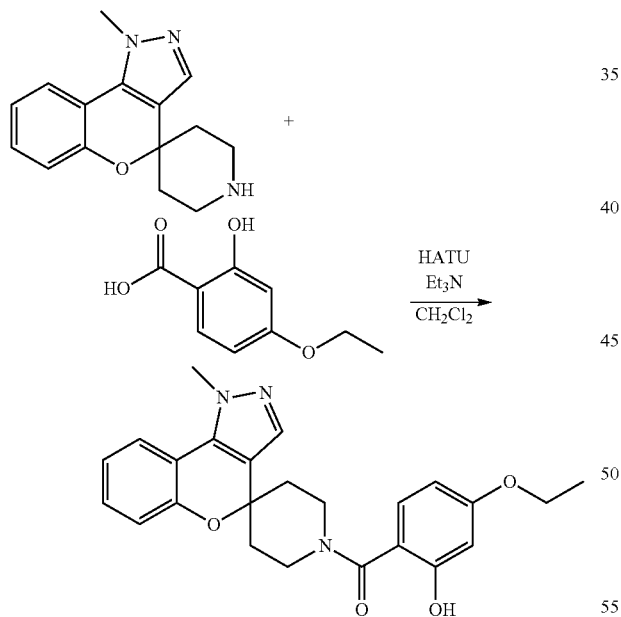

In a vial were added 4-ethoxy-2-hydroxybenzoic acid (0.40 mmol) followed by HATU (170 mg, 0.44 mmol), DMF (0.7 mL), and triethylamine (220 μL, 1.6 mmol). The mixture was stirred for 10 minutes before 1-methyl-1H-spiro[chromeno[4,3-c]pyrazole-4,4'-piperidine] (100 mg, 0.40 mmol) was added. The reaction mixture was allowed to stir at 25° C. for 12 hours before it was filtered and purified by HPLC (1-99%) MeOH:H$_2$O to yield (4-ethoxy-2-hydroxyphenyl)(1-methyl-1H-spiro[chromeno[4,3-c]pyrazole-4,4'-piperidine]-1'-yl)methanone (53 mg, 32%). ESI-MS m/z calc. 419.5. found 420.4 (M+1)$^+$. Retention time: 2.96 minutes (4 min run).

Step 2: (4-Ethoxy-2-isopropoxy-phenyl)-(1-methyl-1H-spiro[chromeno[4,3-c]pyrazole-4,4'-piperidine]-1'-yl)methanone

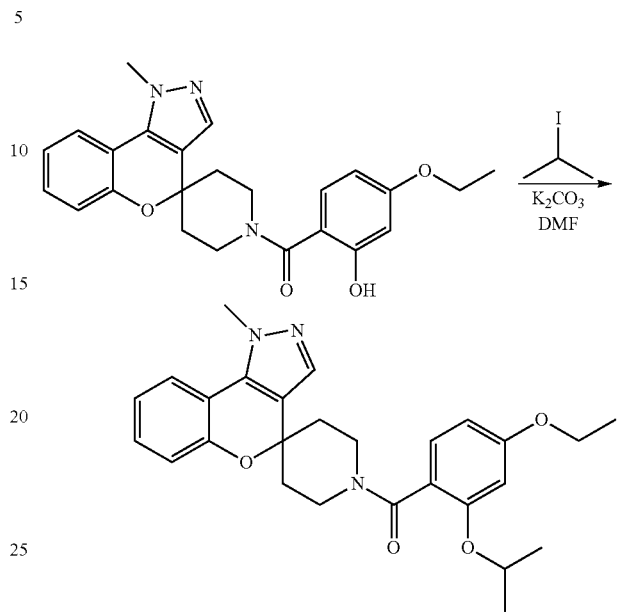

To a vial containing a solution of (4-ethoxy-2-hydroxyphenyl)(1-methyl-1H-spiro[chromeno[4,3-c]pyrazole-4,4'-piperidine]-1'-yl)methanone (41 mg, 0.1 mmol) in DMF (0.8 mL) was added K$_2$CO$_3$ (69 mg, 0.5 mmol), and 2-iodopropane (15 μL, 0.15 mmol). The mixture was stirred for 3 hours at 25° C. The crude reaction mixture was filtered and purified by HPLC (1-99%) MeOH:H$_2$O to yield (4-ethoxy-2-isopropoxy-phenyl)-(1-methyl-1H-spiro[chromeno[4,3-c]pyrazole-4,4'-piperidine]-1'-yl)methanone (17 mg, 33%). ESI-MS m/z calc. 461.5. found 462.2 (M+1)$^+$. Retention time: 3.16 minutes (4 min run).

(2-Isopropoxy-4-methoxyphenyl)(1-methyl-1H-spiro[chromeno[4,3-c]pyrazole-4,4'-piperidine]-1'-yl)methanone was synthesized using the procedures described above. ESI-MS m/z calc. 447.2. found 448.4 (M+1)$^+$; Retention time: 3.03 minutes (4 min run).

[3-(Hydroxymethyl)-4-isopropoxy-phenyl]-(1-methyl-1H-spiro[chromeno[4,3-c]pyrazole-4,4'-piperidine]-1'-yl)methanone Step 1: 2-Isopropoxy-5-(1-methylspiro[chromeno[4,3-c]pyrazole-4,4'-piperidine]-1'-carbonyl)benzaldehyde

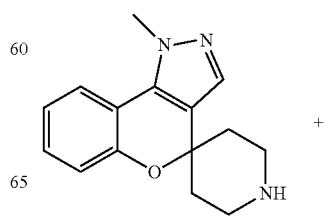

-continued

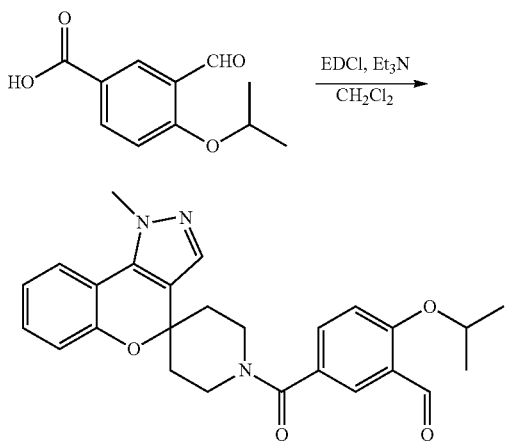

1-Methylspiro[chromeno[4,3-c]pyrazole-4,4'-piperidine] (250 mg, 0.76 mmol), 3-formyl-4-isopropoxy-benzoic acid (160 mg, 0.76 mmol), EDCI (160 mg, 0.84 mmol), and Et$_3$N (430 μL, 3.1 mmol) were combined in dichloromethane (7.1 mL) and the reaction mixture was stirred at room temperature for 48 hours. The reaction mixture was washed with a 1M HCl (×2), a saturated aqueous solution of NaHCO$_3$ (×2) and a saturated aqueous solution of NaCl. The organic layer was dried over Na$_2$SO$_4$, filtered and the solvent was evaporated under reduced pressure. The crude product was purified by column chromatography on silica gel (0-30% ethyl acetate in dichloromethane) to yield 2-isopropoxy-5-(1-methylspiro[chromeno[4,3-c]pyrazole-4,4'-piperidine]-4-carbonyl)benzaldehyde (117 mg, 34%) as a light yellow solid. ESI-MS m/z calc. 445.2. found 446.3 (M+1)$^+$; Retention time: 1.74 minutes (3 min run).

Step 2: [3-(Hydroxymethyl)-4-isopropoxy-phenyl]-(1-methyl-1H-spiro[chromeno[4,3-c]pyrazole-4,4'-piperidine]-1'-yl)methanone

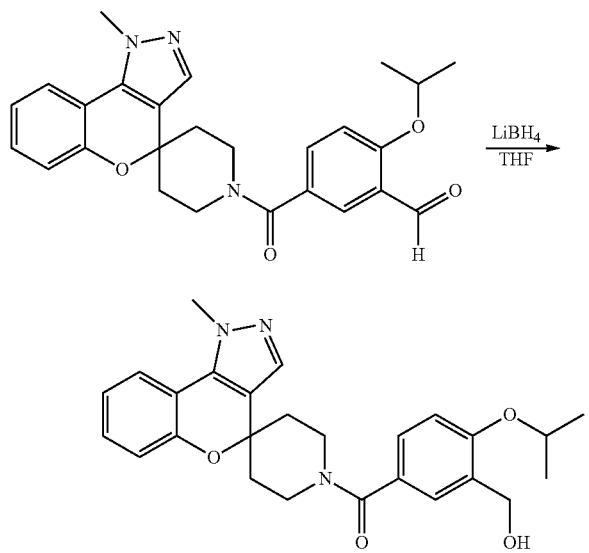

2-Isopropoxy-5-(1-methylspiro[chromeno[4,3-c]pyrazole-4,4'-piperidine]-1'-carbonyl)benzaldehyde (110 mg, 0.25 mmol) was dissolved in THF (3 mL) and LiBH$_4$ (11 mg, 0.50 mmol) was added. The reaction was stirred at room temperature for 1.5 h before being quenched with methanol (3 mL). The reaction was neutralized by the addition of a saturated sodium bicarbonate solution and was extracted with ethyl acetate (3×). The combined organic layers were dried over Na$_2$SO$_4$, filtered and the solvent was evaporated under reduced pressure. The crude product was purified by column chromatography on silica gel (0-100% ethyl acetate in hexane) to yield [3-(hydroxymethyl)-4-isopropoxy-phenyl]-(1-methylspiro[chromeno[4,3-c]pyrazole-4,4'-piperidine]-1'-yl)methanone (74 mg, 65%) as a white solid. ESI-MS m/z calc. 447.5. found 448.3 (M+1)$^+$. Retention time: 1.59 minutes (3 min run).

(7-Chlorospiro[benzo[b]pyrrolo[1,2-d][1,4]oxazine-4,4'-piperidine]-1'-yl)(4-(2-hydroxyethyl)-3-methoxyphenyl)methanone Step 1: 2-(4-(7-Chlorospiro[benzo[b]pyrrolo[1,2-d][1,4]oxazine-4,4'-piperidine]-1'-ylcarbonyl)-2-methoxyphenyl)acetaldehyde

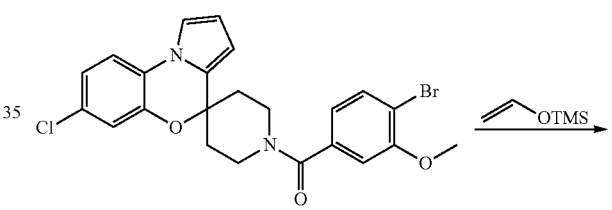

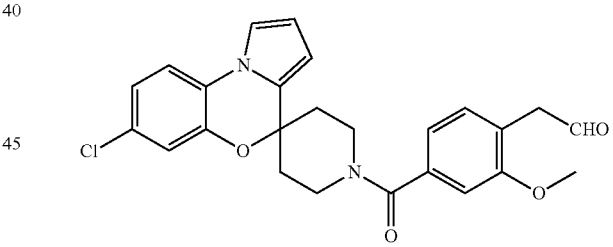

To a microwave vial was added Pd(tBu$_3$P)$_2$ (128 mg, 0.250 mmol) and difluorozinc (259 mg, 2.50 mmol). The vial was capped and purged with nitrogen for 10 minutes. DMF (1 mL) was added and the mixture was stirred for 10 minutes. A solution of (4-bromo-3-methoxy-phenyl)-(7'-chlorospiro[piperidine-4,4'-pyrrolo[2,1-c][1,4]benzoxazine]-1-yl)methanone (244 mg, 0.500 mmol) in DMF (1.5 mL) was added followed by trimethyl(vinyloxy)silane (581 mg, 5.00 mmol). The reaction mixture was heated at 80° C. for 1 h before it was quenched with brine and extracted with EtOAc (3×). The combined organic layers were dried over sodium sulfate and the solvent was removed. The crude reaction was purified by silica gel chromatography (5%-80% ethyl acetate/hexanes) to give 2-(4-(7-chlorospiro[benzo[b]pyrrolo[1,2-d][1,4]oxazine-4,4'-piperidine]-1'-ylcarbon-yl)-2-methoxyphenyl)acetaldehyde.

Step 2: (7-Chlorospiro[benzo[b]pyrrolo[1,2-d][1,4]oxazine-4,4'-piperidine]-1'-yl)(4-(2-hydroxyethyl)-3-methoxyphenyl)methanone

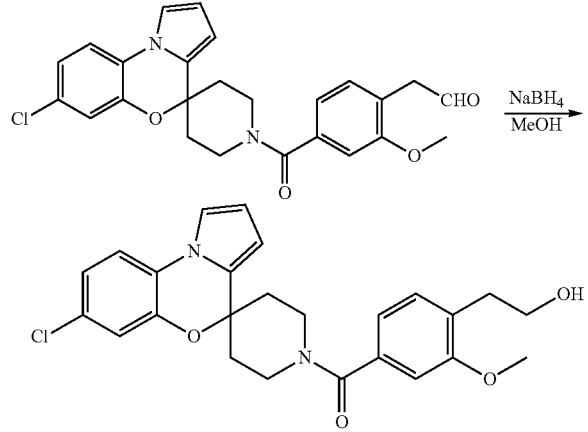

To 2-(4-(7-chlorospiro[benzo[b]pyrrolo[1,2-d][1,4]oxazine-4,4'-piperidine]-1'-ylcarbon-yl)-2-methoxyphenyl)acetaldehyde (from Step 1) was added MeOH (1 mL) followed by NaBH$_4$ (95 mg, 2.5 mmol) and the reaction was stirred for 30 minutes at ambient temperature. After 30 minutes, the mixture was filtered and the filtrate was purified by prep-HPLC (1-99% MeOH:H$_2$O) to give (7-chlorospiro[benzo[b]pyrrolo[1,2-d][1,4]-oxazine-4,4'-piperidine]-1'-yl)(4-(2-hydroxyethyl)-3-methoxyphenyl)methanone (16 mg, 7%). ESI-MS m/z calc. 452.2. found 453.2 (M+1)$^+$. Retention time: 2.91 minutes (4.5 min run).

(7-Chlorospiro[benzo[b]pyrrolo[1,2-d][1,4]oxazine-4,4'-piperidine]-1'-yl)(3-fluoro-4-(1-hydroxy-2-methylpropan-2-yl)phenyl)methanone [ESI-MS m/z calc. 468.2. found 469.4 (M+1)$^+$. Retention time: 3.06 minutes (4.5 min run)] and (7-chlorospiro[benzo[b]pyrrolo[1,2-d][1,4]oxazine-4,4'-piperidine]-1'-yl)(4-(1-hydroxy-2-methylpropan-2-yl)phenyl)methanone [ESI-MS m/z calc. 450.2. found 451.2 (M+1)$^+$. Retention time: 9.72 minutes (15 min run)] were prepared using the procedures described above.

(4-(Isopropylsulfonyl)-3-methoxyphenyl)(1-methyl-1H-spiro[chromeno[4,3-e]pyrazole-4,4'-piperidine]-1'-yl)methanone

Step 1: (4-(Isopropylthio)-3-methoxyphenyl)(1-methyl-1H-spiro[chromeno[4,3-c]pyrazole-4,4'-piperidine]-1'-yl)methanone

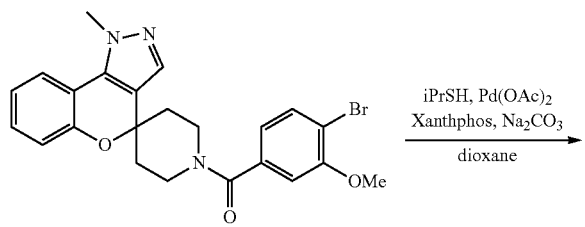

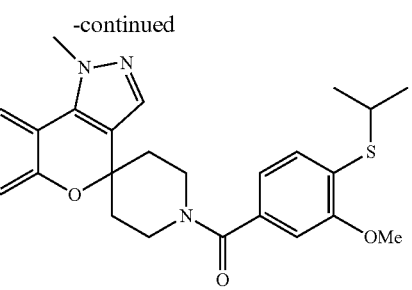

(4-Bromo-3-methoxy-phenyl)-(1-methylspiro[chromeno[4,3-c]pyrazole-4,4'-piperidine]-1'-yl)methanone (300 mg, 0.64 mmol), propane-2-thiol (30 µL, 0.32 mmol), (5-diphenylphosphanyl-9,9-dimethyl-xanthen-4-yl)-diphenyl-phosphane (22 mg, 0.038 mmol), palladium acetate (4.3 mg, 0.019 mmol), and sodium carbonate (680 mg, 6.4 mmol) were combined in 1,4-dioxane (1.3 mL). The reaction mixture was heated at 100° C. for 4 hours. A second aliquot of propane-2-thiol (30 µL, 0.32 mmol) was added and the reaction mixture was stirred for 16 hours. The crude reaction mixture was filtered and then evaporated to dryness. The crude material was purified by column chromatography utilizing a gradient of 0-100% ethyl acetate in dichloromethane to provide a mixture of (4-(isopropylthio)-3-methoxyphenyl)(1-methyl-1H-spiro[chromeno[4,3-c]pyrazole-4,4'-piperidine]-1'-yl)methanone and (4-bromo-3-methoxy-phenyl)-(1-methyl-spiro[chromeno[4,3-c]pyrazole-4,4'-piperidine]-1'-yl)methanon.

Step 2: (4-(Isopropylsulfonyl)-3-methoxyphenyl)(1-methyl-1H-spiro[chromeno[4,3-c]pyrazole-4,4'-piperidine]-1'-yl)methanone

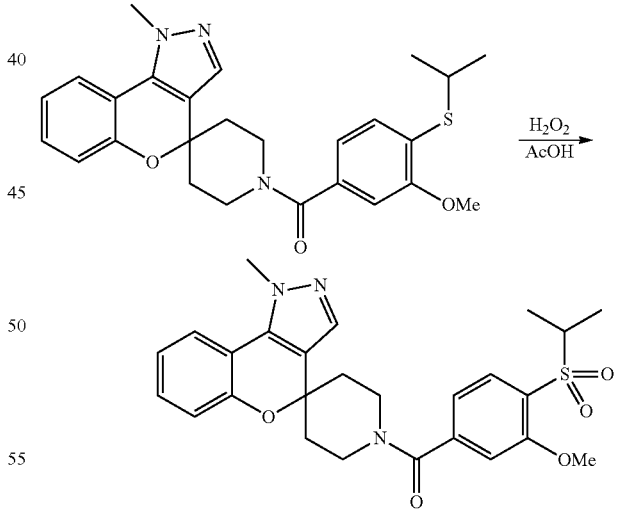

(4-Isopropylsulfanyl-3-methoxy-phenyl)-(1-methylspiro[chromeno[4,3-c]pyrazole-4,4'-piperidine]-1'-yl)methanone (291 mg, 0.6277 mmol) was dissolved in acetic acid (3 mL) and hydrogen peroxide (200 µL, 6.527 mmol) was added. The reaction mixture was heated at 80° C. for 40 minutes before it was partitioned between ethyl acetate (15 mL) and water (10 mL). The organic layer was washed with a saturated aqueous solution of sodium chloride, dried over sodium sulfate and then purified by column chromatography utilizing a gradient of 0-5% methanol in dichloromethane to yield (4-isopropyl-sulfonyl-3-methoxy-phenyl)-(1-methylspiro[chromeno[4,3-c]pyrazole-4,4'-piperidine]-1'-yl)methanone (51 mg, 24%) as a white solid. ESI-MS m/z calc. 495.2. found 496.5 (M+1)$^+$. Retention time: 1.52 minutes (3 min run). $^1$H NMR (400 MHz, DMSO) δ 7.83 (d, J=8.0 Hz, 1H), 7.74 (d, J=7.6 Hz, 1H), 7.45 (s, 1H), 7.34 (s, 1H), 7.29 (t, J=7.8 Hz, 1H), 7.22 (d, J=8.0 Hz, 7.15-7.06 (m, 2H), 4.45-4.31 (m, 1H), 4.10 (s, 3H), 3.97 (s, 3H), 3.68 (septet, J=6.7 Hz, 1H), 3.59-3.22 (m, 3H), 2.10-1.82 (m, 4H), 1.17 (d, J=6.9 Hz, 6H).

(4-(tert-Butylsulfonyl)-3-methoxyphenyl)(1-methyl-1H-spiro[chromeno[4,3-c]pyrazole-4,4'-piperidine]-1'-yl)methanone was also synthesized using the procedures described above. (4-(tert-Butylsulfonyl)-3-methylphenyl)(1-methyl-1H-spiro-[chromeno[4,3-c]pyrazole-4,4'-piperidine]-1'-yl)methanone and (4-(ethylsulfonyl)-3-methylphenyl)(1-methyl-1H-spiro[chromeno[4,3-c]pyrazole-4,4'-piperidine]-1'-yl)methanone were synthesized from (4-bromo-3-methylphenyl)(1-methyl-1H-spiro[chromeno[4,3-c]pyrazole-4,4'-piperidine]-1'-yl)methanone using the procedures described above.

7-Chloro-1'-(4-isopropoxy-3-methylbenzoyl)-N-methylspiro[benzo[b]pyrrolo[1,2-d][1,4]oxazine-4,4'-piperidine]-1-carboxamide Step 1: 7-Chloro-1'-(4-isopropoxy-3-methylbenzoyl)spiro[benzo[b]-pyrrolo[1,2-d][1,4]oxazine-4,4'-piperidine]-1-carboxylic acid

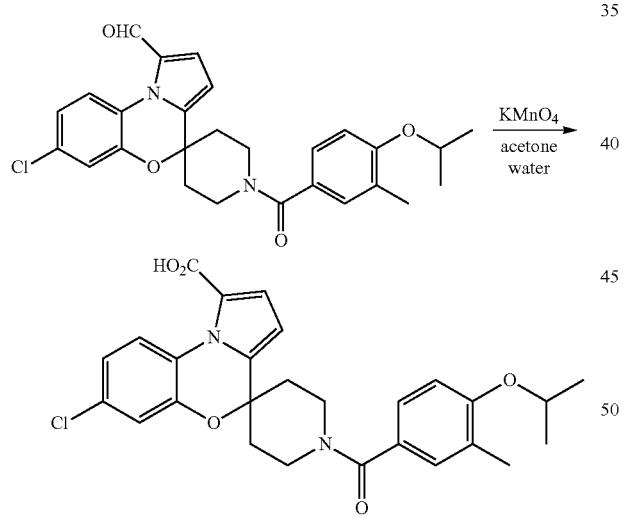

To a solution of 7-chloro-1'-(4-isopropoxy-3-methylbenzoyl)spiro-[benzo[b]pyrrolo[1,2-d][1,4]oxazine-4,4'-piperidine]-1-carbaldehyde (130 mg, 0.27 mmol) in acetone (1.5 mL) was added a solution of potassium permanganate (43 mg, 16 μL, 0.27 mmol) in water (1.5 mL) and acetone (1.5 mL) dropwise at 0° C. The mixture was allowed to stir at room temperature for 2 h before it was concentrated onto Celite from methanol. Column chromatography on the residue (0-20% EtOAc/CH$_2$Cl$_2$) gave 7-chloro-1'-(4-isopropoxy-3-methylbenzoyl)spiro[benzo[b]-pyrrolo[1,2-d][1,4]oxazine-4,4'-piperidine]-1-carboxylic acid (13%).

Step 2: 7-Chloro-1'-(4-isopropoxy-3-methylbenzoyl)-N-methylspiro[benzo[b]pyrrolo[1,2-d][1,4]oxazine-4,4'-piperidine]-1-carboxamide

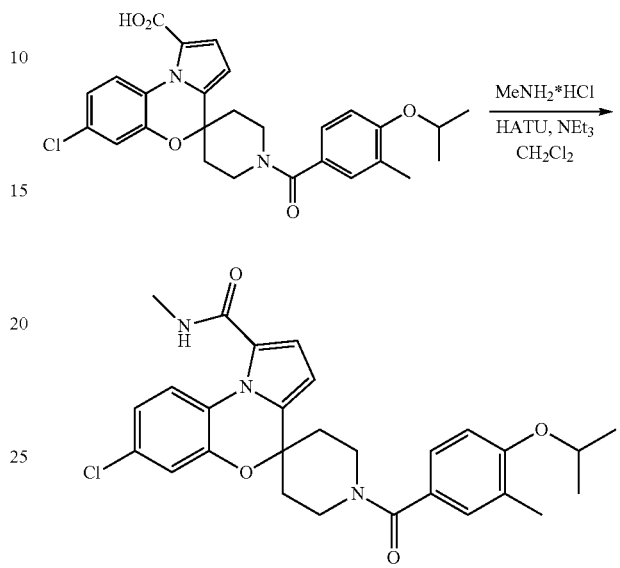

7-Chloro-1'-(4-isopropoxy-3-methylbenzoyl)spiro[benzo[b]-pyrrolo[1,2-d][1,4]oxazine-4,4'-piperidine]-1-carboxylic acid (17 mg, 0.034 mmol), methanamine hydrochloride (2.3 mg, 0.034 mmol), and Et$_3$N (19 μL, 0.14 mmol) were taken up in dry dichloromethane (0.5 mL). HATU (13 mg, 0.034 mmol) was added and the mixture was allowed to stir for 15 min at room temperature. The mixture was purified by prep-HPLC to provide 7-chloro-1'-(4-isopropoxy-3-methyl-benzoyl)-N-methylspiro[benzo[b]pyrrolo[1,2-d][1,4]oxazine-4,4'-piperidine]-1-carboxamide. ESI-MS m/z calc. 507.2. found 508.0 (M+1)$^+$. Retention time: 1.92 minutes (3 min run).

(2-Methoxy-4-(methylsulfonyl)phenyl)(1-methyl-1H-spiro[chromeno[4,3-e]pyrazole-4,4'-piperidine]-1'-yl)methanone Step 1: (2-Methoxy-4-(methylthio)phenyl)(1-methyl-1H-spiro[chromeno[4,3-c]pyrazole-4,4'-piperidine]-1'-yl)methanone

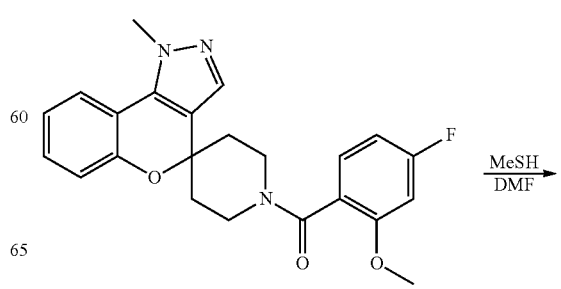

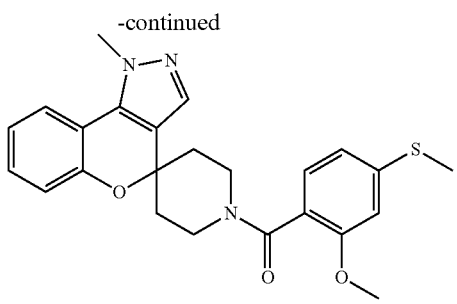

A mixture of (4-fluoro-2-methoxyphenyl)(1-methyl-1H-spiro[chromeno[4,3-c]pyrazole-4,4'-piperidine]-1'-yl)methanone (500 mg, 1.23 mmol) and methanethiol (172 mg, 2.45 mmol) in DMF (5 mL) was heated at 80° C. for 36 h. The reaction led to the desired product as well as O-demethylated version of the product. To the crude reaction mixture was added 3 eq of iodomethane to remethylate to the desired product. The reaction mixture was washed with 1N HCl, sat. aq. NaHCO$_3$, and brine. The organics were dried over sodium sulfate and evaporated. The crude product was purified by column chromatography eluting with 50-100% ethyl acetate in hexanes to give (2-methoxy-4-(methylthio)phenyl)(1-methyl-1H-spiro[chromeno[4,3-c]pyrazole-4,4'-piperidine]-1'-yl)methanone (60%). ESI-MS m/z calc. 435.2. found 436.1 (M+1)$^+$. Retention time: 1.53 minutes (3 min run).

Step 2: (2-Methoxy-4-(methylsulfonyl)phenyl)(1-methyl-1H-spiro[chromeno[4,3-c]pyrazole-4,4'-piperidine]-1'-yl)methanone

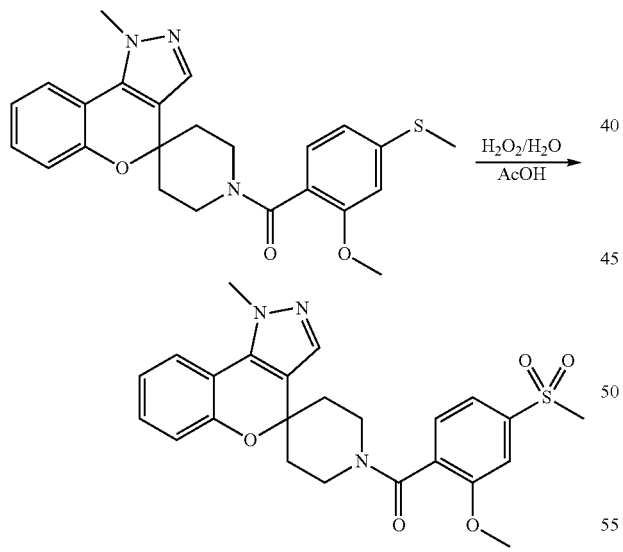

A mixture of (2-methoxy-4-(methylthio)phenyl)(1-methyl-1H-spiro[chromeno[4,3-c]pyrazole-4,4'-piperidine]-1'-yl)methanone (320 mg, 0.74 mmol) and 30% hydrogen peroxide (250 µL) in acetic acid (3 mL) was heated at 80° C. for 45 min. The mixture was diluted with water and was extracted with ethyl acetate. The organics were washed with sat. aq. NaHCO$_3$ and brine. The organics were dried over sodium sulfate and evaporated to dryness. The crude material was purified by column chromatography eluting with 70-100% ethyl acetate in hexanes to give (2-methoxy-4-(methylsulfonyl)phenyl)(1-methyl-1H-spiro[chromeno[4,3-c]pyrazole-4,4'-piperidine]-1'-yl)methanone. ESI-MS m/z calc. 467.2. found 468.2 (M+1)$^+$. Retention time: 1.29 minutes (3 min run). $^1$H NMR (400 MHz, DMSO) δ 7.76-7.70 (m, 1H), 7.63-7.41 (m, 4H), 7.28 (t, J=7.7 Hz, 1H), 7.18-7.04 (m, 2H), 4.46-4.35 (m, 1H), 4.14-4.05 (m, 3H), 3.98-3.90 (m, 3H), 3.53-3.36 (m, 1H), 3.28 (s, 3H), 3.30-3.14 (m, 2H), 2.09-1.77 (m, 4H).

(4-(Isopropylsulfonyl)-2-methoxyphenyl)(1-methyl-1H-spiro[chromeno[4,3-c]pyrazole-4,4'-piperidine]-1'-yl) methanone was also synthesized using the procedures described above. (1-Methyl-1H-spiro[chromeno[4,3-c]pyrazole-4,4'-piperidine]-1'-yl)(3-methyl-4-(methylsulfonyl)phenyl)methanone was synthesized from (4-fluoro-3-methylphenyl)(1-methyl-1H-spiro[chromeno[4,3-c]pyrazole-4,4'-piperidine]-1'-yl)methanone using the procedures described above.
(4-(Isopropylsulfonyl)-2-methylphenyl)(1-methyl-1'-1-spiro[chromeno[4,3-c]pyrazole-4,4'-piperidine]-1'-yl) methanone was synthesized from (4-fluoro-2-methylphenyl)(1-methyl-1H-spiro[chromeno[4,3-c]pyrazole-4,4'-piperidine]-1'-yl)methanone using the procedures above.

N,N-Dimethyl-2-(1-methylspiro[chromeno[4,3-c]pyrazole-4,4'-piperidine]-1'-carbonyl)benzamide Step 1: 2-(1-Methylspiro[chromeno[4,3-c]pyrazole-4,4'-piperidine]-1'-carbonyl)benzoic acid

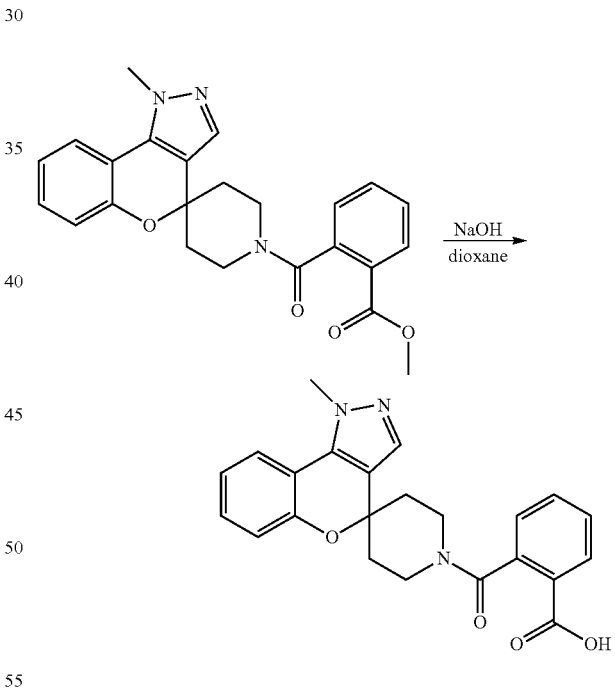

A mixture of methyl 2-(1-methylspiro[chromeno[4,3-c]pyrazole-4,4'-piperidine]-1'-carbonyl)benzoate (500 mg, 1.17 mmol), NaOH (5.0 mL of 1.0 M, 5.0 mmol), and 1,4-dioxane (5 mL) was heated at 80° C. for 1.5 h. The mixture was cooled to rt before it was concentrated in vacuo. The solid residue was taken up in water and was washed with ethyl acetate which was discarded. The aqueous layer was acidified with 1N HCl and was extracted with ethyl acetate (2×). The combined organics were washed with brine, dried over sodium sulfate, and were concentrated in vacuo to give 2-(1-methylspiro[chromeno[4,3-c]pyrazole-4,4'-piperidine]-1'-carbonyl)benzoic acid (33 mg, 75%) as a white solid. ESI-MS m/z calc. 403.2. found 404.2 (M+1)+; Retention time: 2.31 minutes (3 min run). $^1$H NMR (400 MHz, DMSO) δ 13.22 (s, 1H), 7.93 (d, J=7.7 Hz, 1H), 7.73 (d, J=7.6 Hz, 1H), 7.65 (t, J=7.4 Hz, 1H), 7.52 (t, J=7.6 Hz, 1H), 7.36 (br s, 2H), 7.28 (t, J=7.7 Hz, 1H), 7.08 (dd, J=13.8, 6.3 Hz, 2H), 4.39 (br s, 1H), 4.10 (s, 3H), 3.30-3.12 (m, 2H), 2.05-1.86 (m, 4H), 1.85-1.74 (m, 1H).

Step 2: N,N-Dimethyl-2-(1-methylspiro[chromeno[4,3-c]pyrazole-4,4'-piperidine]-1'-carbonyl)benzamide

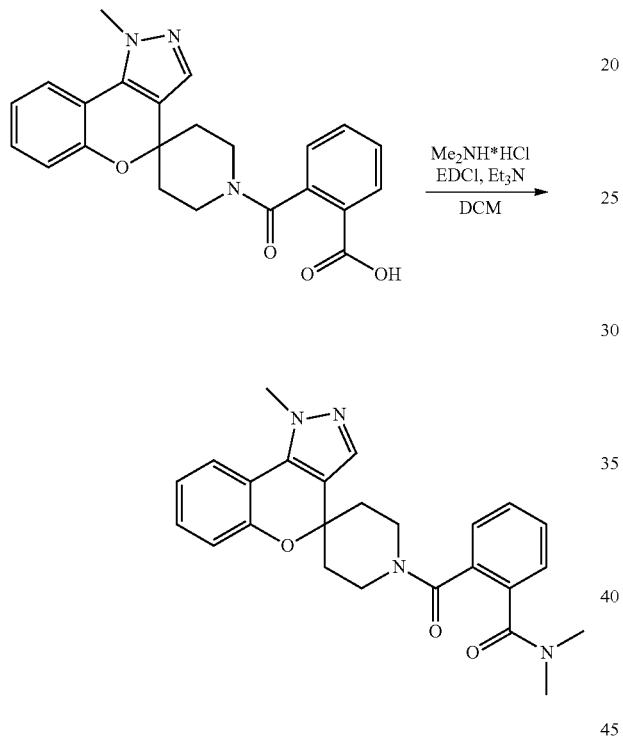

Et$_3$N (170 µL, 1.2 mmol) was added to a mixture of 2-(1-methylspiro[chromeno[4,3-c]pyrazole-4,4'-piperidine]-1'-carbonyl)benzoic acid (100 mg, 0.25 mmol), N-methylmethanamine hydrochloride (30 mg, 0.37 mmol), EDCI (48 mg, 0.25 mmol), and CH$_2$Cl$_2$ (1.5 mL) at ambient temperature. The mixture was allowed to stir for 16 h before it was diluted with CH$_2$Cl$_2$ and was washed with 1N HCl. The layers were separated and the organic layer was washed with 1N NaOH, and then brine before it was dried over sodium sulfate and was concentrated in vacuo to give N,N-dimethyl-2-(1-methylspiro[chromeno[4,3-c]pyrazole-4,4'-piperidine]-1'-carbonyl)benzamide (38 mg) as a white solid. ESI-MS m/z calc. 430.2. found 431.3 (M+1)+; Retention time: 2.24 minutes (3 min run). $^1$H NMR (400 MHz, CDCl$_3$) δ 7.56 (d, J=7.7 Hz, 1H), 7.45-7.37 (m, 3H), 7.46-7.22 (m, 2H), 7.30-7.21 (m, 1H), 7.13-7.00 (m, 2H), 4.52 (d, J=13.5 Hz, 1H), 4.19 (s, 3H), 3.74-3.51 (m, 2H), 3.31 (t, J=11.9 Hz, 1H), 3.09 (s, 3H), 2.94 (s, 3H), 2.24-2.02 (m, J=13.9 Hz, 2H), 2.02-1.76 (m, 2H).

N-isopropyl-4-(1-methyl-1H-spiro[chromeno[4,3-c]pyrazole-4,4'-piperidine]-1'-ylcarbonyl)benzamide was synthesized from 4-(1-methyl-1H-spiro[chromeno[4,3-c]pyrazole-4,4'-piperidine]-1'-ylcarbonyl)benzoic acid using the procedures described above.

(S)-(4-(Tetrahydrofuran-3-ylsulfonyl)phenyl)(1-(trifluoromethyl)spiro[benzo[b]pyrrolo[1,2-d][1,4]oxazine-4,4'-piperidine]-1'-yl)methanone and (R)-(4-(tetrahydrofuran-3-ylsulfonyl)phenyl)(1-(trifluoromethyl)spiro[benzo[b]pyrrolo[1,2-d][1,4]oxazine-4,4'-piperidine]-1'-yl)methanone

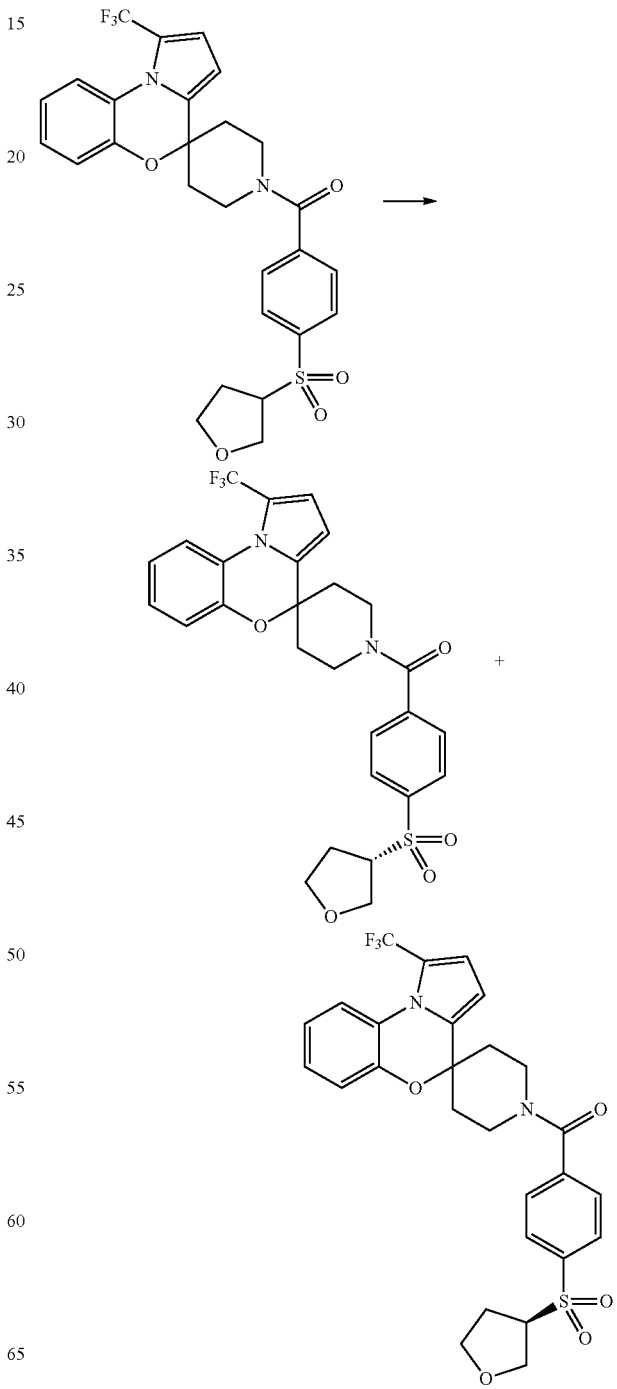

(4-(Tetrahydrofuran-3-ylsulfonyl)phenyl)(1-(trifluoromethyl)spiro[benzo[b]pyrrolo[1,2-d][1,4]oxazine-4,4'-piperidine]-1'-yl)methanone was subjected to chiral SFC (column: Phenomenex Lux Cellulose-2 (250×10 mm), 5 µm; mobile phase: 40% IPA w/0.2% DEA, 60% CO$_2$; concentration: 30 mg/mL in MeOH; injection volume: 20 µA; pressure: 100 bar; detection wavelength: 254 nm) to give two peaks. For each enantiomer, the solvent was evaporated and the residue was dissolved in ethyl acetate. The solution was washed with aqueous 1M hydrochloric acid (1×1 mL), a saturated aqueous solution of sodium bicarbonate (1×1 mL) and a saturated aqueous solution of sodium chloride (1×1 mL). The organic layer was dried over sodium sulfate, filtered and the solvent was evaporated under reduced pressure to yield [4-[(3S)-tetrahydrofuran-3-yl]sulfonylphenyl]-[1'-(trifluoromethyl)spiro[piperidine-4,4'-pyrrolo[2,1-c][1,4]benzoxazine]-1-yl]methanone as a yellow solid (peak 1, the stereochemistry was randomly assigned): ESI-MS m/z calc. 546.1. found 547.2 (M+1)$^+$; Retention time: 1.93 minutes (3 min run); NMR (400 MHz, DMSO) δ 7.99 (d, J=8.4 Hz, 2H), 7.74 (d, J=8.3 Hz, 2H), 7.57 (d, J=8.0 Hz, 1H), 7.37-7.14 (m, 3H), 7.03 (d, J=3.9 Hz, 1H), 6.40 (d, J=4.0 Hz, 1H), 4.53-4.36 (m, 1H), 4.33-4.19 (m, 1H), 4.08-3.94 (m, 1H), 3.91-3.58 (m, 3H), 3.56-3.16 (m, 3H), 2.19-1.82 (m, 6H) and [4[(3R)-tetrahydrofuran-3-yl]sulfonylphenyl]-[1'-(trifluoromethyl)spiro[piperidine-4,4'-pyrrolo[2,1-c][1,4]benzoxazine]-1-yl]methanone as a yellow solid (peak 2, the stereochemistry was randomly assigned): ESI-MS m/z calc. 546.1. found 547.2 (M+1)$^+$; Retention time: 1.93 minutes (3 min run); $^1$H NMR (400 MHz, DMSO) δ 7.99 (d, J=8.3 Hz, 2H), 7.74 (d, J=8.3 Hz, 2H), 7.57 (d, J=8.2 Hz, 1H), 7.36-7.14 (m, 3H), 7.03 (d, J=3.9 Hz, 1H), 6.40 (d, J=4.0 Hz, 1H), 4.54-4.36 (m, 1H), 4.33-4.17 (m, 1H), 4.09-3.95 (m, 1H), 3.90-3.59 (m, 3H), 3.58-3.12 (m, 3H), 2.24-1.77 (m, 6H).

7-(Hydroxymethyl)-1'-(4-(isopropylsulfonyl)benzoyl)spiro[benzo-[b]pyrrolo[1,2-d][1,4]oxazine-4,4'-piperidine]-1-carbonitrile

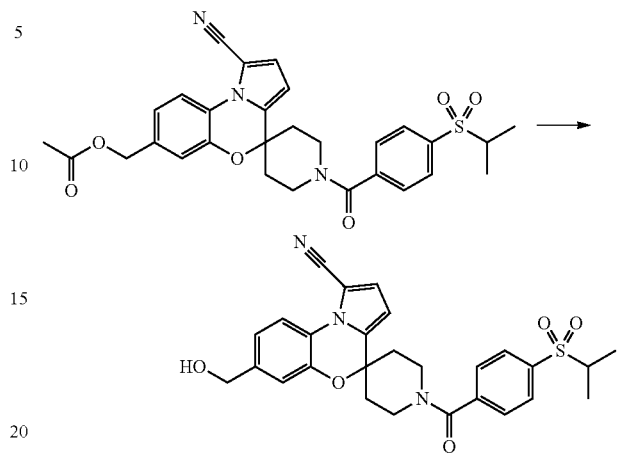

(1-Cyano-1'-(4-(isopropylsulfonyl)benzoyl)spiro[benzo[b]pyrrolo[1,2-d][1,4]oxazine-4,4'-piperidine]-7-yl)methyl acetate (16.2 mg, 0.0297 mmol) was treated with 1M LiOH (1 mL), THF (5 mL) and MeOH (1 mL). The mixture was stirred at room temperature over night. The volatiles were removed and the residue was neutralized with 1N HCl. The mixture was extracted with CH$_2$Cl$_2$ (2×). The combined organics were dried over sodium sulfate, filtered and concentrated under reduced pressure to give 7'-(hydroxymethyl)-1-(4-isopropylsulfonylbenzoyl)spiro[piperidine-4,4'-pyrrolo[2,1-c][1,4]benzoxazine]-1'-carbonitrile (11.3 mg, 75%). ESI-MS m/z calc. 505.58. found 506.5 (M+1)$^+$; Retention time 1.49 minutes (3 min run). NMR (400 MHz, DMSO) δ 7.93 (dd, J=8.2, 6.5 Hz, 3H), 7.73 (d, J=8.3 Hz, 2H), 7.32 (d, J=4.0 Hz, 1H), 7.25 (s, 1H), 7.15 (d, J=8.4 Hz, 1H), 6.45 (d, J=4.1 Hz, 1H), 5.39-5.30 (m, 1H), 4.51 (s, 2H), 3.81-3.64 (m, 1H), 3.54-3.42 (m, 2H), 3.41-3.37 (m, 1H), 2.20-2.12 (m, 1H), 2.13-2.03 (m, 1H), 2.01 (t, J=5.9 Hz, 1H), 1.57 (dd, J=12.5, 6.2 Hz, 1H), 1.17 (d, J=6.8 Hz, 6H).

Table 2 below recites the analytical data for the compounds of Table 1.

TABLE 2

| Cmpd No. | LC/MS M + 1 | LC/RT min | $^1$H NMR |
|---|---|---|---|
| 1 | 523.25 | 2.48 | |
| 2 | 436.08 | 2.13 | |
| 3 | 430.70 | 1.61 | 1H NMR (400 MHz, CDCl3) d 8.12 (d, J = 7.9 Hz, 1H), 7.42 (d, J = 7.4 Hz, 1H), 7.27-7.05 (m, 4H), 7.02 (dd, J = 7.0, 4.0 Hz, 1H), 6.10 (dd, J = 14.8, 3.9 Hz, 1H), 4.86-4.72 (m, 2H), 4.70-4.55 (m, 1H), 3.88 (d, J = 4.8 Hz, 3H), 3.62-3.51 (m, 1H), 3.48-3.17 (m, 3H), 2.32-1.87 (m, 6H), 1.78-1.62 (m, 1H). |
| 4 | 432.70 | 1.56 | |
| 5 | 432.30 | 1.96 | |
| 6 | 483.16 | 1.98 | |
| 7 | 431.00 | 2.19 | |
| 8 | 485.30 | 1.62 | |
| 9 | 485.50 | 1.79 | 1H NMR (400 MHz, CDCl3) d 7.69-7.61 (m, 3H), 7.43 (d, J = 8.2 Hz, 2H), 7.23-7.01 (m, 3H), 6.81 (d, J = 3.9 Hz, 1H), 6.06 (d, J = 3.9 Hz, 1H), 4.92 (d, J = 8.0 Hz, 2H), 4.82 (d, J = 8.0 Hz, 2H), 4.66 (bs, 1H), 3.80-3.15 (m, 4H), 2.32-1.67 (m, 4). |
| 10 | 462.20 | 3.16 | |
| 11 | 533.50 | 2.13 | 1H NMR (400 MHz, DMSO) d 7.98 (d, J = 8.1 Hz, 2H), 7.73 (d, J = 8.0 Hz, 2H), 7.57 (d, J = 8.1 Hz, 1H), 7.34-7.25 (m, 2H), 7.25-7.16 (m, 1H), 7.03 (d, J = 3.9 Hz, 1H), 6.40 (d, J = 3.9 Hz, 1H), 4.49-4.39 (m, 1H), 3.58-3.37 (m, 3H), 3.27 (d, J = 6.5 Hz, 2H), |

TABLE 2-continued

| Cmpd No. | LC/MS M + 1 | LC/RT min | ¹H NMR |
|---|---|---|---|
| | | | 2.17-1.96 (m, 4H), 1.93-1.80 (m, 1H), 0.98 (d, J = 6.7 Hz, 6H). |
| 12 | 563.40 | 1.91 | 1H NMR (400 MHz, DMSO) d 7.88 (d, J = 8.4 Hz, 2H), 7.61-7.53 (m, 3H), 7.36-7.24 (m, 2H), 7.24-7.16 (m, 1H), 7.02 (d, J = 4.0 Hz, 1H), 6.41 (d, J = 4.0 Hz, 1H), 4.55-4.34 (m, 1H), 3.62-3.38 (m, 2H), 3.29-3.06 (m, 1H), 2.22-1.79 (m, 4H), 1.34 (s, 6H). |
| 13 | 462.50 | 1.98 | |
| 14 | 429.30 | 1.51 | |
| 15 | 469.97 | 3.72 | |
| 16 | 420.30 | 1.75 | |
| 17 | 493.50 | 1.53 | 1H NMR (400 MHz, DMSO) d 8.00 (d, J = 7.9 Hz, 1H), 7.86 (d, J = 8.2 Hz, 2H), 7.73 (t, J = 5.8 Hz, 1H), 7.67 (d, J = 8.1 Hz, 2H), 7.36-7.28 (m, 3H), 7.27-7.17 (m, 1H), 6.47 (d, J = 4.0 Hz, 1H), 4.76-4.64 (m, 1H), 4.52-4.46 (m, 1H), 3.58-3.14 (m, 4H), 2.85-2.76 (m, 2H), 2.15-2.00 (m, 3H), 1.98-1.84 (m, 1H). |
| 18 | 448.34 | 1.83 | |
| 19 | 534.50 | 1.64 | |
| 20 | 491.14 | 2.03 | |
| 21 | 445.08 | 2.10 | |
| 22 | 424.10 | 1.77 | 1H NMR (400 MHz, CDCl3) d 12.26, 7.52, 7.26, 7.24, 7.09, 7.01, 6.99, 6.32, 6.30, 6.01, 5.97, 5.94, 4.76, 4.73, 4.65, 4.61, 3.68, 3.65, 3.62, 3.51, 3.48, 3.44, 3.40, 3.37, 3.27, 3.25, 3.22, 2.30, 2.26, 2.21, 2.17, 2.13, 2.07, 2.01, 1.99, 1.96, 1.91, 1.76, 1.73, 1.70, 1.59, 1.25, 0.07. |
| 23 | 473.30 | 1.83 | 1H NMR (400 MHz, CDCl3) d 7.66 (d, J = 8.0 Hz, 1H), 7.42 (d, J = 7.5 Hz, 1H), 7.26-7.03 (m, 5H), 6.81 (dd, J = 7.0, 4.1 Hz, 1H), 6.06 (dd, J = 16.3, 3.9 Hz, 1H), 4.86-4.60 (m, 3H), 3.88 (s, 3H), 3.64-3.18 (m, 4H), 2.31-1.87 (m, 4H). |
| 24 | 418.00 | 1.85 | |
| 25 | 465.50 | 6.80 | |
| 26 | 513.50 | 1.80 | |
| 27 | 393.07 | 2.72 | |
| 28 | 432.50 | 1.83 | 1H NMR (400 MHz, DMSO) d 7.74 (d, J = 7.4 Hz, 1H), 7.47 (s, 1H), 7.42-7.36 (m, 2H), 7.28 (t, J = 7.4 Hz, 1H), 7.15-7.05 (m, 2H), 7.05-6.99 (m, 2H), 4.44-4.13 (m, 1H), 4.10 (s, 3H), 3.72-3.39 (m, 2H), 3.31-3.17 (m, 1H), 2.02-1.85 (m, 4H), 1.33 (s, 9H). |
| 29 | 443.20 | 2.17 | |
| 30 | 481.40 | 2.79 | |
| 31 | 497.10 | 1.84 | |
| 32 | 443.70 | 2.34 | 1H NMR (400 MHz, CDCl3) d 6.90-6.77 (m, 7H), 6.68-6.52 (m, 4H), 6.34 (d, J = 8.0 Hz, 1H), 5.85 (dd, J = 5.8, 2.9 Hz, 1H), 5.55 (d, J = 3.6 Hz, 1H), 4.44 (br s, 1H), 4.10 (d, J = 2.3 Hz, 1H), 3.79 (br s, 1H), 2.05-1.87 (m, 4H), 1.74 (d, J = 2.2 Hz, 3H), 1.61 (s, 3H), 1.11 (d, J = 2.3 Hz, 12H), 0.89 (dd, J = 6.0, 2.3 Hz, 6H). |
| 33 | 444.17 | 2.42 | |
| 34 | 493.50 | 1.80 | |
| 35 | 485.19 | 1.83 | |
| 36 | 472.30 | 2.16 | |
| 37 | 485.50 | 1.88 | |
| 38 | 435.50 | 2.38 | |
| 39 | 438.50 | 1.70 | 1H NMR (400 MHz, DMSO) d 7.72, 7.70, 7.52, 7.47, 7.45, 7.31, 7.31, 7.15, 7.14, 7.13, 6.30, 6.30, 6.29, 6.14, 6.13, 6.10, 6.08, 5.76, 4.39, 4.35, 3.46, 3.34, 3.18, 3.14, 3.12, 2.89, 2.79, 2.77, 2.75, 2.73, 2.67, 2.50, 2.33, 2.02, 1.98, 1.93, 1.90, 1.86, 1.83, 1.19, 1.17, −0.00. |
| 40 | 443.00 | 1.78 | |
| 41 | 453.50 | 1.78 | 1H NMR (400 MHz, DMSO) d 7.87 (d, J = 2.0 Hz, 1H), 7.86-7.81 (m, 1H), 7.67 (d, J = 7.6 Hz, 1H), 7.50 (s, 1H), 7.36 (d, J = 8.6 Hz, 1H), 7.22-7.02 (m, 3H), 6.28 (t, J = 3.1 Hz, 1H), 6.16 (d, J = 2.3 Hz, 1H), 4.52-4.18 (m, 1H), 4.00 (s, 3H), 3.58 (s, 3H), 3.28 (s, 3H), 1.98 (s, 4H). |
| 42 | 446.00 | 1.99 | 1H NMR (400 MHz, CDCl3) d 8.18-8.12 (m, 1H), 7.26-7.13 (m, 5H), 7.07-6.96 (m, 2H), 6.15-6.10 (m, 1H), 4.61 (dt, J = 12.0, 6.0 Hz, 2H), 3.44 (s, 3H), 2.07 (dt, J = 47.5, 23.6 Hz, 5H), 1.46-1.36 (m, 6H). |
| 43 | 414.00 | 1.13 | |
| 44 | 392.20 | 2.97 | |

TABLE 2-continued

| Cmpd No. | LC/MS M + 1 | LC/RT min | ¹H NMR |
|---|---|---|---|
| 45 | 495.50 | 1.89 | 1H NMR (400 MHz, CDCl3) d 7.25 (d, J = 6.6 Hz, 1H), 7.14-7.07 (m, 3H), 7.04-6.96 (m, 3H), 6.32 (t, J = 3.2 Hz, 1H), 6.03 (dd, J = 3.5, 1.3 Hz, 1H), 5.00 (d, J = 7.6 Hz, 2H), 4.86 (d, J = 7.6 Hz, 2H), 4.72-4.57 (m, 1H), 3.84 (s, 3H), 3.77-3.49 (m, 2H), 3.45-3.23 (m, 1H), 3.09 (s, 3H), 2.26-1.75 (m, 4H). |
| 46 | 509.00 | 1.67 | |
| 47 | 462.30 | 2.46 | |
| 48 | 463.50 | 1.88 | |
| 49 | 507.50 | 1.56 | 1H NMR (400 MHz, DMSO) d 8.00 (d, J = 8.0 Hz, 1H), 7.87 (d, J = 8.2 Hz, 2H), 7.65 (d, J = 8.1 Hz, 3H), 7.34 (d, J = 4.0 Hz, 1H), 7.31 (d, J = 4.2 Hz, 2H), 7.28-7.18 (m, 1H), 6.47 (d, J = 4.0 Hz, 1H), 4.72-4.68 (m, 1H), 4.50-4.38 (m, 1H), 3.55-3.38 (m, 2H), 3.29-3.15 (m, 1H), 3.16-3.07 (m, 2H), 2.14-2.04 (m, 3H), 1.95-1.86 (m, 1H), 0.90 (d, J = 6.2 Hz, 3H). |
| 50 | 485.50 | 2.18 | 1H NMR (400 MHz, CDCl3) d 7.67 (d, J = 8.0 Hz, 1H), 7.39 (dd, J = 21.6, 8.1 Hz, 4H), 7.20-7.05 (m, 3H), 6.81 (d, J = 3.9 Hz, 1H), 6.06 (d, J = 3.9 Hz, 1H), 4.75-4.55 (m, 1H), 4.44-4.40 (m, 1H), 3.81-3.20 (m, 3H), 2.28-1.72 (m, 7H), 0.98 (d, J = 6.7 Hz, 3H), 0.82 (d, J = 6.8 Hz, 3H). |
| 51 | 478.30 | 1.62 | |
| 52 | 435.50 | 1.86 | |
| 53 | 480.50 | 1.54 | 1H NMR (400 MHz, DMSO) d 7.79 (s, 1H), 7.76-7.69 (m, 2H), 7.66-7.42 (m, 2H), 7.28 (t, J = 7.6 Hz, 1H), 7.17-7.03 (m, 2H), 4.50-4.37 (m, 1H), 4.10 (s, 3H), 3.54-3.39 (m, 2H), 3.37-3.09 (m, 2H), 2.44-2.30 (m, 3H), 2.11-1.70 (m, 4H), 1.17 (d, J = 6.8 Hz, 6H). |
| 54 | 458.37 | 1.59 | 1H NMR (400 MHz, CDCl3) d 8.16-8.09 (m, 1H), 7.49 (d, J = 7.9 Hz, 1H), 7.25-7.18 (m, 3H), 7.17-7.11 (m, 2H), 7.02 (d, J = 4.0 Hz, 1H), 6.10 (d, J = 4.0 Hz, 1H), 4.66 (s, 1H), 3.98 (d, J = 11.1 Hz, 1H), 3.82-3.71 (m, 1H), 3.68 (d, J = 11.1 Hz, 1H), 3.63-3.24 (m, 2H), 2.55 (s, 3H), 2.25-2.13 (m, 1H), 2.03-1.73 (m, 4H), 1.58 (s, 3H). |
| 55 | 421.10 | 2.62 | |
| 56 | 430.50 | 1.95 | |
| 57 | 481.14 | 2.45 | |
| 58 | 400.21 | 2.33 | |
| 59 | 433.10 | 1.61 | |
| 60 | 427.23 | 2.10 | |
| 61 | 408.20 | 1.66 | |
| 62 | 444.50 | 2.71 | |
| 63 | 427.50 | 2.07 | 1H NMR (400 MHz, CDCl3) d 7.26 (d, J = 8.7 Hz, 1H), 7.13-7.06 (m, 4H), 7.02 (dd, J = 8.5, 2.2 Hz, 1H), 6.99-6.93 (m, 1H), 6.34 (t, J = 3.2 Hz, 1H), 6.06-6.01 (m, 1H), 4.61 (s, 1H), 3.92 (s, 3H), 3.73 (s, 1H), 3.49 (s, 1H), 3.36 (s, 1H), 2.26-1.73 (m, 4H). |
| 64 | 480.20 | 1.69 | |
| 65 | 442.70 | 1.85 | 1H NMR (400 MHz, CDCl3) d 8.12 (d, J = 7.1 Hz, 1H), 7.47-7.30 (m, 4H), 7.26-7.18 (m, 2H), 7.17-7.07 (m, 2H), 7.01 (t, J = 5.5 Hz, 1H), 6.10 (d, J = 4.0 Hz, 1H), 4.67 (m, 1H), 4.43 (m, 1H), 3.51 (m, 4H), 2.32-1.71 (m, 6H), 0.97 (d, J = 6.7 Hz, 3H), 0.82 (d, J = 6.8 Hz, 3H). |
| 66 | 448.50 | 3.26 | |
| 67 | 494.30 | 2.33 | |
| 68 | 501.30 | 2.06 | |
| 69 | 471.19 | 2.83 | H NMR (400.0 MHz, DMSO) d 7.76-7.65 (m, 3H), 7.50-7.49 (m, 1H), 7.30 (d, J = 8.6 Hz, 1H), 7.17-7.05 (m, 3H), 6.29-6.28 (m, 1H), 6.17-6.16 (m, 1H), 4.61-4.18 (m, 1H), 4.12 (t, J = 6.2 Hz, 2H), 3.83-3.05 (m, 3H), 1.98 (s, 4H), 1.78-1.73 (m, 2H) and 0.99 (t, J = 7.4 Hz, 3H) ppm. |
| 70 | 499.30 | 1.88 | |
| 71 | 441.16 | 2.20 | |
| 72 | 551.50 | 2.20 | 1H NMR (400 MHz, CDCl3) d 7.59 (d, J = 8.8 Hz, 1H), 7.15 (d, J = 2.3 Hz, 1H), 7.07 (dd, J = 8.8, 2.3 Hz, 1H), 7.01 (d, J = 1.7 Hz, 1H), 6.98 (dd, J = 8.2, 1.8 Hz, 1H), 6.90 (d, J = 8.2 Hz, 1H), 6.81 (d, J = 3.9 Hz, 1H), 6.06 (d, J = 3.9 Hz, 1H), 4.22-4.15 (m, 3H), 3.88 (s, 3H), 3.81-3.76 (m, 2H), 3.44 (s, 3H), 3.53-3.30 (m, 3H), 2.18-1.80 (m, 4H). |
| 73 | 501.23 | 2.14 | |
| 74 | 477.30 | 2.04 | |

TABLE 2-continued

| Cmpd No. | LC/MS M + 1 | LC/RT min | ¹H NMR |
|---|---|---|---|
| 75 | 495.20 | 2.01 | |
| 76 | 400.50 | 1.68 | 1H NMR (400 MHz, DMSO) d 9.75 (s, 1H), 7.99 (d, J = 7.9 Hz, 1H), 7.34 (d, J = 3.7 Hz, 1H), 7.31 (d, J = 4.1 Hz, 2H), 7.26-7.21 (m, 1H), 7.20 (s, 1H), 7.13 (d, J = 8.1 Hz, 1H), 6.80 (d, J = 8.2 Hz, 1H), 6.49 (d, J = 3.9 Hz, 1H), 3.08 (s, 1H), 2.13 (s, 3H), 2.05-1.91 (m, 4H). |
| 77 | 376.26 | 1.95 | |
| 78 | 534.30 | 1.99 | 1H NMR (400 MHz, CDCl3) d 7.96 (d, J = 8.2 Hz, 2H), 7.87 (dd, J = 7.6, 1.4 Hz, 1H), 7.64-7.58 (m, 3H), 7.37-7.29 (m, 1H), 7.13-7.01 (m, 2H), 4.67 (d, J = 12.7 Hz, 1H), 3.75-3.58 (m, 1H), 3.58-3.49 (m, 1H), 3.47-3.33 (m, 1H), 2.32 (d, J = 12.4 Hz, 1H), 2.21-2.07 (m, 1H), 2.03-1.84 (m, 1H), 1.84-1.64 (m, 1H), 1.36 (s, 9H). |
| 79 | 400.21 | 2.13 | |
| 80 | 424.16 | 1.71 | |
| 81 | 409.11 | 2.01 | |
| 82 | 490.30 | 2.07 | |
| 83 | 463.10 | 1.65 | |
| 84 | 458.25 | 1.87 | |
| 85 | 491.19 | 2.04 | |
| 86 | 427.25 | 2.27 | |
| 87 | 391.24 | 1.79 | |
| 88 | 426.24 | 1.77 | |
| 89 | 461.22 | 2.22 | |
| 90 | 499.50 | 4.71 | |
| 91 | 476.30 | 2.12 | |
| 92 | 414.50 | 1.36 | |
| 93 | 468.20 | 1.29 | 1H NMR (400 MHz, DMSO) d 7.76-7.70 (m, 1H), 7.63-7.41 (m, 4H), 7.28 (t, J = 7.7 Hz, 1H), 7.18-7.04 (m, 2H), 4.46-4.35 (m, 1H), 4.14-4.05 (m, 3H), 3.98-3.90 (m, 3H), 3.53-3.36 (m, 1H), 3.28 (s, 3H), 3.30-3.14 (m, 2H), 2.09-1.77 (m, 4H). |
| 94 | 462.20 | 1.71 | 1H NMR (400 MHz, DMSO) d 7.73 (d, J = 7.7 Hz, 1H), 7.44 (d, J = 12.9 Hz, 1H), 7.27 (t, J = 7.7 Hz, 1H), 7.22-7.01 (m, 3H), 6.67-6.56 (m, 2H), 4.39 (d, J = 12.8 Hz, 1H), 4.09 (s, 3H), 3.79 (s, 3H), 3.50-3.34 (m, 1H), 3.31-3.11 (m, 2H), 2.07-1.93 (m, 1H), 1.93-1.72 (m, 3H), 1.34 (s, 9H). |
| 95 | 501.30 | 2.53 | |
| 96 | 441.16 | 2.28 | |
| 97 | 435.10 | 1.37 | |
| 98 | 434.20 | 1.55 | |
| 99 | 400.20 | 0.71 | 1H NMR (400 MHz, DMSO) d 8.62 (d, J = 6.8 Hz, 1H), 8.03 (s, 1H), 7.73 (d, J = 7.7 Hz, 1H), 7.64 (s, 1H), 7.45 (s, 1H), 7.28 (t, J = 7.6 Hz, 2H), 7.13 (d, J = 8.1 Hz, 1H), 7.07 (t, J = 7.6 Hz, 1H), 6.96 (t, J = 6.8 Hz, 1H), 4.46 (d, J = 13.1 Hz, 1H), 4.10 (s, 3H), 3.52-3.13 (m, 3H), 2.13-1.75 (m, 4H). |
| 100 | 438.50 | 1.36 | |
| 101 | 458.34 | 1.64 | 1H NMR (400 MHz, CDCl3) d 8.12 (d, J = 8.2 Hz, 1H), 7.42 (t, J = 8.0 Hz, 1H), 7.21 (dd, J = 11.1, 4.2 Hz, 1H), 7.12 (dd, J = 13.0, 5.0 Hz, 2H), 7.01 (d, J = 4.0 Hz, 1H), 6.99 (d, J = 8.4 Hz, 1H), 6.90 (d, J = 7.6 Hz, 1H), 6.12 (d, J = 4.0 Hz, 1H), 4.61 (d, J = 13.2 Hz, 1H), 3.88 (d, J = 1.0 Hz, 6H), 3.52 (s, 2H), 3.25 (t, J = 11.9 Hz, 1H), 2.15 (d, J = 14.1 Hz, 1H), 2.07 (s, 1H), 1.96 (t, J = 12.6 Hz, 2H), 1.64 (s, 1H). |
| 102 | 376.15 | 1.42 | |
| 103 | 469.40 | 3.06 | |
| 104 | 444.24 | 2.10 | |
| 105 | 407.40 | 3.18 | |
| 106 | 451.20 | 9.72 | |
| 107 | 477.14 | 2.03 | |
| 108 | 478.30 | 1.92 | 1H NMR (400 MHz, CDCl3) d 7.52, 7.49, 7.47, 7.33, 7.31, 7.29, 7.29, 7.27, 7.26, 7.26, 7.23, 7.21, 7.19, 7.16, 7.14, 7.08, 7.04, 7.02, 6.99, 6.83, 6.64, 6.46, 5.30, 4.69, 4.66, 4.13, 3.99, 3.61, 3.58, 3.54, 3.51, 3.40, 3.36, 3.33, 3.30, 3.27, 2.20, 2.17, 2.07, 2.04, 2.01, 1.97, 1.96, 1.94, 1.93, 1.91, 1.90, 1.76, 1.62, 1.57, 1.52. |
| 109 | 404.30 | 2.33 | |
| 110 | 430.27 | 2.43 | |
| 111 | 423.24 | 2.07 | |
| 112 | 461.50 | 2.68 | |
| 113 | 411.20 | 1.45 | |

TABLE 2-continued

| Cmpd No. | LC/MS M + 1 | LC/RT min | ¹H NMR |
|---|---|---|---|
| 114 | 475.30 | 1.78 | |
| 115 | 418.00 | 1.83 | |
| 116 | 493.25 | 2.19 | |
| 117 | 436.50 | 1.80 | |
| 118 | 457.23 | 2.52 | |
| 119 | 452.30 | 1.16 | 1H NMR (400 MHz, DMSO) d 7.97 (s, 1H), 7.95-7.89 (m, 2H), 7.77-7.68 (m, 3H), 7.26-7.21 (m, 2H), 7.19-7.12 (m, 2H), 4.36-4.23 (m, 1H), 3.59-3.40 (m, 4H), 2.18-2.00 (m, 3H), 1.99-1.87 (m, 1H), 1.17 (d, J = 6.8 Hz, 6H). |
| 120 | 438.50 | 1.73 | 1H NMR (400 MHz, CDCl3) d 7.54, 7.44, 7.42, 7.30, 7.28, 7.28, 7.23, 7.13, 7.12, 7.12, 7.06, 7.05, 7.04, 7.03, 7.02, 6.55, 6.55, 6.37, 6.36, 6.36, 6.28, 6.28, 6.26, 6.26, 6.06, 6.05, 5.32, 5.30, 5.29, 5.27, 5.25, 5.23, 4.62, 4.59, 3.76, 3.72, 3.63, 3.60, 3.57, 3.52, 3.51, 3.32, 3.28, 3.25, 2.22, 2.19, 2.12, 2.08, 2.03, 2.03, 1.98, 1.95, 1.91, 1.88, 1.65, 1.60, 1.55, 1.53, 1.39, 1.38, 1.23, 1.22, 0.98. |
| 121 | 474.28 | 1.81 | |
| 122 | 544.24 | 2.13 | |
| 123 | 505.10 | 2.06 | 1H NMR (400 MHz, DMSO) d 7.96 (d, J = 7.9 Hz, 1H), 7.62-7.49 (m, 3H), 7.35-7.25 (m, 2H), 7.25-7.17 (m, 1H), 7.03 (d, J = 3.9 Hz, 1H), 6.41 (d, J = 4.0 Hz, 1H), 4.51-4.36 (m, 1H), 3.58-3.14 (m, 3H), 3.25 (s, 3H), 2.68 (s, 3H), 2.19-1.81 (m, 4H). |
| 124 | 388.27 | 1.77 | |
| 125 | 454.50 | 1.98 | 1H NMR (400 MHz, CDCl3) d 8.14, 8.12, 8.02, 7.52, 7.31, 7.26, 7.24, 7.21, 7.19, 7.16, 7.14, 7.12, 7.03, 7.02, 6.81, 6.62, 6.44, 6.12, 6.11, 4.71, 3.97, 3.59, 3.56, 3.54, 3.50, 3.48, 3.42, 3.40, 3.33, 3.29, 3.26, 3.23, 2.96, 2.88, 2.80, 2.21, 2.18, 2.14, 2.10, 2.06, 2.02, 1.97, 1.77, 1.57, 0.94. |
| 126 | 485.16 | 2.32 | |
| 127 | 426.30 | 1.83 | |
| 128 | 418.30 | 2.44 | |
| 129 | 477.26 | 2.16 | |
| 130 | 458.50 | 2.11 | |
| 131 | 485.16 | 2.33 | |
| 132 | 475.30 | 1.87 | |
| 133 | 515.24 | 2.28 | |
| 134 | 501.30 | 2.06 | |
| 135 | 452.50 | 1.93 | |
| 136 | 441.16 | 2.50 | |
| 137 | 432.50 | 1.46 | |
| 138 | 453.28 | 2.18 | |
| 139 | 483.30 | 1.40 | |
| 140 | 465.50 | 4.00 | |
| 141 | 452.30 | 1.46 | 1H NMR (400 MHz, DMSO) d 7.96 (d, J = 7.9 Hz, 1H), 7.74 (d, J = 7.7 Hz, 1H), 7.56-7.50 (m, 2H), 7.46 (s, 1H), 7.29 (t, J = 7.7 Hz, 1H), 7.15-7.05 (m, 2H), 4.44-4.32 (m, 1H), 4.10 (s, 3H), 3.61-3.36 (m, 2H), 3.26 (s, 3H), 2.68 (s, 3H), 2.11-1.81 (m, 5H). |
| 142 | 465.40 | 3.02 | |
| 143 | 458.10 | 2.66 | |
| 144 | 462.19 | 2.11 | |
| 145 | 442.18 | 2.57 | |
| 146 | 478.30 | 2.22 | |
| 147 | 410.50 | 1.55 | 1H NMR (400 MHz, CDCl3) d 7.42, 7.42, 7.40, 7.40, 7.24, 7.24, 7.23, 7.22, 7.17, 7.12, 7.11, 7.09, 7.04, 6.94, 6.93, 6.86, 6.86, 6.84, 6.73, 6.38, 6.30, 6.18, 6.17, 6.16, 6.11, 6.09, 6.07, 5.92, 5.91, 5.70, 4.51, 4.47, 3.60, 3.42, 3.37, 3.33, 3.29, 3.25, 3.17, 3.14, 3.11, 2.89, 2.47, 2.02, 1.99, 1.94, 1.93, 1.89, 1.86, 1.62, 1.11, 1.08, 0.73, 0.71, 0.49, 0.47, 0.45, −0.00. |
| 148 | 447.15 | 2.25 | |
| 149 | 487.30 | 1.93 | |
| 150 | 445.30 | 2.02 | 1H NMR (400 MHz, CDCl3) d 7.80 (d, J = 8.1 Hz, 2H), 7.57 (d, J = 7.8 Hz, 1H), 7.51 (d, J = 8.0 Hz, 2H), 7.32-7.22 (m, 2H), 7.10-7.00 (m, 2H), 5.92 (d, J = 6.7 Hz, 1H), 4.61 (d, J = 10.7 Hz, 1H), 4.29 (dq, J = 13.5, 6.6 Hz, 1H), 4.17 (s, 3H), 3.58 (s, 2H), 3.38 (t, J = 12.4 Hz, 1H), 2.29-2.13 (m, 1H), 2.08-1.90 (m, 1H), 1.78 (s, 1H), 1.28 (d, J = 6.5 Hz, 7H). |
| 151 | 547.20 | 1.93 | 1H NMR (400 MHz, DMSO) d 7.99 (d, J = 8.4 Hz, 2H), 7.74 (d, J = 8.3 Hz, 2H), 7.57 (d, J = 8.0 Hz, 1H), 7.37-7.14 (m, 3H), 7.03 (d, J = 3.9 Hz, 1H), 6.40 (d, J = 4.0 Hz, 1H), 4.53-4.36 (m, 1H), 4.33-4.19 (m, |

TABLE 2-continued

| Cmpd No. | LC/MS M + 1 | LC/RT min | ¹H NMR |
|---|---|---|---|
| | | | 1H), 4.08-3.94 (m, 1H), 3.91-3.58 (m, 3H), 3.56-3.16 (m, 3H), 2.19-1.82 (m, 6H). |
| 152 | 445.15 | 2.43 | |
| 153 | 418.50 | 1.62 | 1H NMR (400 MHz, CDCl3) d 7.38 (s, 1H), 7.31 (d, J = 7.8 Hz, 1H), 7.28-7.22 (m, 2H), 7.22-7.06 (m, 4H), 6.82 (d, J = 9.0 Hz, 1H), 4.56 (sept, J = 5.8 Hz, 1H), 4.43-3.76 (m, 2H), 3.65-3.37 (m, 2H), 2.36-2.15 (m, 2H), 2.21 (s, 3H), 2.14-2.00 (m, 2H), 1.33 (t, J = 10.2 Hz, 6H). |
| 154 | 422.50 | 1.74 | 1H NMR (400 MHz, CDCl3) d 7.51, 7.49, 7.29, 7.28, 7.26, 7.14, 7.12, 7.11, 7.09, 7.07, 7.05, 7.03, 7.01, 7.00, 5.30, 4.67, 4.50, 4.48, 4.46, 4.44, 3.99, 3.99, 3.64, 3.61, 3.57, 3.53, 3.50, 3.39, 3.35, 3.33, 3.29, 2.22, 2.19, 2.03, 1.96, 1.92, 1.89, 1.77, 1.73, 1.57, 1.54, 1.52, 1.23, 1.21. |
| 155 | 444.24 | 1.86 | |
| 156 | 458.00 | 1.89 | 1H NMR (400 MHz, CDCl3) d 8.15 (d, J = 7.9 Hz, 1H), 7.24 (t, J = 7.7 Hz, 1H), 7.20-7.12 (m, 2H), 7.04 (d, J = 3.2 Hz, 2H), 6.99 (dd, J = 8.2, 1.5 Hz, 1H), 6.89 (d, J = 8.2 Hz, 1H), 6.12 (d, J = 4.0 Hz, 1H), 4.59 (dt, J = 12.2, 6.1 Hz, 2H), 3.89 (s, 3H), 3.57 (d, J = 110.2 Hz, 2H), 2.82 (s, 3H), 2.38-1.77 (m, 5H), 1.40 (d, J = 6.0 Hz, 6H). |
| 157 | 427.20 | 2.21 | |
| 158 | 432.00 | 1.83 | 1H NMR (400 MHz, CDCl3) d 7.56 (d, J = 7.7 Hz, 1H), 7.33-6.98 (m, 5H), 6.73 (d, J = 9.0 Hz, 2H), 4.65 (d, J = 12.8 Hz, 1H), 4.55 (dt, J = 12.1, 6.1 Hz, 1H), 4.14 (s, 3H), 3.62-3.24 (m, 3H), 2.32 (s, 3H), 2.26-1.60 (m, 5H), 1.32 (d, J = 6.0 Hz, 6H). |
| 159 | 373.20 | 2.99 | |
| 160 | 402.50 | 1.76 | |
| 161 | 457.50 | 2.19 | |
| 162 | 416.21 | 2.31 | |
| 163 | 411.20 | 2.08 | |
| 164 | 503.30 | 2.06 | 1H NMR (400 MHz, DMSO) ? 7.57 (d, J = 8.2 Hz, 1H), 7.38-7.24 (m, 2H), 7.24-7.17 (m, 1H), 6.98 (t, J = 22.1 Hz, 2H), 6.84 (d, J = 8.6 Hz, 1H), 6.40 (s, 1H), 4.46 (d, J = 12.7 Hz, 1H), 3.81 (d, J = 6.3 Hz, 6H), 3.75 (s, 3H), 3.36 (s, 2H), 3.15 (s, 1H), 1.94 (dd, J = 33.5, 13.8 Hz, 4H). |
| 165 | 462.50 | 3.04 | |
| 166 | 449.50 | 2.14 | |
| 167 | 440.50 | 1.78 | 1H NMR (400 MHz, CDCl3) d 7.51, 7.49, 7.43, 7.42, 7.40, 7.38, 7.36, 7.31, 7.29, 7.27, 7.26, 7.24, 7.21, 7.19, 7.12, 7.10, 7.07, 7.05, 7.03, 7.00, 6.76, 6.58, 6.56, 6.39, 4.66, 4.50, 4.48, 4.46, 4.44, 3.62, 3.59, 3.55, 3.52, 3.49, 3.47, 3.45, 3.38, 3.33, 3.29, 2.18, 2.07, 2.04, 2.01, 1.97, 1.93, 1.91, 1.80, 1.76, 1.62, 1.60, 1.57, 1.54, 1.52, 1.23, 1.21, 1.19. |
| 168 | 451.10 | 1.65 | 1H NMR (400 MHz, DMSO) d 7.71 (dd, J = 8.9, 5.6 Hz, 1H), 7.62 (d, J = 8.1 Hz, 1H), 7.50 (dd, J = 2.9, 1.4 Hz, 1H), 7.11 (dd, J = 9.6, 2.8 Hz, 1H), 7.03-6.89 (m, 3H), 6.28 (t, J = 3.2 Hz, 1H), 6.19 (dd, J = 3.4, 1.4 Hz, 1H), 4.53-4.24 (m, 1H), 3.83 (s, 3H), 3.71-3.36 (m, 3H), 2.05-1.83 (m, 4H), 1.48 (s, 6H). |
| 169 | 456.50 | 1.71 | 1H NMR (400 MHz, DMSO) d 7.74 (d, J = 7.7 Hz, 1H), 7.46 (s, 1H), 7.35-6.92 (m, 7H), 4.43-4.29 (m, 1H), 4.10 (s, 3H), 3.87 (s, 3H), 3.65-3.19 (m, 3H), 2.11-1.80 (m, 4H). |
| 170 | 499.30 | 7.77 | |
| 171 | 459.50 | 1.99 | |
| 172 | 497.21 | 2.04 | |
| 173 | 417.02 | 2.57 | |
| 174 | 446.30 | 2.61 | |
| 175 | 462.30 | 1.81 | |
| 176 | 516.00 | 1.79 | |
| 177 | 415.19 | 2.05 | |
| 178 | 528.26 | 2.45 | |
| 179 | 445.15 | 2.42 | |
| 180 | 466.50 | 1.61 | |
| 181 | 457.50 | 2.15 | |
| 182 | 430.70 | 1.75 | |
| 183 | 469.50 | 1.78 | |
| 184 | 405.50 | 4.54 | 1H NMR (400 MHz, DMSO) d 7.66 (dd, J = 7.6, 1.4 Hz, 1H), 7.55-7.46 (m, 1H), 7.42 (d, J = 8.7 Hz, 2H), 7.23-7.05 (m, 3H), 6.98 (d, J = 8.7 Hz, 2H), 6.28 (t, J = 3.2 Hz, 1H), 6.22-6.14 (m, 1H), 4.93-4.81 (m, |

TABLE 2-continued

| Cmpd No. | LC/MS M + 1 | LC/RT min | ¹H NMR |
|---|---|---|---|
| | | | 1H), 4.50-4.06 (m, 1H), 4.03 (t, J = 12.1, 7.2 Hz, 2H), 3.77-3.67 (m, 2H), 3.56-3.06 (m, 3H), 2.07-1.78 (m, 4H). |
| 185 | 446.08 | 2.33 | |
| 186 | 399.23 | 2.13 | |
| 187 | 420.30 | 1.55 | |
| 188 | 432.20 | 1.76 | |
| 189 | 439.14 | 2.03 | |
| 190 | 448.30 | 2.35 | |
| 191 | 503.30 | 2.06 | |
| 192 | 423.20 | 2.18 | |
| 193 | 465.50 | 2.27 | |
| 194 | 444.50 | 1.73 | 1H NMR (400 MHz, CDCl3) d 7.58, 7.56, 7.52, 7.32, 7.31, 7.30, 7.29, 7.28, 7.26, 7.23, 7.21, 7.19, 7.16, 7.14, 7.10, 7.07, 7.05, 7.03, 7.00, 6.84, 6.64, 6.46, 6.10, 4.68, 4.65, 4.16, 3.99, 3.64, 3.60, 3.58, 3.55, 3.49, 3.47, 3.39, 3.36, 3.33, 3.30, 2.22, 2.19, 2.06, 1.97, 1.93, 1.90, 1.75, 1.62, 1.57, 1.53, 1.52, 1.25, 1.23, 1.21, 1.19. |
| 195 | 489.30 | 1.70 | |
| 196 | 493.50 | 1.74 | |
| 197 | 430.50 | 4.47 | 1H NMR (400 MHz, DMSO) d 8.00 (d, J = 7.9 Hz, 1H), 7.42 (d, J = 8.6 Hz, 2H), 7.32 (dd, J = 10.2, 4.1 Hz, 3H), 7.28-7.17 (m, 1H), 6.99 (d, J = 8.6 Hz, 2H), 6.48 (d, J = 4.0 Hz, 1H), 4.88 (t, J = 5.5 Hz, 1H), 4.58-4.08 (m, 1H), 4.03 (t, J = 4.9 Hz, 2H), 3.72 (q, J = 10.1, 5.2 Hz, 2H), 3.67-3.09 (m, 3H), 2.15-1.80 (m, 4H). |
| 198 | 510.50 | 2.31 | |
| 199 | | | |
| 200 | 421.30 | 2.58 | |
| 201 | 365.25 | 1.95 | |
| 202 | 446.50 | 6.06 | 1H NMR (400 MHz, DMSO) d 7.73 (d, J = 6.8 Hz, 1H), 7.48 (s, 1H), 7.28 (t, J = 7.3 Hz, 1H), 7.16-6.88 (m, 3H), 6.83 (s, 1H), 4.66-4.50 (m, 1H), 4.39 (d, J = 12.4 Hz, 1H), 4.09 (s, 3H), 3.42 (d, J = 12.2 Hz, 1H), 3.33 (s, 5H), 2.20 (s, 3H), 2.09 (s, 3H), 1.90 (dd, J = 32.3, 19.2 Hz, 4H), 1.27 (d, J = 6.0 Hz, 6H). |
| 203 | 463.50 | 1.87 | |
| 204 | 509.21 | 2.04 | |
| 205 | 448.40 | 3.03 | |
| 206 | 416.50 | 2.03 | 1H NMR (400 MHz, DMSO) d 9.43 (s, 1H), 8.00 (d, J = 7.9 Hz, 1H), 7.34 (s, 1H), 7.31 (d, J = 4.0 Hz, 2H), 7.26-7.21 (m, 1H), 7.00 (d, J = 1.8 Hz, 1H), 6.91 (dd, J = 8.1, 1.9 Hz, 1H), 6.80 (d, J = 8.1 Hz, 1H), 6.48 (d, J = 4.1 Hz, 1H), 5.76 (s, 1H), 3.79 (s, 3H), 3.50-3.38 (m, 1H), 3.30-3.17 (m, 1H), 2.09-1.92 (m, 4H). |
| 207 | 539.50 | 1.95 | |
| 208 | 428.50 | 1.97 | |
| 209 | 464.30 | 1.72 | 1H NMR (400 MHz, DMSO) d 8.02 (s, 1H), 7.87 (d, J = 8.3 Hz, 2H), 7.72-7.64 (m, 3H), 7.53-7.46 (m, 1H), 7.20-7.03 (m, 3H), 6.32-6.26 (m, 1H), 6.20-6.15 (m, 1H), 4.58-4.27 (m, 1H), 3.64-3.14 (m, 3H), 2.15-1.83 (m, 5H), 0.55-0.33 (m, 4H). |
| 210 | 491.36 | 2.63 | |
| 211 | 467.30 | 1.72 | |
| 212 | 404.30 | 1.84 | |
| 213 | 466.50 | 2.24 | |
| 214 | 442.50 | 1.91 | |
| 215 | 402.10 | 2.17 | |
| 216 | 467.10 | 1.77 | |
| 217 | 374.20 | 2.93 | |
| 218 | 413.27 | 2.28 | |
| 219 | 404.40 | 2.86 | |
| 220 | 460.50 | 2.27 | 1H NMR (400 MHz, CDCl3) d 7.75 (d, J = 1.7, 1H), 7.60-7.51 (m, 2H), 7.27 (d, J = 8.5, 1H), 7.11 (d, J = 2.1, 2H), 7.02 (dd, J = 8.5, 2.2, 1H), 6.35 (t, J = 3.2, 1H), 6.05 (dd, J = 3.5, 1.3, 1H), 4.70-4.53 (m, 1H), 3.72-3.51 (m, 2H), 3.44-3.23 (m, 1H), 2.28-1.77 (m, 4H), 1.53 (s, 9H). |
| 221 | 389.50 | 2.00 | |
| 222 | 407.28 | 2.20 | |
| 223 | 517.20 | 2.34 | 1H NMR (400 MHz, CDCl3) d 7.67 (d, J = 8.1 Hz, 1H), 7.22-7.06 (m, 3H), 7.01 (d, J = 1.7 Hz, 1H), 6.98 (dd, J = 8.2, 1.7 Hz, 1H), 6.89 (d, J = 8.2 Hz, 1H), 6.81 (d, J = 3.9 Hz, 1H), 6.05 (d, J = 3.9 Hz, 1H), 4.65-4.25 (m, 1H), 4.23-4.14 (m, 2H), 3.88 (s, 3H), |

TABLE 2-continued

| Cmpd No. | LC/MS M + 1 | LC/RT min | ¹H NMR |
|---|---|---|---|
| | | | 3.82-3.75 (m, 2H), 3.58-3.32 (m, 3H), 3.44 (s, 3H), 2.20-1.80 (m, 4H). |
| 224 | 415.50 | 1.47 | |
| 225 | 424.10 | 1.72 | |
| 226 | 411.30 | 1.20 | |
| 227 | 424.10 | 1.73 | |
| 228 | 523.70 | 6.06 | |
| 229 | 399.23 | 2.25 | |
| 230 | 418.50 | 1.40 | |
| 231 | 486.48 | 1.57 | 1H NMR (400 MHz, DMSO) d 7.57 (d, J = 7.9 Hz, 1H), 7.52 (d, J = 8.3 Hz, 2H), 7.39 (d, J = 8.2 Hz, 2H), 7.29 (q, J = 8.1 Hz, 2H), 7.20 (t, J = 6.7 Hz, 1H), 7.02 (d, J = 4.3 Hz, 1H), 6.42 (d, J = 3.9 Hz, 1H), 4.98 (s, 1H), 4.72 (t, J = 5.7 Hz, 1H), 4.51-4.31 (m, 1H), 3.42 (s, 2H), 1.99 (s, 5H), 1.39 (s, 3H). |
| 232 | 427.20 | 2.20 | |
| 233 | 495.30 | 2.32 | |
| 234 | 481.50 | 1.88 | |
| 235 | 506.30 | 1.59 | |
| 236 | 404.50 | 1.86 | |
| 237 | 501.30 | 3.00 | |
| 238 | 535.22 | 2.28 | 1H NMR (400 MHz, DMSO) d 7.80-7.67 (m, 3H), 7.56-7.47 (m, 1H), 7.37-7.26 (m, 2H), 7.14 (dd, J = 8.5, 2.3 Hz, 1H), 6.30 (t, J = 3.2 Hz, 1H), 6.23-6.14 (m, 1H), 4.76-4.06 (m, 3H), 3.82-3.40 (m, 5H), 3.23 (s, 3H), 2.13-1.83 (m, 6H). |
| 239 | 403.18 | 2.79 | |
| 240 | 450.30 | 1.45 | |
| 241 | 345.50 | 1.84 | |
| 242 | 396.00 | 2.91 | |
| 243 | 479.30 | 1.53 | 1H NMR (400 MHz, DMSO) d 8.02 (s, 1H), 7.87 (d, J = 8.3 Hz, 2H), 7.74 (d, J = 7.7 Hz, 1H), 7.69 (d, J = 8.2 Hz, 2H), 7.52-7.42 (m, 1H), 7.34-7.25 (m, 1H), 7.16-7.02 (m, 2H), 4.47-4.29 (m, 1H), 4.10 (s, 3H), 3.60-3.22 (m, 3H), 2.15-1.80 (m, 5H), 0.53-0.33 (m, 4H). |
| 244 | 506.24 | 2.45 | |
| 245 | 508.00 | 1.92 | |
| 246 | 436.50 | 1.81 | |
| 247 | 433.30 | 1.92 | 1H NMR (400 MHz, DMSO) d 7.67 (d, J = 7.6 Hz, 1H), 7.56-7.43 (m, 1H), 7.19-7.04 (m, 3H), 7.04-6.96 (m, 3H), 6.28 (t, J = 3.1 Hz, 1H), 6.22-6.10 (m, 1H), 4.64-4.53 (m, 1H), 4.52-3.92 (m, 1H), 3.77 (s, 3H), 3.61-3.09 (m, 3H), 1.96 (s, 4H), 1.26 (d, J = 6.0 Hz, 6H). |
| 248 | 509.20 | 1.72 | |
| 249 | 461.00 | 1.92 | 1H NMR (400 MHz, DMSO) d 7.83-7.64 (m, 3H), 7.53-7.46 (m, 1H), 7.33 (d, J = 8.7 Hz, 1H), 7.10 (dd, J = 9.6, 2.7 Hz, 1H), 7.00-6.88 (m, 1H), 6.28 (t, J = 3.1 Hz, 1H), 6.19-6.13 (m, 1H), 4.58-4.16 (m, 1H), 3.94 (s, 3H), 3.56 (s, 3H), 2.05-1.79 (m, 4H). |
| 250 | 478.10 | 1.83 | 1H NMR (400 MHz, CDCl3) d 7.61, 7.59, 7.52, 7.43, 7.38, 7.36, 7.31, 7.26, 7.15, 7.14, 7.10, 7.09, 7.07, 7.07, 7.04, 6.99, 6.83, 6.82, 6.54, 6.39, 6.34, 6.23, 6.20, 6.18, 6.07, 6.06, 6.03, 4.61, 4.58, 3.72, 3.69, 3.56, 3.49, 3.38, 3.25, 3.22, 3.19, 2.80, 2.19, 2.15, 2.07, 2.04, 2.01, 1.96, 1.89, 1.87, 1.59, 1.36, 1.25, 0.97. |
| 251 | 418.20 | 1.89 | |
| 252 | 440.19 | 2.18 | |
| 253 | 480.30 | 2.25 | |
| 254 | 389.50 | 5.76 | |
| 255 | 419.30 | 1.64 | |
| 256 | 448.50 | 1.70 | 1H NMR (400 MHz, DMSO) d 7.74 (d, J = 7.7 Hz, 1H), 7.47 (d, J = 0.5 Hz, 1H), 7.29 (t, J = 7.8 Hz, 1H), 7.15-6.96 (m, 5H), 4.60 (hept, J = 5.9 Hz, 1H), 4.51-4.05 (m, 1H), 4.10 (s, 3H), 3.78 (s, 3H), 3.59-3.20 (m, 3H), 2.10-1.75 (m, 4H), 1.26 (d, J = 5.7 Hz, 6H). |
| 257 | 435.50 | 2.21 | 1H NMR (400 MHz, CDCl3) d 7.31-7.24 (m, 1H), 7.21 (dd, J = 7.5, 1.2 Hz, 1H), 7.17 (d, J = 7.5 Hz, 1H), 7.07-6.98 (m, 4H), 4.93-4.36 (m, 1H), 3.90 (s, 3H), 3.68-3.13 (m, 3H), 2.98 (s, 3H), 2.65 (q, J = 7.5 Hz, 2H), 2.27-1.98 (m, 4H), 1.19 (t, J = 7.5 Hz, 3H). |
| 258 | 444.20 | 2.21 | |
| 259 | 404.50 | 1.85 | |
| 260 | 501.00 | 1.82 | |
| 261 | 453.30 | 3.01 | |

TABLE 2-continued

| Cmpd No. | LC/MS M + 1 | LC/RT min | ¹H NMR |
|---|---|---|---|
| 262 | 433.20 | 1.70 | 1H NMR (400 MHz, DMSO) d 7.76 (s, 1H), 7.59 (dd, J = 7.6, 1.6 Hz, 1H), 7.46 (s, 2H), 7.25-7.17 (m, 1H), 7.06-6.96 (m, 2H), 4.69 (dt, J = 12.1, 6.0 Hz, 1H), 4.31 (d, J = 12.7 Hz, 1H), 3.86 (s, 3H), 3.54 (s, 1H), 3.33 (t, J = 11.1 Hz, 1H), 2.35 (s, 3H), 2.09-1.99 (m, 2H), 1.90 (d, J = 11.2 Hz, 3H), 1.31 (d, J = 6.0 Hz, 7H). |
| 263 | 499.30 | 7.77 | |
| 264 | 359.00 | 1.95 | |
| 265 | 479.00 | 2.06 | |
| 266 | 481.50 | 1.91 | 1H NMR (400 MHz, DMSO) d 7.87 (d, J = 2.2 Hz, 1H), 7.78 (dd, J = 8.6, 2.2 Hz, 1H), 7.67 (dd, J = 7.6, 1.6 Hz, 1H), 7.50 (dd, J = 2.9, 1.3 Hz, 1H), 7.37 (d, J = 8.8 Hz, 1H), 7.20-7.03 (m, 3H), 6.28 (t, J = 3.2 Hz, 1H), 6.16 (dd, J = 3.4, 1.3 Hz, 1H), 5.03-4.85 (m, 1H), 4.57-4.05 (m, 1H), 3.80-3.37 (m, 3H), 3.28 (s, 3H), 2.06-1.83 (m, 4H), 1.36 (d, J = 6.0 Hz, 6H). |
| 267 | 464.50 | 2.13 | 1H NMR (400 MHz, DMSO) d 7.53 (s, 1H), 7.48 (dd, J = 9.5, 2.5 Hz, 1H), 7.28-7.23 (m, 2H), 7.19-7.10 (m, 2H), 7.00-6.95 (m, 1H), 4.64 (sept, J = 6.0 Hz, 1H), 4.45 (q, J = 7.2 Hz, 2H), 4.34-4.10 (m, 1H), 3.87-3.39 (m, 2H), 3.32-3.08 (m, 1H), 2.15 (s, 3H), 2.00-1.83 (m, 4H), 1.37 (t, J = 7.2 Hz, 3H), 1.29 (d, J = 6.0 Hz, 6H). |
| 268 | 431.15 | 2.18 | |
| 269 | 505.30 | 2.68 | |
| 270 | 517.50 | 1.98 | 1H NMR (400 MHz, DMSO) d 7.97 (d, J = 8.3 Hz, 2H), 7.73 (d, J = 8.3 Hz, 2H), 7.58 (d, J = 8.1 Hz, 1H), 7.34-7.25 (m, 2H), 7.25-7.17 (m, 1H), 7.03 (d, J = 3.9 Hz, 1H), 6.40 (d, J = 3.9 Hz, 1H), 4.52-4.37 (m, 1H), 3.61-3.38 (m, 2H), 3.29-3.13 (m, 1H), 2.97-2.86 (m, 1H), 2.18-1.98 (m, 3H), 1.95-1.84 (m, 1H), 1.19-1.11 (m, 2H), 1.11-1.01 (m, 2H). |
| 271 | 433.50 | 1.25 | |
| 272 | 404.50 | 1.98 | 1H NMR (400 MHz, CDCl3) d 7.73 (dd, J = 17.9, 8.3 Hz, 3H), 7.58 (t, J = 7.7 Hz, 1H), 7.29 (d, J = 7.3 Hz, 2H), 7.13 (d, J = 1.7 Hz, 2H), 7.05 (dd, J = 8.5, 1.9 Hz, 1H), 6.37 (t, J = 3.1 Hz, 1H), 6.10-6.03 (m, 1H), 4.65 (br s, 1H), 3.60 (br s, 2H), 3.36 (br s, 1H), 2.22 (br s, 1H), 2.07 (br s, 2H), 1.88 (br s, 1H), 1.62 (d, J = 2.4 Hz, 3H). |
| 273 | 437.26 | 2.35 | |
| 274 | 446.30 | 2.60 | 1H NMR (400 MHz, CDCl3) d 7.54 (dt, J = 3.0, 1.3 Hz, 1H), 7.31-7.20 (m, 3H), 7.10-6.95 (m, 2H), 6.83 (d, J = 8.2 Hz, 1H), 4.65 (br s, 1H), 4.56 (sept, J = 6.0 Hz, 1H), 4.08 (s, 3H), 3.70-3.21 (m, 3H), 2.30 (s, 3H), 2.21 (s, 3H), 2.17-1.82 (m, 4H), 1.35 (d, J = 1.1 Hz, 3H), 1.34 (d, J = 1.1 Hz, 3H). |
| 275 | 397.50 | 2.07 | 1H NMR (400 MHz, CDCl3) d 7.46-7.37 (m, 1H), 7.30-7.27 (m, 4H), 7.25-7.10 (m, 5H), 7.04 (dd, J = 8.5, 2.2 Hz, 1H), 6.36 (t, J = 3.2 Hz, 1H), 6.07 (d, J = 3.2 Hz, 1H), 4.65 (br. s, 1H), 3.57 (br. dd, J = 43.9, 16.6 Hz, 2H), 3.35 (br. s, 1H), 2.20 (br. s, 1H), 2.06 (br. s, 2H), 1.87 (br. s, 1H), 1.59 (s, 6H). |
| 276 | 448.10 | 1.54 | |
| 277 | 447.15 | 2.32 | |
| 278 | 502.50 | 1.97 | |
| 279 | 547.20 | 1.93 | 1H NMR (400 MHz, DMSO) d 7.99 (d, J = 8.3 Hz, 2H), 7.74 (d, J = 8.3 Hz, 2H), 7.57 (d, J = 8.2 Hz, 1H), 7.36-7.14 (m, 3H), 7.03 (d, J = 3.9 Hz, 1H), 6.40 (d, J = 4.0 Hz, 1H), 4.54-4.36 (m, 1H), 4.33-4.17 (m, 1H), 4.09-3.95 (m, 1H), 3.90-3.59 (m, 3H), 3.58-3.12 (m, 3H), 2.24-1.77 (m, 6H). |
| 280 | 444.10 | 2.40 | |
| 281 | 448.50 | 1.70 | 1H NMR (400 MHz, DMSO) d 7.74 (s, 1H), 7.61-7.56 (m, 1H), 7.20 (td, J = 8.2, 1.5 Hz, 1H), 7.05-6.94 (m, 5H), 4.60 (hept, J = 5.6 Hz, 1H), 4.21 (s, 1H), 3.87 (s, 3H), 3.78 (s, 3H), 3.60-3.32 (m, 3H), 2.06-1.78 (m, 4H), 1.26 (d, J = 6.0 Hz, 6H). |
| 282 | 499.30 | 1.84 | |
| 283 | 460.20 | 2.51 | |
| 284 | 426.30 | 1.67 | |
| 285 | 436.00 | 1.86 | 1H NMR (400 MHz, CDCl3) d 8.15 (d, J = 7.9 Hz, 1H), 7.39 (ddd, J = 31.5, 15.1, 7.3 Hz, 3H), 7.19 (dt, J = 14.9, 8.2 Hz, 4H), 7.05 (d, J = 3.7 Hz, 1H), 6.76 (s, 0H), 6.58 (d, J = 7.0 Hz, 1H), 6.39 (s, 0H), 6.13 (d, J = 3.8 Hz, |

TABLE 2-continued

| Cmpd No. | LC/MS M + 1 | LC/RT min | ¹H NMR |
|---|---|---|---|
| | | | 1H), 4.76 (d, J = 10.5 Hz, 1H), 3.69-3.17 (m, 3H), 2.32-1.91 (m, 5H). |
| 286 | 495.00 | 1.47 | |
| 287 | 481.50 | 1.71 | 1H NMR (400 MHz, CDCl3) d 7.34-7.23 (m, 2H), 7.14-7.08 (m, 2H), 7.07-6.99 (m, 3H), 6.34 (t, J = 3.2 Hz, 1H), 6.04 (dd, J = 3.5, 1.3 Hz, 1H), 5.02 (d, J = 7.2 Hz, 2H), 4.87 (d, J = 7.2 Hz, 2H), 4.75-4.51 (m, 1H), 3.91 (s, 3H), 3.82-3.43 (m, 3H), 2.29-1.72 (m, 4H). |
| 288 | 487.27 | 2.04 | |
| 289 | 462.50 | 1.93 | 1H NMR (400 MHz, CDCl3) d 7.02 (dd, J = 8.6, 1.6 Hz, 1H), 6.83-6.78 (m, 4H), 6.37 (d, J = 8.1 Hz, 1H), 6.21-6.14 (m, 2H), 4.12 (dt, J = 16.6, 6.0 Hz, 1H), 3.67 (t, J = 2.5 Hz, 3H), 3.38 (t, J = 2.5 Hz, 3H), 3.04 (s, 2H), 1.76 (s, 3H), 1.64 (s, 2H), 1.44 (s, 2H), 1.18 (d, J = 1.5 Hz, 3H), 0.94-0.85 (m, 6H). |
| 290 | 402.60 | 2.71 | |
| 291 | 537.50 | 2.20 | |
| 292 | 460.50 | 1.76 | |
| 293 | 460.50 | 1.46 | |
| 294 | 474.30 | 2.38 | |
| 295 | 426.00 | 2.12 | |
| 296 | 511.00 | 1.73 | |
| 297 | 476.30 | 5.18 | 1H NMR (400 MHz, DMSO) d 8.00 (d, J = 8.0 Hz, 1H), 7.93 (d, J = 8.2 Hz, 2H), 7.73 (d, J = 8.2 Hz, 2H), 7.35 (d, J = 4.0 Hz, 1H), 7.31 (d, J = 4.2 Hz, 2H), 7.27-7.20 (m, J = 8.9, 4.5 Hz, 1H), 6.47 (d, J = 4.0 Hz, 1H), 4.46 (d, J = 12.8 Hz, 1H), 3.59-3.38 (m, 3H), 3.23 (s br, 1H), 2.07 (sbr, 3H), 1.90 (d, J = 12.6 Hz, 1H), 1.17 (d, J = 6.8 Hz, 6H). |
| 298 | 463.20 | 2.08 | |
| 299 | 424.30 | 1.79 | |
| 300 | 507.00 | 1.96 | |
| 301 | 396.25 | 1.68 | |
| 302 | 444.17 | 2.03 | |
| 303 | 481.50 | 1.89 | |
| 304 | 422.15 | 2.19 | |
| 305 | 467.50 | 2.29 | |
| 306 | 443.70 | 1.74 | 1H NMR (400 MHz, DMSO) d 7.85 (d, J = 1.8 Hz, 1H), 7.74 (d, J = 8.1 Hz, 2H), 7.45 (s, 1H), 7.37-7.25 (m, 2H), 7.14-7.05 (m, 2H), 4.90-4.81 (m, 1H), 4.40-4.22 (m, 1H), 4.10 (s, 3H), 3.63-3.42 (m, 2H), 3.30-3.18 (m, 1H), 2.07-1.81 (m, 4H), 1.34 (d, J = 6.0 Hz, 6H). |
| 307 | 462.20 | 1.74 | |
| 308 | 442.70 | 1.78 | |
| 309 | 428.50 | 1.75 | |
| 310 | 458.00 | 1.77 | 1H NMR (400 MHz, CDCl3) d 8.13 (d, J = 8.3 Hz, 1H), 7.26-7.12 (m, 4H), 7.03 (d, J = 4.0 Hz, 1H), 6.96 (d, J = 2.4 Hz, 1H), 6.81 (dd, J = 8.4, 2.4 Hz, 1H), 6.12 (d, J = 3.9 Hz, 1H), 4.75-4.47 (m, 4H), 3.90-3.50 (m, 3H), 3.33 (s, 1H), 2.21 (d, J = 9.7 Hz, 1H), 2.12-1.99 (m, 2H), 1.86 (s, 1H), 1.35 (d, J = 6.0 Hz, 6H). |
| 311 | 507.30 | 1.67 | |
| 312 | 485.20 | 2.22 | |
| 313 | 462.20 | 1.62 | 1H NMR (400 MHz, DMSO) d 7.74 (d, J = 7.6 Hz, 1H), 7.47 (s, 1H), 7.29 (t, J = 7.7 Hz, 1H), 7.16-6.99 (m, 4H), 6.95 (dd, J = 8.1, 1.5 Hz, 1H), 4.47-4.17 (m, 1H), 4.10 (s, 3H), 3.77 (s, 3H), 3.72-3.33 (m, 3H), 2.10-1.81 (m, 4H), 1.29 (s, 9H). |
| 314 | 417.50 | 2.26 | |
| 315 | 431.70 | 2.32 | |
| 316 | 434.50 | 1.29 | |
| 317 | 413.27 | 2.35 | |
| 318 | 446.00 | 2.03 | 1H NMR (400 MHz, CDCl3) d 8.14 (d, J = 7.7 Hz, 1H), 7.36 (t, J = 8.3 Hz, 1H), 7.24 (t, J = 7.7 Hz, 1H), 7.20-7.11 (m, 2H), 7.04 (d, J = 4.0 Hz, 1H), 6.74 (dd, J = 8.6, 2.0 Hz, 1H), 6.60 (dd, J = 11.9, 2.1 Hz, 1H), 6.12 (d, J = 4.0 Hz, 1H), 4.71 (d, J = 13.0 Hz, 1H), 4.56 (dt, J = 12.1, 6.1 Hz, 1H), 3.59 (d, J = 6.8 Hz, 2H), 3.31 (t, J = 12.6 Hz, 1H), 2.29-1.82 (m, 5H), 1.36 (d, J = 6.0 Hz, 6H). |
| 319 | 453.40 | 2.63 | |
| 320 | 442.20 | 2.41 | |
| 321 | 458.50 | 1.87 | 1H NMR (400 MHz, CDCl3) d 7.51, 7.49, 7.47, 7.45, 7.43, 7.42, 7.38, 7.36, 7.34, 7.32, 7.30, 7.28, 7.26, |

TABLE 2-continued

| Cmpd No. | LC/MS M + 1 | LC/RT min | ¹H NMR |
|---|---|---|---|
| | | | 7.26, 7.24, 7.22, 7.13, 7.11, 7.07, 7.05, 7.04, 6.99, 5.30, 4.67, 4.50, 4.48, 4.46, 4.44, 3.62, 3.58, 3.55, 3.52, 3.37, 3.33, 3.29, 2.23, 2.20, 2.03, 1.94, 1.90, 1.74, 1.57, 1.54, 1.53, 1.20. |
| 322 | 411.10 | 1.47 | |
| 323 | 427.70 | 1.24 | 1H NMR (400 MHz, DMSO) d 8.59 (bs, 3H), 8.00 (d, J = 7.9 Hz, 1H), 7.63 (d, J = 8.4 Hz, 2H), 7.54 (d, J = 8.3 Hz, 2H), 7.36-7.29 (m, 3H), 7.29-7.16 (m, 1H), 6.48 (d, J = 4.1 Hz, 1H), 4.51-4.38 (m, 1H), 3.70-3.47 (m, 2H), 3.20 (s, 1H), 2.18-1.88 (m, 4H), 1.65 (s, 6H). |
| 324 | 431.02 | 2.80 | |
| 325 | 432.50 | 1.13 | |
| 326 | 447.50 | 2.08 | |
| 327 | 465.50 | 1.81 | 1H NMR (400 MHz, CDCl3) d 7.97-7.91 (m, 2H), 7.64-7.57 (m, 2H), 7.36 (d, J = 7.3 Hz, 1H), 7.16-7.13 (m, 1H), 7.11-7.01 (m, 3H), 6.36-6.29 (m, 1H), 6.07-5.99 (m, 1H), 4.71-4.59 (m, 1H), 3.70-3.27 (m, 3H), 2.33-1.75 (m, 4H), 1.36 (s, 9H). |
| 328 | 442.50 | 1.86 | 1H NMR (400 MHz, CDCl3) d 7.52, 7.49, 7.47, 7.26, 7.21, 7.15, 7.13, 7.10, 7.08, 7.08, 7.07, 7.06, 7.04, 7.04, 7.02, 7.02, 4.66, 4.13, 3.99, 3.99, 3.81, 3.61, 3.58, 3.55, 3.48, 3.46, 3.44, 3.39, 3.36, 3.33, 3.30, 3.27, 2.21, 2.17, 2.01, 1.97, 1.94, 1.93, 1.90, 1.89, 1.75, 1.73, 1.69, 1.62, 1.57, 1.53. |
| 329 | 496.26 | 1.95 | |
| 330 | 506.30 | 2.17 | |
| 331 | 443.12 | 2.43 | |
| 332 | 407.50 | 5.96 | |
| 333 | 500.30 | 1.59 | |
| 334 | 472.30 | 1.74 | 1H NMR (400 MHz, CDCl3) d 8.12 (d, J = 7.3 Hz, 1H), 7.37 (d, J = 8.5 Hz, 2H), 7.24-7.18 (m, 1H), 7.18-7.09 (m, 2H), 7.02 (d, J = 3.8 Hz, 1H), 6.86 (d, J = 8.5 Hz, 2H), 6.11 (d, J = 3.8 Hz, 1H), 4.64 (s, 1H), 3.91-3.26 (m, 4H), 2.26-1.77 (m, 6H), 1.61 (s, 6H). |
| 335 | 477.22 | 2.26 | |
| 336 | 496.20 | 1.42 | 1H NMR (400 MHz, DMSO) d.7.77-7.69 (m, 1H), 7.63-7.40 (m, 4H), 7.28 (t, J = 7.7 Hz, 1H), 7.18-7.02 (m, 2H), 4.41 (d, J = 12.1 Hz, 1H), 4.15-4.05 (m, 3H), 3.98-3.88 (m, 3H), 3.60-3.49 (m, 1H), 3.49-3.35 (m, 1H), 3.30-3.11 (m, 2H), 2.10-1.76 (m, 4H), 1.22-1.14 (m, 6H). |
| 337 | 480.30 | 2.10 | |
| 338 | 442.70 | 2.13 | |
| 339 | 433.50 | 2.40 | |
| 340 | 444.50 | 1.70 | |
| 341 | 479.30 | 2.16 | |
| 342 | 459.20 | 2.68 | |
| 343 | 404.07 | 1.95 | |
| 344 | 495.20 | 1.49 | |
| 345 | 440.12 | 2.32 | |
| 346 | 418.27 | 1.54 | |
| 347 | 471.20 | 2.52 | 1H NMR (400 MHz, CDCl3) d 7.67 (d, J = 8.1 Hz, 1H), 7.21-7.05 (m, 4H), 6.97-6.89 (m, 2H), 6.81 (d, J = 3.9 Hz, 1H), 6.06 (d, J = 3.9 Hz, 1H), 4.96-4.23 (m, 1H), 3.84 (s, 3H), 3.64-3.14 (m, 3H), 2.64 (q, J = 7.5 Hz, 2H), 2.25-1.75 (m, 4H), 1.17 (t, J = 7.5 Hz, 3H). |
| 348 | 509.70 | 1.92 | |
| 349 | 391.20 | 3.01 | |
| 350 | 430.40 | 2.91 | |
| 351 | 387.20 | 2.50 | |
| 352 | 433.30 | 2.36 | 1H NMR (400 MHz, DMSO) d 7.66 (d, J = 7.7 Hz, 1H), 7.51-7.47 (m, 1H), 7.18-6.95 (m, 6H), 6.28 (t, J = 3.1 Hz, 1H), 6.17 (d, J = 3.4 Hz, 1H), 4.58-4.04 (m, 1H), 3.94 (t, J = 6.5 Hz, 2H), 3.78 (s, 3H), 3.59-3.13 (m, 3H), 2.03-1.86 (m, 4H), 1.73 (sextet, J = 6.8 Hz, 2H), 0.97 (t, J = 7.4 Hz, 3H). |
| 353 | 426.20 | 2.97 | |
| 354 | 422.19 | 2.00 | |
| 355 | 450.30 | 1.53 | 1H NMR (400 MHz, DMSO) ? 7.73 (d, J = 7.4 Hz, 1H), 7.46 (s, 1H), 7.28 (t, J = 7.2 Hz, 1H), 7.19-6.80 (m, 4H), 4.39 (s, 1H), 4.10 (s, 3H), 3.79 (d, J = 22.0 Hz, 9H), 3.42 (s, 1H), 3.27-3.14 (m, 1H), 1.92 (d, J = 49.8 Hz, 4H). |
| 356 | 447.13 | 2.84 | |

TABLE 2-continued

| Cmpd No. | LC/MS M + 1 | LC/RT min | ¹H NMR |
|---|---|---|---|
| 357 | 479.30 | 1.54 | 1H NMR (400 MHz, DMSO) ? 7.96 (d, J = 7.9 Hz, 1H), 7.58-7.50 (m, 3H), 7.37 (d, J = 4.1 Hz, 1H), 7.25-7.13 (m, J = 9.4, 8.0, 1.6 Hz, 2H), 7.08-6.99 (m, 1H), 6.38 (d, J = 4.0 Hz, 1H), 4.45 (d, J = 12.4 Hz, 1H), 3.47 (dd, J = 22.7, 14.5 Hz, 2H), 3.25 (s, 3H), 3.23-3.10 (m, 1H), 2.68 (s, 3H), 2.49 (s, 3H), 2.14-2.00 (m, 1H), 1.94 (s br, 2H), 1.80 (d, J = 13.9 Hz, 1H). |
| 358 | 420.17 | 1.59 | |
| 359 | 431.00 | 2.31 | |
| 360 | 453.30 | 1.75 | |
| 361 | 428.10 | 2.54 | |
| 362 | 476.20 | 2.95 | |
| 363 | 490.30 | 1.86 | 1H NMR (400 MHz, CDCl3) d 8.13 (d, J = 7.3 Hz, 1H), 8.03 (d, J = 7.6 Hz, 1H), 7.39 (d, J = 8.0 Hz, 2H), 7.22 (t, J = 7.8 Hz, 1H), 7.15 (t, J = 7.2 Hz, 2H), 7.03 (d, J = 4.0 Hz, 1H), 6.11 (d, J = 3.9 Hz, 1H), 4.73-4.64 (m, 1H), 3.62-3.51 (m, 2H), 3.40-3.30 (m, 1H), 3.30-3.20 (m, 1H), 2.72 (s, 3H), 2.29-2.17 (m, 1H), 2.12-1.97 (m, 2H), 1.87-1.75 (m, 1H), 1.31 (d, J = 6.8 Hz, 6H). |
| 364 | 458.50 | 1.58 | |
| 365 | 448.20 | 1.74 | |
| 366 | 509.50 | 1.86 | |
| 367 | 447.50 | 2.22 | 1H NMR (400 MHz, CDCl3) d 7.72 (d, J = 10.5 Hz, 2H), 7.66 (d, J = 7.6 Hz, 1H), 7.58 (t, J = 7.5 Hz, 1H), 7.33-7.25 (m, 3H), 7.13 (d, J = 1.9 Hz, 2H), 7.04 (dd, J = 8.5, 2.1 Hz, 1H), 6.36 (t, J = 3.1 Hz, 1H), 6.11-6.04 (m, 1H), 4.67 (s, 1H), 3.61 (br. s, 2H), 3.38 (br. s, 1H), 2.22 (br. s, 1H), 2.08 (br. s, 2H), 1.88 (br. s, 1H), 1.60 (s, 5H). |
| 368 | 490.30 | 2.07 | |
| 369 | 430.70 | 1.81 | |
| 370 | 466.10 | 3.39 | |
| 371 | 363.50 | 1.89 | |
| 372 | 460.30 | 2.18 | |
| 373 | | | |
| 374 | 481.50 | 1.94 | |
| 375 | 472.50 | 1.90 | 1H NMR (400 MHz, CDCl3) d 7.98 (d, J = 8.2 Hz, 1H), 7.41 (s, 1H), 7.37 (d, J = 8.4 Hz, 1H), 6.99 (d, J = 4.0 Hz, 1H), 6.96 (s, 1H), 6.93 (d, J = 8.7 Hz, 1H), 6.89 (d, J = 8.4 Hz, 1H), 6.07 (d, J = 4.0 Hz, 1H), 4.67 (s, 2H), 4.66-4.60 (m, 1H), 4.06-3.26 (m, 3H), 2.36 (s, 3H), 2.19-1.82 (m, 5H), 1.37 (d, J = 6.0 Hz, 6H). |
| 376 | 471.50 | 3.29 | |
| 377 | 405.10 | 2.51 | |
| 378 | | | |
| 379 | 445.50 | 1.50 | |
| 380 | 467.31 | 2.27 | |
| 381 | 426.12 | 1.68 | 1H NMR (400 MHz, CDCl3) ? 7.57 (dd, J = 7.7, 1.4 Hz, 1H), 7.45-7.34 (m, 2H), 7.33-7.17 (m, 4H), 7.14-7.00 (m, 2H), 6.58 (dd, J = 77.9, 70.8 Hz, 1H), 4.66 (t, J = 13.1 Hz, 1H), 4.16 (s, 3H), 3.68-3.51 (m, 1H), 3.43-3.27 (m, 2H), 2.26-2.15 (m, 1H), 2.13-1.99 (m, 1H), 1.99-1.88 (m, 1H), 1.82-1.66 (m, 1H). |
| 382 | 462.50 | 1.85 | |
| 383 | 408.50 | 1.62 | |
| 384 | 391.30 | 1.38 | |
| 385 | 427.25 | 2.45 | |
| 386 | 429.20 | 2.00 | |
| 387 | 486.20 | 2.05 | |
| 388 | 444.10 | 1.65 | |
| 390 | 443.12 | 2.21 | |
| 391 | 532.20 | 1.71 | |
| 392 | 502.00 | 2.20 | 1H NMR (400 MHz, CDCl3) d 8.06 (t, J = 10.1 Hz, 1H), 7.70 (s, 1H), 7.64 (dd, J = 8.6, 1.6 Hz, 1H), 7.17 (d, J = 2.2 Hz, 1H), 7.10 (dd, J = 8.7, 2.2 Hz, 1H), 7.03 (dd, J = 10.4, 6.3 Hz, 2H), 6.13 (d, J = 4.0 Hz, 1H), 4.61 (s, 1H), 3.96 (d, J = 20.2 Hz, 3H), 3.89-3.06 (m, 3H), 2.16-1.81 (m, 4H). |
| 393 | 434.50 | 1.91 | |
| 394 | 451.30 | 7.62 | |
| 395 | 417.50 | 2.30 | |
| 396 | 406.20 | 1.19 | 1H NMR (400 MHz, DMSO) d 9.44 (s, 1H), 7.73 (d, J = 7.7 Hz, 1H), 7.47 (s, 1H), 7.29 (t, J = 7.7 Hz, 1H), 7.16-7.05 (m, 2H), 7.00 (s, 1H), 6.91 (d, J = 8.1 Hz, 1H), 6.81 (d, J = 8.0 Hz, 1H), 4.10 (s, 3H), |

TABLE 2-continued

| Cmpd No. | LC/MS M + 1 | LC/RT min | ¹H NMR |
|---|---|---|---|
| | | | 4.18-4.02 (m, 1H), 3.79 (s, 3H), 3.54-3.25 (m, 3H), 2.06-1.78 (m, 4H). |
| 397 | 407.24 | 2.16 | |
| 398 | 490.50 | 1.47 | |
| 399 | 447.50 | 7.60 | H NMR (400.0 MHz, DMSO) d 7.68-7.65 (m, 1H), 7.50-7.49 (m, 1H), 7.40 (d, J = 7.9 Hz, 1H), 7.17-6.98 (m, 5H), 6.29-6.28 (m, 1H), 6.18-6.17 (m, 1H), 4.49-4.34 (m, 1H), 3.83 (s, 3H), 3.80-3.41 (m, 3H), 3.13 (s, 3H), 2.11-1.81 (m, 4H) and 1.50 (s, 6H) ppm. |
| 400 | 465.21 | 2.23 | |
| 401 | 420.00 | 1.89 | 1H NMR (400 MHz, CDCl3) d 8.14 (d, J = 8.1 Hz, 1H), 7.76-7.67 (m, 1H), 7.58-7.49 (m, 2H), 7.38-7.32 (m, 1H), 7.24 (t, J = 7.5 Hz, 1H), 7.20-7.13 (m, 2H), 7.04 (d, J = 3.9 Hz, 1H), 6.12 (s, 1H), 4.72 (s, 1H), 3.37 (dd, J = 46.1, 33.5 Hz, 3H), 2.20 (s, 1H), 1.96 (dd, J = 56.3, 18.6 Hz, 3H). |
| 402 | 453.28 | 2.25 | |
| 403 | 490.40 | 3.05 | |
| 404 | 543.00 | 1.75 | |
| 405 | 376.50 | 1.43 | |
| 406 | 444.40 | 1.51 | 1H NMR (400 MHz, CDCl3) d 8.12 (d, J = 7.9 Hz, 1H), 7.52 (d, J = 8.1 Hz, 2H), 7.44 (d, J = 8.2 Hz, 2H), 7.25-7.19 (m, 1H), 7.17-7.11 (m, 2H), 7.02 (d, J = 3.9 Hz, 1H), 6.10 (d, J = 4.0 Hz, 1H), 4.66 (s, 1H), 3.78 (d, J = 11.1 Hz, 1H), 3.65 (d, J = 11.1 Hz, 1H), 3.49 (s, 1H), 3.33 (s, 3H), 2.10 (s, 1H), 1.84 (s, 4H), 1.53 (s, 3H). |
| 407 | 497.50 | 2.03 | |
| 408 | 486.35 | 1.70 | 1H NMR (400 MHz, CDCl3) d 8.12 (d, J = 8.5 Hz, 1H), 7.25-7.17 (m, 3H), 7.18-7.10 (m, 2H), 7.02 (d, J = 4.0 Hz, 1H), 6.70 (d, J = 9.0 Hz, 1H), 6.10 (d, J = 4.0 Hz, 1H), 4.66 (s, 1H), 3.74 (dd, J = 103.4, 60.3 Hz, 4H), 2.23 (s, 3H), 2.02 (dd, J = 92.2, 67.9 Hz, 5H), 1.61 (s, 6H). |
| 409 | 412.50 | 1.69 | |
| 410 | 446.50 | 6.31 | 1H NMR (400 MHz, CDCl3) d 7.50 (d, J = 7.8 Hz, 1H), 7.31 (s, 1H), 7.29-7.22 (m, 3H), 7.11-7.02 (m, 2H), 6.82 (d, J = 8.1 Hz, 1H), 4.56 (sept, J = 6.1 Hz, 1H), 4.50 (s, 1H), 4.48 (q, J = 7.3 Hz, 2H), 3.84 (s, 1H), 3.48 (s, 2H), 2.21 (s, 3H), 2.10 (s, 1H), 1.90 (s, 2H), 1.75 (s, 1H), 1.55 (t, J = 7.3 Hz, 3H), 1.35 (d, J = 6.0 Hz, 6H). |
| 411 | 518.30 | 1.55 | |
| 412 | 432.30 | 1.76 | |
| 413 | 534.50 | 2.07 | |
| 414 | 433.70 | 1.91 | |
| 415 | 417.13 | 2.89 | |
| 416 | 460.00 | 2.08 | |
| 417 | 481.20 | 3.03 | |
| 418 | 432.50 | 1.29 | 1H NMR (400 MHz, CDCl3) d 7.64 (d, J = 8.2 Hz, 2H), 7.57 (d, J = 7.7 Hz, 1H), 7.44 (d, J = 8.2 Hz, 2H), 7.29-7.23 (m, 3H), 7.10-7.02 (m, 2H), 4.93 (d, J = 7.0 Hz, 2H), 4.83 (d, J = 7.0 Hz, 2H), 4.60 (bs, 1H), 4.15 (s, 3H), 3.80-3.21 (m, 4H), 2.29-1.44 (m, 4H). |
| 419 | 426.50 | 7.85 | H NMR (400.0 MHz, DMSO) d 7.93 (d, J = 1.7 Hz, 1H), 7.73 (m, 1H), 7.68-7.63 (m, 2H), 7.50 (m, 1H), 7.17-7.05 (m, 3H), 6.29 (t, J = 3.2 Hz, 1H), 6.16 (dd, J = 1.3, 3.4 Hz, 1H), 4.48-4.34 (m, 1H), 3.59-3.41 (m, 2H), 3.23 (m, 1H), 2.10-1.85 (m, 4H) and 1.48 (s, 9H) ppm. |
| 420 | 464.20 | 2.38 | |
| 421 | 411.23 | 2.18 | |
| 422 | 430.70 | 1.77 | |
| 423 | 480.30 | 2.31 | |
| 424 | 489.50 | 2.04 | 1H NMR (400 MHz, CDCl3) d 7.71-7.59 (m, 2H), 7.23-7.06 (m, 5H), 6.81 (d, J = 3.9 Hz, 1H), 6.06 (d, J = 3.9 Hz, 1H), 4.63 (s, 1H), 3.68 (s, 1H), 3.56 (s, 1H), 3.31 (s, 1H), 2.16 (s, 1H), 2.03-1.90 (m, 1H), 1.82 (d, J = 21.3 Hz, 1H), 1.64 (s, 6H). |
| 425 | 448.50 | 1.32 | |
| 426 | 490.30 | 1.83 | 1H NMR (400 MHz, CDCl3) d 8.13 (d, J = 7.4 Hz, 1H), 7.76 (d, J = 9.1 Hz, 2H), 7.43-7.36 (m, 1H), 7.22 (d, J = 8.0 Hz, 1H), 7.15 (t, J = 7.0 Hz, 2H), 7.03 (d, J = 3.9 Hz, 1H), 6.14-6.06 (m, 1H), 4.76 (d, J = 13.5 Hz, 1H), 3.52 (t, J = 12.1 Hz, 1H), 3.41-3.24 (m, 2H), 3.24-3.16 (m, 1H), 2.44 (d, J = 13.7 Hz, 3H), 2.25 (d, |

TABLE 2-continued

| Cmpd No. | LC/MS M + 1 | LC/RT min | ¹H NMR |
|---|---|---|---|
| | | | J = 15.6 Hz, 1H), 2.10-1.95 (m, 3H), 1.84-1.73 (m, 1H), 1.31 (d, J = 6.9 Hz, 6H). |
| 427 | 476.30 | 2.12 | |
| 428 | 489.25 | 1.95 | |
| 429 | 446.20 | 2.49 | |
| 430 | 418.30 | 1.90 | |
| 431 | 506.50 | 1.49 | 1H NMR (400 MHz, DMSO) d 7.93 (dd, J = 8.2, 6.5 Hz, 3H), 7.73 (d, J = 8.3 Hz, 2H), 7.32 (d, J = 4.0 Hz, 1H), 7.25 (s, 1H), 7.15 (d, J = 8.4 Hz, 1H), 6.45 (d, J = 4.1 Hz, 1H), 5.39-5.30 (m, 1H), 4.51 (s, 2H), 3.81-3.64 (m, 1H), 3.54-3.42 (m, 2H), 3.41-3.37 (m, 1H), 2.20-2.12 (m, 1H), 2.13-2.03 (m, 1H), 2.01 (t, J = 5.9 Hz, 1H), 1.57 (dd, J = 12.5, 6.2 Hz, 1H), 1.17 (d, J = 6.8 Hz, 6H). |
| 432 | 411.23 | 2.18 | |
| 433 | 404.20 | 1.75 | |
| 434 | 443.20 | 2.12 | |
| 435 | 466.50 | 1.72 | |
| 436 | 490.30 | 1.90 | 1H NMR (400 MHz, CDCl3) d 8.13 (d, J = 7.5 Hz, 1H), 7.98 (d, J = 8.3 Hz, 2H), 7.62 (d, J = 8.3 Hz, 2H), 7.26-7.21 (m, 1H), 7.15 (t, J = 7.2 Hz, 2H), 7.03 (d, J = 4.0 Hz, 1H), 6.11 (d, J = 4.0 Hz, 1H), 4.69 (d, J = 11.9 Hz, 1H), 3.66-3.48 (m, 2H), 3.40-3.28 (m, 1H), 3.00 (d, J = 6.5 Hz, 2H), 2.30-2.16 (m, 2H), 2.12-1.98 (m, 2H), 1.88-1.75 (m, 1H), 1.08 (s, 3H), 1.07 (s, 3H). |
| 437 | 475.30 | 1.76 | |
| 438 | 444.20 | 5.86 | 1H NMR (400 MHz, CDCl3) d 8.24 (d, J = 2.8 Hz, 1H), 7.73 (d, J = 8.7 Hz, 1H), 7.67 (d, J = 8.2 Hz, 1H), 7.31 (dd, J = 8.7, 2.9 Hz, 1H), 7.21-7.05 (m, 3H), 6.80 (d, J = 3.9 Hz, 1H), 6.08 (d, J = 3.9 Hz, 1H), 4.65 (d, J = 12.3 Hz, 1H), 4.10 (d, J = 12.5 Hz, 1H), 3.90 (s, 3H), 3.61 (t, J = 13.0 Hz, 1H), 3.33 (t, J = 12.4 Hz, 1H), 2.23-1.98 (m, J = 17.2 Hz, 4H). |
| 439 | 412.30 | 1.35 | |
| 440 | 490.30 | 1.84 | 1H NMR (400 MHz, CDCl3) d 8.00 (d, J = 8.1 Hz, 1H), 7.95 (d, J = 8.3 Hz, 2H), 7.61 (d, J = 8.3 Hz, 2H), 7.00 (d, J = 4.0 Hz, 1H), 6.94 (d, J = 10.0 Hz, 2H), 6.09 (d, J = 4.0 Hz, 1H), 4.69 (d, J = 11.7 Hz, 1H), 3.65-3.47 (m, 2H), 3.34 (t, J = 12.1 Hz, 1H), 3.21 (dt, J = 13.7, 6.9 Hz, 1H), 2.36 (s, 3H), 2.29-2.16 (m, 1H), 2.11-1.95 (m, 2H), 1.90-1.71 (m, 1H), 1.31 (d, J = 6.9 Hz, 6H). |
| 441 | 457.27 | 2.43 | |
| 442 | 430.40 | 2.95 | |
| 443 | 417.50 | 1.86 | |
| 444 | 400.00 | 1.35 | |
| 445 | 485.50 | 1.75 | 1H NMR (400 MHz, CDCl3) d 8.59, 8.57, 7.52, 7.31, 7.26, 7.23, 7.22, 7.21, 7.16, 7.14, 7.13, 7.11, 7.09, 7.01, 6.99, 6.97, 6.93, 6.15, 4.74, 4.70, 4.14, 4.12, 4.10, 4.08, 3.51, 3.29, 3.08, 2.21, 2.17, 2.08, 2.07, 2.05, 2.04, 2.01, 1.61, 1.56, 1.51, 1.47, 1.45, 1.44. |
| 446 | 458.50 | 1.78 | |
| 447 | 432.50 | 1.46 | |
| 448 | 431.20 | 2.24 | 1H NMR (400 MHz, CDCl3) d 7.56 (d, J = 7.7 Hz, 1H), 7.45-7.37 (m, 3H), 7.46-7.22 (m, 2H), 7.30-7.21 (m, 1H), 7.13-7.00 (m, 2H), 4.52 (d, J = 13.5 Hz, 1H), 4.19 (s, 3H), 3.74-3.51 (m, 2H), 3.31 (t, J = 11.9 Hz, 1H), 3.09 (s, 3H), 2.94 (s, 3H), 2.24-2.02 (m, J = 13.9 Hz, 2H), 2.02-1.76 (m, 2H). |
| 449 | 463.50 | 1.98 | |
| 450 | 414.25 | 2.26 | |
| 451 | 463.30 | 2.27 | 1H NMR (400 MHz, CDCl3) d 7.49 (t, J = 7.7 Hz, 1H), 7.40 (d, J = 7.6 Hz, 1H), 7.29 (dd, J = 11.7, 6.5 Hz, 4H), 7.12 (d, J = 1.8 Hz, 2H), 7.04 (dd, J = 8.5, 2.1 Hz, 1H), 6.36 (t, J = 3.2 Hz, 1H), 6.07 (d, J = 3.3 Hz, 1H), 4.65 (br s, 1H), 3.62 (br s, 2H), 3.36 (br s, 1H), 2.21 (br s, 1H), 2.08 (br s, 2H), 1.87 (br s, 1H), 1.62 (s, 2H). |
| 452 | 444.10 | 1.79 | |
| 453 | 418.10 | 2.33 | |
| 454 | 460.50 | 1.44 | |
| 455 | 472.00 | 1.63 | 1H NMR (400 MHz, CDCl3) d 8.63 (s, 1H), 7.83 (dd, J = 8.1, 1.6 Hz, 1H), 7.70 (d, J = 8.1 Hz, 1H), 7.49 (d, J = 8.1 Hz, 1H), 7.17 (tt, J = 15.4, 7.6 Hz, 3H), 6.84 (d, J = 3.9 Hz, 1H), 6.08 (d, J = 3.9 Hz, 1H), 4.65 (d, J = 20.8 Hz, |

TABLE 2-continued

| Cmpd No. | LC/MS M + 1 | LC/RT min | ¹H NMR |
|---|---|---|---|
| | | | 1H), 3.68 (s, 2H), 3.37 (s, 1H), 2.82 (s, 1H), 2.30-1.99 (m, 3H), 1.90 (s, 1H), 1.58 (s, 6H). |
| 456 | 505.30 | 1.96 | 1H NMR (400 MHz, DMSO) d 7.96 (d, J = 8.0 Hz, 2H), 7.74 (d, J = 8.0 Hz, 2H), 7.57 (d, J = 8.0 Hz, 1H), 7.34-7.17 (m, 3H), 7.03 (d, J = 3.9 Hz, 1H), 6.40 (d, J = 3.9 Hz, 1H), 4.51-4.37 (m, 1H), 3.62-3.11 (m, 3H), 3.35 (q, J = 7.3 Hz, 2H), 2.19-1.75 (m, 4H), 1.12 (t, J = 7.3 Hz, 3H). |
| 457 | 472.25 | 1.52 | |
| 458 | 459.50 | 2.01 | |
| 459 | 429.50 | 2.30 | |
| 460 | 429.30 | 1.57 | |
| 461 | 394.10 | 1.76 | |
| 462 | 458.50 | 1.68 | 1H NMR (400 MHz, CDCl3) d 8.12 (d, J = 7.6 Hz, 1H), 7.34 (d, J = 8.4 Hz, 1H), 7.25-7.18 (m, 2H), 7.18-7.09 (m, 2H), 7.01 (d, J = 4.0 Hz, 1H), 6.63 (d, J = 8.5 Hz, 1H), 6.10 (d, J = 4.0 Hz, 1H), 5.70-5.30 (m, 2H), 4.63 (s, 2H), 3.68-3.23 (m, 2H), 2.27 (s, 3H), 2.21-2.02 (m, 2H), 1.99-1.74 (m, 2H). |
| 463 | 429.30 | 1.53 | |
| 464 | 418.30 | 2.38 | |
| 465 | 404.30 | 1.67 | |
| 466 | 449.10 | 1.41 | |
| 467 | 418.30 | 1.95 | |
| 468 | 462.30 | 2.33 | |
| 469 | 508.30 | 1.58 | |
| 470 | 406.20 | 2.80 | |
| 471 | 461.22 | 2.52 | |
| 472 | 524.30 | 2.18 | |
| 473 | 432.70 | 1.60 | |
| 474 | 435.50 | 1.63 | |
| 475 | 427.50 | 2.12 | 1H NMR (400 MHz, CDCl3) d 7.26 (d, J = 8.4 Hz, 1H), 7.13-7.07 (m, 2H), 7.05-6.96 (m, 2H), 6.94-6.85 (m, 2H), 6.33 (t, J = 3.2 Hz, 1H), 6.08-5.98 (m, 1H), 4.69 (d, J = 13.1 Hz, 1H), 3.80 (s, 3H), 3.63-3.44 (m, 2H), 3.33 (t, J = 12.8 Hz, 1H), 2.19 (d, J = 13.8 Hz, 1H), 2.09-1.96 (m, 2H), 1.60 (s, 1H). |
| 476 | 408.40 | 2.86 | |
| 477 | 443.10 | 2.62 | |
| 478 | 423.50 | 2.17 | 1H NMR (400 MHz, CDCl3) d 7.30 (dt, J = 8.4, 6.8 Hz, 3H), 7.12 (d, J = 2.0 Hz, 2H), 7.01 (ddd, J = 20.7, 10.7, 4.8 Hz, 4H), 6.36 (t, J = 3.1 Hz, 1H), 6.06 (d, J = 2.9 Hz, 1H), 4.65 (br s, 1H), 4.07 (q, J = 7.0 Hz, 2H), 3.71 (br s, 1H), 3.55 (br s, 1H), 3.33 (br s, 1H), 2.19 (br s, 1H), 2.05 (br s, 2H), 1.86 (br s, 1H), 1.62 (br s, 3H), 1.44 (t, J = 7.0 Hz, 3H). |
| 479 | 486.00 | 2.03 | 1H NMR (400 MHz, CDCl3) d 8.10 (dd, J = 9.0, 5.2 Hz, 1H), 7.70 (s, 1H), 7.64 (d, J = 8.5 Hz, 1H), 7.03 (dd, J = 10.3, 6.1 Hz, 2H), 6.94-6.82 (m, 2H), 6.11 (d, J = 4.0 Hz, 1H), 4.61 (s, 1H), 3.95 (s, 3H), 3.49 (s, 3H), 2.03 (d, J = 66.9 Hz, 4H). |
| 480 | 456.50 | 1.82 | |
| 481 | 437.00 | 2.05 | 1H NMR (400 MHz, CDCl3) d 8.16-7.94 (m, 1H), 7.60 (d, J = 8.1 Hz, 2H), 7.47 (d, J = 8.1 Hz, 2H), 7.17-7.10 (m, 1H), 7.10-7.00 (m, 2H), 6.93 (d, J = 4.0 Hz, 1H), 6.02 (d, J = 4.0 Hz, 1H), 4.60 (d, J = 10.9 Hz, 1H), 3.51 (s, 2H), 3.41-3.08 (m, 1H), 2.13 (d, J = 11.5 Hz, 1H), 1.95 (s, 3H), 1.78 (d, J = 8.8 Hz, 1H). |
| 482 | 481.50 | 2.23 | |
| 483 | 533.50 | 2.10 | 1H NMR (400 MHz, DMSO) d 7.89 (d, J = 8.0 Hz, 2H), 7.73 (d, J = 8.0 Hz, 2H), 7.57 (d, J = 8.0 Hz, 1H), 7.35-7.25 (m, 2H), 7.25-7.16 (m, 1H), 7.03 (d, J = 3.9 Hz, 1H), 6.40 (d, J = 3.9 Hz, 1H), 4.53-4.37 (m, 1H), 3.57-3.14 (m, 3H), 2.17-1.78 (m, 4H), 1.26 (s, 9H). |
| 484 | 477.22 | 2.20 | |
| 485 | 432.50 | 1.96 | 1H NMR (400 MHz, CDCl3) d 8.15, 8.13, 7.54, 7.28, 7.26, 7.24, 7.22, 7.17, 7.16, 7.14, 7.12, 7.04, 7.03, 7.02, 7.00, 6.97, 6.95, 6.12, 4.76, 4.73, 4.16, 4.14, 4.13, 4.11, 3.55, 3.31, 2.24, 2.20, 2.07, 2.05, 2.03, 2.02, 2.00, 1.99, 1.63, 1.58, 1.54, 1.49, 1.48, 1.46. |
| 486 | 436.50 | 1.46 | |
| 487 | 443.70 | 1.83 | |
| 488 | 497.50 | 1.78 | |
| 489 | 423.30 | 6.50 | |
| 490 | 456.00 | 2.20 | 1H NMR (400 MHz, CDCl3) d 7.28-7.22 (m, 2H), 7.18 (t, J = 7.9 Hz, 1H), 7.09 (d, J = 3.7 Hz, 1H), |

TABLE 2-continued

| Cmpd No. | LC/MS M + 1 | LC/RT min | ¹H NMR |
|---|---|---|---|
| | | | 7.03 (dd, J = 13.1, 7.9 Hz, 2H), 6.82 (d, J = 8.4 Hz, 1H), 6.18 (d, J = 4.0 Hz, 1H), 4.57 (dt, J = 12.1, 6.0 Hz, 2H), 3.43 (d, J = 6.4 Hz, 3H), 2.70 (s, 3H), 2.22 (d, J = 3.5 Hz, 3H), 2.05 (t, J = 15.1 Hz, 5H), 1.36 (d, J = 6.0 Hz, 7H). |
| 491 | 374.20 | 2.04 | |
| 492 | 467.20 | 2.50 | 1H NMR (400 MHz, DMSO) d 7.71 (d, J = 8.6 Hz, 1H), 7.52 (d, J = 1.5 Hz, 1H), 7.29 (d, J = 2.2 Hz, 1H), 7.14 (dd, J = 8.6, 2.2 Hz, 1H), 7.07-6.95 (m, 3H), 6.30 (t, J = 3.1 Hz, 1H), 6.20 (d, J = 3.3 Hz, 1H), 4.63-4.07 (m, 1H), 3.94 (t, J = 6.5 Hz, 2H), 3.79 (s, 3H), 3.59-3.14 (m, 3H), 2.08-1.86 (m, 4H), 1.73 (sextet, J = 7.0 Hz, 2H), 0.97 (t, J = 7.4 Hz, 3H). |
| 493 | 451.23 | 2.25 | |
| 494 | 453.30 | 1.40 | 1H NMR (400 MHz, DMSO) d 7.84 (d, J = 8.2 Hz, 2H), 7.74 (d, J = 7.7 Hz, 1H), 7.69 (d, J = 8.1 Hz, 2H), 7.48 (s, 1H), 7.46 (s, 1H), 7.33-7.25 (m, 1H), 7.15-7.04 (m, 2H), 4.45-4.34 (m, 1H), 4.10 (s, 3H), 3.61-3.21 (m, 3H), 2.44 (s, 3H), 2.08-1.82 (m, 4H). |
| 495 | 465.50 | 4.00 | |
| 496 | 420.30 | 3.60 | 1H NMR (400 MHz, DMSO) d 7.73 (dd, J = 7.7, 1.1 Hz, 1H), 7.47 (s, 1H), 7.41 (d, J = 8.6 Hz, 2H), 7.33-7.25 (m, 1H), 7.16-7.04 (m, 2H), 6.99 (d, J = 8.7 Hz, 2H), 4.88 (t, J = 5.4 Hz, 1H), 4.49-4.16 (m, 1H), 4.10 (s, 3H), 4.03 (t, J = 4.9 Hz, 2H), 3.77-3.67 (m, 2H), 3.66-3.18 (m, 3H), 2.02-1.83 (m, 4H). |
| 497 | 481.10 | 2.03 | 1H NMR (400 MHz, DMSO) d 7.71 (d, J = 8.6 Hz, 1H), 7.52 (dd, J = 2.8, 1.3 Hz, 1H), 7.41 (d, J = 7.9 Hz, 1H), 7.29 (d, J = 2.3 Hz, 1H), 7.14 (dd, J = 8.6, 2.3 Hz, 1H), 7.05 (d, J = 1.3 Hz, 1H), 7.01 (dd, J = 7.8, 1.3 Hz, 1H), 6.30 (t, J = 3.2 Hz, 1H), 6.20 (dd, J = 3.5, 1.2 Hz, 1H), 4.55-4.25 (m, 1H), 3.83 (s, 3H), 3.74-3.39 (m, 3H), 3.13 (s, 3H), 2.06-1.86 (m, 4H), 1.50 (s, 6H). |
| 498 | 505.30 | 2.56 | 1H NMR (400 MHz, CDCl3) d 7.59 (d, J = 8.8 Hz, 1H), 7.18-7.10 (m, 2H), 7.07 (dd, J = 8.8, 2.4 Hz, 1H), 6.96-6.87 (m, 2H), 6.81 (d, J = 3.6 Hz, 1H), 6.07 (d, J = 3.8 Hz, 1H), 4.92-4.24 (m, 1H), 3.85 (s, 3H), 3.66-3.03 (m, 3H), 2.64 (q, J = 7.5 Hz, 2H), 2.31-1.75 (m, 4H), 1.18 (t, J = 7.5 Hz, 3H). |
| 499 | 404.27 | 1.44 | |
| 500 | 418.40 | 3.93 | |
| 501 | 481.50 | 4.04 | |
| 502 | 424.30 | 1.63 | 1H NMR (400 MHz, CDCl3) d 8.24, 7.04, 7.02, 6.84, 6.82, 6.69, 6.65, 6.64, 6.61, 6.56, 6.46, 6.45, 6.38, 6.38, 6.36, 6.36, 6.25, 6.22, 5.90, 5.70, 5.69, 5.68, 5.51, 5.49, 5.44, 5.43, 5.30, 5.28, 5.22, 4.02, 3.99, 3.36, 3.10, 2.97, 2.92, 2.86, 2.84, 2.74, 2.69, 2.66, 2.63, 1.99, 1.92, 1.86, 1.81, 1.76, 1.71, 1.60, 1.54, 1.50, 1.45, 1.44, 1.41, 1.38, 1.26, 1.21, 0.79, −1.64. |
| 503 | 483.97 | 3.83 | |
| 504 | 516.00 | 1.88 | 1H NMR (400 MHz, CDCl3) d 8.38 (d, J = 8.1 Hz, 1H), 8.19-8.09 (m, 1H), 7.97 (s, 1H), 7.82 (d, J = 8.1 Hz, 1H), 7.22 (d, J = 7.8 Hz, 1H), 7.19-7.11 (m, 2H), 7.03 (d, J = 4.0 Hz, 1H), 6.13 (d, J = 4.0 Hz, 1H), 4.69 (d, J = 11.7 Hz, 1H), 3.86-3.28 (m, 3H), 3.20 (s, 3H), 2.11 (d, J = 50.6 Hz, 16H), 1.99-1.79 (m, 2H). |
| 505 | 503.95 | 4.25 | |
| 506 | 418.50 | 1.47 | 1H NMR (400 MHz, CDCl3) d 7.64-7.50 (m, 3H), 7.44 (t, J = 12.1 Hz, 2H), 7.33-7.21 (m, 2H), 7.06 (dd, J = 15.7, 8.0 Hz, 2H), 4.60 (m, 1H), 4.17 (s, 3H), 3.82-3.49 (m, 2H), 3.43 (m, 1H), 2.33-1.69 (m, 5H), 1.59 (s, 6H). |
| 507 | 463.00 | 1.34 | |
| 508 | 469.50 | 1.86 | 1H NMR (400 MHz, CDCl3) d 7.96 (d, J = 8.3 Hz, 2H), 7.63 (d, J = 8.3 Hz, 2H), 7.29 (d, J = 22.7 Hz, 1H), 7.11-7.01 (m, 4H), 6.92 (t, J = 3.8 Hz, 1H), 6.12 (d, J = 3.3 Hz, 1H), 4.67 (d, J = 12.5 Hz, 1H), 3.69-3.46 (m, 2H), 3.40-3.27 (m, 1H), 3.21 (dt, J = 13.7, 6.8 Hz, 2H), 2.15 (d, J = 56.6 Hz, 4H), 1.54 (s, 1H), 1.31 (d, J = 6.9 Hz, 8H). |
| 509 | | | 1H NMR (400 MHz, DMSO) d 8.00 (d, J = 7.9 Hz, 1H), 7.96 (d, J = 7.9 Hz, 1H), 7.58-7.50 (m, J = 8.6 Hz, 2H), 7.35 (d, J = 4.0 Hz, 1H), 7.34-7.28 (m, J = 4.1 Hz, 2H), 7.28-7.20 (m, 1H), 6.48 (d, J = 4.0 Hz, 1H), 4.45 (d, J = 12.5 Hz, 1H), 3.59-3.42 (m, J = 20.8 Hz, 2H), 3.25 (s, 3H), 3.19 (br d, 1H), 2.68 (s, |

TABLE 2-continued

| Cmpd No. | LC/MS M + 1 | LC/RT min | ¹H NMR |
|---|---|---|---|
| | | | 3H), 2.16-2.00 (m, J = 22.8 Hz, 3H), 1.90 (d, J = 13.1 Hz, 1H). |
| 510 | 408.26 | 1.60 | |
| 511 | 428.50 | 2.07 | |
| 512 | 449.00 | 3.32 | |
| 513 | 457.50 | 1.82 | 1H NMR (400 MHz, CDCl3) d 8.04 (d, J = 8.4 Hz, 2H), 7.76 (d, J = 7.3 Hz, 1H), 7.68 (t, J = 7.6 Hz, 1H), 7.29 (t, J = 4.1 Hz, 2H), 7.13 (d, J = 1.9 Hz, 2H), 7.04 (dd, J = 8.5, 1.8 Hz, 1H), 6.36 (t, J = 3.1 Hz, 1H), 6.07 (d, J = 3.4 Hz, 1H), 4.67 (br s, 1H), 3.59 (br s, 2H), 3.38 (br s, 1H), 3.10 (s, 3H), 2.22 (br s, 1H), 2.06 (br s, 2H), 1.89 (br s, 1H), 1.62 (s, 4H). |
| 514 | 488.00 | 1.79 | 1H NMR (400 MHz, CDCl3) d 7.41 (d, J = 7.9 Hz, 1H), 7.25 (d, J = 8.1 Hz, 2H), 7.19-7.02 (m, 3H), 6.83 (d, J = 8.1 Hz, 1H), 6.26 (d, J = 3.4 Hz, 1H), 5.99 (d, J = 3.5 Hz, 1H), 5.68 (s, 1H), 4.71 (d, J = 4.7 Hz, 2H), 4.57 (dt, J = 12.0, 6.1 Hz, 2H), 4.00-3.30 (m, 3H), 2.23 (s, 3H), 2.20-1.75 (m, 4H), 1.36 (d, J = 6.0 Hz, 6H). |
| 515 | 492.20 | 2.44 | |
| 516 | 414.50 | 1.58 | 1H NMR (400 MHz, DMSO) d 7.99 (d, J = 7.8 Hz, 1H), 7.41 (d, J = 7.5 Hz, 1H), 7.38-7.13 (m, 6H), 6.50 (t, J = 4.4 Hz, 1H), 5.15 (t, J = 5.3 Hz, 1H), 4.52 (d, J = 5.4 Hz, 3H), 3.53-3.03 (m, 4H), 2.23-1.66 (m, 6H). |
| 517 | 446.14 | 2.39 | |
| 518 | 478.20 | 2.62 | |
| 519 | 418.00 | 1.81 | 1H NMR (400 MHz, CDCl3) d 8.14 (d, J = 8.1 Hz, 1H), 7.38-7.31 (m, 1H), 7.23 (dd, J = 8.7, 6.6 Hz, 1H), 7.20-7.12 (m, 2H), 7.04 (d, J = 4.0 Hz, 1H), 6.82-6.71 (m, 2H), 6.11 (dd, J = 10.3, 4.0 Hz, 1H), 4.79 (d, J = 13.3 Hz, 1H), 3.88 (d, J = 7.4 Hz, 3H), 3.62-3.24 (m, 3H), 2.31-2.17 (m, 1H), 2.17-1.81 (m, 3H). |
| 520 | 394.30 | 1.83 | |
| 521 | 467.30 | 1.47 | 1H NMR (400 MHz, DMSO) d 7.85 (d, J = 8.1 Hz, 2H), 7.79-7.52 (m, 4H), 7.46 (s, 1H), 7.33-7.25 (m, 1H), 7.15-7.04 (m, 2H), 4.46-4.32 (m, 1H), 4.10 (s, 3H), 3.64-3.20 (m, 3H), 2.81 (q, J = 7.2 Hz, 2H), 2.09-1.81 (m, 4H), 0.98 (t, J = 7.2 Hz, 3H). |
| 522 | 476.30 | 1.80 | 1H NMR (400 MHz, CDCl3) d 8.09 (d, J = 8.6 Hz, 1H), 7.99 (d, J = 8.1 Hz, 1H), 7.41 (s, 1H), 7.40 (d, J = 7.0 Hz, 1H), 7.00 (d, J = 4.0 Hz, 1H), 6.95 (s, 1H), 6.94 (d, J = 10.2 Hz, 1H), 6.09 (d, J = 4.0 Hz, 1H), 4.68 (d, J = 11.8 Hz, 1H), 3.65-3.53 (m, 2H), 3.32 (t, J = 12.6 Hz, 1H), 3.09 (s, 3H), 2.75 (s, 3H), 2.36 (s, 3H), 2.27-2.17 (m, 1H), 2.11-1.96 (m, 2H), 1.86-1.75 (m, 1H). |
| 523 | 467.50 | 1.43 | 1H NMR (400 MHz, DMSO) d 7.85 (d, J = 8.0 Hz, 1H), 7.74 (s, 1H), 7.64-7.55 (m, 2H), 7.49 (s, 1H), 7.45 (d, J = 8.2 Hz, 1H), 7.25-7.16 (m, 1H), 7.06-6.94 (m, 2H), 4.33 (d, J = 11.7 Hz, 1H), 3.88 (s, 3H), 3.62-3.48 (m, 1H), 3.48-3.34 (m, 2H), 2.60 (s, 3H), 2.46 (d, J = 4.9 Hz, 3H), 2.10-1.98 (m, 1H), 1.97-1.82 (m, 3H). |
| 524 | 432.50 | 1.18 | |
| 525 | 432.70 | 1.51 | |
| 526 | 458.28 | 1.76 | |
| 527 | 463.10 | 1.68 | |
| 528 | 458.50 | 1.80 | 1H NMR (400 MHz, CDCl3) d 7.52, 7.50, 7.33, 7.30, 7.29, 7.27, 7.24, 7.22, 7.17, 7.15, 7.12, 7.08, 7.07, 7.05, 7.01, 6.84, 6.65, 6.47, 4.69, 4.65, 4.51, 4.49, 4.47, 4.45, 4.00, 3.65, 3.61, 3.58, 3.56, 3.51, 3.50, 3.48, 3.46, 3.40, 3.36, 3.34, 3.30, 2.23, 2.19, 2.07, 2.02, 1.98, 1.97, 1.94, 1.93, 1.91, 1.76, 1.63, 1.61, 1.58, 1.55, 1.53, 1.23, 1.22, 1.20. |
| 529 | 465.10 | 2.37 | |
| 530 | 484.50 | 5.64 | |
| 531 | 501.30 | 2.01 | 1H NMR (400 MHz, DMSO) d 7.57 (d, J = 8.1 Hz, 1H), 7.49 (s, 1H), 7.36-7.25 (m, 3H), 7.20 (t, J = 7.7 Hz, 1H), 7.04-6.95 (m, 2H), 6.41 (d, J = 3.9 Hz, 1H), 5.11-5.03 (m, 1H), 4.71-4.62 (m, 1H), 4.48 (s, 2H), 4.43-4.02 (m, 1H), 3.88-3.12 (m, 3H), 2.09-1.87 (m, 4H), 1.27 (d, J = 6.0 Hz, 6H). |
| 532 | 467.20 | 2.19 | |
| 533 | 462.30 | 2.44 | |
| 534 | 439.28 | 2.04 | |

TABLE 2-continued

| Cmpd No. | LC/MS M + 1 | LC/RT min | ¹H NMR |
|---|---|---|---|
| 535 | 483.10 | 1.47 | 1H NMR (400 MHz, DMSO) d 8.12 (d, J = 3.2 Hz, 1H), 7.57 (d, J = 8.1 Hz, 1H), 7.47 (dd, J = 44.9, 6.9 Hz, 1H), 7.38-7.24 (m, 2H), 7.20 (t, J = 7.0 Hz, 1H), 7.02 (d, J = 4.0 Hz, 1H), 6.70-6.57 (m, 1H), 6.40 (t, J = 4.6 Hz, 1H), 4.57-4.36 (m, 1H), 3.66-3.36 (m, 4H), 3.29-3.17 (m, 2H), 3.18-3.01 (m, 1H), 2.13 (dd, J = 25.2, 12.5 Hz, 1H), 2.08-1.97 (m, 2H), 1.97-1.77 (m, 5H). |
| 536 | 444.50 | 2.18 | 1H NMR (400 MHz, DMSO) d 7.93 (d, J = 1.8, 1H), 7.75-7.69 (m, 2H), 7.64 (d, J = 8.3, 1H), 7.50 (dd, J = 2.8, 1.3, 1H), 7.09 (dd, J = 9.6, 2.8, 1H), 6.94 (td, J = 8.7, 2.8, 1H), 6.29 (t, J = 3.2, 1H), 6.17 (dd, J = 3.4, 1.3, 1H), 4.46-4.34 (m, 1H), 3.62-3.40 (m, 2H), 3.29-3.16 (m, 1H), 2.15-1.83 (m, 4H), 1.46 (s, 9H). |
| 537 | 448.20 | 2.00 | |
| 538 | 431.20 | 2.08 | |
| 539 | 504.24 | 2.09 | |
| 540 | 507.50 | 1.56 | 1H NMR (400 MHz, DMSO) d 8.00 (d, J = 8.0 Hz, 1H), 7.85 (d, J = 8.3 Hz, 2H), 7.70-7.64 (m, 3H), 7.37-7.28 (m, 3H), 7.26-7.18 (m, 1H), 6.47 (d, J = 4.0 Hz, 1H), 4.52-4.35 (m, 2H), 3.60-3.12 (m, 5H), 2.85-2.75 (m, 2H), 2.15-2.02 (m, 3H), 1.95-1.85 (m, 1H), 1.56-1.46 (m, 2H). |
| 541 | 532.30 | 1.95 | 1H NMR (400 MHz, DMSO) d 8.03 (s, 1H), 7.87 (d, J = 7.9 Hz, 2H), 7.69 (d, J = 8.0 Hz, 2H), 7.57 (d, J = 8.0 Hz, 1H), 7.37-7.11 (m, 3H), 7.03 (d, J = 3.7 Hz, 1H), 6.41 (d, J = 3.7 Hz, 1H), 4.55-4.36 (m, 1H), 3.64-3.13 (m, 3H), 2.20-1.81 (m, 5H), 0.54-0.33 (m, 4H). |
| 542 | 454.19 | 1.58 | |
| 543 | 480.30 | 2.24 | 1H NMR (400 MHz, DMSO) d 7.90 (d, J = 8.0 Hz, 1H), 7.74 (d, J = 7.6 Hz, 1H), 7.57-7.49 (m, 2H), 7.46 (s, 1H), 7.29 (t, J = 7.7 Hz, 1H), 7.09 (dd, J = 16.6, 8.0 Hz, 2H), 4.38 (d, J = 11.4 Hz, 1H), 4.10 (s, 3H), 3.58-3.46 (m, 2H), 3.08 (d, J = 6.1 Hz, 2H), 2.65 (s, 3H), 2.08-1.79 (m, 4H), 1.18 (s, 3H), 1.16 (s, 3H). |
| 544 | 436.50 | 1.88 | 1H NMR (400 MHz, MeOD) d 7.70 (d, J = 8.0 Hz, 1H), 7.48 (d, J = 4.6 Hz, 1H), 7.36-7.22 (m, 2H), 7.22-7.04 (m, 4H), 5.11-5.01 (m, 1H), 4.03-3.96 (m, 3H), 3.71-3.37 (m, 4H), 2.24-2.13 (m, 1H), 2.13-1.89 (m, 3H), 1.62-1.53 (m, 6H). |
| 545 | 418.20 | 2.33 | |
| 546 | 388.19 | 1.76 | |
| 547 | 493.50 | 2.16 | |
| 548 | 441.31 | 1.30 | |
| 549 | 490.00 | 1.85 | |
| 550 | 494.22 | 1.77 | |
| 551 | 429.70 | 2.15 | |
| 552 | 454.50 | 1.65 | |
| 553 | 448.50 | 4.80 | |
| 554 | 495.00 | 1.94 | |
| 555 | 429.70 | 2.27 | 1H NMR (400 MHz, CDCl3) d 7.22 (d, J = 7.4 Hz, 1H), 7.16 (s, 2H), 7.04-6.84 (m, 7H), 6.21 (t, J = 3.2 Hz, 1H), 5.89 (d, J = 3.4 Hz, 1H), 4.82 (br. s, 1H), 4.12 (br. s, 1H), 3.75 (s, 3H), 2.54 (q, J = 7.5 Hz, 2H), 2.45-1.84 (m, 8H), 1.48 (s, 4H), 1.07 (t, J = 7.5 Hz, 3H). |
| 556 | 453.30 | 1.84 | |
| 557 | 510.30 | 2.27 | |
| 558 | 520.50 | 1.95 | 1H NMR (400 MHz, DMSO) d 7.84 (d, J = 7.9 Hz, 1H), 7.63-7.54 (m, 2H), 7.49 (s, 1H), 7.46 (d, J = 8.8 Hz, 1H), 7.35-7.25 (m, 2H), 7.25-7.17 (m, 1H), 7.03 (d, J = 3.9 Hz, 1H), 6.42 (d, J = 4.0 Hz, 1H), 4.45 (d, J = 10.7 Hz, 1H), 3.61-3.40 (m, 2H), 3.27-3.14 (m, 1H), 2.60 (s, 3H), 2.45 (d, J = 4.9 Hz, 3H), 2.17-1.95 (m, 3H), 1.95-1.81 (m, 1H). |
| 559 | 458.50 | 1.79 | |
| 560 | 392.26 | 1.64 | |
| 561 | 457.10 | 2.35 | |
| 562 | 384.10 | 2.16 | |
| 563 | 379.50 | 2.01 | |
| 564 | 442.20 | 6.16 | 1H NMR (400 MHz, CDCl3) d 8.41 (s, 1H), 7.71-7.58 (m, 3H), 7.22-7.04 (m, 3H), 6.80 (d, J = 3.9 Hz, 1H), 6.07 (d, J = 3.9 Hz, 1H), 4.67 (d, J = 13.3 Hz, 1H), 3.99 (d, J = 12.8 Hz, 1H), 3.65-3.52 (m, 1H), 3.33 (td, J = 13.0, 2.9 Hz, 1H), 2.71 (q, J = 7.6 Hz, 2H), |

TABLE 2-continued

| Cmpd No. | LC/MS M + 1 | LC/RT min | ¹H NMR |
|---|---|---|---|
| | | | 2.18 (d, J = 15.2 Hz, 1H), 2.13-1.98 (m, 3H), 1.27 (t, J = 7.6 Hz, 3H). |
| 565 | 419.50 | 1.32 | 1H NMR (400 MHz, CDCl3) d 7.58, 7.56, 7.53, 7.51, 7.41, 7.39, 7.27, 7.26, 7.25, 7.24, 7.08, 7.05, 7.04, 7.01, 6.99, 6.53, 6.27, 6.25, 5.29, 5.27, 5.26, 5.24, 5.22, 4.56, 4.52, 4.33, 4.15, 4.14, 3.95, 3.68, 3.65, 3.62, 3.59, 3.50, 3.48, 3.46, 3.44, 3.35, 3.32, 3.29, 3.16, 3.14, 2.95, 2.21, 2.18, 2.11, 2.07, 2.00, 1.94, 1.90, 1.86, 1.83, 1.80, 1.58, 1.37, 1.35, 1.22, 1.20, 1.18, 0.06. |
| 566 | 428.20 | 5.72 | 1H NMR (400 MHz, CDCl3) d 8.41 (s, 1H), 7.77-7.56 (m, 3H), 7.24-7.05 (m, 3H), 6.80 (d, J = 3.9 Hz, 1H), 6.08 (d, J = 3.9 Hz, 1H), 4.76-4.61 (m, 1H), 4.05-3.91 (m, 1H), 3.69-3.52 (m, 1H), 3.43-3.24 (m, 1H), 2.39 (s, 3H), 2.28-1.98 (m, 4H). |
| 567 | 465.10 | 1.88 | 1H NMR (400 MHz, DMSO) d 7.71 (dd, J = 9.0, 5.6 Hz, 1H), 7.50 (dd, J = 2.8, 1.3 Hz, 1H), 7.41 (d, J = 8.0 Hz, 1H), 7.11 (dd, J = 9.6, 2.7 Hz, 1H), 7.05 (d, J = 1.2 Hz, 1H), 7.01 (dd, J = 7.9, 1.2 Hz, 1H), 6.99-6.90 (m, 1H), 6.28 (t, J = 3.2 Hz, 1H), 6.18 (dd, J = 3.6, 1.3 Hz, 1H), 4.52-4.26 (m, 1H), 3.83 (s, 3H), 3.70-3.40 (m, 3H), 3.13 (s, 3H), 2.06-1.85 (m, 4H), 1.50 (s, 6H). |
| 568 | 457.10 | 2.81 | |
| 569 | 450.40 | 2.51 | |
| 570 | 458.50 | 6.03 | |
| 571 | 444.40 | 1.51 | 1H NMR (400 MHz, CDCl3) d 8.12 (d, J = 7.7 Hz, 1H), 7.51 (d, J = 8.3 Hz, 2H), 7.43 (d, J = 8.3 Hz, 2H), 7.24-7.19 (m, 1H), 7.17-7.10 (m, 2H), 7.02 (d, J = 4.0 Hz, 1H), 6.10 (d, J = 4.0 Hz, 1H), 4.67 (s, 1H), 3.78 (d, J = 11.1 Hz, 1H), 3.64 (d, J = 11.1 Hz, 1H), 3.60-3.23 (m, 2H), 2.07 (s, 2H), 1.88 (s, 4H), 1.53 (s, 3H). |
| 572 | 501.30 | 1.82 | |
| 573 | 431.14 | 2.94 | |
| 574 | 458.25 | 1.77 | |
| 575 | 441.20 | 2.18 | |
| 576 | 469.50 | 1.79 | |
| 577 | 509.13 | 1.78 | |
| 578 | 439.24 | 1.99 | |
| 579 | 451.30 | 1.76 | 1H NMR (400 MHz, CDCl3) d 7.97-7.91 (m, 2H), 7.64-7.59 (m, 2H), 7.39-7.32 (m, 1H), 7.17-7.13 (m, 1H), 7.11-7.00 (m, 3H), 6.34 (t, J = 3.2 Hz, 1H), 6.06-6.00 (m, 1H), 4.71-4.59 (m, 1H), 3.70-3.31 (m, 3H), 3.27-3.14 (m, 1H), 2.29-1.76 (m, 4H), 1.31 (d, J = 6.9 Hz, 6H). |
| 580 | 499.50 | 1.58 | |
| 581 | 452.00 | 1.89 | |
| 582 | 466.30 | 1.52 | 1H NMR (400 MHz, DMSO) d 7.96 (d, J = 7.9 Hz, 1H), 7.67 (d, J = 7.7 Hz, 1H), 7.59-7.45 (m, 3H), 7.29 (t, J = 7.7 Hz, 1H), 7.17-7.04 (m, 2H), 4.54-4.33 (m, 3H), 3.61-3.36 (m, 3H), 3.26 (s, 3H), 2.68 (s, 3H), 2.10-1.80 (m, 4H), 1.38 (t, J = 7.2 Hz, 3H). |
| 583 | 432.70 | 1.54 | |
| 584 | 520.30 | 1.96 | |
| 585 | 449.30 | 5.90 | |
| 586 | 496.50 | 1.52 | 1H NMR (400 MHz, DMSO) d 7.83 (d, J = 8.0 Hz, 1H), 7.74 (d, J = 7.6 Hz, 1H), 7.45 (s, 1H), 7.34 (s, 1H), 7.29 (t, J = 7.8 Hz, 1H), 7.22 (d, J = 8.0 Hz, 1H), 7.15-7.06 (m, 2H), 4.45-4.31 (m, 1H), 4.10 (s, 3H), 3.97 (s, 3H), 3.68 (septet, J = 6.7 Hz, 1H), 3.59-3.22 (m, 3H), 2.10-1.82 (m, 4H), 1.17 (d, J = 6.9 Hz, 6H). |
| 587 | 468.10 | 2.70 | |
| 588 | 483.70 | 4.21 | |
| 589 | 544.20 | 1.95 | |
| 590 | 520.30 | 1.93 | 1H NMR (400 MHz, DMSO) d 7.85 (d, J = 8.2 Hz, 2H), 7.72-7.65 (m, 3H), 7.58 (d, J = 8.0 Hz, 1H), 7.34-7.25 (m, 2H), 7.25-7.17 (m, 1H), 7.03 (d, J = 3.9 Hz, 1H), 6.40 (d, J = 4.0 Hz, 1H), 4.52-4.38 (m, 1H), 3.60-3.12 (m, 3H), 2.80 (q, J = 7.2 Hz, 2H), 2.15-1.80 (m, 4H), 0.98 (t, J = 7.2 Hz, 3H). |
| 591 | 400.31 | 1.17 | |
| 592 | 479.30 | 1.82 | |
| 593 | 458.20 | 2.41 | 1H NMR (400 MHz, CDCl3) d 7.56 (d, J = 7.7 Hz, 1H), 7.38 (t, J = 8.1 Hz, 1H), 7.33-7.20 (m, 3H), 7.18-6.99 (m, 3H), 6.93 (t, J = 9.3 Hz, 1H), 4.67 (t, J = 15.1 Hz, 1H), 4.54-4.29 (m, 2H), 4.15 (s, 3H), |

TABLE 2-continued

| Cmpd No. | LC/MS M + 1 | LC/RT min | ¹H NMR |
|---|---|---|---|
| | | | 3.71-3.48 (m, 1H), 3.48-3.23 (m, 2H), 2.20 (t, J = 11.8 Hz, 1H), 2.10-1.64 (m, 3H). |
| 594 | 494.50 | 1.76 | 1H NMR (400 MHz, MeOD) d 8.01 (d, J = 8.4 Hz, 2H), 7.76 (d, J = 8.4 Hz, 2H), 7.70 (d, J = 7.8 Hz, 1H), 7.50 (s, 1H), 7.31 (t, J = 7.8 Hz, 1H), 7.17 (d, J = 8.1 Hz, 1H), 7.13 (t, J = 7.6 Hz, 1H), 5.18-5.01 (m, 1H), 3.75-3.62 (m, 1H), 3.62-3.40 (m, 4H), 2.19-1.89 (m, 4H), 1.58 (d, J = 3.8 Hz, 6H), 1.29 (d, J = 6.9 Hz, 6H). |
| 595 | 400.30 | 1.30 | |
| 596 | 463.00 | 1.86 | |
| 597 | 411.20 | 2.12 | |
| 598 | 432.50 | 1.47 | |
| 599 | 436.00 | 1.86 | |
| 600 | 414.34 | 1.45 | |
| 601 | 470.29 | 2.20 | |
| 602 | 461.50 | 3.23 | |
| 603 | 430.27 | 2.39 | |
| 604 | 500.29 | 1.99 | |
| 605 | 423.50 | 2.17 | 1H NMR (400 MHz, DMSO) d 7.71 (dd, J = 8.5, 4.5 Hz, 1H), 7.52 (d, J = 4.6 Hz, 1H), 7.37-7.23 (m, 2H), 7.20-7.01 (m, 3H), 6.35-6.26 (m, 1H), 6.18 (dd, J = 9.0, 2.4 Hz, 1H), 4.57-4.39 (m, 1H), 3.78-3.65 (m, J = 9.6 Hz, 3H), 3.54-3.11 (m, 3H), 2.25 (s, 3H), 2.12-1.80 (m, 4H). |
| 606 | 483.70 | 4.20 | |
| 607 | 481.00 | 1.49 | |
| 608 | 432.70 | 1.89 | |
| 609 | 467.50 | 1.93 | |
| 610 | 446.30 | 1.97 | |
| 611 | 431.06 | 2.72 | |
| 612 | 465.10 | 2.01 | |
| 613 | 466.30 | 4.17 | |
| 614 | 471.30 | 1.62 | |
| 615 | 511.24 | 2.14 | |
| 616 | 509.32 | 2.04 | |
| 617 | 466.30 | 2.30 | |
| 618 | 479.30 | 7.06 | 1H NMR (400 MHz, CDCl3) d 7.67 (d, J = 8.2 Hz, 1H), 7.46-7.34 (m, 2H), 7.30 (t, J = 7.0 Hz, 1H), 7.25-7.05 (m, 4H), 6.81 (d, J = 3.5 Hz, 1H), 6.56 (dd, J = 77.9, 70.7 Hz, 1H), 6.11-6.02 (m, 1H), 4.72 (d, J = 10.8 Hz, 1H), 3.63-3.20 (m, 3H), 2.26-1.93 (m, 4H), 1.60 (s, 1H). |
| 619 | 444.10 | 1.85 | |
| 620 | 420.10 | 1.83 | |
| 621 | 519.50 | 6.38 | |
| 622 | 458.50 | 1.66 | |
| 623 | 460.20 | 2.52 | |
| 624 | 427.23 | 2.05 | |
| 625 | 362.23 | 1.69 | |
| 626 | 474.30 | 1.64 | |
| 627 | 423.24 | 2.12 | |
| 628 | 501.10 | 2.35 | |
| 629 | 443.60 | 2.94 | |
| 630 | 411.23 | 2.13 | |
| 631 | 489.50 | 2.62 | |
| 632 | 493.50 | 1.89 | |
| 633 | 442.50 | 1.70 | |
| 634 | 505.50 | 1.90 | |
| 635 | 453.20 | 2.91 | |
| 636 | 478.10 | 6.14 | |
| 637 | 448.50 | 1.43 | |
| 638 | 416.21 | 2.36 | |
| 639 | 461.22 | 2.40 | |
| 640 | 487.40 | 1.57 | 1H NMR (400 MHz, DMSO) d 7.57 (d, J = 7.7 Hz, 1H), 7.52 (d, J = 8.3 Hz, 2H), 7.39 (d, J = 8.3 Hz, 2H), 7.34-7.26 (m, 2H), 7.20 (t, J = 8.0 Hz, 1H), 7.02 (d, J = 4.0 Hz, 1H), 6.42 (d, J = 4.0 Hz, 1H), 4.98 (s, 1H), 4.72 (t, J = 5.9 Hz, 1H), 4.41 (s, 2H), 3.44-3.39 (m, 2H), 2.19-1.83 (m, 5H), 1.39 (s, 3H). |
| 641 | 450.50 | 2.48 | |
| 642 | 391.24 | 2.03 | |
| 643 | 480.20 | 1.70 | 1H NMR (400 MHz, DMSO) d 7.90 (d, J = 8.1 Hz, 2H), 7.77-7.70 (m, 3H), 7.46 (s, 1H), 7.29 (t, J = 7.7 Hz, 1H), 7.14-7.04 (m, 2H), 4.46-4.33 (m, 1H), 4.10 (s, 3H), 3.61-3.47 (m, 3H), 2.10-1.76 (m, 4H), 1.26 (s, 9H). |

TABLE 2-continued

| Cmpd No. | LC/MS M + 1 | LC/RT min | ¹H NMR |
|---|---|---|---|
| 644 | 414.50 | 1.51 | |
| 645 | 427.23 | 2.02 | |
| 646 | 450.30 | 1.50 | 1H NMR (400 MHz, DMSO) ? 7.76 (d, J = 29.4 Hz, 1H), 7.59 (dd, J = 7.5, 1.4 Hz, 1H), 7.24-7.16 (m, 1H), 7.07-6.90 (m, 3H), 6.84 (d, J = 8.6 Hz, 1H), 4.14 (d, J = 35.3 Hz, 2H), 3.87 (s, 3H), 3.82 (s, 6H), 3.76 (d, J = 4.8 Hz, 3H), 3.31 (d, J = 13.6 Hz, 2H), 1.89 (dd, J = 46.8, 33.8 Hz, 4H). |
| 647 | 447.50 | 2.07 | |
| 648 | 487.10 | 2.63 | |
| 649 | 388.27 | 1.74 | |
| 650 | 436.30 | 1.83 | |
| 651 | 411.10 | 1.53 | |
| 652 | 411.20 | 1.42 | |
| 653 | 478.20 | 2.59 | |
| 654 | 488.20 | 1.81 | |
| 655 | 442.00 | 2.19 | 1H NMR (400 MHz, CDCl3) d 8.14 (d, J = 8.0 Hz, 1H), 7.27-7.20 (m, 3H), 7.19-7.12 (m, 2H), 7.04 (d, J = 4.0 Hz, 1H), 6.84 (d, J = 8.1 Hz, 1H), 6.12 (d, J = 4.0 Hz, 1H), 4.74-4.25 (m, m, 2H), 3.44 (m, 3H), 2.22 (s, 3H), 2.20-1.75 (m, 4H), 1.36 (d, J = 6.0 Hz, 6H). |
| 656 | 472.39 | 2.29 | |
| 657 | 411.27 | 2.10 | |
| 658 | 486.20 | 2.24 | 1H NMR (400 MHz, DMSO) d 7.57 (d, J = 8.1 Hz, 1H), 7.50-7.42 (m, 2H), 7.30 (dtd, J = 9.3, 8.0, 1.5 Hz, 2H), 7.25-7.17 (m, 1H), 7.01 (d, J = 4.0 Hz, 1H), 6.41 (d, J = 4.0 Hz, 1H), 4.69 (hept, J = 6.1 Hz, 1H), 4.44 (d, J = 12.9 Hz, 1H), 3.93 (d, J = 12.3 Hz, 1H), 3.31-3.13 (m, 1H), 2.34 (s, 3H), 2.11-1.83 (m, 4H), 1.32 (t, J = 10.2 Hz, 6H). |
| 659 | 422.04 | 1.92 | |
| 660 | 453.50 | 1.67 | |
| 661 | 407.50 | 2.03 | |
| 662 | 484.20 | 2.05 | |
| 663 | 492.30 | 1.82 | |
| 664 | 474.32 | 1.78 | |
| 665 | 452.00 | 2.04 | |
| 666 | 450.10 | 1.09 | |
| 667 | 472.22 | 1.61 | |
| 668 | 478.30 | 2.02 | |
| 669 | 447.50 | 2.11 | |
| 670 | 410.50 | 1.59 | 1H NMR (400 MHz, CDCl3) d 7.74, 7.73, 7.52, 7.42, 7.41, 7.39, 7.39, 7.28, 7.26, 7.10, 7.10, 7.04, 7.04, 7.02, 7.01, 6.56, 6.53, 6.34, 6.34, 6.33, 6.03, 6.02, 4.12, 3.58, 3.48, 2.16, 2.12, 2.01, 1.97, 1.94, 1.57. |
| 671 | 386.30 | 1.59 | 1H NMR (400 MHz, DMSO) d 9.84 (s, 1H), 8.00 (d, J = 8.1 Hz, 1H), 7.37-7.28 (m, 5H), 7.27-7.19 (m, 1H), 6.79 (d, J = 8.5 Hz, 2H), 6.48 (d, J = 4.0 Hz, 1H), 2.11-1.89 (m, 4H). |
| 672 | 390.21 | 1.57 | 1H NMR (400 MHz, CDCl3) d 7.56 (d, J = 7.7 Hz, 1H), 7.43-7.19 (m, 4H), 6.89-7.16 (m, 3H), 6.92 (d, J = 8.3 Hz, 1H), 4.67 (m, 1H), 4.16 (d, J = 2.0 Hz, 3H), 3.86 (d, J = 4.5 Hz, 3H), 3.66-3.28 (m, 3H), 2.19 (d, J = 14.1 Hz, 1H), 2.06-1.59 (m, 3H). |
| 673 | 424.30 | 1.88 | |
| 674 | 422.50 | 1.72 | |
| 675 | 506.30 | 1.87 | 1H NMR (400 MHz, DMSO) d 7.84 (d, J = 8.1 Hz, 2H), 7.69 (d, J = 8.1 Hz, 2H), 7.65-7.43 (m, 2H), 7.34-7.25 (m, 2H), 7.25-7.17 (m, 1H), 7.03 (d, J = 4.0 Hz, 1H), 6.41 (d, J = 4.0 Hz, 1H), 4.51-4.38 (m, 1H), 3.61-3.12 (m, 3H), 2.44 (s, 3H), 2.16-1.82 (m, 4H). |
| 676 | 451.50 | 2.46 | |
| 677 | 474.00 | 1.79 | 1H NMR (400 MHz, CDCl3) d 8.23 (s, 1H), 7.40 (d, J = 7.8 Hz, 1H), 7.24 (d, J = 8.3 Hz, 2H), 7.20-7.04 (m, 3H), 6.83 (d, J = 8.1 Hz, 1H), 6.28 (d, J = 3.5 Hz, 1H), 5.99 (d, J = 3.6 Hz, 1H), 5.89 (s, 1H), 4.77 (d, J = 5.0 Hz, 2H), 4.57 (dt, J = 12.1, 6.0 Hz, 2H), 3.50 (s, 3H), 2.21 (s, 3H), 2.00 (t, J = 23.8 Hz, 4H), 1.36 (d, J = 6.0 Hz, 6H). |
| 678 | 475.30 | 1.69 | |
| 679 | 510.00 | 1.91 | |
| 680 | 490.50 | 1.49 | |
| 681 | 481.50 | 2.23 | |
| 682 | 485.50 | 2.07 | |
| 683 | 479.30 | 1.78 | |
| 684 | 500.00 | 1.77 | 1H NMR (400 MHz, CDCl3) d 8.39 (d, J = 8.1 Hz, 1H), 8.18-8.10 (m, 1H), 7.87 (d, J = 8.1 Hz, 1H), |

TABLE 2-continued

| Cmpd No. | LC/MS M + 1 | LC/RT min | ¹H NMR |
|---|---|---|---|
| | | | 7.80 (s, 1H), 7.24 (dd, J = 14.9, 7.2 Hz, 1H), 7.19-7.11 (m, 2H), 7.03 (d, J = 4.0 Hz, 1H), 6.12 (d, J = 4.0 Hz, 1H), 4.68 (s, 1H), 3.59 (s, 2H), 3.38 (d, J = 14.2 Hz, 1H), 2.81 (s, 1H), 2.77 (s, 3H), 2.35-1.96 (m, 6H), 1.95-1.70 (m, 2H). |
| 685 | 549.60 | 1.87 | 1H NMR (400 MHz, DMSO) d 7.89 (d, J = 8.2 Hz, 2H), 7.70 (d, J = 8.3 Hz, 2H), 7.57 (d, J = 8.1 Hz, 1H), 7.36-7.14 (m, 3H), 7.03 (d, J = 3.9 Hz, 1H), 6.40 (d, J = 3.9 Hz, 1H), 5.14-4.98 (m, 1H), 4.55-4.36 (m, 1H), 3.58-3.37 (m, 4H), 3.30-3.10 (m, 1H), 2.20-1.77 (m, 4H), 1.21 (s, 6H). |
| 686 | 472.00 | 2.00 | 1H NMR (400 MHz, DMSO) d 8.00 (d, J = 7.9 Hz, 1H), 7.33 (dd, J = 11.7, 4.1 Hz, 3H), 7.23 (dt, J = 8.7, 4.5 Hz, 1H), 7.04 (dd, J = 14.8, 4.9 Hz, 2H), 6.48 (d, J = 4.1 Hz, 1H), 3.77 (s, 3H), 3.47-3.21 (m, 98H), 2.52 (dd, J = 11.8, 10.2 Hz, 24H), 2.02 (s, 5H), 1.29 (s, 9H). |
| 687 | | | |
| 688 | 481.40 | 2.79 | |
| 689 | 432.70 | 1.90 | |
| 690 | 495.18 | 1.93 | |
| 691 | 435.28 | 2.40 | |
| 692 | 408.26 | 1.75 | |
| 693 | 523.50 | 6.07 | |
| 694 | 448.50 | 1.93 | |
| 695 | 519.26 | 2.42 | |
| 696 | 541.21 | 2.20 | |
| 697 | 437.50 | 2.00 | 1H NMR (400 MHz, DMSO) d 7.71 (d, J = 8.6 Hz, 1H), 7.52 (dd, J = 2.9, 1.3 Hz, 1H), 7.29 (d, J = 2.3 Hz, 1H), 7.20 (d, J = 7.6 Hz, 1H), 7.14 (dd, J = 8.6, 2.3 Hz, 1H), 7.00-6.92 (m, 2H), 6.30 (t, J = 3.2 Hz, 1H), 6.20 (dd, J = 3.4, 1.3 Hz, 1H), 4.51-4.30 (m, 1H), 3.82 (s, 3H), 3.67-3.41 (m, 2H), 3.29-3.15 (m, 1H), 2.58 (q, J = 7.5 Hz, 2H), 2.06-1.86 (m, 4H), 1.13 (t, J = 7.5 Hz, 3H). |
| 698 | 472.30 | 2.03 | |
| 699 | 408.50 | 1.81 | |
| 700 | 390.50 | 3.87 | |
| 701 | 388.30 | 2.40 | |
| 702 | 426.20 | 2.99 | |
| 703 | 439.21 | 2.15 | |
| 704 | 450.20 | 1.83 | 1H NMR (400 MHz, DMSO) d 7.74 (d, J = 7.6 Hz, 1H), 7.45 (s, 1H), 7.37 (t, J = 8.2 Hz, 1H), 7.28 (t, J = 7.5 Hz, 1H), 7.14 (d, J = 7.9 Hz, 1H), 7.09 (t, J = 7.6 Hz, 1H), 6.94-6.91 (m, 1H), 6.90 (s, 1H), 4.39 (d, J = 13.0 Hz, 1H), 4.10 (s, 3H), 3.58-3.43 (m, 1H), 3.42-3.38 (m, 1H), 3.31-3.20 (m, 1H), 2.07-1.97 (m, 1H), 1.97-1.80 (m, 3H), 1.35 (s, 9H). |
| 705 | 454.50 | 1.88 | 1H NMR (400 MHz, MeOD) d 7.70 (d, J = 7.2 Hz, 1H), 7.56-7.45 (m, 2H), 7.43-7.33 (m, 2H), 7.34-7.26 (m, 2H), 7.20-7.08 (m, 2H), 7.08-6.65 (m, 1H), 5.14-5.00 (m, 1H), 3.71-3.55 (m, 1H), 3.49-3.36 (m, 3H), 2.24-1.88 (m, 4H), 1.62-1.52 (m, 6H). |
| 706 | 454.50 | 1.90 | |
| 707 | 413.20 | 1.86 | |
| 708 | 413.27 | 2.45 | |
| 709 | 432.30 | 2.01 | |
| 710 | 432.40 | 3.14 | |
| 711 | 432.70 | 1.62 | 1H NMR (400 MHz, CDCl3) d 7.57 (d, J = 7.7 Hz, 1H), 7.43 (d, J = 8.2 Hz, 2H), 7.37 (d, J = 8.1 Hz, 2H), 7.32-7.20 (m, 2H), 7.06 (dd, J = 15.4, 7.8 Hz, 2H), 4.60 (m, 1H), 4.42 (m, 1H), 4.18 (s, 3H), 3.80-3.26 (m, 3H), 2.32-1.71 (m, 7H), 0.96 (d, 6.2 Hz, 3H), 0.82 (d, J = 6.8 Hz, 3H). |
| 712 | 501.30 | 2.55 | |
| 713 | 460.50 | 1.75 | |
| 714 | 467.30 | 1.53 | 1H NMR (400 MHz, CDCl3) d 7.84 (d, J = 8.1 Hz, 2H), 7.61 (d, J = 8.1 Hz, 2H), 7.58 (d, J = 7.7 Hz, 1H), 7.30-7.23 (m, 2H), 7.11-7.03 (m, 2H), 4.77-4.49 (m, 1H), 4.16 (s, 3H), 3.77-3.31 (m, 3H), 2.73 (s, 6H), 2.34-1.71 (m, 4H). |
| 715 | 434.17 | 2.23 | |
| 716 | 462.20 | 2.73 | |
| 717 | 417.50 | 6.92 | |
| 718 | 410.50 | 1.65 | 1H NMR (400 MHz, CDCl3) d 8.85, 7.52, 7.34, 7.33, 7.33, 7.32, 7.31, 7.30, 7.29, 7.28, 7.26, 7.11, 7.11, 7.10, 7.09, 7.04, 7.04, 7.02, 7.02, 6.61, 6.59, 6.35, |

TABLE 2-continued

| Cmpd No. | LC/MS M + 1 | LC/RT min | ¹H NMR |
|---|---|---|---|
| | | | 6.34, 6.33, 6.16, 6.14, 6.13, 6.11, 6.04, 6.03, 6.02, 4.64, 4.63, 4.61, 3.97, 3.70, 3.66, 3.64, 3.64, 3.61, 3.60, 3.58, 3.57, 3.56, 3.55, 3.52, 3.49, 3.39, 3.38, 3.35, 3.35, 3.34, 3.33, 3.32, 3.31, 3.30, 3.27, 3.27, 2.25, 2.22, 2.15, 2.14, 2.11, 2.08, 2.08, 2.02, 2.01, 2.00, 1.99, 1.98, 1.95, 1.94, 1.93, 1.92, 1.91, 1.90, 1.88, 1.87, 1.85, 1.83, 1.81, 1.80, 1.78, 1.76, 1.75, 1.70, 1.14. |
| 719 | 415.26 | 1.98 | |
| 720 | 465.18 | 2.20 | |
| 721 | 491.50 | 1.83 | 1H NMR (400 MHz, CDCl3) d 8.13 (d, J = 7.9 Hz, 1H), 7.94 (d, J = 8.3 Hz, 2H), 7.56 (d, J = 8.2 Hz, 2H), 7.22 (d, J = 7.5 Hz, 1H), 7.15 (t, J = 7.3 Hz, 2H), 7.02 (d, J = 4.0 Hz, 1H), 6.11 (d, J = 4.0 Hz, 1H), 4.75-4.63 (m, 1H), 4.26 (d, J = 7.6 Hz, 1H), 3.65-3.54 (m, 2H), 3.54-3.46 (m, 1H), 3.42-3.27 (m, 1H), 2.32-2.16 (m, 1H), 2.14-1.95 (m, J = 10.9 Hz, 2H), 1.91-1.77 (m, 1H), 1.11 (d, J = 6.5 Hz, 6H). |
| 722 | 471.50 | 1.96 | 1H NMR (400 MHz, CDCl3) d 7.67 (d, J = 8.4 Hz, 1H), 7.52 (d, J = 8.4 Hz, 2H), 7.40 (d, J = 8.4 Hz, 2H), 7.22-7.03 (m, 3H), 6.81 (d, J = 3.9 Hz, 1H), 6.06 (d, J = 3.9 Hz, 1H), 4.65 (s, 1H), 4.12 (q, J = 7.1 Hz, 1H), 3.84-3.16 (m, 5H), 2.31-1.67 (m, 6H), 1.66-1.47 (m, 9H). |
| 723 | 509.60 | 3.38 | |
| 724 | 409.50 | 2.06 | 1H NMR (400 MHz, DMSO) d 7.71 (d, J = 8.6 Hz, 1H), 7.52 (dd, J = 2.9, 1.4 Hz, 1H), 7.36 (t, J = 7.8 Hz, 1H), 7.29 (d, J = 2.3 Hz, 1H), 7.14 (dd, J = 8.6, 2.3 Hz, 1H), 7.04-6.95 (m, 3H), 6.30 (t, J = 3.2 Hz, 1H), 6.21 (dd, J = 3.4, 1.3 Hz, 1H), 4.49-4.33 (m, 1H), 3.79 (s, 3H), 3.60-3.15 (m, 3H), 2.12-1.80 (m, 4H). |
| 725 | 463.50 | 1.98 | |
| 726 | 472.50 | 1.58 | |
| 727 | 447.10 | 2.63 | H NMR (400.0 MHz, DMSO) d 7.68-7.65 (m, 1H), 7.50-7.48 (m, 1H), 7.19-6.90 (m, 6H), 6.29-6.28 (m, 1H), 6.18-6.17 (m, 1H), 4.60-4.10 (m, 1H), 3.98-3.08 (m, 6H), 1.96 (s, 4H) and 1.29 (s, 9H) ppm. |
| 728 | 424.50 | 1.66 | 1H NMR (400 MHz, CDCl3) d 7.56, 7.55, 7.54, 7.54, 7.37, 7.37, 7.36, 7.35, 7.31, 7.26, 7.24, 7.08, 7.08, 7.01, 7.01, 6.99, 6.98, 6.33, 6.32, 6.31, 6.27, 6.25, 6.23, 6.07, 6.06, 5.30, 4.66, 4.63, 4.02, 3.58, 3.45, 3.42, 3.32, 3.29, 3.26, 2.17, 2.14, 2.10, 2.09, 2.07, 2.04, 2.01, 1.59, 1.37, 1.35, 1.33, 1.21, 1.19, 0.07. |
| 729 | 493.25 | 2.22 | |
| 730 | 420.30 | 1.73 | |
| 731 | 509.50 | 2.11 | |
| 732 | 443.40 | 6.14 | 1H NMR (400 MHz, CDCl3) d 7.67 (d, J = 8.1 Hz, 1H), 7.15 (ddd, J = 26.0, 23.5, 13.3 Hz, 5H), 6.81 (d, J = 2.7 Hz, 1H), 6.72 (s, 1H), 6.06 (s, 1H), 3.47 (d, J = 19.7 Hz, 3H), 2.23 (s, 3H), 2.08 (s, 2H), 2.02-1.79 (m, 2H). |
| 733 | 446.00 | 1.45 | |
| 734 | 473.30 | 4.94 | |
| 735 | 417.00 | 2.24 | |
| 736 | 488.30 | 1.85 | |
| 737 | 451.30 | 2.51 | |
| 738 | 422.50 | 1.70 | 1H NMR (400 MHz, CDCl3) d 7.57, 7.55, 7.52, 7.31, 7.29, 7.27, 7.26, 7.26, 7.23, 7.13, 7.11, 7.09, 7.06, 7.05, 7.03, 7.01, 6.99, 6.97, 6.95, 4.67, 4.64, 4.15, 4.13, 4.11, 4.09, 3.94, 3.61, 3.50, 3.49, 3.47, 3.45, 3.34, 2.22, 2.18, 2.04, 2.01, 1.98, 1.97, 1.94, 1.93, 1.91, 1.90, 1.78, 1.57, 1.48, 1.46, 1.44, 1.25, 1.22, 1.21, 1.19. |
| 739 | 427.18 | 2.21 | |
| 740 | 426.00 | 1.42 | |
| 741 | 410.30 | 1.60 | 1H NMR (400 MHz, CDCl3) d 7.52, 7.38, 7.36, 7.28, 7.26, 7.10, 7.09, 7.04, 7.03, 7.02, 7.01, 6.55, 6.35, 6.34, 6.33, 6.21, 6.19, 6.03, 6.03, 5.30, 4.60, 4.56, 4.13, 4.11, 3.67, 3.60, 3.56, 3.29, 3.26, 3.23, 2.20, 2.17, 2.08, 2.05, 1.96, 1.87, 1.55, 1.28, 1.26. |
| 742 | 480.50 | 1.90 | 1H NMR (400 MHz, DMSO) d 7.52 (s, 1H), 7.48 (dd, J = 9.4, 2.3 Hz, 1H), 7.20-7.09 (m, 2H), 7.02 (s, 1H), 6.99 (s, 2H), 4.60 (hept, J = 5.8 Hz, 1H), 4.45 (q, J = 7.2 Hz, 2H), 4.36-4.18 (m, 1H), 3.76 (s, 3H), 3.70-3.39 (m, 2H), 3.28-3.13 (m, 1H), 2.02-1.84 (m, 4H), 1.37 (t, J = 7.2 Hz, 3H), 1.26 (d, J = 6.0 Hz, 6H). |
| 743 | 515.20 | 2.33 | |

TABLE 2-continued

| Cmpd No. | LC/MS M + 1 | LC/RT min | ¹H NMR |
|---|---|---|---|
| 744 | 442.18 | 2.52 | |
| 745 | 446.50 | 5.70 | 1H NMR (400 MHz, DMSO) d 7.74 (d, J = 7.6 Hz, 1H), 7.48 (s, 1H), 7.29 (t, J = 7.7 Hz, 1H), 7.16-7.05 (m, 4H), 4.31 (s, 1H), 4.23-4.16 (m, 1H), 4.10 (s, 3H), 3.44 (d, J = 53.4 Hz, 2H), 2.23 (s, 6H), 1.92 (d, J = 6.6 Hz, 4H), 1.24 (d, J = 6.1 Hz, 6H). |
| 746 | 404.70 | 1.35 | 1H NMR (400 MHz, CDCl3) d 7.57 (d, J = 7.7 Hz, 1H), 7.41 (d, J = 7.5 Hz, 1H), 7.33-7.11 (m, 4H), 7.10-7.02 (m, 2H), 4.78-4.65 (m, 3H), 4.15 (s, 3H), 3.57-3.48 (m, 1H), 3.45-3.31 (m, 2H), 2.33 (d, J = 21.1 Hz, 3H), 2.26-2.19 (m, 1H), 2.04-1.88 (m, 2H), 1.84-1.64 (m, 2H). |
| 747 | 450.30 | 1.47 | |
| 748 | 420.26 | 1.77 | |
| 749 | 429.50 | 2.02 | |
| 750 | 432.30 | 2.22 | |
| 751 | 539.50 | 6.58 | |
| 752 | 480.30 | 2.05 | 1H NMR (400 MHz, CDCl3) d 7.87 (d, J = 7.7 Hz, 1H), 7.58 (d, J = 11.1 Hz, 1H), 7.47-7.35 (m, 2H), 7.35-7.25 (m, 2H), 7.21 (t, J = 8.7 Hz, 1H), 7.11-6.98 (m, 2H), 6.58 (t, J = 74.7 Hz, 1H), 4.78-4.62 (m, 1H), 3.71-3.51 (m, 1H), 3.47-3.26 (m, 2H), 2.37-2.22 (m, 1H), 2.16-1.81 (m, 3H). |
| 753 | 427.25 | 2.39 | |
| 754 | 446.30 | 2.46 | |
| 755 | 472.00 | 2.10 | |
| 756 | 512.21 | 1.83 | |
| 757 | 480.22 | 1.51 | |
| 758 | 473.50 | 4.90 | |
| 759 | 539.50 | 2.07 | |
| 760 | 522.24 | 1.80 | |
| 761 | 448.30 | 1.70 | |
| 762 | 428.50 | 1.71 | 1H NMR (400 MHz, CDCl3) d 8.12 (d, J = 7.5 Hz, 1H), 7.53 (d, J = 8.3 Hz, 2H), 7.41 (d, J = 8.2 Hz, 2H), 7.29-7.09 (m, 3H), 7.01 (t, J = 5.6 Hz, 1H), 6.10 (d, J = 4.0 Hz, 1H), 4.67 (m, 1H), 3.74 (m, 1H), 3.49 (m, 1H), 3.32 (m, 1H), 1.75-2.25 (m, 4H), 1.73 (s, 1H), 1.58 (s, 6H). |
| 763 | 408.24 | 1.83 | |
| 764 | 417.13 | 2.89 | |
| 765 | 427.25 | 2.67 | |
| 766 | 406.50 | 1.84 | |
| 767 | 479.30 | 1.49 | |
| 768 | 511.50 | 1.69 | |
| 769 | 432.50 | 2.00 | 1H NMR (400 MHz, CDCl3) d 8.19-8.02 (m, 1H), 7.29-6.89 (m, 10H), 6.09 (t, J = 3.5 Hz, 1H), 4.74 (d, J = 13.4 Hz, 1H), 4.49-3.96 (m, 2H), 3.69-3.26 (m, 3H), 3.24 (d, J = 13.2 Hz, 1H), 2.21 (d, J = 15.7 Hz, 2H), 2.10-1.87 (m, 2H), 1.74 (d, J = 12.5 Hz, 0H), 1.55 (d, J = 3.0 Hz, 1H), 1.38 (td, J = 6.9, 3.7 Hz, 3H). |
| 770 | 446.30 | 2.05 | 1H NMR (400 MHz, CDCl3) d 8.12 (d, J = 7.5 Hz, 1H), 7.25 (d, J = 11.0 Hz, 3H), 7.14 (ddd, J = 18.7, 16.0, 7.7 Hz, 4H), 6.99 (dt, J = 22.4, 5.5 Hz, 3H), 6.11 (s, 1H), 4.73 (d, J = 10.9 Hz, 1H), 4.60-4.46 (m, 1H), 3.52 (s, 2H), 3.28 (s, 1H), 2.22 (s, 0H), 2.28-2.12 (m, 1H), 2.13-1.90 (m, 3H), 1.55 (s, 1H), 1.36 (d, J = 6.0 Hz, 5H). |
| 771 | 420.30 | 1.63 | |
| 772 | | | |
| 773 | 408.22 | 1.74 | |
| 774 | 404.30 | 1.63 | |
| 775 | 515.50 | 2.14 | |
| 776 | 401.22 | 2.21 | |
| 777 | 469.40 | 2.92 | |
| 778 | 527.30 | 6.81 | |
| 779 | 414.25 | 2.43 | |
| 780 | 469.50 | 2.15 | 1H NMR (400 MHz, CDCl3) d 7.74 (s, 1H), 7.66 (dd, J = 8.6, 1.7 Hz, 1H), 7.31 (d, J = 7.4 Hz, 1H), 7.10-6.97 (m, 5H), 6.29 (t, J = 3.2 Hz, 1H), 6.01-5.94 (m, 1H), 4.88 (br. s, 1H), 4.13 (br. s, 1H), 3.92 (s, 3H), 2.59-2.15 (m, 5H), 2.06 (br. s, 3H), 1.57 (s, 3H). |
| 781 | 476.30 | 1.64 | 1H NMR (400 MHz, CDCl3) d 8.22-8.05 (m, 1H), 7.50 (q, J = 8.2 Hz, 4H), 7.27-7.19 (m, 4H), 7.19-7.09 (m, 2H), 7.01 (t, J = 6.2 Hz, 1H), 6.10 (d, J = 4.0 Hz, 1H), 4.67 (s, 1H), 4.31-4.12 (m, 1H), 3.62 (d, J = 39.1 Hz, 2H), 3.33 (s, 1H), 2.72 (d, J = 20.1 Hz, 3H), |

TABLE 2-continued

| Cmpd No. | LC/MS M + 1 | LC/RT min | ¹H NMR |
|---|---|---|---|
| | | | 2.12 (d, J = 47.3 Hz, 2H), 2.01 (s, 4H), 1.82 (t, J = 13.7 Hz, 4H), 1.58 (d, J = 20.4 Hz, 3H). |
| 782 | 458.50 | 1.55 | 1H NMR (400 MHz, CDCl3) d 8.15-8.07 (m, 1H), 7.50 (d, J = 8.0 Hz, 1H), 7.25-7.16 (m, 3H), 7.16-7.08 (m, 2H), 7.02 (d, J = 4.0 Hz, 1H), 6.10 (d, J = 4.0 Hz, 1H), 4.74-4.57 (m, 1H), 4.00 (d, J = 11.1 Hz, 1H), 3.85-3.71 (m, 1H), 3.69 (d, J = 11.1 Hz, 1H), 3.63-3.23 (m, J = 86.9 Hz, 2H), 2.56 (s, 3H), 2.23-2.07 (m, 2H), 1.99-1.72 (m, 5H), 1.58 (s, 3H). |
| 783 | 497.50 | 2.02 | |
| 784 | 462.50 | 1.67 | 1H NMR (400 MHz, CDCl3) d 8.21-8.06 (m, 1H), 7.84-7.80 (m, 2H), 7.48-7.35 (m, 1H), 7.29-7.18 (m, 1H), 7.19-7.08 (m, 2H), 7.02 (d, J = 3.9 Hz, 1H), 6.12-6.08 (m, 1H), 4.75 (d, J = 13.8 Hz, 1H), 3.57-3.48 (m, 1H), 3.42-3.21 (m, 2H), 3.05 (s, 3H), 2.44 (d, J = 13.0 Hz, 3H), 2.28-2.21 (m, 1H), 2.15-1.88 (m, 2H), 1.84-1.69 (m, 1H). |
| 785 | 544.20 | 1.95 | |
| 786 | 431.15 | 2.18 | |
| 787 | 431.19 | 2.17 | |
| 788 | 476.40 | 3.02 | |
| 789 | 460.50 | 1.46 | |
| 790 | 395.11 | 1.86 | |
| 791 | 449.10 | 2.35 | H NMR (400.0 MHz, DMSO) d 7.67-7.65 (m, 1H), 7.50-7.49 (m, 1H), 7.17-6.99 (m, 6H), 6.29-6.26 (m, 1H), 6.18-6.17 (m, 1H), 4.35 (s, 1H), 4.12-4.10 (m, 2H), 3.82-3.78 (m, 3H), 3.67-3.65 (m, 2H), 3.40 (s, 3H), 3.33-3.30 (m, 3H) and 1.95 (s, 4H) ppm. |
| 792 | 451.30 | 1.98 | |
| 793 | 471.30 | 1.88 | |
| 794 | 521.30 | 1.84 | 1H NMR (400 MHz, DMSO) d 7.97 (d, J = 8.1 Hz, 2H), 7.71 (d, J = 8.1 Hz, 2H), 7.57 (d, J = 8.1 Hz, 1H), 7.34-7.16 (m, 3H), 7.03 (d, J = 4.0 Hz, 1H), 6.40 (d, J = 4.0 Hz, 1H), 4.90 (t, J = 4.9 Hz, 1H), 4.52-4.37 (m, 1H), 3.75-3.65 (m, 2H), 3.58-3.36 (m, 4H), 3.28-3.15 (m, 1H), 2.20-1.77 (m, 4H). |
| 795 | 457.00 | 2.13 | |
| 796 | 450.50 | 1.52 | |
| 797 | 388.30 | 2.41 | |
| 798 | 415.19 | 2.09 | |
| 799 | 452.00 | 2.01 | |
| 800 | 450.27 | 1.76 | |
| 801 | 418.50 | 1.75 | 1H NMR (400 MHz, DMSO) d 7.74 (d, J = 7.7 Hz, 1H), 7.47 (s, 1H), 7.29 (t, J = 7.8 Hz, 1H), 7.13 (s, 4H), 4.33 (s, 1H), 4.10 (s, 3H), 3.68 (s, 5H), 2.25 (s, 6H), 2.07 (s, 1H), 1.91 (s, 4H). |
| 802 | 432.70 | 3.15 | |
| 803 | 435.50 | 7.08 | |
| 804 | 537.50 | 2.08 | 1H NMR (400 MHz, DMSO) d 7.93 (d, J = 8.0 Hz, 2H), 7.73 (d, J = 8.0 Hz, 2H), 7.58 (dd, J = 9.0, 5.2 Hz, 1H), 7.29 (dd, J = 9.1, 2.7 Hz, 1H), 7.10 (td, J = 8.7, 2.9 Hz, 1H), 7.03 (d, J = 3.9 Hz, 1H), 6.41 (d, J = 3.9 Hz, 1H), 4.54-4.37 (m, 1H), 3.64-3.16 (m, 4H), 2.18-1.81 (m, 4H), 1.17 (d, J = 6.8 Hz, 6H). |
| 805 | 472.30 | 3.09 | |
| 806 | 434.20 | 1.94 | |
| 807 | 422.04 | 1.88 | |
| 808 | 491.15 | 1.91 | |
| 809 | 404.20 | 1.77 | |
| 810 | 442.50 | 2.02 | 1H NMR (400 MHz, CDCl3) d 8.12 (d, J = 7.6 Hz, 1H), 7.46-7.38 (m, 4H), 7.22 (t, J = 7.3 Hz, 1H), 7.16-7.11 (m, 2H), 7.02 (d, J = 4.0 Hz, 1H), 6.10 (d, J = 4.0 Hz, 1H), 5.19 (d, J = 11.0 Hz, 2H), 4.97 (s, 1H), 3.83-3.25 (m, 3H), 2.26-1.79 (m, 5H), 1.60 (s, 6H). |
| 811 | 426.10 | 1.68 | |
| 812 | 451.20 | 2.38 | 1H NMR (400 MHz, DMSO) d 7.71 (dd, J = 8.9, 5.6 Hz, 1H), 7.53-7.47 (m, 1H), 7.11 (dd, J = 9.6, 2.6 Hz, 1H), 7.05-6.98 (m, 3H), 6.94 (td, J = 8.8, 2.7 Hz, 1H), 6.28 (t, J = 3.1 Hz, 1H), 6.18 (d, J = 3.4 Hz, 1H), 4.58-4.02 (m, 1H), 3.94 (t, J = 6.5 Hz, 2H), 3.79 (s, 3H), 3.59-3.09 (m, 3H), 2.06-1.86 (m, 4H), 1.73 (sextet, J = 6.8 Hz, 2H), 0.97 (t, J = 7.4 Hz, 3H). |
| 813 | 518.50 | 1.80 | |
| 814 | 458.28 | 2.17 | |
| 815 | 483.50 | 1.97 | 1H NMR (400 MHz, CDCl3) d 7.67 (d, J = 8.1 Hz, 1H), 7.53-7.35 (m, 4H), 7.23-7.03 (m, 3H), 6.81 (d, J = 3.9 Hz, 1H), 6.06 (d, J = 3.9 Hz, 1H), 4.64 (bs, |

TABLE 2-continued

| Cmpd No. | LC/MS M + 1 | LC/RT min | ¹H NMR |
|---|---|---|---|
| | | | 1H), 4.03 (d, J = 8.3 Hz, 1H), 3.81-3.23 (m, 3H), 2.32-1.70 (m, 5H), 1.29-1.05 (m, 1H), 0.72-0.28 (m, 4H). |
| 816 | 399.26 | 1.67 | |
| 817 | 431.70 | 2.10 | |
| 818 | 485.00 | 2.38 | |
| 819 | 521.00 | 1.85 | 1H NMR (400 MHz, CDCl3) d 8.59 (d, J = 8.3 Hz, 1H), 7.69 (s, 1H), 7.64 (d, J = 8.5 Hz, 1H), 7.24 (t, J = 7.2 Hz, 2H), 7.19-7.12 (m, 2H), 7.04 (d, J = 8.5 Hz, 1H), 6.15 (d, J = 4.1 Hz, 1H), 4.57 (s, 1H), 3.94 (s, 3H), 3.47 (s, 3H), 3.08 (s, 3H), 2.27-1.67 (m, 4H). |
| 820 | 491.30 | 1.57 | |
| 821 | 466.30 | 2.21 | |
| 822 | 462.50 | 2.09 | |
| 823 | 454.33 | 2.16 | |
| 824 | 495.50 | 1.60 | |
| 825 | 463.50 | 2.20 | |
| 826 | 468.00 | 1.98 | |
| 827 | 447.50 | 1.54 | 1H NMR (400 MHz, CDCl3) d 7.35 (d, J = 7.4 Hz, 1H), 7.29 (d, J = 8.0 Hz, 1H), 7.15 (dd, J = 2.8, 1.3 Hz, 1H), 7.11-6.99 (m, 5H), 6.33 (t, J = 3.2 Hz, 1H), 6.04 (dd, J = 3.5, 1.3 Hz, 1H), 5.02 (d, J = 7.2 Hz, 2H), 4.86 (d, J = 7.1 Hz, 2H), 4.72-4.54 (m, 1H), 3.90 (s, 3H), 3.78-3.24 (m, 3H), 2.35-1.76 (m, 4H). |
| 828 | 444.30 | 2.54 | |
| 829 | 505.50 | 1.89 | |
| 830 | 419.20 | 1.66 | |
| 831 | 420.30 | 1.75 | |
| 832 | 520.30 | 1.98 | 1H NMR (400 MHz, CDCl3) d 8.10 (d, J = 8.3 Hz, 1H), 7.95 (d, J = 8.3 Hz, 2H), 7.61 (d, J = 8.3 Hz, 2H), 7.17 (s, 1H), 7.09 (d, J = 8.3 Hz, 1H), 7.02 (d, J = 4.0 Hz, 1H), 6.10 (d, J = 4.0 Hz, 1H), 4.75-4.63 (m, 1H), 4.45 (s, 2H), 3.64-3.46 (m, 2H), 3.43 (s, 3H), 3.41-3.29 (m, 1H), 3.26-3.17 (m, 1H), 2.29-2.19 (m, 1H), 2.10-1.99 (m, 2H), 1.81 (s, 1H), 1.31 (d, J = 6.9 Hz, 6H). |
| 833 | 407.15 | 2.20 | |
| 834 | 433.20 | 1.72 | |
| 835 | 495.21 | 1.93 | |
| 836 | 513.50 | 8.20 | |
| 837 | 461.50 | 1.88 | |
| 838 | 458.50 | 5.96 | |
| 839 | 428.00 | 2.08 | 1H NMR (400 MHz, CDCl3) d 8.05 (d, J = 8.0 Hz, 1H), 7.18-7.02 (m, 4H), 6.95 (d, J = 4.0 Hz, 1H), 6.85 (d, J = 8.4 Hz, 2H), 6.03 (d, J = 4.0 Hz, 1H), 4.59 (s, 1H), 3.78 (s, 3H), 3.37 (d, J = 81.3 Hz, 3H), 2.57 (q, J = 7.5 Hz, 2H), 2.35-1.60 (m, 4H), 1.11 (t, J = 7.5 Hz, 3H). |
| 840 | 547.50 | 5.88 | 1H NMR (400 MHz, DMSO) d 8.08-7.93 (m, 2H), 7.84-7.69 (m, 2H), 7.57 (d, J = 8.1 Hz, 1H), 7.38-7.12 (m, 3H), 7.11-6.96 (m, 1H), 6.48-6.31 (m, 1H), 4.53-4.18 (m, 2H), 4.07-3.97 (m, 1H), 3.88-3.71 (m, 2H), 3.69-3.59 (m, 1H), 3.60-3.37 (m, 2H), 3.31-3.13 (m, 1H), 2.23-1.78 (m, 6H). |
| 841 | 416.50 | 1.84 | |
| 842 | 450.97 | 3.18 | |
| 843 | 450.97 | 3.12 | |
| 844 | 505.30 | 5.49 | 1H NMR (400 MHz, DMSO) d 8.00 (d, J = 8.0 Hz, 1H), 7.89 (d, J = 8.2 Hz, 2H), 7.73-7.60 (m, 3H), 7.34 (d, J = 4.0 Hz, 1H), 7.31 (d, J = 4.2 Hz, 2H), 7.27-7.20 (m, 1H), 6.47 (d, J = 4.0 Hz, 1H), 4.57-4.36 (m, 1H), 3.60-3.37 (m, 2H), 3.28-3.09 (m, 1H), 2.18-1.77 (m, 4H), 1.10 (s, 9H). |
| 845 | 408.20 | 2.19 | |
| 846 | 473.30 | 1.83 | 1H NMR (400 MHz, DMSO) d 7.57 (d, J = 8.1 Hz, 1H), 7.42 (d, J = 8.6 Hz, 2H), 7.38-7.16 (m, 3H), 7.01 (d, J = 4.0 Hz, 1H), 6.99 (d, J = 8.6 Hz, 2H), 6.41 (d, J = 4.0 Hz, 1H), 4.88 (t, J = 5.5 Hz, 1H), 4.49-4.09 (m, 1H), 4.03 (t, J = 4.9 Hz, 2H), 3.80-3.66 (m, 2H), 3.66-3.15 (m, 3H), 2.15-1.80 (m, 4H). |
| 847 | | | |
| 848 | 433.50 | 1.78 | |
| 849 | 427.50 | 1.50 | 1H NMR (400 MHz, CDCl3) d 8.57 (s, 1H), 8.06 (d, J = 7.5 Hz, 1H), 7.65 (dd, J = 8.2, 2.3 Hz, 1H), 7.34 (d, J = 8.2 Hz, 1H), 7.18-7.03 (m, 3H), 6.95 (d, J = 4.0 Hz, 1H), 6.03 (d, J = 4.0 Hz, 1H), 4.69-4.48 (m, 1H), 3.81-3.11 (m, 3H), 2.24-1.72 (m, 4H), 1.31 (s, 9H). |

TABLE 2-continued

| Cmpd No. | LC/MS M + 1 | LC/RT min | ¹H NMR |
|---|---|---|---|
| 850 | 447.30 | 2.07 | |
| 851 | 530.00 | 1.82 | 1H NMR (400 MHz, CDCl3) d 7.29 (d, J = 5.9 Hz, 3H), 7.12 (d, J = 2.1 Hz, 2H), 7.09-6.99 (m, 3H), 6.91 (d, J = 8.2 Hz, 1H), 6.36 (t, J = 3.2 Hz, 1H), 6.06 (d, J = 3.2 Hz, 1H), 4.61 (s, 1H), 4.48 (t, J = 5.3 Hz, 2H), 3.89 (s, 3H), 3.88-3.28 (m, J = 5.2 Hz, 5H), 3.24 (q, J = 7.4 Hz, 2H), 3.20 (s, 3H), 2.82 (s, 2H), 2.12-1.75 (m, 4H), 1.41 (t, J = 7.3 Hz, 2H). |
| 852 | 431.70 | 2.38 | |
| 853 | 420.50 | 1.38 | 1H NMR (400 MHz, CDCl3) d 7.57 (d, J = 7.7 Hz, 1H), 7.42 (d, J = 7.5 Hz, 1H), 7.35-7.21 (m, 3H), 7.17 (t, J = 7.9 Hz, 1H), 7.13-7.00 (m, 2H), 4.88-4.80 (m, 1H), 4.77-4.54 (m, 2H), 4.15 (d, J = 3.1 Hz, 3H), 3.90 (d, J = 11.6 Hz, 3H), 3.72-3.24 (m, 3H), 2.32-1.60 (m, 5H). |
| 854 | 441.50 | 1.30 | 1H NMR (400 MHz, DMSO) d 9.30 (bs, 1H), 9.14 (bs, 1H), 8.00 (d, J = 7.9 Hz, 1H), 7.45 (d, J = 8.6 Hz, 2H), 7.37-7.29 (m, 3H), 7.28-7.16 (m, 1H), 6.93 (d, J = 8.6 Hz, 2H), 6.47 (d, J = 4.0 Hz, 1H), 5.17-5.09 (m, 1H), 4.49-4.40 (m, 3H), 4.04-3.95 (m, 3H), 2.12-1.90 (m, 4H). |
| 855 | 449.10 | 2.22 | 1H NMR (400 MHz, DMSO) d 7.71 (dd, J = 8.9, 5.6 Hz, 1H), 7.49 (dd, J = 2.8, 1.3 Hz, 1H), 7.27 (d, J = 7.9 Hz, 1H), 7.10 (dd, J = 9.6, 2.8 Hz, 1H), 7.01 (d, J = 1.3 Hz, 1H), 6.98-6.90 (m, 2H), 6.28 (t, J = 3.2 Hz, 1H), 6.18 (dd, J = 3.4, 1.2 Hz, 1H), 4.51-4.26 (m, 1H), 3.84 (s, 3H), 3.73-3.40 (m, 3H), 2.05-1.85 (m, 4H), 1.34 (s, 9H). |
| 856 | 394.50 | 1.39 | 1H NMR (400 MHz, DMSO) d 10.41 (s, 1H), 7.73 (d, J = 7.7 Hz, 1H), 7.46 (s, 1H), 7.32-7.23 (m, 2H), 7.15-7.04 (m, 3H), 6.98 (t, J = 8.5 Hz, 1H), 4.10 (s, 3H), 3.52-3.19 (m, 4H), 1.99-1.85 (m, 4H). |
| 857 | 477.00 | 2.04 | 1H NMR (400 MHz, DMSO) d 7.77 (d, J = 8.6 Hz, 1H), 7.74-7.67 (m, 2H), 7.56-7.50 (m, 1H), 7.33 (d, J = 8.6 Hz, 1H), 7.31-7.27 (m, 1H), 7.14 (dd, J = 8.8, 2.0 Hz, 1H), 6.30 (t, J = 2.6 Hz, 1H), 6.22-6.16 (m, 1H), 4.65-4.21 (m, 1H), 3.94 (s, 3H), 3.74-3.38 (m, 3H), 2.06-1.83 (m, 4H). |
| 858 | 443.12 | 2.15 | |
| 859 | 452.30 | 1.46 | 1H NMR (400 MHz, DMSO) d 7.96 (d, J = 8.0 Hz, 2H), 7.79-7.68 (m, 3H), 7.46 (s, 1H), 7.29 (t, J = 7.7 Hz, 1H), 7.16-7.03 (m, 2H), 4.47-4.32 (m, 1H), 4.10 (s, 3H), 3.62-3.20 (m, 3H), 3.35 (q, J = 7.4 Hz, 2H), 2.10-1.82 (m, 4H), 1.12 (t, J = 7.3 Hz, 3H). |
| 860 | 430.70 | 1.77 | |
| 861 | 413.27 | 2.23 | |
| 862 | 471.19 | 1.69 | |
| 863 | 474.50 | 1.81 | |
| 864 | 442.50 | 1.53 | 1H NMR (400 MHz, CDCl3) d 8.17-8.03 (m, 1H), 7.63 (d, J = 8.2 Hz, 2H), 7.41 (t, J = 9.3 Hz, 2H), 7.25-7.18 (m, 1H), 7.18-7.08 (m, 2H), 7.02 (d, J = 4.0 Hz, 1H), 6.09 (d, J = 4.0 Hz, 1H), 4.95 (d, J = 7.3 Hz, 2H), 4.82 (d, J = 7.3 Hz, 2H), 4.67 (bs, 1H), 3.81-3.21 (m, 4H), 2.34-1.50 (m, 4H). |
| 865 | 418.00 | 2.02 | 1H NMR (400 MHz, CDCl3) d 8.20-8.08 (m, 1H), 7.45 (s, 1H), 7.32-7.21 (m, 4H), 7.16 (dd, J = 7.0, 5.5 Hz, 2H), 7.04 (d, J = 4.0 Hz, 1H), 6.13 (d, J = 4.0 Hz, 1H), 4.67 (s, 1H), 3.98-3.04 (m, 3H), 2.42 (s, 3H), 2.33-1.71 (m, 5H). |
| 866 | 434.20 | 1.93 | |
| 867 | 414.50 | 1.47 | 1H NMR (400 MHz, DMSO) d 8.10 (s, 1H), 7.76-7.69 (m, 2H), 7.55-7.42 (m, 2H), 7.28 (t, J = 7.7 Hz, 1H), 7.21 (d, J = 7.0 Hz, 1H), 7.13 (d, J = 8.1 Hz, 1H), 7.07 (t, J = 7.6 Hz, 1H), 4.63-4.31 (m, 1H), 4.09 (s, 3H), 4.08 (s, 3H), 3.64-3.19 (m, 3H), 2.18-1.67 (m, 4H). |
| 868 | 390.30 | 2.35 | |
| 869 | 490.00 | 1.82 | |
| 870 | 413.30 | 2.19 | 1H NMR (400 MHz, CDCl3) d 7.46-7.27 (m, 7H), 7.12 (d, J = 2.1 Hz, 2H), 7.04 (dd, J = 8.5, 2.2 Hz, 1H), 6.36 (t, J = 3.2 Hz, 1H), 6.07 (d, J = 3.4 Hz, 1H), 5.32 (s, 1H), 4.65 (br. s, 1H), 3.64 (br. s, 2H), 3.35 (br. s, 1H), 2.20 (br. s, 1H), 2.05 (br.s, 2H), 1.86 (br. s, 1H), 1.59 (s, 6H). |

Assays for Detecting and Measuring NaV Inhibition Properties of Compound

E-VIPR Optical Membrane Potential Assay Method with Electrical Stimulation

Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

24 hours before the assay on E-VIPR, HEK cells expressing human NaV subtype, like NaV 1.7, are seeded in 384-well poly-lysine coated plates at 15,000-20,000 cells per well. Other subtypes are performed in an analogous mode in a cell line expressing the NaV of interest. HEK cells are grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

Reagents and Solutions 100 mg/mL Pluronic F-127 (Sigma #P2443), in dry DMSO

Compound Plates: 384-well round bottom plate, e.g. Corning 384-well Polypropylene Round Bottom #3656

Cell Plates: 384-well tissue culture treated plate, e.g. Greiner #781091-1B 10 mM $DiSBAC_6(3)$ (Aurora #00-100-010) in dry DMSO 10 mM CC2-DMPE (Aurora #00-100-008) in dry DMSO 200 mM ABSC1 in $H_2O$ Bath1 buffer. Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).

Hexyl Dye Solution: Bath1 Buffer+0.5% β-cyclodextrin (make this prior to use, Sigma #C4767), 8 µM CC2-DMPE+ 2.5 µM $DiSBAC_6(3)$. To make the solution Add volume of 10% Pluronic F127 stock equal to volumes of CC2-DMPE+ $DiSBAC_6(3)$. The order of preparation is first mix Pluronic and CC2-DMPE, then add $DiSBAC_6(3)$ while vortexing, then add Bath1+β-Cyclodextrin.

Assay Protocol

1) Pre-spot compounds (in neat DMSO) into compound plates. Vehicle control (neat DMSO), the positive control (20 mM DMSO stock tetracaine, 125 µM final in assay) and test compounds are added to each well at 160× desired final concentration in neat DMSO. Final compound plate volume will be 80 µL (80-fold intermediate dilution from 1 µL DMSO spot; 160-fold final dilution after transfer to cell plate). Final DMSO concentration for all wells in assay is 0.625%.

2) Prepare Hexyl Dye Solution.

3) Prepare cell plates. On the day of the assay, medium is aspirated and cells are washed three times with 100 µL of Bath1 Solution, maintaining 25 µL residual volume in each well.

4) Dispense 25 µL per well of Hexyl Dye Solution into cell plates. Incubate for 20-35 minutes at room temp or ambient conditions.

5) Dispense 80 µL per well of Bath1 into compound plates. Acid Yellow-17 (1 mM) is added and Potassium Chloride can be altered from 4.5 to 20 mM depending on the NaV subtype and assay sensitivity.

6) Wash cell plates three times with 100 µL per well of Bath1, leaving 25 of residual volume. Then transfer 25 uL per well from Compound Plates to Cell Plates. Incubate for 20-35 minutes at room temp/ambient condition 7) Read Plate on E-VIPR. Use the current-controlled amplifier to deliver stimulation wave pulses for typically 9 seconds and a scan rate of 400 Hz. A pre-stimulus recording is performed for 0.5 seconds to obtain the un-stimulated intensities baseline. The stimulatory waveform is applied for 9 seconds followed by 0.5 seconds of post-stimulation recording to examine the relaxation to the resting state. The stimulatory waveform of the electrical stimulation is specific for each cell type and can vary the magnitude, duration and frequency of the applied current to provide an optimal assay signal.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\,nm} - background_{460\,nm})}{(intensity_{580\,nm} - background_{580\,nm})}.$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated and reported as a function of time.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

IonWorks Assays.

Sodium currents were recorded using the automated patch clamp system, IonWorks (Molecular Devices Corporation, Inc.). Cells expressing Nav subtypes are harvested from tissue culture and placed in suspension at 0.5-4 million cells per mL Bath1. The IonWorks instrument measures changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents are measured at the test potential.

1-Benzazepin-2-one Binding Assay

The sodium channel inhibiting properties of the compounds of the invention can also be determined by assay methods described in Williams, B. S. et al., "Characterization of a New Class of Potent Inhibitors of the Voltage-Gated Sodium Channel NaV 1.7," *Biochemistry*, 2007, 46, 14693-14703, the entire contents of which are incorporated herein by reference.

The exemplified compounds of Table 1 herein are active against one or more sodium channels as measured using the assays described herein above as presented in Table 3.

TABLE 3

| Cmpd. No. | Binned Activity Data |
| --- | --- |
| 1 | |
| 2 | + |
| 3 | +++ |
| 4 | +++ |
| 5 | +++ |
| 6 | |
| 7 | +++ |
| 8 | ++ |
| 9 | +++ |
| 10 | |
| 11 | +++ |
| 12 | ++ |
| 13 | +++ |
| 14 | +++ |
| 15 | + |
| 16 | +++ |
| 17 | ++ |
| 18 | |
| 19 | |
| 20 | |
| 21 | +++ |
| 22 | ++ |
| 23 | +++ |
| 24 | +++ |
| 25 | |
| 26 | +++ |
| 27 | +++ |
| 28 | ++ |
| 29 | +++ |
| 30 | +++ |
| 31 | +++ |
| 32 | +++ |
| 33 | |
| 34 | +++ |
| 35 | |
| 36 | +++ |
| 37 | +++ |
| 38 | +++ |
| 39 | +++ |
| 40 | ++ |
| 41 | +++ |
| 42 | +++ |
| 43 | ++ |
| 44 | +++ |
| 45 | +++ |
| 46 | + |
| 47 | +++ |
| 48 | +++ |
| 49 | + |
| 50 | +++ |
| 51 | +++ |
| 52 | +++ |
| 53 | +++ |
| 54 | +++ |
| 55 | +++ |
| 56 | +++ |
| 57 | +++ |
| 58 | |
| 59 | +++ |
| 60 | +++ |
| 61 | |
| 62 | +++ |
| 63 | +++ |
| 64 | |
| 65 | +++ |
| 66 | +++ |
| 67 | +++ |
| 68 | |
| 69 | +++ |
| 70 | +++ |
| 71 | |
| 72 | |
| 73 | |
| 74 | +++ |
| 75 | |
| 76 | +++ |
| 77 | |
| 78 | +++ |
| 79 | |
| 80 | + |
| 81 | +++ |
| 82 | +++ |
| 83 | +++ |
| 84 | ++ |
| 85 | |
| 86 | |
| 87 | + |
| 88 | |
| 89 | |
| 90 | +++ |
| 91 | |
| 92 | ++ |
| 93 | ++ |
| 94 | +++ |
| 95 | +++ |
| 96 | |
| 97 | +++ |
| 98 | +++ |
| 99 | +++ |
| 100 | |
| 101 | +++ |
| 102 | + |
| 103 | +++ |
| 104 | + |
| 105 | +++ |

TABLE 3-continued

| Cmpd. No. | Binned Activity Data |
|---|---|
| 106 | +++ |
| 107 | |
| 108 | +++ |
| 109 | +++ |
| 110 | |
| 111 | +++ |
| 112 | +++ |
| 113 | +++ |
| 114 | +++ |
| 115 | +++ |
| 116 | +++ |
| 117 | +++ |
| 118 | |
| 119 | ++ |
| 120 | |
| 121 | +++ |
| 122 | |
| 123 | +++ |
| 124 | |
| 125 | +++ |
| 126 | +++ |
| 127 | + |
| 128 | +++ |
| 129 | +++ |
| 130 | +++ |
| 131 | +++ |
| 132 | |
| 133 | |
| 134 | |
| 135 | +++ |
| 136 | |
| 137 | + |
| 138 | +++ |
| 139 | +++ |
| 140 | +++ |
| 141 | +++ |
| 142 | +++ |
| 143 | ++ |
| 144 | |
| 145 | +++ |
| 146 | +++ |
| 147 | +++ |
| 148 | |
| 149 | |
| 150 | + |
| 151 | +++ |
| 152 | |
| 153 | +++ |
| 154 | +++ |
| 155 | +++ |
| 156 | +++ |
| 157 | |
| 158 | +++ |
| 159 | +++ |
| 160 | + |
| 161 | +++ |
| 162 | |
| 163 | |
| 164 | +++ |
| 165 | +++ |
| 166 | +++ |
| 167 | +++ |
| 168 | +++ |
| 169 | ++ |
| 170 | +++ |
| 171 | +++ |
| 172 | +++ |
| 173 | +++ |
| 174 | +++ |
| 175 | +++ |
| 176 | +++ |
| 177 | |
| 178 | |
| 179 | |
| 180 | +++ |
| 181 | +++ |
| 182 | ++ |

TABLE 3-continued

| Cmpd. No. | Binned Activity Data |
|---|---|
| 183 | +++ |
| 184 | +++ |
| 185 | |
| 186 | +++ |
| 187 | +++ |
| 188 | +++ |
| 189 | +++ |
| 190 | +++ |
| 191 | +++ |
| 192 | |
| 193 | +++ |
| 194 | +++ |
| 195 | +++ |
| 196 | +++ |
| 197 | +++ |
| 198 | +++ |
| 199 | +++ |
| 200 | +++ |
| 201 | |
| 202 | +++ |
| 203 | +++ |
| 204 | |
| 205 | +++ |
| 206 | +++ |
| 207 | +++ |
| 208 | +++ |
| 209 | +++ |
| 210 | |
| 211 | +++ |
| 212 | +++ |
| 213 | +++ |
| 214 | + |
| 215 | +++ |
| 216 | +++ |
| 217 | ++ |
| 218 | +++ |
| 219 | +++ |
| 220 | +++ |
| 221 | |
| 222 | +++ |
| 223 | +++ |
| 224 | +++ |
| 225 | |
| 226 | |
| 227 | ++ |
| 228 | +++ |
| 229 | |
| 230 | +++ |
| 231 | + |
| 232 | |
| 233 | ++ |
| 234 | |
| 235 | +++ |
| 236 | + |
| 237 | +++ |
| 238 | +++ |
| 239 | +++ |
| 240 | ++ |
| 241 | + |
| 242 | + |
| 243 | +++ |
| 244 | |
| 245 | ++ |
| 246 | +++ |
| 247 | +++ |
| 248 | |
| 249 | +++ |
| 250 | ++ |
| 251 | +++ |
| 252 | ++ |
| 253 | +++ |
| 254 | |
| 255 | +++ |
| 256 | +++ |
| 257 | +++ |
| 258 | +++ |
| 259 | +++ |

TABLE 3-continued

| Cmpd. No. | Binned Activity Data |
|---|---|
| 260 | ++ |
| 261 | |
| 262 | +++ |
| 263 | +++ |
| 264 | |
| 265 | +++ |
| 266 | |
| 267 | +++ |
| 268 | |
| 269 | +++ |
| 270 | +++ |
| 271 | + |
| 272 | + |
| 273 | |
| 274 | +++ |
| 275 | |
| 276 | +++ |
| 277 | +++ |
| 278 | |
| 279 | +++ |
| 280 | |
| 281 | +++ |
| 282 | +++ |
| 283 | +++ |
| 284 | +++ |
| 285 | +++ |
| 286 | +++ |
| 287 | +++ |
| 288 | |
| 289 | +++ |
| 290 | +++ |
| 291 | +++ |
| 292 | +++ |
| 293 | +++ |
| 294 | |
| 295 | +++ |
| 296 | +++ |
| 297 | +++ |
| 298 | +++ |
| 299 | + |
| 300 | +++ |
| 301 | |
| 302 | |
| 303 | +++ |
| 304 | +++ |
| 305 | +++ |
| 306 | +++ |
| 307 | +++ |
| 308 | +++ |
| 309 | + |
| 310 | +++ |
| 311 | +++ |
| 312 | +++ |
| 313 | +++ |
| 314 | +++ |
| 315 | +++ |
| 316 | +++ |
| 317 | + |
| 318 | +++ |
| 319 | ++ |
| 320 | |
| 321 | +++ |
| 322 | ++ |
| 323 | ++ |
| 324 | + |
| 325 | ++ |
| 326 | +++ |
| 327 | +++ |
| 328 | +++ |
| 329 | |
| 330 | +++ |
| 331 | + |
| 332 | |
| 333 | +++ |
| 334 | + |
| 335 | |
| 336 | +++ |

TABLE 3-continued

| Cmpd. No. | Binned Activity Data |
|---|---|
| 337 | +++ |
| 338 | +++ |
| 339 | |
| 340 | +++ |
| 341 | + |
| 342 | +++ |
| 343 | + |
| 344 | |
| 345 | +++ |
| 346 | +++ |
| 347 | +++ |
| 348 | +++ |
| 349 | +++ |
| 350 | +++ |
| 351 | |
| 352 | +++ |
| 353 | + |
| 354 | |
| 355 | +++ |
| 356 | |
| 357 | +++ |
| 358 | ++ |
| 359 | +++ |
| 360 | +++ |
| 361 | +++ |
| 362 | +++ |
| 363 | +++ |
| 364 | +++ |
| 365 | |
| 366 | +++ |
| 367 | +++ |
| 368 | |
| 369 | +++ |
| 370 | +++ |
| 371 | |
| 372 | +++ |
| 373 | +++ |
| 374 | |
| 375 | +++ |
| 376 | +++ |
| 377 | +++ |
| 378 | +++ |
| 379 | +++ |
| 380 | |
| 381 | +++ |
| 382 | +++ |
| 383 | +++ |
| 384 | + |
| 385 | |
| 386 | |
| 387 | +++ |
| 388 | +++ |
| 390 | |
| 391 | ++ |
| 392 | +++ |
| 393 | +++ |
| 394 | |
| 395 | +++ |
| 396 | +++ |
| 397 | |
| 398 | ++ |
| 399 | +++ |
| 400 | |
| 401 | +++ |
| 402 | |
| 403 | +++ |
| 404 | +++ |
| 405 | + |
| 406 | +++ |
| 407 | +++ |
| 408 | ++ |
| 409 | + |
| 410 | +++ |
| 411 | + |
| 412 | |
| 413 | +++ |
| 414 | +++ |

TABLE 3-continued

| Cmpd. No. | Binned Activity Data |
|---|---|
| 415 | +++ |
| 416 | +++ |
| 417 | +++ |
| 418 | ++ |
| 419 | +++ |
| 420 | +++ |
| 421 | |
| 422 | ++ |
| 423 | +++ |
| 424 | +++ |
| 425 | + |
| 426 | +++ |
| 427 | +++ |
| 428 | |
| 429 | +++ |
| 430 | +++ |
| 431 | +++ |
| 432 | |
| 433 | +++ |
| 434 | +++ |
| 435 | +++ |
| 436 | +++ |
| 437 | +++ |
| 438 | +++ |
| 439 | +++ |
| 440 | +++ |
| 441 | |
| 442 | +++ |
| 443 | +++ |
| 444 | + |
| 445 | ++ |
| 446 | +++ |
| 447 | +++ |
| 448 | ++ |
| 449 | +++ |
| 450 | |
| 451 | |
| 452 | +++ |
| 453 | +++ |
| 454 | ++ |
| 455 | + |
| 456 | +++ |
| 457 | |
| 458 | |
| 459 | |
| 460 | +++ |
| 461 | |
| 462 | ++ |
| 463 | +++ |
| 464 | +++ |
| 465 | +++ |
| 466 | +++ |
| 467 | |
| 468 | +++ |
| 469 | ++ |
| 470 | ++ |
| 471 | |
| 472 | +++ |
| 473 | +++ |
| 474 | ++ |
| 475 | +++ |
| 476 | +++ |
| 477 | +++ |
| 478 | +++ |
| 479 | + |
| 480 | +++ |
| 481 | + |
| 482 | |
| 483 | +++ |
| 484 | +++ |
| 485 | +++ |
| 486 | +++ |
| 487 | +++ |
| 488 | |
| 489 | ++ |
| 490 | +++ |
| 491 | + |

TABLE 3-continued

| Cmpd. No. | Binned Activity Data |
|---|---|
| 492 | |
| 493 | |
| 494 | +++ |
| 495 | +++ |
| 496 | + |
| 497 | +++ |
| 498 | |
| 499 | ++ |
| 500 | +++ |
| 501 | +++ |
| 502 | +++ |
| 503 | +++ |
| 504 | +++ |
| 505 | ++ |
| 506 | +++ |
| 507 | + |
| 508 | +++ |
| 509 | +++ |
| 510 | |
| 511 | +++ |
| 512 | +++ |
| 513 | +++ |
| 514 | +++ |
| 515 | +++ |
| 516 | +++ |
| 517 | +++ |
| 518 | +++ |
| 519 | +++ |
| 520 | |
| 521 | +++ |
| 522 | +++ |
| 523 | +++ |
| 524 | +++ |
| 525 | +++ |
| 526 | |
| 527 | |
| 528 | +++ |
| 529 | +++ |
| 530 | +++ |
| 531 | +++ |
| 532 | +++ |
| 533 | +++ |
| 534 | +++ |
| 535 | +++ |
| 536 | +++ |
| 537 | +++ |
| 538 | +++ |
| 539 | |
| 540 | ++ |
| 541 | +++ |
| 542 | ++ |
| 543 | +++ |
| 544 | +++ |
| 545 | |
| 546 | +++ |
| 547 | +++ |
| 548 | |
| 549 | +++ |
| 550 | ++ |
| 551 | +++ |
| 552 | +++ |
| 553 | ++ |
| 554 | +++ |
| 555 | +++ |
| 556 | ++ |
| 557 | +++ |
| 558 | +++ |
| 559 | +++ |
| 560 | |
| 561 | +++ |
| 562 | +++ |
| 563 | |
| 564 | ++ |
| 565 | |
| 566 | + |
| 567 | +++ |
| 568 | +++ |

TABLE 3-continued

| Cmpd. No. | Binned Activity Data |
|---|---|
| 569 | + |
| 570 | +++ |
| 571 | +++ |
| 572 | ++ |
| 573 | +++ |
| 574 | +++ |
| 575 | |
| 576 | +++ |
| 577 | |
| 578 | +++ |
| 579 | +++ |
| 580 | +++ |
| 581 | +++ |
| 582 | +++ |
| 583 | +++ |
| 584 | |
| 585 | ++ |
| 586 | + |
| 587 | +++ |
| 588 | +++ |
| 589 | +++ |
| 590 | +++ |
| 591 | |
| 592 | +++ |
| 593 | +++ |
| 594 | +++ |
| 595 | +++ |
| 596 | +++ |
| 597 | |
| 598 | +++ |
| 599 | +++ |
| 600 | +++ |
| 601 | +++ |
| 602 | +++ |
| 603 | |
| 604 | |
| 605 | +++ |
| 606 | +++ |
| 607 | ++ |
| 608 | +++ |
| 609 | +++ |
| 610 | +++ |
| 611 | +++ |
| 612 | +++ |
| 613 | +++ |
| 614 | ++ |
| 615 | |
| 616 | |
| 617 | +++ |
| 618 | +++ |
| 619 | + |
| 620 | +++ |
| 621 | +++ |
| 622 | +++ |
| 623 | +++ |
| 624 | |
| 625 | |
| 626 | +++ |
| 627 | +++ |
| 628 | +++ |
| 629 | |
| 630 | |
| 631 | +++ |
| 632 | +++ |
| 633 | +++ |
| 634 | |
| 635 | +++ |
| 636 | +++ |
| 637 | +++ |
| 638 | |
| 639 | |
| 640 | +++ |
| 641 | |
| 642 | ++ |
| 643 | ++ |
| 644 | + |
| 645 | |

TABLE 3-continued

| Cmpd. No. | Binned Activity Data |
|---|---|
| 646 | +++ |
| 647 | |
| 648 | |
| 649 | |
| 650 | +++ |
| 651 | +++ |
| 652 | +++ |
| 653 | +++ |
| 654 | |
| 655 | +++ |
| 656 | |
| 657 | + |
| 658 | +++ |
| 659 | + |
| 660 | +++ |
| 661 | |
| 662 | ++ |
| 663 | +++ |
| 664 | +++ |
| 665 | +++ |
| 666 | ++ |
| 667 | + |
| 668 | +++ |
| 669 | +++ |
| 670 | + |
| 671 | +++ |
| 672 | +++ |
| 673 | +++ |
| 674 | ++ |
| 675 | +++ |
| 676 | |
| 677 | +++ |
| 678 | +++ |
| 679 | ++ |
| 680 | +++ |
| 681 | +++ |
| 682 | +++ |
| 683 | +++ |
| 684 | +++ |
| 685 | ++ |
| 686 | +++ |
| 687 | +++ |
| 688 | +++ |
| 689 | +++ |
| 690 | ++ |
| 691 | |
| 692 | |
| 693 | +++ |
| 694 | +++ |
| 695 | |
| 696 | |
| 697 | +++ |
| 698 | +++ |
| 699 | +++ |
| 700 | +++ |
| 701 | ++ |
| 702 | ++ |
| 703 | +++ |
| 704 | +++ |
| 705 | +++ |
| 706 | +++ |
| 707 | |
| 708 | |
| 709 | +++ |
| 710 | +++ |
| 711 | +++ |
| 712 | |
| 713 | +++ |
| 714 | ++ |
| 715 | |
| 716 | +++ |
| 717 | |
| 718 | ++ |
| 719 | |
| 720 | |
| 721 | +++ |
| 722 | +++ |

TABLE 3-continued

| Cmpd. No. | Binned Activity Data |
|---|---|
| 723 | +++ |
| 724 | +++ |
| 725 | +++ |
| 726 | +++ |
| 727 | +++ |
| 728 | +++ |
| 729 | +++ |
| 730 | |
| 731 | |
| 732 | +++ |
| 733 | ++ |
| 734 | +++ |
| 735 | +++ |
| 736 | + |
| 737 | +++ |
| 738 | ++ |
| 739 | +++ |
| 740 | +++ |
| 741 | ++ |
| 742 | ++ |
| 743 | |
| 744 | +++ |
| 745 | +++ |
| 746 | ++ |
| 747 | + |
| 748 | ++ |
| 749 | |
| 750 | +++ |
| 751 | +++ |
| 752 | +++ |
| 753 | |
| 754 | + |
| 755 | +++ |
| 756 | |
| 757 | |
| 758 | +++ |
| 759 | +++ |
| 760 | |
| 761 | +++ |
| 762 | +++ |
| 763 | ++ |
| 764 | +++ |
| 765 | +++ |
| 766 | |
| 767 | +++ |
| 768 | +++ |
| 769 | +++ |
| 770 | +++ |
| 771 | +++ |
| 772 | +++ |
| 773 | +++ |
| 774 | +++ |
| 775 | |
| 776 | |
| 777 | +++ |
| 778 | +++ |
| 779 | |
| 780 | |
| 781 | ++ |
| 782 | +++ |
| 783 | |
| 784 | +++ |
| 785 | +++ |
| 786 | |
| 787 | |
| 788 | +++ |
| 789 | + |
| 790 | +++ |
| 791 | +++ |
| 792 | +++ |
| 793 | +++ |
| 794 | + |
| 795 | |
| 796 | +++ |
| 797 | +++ |
| 798 | |
| 799 | +++ |

TABLE 3-continued

| Cmpd. No. | Binned Activity Data |
|---|---|
| 800 | |
| 801 | +++ |
| 802 | |
| 803 | |
| 804 | + |
| 805 | +++ |
| 806 | |
| 807 | + |
| 808 | +++ |
| 809 | |
| 810 | +++ |
| 811 | + |
| 812 | +++ |
| 813 | |
| 814 | + |
| 815 | +++ |
| 816 | |
| 817 | +++ |
| 818 | +++ |
| 819 | +++ |
| 820 | +++ |
| 821 | +++ |
| 822 | +++ |
| 823 | |
| 824 | +++ |
| 825 | |
| 826 | +++ |
| 827 | |
| 828 | +++ |
| 829 | |
| 830 | +++ |
| 831 | +++ |
| 832 | + |
| 833 | +++ |
| 834 | +++ |
| 835 | |
| 836 | +++ |
| 837 | +++ |
| 838 | ++ |
| 839 | +++ |
| 840 | +++ |
| 841 | +++ |
| 842 | + |
| 843 | ++ |
| 844 | +++ |
| 845 | +++ |
| 846 | +++ |
| 847 | +++ |
| 848 | +++ |
| 849 | + |
| 850 | |
| 851 | +++ |
| 852 | +++ |
| 853 | +++ |
| 854 | ++ |
| 855 | +++ |
| 856 | +++ |
| 857 | +++ |
| 858 | +++ |
| 859 | ++ |
| 860 | +++ |
| 861 | +++ |
| 862 | +++ |
| 863 | +++ |
| 864 | +++ |
| 865 | |
| 866 | +++ |
| 867 | +++ |
| 868 | ++ |
| 869 | +++ |
| 870 | +++ |

IC50: +++ <= 2.0 μM < ++ <= 5.0 μM < +

Many modifications and variations of the embodiments described herein may be made without departing from the

We claim:
1. A compound of formula I:

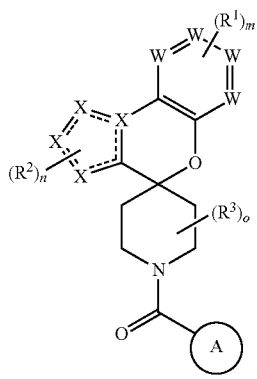

or a pharmaceutically acceptable salt thereof,
wherein, independently for each occurrence and optionally substituted, as valency allows, with one or more substituents selected from the group consisting of halo, cyano, oxoalkoxy, hydroxy, amino, nitro, aryl, haloalkyl, and alkyl:
$R^1$ is C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl or (C1-C6)-$R^8$ wherein up to two $CH_2$ units may be replaced with O, CO, S, SO, $SO_2$, $NR^7$;
$R^2$ is H, C1-C6 alkyl, C1-C6 haloalkyl, C3-C8 cycloalkyl, halo, aryl, an electron withdrawing group, $CH_2CF_3$, $CHF_2$, $CF_3$, CN, OH, $OR^7$, $CON(R^7)_2$, $SO_2R^7$, $SR^7$, $SOR^7$, $SO_2N(R^7)_2$, or (C1-C6)-$R^8$ wherein up to two $CH_2$ units may be replaced with O, CO, S, SO, $SO_2$, $CF_2$, or $NR^7$;
$R^3$ is halo, C1-C6 alkyl or C3-C8 cycloalkyl, wherein up to two $CH_2$ units may be replaced by O, CO, S, SO, $SO_2$, or $NR^8$, or 2 occurrences of $R^3$ taken together form a C3-C8 cycloalkyl group;
$R^7$ is H, C1-C6 alkyl, $CHF_2$, $CF_3$, or C3-C8 cycloalkyl, or 2 $R^7$ taken together with the atoms to which they are attached form a heterocyclic or heteroaromatic ring;
$R^8$ is H, $CF_3$, $CO_2R^7$, OH, aryl, heteroaryl, C3-C8 cycloalkyl, heterocycloalkyl, $N(R^7)_2$, $NR^7COR^7$, $CON(R^7)_2$, CN, or $SO_2R^7$;
A is aryl, heteroaryl or heterocyclic;
X is N, S, or $CR^2$ wherein at least one X is N;
W is N or CH, wherein up to 2 W are N;
a - - - - line denotes an optionally double bond depending on the identity of X;
m is an integer from 0 to 4 inclusive;
n is an integer from 0 to 3 inclusive; and
o is an integer from 0 to 4 inclusive.
2. The compound of claim 1, wherein all W's are CH.
3. The compound of claim 1, wherein one W is N.
4. The compound of claim 1, wherein $R^1$ is C1-C6 alkyl, C1-C6 alkoxy, halo, CN, $CON(R^7)_2$, or (C1-C6)-$R^8$ wherein up to two $CH_2$ units may be replaced with O or $NR^7$.
5. The compound of claim 1, wherein $R^1$ is F, Cl, $CH_3$, CN, $OCH_3$, $CH_2OH$, $CH_2N(CH_3)_2$, $CH_2NH_2$, $CONHCH_3$, $CON(CH_3)_2$, $CH_2OCH_3$.
6. The compound of claim 1, wherein $R^2$ is C1-C6 alkyl, C1-C6 haloalkyl, halo, CN, $CF_3$, $CON(R^7)_2$, $SO_2R^7$, or (C1-C6)-$R^8$ wherein up to two $CH_2$ units may be replaced with O, CO, S, SO, $SO_2$, $CF_2$, or $NR^7$.
7. The compound of claim 1, wherein $R^2$ is $CH_3$, $CF_3$, $CHF_2$, $C_2H_5$, $CH_2OH$, F, CN, $(CH_2)_2OCH_3$, $SO_2CH_3$, $SOCH_3$, $CH_2CF_3$, $CH_2NH_2$, $CH_2NHCOCH_3$, $CH_2NHCOH$, $COCH_3$, or $CONHCH_3$.
8. The compound of claim 1, wherein $R^3$ is C1-C6 alkyl.
9. The compound of claim 1, wherein $R^3$ is methyl.
10. The compound of claim 1, wherein 2 occurrences of $R^3$ taken together form a C3-C8 cycloalkyl group.
11. The compound of claim 1, wherein A is

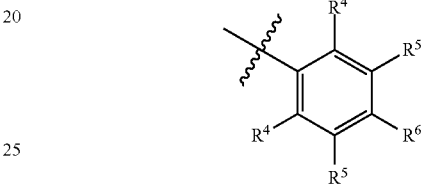

wherein:
$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CHF_2$, $CF_3$, $OCF_3$, $OCHF_2$, heterocycloalkyl, aryl, heteroaryl, or a straight chain, branched, or cyclic (C1-C8)-$R^8$ wherein up to three $CH_2$ units may be replaced with O, CO, S, SO, $SO_2$, or $NR^7$;
$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ wherein up to three $CH_2$ units may be replaced with O, CO, S, SO, $SO_2$, or $NR^7$;
$R^6$ is H, C1-C6 alkyl, C3-C8 cycloalkyl, C1-C6 alkoxy, halo, CN, OH, $OR^7$, $N(R^7)_2$, $NR^7SO_2R^7$, $SR^7$, $SOR^7$, $SO_2R^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl, or a straight chain, branched, or cyclic (C1-C8)-$R^8$ wherein up to three $CH_2$ units may be replaced with O, CO, S, SO, $SO_2$, or $NR^7$; or
two occurrences of $R^4$ and $R^5$, or $R^5$ and $R^6$ are both C1-C6 alkyl and together with the carbons to which they are attached form an optionally substituted ring comprising up to 2 heteroatoms.
12. The compound of claim 11, wherein $R^4$ is H, C1-C6 alkyl, C1-C6 alkoxy, halo, CN, OH, $OR^7$, $CON(R^7)_2$, $NR^7SO_2R^7$, $SO_2R^7$, $SOR^7$, $SR^7$, $CO_2R^7$, $NR^7CO_2R^7$, $CHF_2$, $CF_3$, $OCF_3$, $OCHF_2$, heteroaryl, or a straight chain, branched, or cyclic (C1-C8)-$R^8$ wherein up to three $CH_2$ units may be replaced with O, CO, S, SO, $SO_2$, or $NR^7$.
13. The compound of claim 11, wherein $R^4$ is H, F, Cl, OH, $CH_3$, $CHF_2$, $CF_3$, $OCH_3$, $OCHF_2$, $OCF_3$, $SO_2CH_3$, CN, $NHSO_2CH_3$, $C_2H_5$, $OC_2H_5$, $OCF_2CHFCl$, $OCH_2CF_3$, $O(CH_2)_2CH_3$, $OCH(CH_3)_2$, $O(CH_2)_2OH$, $OCH_2OCH_3$, $CO_2CH_3$, $CH_2OH$, $SCH_3$, $CON(CH_3)_2$, $NHCO_2tBu$,

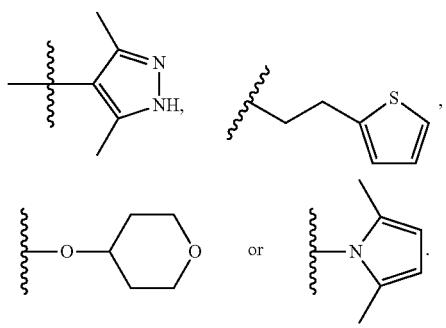

14. The compound of claim 11, wherein $R^5$ is H, C1-C6 alkyl, C1-C6 alkoxy, halo, CN, OH, $OR^7$, $NR^7SO_2R^7$, $SO_2R^7$, $SR^7$, $SOR^7$, $CO_2R^7$, $CON(R^7)_2$, $SO_2N(R^7)_2$, $CF_3$, $OCF_3$, or a straight chain, branched, or cyclic (C1-C8)-$R^8$ wherein up to three $CH_2$ units may be replaced with O, CO, S, SO, $SO_2$, or $NR^7$.

15. The compound of claim 11, wherein $R^5$ is H, F, Cl, $CH_3$, $C_2H_5$, $CH(CH_3)_2$, tBu, OH, $OCH_3$, $OC_2H_5$, $OCH(CH_3)_2$, $CH_2OH$, $CF_3$, $OCF_3$, CN, $CO_2CH_3$, $CONH_2$, $N(CH_3)$ $SO_2CH_3$, $SO_2NH_2$ or $SO_2CH_3$.

16. The compound of claim 11, wherein $R^6$ is H, C1-C6 alkyl, C3-C8 cycloalkyl, C1-C6 alkoxy, halo, CN, OH, $OR^7$, $SR^7$, SOW, $SO_2R^7$, $NR^7COR^7$, $SO_2N(R^7)_2$, $CON(R^7)_2$, $CF_3$, $OCF_3$, $OCHF_2$, heterocycloalkyl, heteroaryl or a straight chain, branched, or cyclic (C1-C8)-$R^8$ wherein up to three $CH_2$ units may be replaced with O, CO, S, SO, $SO_2$, or $NR^7$.

17. The compound of claim 11, wherein $R^6$ is H, F, Cl, $CH_3$, $CF_3$, $OCH_3$, $OC_2H_5$, $CH_2CH_2OH$, $OCF_3$, $OCHF_2$, $SOCH(CH_3)_2$, $SO_2CH_3$, $SO_2CH(CH_3)_2$, $SO_2CHF_2$, $SO_2CF_3$, $SO_2C_2H_5$, $SO_2CH_2CH(CH_3)_2$, $SO_2tBu$, OH, CN, $CH_2CH_3$, $OCH_2CF_3$, $O(CH_2)_2OH$, $NHC(=O)CH_3$, $OCH_2C(=O)NH_2$,

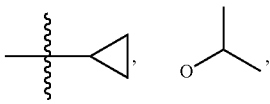

$O(CH_2)_2CH_3$,

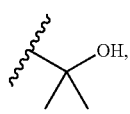

$O(CH_2)_3OH$, $O(CH_2)_2OCH_3$,

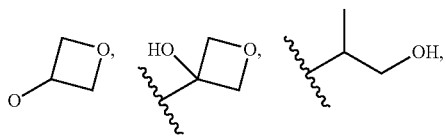

$O(CH_2)_2OCF_3$,

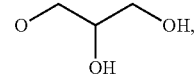

$O(CH_2)_2SO_2CH_3$, tBu,

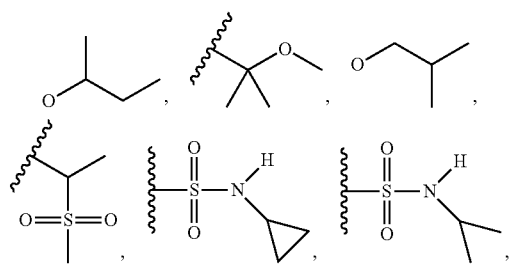

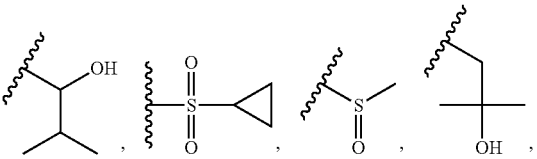

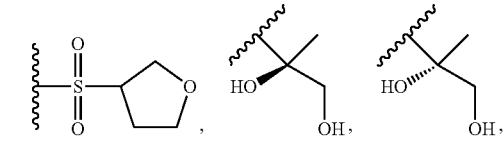

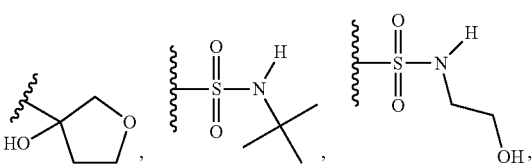

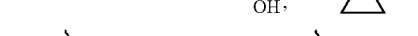

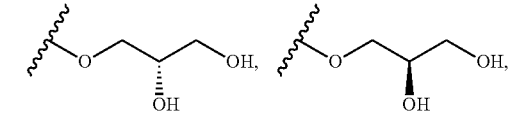

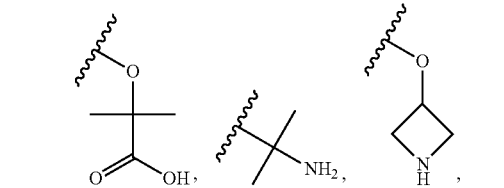

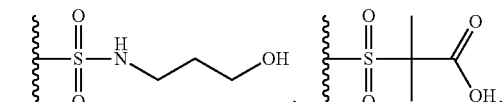

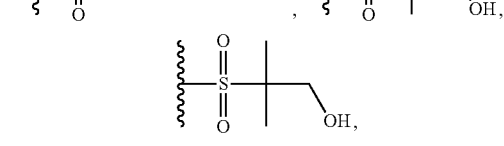

OtBu,

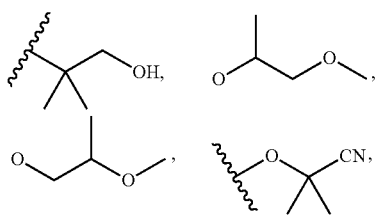

O(CH₂)₃OCH₃, O(CH₂)₂OC₂H₅,

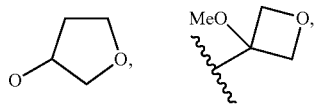 [SMILES: OC1CCOC1 ; *C1(OC)COC1]

O(CH₂)₂N(CH₃)₂,

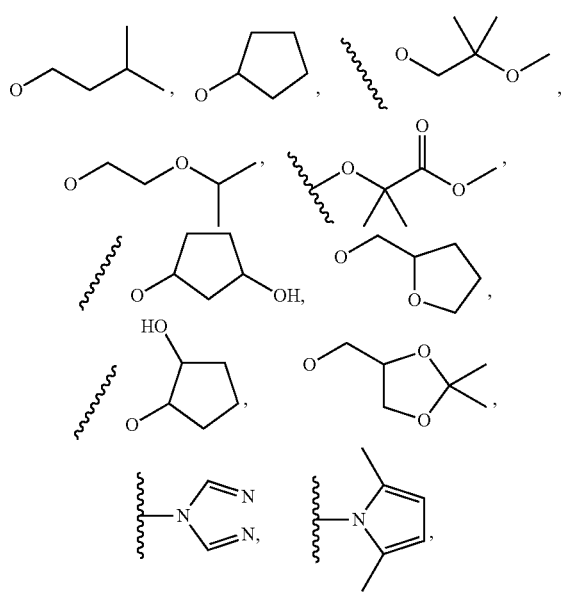

OCH₂Ph, SO₂NHCH₃, SO₂N(CH₃)₂, SO₂NHCH₂CH₃, SO₂N(CH₃)CH(CH₃)₂, SO₂CH₂CH₂OH, CONHCH(CH₃)₂ or OCH₂CO₂H.

18. The compound of claim 11, wherein two occurrences of $R^4$ and $R^5$ are both C1-C6 alkyl and together with the carbons to which they are attached form an optionally substituted ring comprising up to 2 heteroatoms.

19. The compound of claim 11, wherein two occurrences of $R^5$ and $R^6$ are C1-C6 alkyl and together with the carbons to which they are attached form an optionally substituted ring comprising up to 2 heteroatoms.

20. The compound of claim 11, wherein $R^4$ is H.

21. The compound of claim 11, wherein $R^5$ is halo, $CF_3$, C1-C6 alkyl, or C1-C6 alkoxy.

22. The compound of claim 11, wherein $R^5$ is C1-C6 alkoxy.

23. The compound of claim 11, wherein $R^6$ is C1-C6 alkyl or C1-C6 alkoxy.

24. The compound of claim 11, wherein $R^6$ is C1-C6 alkyl.

25. The compound of claim 11, wherein $R^4$ is H or alkoxy; $R^5$ is H, halo, $CF_3$, C1-C6 alkyl, or C1-C6 alkoxy; and $R^6$ is H, (C1-C6)-$R^8$ wherein two methylene units have been replaced with O, or $SO_2R^7$.

26. The compound of claim 11, wherein $R^4$ is H or $OCHF_2$, and $R^5$ and $R^6$ are H.

27. The compound of claim 11, wherein $R^4$ and $R^5$ are H, and $R^6$ is (C1-C6)-$R^8$ wherein two methylene units have been replaced with O.

28. The compound of claim 11, wherein $R^4$ is halo, $R^5$ is H, and $R^6$ is alkoxy.

29. The compound of claim 11, wherein $R^4$ and $R^5$ are H, and $R^6$ is $SO_2R^7$.

30. The compound of claim 11, wherein

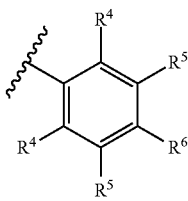

is selected from:

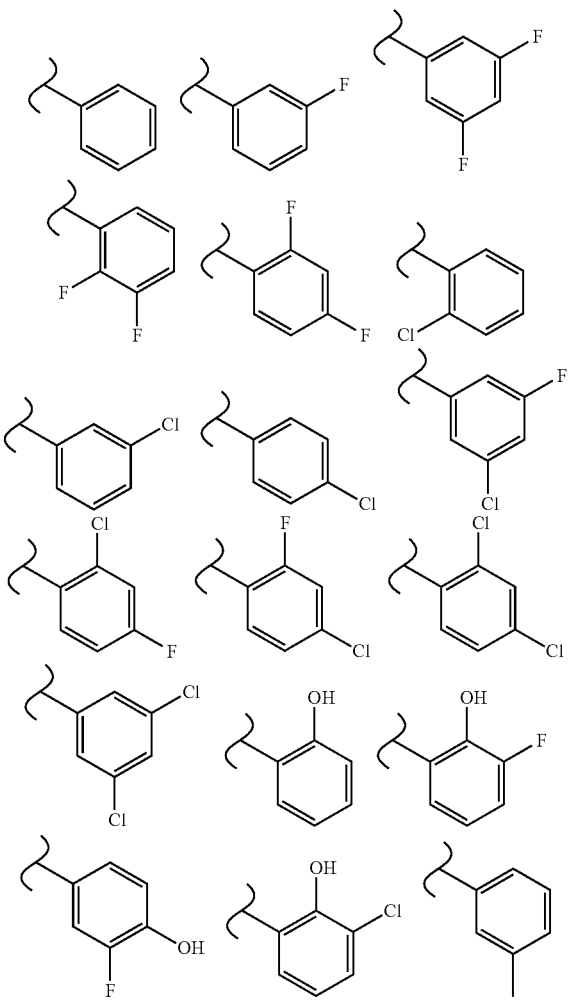

755
-continued
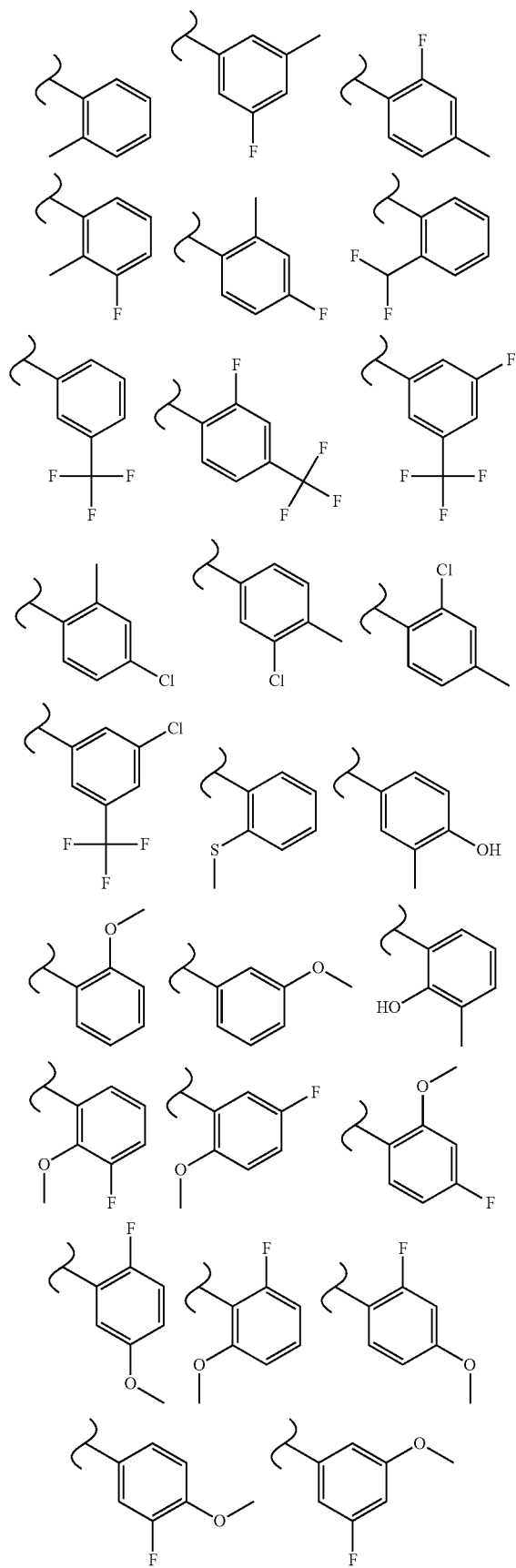
756
-continued
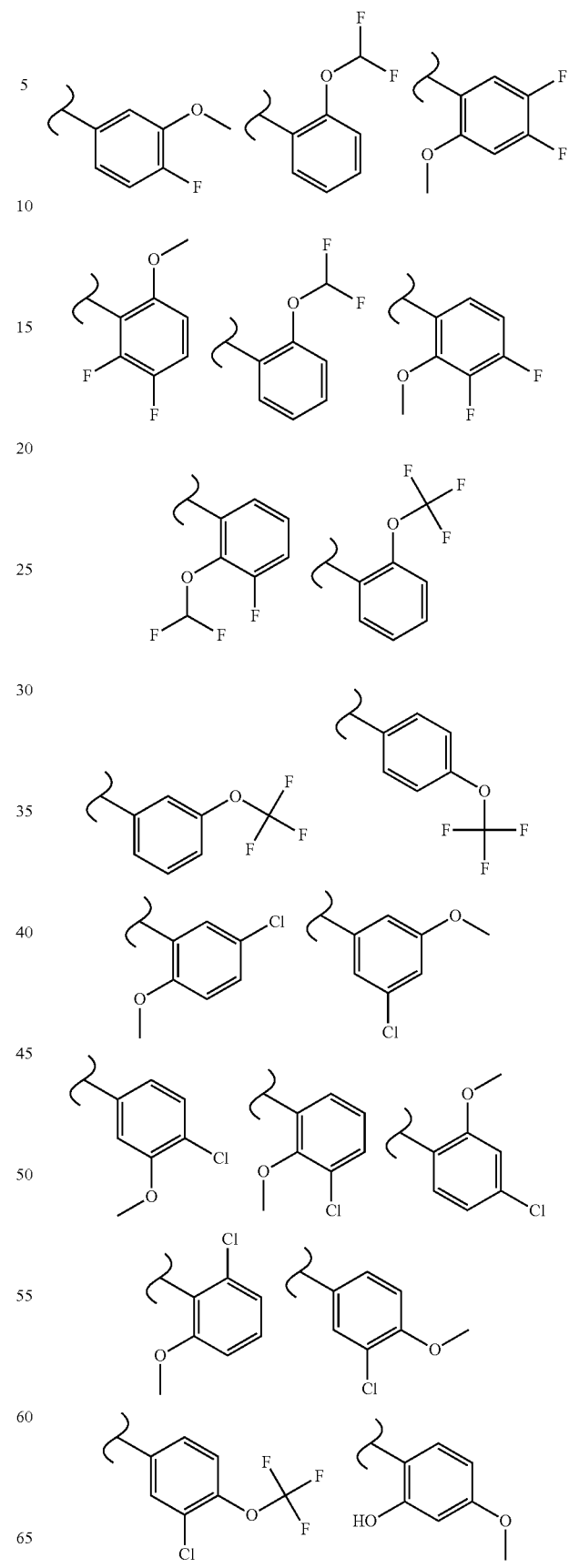

757
-continued
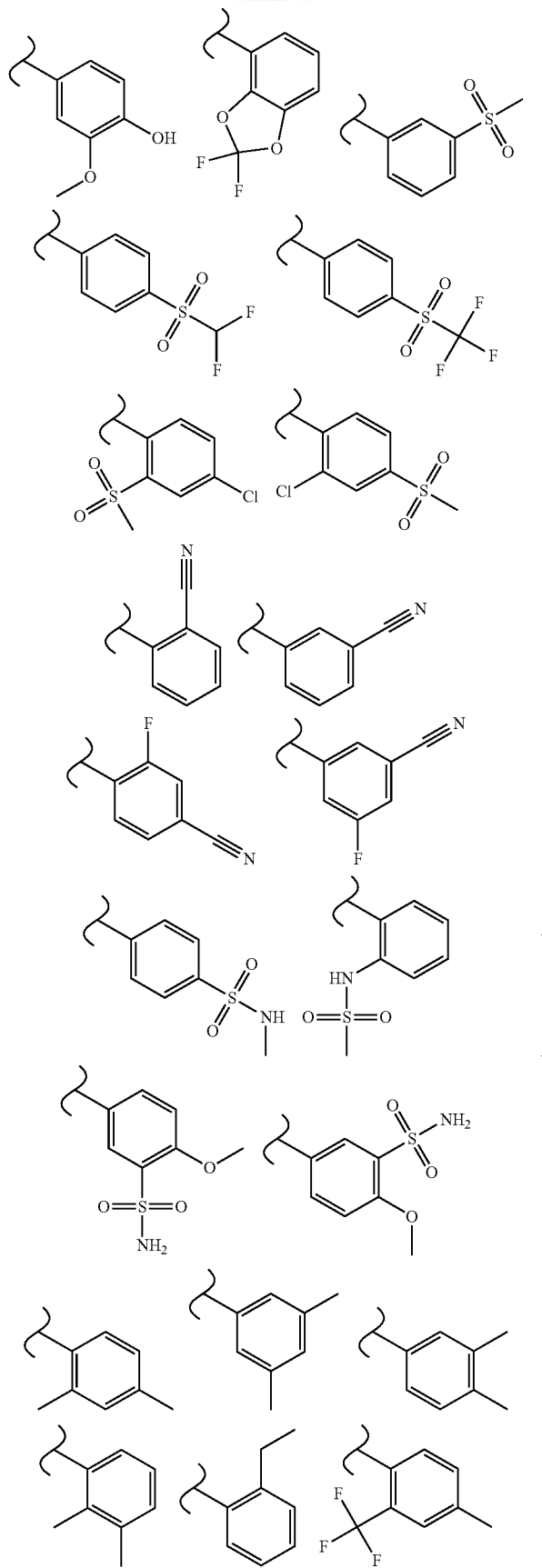
758
-continued
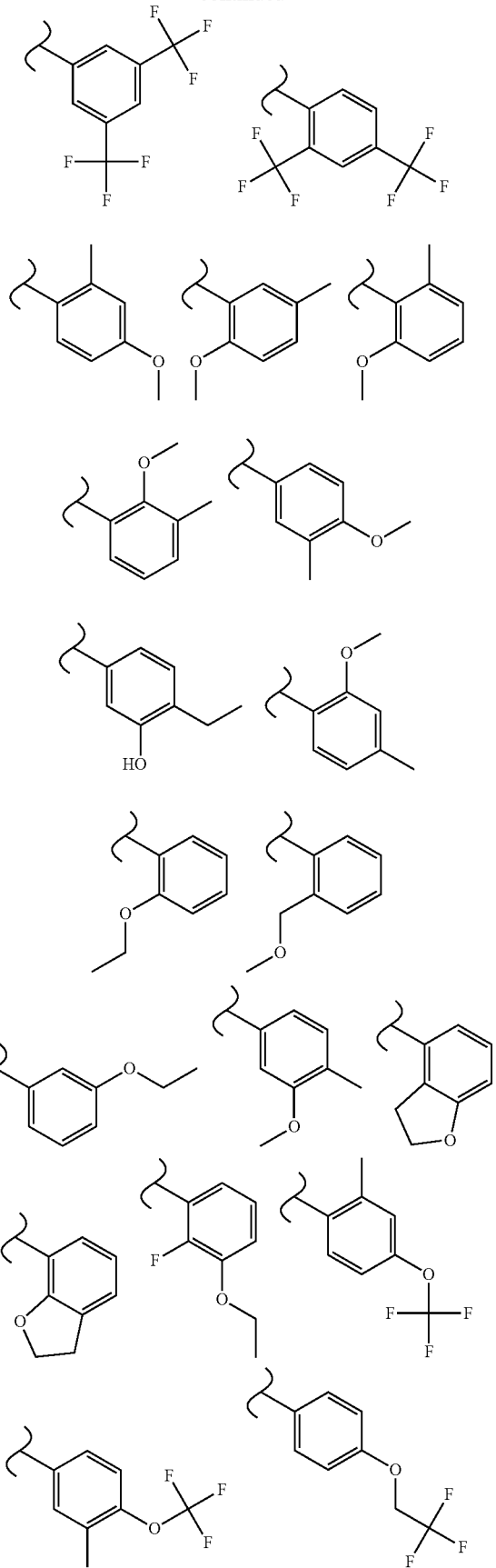

759
-continued
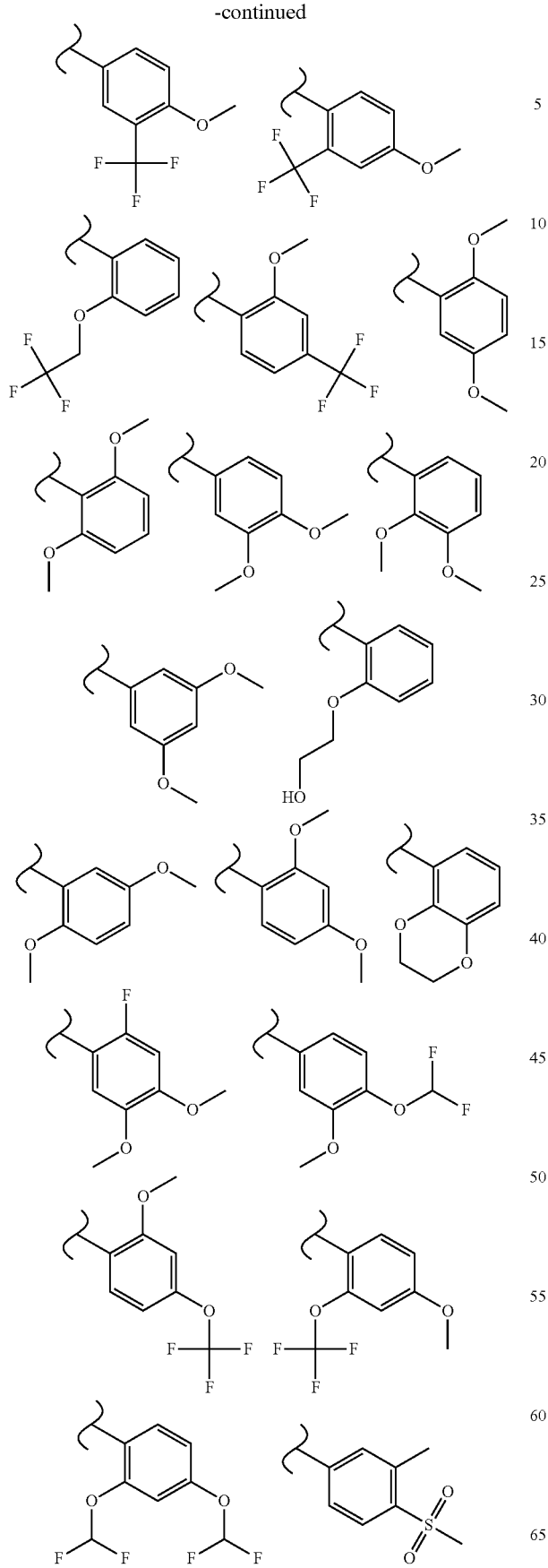
760
-continued
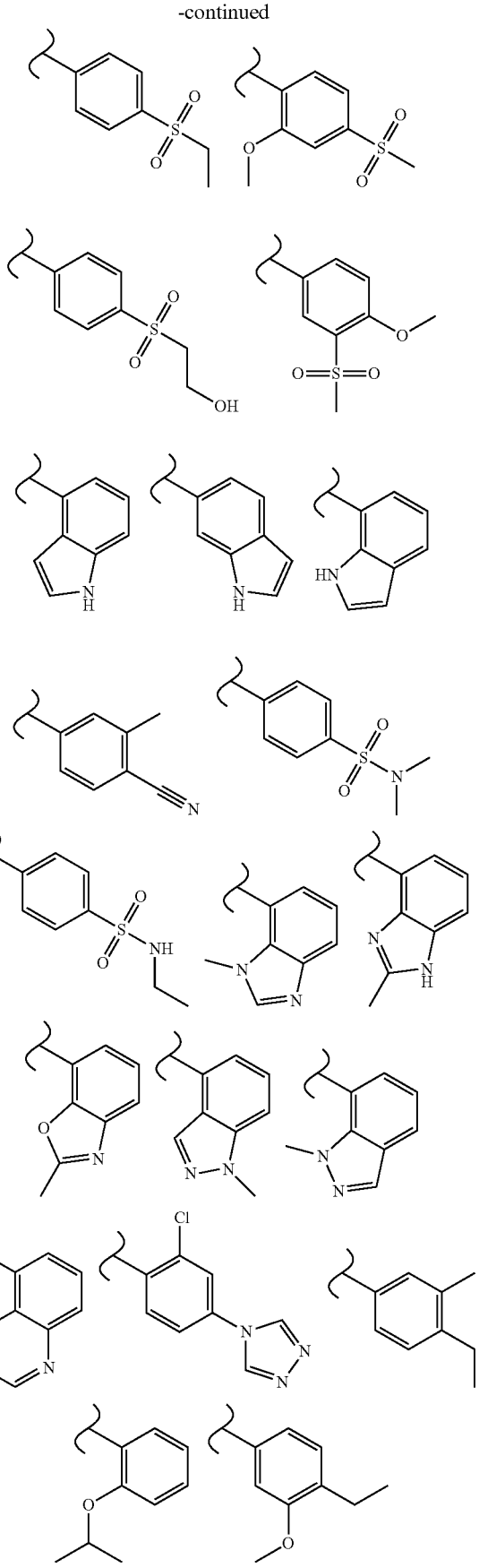

761
-continued
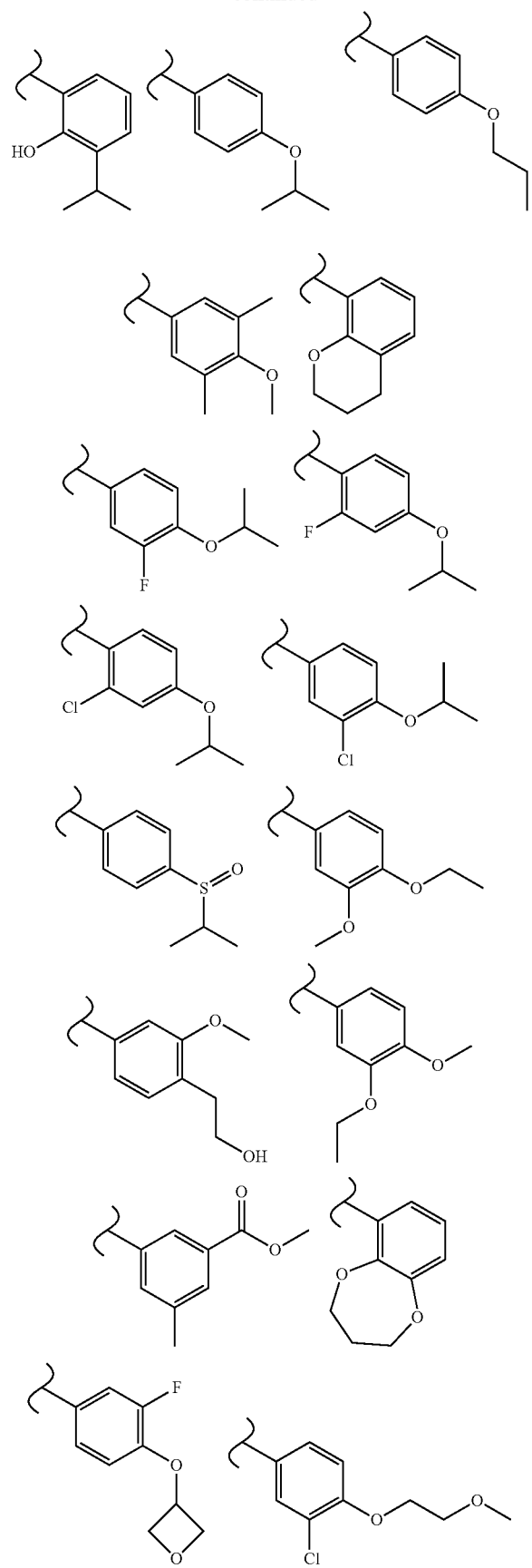
762
-continued
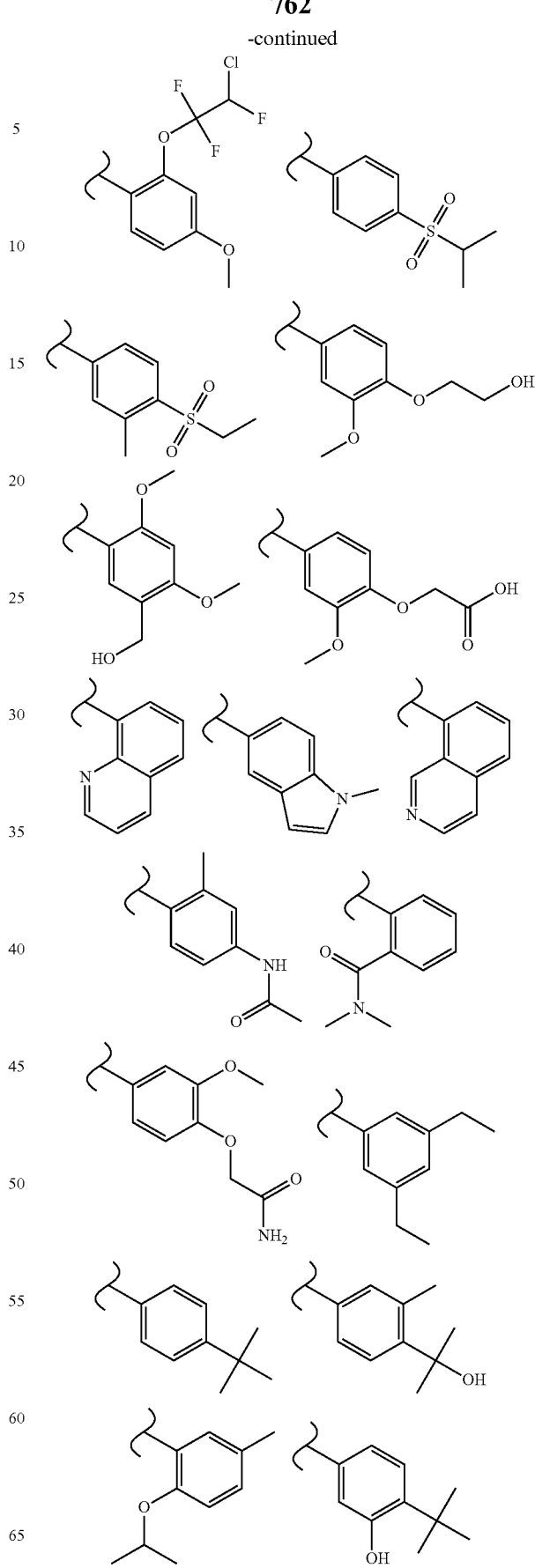

763
-continued
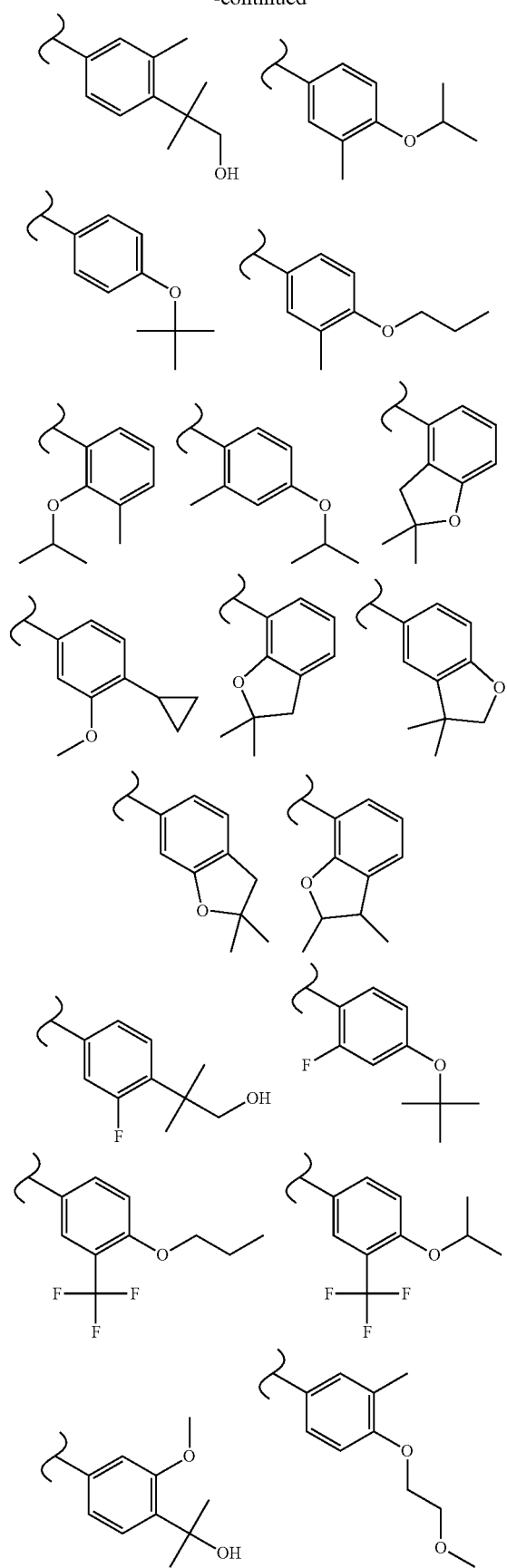
764
-continued
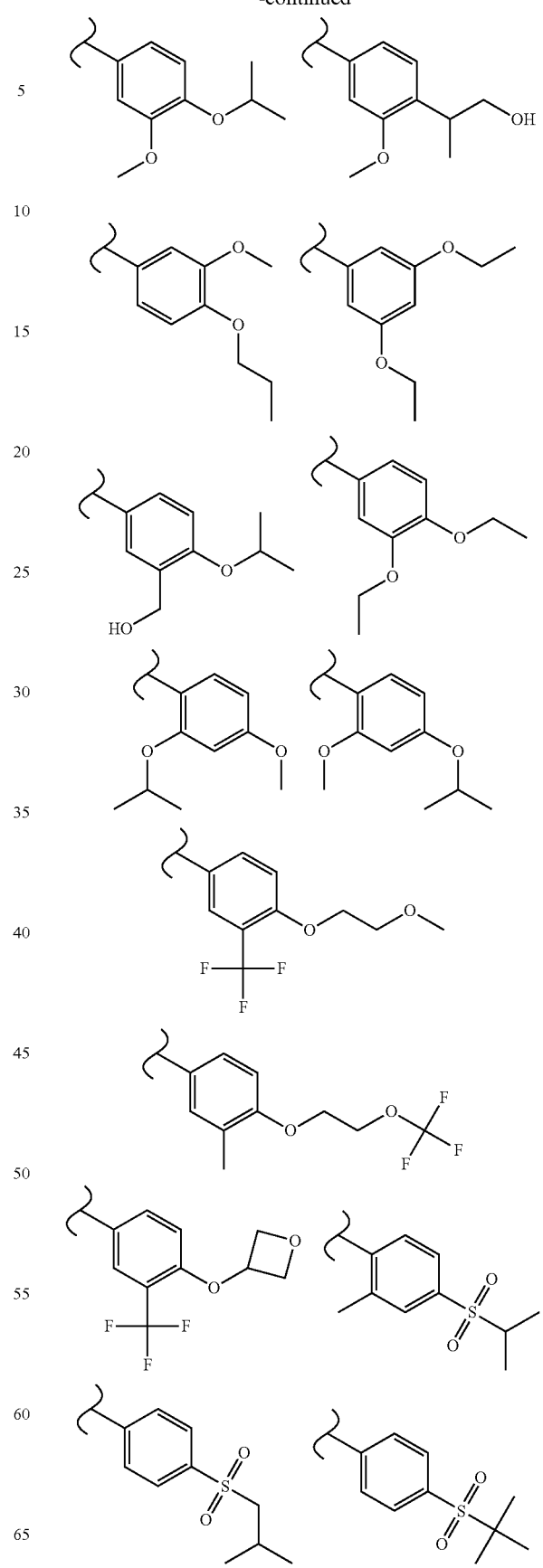

765
-continued
766
-continued
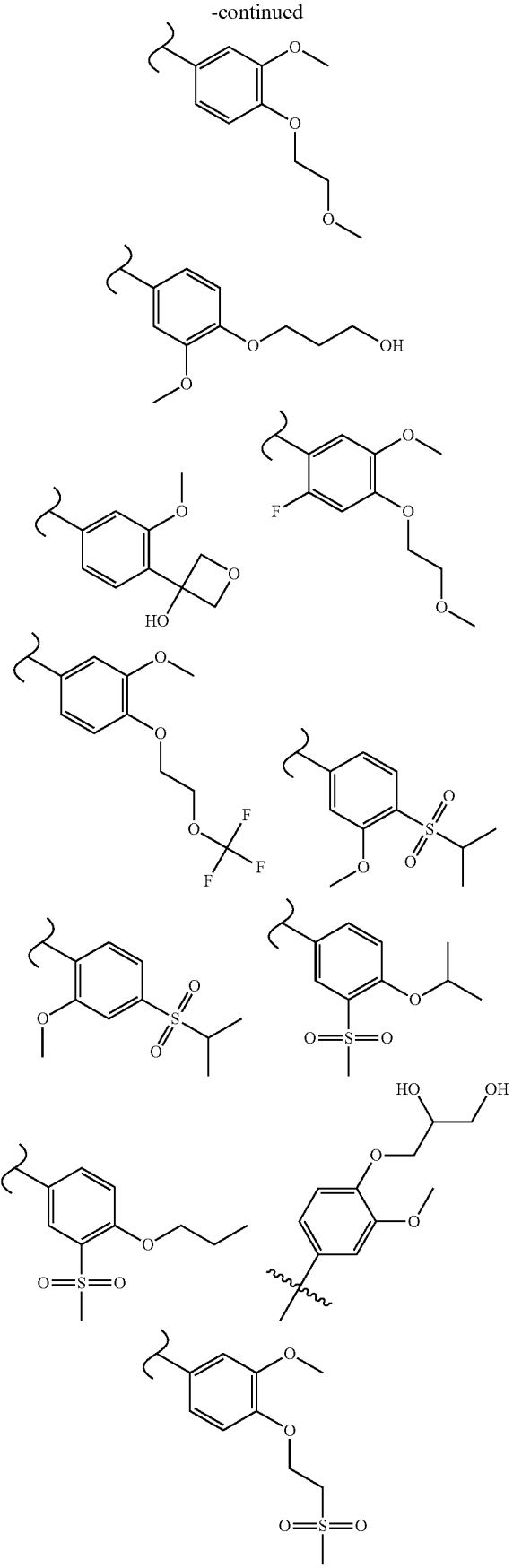
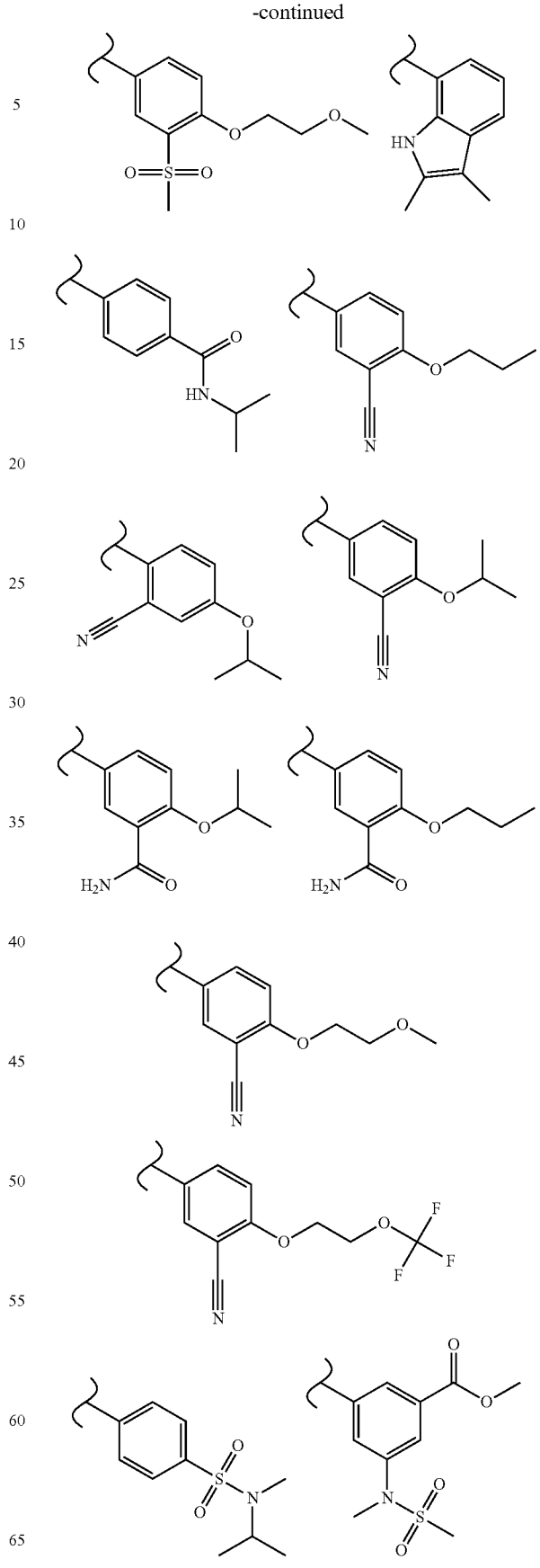

767
-continued
768
-continued
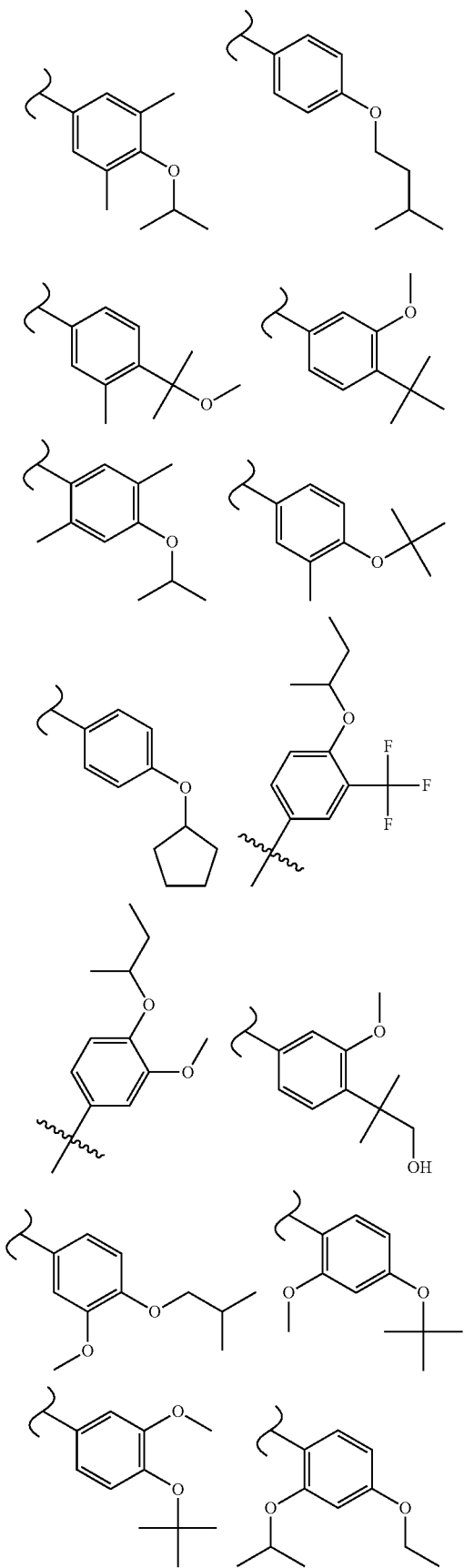
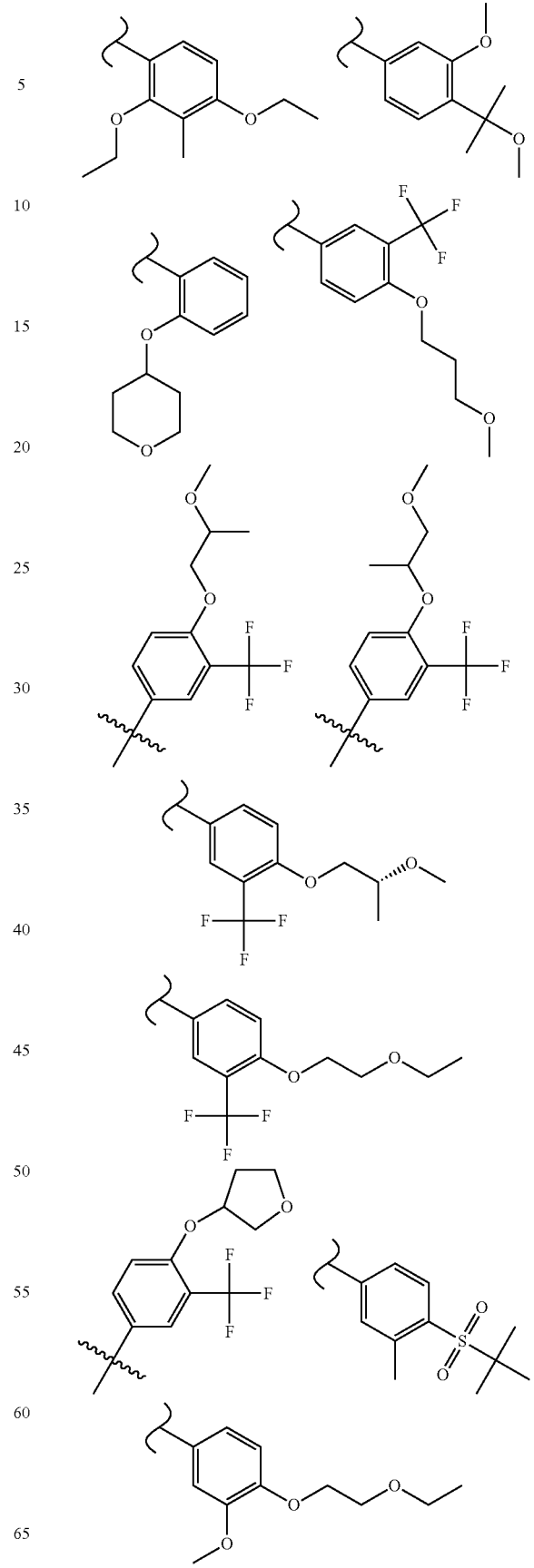

769
-continued
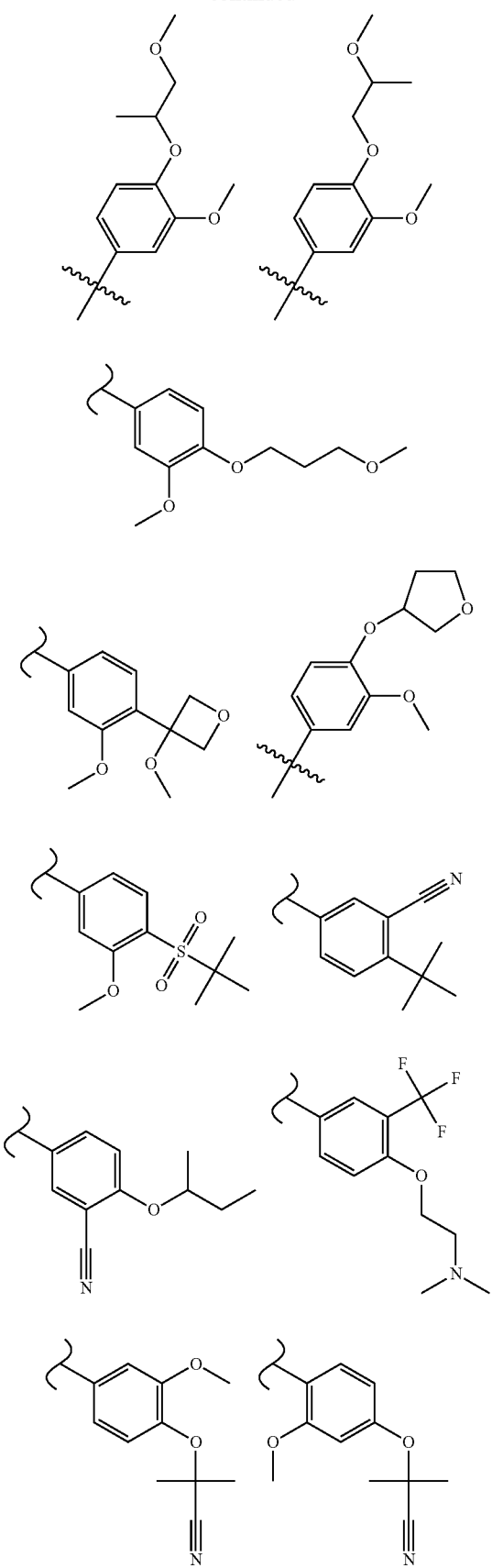
770
-continued
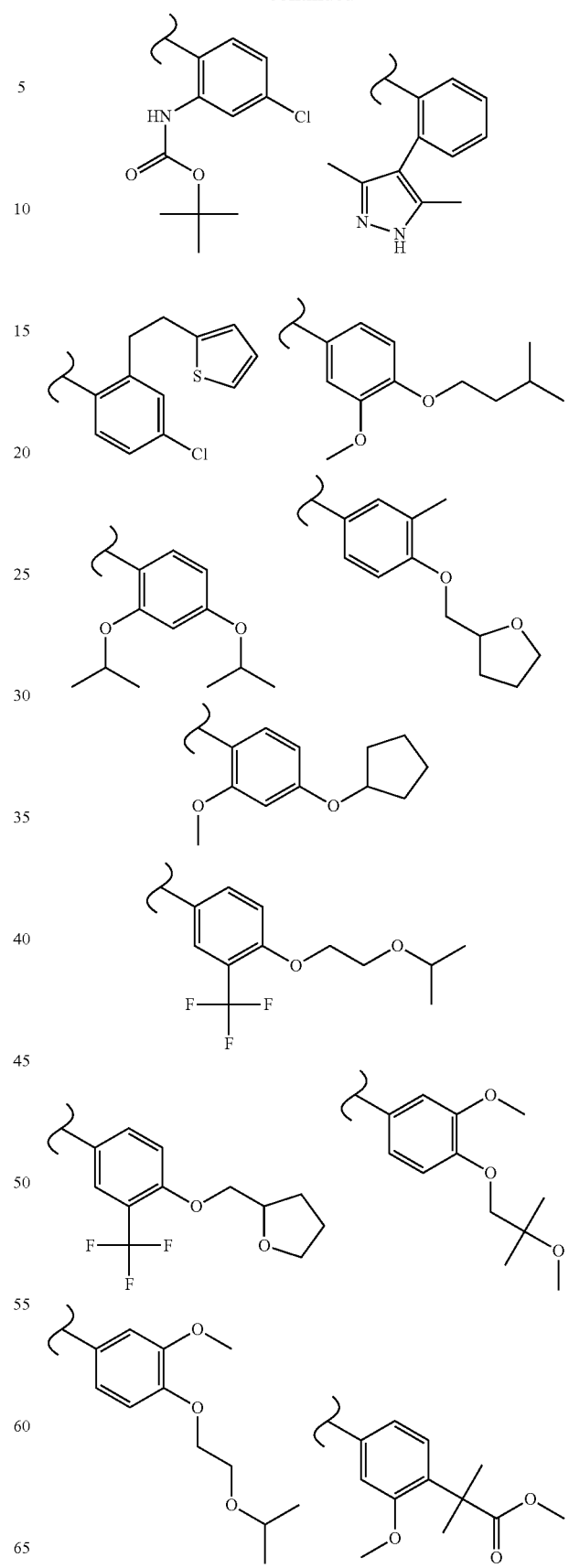

771
-continued
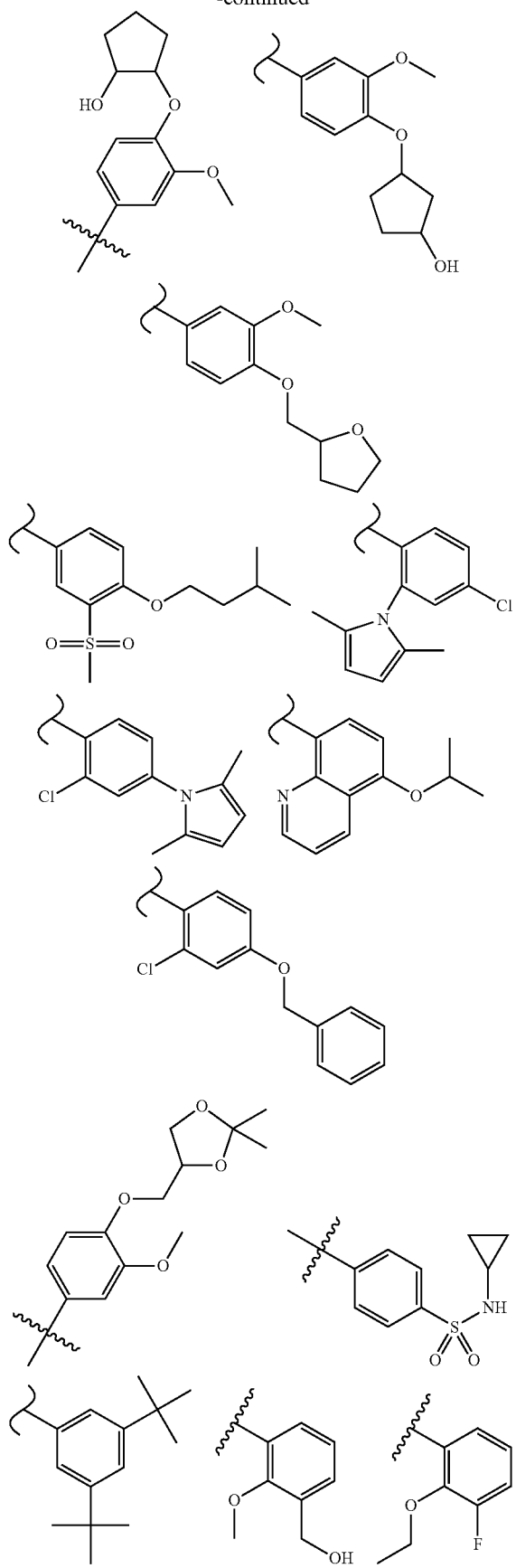
772
-continued
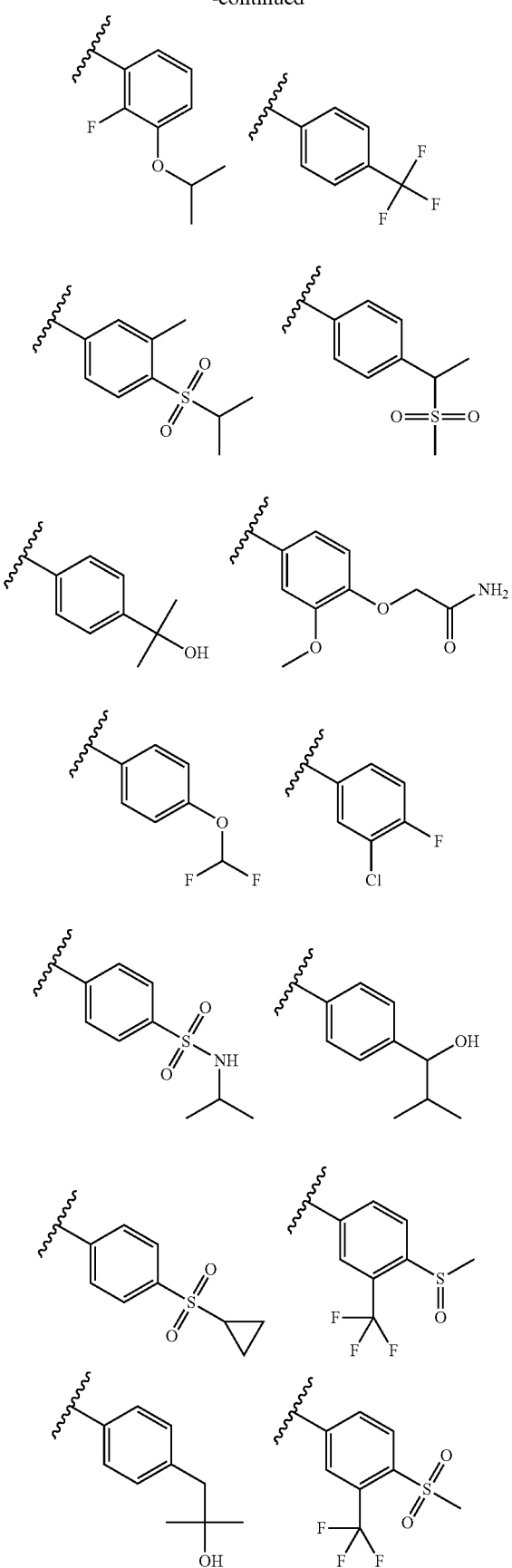

773
-continued
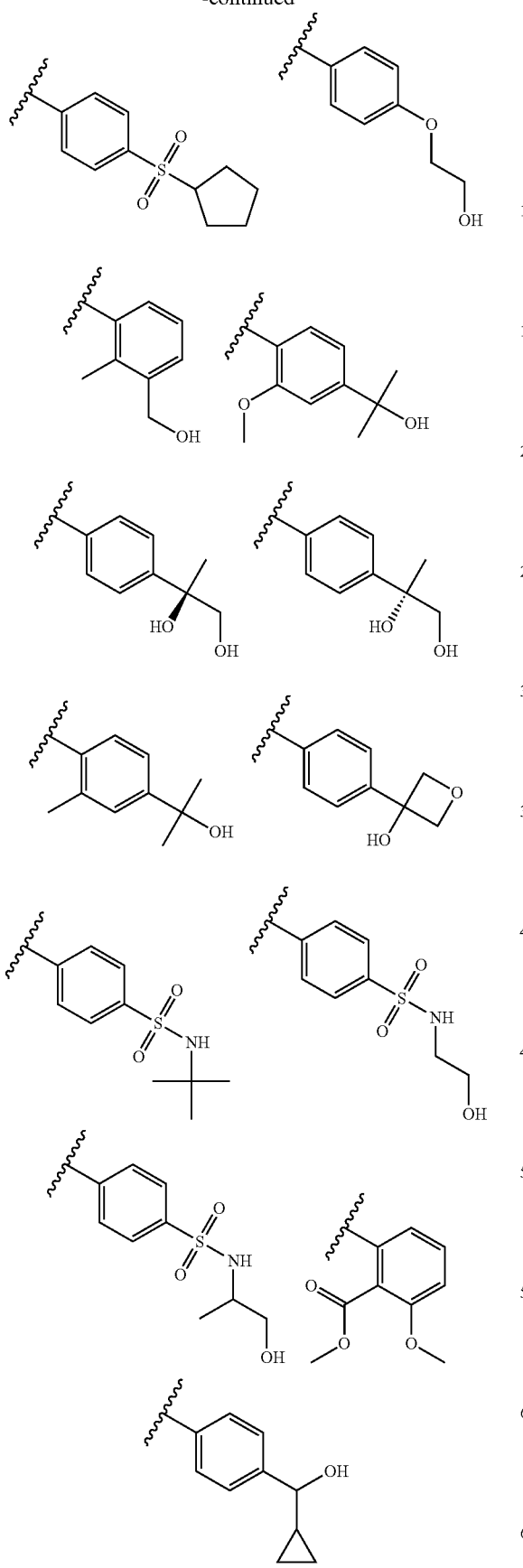
774
-continued
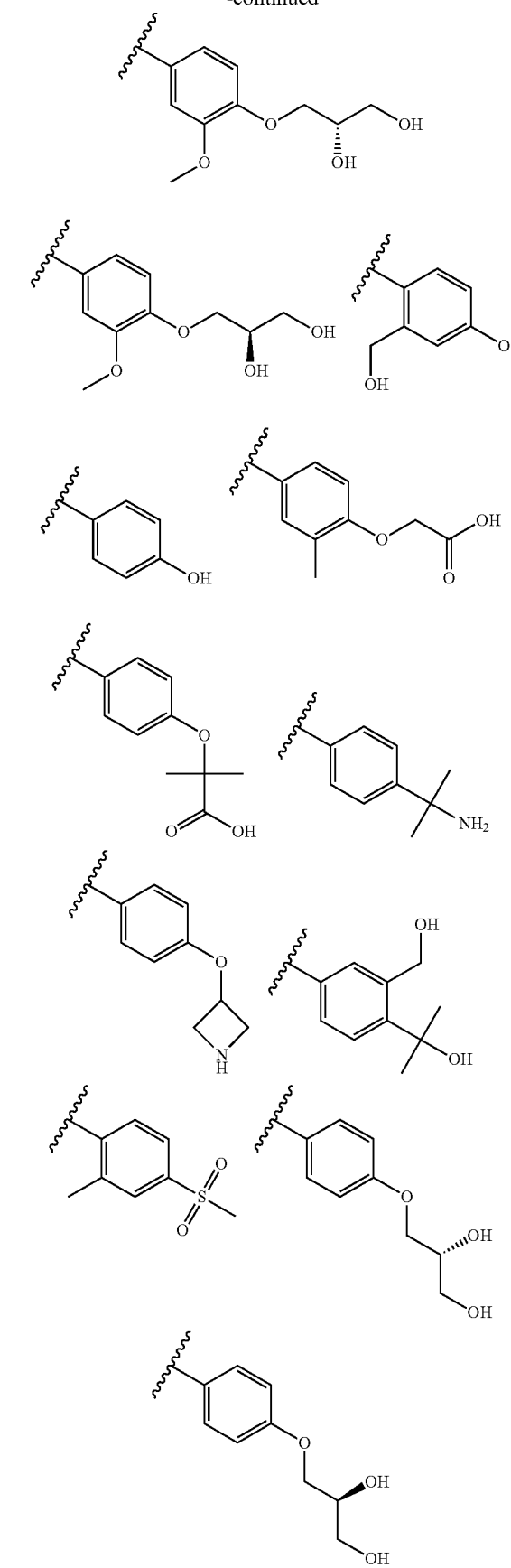

-continued
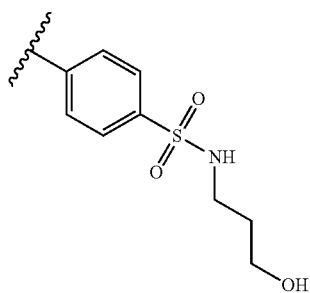
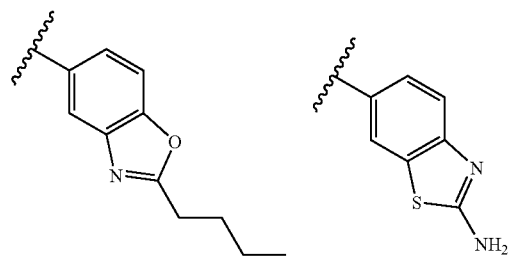
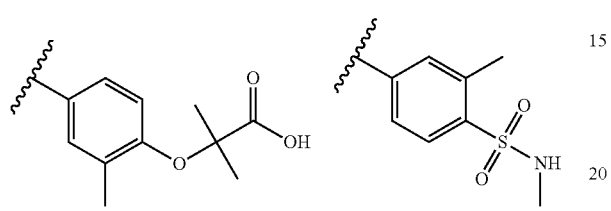
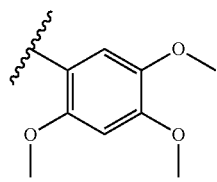
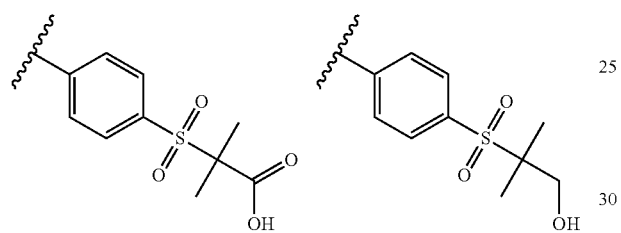
31. The compound of claim 1, wherein A is heteroaryl or heterocyclic.
32. The compound of claim 31, wherein A is selected from:
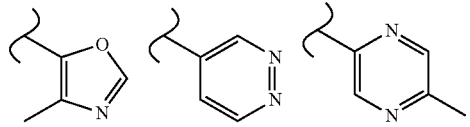
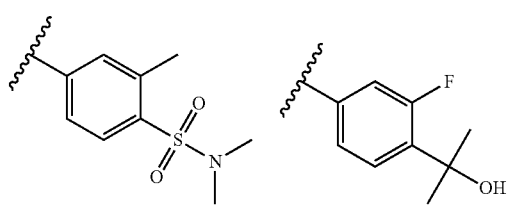
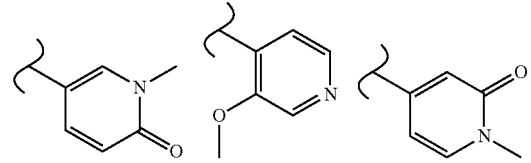
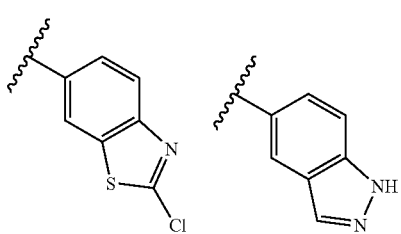
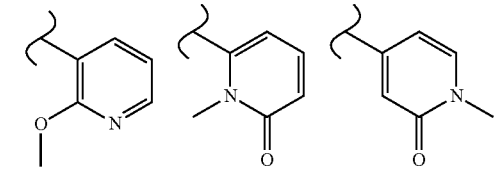
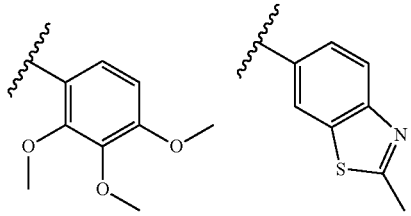
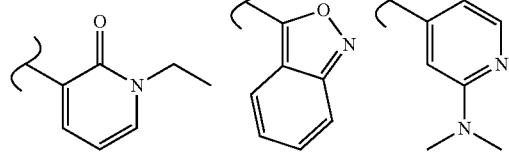
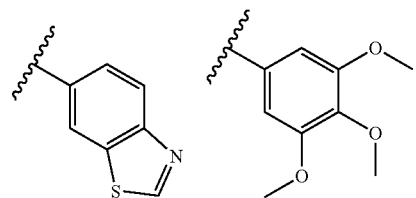
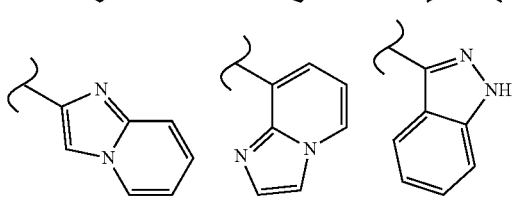

777
-continued
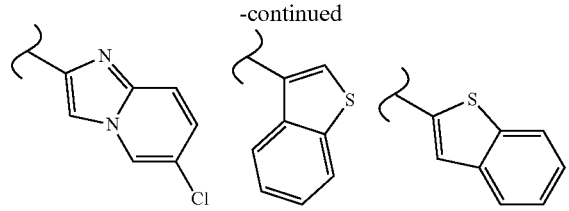
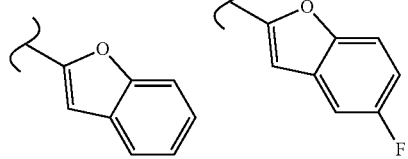
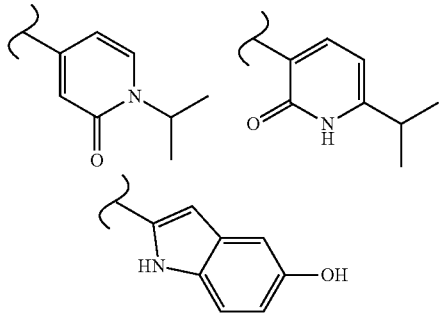
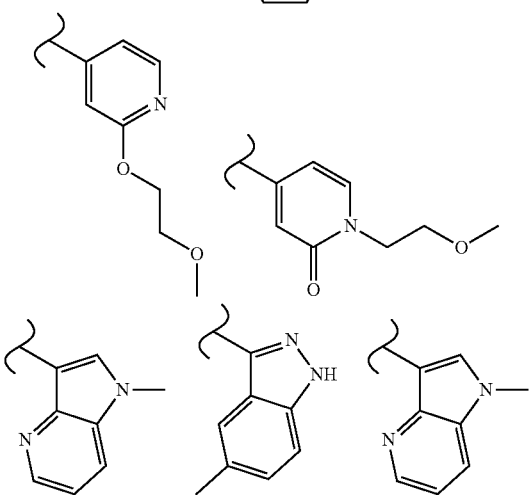
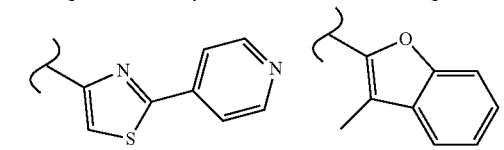
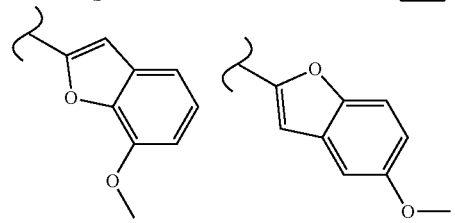
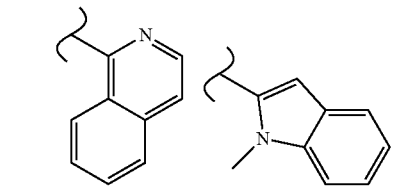
778
-continued
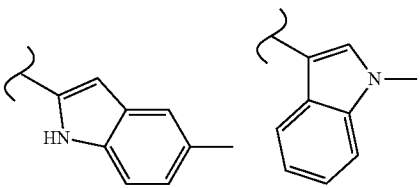
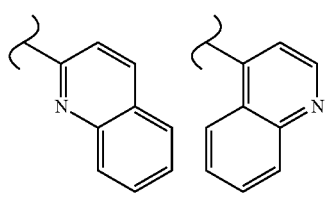
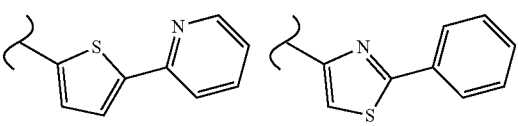
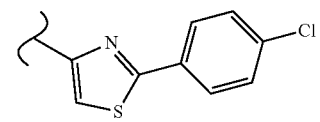
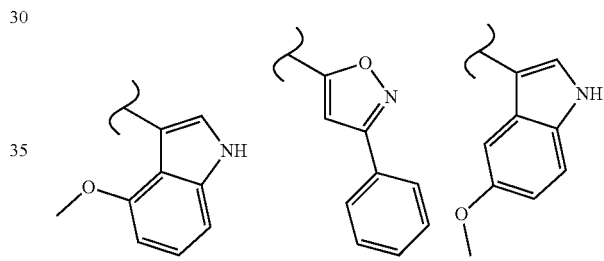
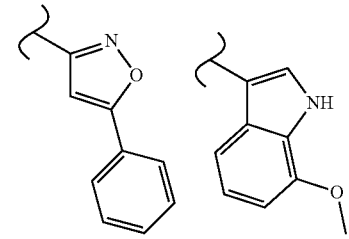
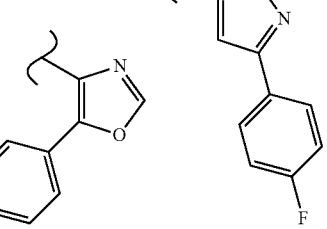
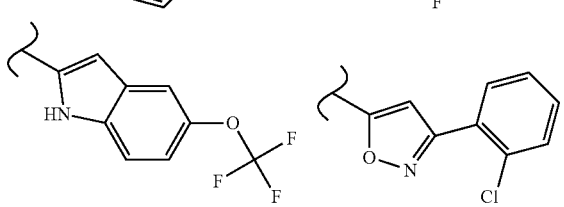

779
-continued
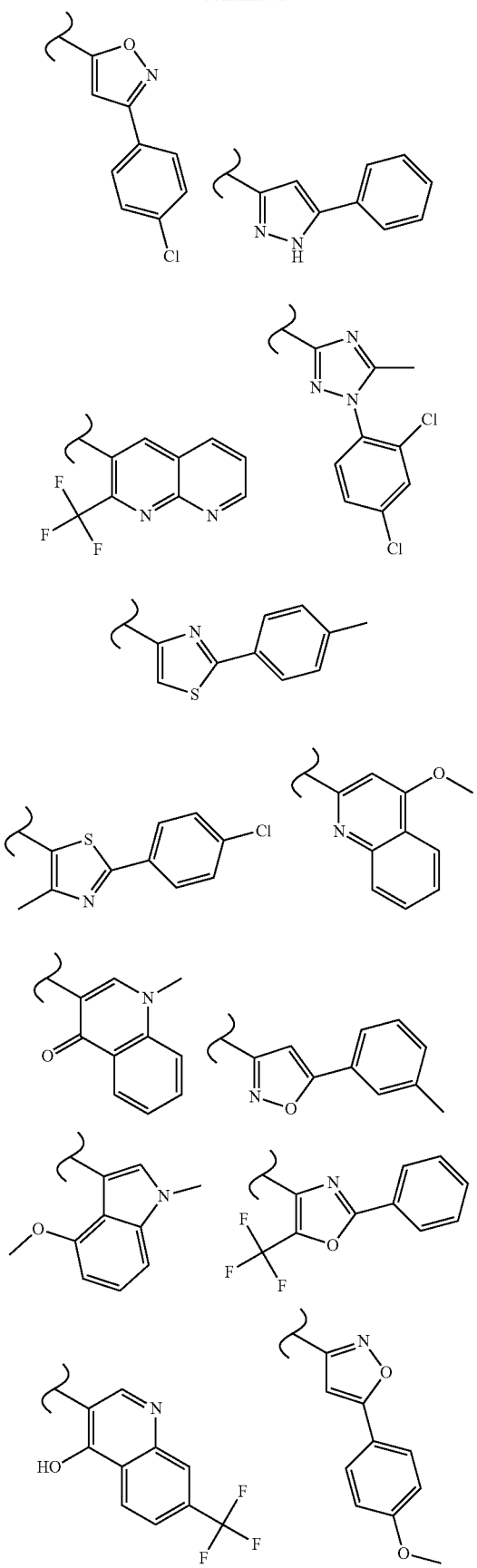
780
-continued
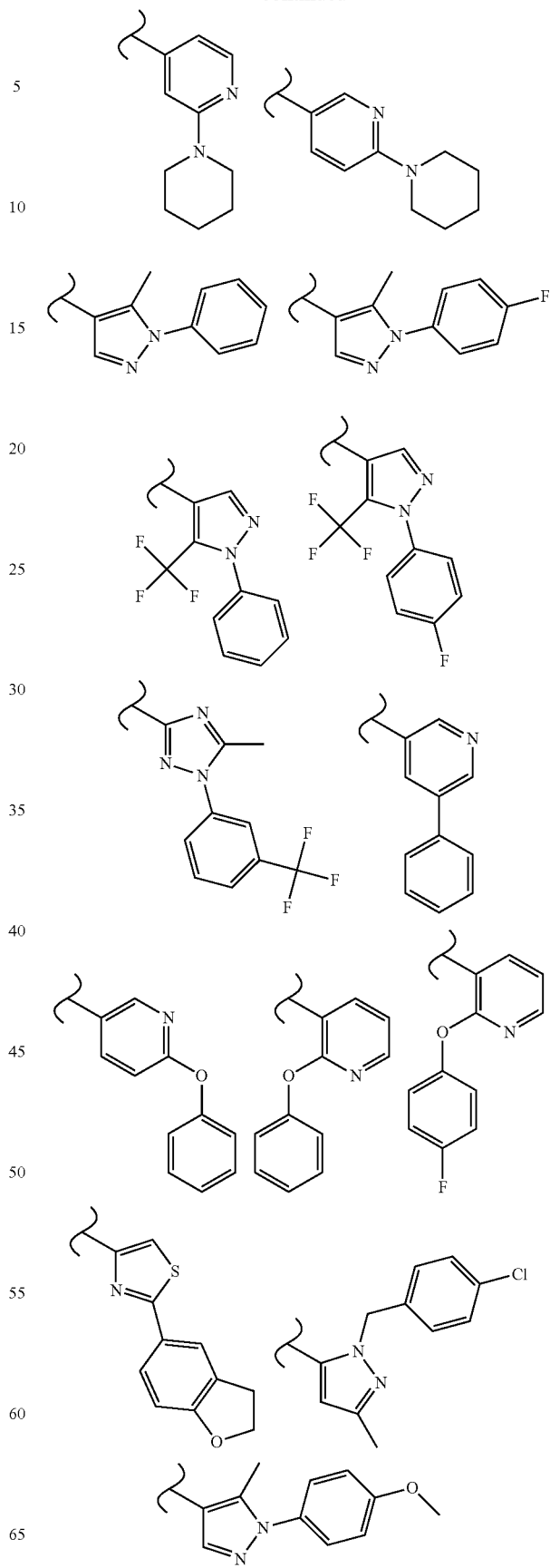

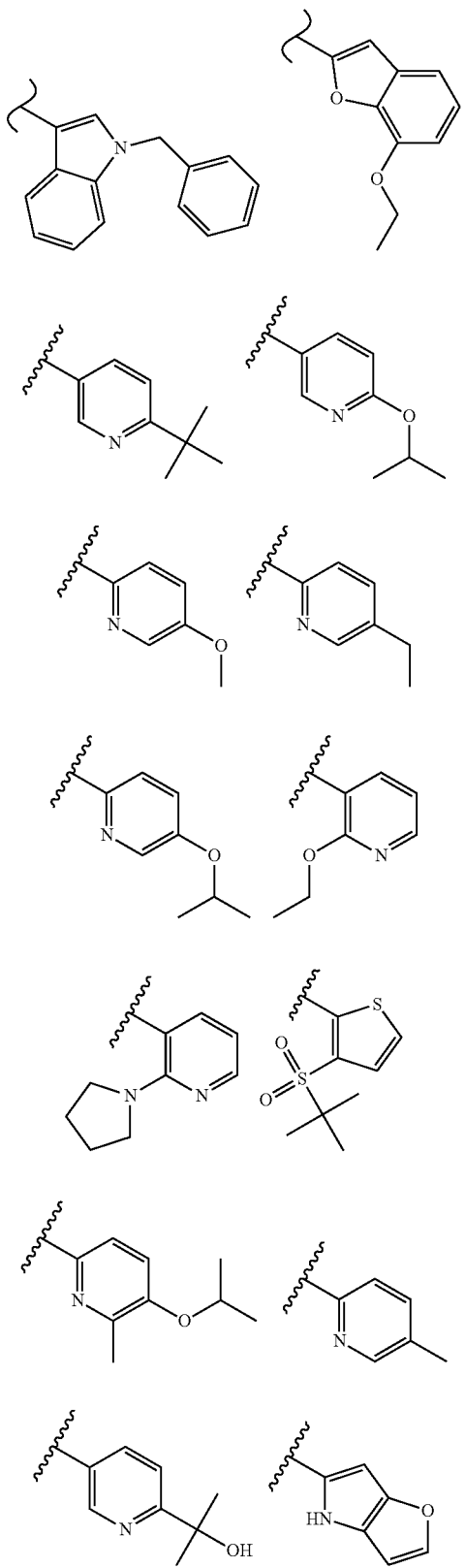

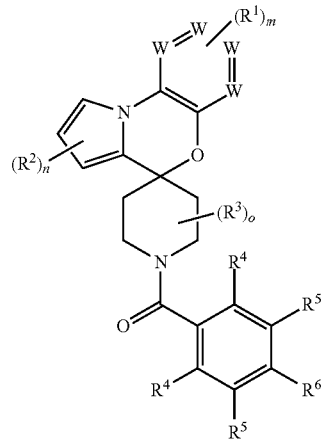

33. The compound of claim 1, wherein the compound has formula IA:

wherein:
R⁴ is H, C1-C6 alkyl, C3-C8 cycloalkyl, C1-C6 alkoxy, halo, CN, OH, OR⁷, N(R⁷)₂, NR⁷SO₂R⁷, SO₂R⁷, SR⁷, SOR⁷, CO₂R⁷, NR⁷COR⁷, NR⁷CO₂R⁷, CON(R⁷)₂, SO₂N(R⁷)₂, CF₃, OCF₃, OCHF₂, heterocycloalkyl, aryl, heteroaryl or a straight chain, branched, or cyclic (C1-C8)-R⁸ wherein up to three CH₂ units may be replaced with O, CO, S, SO, SO₂, or NR⁷;

R⁵ is H, C1-C6 alkyl, C3-C8 cycloalkyl, C1-C6 alkoxy, C3-C8 cycloalkoxy, halo, CN, OH, OR⁷, N(R⁷)₂, NR⁷SO₂R⁷, SO₂R⁷, SR⁷, SOR⁷, CO₂R⁷, NR⁷COR⁷, NR⁷CO₂R⁷, CON(R⁷)₂, SO₂N(R⁷)₂, CF₃, OCF₃, OCHF₂, heterocycloalkyl, aryl, heteroaryl or a straight chain, branched, or cyclic (C1-C8)-R⁸ wherein up to three CH₂ units may be replaced with O, CO, S, SO, SO₂, or NR⁷;

R⁶ is H, C1-C6 alkyl, C3-C8 cycloalkyl, C1-C6 alkoxy, halo, CN, OH, OR⁷, N(R⁷)₂, NR⁷SO₂R⁷, SOR⁷, SO₂R⁷, SR⁷, CO₂R⁷, NR⁷COR⁷, NR⁷CO₂R⁷, CON(R⁷)₂, SO₂N(R⁷)₂, CF₃, OCF₃, OCHF₂, heterocycloalkyl, aryl, heteroaryl or a straight chain, branched, or cyclic (C1-C8)-R⁸ wherein up to three CH₂ units may be replaced with O, CO, S, SO, SO₂, or NR⁷; or two occurrences of R⁴ and R⁵, or R⁵ and R⁶ are both C1-C6 alkyl and together with the carbons to which they are attached form an optionally substituted ring comprising up to 2 heteroatoms.

34. The compound of claim 33, wherein R¹ is C1-C6 alkyl, C1-C6 alkoxy, halo, CN, CON(R⁷)₂, or (C1-C6)-R⁸ wherein up to two CH₂ units may be replaced with O or NR⁷.

35. The compound of claim 33, wherein R¹ is F, Cl, CN, CH₃, CH₂OH, CH₂N(CH₃)₂, CH₂NH₂, CONHCH₃, CON(CH₃)₂, CH₂OCH₃.

36. The compound of claim 33, wherein R² is C1-C6 alkyl, CN, CF₃, CON(R⁷)₂, SO₂R⁷, or (C1-C6)-R⁸ wherein up to two CH₂ units may be replaced with O, CO, S, SO, SO₂, or NR⁷.

37. The compound of claim 33, wherein R² is CH₃, CF₃, CH₂OH, CN, SO₂CH₃, SOCH₃, CH₂NH₂, CH₂NHCOCH₃, CH₂NHCOH, COCH₃, or CONHCH₃.

38. The compound of claim 33, wherein R³ is C1-C6 alkyl or 2 occurrences of R³ taken together form a C3-C8 cycloalkyl group.

39. The compound of claim 33, wherein R³ is CH₃.

40. The compound of claim 33, wherein 2 occurrences of R³ taken together form a C3-C8 cycloalkyl group.

41. The compound of claim 33, wherein $R^4$ is H, C1-C6 alkyl, C1-C6 alkoxy, halo, CN, OH, $OR^7$, $CHF_2$, $CF_3$, $OCF_3$, $OCHF_2$, $SO_2R^7$, $SR^7$, $SOR^7$, $NR^7CO_2R^7$, heteroaryl, or a straight chain, branched, or cyclic (C1-C8)-$R^8$ wherein up to three $CH_2$ units may be replaced with O, CO, S, SO, $SO_2$, or $NR^7$.

42. The compound of claim 33, wherein $R^4$ is H, F, Cl, OH, $CH_3$, $CHF_2$, $CF_3$, $OCH_3$, $OCHF_2$, $OCF_3$, $CO_2CH_3$, $CH_2OH$, $SO_2CH_3$, CN, $NHCO_2tBu$, $C_2H_5$, $OCF_2CHFCl$,

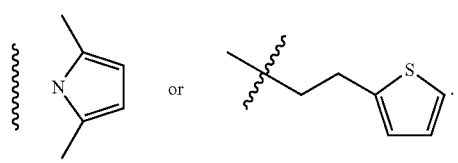

43. The compound of claim 33, wherein $R^5$ is H, C1-C6 alkyl, C1-C6 alkoxy, halo, CN, OH, $OR^7$, $NR^7SO_2R^7$, $SO_2R^7$, $SR^7$, $SOR^7$, $CO_2R^7$, $CON(R^7)_2$, $SO_2N(R^7)_2$, $CF_3$, $OCF_3$, or a straight chain, branched, or cyclic (C1-C8)-$R^8$ wherein up to three $CH_2$ units may be replaced with O, CO, S, SO, $SO_2$, or $NR^7$.

44. The compound of claim 33, wherein $R^5$ is H, F, Cl, $CH_3$, $C_2H_5$, tBu, OH, $OCH_3$, $OC_2H_5$, $OCH(CH_3)_2$, $CH_2OH$, $CF_3$, $OCF_3$, CN, $CO_2CH_3$, $CONH_2$, $N(CH_3)SO_2CH_3$, $SO_2NH_2$ or $SO_2CH_3$.

45. The compound of claim 33, wherein $R^6$ is H, C1-C6 alkyl, C3-C8 cycloalkyl, C1-C6 alkoxy, halo, CN, OH, $OR^7$, $SO_2R^7$, $SR^7$, $SOR^7$, $NR^7COR^7$, $SO_2N(R^7)_2$, $CF_3$, $OCF_3$, heteroaryl, or a straight chain, branched, or cyclic (C1-C8)-$R^8$, wherein up to three $CH_2$ units may be replaced with O, CO, S, SO, $SO_2$, or $NR^7$.

46. The compound of claim 33, wherein $R^6$ is H, F, $CH_3$, $CF_3$, $OCH_3$, $OCF_3$, $SO_2CH_3$, $SO_2C_2H_5$, $SO_2CH(CH_3)_2$, $SO_2CH_2CH(CH_3)_2$, $SO_2tBu$, $SO_2CHF_2$, CN, $CH_2CH_3$, tBu, $CH_2CH_2OH$, $C(CH_3)_2OH$, $OCH_2CF_3$, $O(CH_2)_2OH$, $NHC(=O)CH_3$, $OCH_2C(=O)NH_2$,

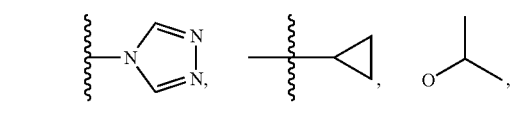

$O(CH_2)_2CH_3$,

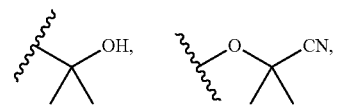

$O(CH_2)_3OH$, $O(CH_2)_2OCH_3$,

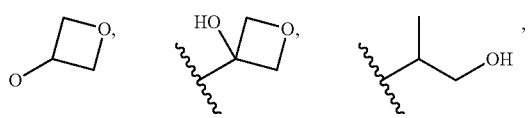

$O(CH_2)_2OCF_3$,

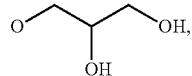

$O(CH_2)_2SO_2CH_3$,

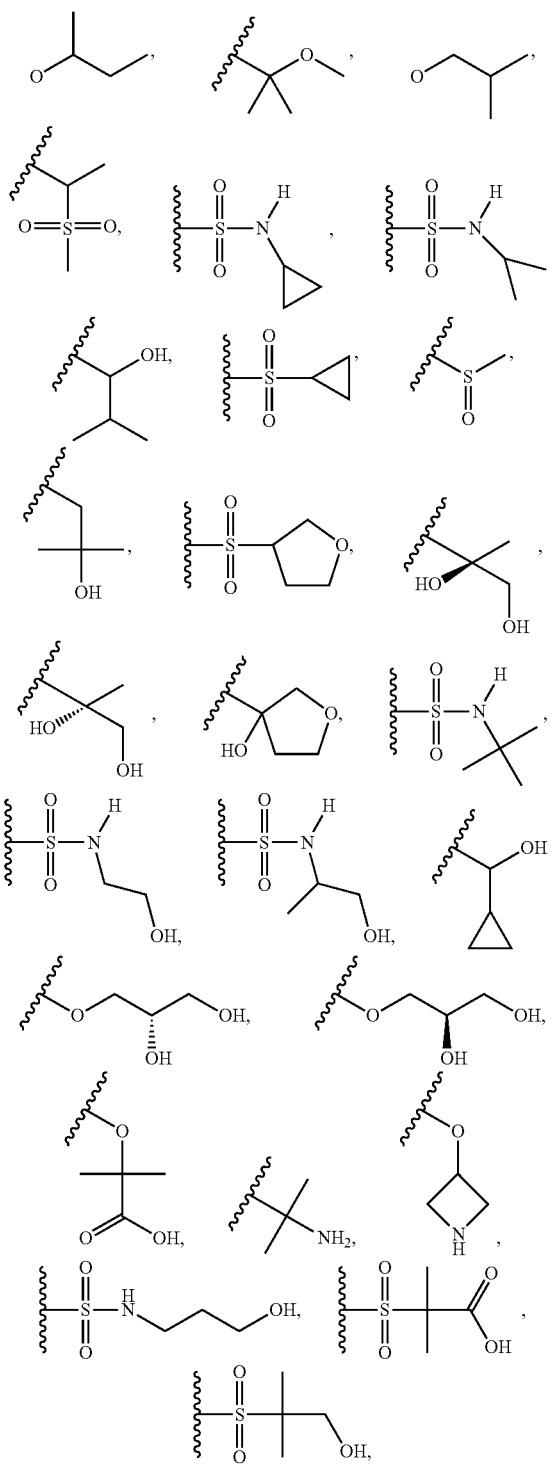

OtBu,
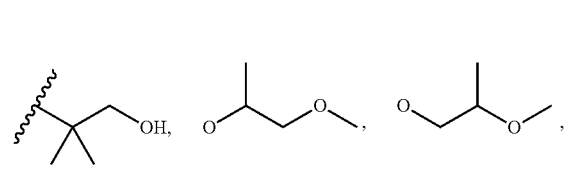
O(CH$_2$)$_3$OCH$_3$, O(CH$_2$)$_2$OC$_2$H$_5$,
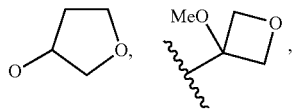
O(CH$_2$)$_2$N(CH$_3$)$_2$,
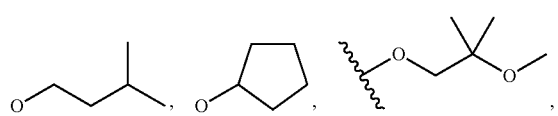
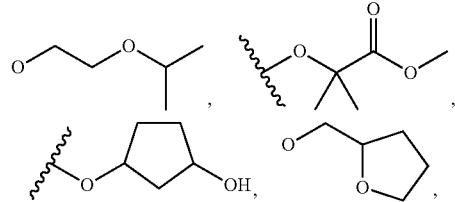
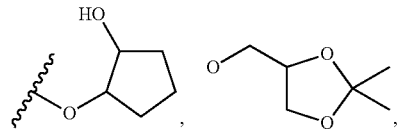
OCH$_2$Ph, SO$_2$NHCH$_3$, SO$_2$NHCH$_2$CH$_3$, SO$_2$CH$_2$CH$_2$OH or OCH$_2$CO$_2$H.
47. The compound of claim 33, wherein o is 2, and the two occurrences of R$^3$ form a C3-C8 cycloalkyl group.
48. The compound of claim 33, wherein
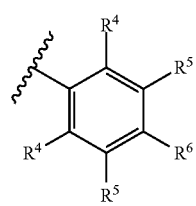
is selected from:
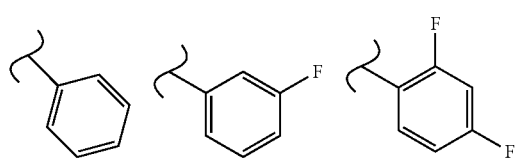
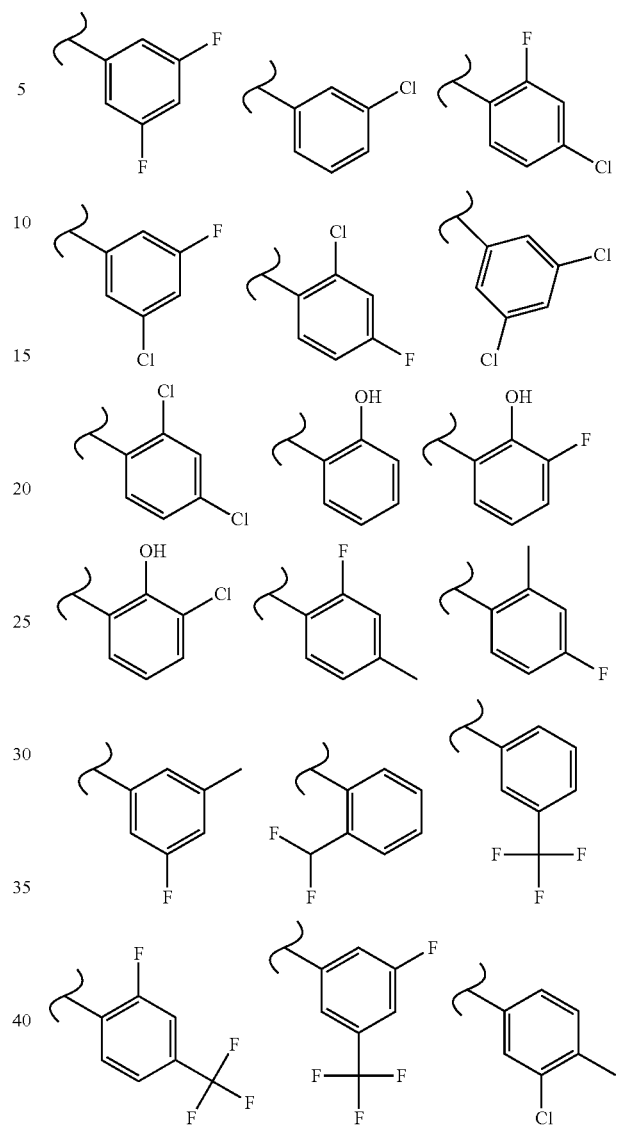
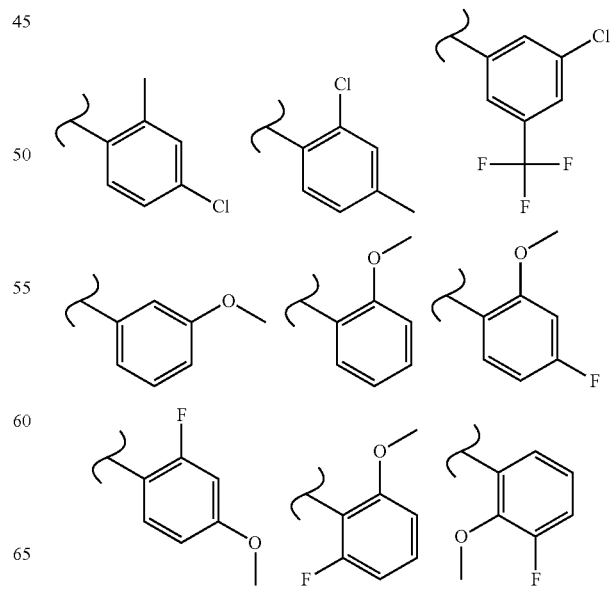

787
-continued
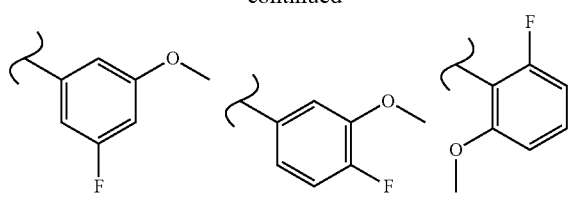
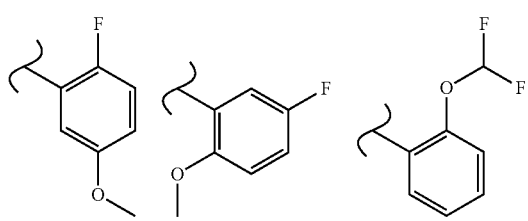
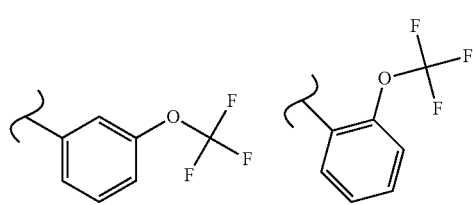
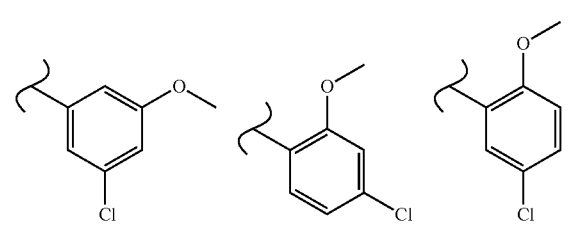
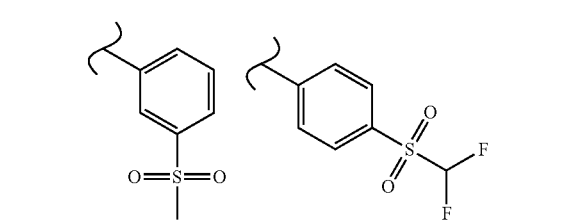
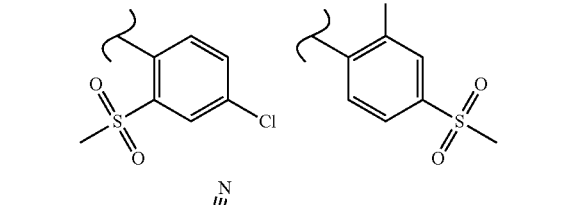
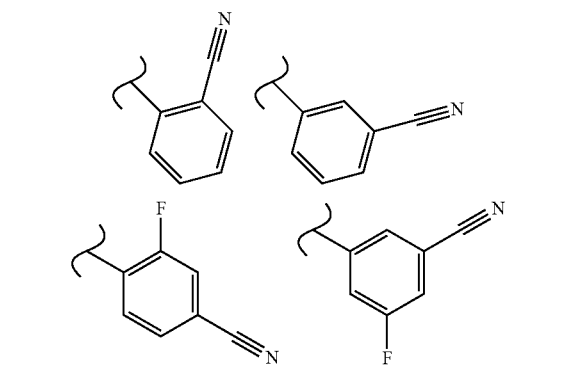
788
-continued
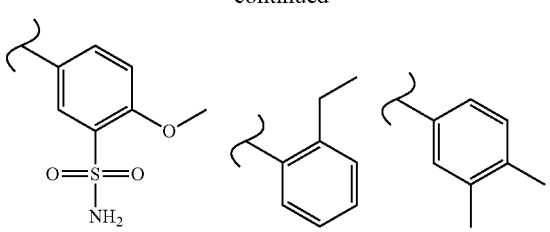
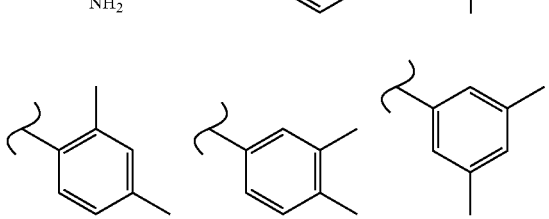
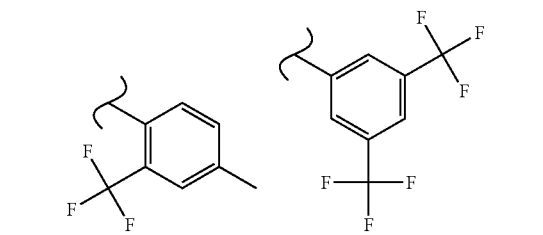
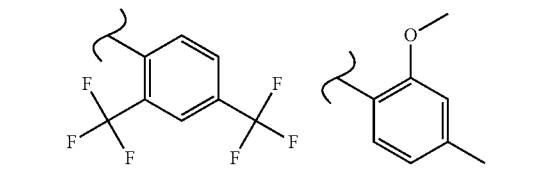
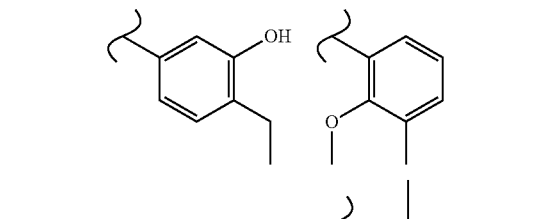
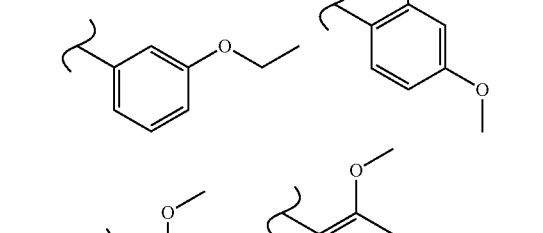
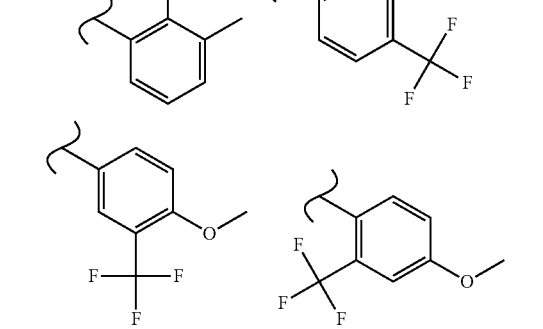

789
-continued
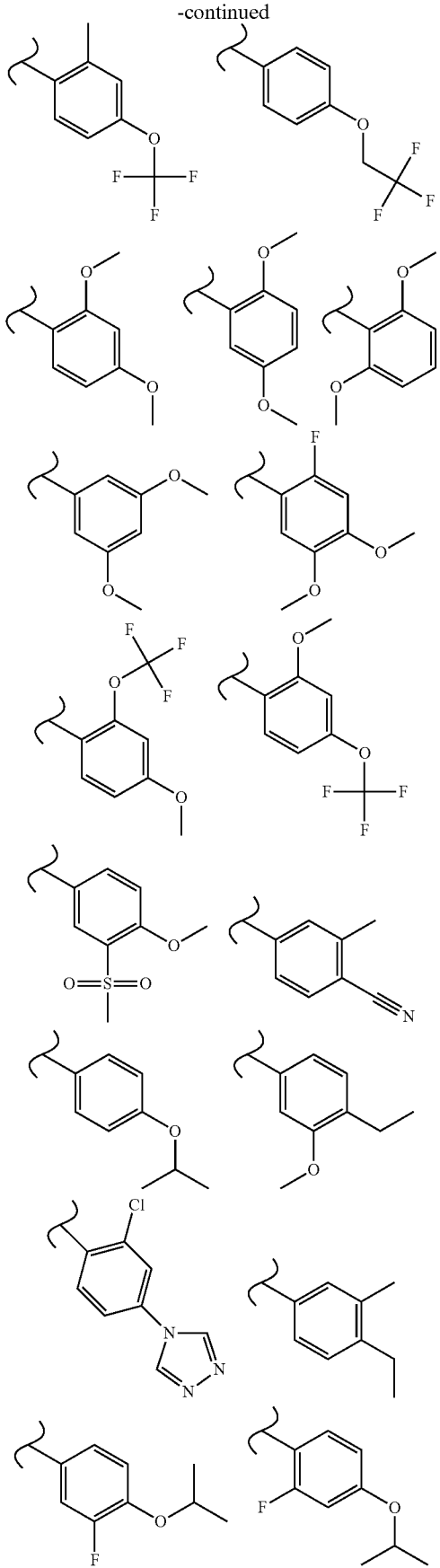
790
-continued
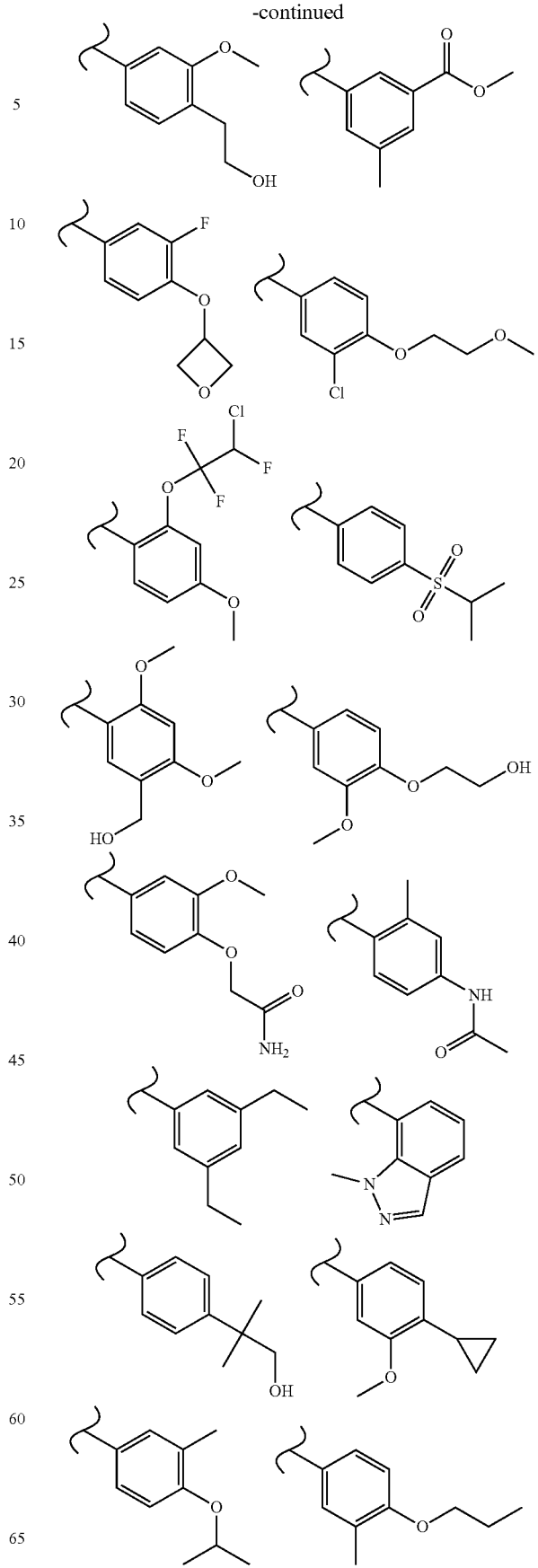

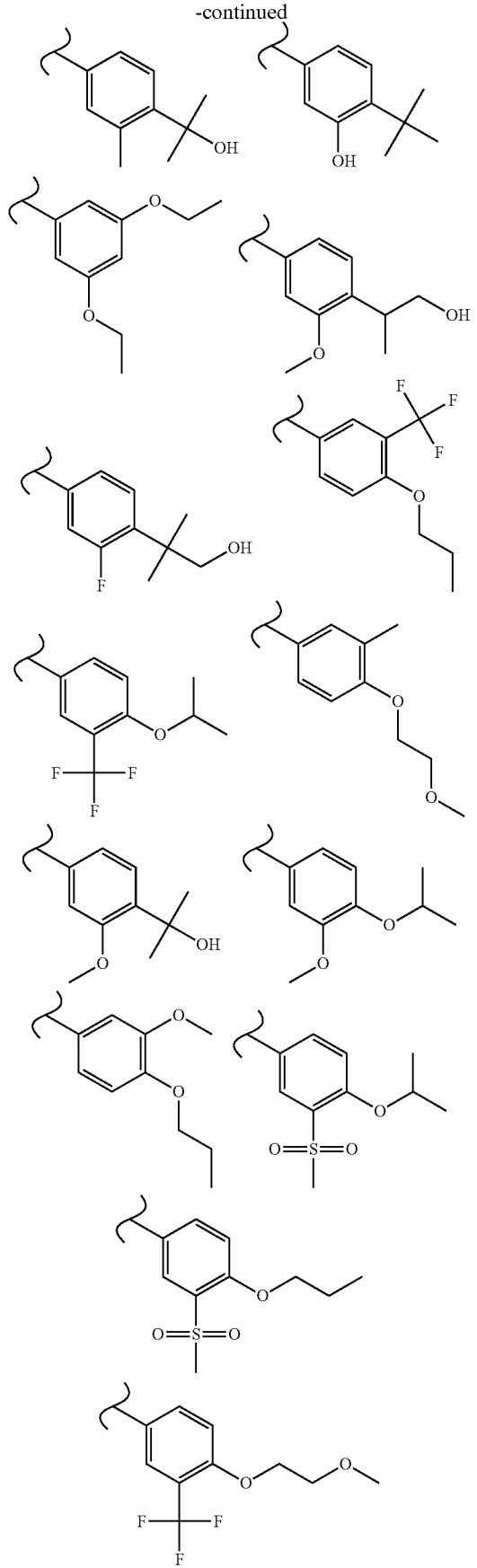
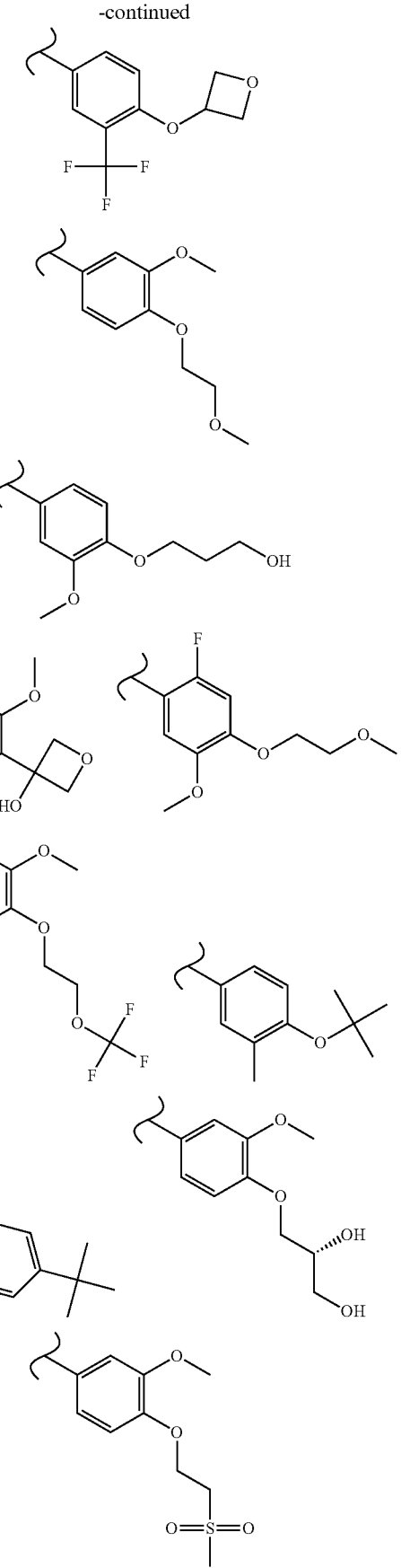

793
-continued
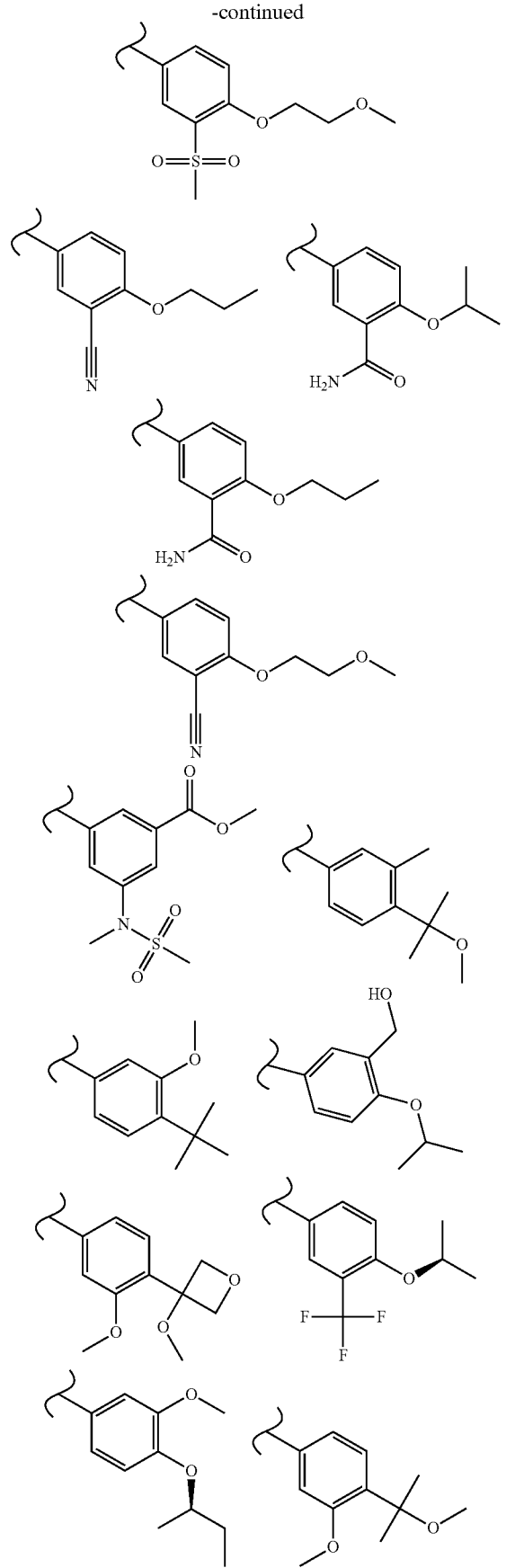
794
-continued
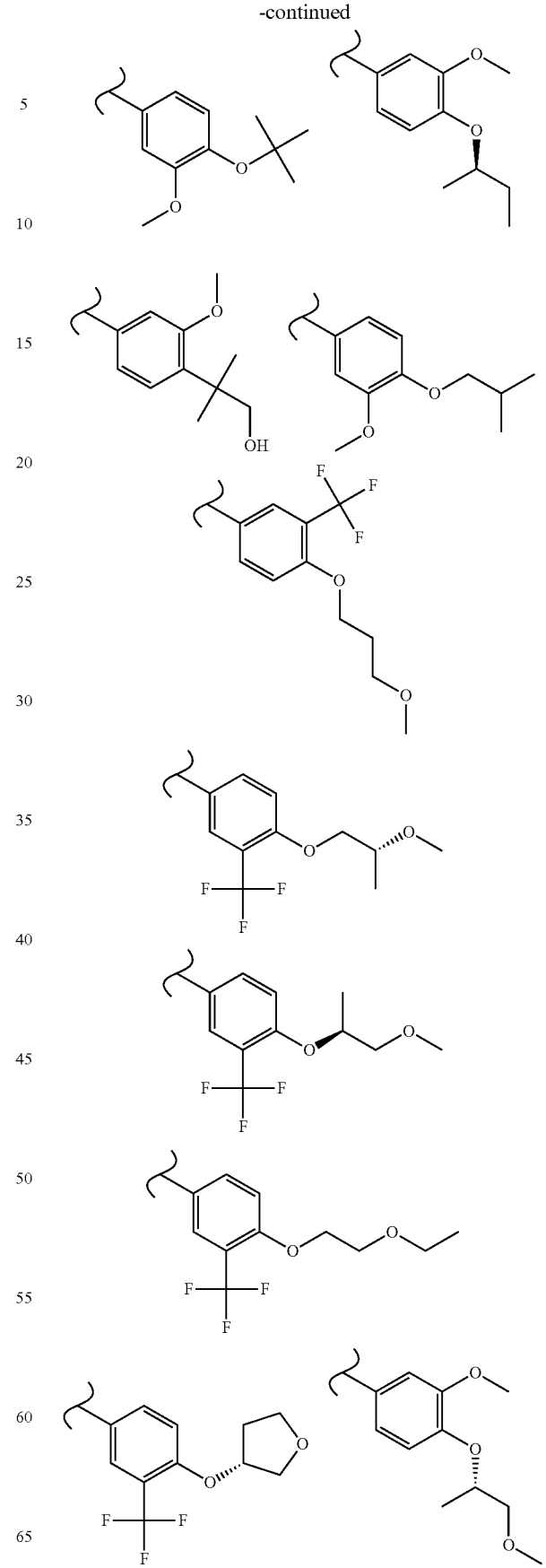

795
-continued
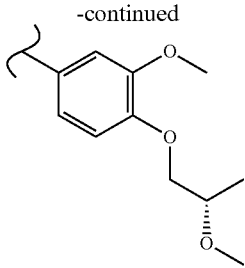
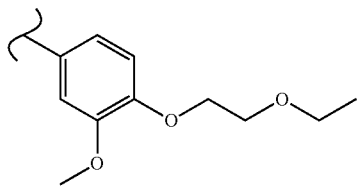
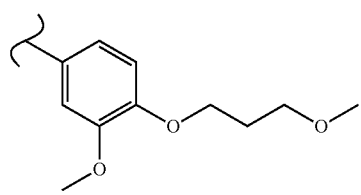
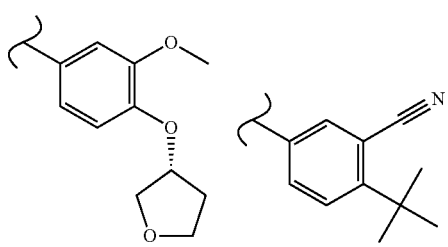
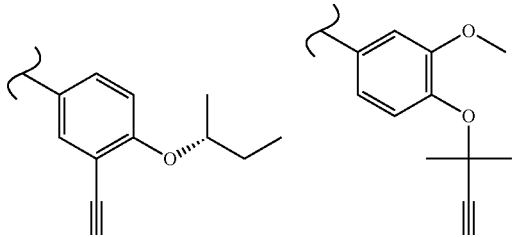
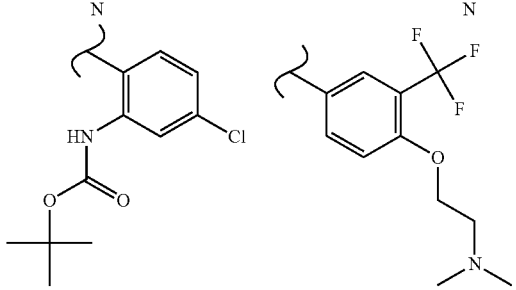
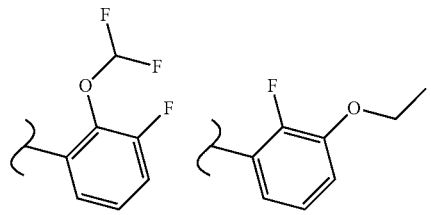
796
-continued
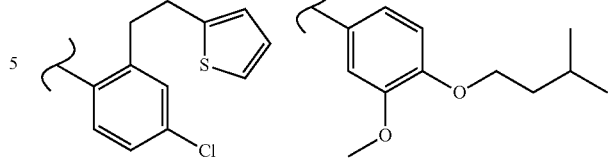
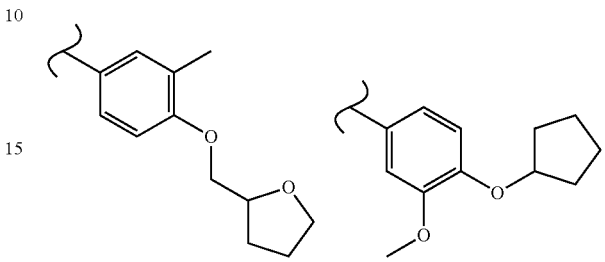
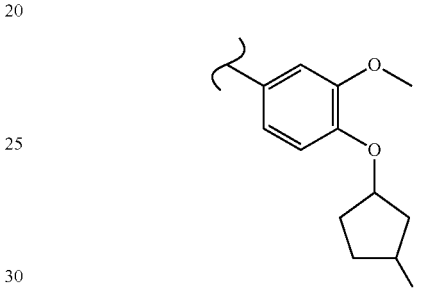
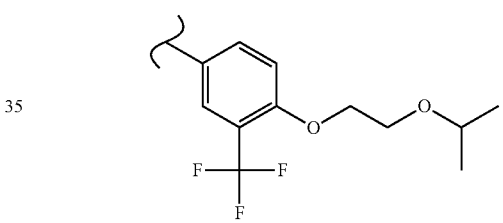
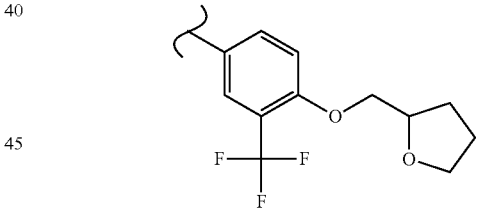
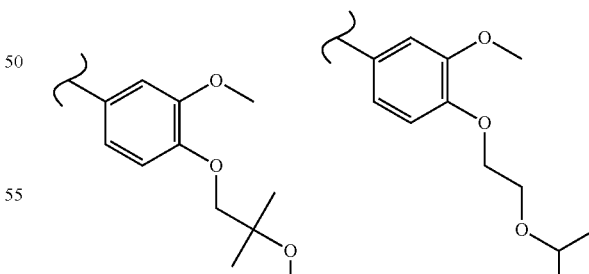
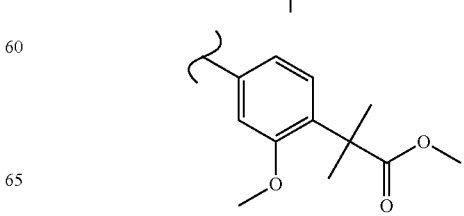

797
-continued
798
-continued
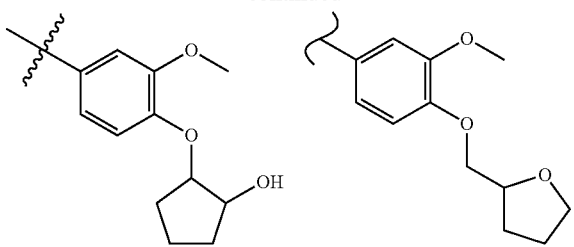
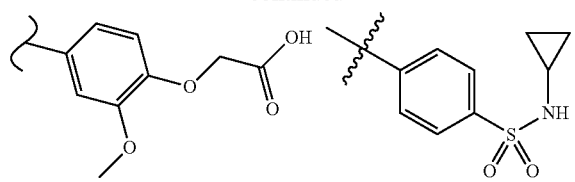
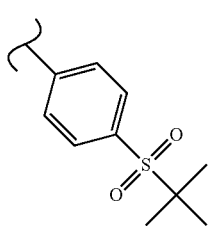
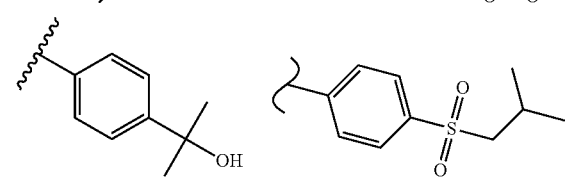
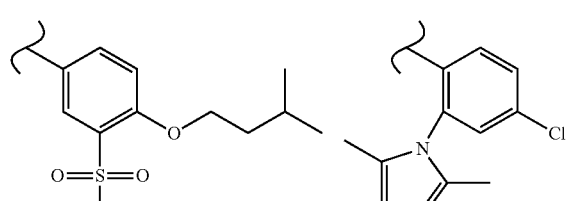

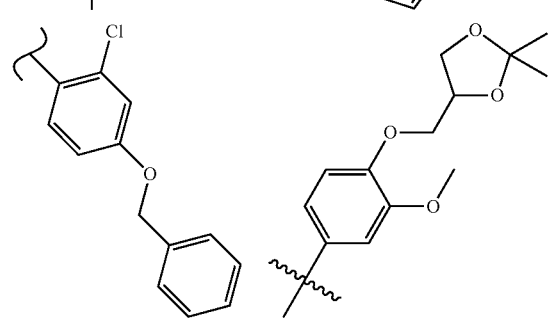
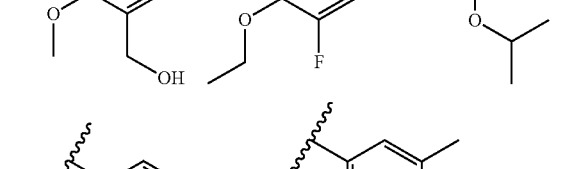
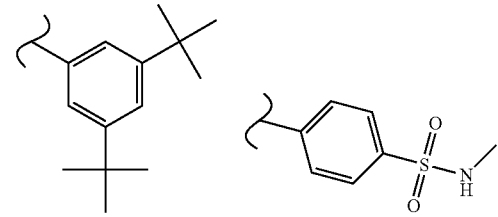
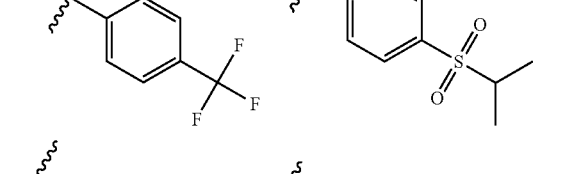
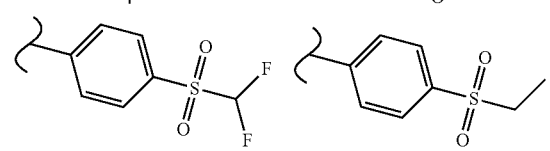
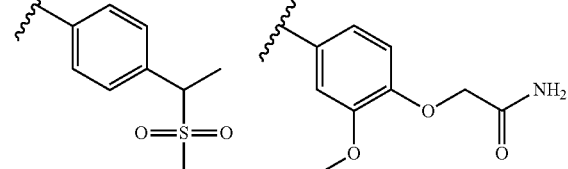
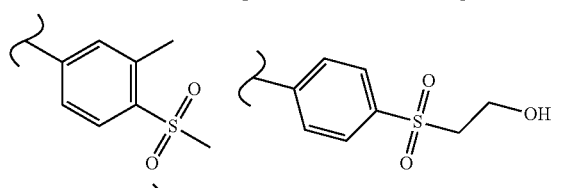
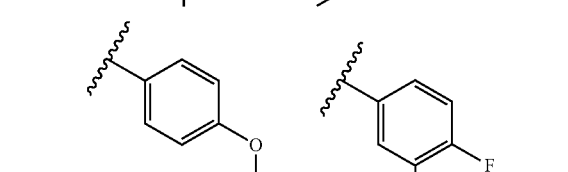
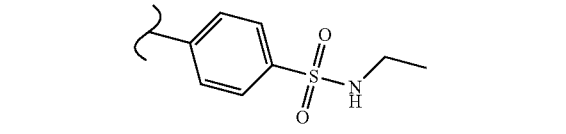
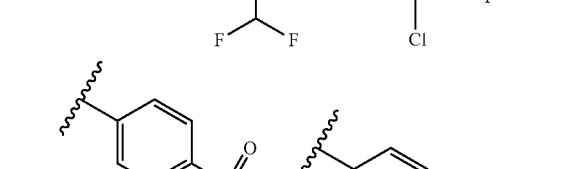
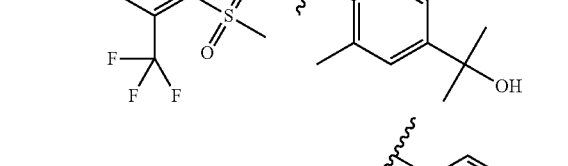
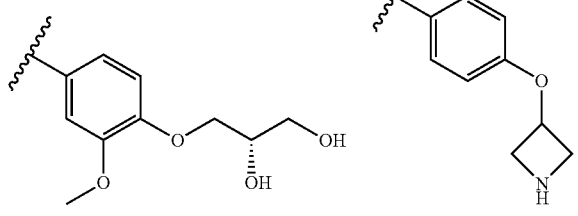

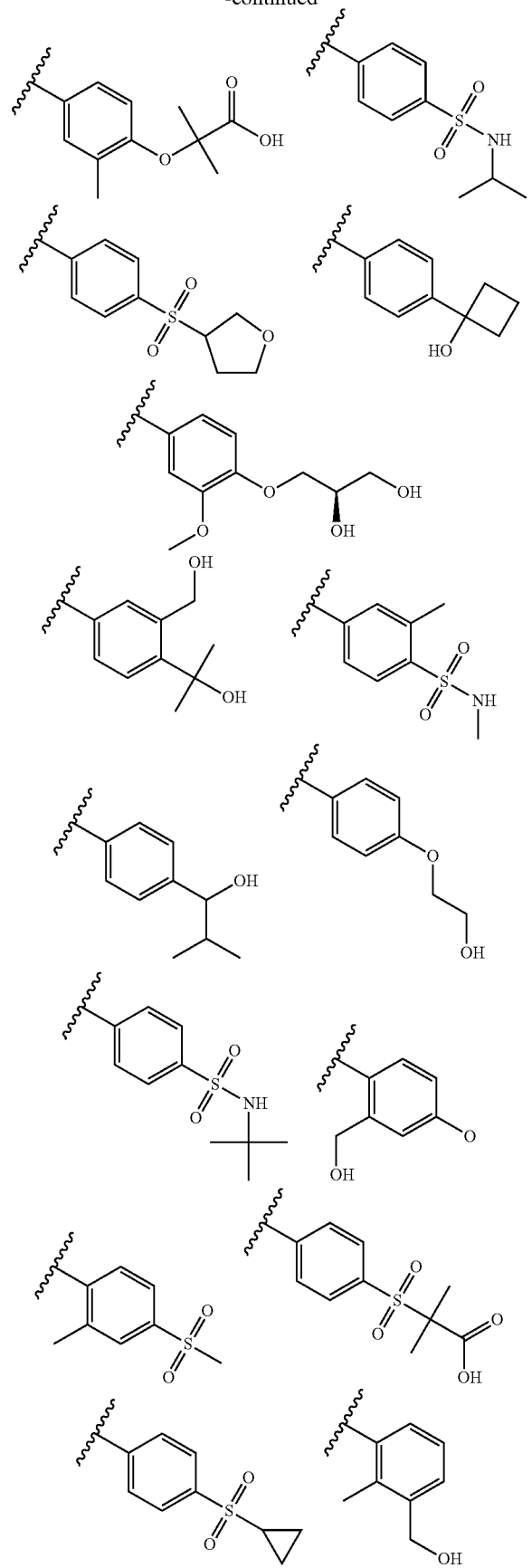
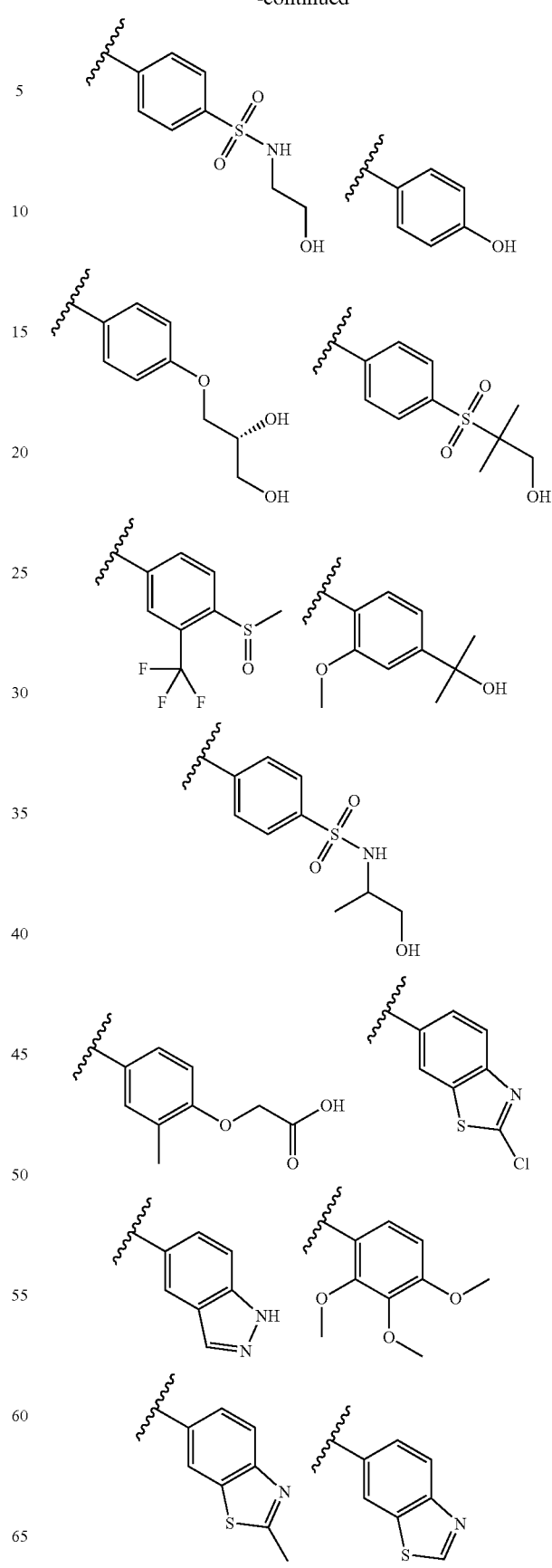

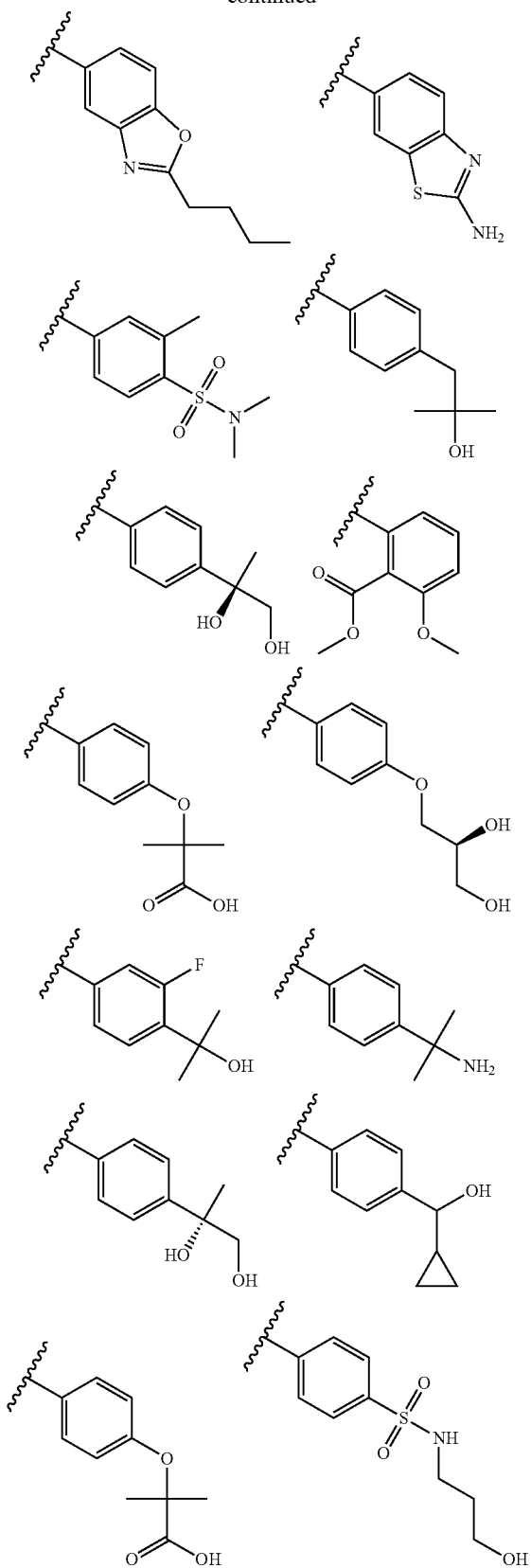

49. The compound of claim 1, wherein the compound has formula IB:

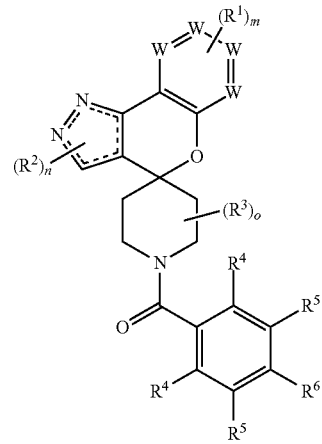

wherein:

$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R)_2$, $SO_2N(R^7)_2$, $CF_3$, $OCF_3$, $OCHF_2$, heterocycloalkyl, aryl, heteroaryl or a straight chain, branched, or cyclic (C1-C8)-$R^8$ wherein up to three $CH_2$ units may be replaced with O, CO, S, SO, $SO_2$, or $NR^7$;

$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl or a straight chain, branched, or cyclic (C1-C8)-$R^8$ wherein up to three $CH_2$ units may be replaced with O, CO, S, SO, $SO_2$, or $NR^7$;

$R^6$ is H, C1-C6 alkyl, C3-C8 cycloalkyl, C1-C6 alkoxy, halo, CN, OH, $OR^7$, $N(R^7)_2$, $NR^7SO_2R^7$, $SOR^7$, $SO_2R^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, aryl, heteroaryl or a straight chain, branched, or cyclic (C1-C8)-$R^8$ wherein up to three $CH_2$ units may be replaced with O, CO, S, SO, $SO_2$, or $NR^7$; or two occurrences of $R^4$ and $R^5$, or $R^5$ and $R^6$ are both C1-C6 alkyl and together with the carbons to which they are attached form an optionally substituted ring comprising up to 2 heteroatoms.

50. The compound of claim 49, wherein $R^1$ is halo or C1-C6 alkoxy.

51. The compound of claim 49, wherein $R^1$ is F, Cl or $OCH_3$.

52. The compound of claim 49, wherein $R^2$ is C1-C6 alkyl, $CF_3$ or (C1-C6)-$R^8$ wherein up to two $CH_2$ units may be replaced with O, CO, S, SO, $SO_2$, or $NR^7$.

53. The compound of claim 49, wherein $R^2$ is $CH_3$, $CF_3$, $C_2H_5$, $CH(CH_3)_2$, $CH_2CF_3$, or $(CH_2)_2OCH_3$.

54. The compound of claim 49, wherein $R^4$ is H, C1-C6 alkyl, C1-C6 alkoxy, halo, CN, OH, $OR^7$, $CON(R^7)_2$, $NR^7SO_2R^7$, $SO_2R^7$, $SR^7$, $SOR^7$, $CO_2R^7$, $NR^7CO_2R^7$, $CHF_2$, $CF_3$, $OCF_3$, $OCHF_2$, heteroaryl, or a straight chain, branched, or cyclic (C1-C8)-$R^8$ wherein up to three $CH_2$ units may be replaced with O, CO, S, SO, $SO_2$, or $NR^7$.

55. The compound of claim 49, wherein $R^4$ is H, F, Cl, OH, $CH_3$, $CHF_2$, $CF_3$, $OCH_3$, $OCHF_2$, $OCF_3$, $SO_2CH_3$, CN, $NHSO_2CH_3$, $C_2H_5$, $OC_2H_5$, $OCF_2CHFCl$, $OCH_2CF_3$, $O(CH_2)_2CH_3$, $OCH_2OCH_3$, $OCH(CH_3)_2$, $O(CH_2)_2OH$, $SCH_3$, $CON(CH_3)_2$, $NHCO_2tBu$,

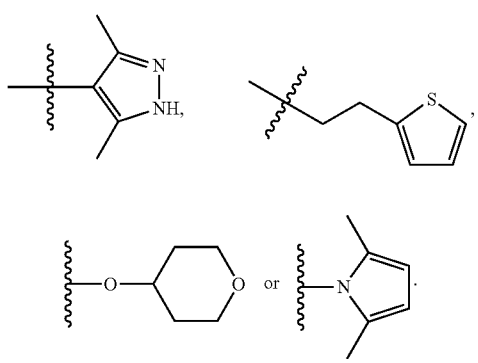

56. The compound of claim 49, wherein $R^5$ is H, C1-C6 alkyl, C1-C6 alkoxy, halo, CN, OH, $OR^7$, $CF_3$, $OCF_3$, $SO_2R^7$, $SR^7$, $SOR^7$, or a straight chain, branched, or cyclic (C1-C8)-$R^8$ wherein up to three $CH_2$ units may be replaced with O, CO, S, SO, $SO_2$, or $NR^7$.

57. The compound of claim 49, wherein $R^5$ is H, F, Cl, $CH_3$, $CF_3$, $OCH_3$, $CH(CH_3)_2$, $OCH_2CH_3$, $CH_2OH$, $OCF_3$, CN, $SO_2CH_3$ or tBu.

58. The compound of claim 49, wherein $R^6$ is H, C1-C6 alkyl, C3-C8 cycloalkyl, C1-C6 alkoxy, halo, OH, $OR^7$, $SOR^7$, $SO_2R^7$, $SR^7$, $SO_2N(R^7)_2$, $CON(R)_2$, $CF_3$, $OCF_3$, $OCHF_2$, heterocycloalkyl, heteroaryl, a straight chain, branched, or cyclic (C1-C8)-$R^8$, wherein up to three $CH_2$ units may be replaced with O, CO, S, SO, $SO_2$, or $NR^7$.

59. The compound of claim 49, wherein $R^6$ is H, F, Cl, OH, $CH_3$, $CF_3$, $OCH_3$, $OCF_3$, $OCHF_2$, $SOCH(CH_3)_2$, $SO_2CH_3$, $SO_2CHF_2$, $SO_2CF_3$, $SO_2C_2H_5$, $SO_2CH(CH_3)_2$, $SO_2CH_2CH(CH_3)_2$, $SO_2tBu$, $SO_2NHCH_3$, $SO_2N(CH_3)_2$, $SO_2NHCH_2CH_3$, $SO_2N(CH_3)CH(CH_3)_2$, $CONHCH(CH_3)_2$, $CH_2CH_3$, $OCH_2CH_3$,

$O(CH_2)_2CH_3$,

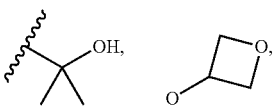

$O(CH_2)_2OCH_3$, $O(CH_2)_2OCF_3$, tBu,

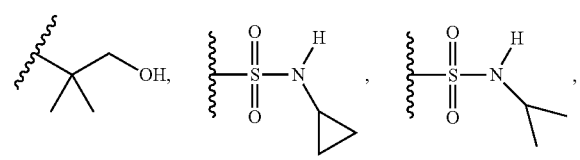

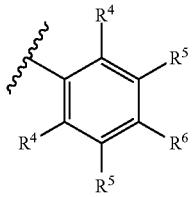

OtBu,

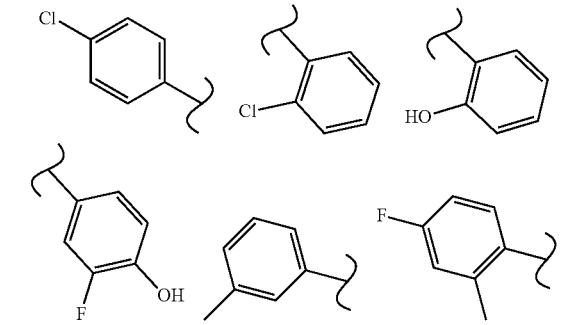

or $OCH_2Ph$.

60. The compound of claim 49, wherein two occurrences of $R^4$ and $R^5$ are both C1-C6 alkyl and together with the carbons to which they are attached form an optionally substituted ring comprising up to 2 heteroatoms.

61. The compound of claim 49, wherein two occurrences of $R^5$ and $R^6$ are both C1-C6 alkyl and together with the carbons to which they are attached form an optionally substituted ring comprising up to 2 heteroatoms.

62. The compound of claim 49, wherein is selected from:

805
-continued
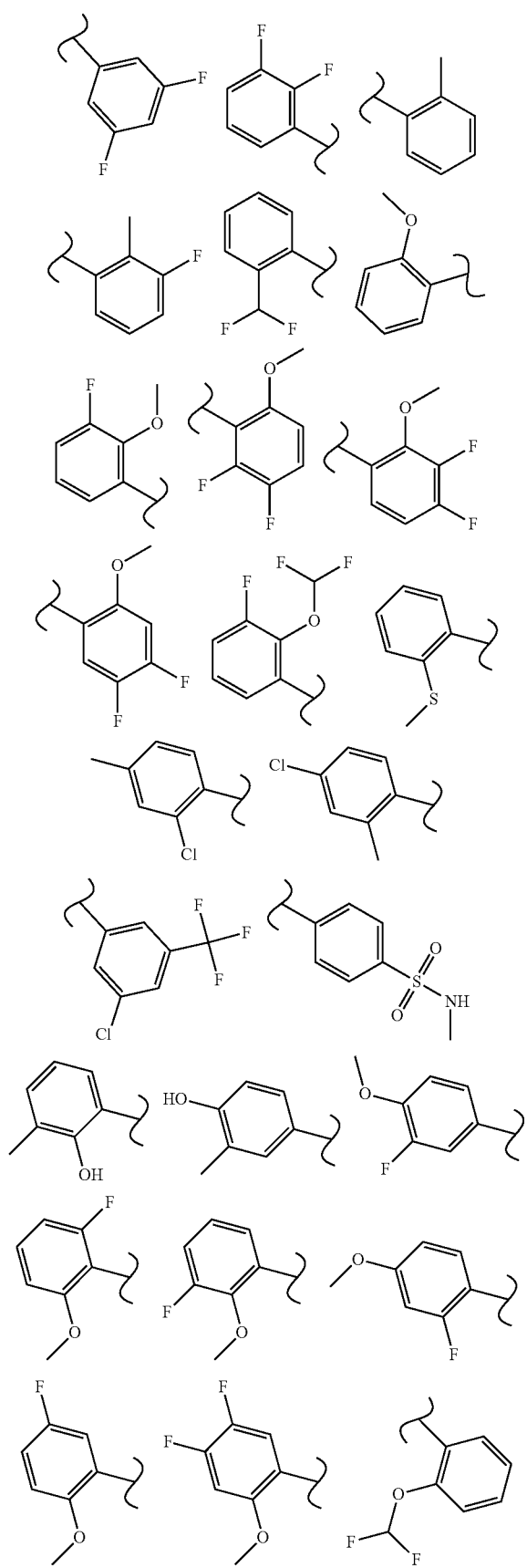
806
-continued
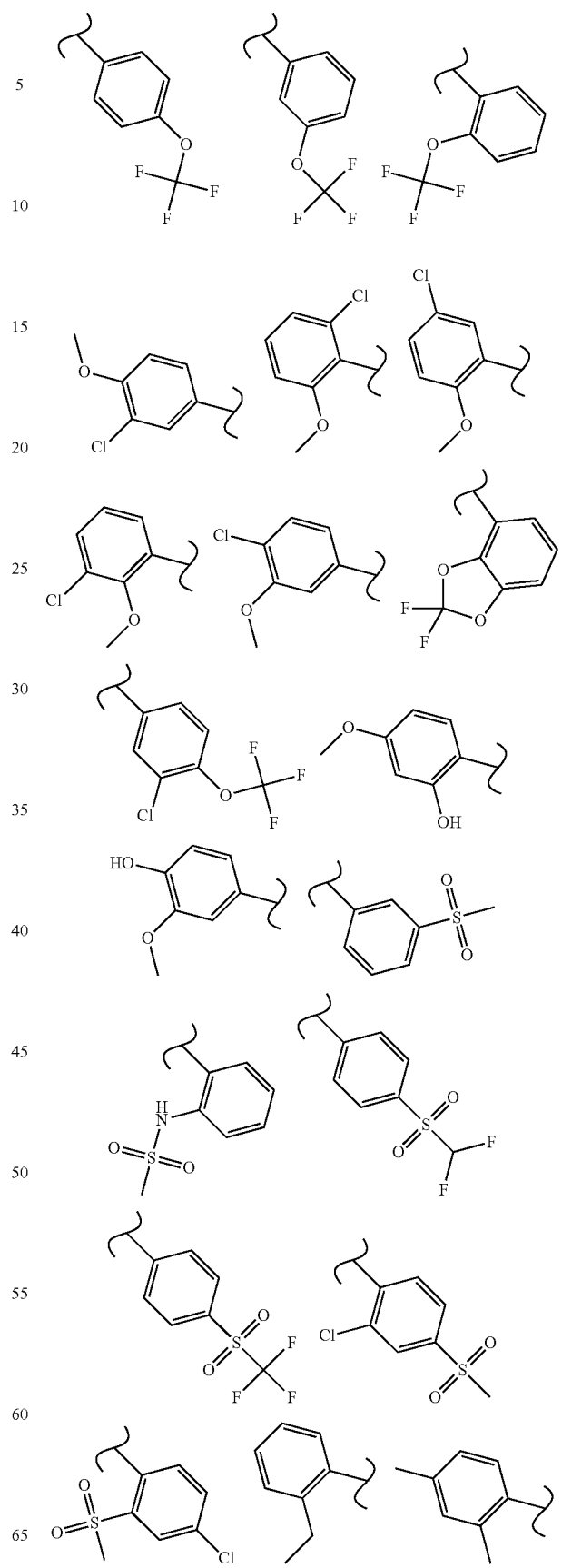

807
-continued
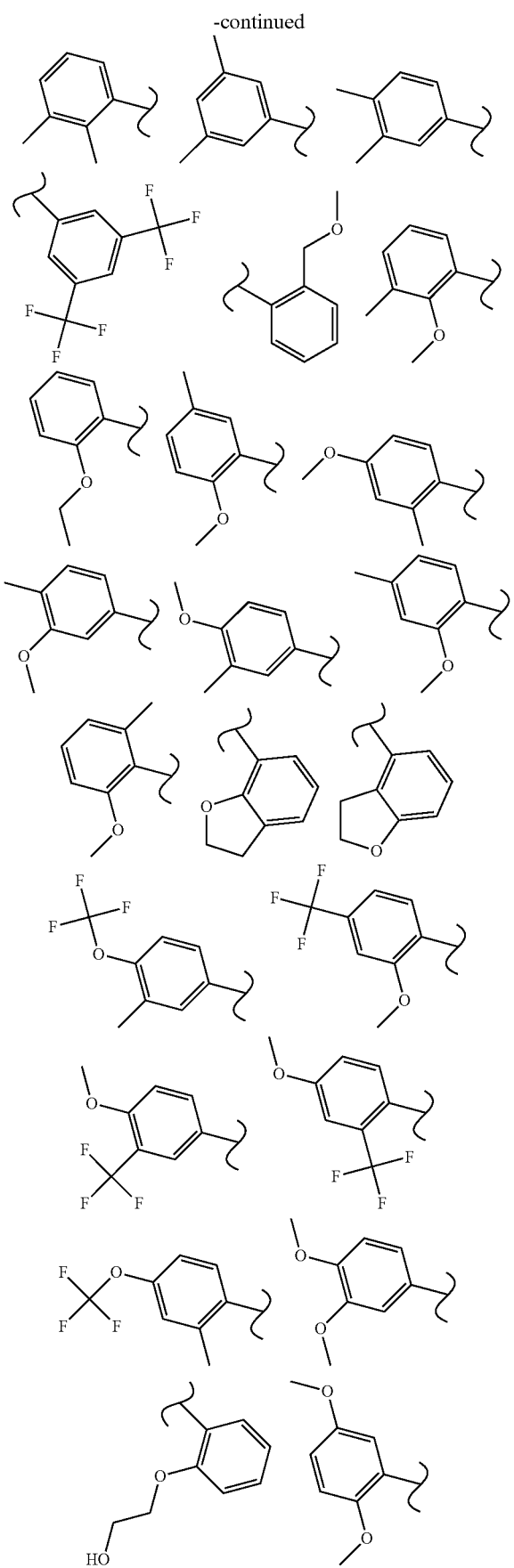
808
-continued
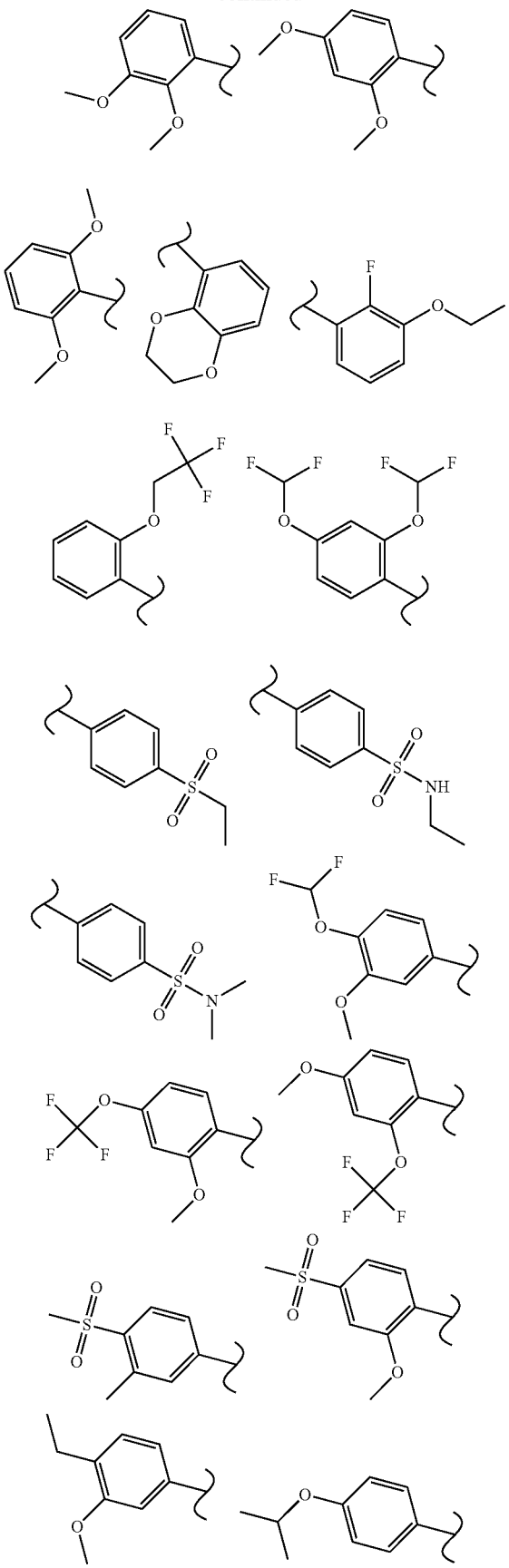

809
-continued
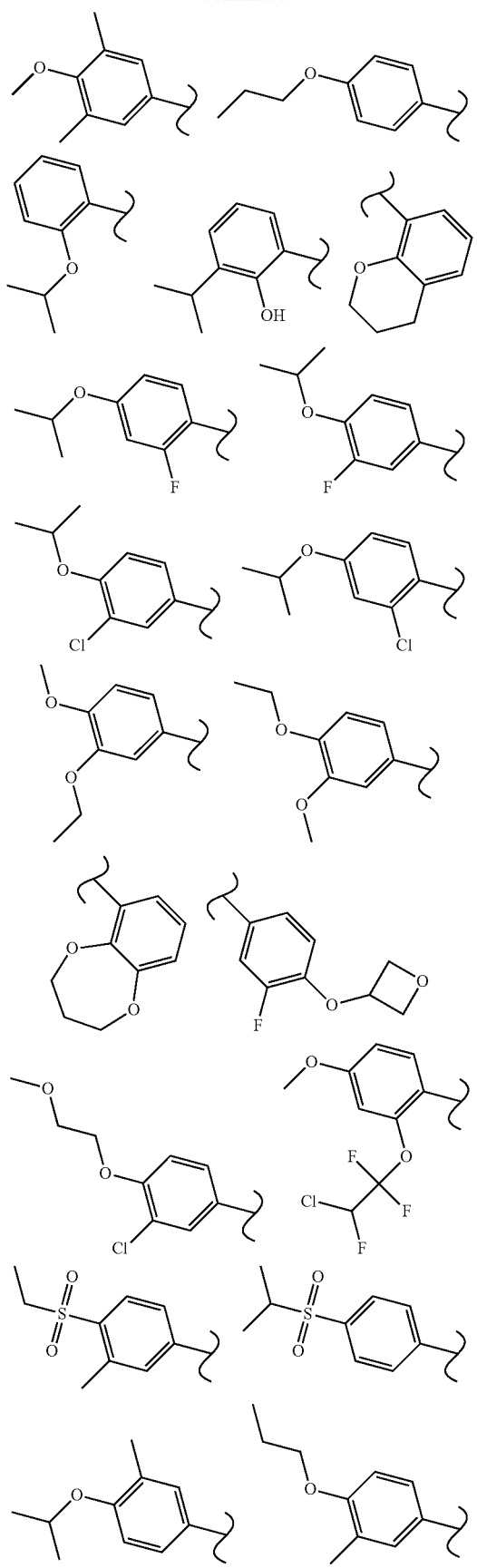
810
-continued
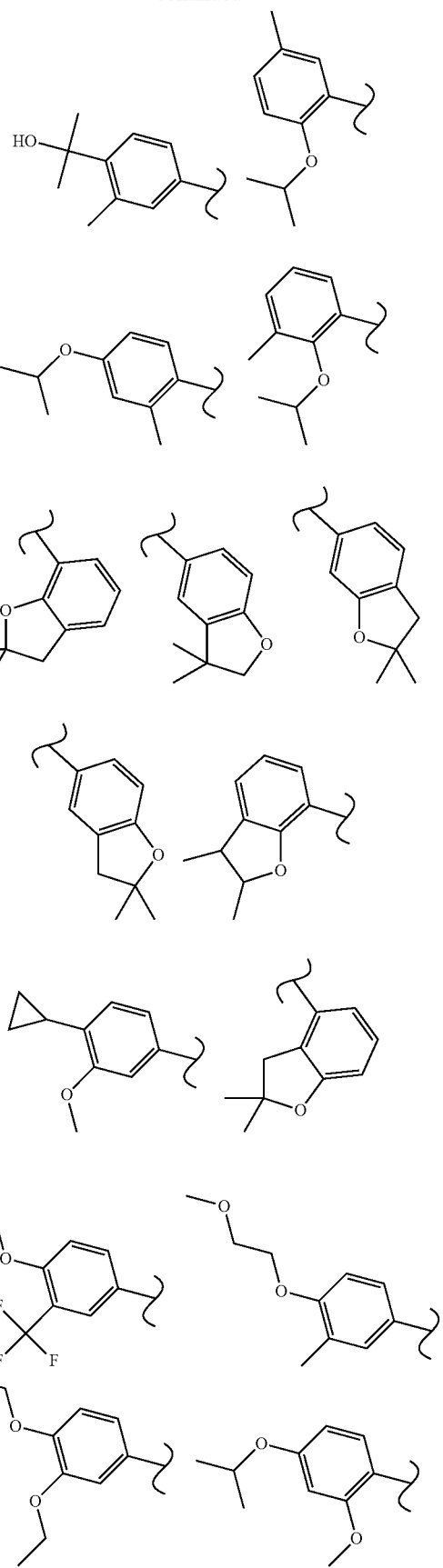

811
-continued
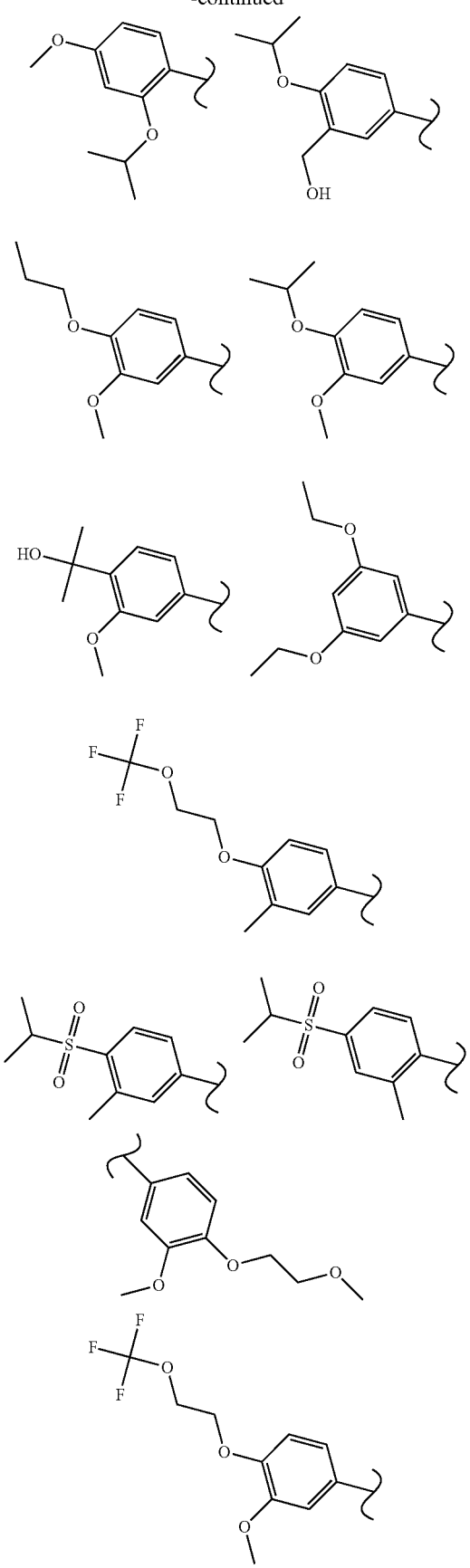
812
-continued
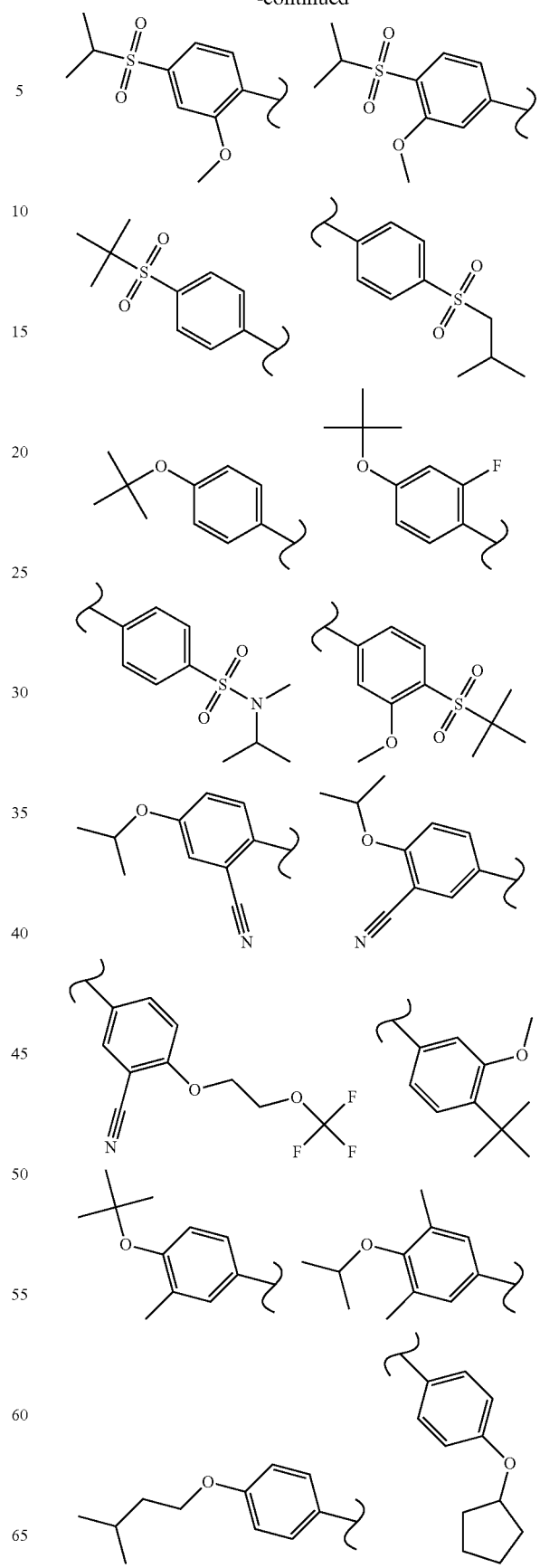

813
-continued
814
-continued
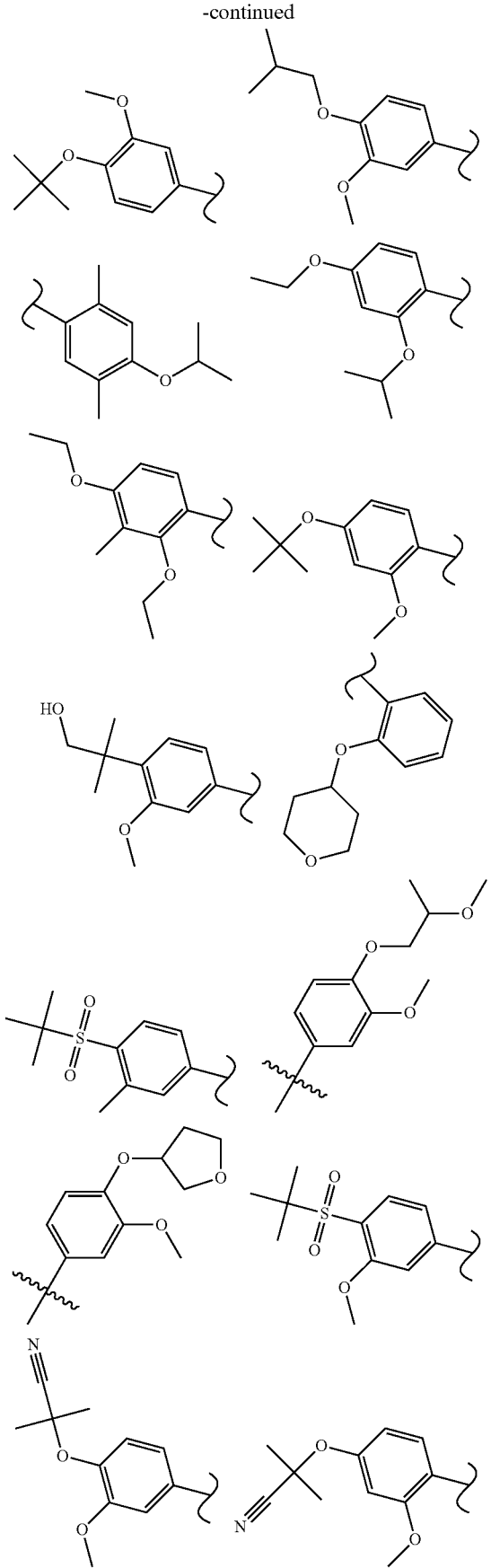
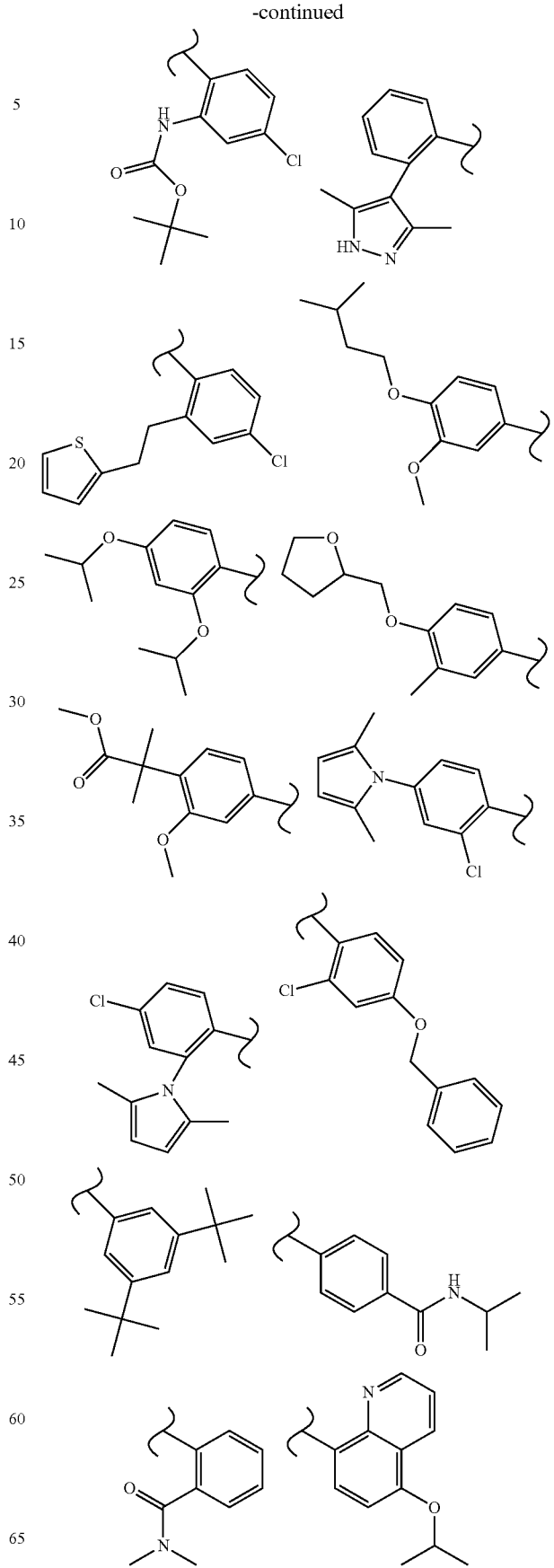

815
-continued
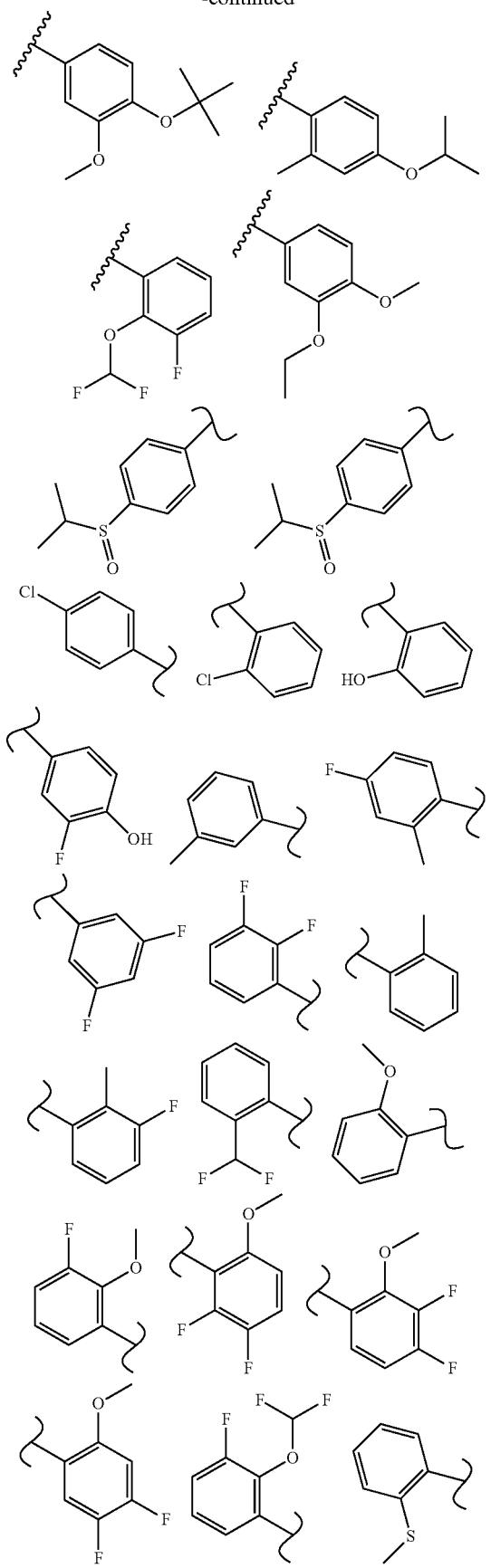
816
-continued
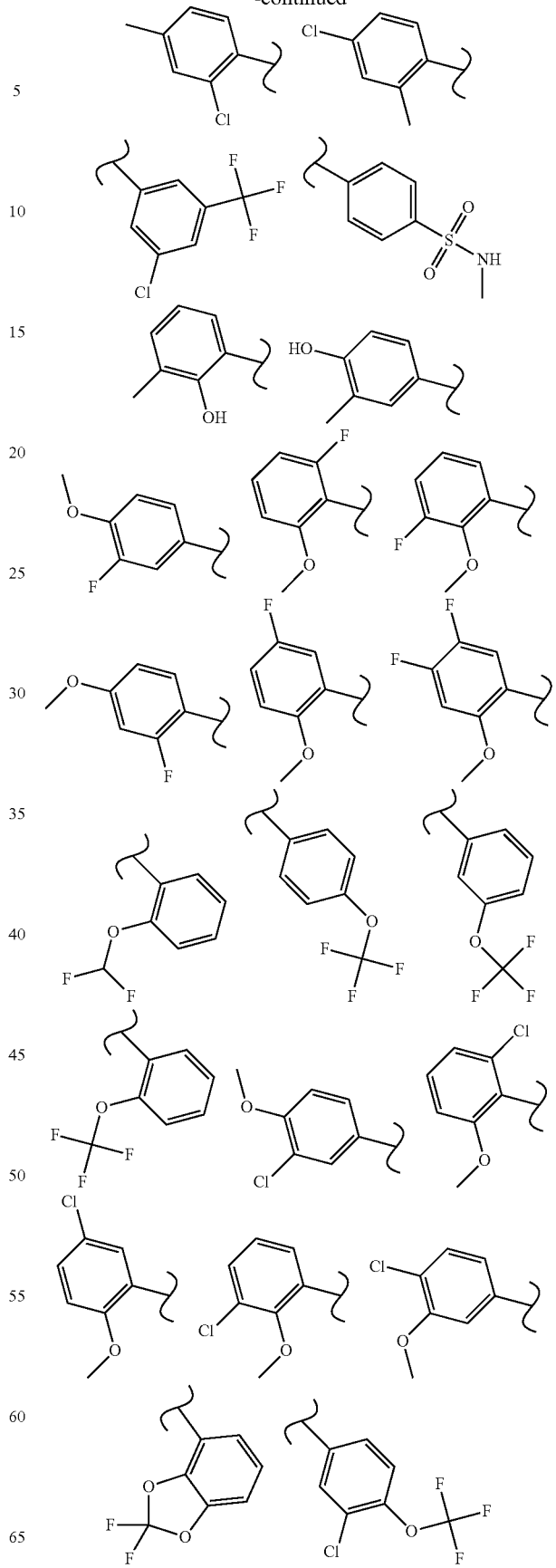

817
-continued
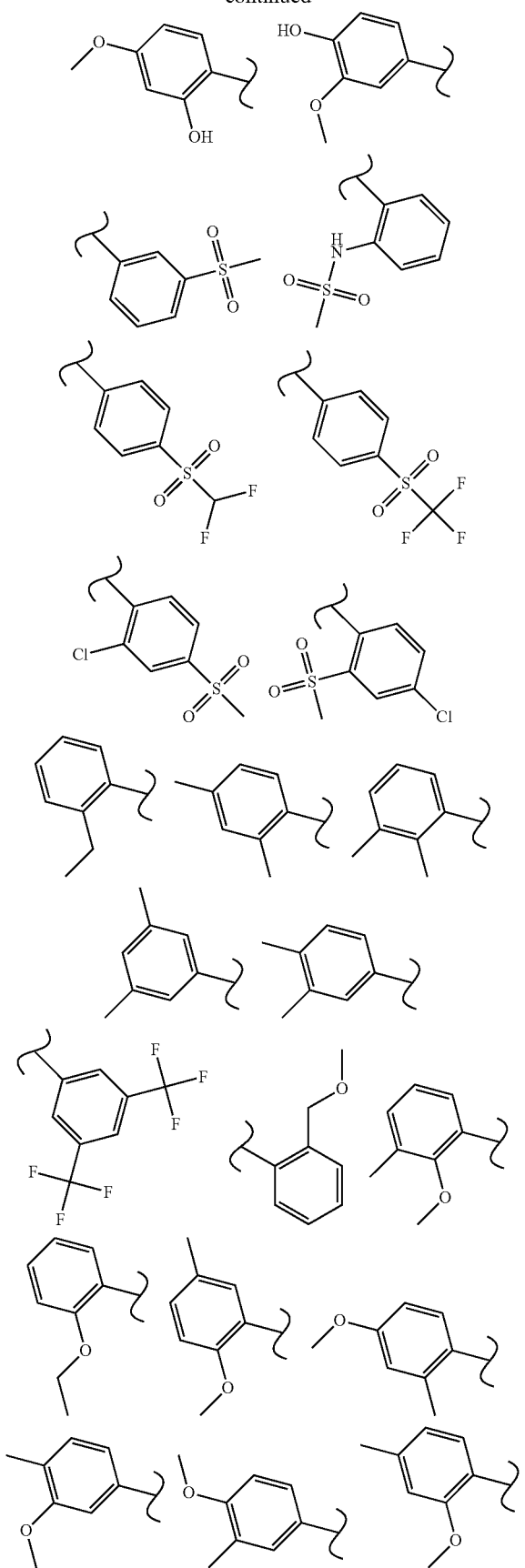
818
-continued
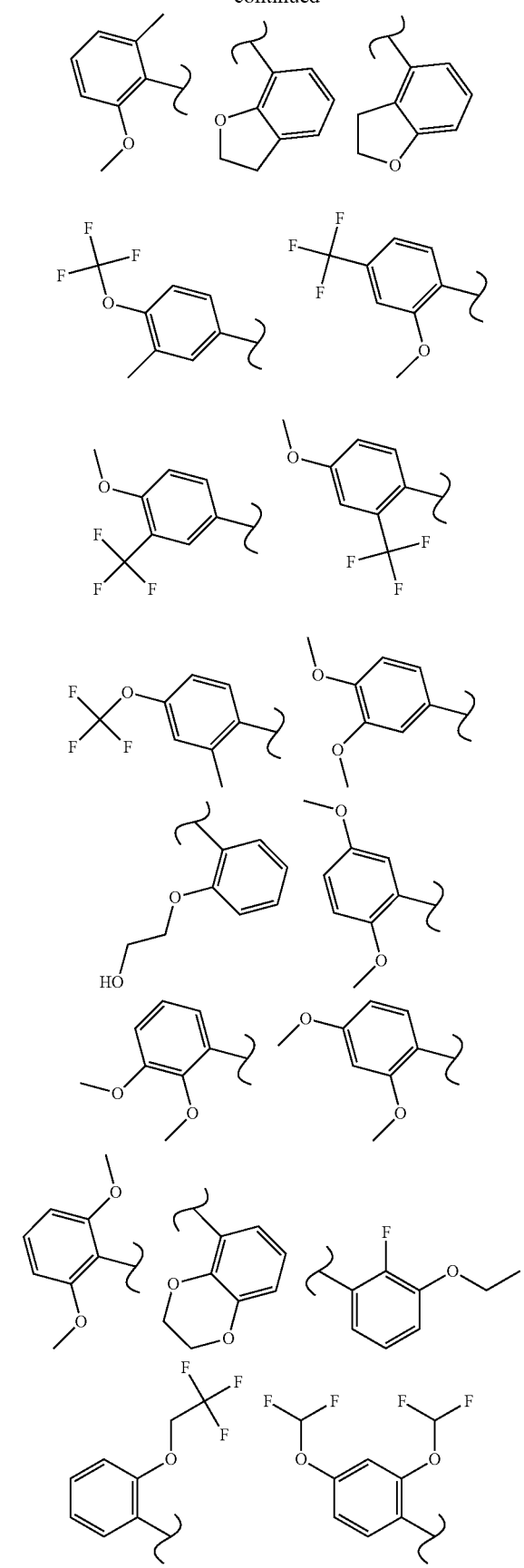

819
-continued
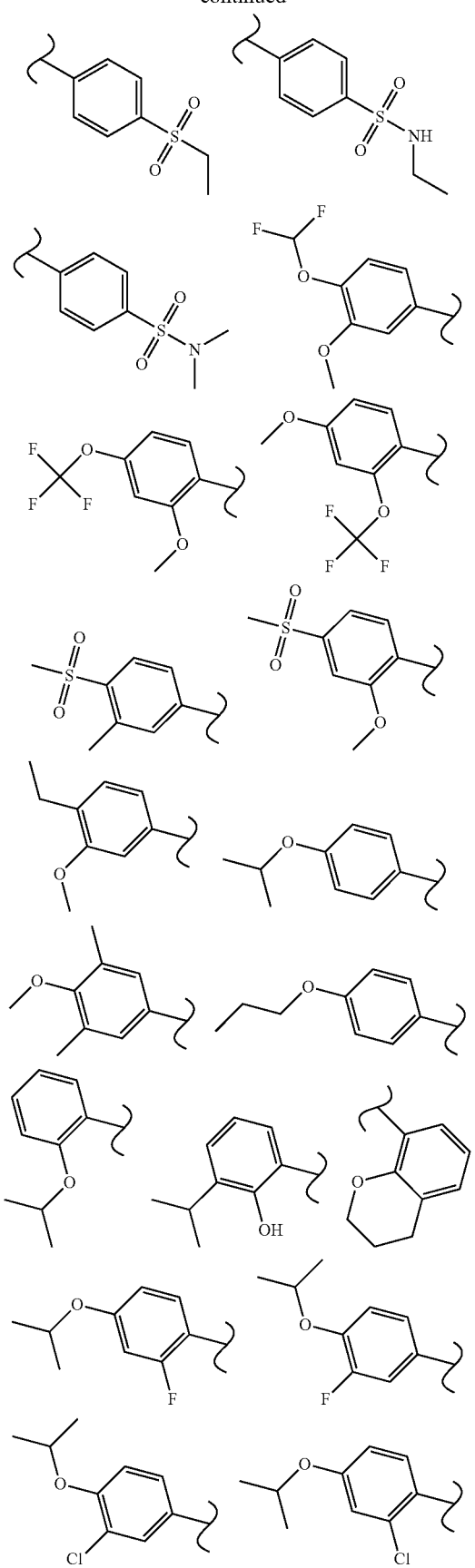
820
-continued
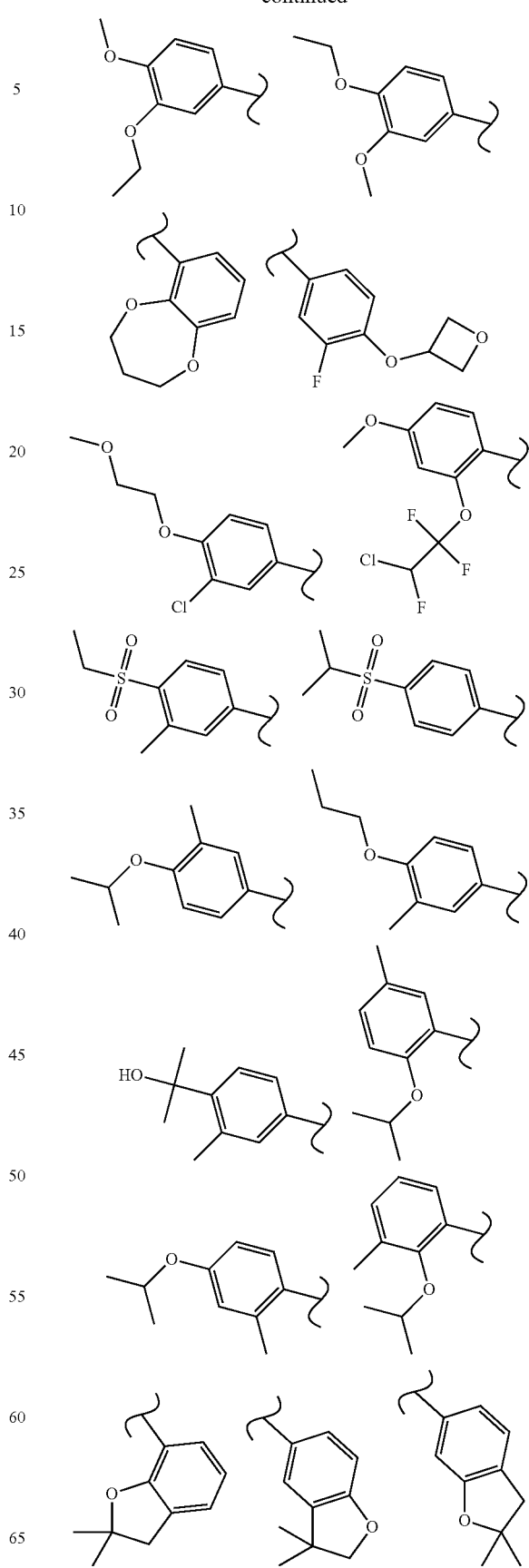

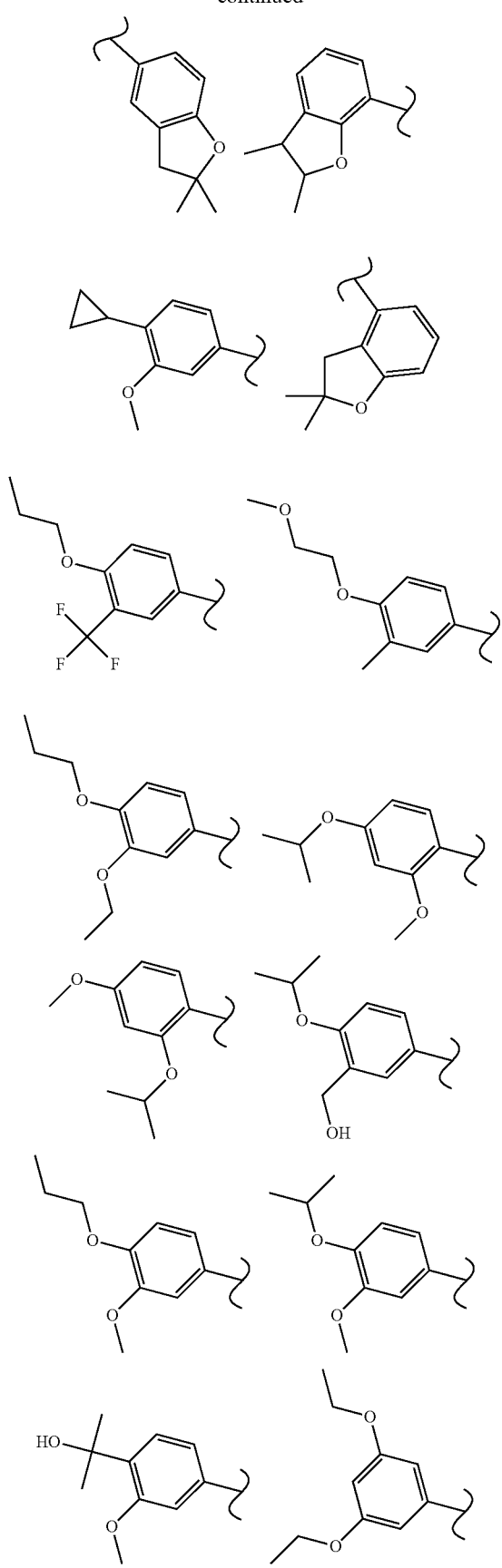
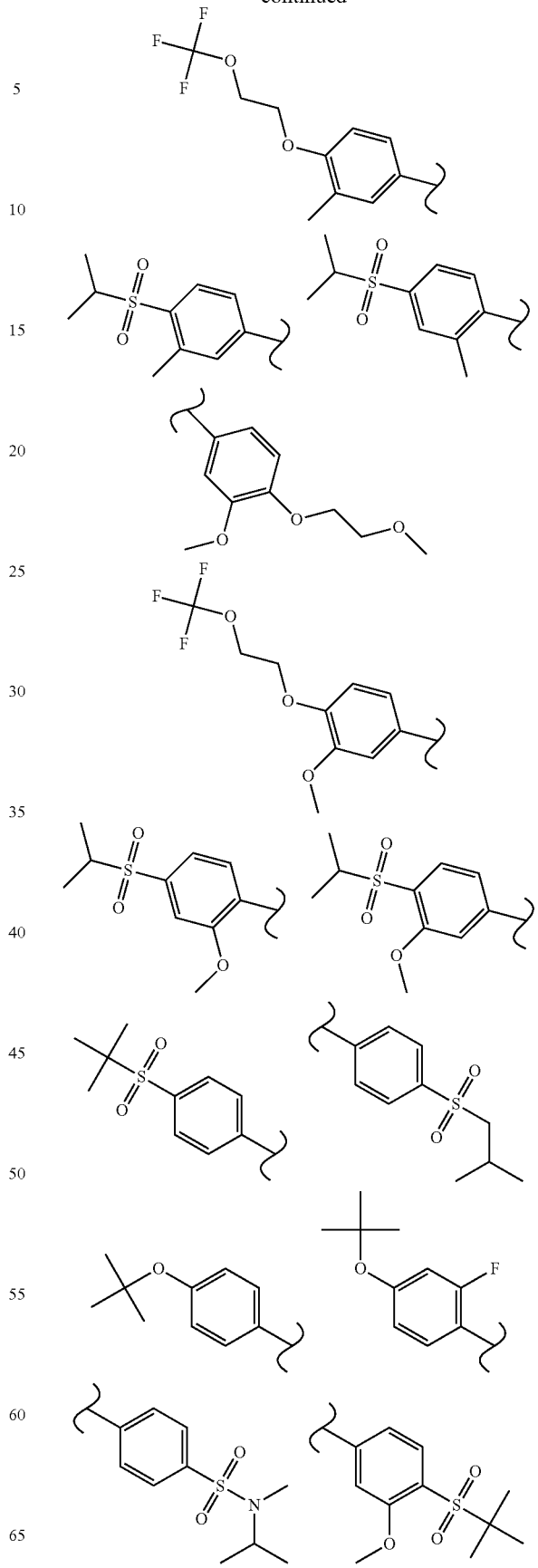

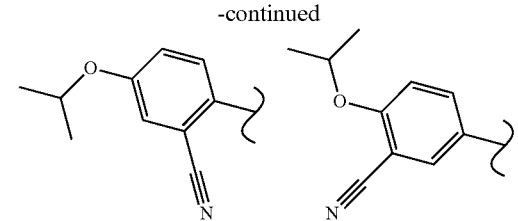
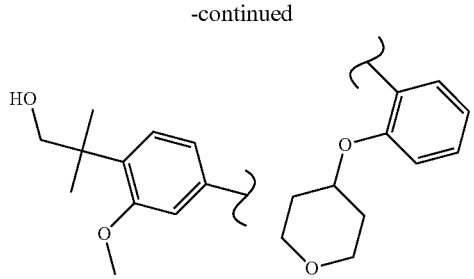
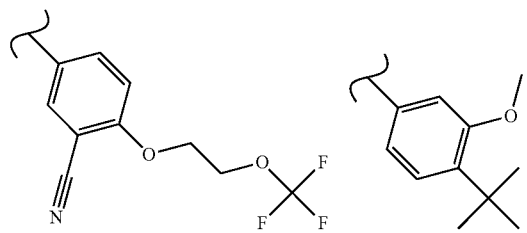
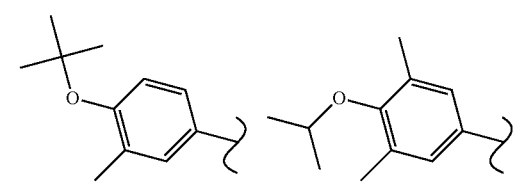
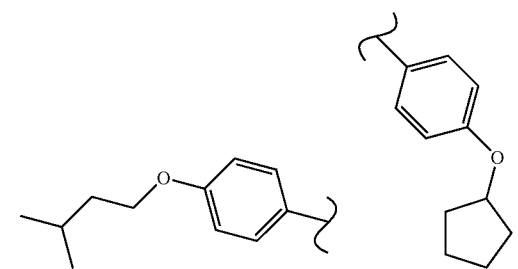
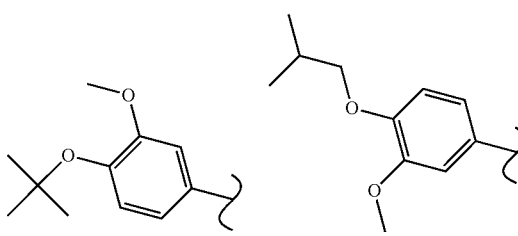
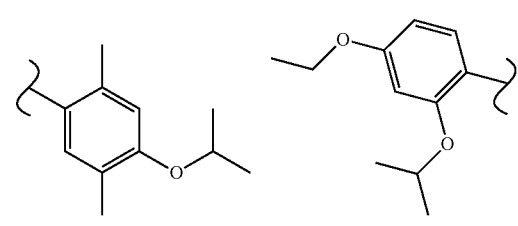
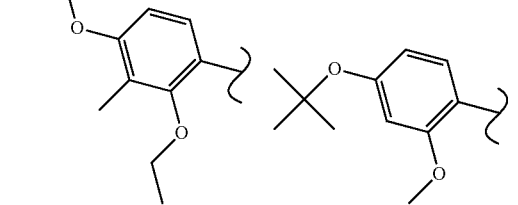
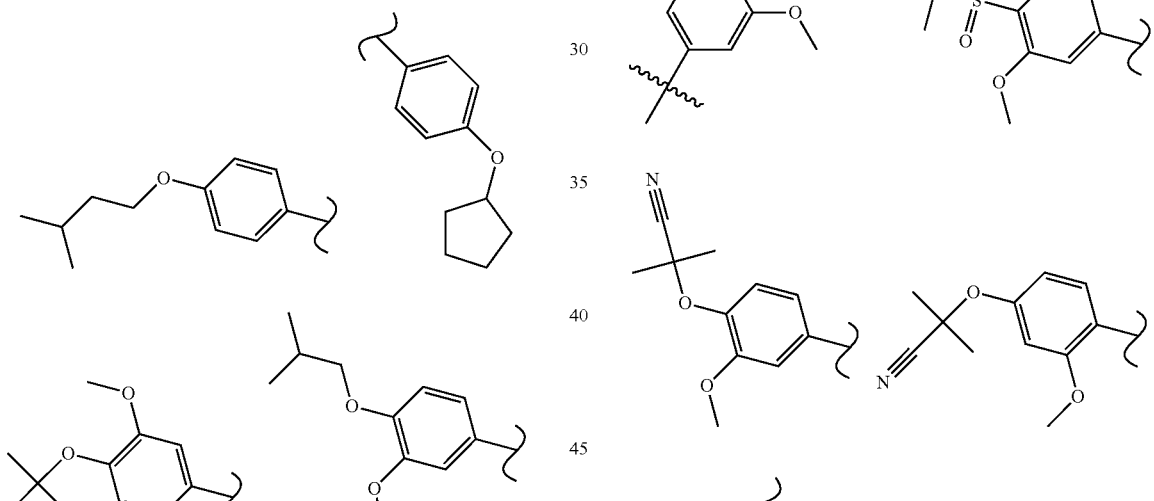
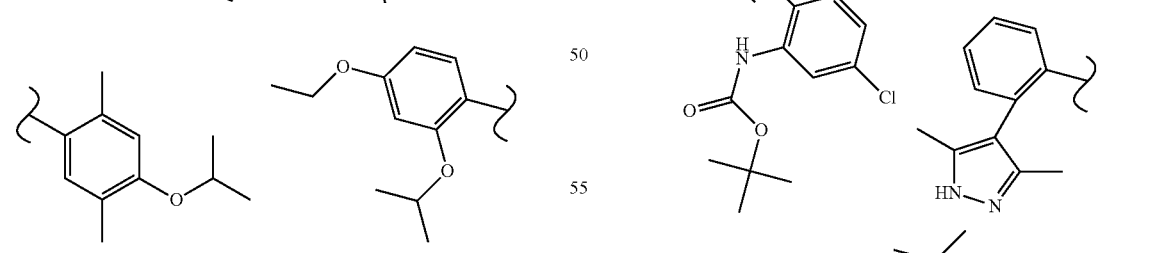
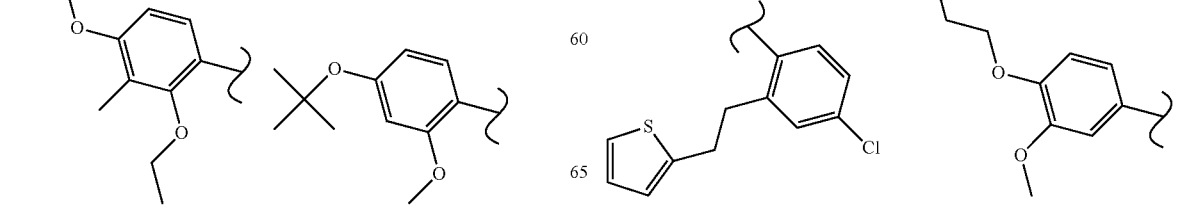

825
-continued
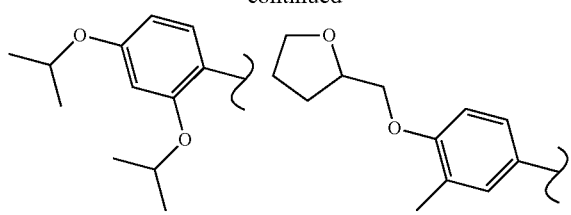
826
-continued
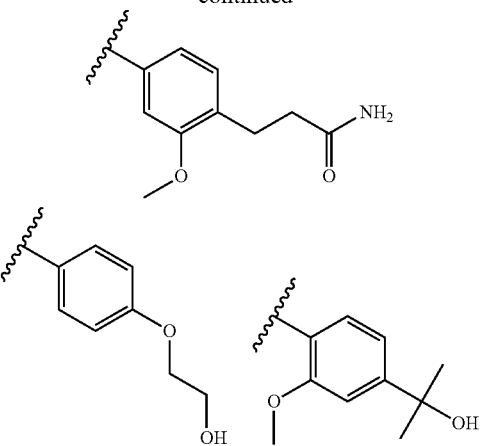
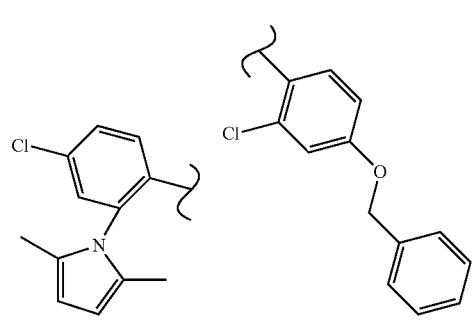
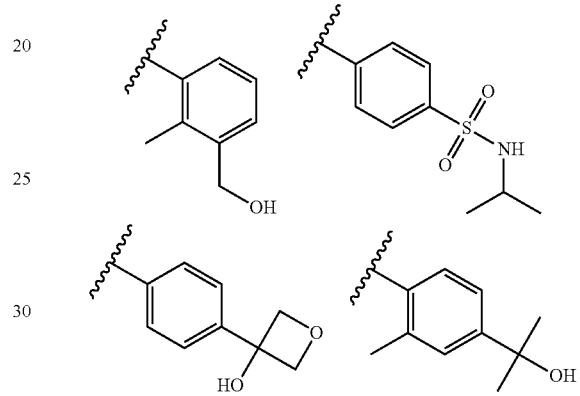
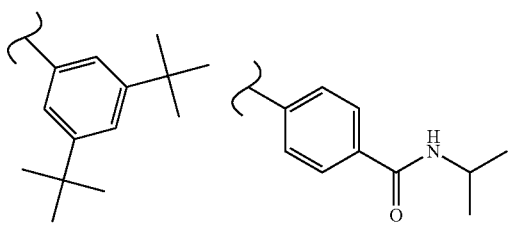
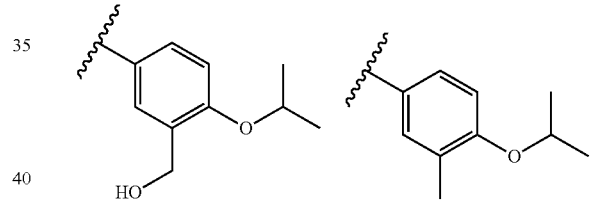
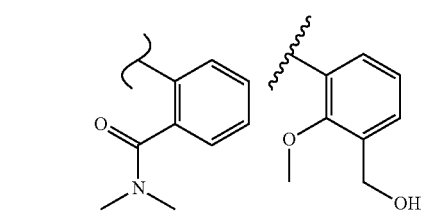
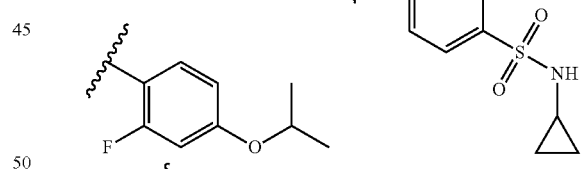
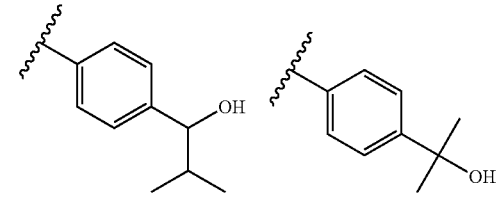
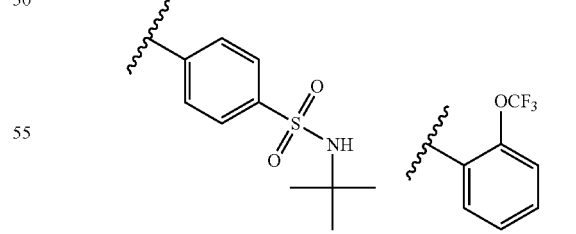
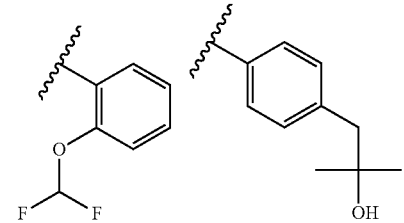
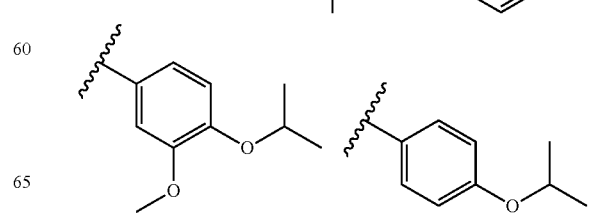

-continued
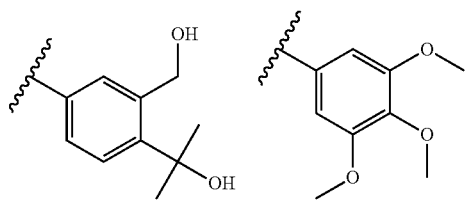
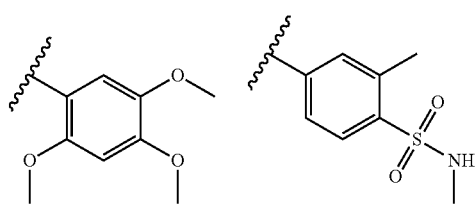
63. The compound of claim 1, wherein the compound is selected from Table 1:
-continued
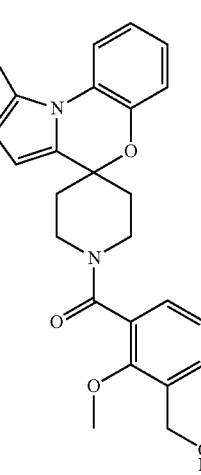
1
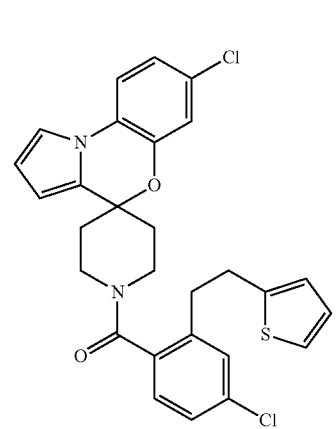
4
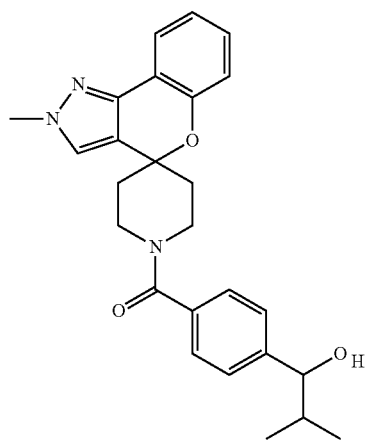
2
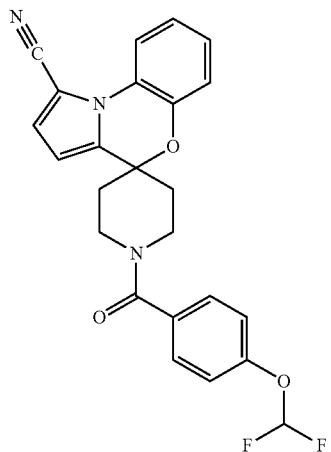
5
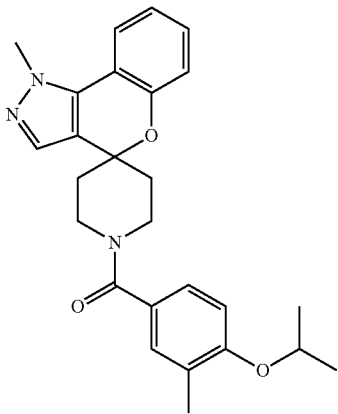

6
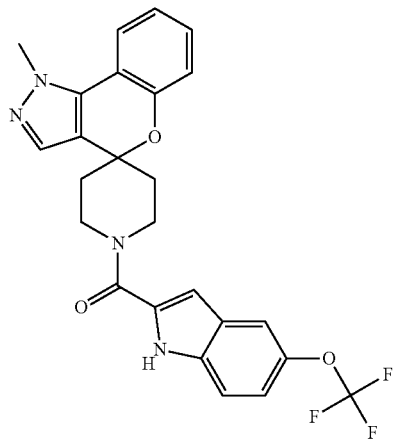
7
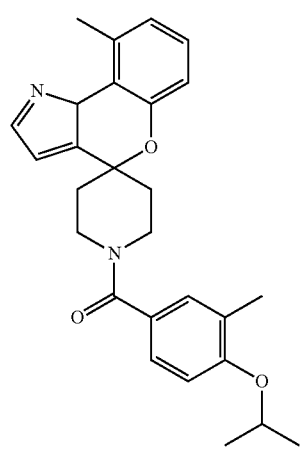
8
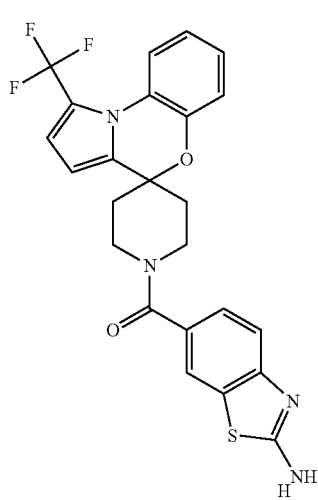
9
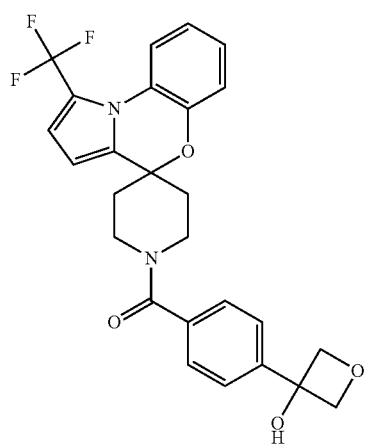
10
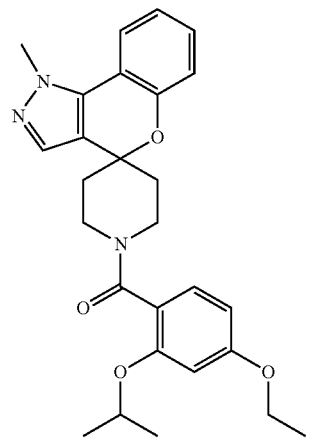
11
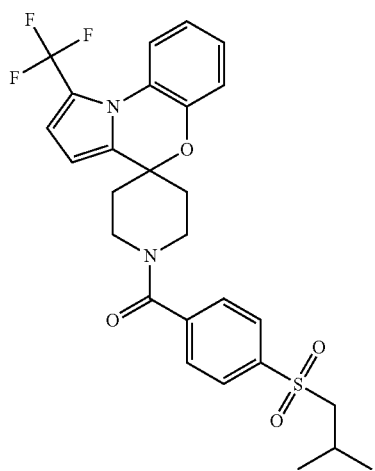

12
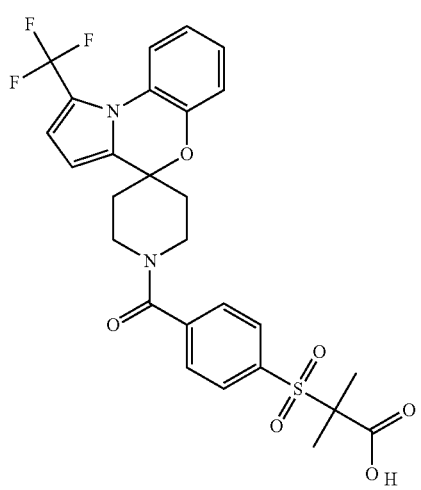
15
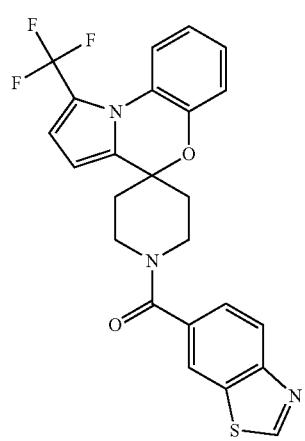
13
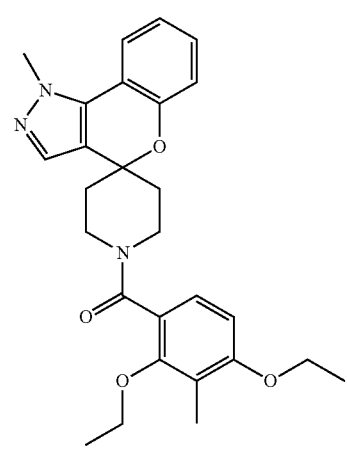
16
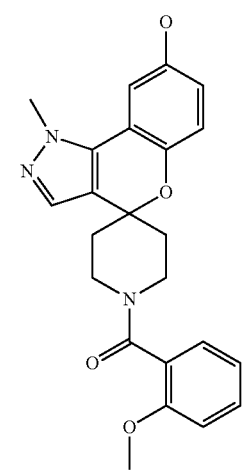
14
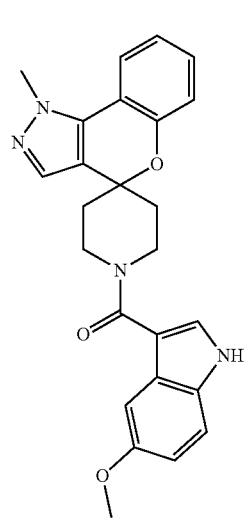
17
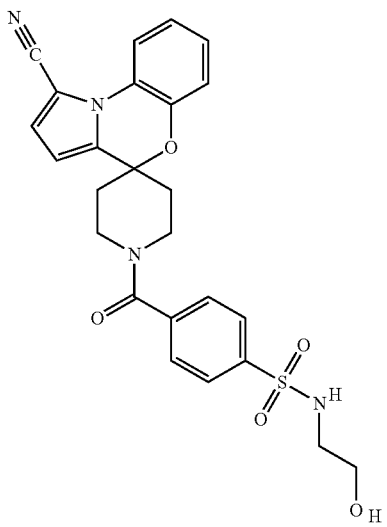

18
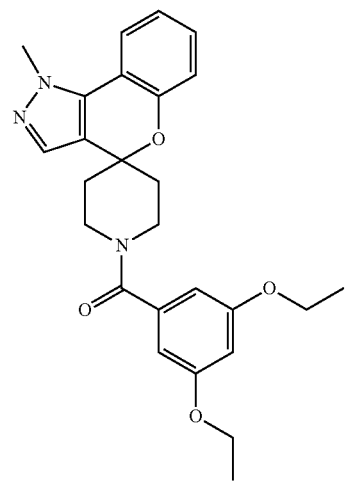
19
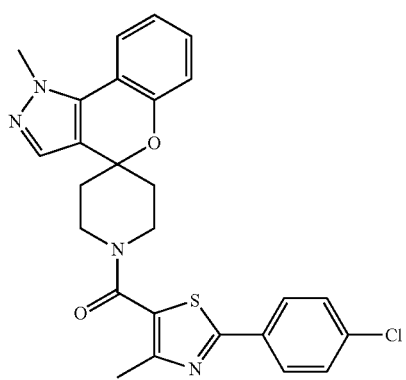
20
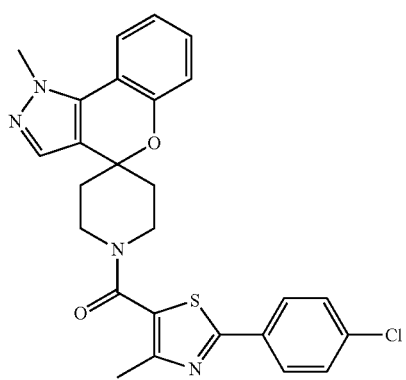
21
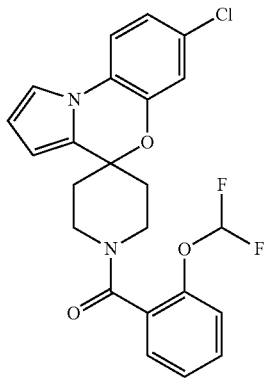
22
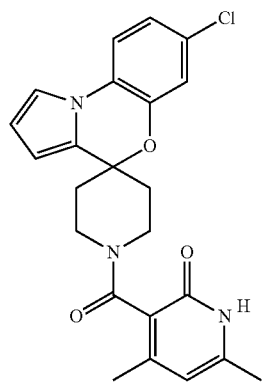
23
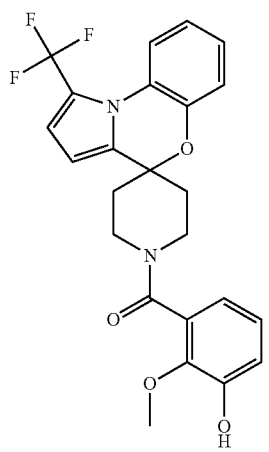
24
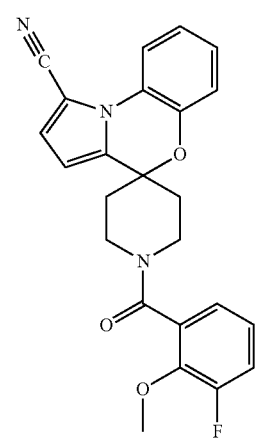

835
-continued
836
-continued
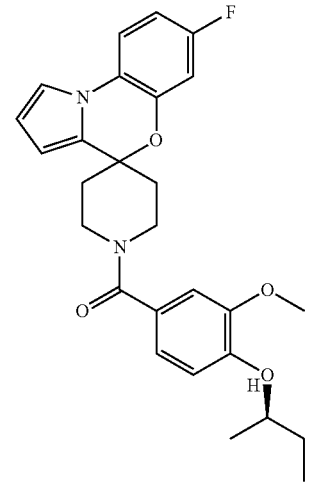
25
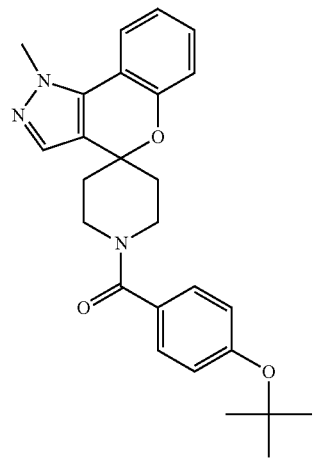
28
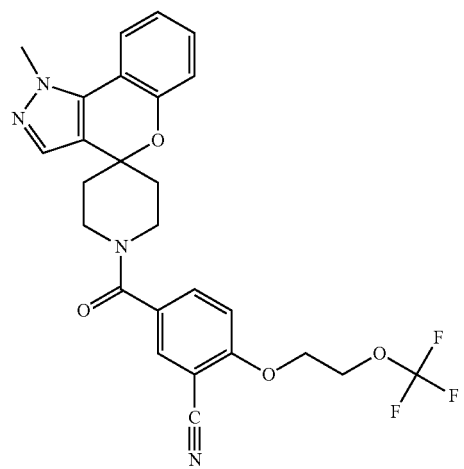
26
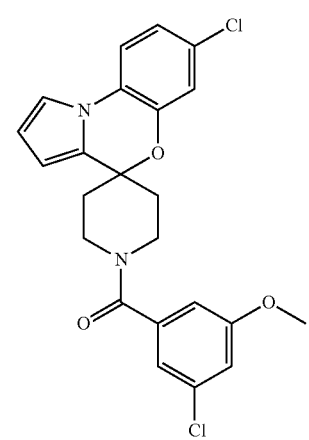
29
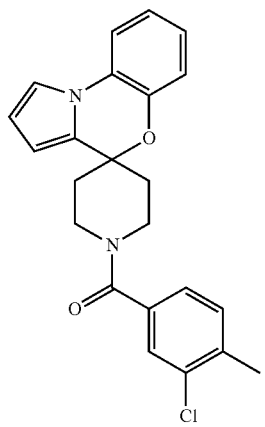
27
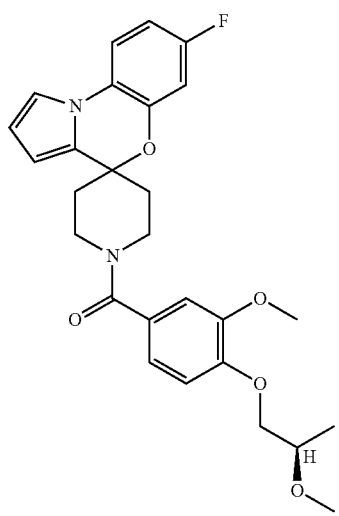
30

-continued
31
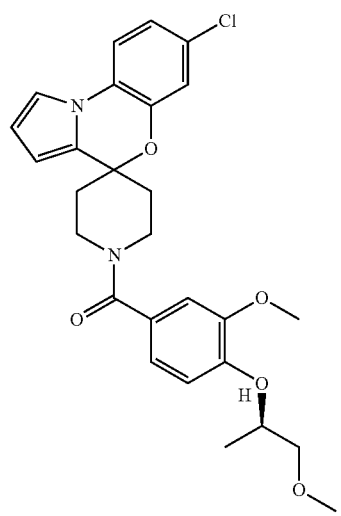
32
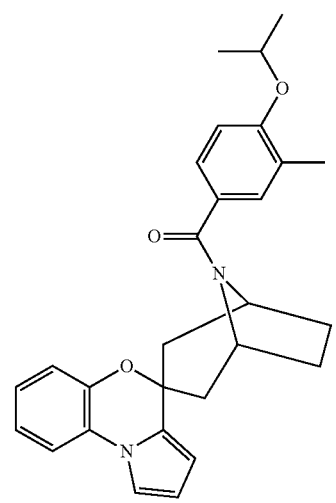
33
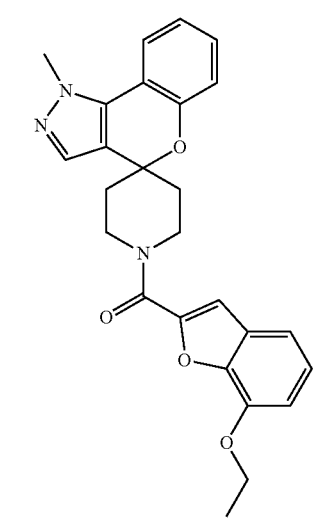
-continued
34
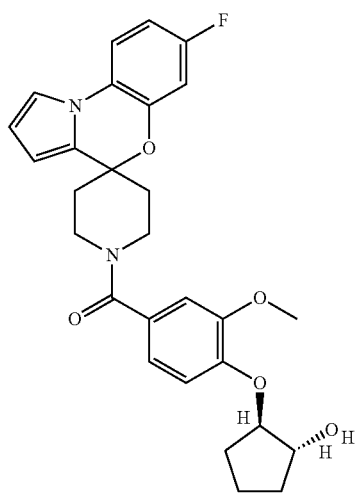
35
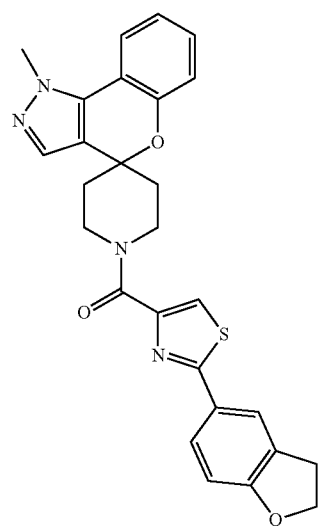
36
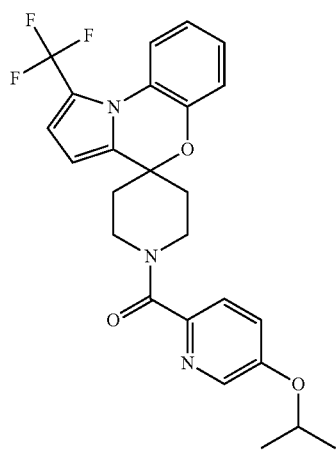

839
-continued
| | |
|---|---|
| 37 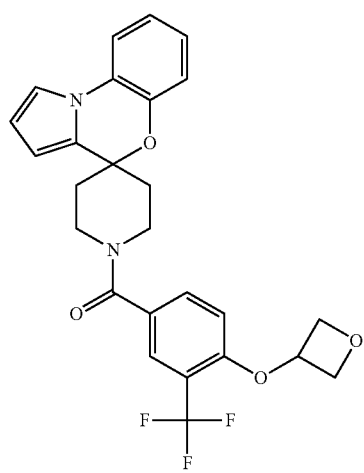 | 40 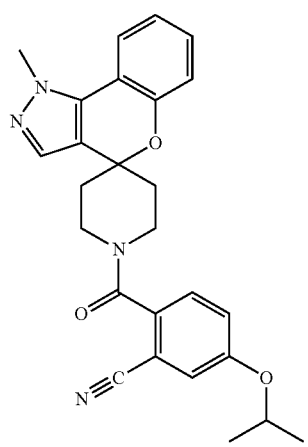 |
| 38 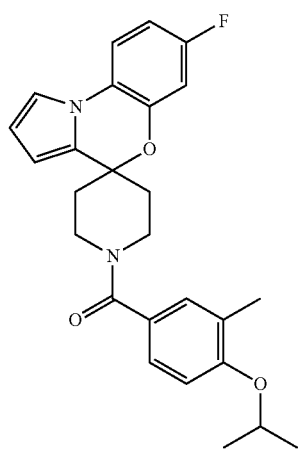 | 41 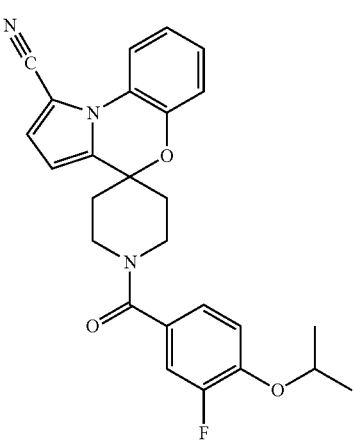 |
| 39 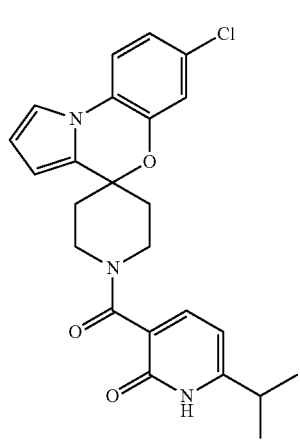 | 42 |
840
-continued

| 43 | 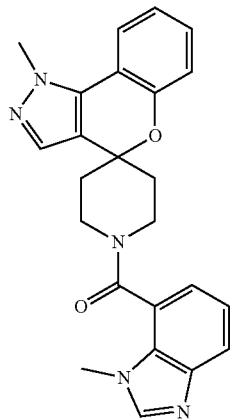 |
| --- | --- |
| 44 | 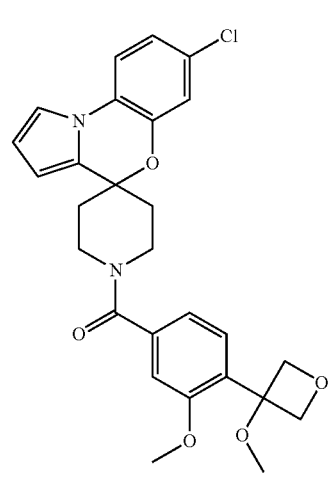 (partial) |
| 45 | 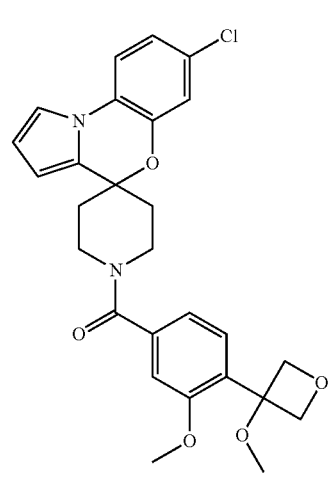 |
| 46 | 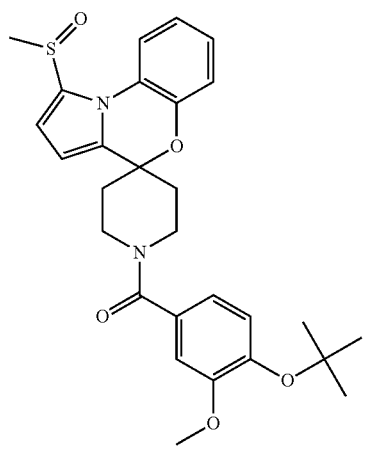 |
| --- | --- |
| 47 | 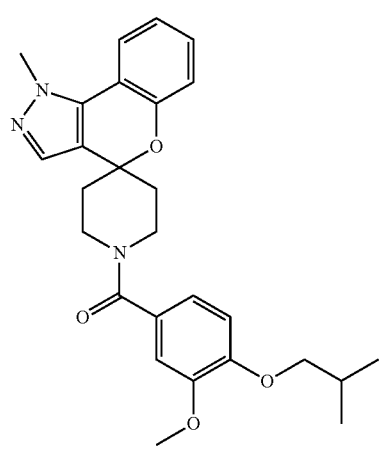 |
| 48 | 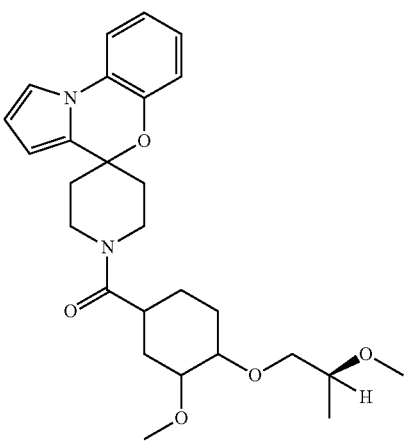 |

49
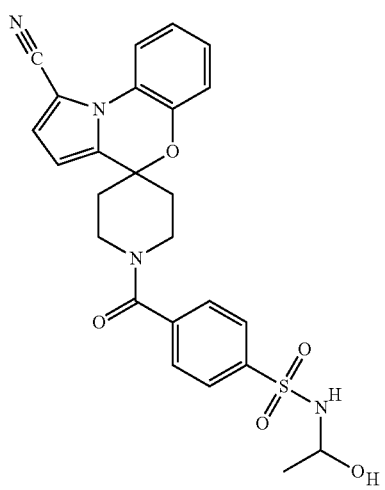
50
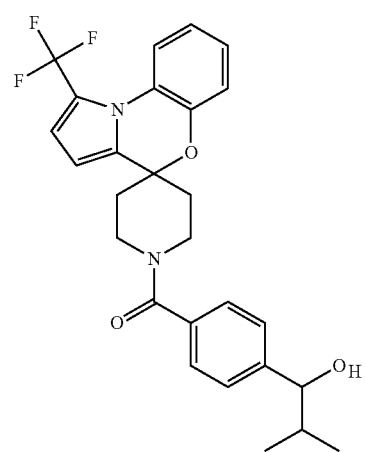
51
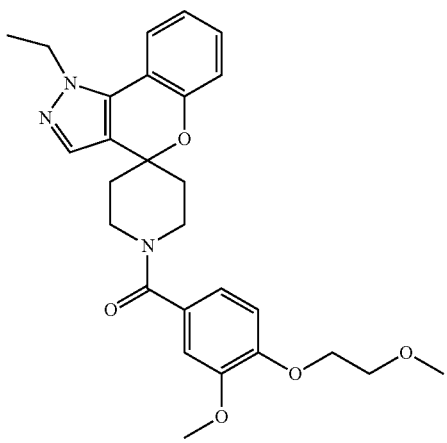
52
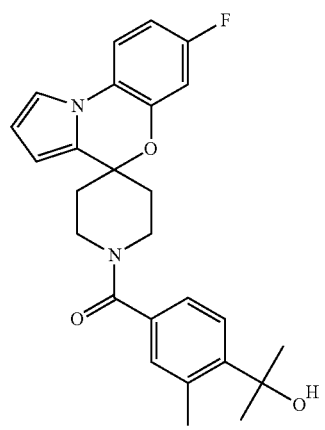
53
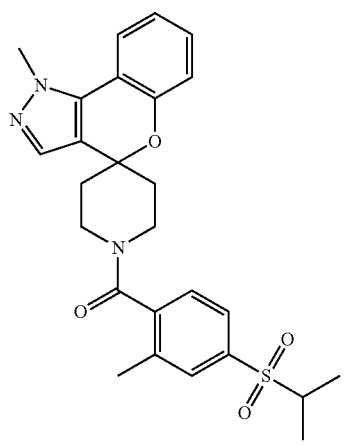
54
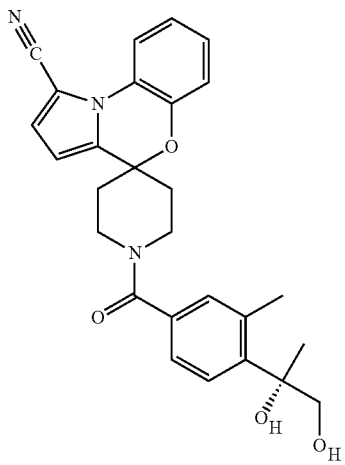

845
-continued
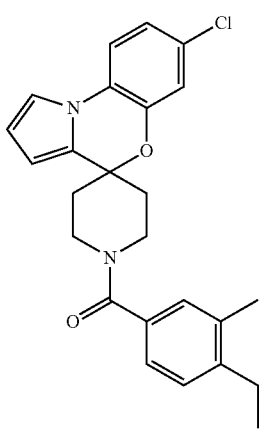
55
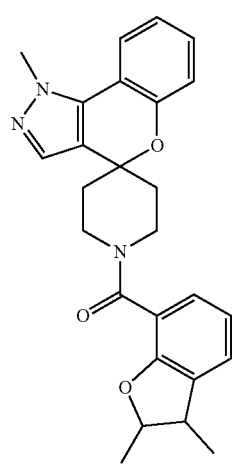
56
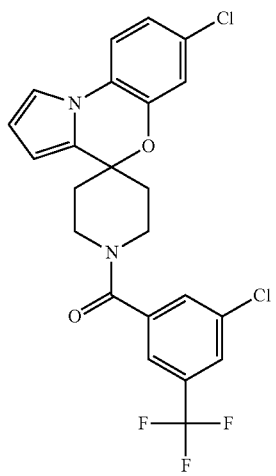
57
846
-continued
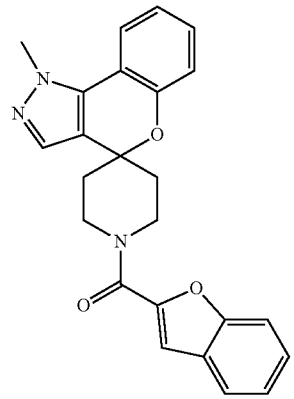
58
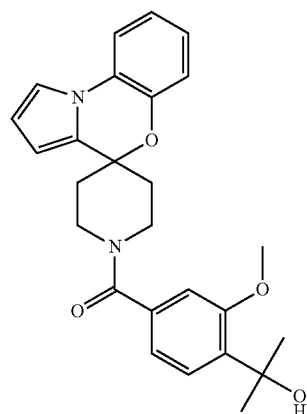
59
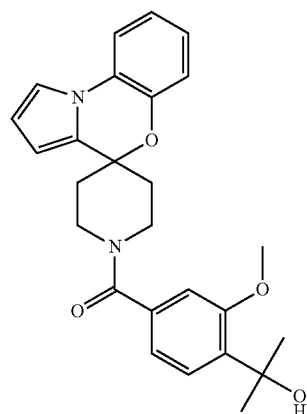
60

61
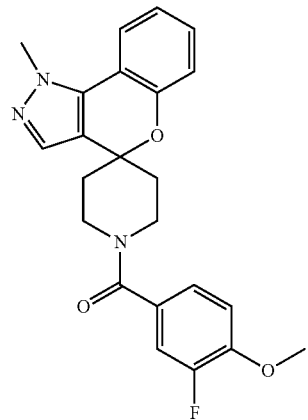
62
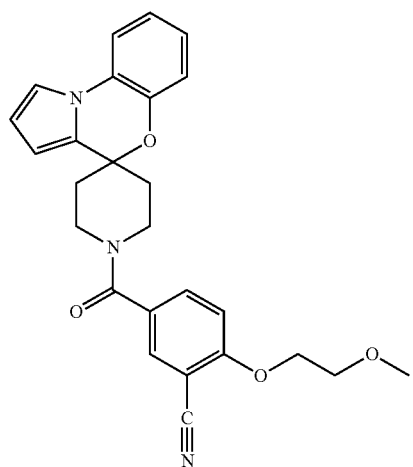
63
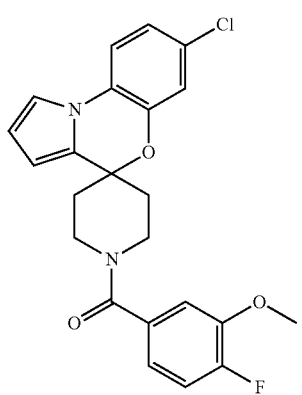
64
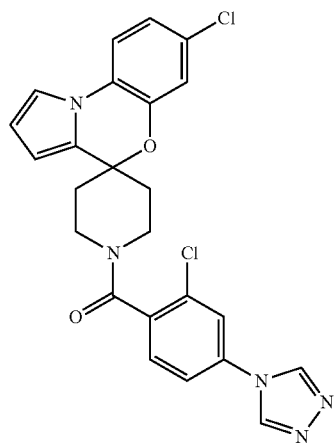
65
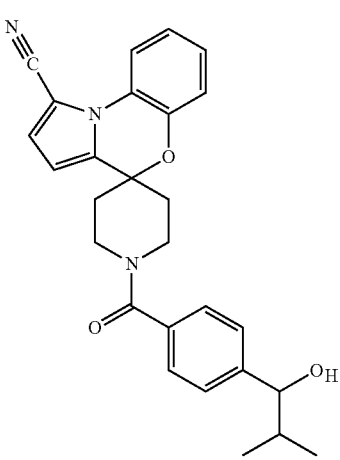
66
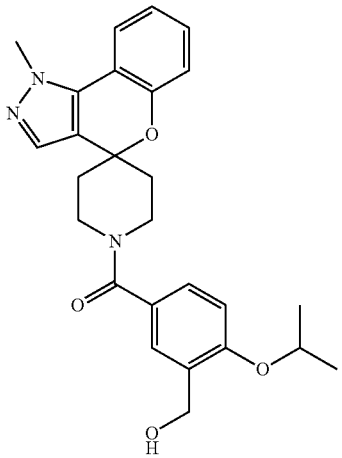

849
-continued
| 67 | 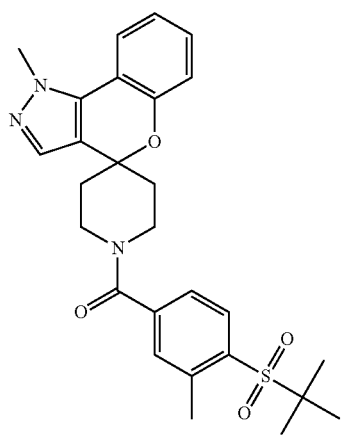 |
| 68 | 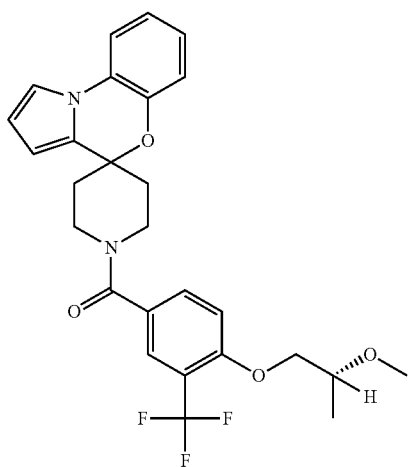 |
| 69 | 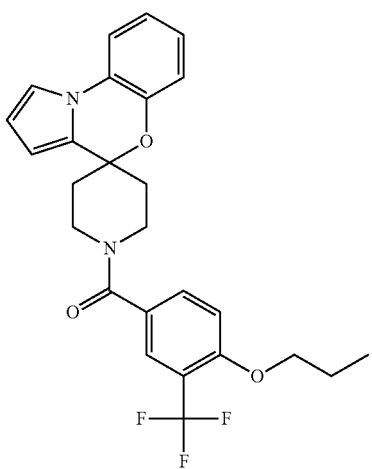 |
850
-continued
| 70 | 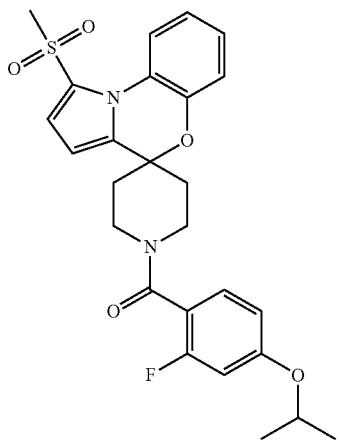 |
| 71 | 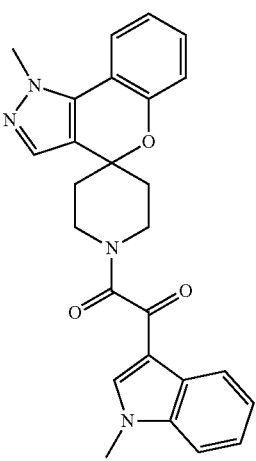 |
| 72 | 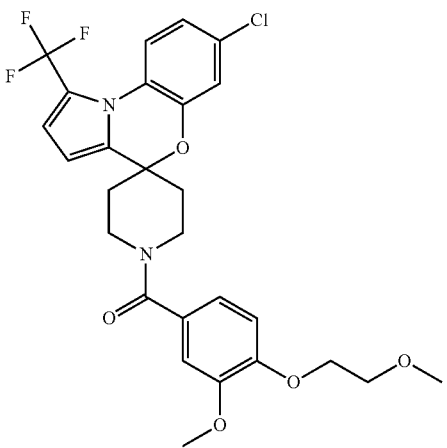 |

73
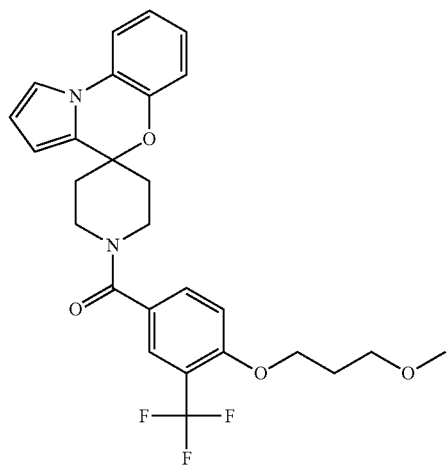
74
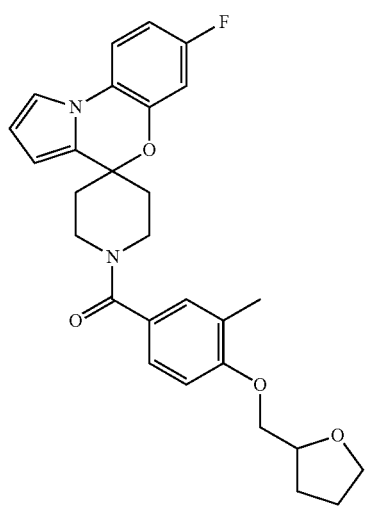
75
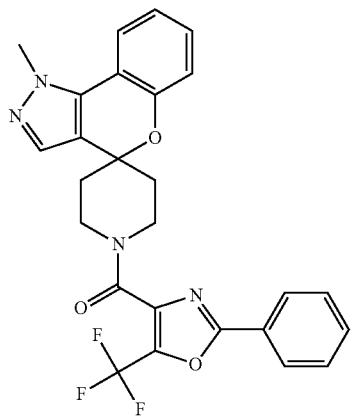
76
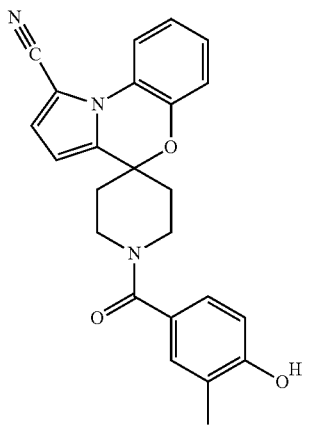
77
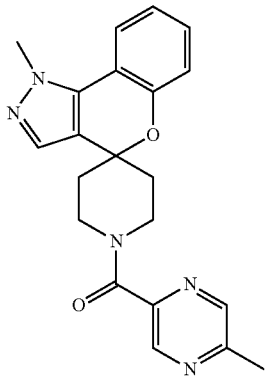
78
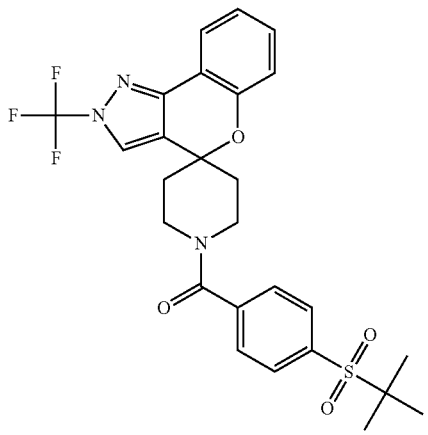

79 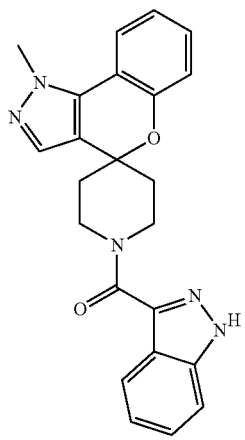
80 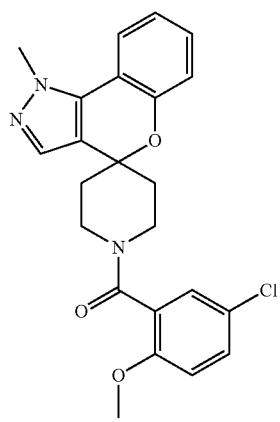
81 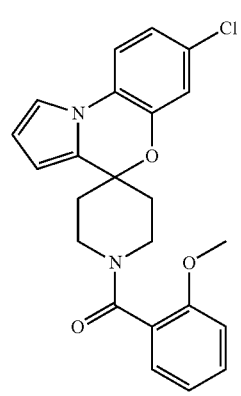
82 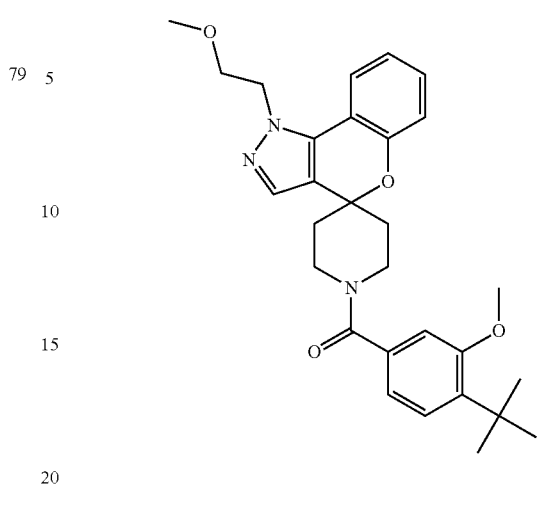
83 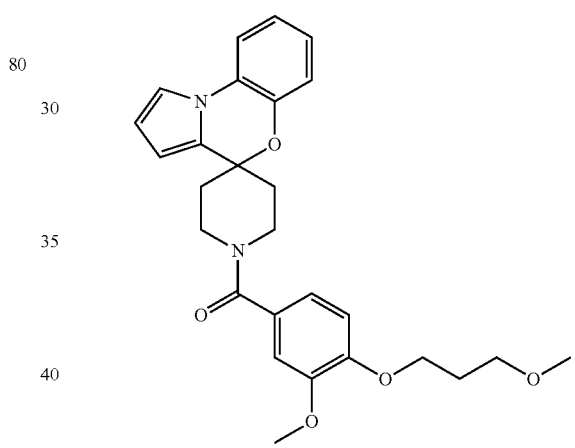
84 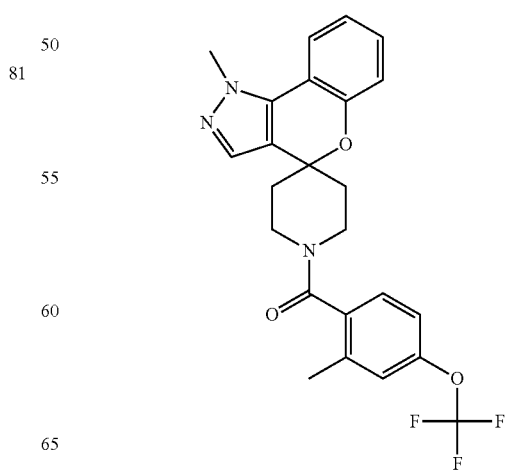

| 85 | 89 |
| --- | --- |
| 86 | |
| | 90 |
| 87 | |
| 88 | 91 |
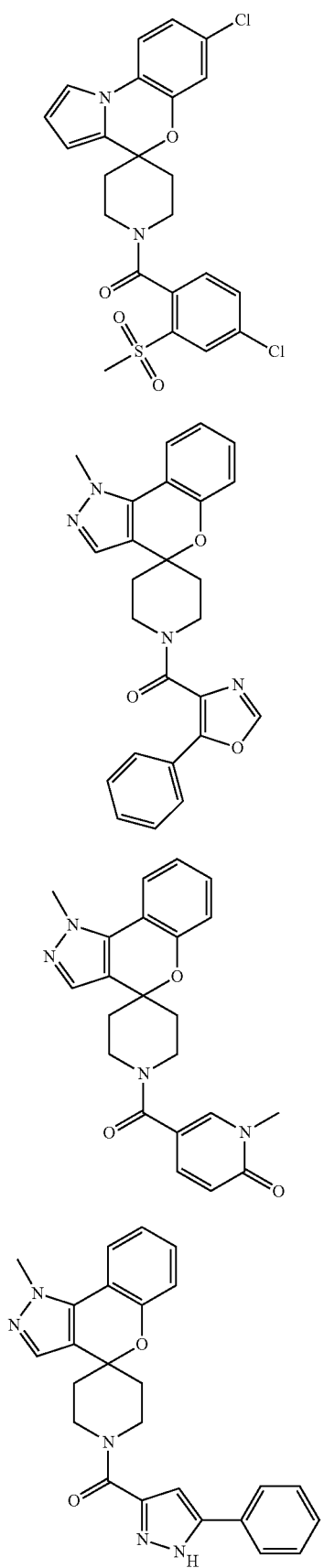
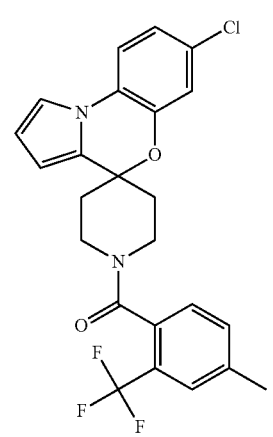
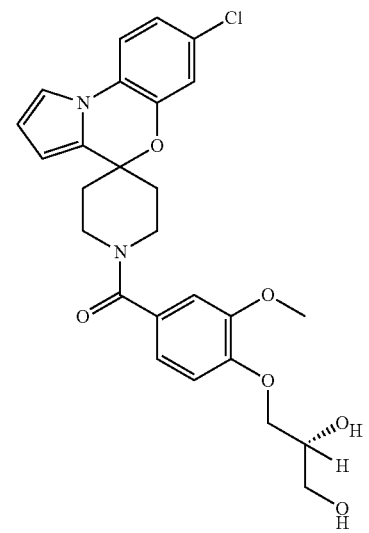
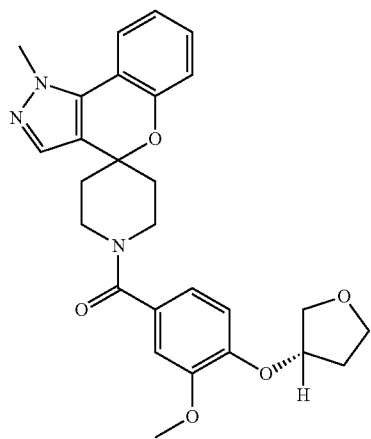

| 857 | 858 |
|---|---|
| 92 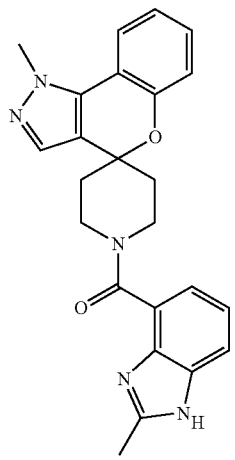 | 95 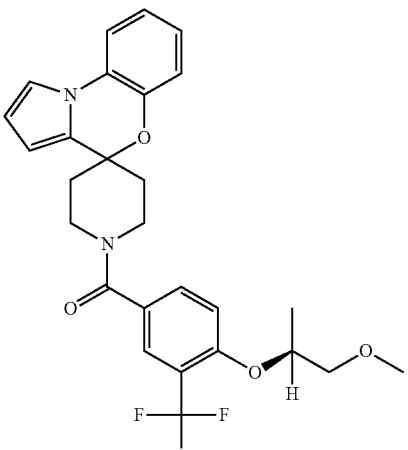 |
| 93 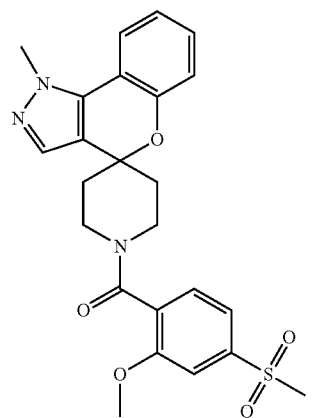 | 96 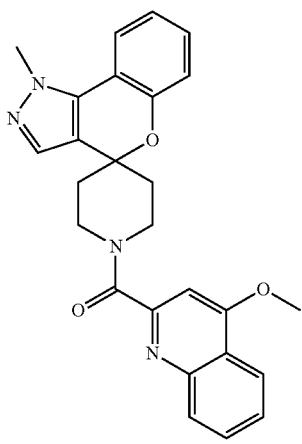 |
| 94 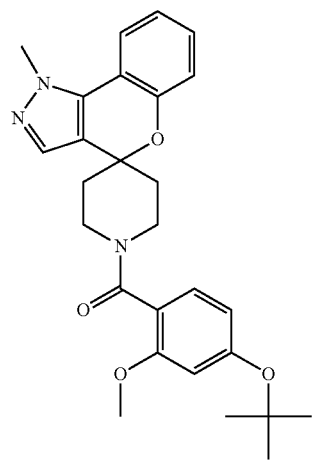 | 97 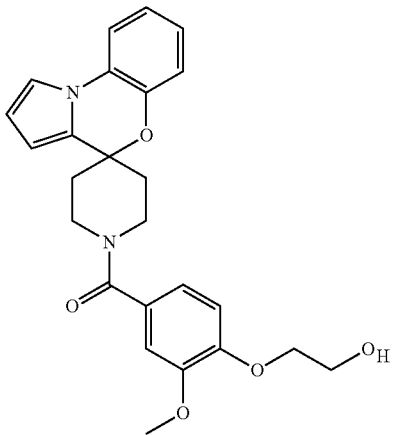 |

859
-continued
98
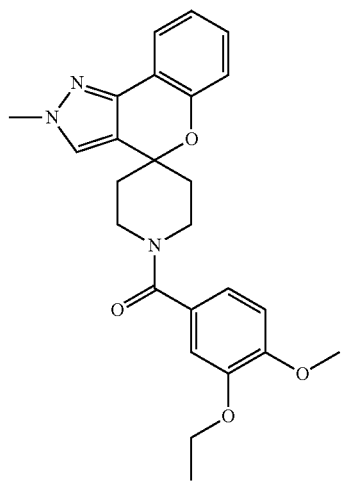
99
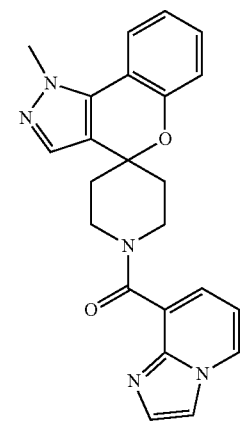
100
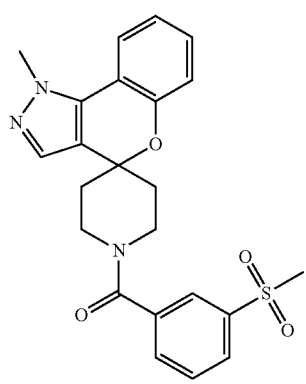
860
-continued
101
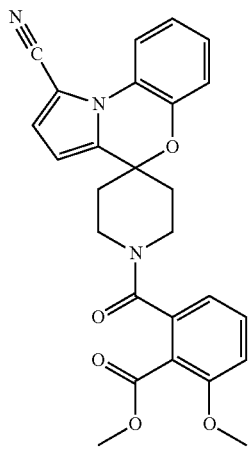
102
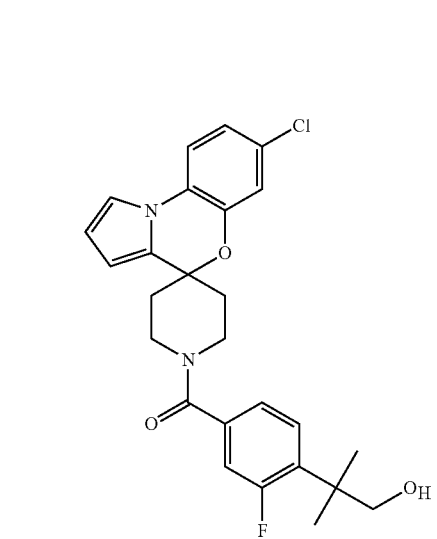
103

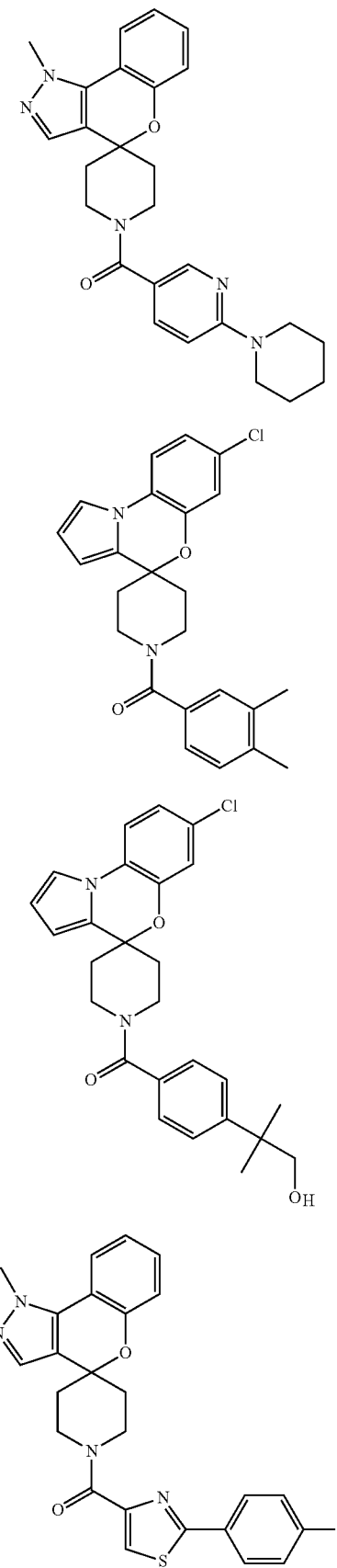
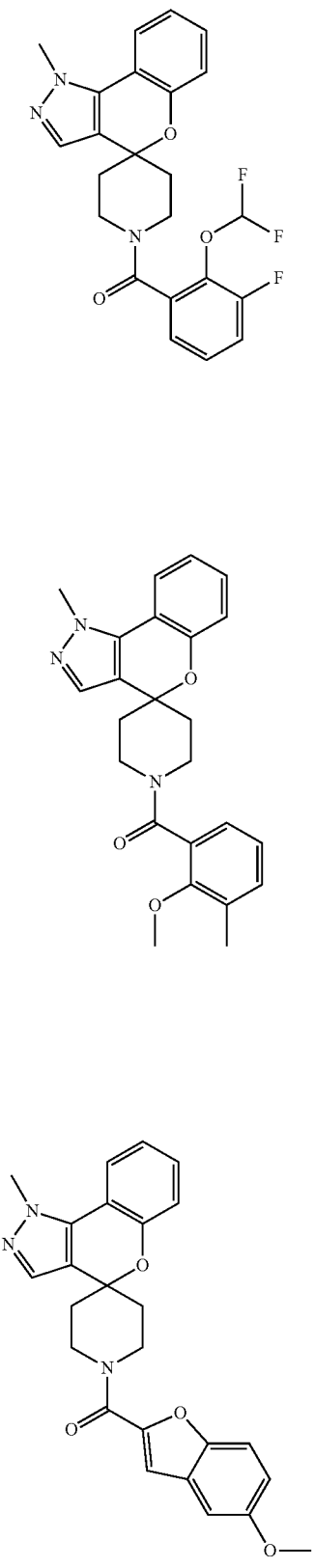

| 111 | 114 |
|---|---|
| 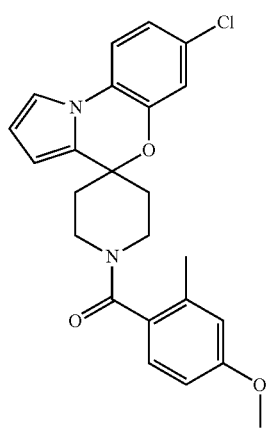 | 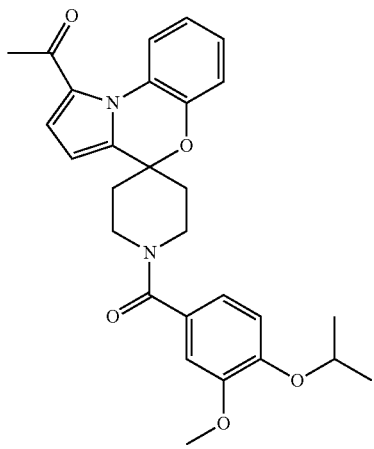 |
| 112 | 115 |
|---|---|
| 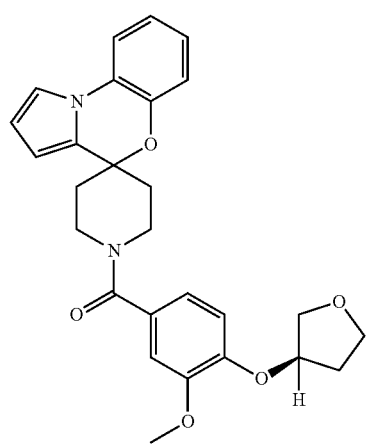 | 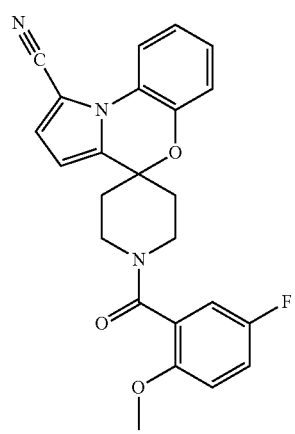 |
| 113 | 116 |
|---|---|
| 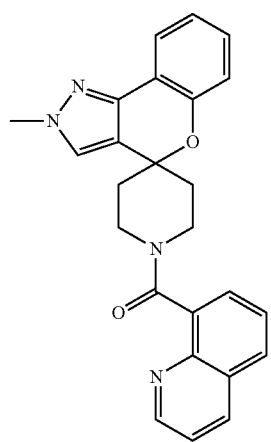 | 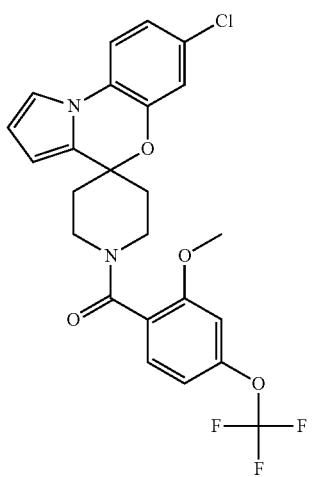 |

| 117 | 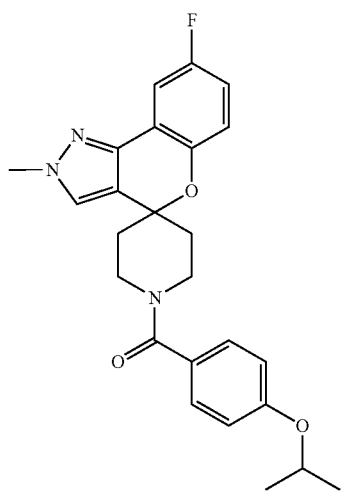 | 120 | 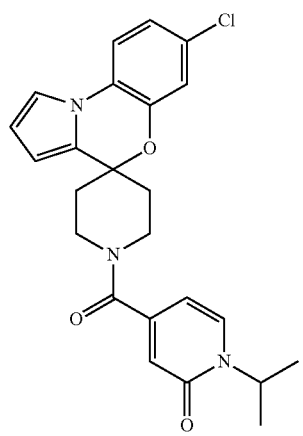 |
| 118 | 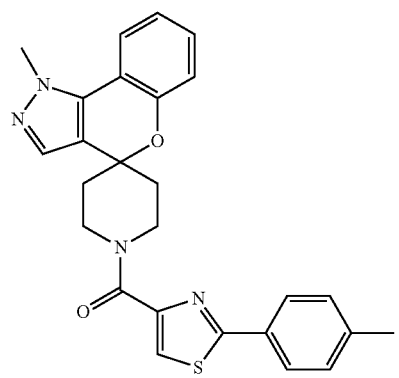 | 121 | 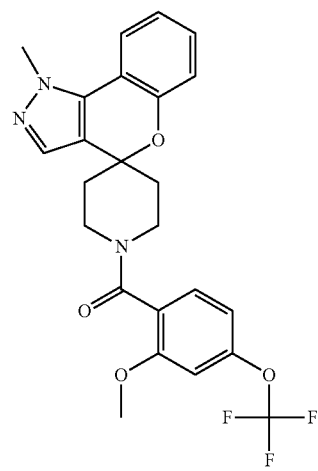 |
| 119 | 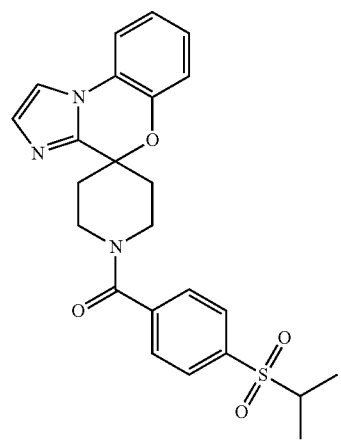 | 122 | 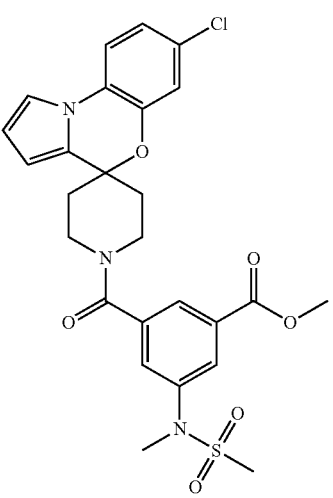 |

123
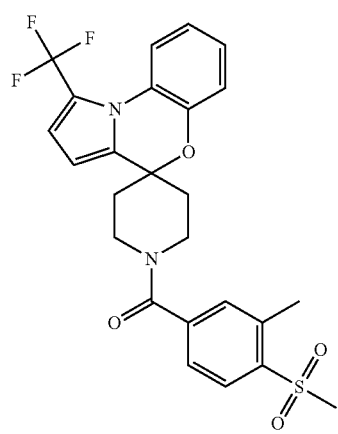
124
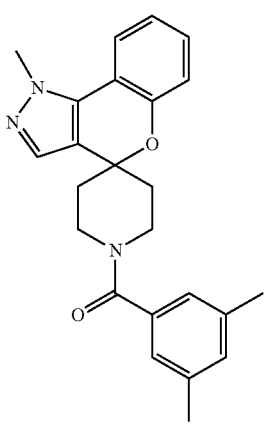
125
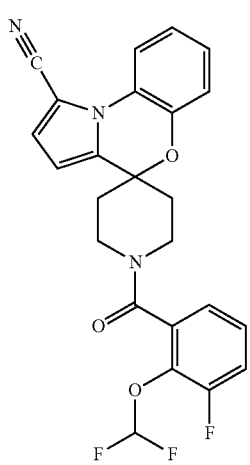
126
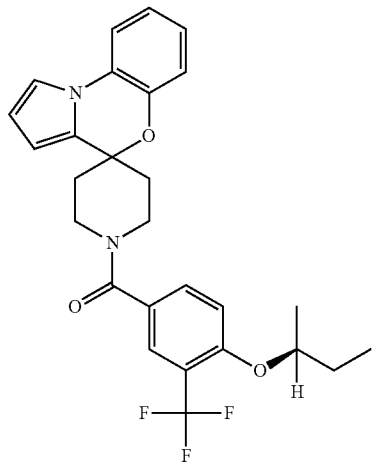
127
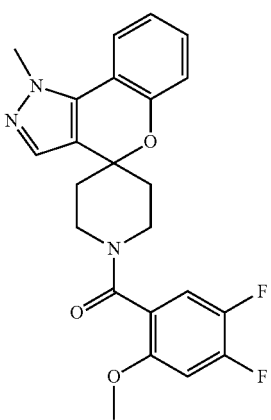
128
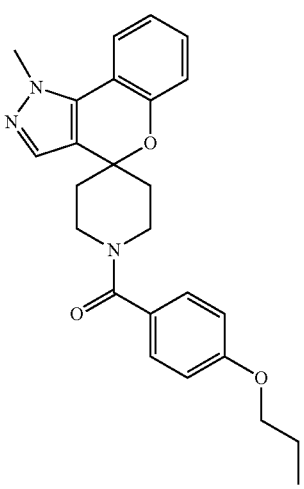

| 129 | 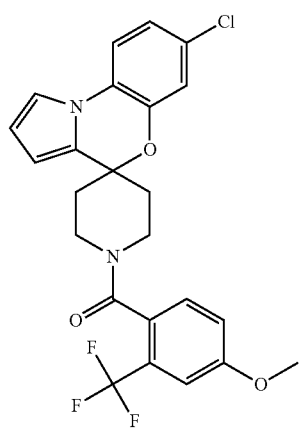 | 132 | 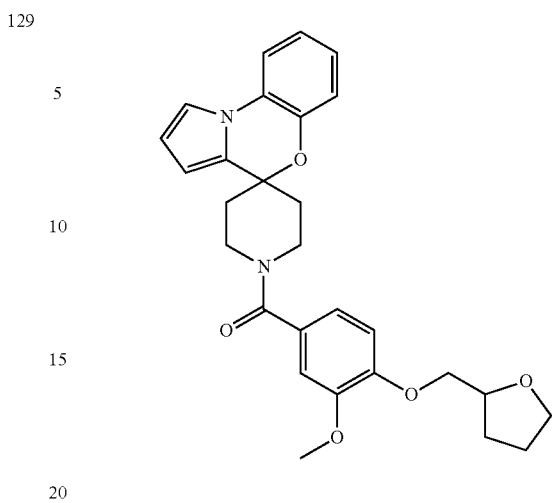 |
| 130 | 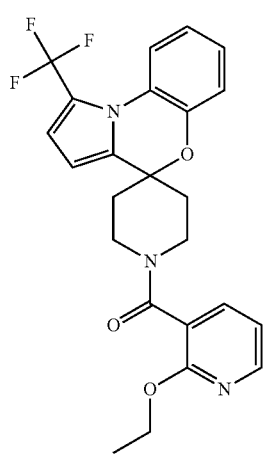 | 133 | 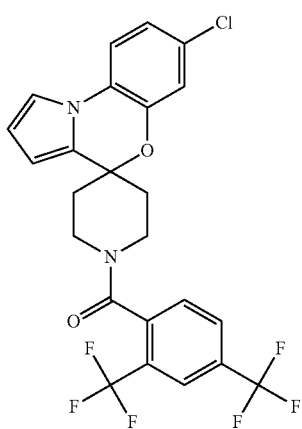 |
| 131 | 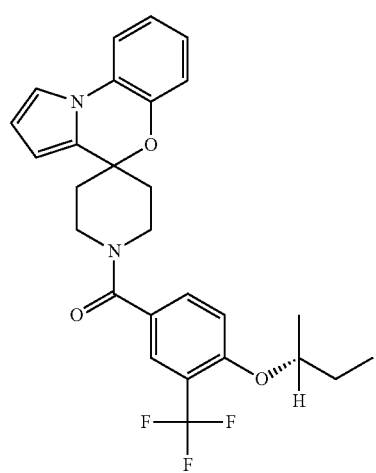 | 134 | 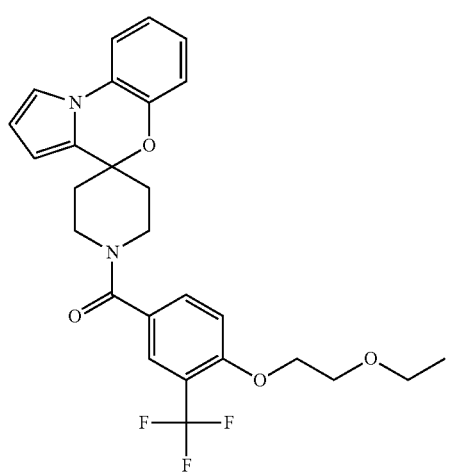 |

871
-continued
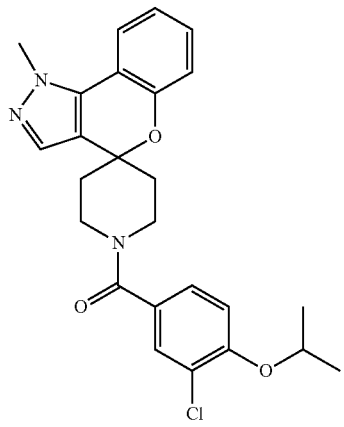
135
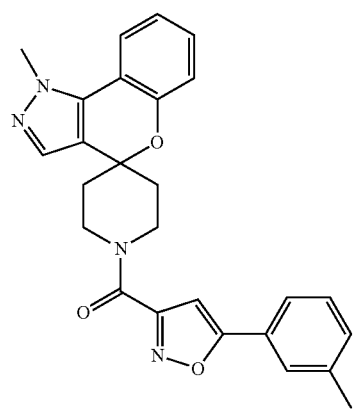
136
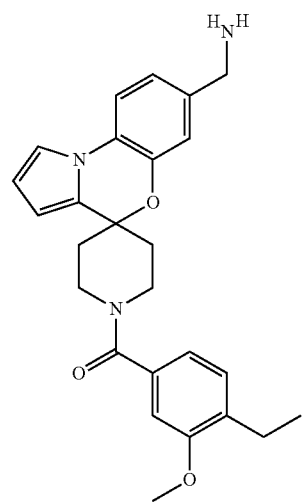
137
872
-continued
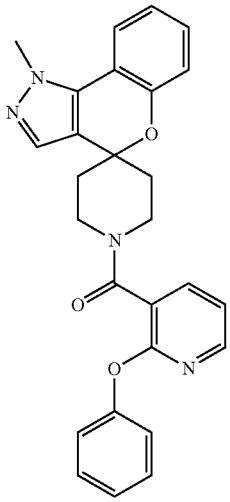
138
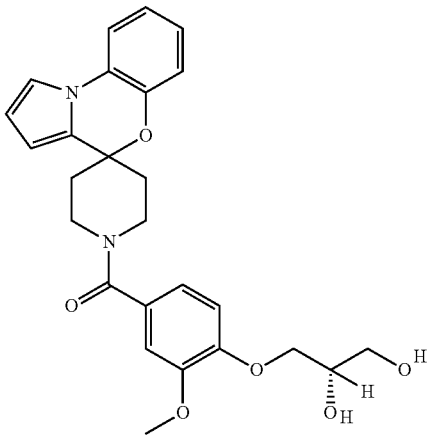
139
140

| 141 | 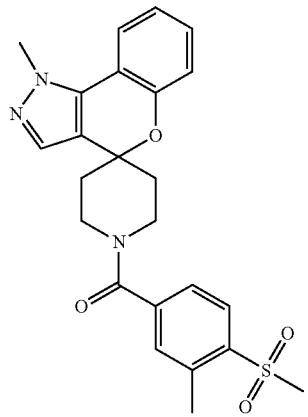 | 144 | 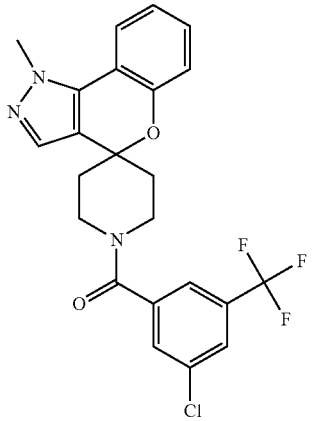 |
| --- | --- | --- | --- |
| 142 | 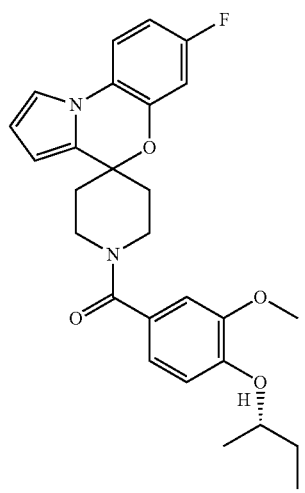 | 145 | 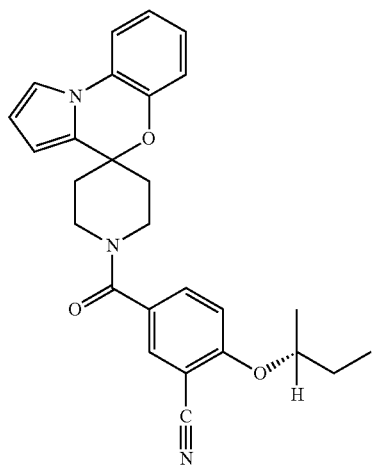 |
| 143 | 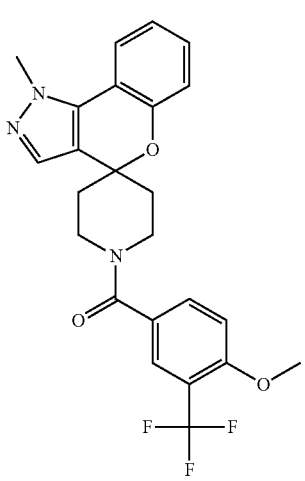 | 146 | 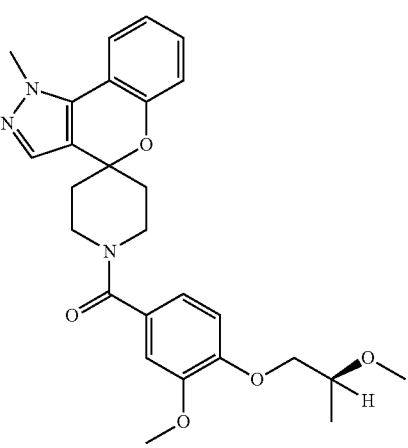 |

875
-continued
876
-continued
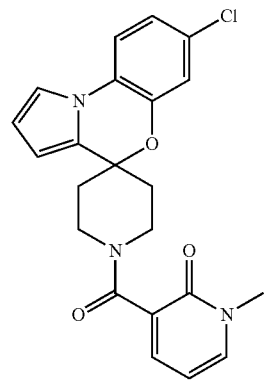
147
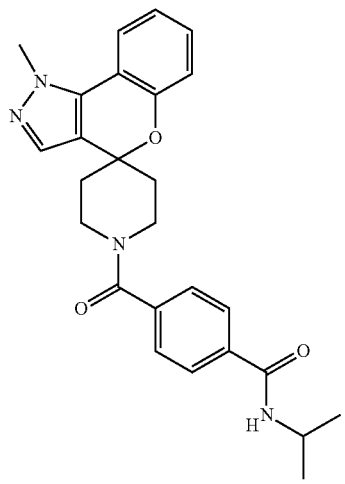
150
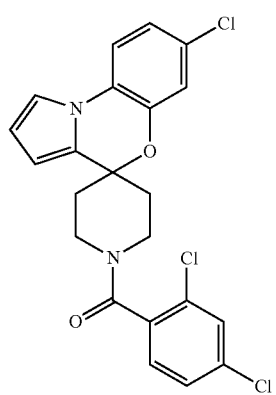
148
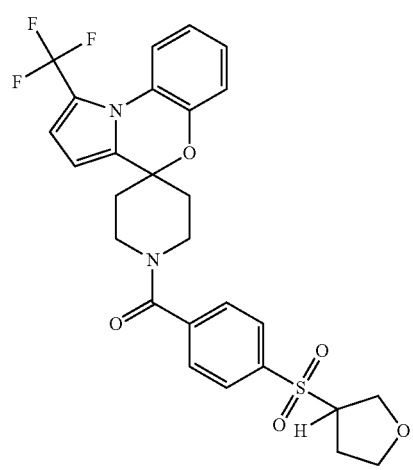
151
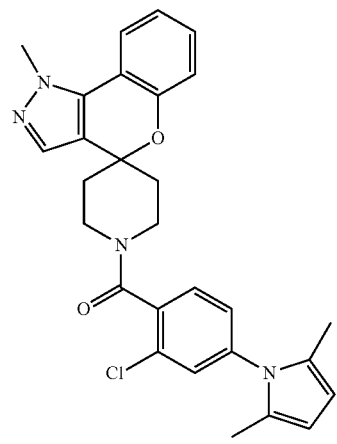
149
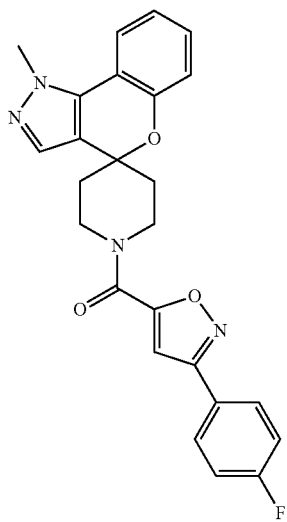
152

153
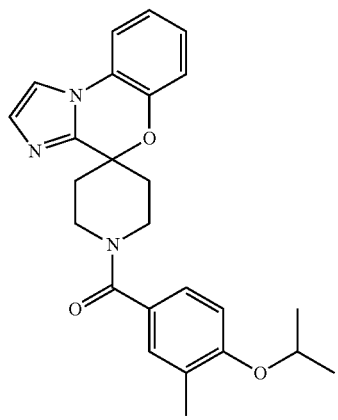
154
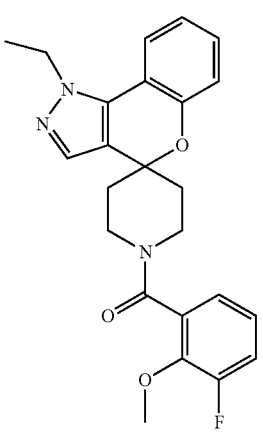
155
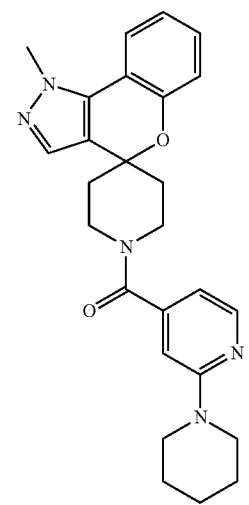
156
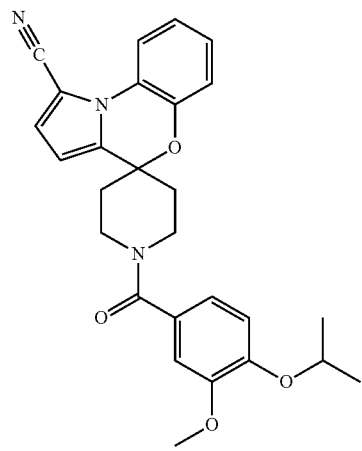
157
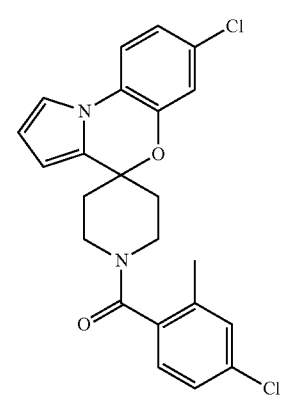
158
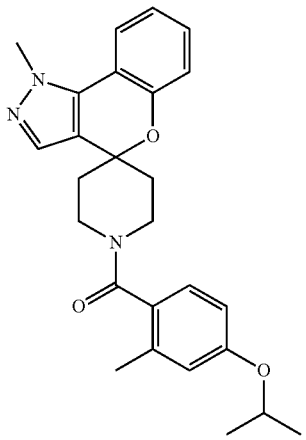

879
-continued
| | |
|---|---|
| 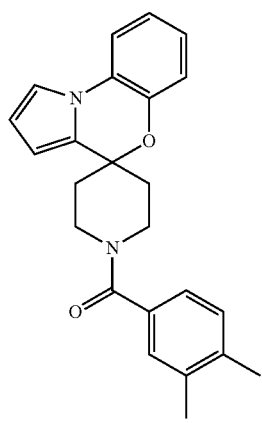 | 159 |
| 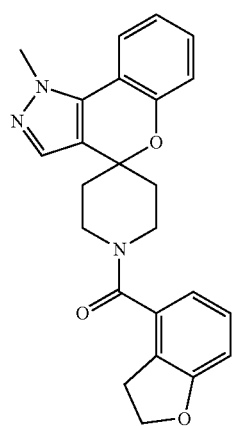 | 160 |
| 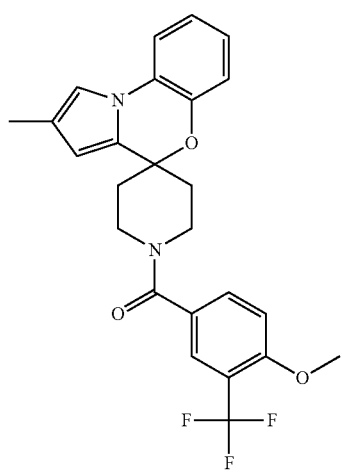 | 161 |
880
-continued
| | |
|---|---|
| 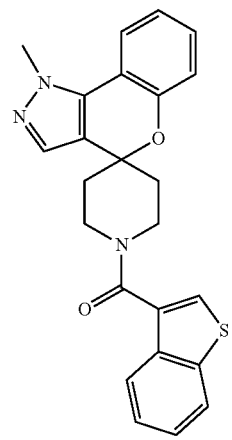 | 162 |
| 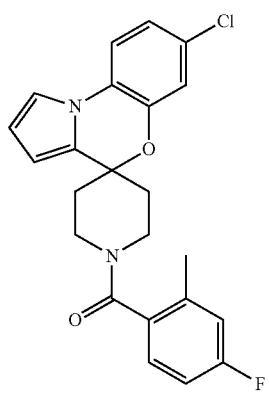 | 163 |
| 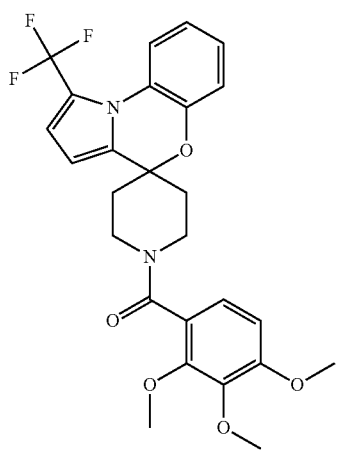 | 164 |

165 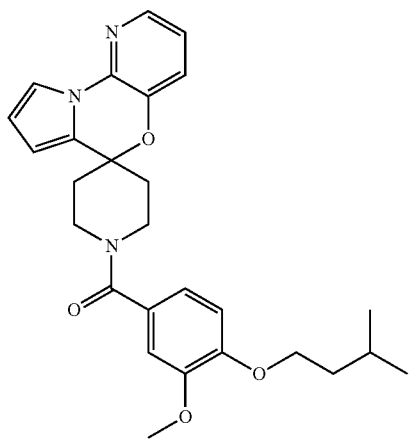
166 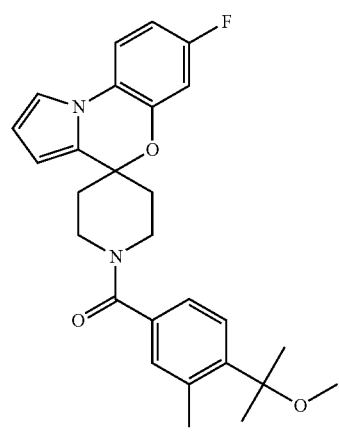
167 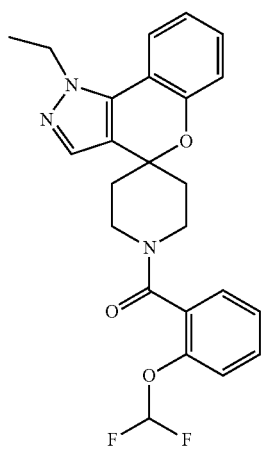
168 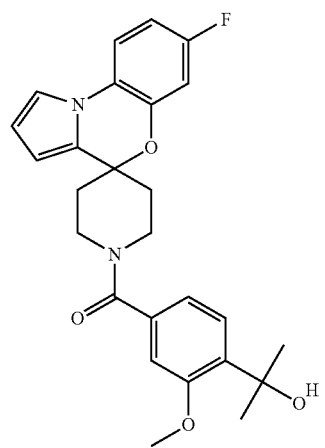
169 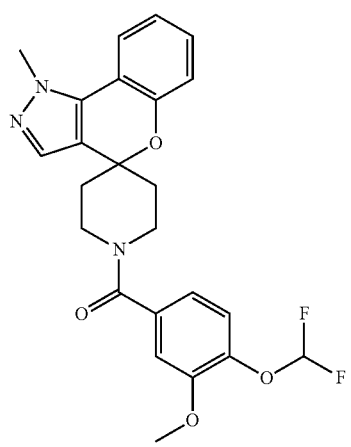
170 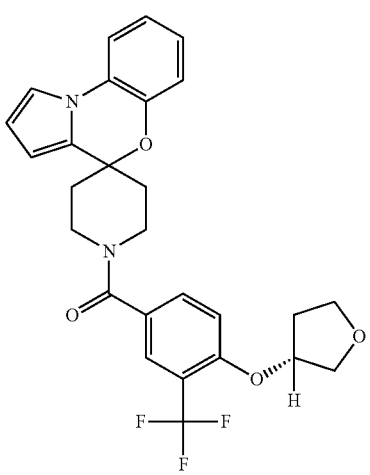

883
-continued
171
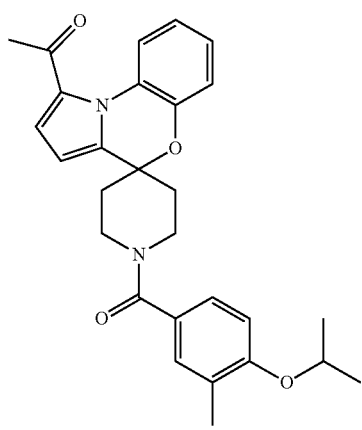
172
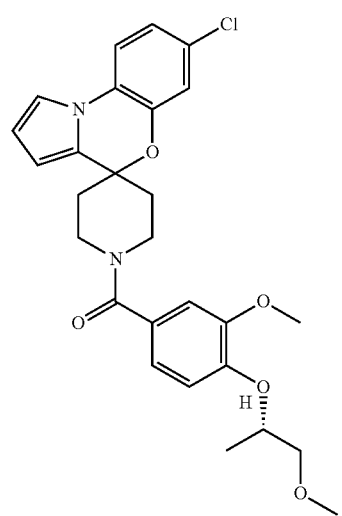
173
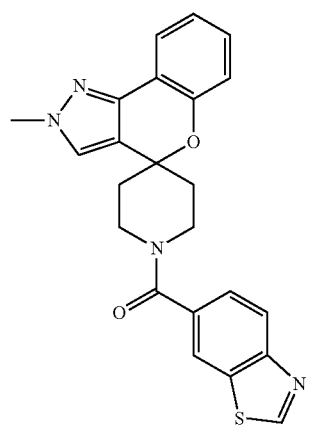
884
-continued
174
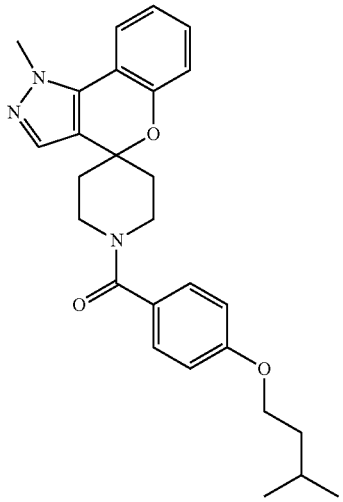
175
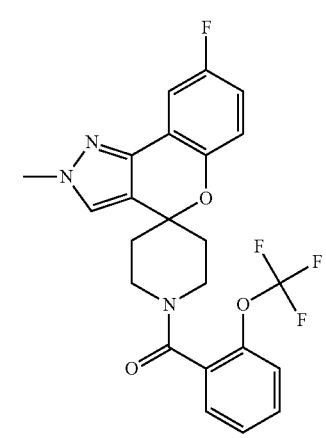
176
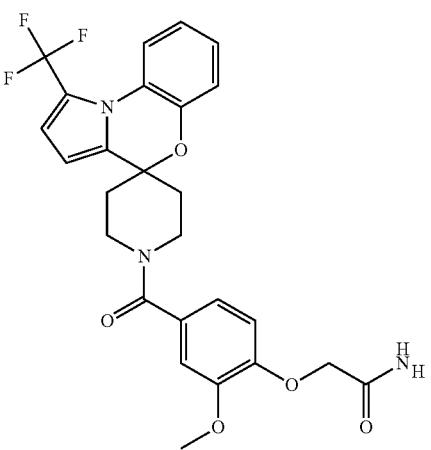

177 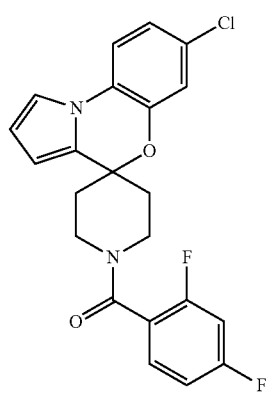
178 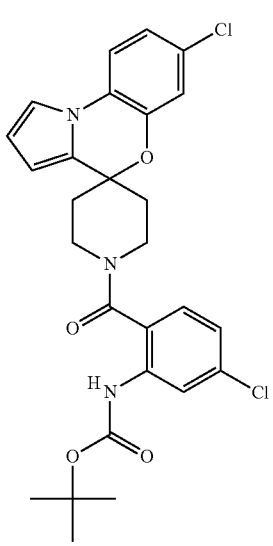
179 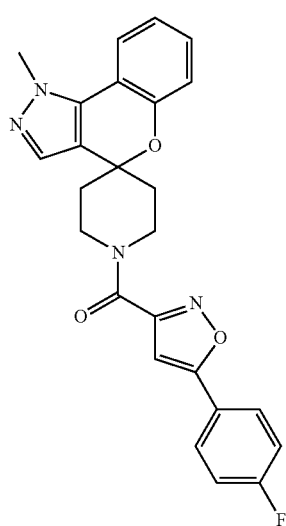
180 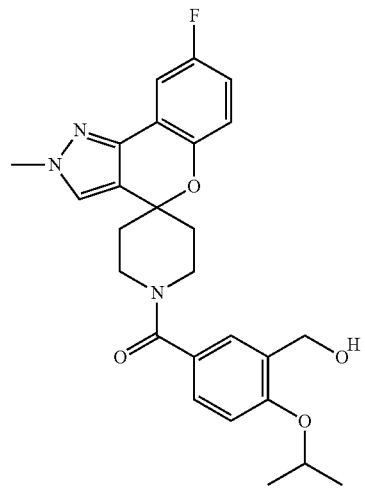
181 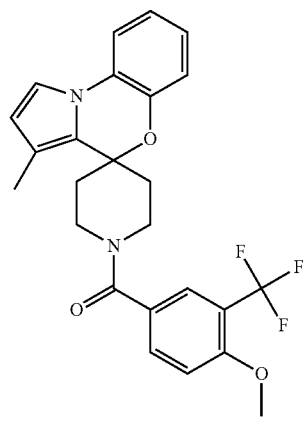
182 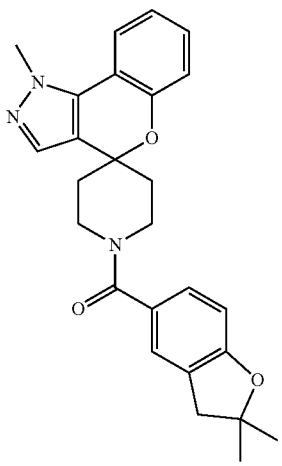

887
-continued
183
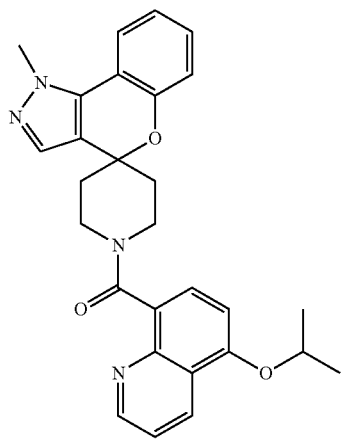
184
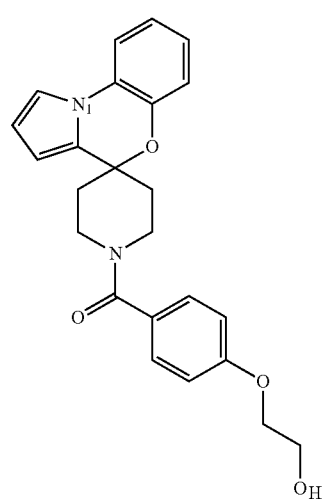
185
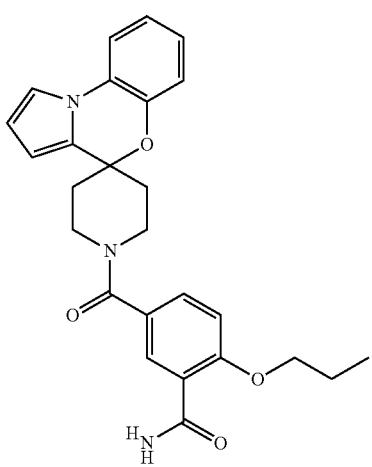
888
-continued
186
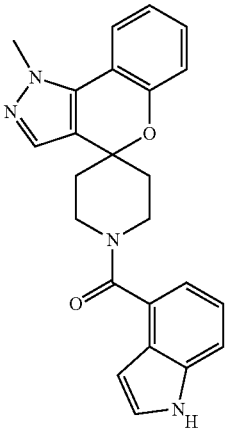
187
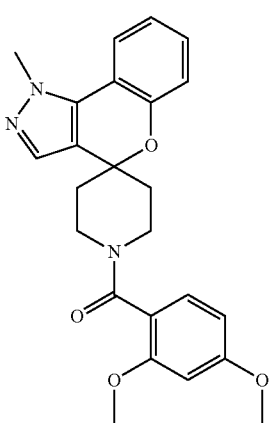
188
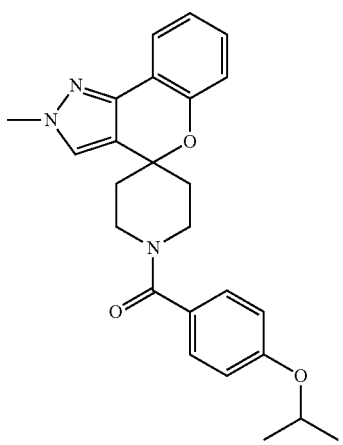

889 890
-continued -continued
189
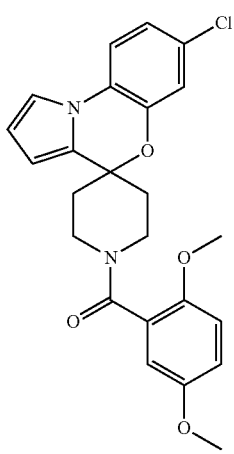
192
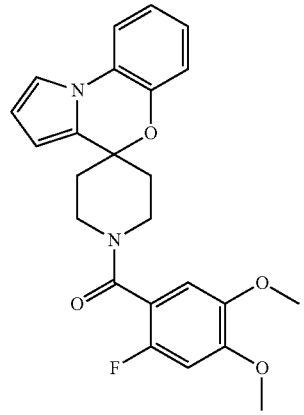
190
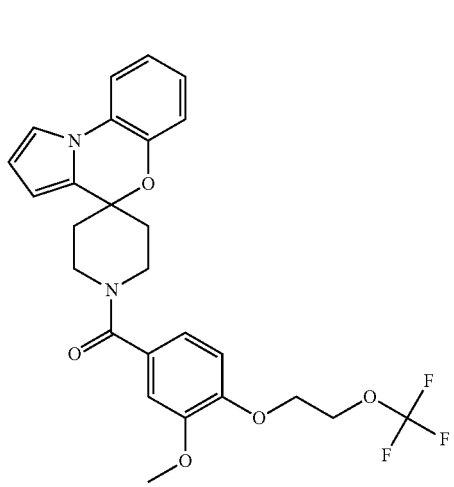
193
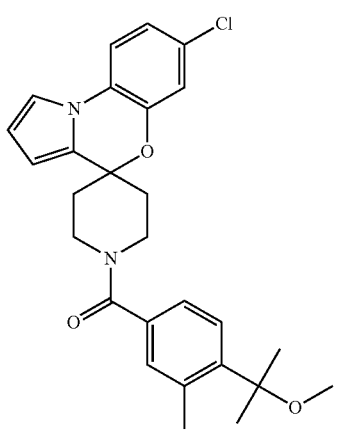
191
194
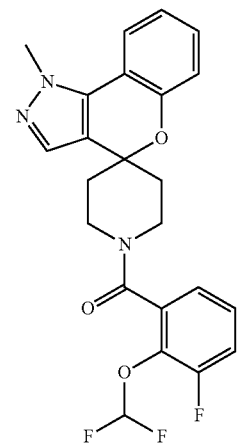

| 195 | 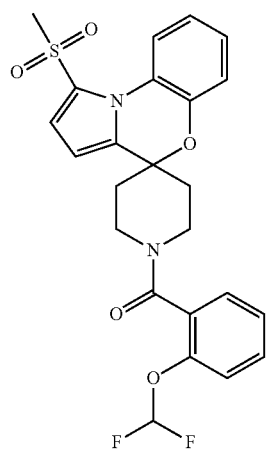 | 198 | 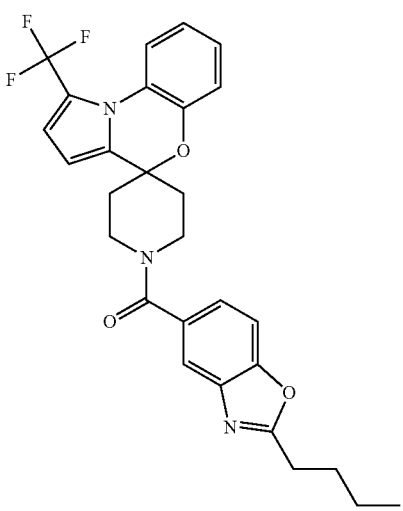 |
| 196 | 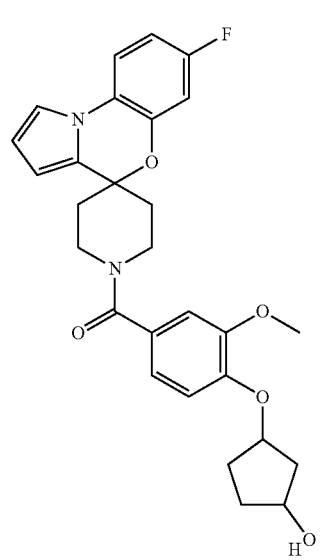 | 199 | 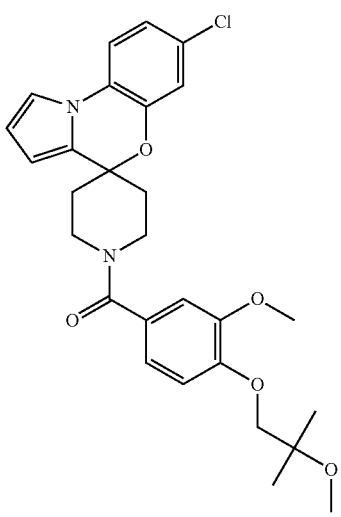 |
| 197 | 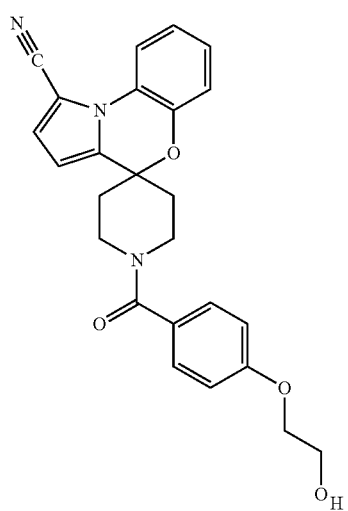 | 200 | 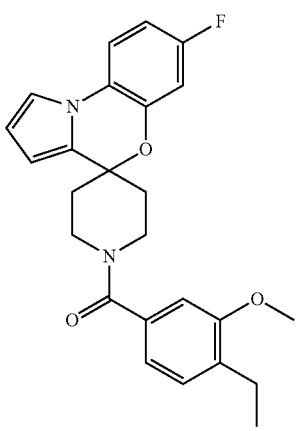 |

201 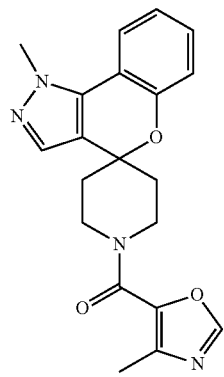
202 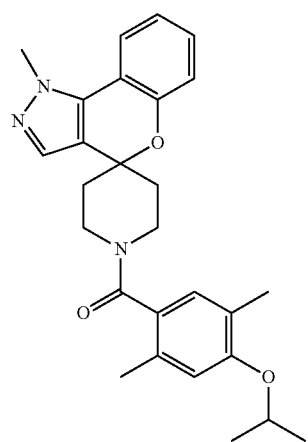
203 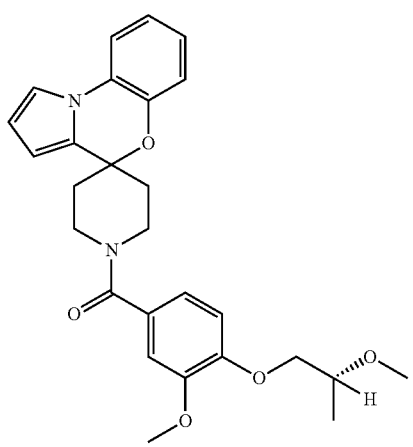
204 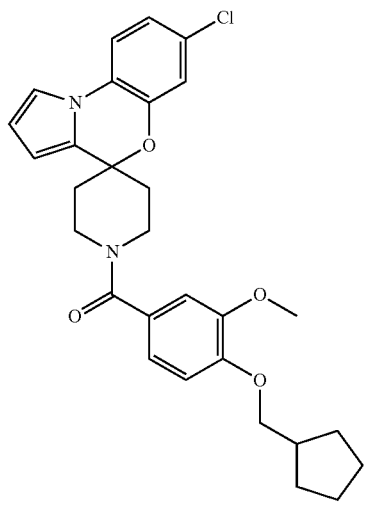
205 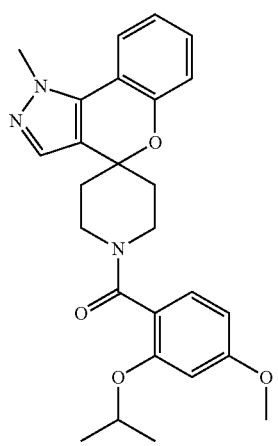
206 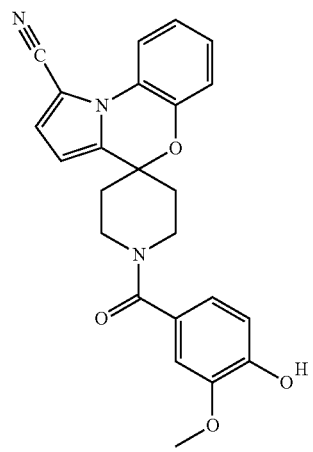

207
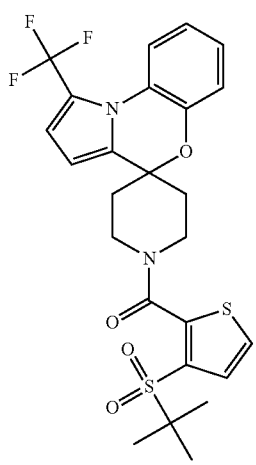
210
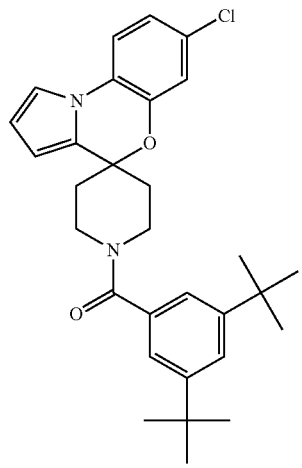
208
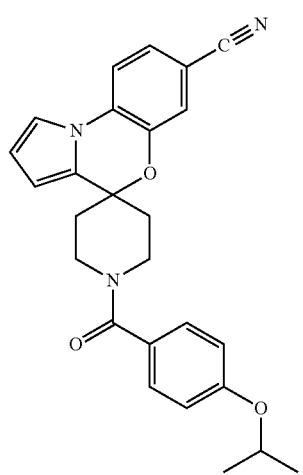
211
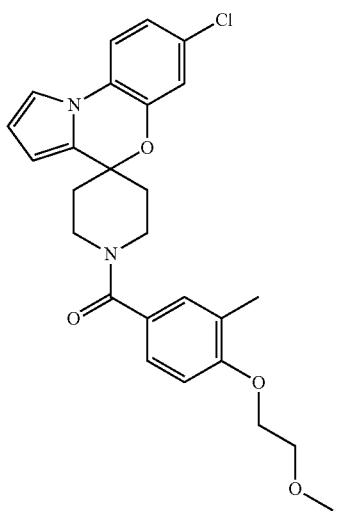
209
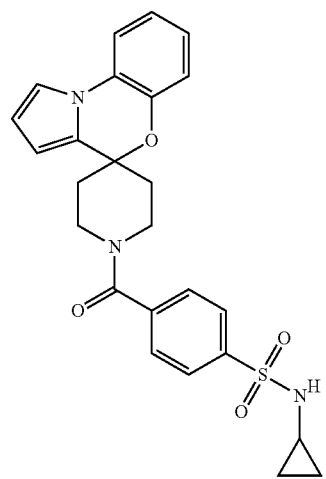
212
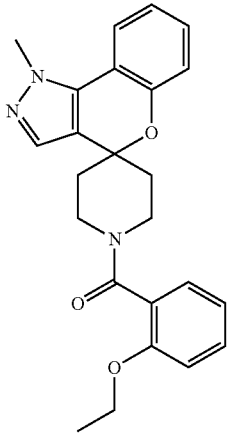

| 213 | 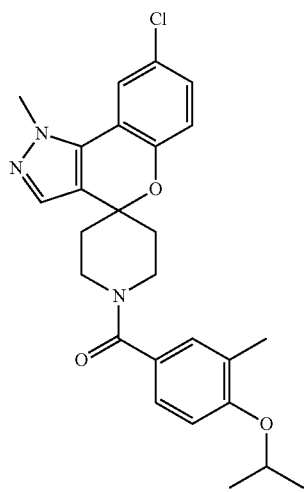 | 216 | 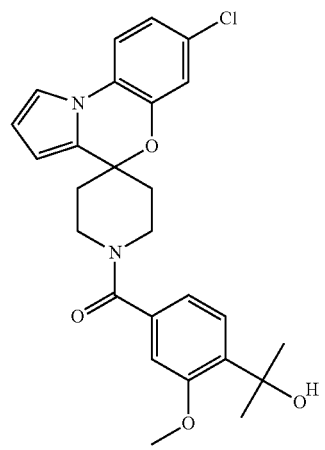 |
| 214 | 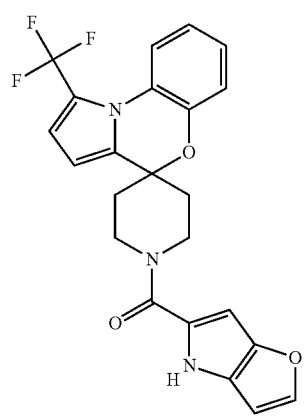 | 217 | 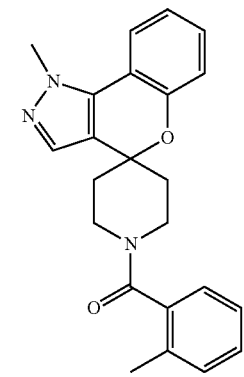 |
| 215 | 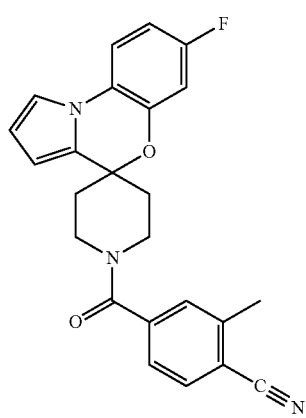 | 218 | 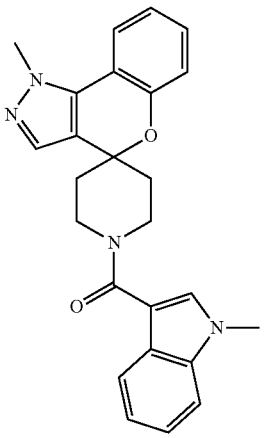 |

899
-continued
900
-continued
219
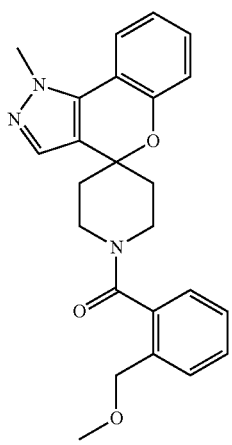
222
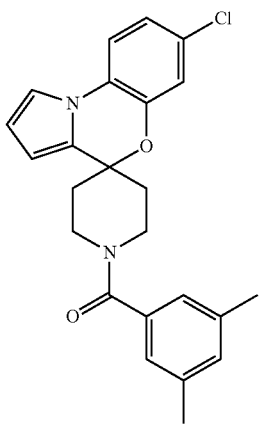
220
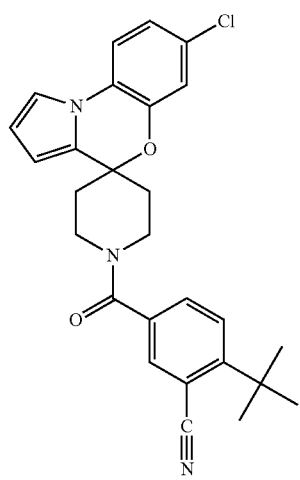
223
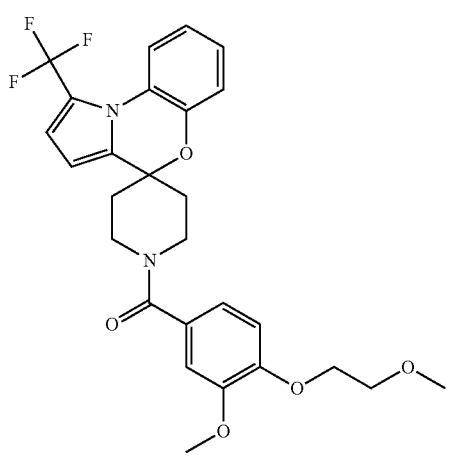
221
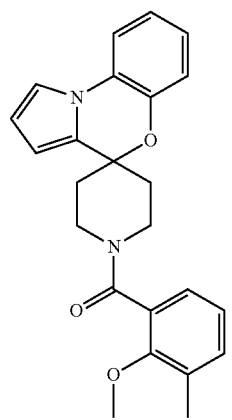
224
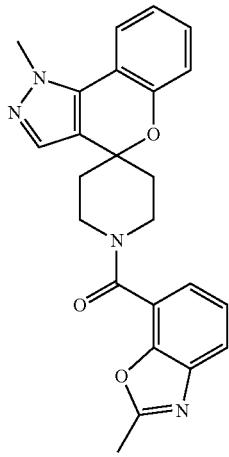

901 902
225
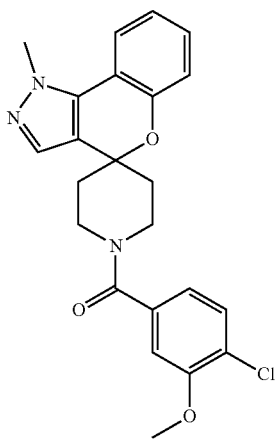
228
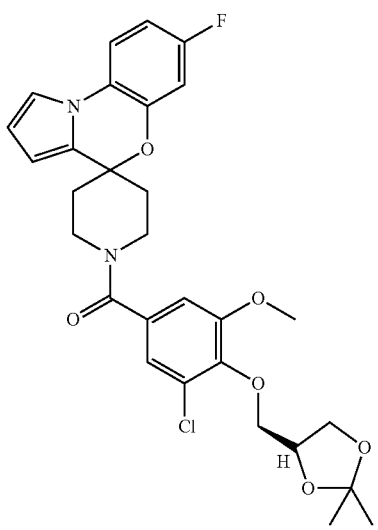
226
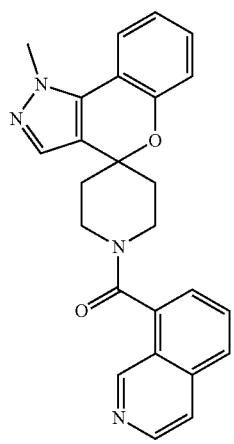
229
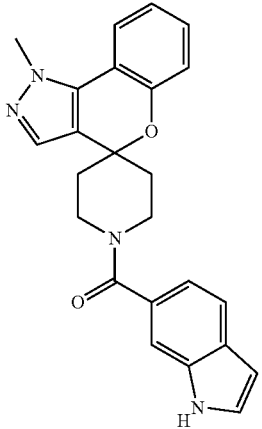
227
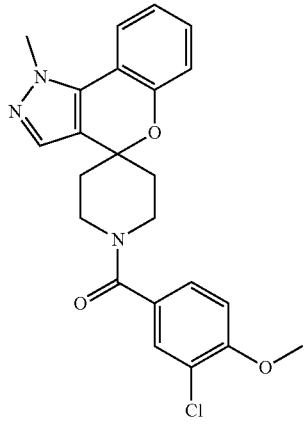
230

903
-continued
234
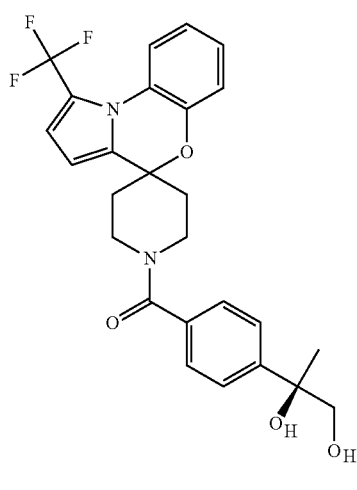
231
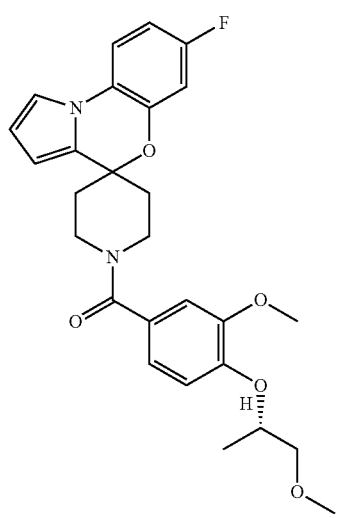
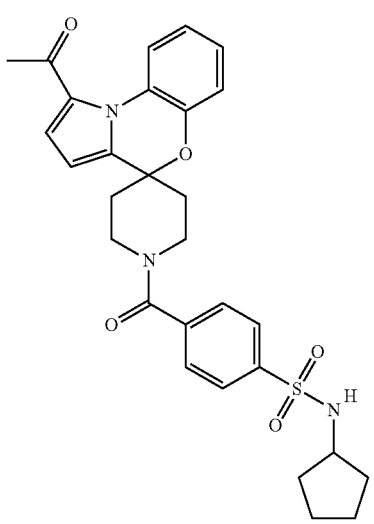
232
235
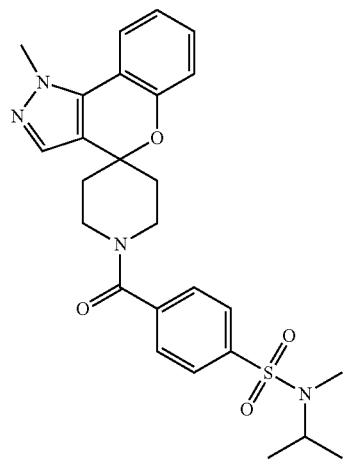
233
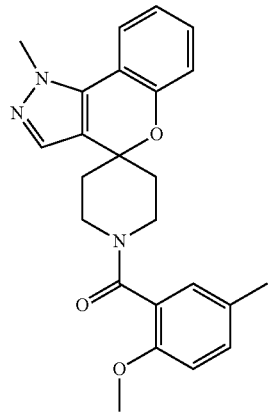
236

237
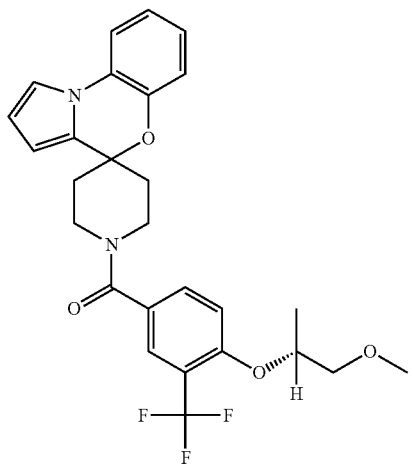
238
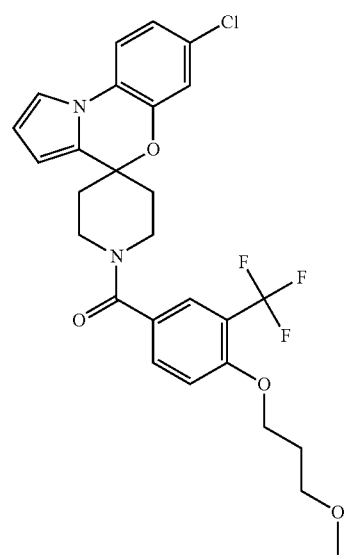
239
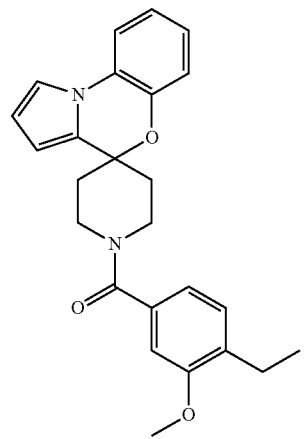
240
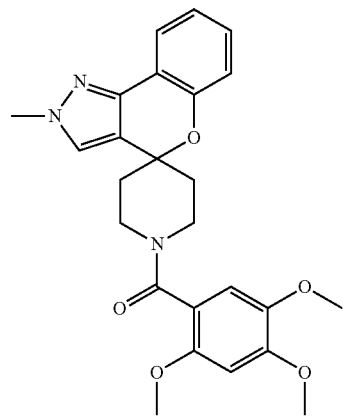
241
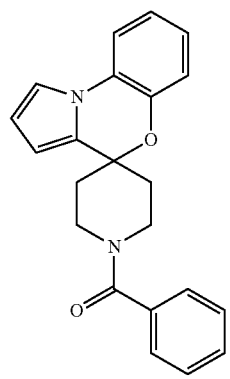
242
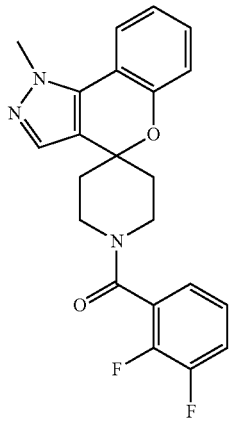

243
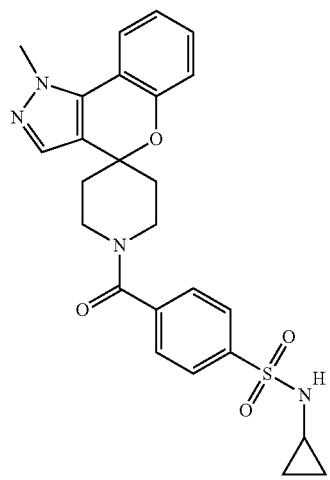
244
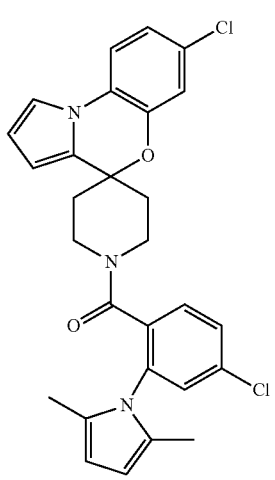
245
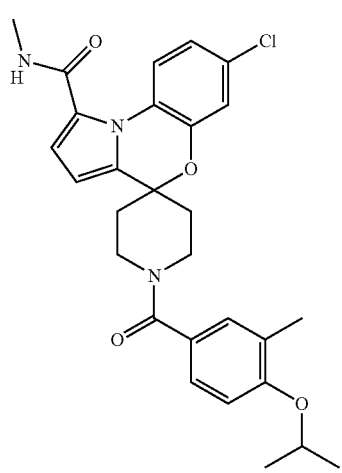
246
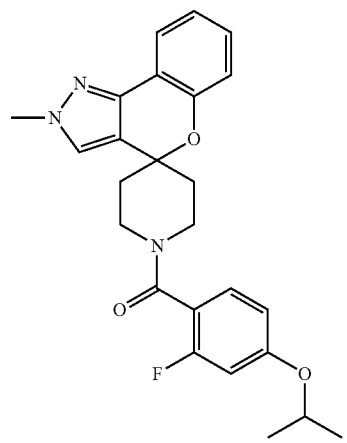
247
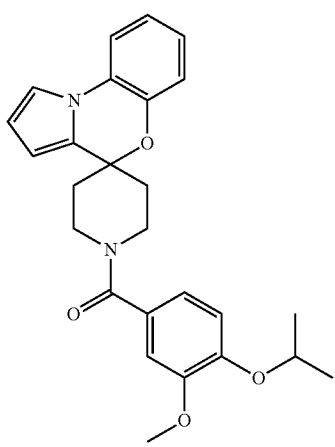
248
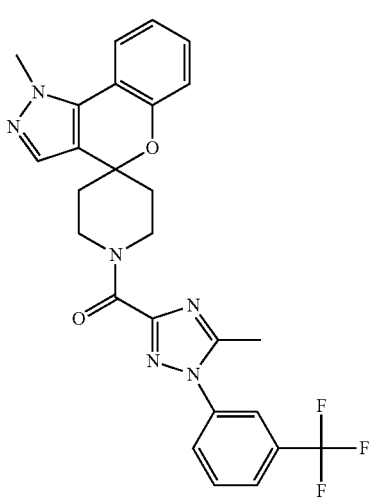

-continued
| | |
|---|---|
| 249 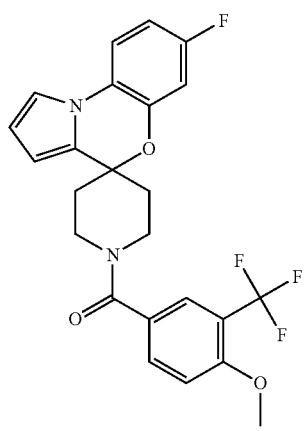 | 252 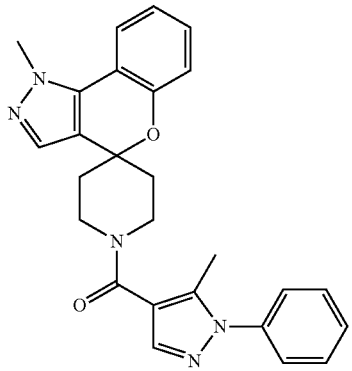 |
| 250 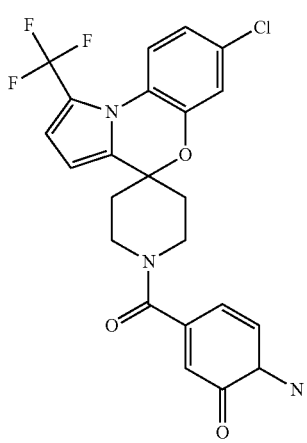 | 253 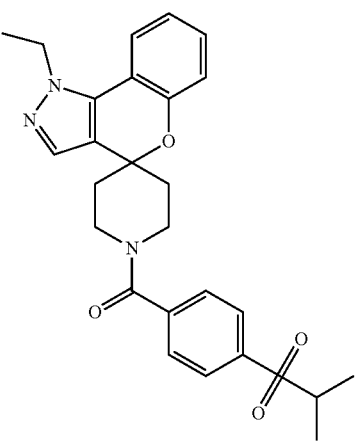 |
| 251 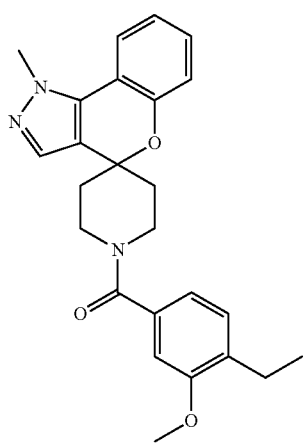 | 254 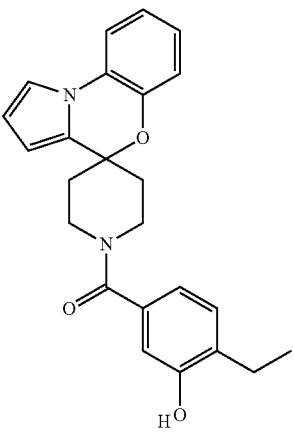 |

255
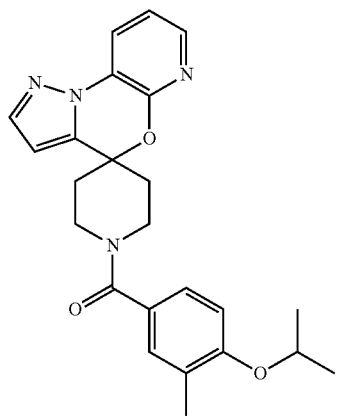
256
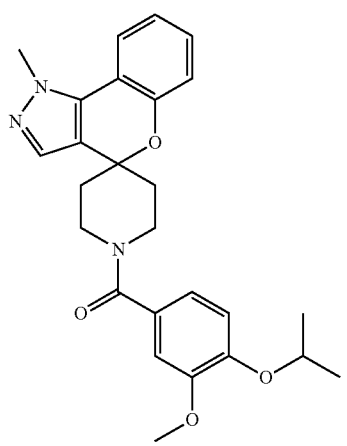
257
258
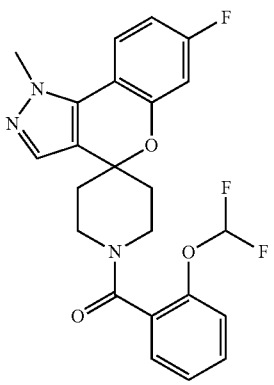
259
260
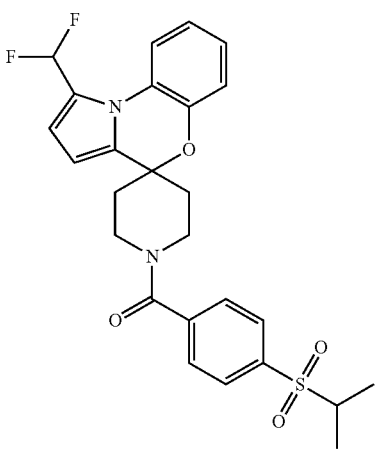

913
-continued
261
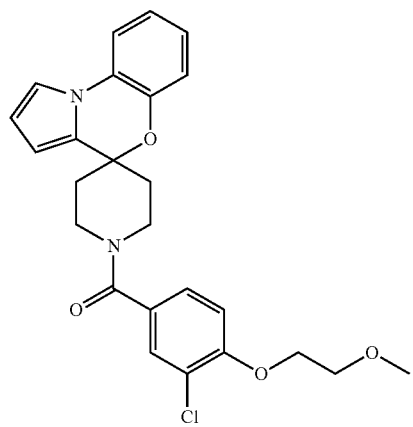
262
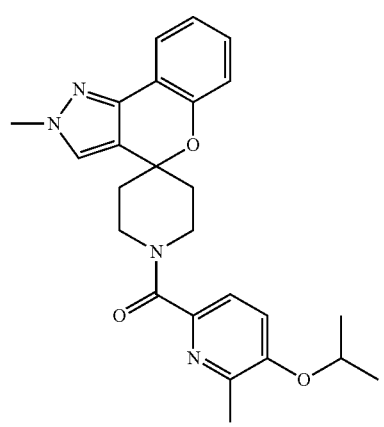
263
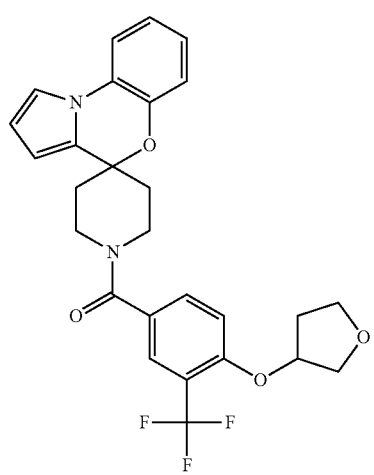
914
-continued
264
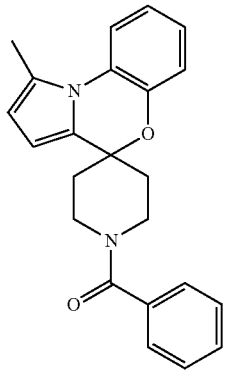
265
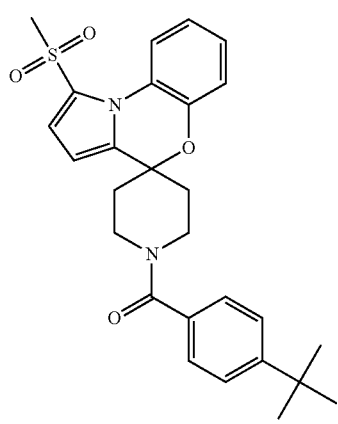
266
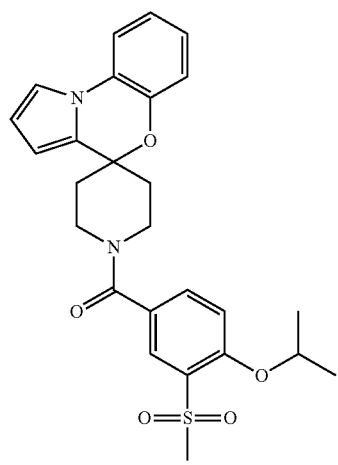

267 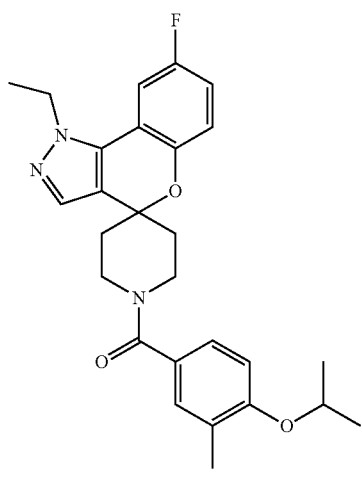
268 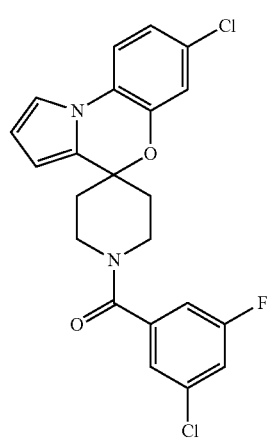
269 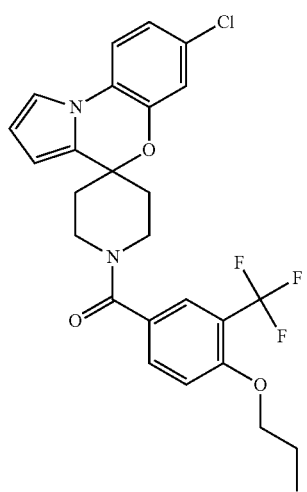
270 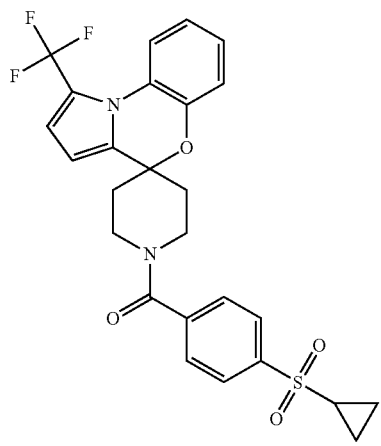
271 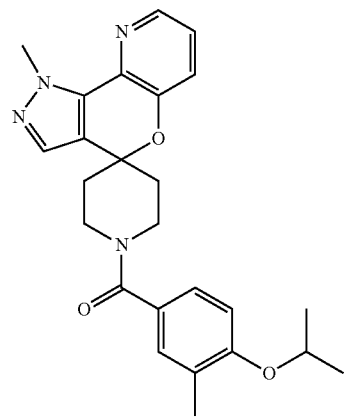
272 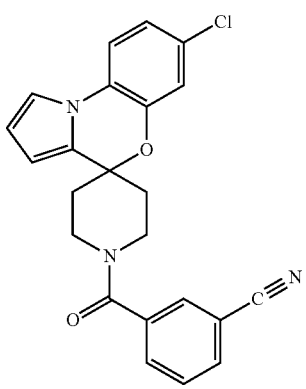

917
-continued
273
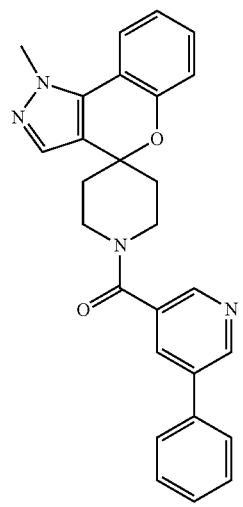
274
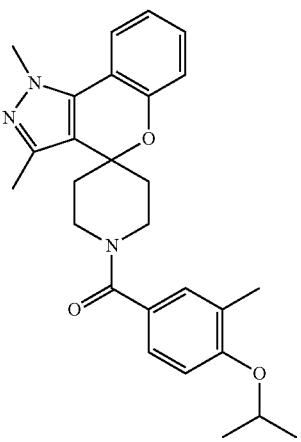
275
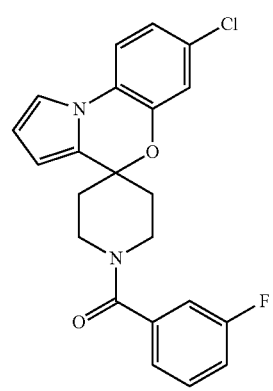
918
-continued
276
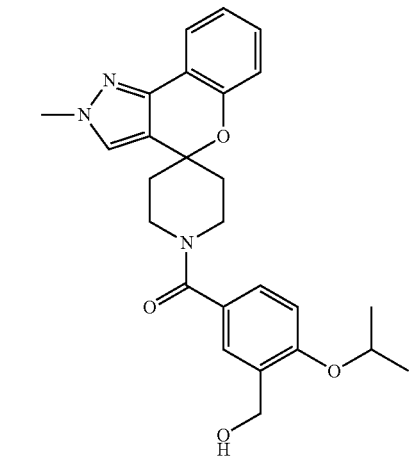
277
278
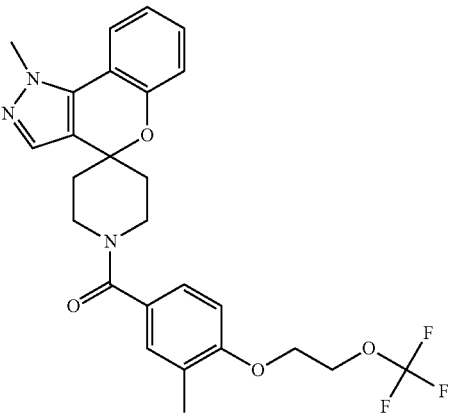

| 279 | 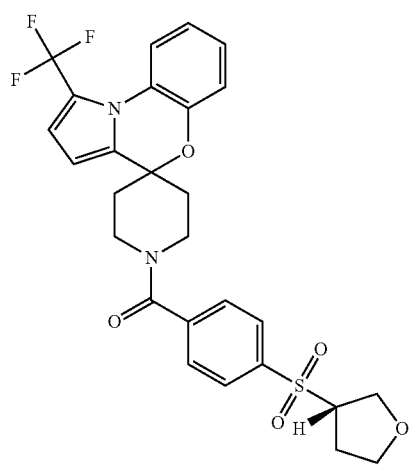 | 282 | 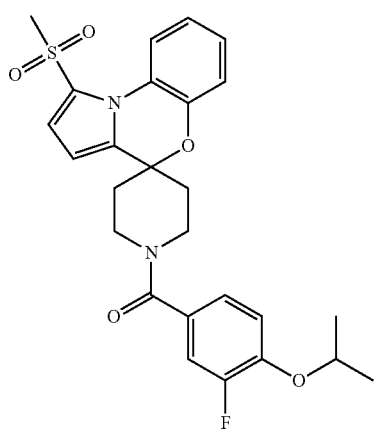 |
| 280 | 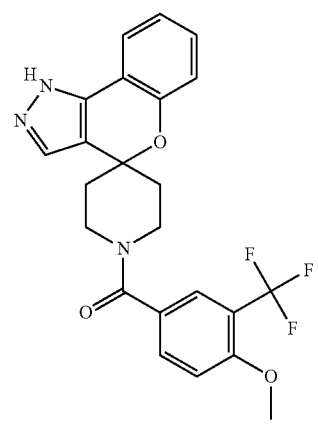 | 283 | 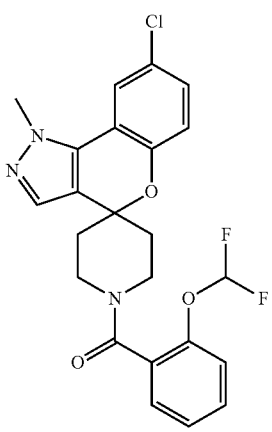 |
| 281 | 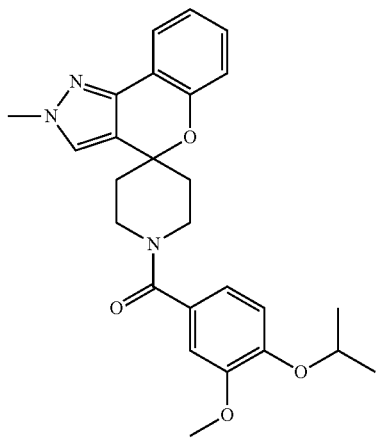 | 284 | 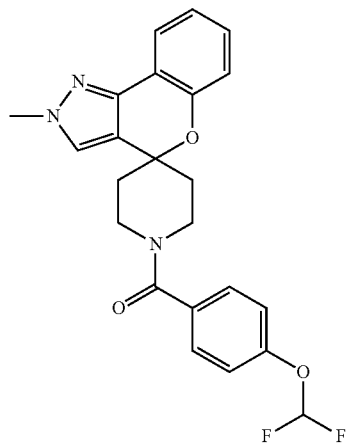 |

| 921 | 922 |
|---|---|
| 285 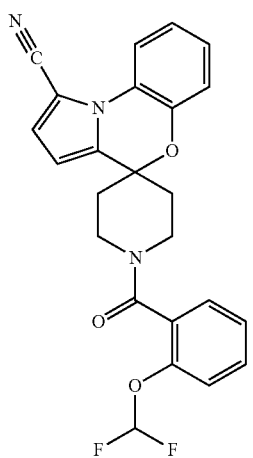 | 288 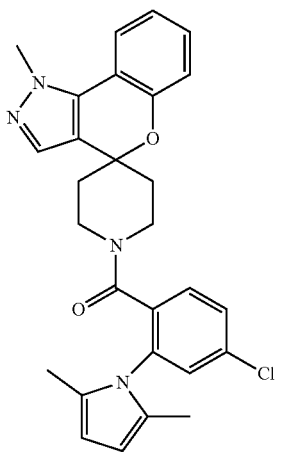 |
| 286 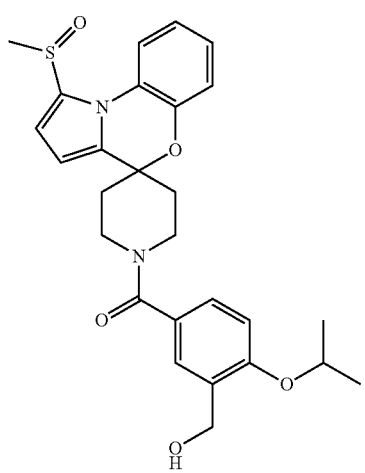 | 289 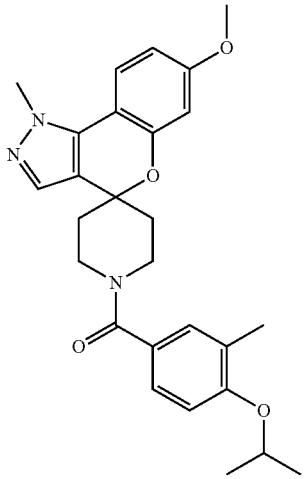 |
| 287 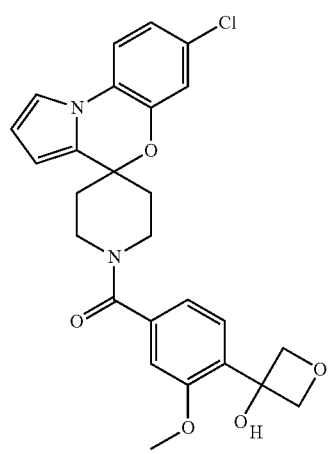 | 290 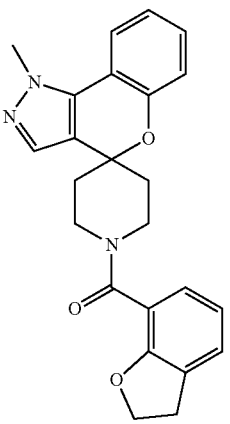 |

923
-continued
291
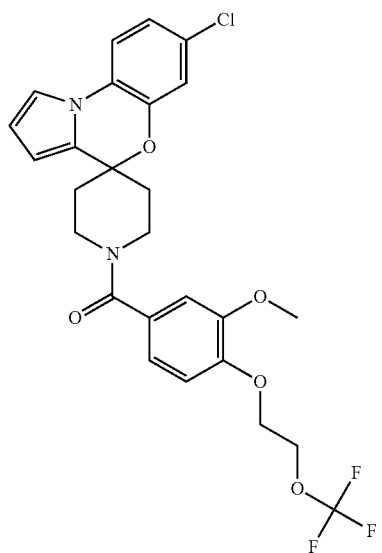
292
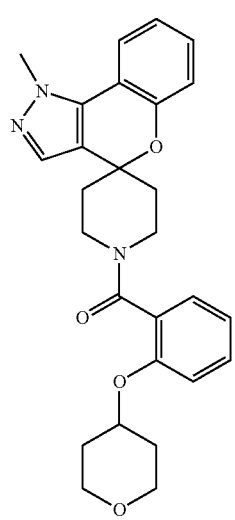
293
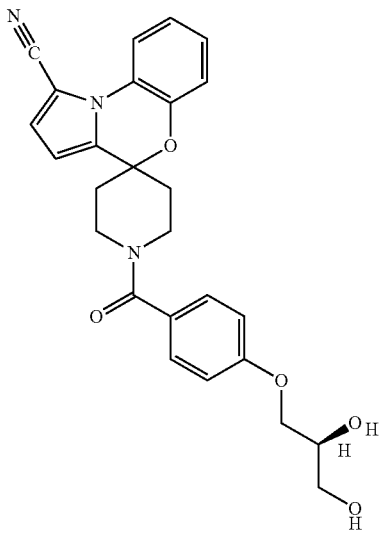
924
-continued
294
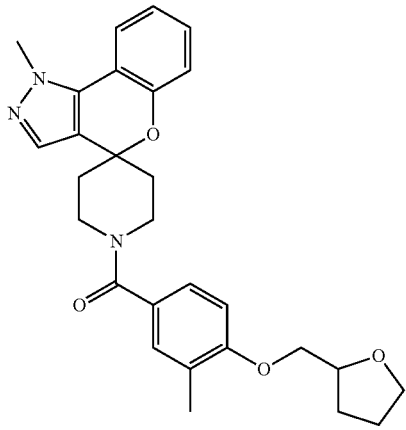
295
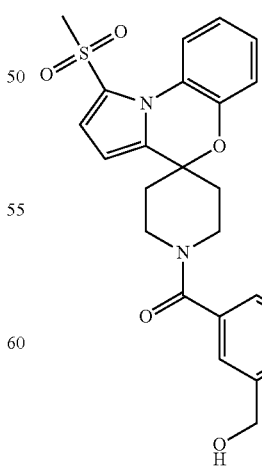
296

| 297 | 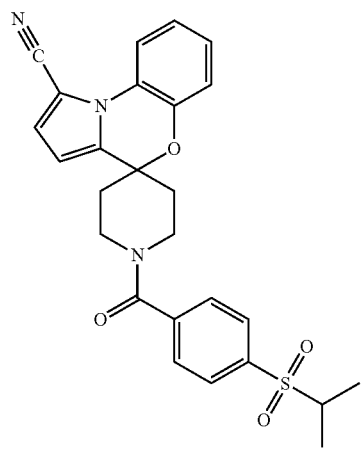 | 300 | 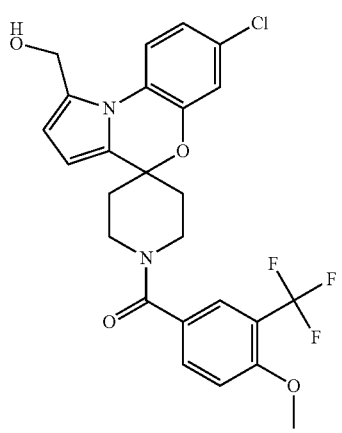 |
| 298 | 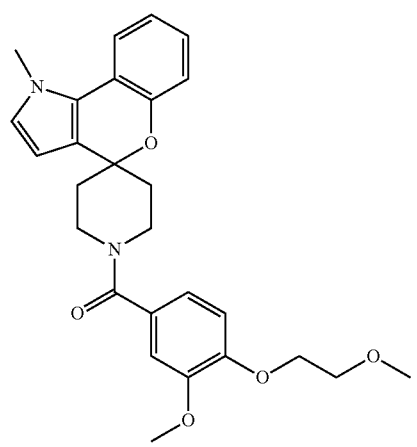 | 301 | 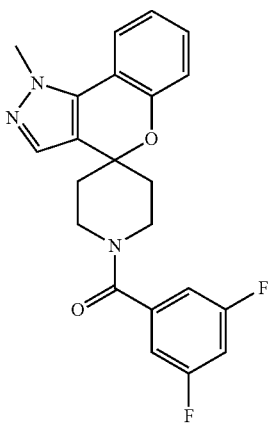 |
| 299 | 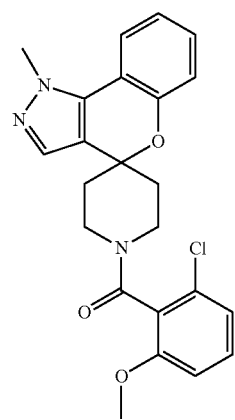 | 302 | 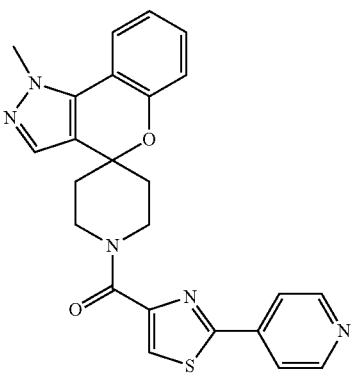 |

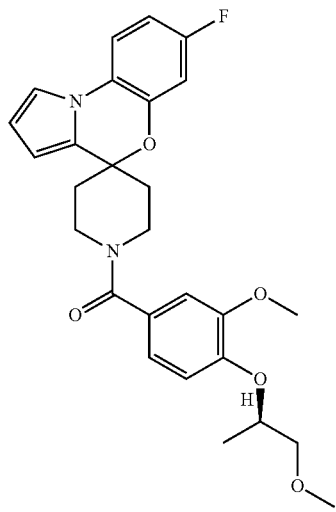
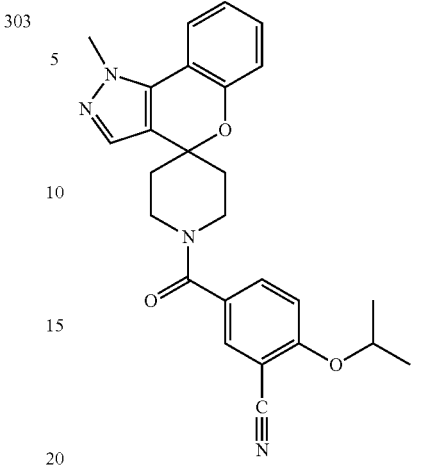
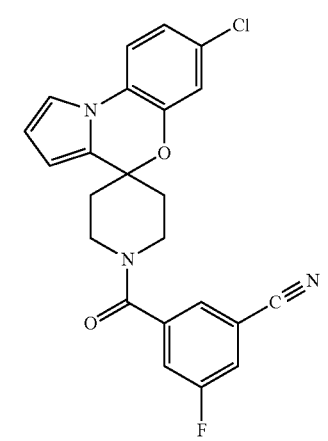
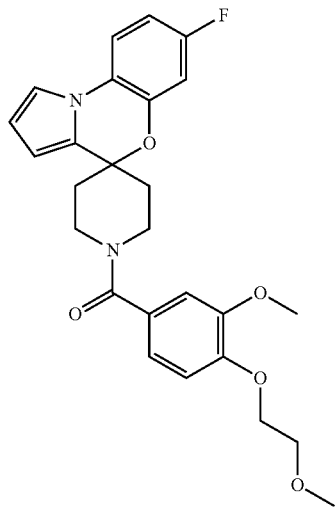

929
-continued
930
-continued
309
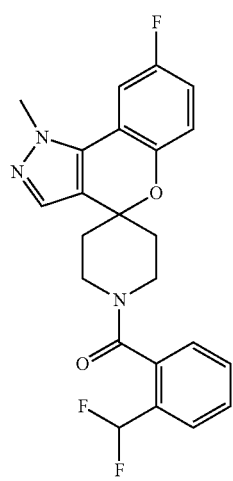
312
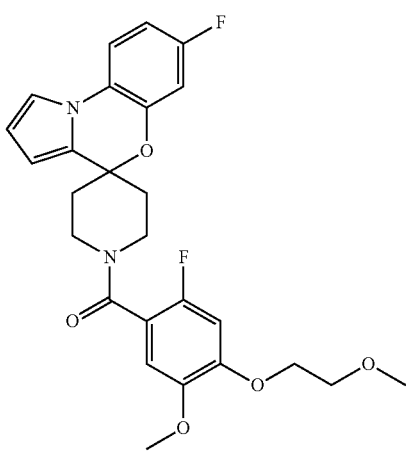
310
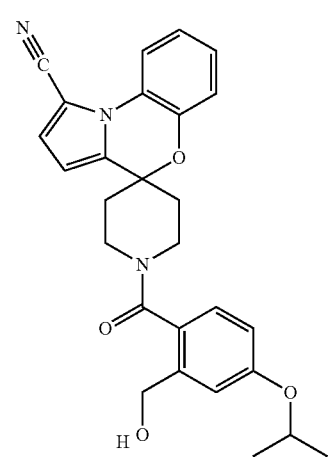
313
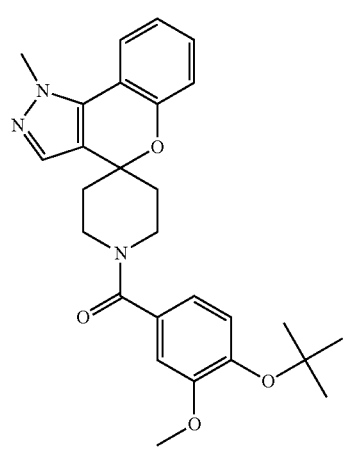
311
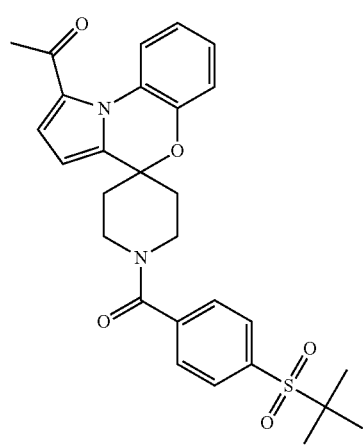
314
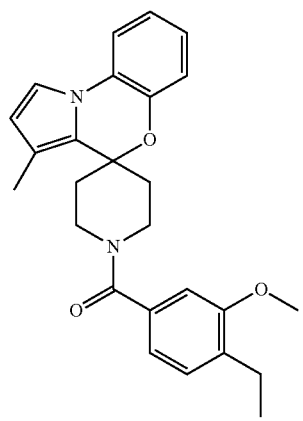

931
-continued
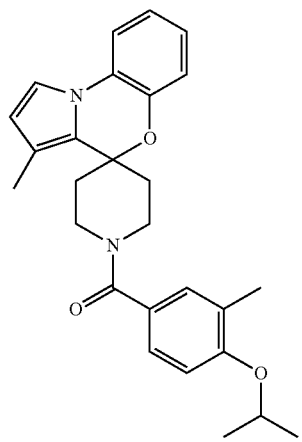
315
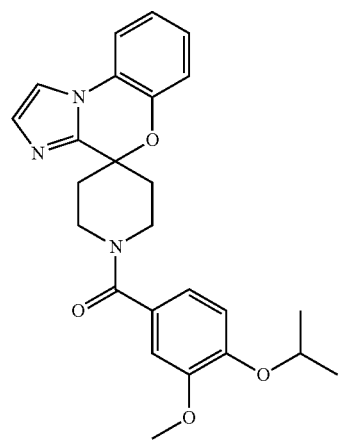
316
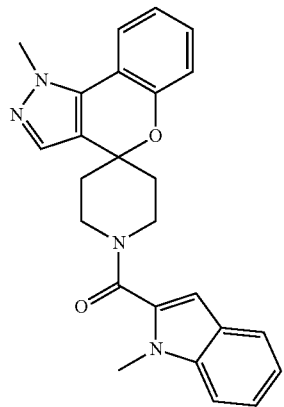
317
932
-continued
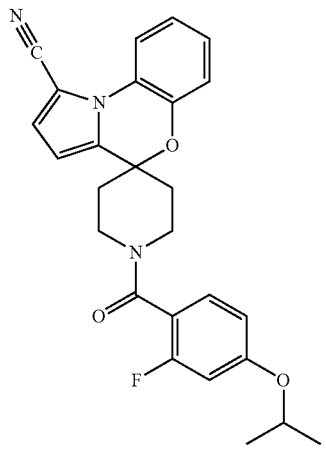
318
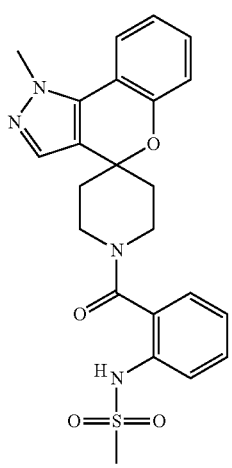
319
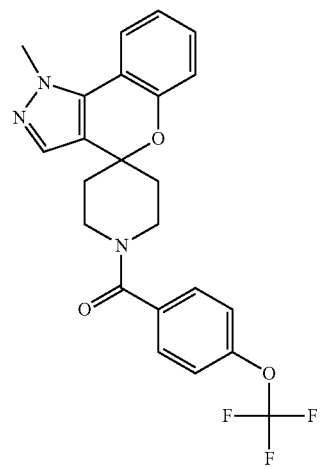
320

| 321 | 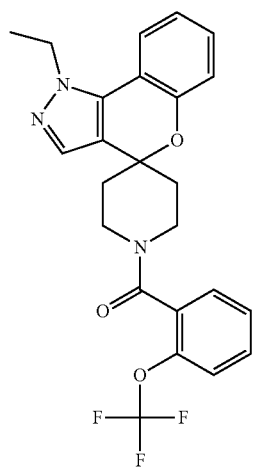 | 324 | 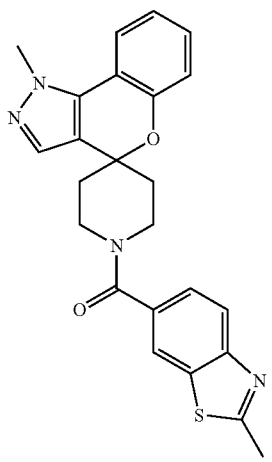 |
| 322 | 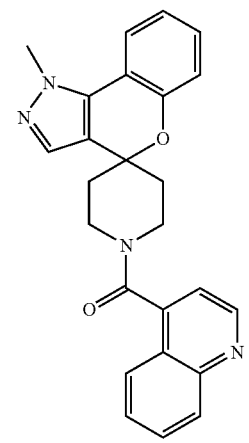 | 325 | 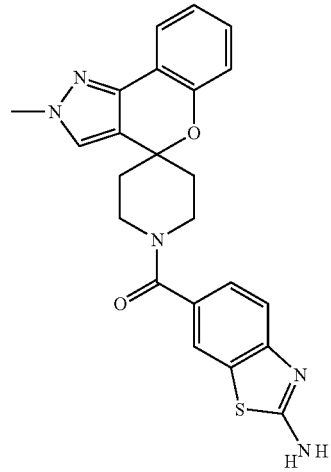 |
| 323 | 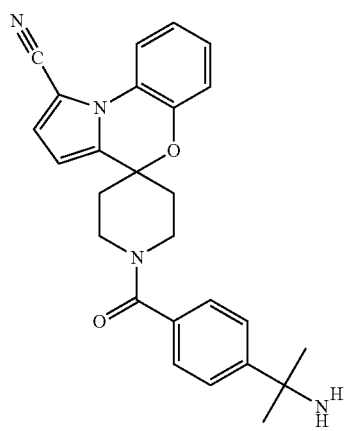 | 326 | 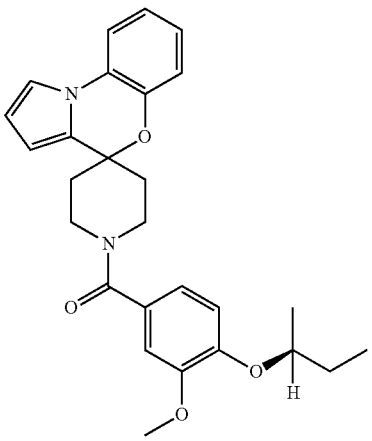 |

| 935 -continued | 936 -continued |
|---|---|
| 327 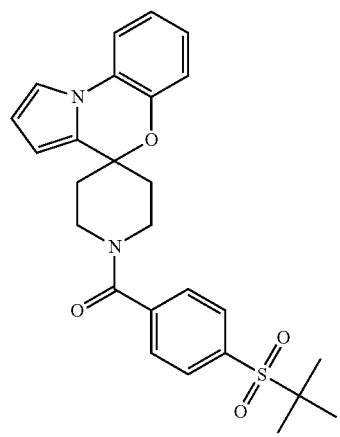 | 330 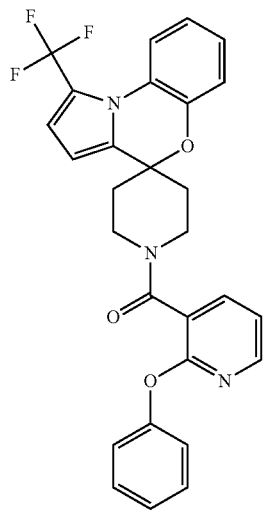 |
| 328 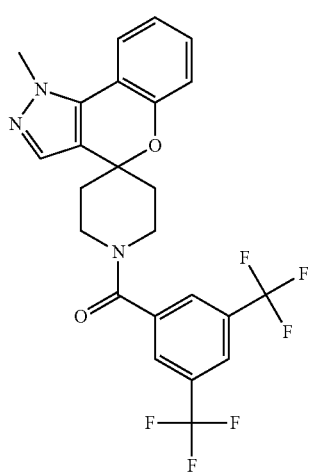 | 331 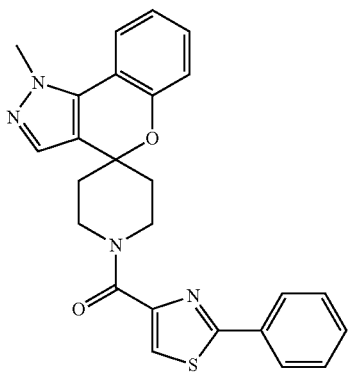 |
| 329 | 332 |

| 937 -continued | 938 -continued |
|---|---|
| 333 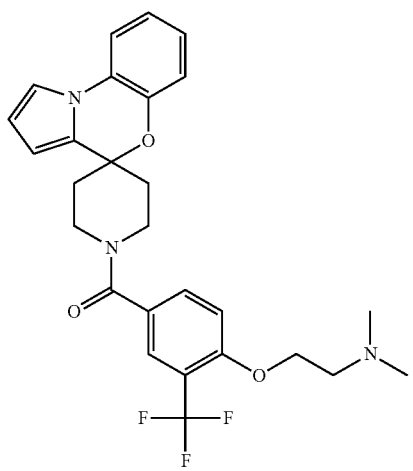 | 336 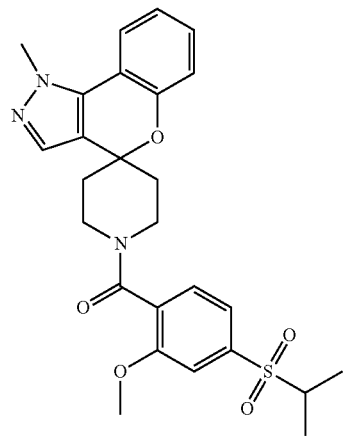 |
| 334 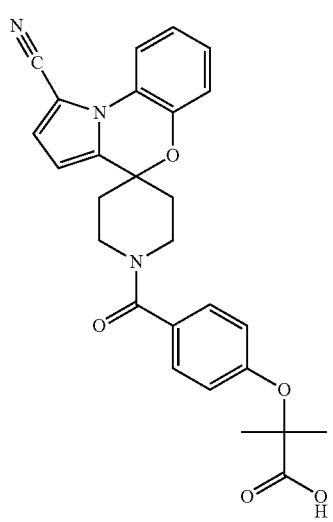 | 337 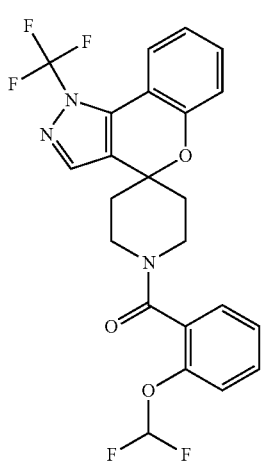 |
| 335 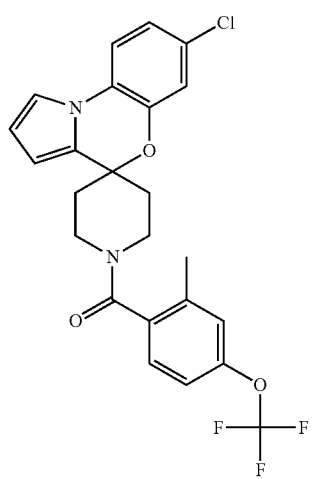 | 338 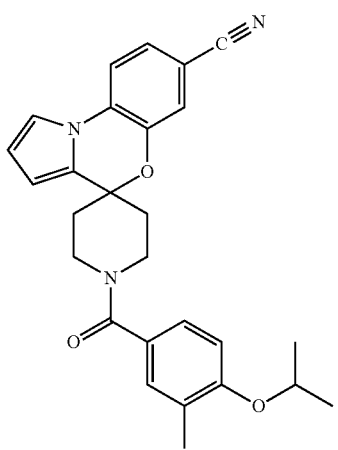 |

| 939 -continued | 940 -continued |
|---|---|
| 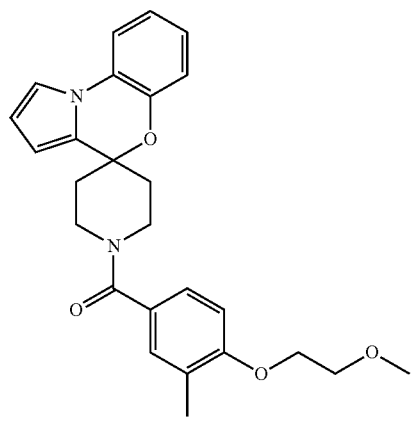 | 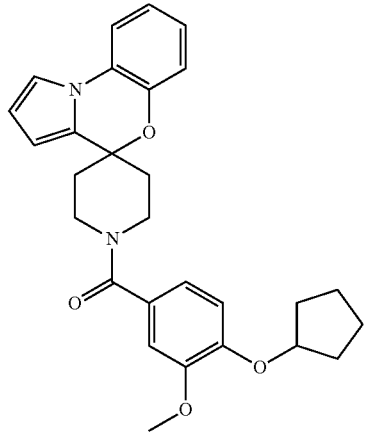
339 |
| 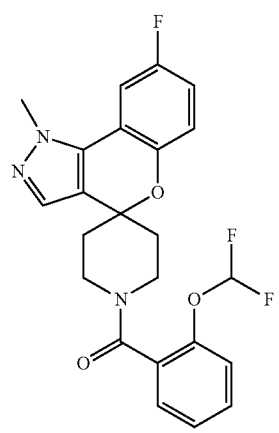 | 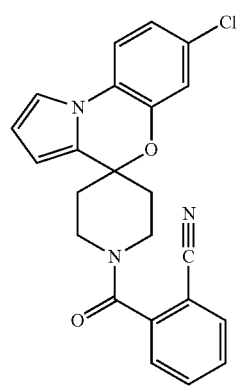
340 |
| 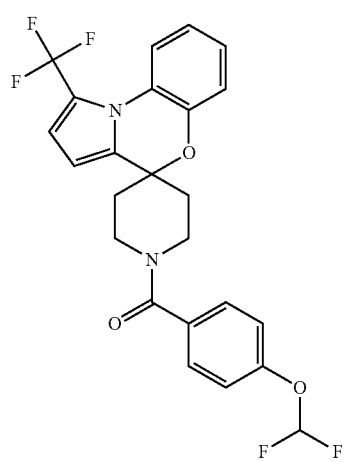 | 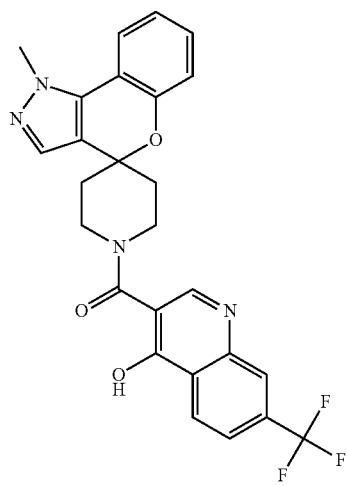
341 |
342
343
344

345
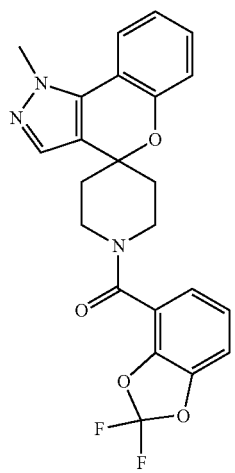
346
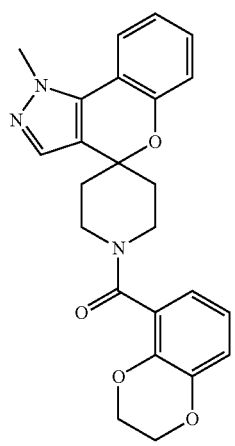
347
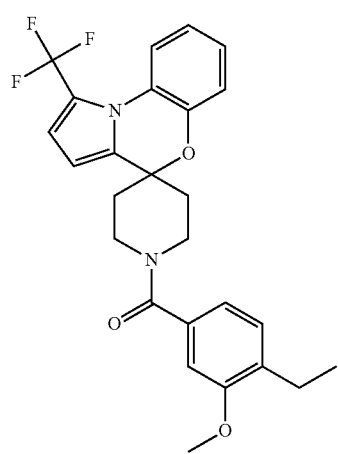
348
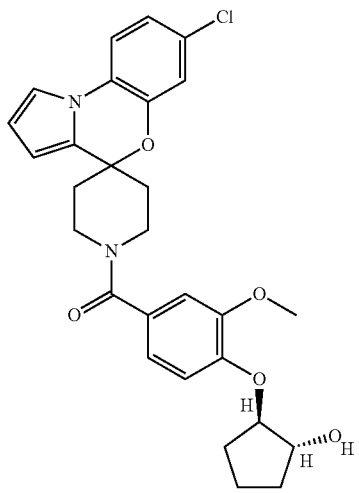
349
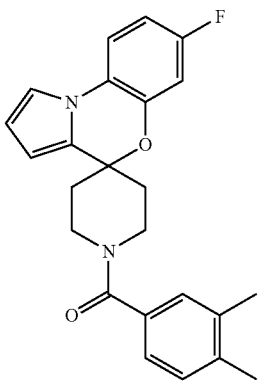
350

943
-continued
944
-continued
351 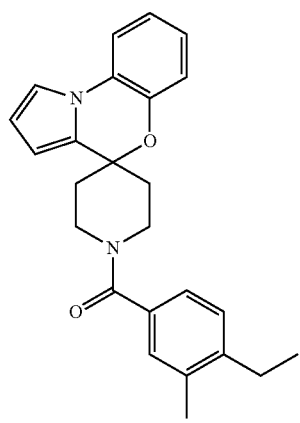
354 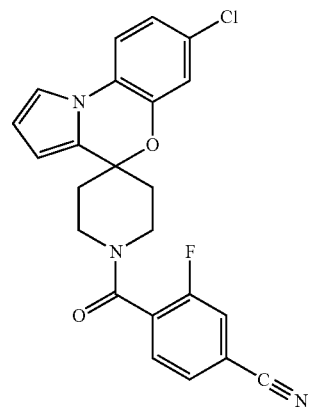
352 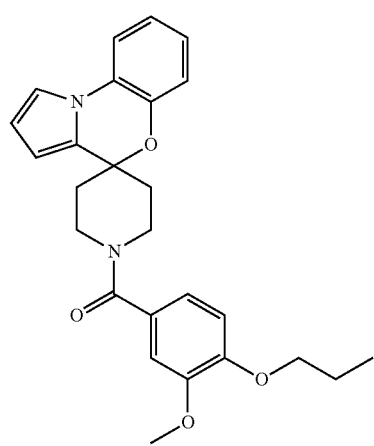
355 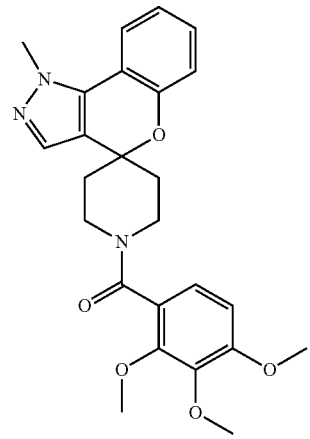
353 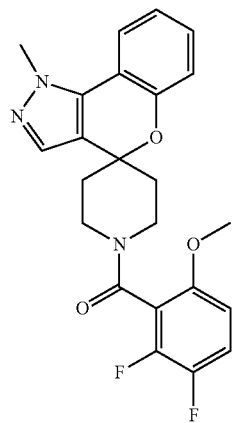
356 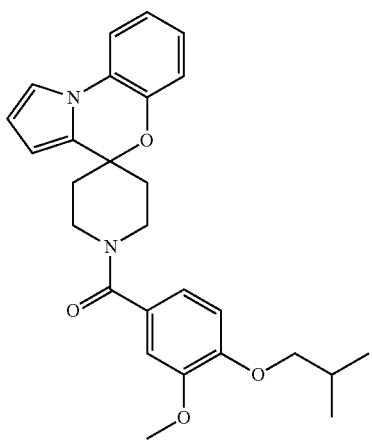

945
-continued
| | |
|---|---|
| 357 | 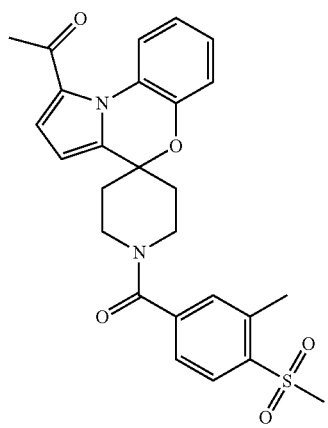 |
| 358 | 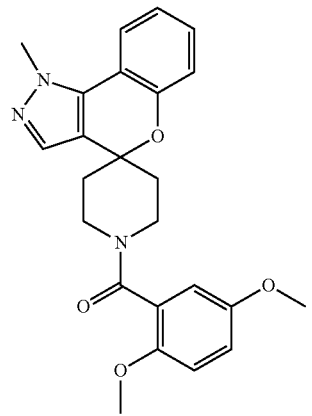 |
| 359 | 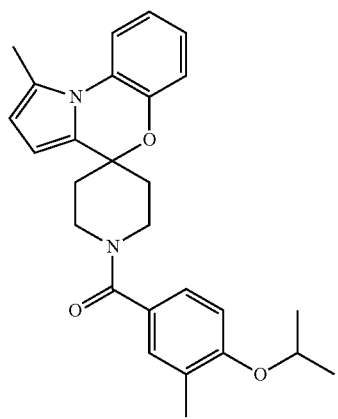 |
946
-continued
| | |
|---|---|
| 360 | 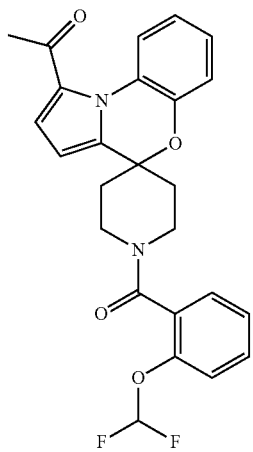 |
| 361 | 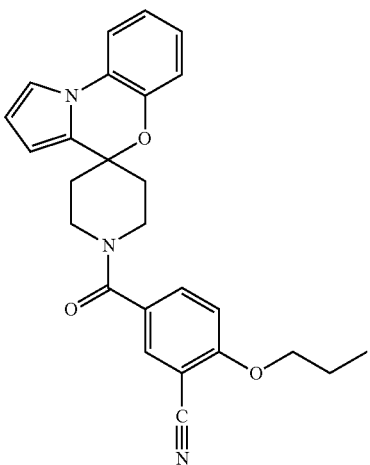 |
| 362 | |

947
-continued
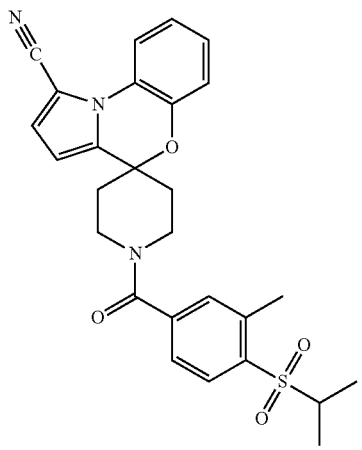
363
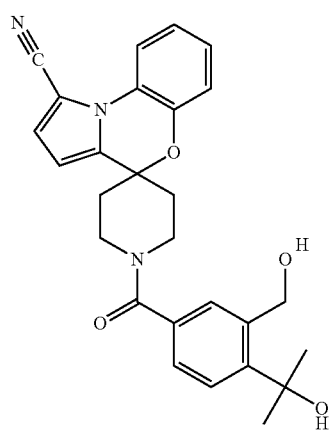
364
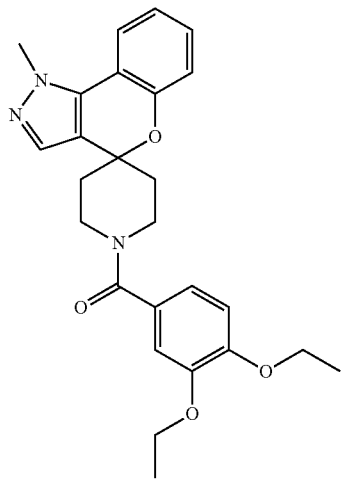
365
948
-continued
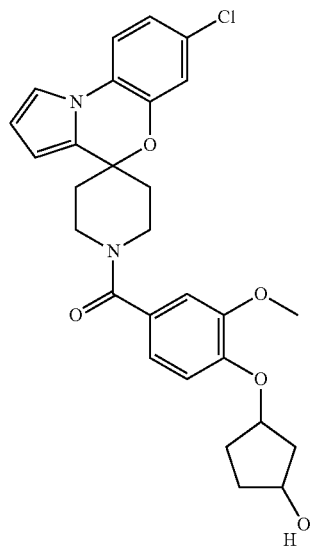
366
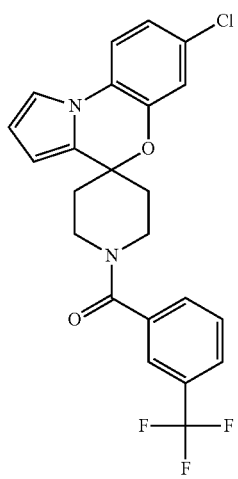
367
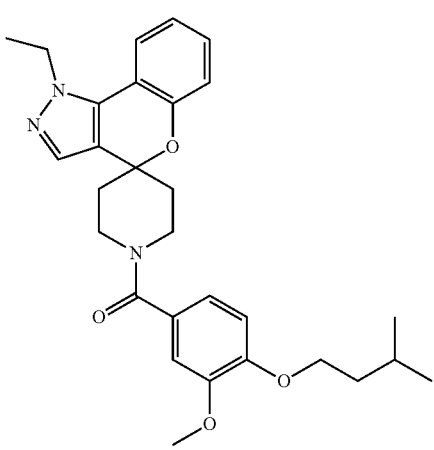
368

949
-continued
369
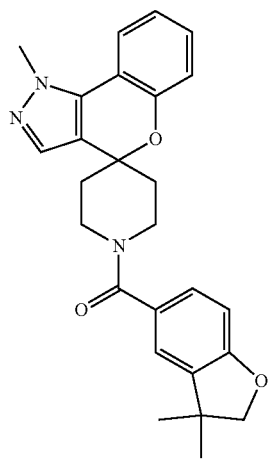
370
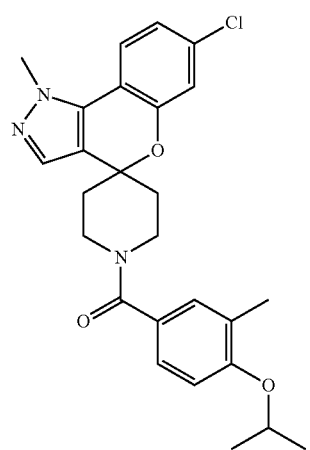
371
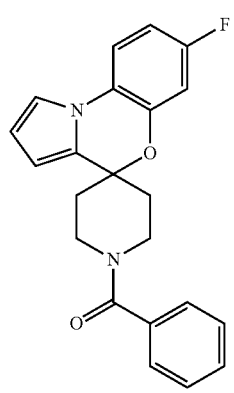
950
-continued
372
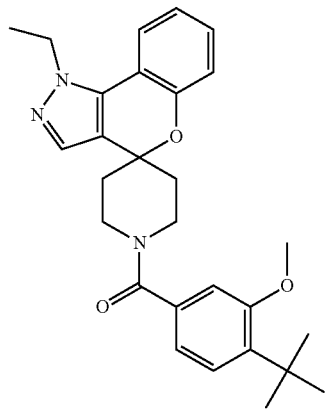
373
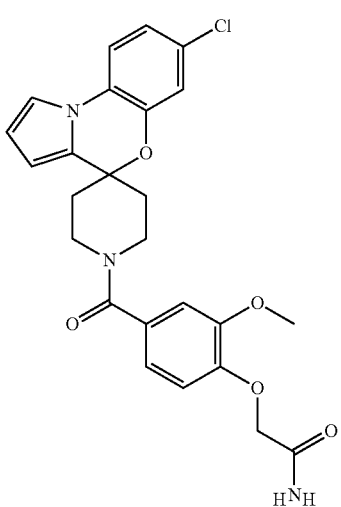
374
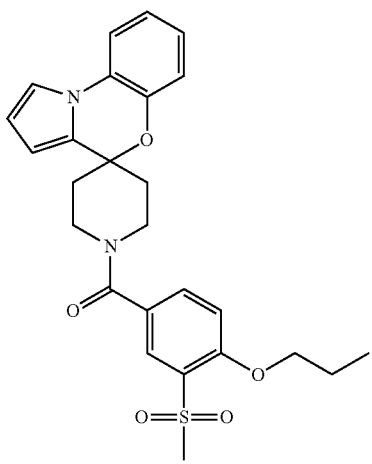

| 951 -continued | 952 -continued |
|---|---|
| 375 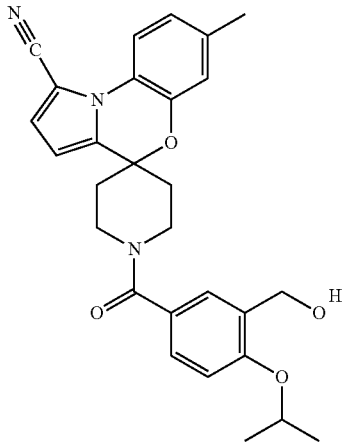 | 378 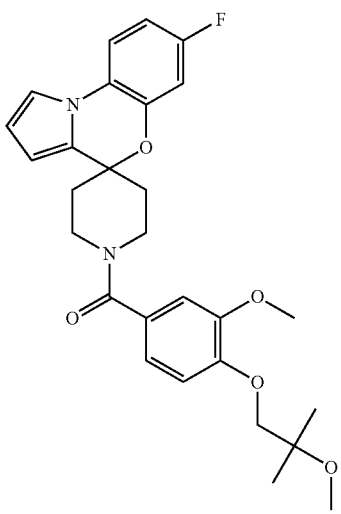 |
| 376 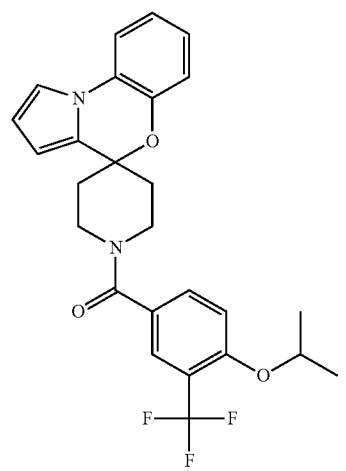 | 379 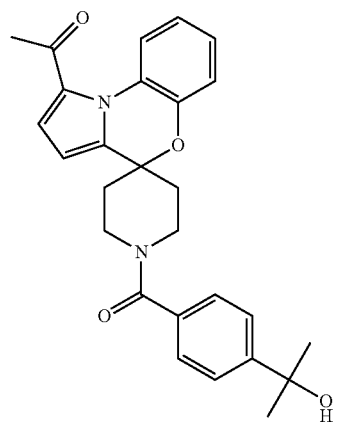 |
| 377 | 380 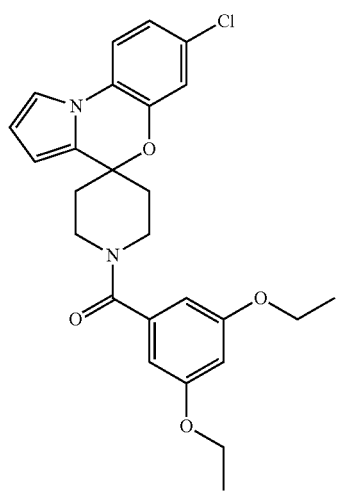 |

381
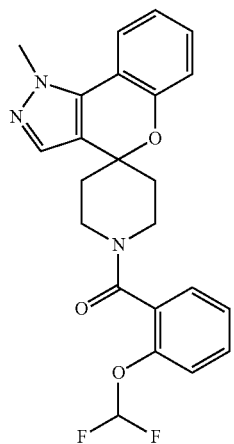
382
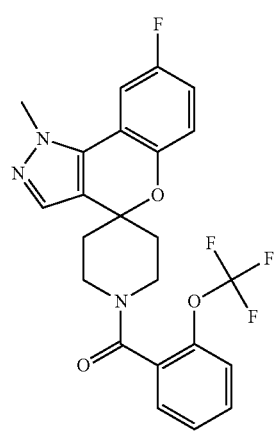
383
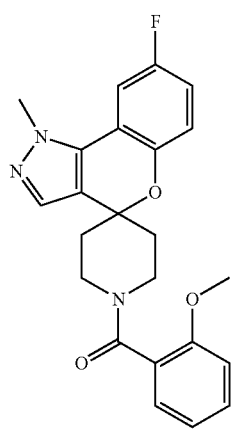
384
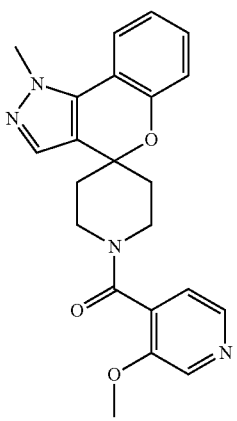
385
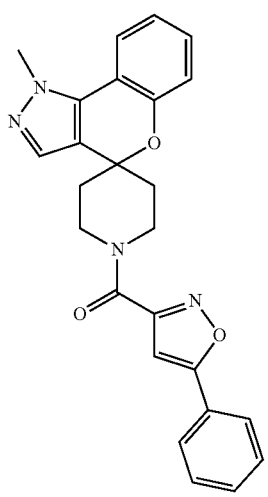
386
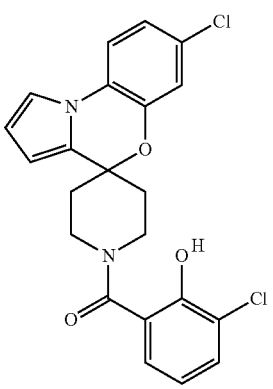

387
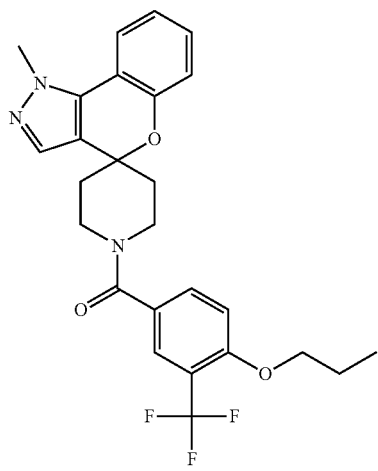
388
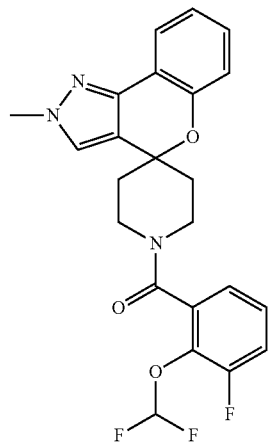
390
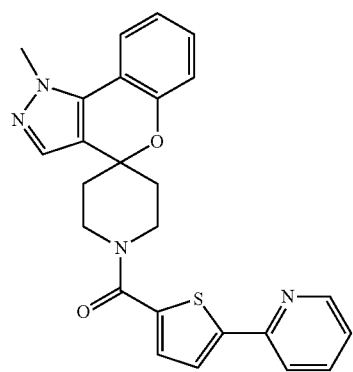
391
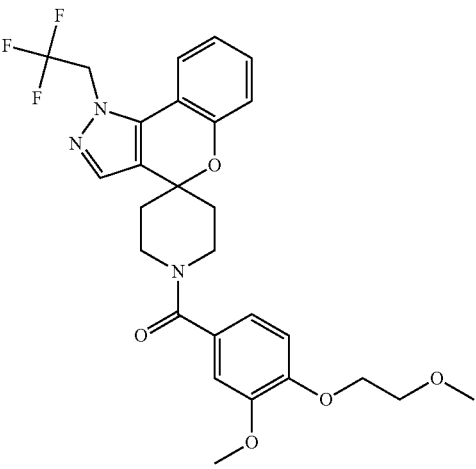
392
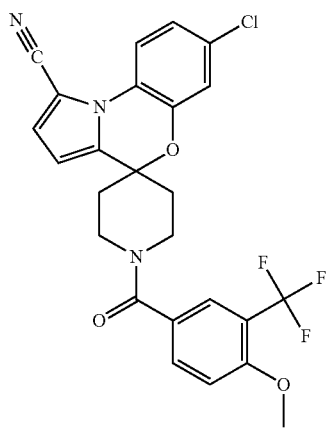
393
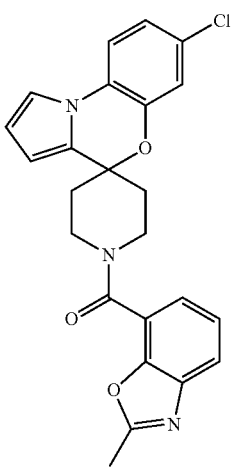

957
-continued
958
-continued
394
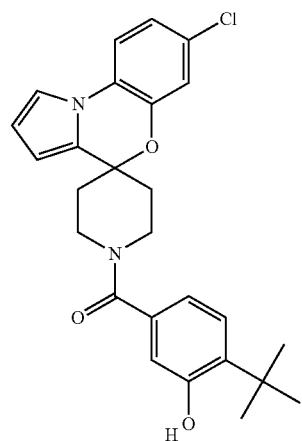
397
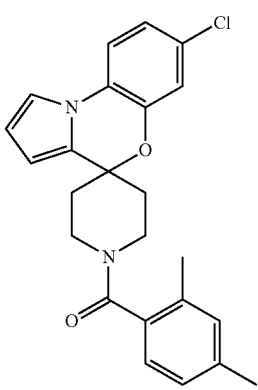
395
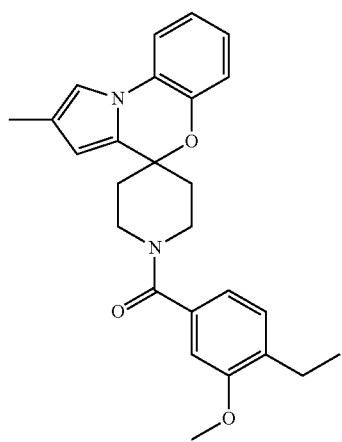
398
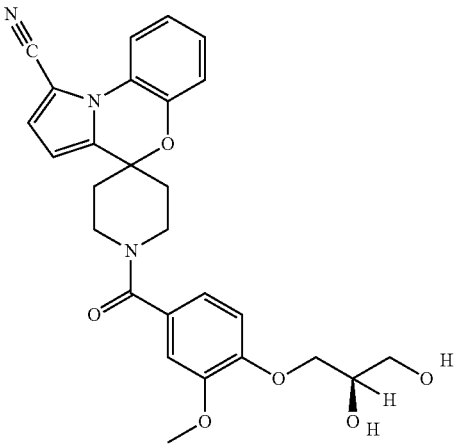
396
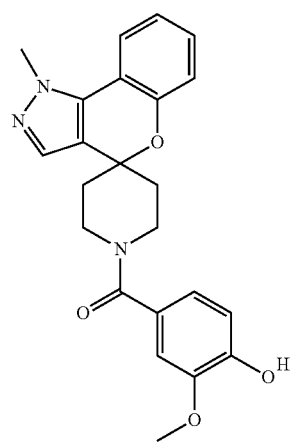
399
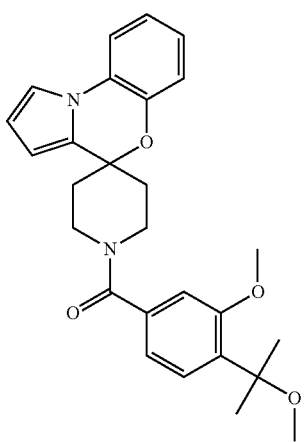

400 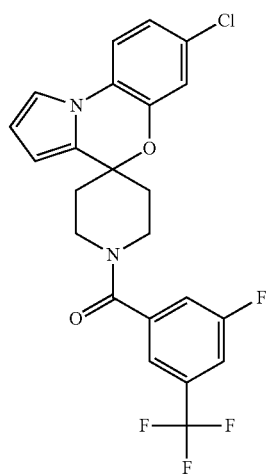
401 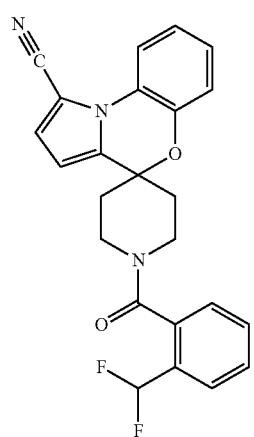
402 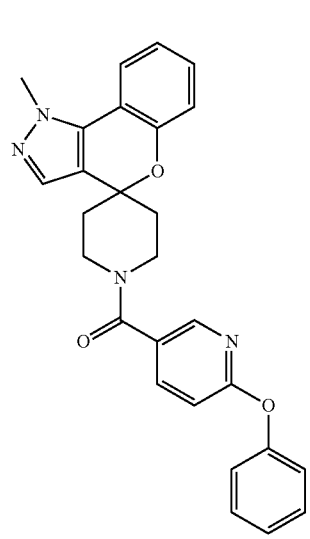
403 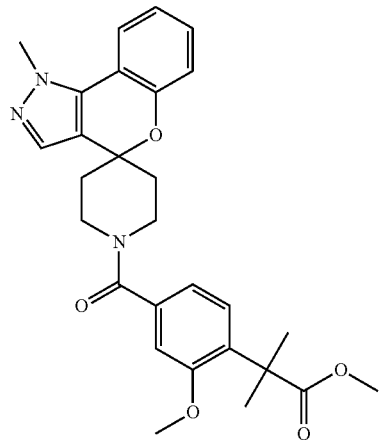
404 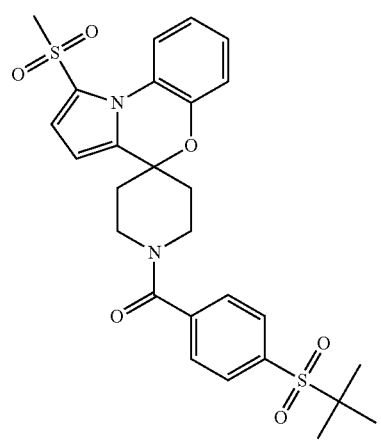
405 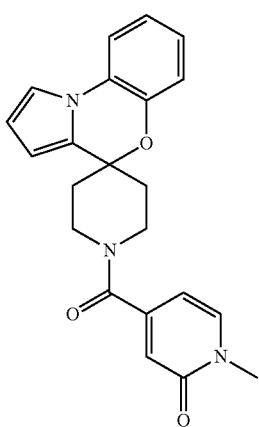

961
-continued
406
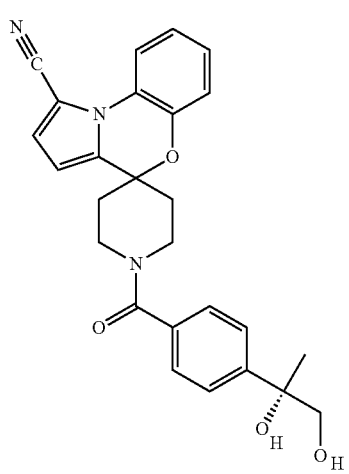
407
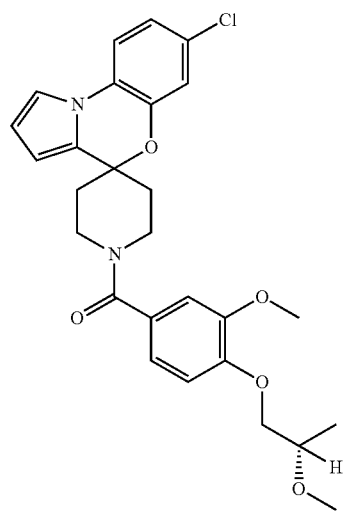
408
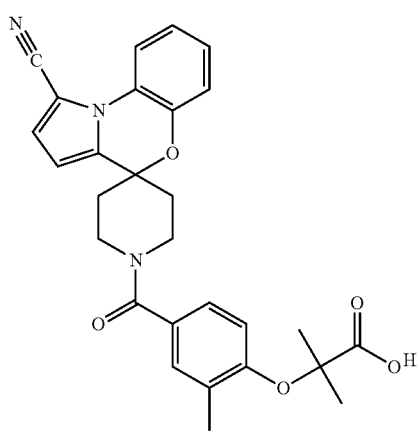
962
-continued
409
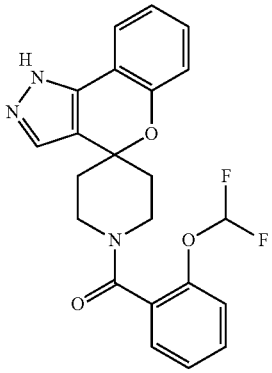
410
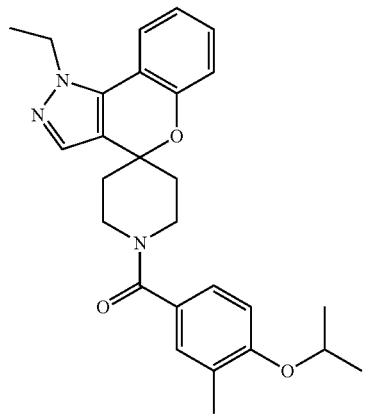
411
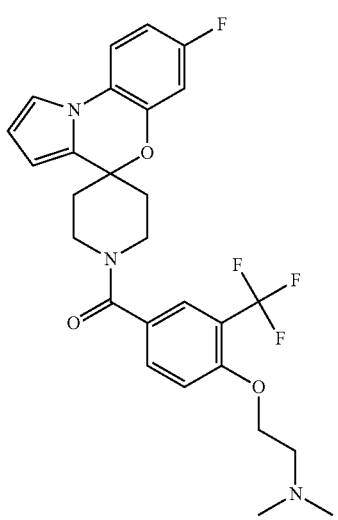

412 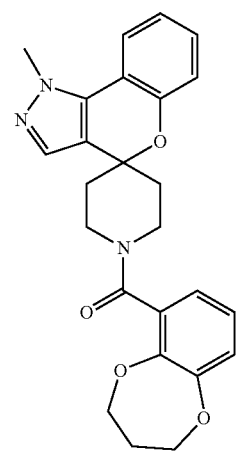
413 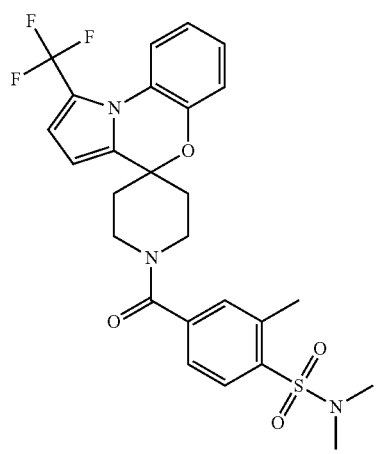
414 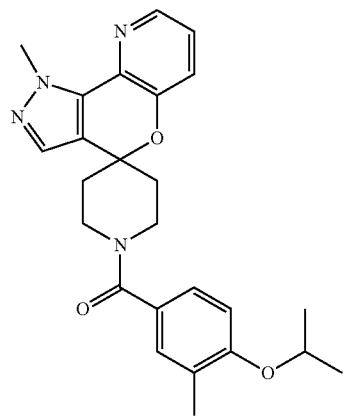
415 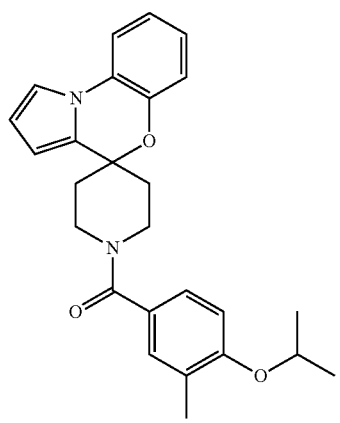
416 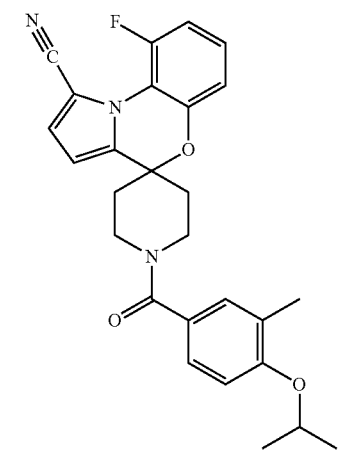
417 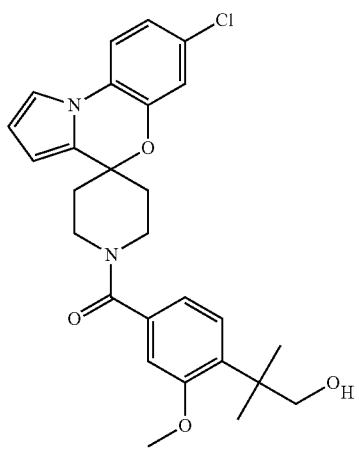

| 965 -continued | 966 -continued |
|---|---|
| 418 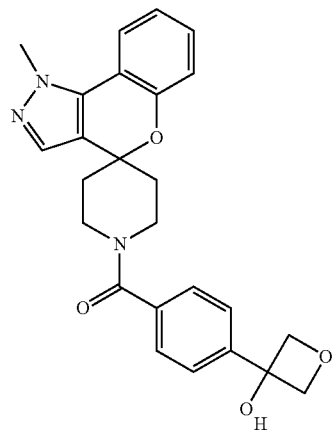 | 421 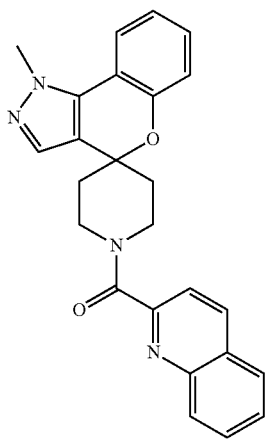 |
| 419 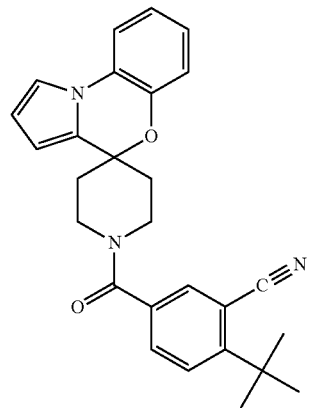 | 422 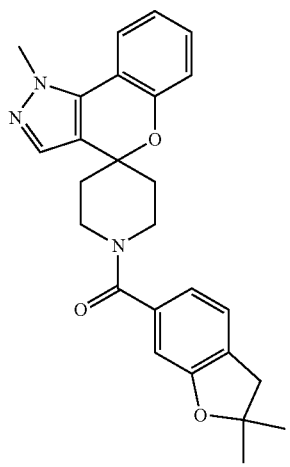 |
| 420 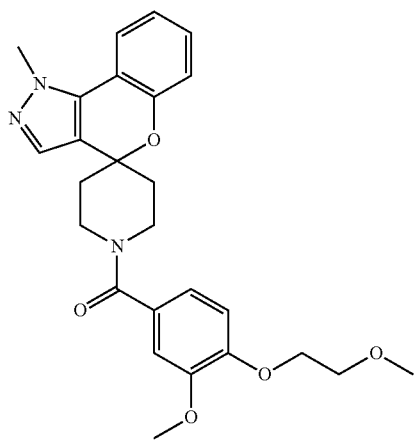 | 423 |

967
-continued
424
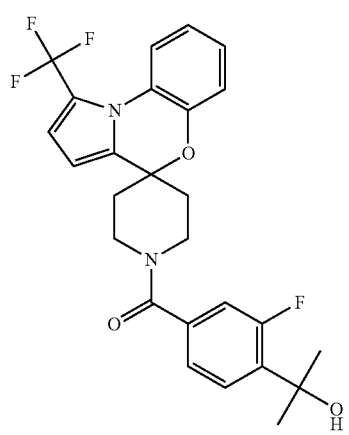
425
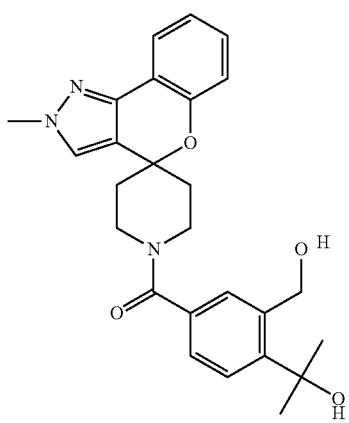
426
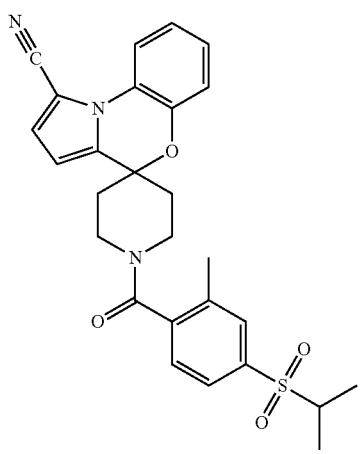
968
-continued
427
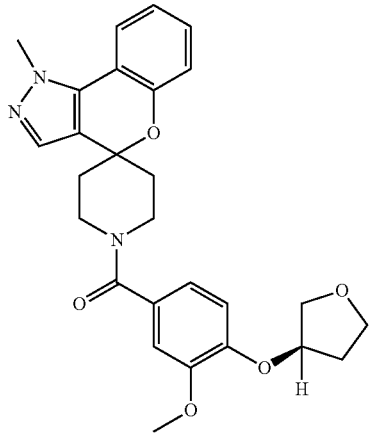
428
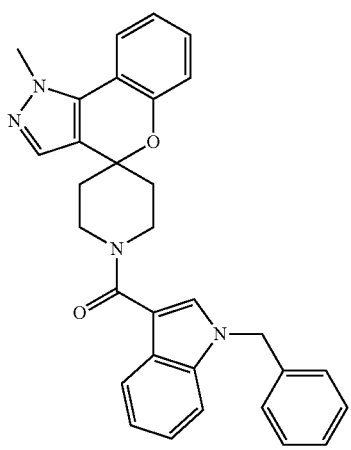
429
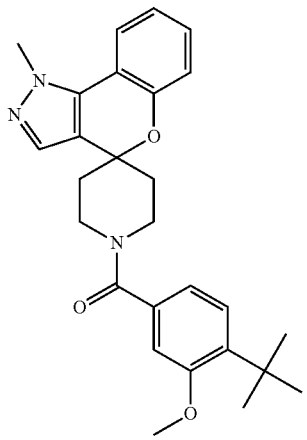

969
-continued
430
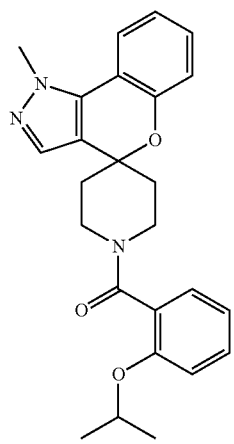
431
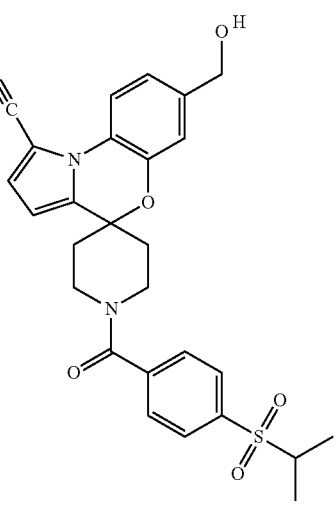
432
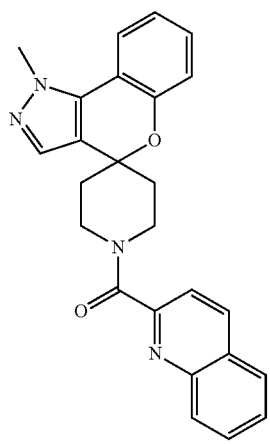
970
-continued
433
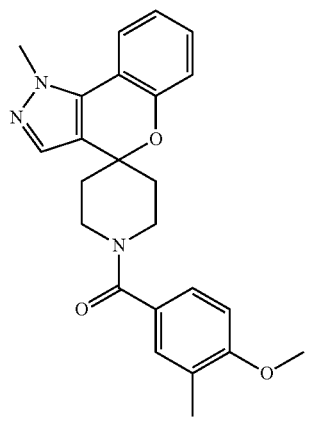
434
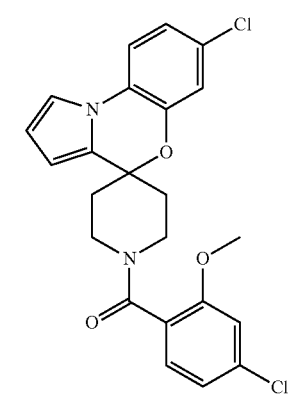
435
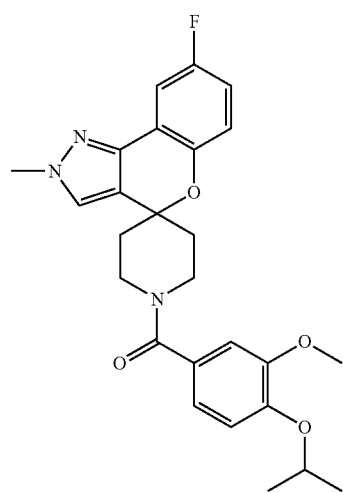

| 971 -continued | 972 -continued |
|---|---|
| 436 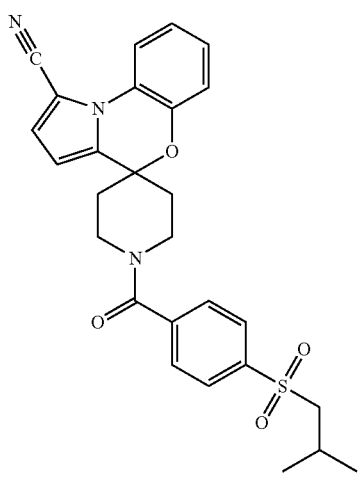 | 439 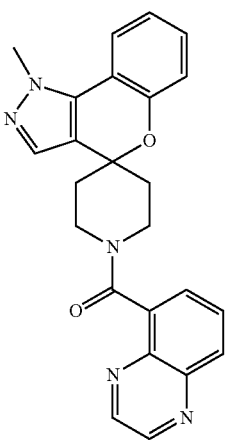 |
| 437 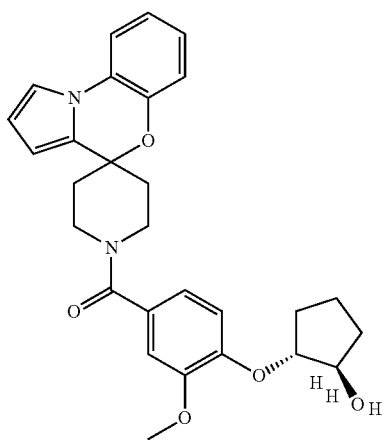 | 440 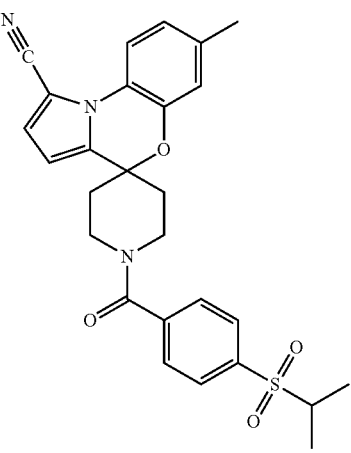 |
| 438 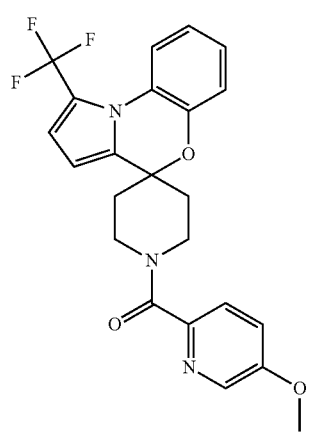 | 441 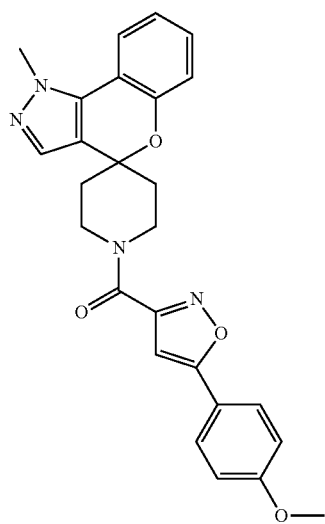 |

973
-continued
442
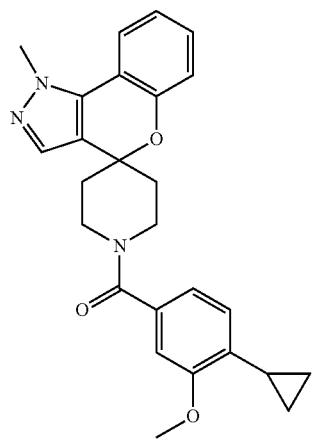
443
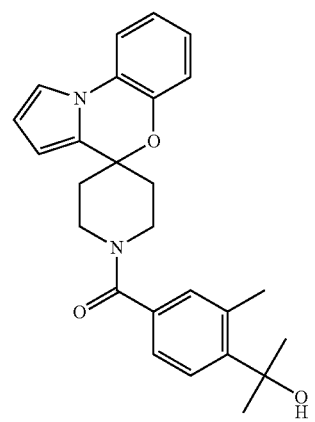
444
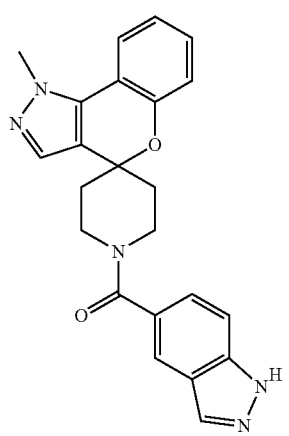
974
-continued
445
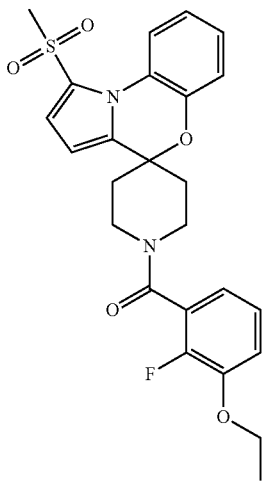
446
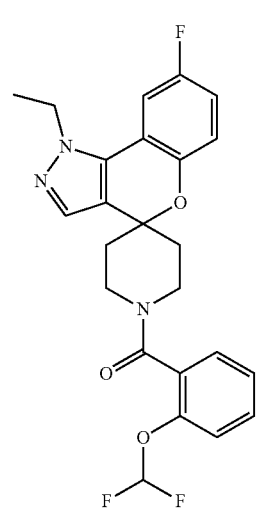
447
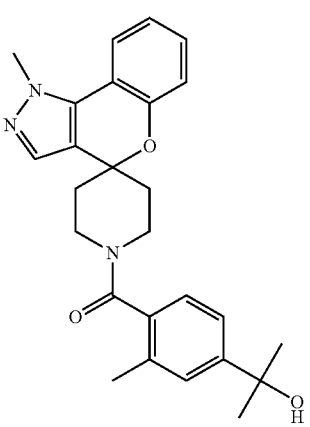

| 975 | 976 |
|---|---|
| -continued | -continued |
| 448 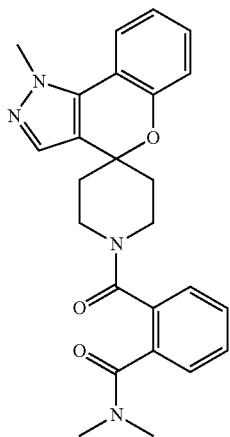 | 451 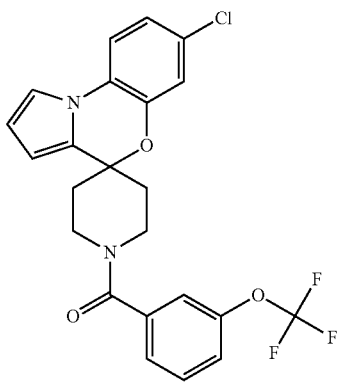 |
| 449 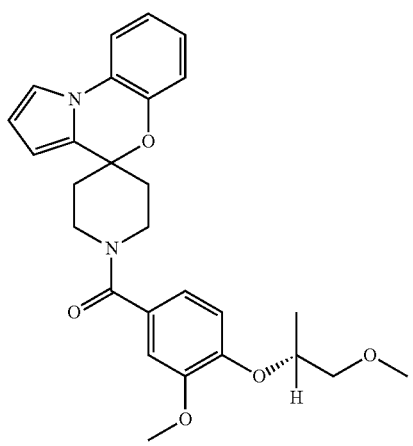 | 452 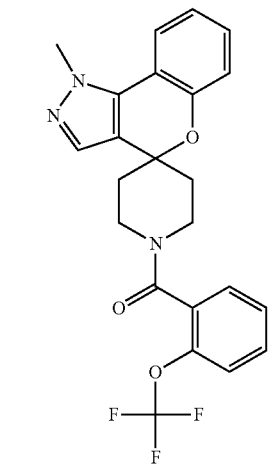 |
| 450 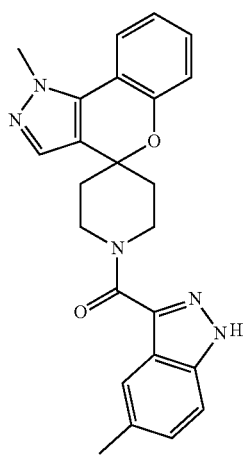 | 453 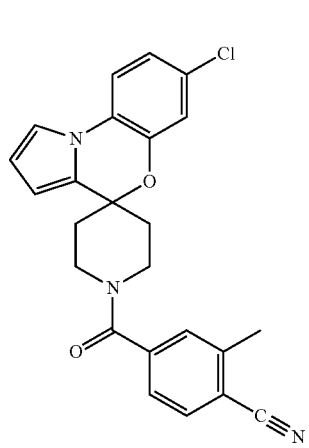 |

| 454 | 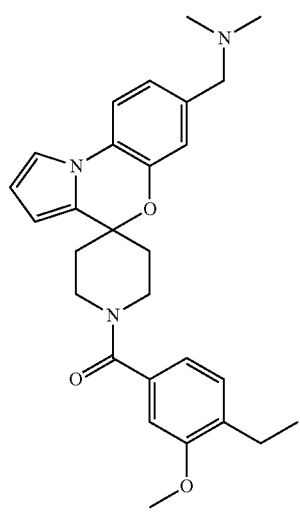 | 457 | 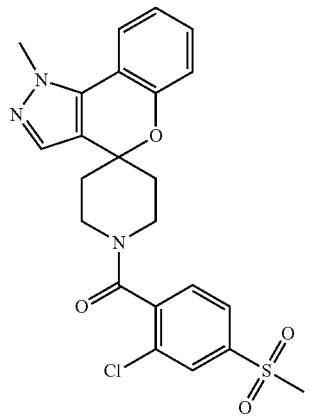 |
| 455 | 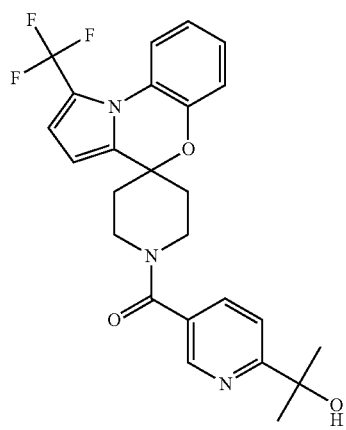 | 458 | 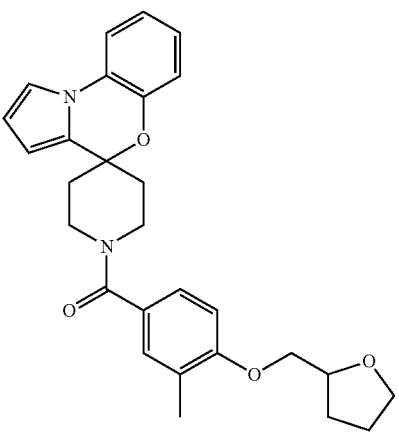 |
| 456 | 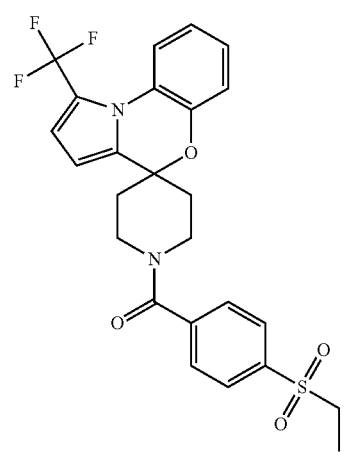 | 459 | 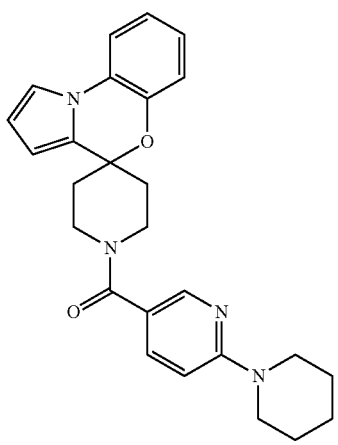 |

979
-continued
460
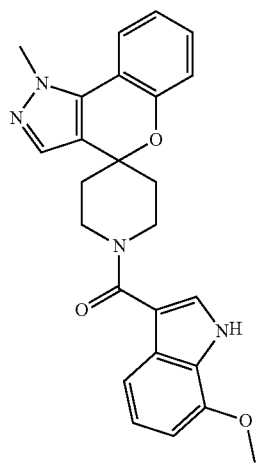
461
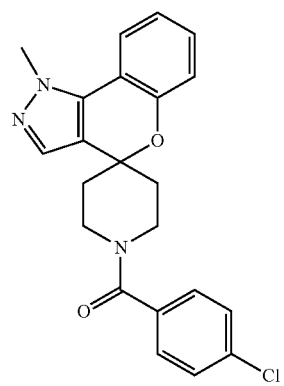
462
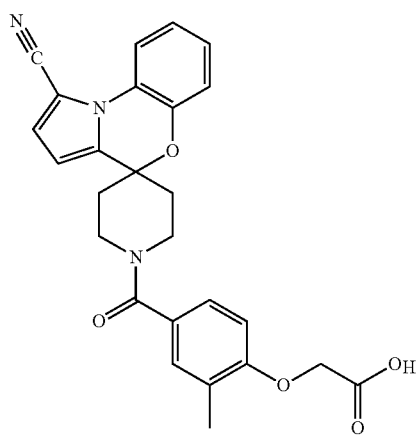
980
-continued
463
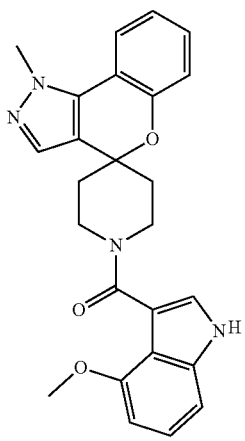
464
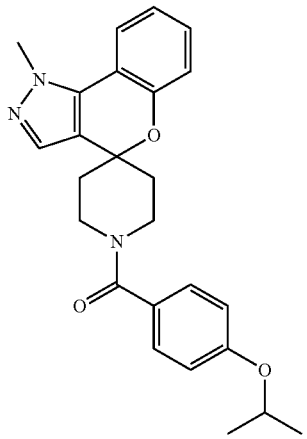
465
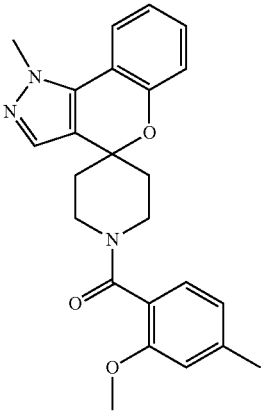

-continued
466
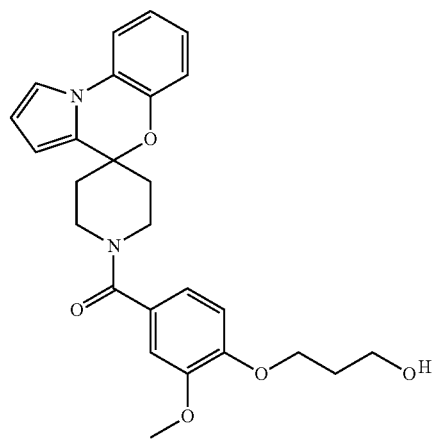
-continued
469
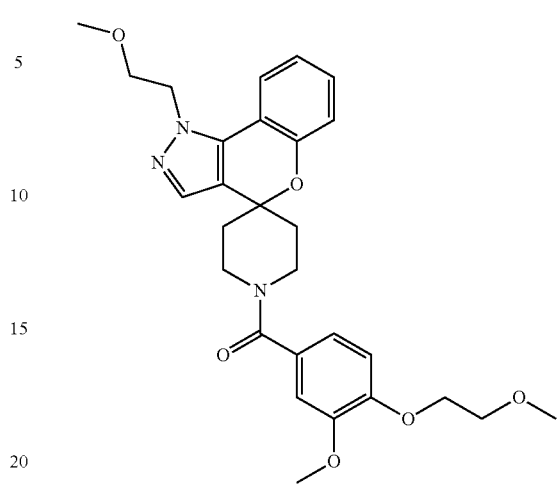
467
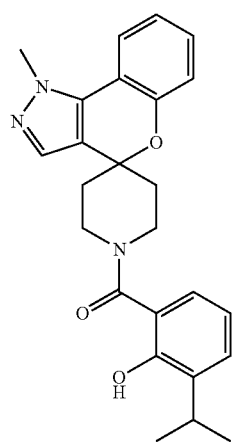
470
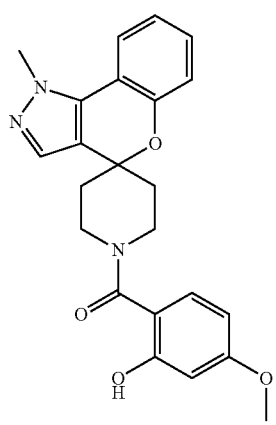
468
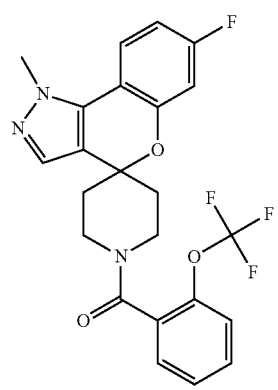
471
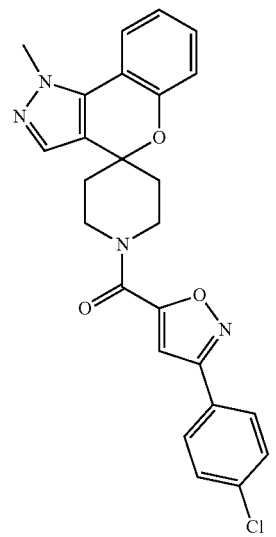

983
-continued
472
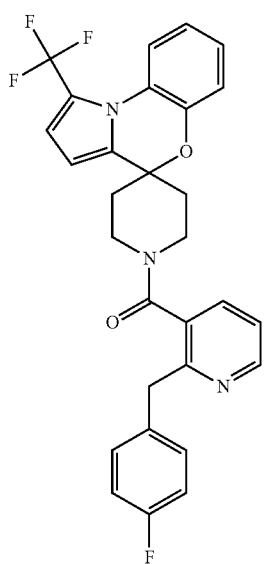
473
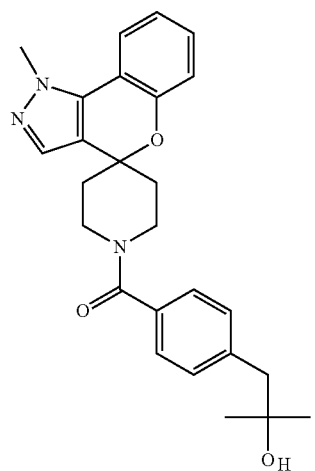
474
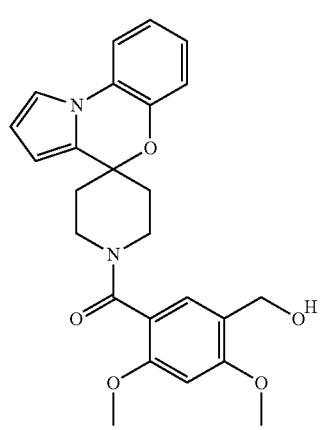
984
-continued
475
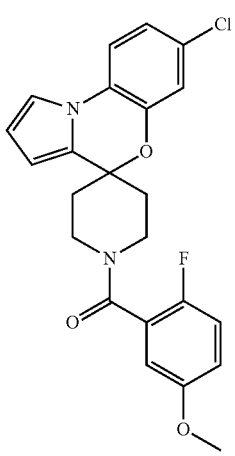
476
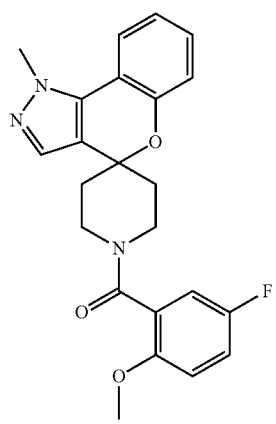
477
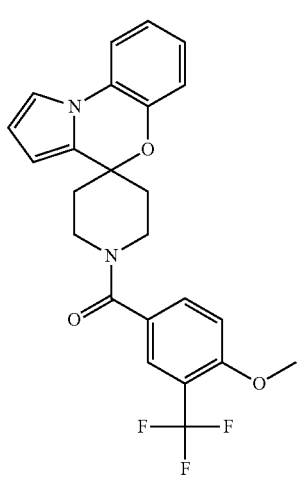

478 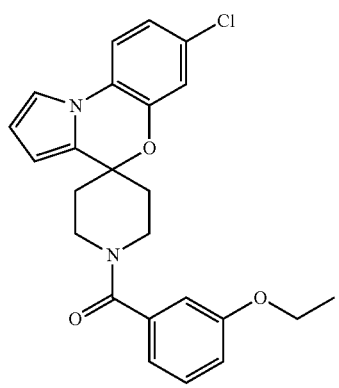
479 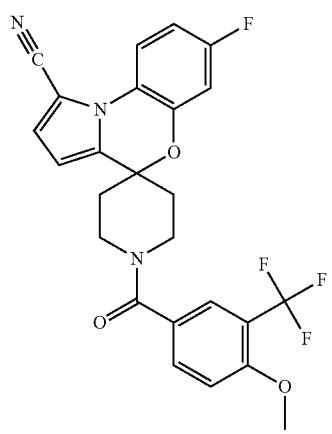
480 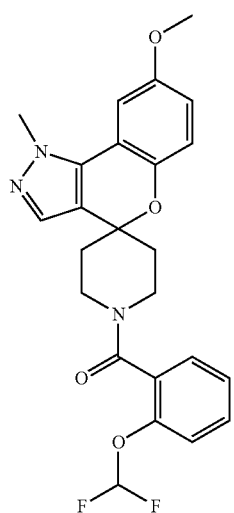
481 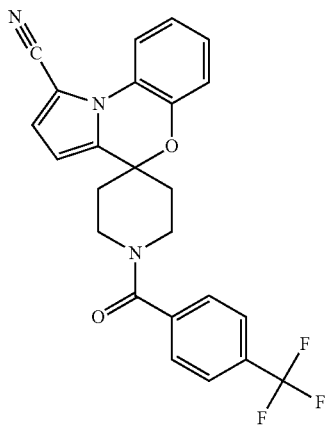
482 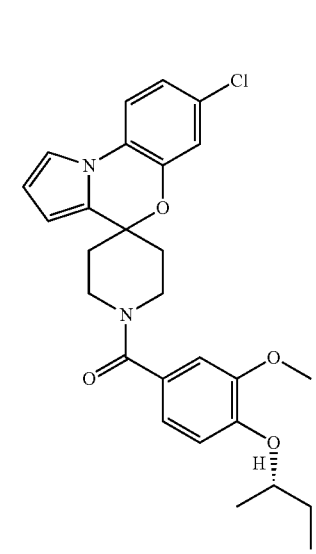
483 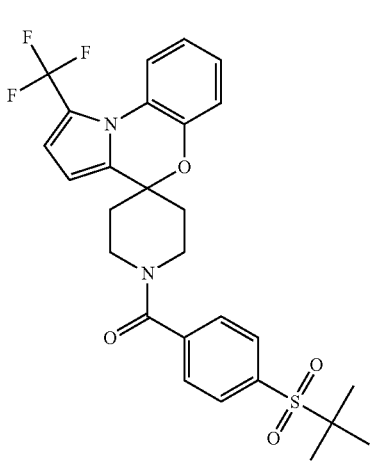

484 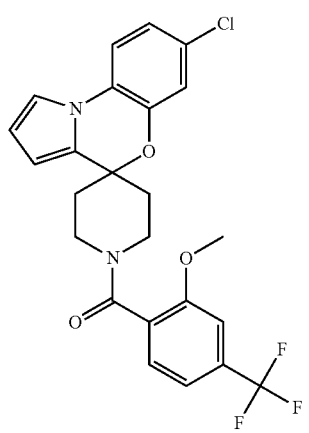
485 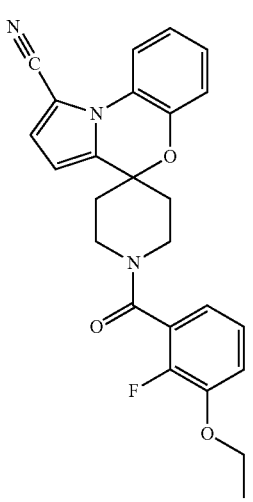
486 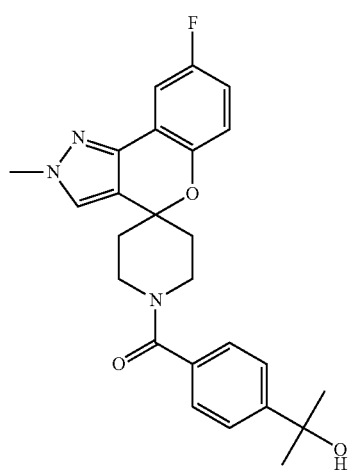
487 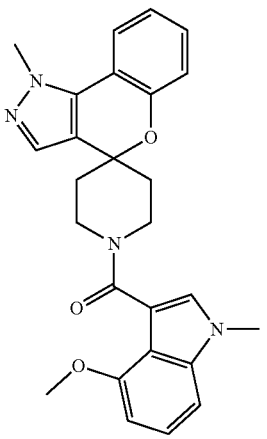
488 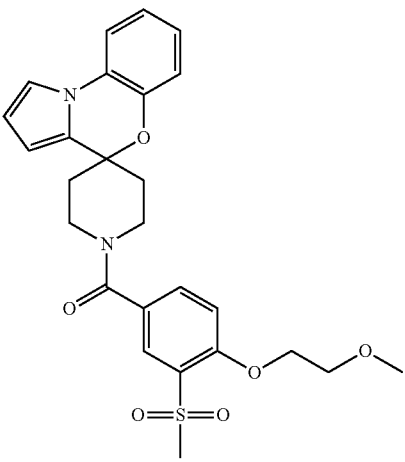
489 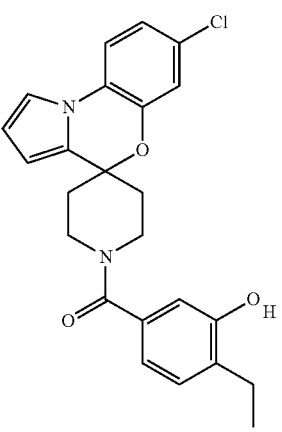

989
490
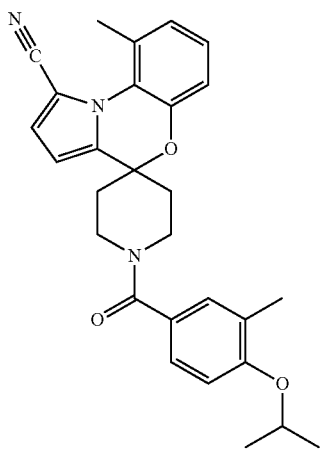
491
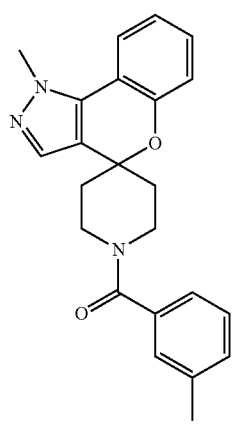
492
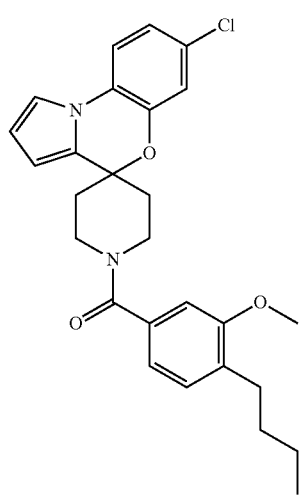
990
493
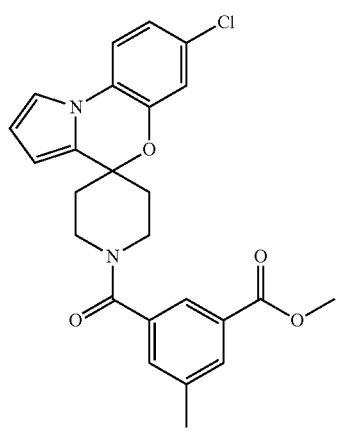
494
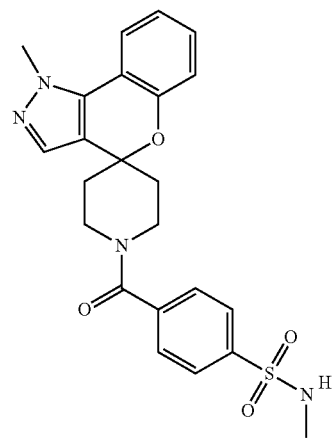
495
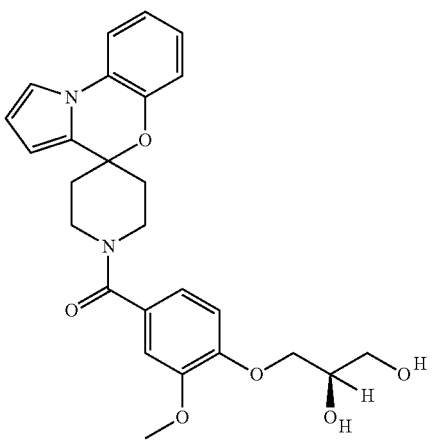

991 496 992 499
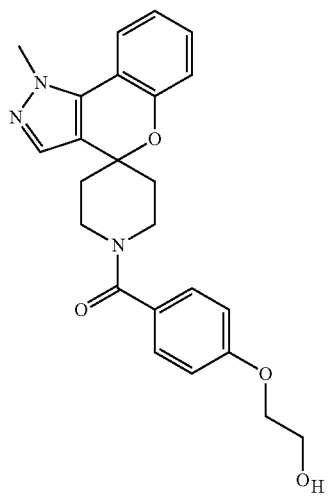
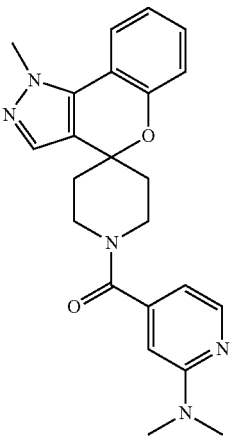
497 500
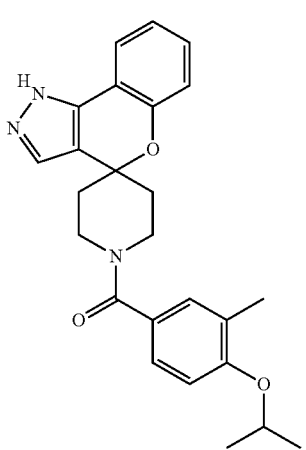
498 501
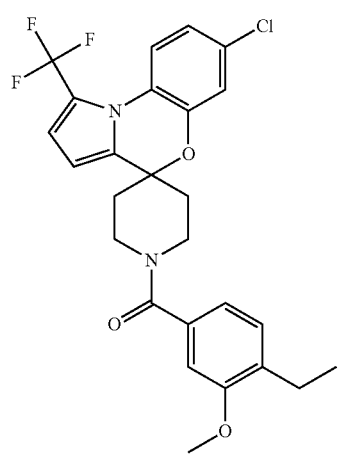
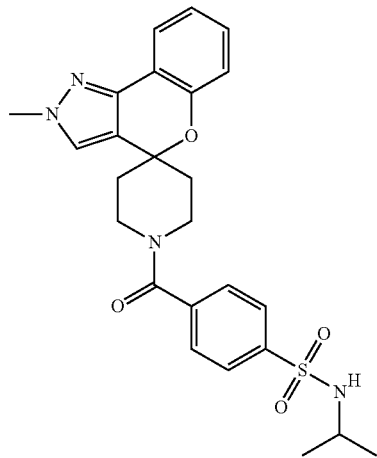

| 993 -continued | 994 -continued |
|---|---|
| 502 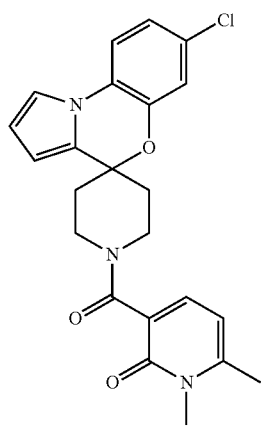 | 505 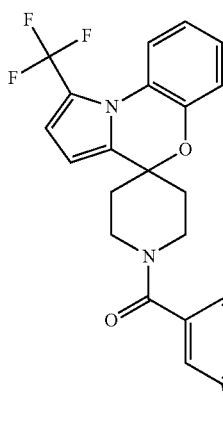 |
| 503 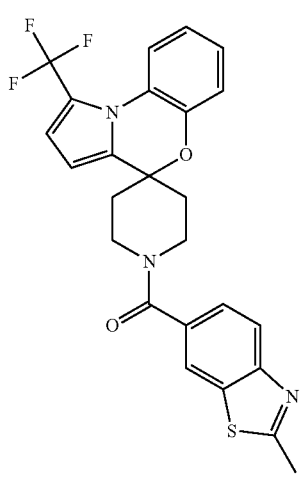 | 506 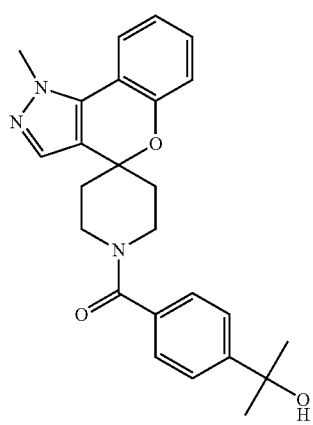 |
| 504 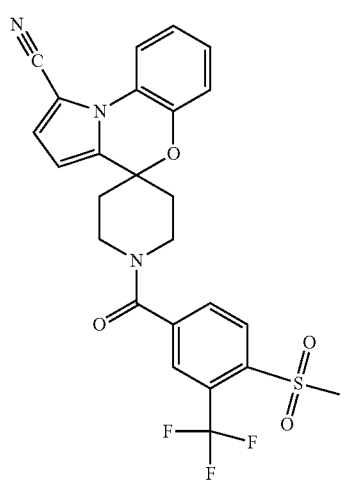 | 507 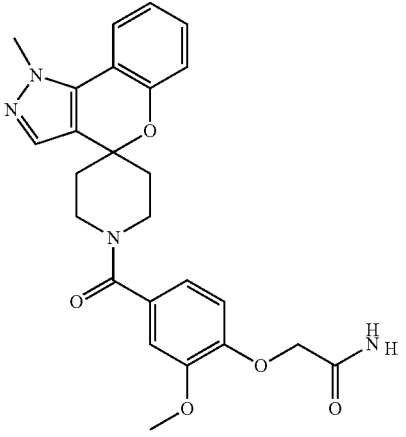 |

| 508 | 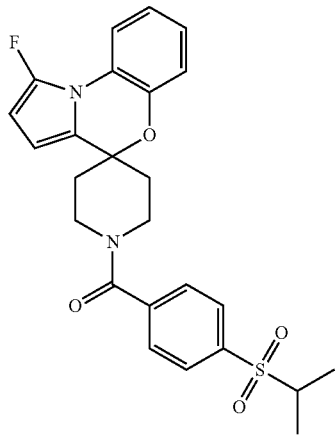 | 511 | 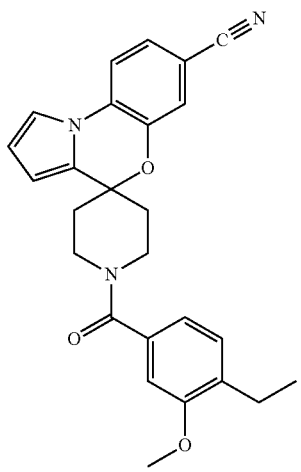 |
| 509 | 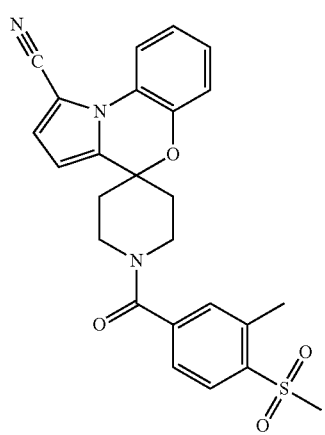 | 512 | 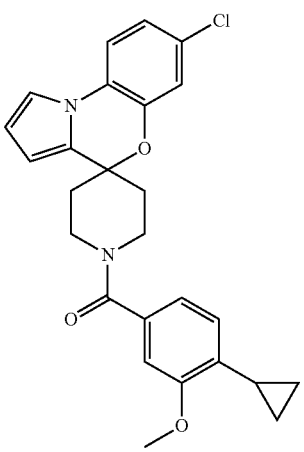 |
| 510 | 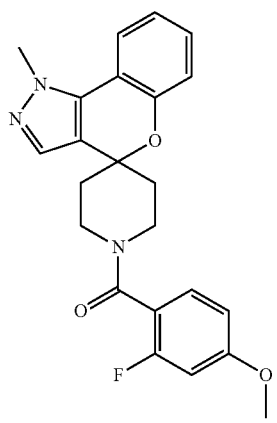 | 513 | 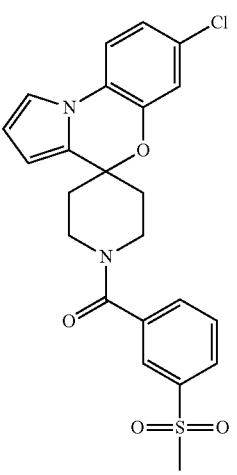 |

514
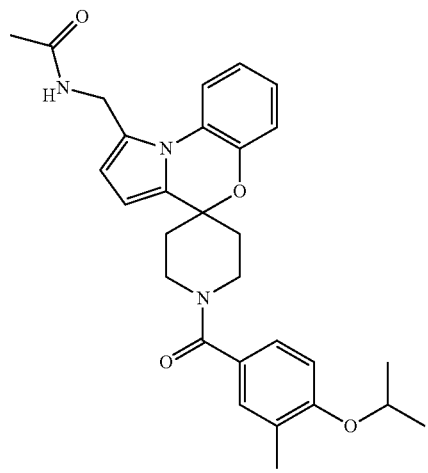
515
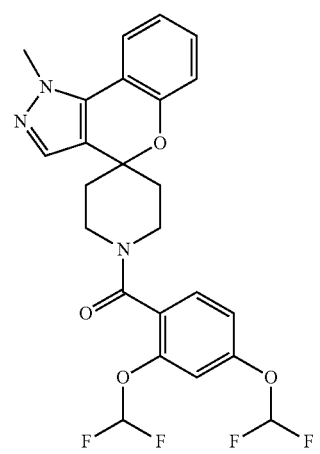
516
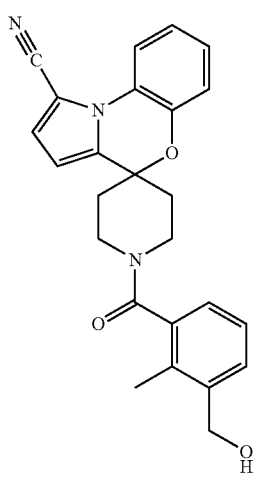
517
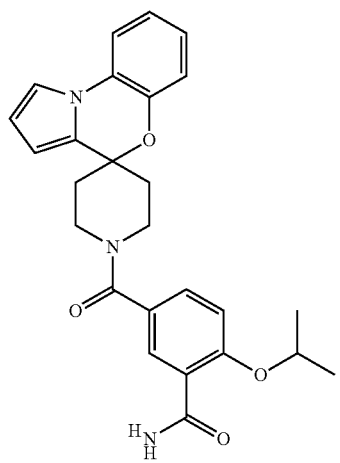
518
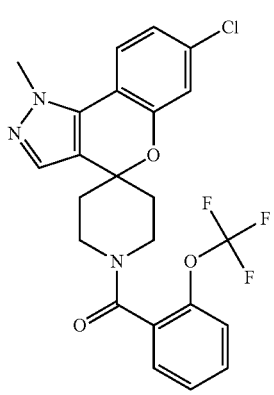
519
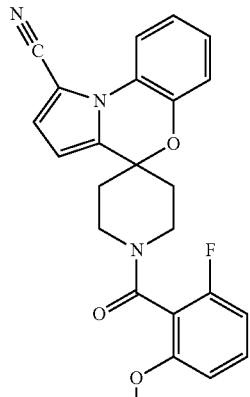
520
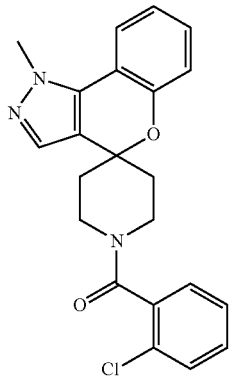

521
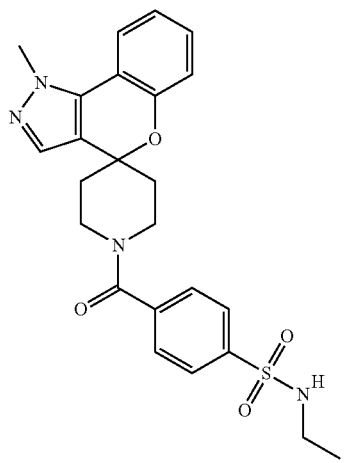
524
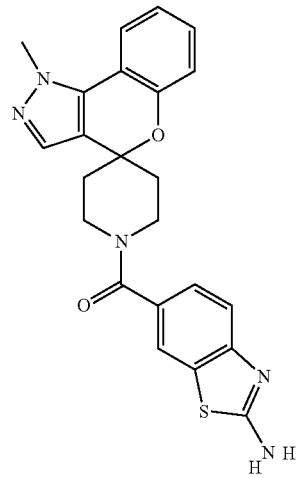
522
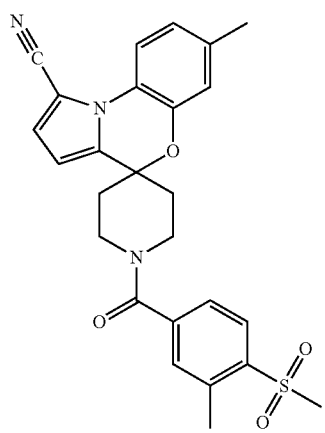
525
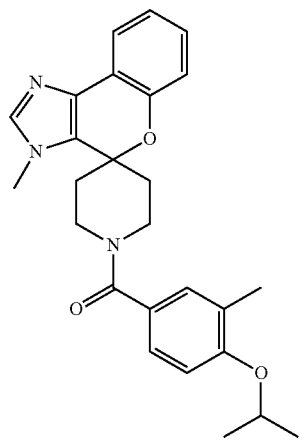
523
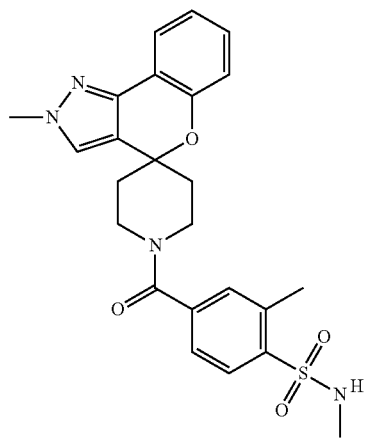
526
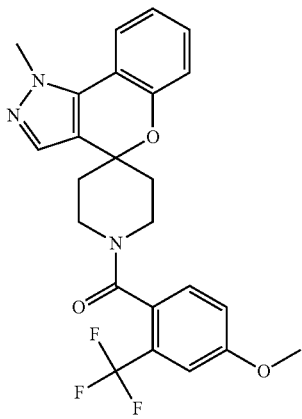

1001 1002
-continued -continued
527 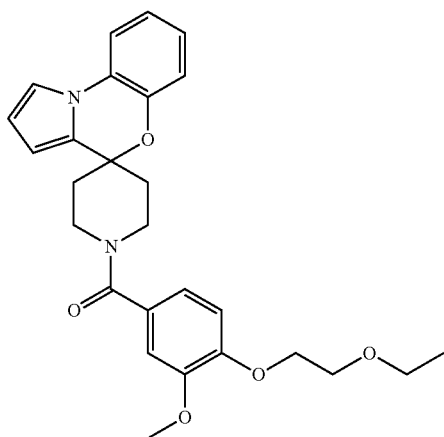
530 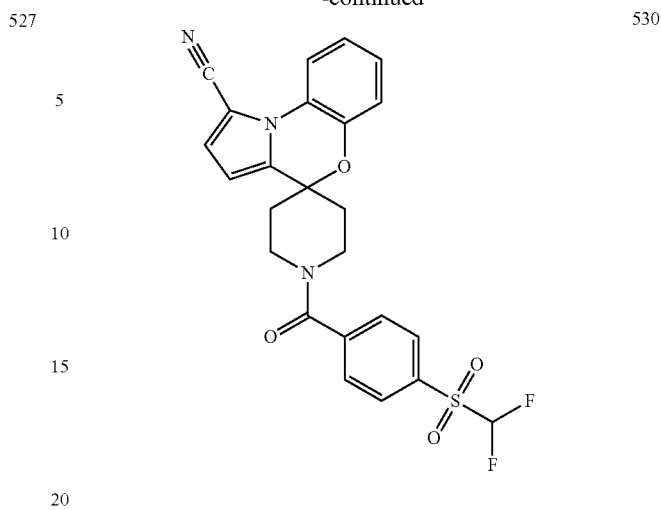
528 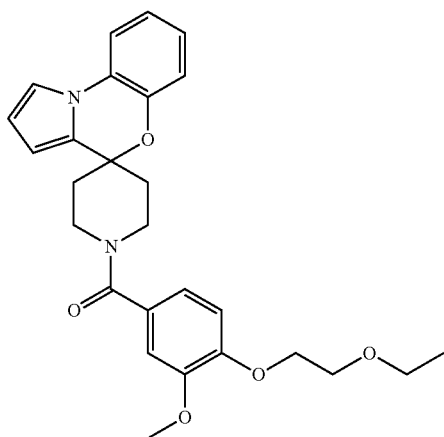
531 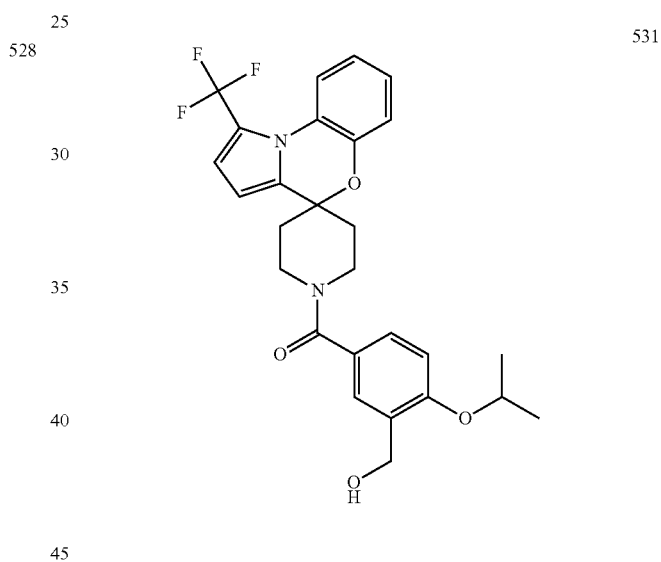
529 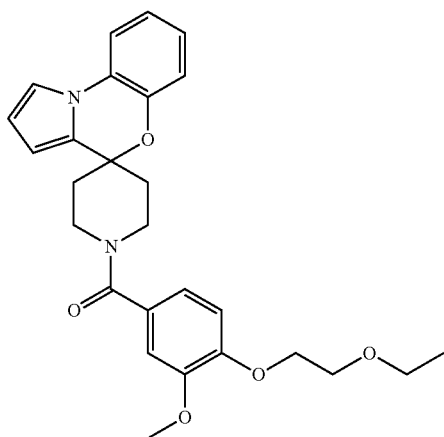
532 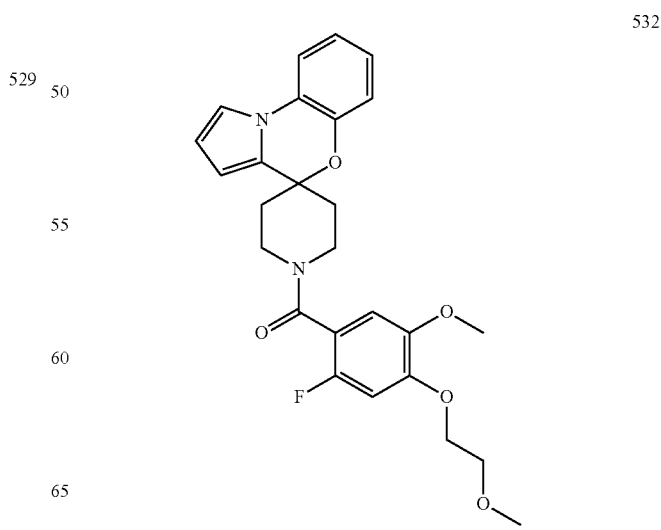

1003
-continued
533
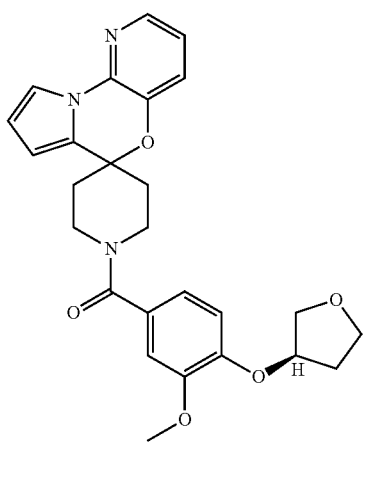
534
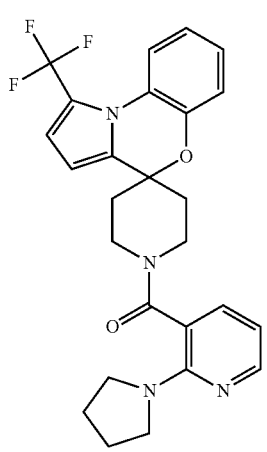
535
1004
-continued
536
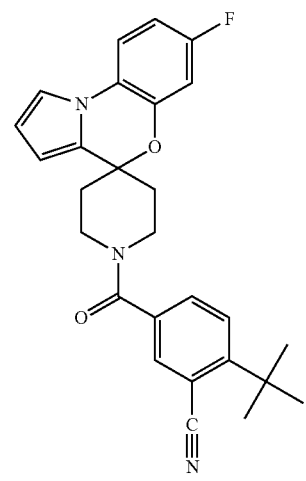
537
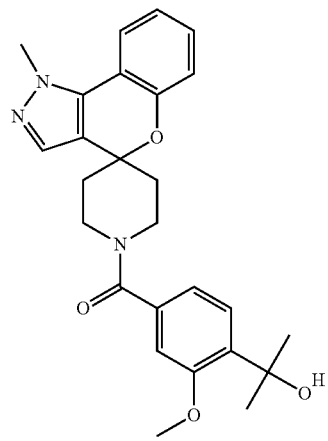
538
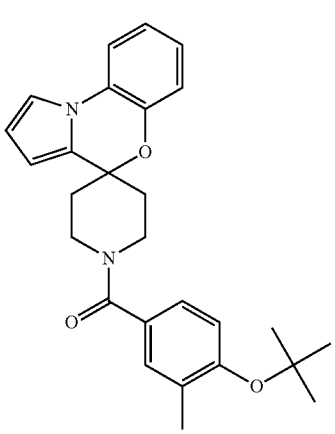

1005
-continued
539
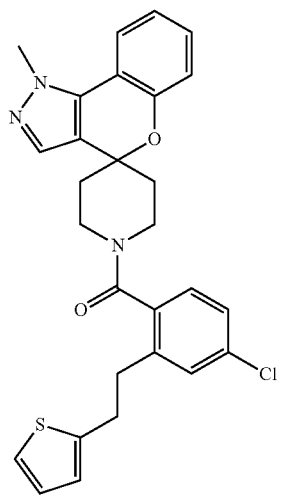
540
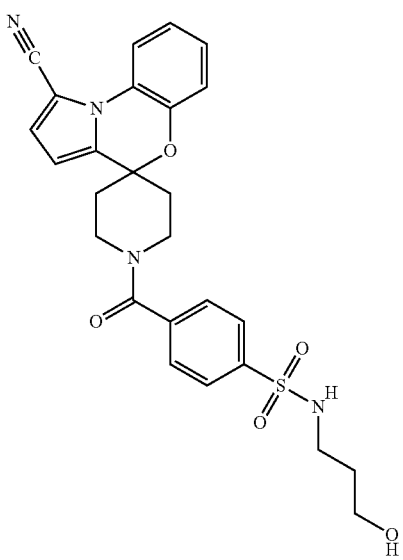
541
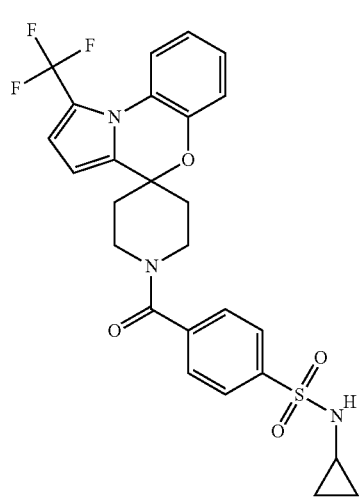
1006
-continued
542
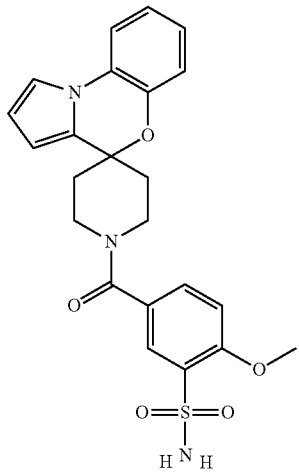
543
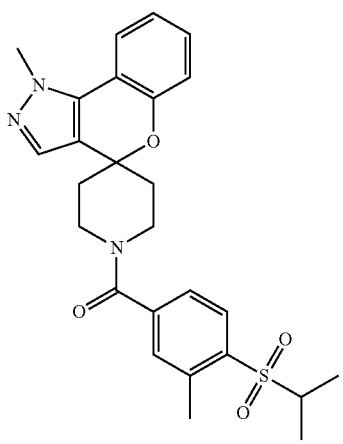
544
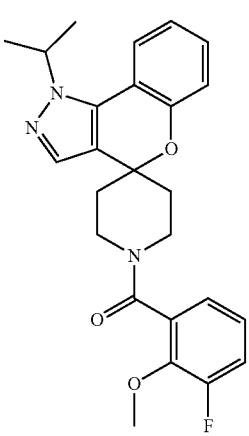

1007 -continued
545
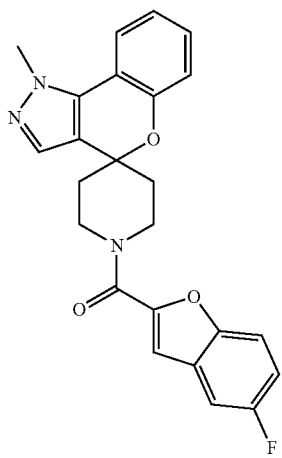
546
547
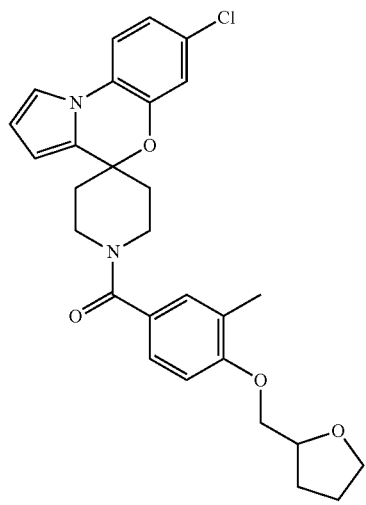
1008 -continued
548
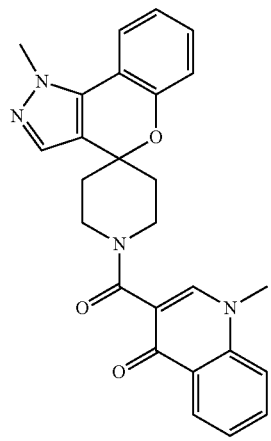
549
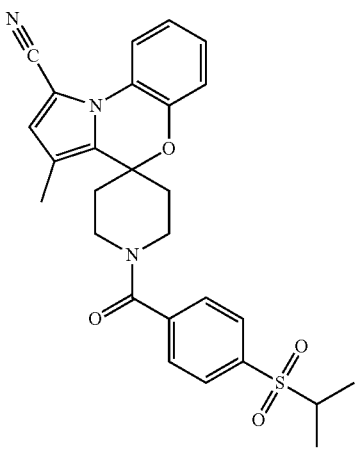
550
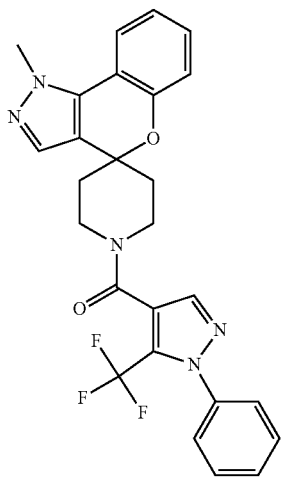

551 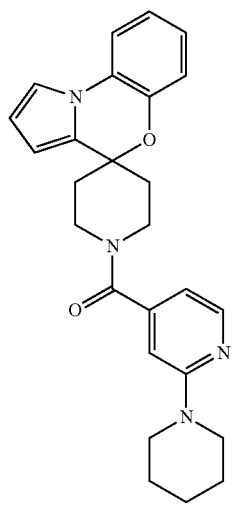
552 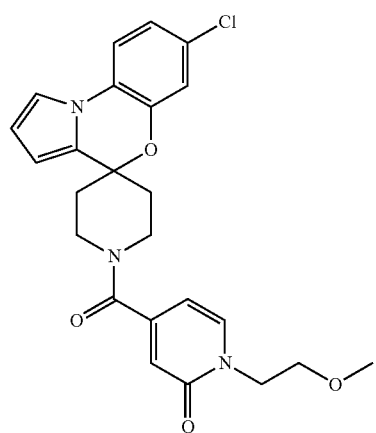
553 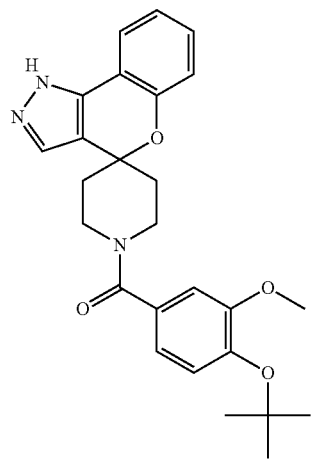
554 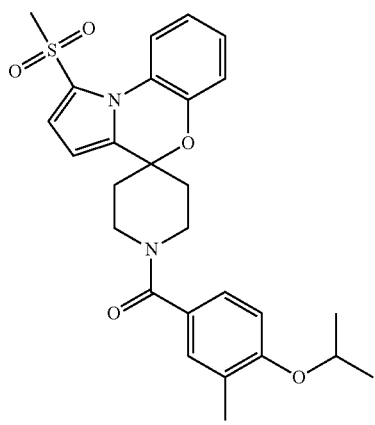
555 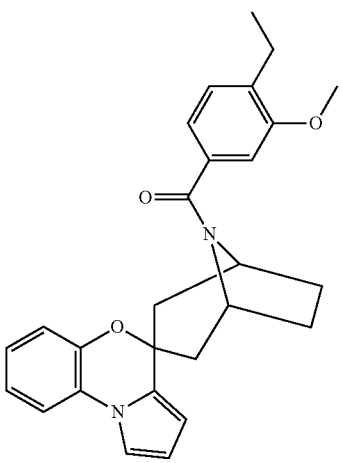
556 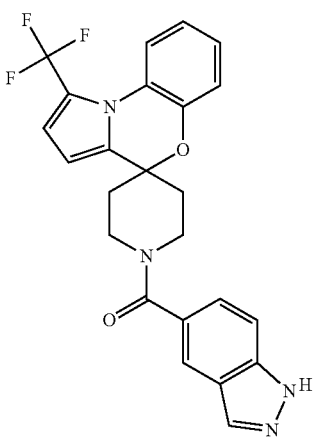

| 557 | 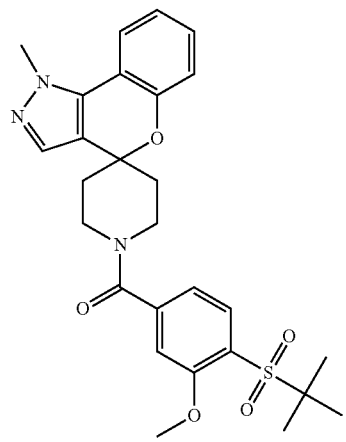 | 560 | 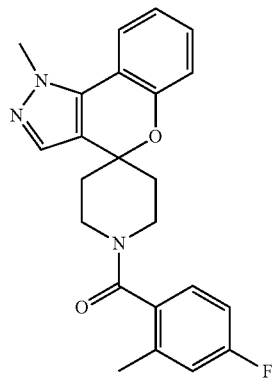 |
| 558 | 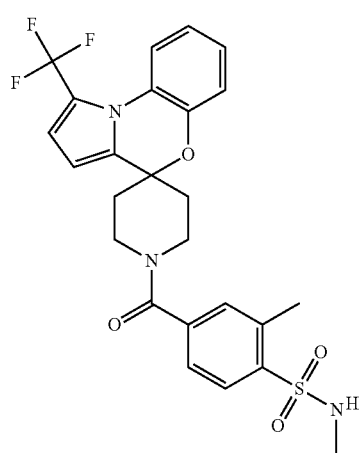 | 561 | 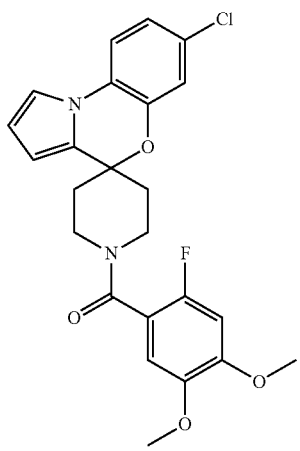 |
| | | 562 | 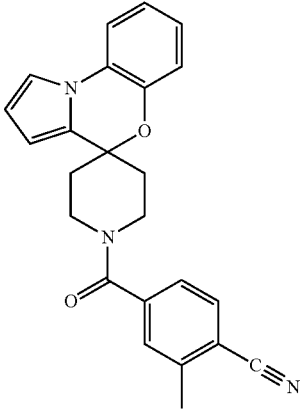 |
| 559 | 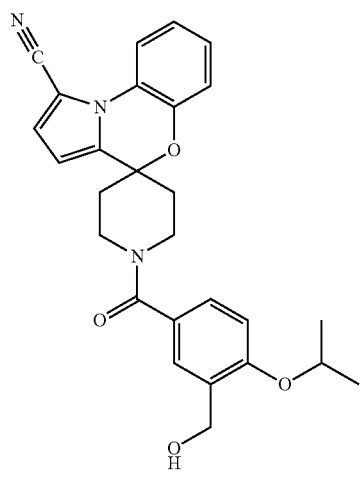 | 563 | 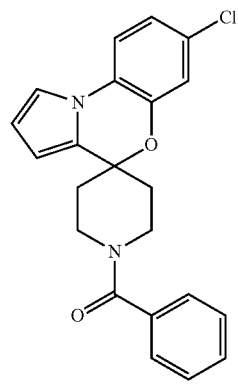 |

1013
-continued
1014
-continued
564
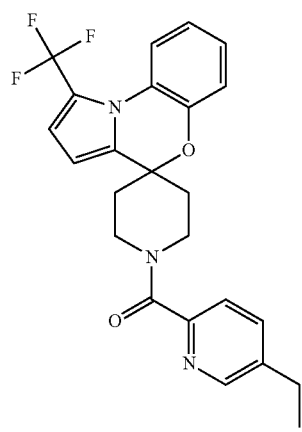
567
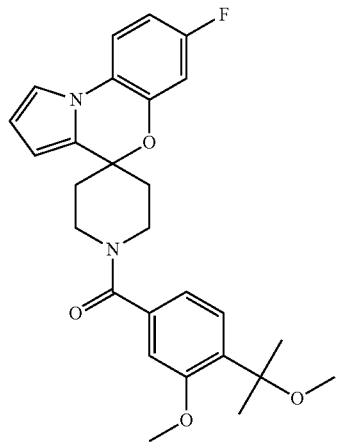
565
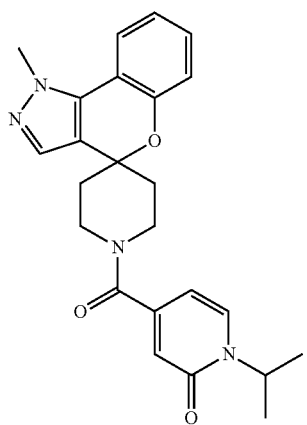
568
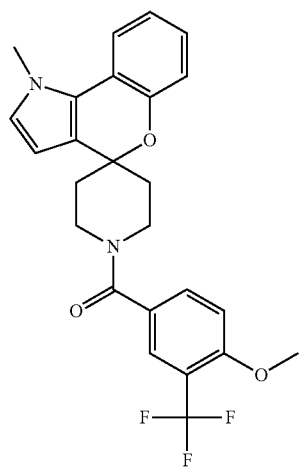
566
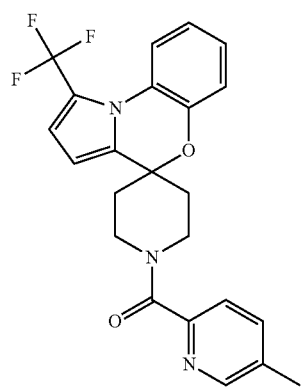
569
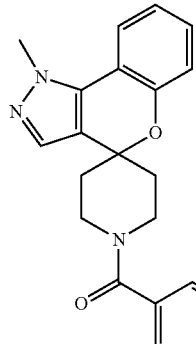

1015
-continued
570
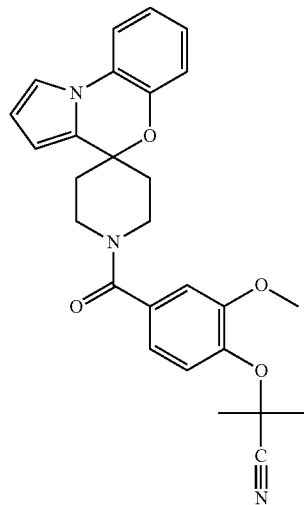
571
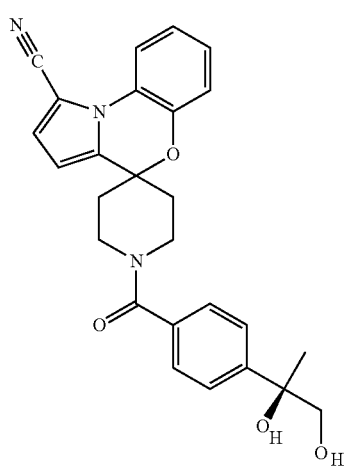
572
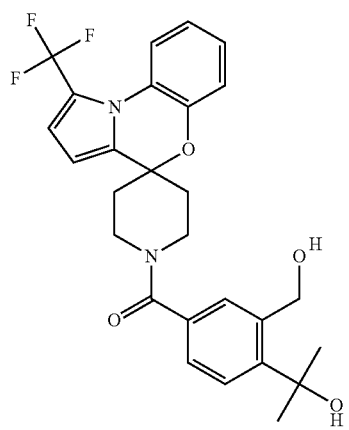
1016
-continued
573
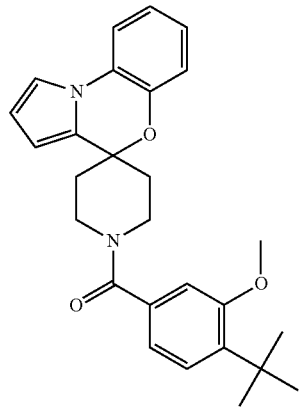
574
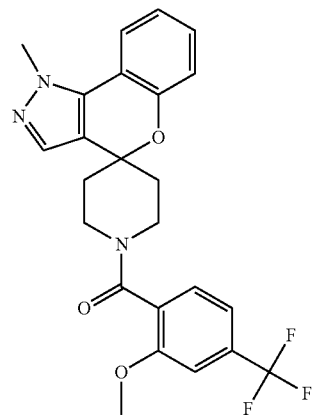
575
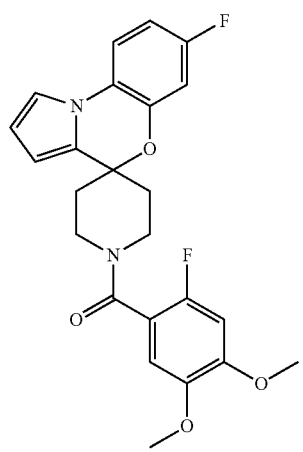

| 1017 -continued | 1018 -continued |
|---|---|
| 576 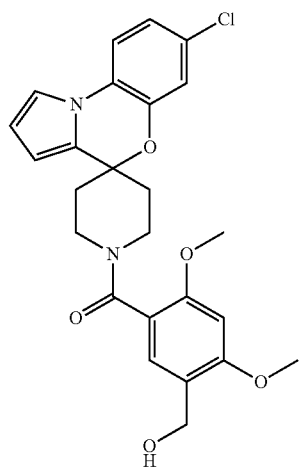 | 579 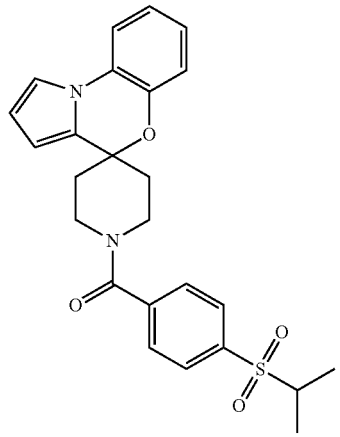 |
| 577 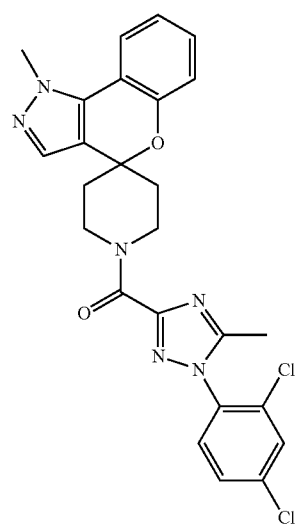 | 580 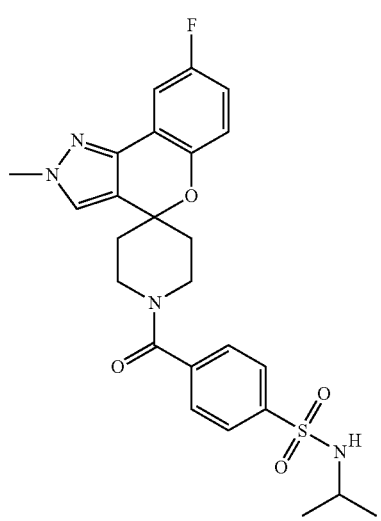 |
| 578 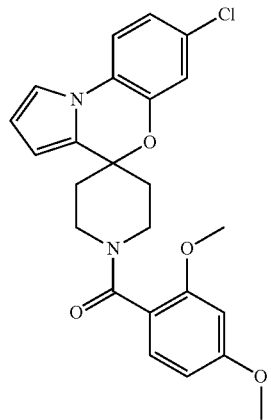 | 581 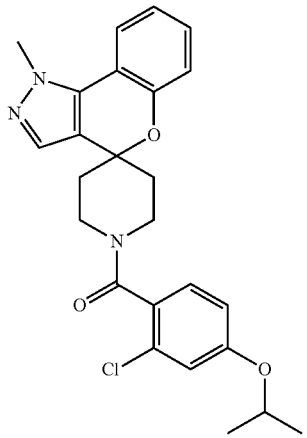 |

1019
-continued
582
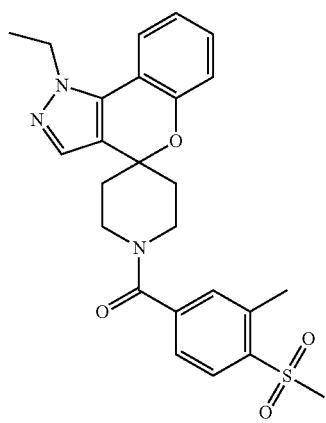
583
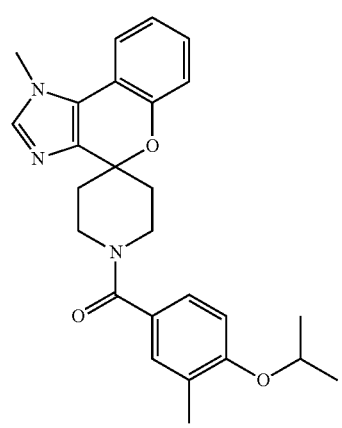
584
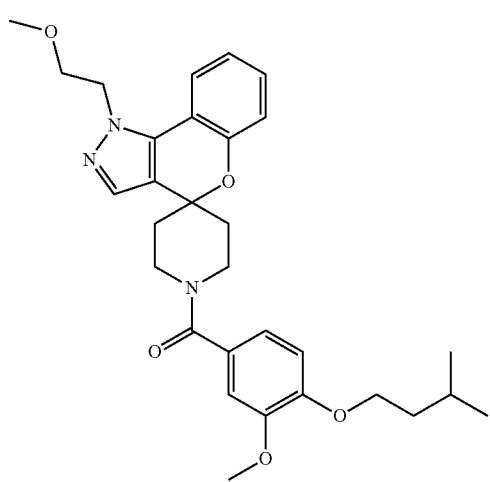
1020
-continued
585
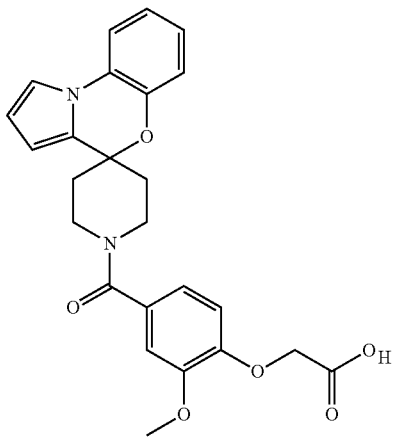
586
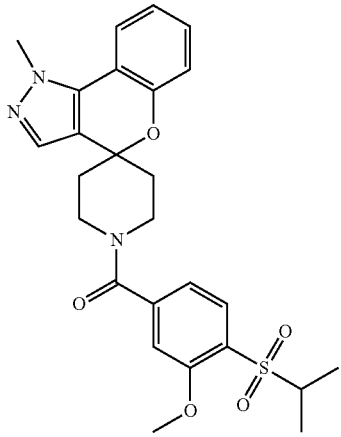
587
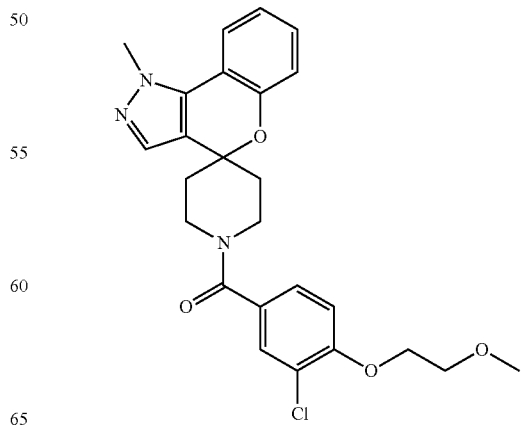

1021
-continued
588
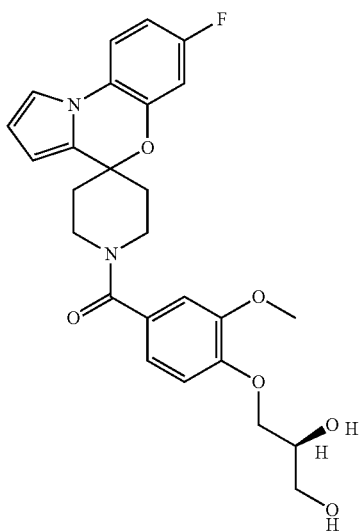
589
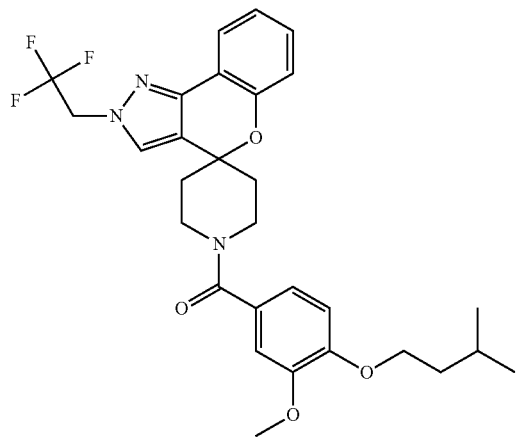
590
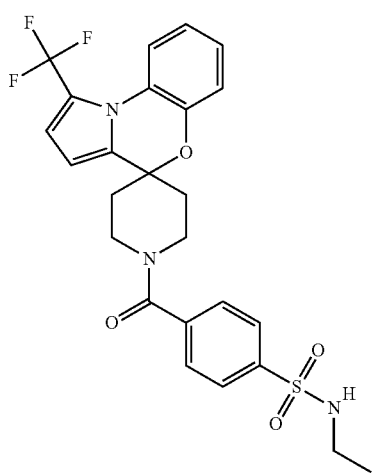
1022
-continued
591
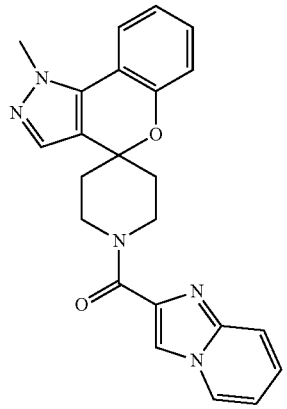
592
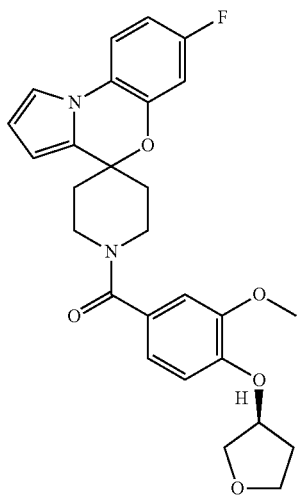
593
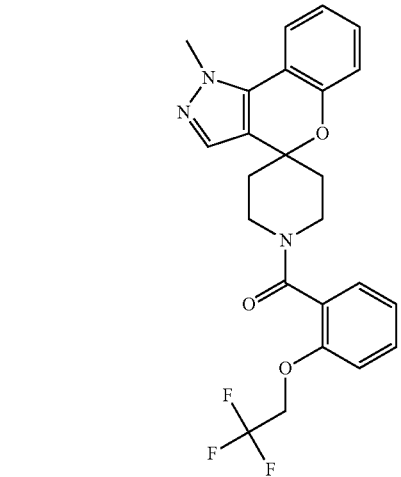

594
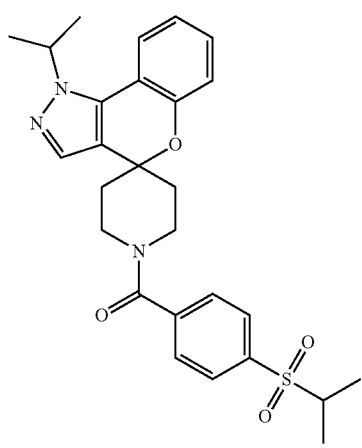
595
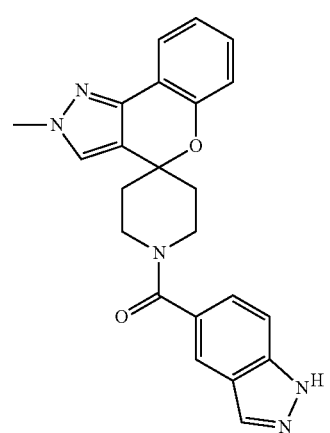
596
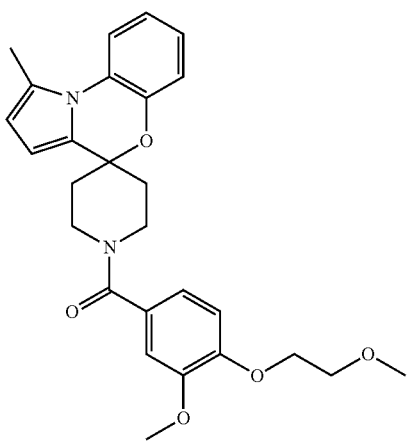
597
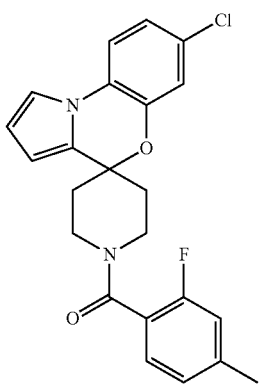
598
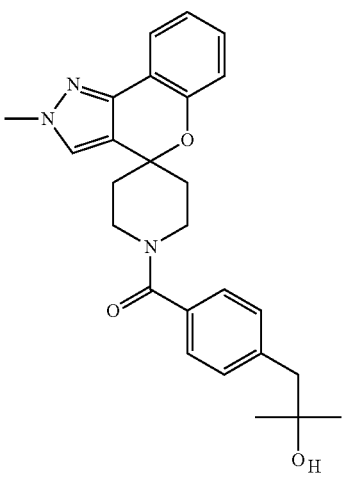
599
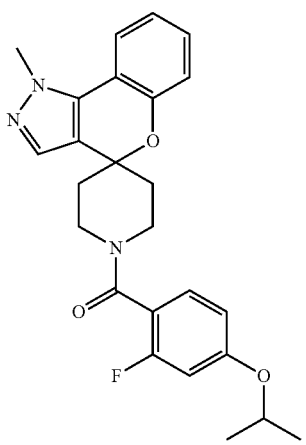

1025
-continued
1026
-continued
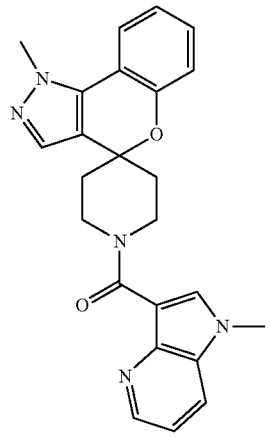
600
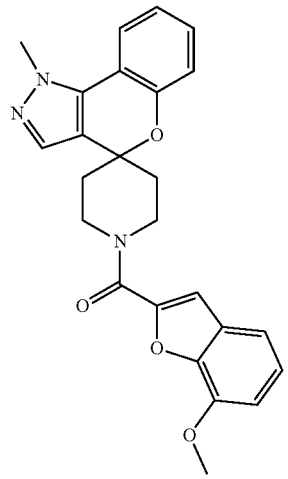
603
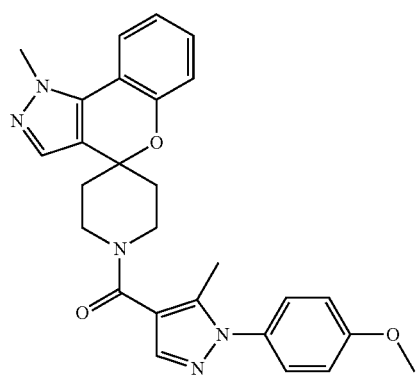
601
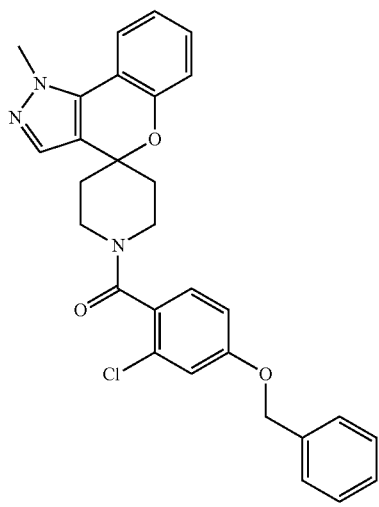
604
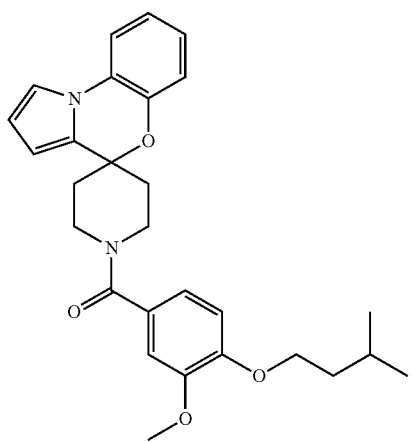
602
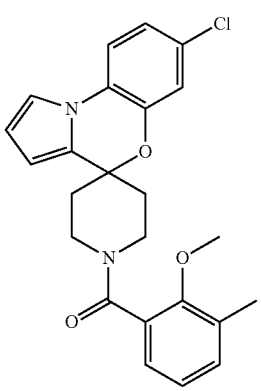
605

1027 -continued
606
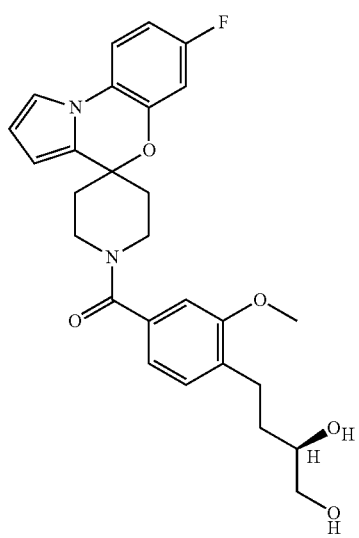
607
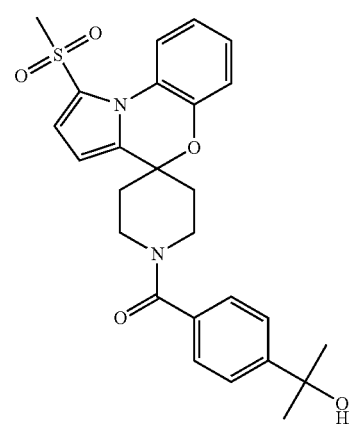
608
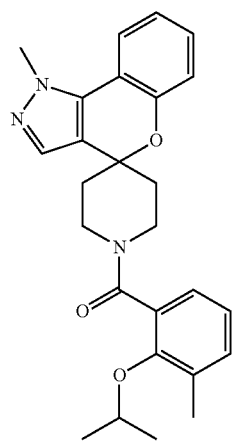
1028 -continued
609
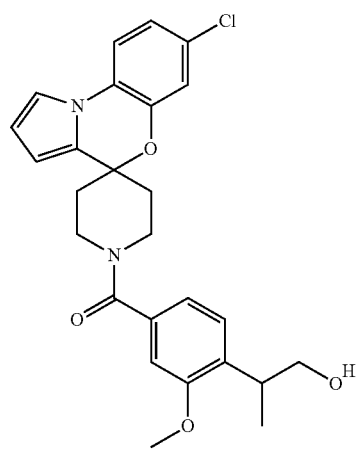
610
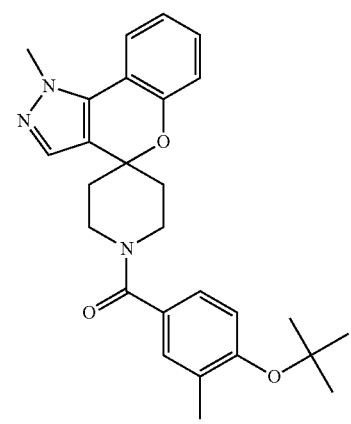
611
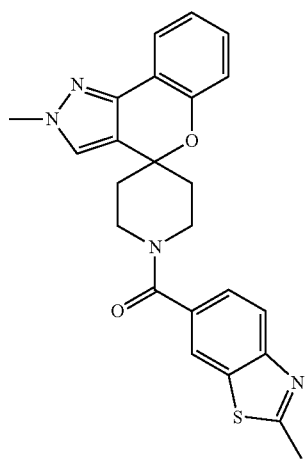

612 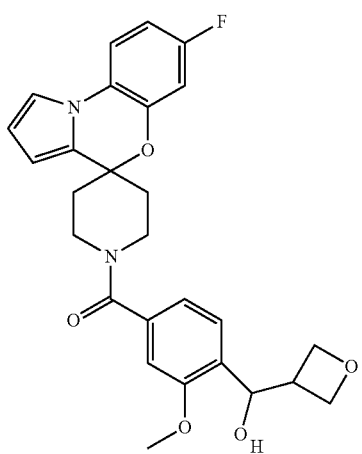
613 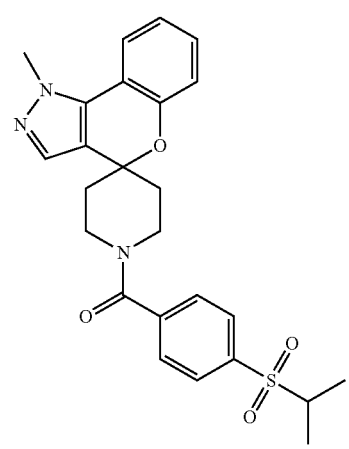
614 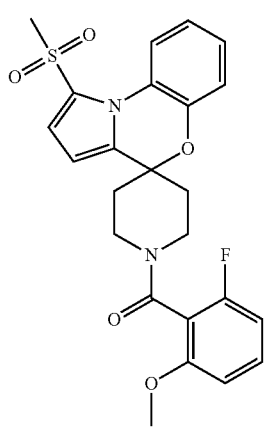
615 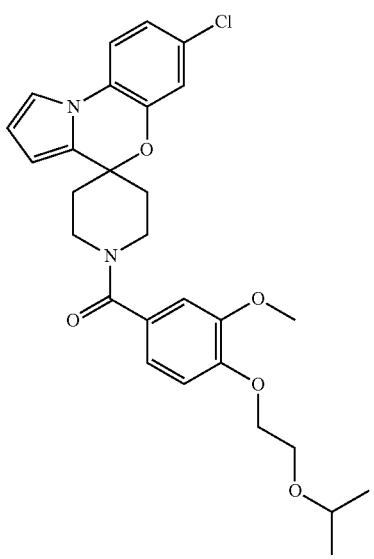
616 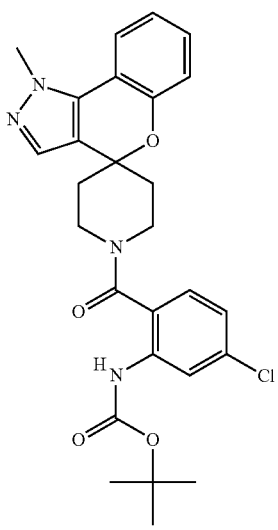
617 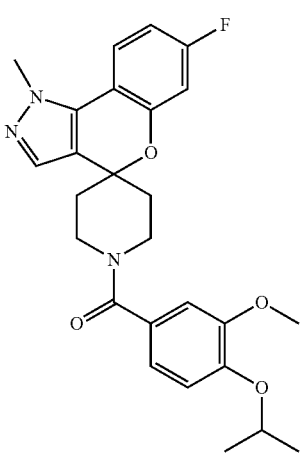

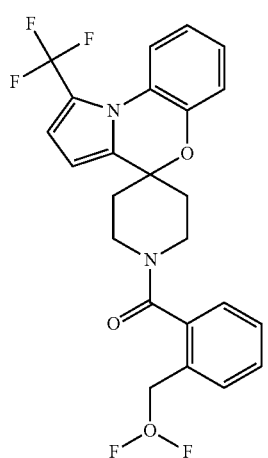
618
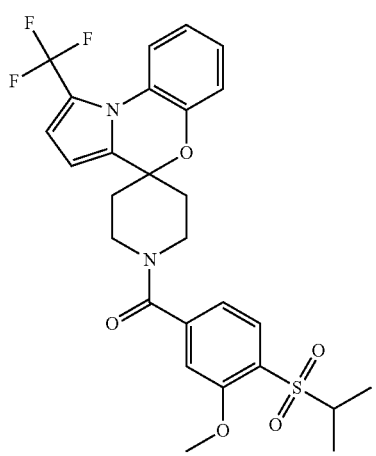
621
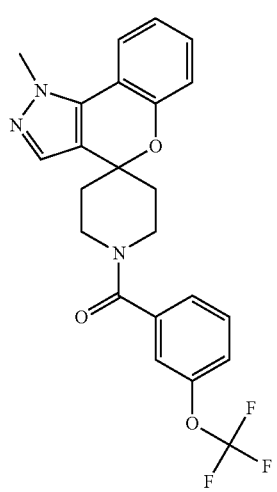
619
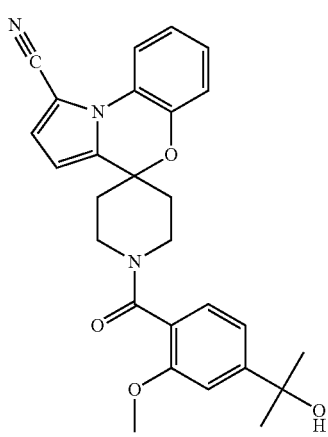
622
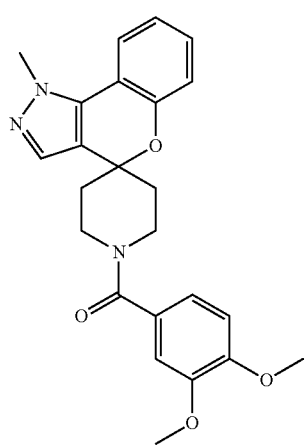
620
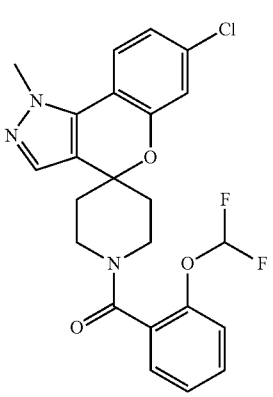
623

1033
-continued
1034
-continued
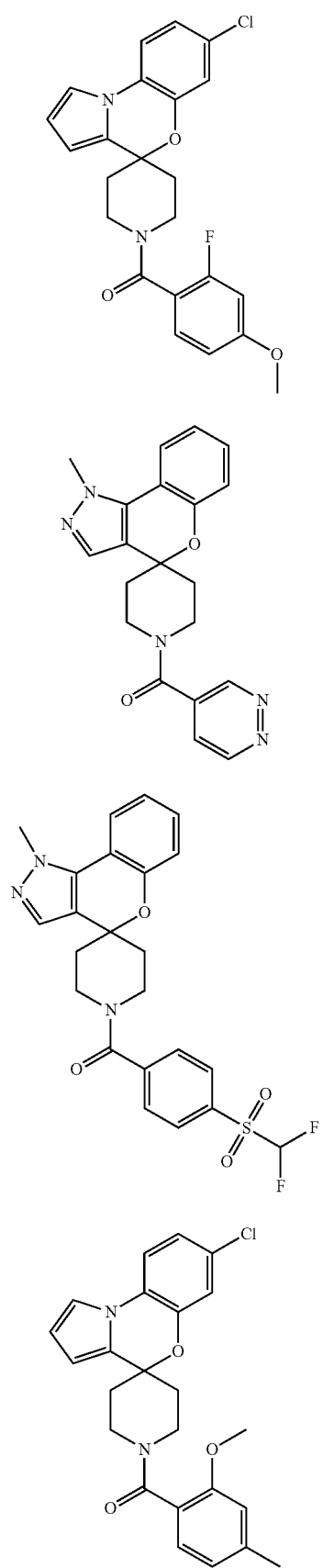
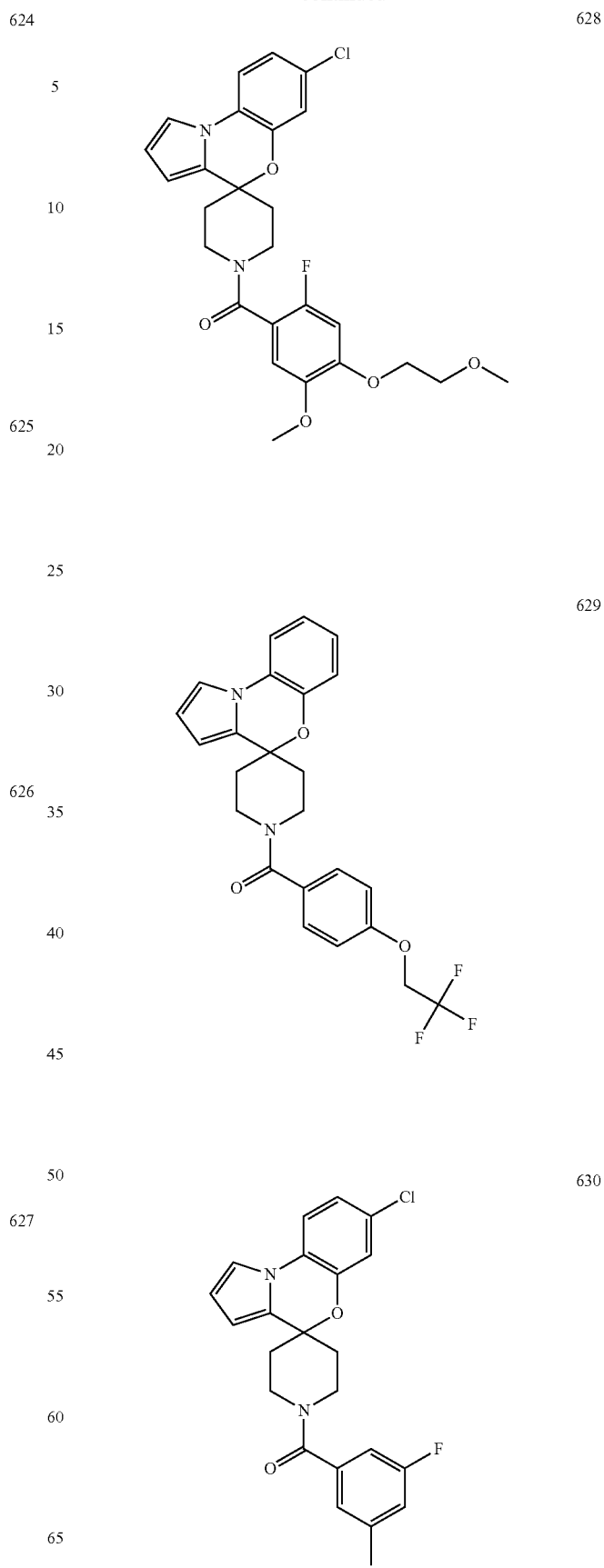

1035
-continued
631
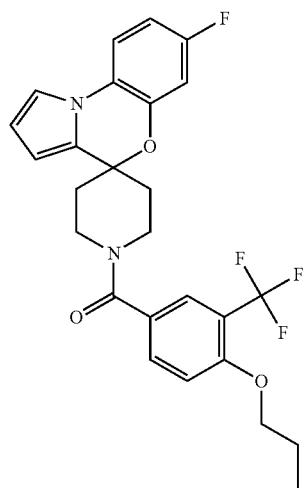
632
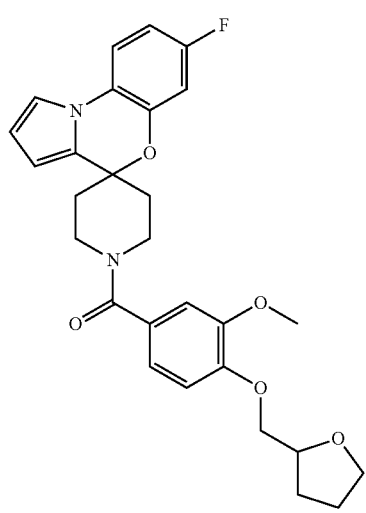
633
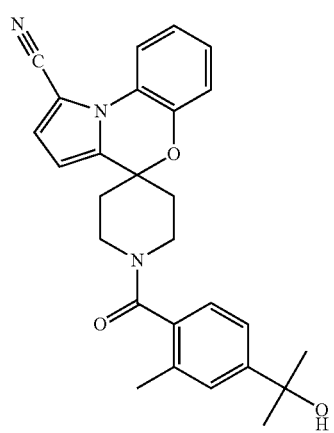
1036
-continued
634
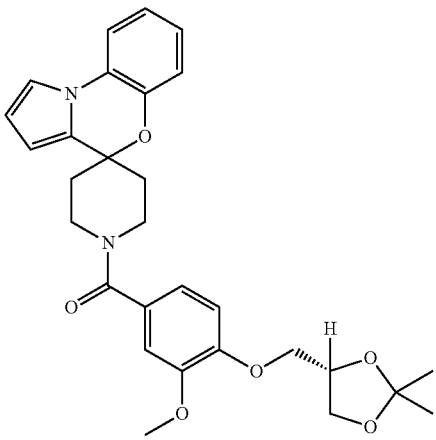
635
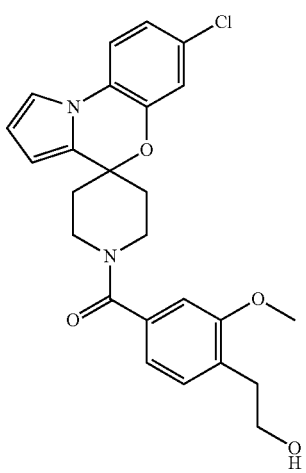
636
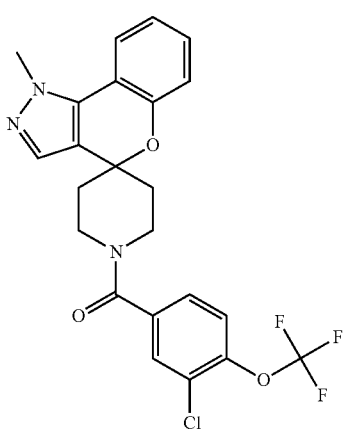

| 1037 | 1038 |
|---|---|
| -continued | -continued |
| 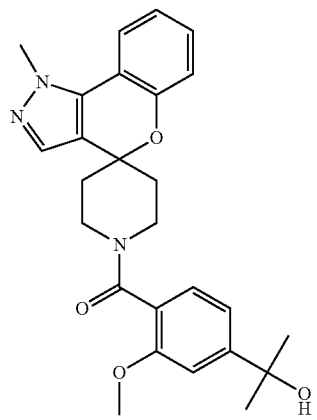 637 | 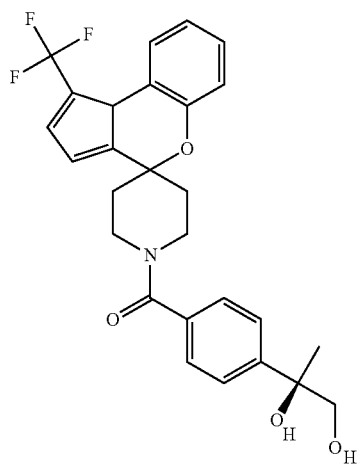 640 |
| 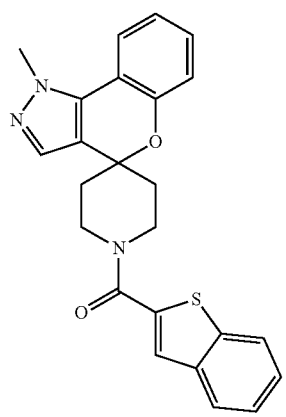 638 | 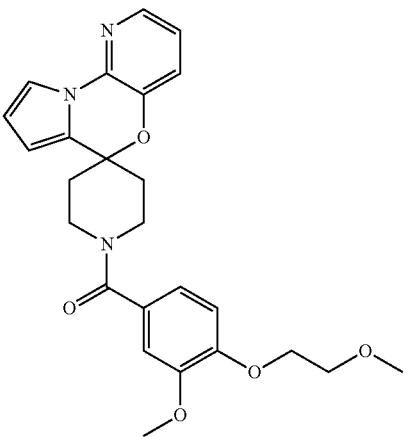 641 |
| 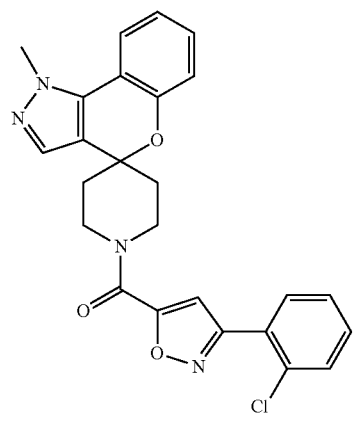 639 | 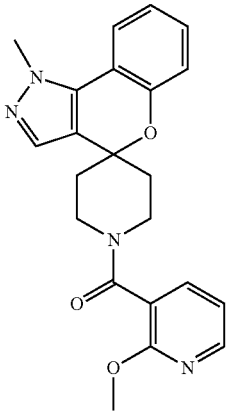 642 |

1039
-continued
643 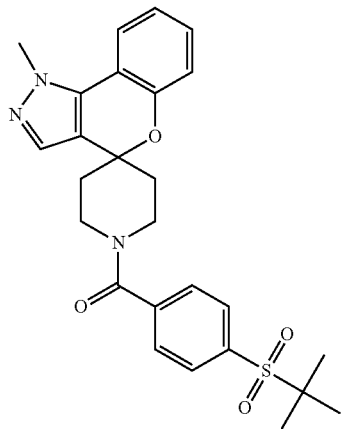
644 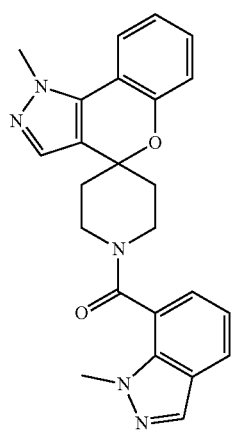
645 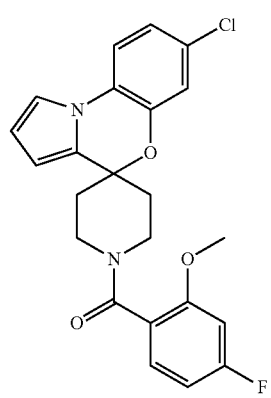
1040
-continued
646 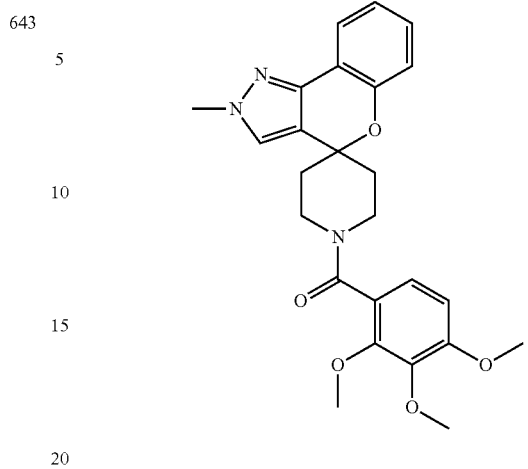
647 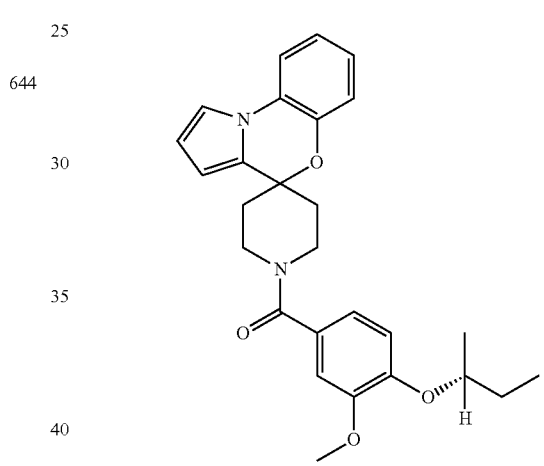
648 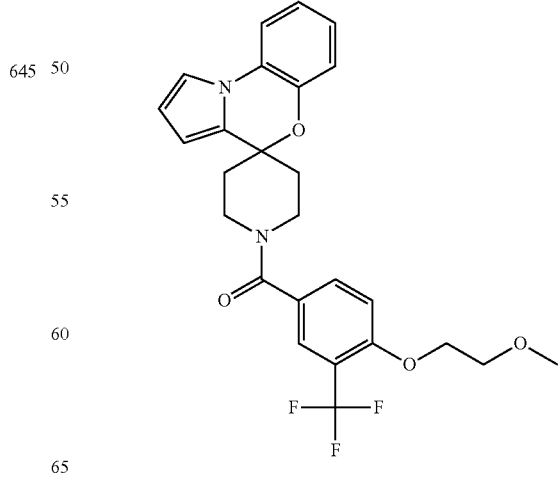

1041
-continued
1042
-continued
649
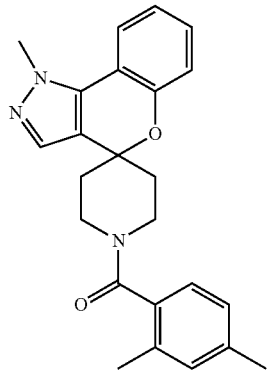
652
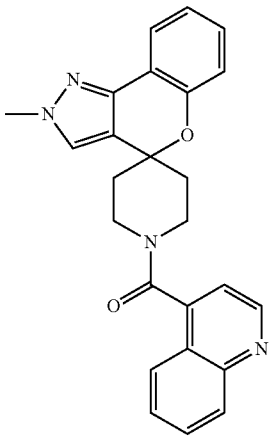
650
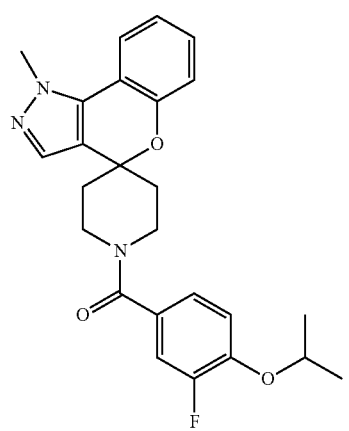
653
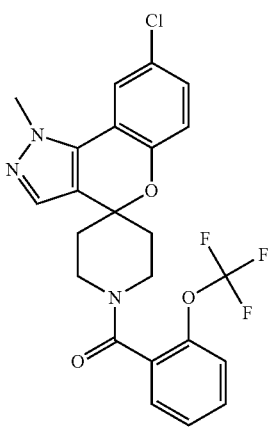
651
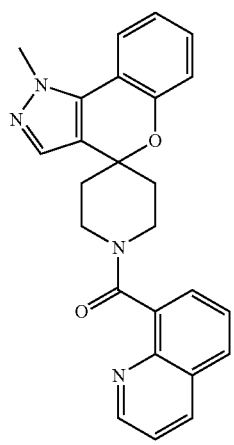
654
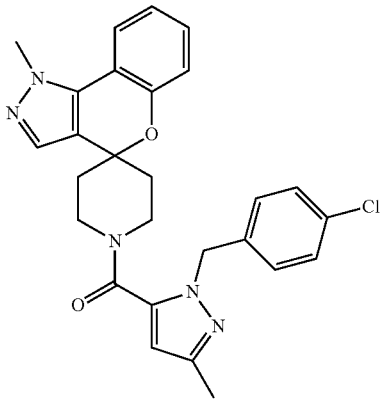

655
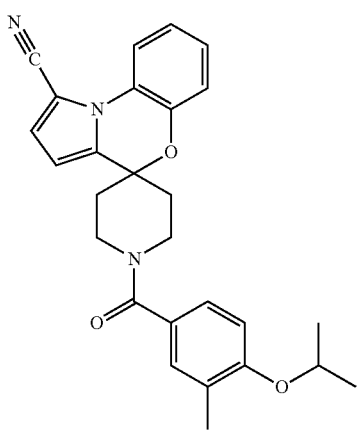
656
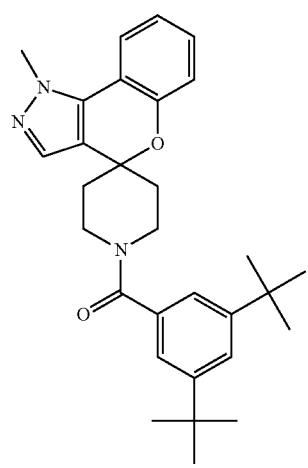
657
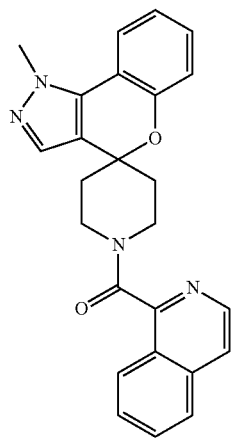
658
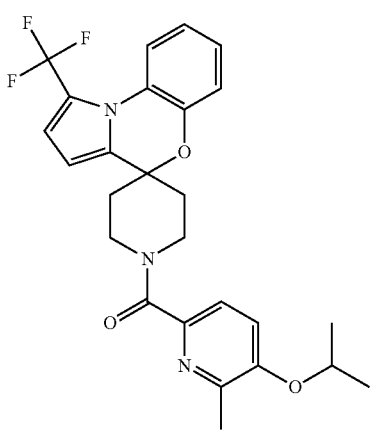
659
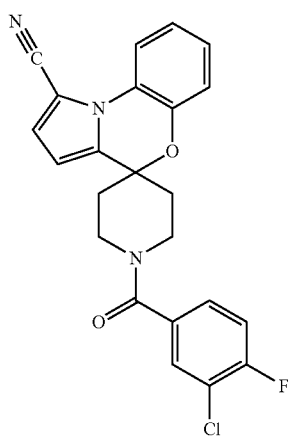
660
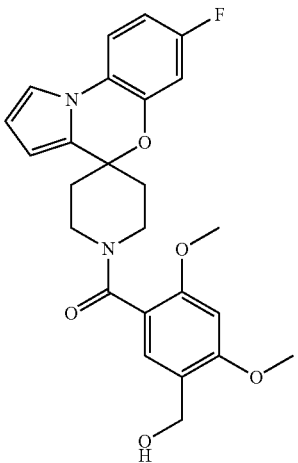

| 1045 -continued | 1046 -continued |
|---|---|
| 661 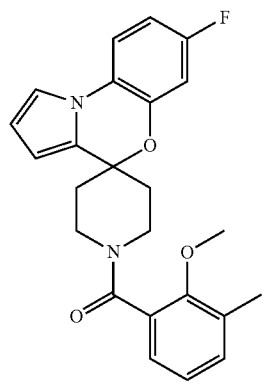 | 664 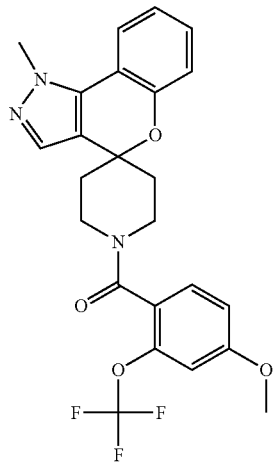 |
| 662 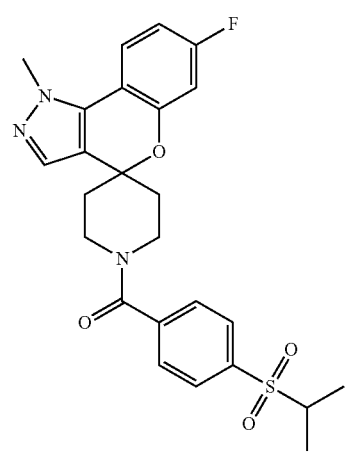 | 665 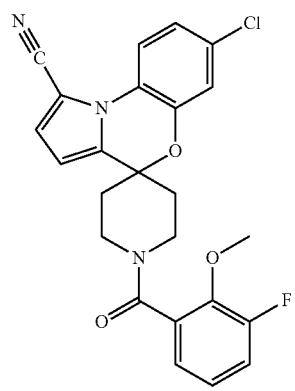 |
| 663 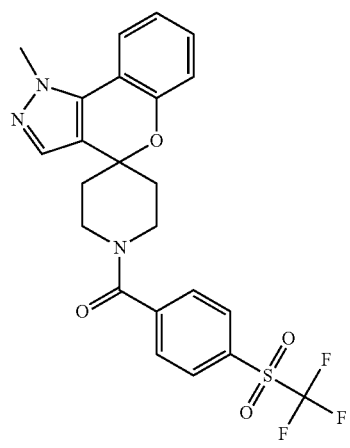 | 666 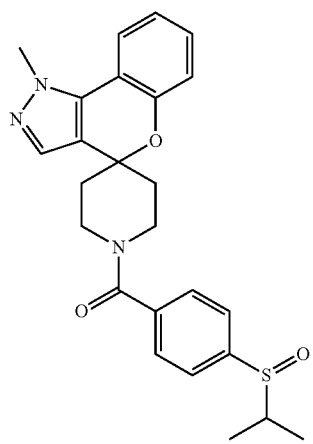 |

667
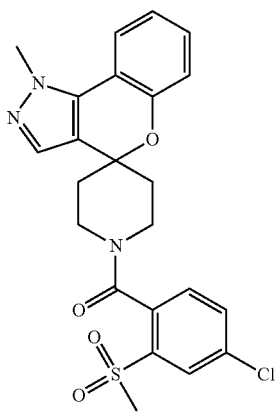
668
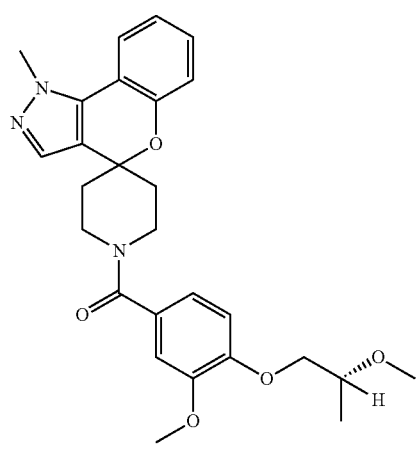
669
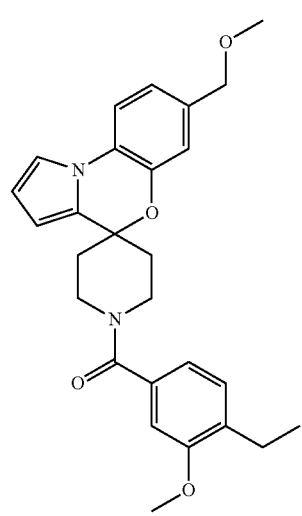
670
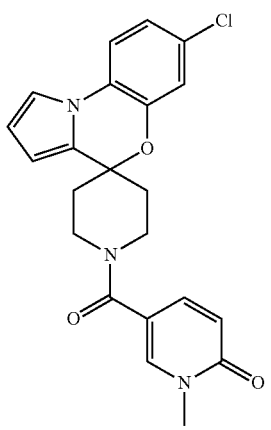
671
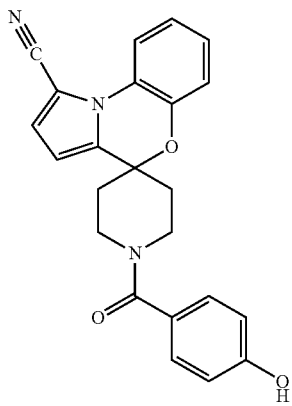
672
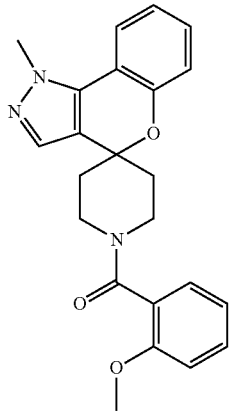

| 673 | 676 |
|---|---|
| 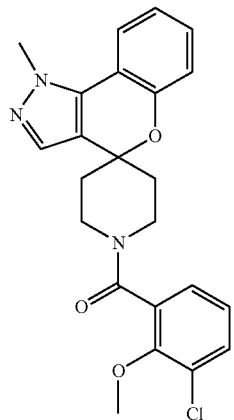 | 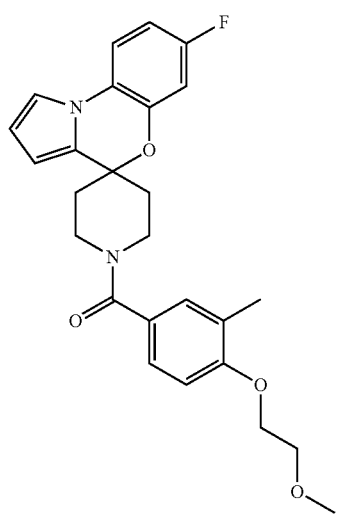 |
| 674 | 677 |
| 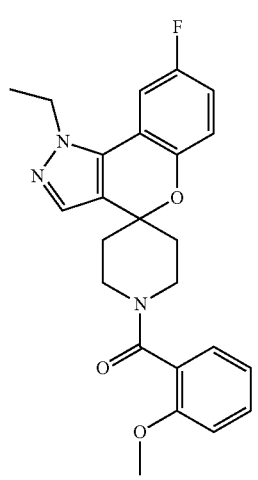 | 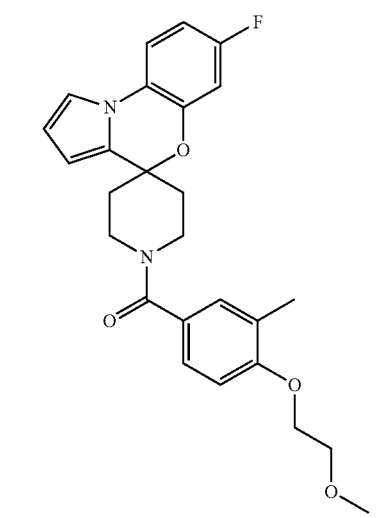 |
| 675 | 678 |
| 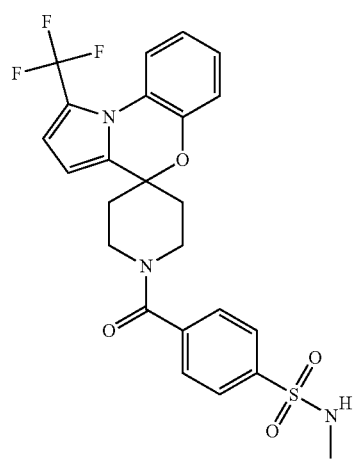 | 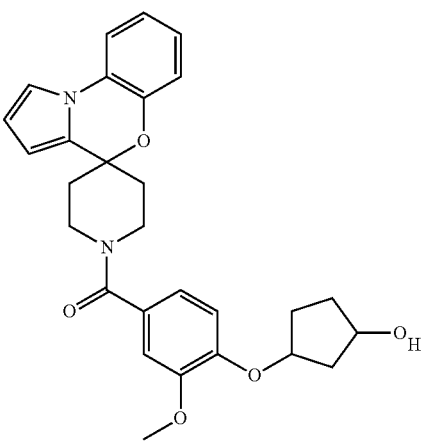 |

| 1051 | 1052 |
|---|---|
| -continued | -continued |
| 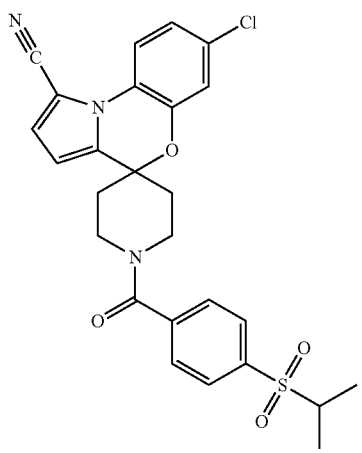 679 | 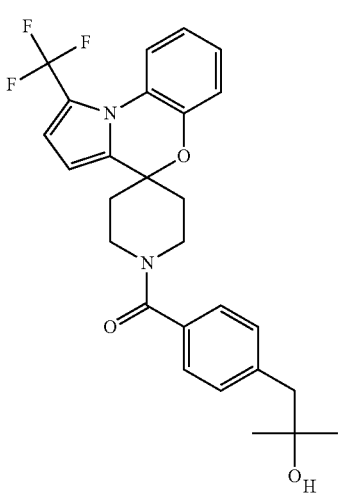 682 |
| 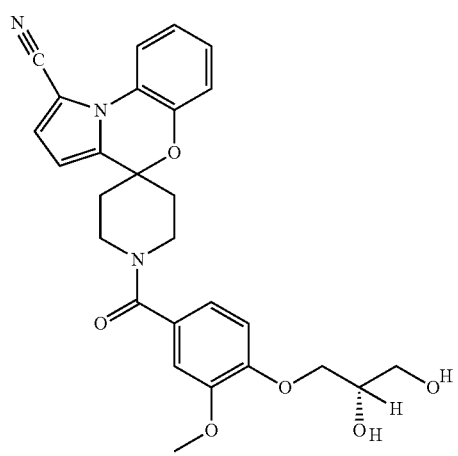 680 | 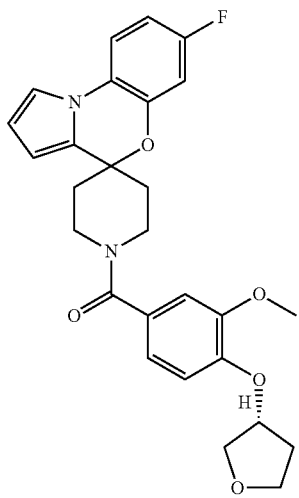 683 |
| 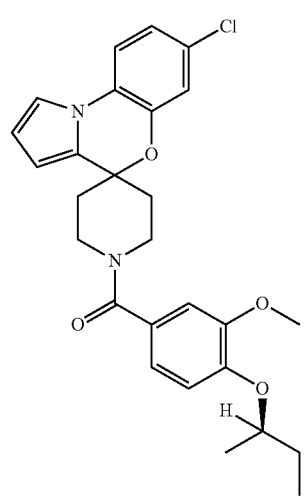 681 | 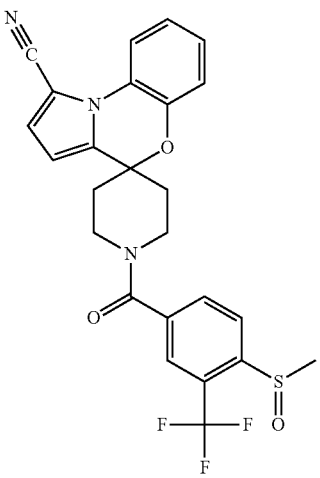 684 |

1053
-continued
685
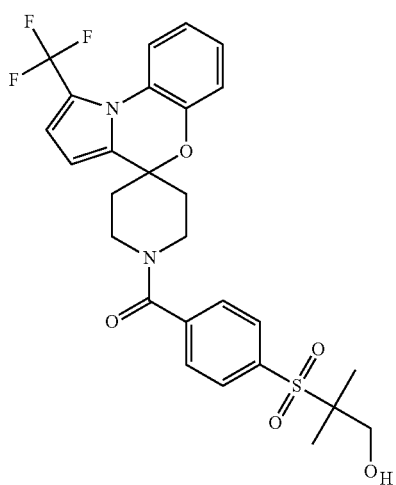
686
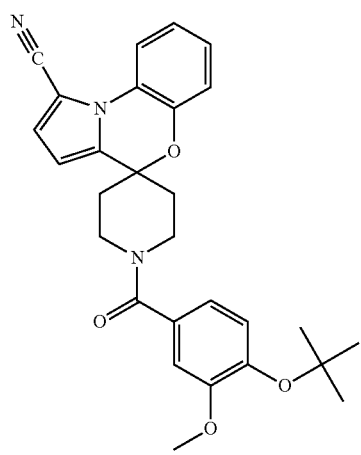
687
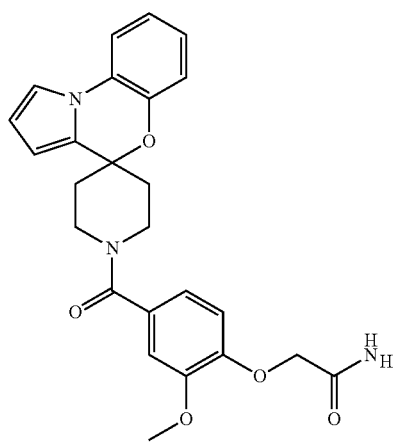
1054
-continued
688
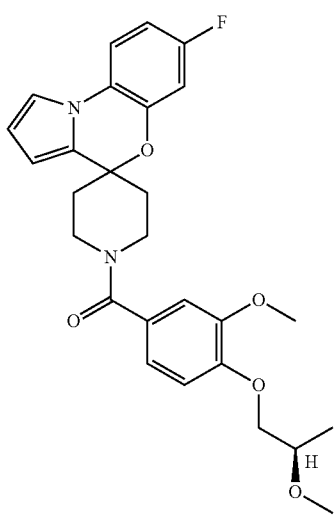
689
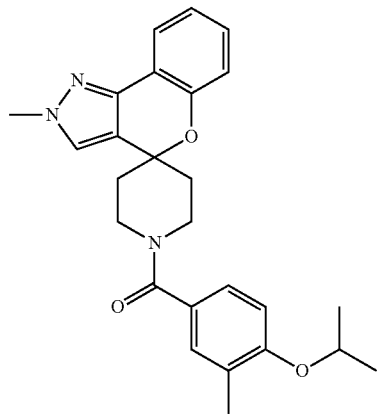
690
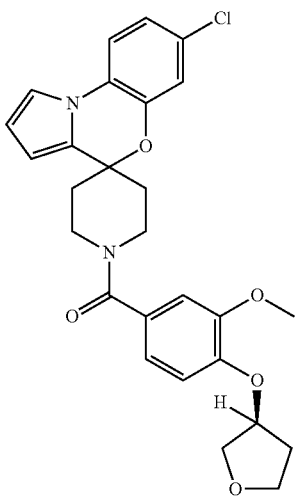

| 1055 -continued | 1056 -continued |
|---|---|
| 691 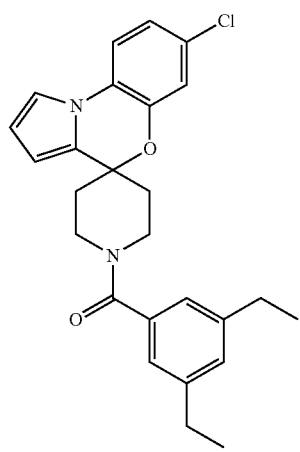 | 694 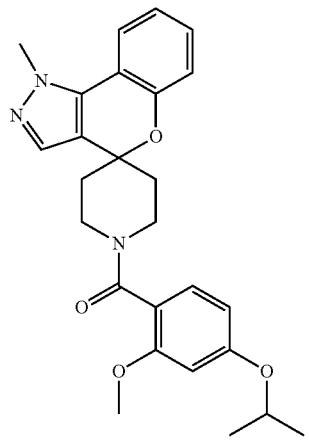 |
| 692 | 695 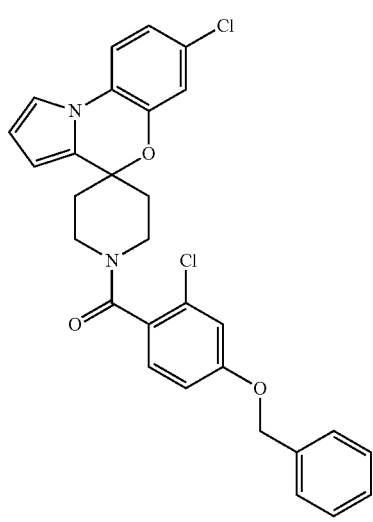 |
| 693 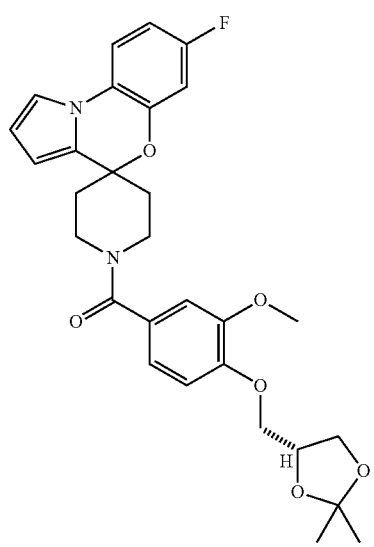 | 696 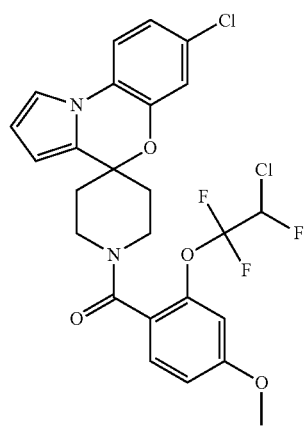 |

1057
-continued
1058
-continued
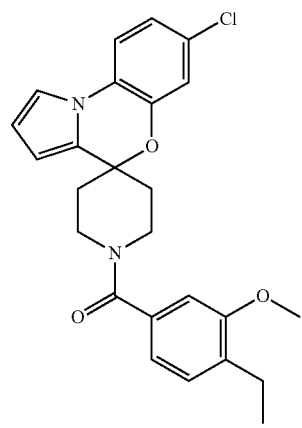
697
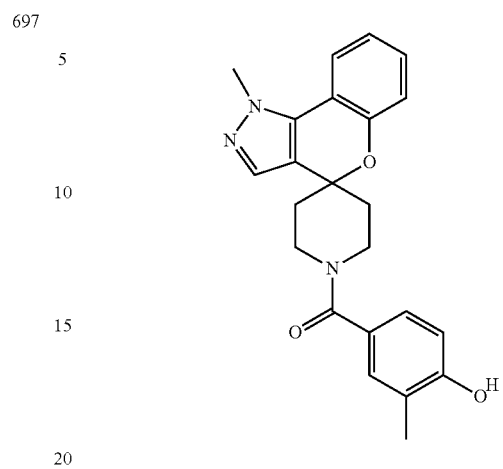
700
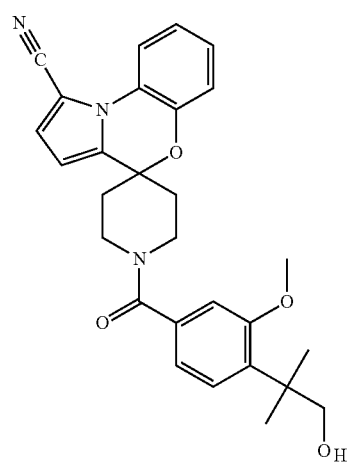
698
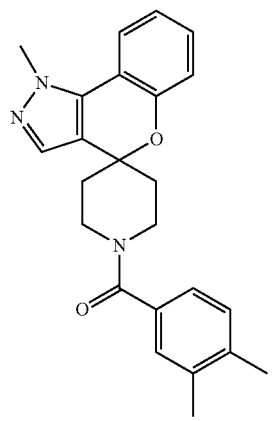
701
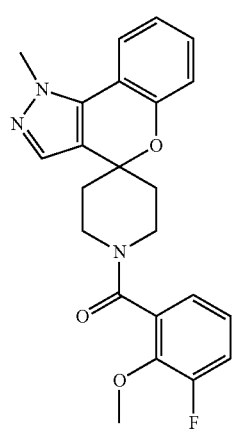
699
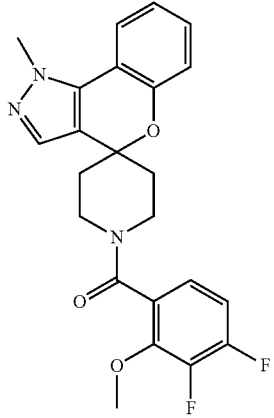
702

| 1059 -continued | 1060 -continued |
|---|---|
| 703 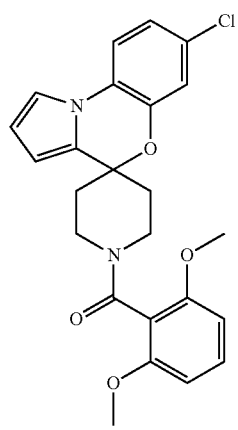 | 706 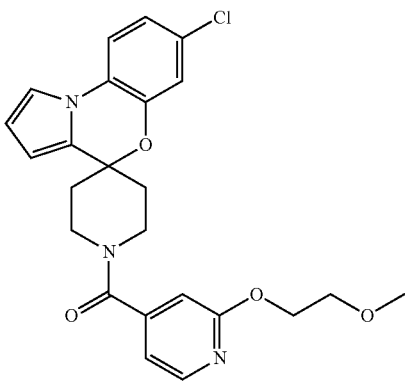 |
| 704 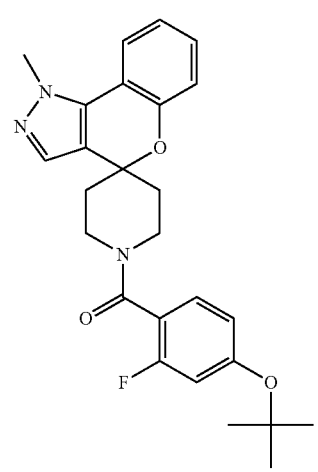 | 707 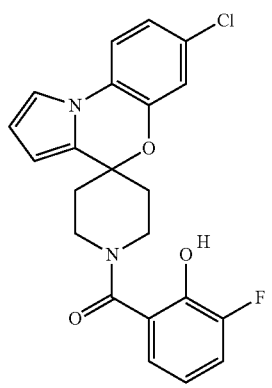 |
| | 708 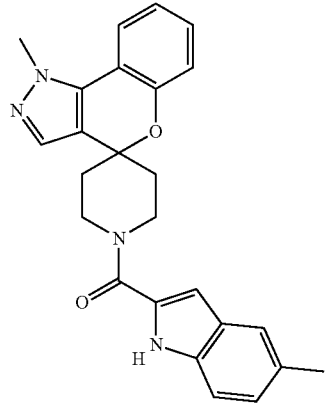 |
| 705 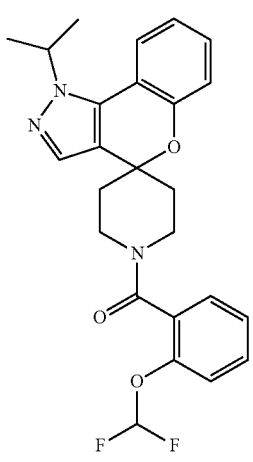 | 709 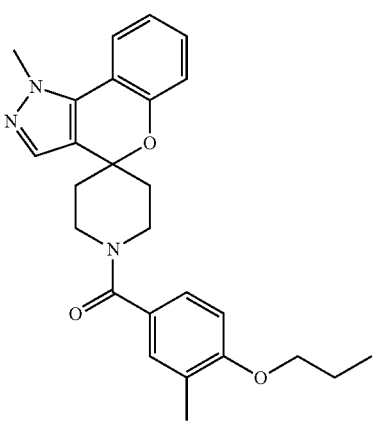 |

| 710 | 713 |
|---|---|
| 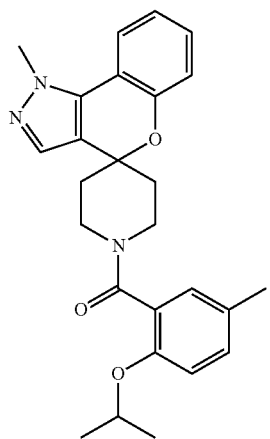 | 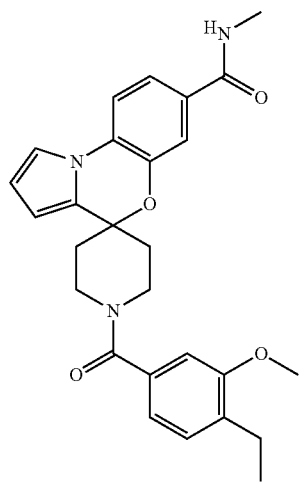 |
| 711 | 714 |
|---|---|
| 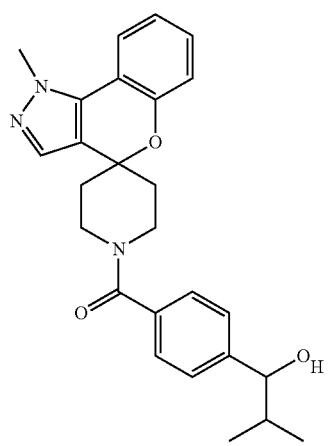 | 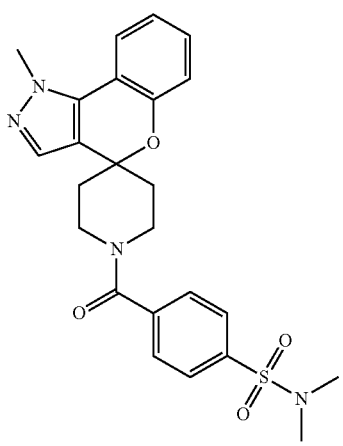 |
| 712 | 715 |
|---|---|
| 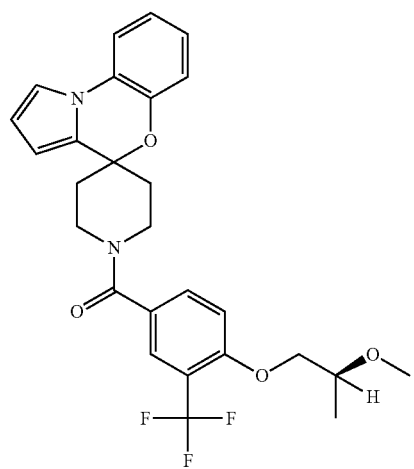 | 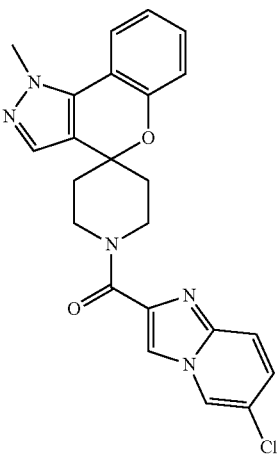 |

716 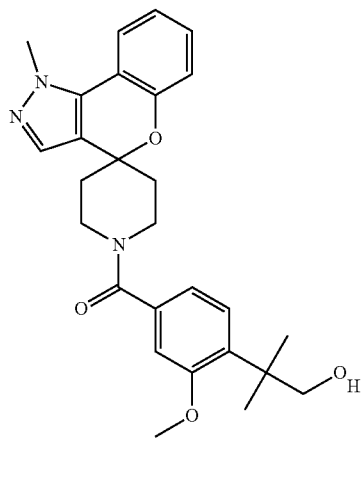
717 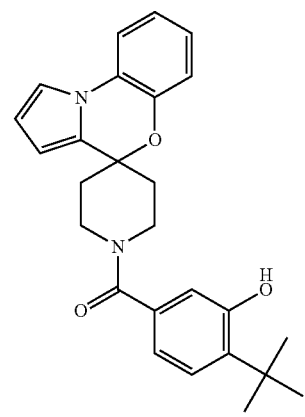
718 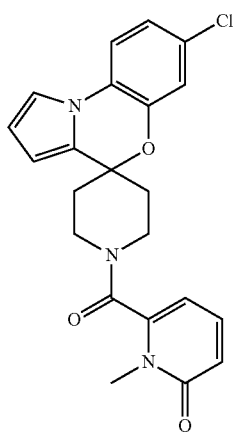
719 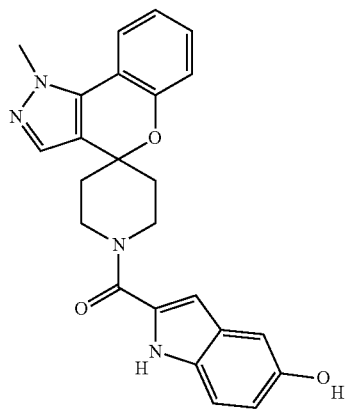
720 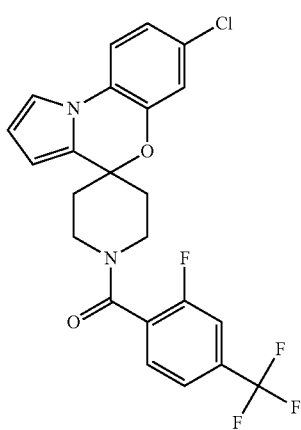
721 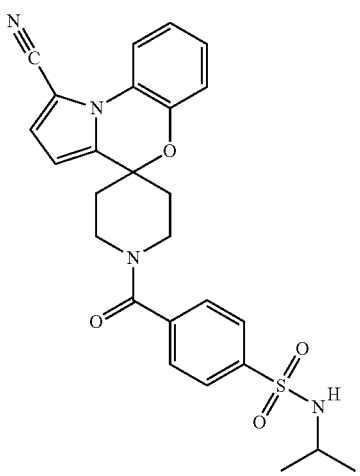

1065
-continued
722 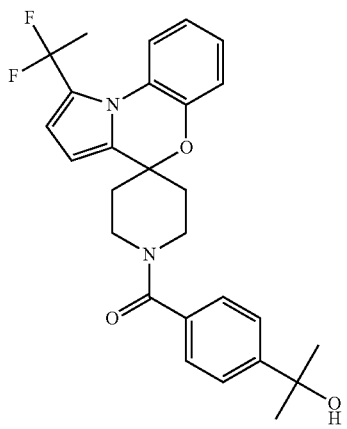
723 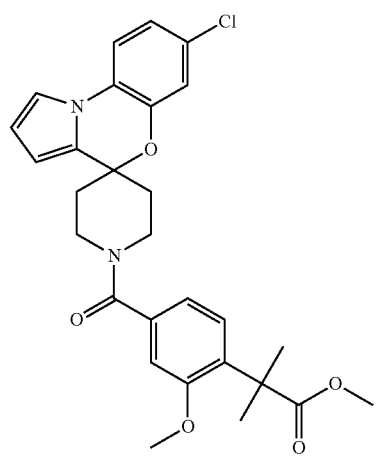
724 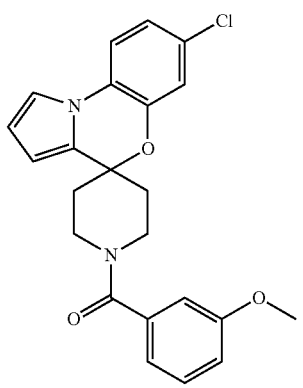
1066
-continued
725 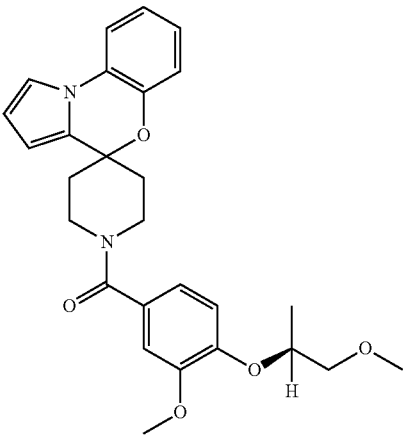
726 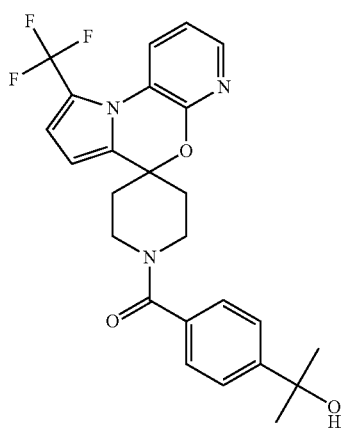
727 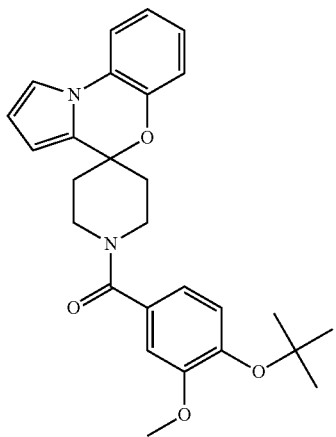

728
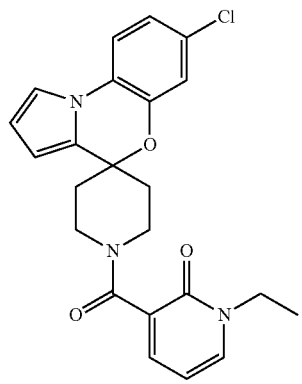
729
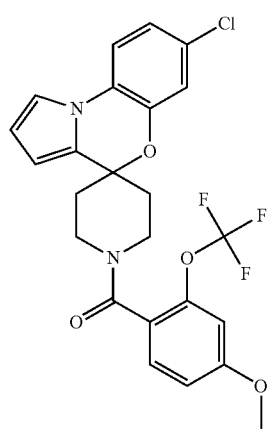
730
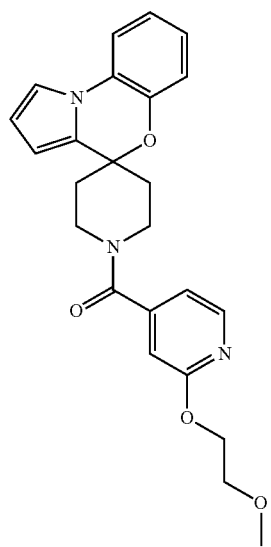
731
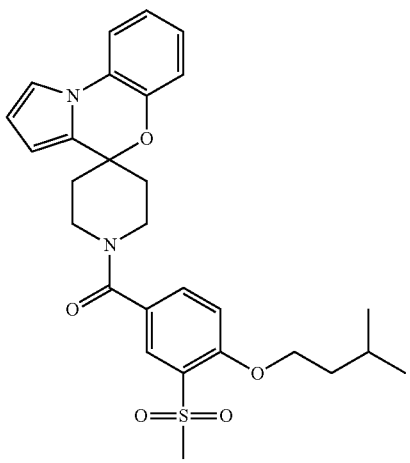
732
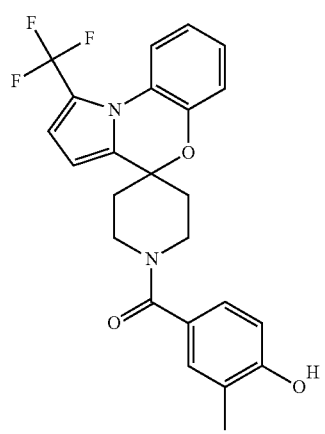
733
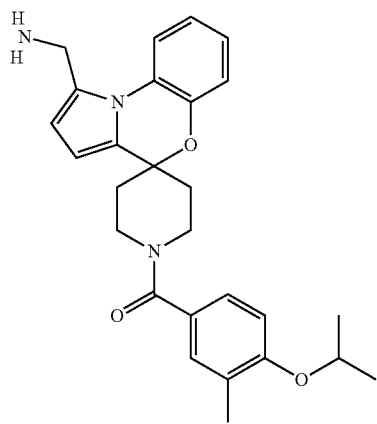

-continued
734
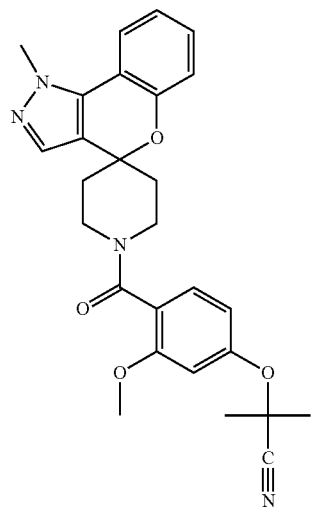
735
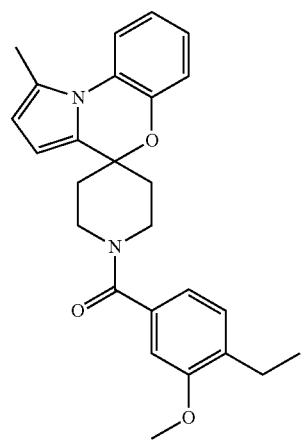
736
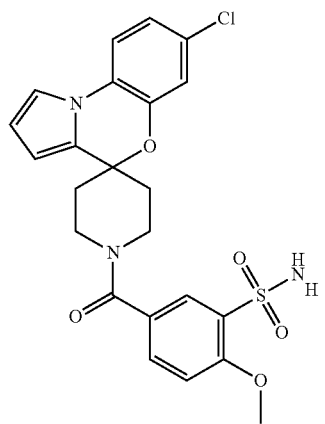
-continued
737
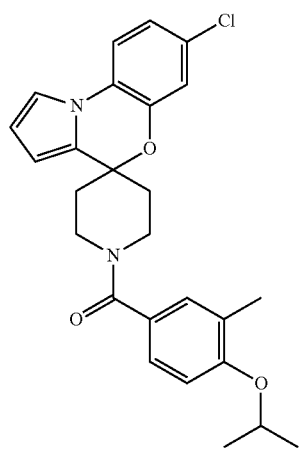
738
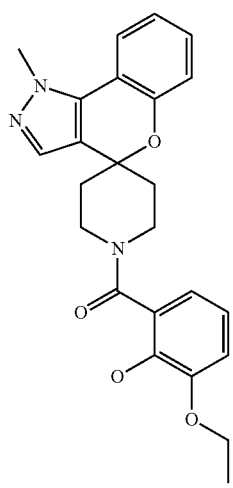
739

740
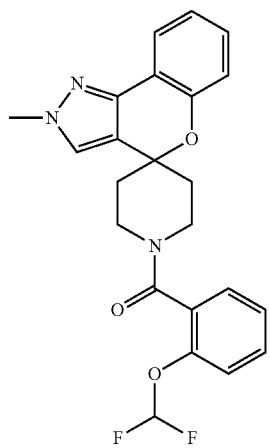
741
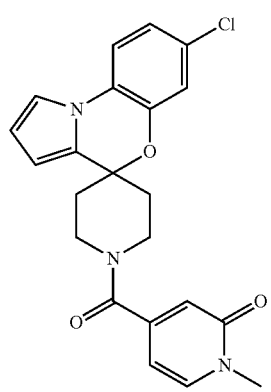
742
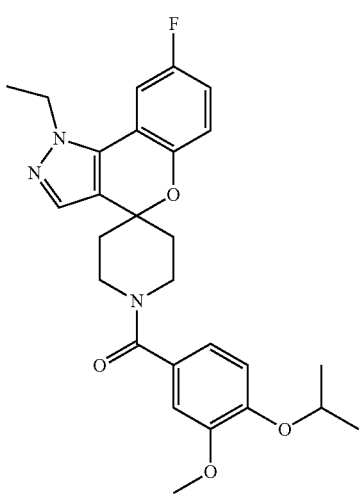
743
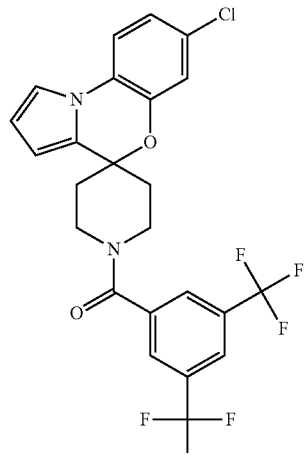
744
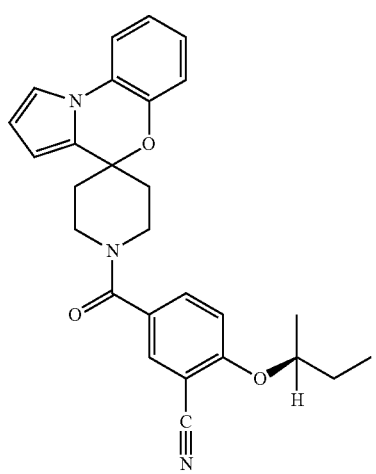
745
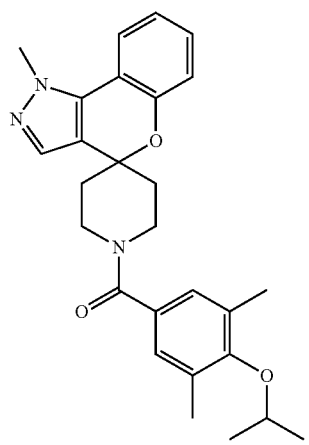

746
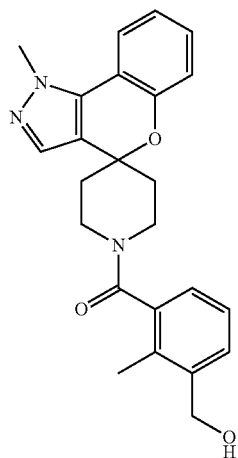
747
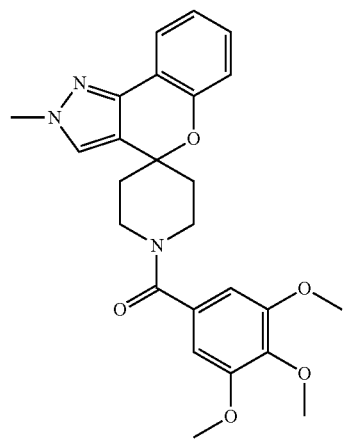
748
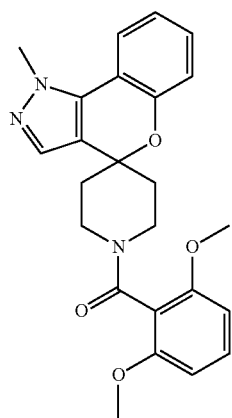
749
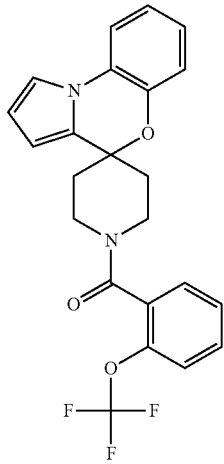
750
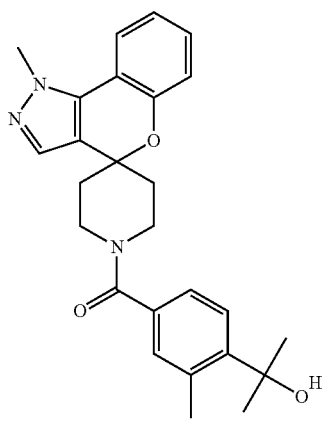
751
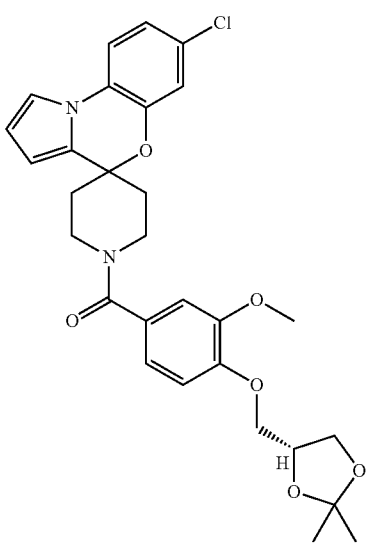

752 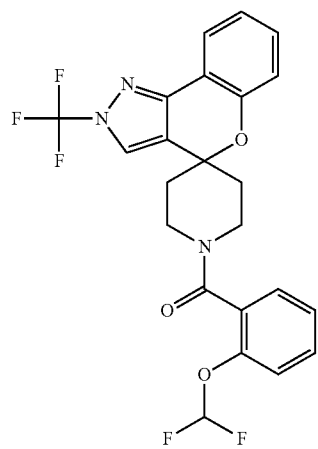
755 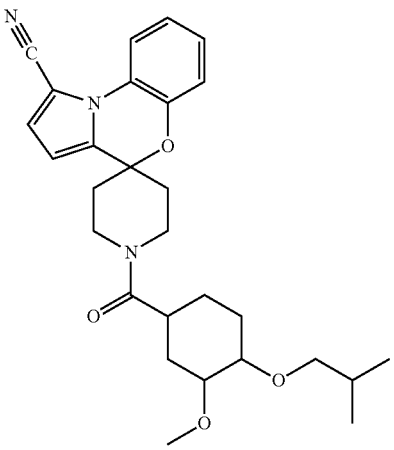
753 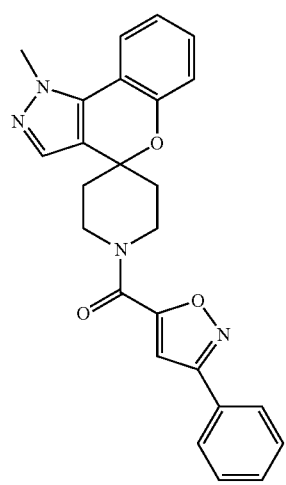
756 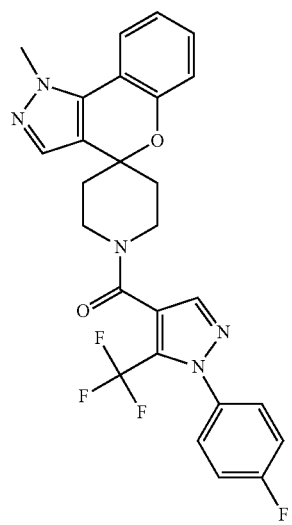
754 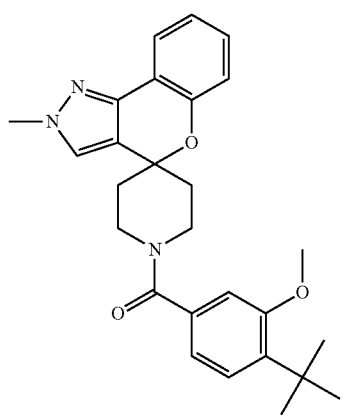
757 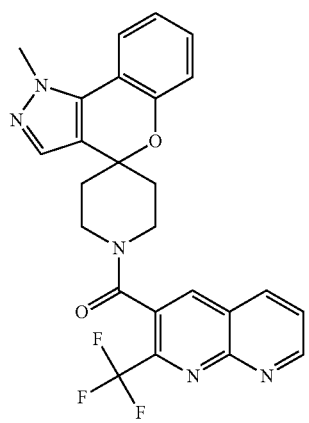

| 1077 | 1078 |
|---|---|
| -continued | -continued |
758
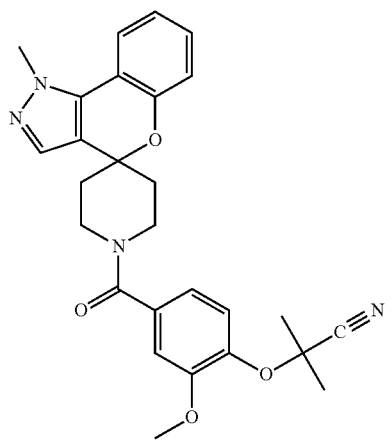
761
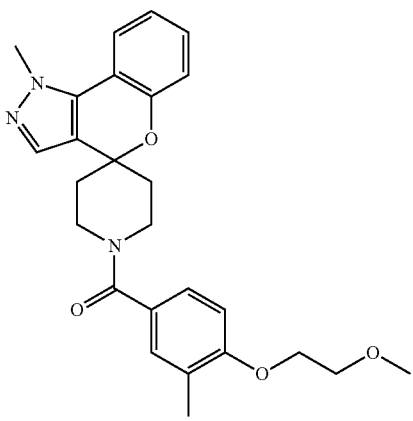
759
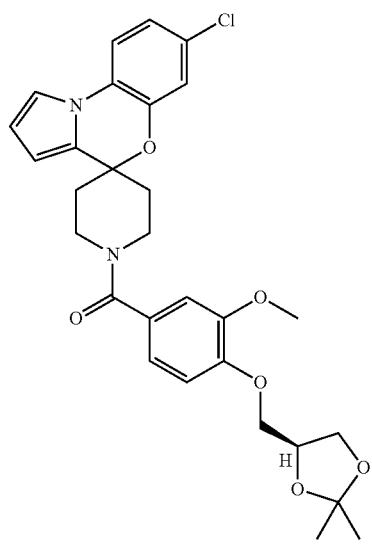
762
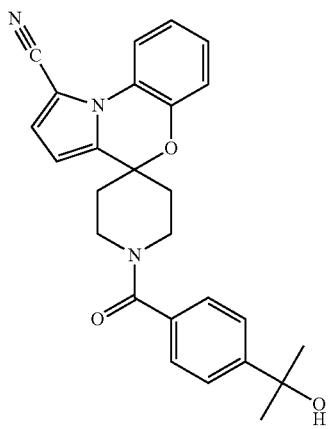
760
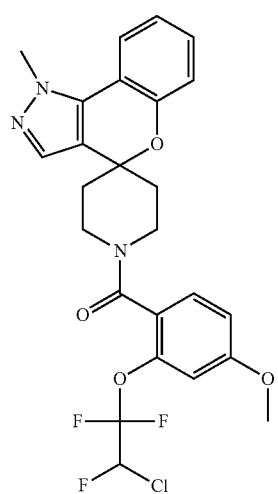
763
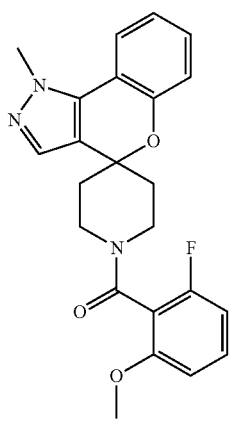

1079
-continued
764
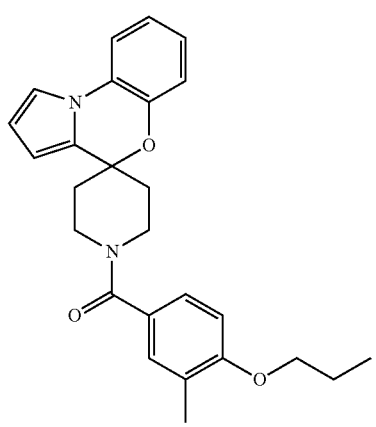
765
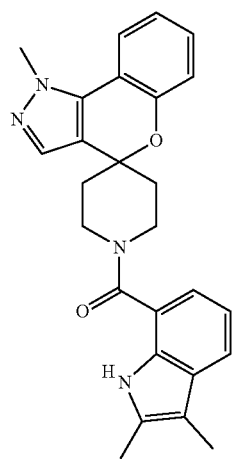
766
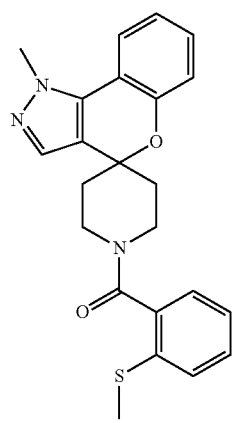
1080
-continued
767
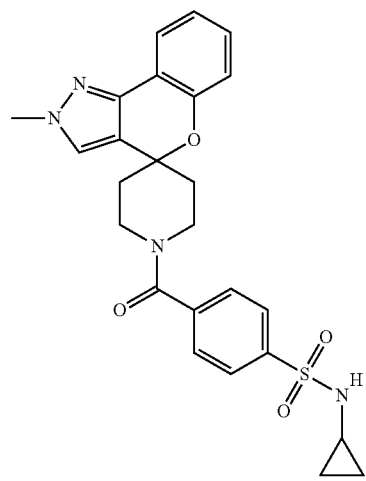
768
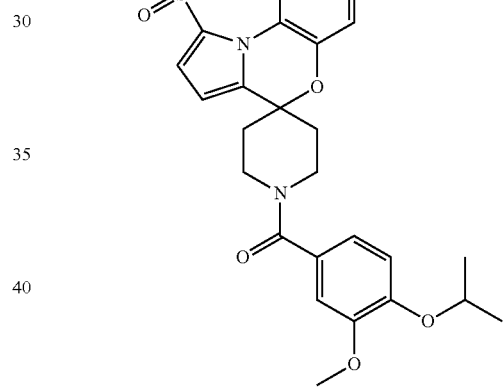
769
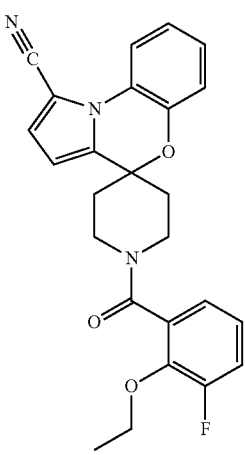

1081
-continued
770
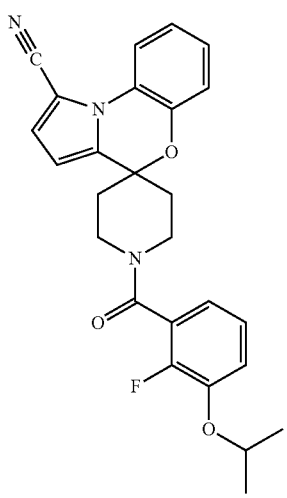
771
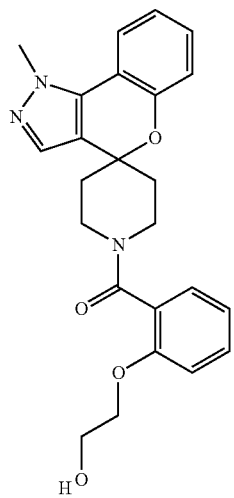
772
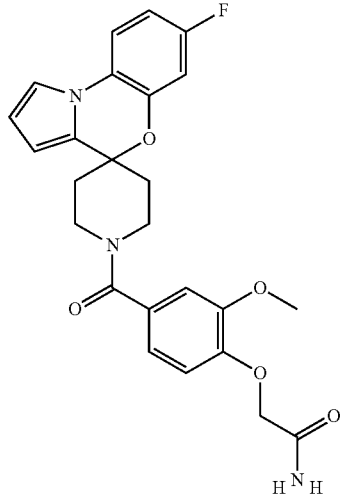
1082
-continued
773
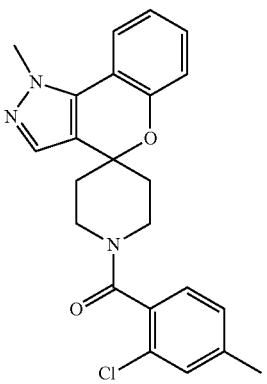
774
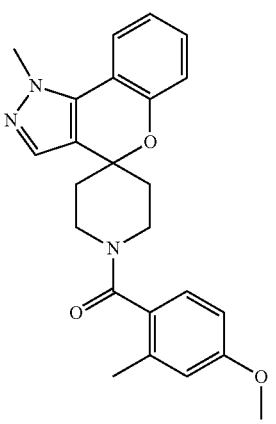
775
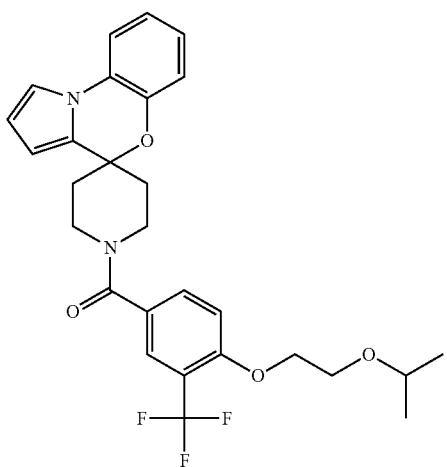

776 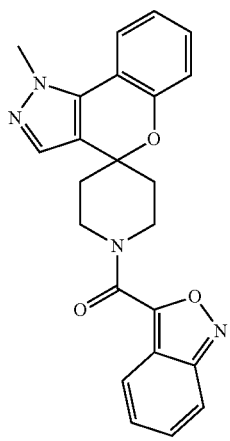
777 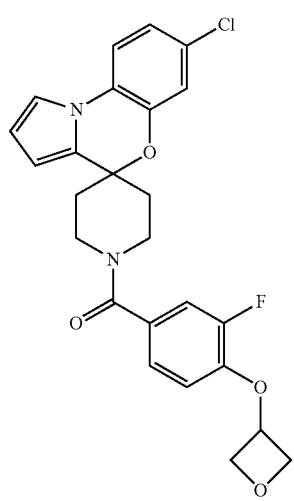
778 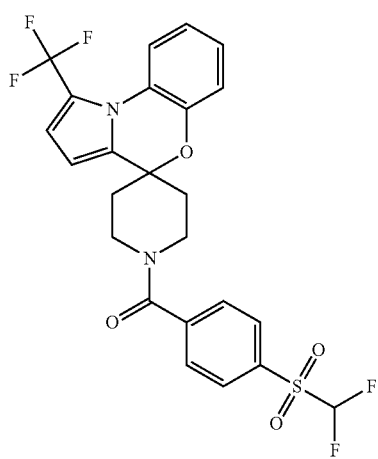
779 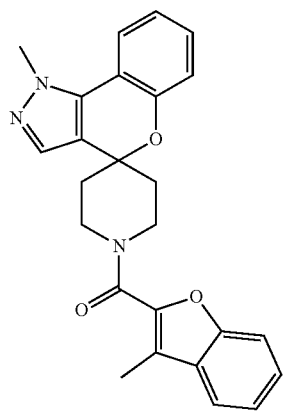
780 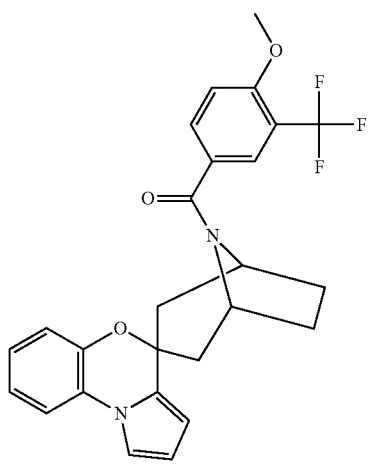
781 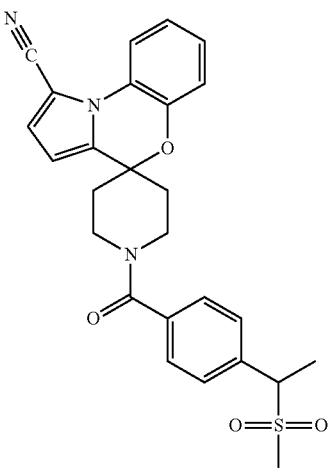

1085
-continued
782
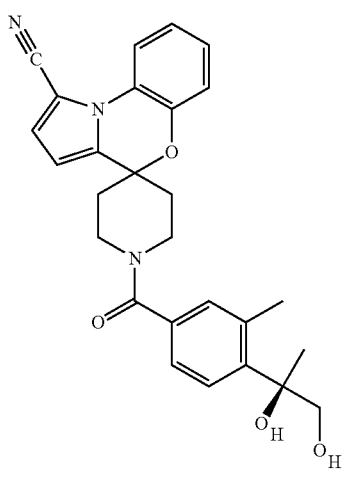
783
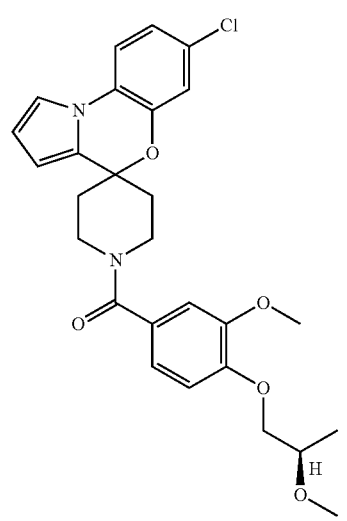
784
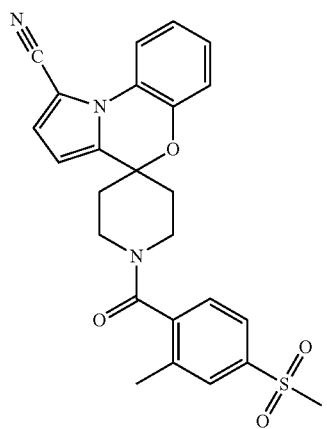
1086
-continued
785
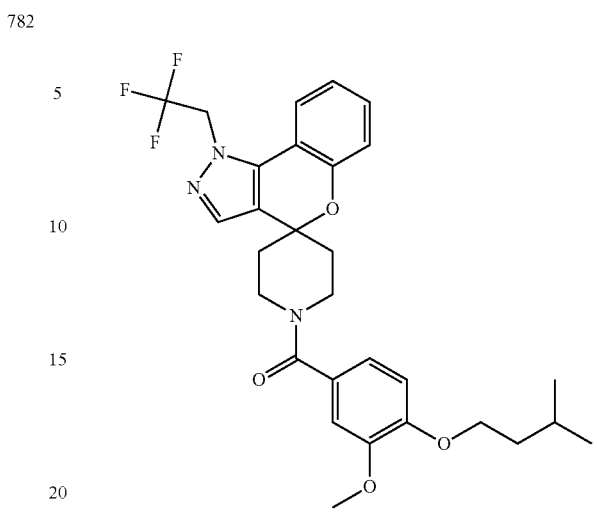
786
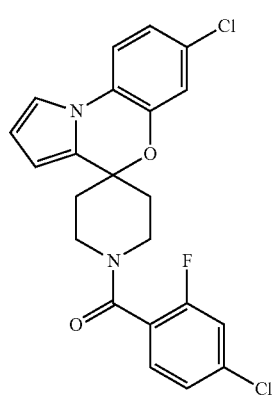
787
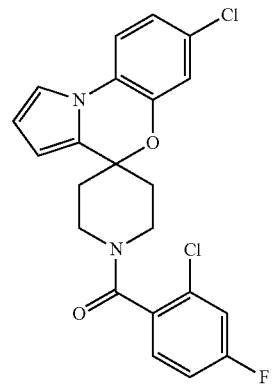

1087 -continued
788
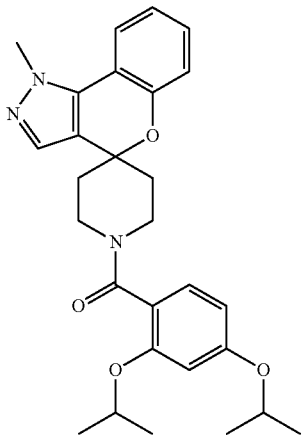
789
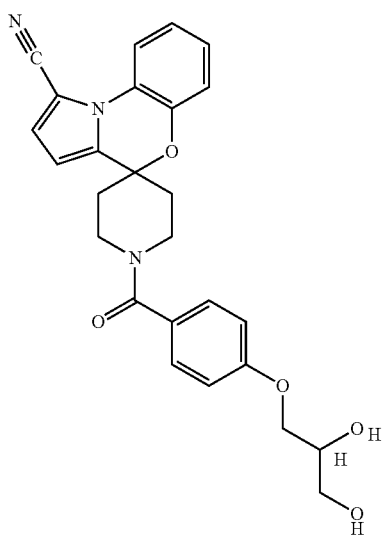
790
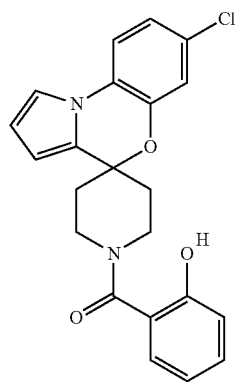
1088 -continued
791
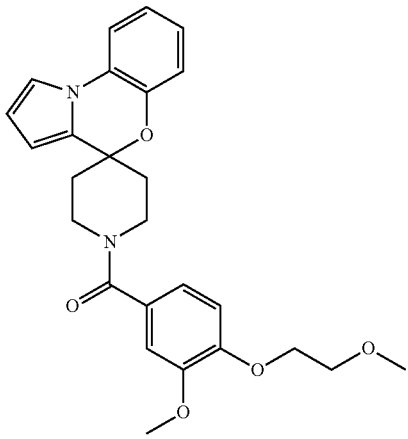
792
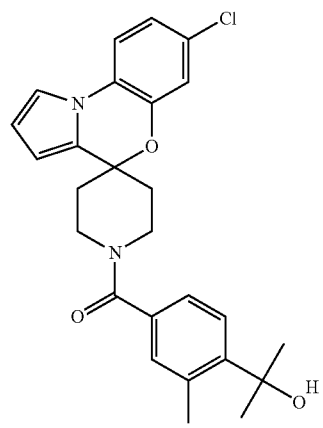
793
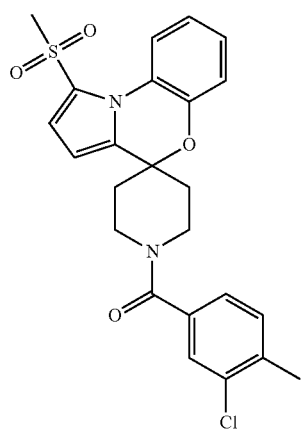

794
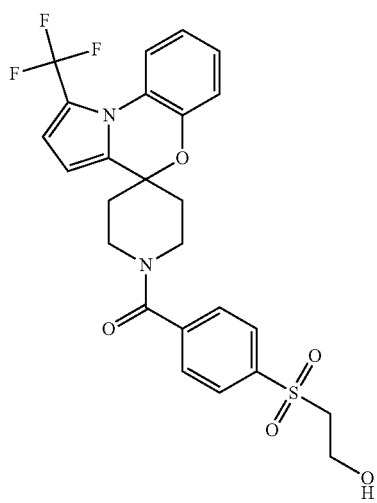
795
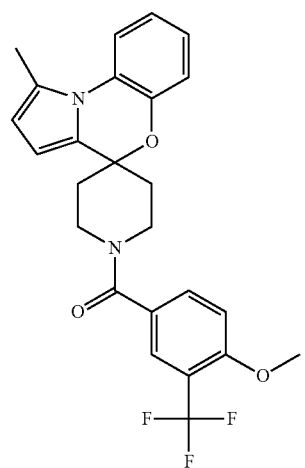
796
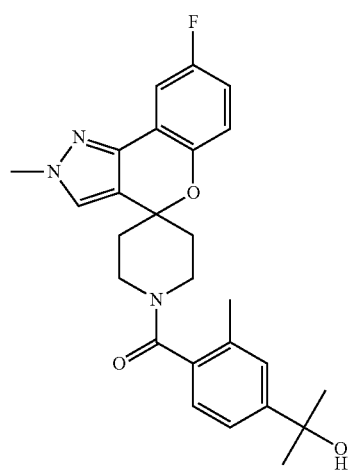
797
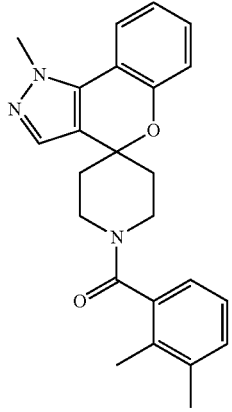
798
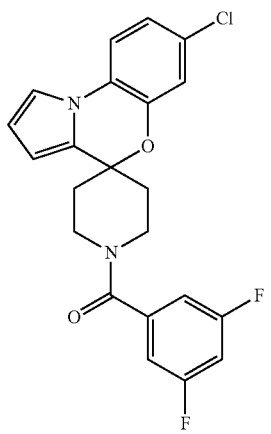
799
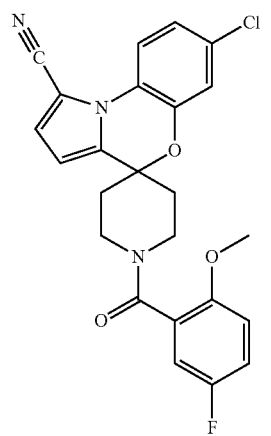

1091
800
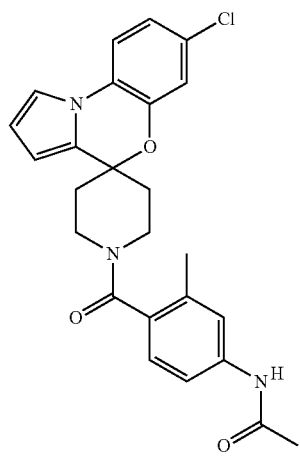
801
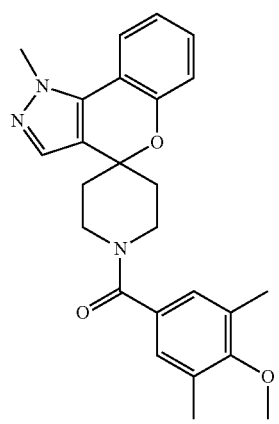
802
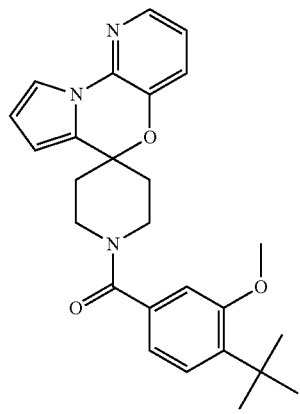
1092
803
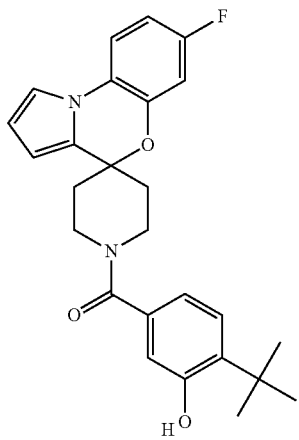
804
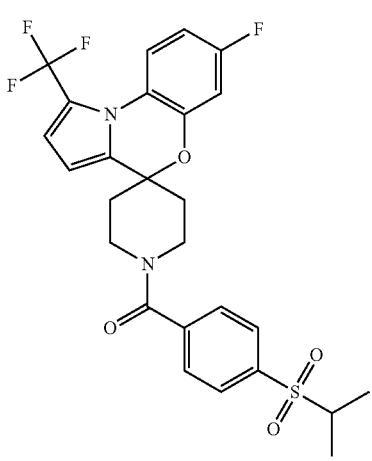
805
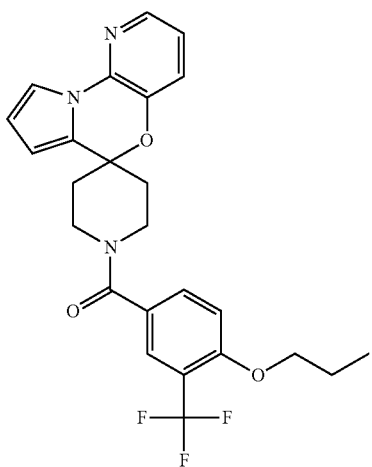

806 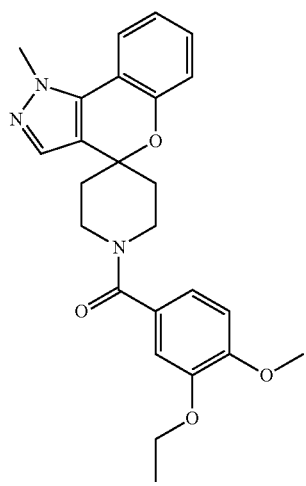
807 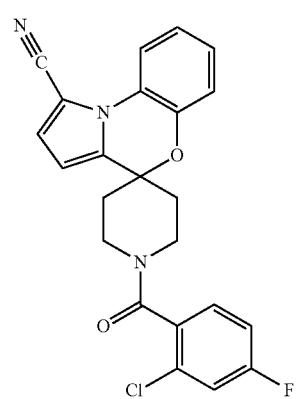
808 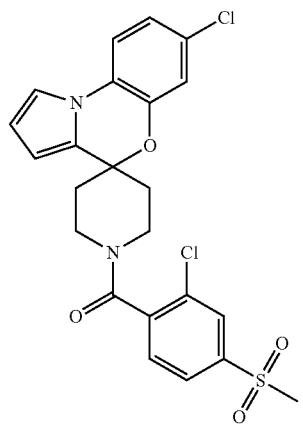
809 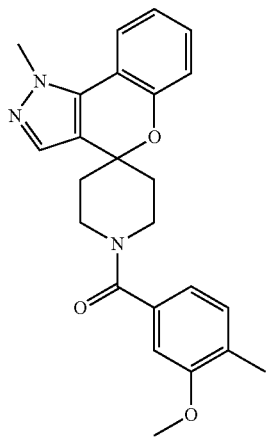
810 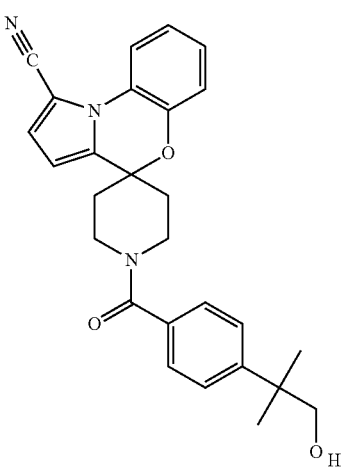
811 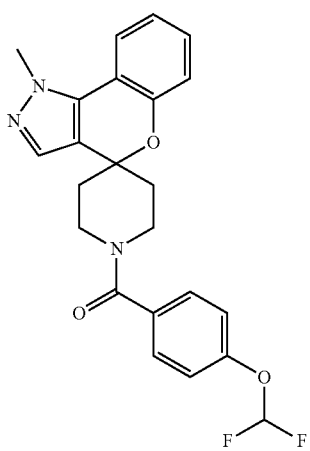

| 812 | 815 |
|---|---|
| 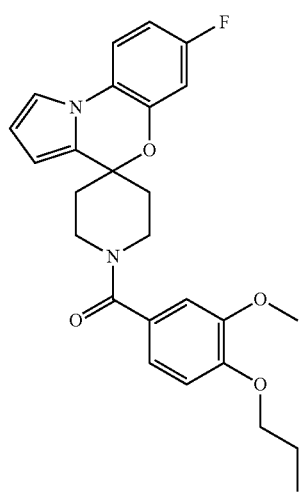 | 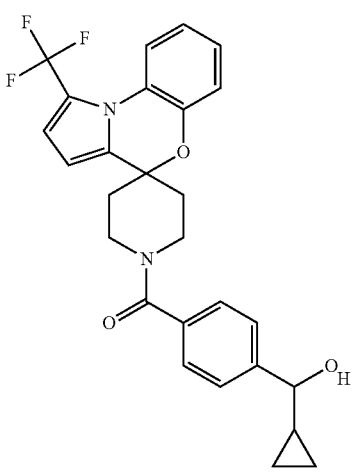 |
| 813 | 816 |
| 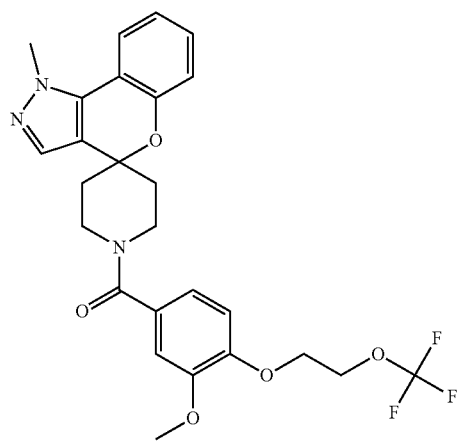 | 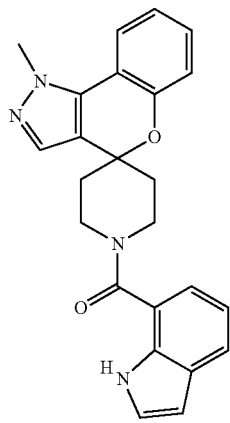 |
| 814 | 817 |
| 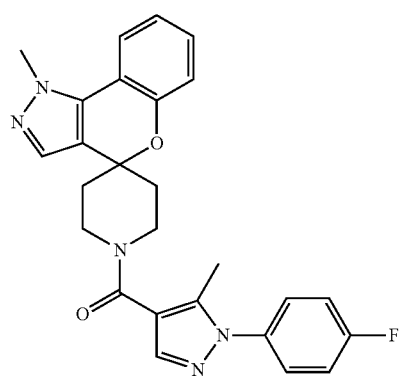 | 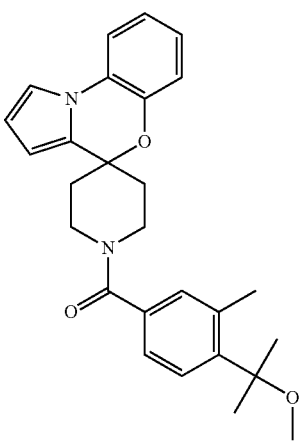 |

818 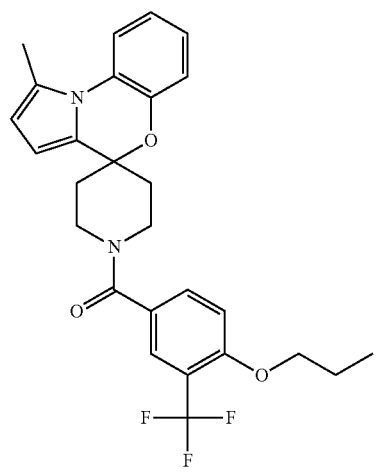
819 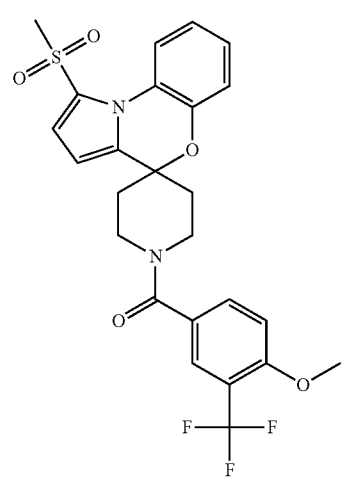
820 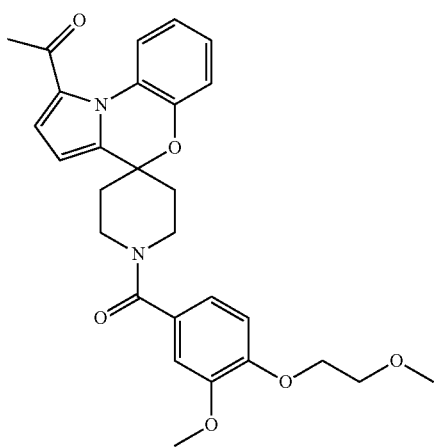
821 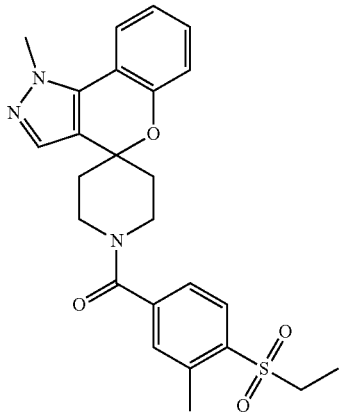
822 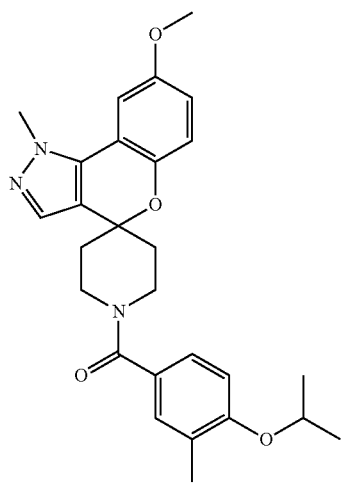
823 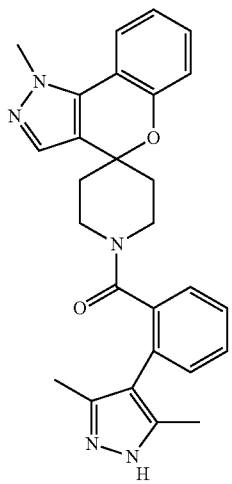

| 1099 -continued | 1100 -continued |
|---|---|
| 824 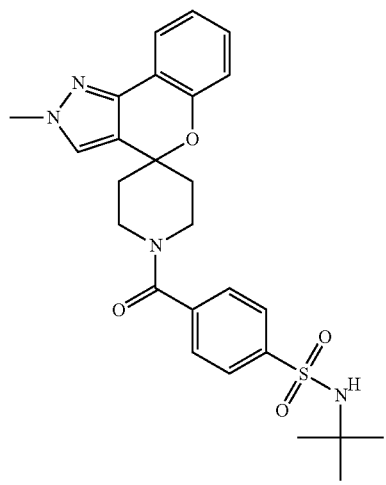 | 827 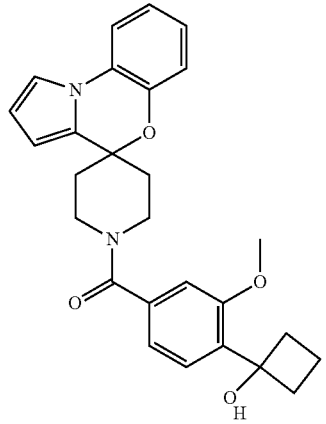 |
| 825 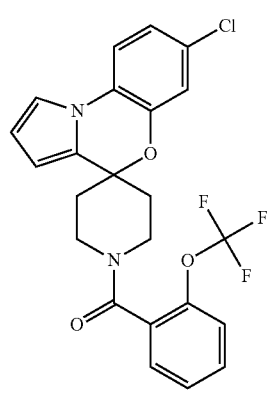 | 828 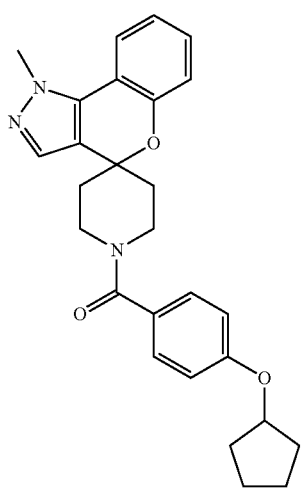 |
| 826 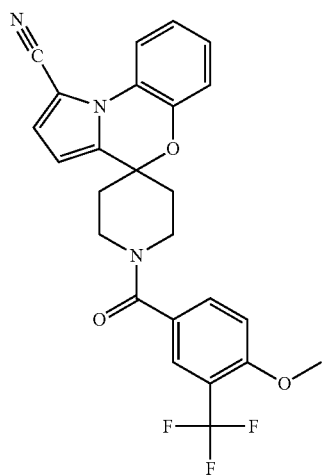 | 829 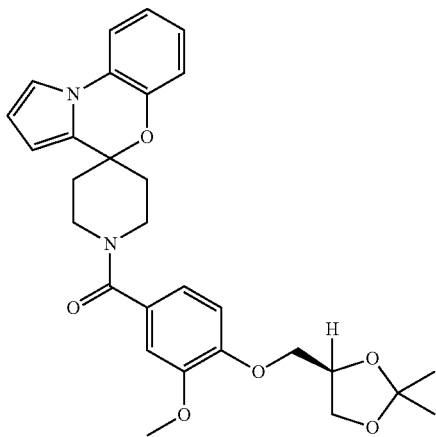 |

| 1101 | 1102 |
|---|---|
| 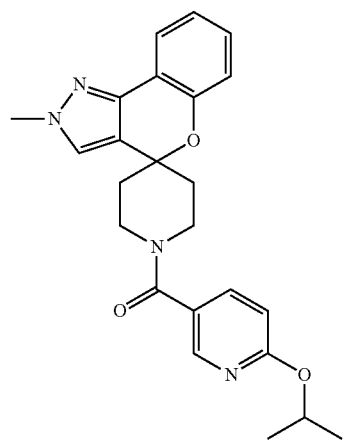 830 | 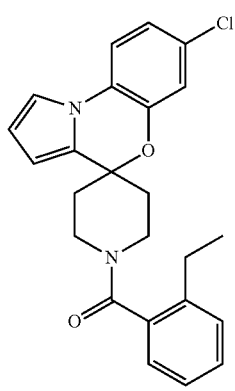 833 |
| 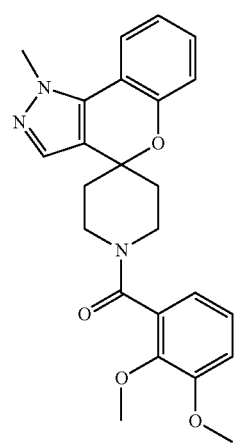 831 | 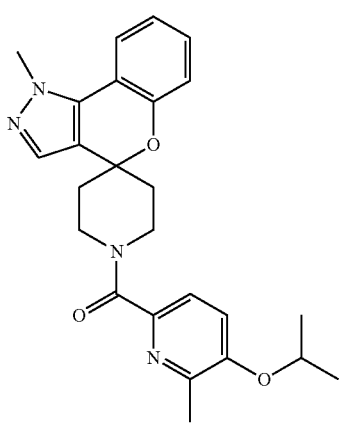 834 |
| 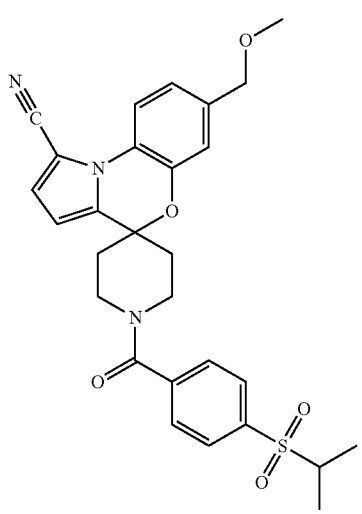 832 | 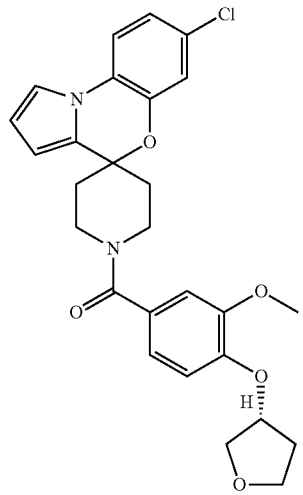 835 |

836
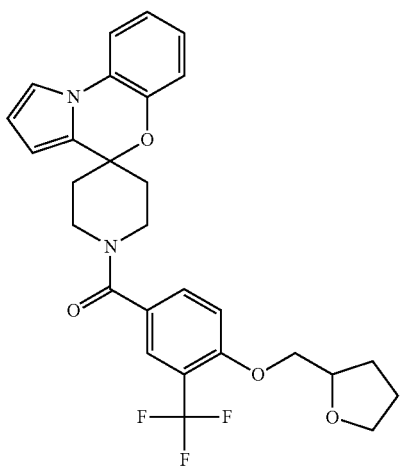
837
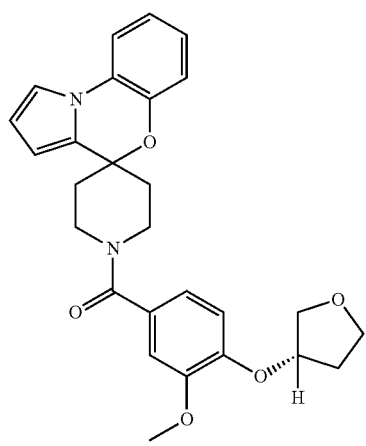
838
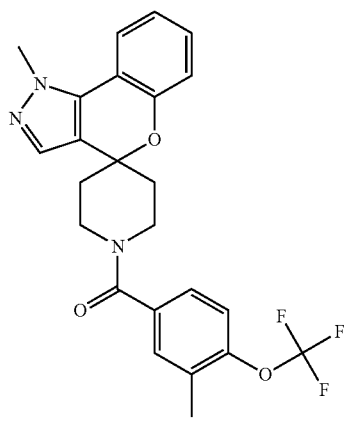
839
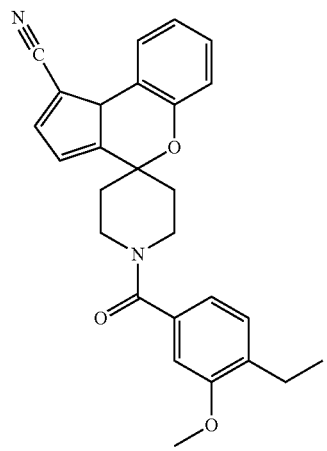
840
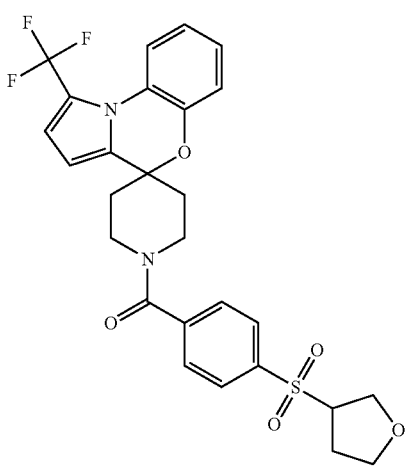
841
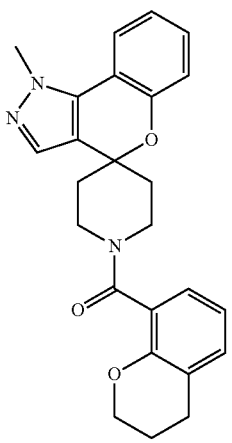

1105
-continued
842
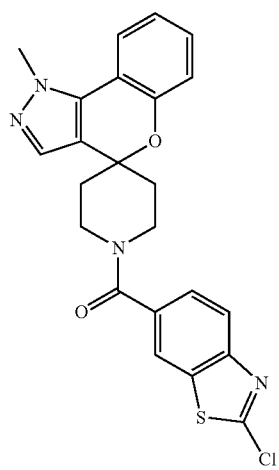
843
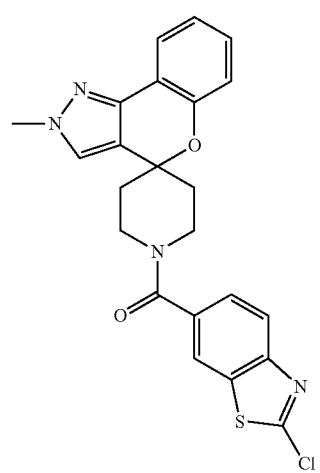
844
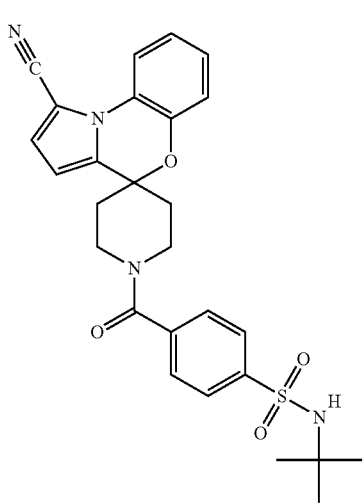
1106
-continued
845
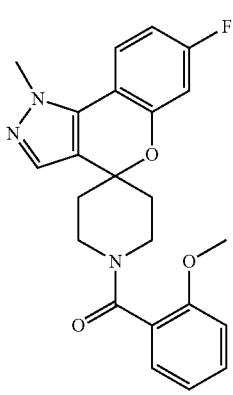
846
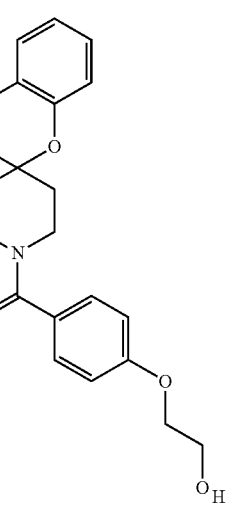
847
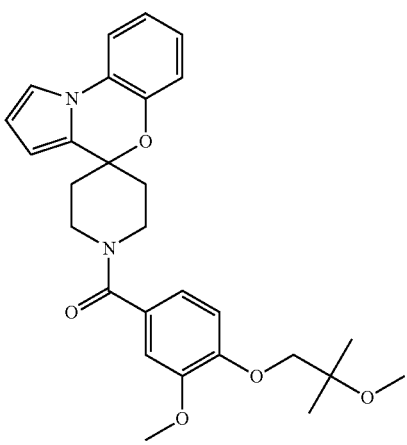

| 1107 -continued | | 1108 -continued | |
|---|---|---|---|
| 848 | 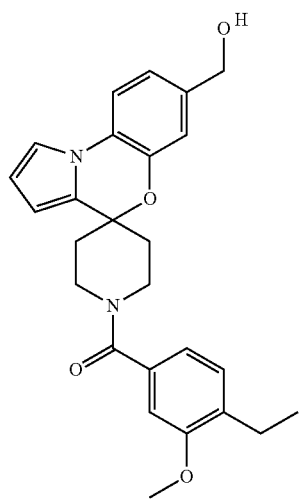 | 851 | 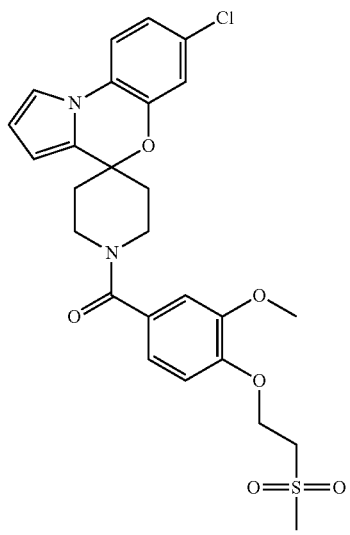 |
| 849 | 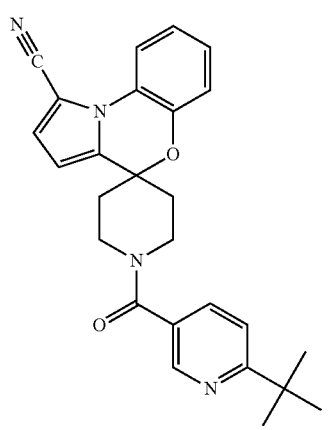 | 852 | 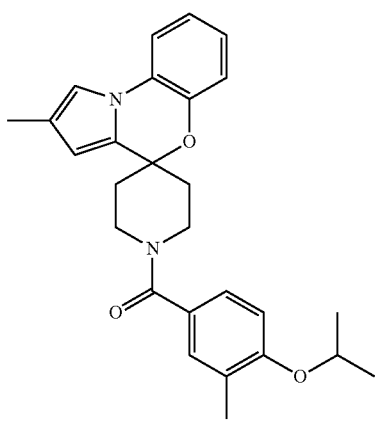 |
| 850 | 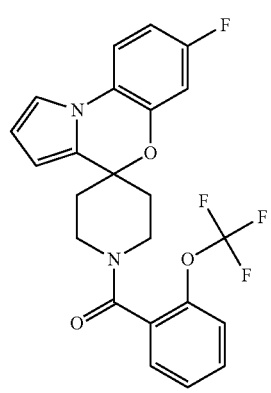 | 853 | 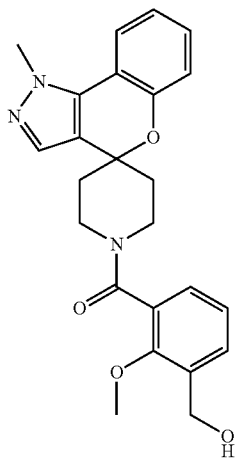 |

1109
-continued
854
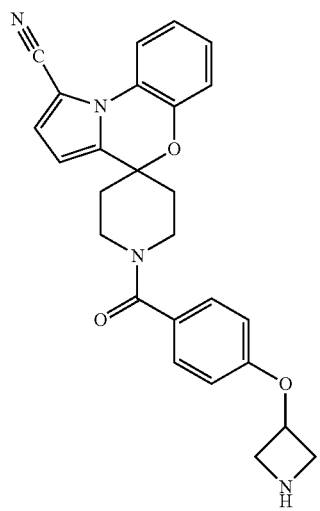
855
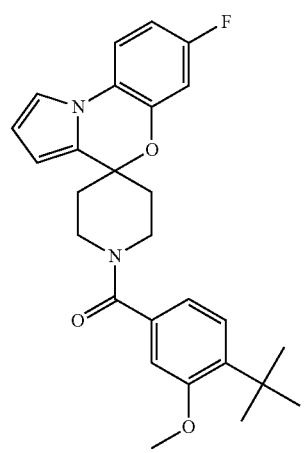
856
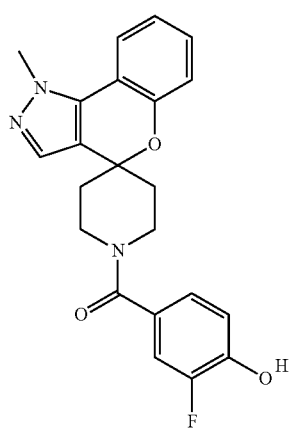
1110
-continued
857
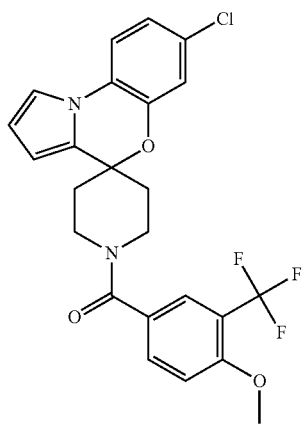
858
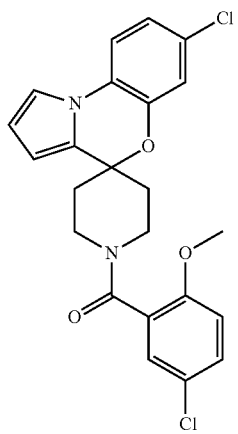
859
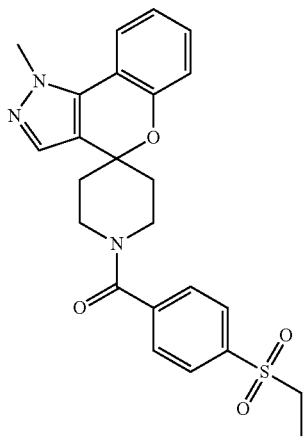

860 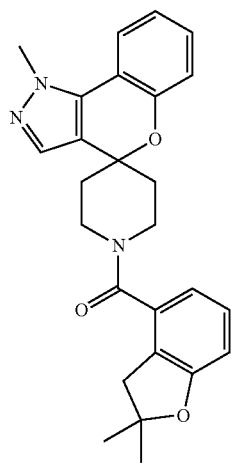
861 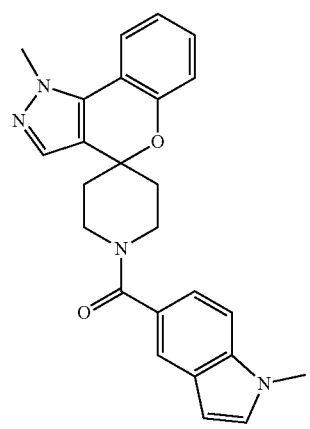
862 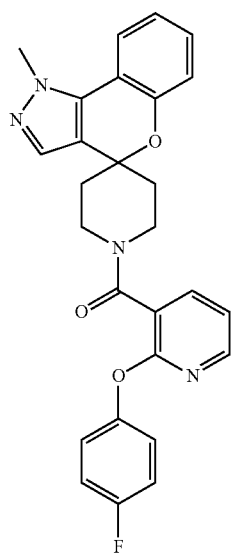
863 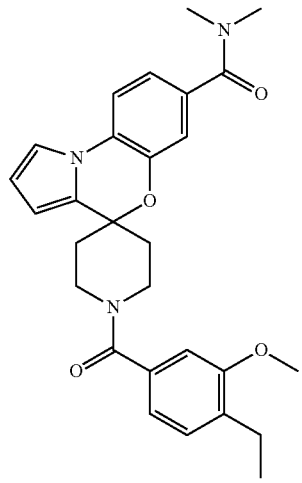
864 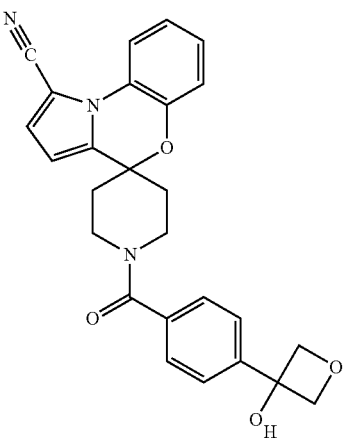
865 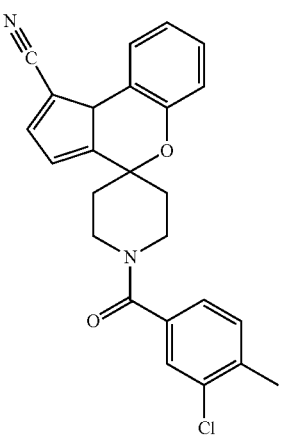

1113
-continued

866
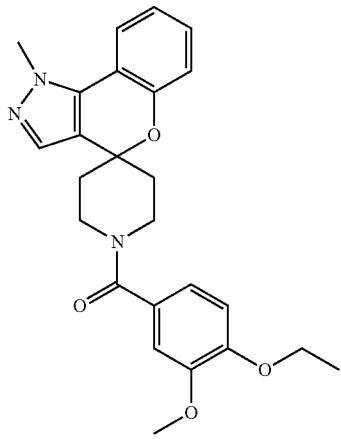

867
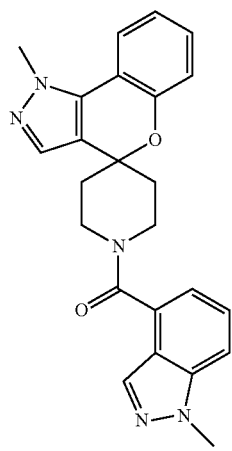

868
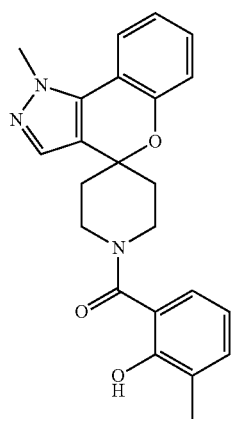

1114
-continued

869
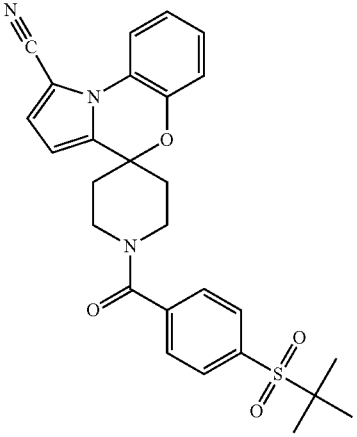

870
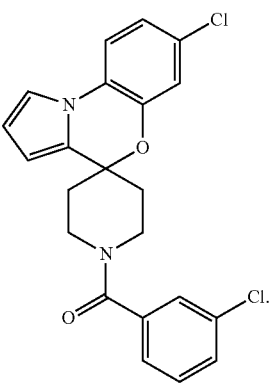

64. A pharmaceutical composition comprising the compound of claim 1 and a pharmaceutically acceptable carrier.

65. A method of inhibiting a voltage-gated sodium ion channel in:
(a) a patient; or
(b) a biological sample;
comprising administering to the patient, or contacting the biological sample, with the compound of claim 1.

66. The method of claim 65, wherein the voltage-gated sodium ion channel is NaV 1.7.

67. A method of treating or lessening the severity in a subject of acute, chronic, neuropathic, or inflammatory pain, migraine, cluster headaches, trigeminal neuralgia, herpatic neuralgia, general neuralgias, epilepsy or epilepsy conditions, neurodegenerative disorders, psychiatric disorders, anxiety, depression, dipolar disorder, myotonia, arrhythmia, movement disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, cerebral ischemia, traumatic brain injury, amyotrophic lateral sclerosis, stress- or exercise induced angina, palpitations, hypertension, migraine, or aboramal gastro-intestinal motility, comprising administering an effective amount of a compound of claim 1.

68. The method according to claim 67, wherein said method is used for treating or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, cluster headaches; chronic and acute neuropathic pain, post-herpatic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, urinary incontinence; hyperactivity bladder; painful bladder syndrome; interstitial cystitis (IC); prostatitis; complex regional pain syndrome (CRPS), type I and type II; widespread pain, paroxysmal extreme pain, pruritis, tinnitus, or angina-induced pain.

* * * * *